(12) United States Patent
Li et al.

(10) Patent No.: US 11,793,881 B2
(45) Date of Patent: Oct. 24, 2023

(54) POLYETHYLENE GLYCOL CONJUGATE MEDICAMENT, PREPARATION METHOD THEREFOR AND USE THEREOF

(71) Applicant: CHONGQING UPGRA BIOTECHNOLOGY CO., LTD., Chongqing (CN)

(72) Inventors: Gaoquan Li, Chongqing (CN); Dajun Li, Chongqing (CN); Qian Zhang, Chongqing (CN); Yusong Wei, Chongqing (CN); Yongchen Peng, Chongqing (CN); Xiangwei Yang, Chongqing (CN); Xiafan Zeng, Chongqing (CN); Gang Mei, Chongqing (CN); Diedie Li, Chongqing (CN); Chengzhi Gao, Chongqing (CN); Xiaoling Ding, Chongqing (CN); Yue Liu, Chongqing (CN); Jia Gao, Chongqing (CN); Yuyang Yi, Chongqing (CN); Yanxia Heng, Chongqing (CN); Xi Liu, Chongqing (CN); Tao Tu, Chongqing (CN); Kai Wang, Chongqing (CN); Liwei Liu, Chongqing (CN); Mei Liu, Chongqing (CN); Qiang Luo, Chongqing (CN); Xiao Tang, Chongqing (CN); Jie Lou, Chongqing (CN); Huiyu Chen, Chongqing (CN); Yue Yang, Chongqing (CN); Yuanqiang Wang, Chongqing (CN)

(73) Assignee: CHONGQING UPGRA BIOTECHNOLOGY CO., LTD., Chongqing (CN)

( * ) Notice: Subject to any disclaimer, the term of this patent is extended or adjusted under 35 U.S.C. 154(b) by 0 days.

(21) Appl. No.: 17/779,649

(22) PCT Filed: Nov. 18, 2020

(86) PCT No.: PCT/CN2020/129705
§ 371 (c)(1),
(2) Date: May 25, 2022

(87) PCT Pub. No.: WO2021/104120
PCT Pub. Date: Jun. 3, 2021

(65) Prior Publication Data
US 2023/0088403 A1 Mar. 23, 2023

(30) Foreign Application Priority Data

| Nov. 28, 2019 | (CN) | 201911190064 |
| Jul. 28, 2020 | (CN) | 202010737415 |
| Jul. 28, 2020 | (CN) | 202010738638 |

(51) Int. Cl.
*A61K 47/60* (2017.01)
*A61P 35/00* (2006.01)
*A61K 45/06* (2006.01)

(52) U.S. Cl.
CPC .............. *A61K 47/60* (2017.08); *A61K 45/06* (2013.01); *A61P 35/00* (2018.01)

(58) Field of Classification Search
None
See application file for complete search history.

(56) References Cited

U.S. PATENT DOCUMENTS

| 2014/0363371 A1 | 12/2014 | Luo et al. |
| 2019/0117790 A1 | 4/2019 | Song et al. |

(Continued)

FOREIGN PATENT DOCUMENTS

| CN | 104105508 A | 10/2014 |
| CN | 104987504 A | 10/2015 |

(Continued)

OTHER PUBLICATIONS

International Search Report, International Application No. PCT/CN2020/129705, dated Feb. 20, 2021 (8 pages).

(Continued)

*Primary Examiner* — Brian J Davis
(74) *Attorney, Agent, or Firm* — Ware, Fressola, Maguire & Barber LLP

(57) ABSTRACT

The present invention relates to a polyethylene glycol conjugate medicament, a preparation method therefor and use thereof, and in particular relates to a polyethylene glycol conjugate medicament represented by formula (I) or a pharmaceutically acceptable salt thereof. The present invention also relates to a method for preparing the polyethylene glycol conjugate medicament or a pharmaceutically acceptable salt thereof, and an intermediate of the same, a pharmaceutical composition comprising the polyethylene glycol conjugate medicament or a pharmaceutically acceptable salt thereof, and use thereof in preparing a medicament.

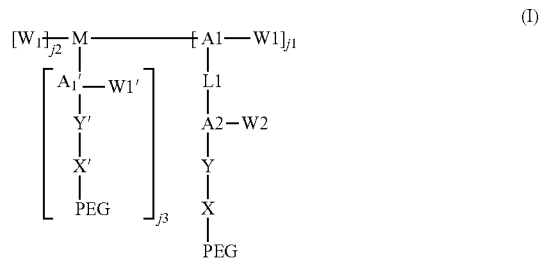

(I)

22 Claims, 7 Drawing Sheets

(56) References Cited

U.S. PATENT DOCUMENTS

2020/0261588 A1    8/2020  Li et al.
2022/0105189 A1    4/2022  Li et al.

FOREIGN PATENT DOCUMENTS

| CN | 105601903 A    | 5/2016  |
|----|----------------|---------|
| CN | 107670048 A    | 2/2018  |
| CN | 107670050 A    | 2/2018  |
| JP | 2022-523752    | 4/2022  |
| WO | 2015027054 A2  | 2/2015  |
| WO | 2017210963 A1  | 12/2017 |

OTHER PUBLICATIONS

Written Opinion, International Application No. PCT/CN2020/129705, dated Feb. 20, 2021 (5 pages).
Office Action and English Translation, Japanese Patent Application No. 2022-531503, dated Nov. 2023 (10 pages). 2022.

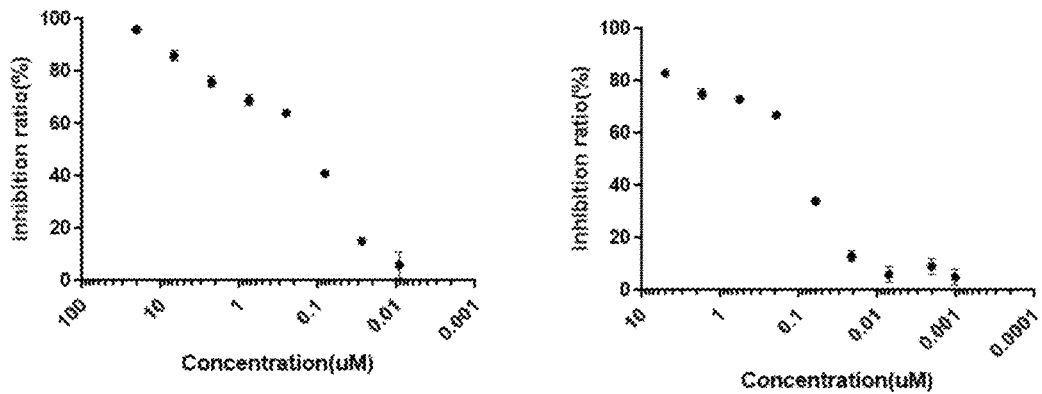
FIG. 3
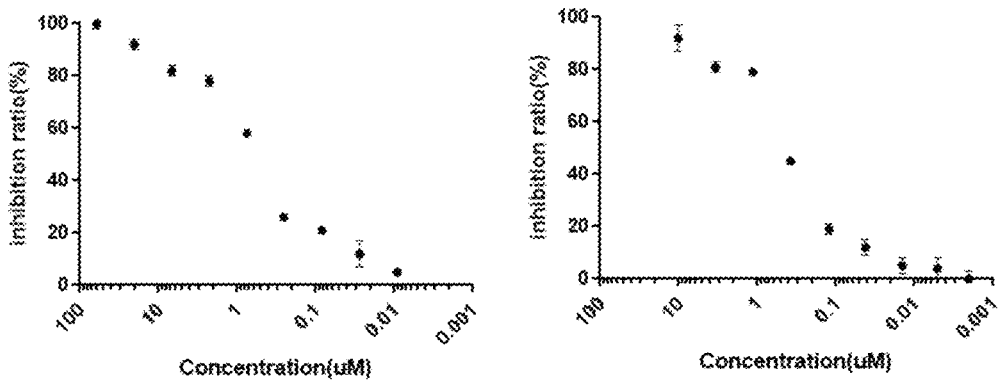
FIG. 4
| 27-134 | | Best-fit values | | 44-2 | | Best-fit values | |
|---|---|---|---|---|---|---|---|
| | | IC50 | 0.6862 | | | IC50 | 0.09375 |
| | | Best-fit values | | | | Best-fit values | |
| | | IC50 | 0.4305 | | | IC50 | 0.1076 |
FIG. 5

POLYETHYLENE GLYCOL CONJUGATE MEDICAMENT, PREPARATION METHOD THEREFOR AND USE THEREOF

TECHNICAL FIELD

The present invention belongs to the technical field of medicine, and relates to a polyethylene glycol conjugated drug, preparation method thereof and use thereof.

BACKGROUND

Pegylated drug has great advantages over the original drug, which can increase water solubility of drug molecules (which is very important for drugs with extremely low solubility such as paclitaxel, camptothecin or platinum); and can prevent or reduce drug agglomeration, immunogenicity and antigenicity. Most small-molecule anticancer drugs can only stay in the blood circulation for a few minutes, while polymer-(anticancer drug) conjugates may stay for tens or hundreds of hours or even longer, which is beneficial from the "enhanced permeability and retention" effect, i.e., the EPR effect, caused by leakage of tumor capillaries. Due to the increased hydrodynamic volume of the polymer-(anticancer drug) conjugates, the renal elimination of the drugs is weakened, the drugs are protected from enzymatic degradation, the half-life of the drugs in plasma is extended, and the bioavailability of the drugs is increased. Moreover, the anticancer drugs can be highly enriched in diseased organs, tissues or cells through the EPR passive targeting or active targeting, thereby greatly reducing the toxic side effects caused by small molecule anticancer drugs spreading all over the body. In addition, the polymer-(anticancer drug) conjugates can limit the cell absorption of drugs to the endocytic pathway, which is conducive to drug delivery to the lysosome, thereby avoiding drug resistance caused by p-glycoprotein pumping out; the polymer-(anticancer drug) conjugates can also stimulate or restore immune function, and this is conducive to killing cancer cells.

The NEKTAR company and the ENZON company in the United States have successfully developed polyethylene glycol conjugated drugs. At present, there are 15 polyethylene glycol conjugated drugs which have been approved by the FDA to enter the market, and in addition, 36 new clinical drugs are in the first-phase, second-phase, third-phase clinical trials or in the NDA phase. However, all the above pegylated drugs are pegylated single drugs.

Chinese patent ZL201510996205.4 discloses that gemcitabine, a chemotherapeutic drug, and AZD7762, a Chk1 inhibitor, are grafted onto a four-arm polyethylene glycol carrier simultaneously. The Chk1 inhibitor has no anticancer effect in itself, but, when combined with gemcitabine, it can enhance the effect of the chemotherapeutic drug. Chinese patents ZL201710761441.7 and ZL201710761572.5 disclose that two anticancer drugs are grafted onto one graft site of polyethylene glycol simultaneously, to thereby realize the inhibition of different cancer cell biological signal channels and targets, and the free combination between different treatment methods.

SUMMARY

The present invention is directed to solving, at least to a certain extent, one of the technical problems in the related art. Therefore, the present invention provides a polyethylene glycol conjugated drug which has excellent tumor inhibition activity. Through the preparation method of the present invention, the polyethylene glycol conjugated drug of the present invention can be prepared efficiently and conveniently.

Polyethylene Glycol Conjugated Drug

In the first aspect of the present invention, the present invention provides a polyethylene glycol conjugated drug of formula (I) or a pharmaceutically acceptable salt thereof.

In the polyethylene glycol conjugated drug of the present invention, multiple identical or different drug molecules are conjugated together by using an amino acid or a polypeptide as a linking chain, and a dicarboxylic acid with an amino group (for example, a natural amino acid with two carboxyl groups) as a linking bridge. The type, ratio and drug loading of the drug can be adjusted. In the formula (I), PEG is a single-arm polyethylene glycol segment, and its number-average molecular weight may be from 2 k to 40 k, such as from 5 k to 10 k or from 10 k to 40 k, such as about 2 k, about 5 k, about 10 k, about 20 k, about 30 k or about 40 k. In certain embodiments, PEG reacts with a carboxyl group on the main chain through a terminal amino group to form an amide bond. Alternatively, PEG reacts with an amino group on the main chain through a terminal carboxyl group to form an amide bond. In certain embodiments, the molecular weight of the PEG comprises the terminal amino group thereof (i.e., the PEG derivative bearing reactive group), and in some embodiments, the molecular weight of the PEG is the molecular weight of polyethylene glycol and X or X' as a whole, which may be from 2 k to 40 k, such as 2 k to 3 k, 3 k to 5 k, 5 k to 10 k, or 10 k to 40 k, such as about 2 k, about 3 k, about 5 k, about 10 k, about 40 k.

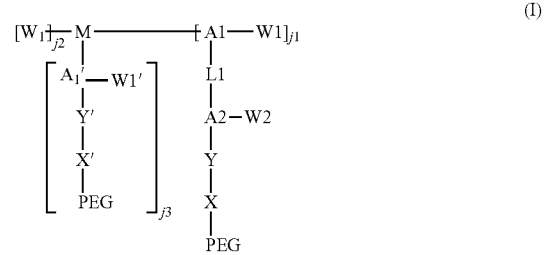

wherein:

M is —C(=O)—$C_{1-6}$ alkylene-C(=O)—, —C(=O)—, —NH—$C_{1-6}$ alkylene-NH—, —C(=O)—$C_{1-6}$ alkylene-NH—,

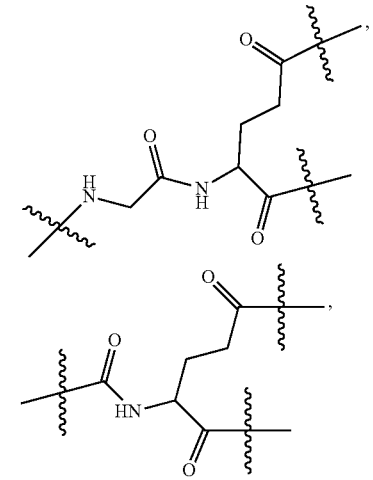

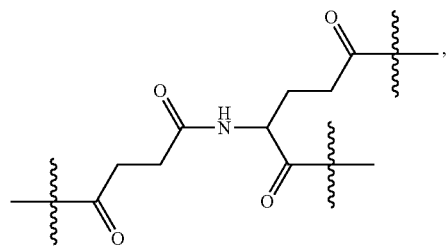
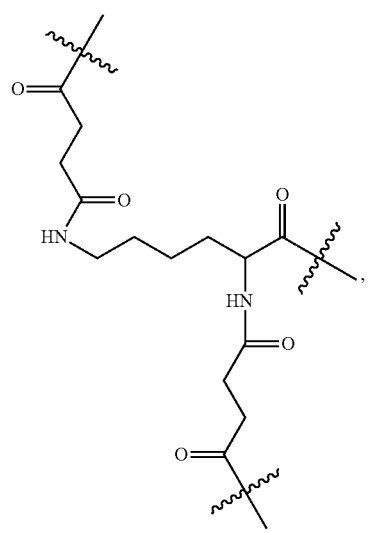
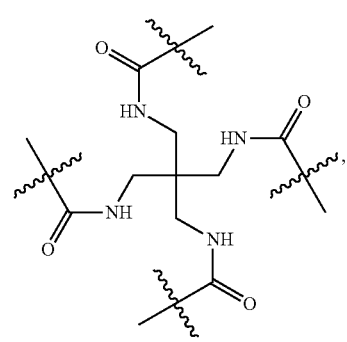
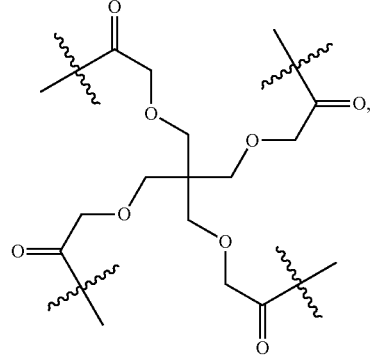
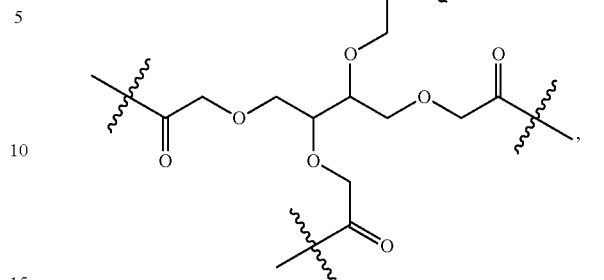
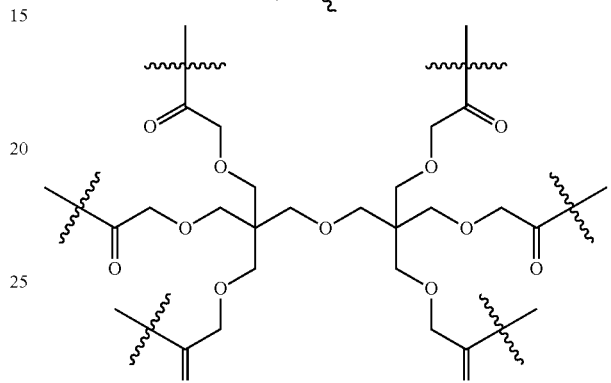
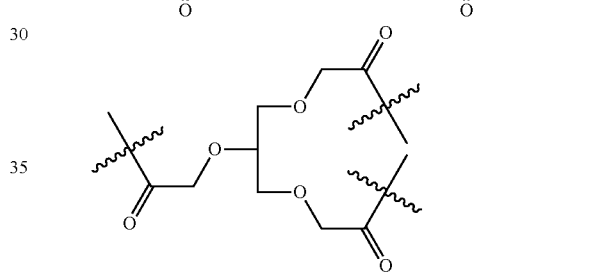
or PEG$_m$; wherein, PEG$_m$ is a single-arm or multi-arm (for example, four-arm, eight-arm, preferably four-arm) polyethylene glycol segment, and its number-average molecular weight is 5 k-40 k, preferably 5 k-10 k or 10 k-40 k, more preferably 5 k or 10 k;
A1, A1' each independently are
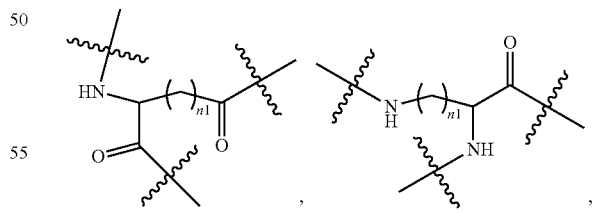
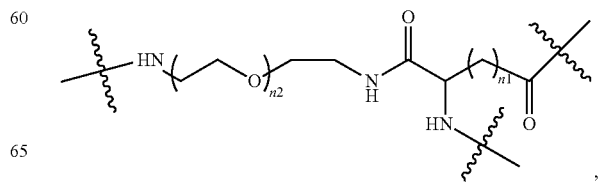

-continued
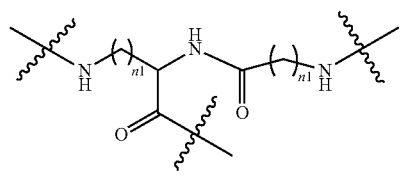
,
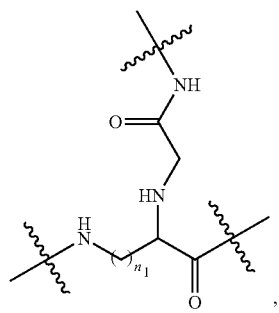
,
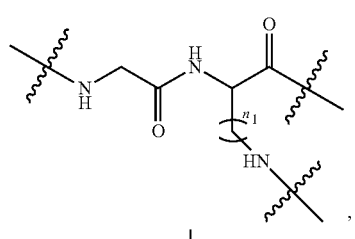
,
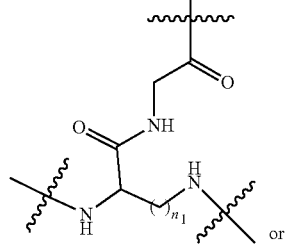
or
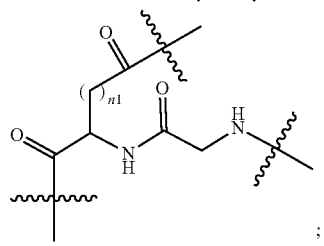
;
A2 independently is a direct bond or
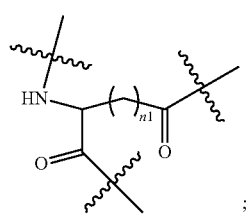
;
L1 independently is a direct bond or —C(=O)—C$_{1-6}$ alkylene-C(=O)—;
W1, W1', W2 each independently are Q1,
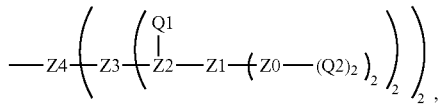
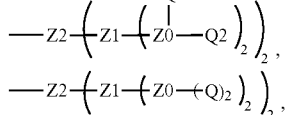
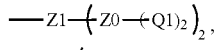
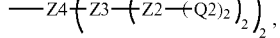
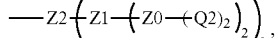
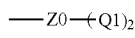
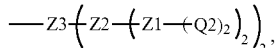
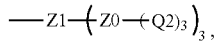
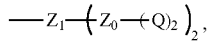
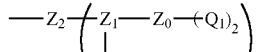
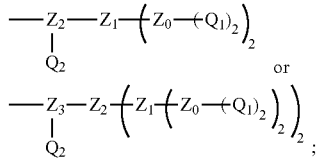
or
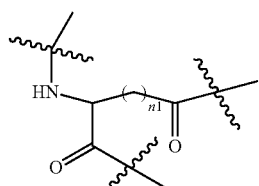
;
Z4, Z3, Z2, Z1, Z0 each independently are
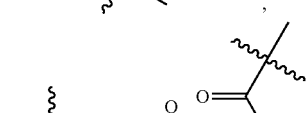
,
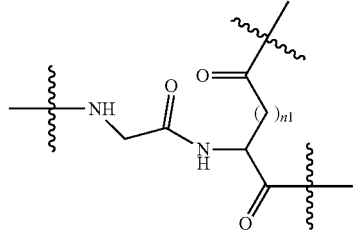
,
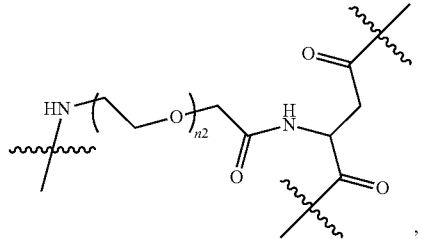
,

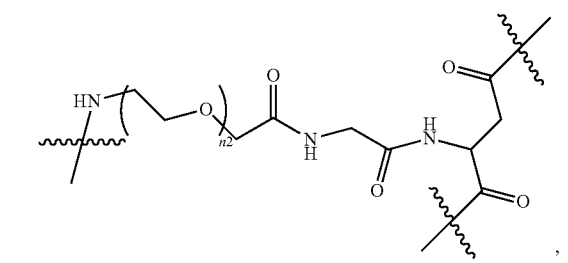
,
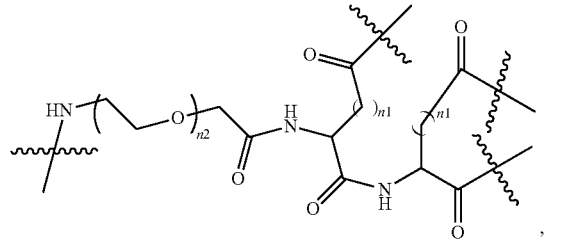
,
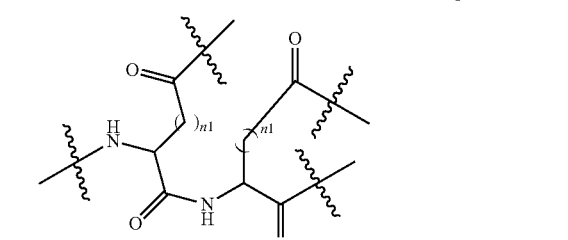
,
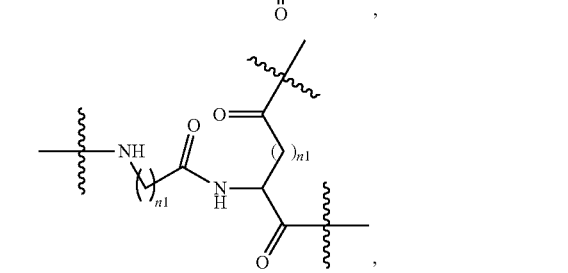
,
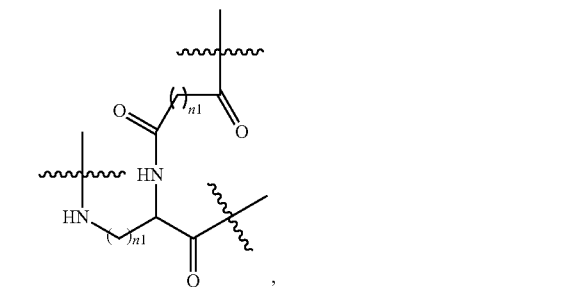
,
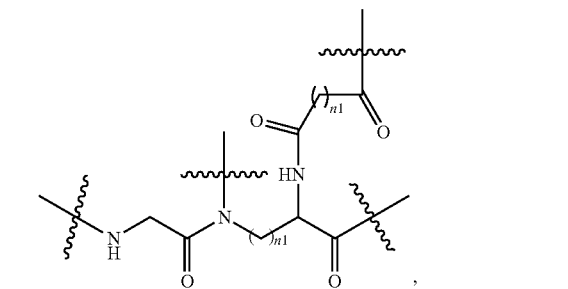
,
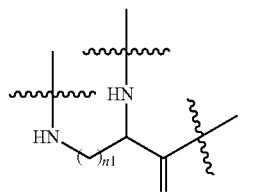
or
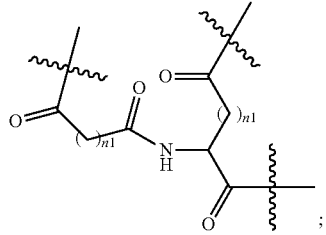
;
Q is —N-AC;
Q1 is —N1-AC1;
Q2 is —N2-AC2;
N, N1, N2 each independently are GFLG, G,
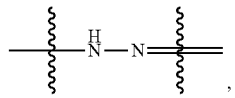
,
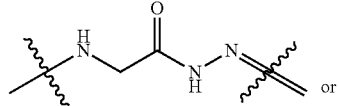 or
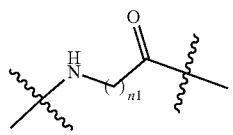
(preferably
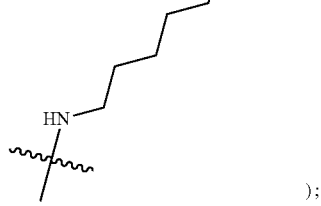
);
AC, AC1, AC2 each independently are drug molecules (for example, drug molecules with anti-tumor activity), preferably PCB, DOX, LPT, SB7, PKA, SN38, PTX or NPB;
n1, n2 each independently are 0, 1, 2, 3, 4, 5 or 6;
Y, Y' each independently are a direct bond, GLFG, —C(=O)—C$_{1-6}$ alkylene-C(=O)—,

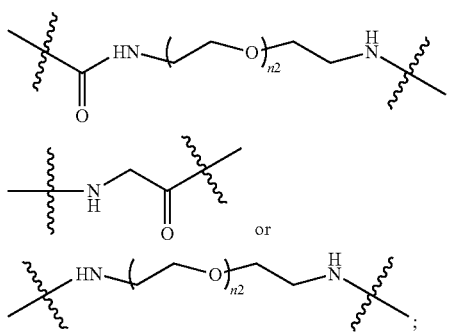

X, X' each independently are

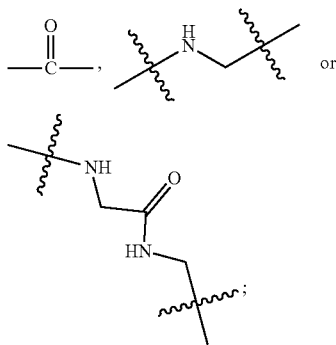

PEG is a single-arm polyethylene glycol segment, and its number-average molecular weight independently is 5 k-40 k;

j1 is 1, 2, 3, 4, 5 or 6;

j2, j3 each independently are 0 or 1.

It should be noted that, in some embodiments, $PEG_m$ is linked to the residual structure of the compound of the formula (I) through carbonyl.

Alternatively, in the polyethylene glycol conjugated drug of the present invention, multiple identical or different drug molecules are conjugated together by using an amino acid or a polypeptide as a linking chain, and a dicarboxylic acid with an amino group (for example, a natural amino acid with two carboxyl groups) as a linking bridge. The type, ratio and drug loading of the drug can be adjusted. In the formula (I), PEG is a single-arm polyethylene glycol segment, and its number-average molecular weight may be from 2 k to 40 k, such as from 5 k to 10 k or from 10 k to 40 k, such as about 2 k, about 5 k, about 10 k, about 20 k, about 30 k or about 40 k. In certain embodiments, PEG reacts with a carboxyl group on the main chain through a terminal amino group to form an amide bond. Alternatively, PEG reacts with an amino group on the main chain through a terminal carboxyl group to form an amide bond. In certain embodiments, the molecular weight of the PEG comprises the terminal amino group thereof (i.e., the PEG derivative bearing reactive group), and in some embodiments, the molecular weight of the PEG is the molecular weight of polyethylene glycol and X or X' as a whole, which may be from 2 k to 40 k, such as 2 k to 3 k, 3 k to 5 k, 5 k to 10 k, or 10 k to 40 k, such as about 2 k, about 3 k, about 5 k, about 10 k, about 40 k.

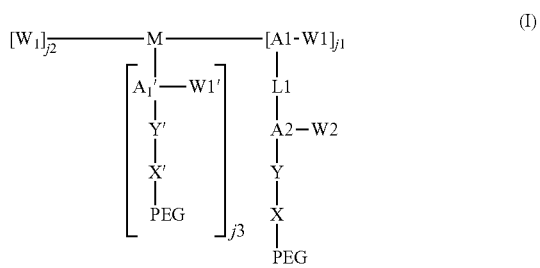

wherein:

M is —C(=O)—$C_{1-6}$ alkylene-C(=O)—, —C(=O)—, —NH—$C_{1-6}$ alkylene-NH—, —C(=O)—$C_{1-6}$ alkylene-NH—,

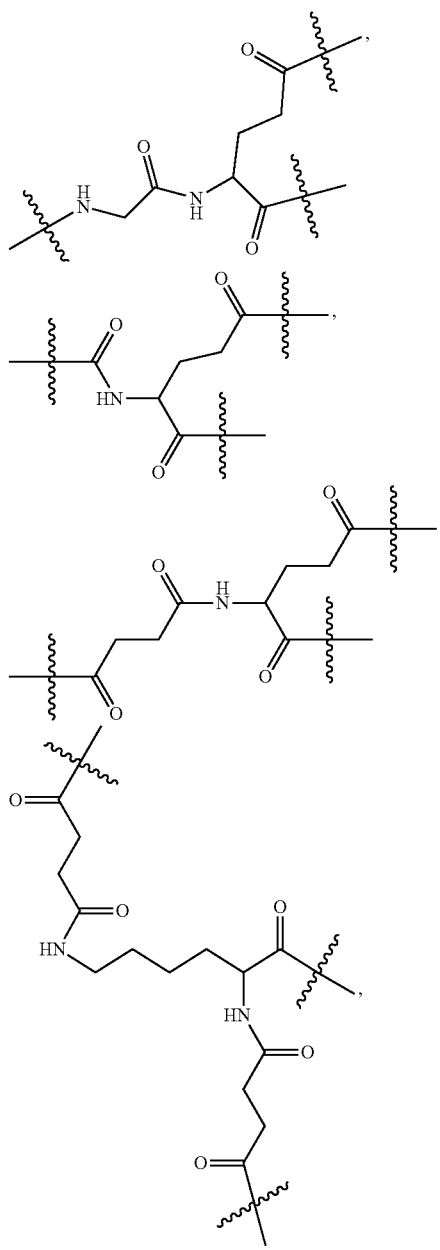

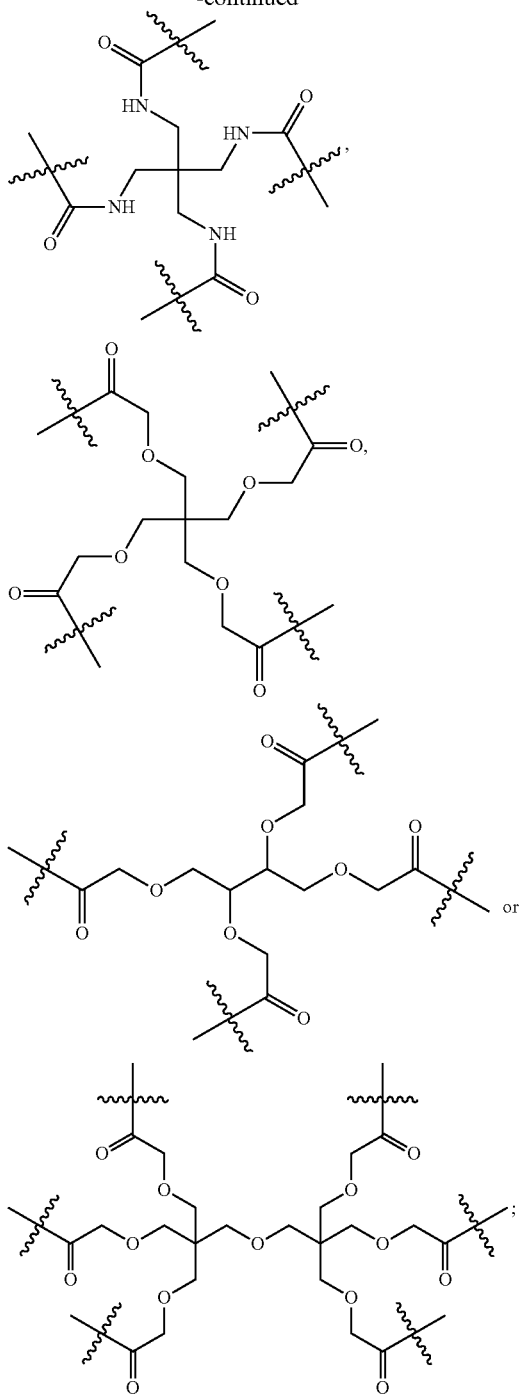
A1, A1' each independently are
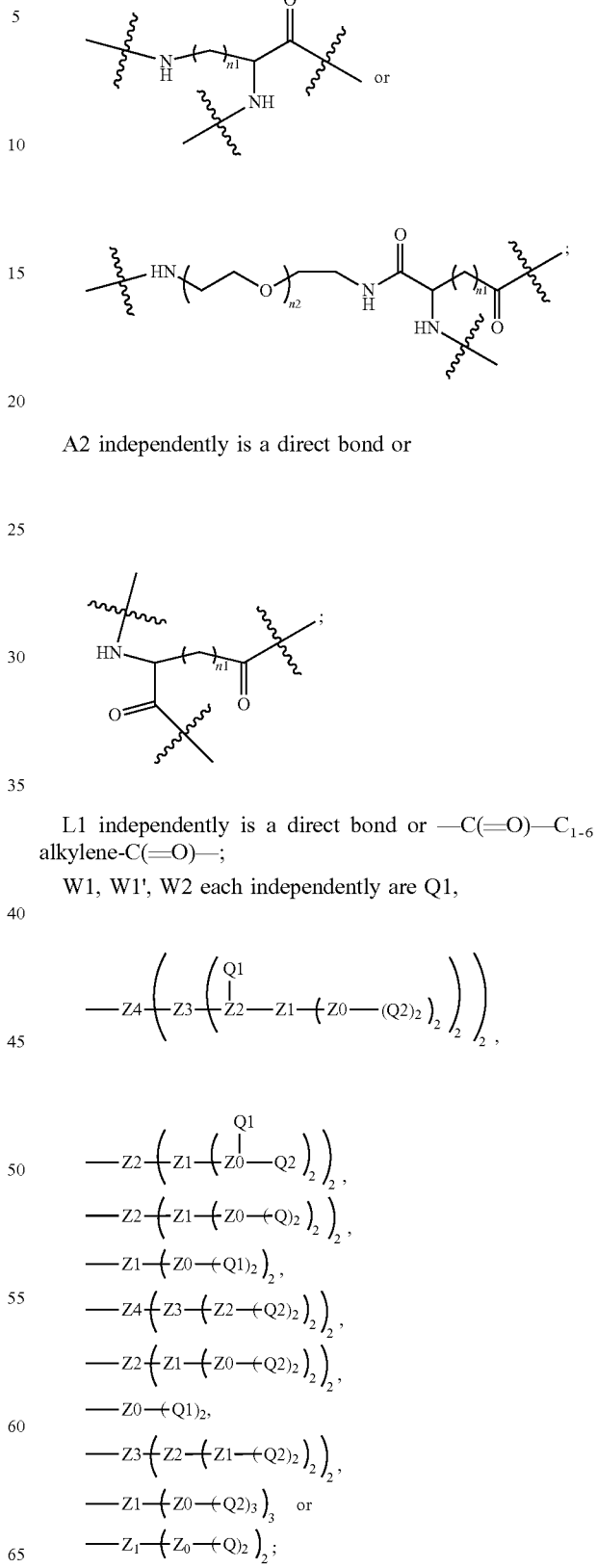
A2 independently is a direct bond or
L1 independently is a direct bond or —C(=O)—C$_{1-6}$ alkylene-C(=O)—;
W1, W1', W2 each independently are Q1, Z4, Z3, Z2, Z1, Z0 each independently are

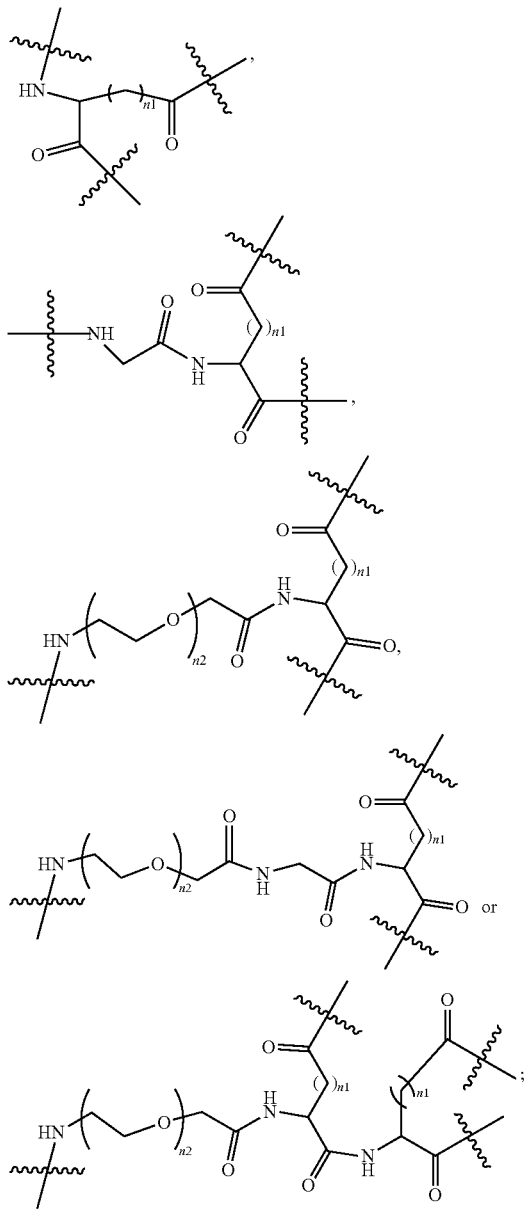

Q is —N-AC;
Q1 is —N1-AC1;
Q2 is —N2-AC2;
N, N1, N2 each independently are GFLG, G,

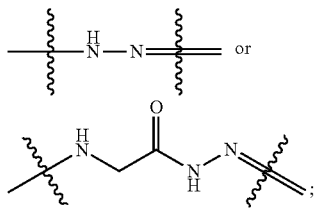

AC, AC1, AC2 each independently are drug molecules (for example, drug molecules with anti-tumor activity), preferably PCB, DOX, LPT, SB7, PKA, SN38 or PTX;

n1, n2 each independently are 0, 1, 2, 3, 4, 5 or 6;

Y, Y' each independently are a direct bond, GLFG, —C(=O)—C$_{1-6}$ alkylene-C(=O)—,

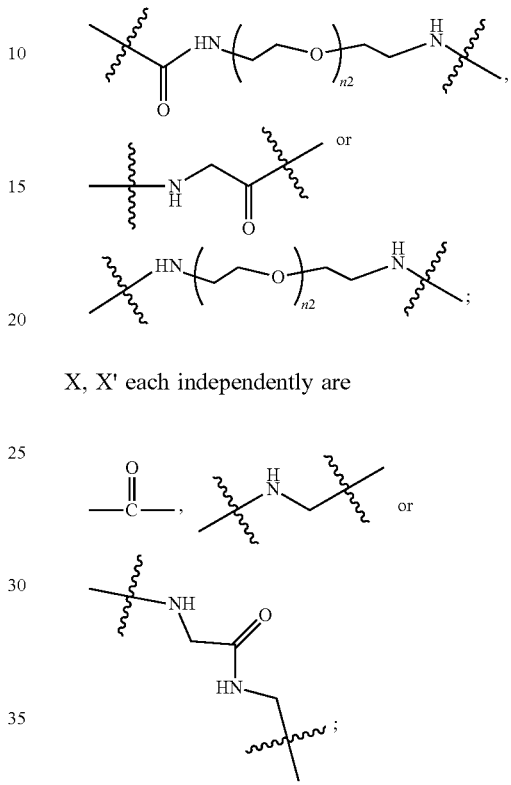

X, X' each independently are

PEG is a single-arm polyethylene glycol segment, and its number-average molecular weight independently is 5 k-40 k;

j1 is 1, 2, 3, 4, 5 or 6;

j2, j3 each independently are 0 or 1.

In some embodiments, the polyethylene glycol conjugated drug has the structure represented by the formula (II), the formula (III), the formula (IV) or the formula (V):

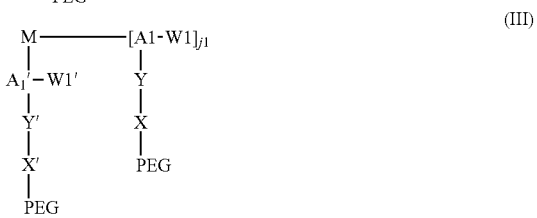

$$M\begin{matrix}\text{---}[A1\text{-}W1]_{j1}\\|\\L1\\|\\A2\text{---}W2\\|\\Y\\|\\X\\|\\PEG\end{matrix} \quad (V)$$
In some embodiments, the polyethylene glycol conjugated drug has the structure represented by the formula (II), wherein:
M is —C(=O)—C$_{1-6}$ alkylene-C(=O)—,
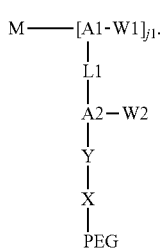,
—NH—C$_{1-6}$ alkylene-NH—,
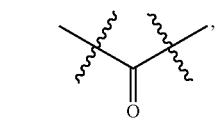 [SMILES: *C(*)=O],
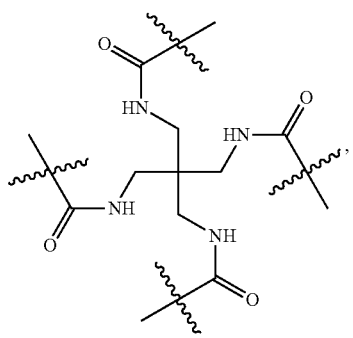,
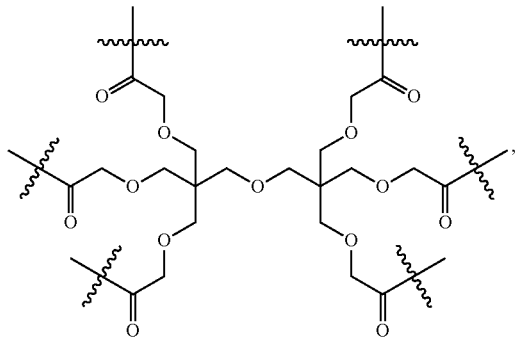,
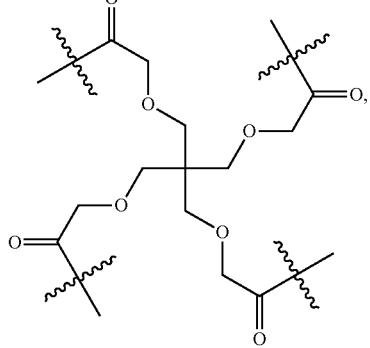,
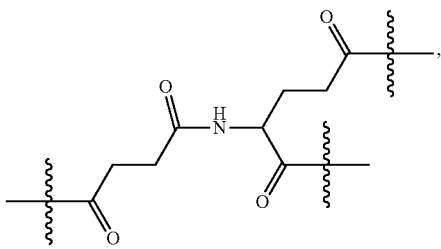,
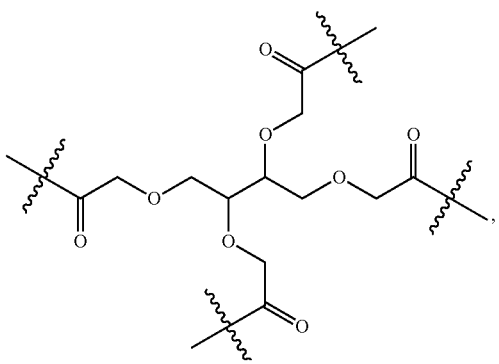,
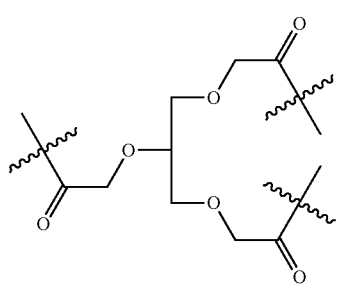,
or PEG$_m$, preferably
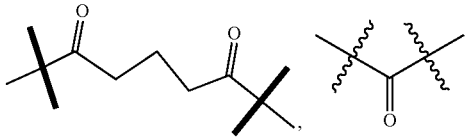,
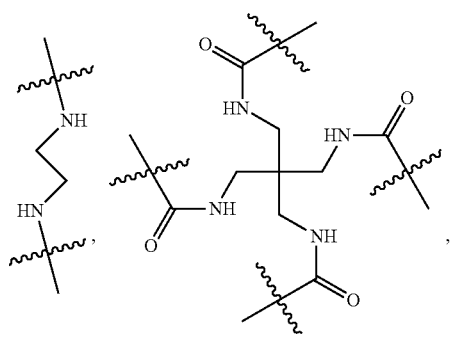, -continued
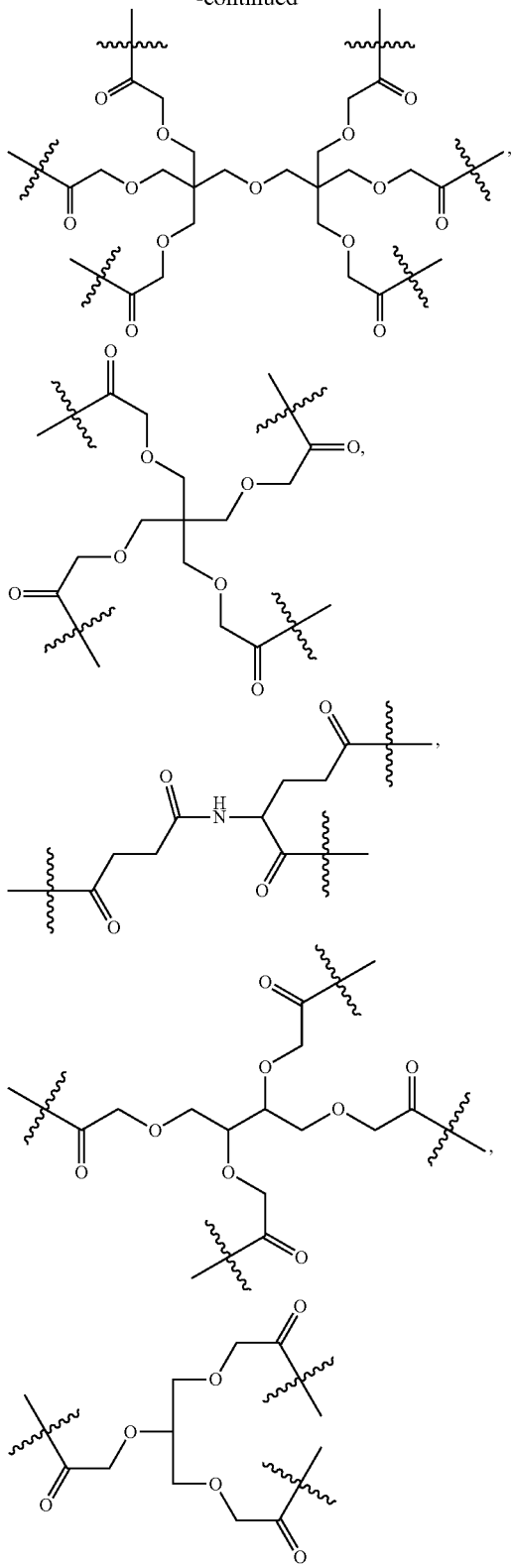
or PEG$_m$, wherein, PEG$_m$ is a single-arm or multi-arm (for example, four-arm, eight-arm, preferably four-arm) polyethylene glycol segment, and its number-average molecular weight is 5 k-40 k, preferably 5 k-10 k or 10 k-40 k, more preferably 5 k or 10 k,
A1 independently is
preferably

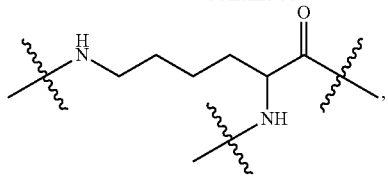
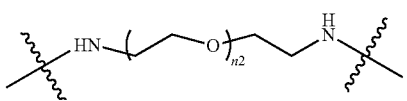
preferably a direct bond,
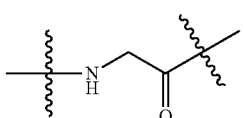
GLFG,
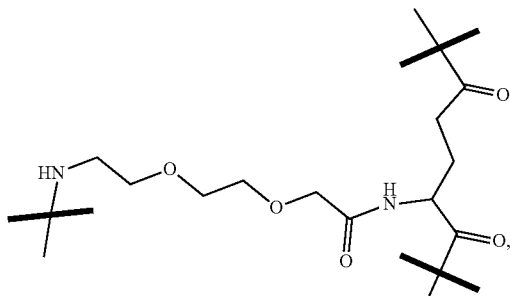
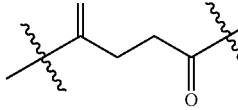
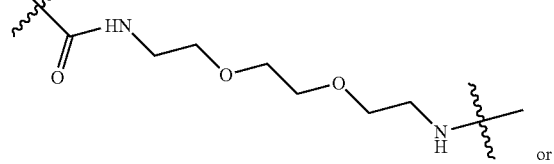
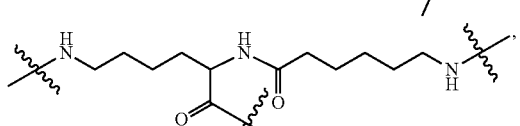
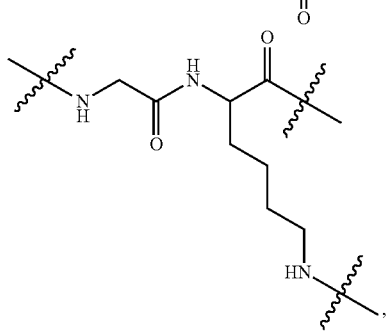
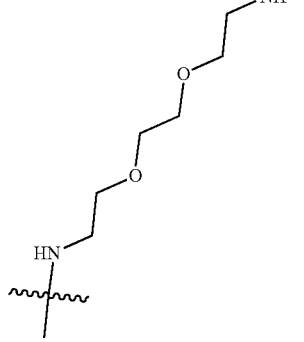
Y independently is a direct bond,
X independently is
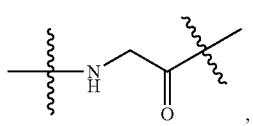
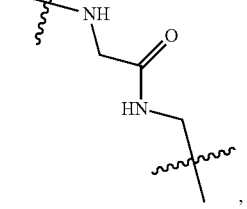
GLFG, —C(=O)—C$_{1-6}$ alkylene-C(=O)—,
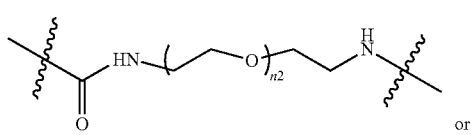 or W1 independently is
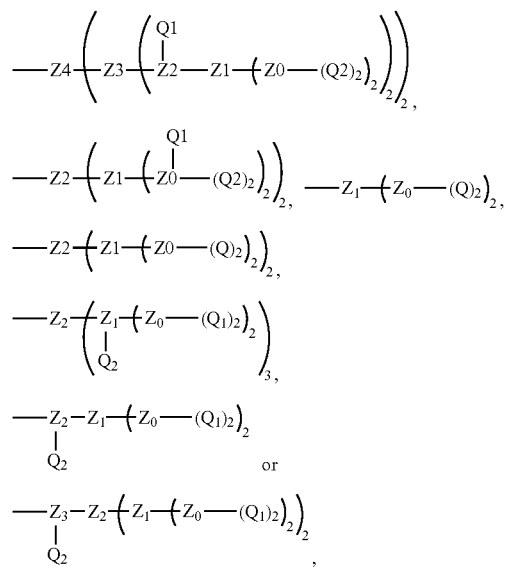
Z4, Z3, Z2, Z1, Z0 each independently are
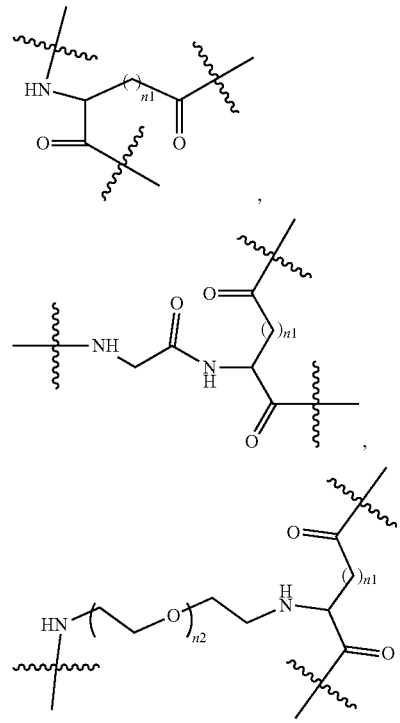
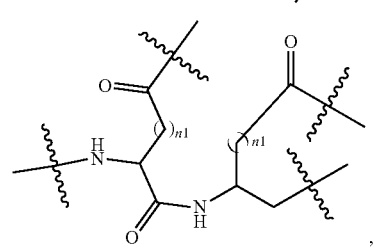
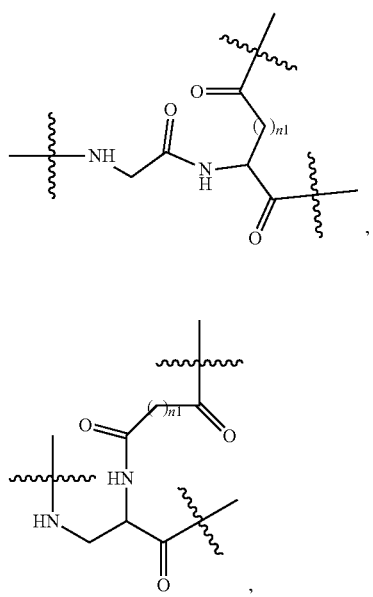
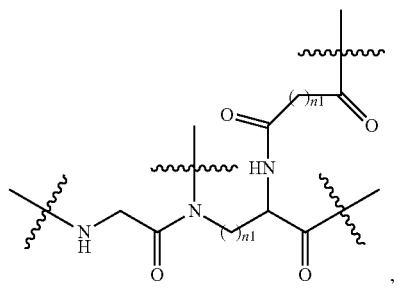
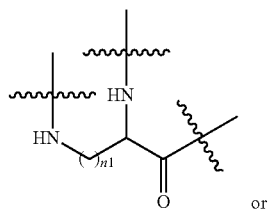
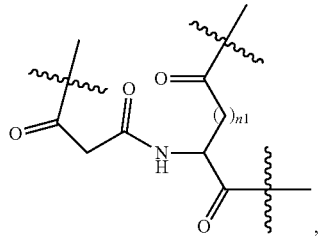
preferably
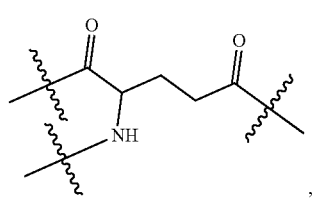

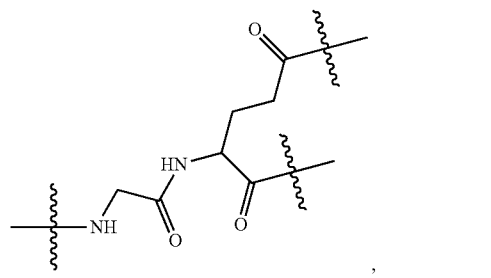
,
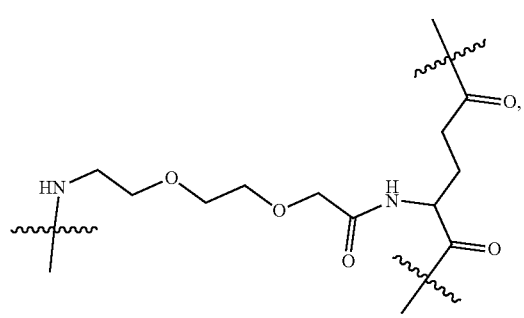
,
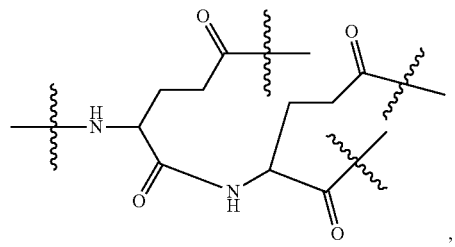
,
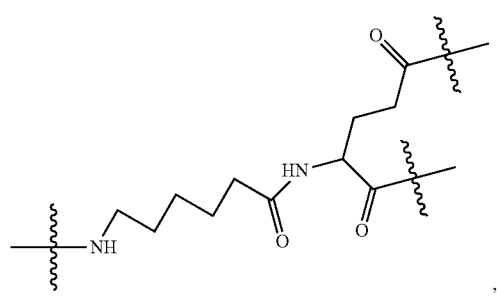
,
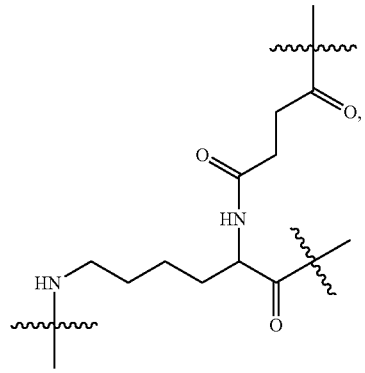
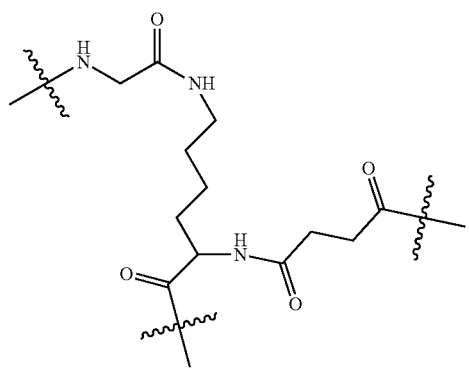
,
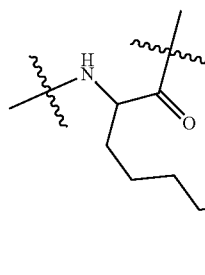
or
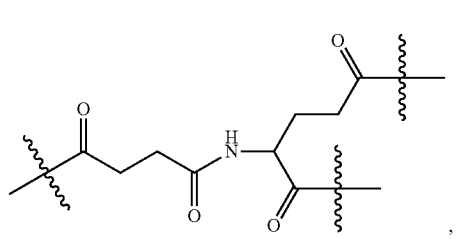
,
Q is —N-AC,
Q1 is —N1-AC1,
Q2 is —N2-AC2,
N, N1, N2 each independently are G, GFLG,
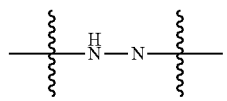
,
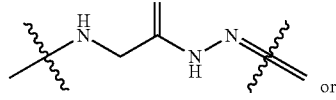
or
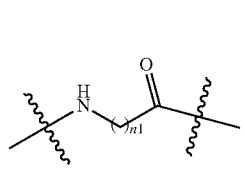

(preferably
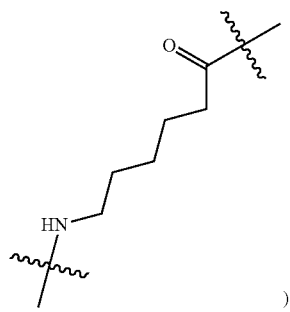
),
AC, AC1, AC2 each independently are SN38, PKA, PCB, LPT, SB7, PTX or NPB, the number-average molecular weight of PEG independently is 5 k-40 k.
Alternatively, in some embodiments, the polyethylene glycol conjugated drug has the structure represented by the formula (II), wherein:
M is —C(=O)—C$_{1-6}$ alkylene-C(=O)—,
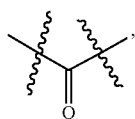,
—NH—C$_{1-6}$ alkylene-NH—,
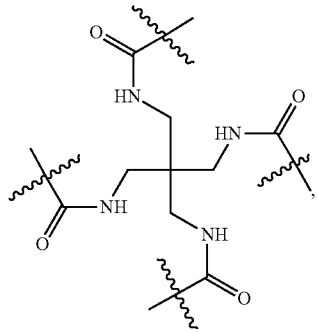
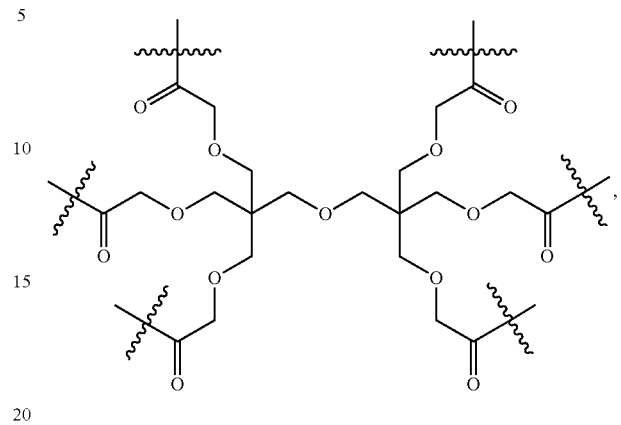
-continued
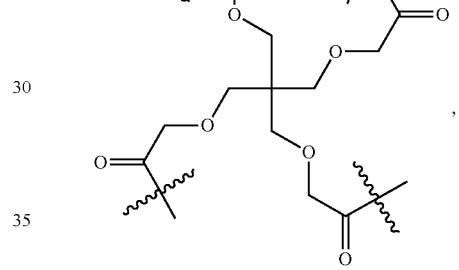,
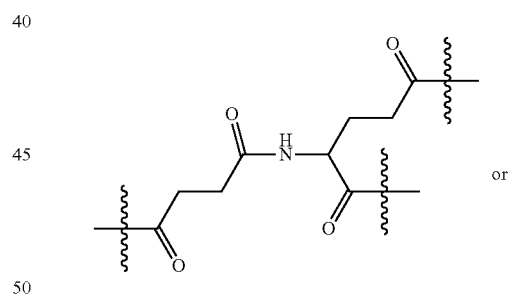 or
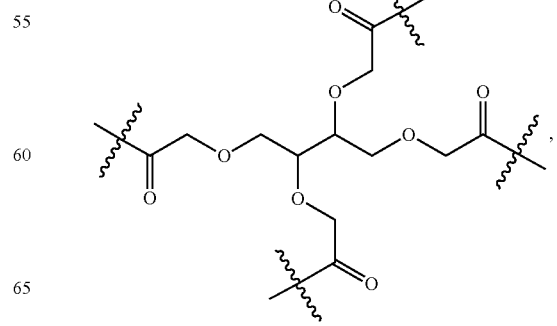, preferably
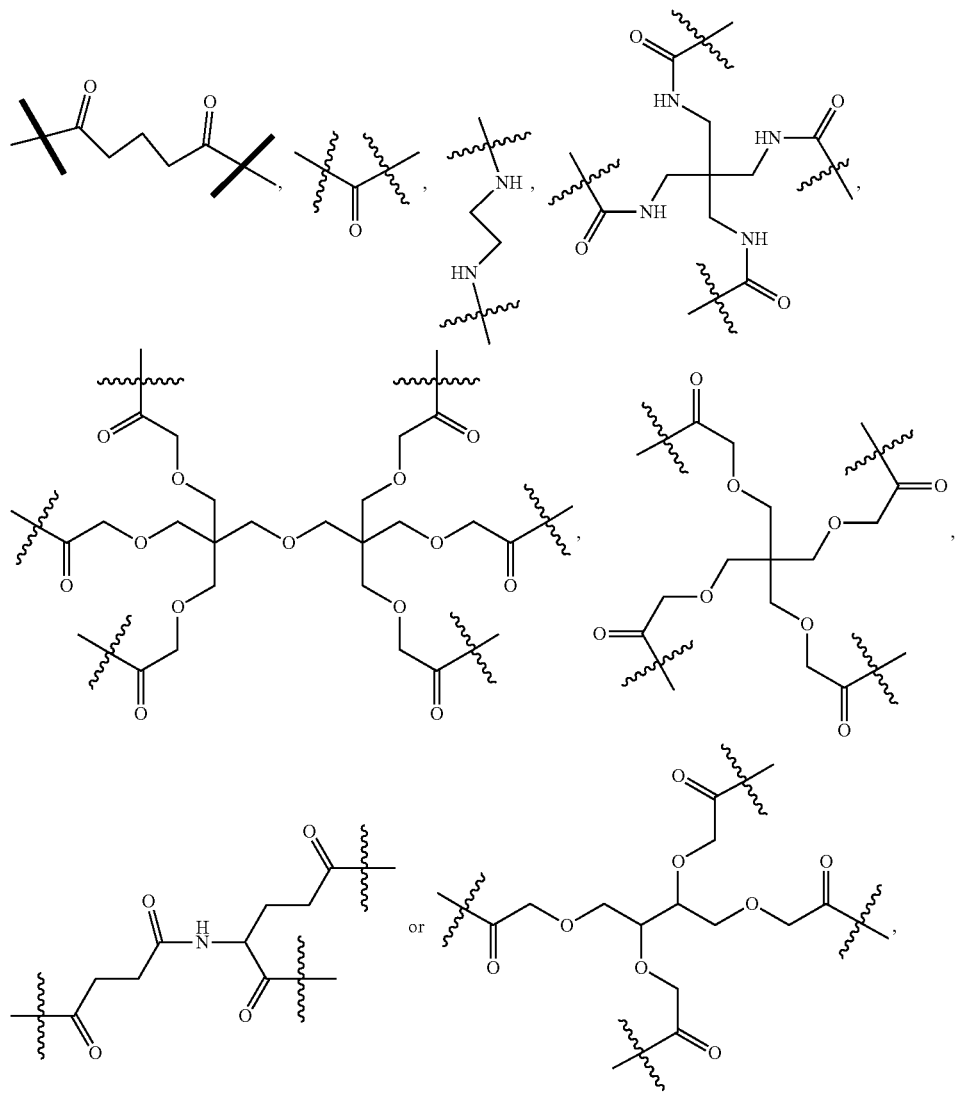
A1 independently is         preferably
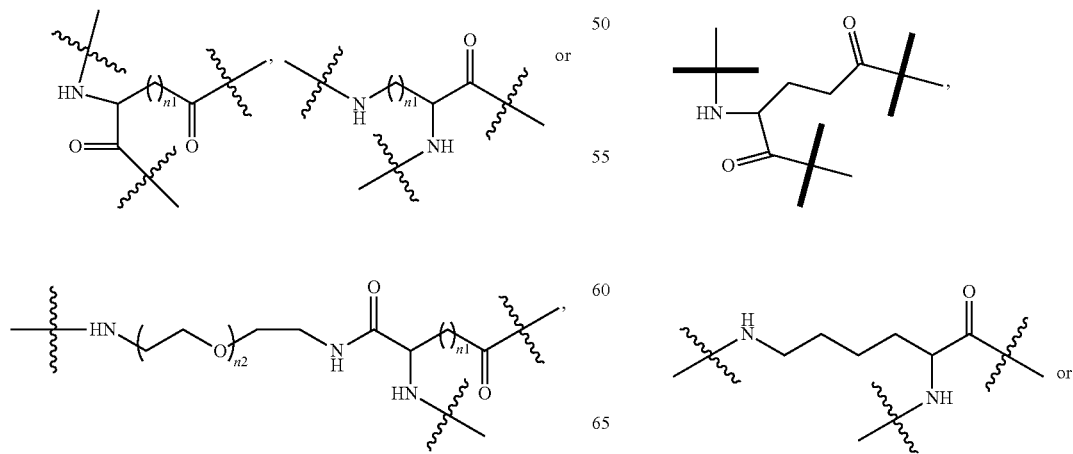

-continued
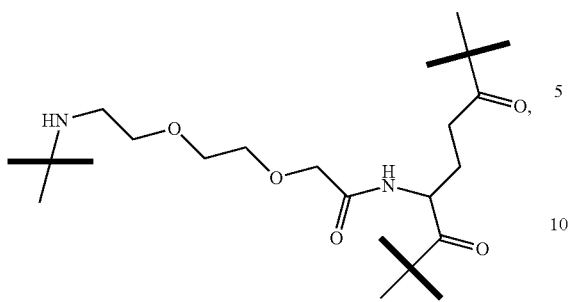
Y independently is a direct bond, GLFG, —C(=O)—C$_{1-6}$alkylene-C(=O)—,
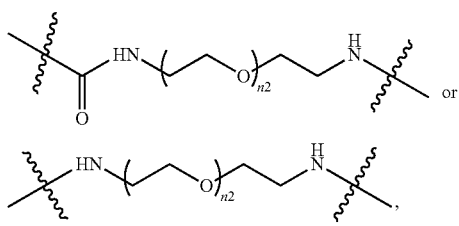 or
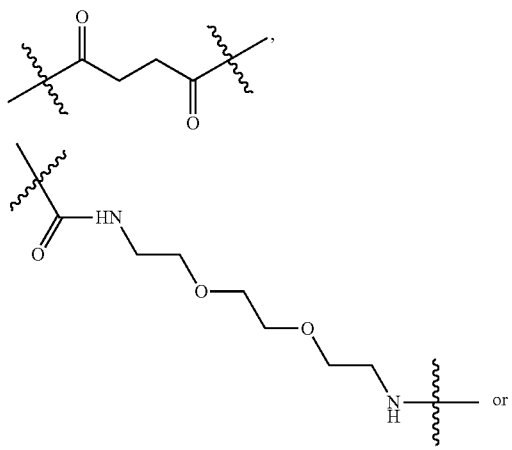
preferably a direct bond, GLFG,
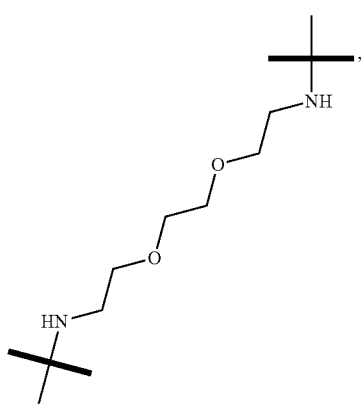
X independently is
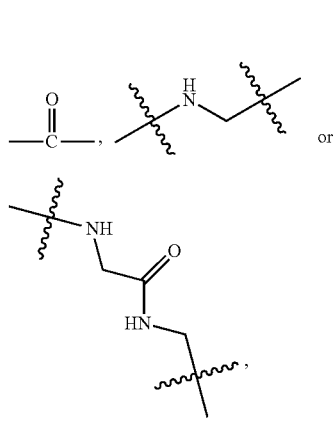
W1 independently is
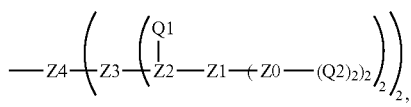
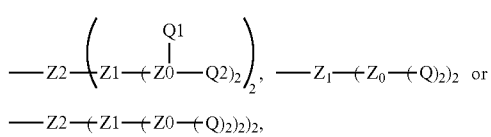
Z4, Z3, Z2, Z1, Z0 each independently are
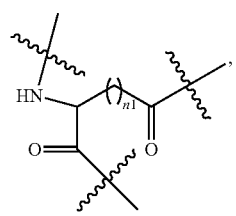
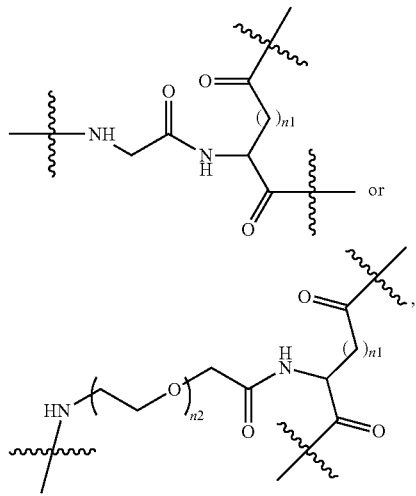

preferably
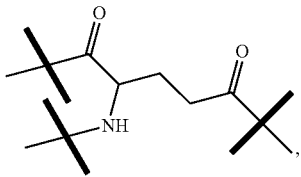
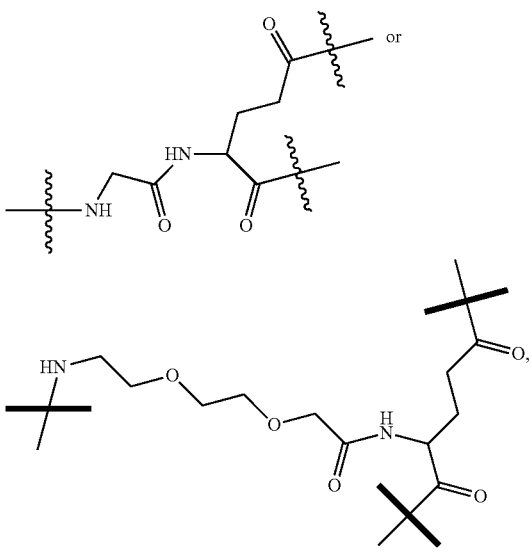
Q is —N-AC,
Q1 is —N1-AC1,
Q2 is —N2-AC2,
N, N1, N2 each independently are G, GFLG,
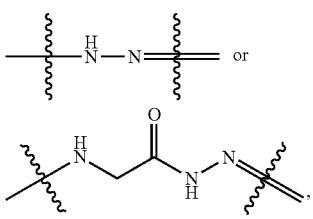
AC, AC1, AC2 each independently are SN38, PKA, PCB, LPT or SB7, the number-average molecular weight of PEG independently is 5 k-40 k.
In some embodiments, wherein:
M is —C(=O)—C$_{1-6}$ alkylene-C(=O)—, A1 is
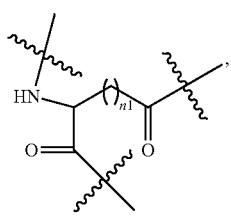
Y is
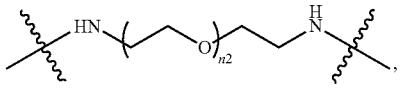
X is
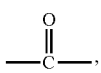
W1 is
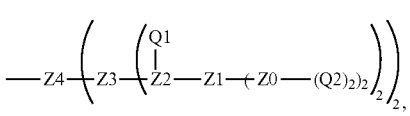
Z4, Z2 and Z1 are
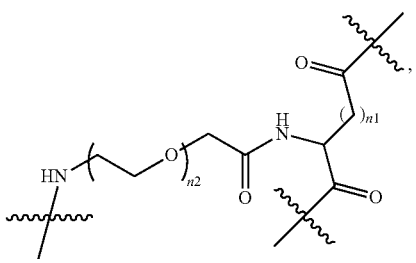
Z3 and Z0 are
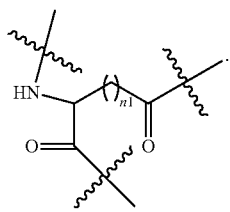
In some specific embodiments, M is
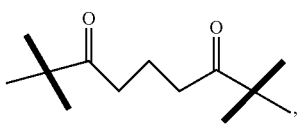

A1 is
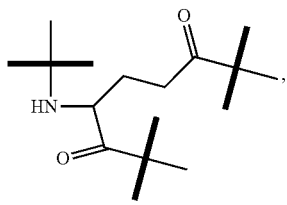
Y is
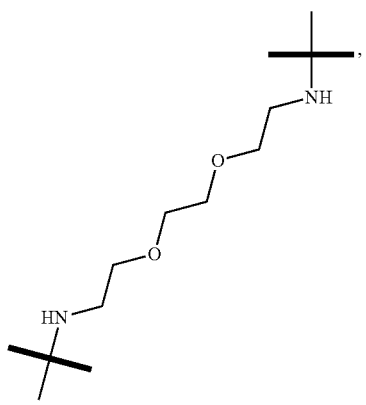
X is
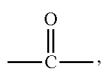
W1 is
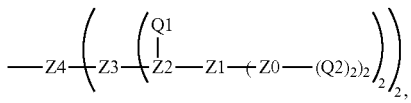
Z4, Z2 and Z1 are
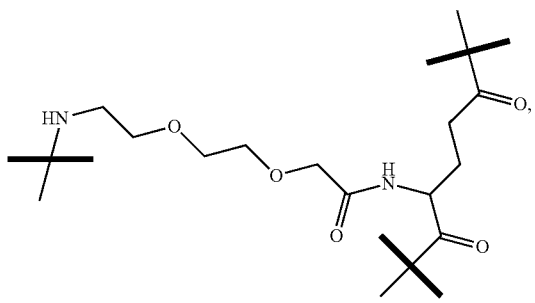
Z3 and Z0 are
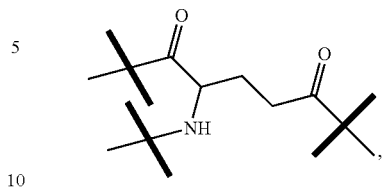
Q1 is —N1-AC1, Q2 is —N2-AC2, N1 and N2 are GFLG, AC1 is PCB, AC2 is PKA.
In some embodiments, M is —NH—C$_{1-6}$alkylene-NH—, A1 is
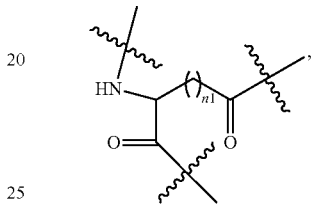
Y is GLFG, X is
W1 is
—Z2—(Z1—(Z0—(Q)$_2$)$_2$)$_2$,
Z2 is
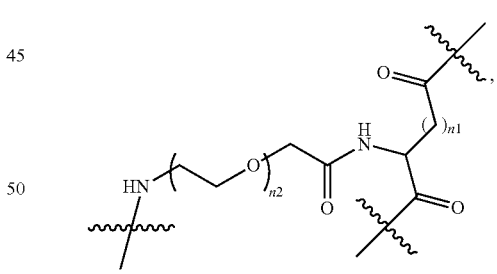
Z1 is
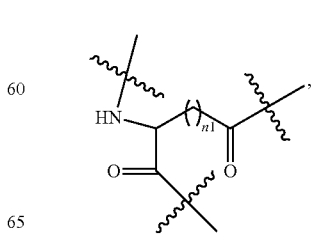

Z0 is
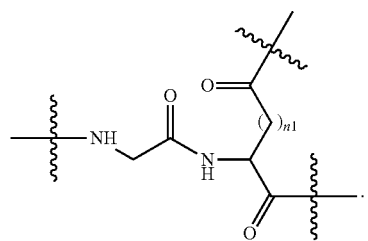
In some specific embodiments, M is
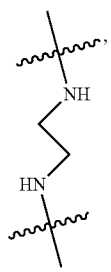 [SMILES: *NCCN*]
A1 is
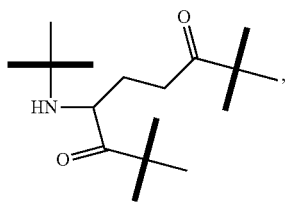
Y is GLFG, X is
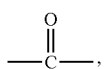
W1 is
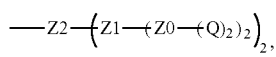
Z2 is
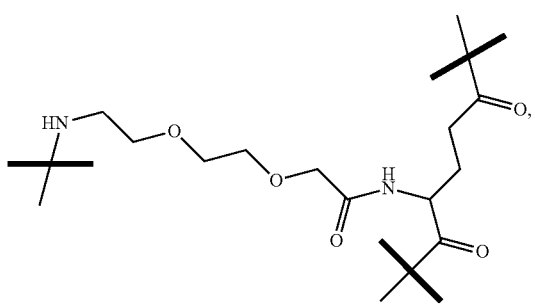
Z1 is
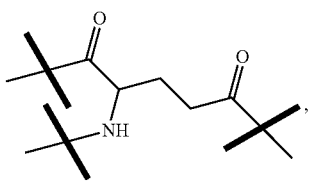
Z0 is
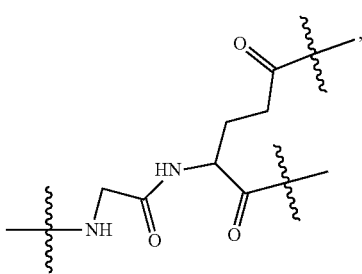 [SMILES: *NCC(=O)NC(CCC(*)=O)C(*)=O]
Q is —N-AC, N is G, AC is SN38.
In some embodiments, M is
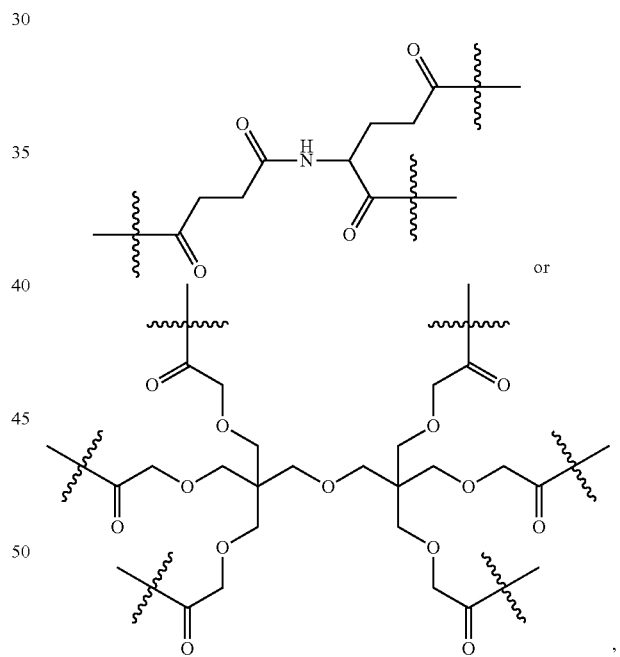
or
A1 is
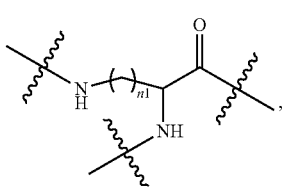

Y is a direct bond or —C(=O)—C$_{1-6}$alkylene-C(=O)—, X is
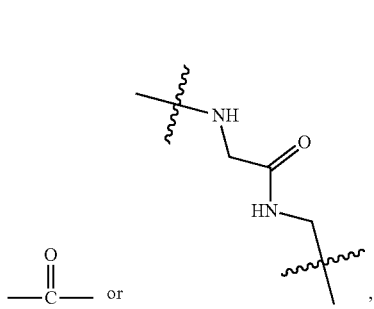
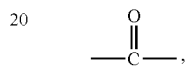 or ,
W1 is
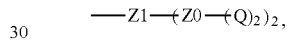
Z1 is
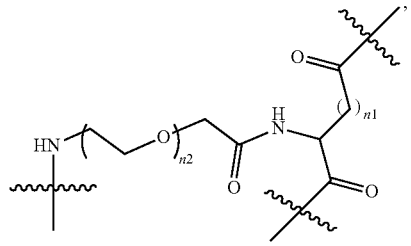
Z0 is
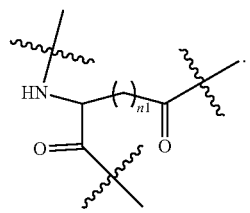
In some specific embodiments, M is
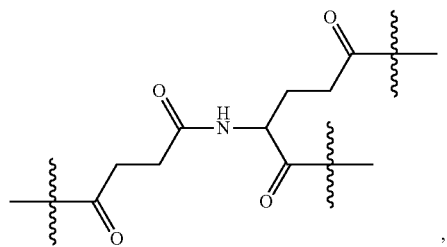 [SMILES: *C(=O)CCC(=O)NC(CCC(*)=O)C(*)=O]
A1 is
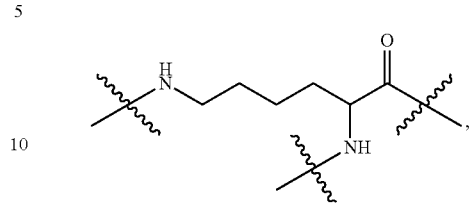
Y is a direct bond, X is
,
W1 is
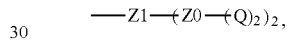
Z1 is
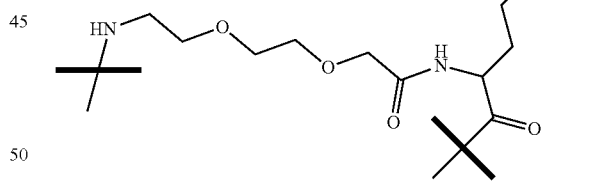
Z0 is
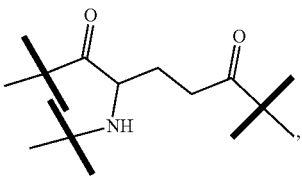,
Q is —N-AC, N is GFLG, AC is LPT.

In some specific embodiments, M is
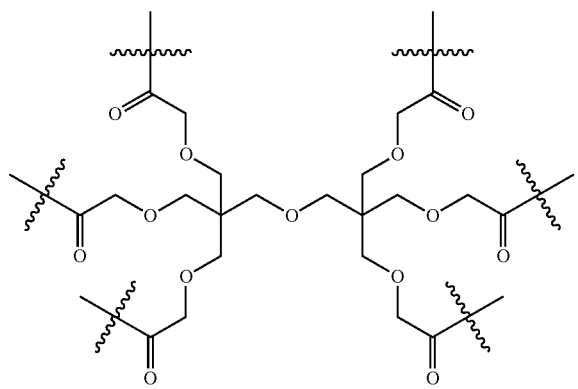
A1 is
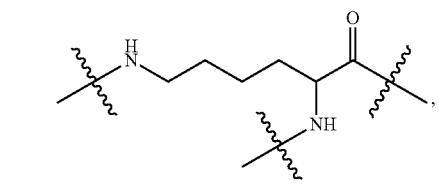
Y is
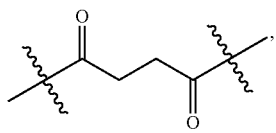
X is
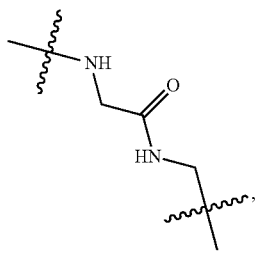
W1 is
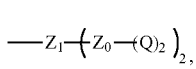
Z1 is
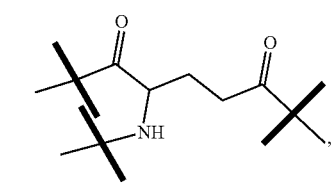
Z0 is
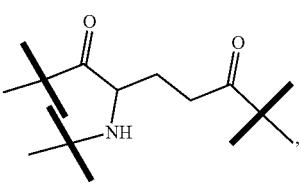
Q is —N-AC, N is GFLG, AC is PCB.
In some embodiments, M is
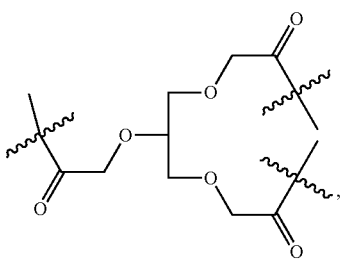 [SMILES: *C(=O)COCC(COCC(*)=O)OCC(*)=O]
A1 is
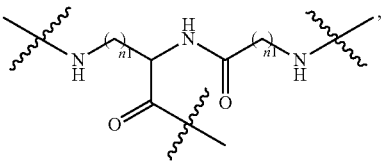 [SMILES: *NCC(=O)NC(CN*)C(*)=O]
Y is a direct bond, X is

W1 is
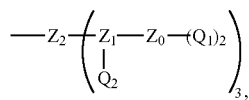
Z2 is
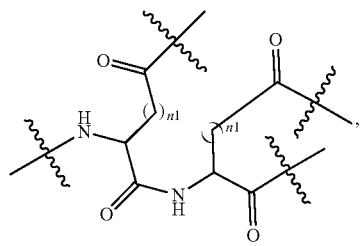 [SMILES: *NC(CC(*)=O)C(=O)NC(CC(*)=O)C(*)=O]
Z1 is
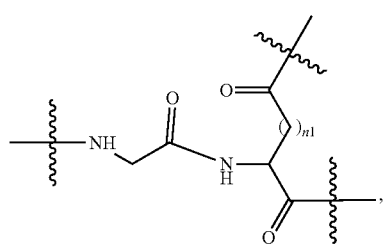 [SMILES: *NCC(=O)NC(CC(*)=O)C(*)=O]
Z0 is
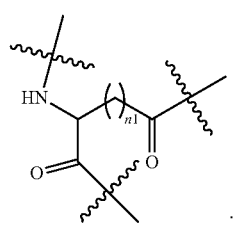
In some specific embodiments, M is
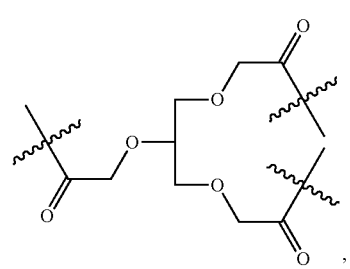 [SMILES: *C(=O)COCC(COCC(*)=O)OCC(*)=O]
A1 is
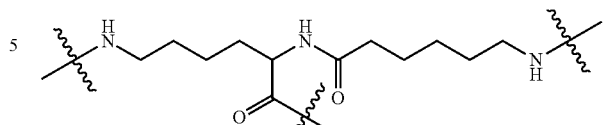
Y is a direct bond, X is
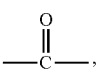
W1 is
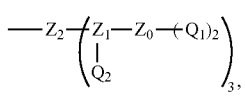
Z2 is
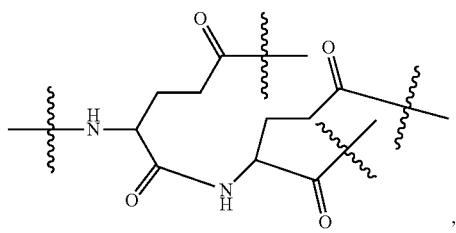 [SMILES: *NC(CCC(*)=O)C(=O)NC(CCC(*)=O)C(*)=O]
Z1 is
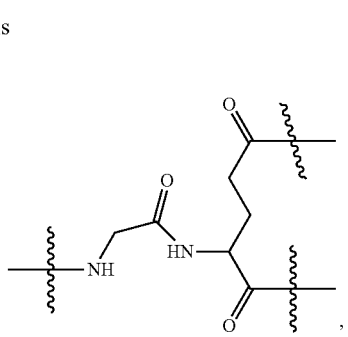
Z0 is
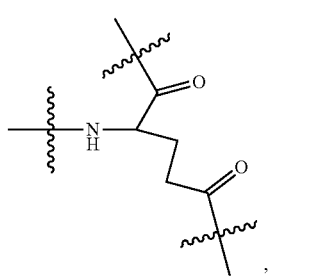 [SMILES: *NC(CCC(*)=O)C(*)=O]
Q1 is —N1-AC1, Q2 is —N2-AC2, N1, N2 are GFLG, AC1 is NPB, AC2 is PCB.

In some embodiments, M is PEG$_m$, PEG$_m$ is a single-arm polyethylene glycol segment, and its number-average molecular weight is 5 k-40 k, preferably 5 k-10 k or 10 k-40 k, more preferably 5 k, A1 is

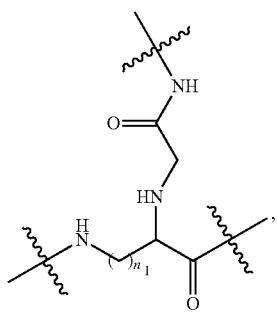

Y is a direct bond, X is

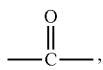

W1 is

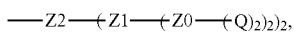

Z2 is

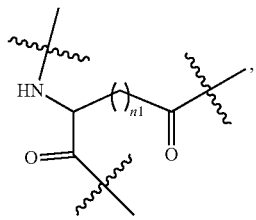

Z1 is

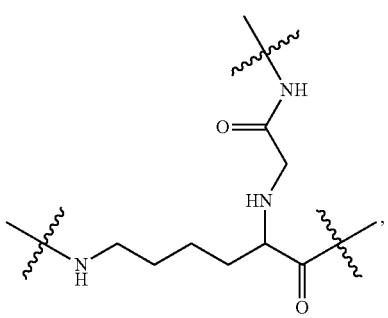 [SMILES: *NCCCCC(NCC(=O)N*)C(*)=O]

Z0 is

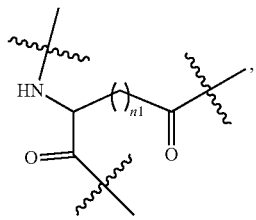

In some specific embodiments, M is PEGm, PEG$_m$, is a single-arm polyethylene glycol segment, and its number-average molecular weight is 5 k-40 k, preferably 5 k-10 k or 10 k-40 k, more preferably 5 k, A1 is

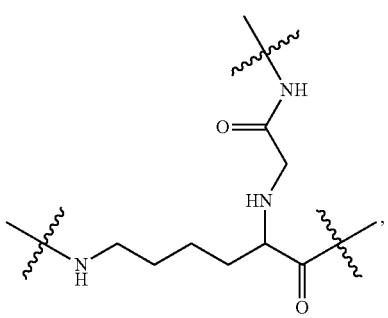 [SMILES: *NCCCCC(NCC(=O)N*)C(*)=O]

Y is a direct bond, X is

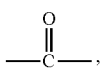

W1 is

—Z2—(Z1—(Z0—(Q)$_2$)$_2$)$_2$,

Z2 is

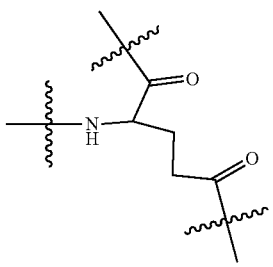

Z1 is

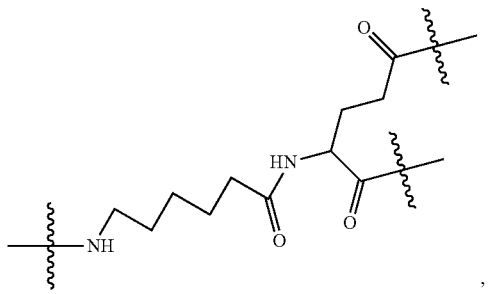 [SMILES: *NCCCCCC(=O)NC(CCC(*)=O)C(*)=O]

Z0 is

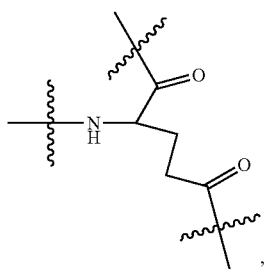 [SMILES: *NC(CCC(*)=O)C(*)=O]

Q is —N-AC, N is G, AC is SN38.

In some embodiments, M is PEGm, $PEG_m$ is a multi-arm (for example, four-arm, eight-arm, preferably four-arm) polyethylene glycol segment, and its number-average molecular weight is 5 k-40 k, preferably 5 k-10 k or 10 k-40 k, more preferably 10 k, A1 is

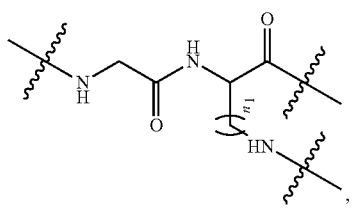

Y is a direct bond, X is

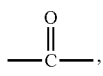

W1 is

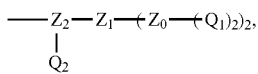

Z2 is

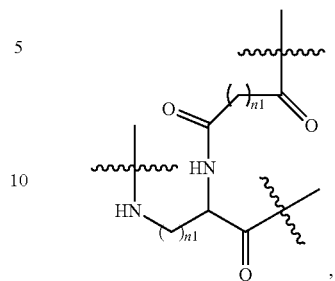

Z1 is

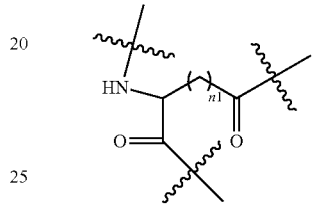

Z0 is

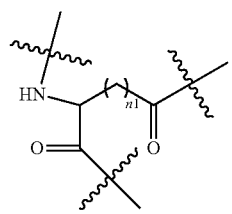

In some specific embodiments, M is PEGm, $PEG_m$, is a multi-arm (for example, four-arm, eight-arm, preferably four-arm) polyethylene glycol segment, and its number-average molecular weight is 5 k-40 k, preferably 5 k-10 k or 10 k-40 k, more preferably 10 k, A1 is

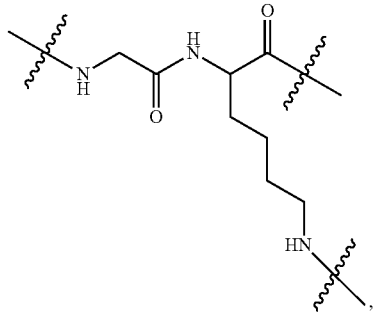 [SMILES: *NCCCCC(NC(=O)CN*)C(*)=O]

Y is a direct bond, X is

W1 is
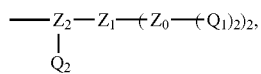
Z2 is
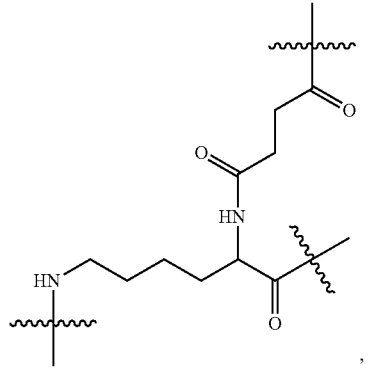 [SMILES: *NCCCCC(NC(=O)CCC(*)=O)C(*)=O]
Z1 is
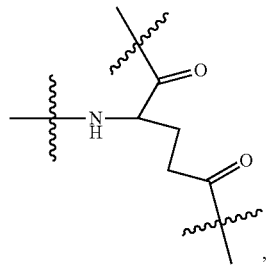 [SMILES: *NC(CCC(*)=O)C(*)=O]
Z0 is
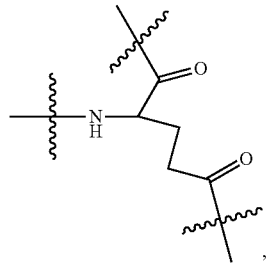 [SMILES: *NC(CCC(*)=O)C(*)=O]
Q1 is —N1-AC1, Q2 is —N2-AC2, N1, N2 are GFLG, AC1 is LPT, AC2 is PCB.
In some embodiments, M is
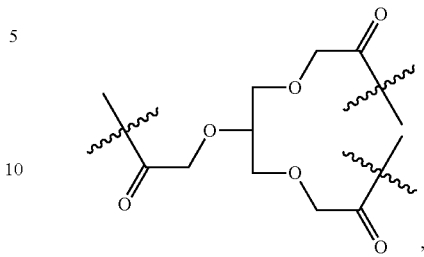
A1 is
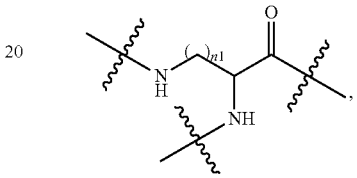
Y is
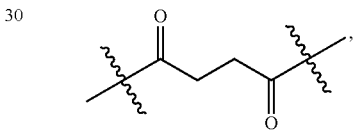
X is
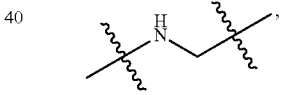
W1 is
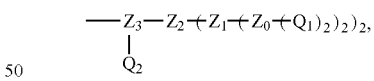
Z3 is
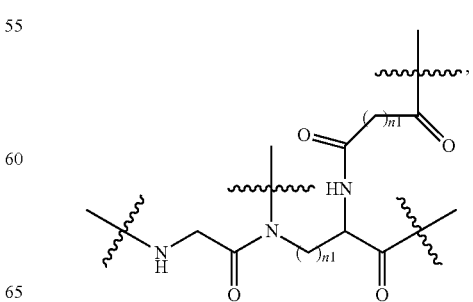

Z2 is
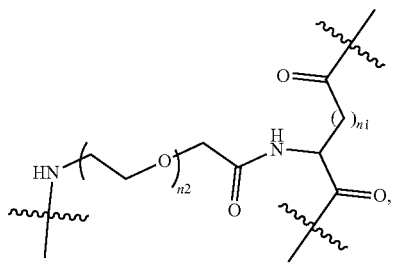
Z1 is
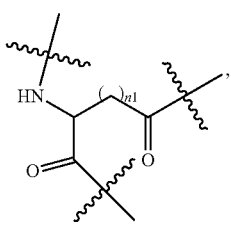
Z0 is
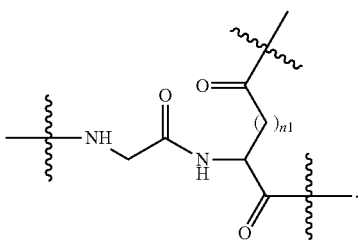
In some specific embodiments, M is
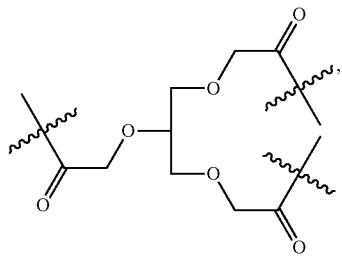 [SMILES: *C(=O)COCC(COCC(*)=O)OCC(*)=O]
A1 is
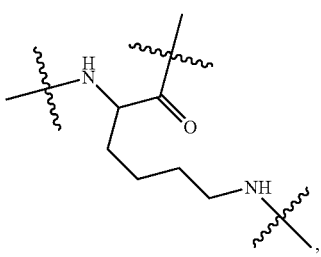 [SMILES: *NCCCCC(N*)C(*)=O]
Y is
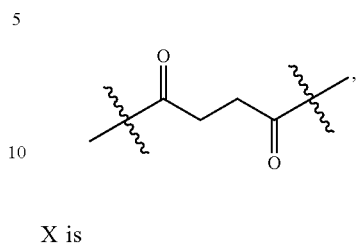
X is
W1 is
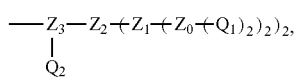
Z3 is
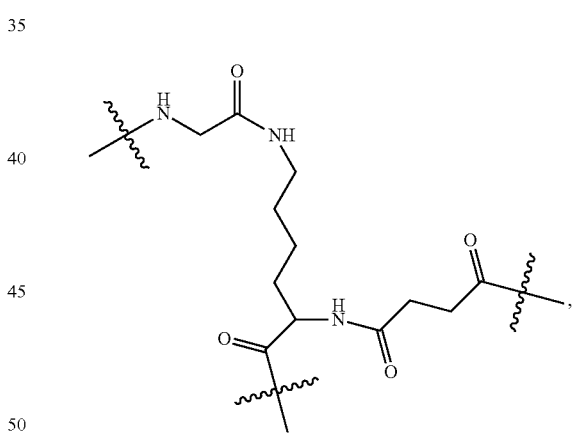
Z2 is
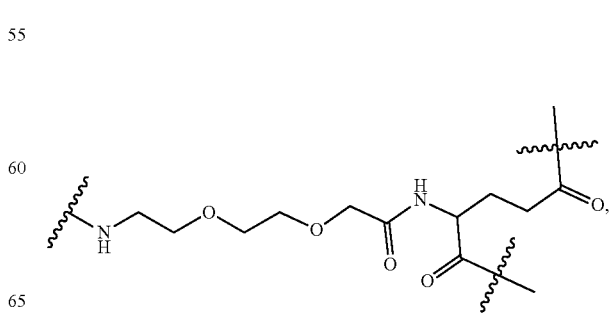

Z1 is
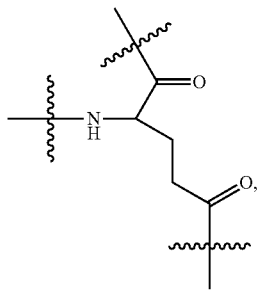 [SMILES: *NC(CCC(*)=O)C(*)=O]
Z0 is
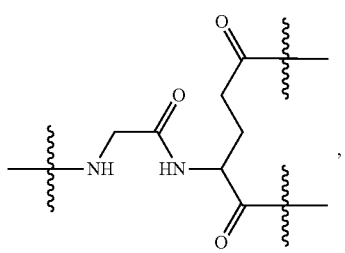 [SMILES: *NCC(=O)NC(CCC(*)=O)C(*)=O]
Q1 is —N1-AC1, Q2 is —N2-AC2, N1, N2 are GFLG, AC1 is LPT, AC2 is PCB.
In some embodiments, M is
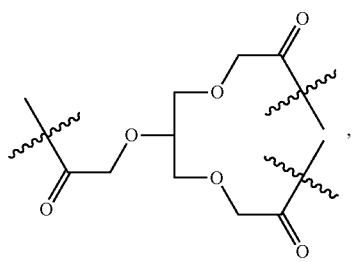 [SMILES: *C(=O)COCC(COCC(*)=O)OCC(*)=O]
A1 is
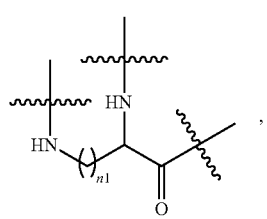
Y is
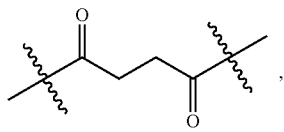 [SMILES: *C(=O)CCC(*)=O]
X is
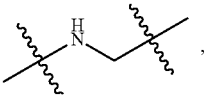 [SMILES: *CN*]
W1 is
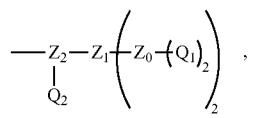
Z2 is
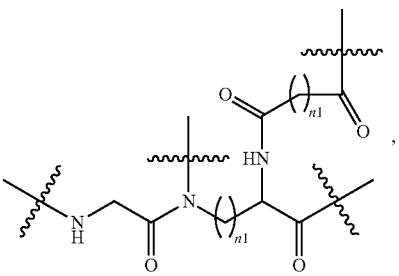
Z1 is
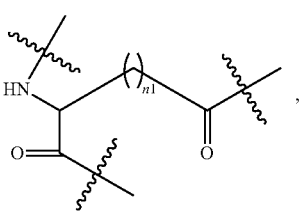
Z0
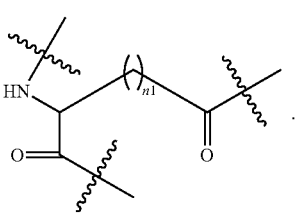

In some specific embodiments, M is
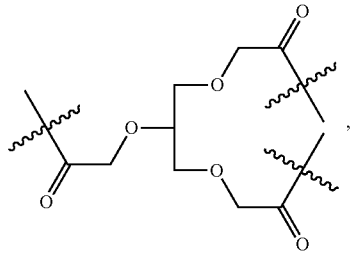 [SMILES: *C(=O)COCC(COCC(*)=O)OCC(*)=O]
A1 is
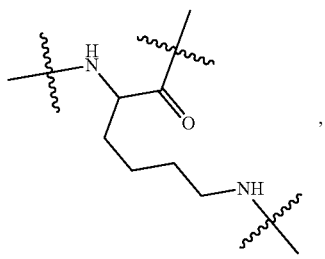 [SMILES: *NCCCCC(N*)C(*)=O]
Y is
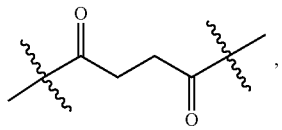 [SMILES: *C(=O)CCC(*)=O]
X is
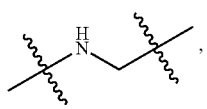
W1 is
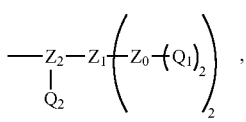
Z2 is
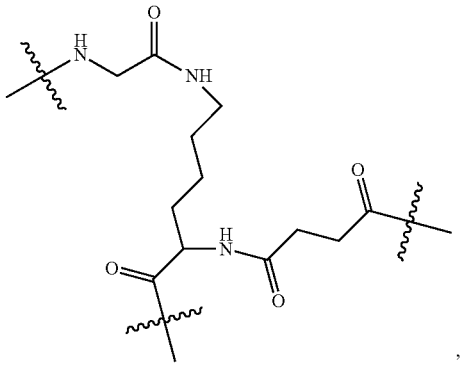 [SMILES: *NCC(=O)NCCCCC(NC(=O)CCC(*)=O)C(*)=O]
Z1 is
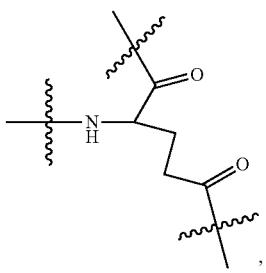 [SMILES: *NC(CCC(*)=O)C(*)=O]
Z0 is
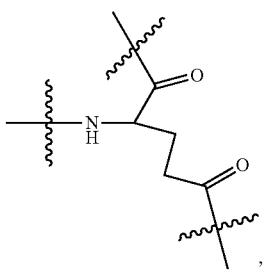 [SMILES: *NC(CCC(*)=O)C(*)=O]
Q1 is —N1-AC1, Q2 is —N2-AC2, N1, N2 are GFLG, AC1 is LPT, AC2 is PCB.
In some embodiments, M is
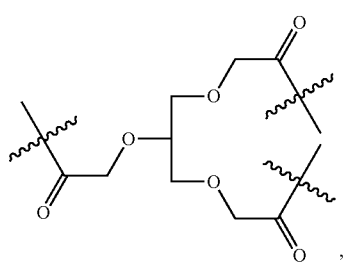 [SMILES: *C(=O)COCC(COCC(*)=O)OCC(*)=O]

A1 is
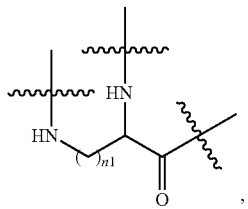
Y is a direct bond, X is
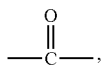
W1 is
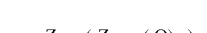
Z1 is
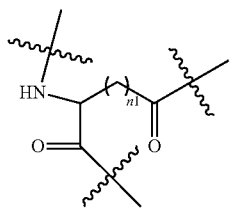
Z0 is
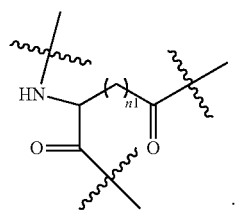
In some specific embodiments, M is
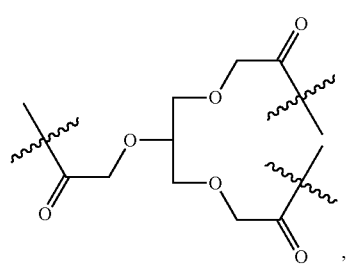 [SMILES: *C(=O)COCC(COCC(*)=O)OCC(*)=O]
A1 is
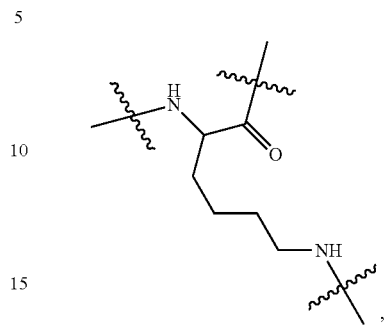
Y is a direct bond, X is
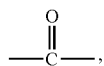
W1 is
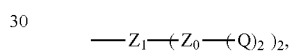
Z1 is
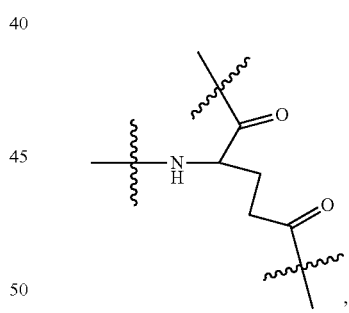
Z0 is
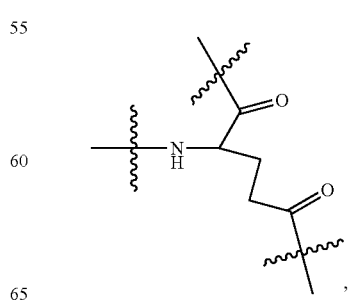

Q is —N-AC, N is
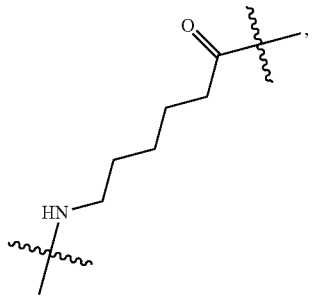 [SMILES: *NCCCCCC(*)=O]
AC is PTX.
In some embodiments, M is
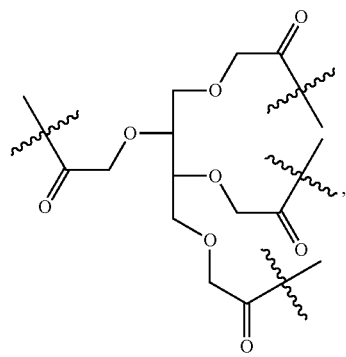 [SMILES: *C(=O)COCC(OCC(*)=O)C(COCC(*)=O)OCC(*)=O]
A1 is
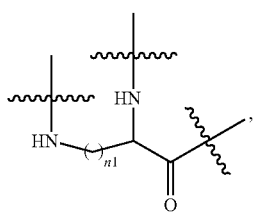 [SMILES: *NCC(N*)C(*)=O]
Y is
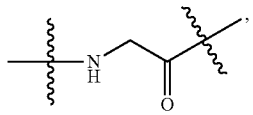 [SMILES: *NCC(*)=O]
X is
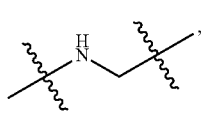
W1 is
$$-Z2-(Z1-(Z0-(Q)_2)_2)_2,$$
Z2 is
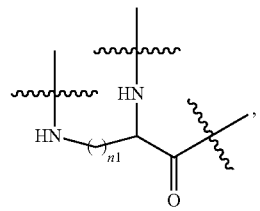 [SMILES: *NCC(N*)C(*)=O]
Z1 is
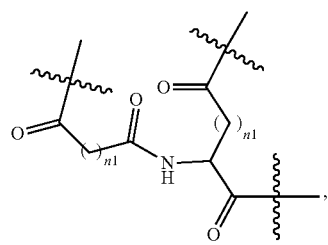 [SMILES: *C(=O)CC(=O)NC(CC(*)=O)C(*)=O]
Z0 is
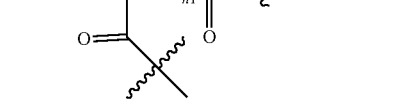
In some specific embodiments, M is
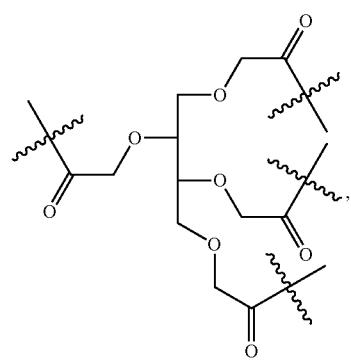 [SMILES: *C(=O)COCC(OCC(*)=O)C(COCC(*)=O)OCC(*)=O]

A1 is
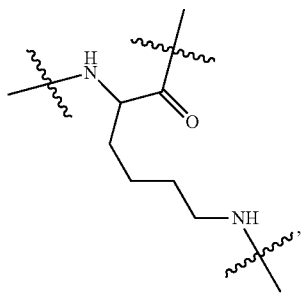 [SMILES: *NCCCCC(N*)C(*)=O]
Y is
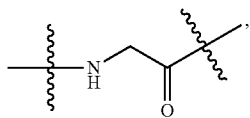 [SMILES: *NCC(*)=O]
X is
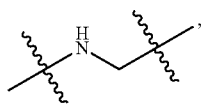
W1 is
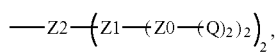
Z2 is
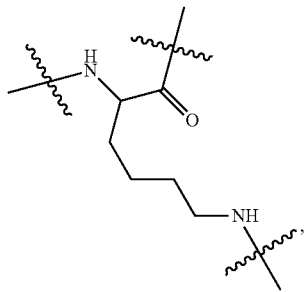 [SMILES: *NCCCCC(N*)C(*)=O]
Z1 is
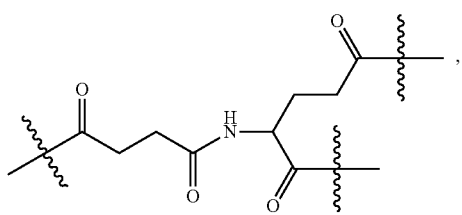 [SMILES: *C(=O)CCC(=O)NC(CCC(*)=O)C(*)=O]
Z0 is
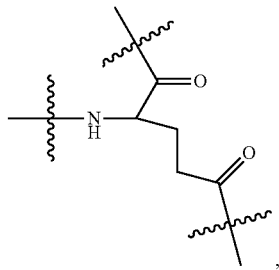 [SMILES: *NC(CCC(*)=O)C(*)=O]
Q is —N-AC, N is G, AC is SN38.
In some embodiments, wherein:
M is
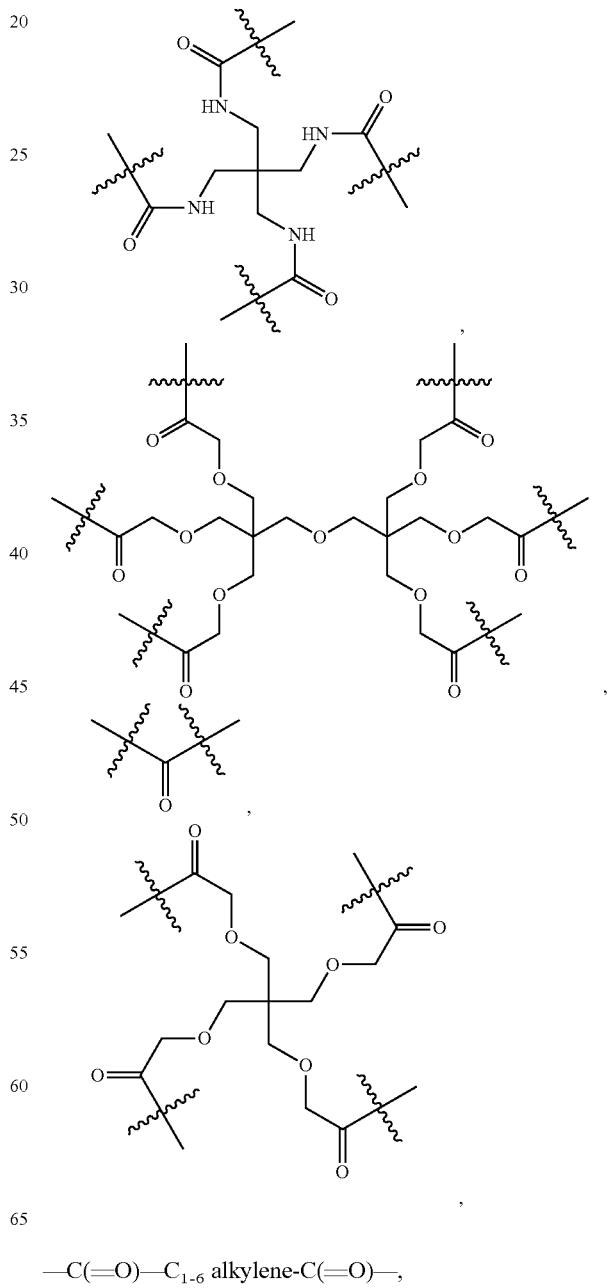
—C(=O)—C$_{1-6}$ alkylene-C(=O)—, X is
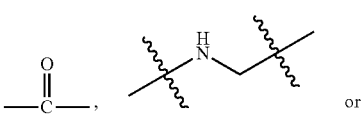,
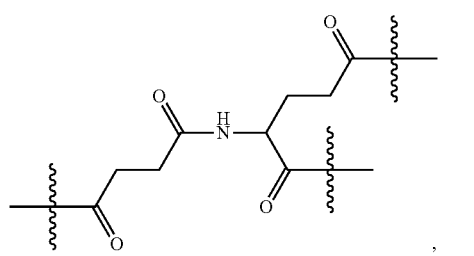
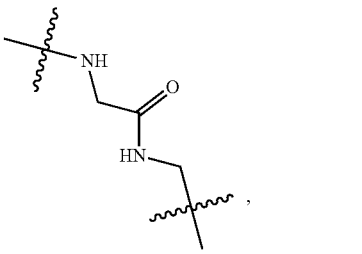,
W1 is
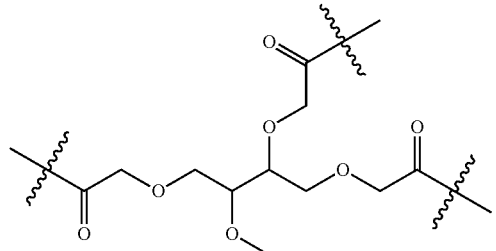 or
$$-Z2\left(-Z1-\left(Z0-Q2\right)_2\right)_2$$  or
$$-Z2\left(-Z1-\left(Z0-(-Q)_2\right)_2\right)_2,$$
Z2 is
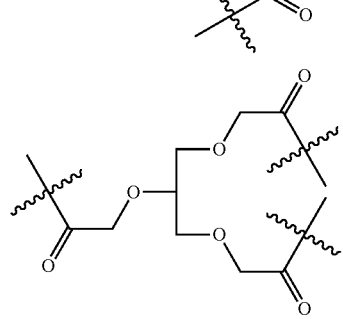,
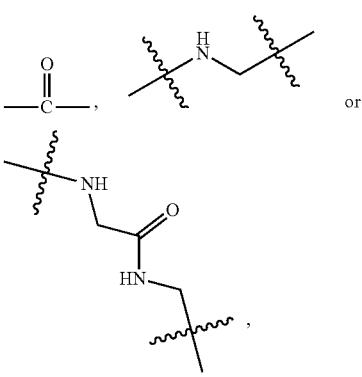
A1 is
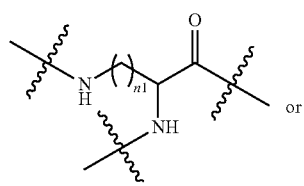 or
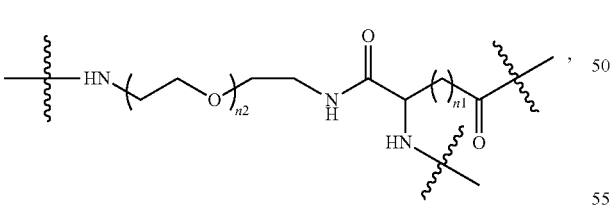,
Y is a direct bond, GLFG, —C(=O)—C$_{1-6}$ alkylene-C(=O)— or
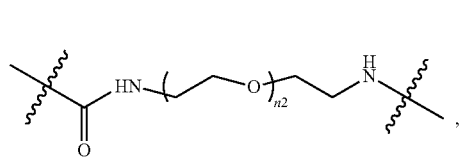,
Z1 is
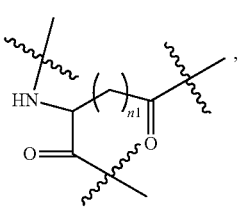, Z0 is
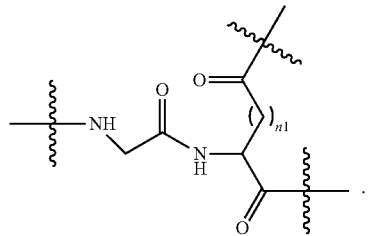
Alternatively, in some embodiments, wherein:
M is
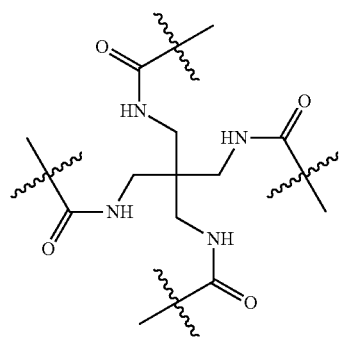
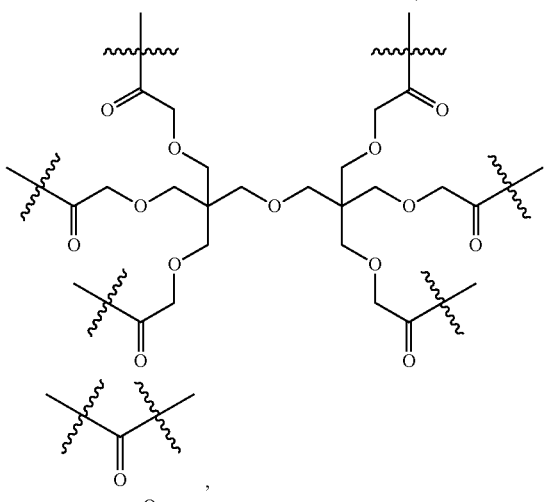
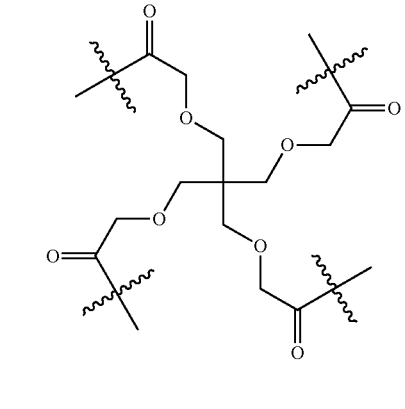
—C(=O)—C$_{1-6}$ alkylene-C(=O)—,
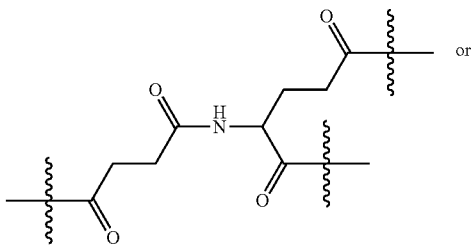
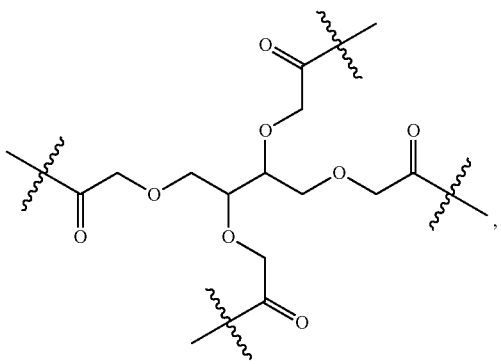
A1 is
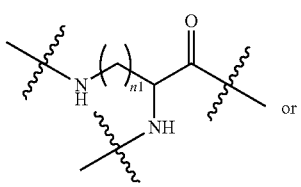
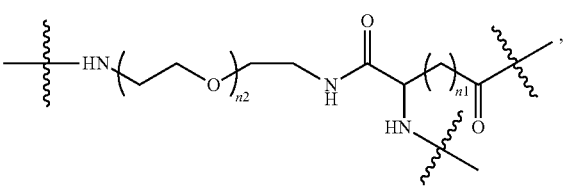
Y is a direct bond, GLFG, —C(=O)—C$_{1-6}$ alkylene-C(=O)— or
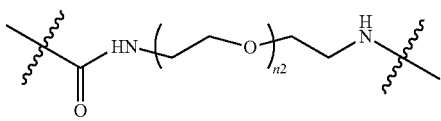
X is
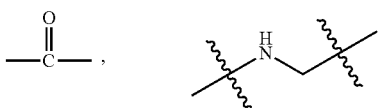

-continued
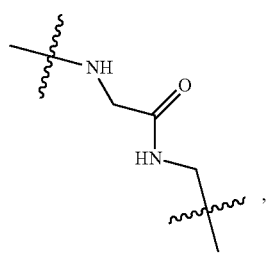
or 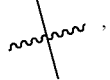,
W1 is
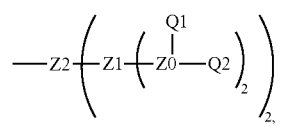
Z2 is
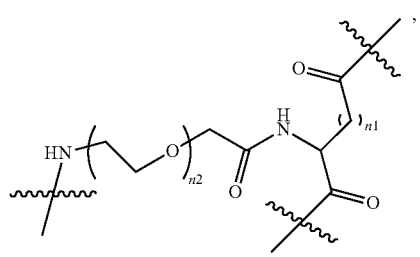
Z1 is
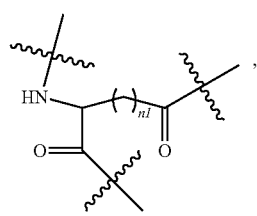
Z0 is
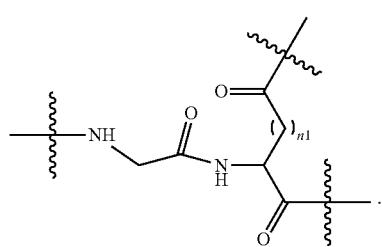
In some specific embodiments, M is
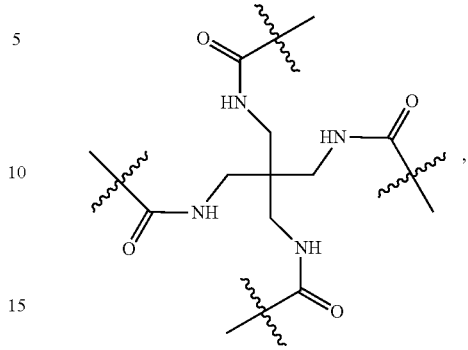,
A1 is
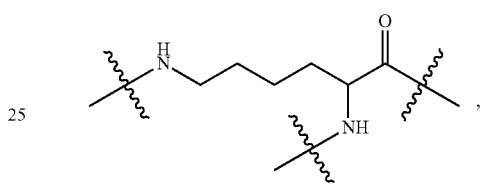,
Y is
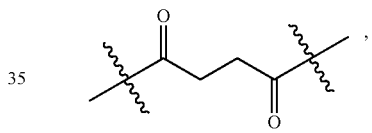,
X is
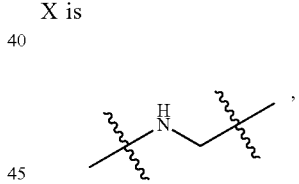,
W1 is
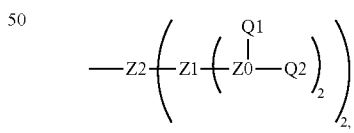
Z2 is
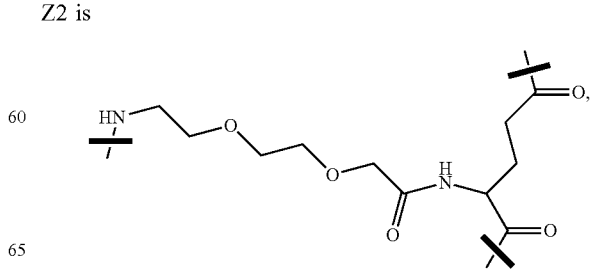

Z1 is
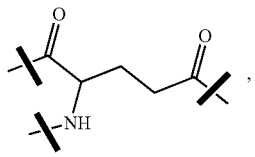
Z0 is
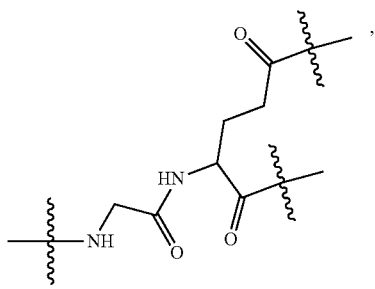 [SMILES: *NCC(=O)NC(CCC(*)=O)C(*)=O]
Q1 is —N1-AC1, Q2 is —N2-AC2, N1 and N2 are GFLG, AC1 is SB7, AC2 is PCB.
In some specific embodiments, M is
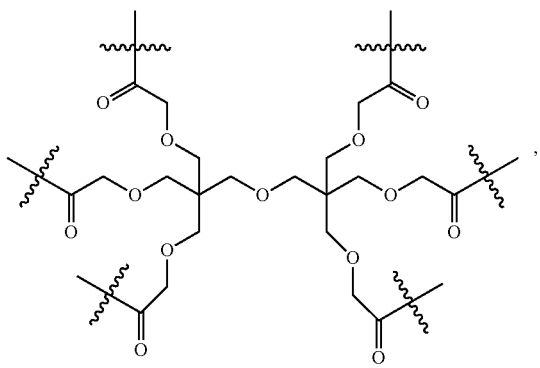 [SMILES: *C(=O)COCC(COCC(*)=O)(COCC(*)=O)COCC(COCC(*)=O)(COCC(*)=O)COCC(*)=O]
A1 is
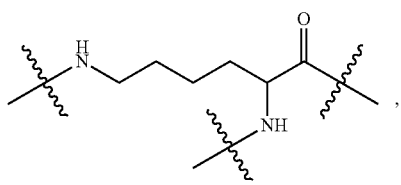 [SMILES: *NCCCCC(N*)C(*)=O]
Y is
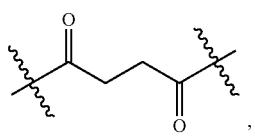 [SMILES: *C(=O)CCC(*)=O]
X is
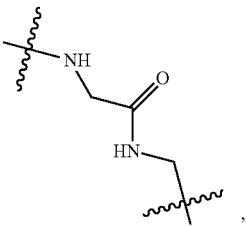 [SMILES: *CNC(=O)CN*]
W1 is
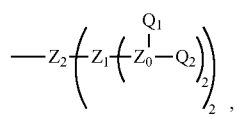
Z2 is
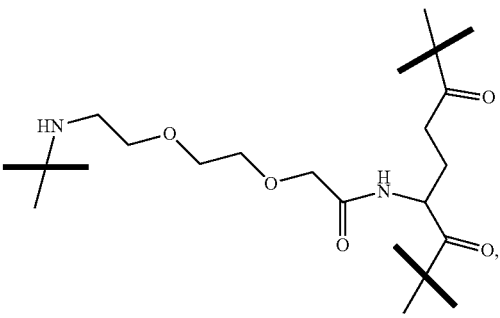
Z1 is
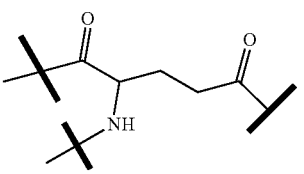
Z0 is
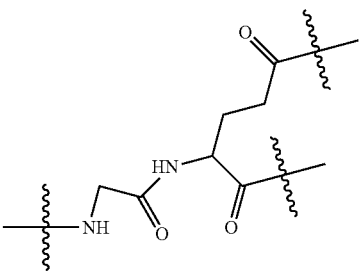
Q1 is —N1-AC1, Q2 is —N2-AC2, N1 and N2 are GFLG, AC1 is SB7, AC2 is PCB.

In some specific embodiments, M is
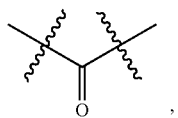
A1 is
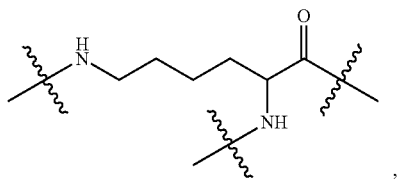 [SMILES: *NCCCCC(N*)C(*)=O]
Y is GLFG, X is
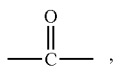
W1 is
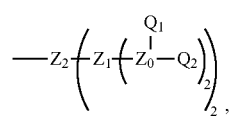
Z2 is
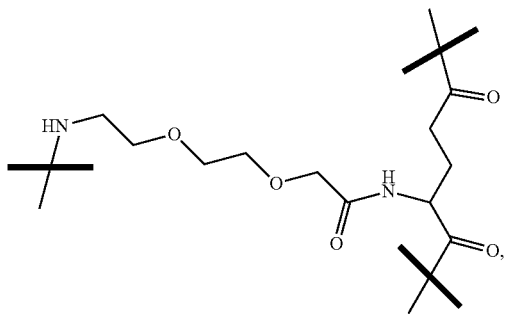
Z1 is
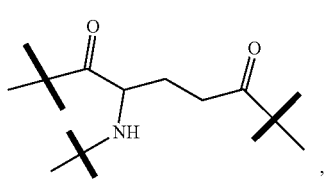
Z0 is
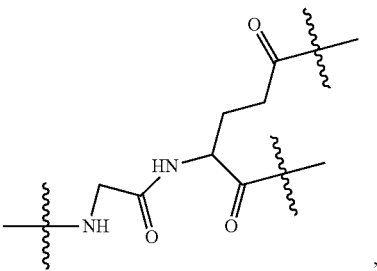 [SMILES: *NCC(=O)NC(CCC(*)=O)C(*)=O]
Q1 is —N1-AC1, Q2 is —N2-AC2, N1 and N2 are GFLG, AC1 is SB7, AC2 is PCB.
In some specific embodiments, M is
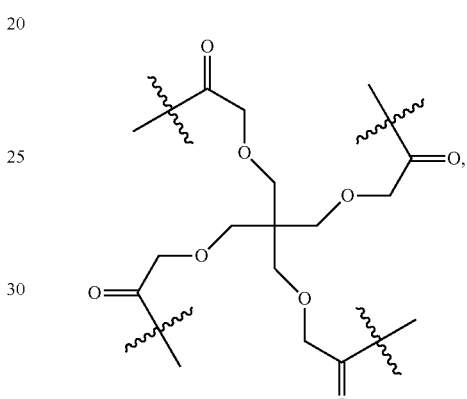
A1 is
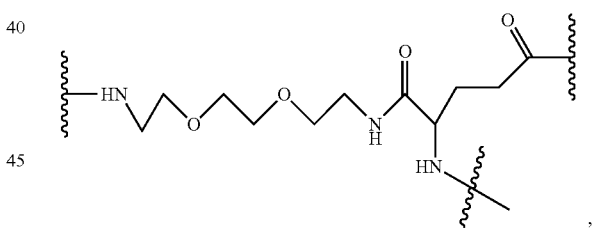
Y is
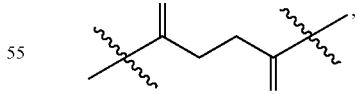
X is
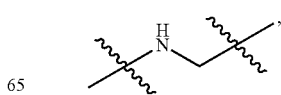

W1 is
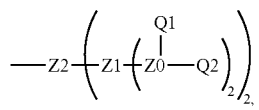
Z2 is
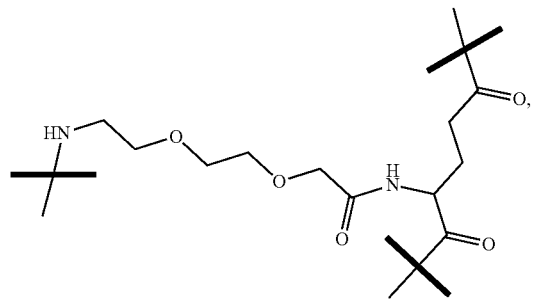
Z1 is
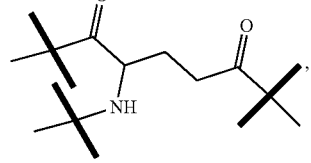
Z0 is
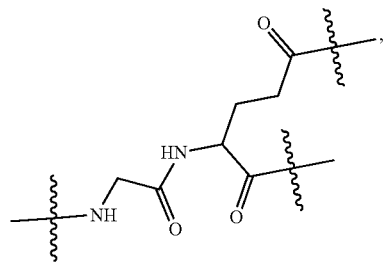 [SMILES: *NCC(=O)NC(CCC(*)=O)C(*)=O]
Q1 is —N1-AC1, Q2 is —N2-AC2, N1 and N2 are GFLG, AC1 is SB7, AC2 is PCB.
In some specific embodiments, M is
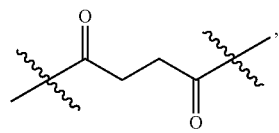 [SMILES: *C(=O)CCC(*)=O]
A1 is
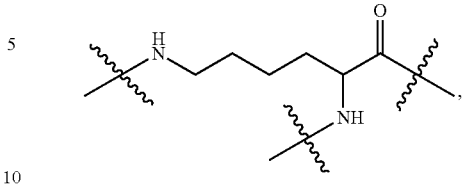
Y is GLFG, X is
W1 is
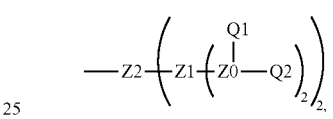
Z2 is
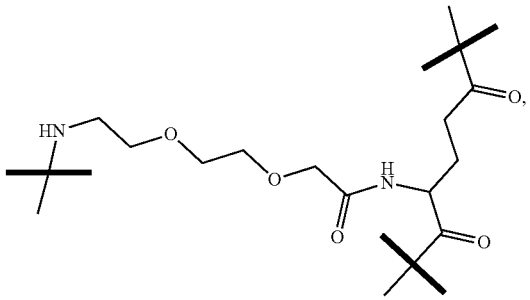
Z1 is
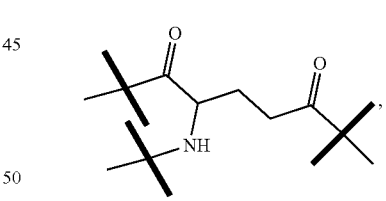
Z0 is
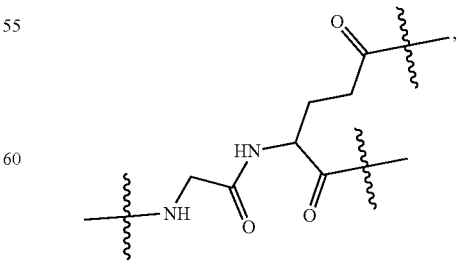
Q1 is —N1-AC1, Q2 is —N2-AC2, N1 and N2 are GFLG, AC1 is SB7, AC2 is PCB.

In some specific embodiments, M is
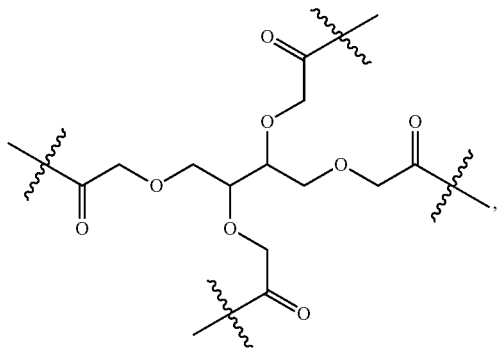 [SMILES: *C(=O)COCC(OCC(*)=O)C(COCC(*)=O)OCC(*)=O]
A1 is
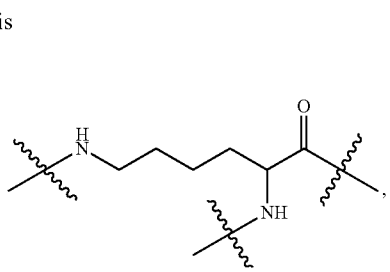
Y is
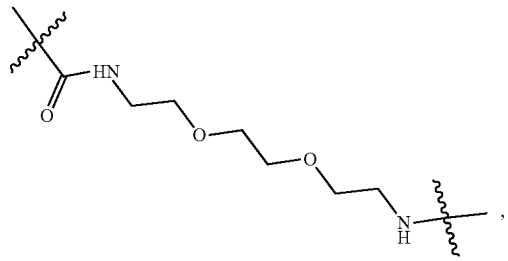 [SMILES: *NCCOCCOCCNC(*)=O]
X is
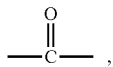,
W1 is
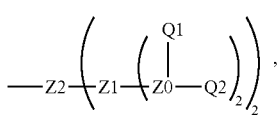,
Z2 is
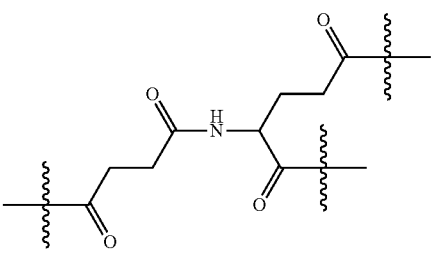
Z1 is
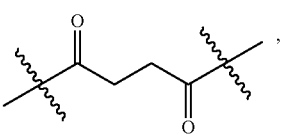,
Z0 is
Q1 is —N1-AC1, Q2 is —N2-AC2, N1 and N2 are GFLG, AC1 is SB7, AC2 is LPT.
In some specific embodiments, M is
 or
, A1 is
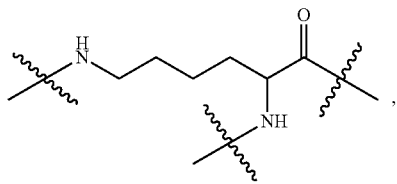
Y is a direct bond, X is
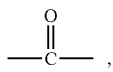,
W1 is
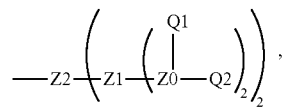,
Z2 is
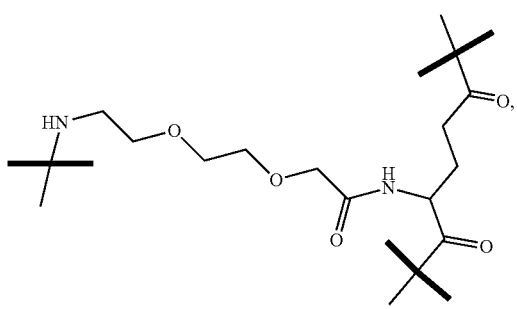
Z1 is
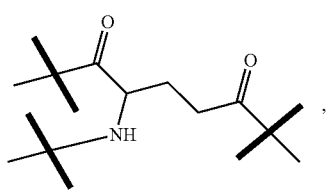,
Z0 is
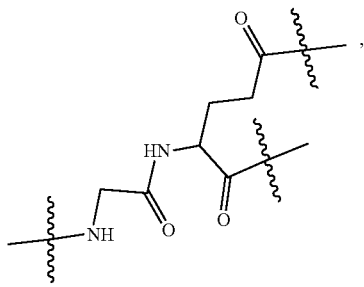 [SMILES: *NCC(=O)NC(CCC(*)=O)C(*)=O]
Q1 is —N1-AC1, Q2 is —N2-AC2, N1 and N2 are GFLG, AC1, AC2 each independently are PCB, SB7 or LPT.
In some specific embodiments, M is
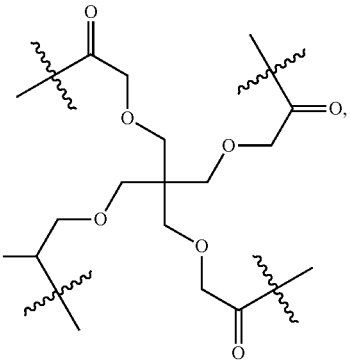
A1 is
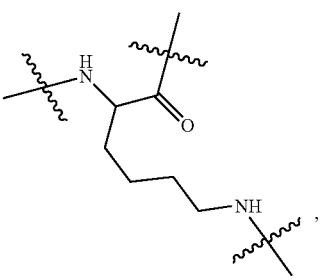 [SMILES: *NCCCCC(N*)C(*)=O],
Y is
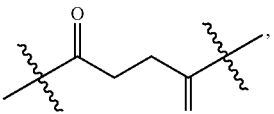,
X is
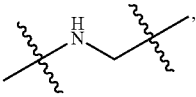 [SMILES: *CN*],
W1 is
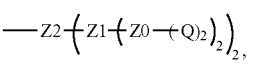, Z2 is
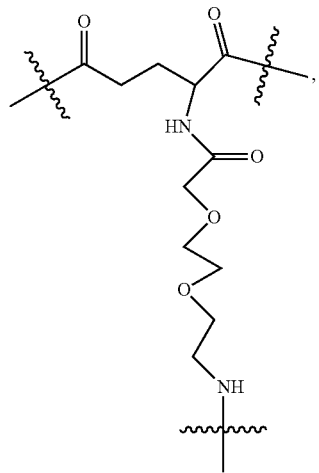 [SMILES: *NCCOCCOCC(=O)NC(CCC(*)=O)C(*)=O]
Z1 is
Z0 is
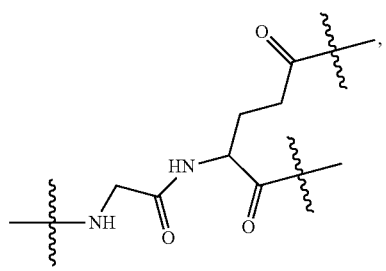 [SMILES: *NCC(=O)NC(CCC(*)=O)C(*)=O]
Q is —N-AC, N is GFLG, AC is PCB.
In some specific embodiments, M is
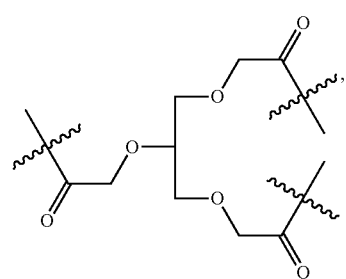 [SMILES: *C(=O)COCC(COCC(*)=O)OCC(*)=O]
A1 is
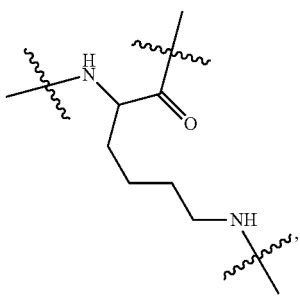 [SMILES: *NCCCCC(N*)C(*)=O]
Y is a direct bond, X is
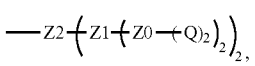
W1 is
—Z2―(Z1―(Z0―(Q)₂)₂)₂,
Z2 is
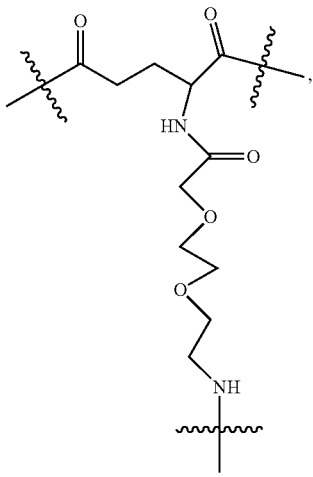 [SMILES: *NCCOCCOCC(=O)NC(CCC(*)=O)C(*)=O]
Z1 is
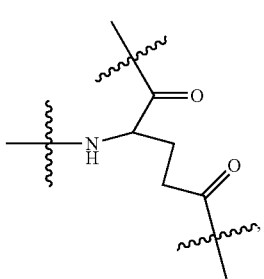 [SMILES: *NC(CCC(*)=O)C(*)=O]

Z0 is
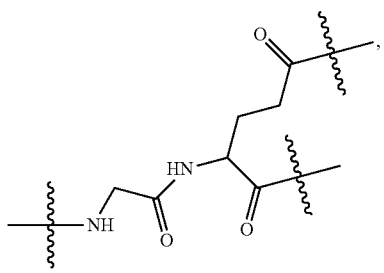 [SMILES: *NCC(=O)NC(CCC(*)=O)C(*)=O]
Q is —N-AC, N is GFLG, AC is NPB.
In some embodiments, the polyethylene glycol conjugated drug has the structure represented by the formula (III), wherein: M is
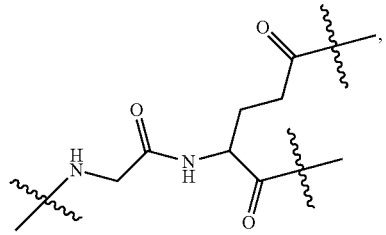 [SMILES: *NCC(=O)NC(CCC(*)=O)C(*)=O]
—C(=O)—C$_{1-6}$ alkylene-NH— or —C(=O)—C$_{1-6}$ alkylene-C(=O)—, preferably
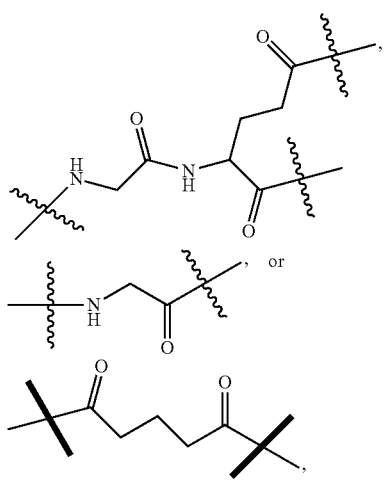
A1, A1' each independently are
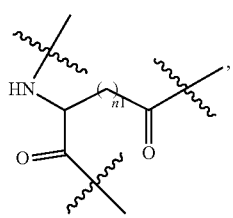
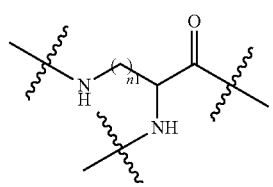
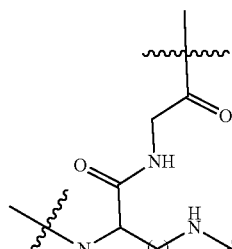
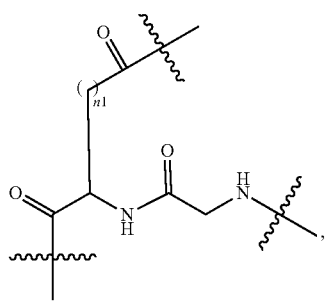
preferably
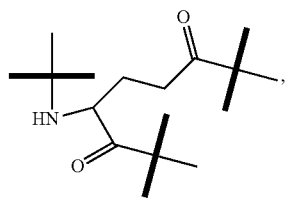
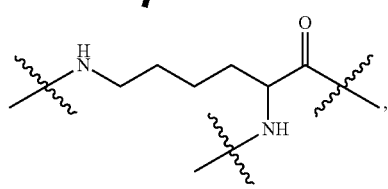
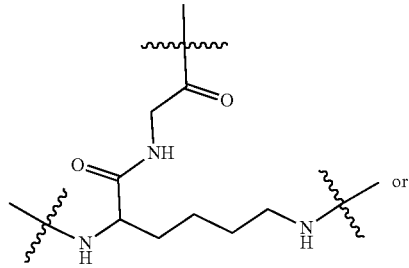

81
-continued
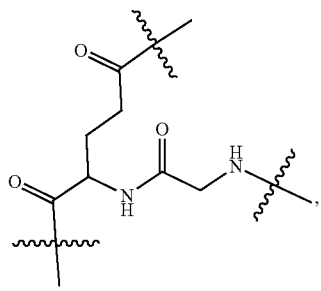
Y, Y' each independently are a direct bond or
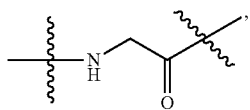
X and X' are
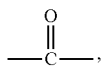
W1, W1' each independently are
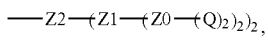
Q1,
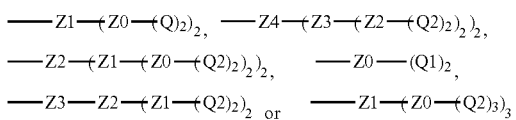
Z4, Z3, Z2, Z1, Z0 each independently are
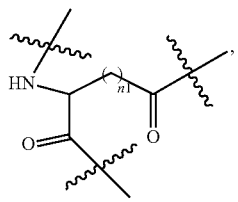
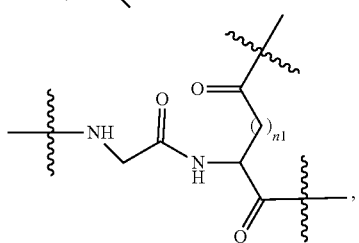
82
-continued
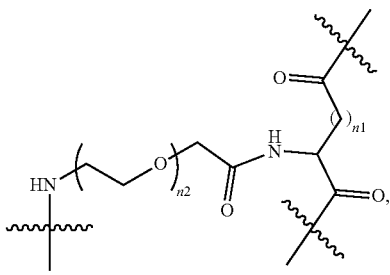
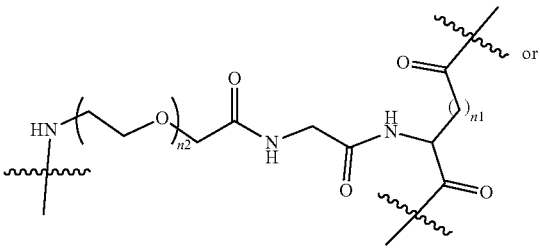
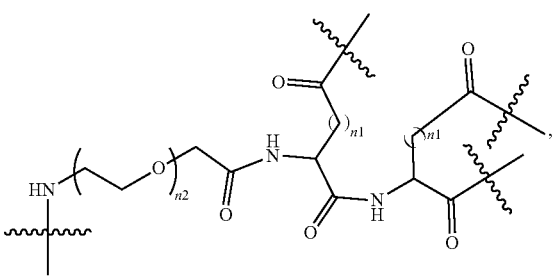
preferably
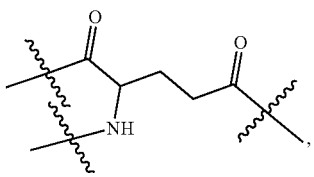
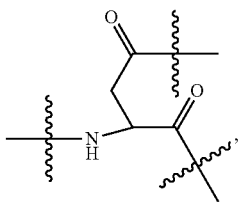
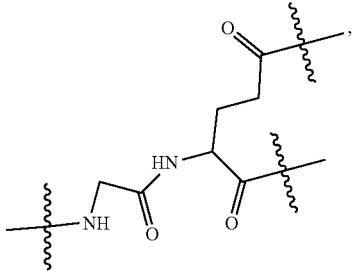

-continued

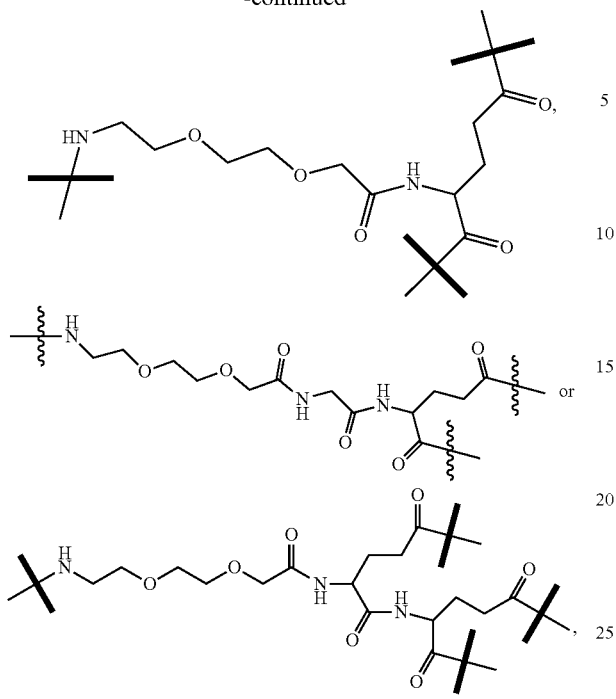

Q is —N-AC,
Q1 is —N1-AC1,
Q2 is —N2-AC2,
N, N1, N2 each independently are GFLG, G,

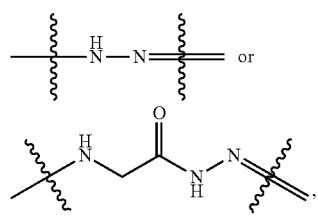

AC, AC1, AC2 each independently are SN38, PKA, PCB, PTX, LPT, SB7 or DOX, the number-average molecular weight of PEG independently is 5 k-40 k.

Alternatively, in some embodiments, the polyethylene glycol conjugated drug has the structure represented by the formula (III), wherein:

M is

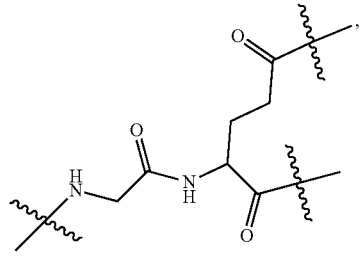 [SMILES: *NCC(=O)NC(CCC(*)=O)C(*)=O]

—C(═O)—$C_{1-6}$ alkylene-NH— or —C(═O)—$C_{1-6}$alkylene-C(═O)—, preferably

A1, A1' each independently are

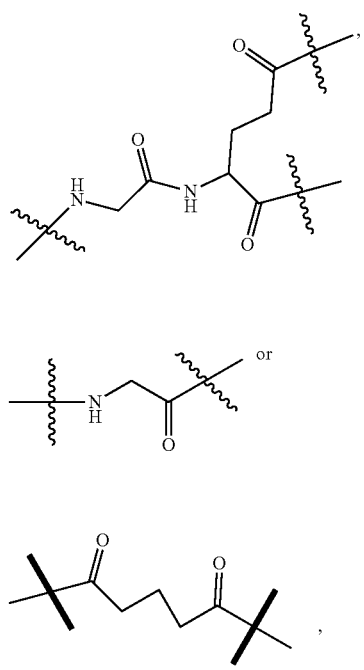

preferably

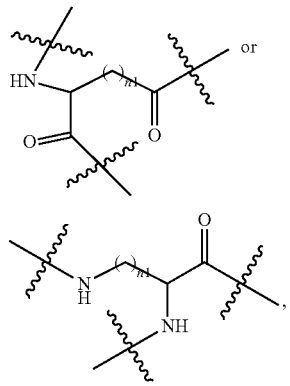

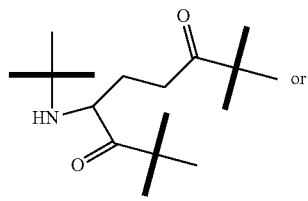

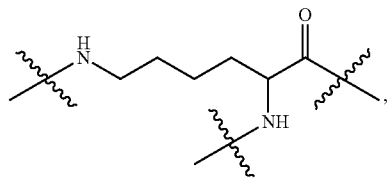

Y, Y' each independently are a direct bond or
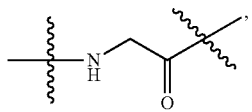 [SMILES: *NCC(*)=O],
X and X' are
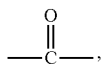,
W1, W1' each independently are Q1,
—Z1—(Z0—(Q1)$_2$)$_2$,  —Z4—(Z3—(Z2—(Q2)$_2$)$_2$)$_2$,
—Z2—(Z1—(Z0—(Q2)$_2$)$_2$)$_2$,  —Z0—(Q1)$_2$,
—Z3—(Z2—(Z1—(Q2)$_2$)$_2$)$_2$  or
—Z1—(Z0—(Q2)$_3$)$_3$,
Z4, Z3, Z2, Z1, Z0 each independently are
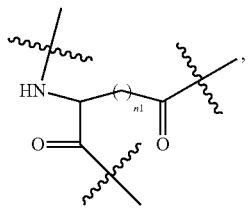,
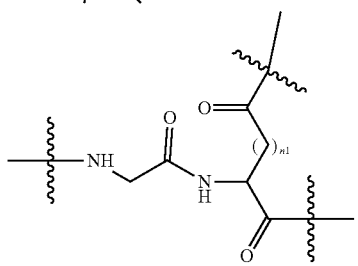,
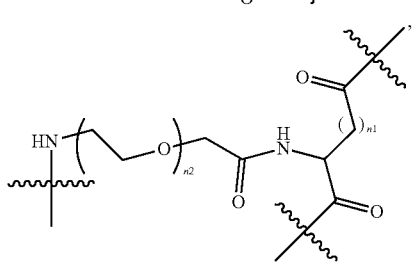,
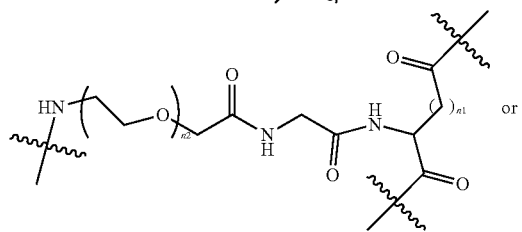 or
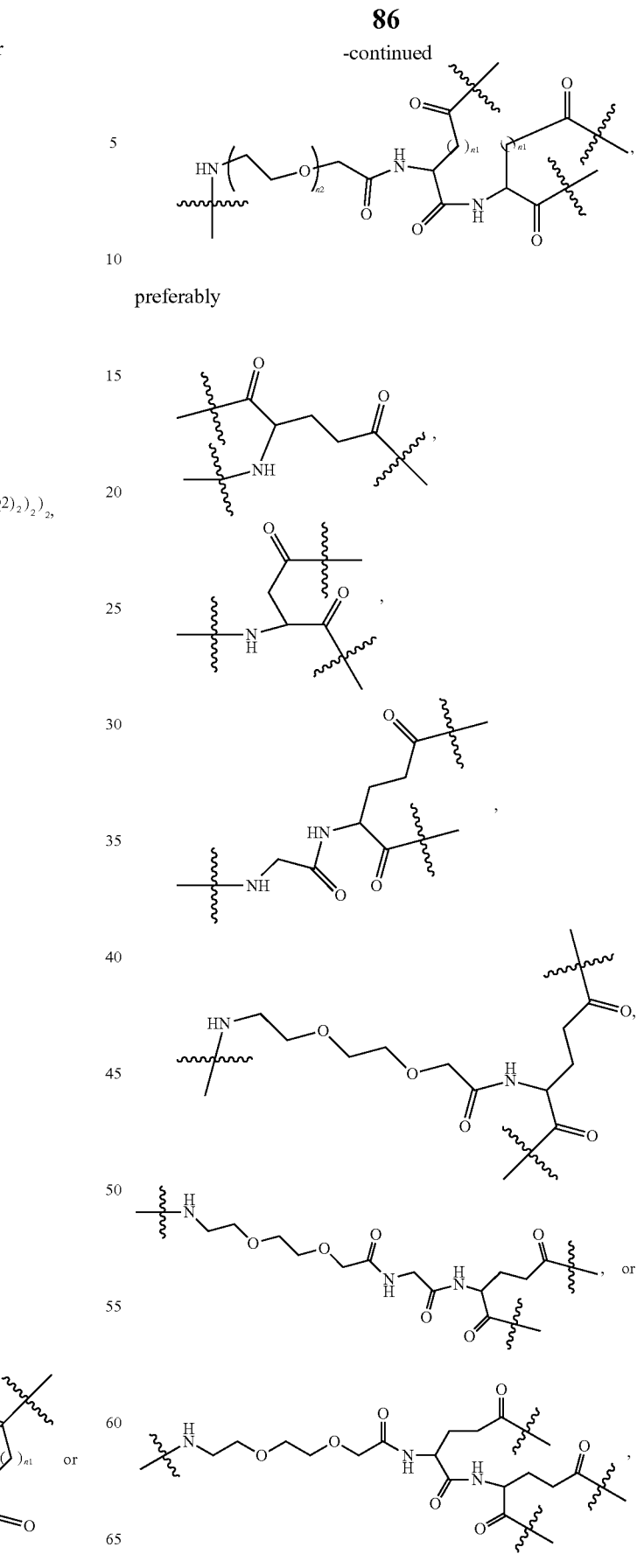
preferably Q1 is —N1-AC1,
Q2 is —N2-AC2,
N1, N2 each independently are GFLG, G,
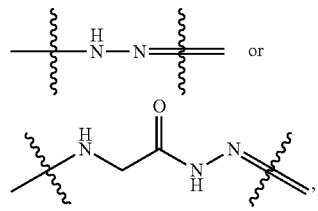 or
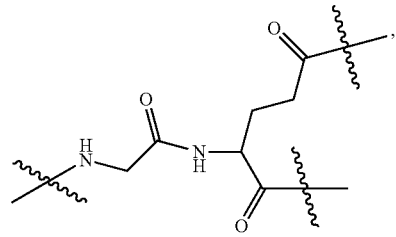 [SMILES: *NCC(=O)NC(CCC(*)=O)C(*)=O]
AC1, AC2 each independently are SN38, PKA, PCB, PTX, LPT, SB7 or DOX,
the number-average molecular weight of PEG independently is 5 k-40 k.
In some embodiments, wherein:
M is
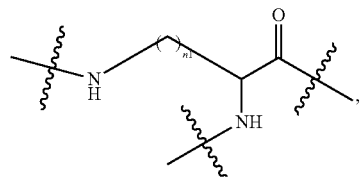
A1 is
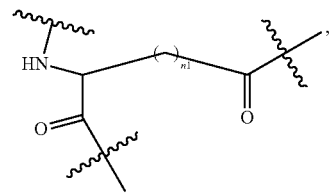
A1' is
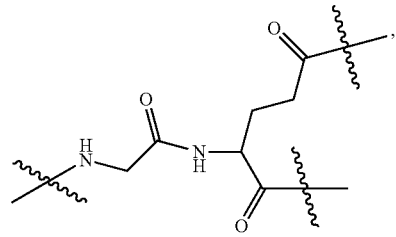 [SMILES: *NCC(=O)NC(CCC(*)=O)C(*)=O]
Y is a direct bond, Y' is
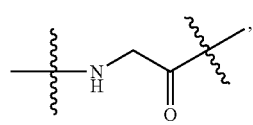 [SMILES: *NCC(*)=O]
W1 is
—Z4—(Z3—(Z2—(Q2)$_2$)$_2$)$_2$,
W1' is
—Z1—(Z0—(Q1)$_2$)$_2$,
Z4, Z2 and Z0 are
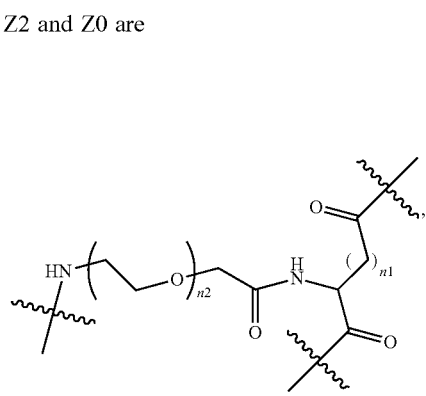
Z3 and Z1 are
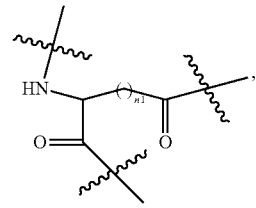
In some specific embodiments, M is
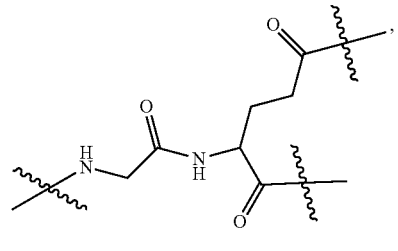 [SMILES: *NCC(=O)NC(CCC(*)=O)C(*)=O]
A1 is
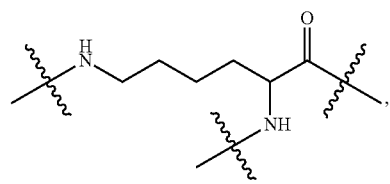 [SMILES: *NCCCCC(N*)C(*)=O]

A1' is
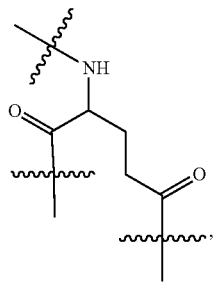 [SMILES: *NC(CCC(*)=O)C(*)=O]
Y is a direct bond, Y' is
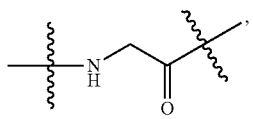 [SMILES: *NCC(*)=O]
W1 is
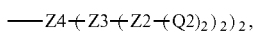
W1' is
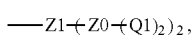
Z4, Z2 and Z0 are
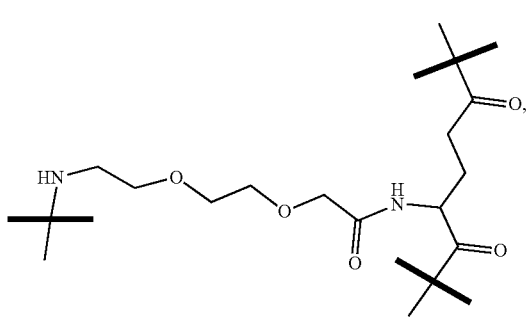
Z3 and Z1 are
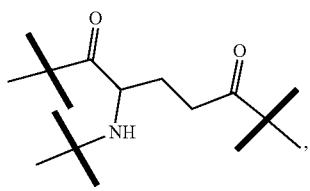
Q1 is —N1-AC1, Q2 is —N2-AC2, N1 is G, N2 is GFLG, AC1 is SN38, AC2 is PKA.
In some embodiments, M is —C(=O)—C$_{1-6}$ alkylene-NH—, A1 is
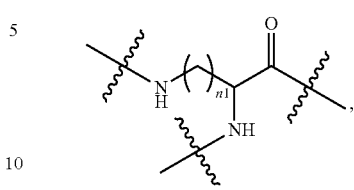
A1' is
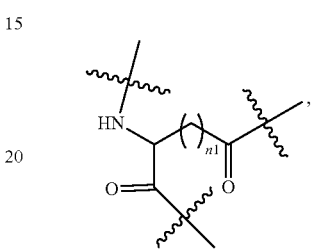
Y is a direct bond, Y' is
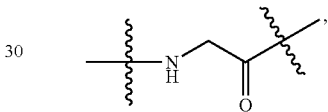
W1 is
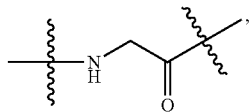 [SMILES: *NCC(*)=O]
W1' is Q1, Z2 and Z0 are
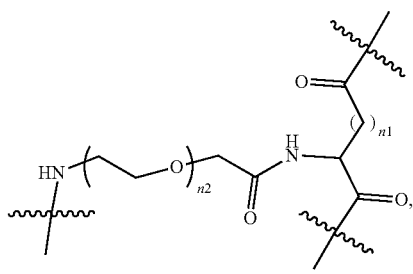
Z1 is
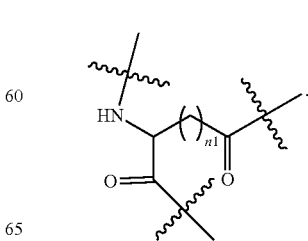

In some specific embodiments, M is
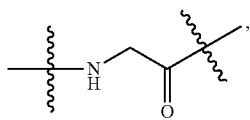 [SMILES: *NCC(*)=O]
A1 is
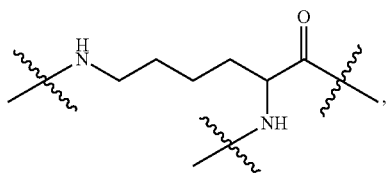 [SMILES: *NCCCCC(N*)C(*)=O]
A1' is
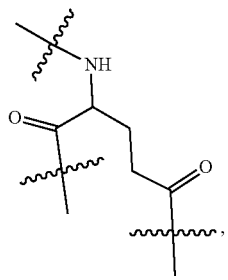 [SMILES: *NC(CCC(*)=O)C(*)=O]
Y is a direct bond, Y' is
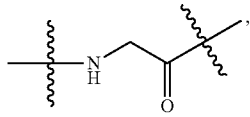 [SMILES: *NCC(*)=O]
W1 is
—Z2―(Z1―(Z0―(Q2)$_2$)$_2$)$_2$,
W1' is Q1, Z2 is
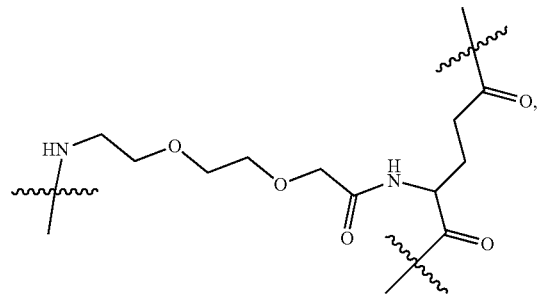 [SMILES: *NCCOCCOCC(=O)NC(CCC(*)=O)C(*)=O]
Z1 is
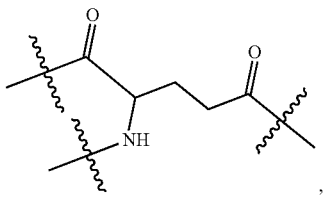 [SMILES: *NC(CCC(*)=O)C(*)=O]
Z0 is
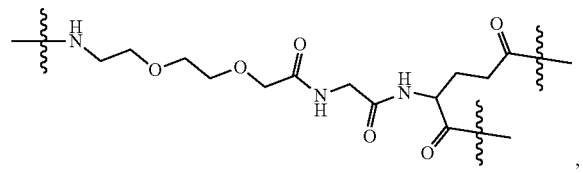 [SMILES: *NCCOCCOCC(=O)NCC(=O)NC(CCC(*)=O)C(*)=O]
Q1 is —N1-AC1, Q2 is —N2-AC2, N1 is G or
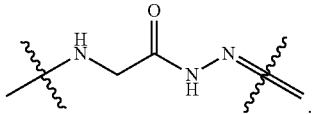 [SMILES: *NCC(=O)NN=*]
N2 is GFLG, AC1 is PTX or DOX, AC2 is PCB or LPT.
In some embodiments, M is —C(=O)—C$_{1-6}$ alkylene-C(=O)—, A1 and A1' are
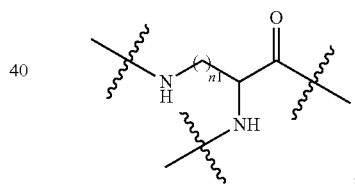
Y and Y' are a direct bond, W1 is
—Z3―(Z2―(Z1―(Q2)$_2$)$_2$)$_2$,
W1' is —Z0-(Q1)$_2$, Z3 and Z1 are
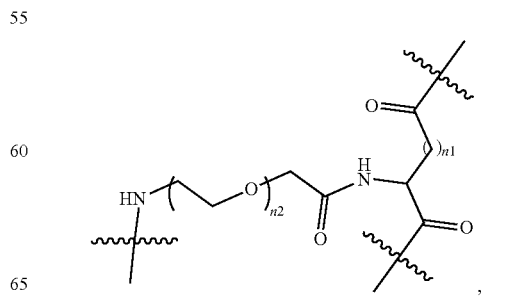

Z2 and Z0 are
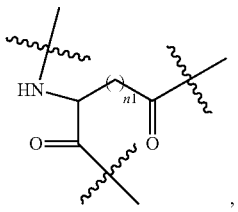
,
In some specific embodiments, M is
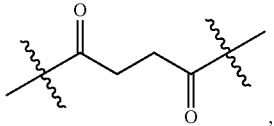 [SMILES: *C(=O)CCC(*)=O]
,
A1 and A1' are
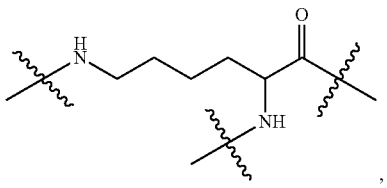 [SMILES: *NCCCCC(N*)C(*)=O]
,
Y and Y' are a direct bond, W1 is
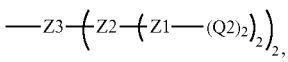
,
W1' is —Z0-(Q1)$_2$, Z3 and Z1 are
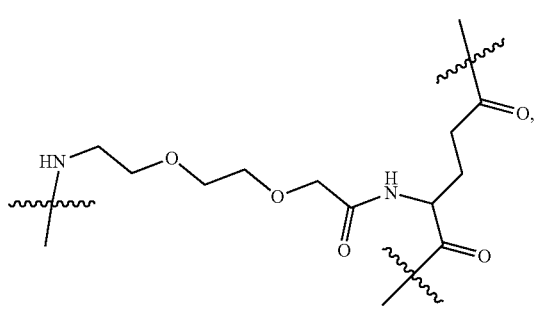 [SMILES: *NCCOCCOCC(=O)NC(CCC(*)=O)C(*)=O]
,
Z2 is
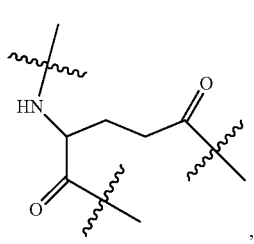 [SMILES: *NC(CCC(*)=O)C(*)=O]
,
Z0 is
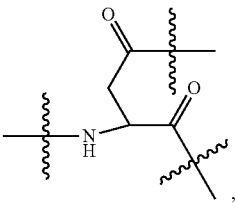 [SMILES: *NC(CC(*)=O)C(*)=O]
,
Q1 is —N1-AC1, Q2 is —N2-AC2, N1 and N2 are GFLG, AC1 is SB7, AC2 is PCB.
In some embodiments, M is —C(=O)—C$_{1-6}$ alkylene-C(=O)—, A1 and A1' are
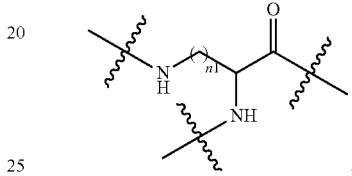
,
Y and Y' are a direct bond, W1 is
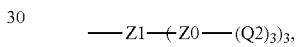,
W1' is Q1, Z1 and Z0 are
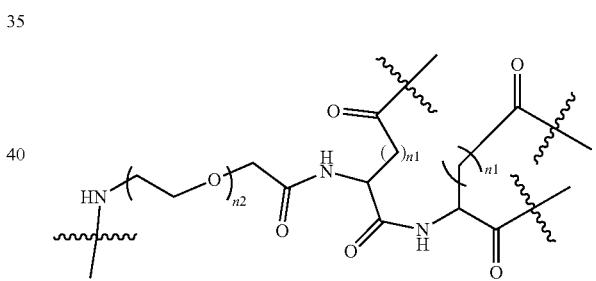
.
In some specific embodiments, M is
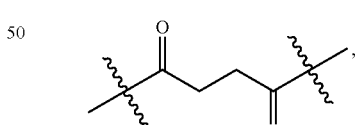
,
A1 and A1' are
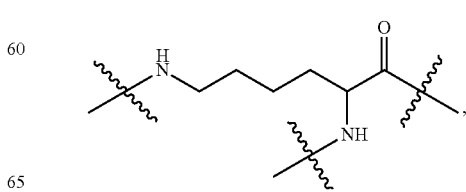
, Y and Y' are a direct bond, W1 is
—Z1—(Z0—(Q2)₃)₃,
W1' is Q1, Z1 and Z0 are
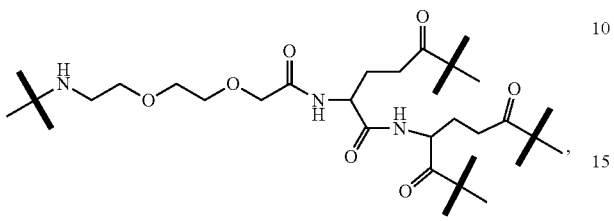
Q1 is —N1-AC1, Q2 is —N2-AC2, N1 and N2 are GFLG, AC1 is PCB, AC2 is LPT.
In some embodiments, M is —C(=O)—C₁₋₆ alkylene-NH—, A1 is
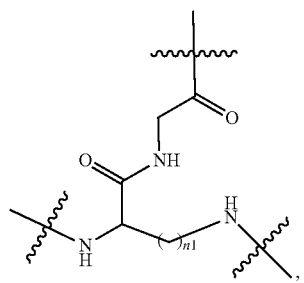
A1' is
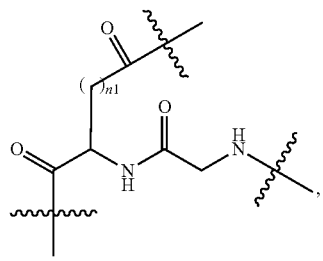
Y and Y' are a direct bond, W1 and W1' are
—Z2—(Z1—(Z0—(Q)₂)₂)₂,
Z2 is
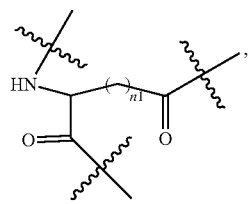
Z1 is
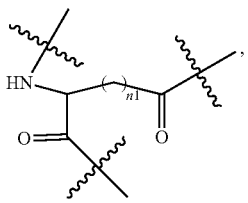
Z0 is
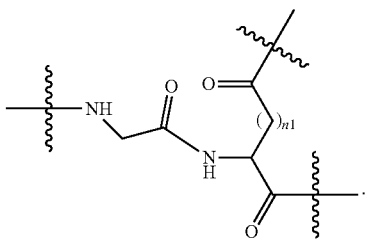
In some specific embodiments, M is
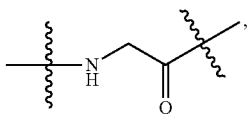 [SMILES: *NCC(*)=O]
A1 is
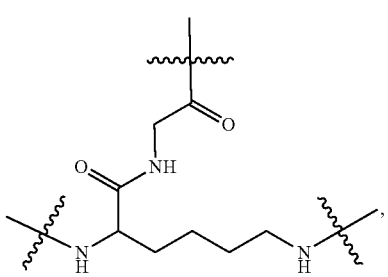 [SMILES: *NCCCCC(N*)C(=O)NCC(*)=O]
A1' is
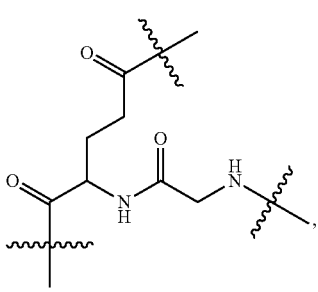 [SMILES: *NCC(=O)NC(CCC(*)=O)C(*)=O]

Y and Y' are a direct bond, W1 and W1' are
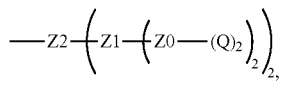
Z2 is
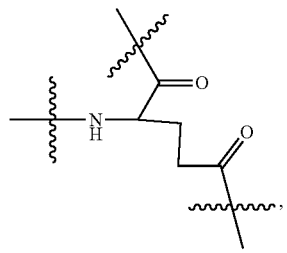 [SMILES: *NC(CCC(*)=O)C(*)=O]
Z1 is
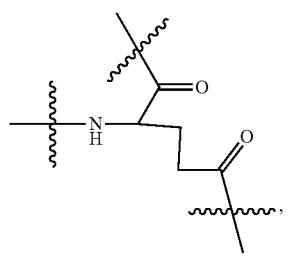 [SMILES: *NC(CCC(*)=O)C(*)=O]
Z0 is
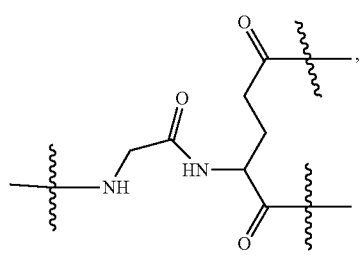 [SMILES: *NCC(=O)NC(CCC(*)=O)C(*)=O]
Q is —N-AC, N is GFLG, AC is SB7.
In some embodiments, the polyethylene glycol conjugated drug has the structure represented by the formula (IV), wherein:
M is
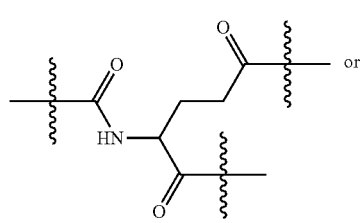 or
-continued
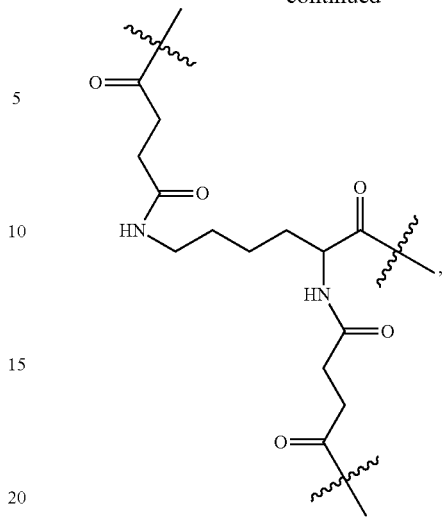
A1 is
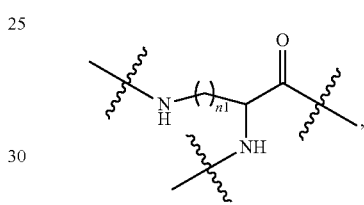
preferably
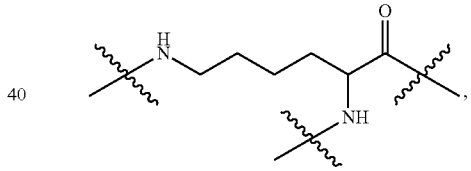
X is
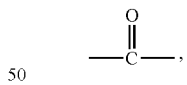
W1 independently is
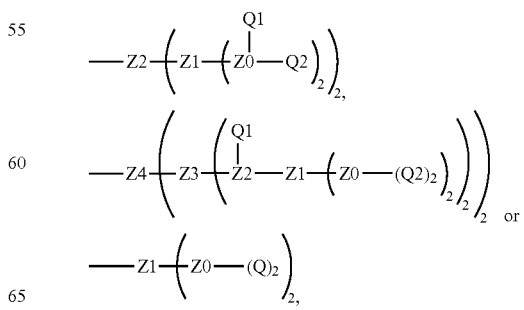 or Z4, Z3, Z2, Z1, Z0 each independently are
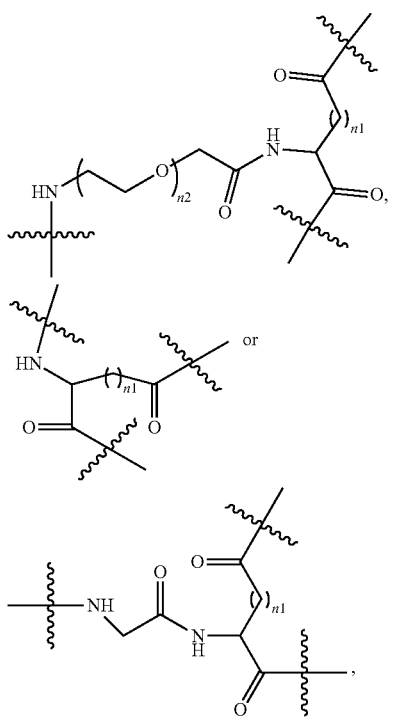
preferably
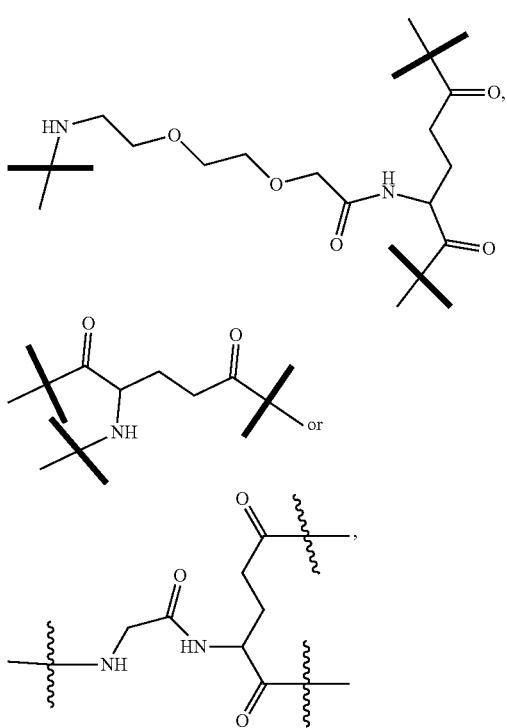
Q is —N-AC,
Q1 is —N1-AC1,
Q2 is —N2-AC2,
N1 and N2 are GFLG,
AC1, AC2 each independently are PCB, SB7, LPT, PKA,
the number-average molecular weight of PEG independently is 5 k-40 k.
In some embodiments, wherein:
M is
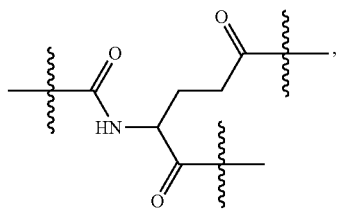 [SMILES: *C(=O)CCC(NC(*)=O)C(*)=O]
W1 is
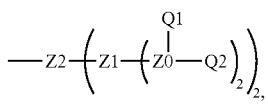
Z2 is
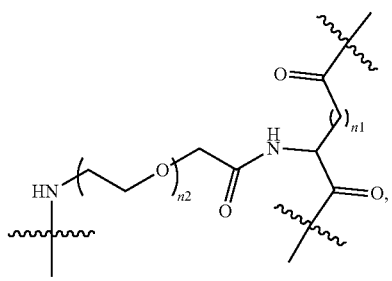
Z1 is
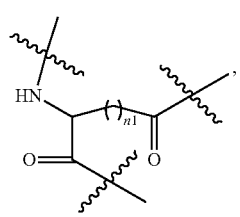
Z0 is
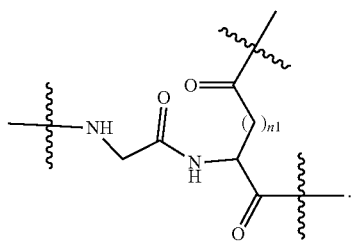

In some specific embodiments, M is
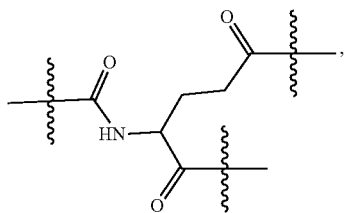 [SMILES: *C(=O)CCC(NC(*)=O)C(*)=O]
W1 is
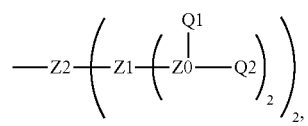
Z2 is
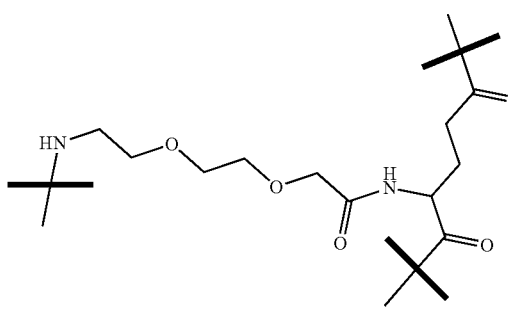
Z1 is
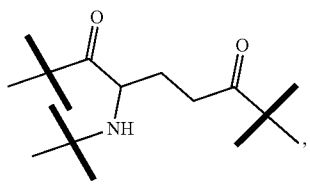
Z0 is
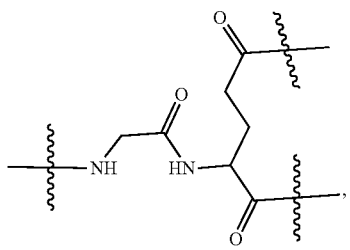 [SMILES: *NCC(=O)NC(CCC(*)=O)C(*)=O]
Q1 is —N1-AC1, Q2 is —N2-AC2, N1 and N2 are GFLG, AC1 is LPT, AC2 is SB7.
In some embodiments, M is
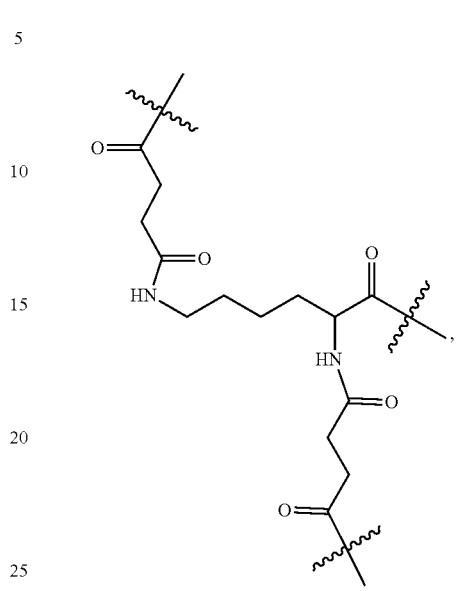
W1 is
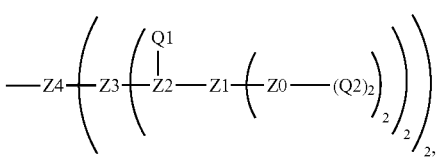
Z4 and Z1 are
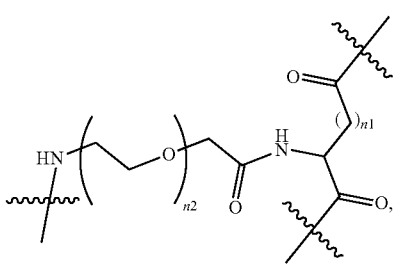
Z3, Z2 and Z0 are
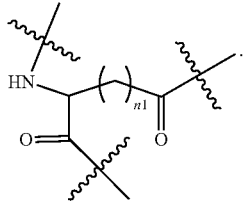

In some specific embodiments, M is
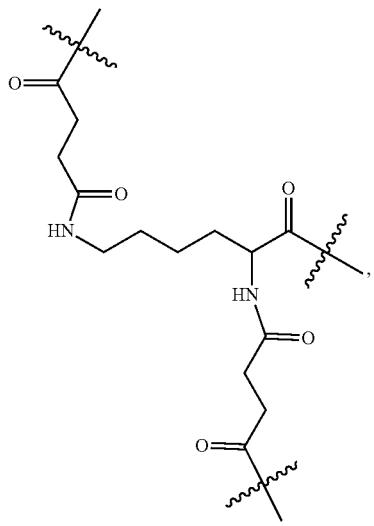 [SMILES: *C(=O)CCC(=O)NCCCCC(NC(=O)CCC(*)=O)C(*)=O]
W1 is
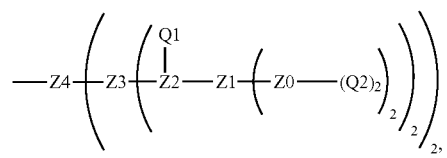
Z4 and Z1 are
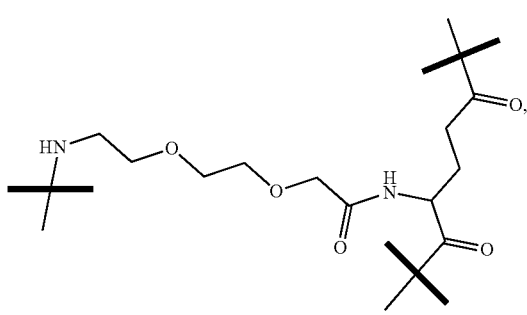
Z3, Z2 and Z0 are
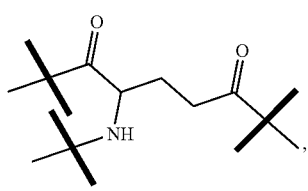
Q1 is —N1-AC1, Q2 is —N2-AC2, N1 and N2 are GFLG, AC1 is PCB, AC2 is PKA.
In some embodiments, M is
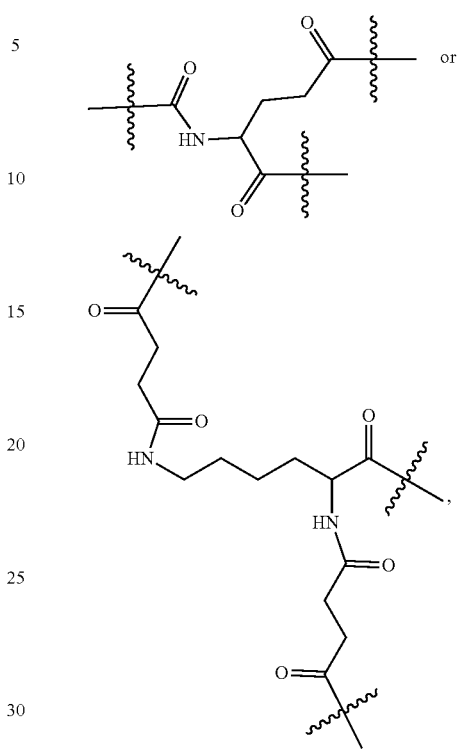 or
W1 is
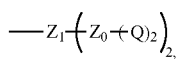
Z1 is
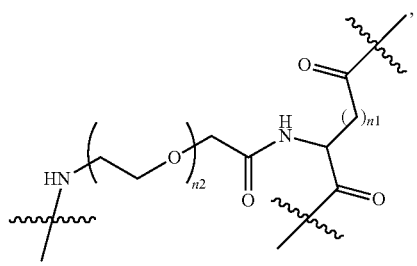
Z0 is
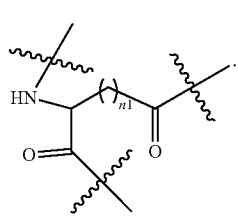

In some specific embodiments, M is
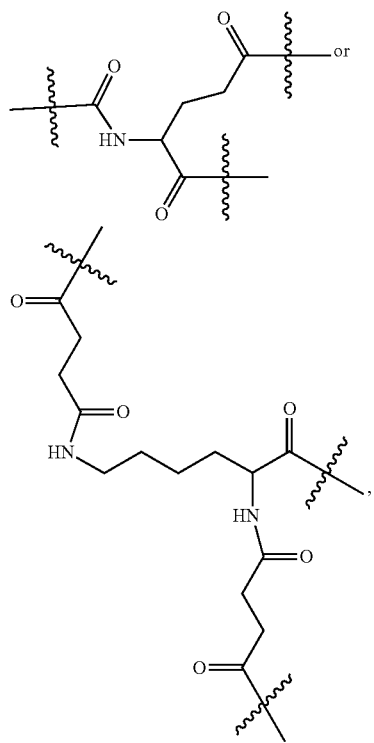
W1 is
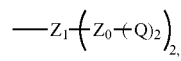
Z1 is
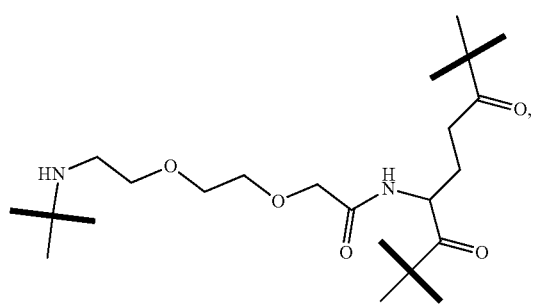
Z0 is
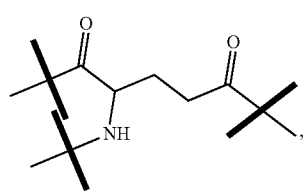
Q is —N-AC, N is GFLG, AC is LPT or PCB.
In some embodiments, the polyethylene glycol conjugated drug has the structure represented by the formula (V), wherein:
L1 is —C(=O)—C$_{1-6}$ alkylene-C(=O)—, preferably
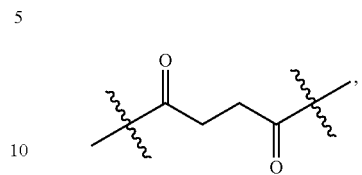
A2 is
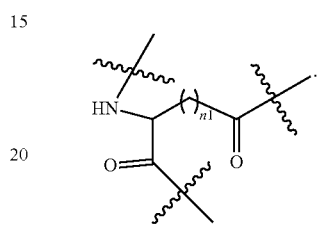
preferably
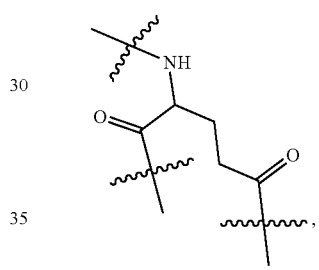
M is
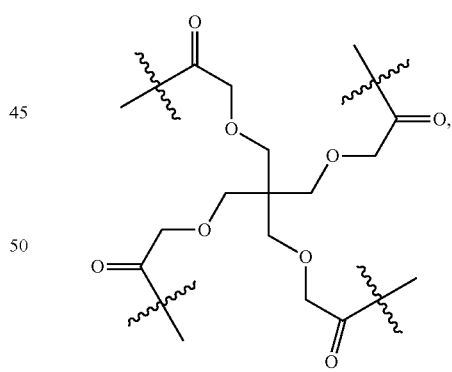
A1 is
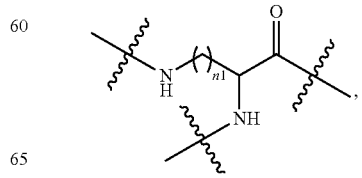

preferably
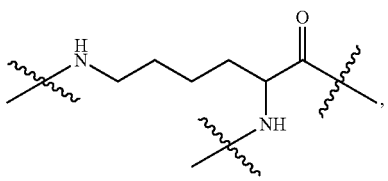 [SMILES: *NCCCCC(N*)C(*)=O]
Y is
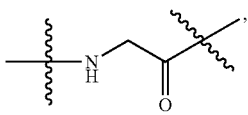 [SMILES: *NCC(*)=O]
X is
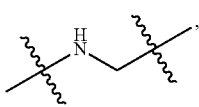
W1, W2 each independently are
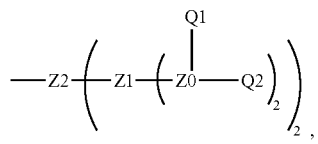
Z2, Z1, Z0 each independently are
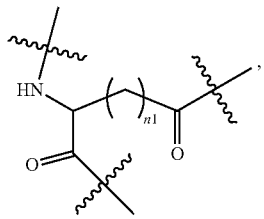
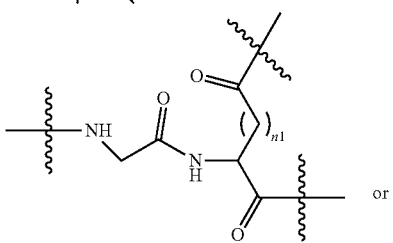 or
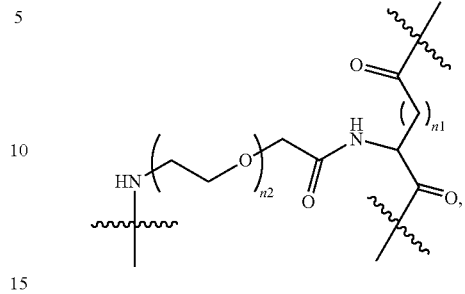
preferably
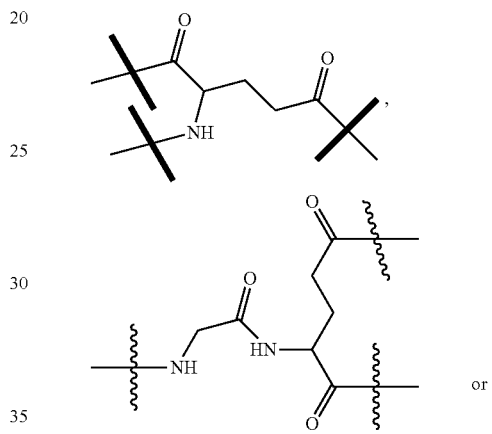
or
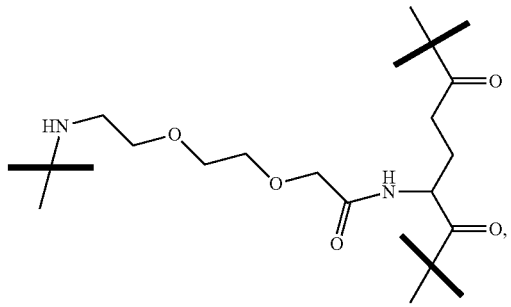
Q1 is —N1-AC1,
Q2 is —N2-AC2,
N1 and N2 are GFLG,
AC1, AC2 each independently are PCB or SB7,
the number-average molecular weight of PEG is 5 k-40 k.
In some embodiments, wherein:
W1 and W2 are
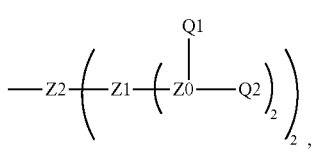

Z2 is
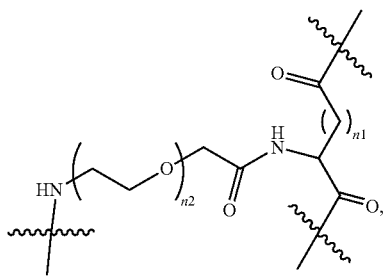
Z1 is
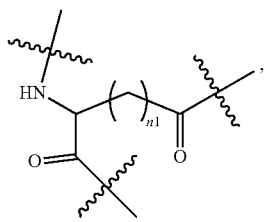
Z0 is
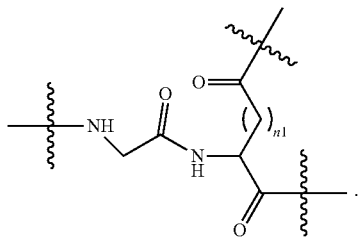
In some specific embodiments, W1 and W2 are
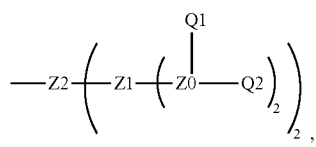
Z2 is
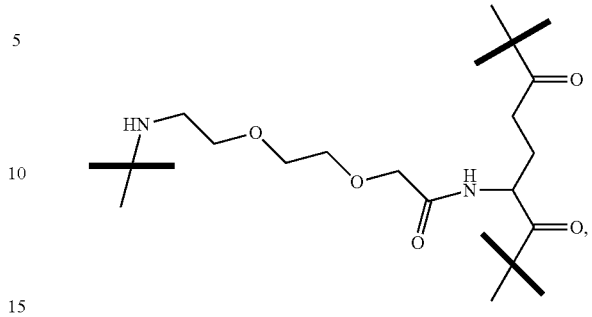
Z1 is
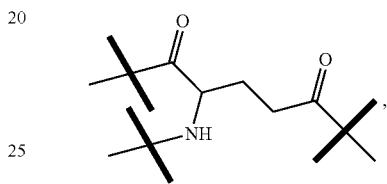
Z0 is
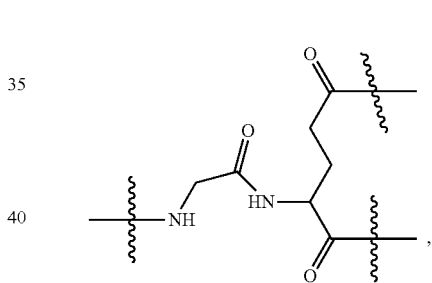
Q1 is —N1-AC1, Q2 is —N2-AC2, N1 and N2 are GFLG, AC1 is PCB, AC2 is SB7.
In the second aspect of the present invention, the present invention provides a polyethylene glycol conjugated drug or a pharmaceutically acceptable salt thereof, the polyethylene glycol conjugated drug being selected from:

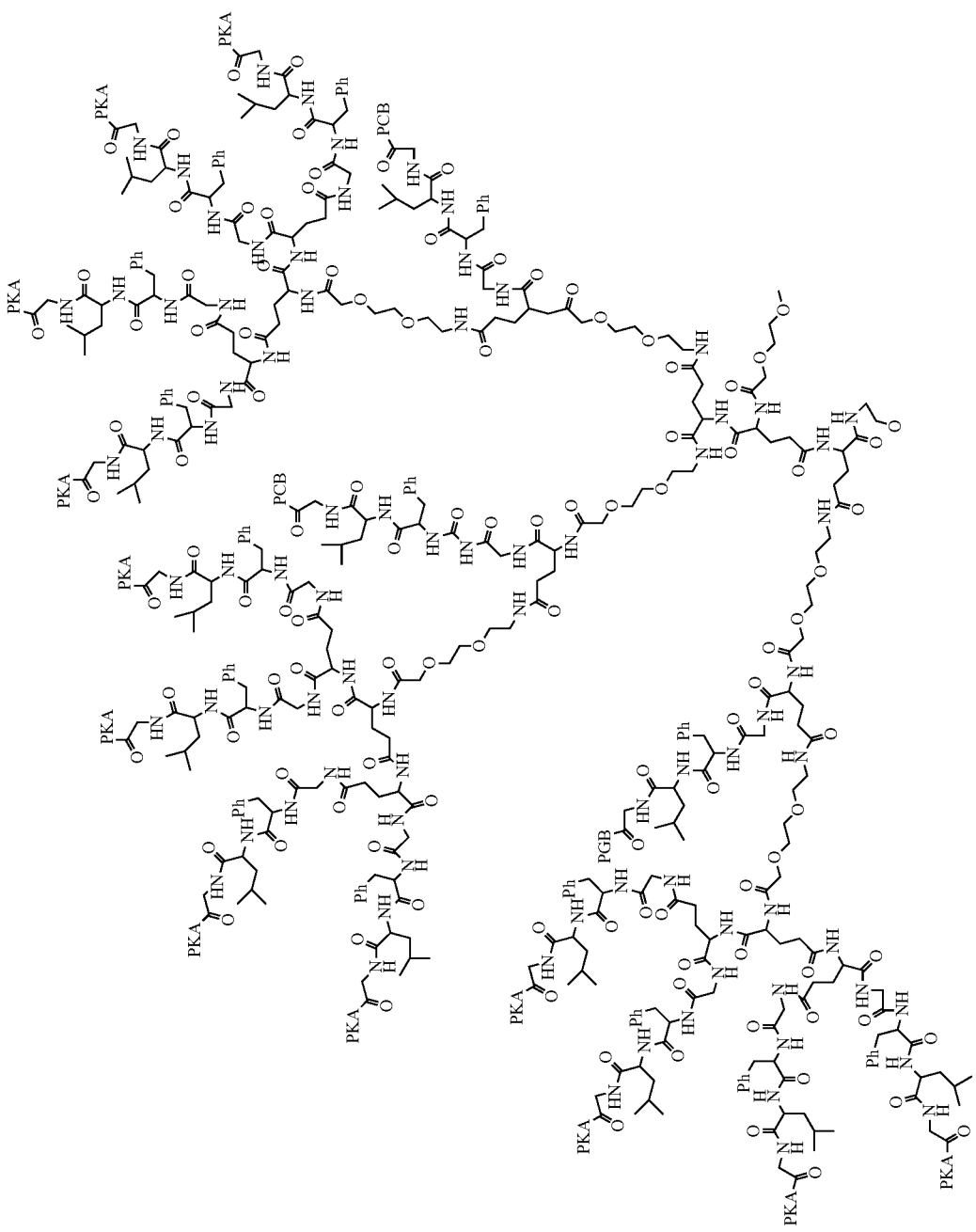

-continued
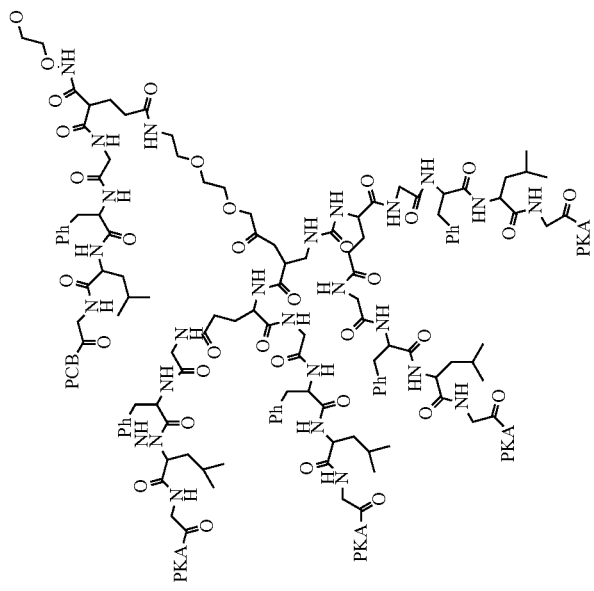

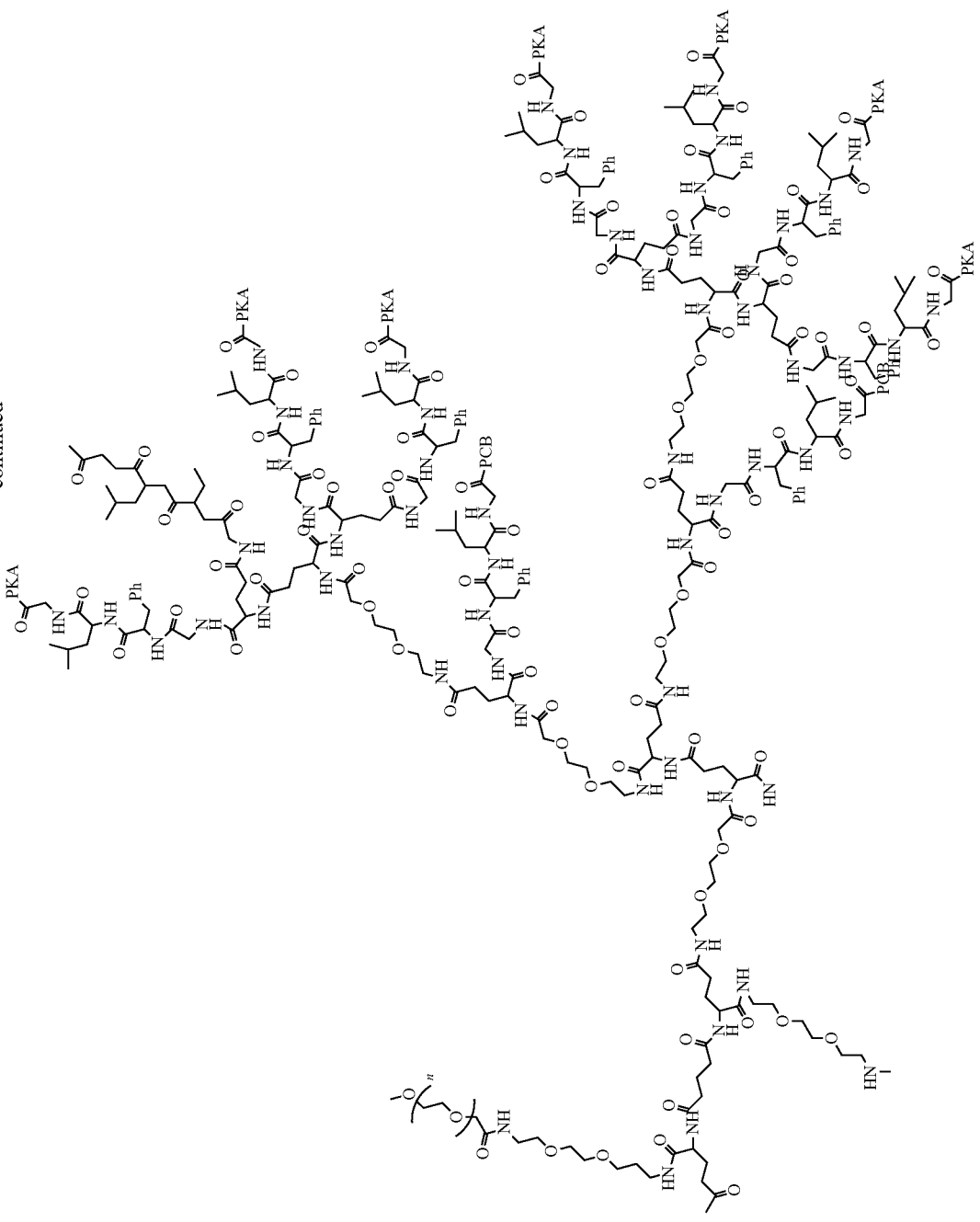
-continued

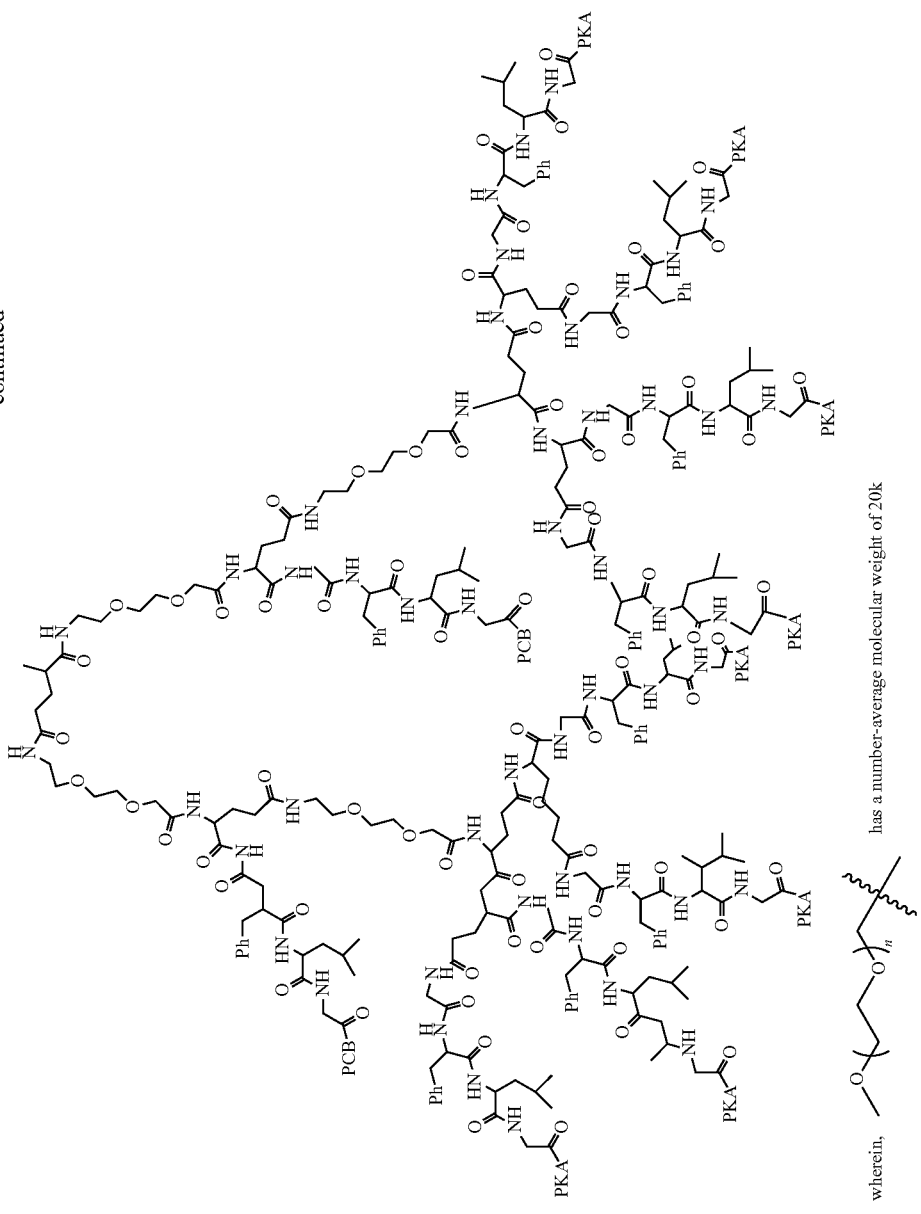

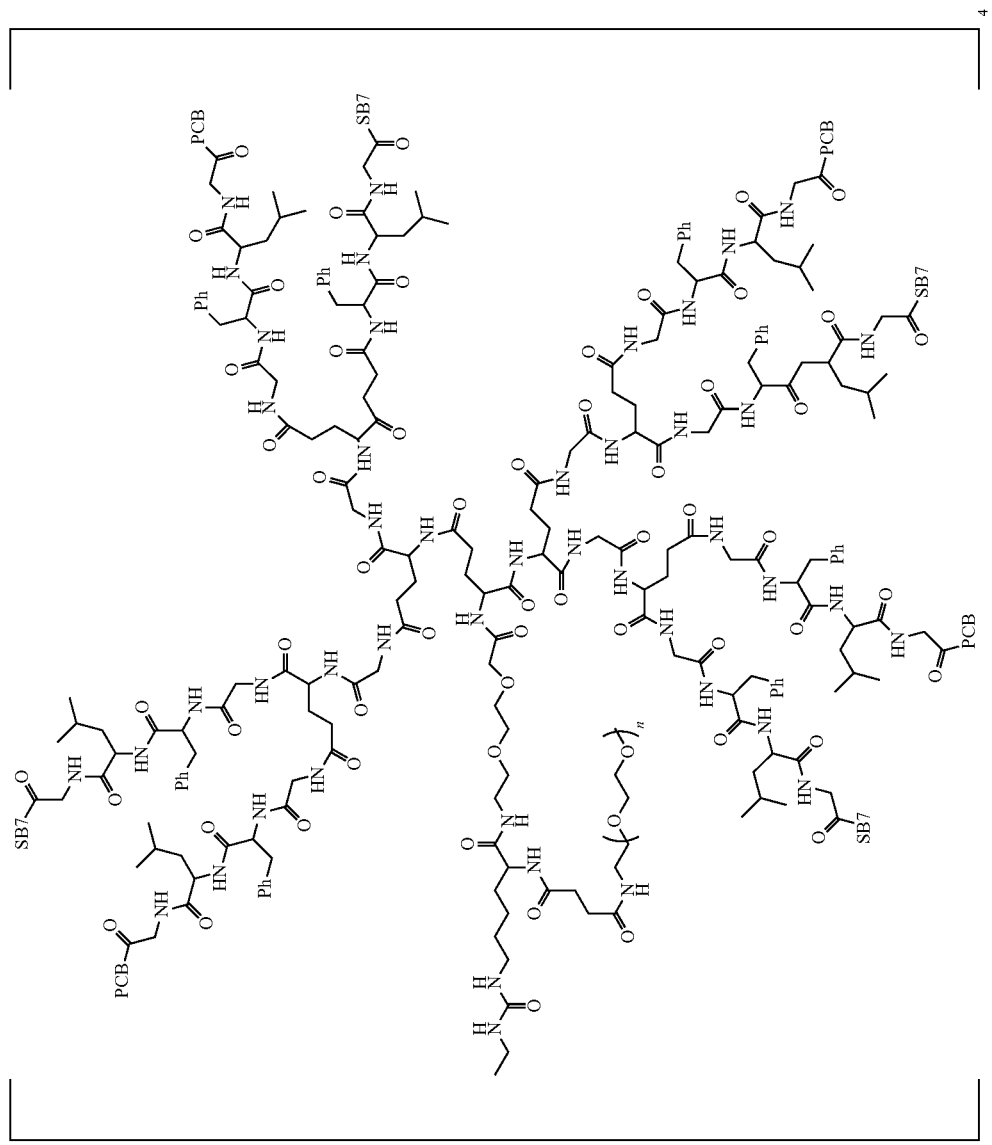
wherein, has a number-average molecular weight of 5k

-continued
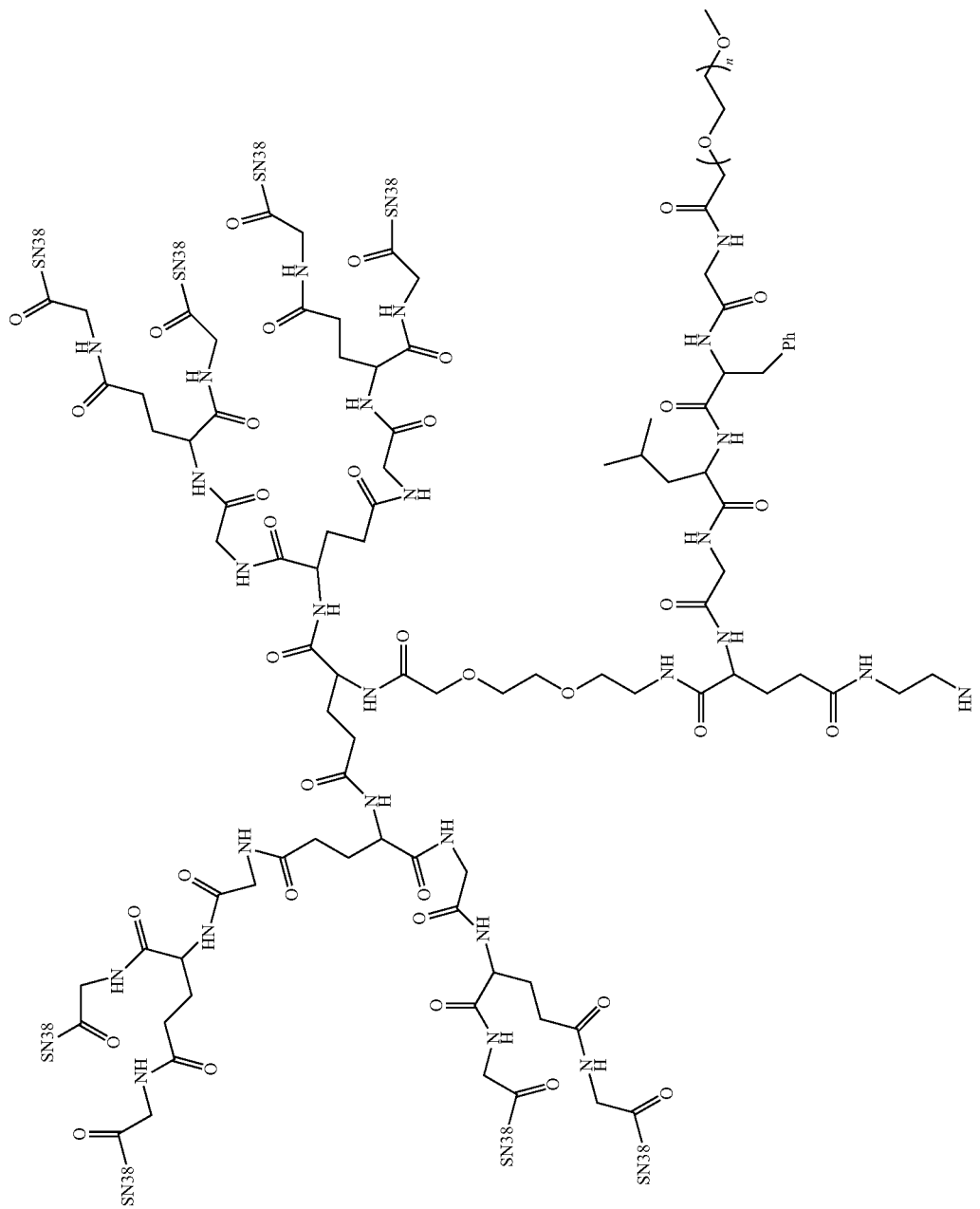

-continued
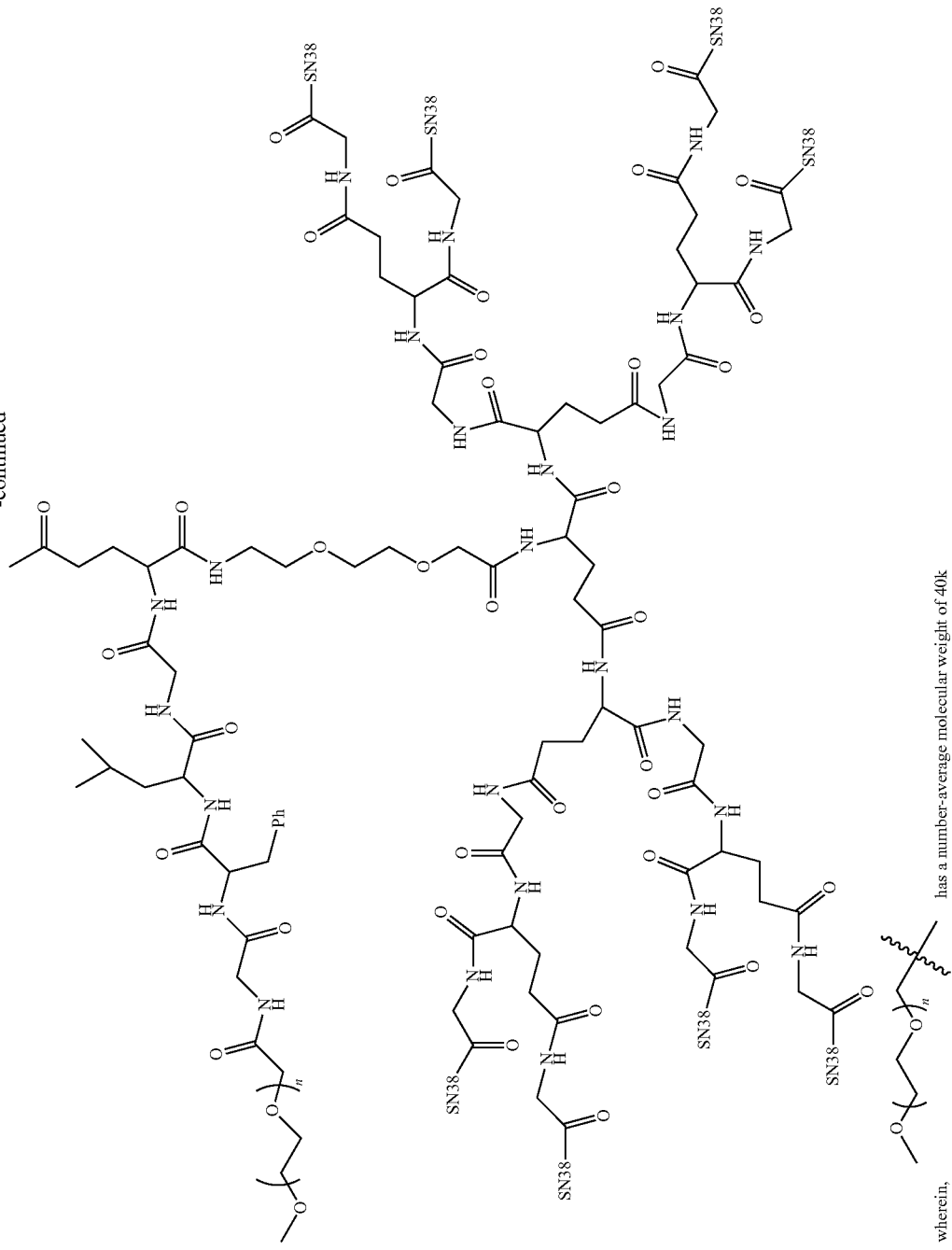
wherein, has a number-average molecular weight of 40k

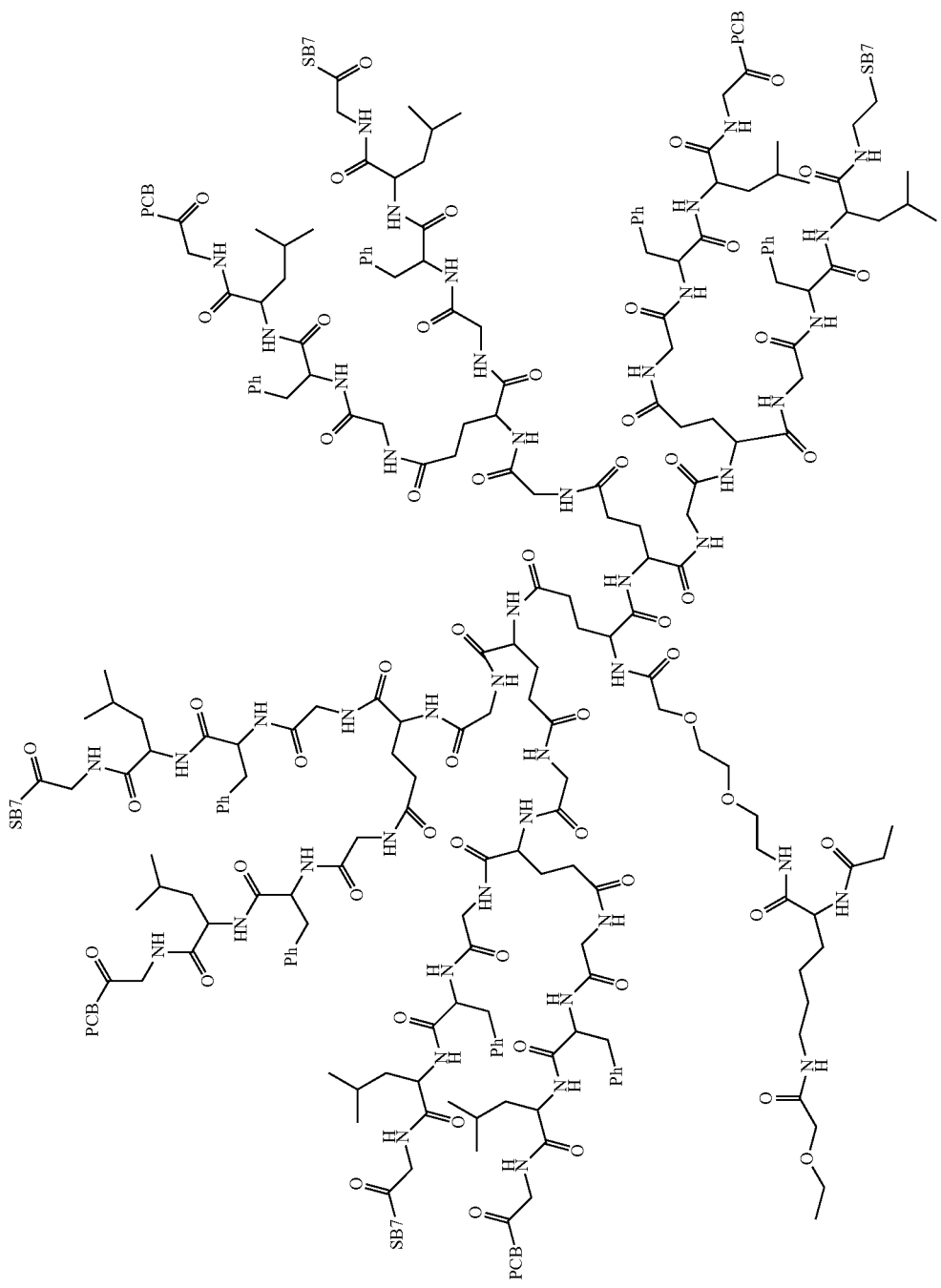

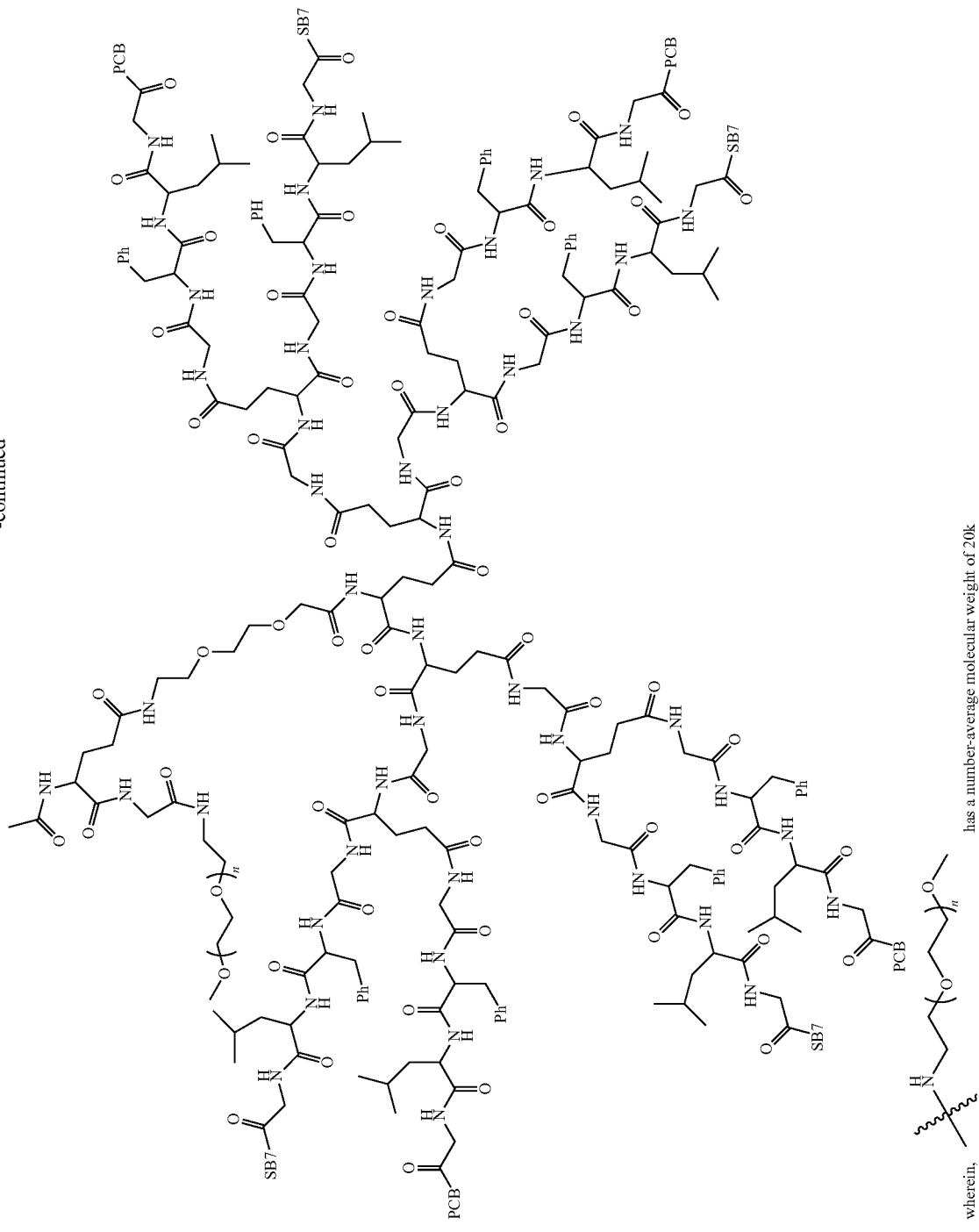

-continued
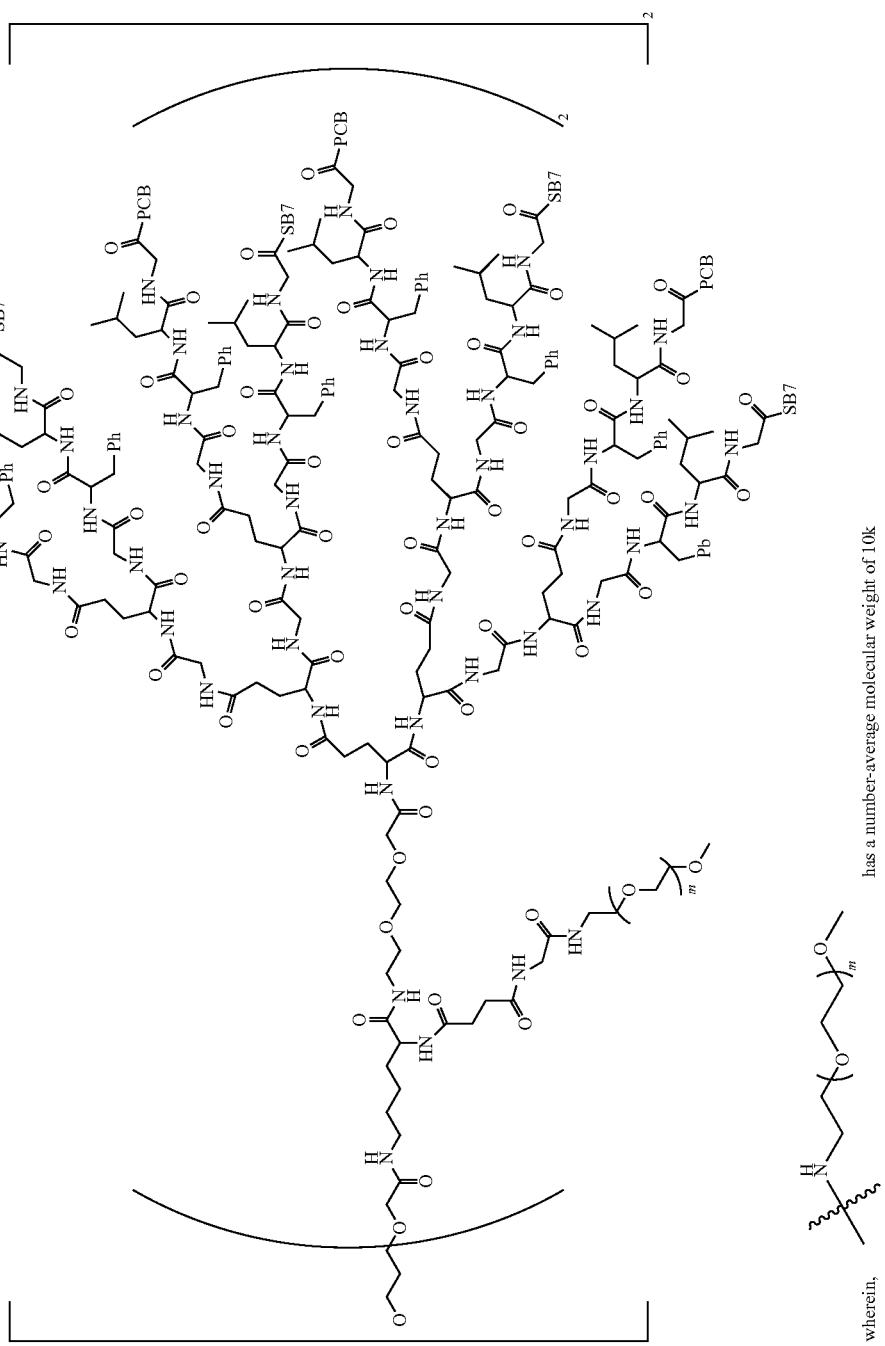
wherein, has a number-average molecular weight of 10k

-continued
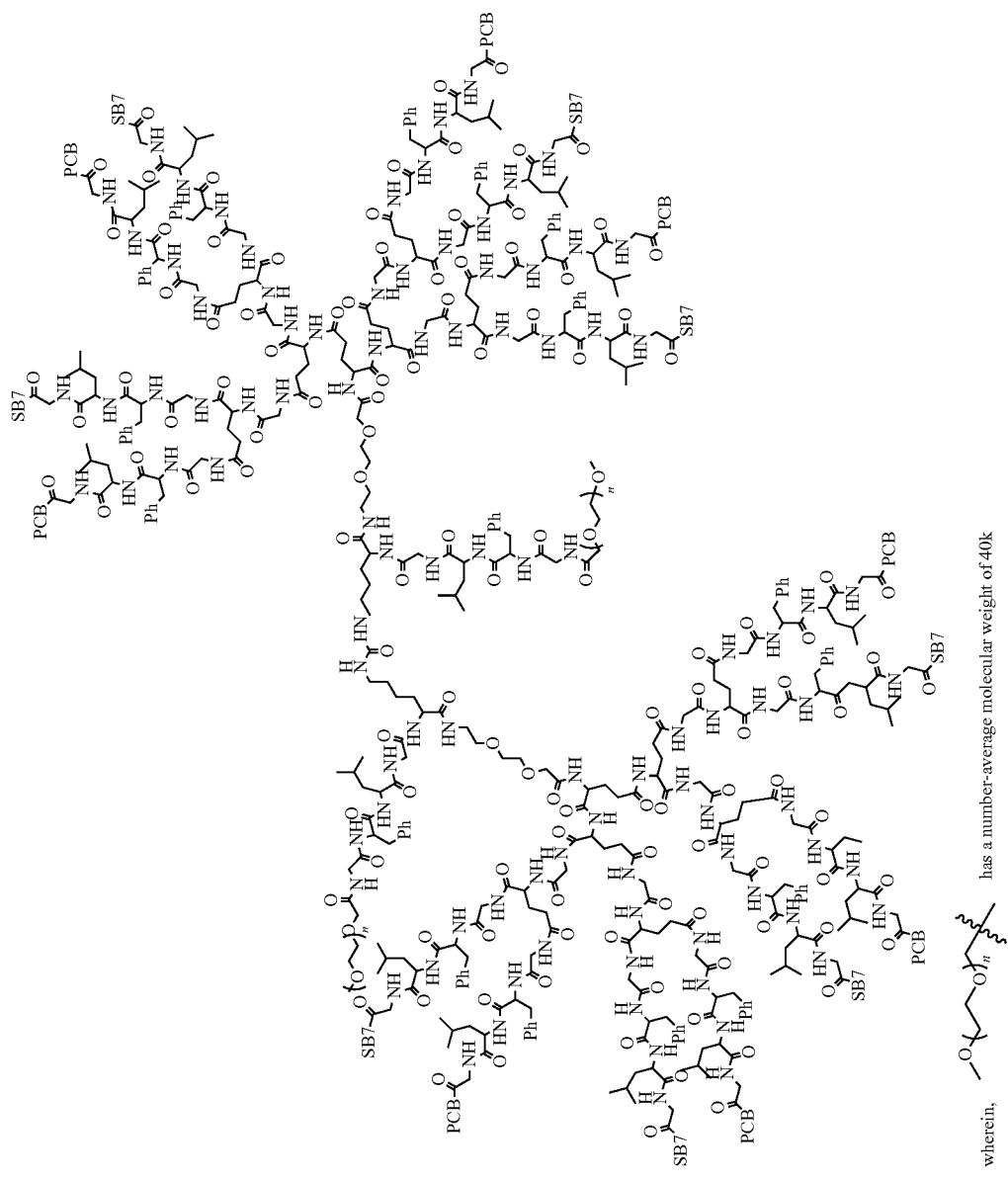
wherein,
has a number-average molecular weight of 40k

-continued
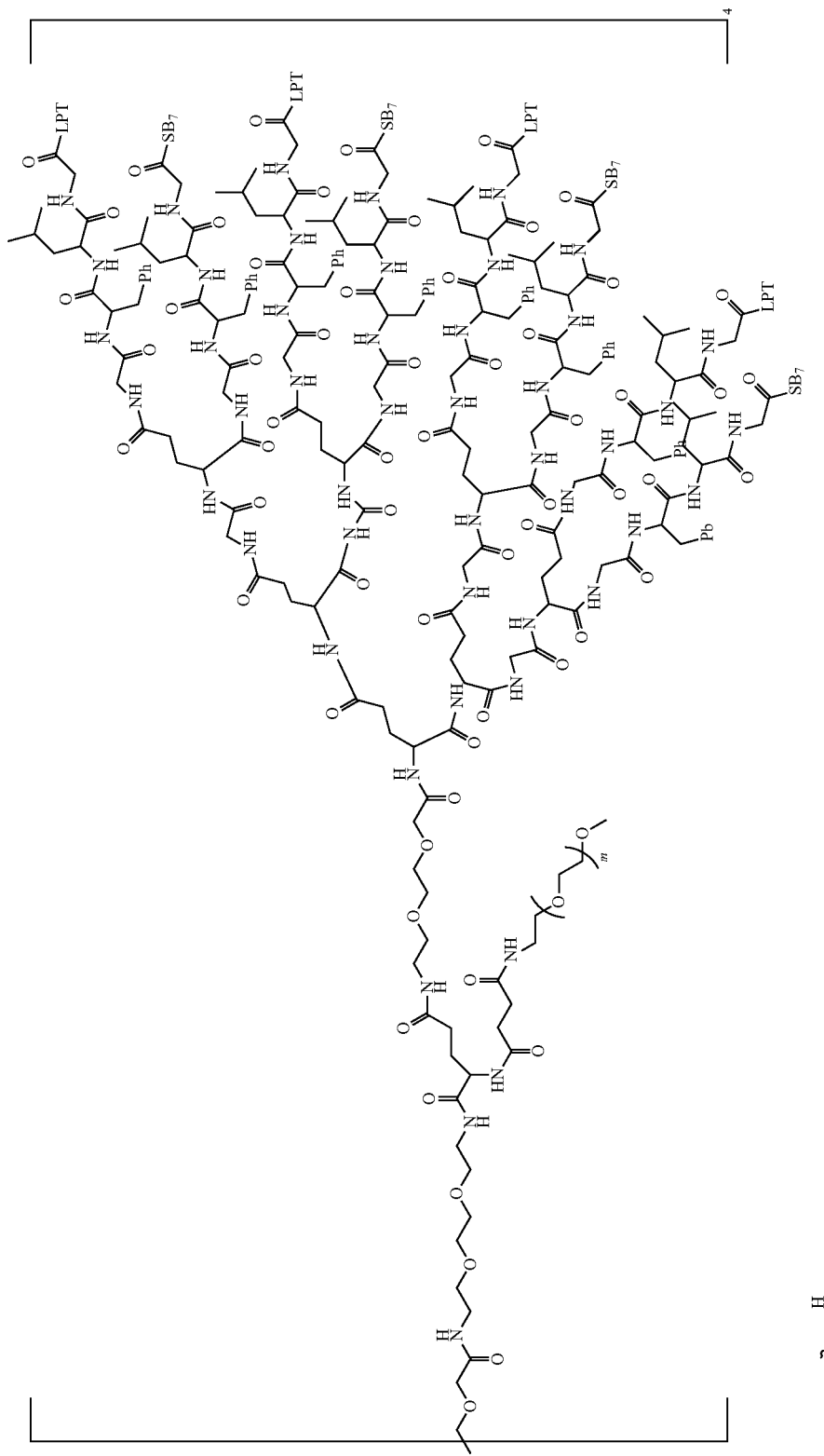
wherein, has a number-average molecular weight of 10k

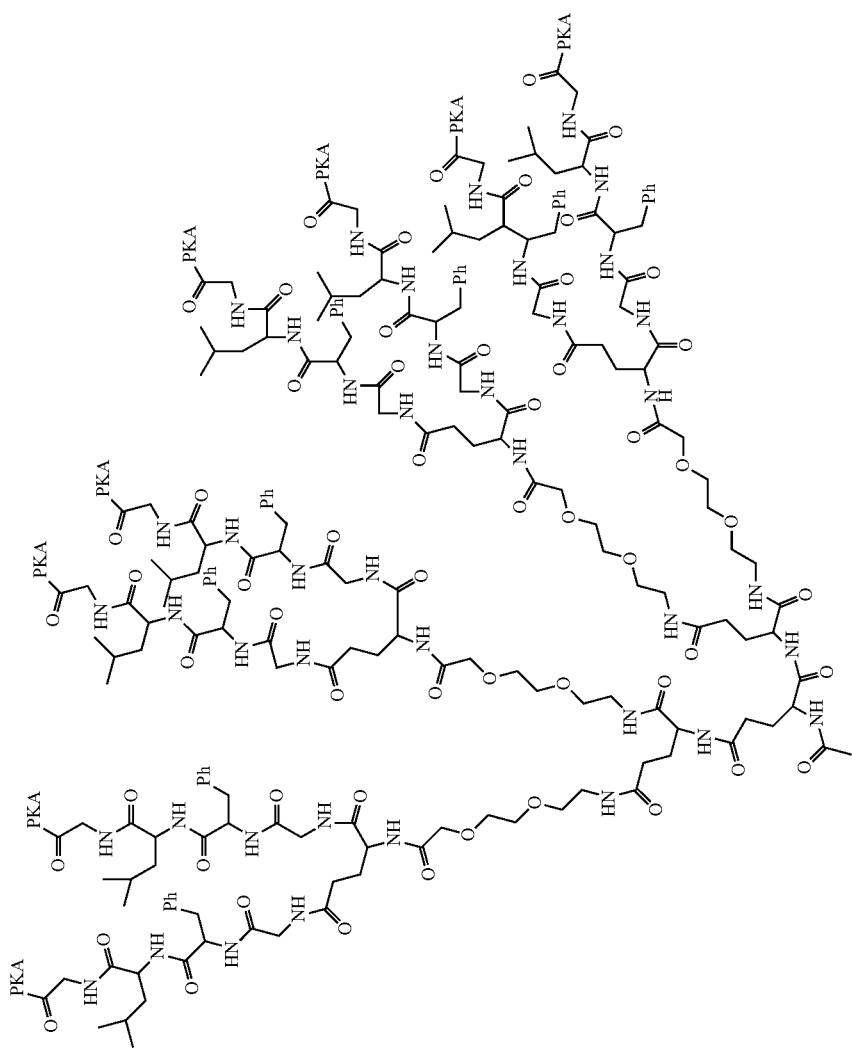

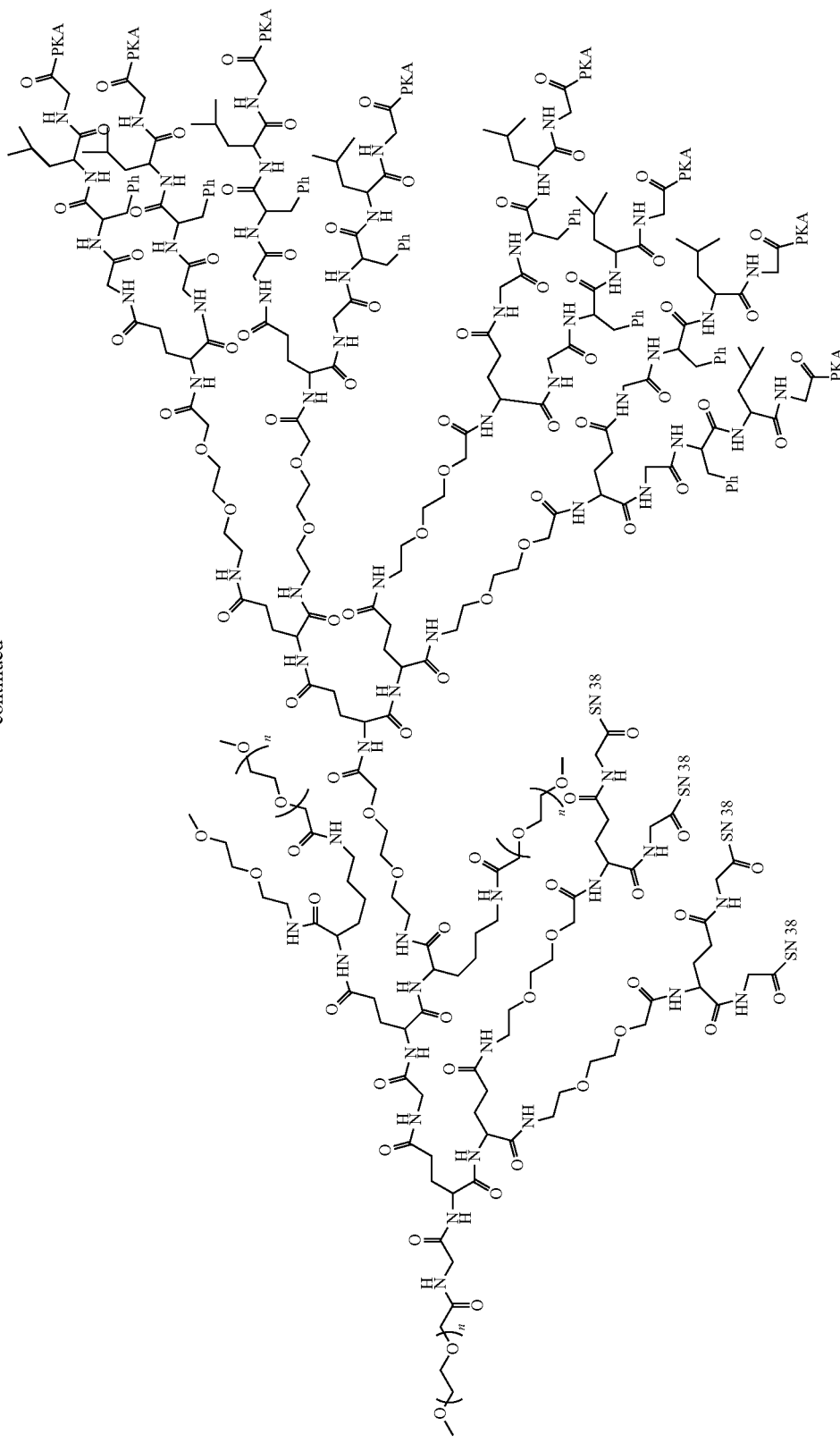
-continued
wherein, 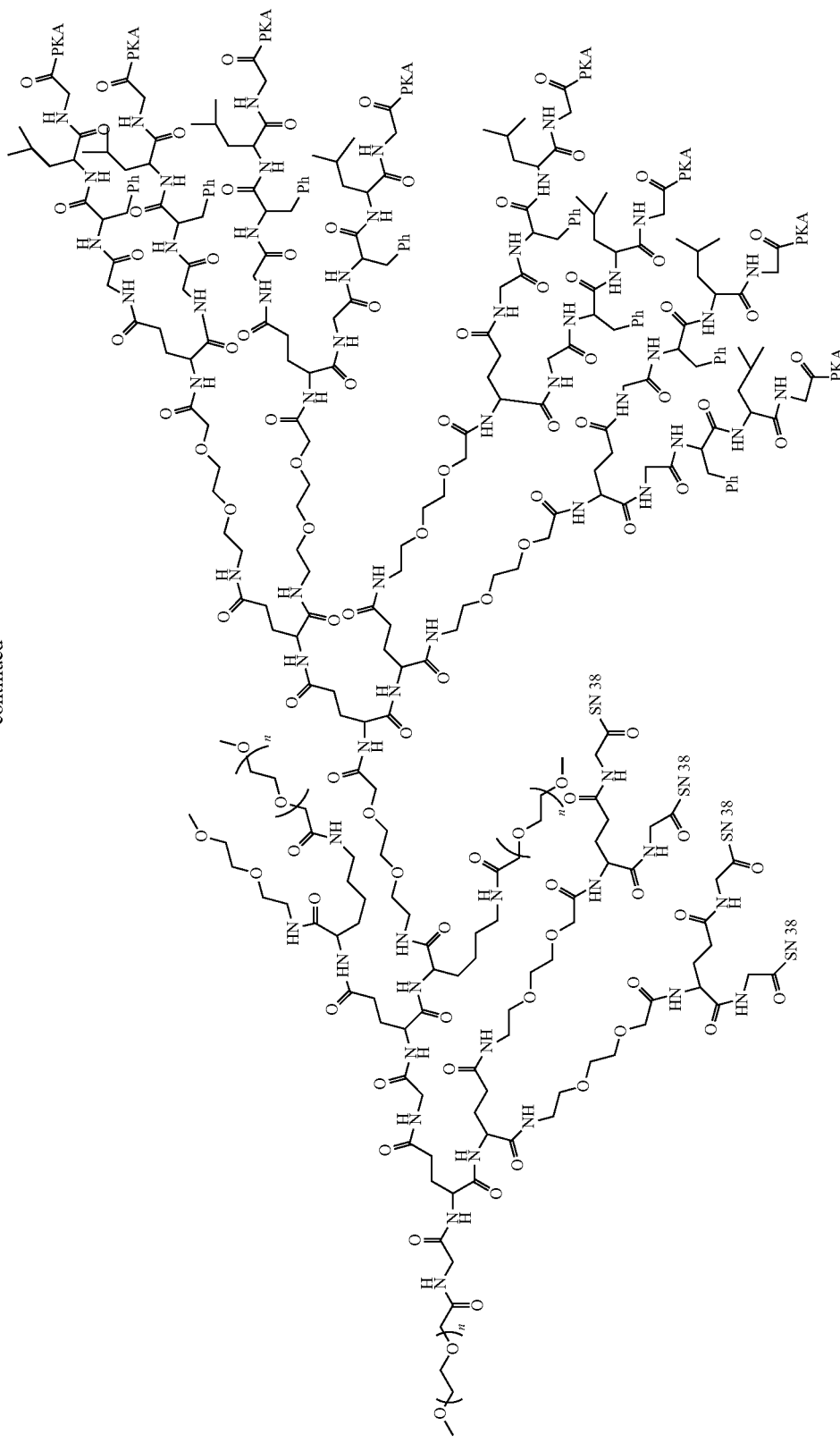 has a number-average molecular weight of 5k -continued
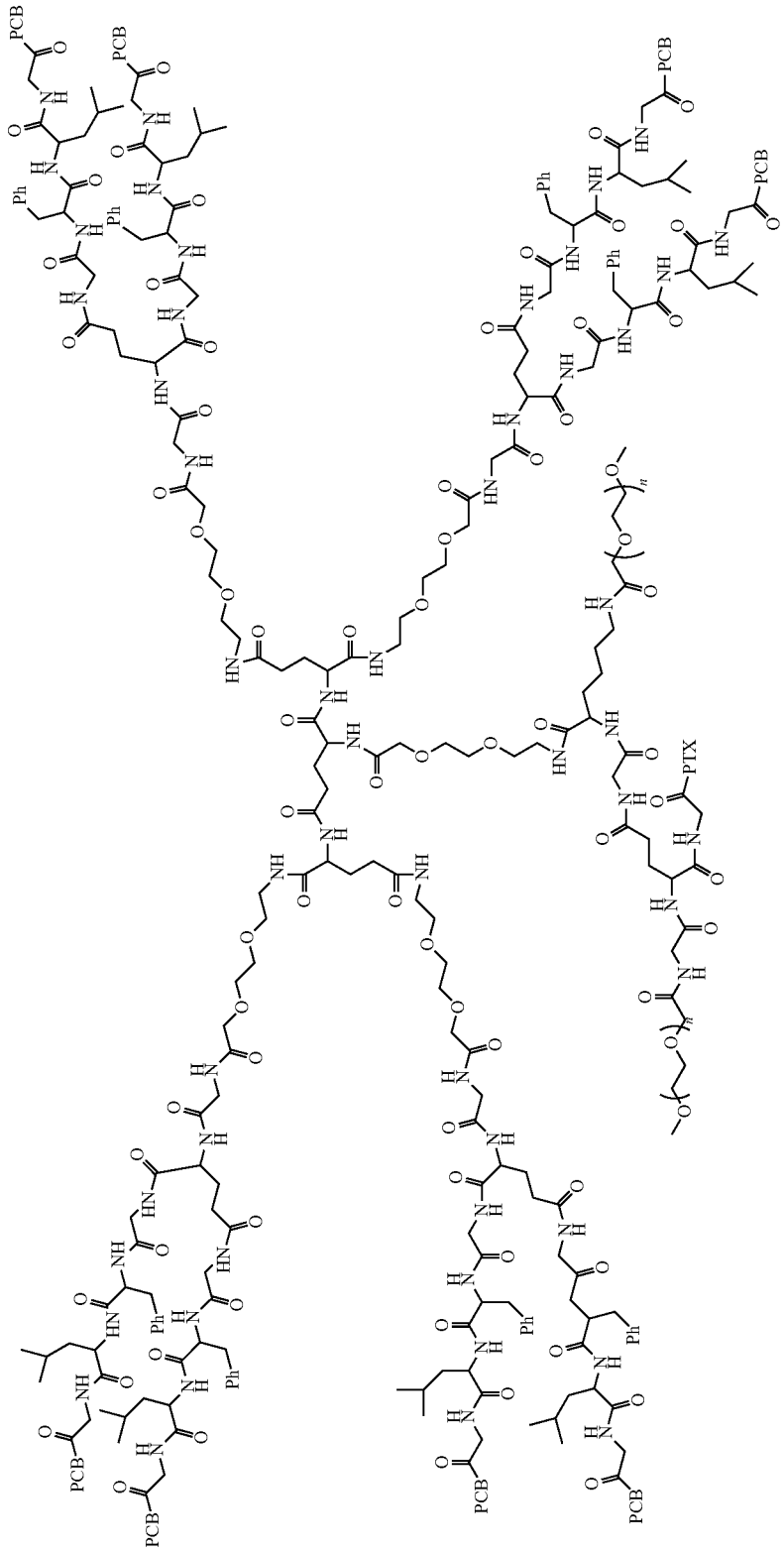
wherein, ~~~O~~~ has a number-average molecular weight of 5k -continued
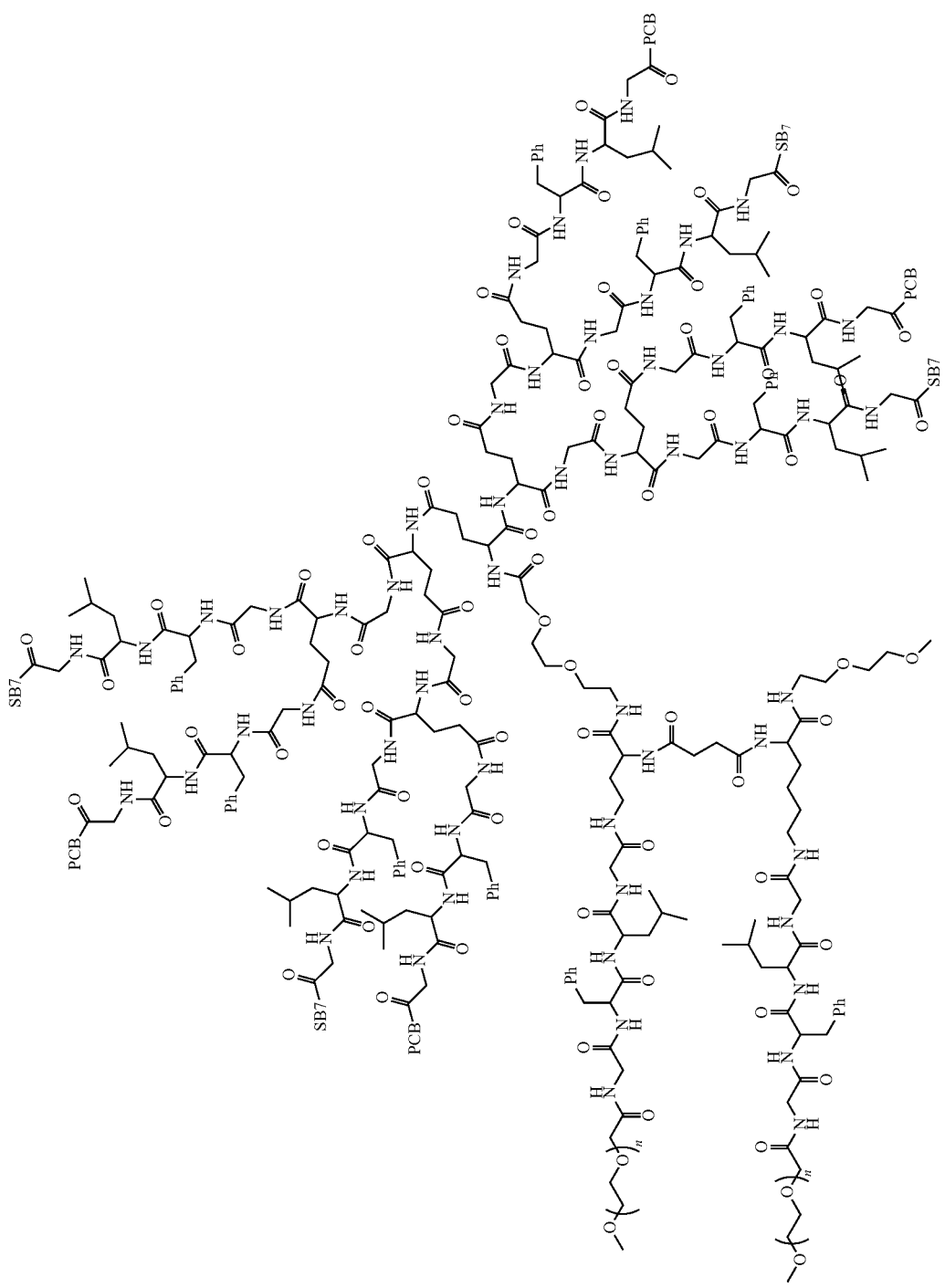

-continued
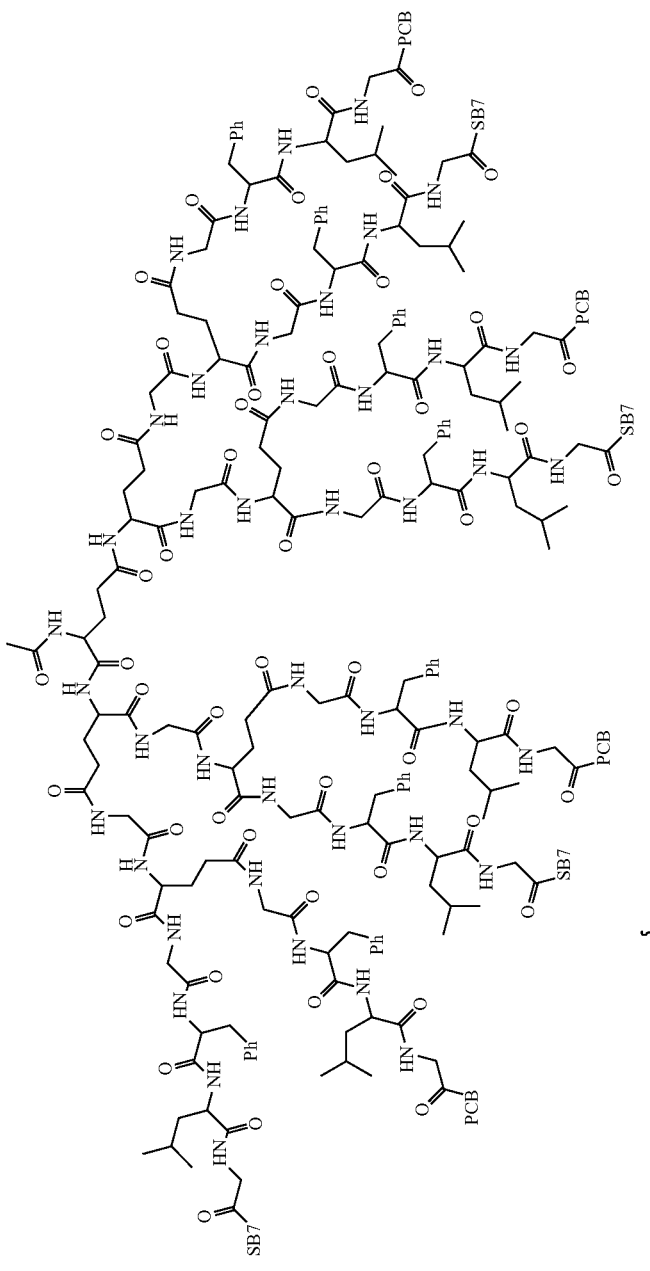
wherein,
 has a number-average molecular weight of 40k -continued
11
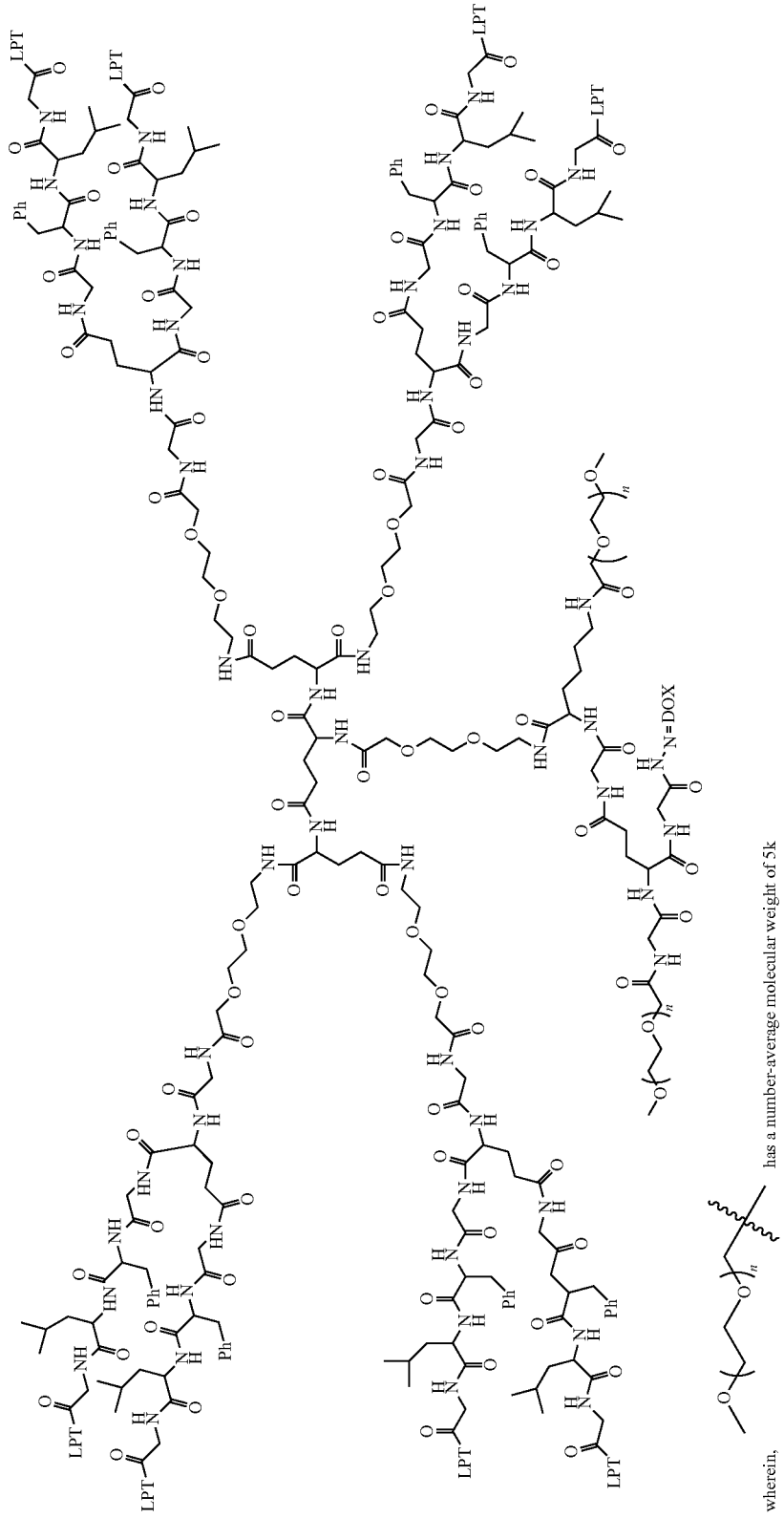
wherein,
~~~O~ has a number-average molecular weight of 5k -continued
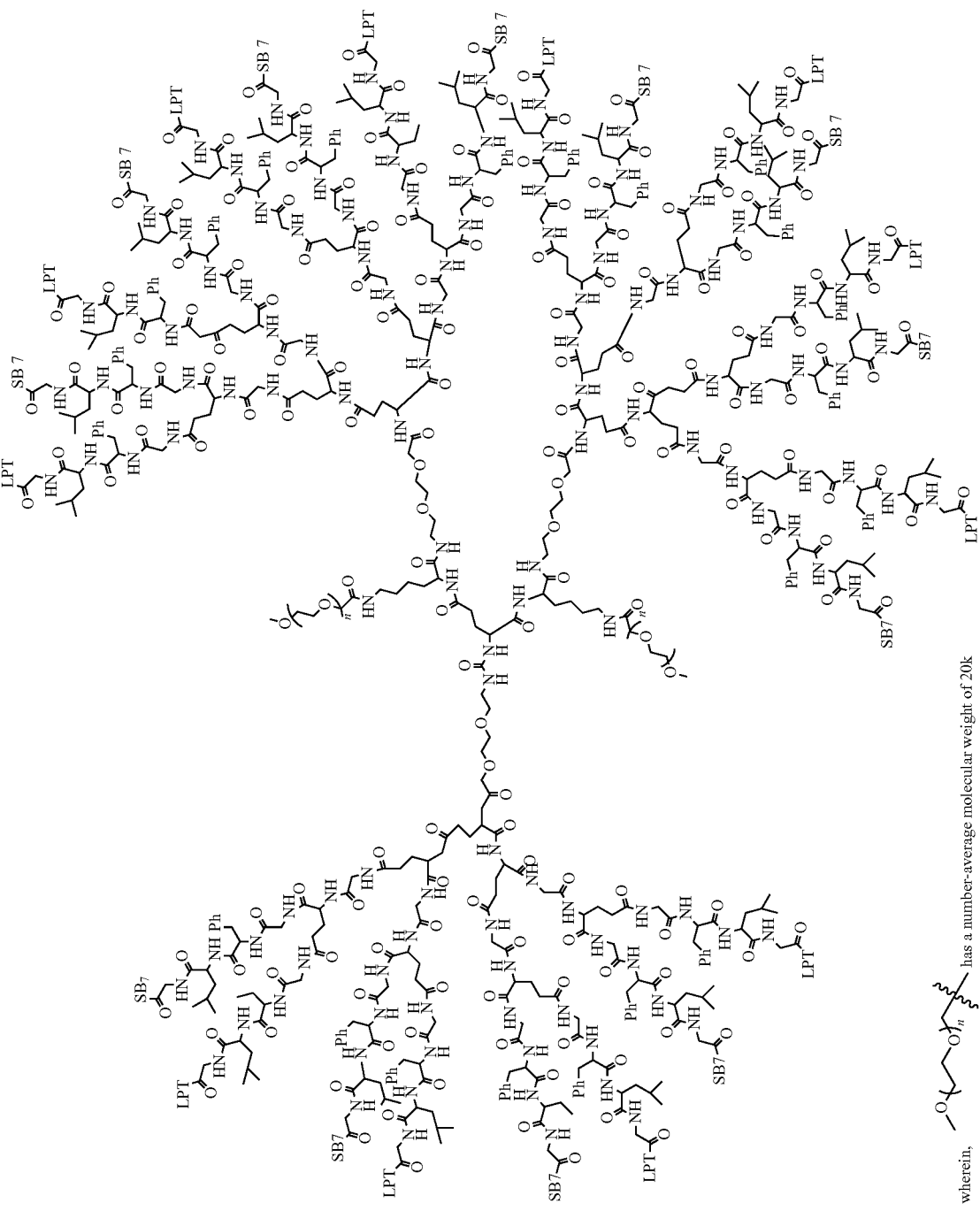
wherein, ～[O⁀]ₙ～ has a number-average molecular weight of 20k

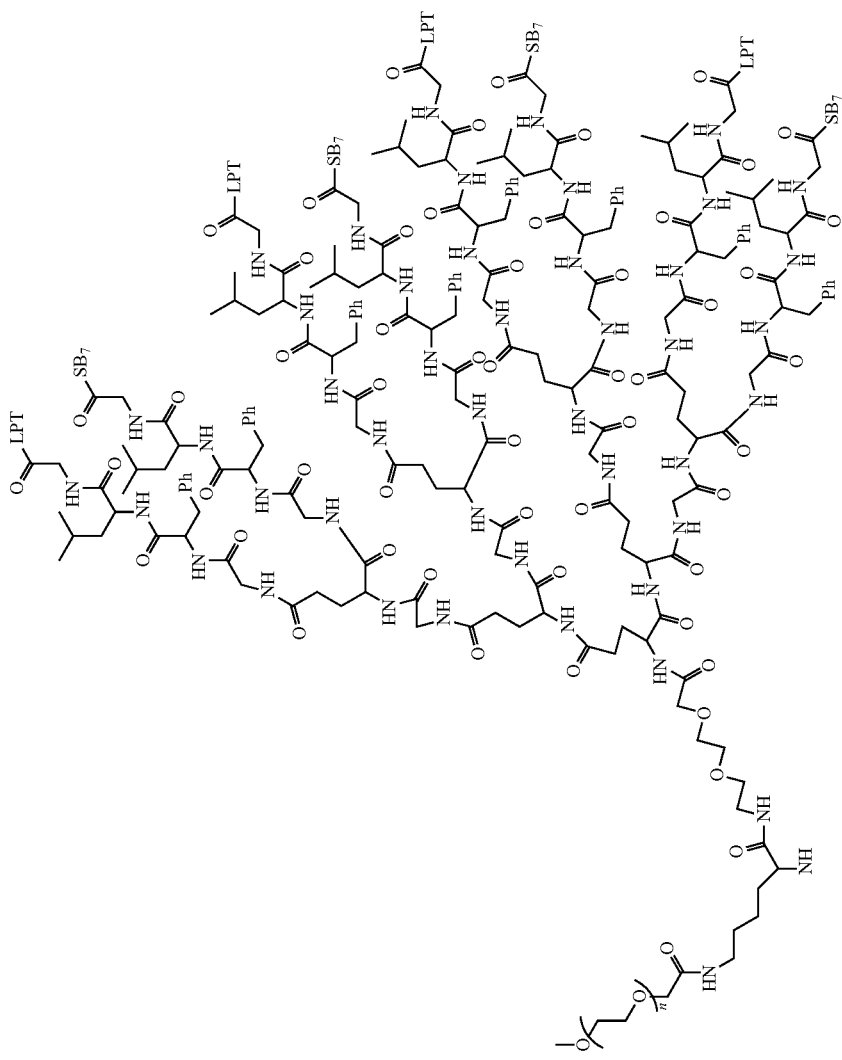

-continued
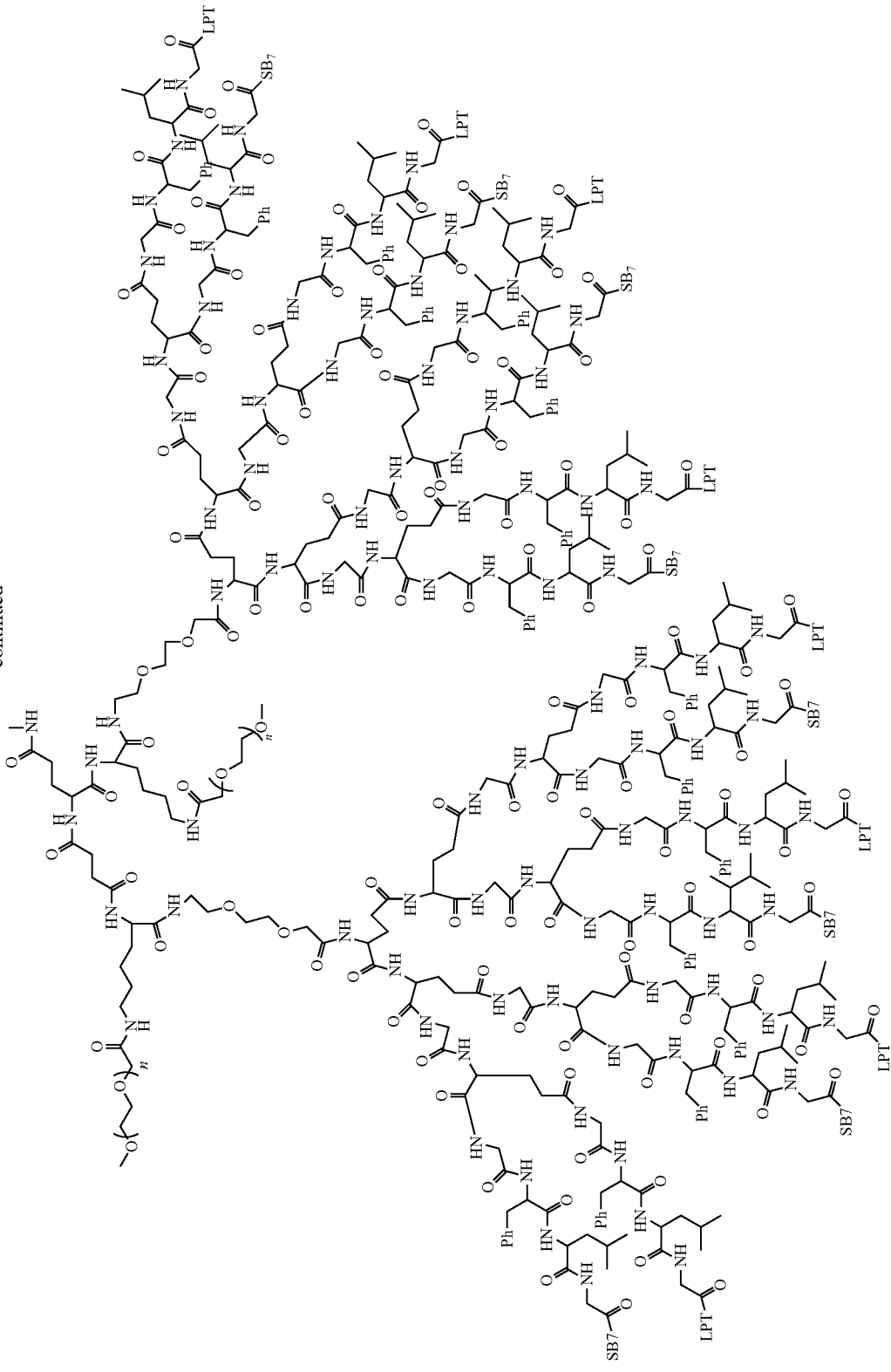
wherein,  has a number-average molecular weight of 10k

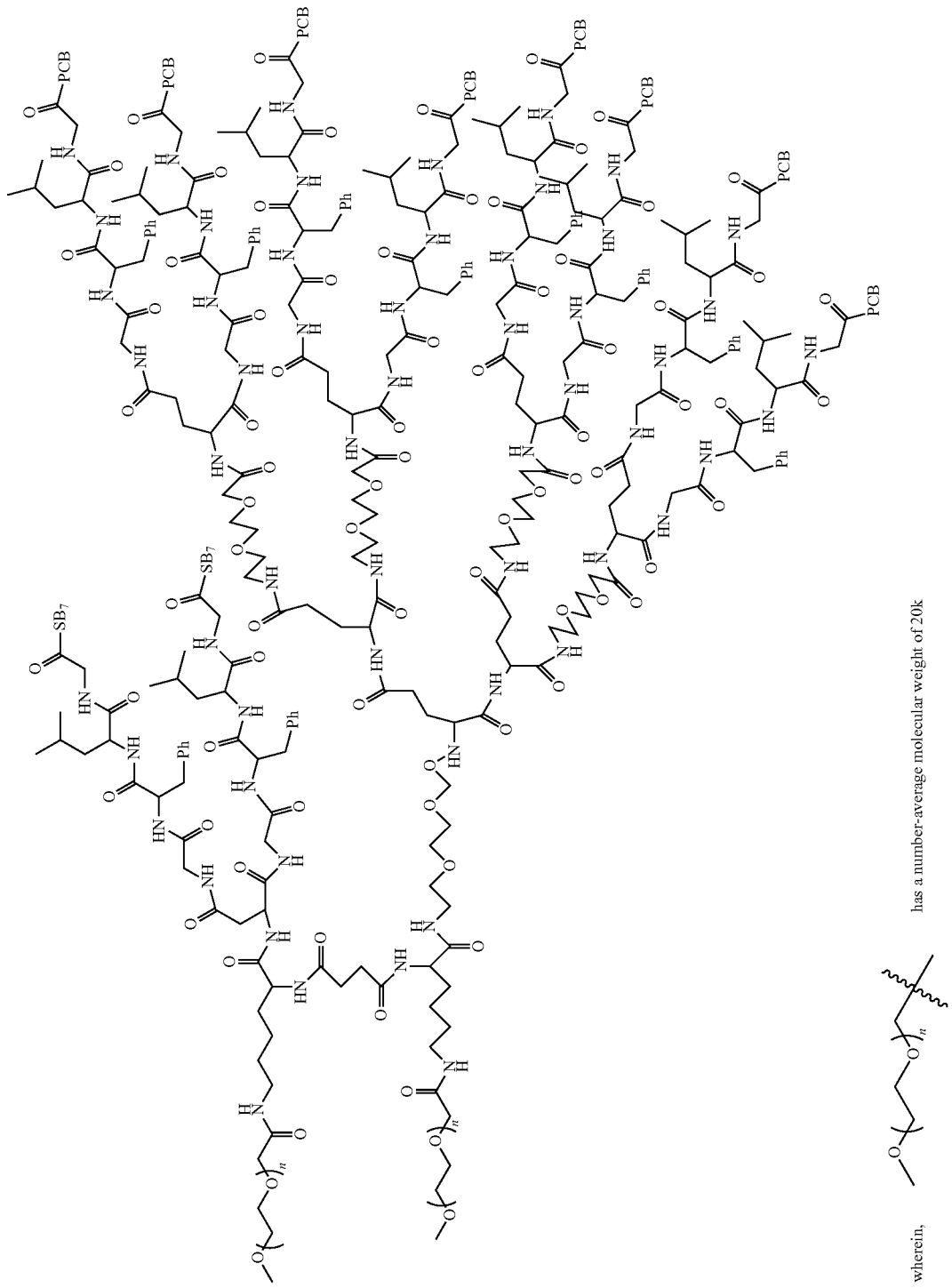
wherein, has a number-average molecular weight of 20k

-continued
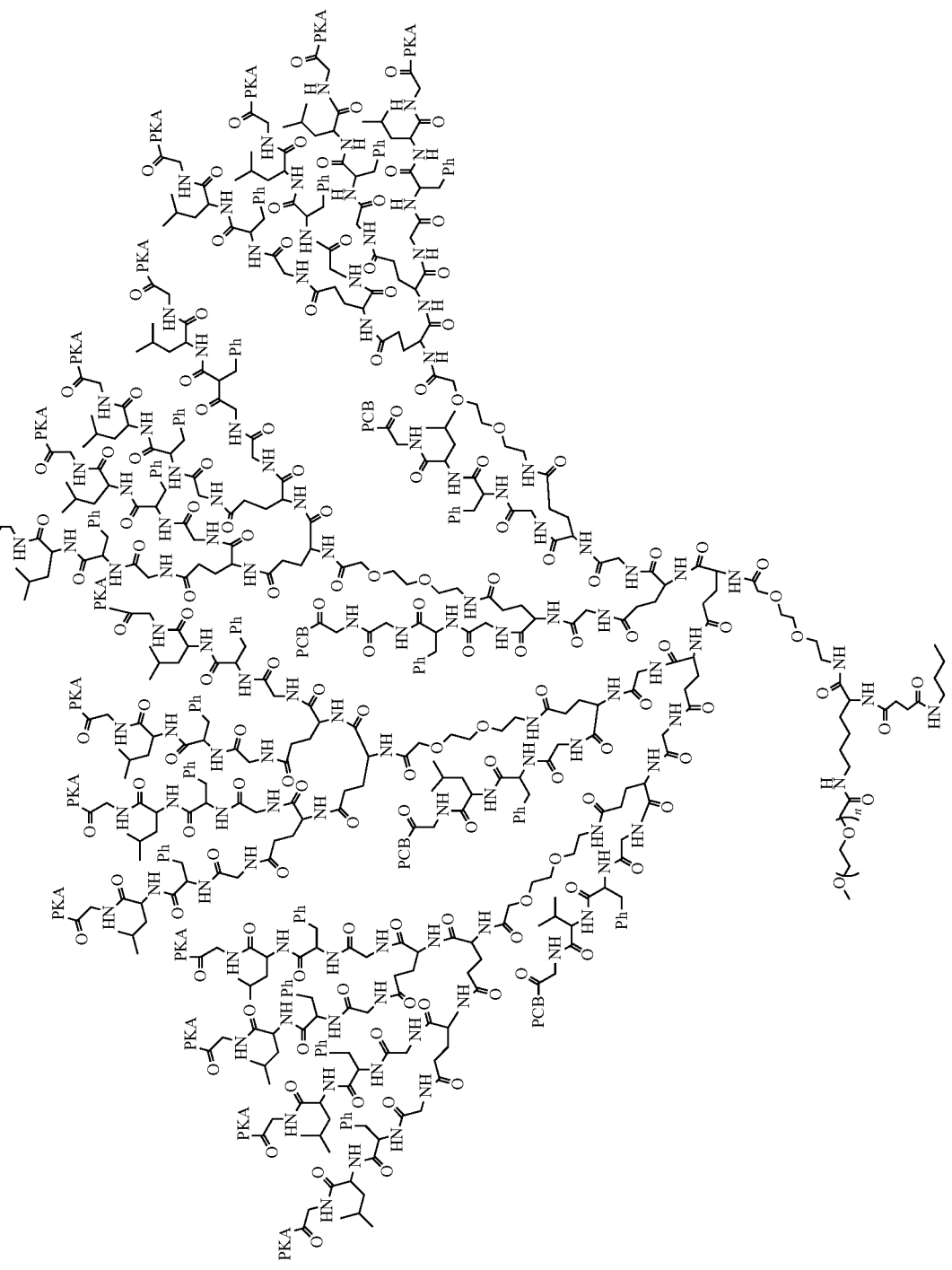

-continued
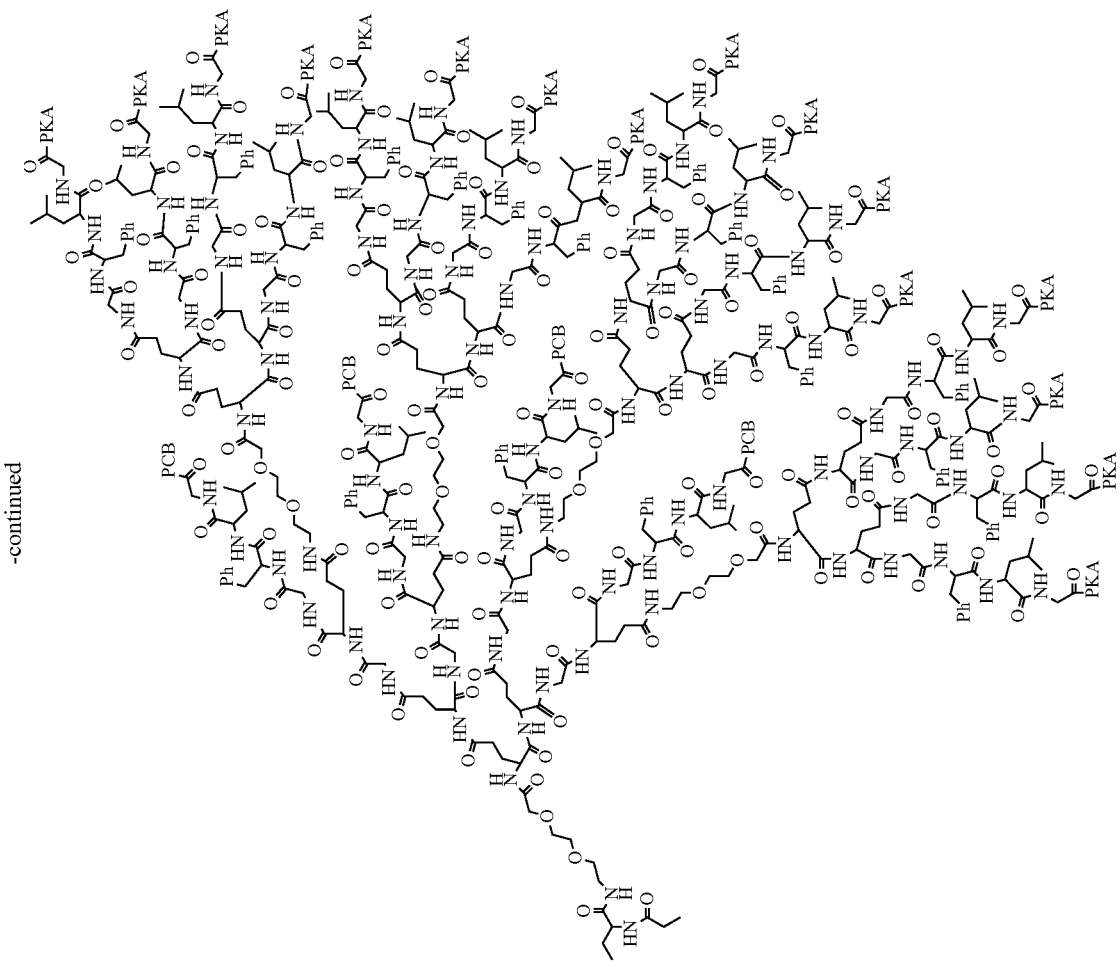

-continued
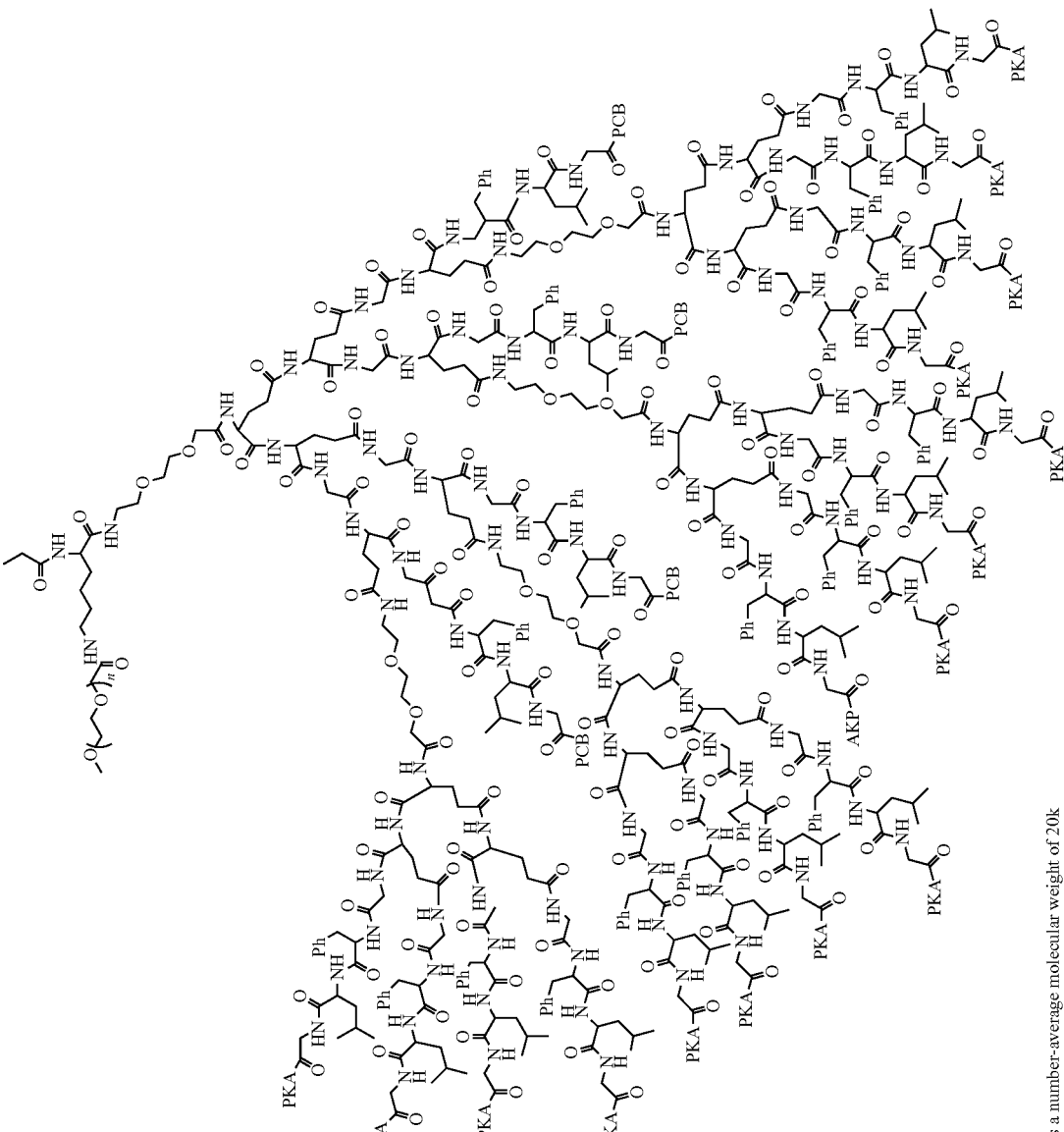
wherein, ⌇⌇⌇O⟨O⟩ₙ has a number-average molecular weight of 20k -continued
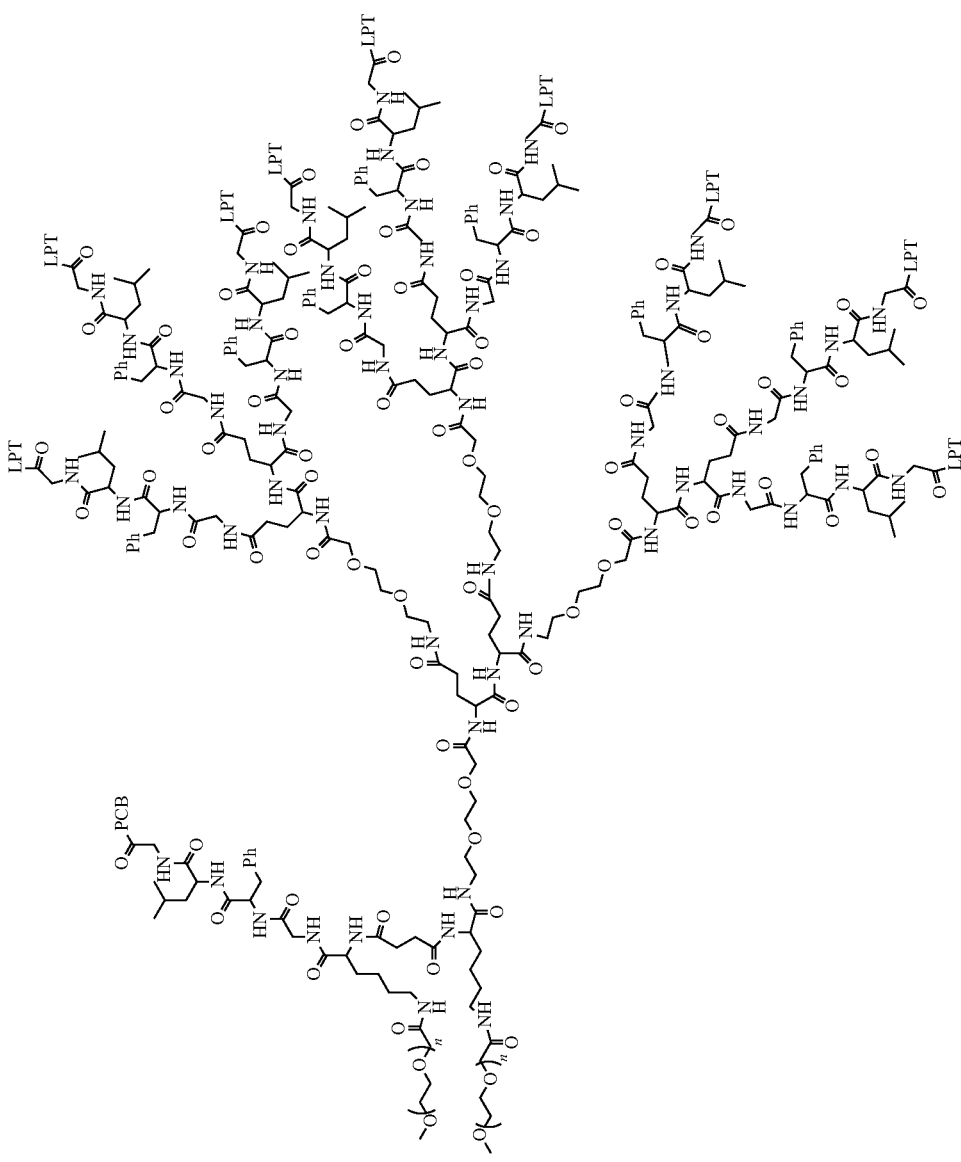
wherein,  has a number-average molecular weight of 20k

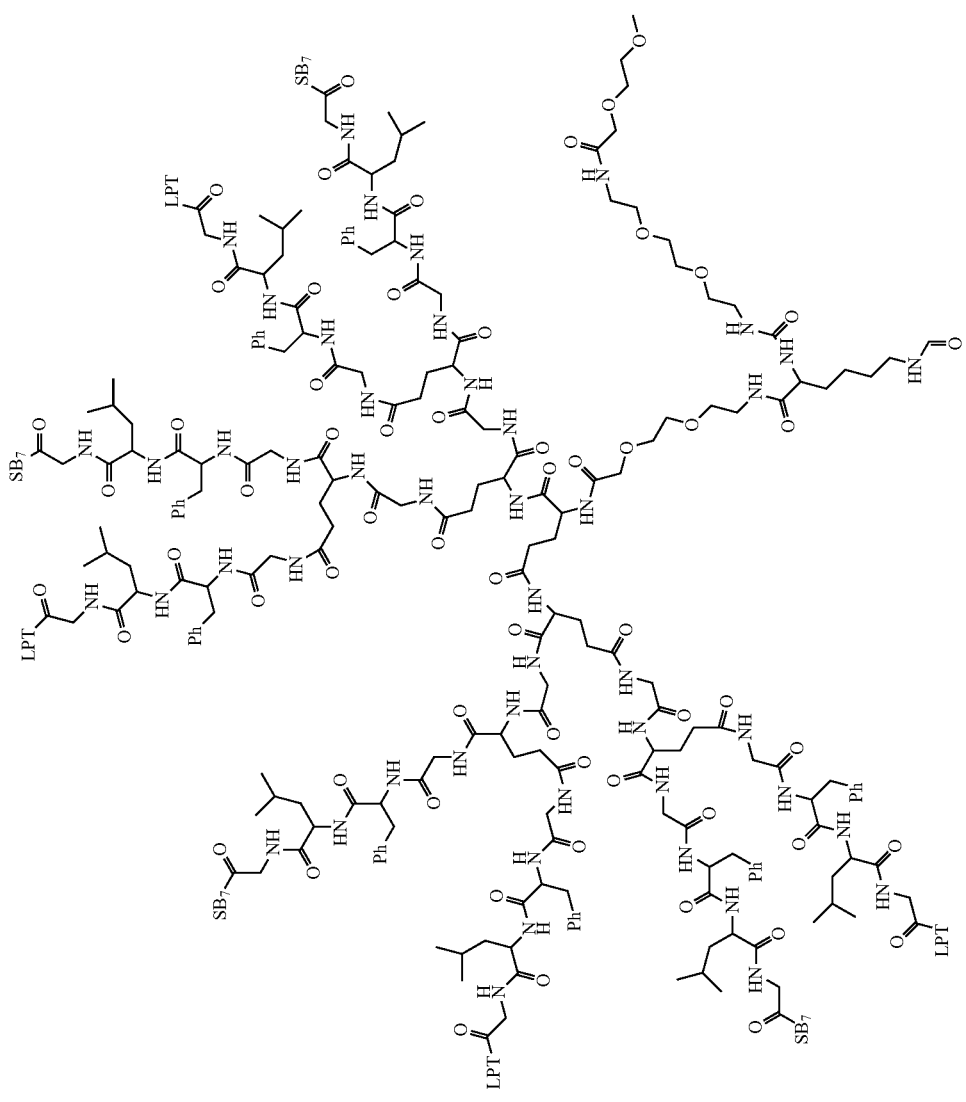

-continued
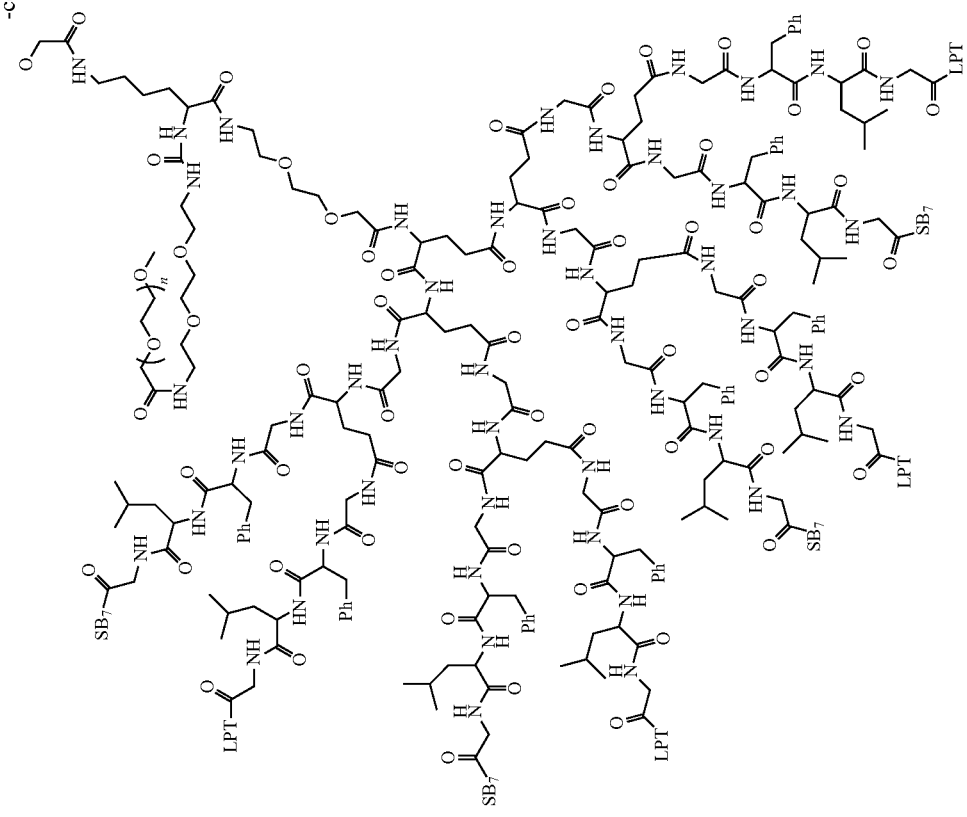

-continued
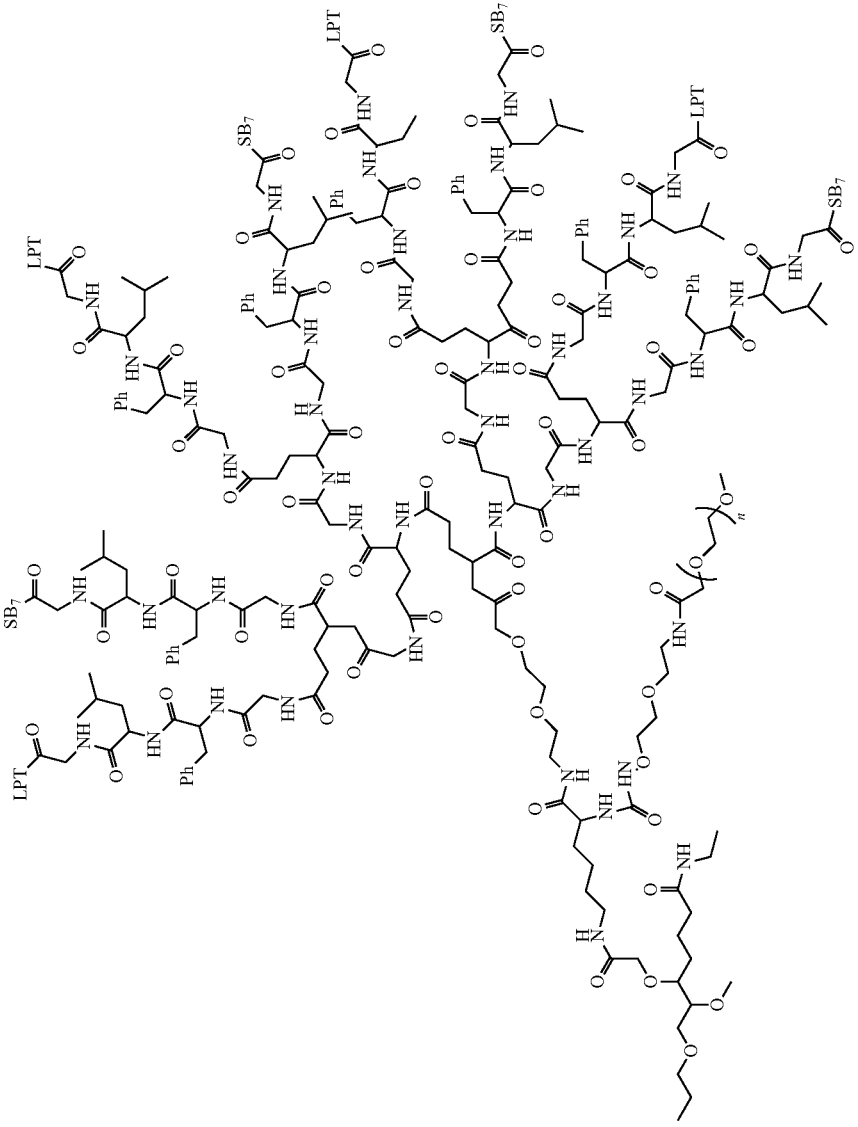

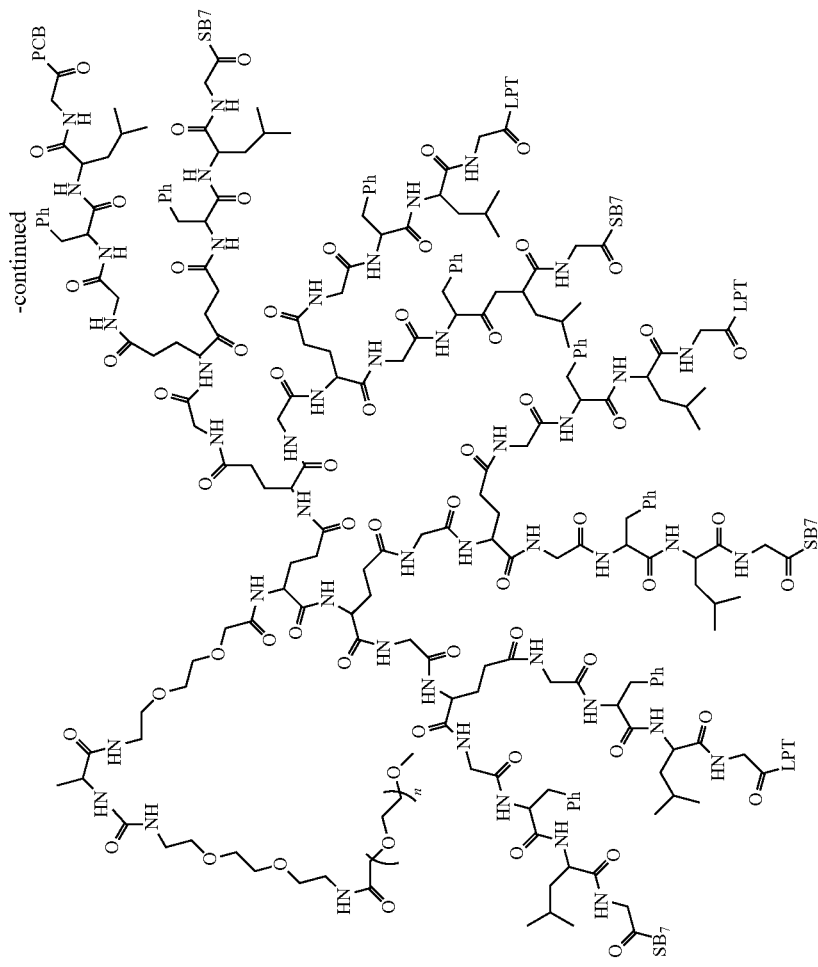

-continued
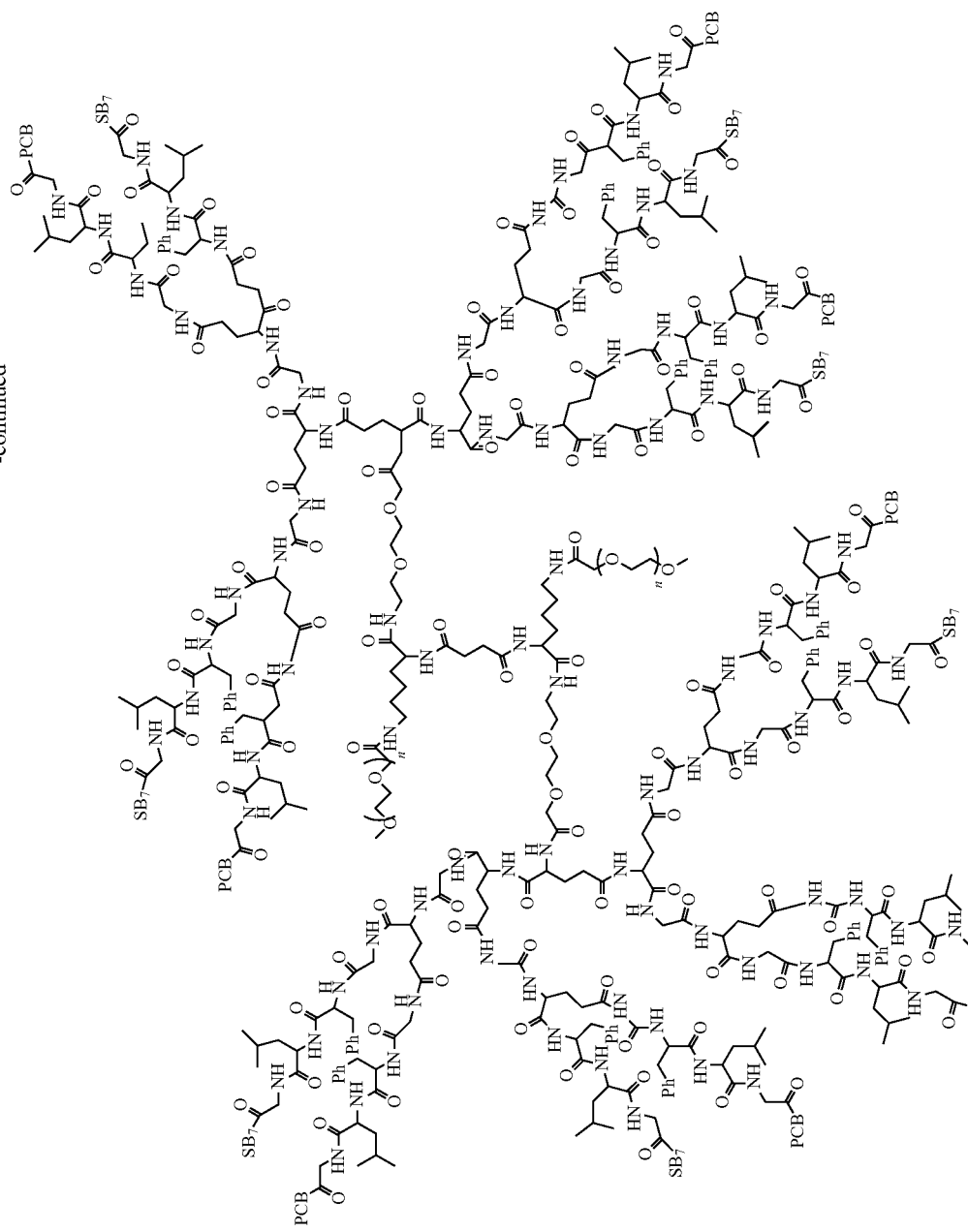
wherein, —O\[O\]ₙ has a number-average molecular weight of 20k

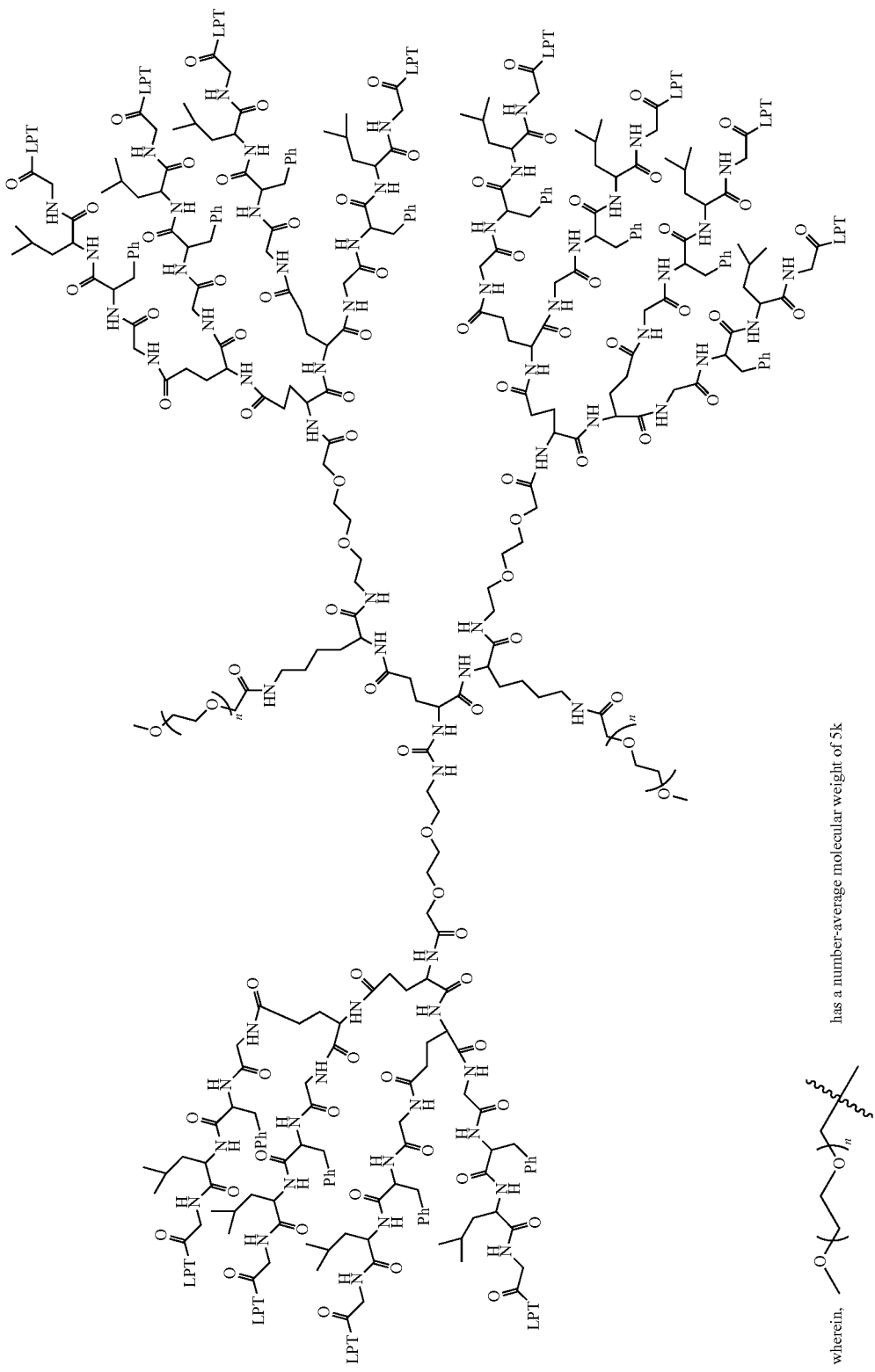

-continued
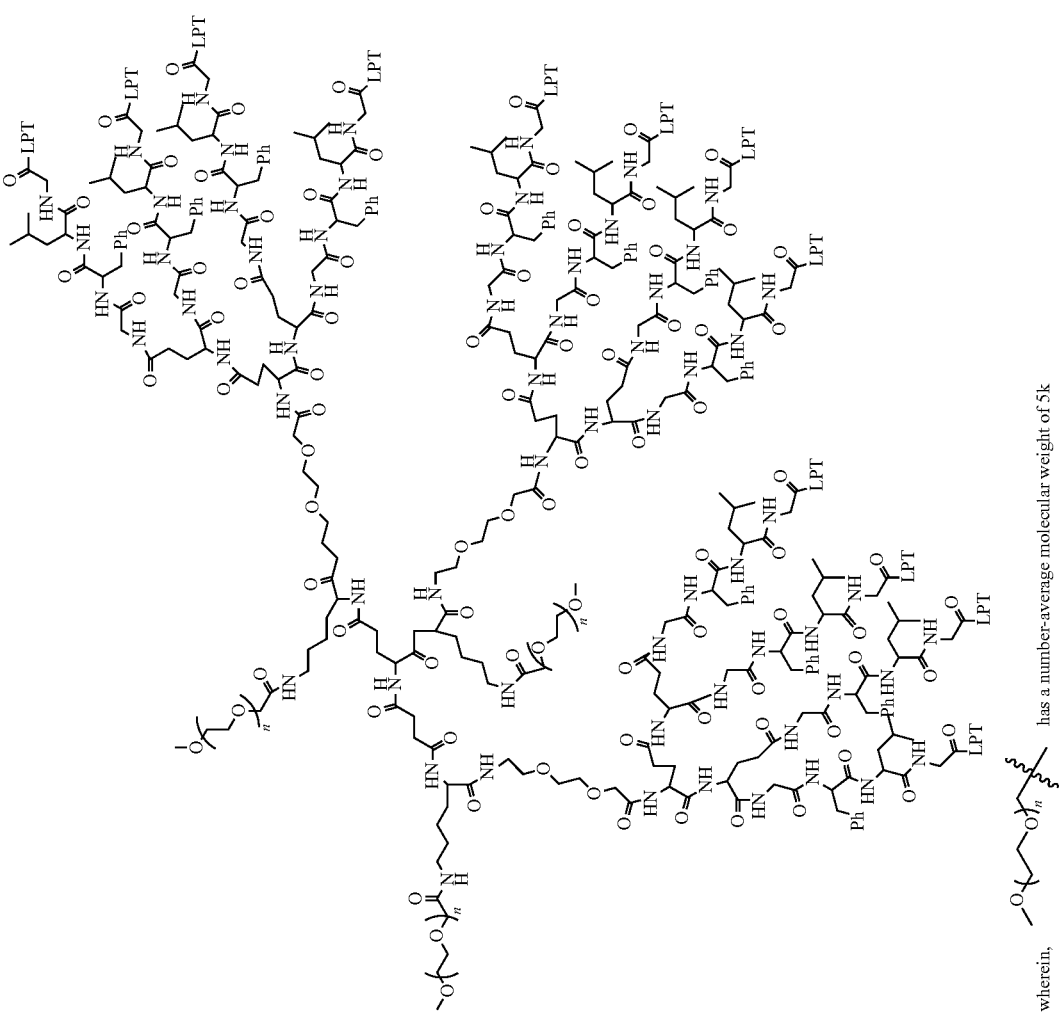
wherein, has a number-average molecular weight of 5k

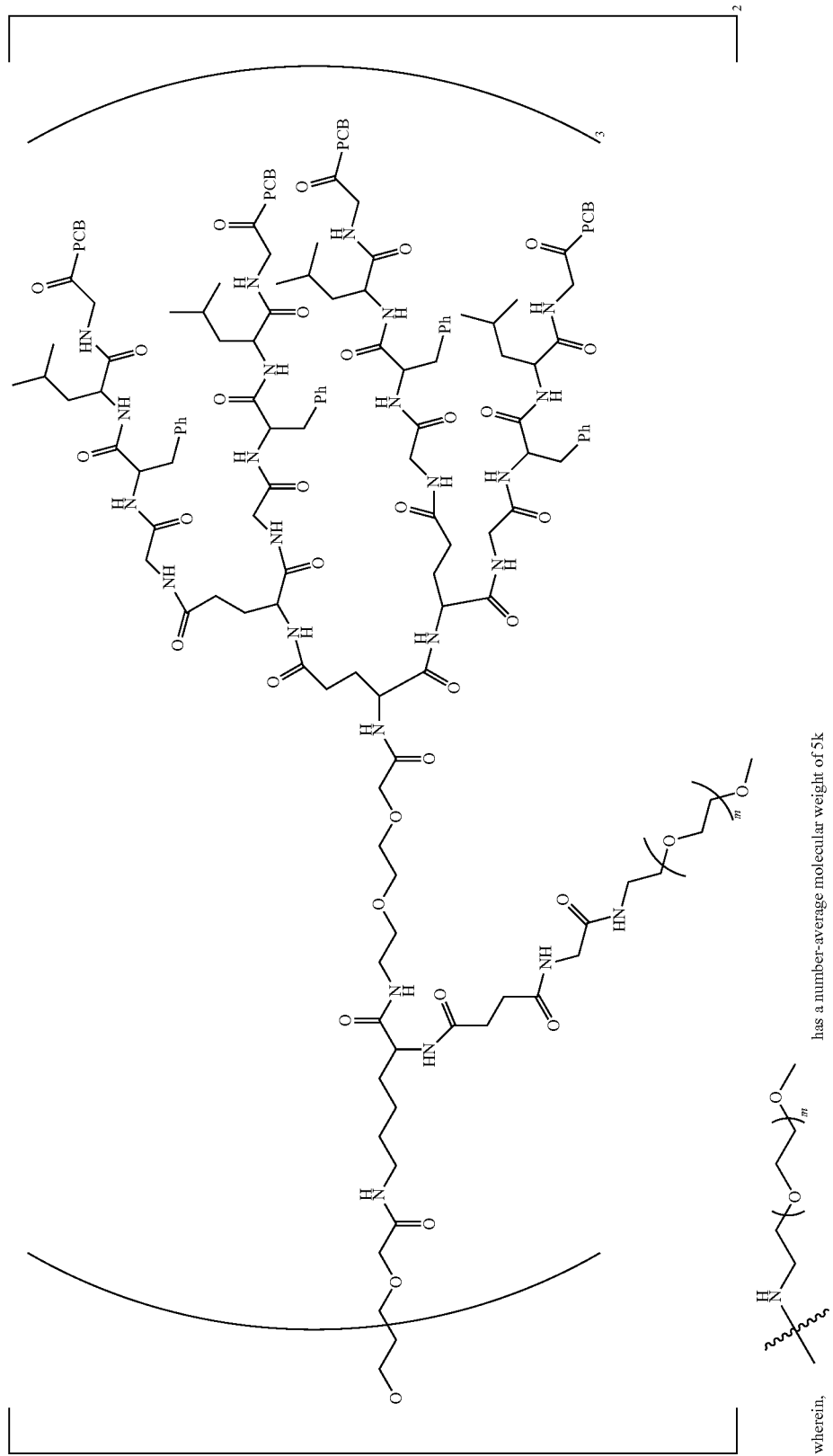
wherein,

-continued
22
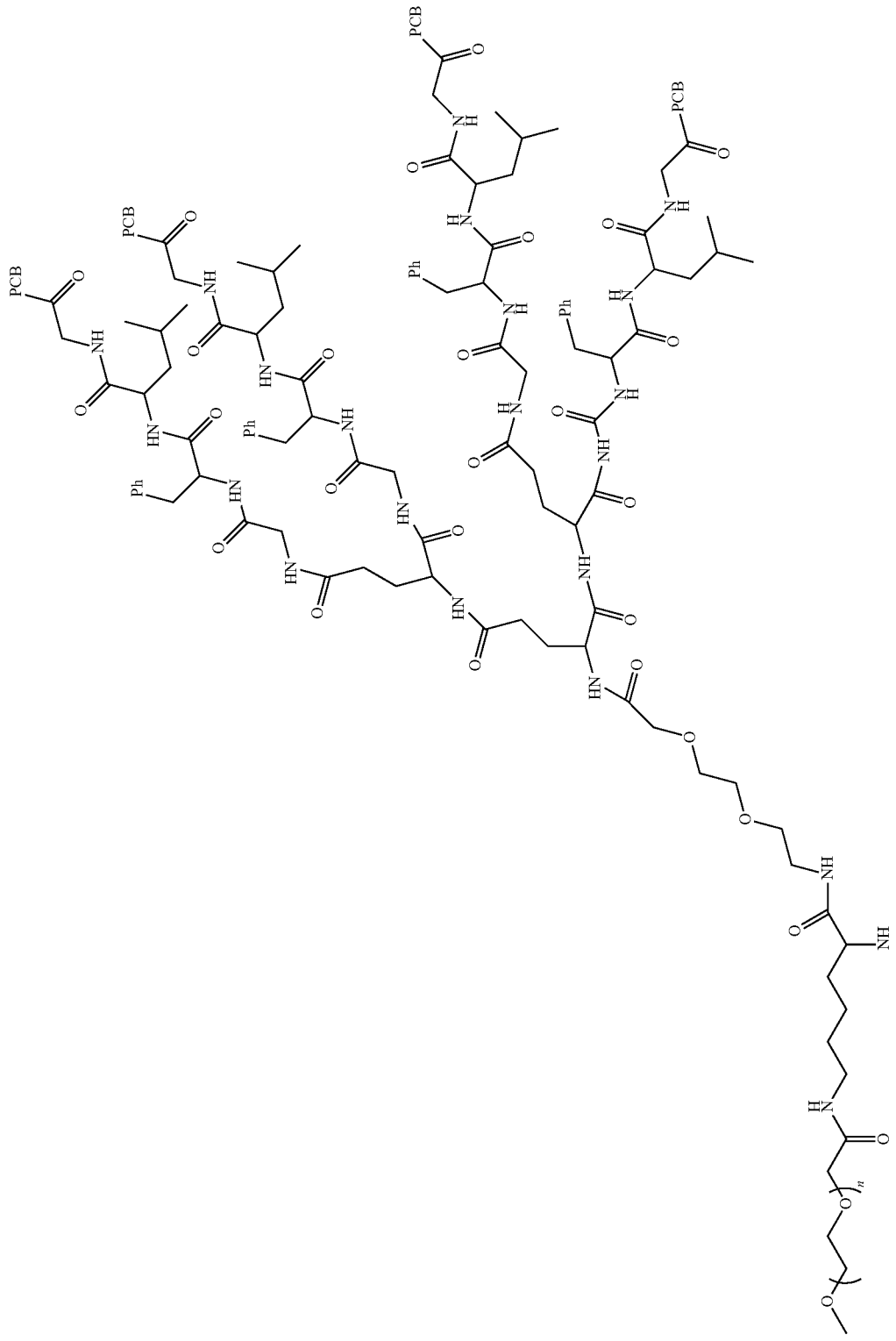

-continued
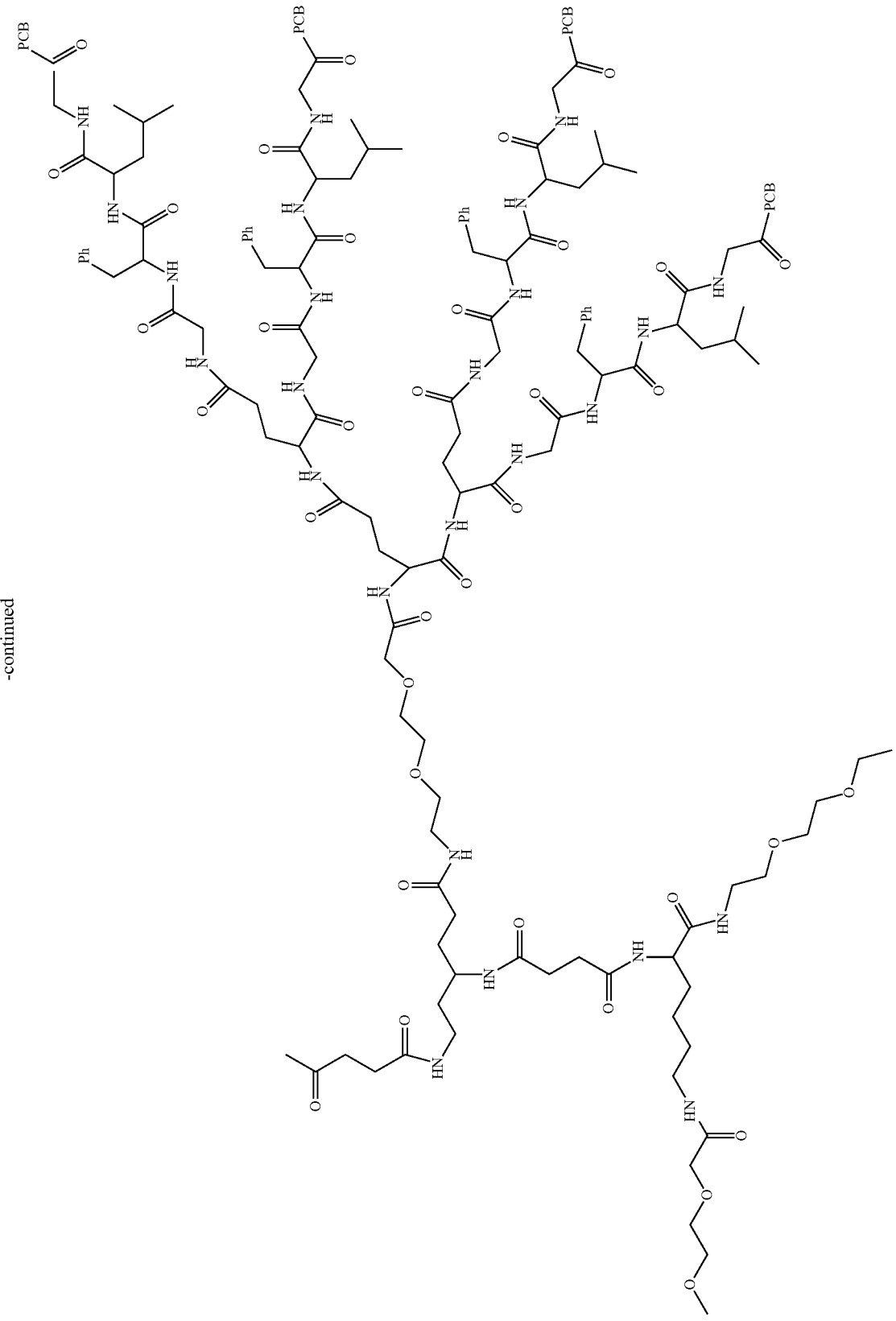

-continued
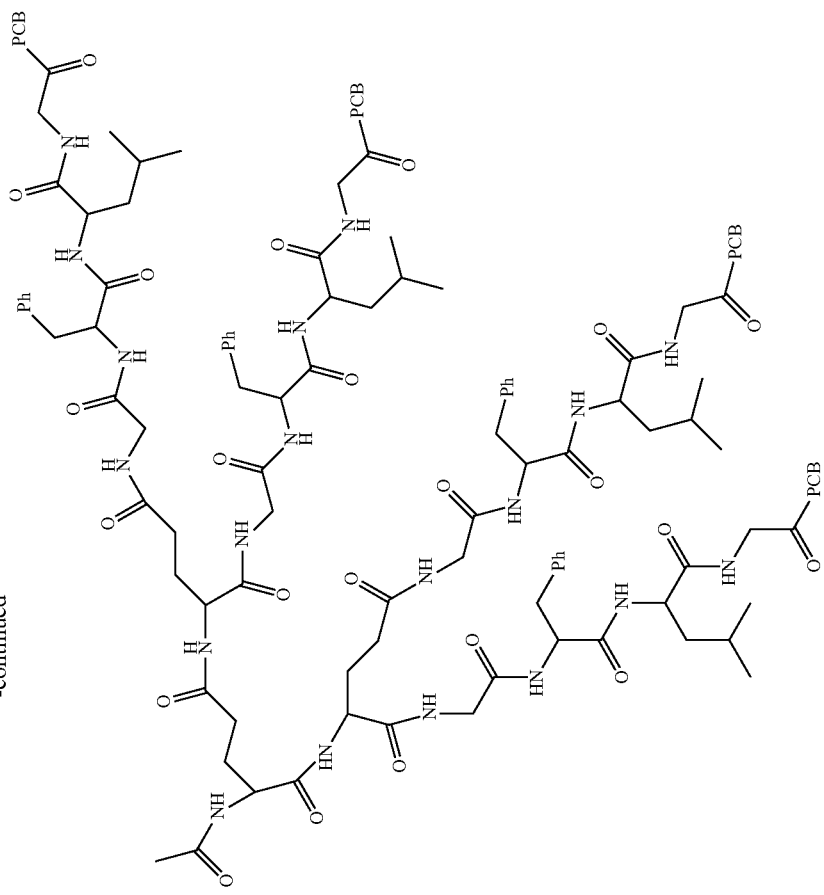
wherein, 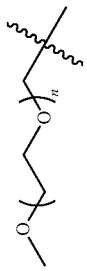 has a number-average molecular weight of 10k

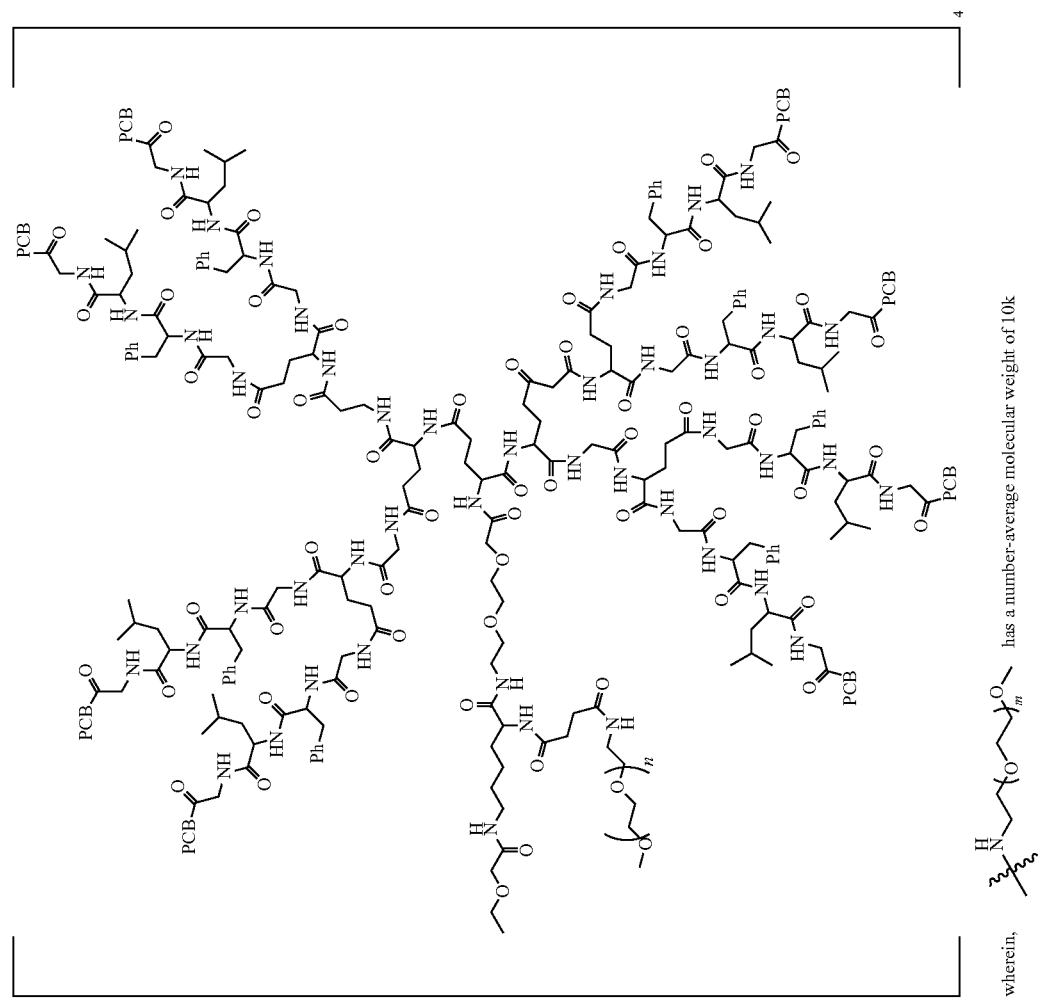

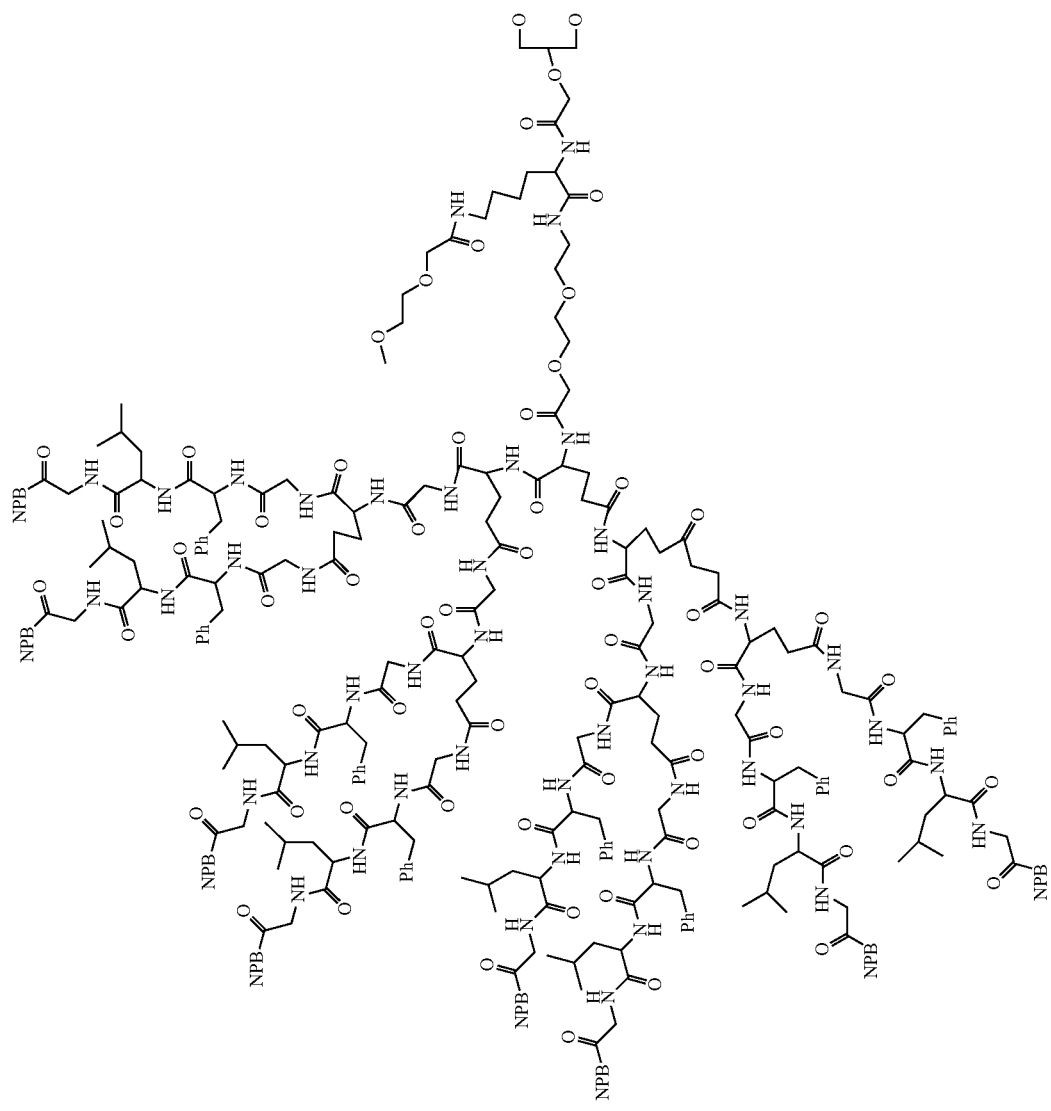

-continued
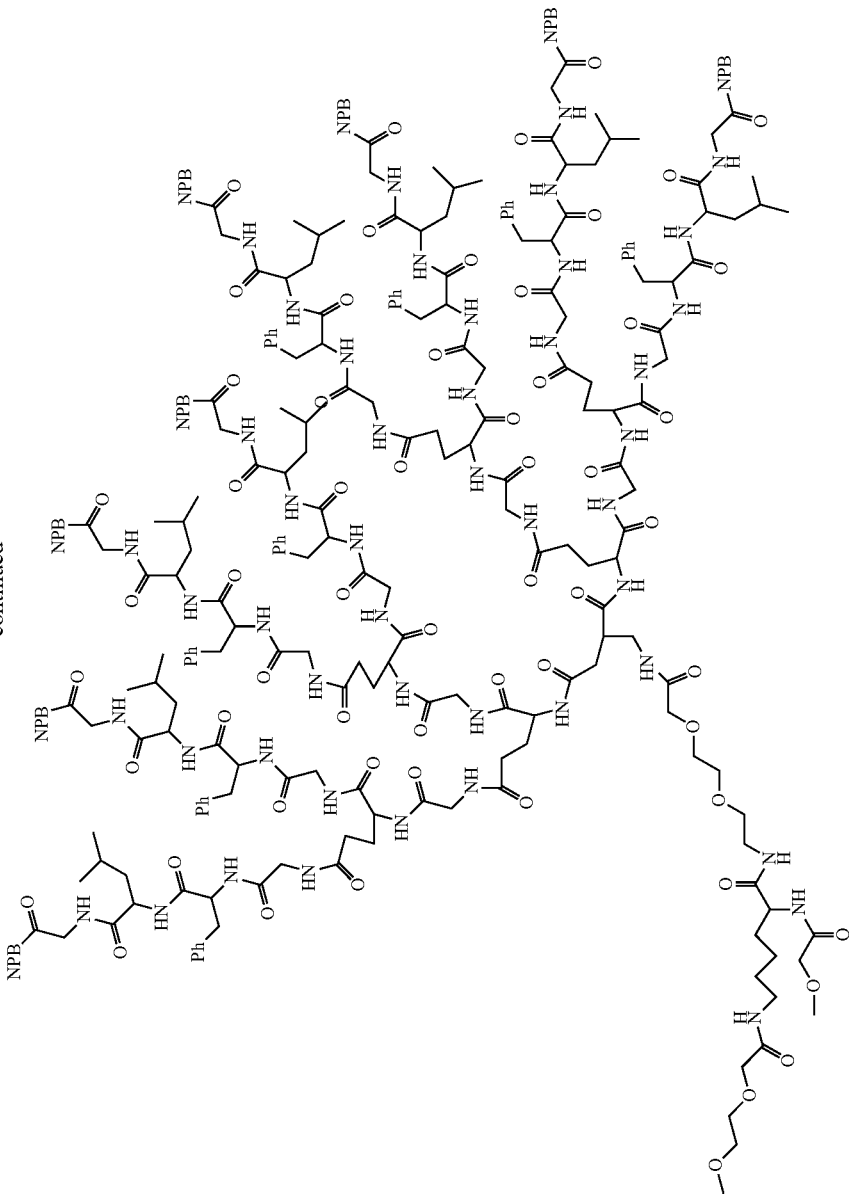

-continued
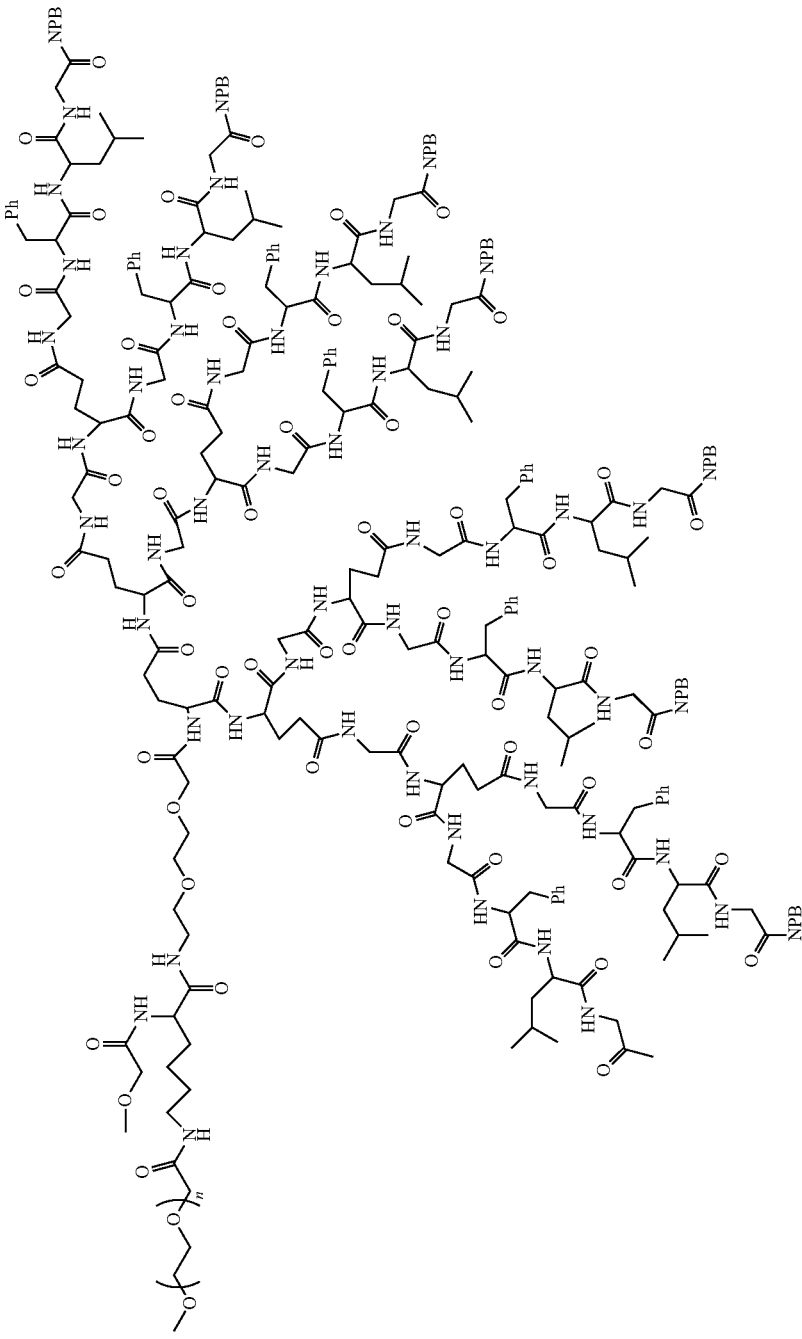
has a number-average molecular weight of 10k
wherein,

-continued
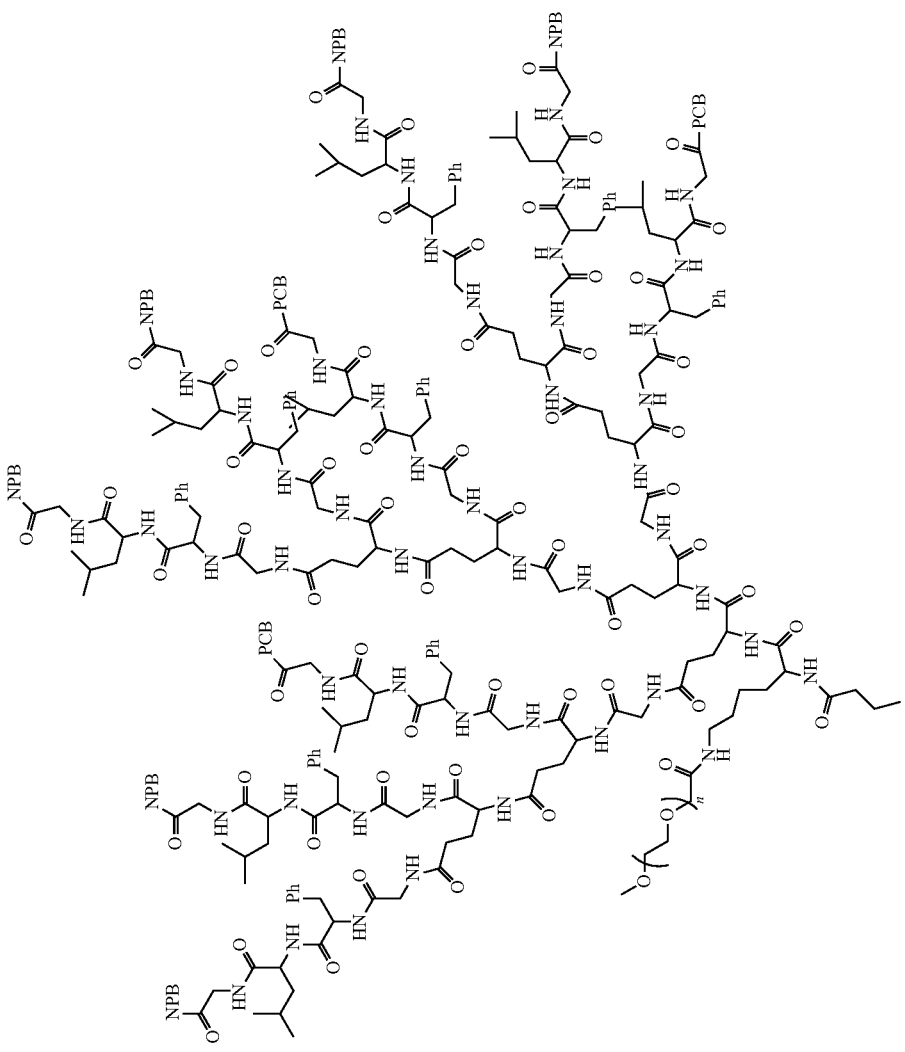

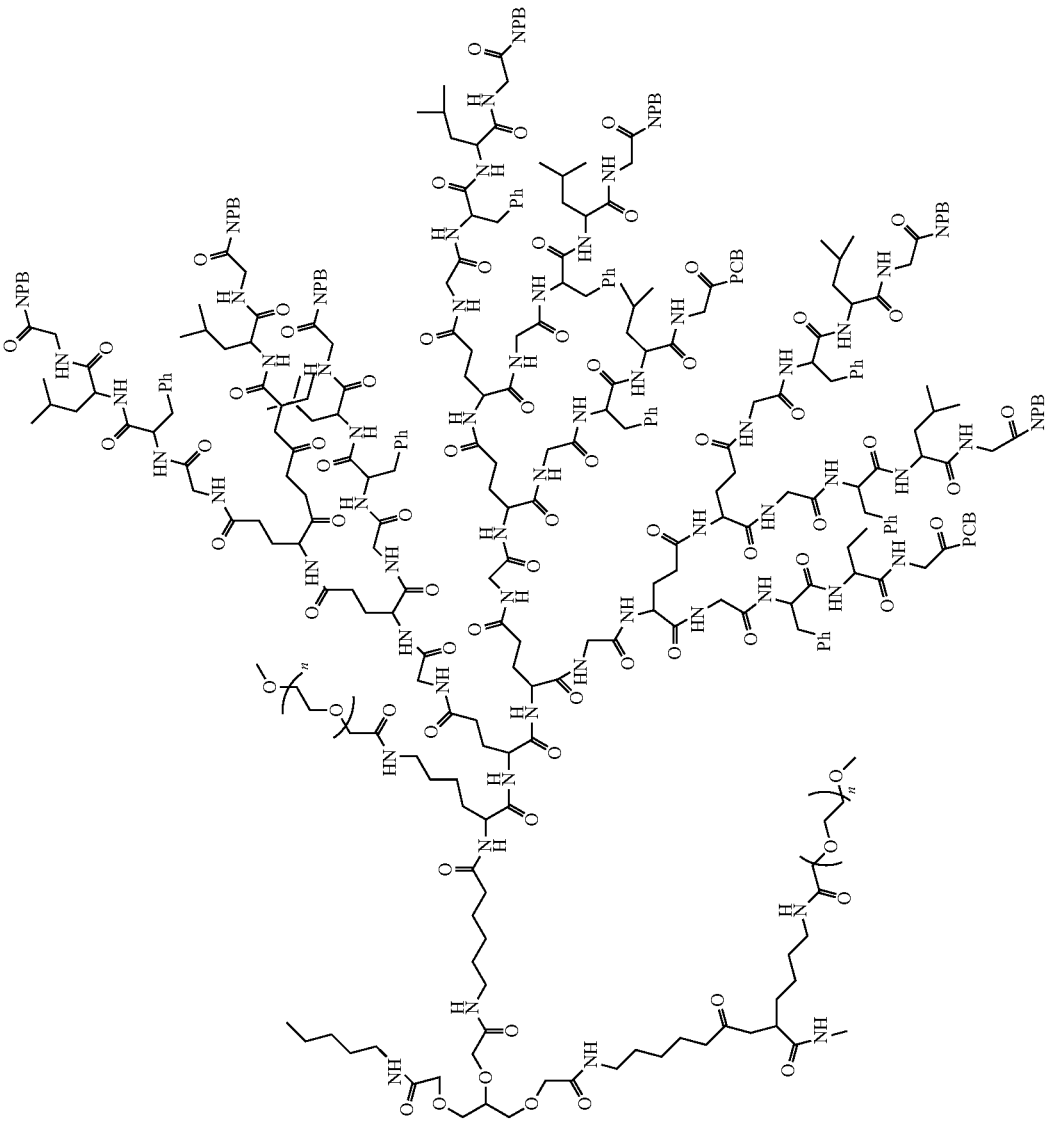

-continued
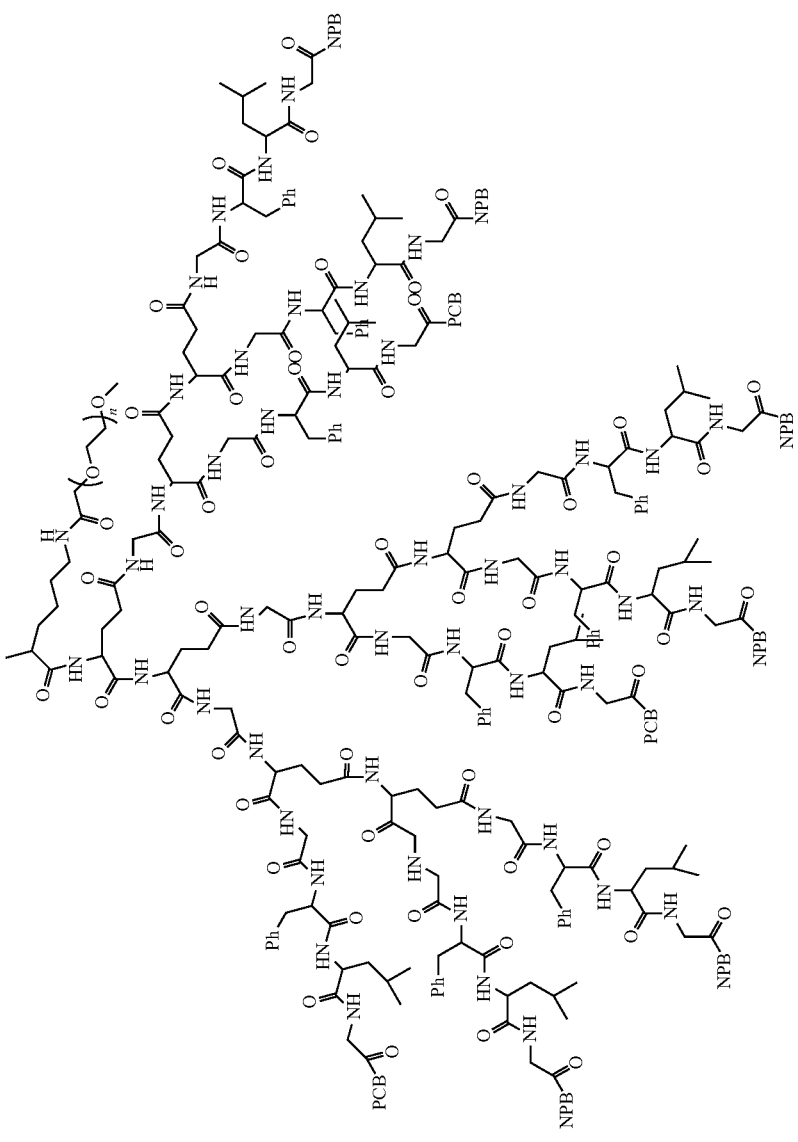
has a number-average molecular weight of 10k
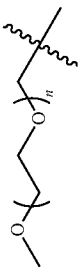
wherein, -continued
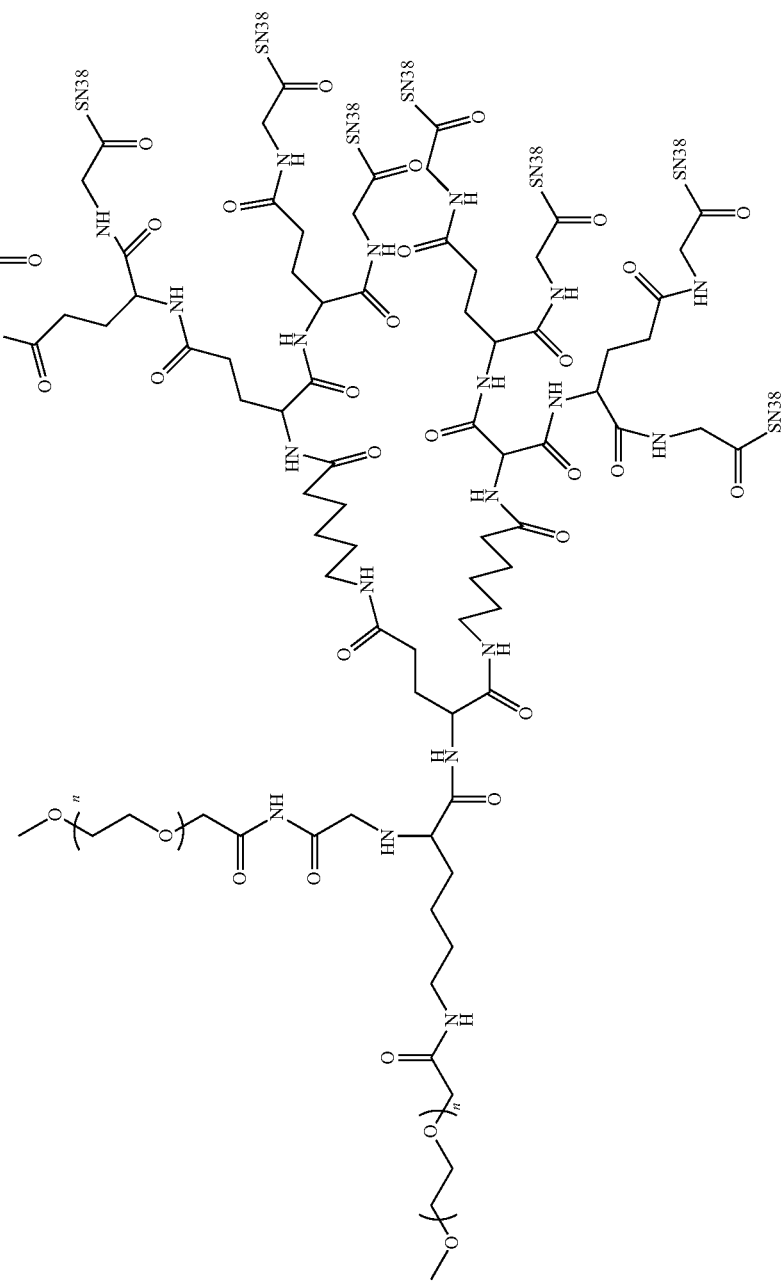
wherein,  has a number-average molecular weight of 5k -continued
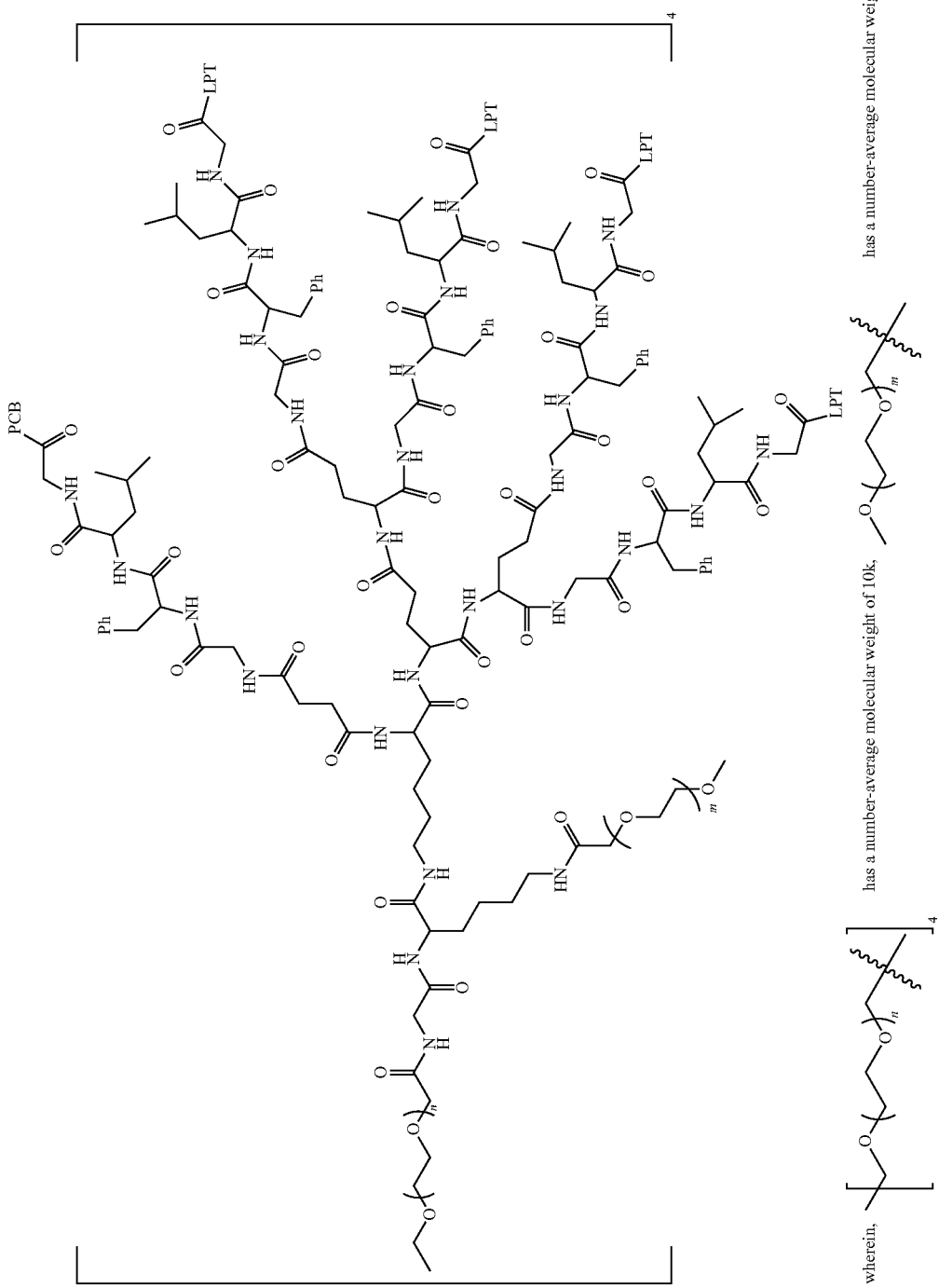
wherein, has a number-average molecular weight of 10k, has a number-average molecular weight of 5k -continued
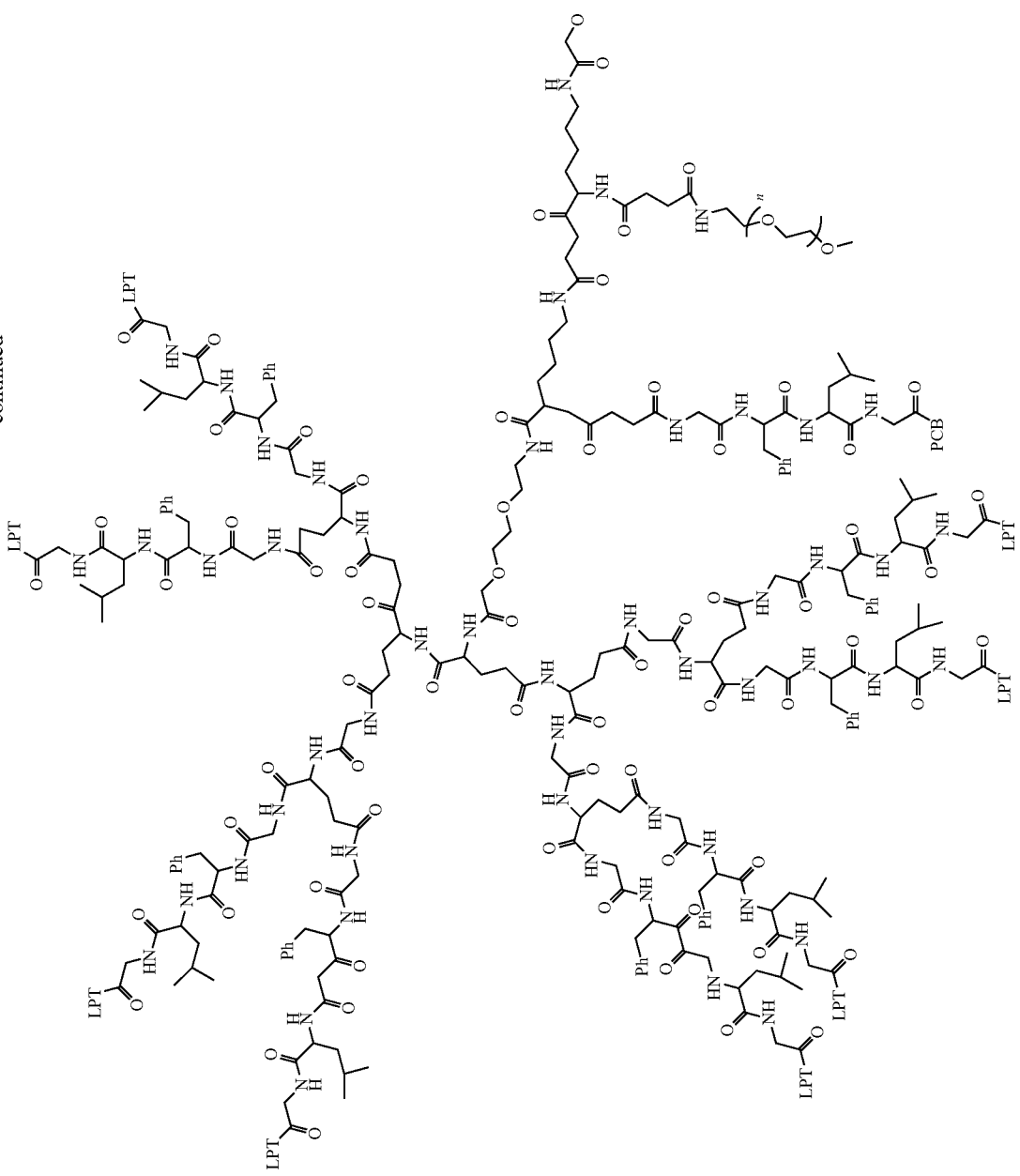

-continued
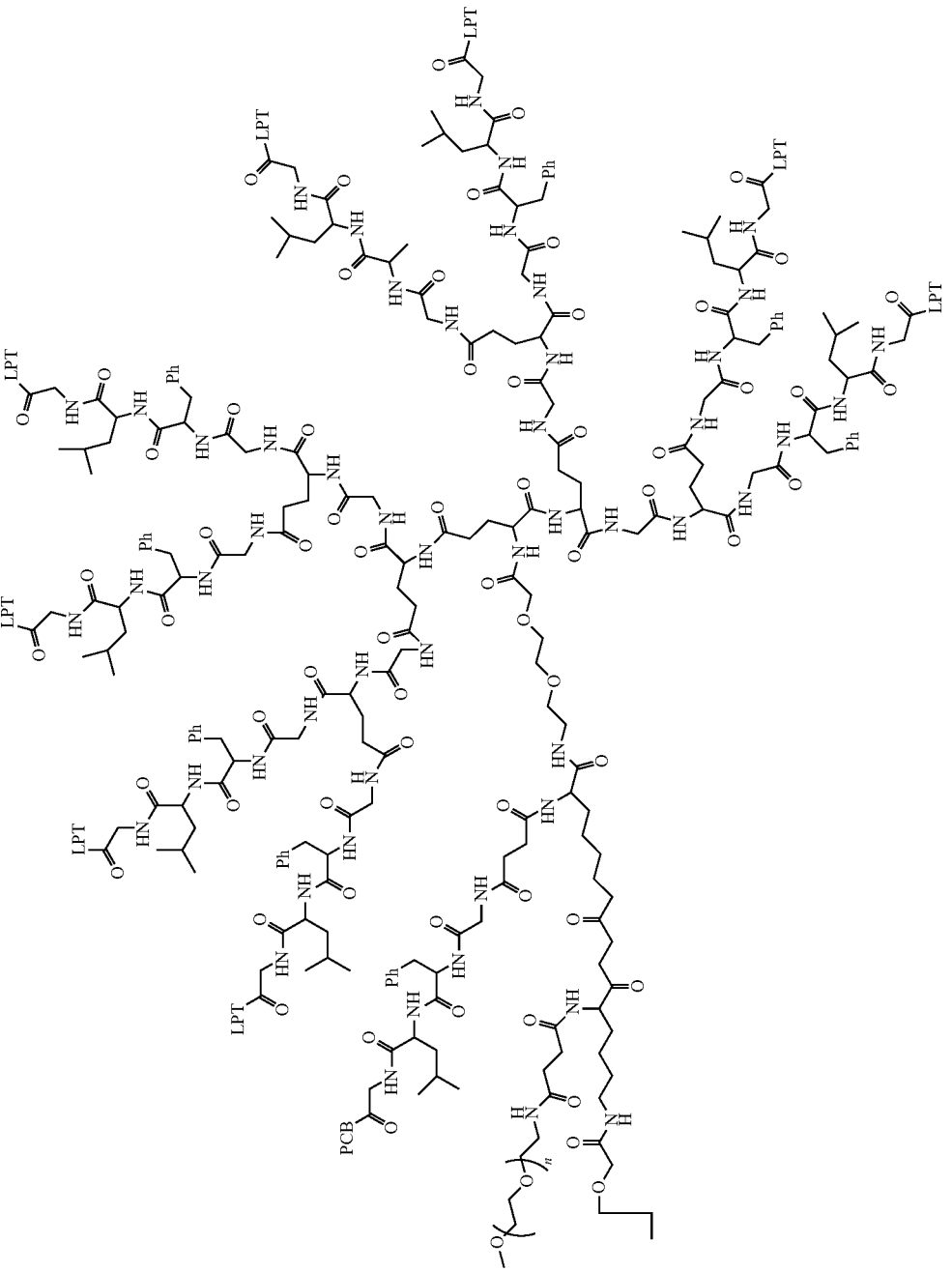

-continued
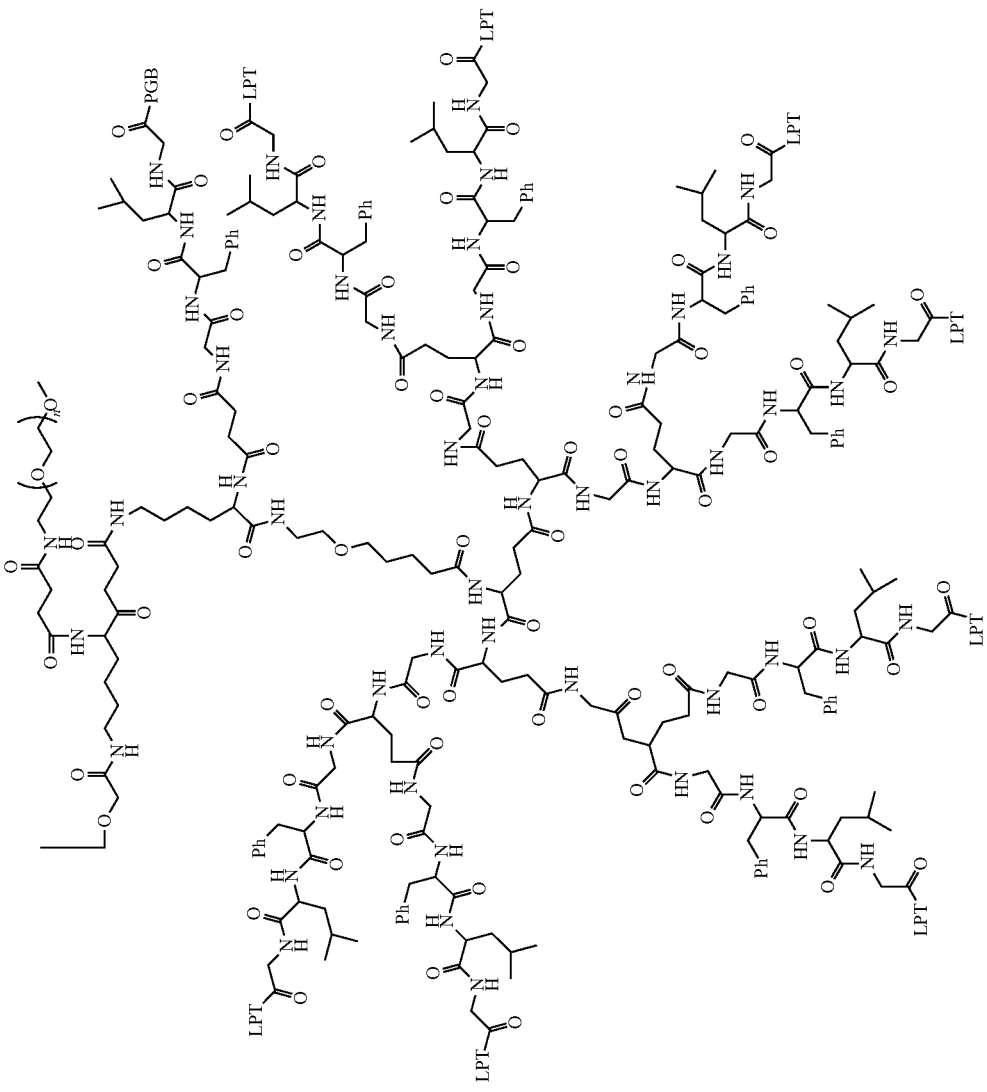
wherein,
has a number-average molecular weight of 10k

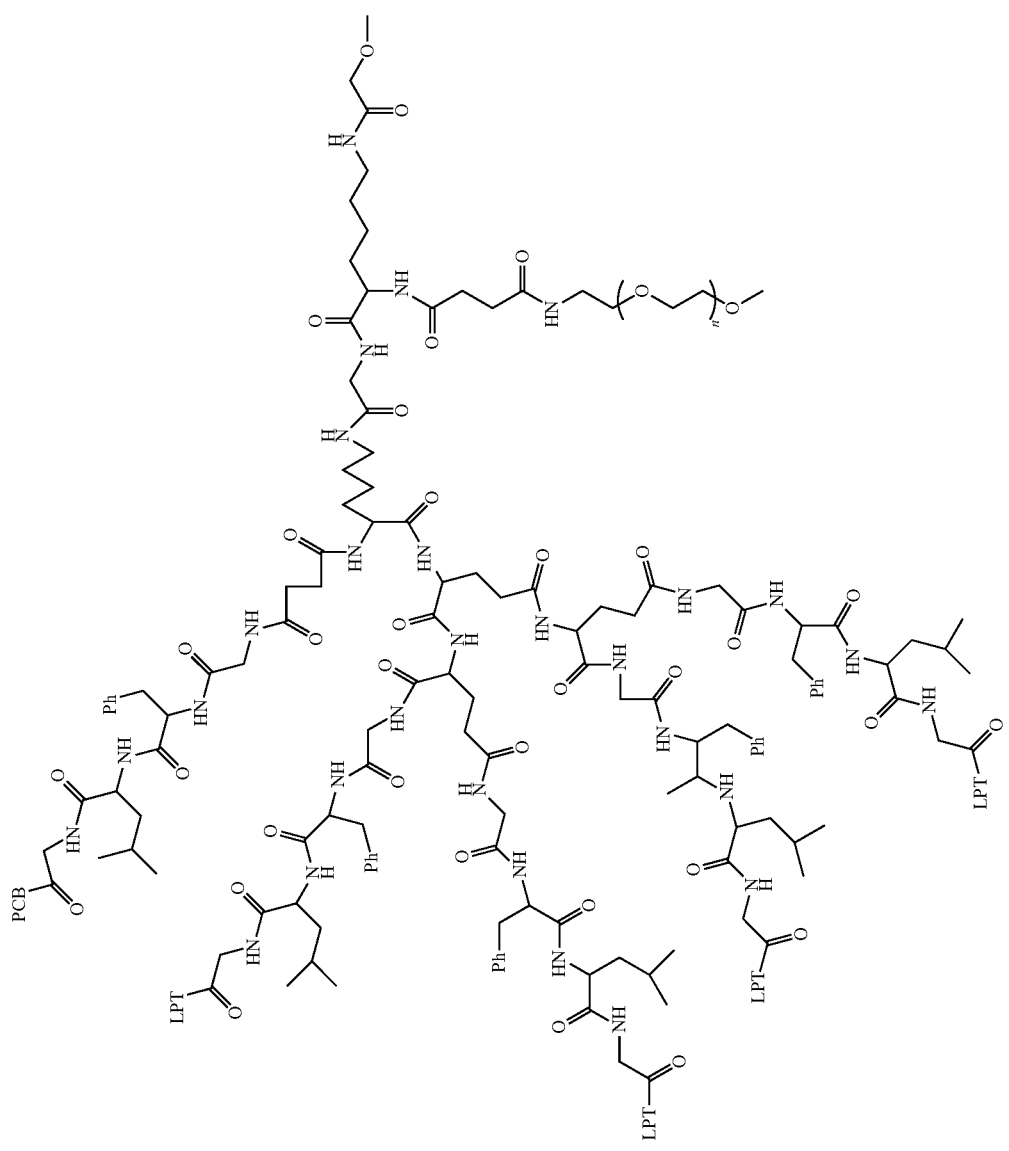

-continued
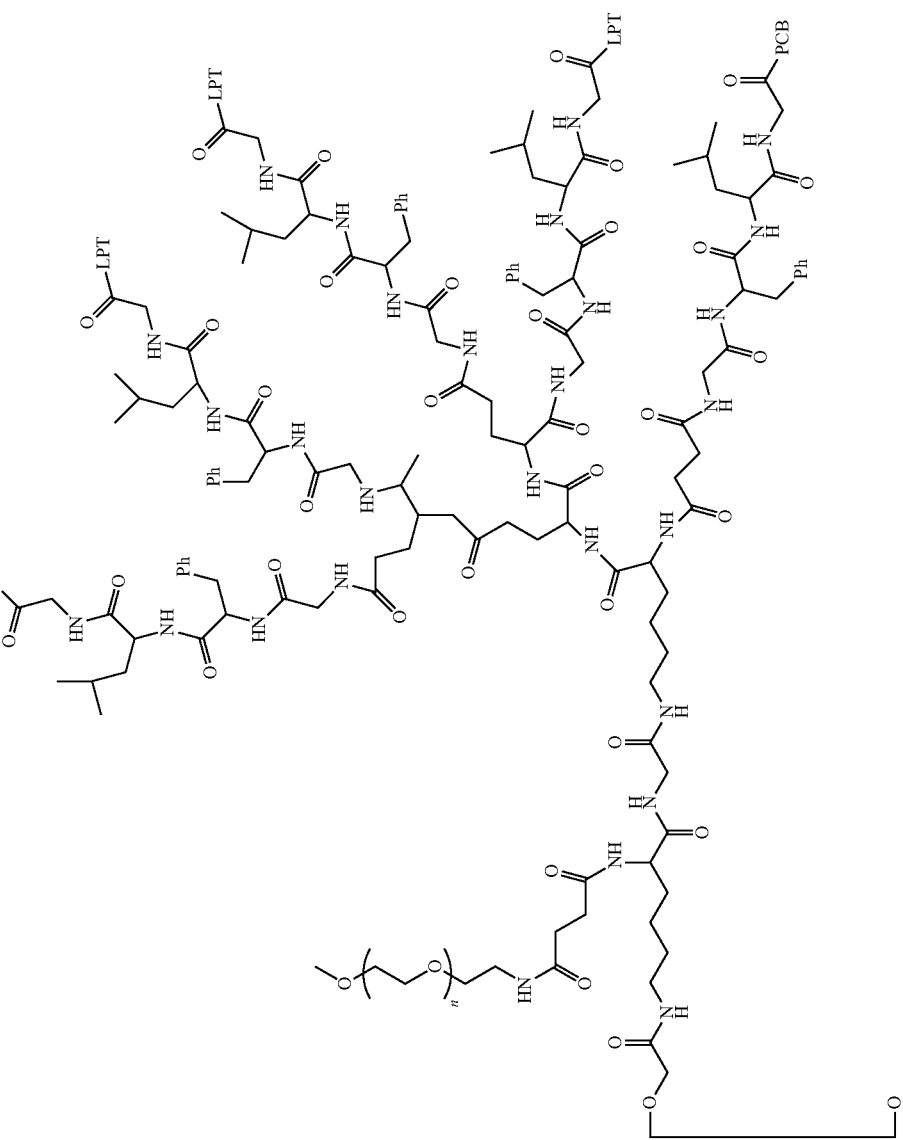

-continued
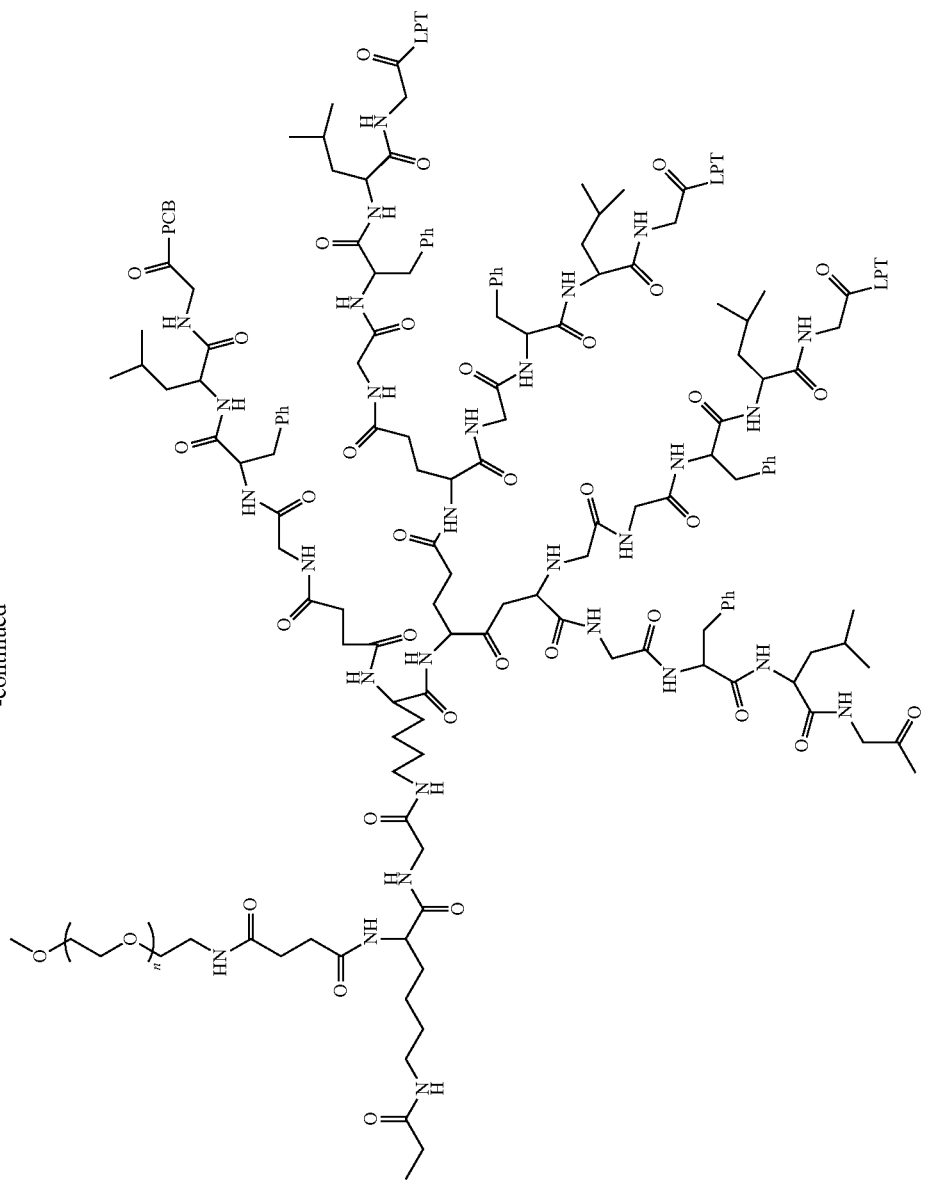
wherein,
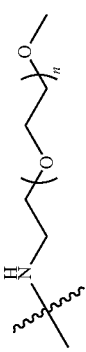
has a number-average molecular weight of 10k -continued
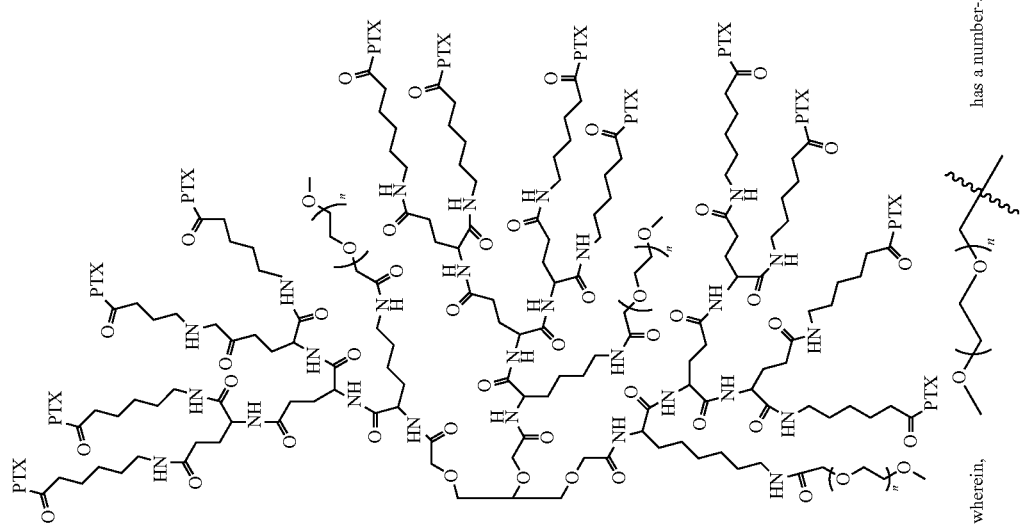
wherein,
has a number-average molecular weight of 5k

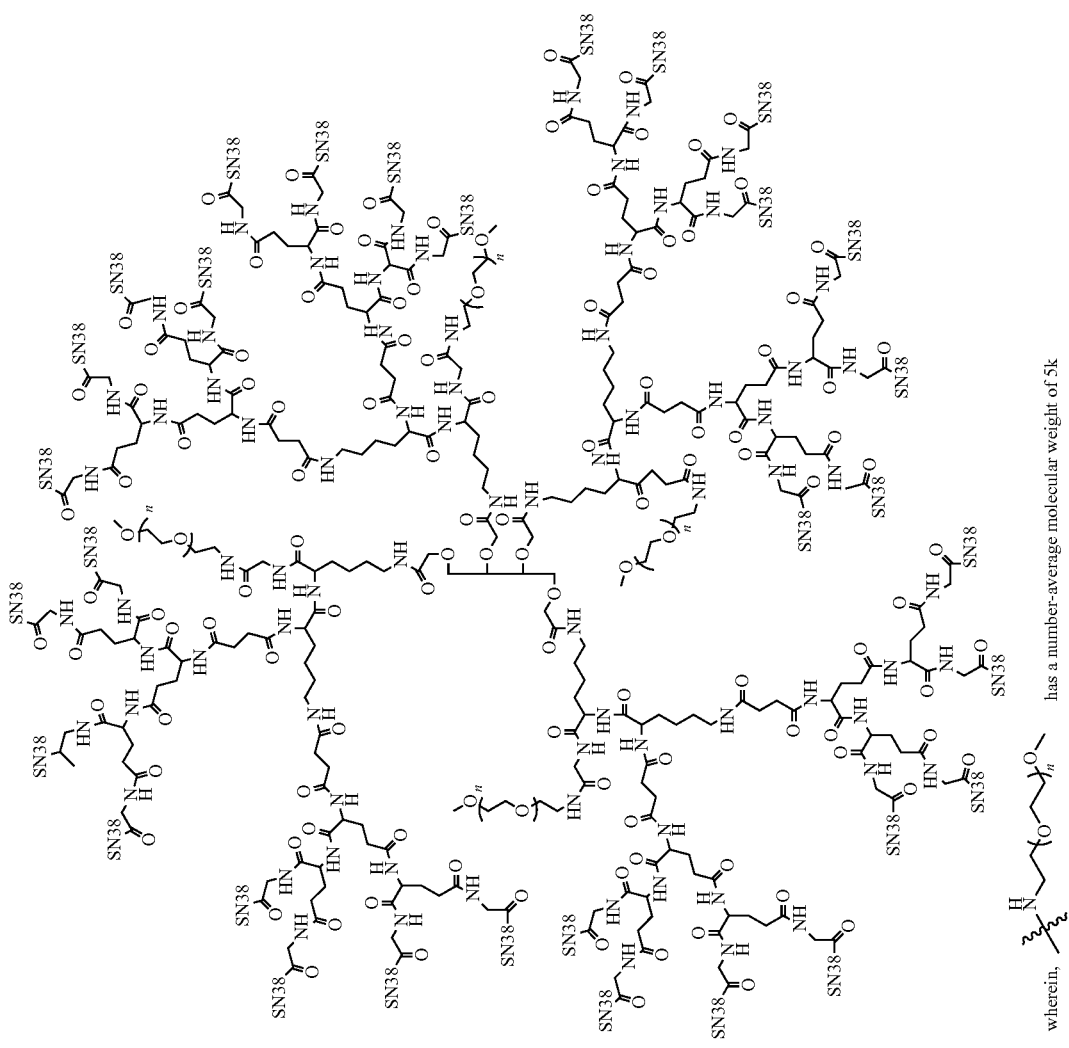

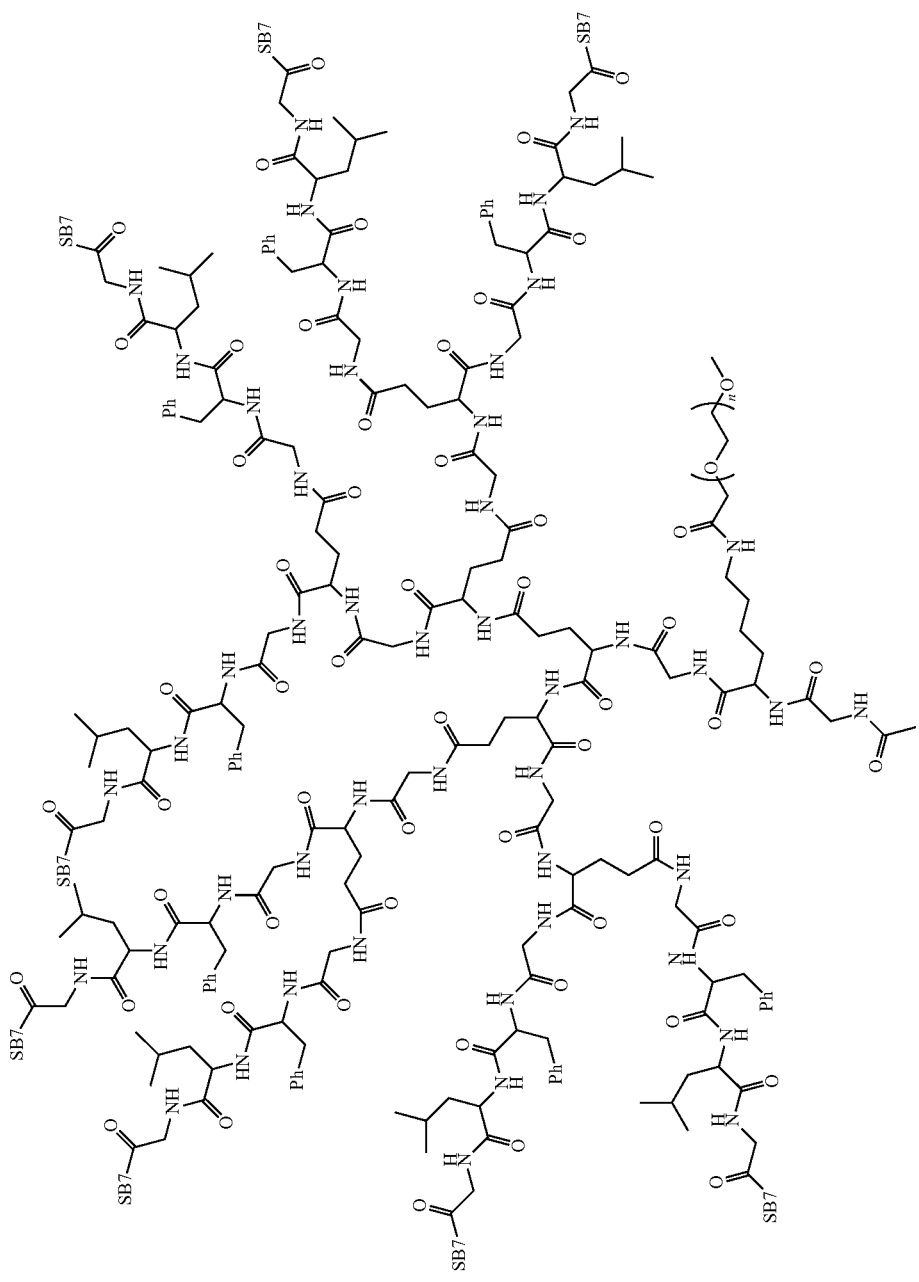

-continued
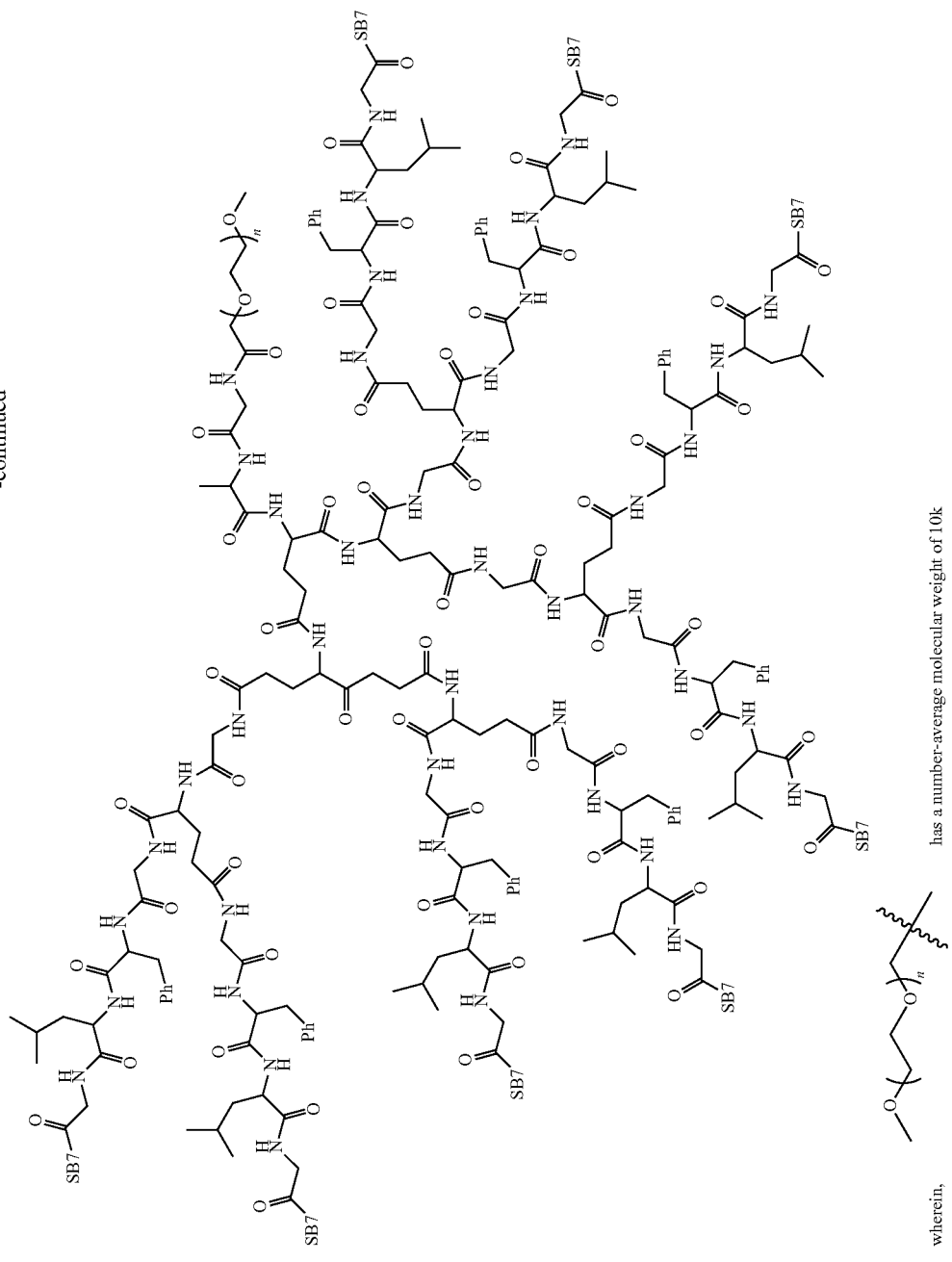
wherein, has a number-average molecular weight of 10k

Intermediate and Preparation Method
In the third aspect of the present invention, the present invention provides an intermediate for preparing the above-mentioned polyethylene glycol conjugated drug of the formula (II) or a pharmaceutically acceptable salt thereof, the intermediate being selected from:
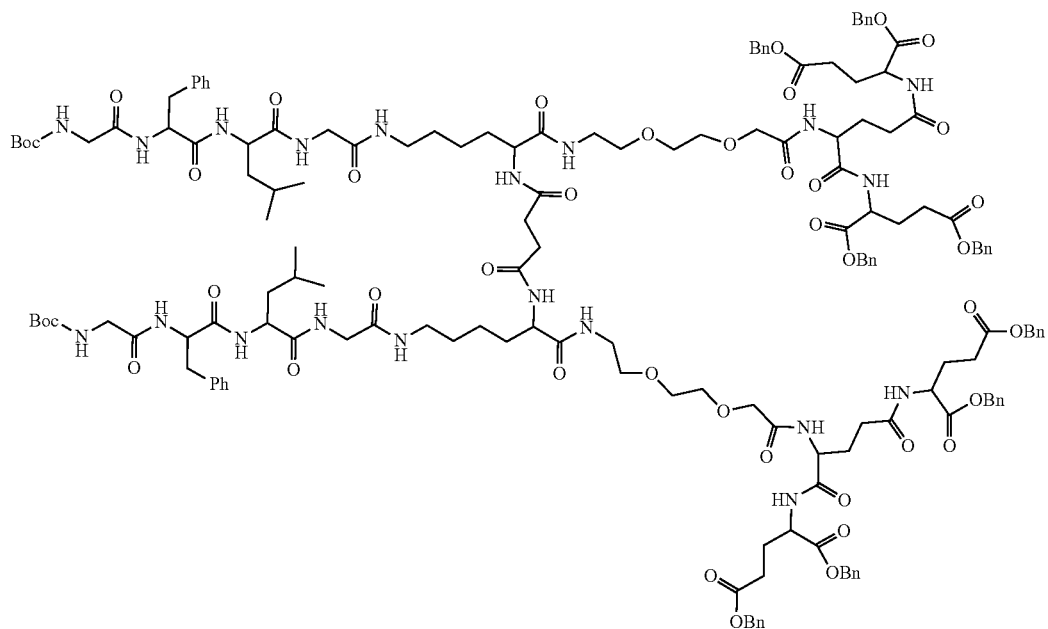
35-11
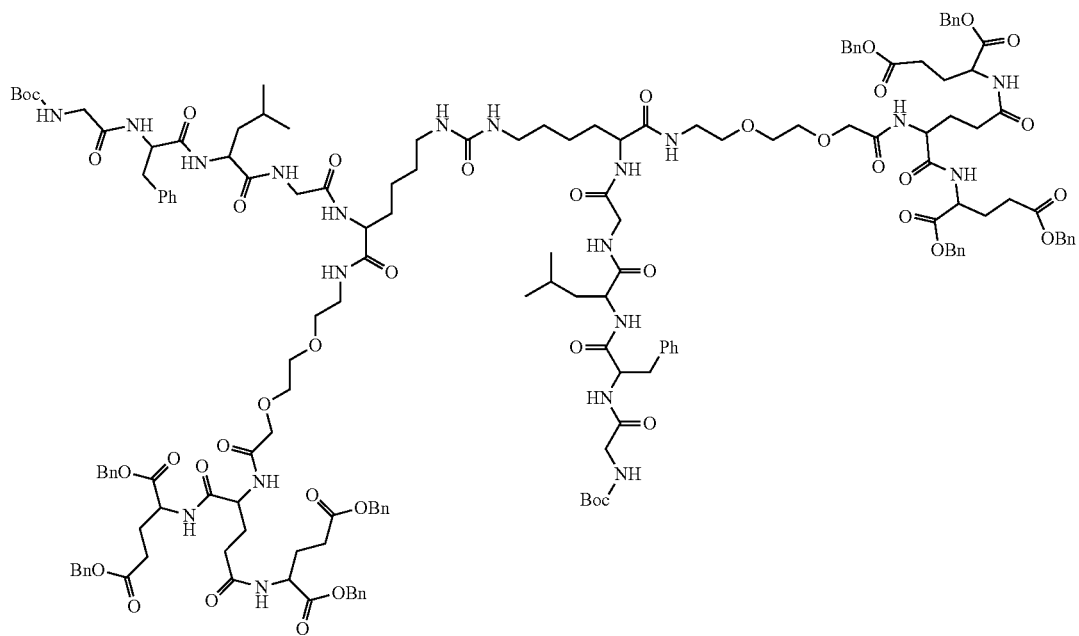
43-11

-continued
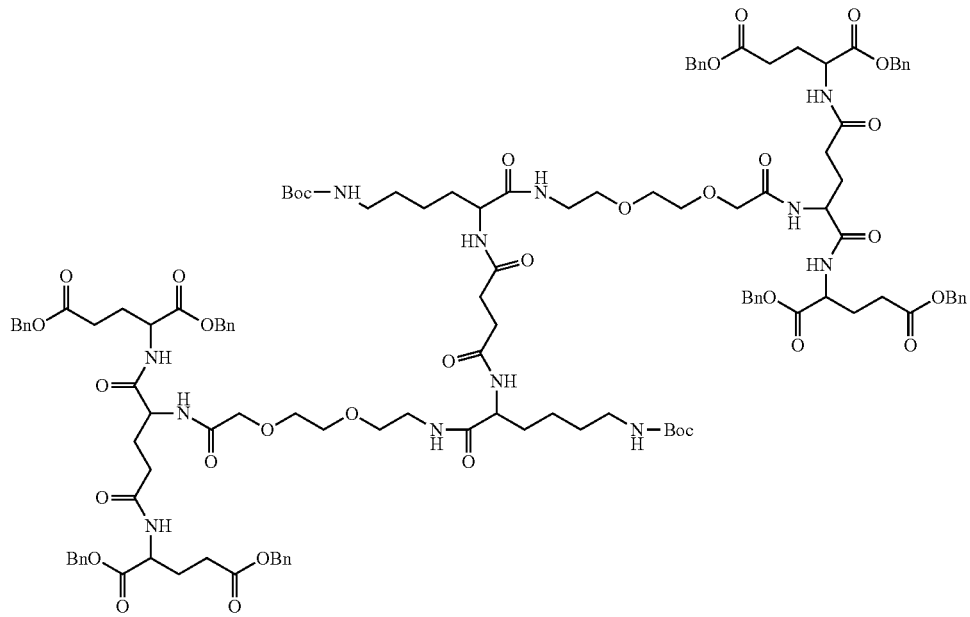
27-121
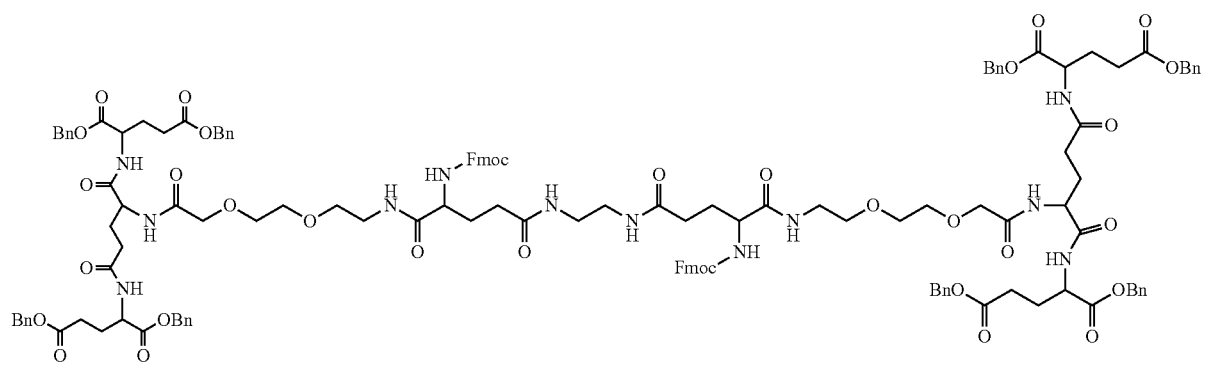
25-221
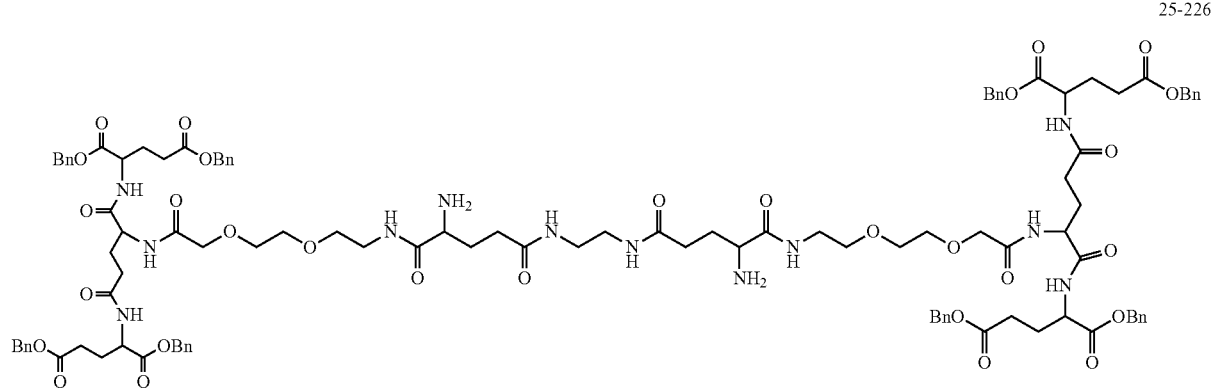
25-226

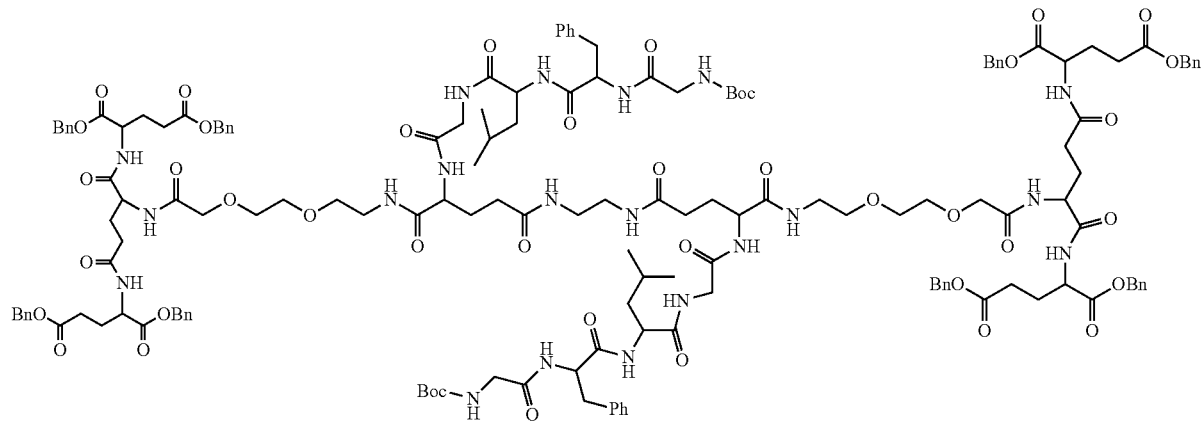
25-227
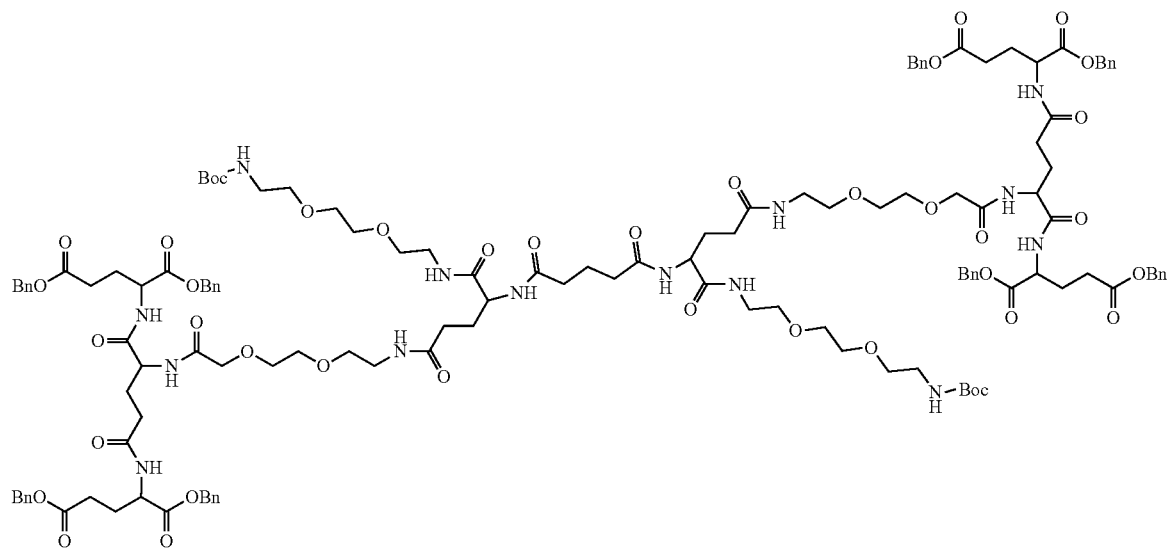
42-34
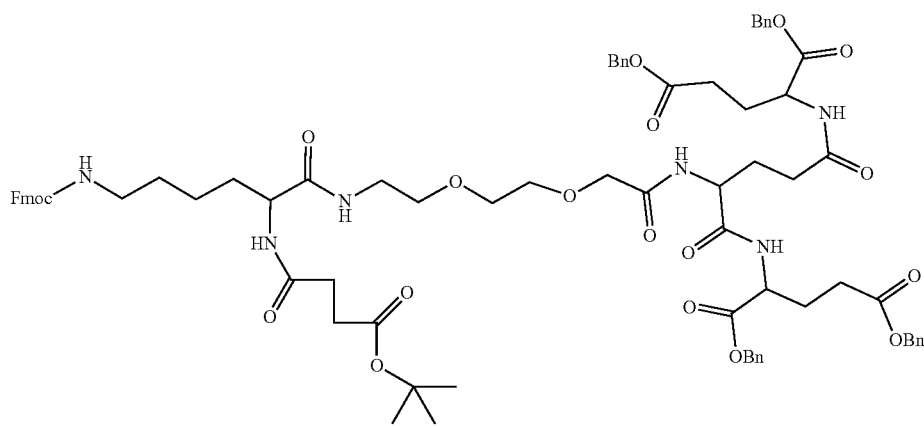
37-45

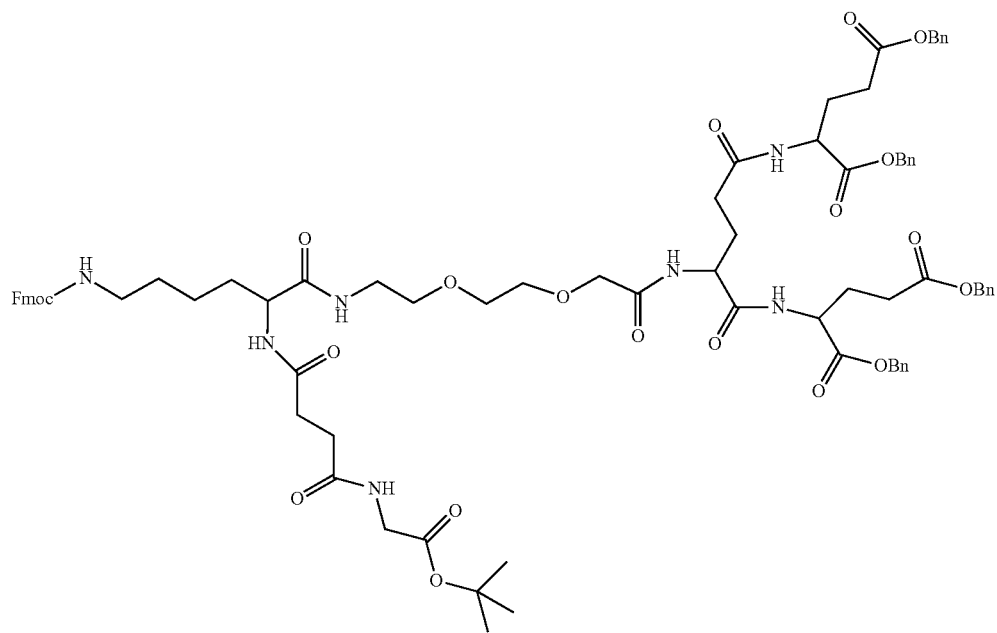
45-6
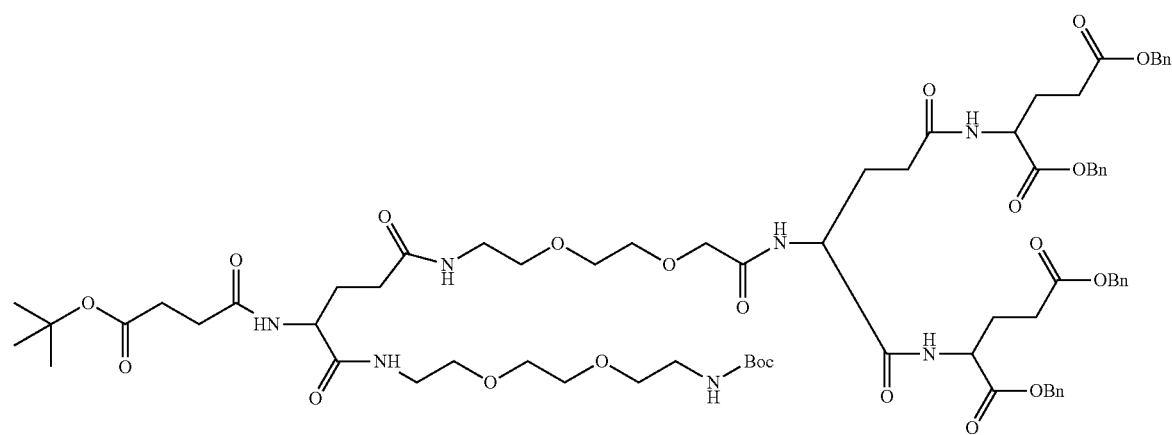
45-9

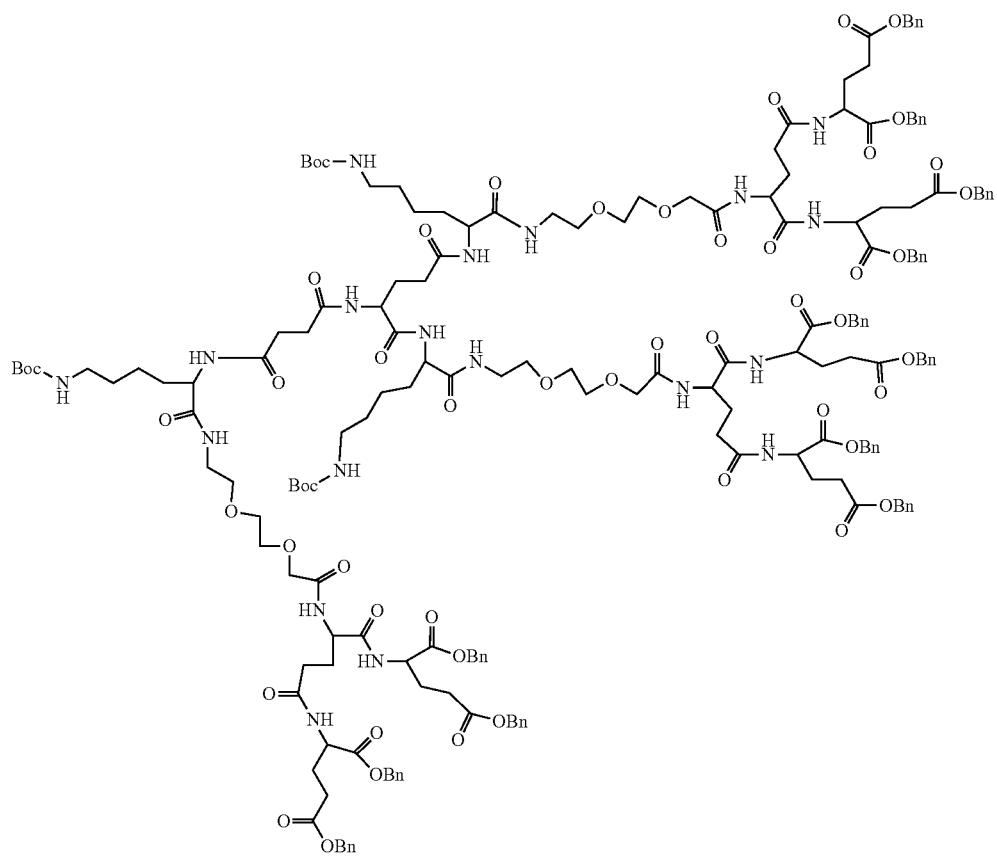
41-27

233 234
-continued
37-81
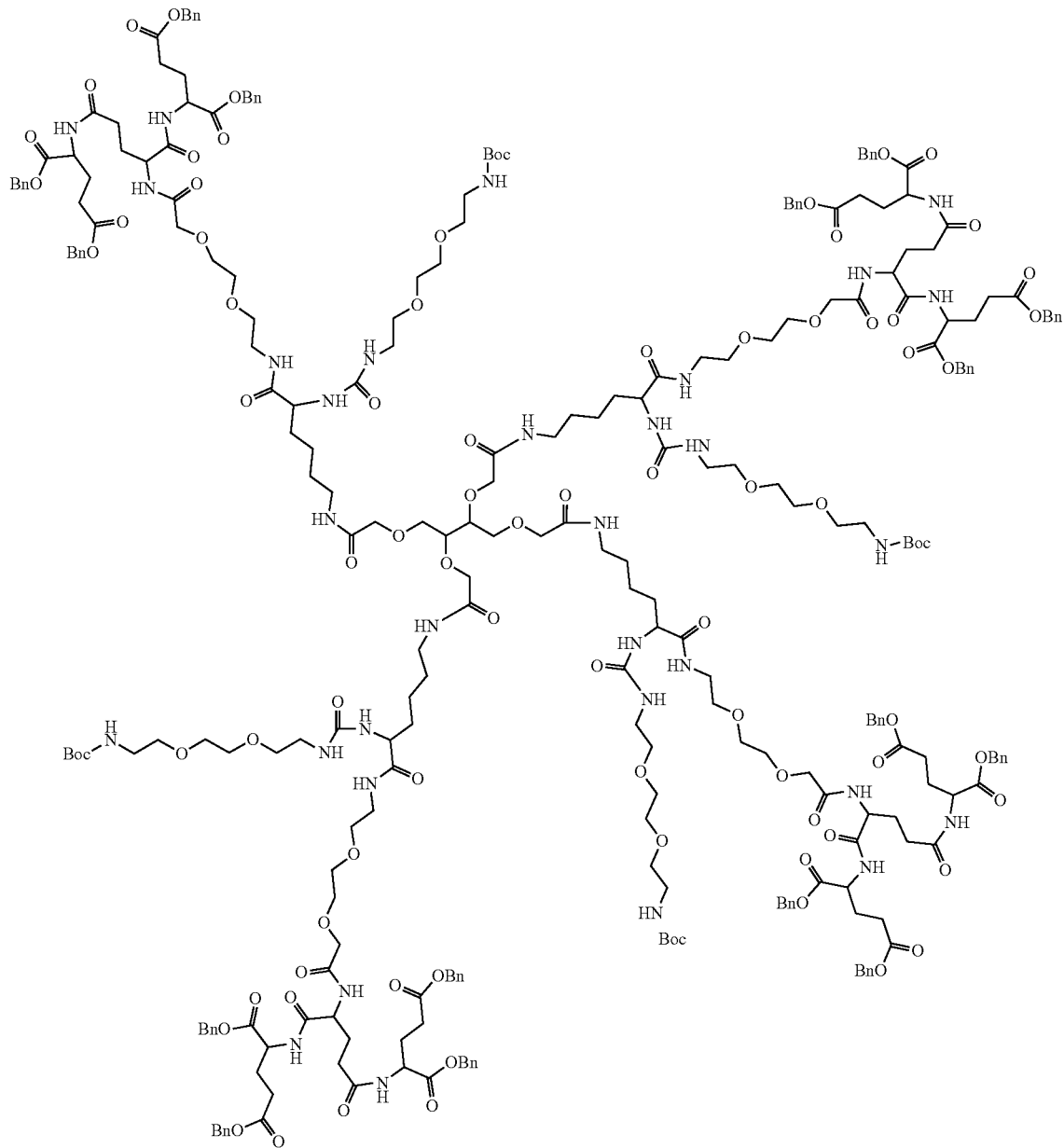
35-90
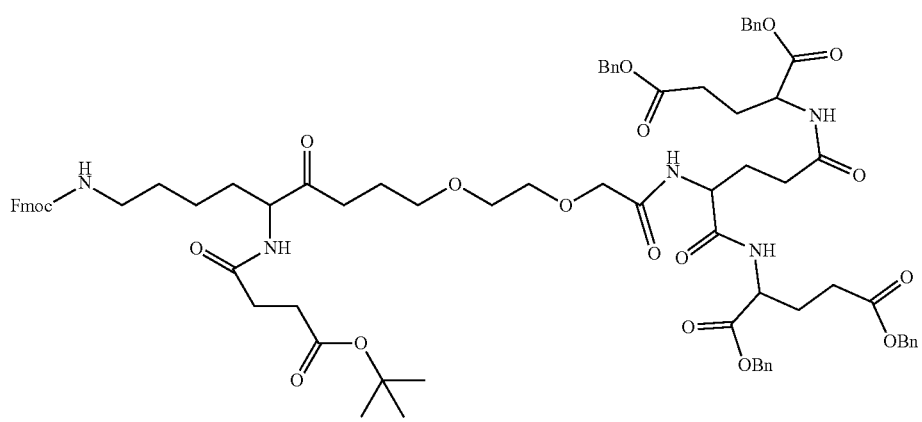

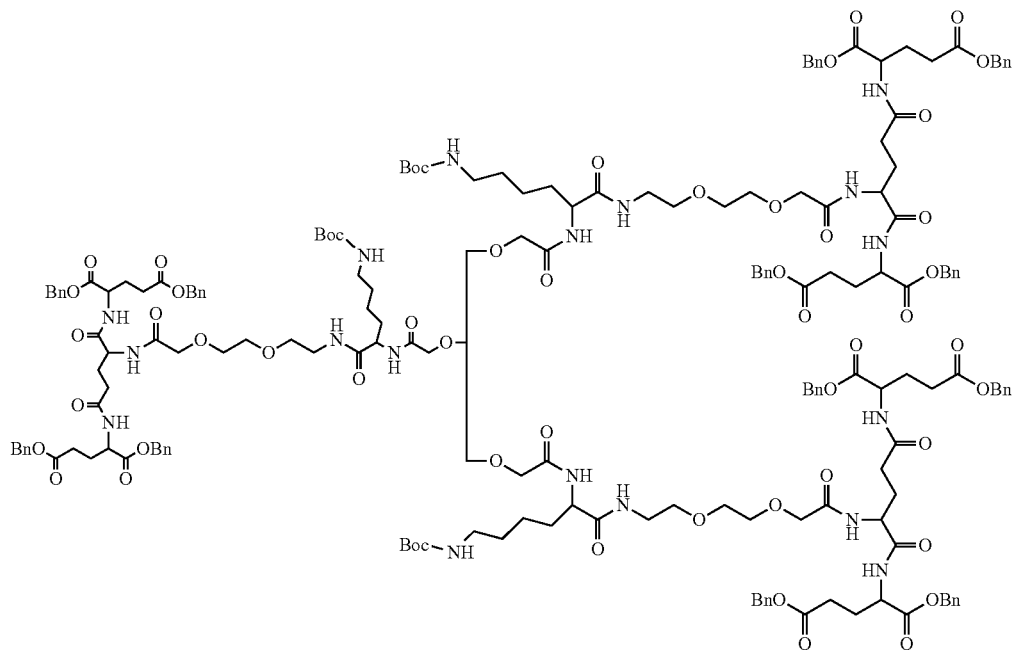
44-161
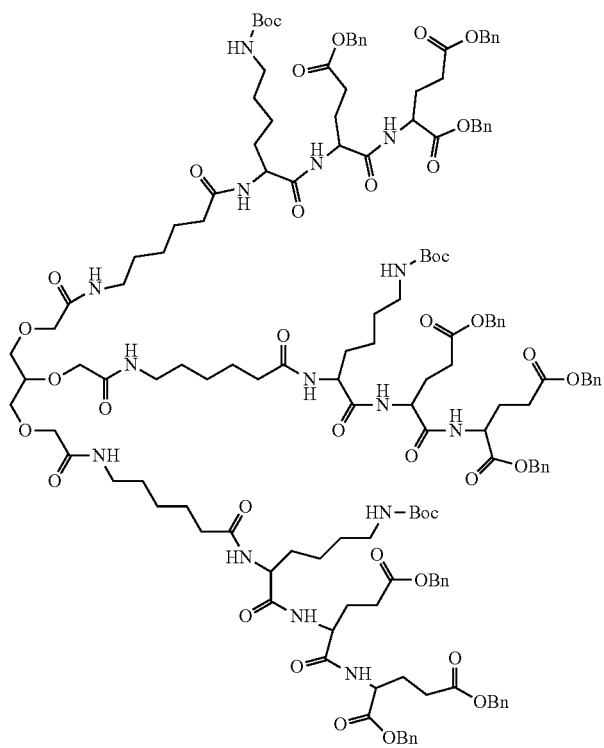
41-119

49-124
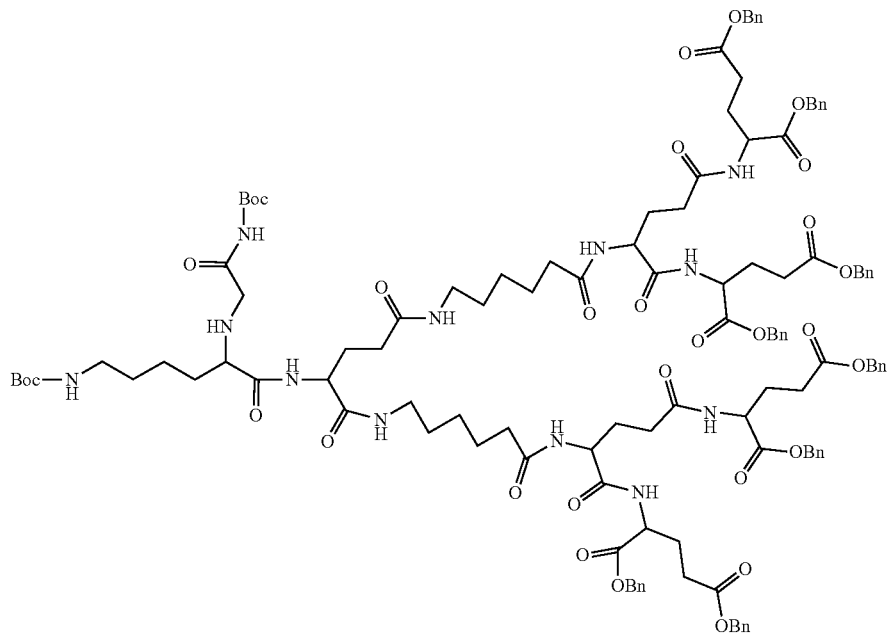
40-171
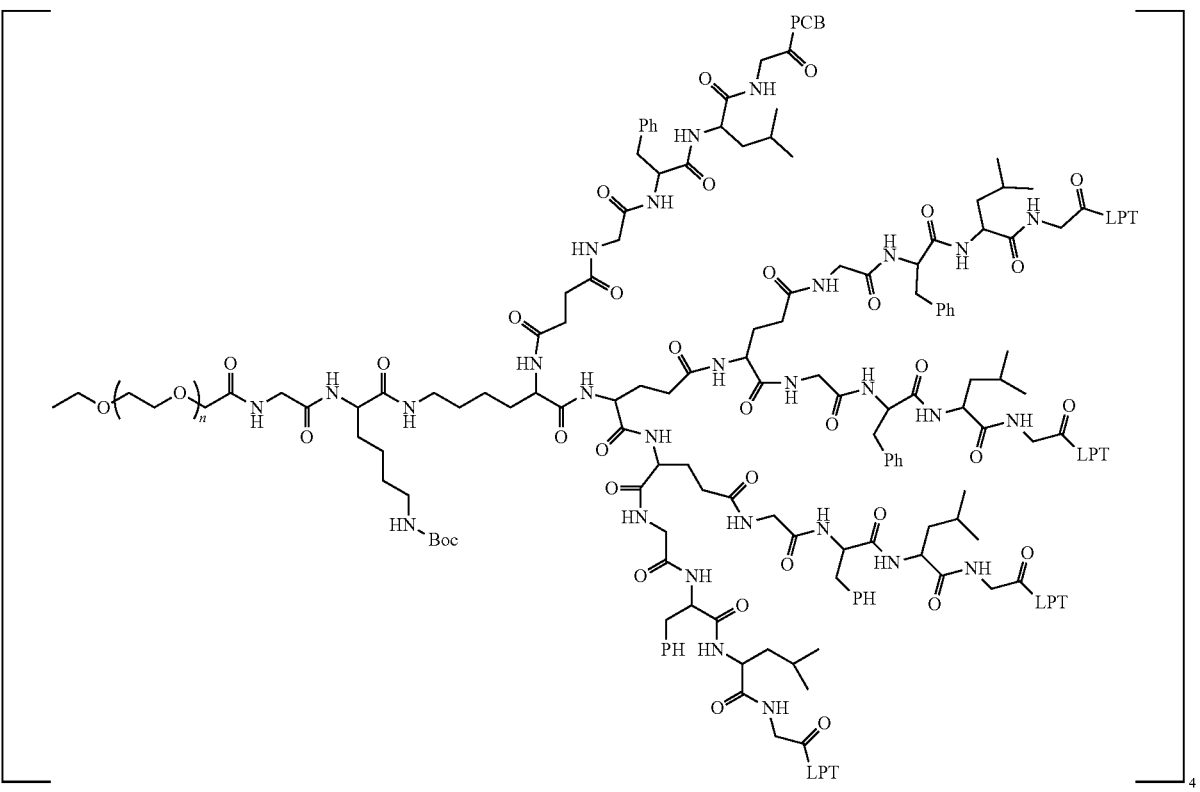

42-134
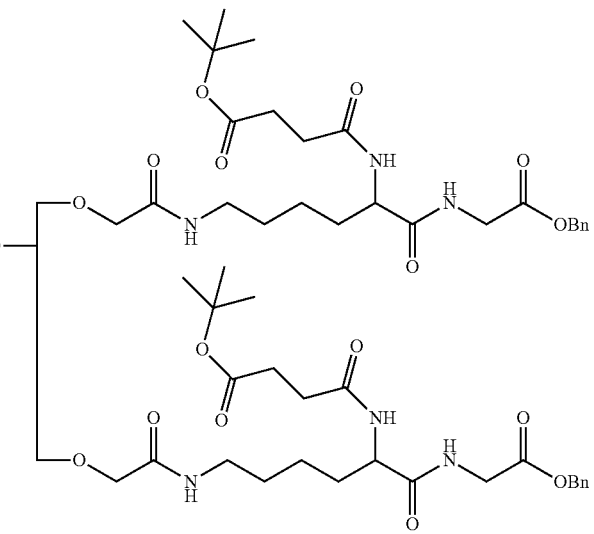
41-131
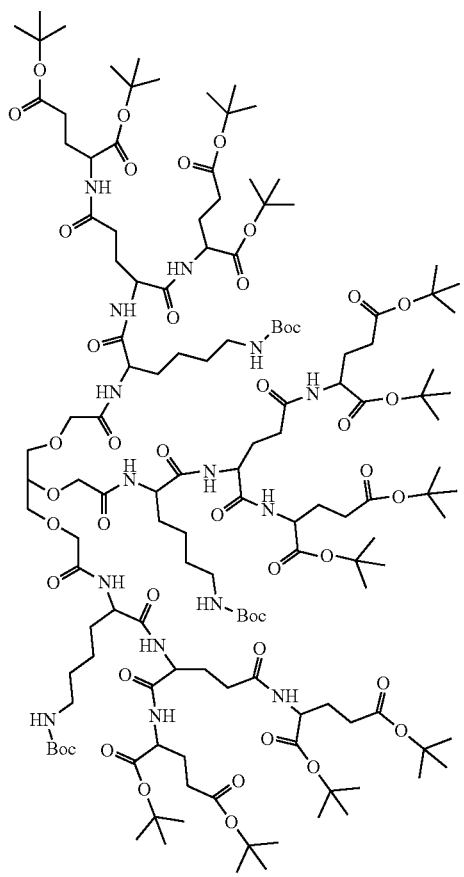
29-248
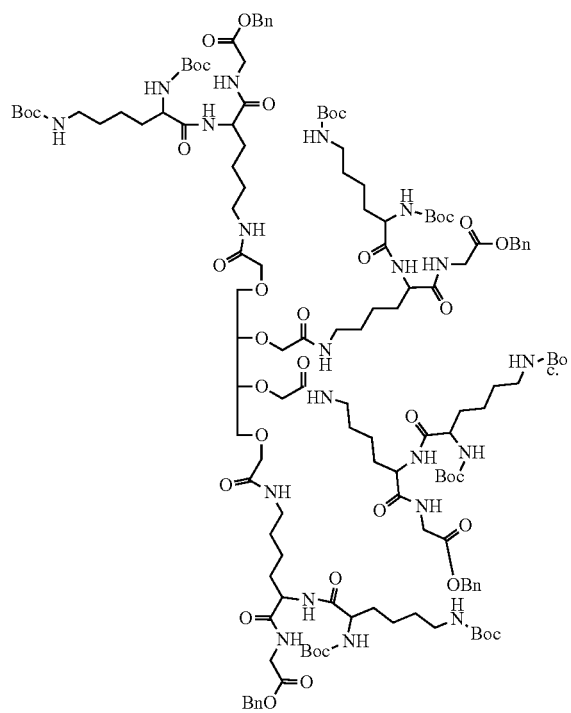

In the fourth aspect of the present invention, the present invention provides a method for preparing the above-mentioned polyethylene glycol conjugated drug of the formula (II) or a pharmaceutically acceptable salt thereof, comprising the following steps:

(1) preparing the intermediate

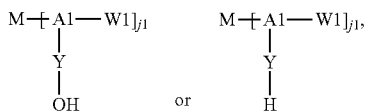

M, A1, W1, Y and j1 being as defined above, wherein: in the preparation of the intermediate

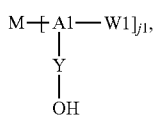

when Y is other than a direct bond, —Y—OH has a terminal carboxyl group, when Y is a direct bond,

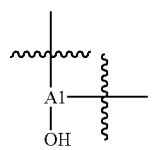

has a terminal carboxyl group,
in the preparation of the intermediate

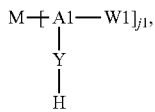

when Y is other than a direct bond, —Y—H has a terminal amino group, when Y is a direct bond,

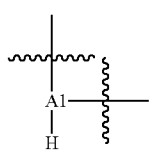

has a terminal amino group;

(2) allowing the PEG with amino group or activated amino group and the intermediate

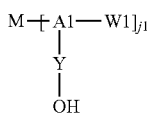

to carry out amidation reaction, or, allowing the PEG with carboxyl group or activated carboxyl group and the intermediate

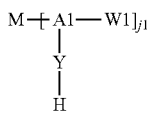

to carry out amidation reaction, to obtain the above-mentioned polyethylene glycol conjugated drug.

In the fifth aspect of the present invention, the present invention provides an intermediate for preparing the above-mentioned polyethylene glycol conjugated drug of the formula (III) or a pharmaceutically acceptable salt thereof, the intermediate being selected from:

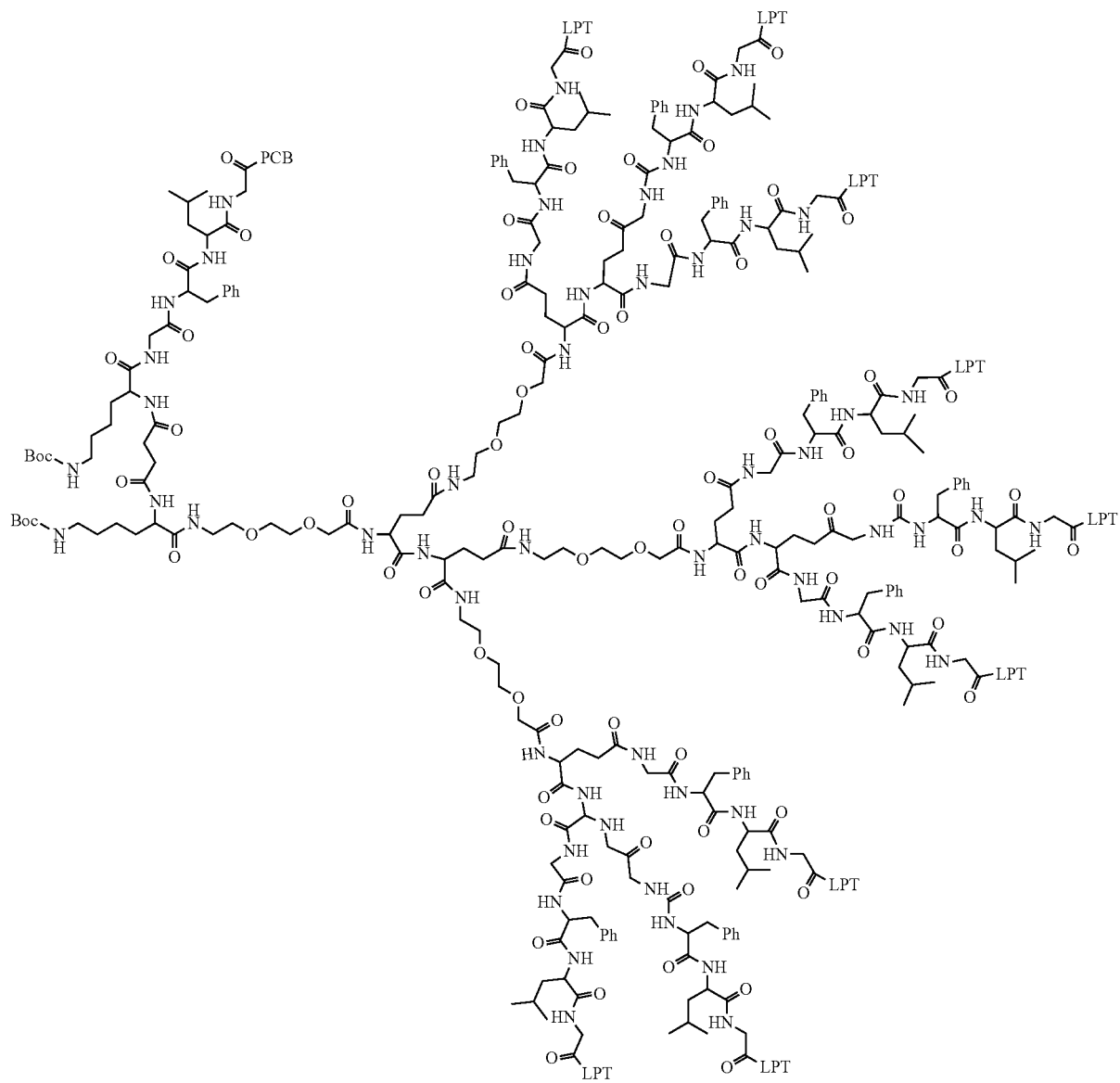

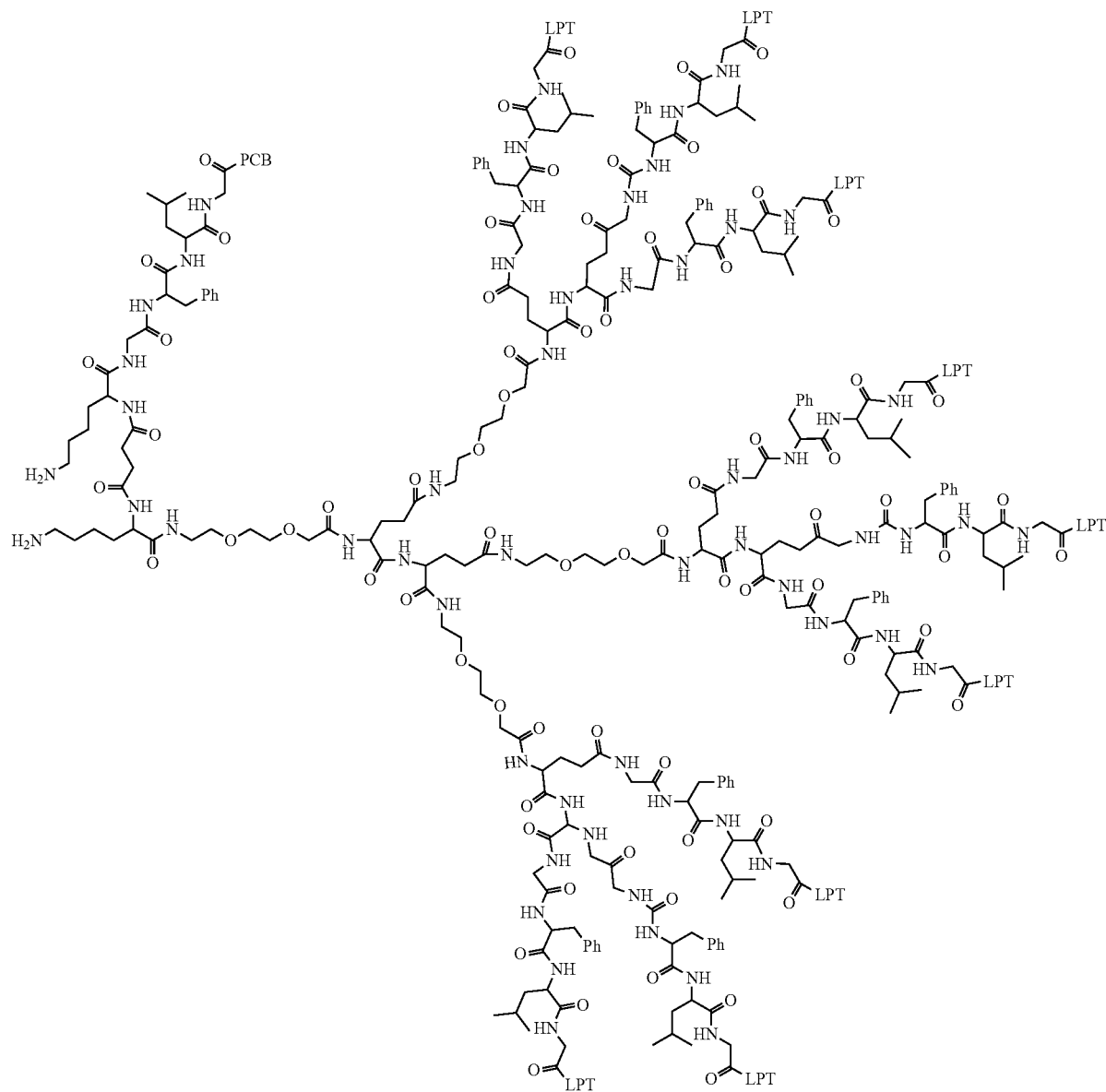
10-97

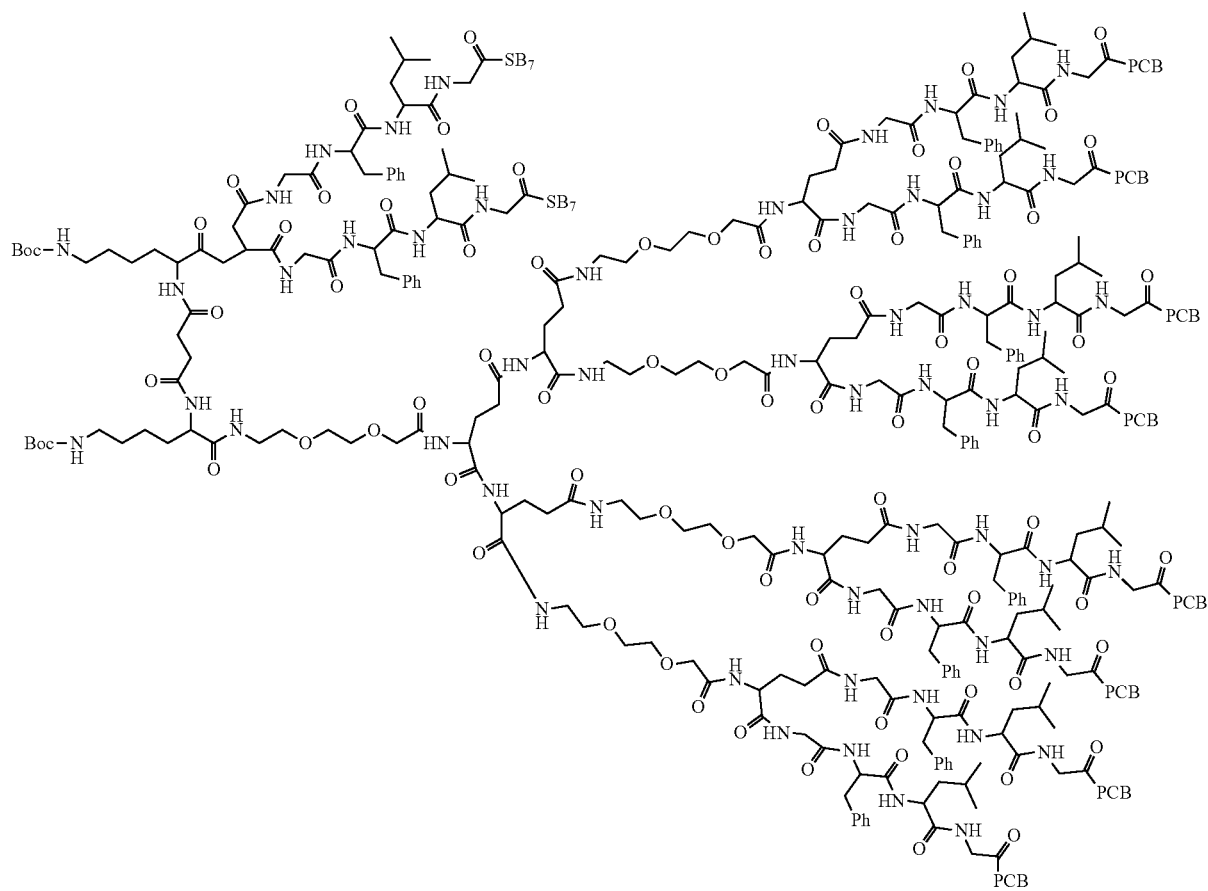
39-14

-continued
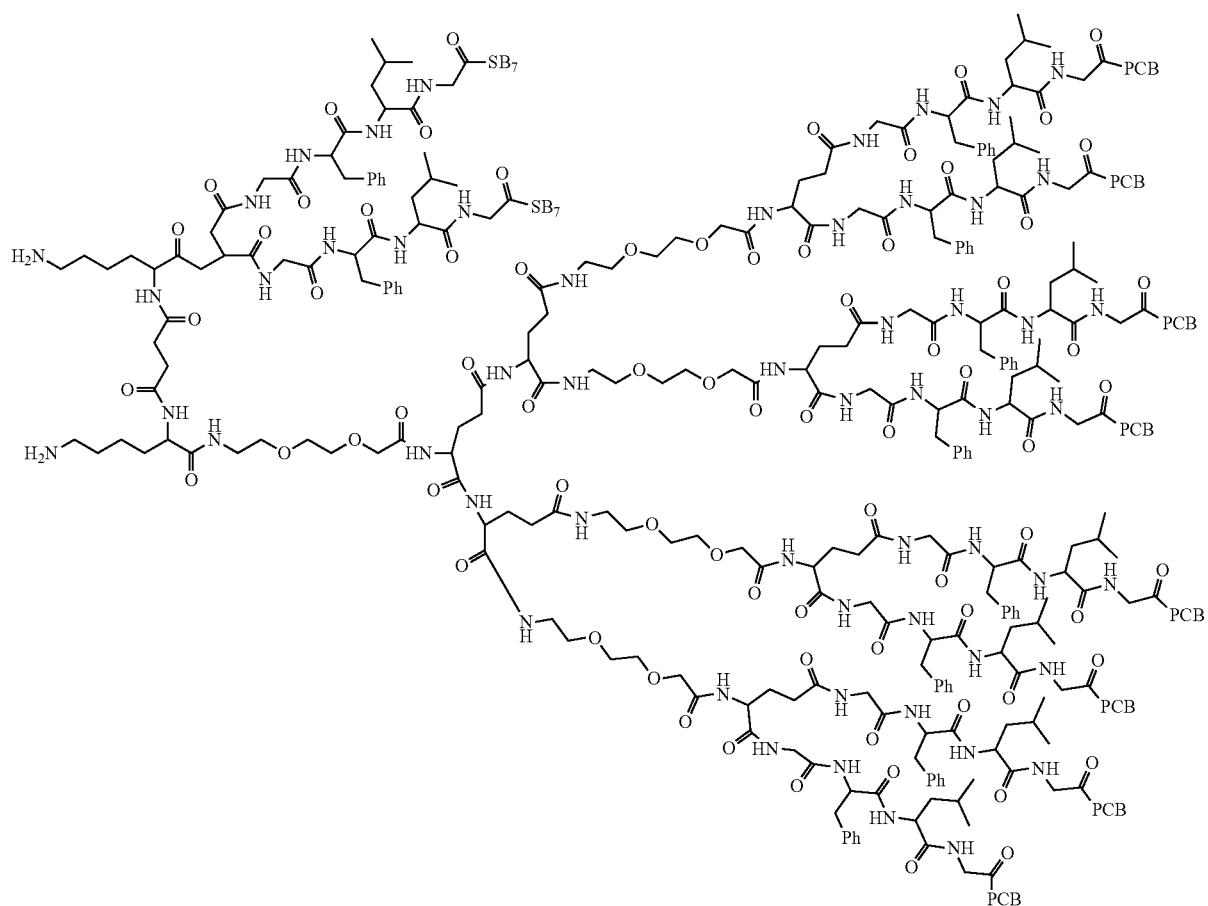
39-15

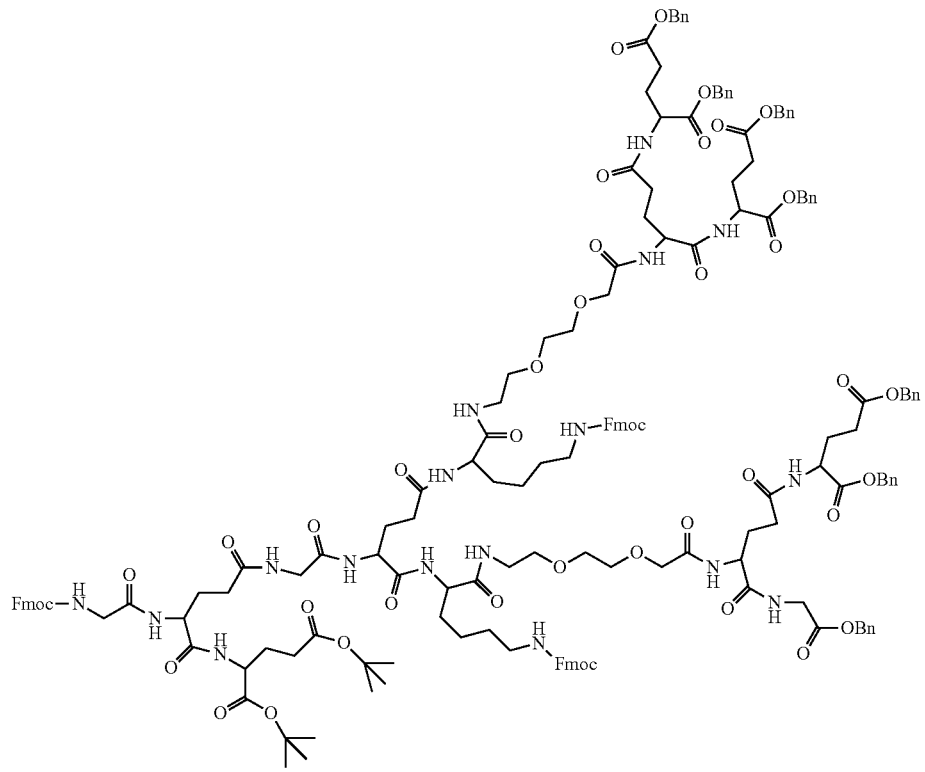
2-210
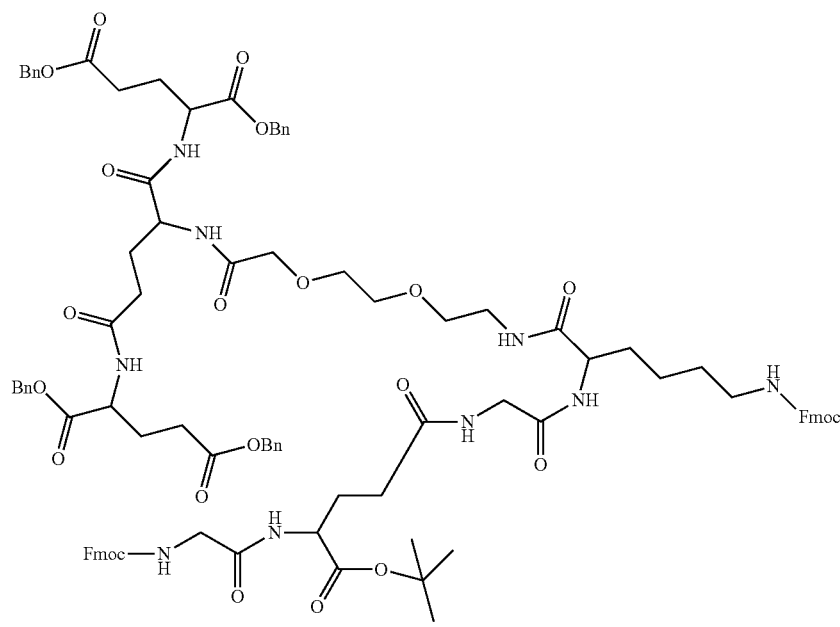
27-202

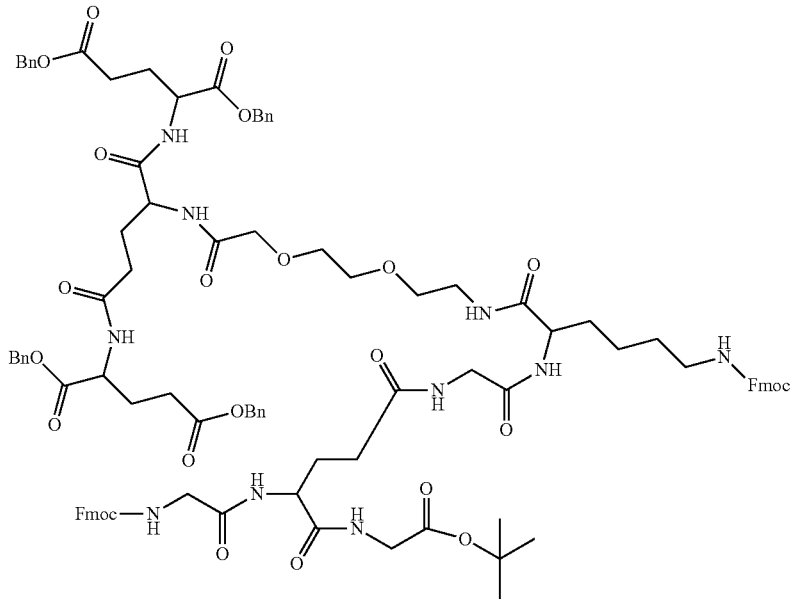
27-218
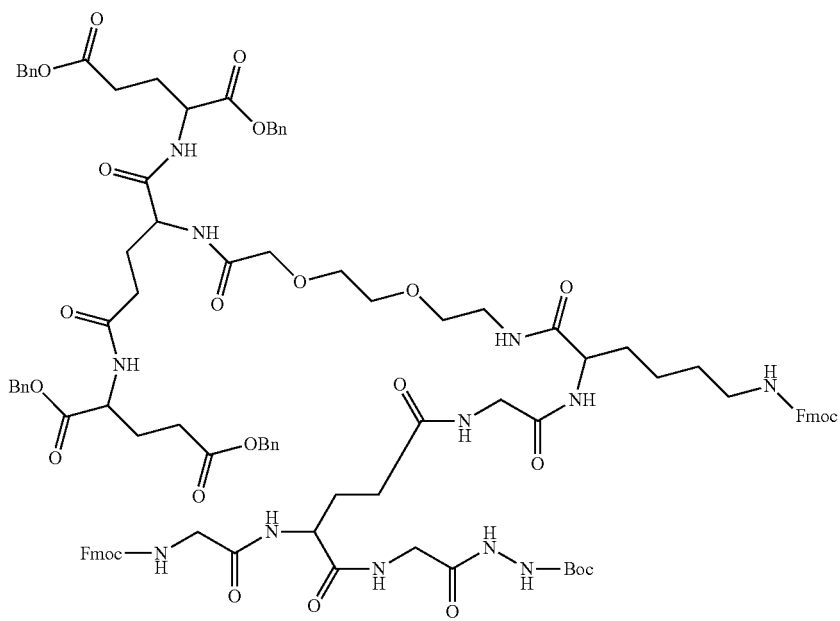
27-224

35-155

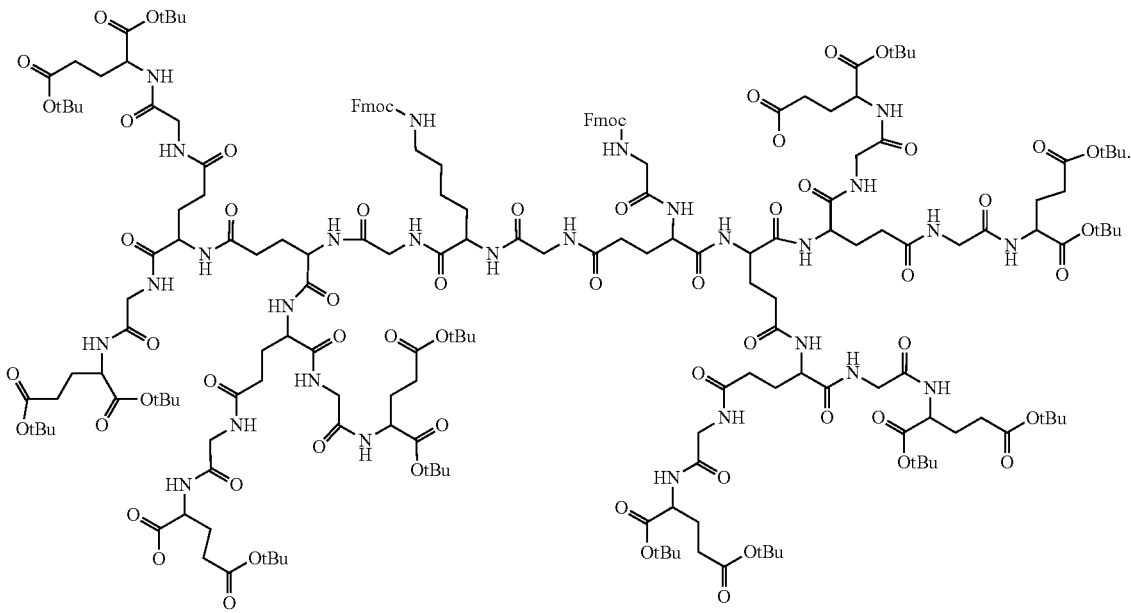

In the sixth aspect of the present invention, the present invention provides a method for preparing the above-mentioned polyethylene glycol conjugated drug of the formula (III) or a pharmaceutically acceptable salt thereof, comprising the following steps:

(1) preparing the intermediate

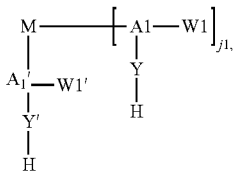

M, A1, A1', W1, W1', Y, Y' and j1 being as defined above, wherein:

when Y or Y' is other than a direct bond, —Y—H or —Y'—H has a terminal amino group, when Y or Y' is a direct bond,

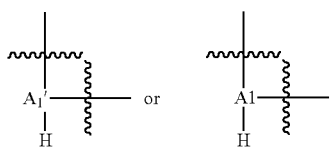

has a terminal amino group;

(2) allowing the PEG with carboxyl group or activated carboxyl group and the intermediate

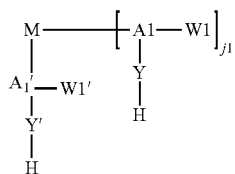

to carry out amidation reaction, to obtain the above-mentioned polyethylene glycol conjugated drug.

In the seventh aspect of the present invention, the present invention provides an intermediate for preparing the above-mentioned polyethylene glycol conjugated drug of the formula (IV) or a pharmaceutically acceptable salt thereof, the intermediate being selected from:

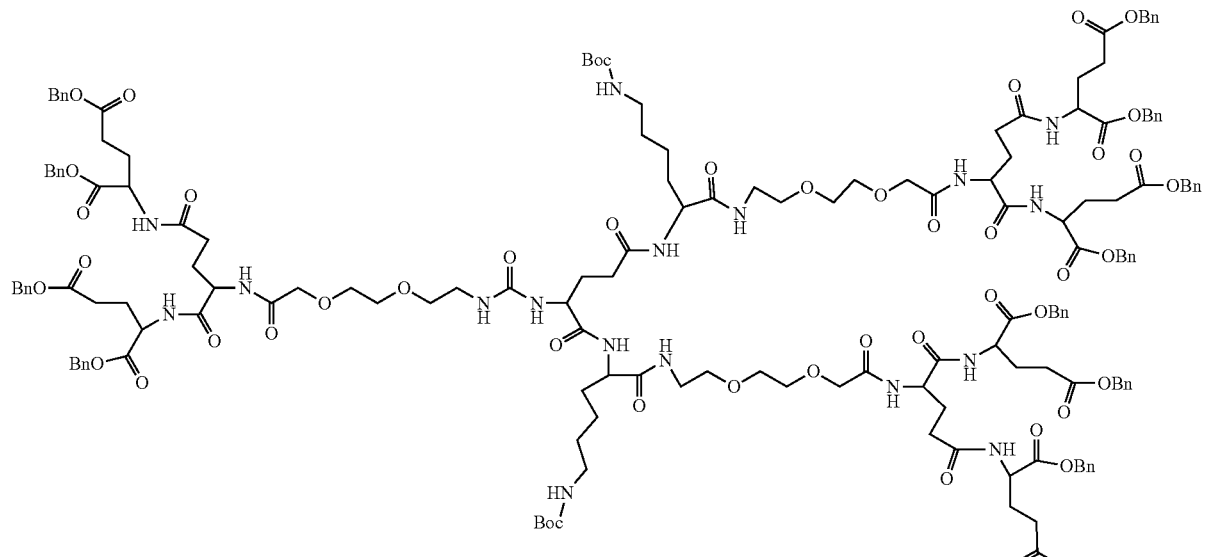
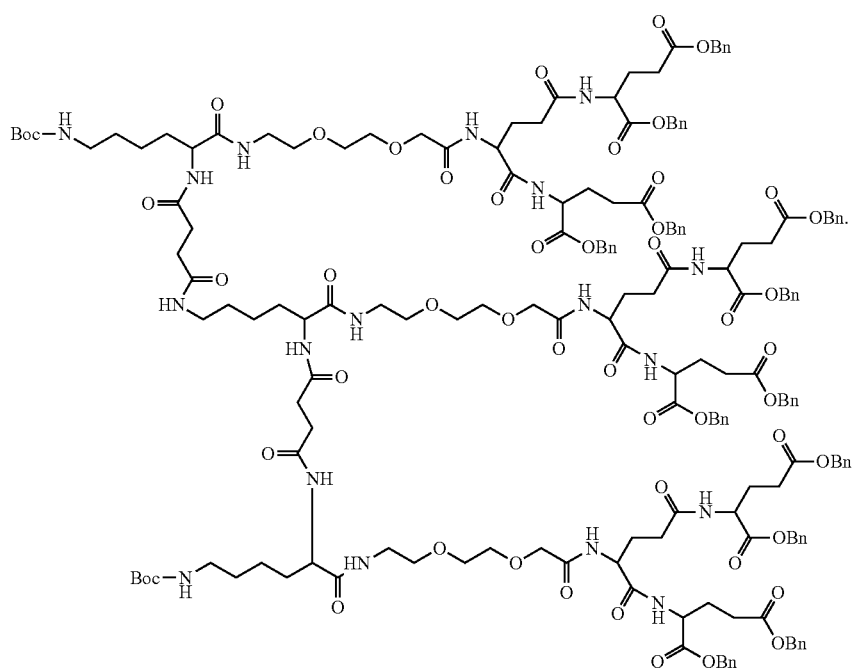
In the eighth aspect of the present invention, the present invention provides a method for preparing the above-mentioned polyethylene glycol conjugated drug of the formula (IV) or a pharmaceutically acceptable salt thereof, comprising the following steps:
(1) preparing the intermediate
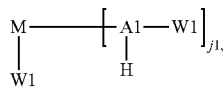
M, A1, W1 and j1 being as defined above, wherein,
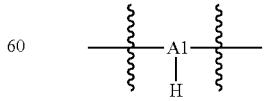
has a terminal amino group;

(2) allowing the PEG with carboxyl group or activated carboxyl group and the intermediate

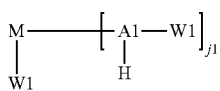

to carry out amidation reaction, to obtain the above-mentioned polyethylene glycol conjugated drug.

In the ninth aspect of the present invention, the present invention provides an intermediate for preparing the above-mentioned polyethylene glycol conjugated drug of the formula (V) or a pharmaceutically acceptable salt thereof, the intermediate being selected from:

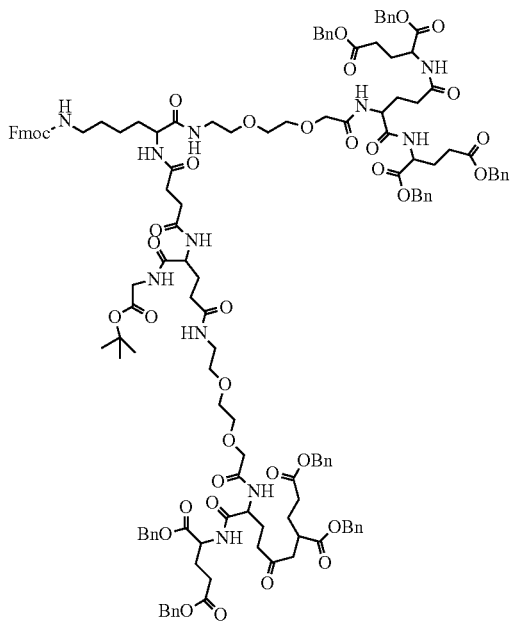

35-36

In the tenth aspect of the present invention, the present invention provides a method for preparing the above-mentioned polyethylene glycol conjugated drug of the formula (V) or a pharmaceutically acceptable salt thereof, comprising the following steps:

(1) preparing the intermediate

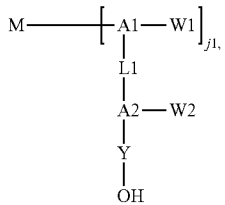

M, A1, A2, W1, W2, L1, Y and j1 being as defined above, wherein, —Y—OH has a terminal carboxyl group;

(2) allowing the PEG with amino group or activated amino group and the intermediate

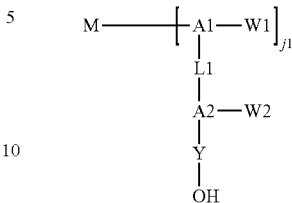

to carry out amidation reaction, to obtain the above-mentioned polyethylene glycol conjugated drug.

Pharmaceutical Composition and Pharmaceutical Use

In one aspect of the present invention, the present application provides a pharmaceutical composition, comprising a therapeutically and/or prophylactically effective amount of the polyethylene glycol conjugated drug or a pharmaceutically acceptable salt thereof according to the present invention; the composition further comprises one or more pharmaceutically acceptable excipients, such as carriers and/or vehicles. The carriers and/or vehicles include, but are not limited to: ion exchangers, alumina, aluminum stearate, lecithin, serum proteins such as human serum protein, buffer substances such as phosphate, glycerin, sorbic acid, potassium sorbate, a mixture of partial glycerides of saturated plant fatty acids, water, salt or electrolyte, such as protamine sulfate, disodium hydrogen phosphate, potassium hydrogen phosphate, sodium chloride, zinc salt, colloidal silica, magnesium trisilicate, polyvinylpyrrolidone, cellulose material, polyethylene glycol, sodium carboxymethyl cellulose, polyacrylate, beeswax, polyethylene-polyoxypropylene block polymer, and lanolin.

The pharmaceutical composition may be prepared into any pharmaceutically acceptable dosage form. The pharmaceutical composition may also be applied to individuals in need of such treatment in any suitable way of administration, such as oral, parenteral, rectal or pulmonary administration. In the case of oral administration, the pharmaceutical composition may be made into conventional solid preparations, such as tablets, capsules, pills, granules, etc.; it may also be made into oral liquid preparations, such as oral solutions and oral suspensions, and syrup. When the pharmaceutical composition is made into oral preparations, suitable fillers, binders, disintegrants, lubricants, etc. may be added. In the case of parenteral administration, the pharmaceutical composition may be made into injection preparations, including injection solutions, sterile powders for injection, and concentrated solutions for injection. When the pharmaceutical composition is made into injection preparations, they may be produced by a conventional method in the current pharmaceutical field. In the case of preparation of injection preparations, it is not required to add additives, or appropriate additives may be added according to the nature of the drug. In the case of rectal administration, the pharmaceutical composition may be made into suppositories and the like. In the case of pulmonary administration, the pharmaceutical composition may be made into an inhalant or a spray. Preferably, the pharmaceutical composition of the present invention may be made into an injection preparation, such as an injection solution. Alternatively, normal saline is used as the carrier of the injection solutions.

In another aspect, the present application provides use of the polyethylene glycol conjugated drug of the present invention or a pharmaceutically acceptable salt thereof in the preparation of a medicament for treating and/or preventing a disease (such as a cancer). The disease refers to a disease treated by the active ingredient in the polyethylene glycol conjugated drug.

In another aspect, the present application provides the polyethylene glycol conjugated drug of the present invention or a pharmaceutically acceptable salt thereof for use in treating and/or preventing a disease (such as a cancer). The disease refers to a disease treated by the active ingredient in the polyethylene glycol conjugated drug.

In the present invention, cancer refers to a disease state characterized by cell proliferative, including but not limited to: colon cancer, leukemia, lymphoma, bladder cancer, bone cancer, brain tumor, medulloblastoma, glioma, breast cancer, adenoma/carcinoid, adrenal cortical cancer, pancreatic islet cell cancer, cervical cancer, endometrial cancer, ovarian cancer, colorectal cancer, skin cancer, esophageal cancer, eye cancer, gallbladder cancer, stomach cancer, head and neck cancer, liver cancer, melanoma, Kaposi's sarcoma, kidney cancer, oral cancer, lung cancer, nasopharyngeal cancer, neuroblastoma, ovarian cancer, pancreatic cancer, thyroid cancer, parathyroid penile cancer, prostate cancer, urethral cancer, vaginal cancer, vulvar cancer, anal cancer, sarcoma, etc., including metastasis of the aforementioned cancers.

In another aspect, the present application provides a method for treating and/or preventing a disease (such as a cancer), comprising administering an effective amount of the polyethylene glycol conjugated drug of the present invention or a pharmaceutically acceptable salt thereof to an individual in need thereof. The dosage regimen may be adjusted to provide the optimum desired response. For example, a single amount of drug may be administered, several divided doses may be administered over time, or the dose may be proportionally reduced or increased as indicated by the urgent need for the treatment. It should be noted that the dose value may vary with the type and severity of the condition to be alleviated, and may include single or multiple doses. It should be further understood that for any particular individual, the specific dosage regimen should be adjusted over time according to the individual's needs and the professional judgment of the person administering the composition or supervising the administration of the composition.

In the present invention, "individual" includes a human or a non-human animal. Exemplary human individuals include human individuals suffering from diseases such as those described herein (referred to as patients) or normal individuals. In the present invention, "non-human animals" include all vertebrates, such as non-mammals (such as birds, amphibians, and reptiles) and mammals, such as non-human primates, livestock and/or domesticated animals (such as sheep, dogs, cats, cows, pigs, and etc.).

Explanation or Definition of Terms

In the present invention, the active ingredient suitable for being conjugated with polyethylene glycol may be a drug molecule with at least one amino group, hydroxyl group, carboxyl group or acyl group, for example, a drug molecule having anti-tumor activity with at least one amino group, hydroxyl group, carboxyl group or acyl group, such as MK2, LPT, PCB, SB7, PKA, NPB and the like, which represent the following meanings:

| Abbreviation | Name | CAS number or structural formula |
|---|---|---|
| MK2 | MK-2206•2HCl | 1032350-13-2 |
| LPT | Lapatinib | 231277-92-2 |
| PCB | Palbociclib | 571190-30-2 |
| SB7 | SB-743921 | 940929-33-9 |
| PKA | A derivative of PKI-587, in said derivative the two terminal methyl groups are removed compared with PKI-587 | (structural formula) |
| NPB | Niraparib (MK-4827) | 1038915-60-4 |

Unless otherwise defined below, the meanings of all technical and scientific terms used herein are intended to be the same as those commonly understood by those skilled in the art. The reference to the technology used herein is intended to refer to the technology generally understood in the art, including those technical changes or equivalent technology substitutions that are obvious to those skilled in the art. Although it is believed that the following terms are well understood by those skilled in the art, the following definitions are still set forth to better explain the present invention.

As used herein, "PEG" is an abbreviation for polyethylene glycol, which refers to a homopolymer with a repeating unit of —$CH_2CH_2O$—, including single-arm polyethylene glycol, multi-arm polyethylene glycol and their derivatives, such as a derivative with a reactive functional group such as amino or carboxyl group at the terminal. In the present invention, the arms of the multi-arm polyethylene glycol preferably have the same degree of polymerization. When referring to the molecular weight of a multi-arm polyethylene glycol, the molecular weight means the total molecular weight of each arm. In the structural formula of the present invention, the letter "m" or "n" in the subscript of the repeating unit of polyethylene glycol represents the degree of polymerization of polyethylene glycol. When the polyethylene glycol is a multi-arm polyethylene glycol, the letter "m" or "n" represents the degree of polymerization of each arm.

In various parts of this specification, substituents for the disclosed compounds of the present invention are disclosed in terms of group species or ranges. It is specifically pointed out that the present invention includes every independent subcombination of each member of these group species and ranges. For example, the term "$C_1$-$C_6$ alkyl" specifically refers to independently disclosed methyl, ethyl, $C_3$ alkyl, $C_4$ alkyl, $C_5$ alkyl and $C_6$ alkyl.

Unless otherwise indicated, the term "alkyl" refers to a saturated, straight-chain or branched-chain, monovalent hydrocarbon group with 1 to 6 carbon atoms ($C_1$-$C_6$ alkyl group), or 1 to 4 carbon atoms ($C_1$-$C_4$ alkyl group), or 1 to 3 carbon atoms ($C_1$-$C_3$ alkyl group), wherein the alkyl group may be independently and optionally substituted by one or more substituents described herein, including but not limited to deuterium, amino, hydroxyl, cyano, F, Cl, Br, I, mercapto, nitro, oxo (=O) and the like. Examples of the alkyl group include, but not limited to, methyl (Me, —$CH_3$), ethyl (Et, —$CH_2CH_3$), n-propyl (n-Pr, —$CH_2CH_2CH_3$), iso-propyl (i-Pr, —$CH(CH_3)_2$), n-butyl (n-Bu, —$CH_2CH_2CH_2CH_3$), iso-butyl (i-Bu, —$CH_2CH(CH_3)_2$), sec-butyl (s-Bu, —CH($CH_3$)$CH_2CH_3$), tert-butyl (t-Bu, —C($CH_3$)$_3$), n-pentyl (—$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2$$CH_2CH_3$), 3-methyl-2-butyl (—CH($CH_3$)CH($CH_3$)$_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2$$CH_2CH_2CH_3$), 3-methyl-2-pentyl (—CH($CH_3$)CH($CH_3$)$CH_2CH_3$), 4-methyl-2-pentyl (—CH($CH_3$)$CH_2CH(CH_3)_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), n-heptyl, n-octyl and the like. The term "alkyl" and its prefix "alk", as used herein, both include straight and branched saturated carbon chains.

The term "alkylene" refers to a saturated divalent hydrocarbon group obtained by removing two hydrogen atoms from a linear or branched saturated alkyl group, such as "$C_1$-$C_6$ alkylene" derived from $C_1$-$C_6$ alkyl, "$C_1$-$C_4$ alkylene" derived from $C_1$-$C_4$ alkyl, "$C_1$-$C_3$ alkylene" derived from $C_1$-$C_3$ alkyl. And the alkylene group may be substituted or unsubstituted, wherein the substituent may be, but not limited to, deuterium, hydroxyl, amino, halogen, cyano, aryl, heteroaryl, alkoxy, alkyl, alkenyl, alkynyl, heterocyclyl, mercapto, nitro or aryloxy. Examples of the alkylene group include, but not limited to, methylene (—$CH_2$—), ethylene (—$CH_2$—$CH_2$—), isopropylidene (—$CH_2$—CH($CH_3$)—), ethane-1,1-diyl, 2-methoxypropane-1,1-diyl, 2-hydroxypropane-1,1-diyl, 2-methyl-2-hydroxypropane-1,1-diyl and the like. Wherein, the meaning of the alkyl group is as described above.

In addition, it should be noted that, unless it is clearly indicated in other ways, the expressions "each . . . independently are" and " . . . and . . . each independently are" used throughout this disclosure are interchangeable, and both should be understood in a broad sense. It can mean that the specific options expressed by the same symbol in different groups do not affect each other, or it can mean that the specific options expressed by the same symbol in the same group do not affect each other.

As used herein, a certain variable being "a direct bond" refers to that the linker group does not exist, and at the same time, the substituent on the linker group correspondingly does not exist. For example, regarding —X—Y—Z, if Y is a direct bond, then it is expressed as —X—Z, and at the same time, the substituent on Y correspondingly does not exist.

As used herein, the "pharmaceutically acceptable salt" of the compound of the present invention includes an acid addition salt and base addition salt of the compound, such as hydrochloride, hexafluorophosphate, and meglumine salt.

As used herein, the wavy line " " in the structural formula means the position where another group is bonded to the structure represented by the structural formula.

As used herein, the term "effective amount" refers to the amount of a compound that will relieve one or more symptoms of the disease being treated to a certain extent after being administered.

As used herein, the term "treating" means reversing, alleviating, or inhibiting the disease or condition to which such term is applied or the progression of one or more symptoms of such a disease or condition, or preventing such a disease or condition or one or more symptoms of such a disease or condition.

Beneficial Effect

The polyethylene glycol conjugated drug of the present invention has excellent anti-tumor activity. Through the preparation method of the present invention, the polyethylene glycol conjugated drug of the present invention can be prepared efficiently and conveniently.

BRIEF DESCRIPTION OF THE DRAWINGS

FIG. 1 shows the preparation of drugs 44-2 and 27-134;

FIG. 2 shows the measured absorbance values of drugs 44-2 and 27-134;

FIG. 3 shows the inhibitory effect of drug 44-2 on MDA-MB-231 cancer cells;

FIG. 4 shows the inhibitory effect of drug 27-134 on Colo205 cancer cells;

FIG. 5 shows the $IC_{50}$ calculation results of drugs 44-2 and 27-134;

DETAILED DESCRIPTION

Figure 6:
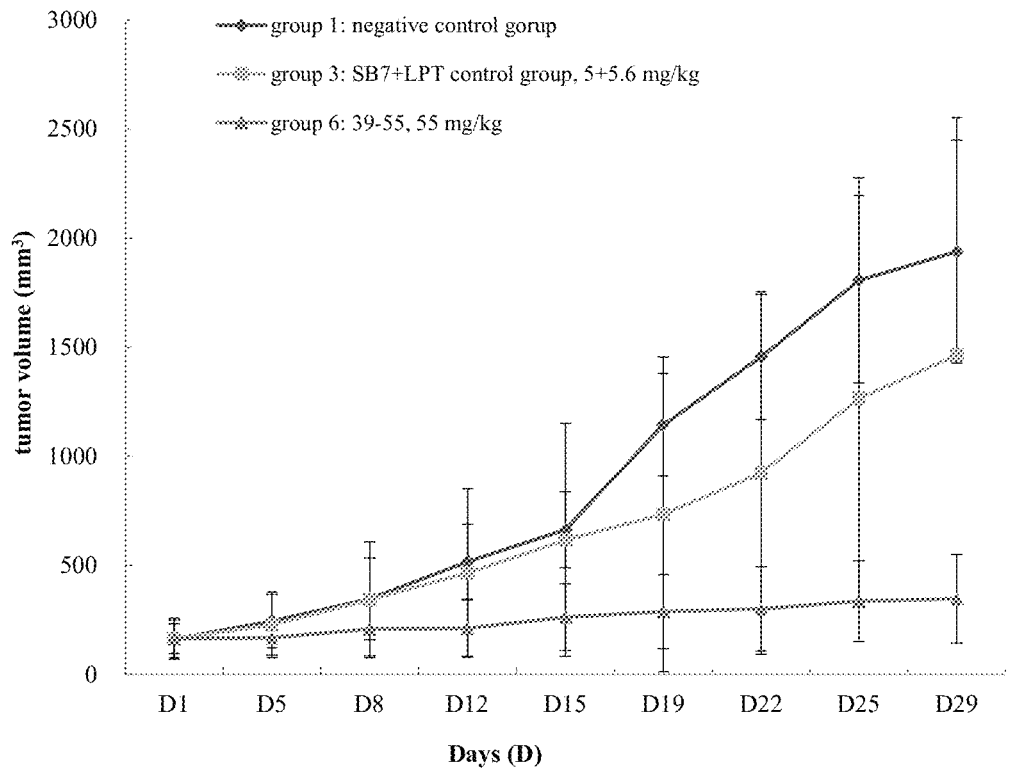
FIG. 6, FIG. 7 and FIG. 8 show the tumor growth trend of each group in Example 3.

The embodiments of the present invention will be described in detail below in conjunction with examples. However, those skilled in the art will understand that the following examples are only used to illustrate the present invention, not to limit the scope of the present invention. Those without specific conditions among the examples are generally implemented under conventional conditions or under conditions recommended by the manufacturers. The reagents or instruments used without specifying the manufacturers are all conventional products that may be purchased commercially.

The meanings of abbreviations in the examples are as follows:

| | | | | |
|---|---|---|---|---|
| G | Glycine residue | | L | Leucine residue |
| F | Phenylalanine residue | | Asp | Aspartic acid residue |
| E | Glutamate residue | | Glu | Glutamate residue |
| DMF | N,N-dimethylformamide | | TFA | Trifluoroacetic acid |
| t-Bu | Tert-butyl | | Bn | Benzyl |
| Boc | Tert-butoxycarbonyl | | Fmoc | Fluorenyl methoxycarbonyl |
| HOBT | 1-hydroxybenzotriazole | | Ts | p-toluenesulfonyl |
| HBTU | O-benzotriazole-tetramethylurea hexafluorophosphate | | LPT | Lapatinib |
| DIEA | N,N-diiso-propylethylamine | | SB7 | SB-743921 |
| EA | Ethyl acetate | | PCB | Palbociclib |
| TMP | 2,4,6-trimethylpyridine | | NPB | Niraparib |
| GFLG | Glycine-phenylalanine-leucine-glycine residue | | | |
| PyAOP | (3H-1,2,3-triazolo[4,5-b]pyridin-3-oxy)tris-1-pyrrolidinylphosphonium hexafluorophosphate | | | |
| LC | $NH_2-CH_2CH_2O-CH_2CH_2O-CH_2-COOH$ or $-NH-CH_2CH_2O-CH_2CH_2O-CH_2-CO-$ | | | |

The source and structure of some raw materials are as follows:
M-NH$_2$-2K•HCl
JenKem, mPEG—CH$_2$CH$_2$—NH$_2$HCl
M-NH$_2$-3K•HCl
JenKem, mPEG—CH$_2$CH$_2$—NH$_2$HCl
M-NH$_2$-5K•HCl
JenKem, mPEG—CH$_2$CH$_2$—NH$_2$HCl
M-SCM-10K

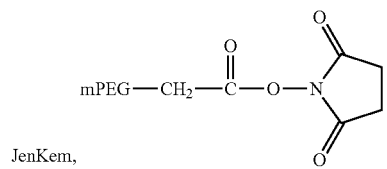

JenKem,

Example 1 Synthesis of Compound

1. Synthesis of 37-14 (Compound No. 10)
Synthetic route is as follows:

40

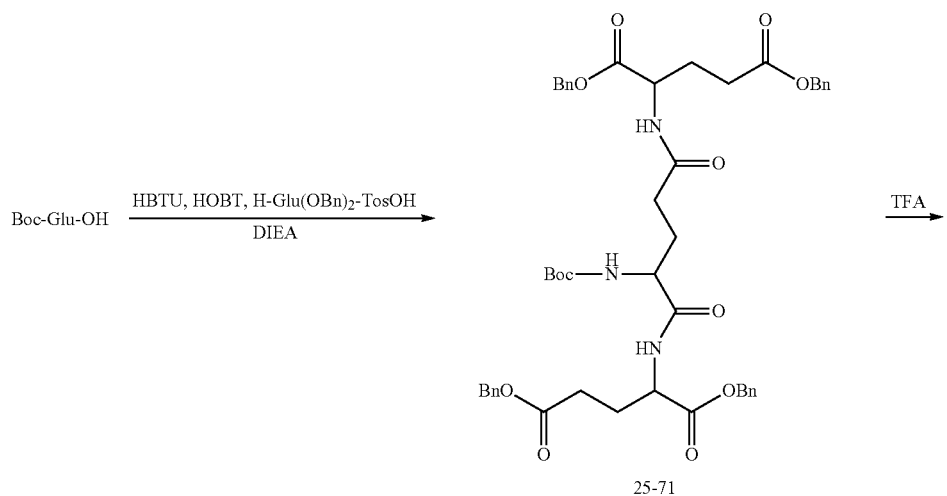

25-71

-continued
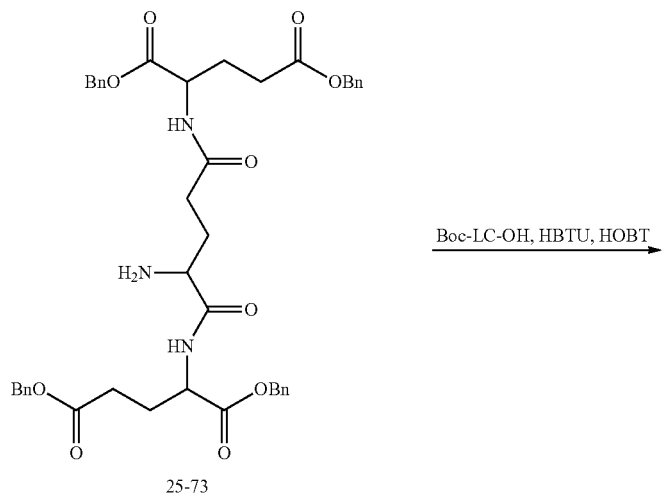
25-73
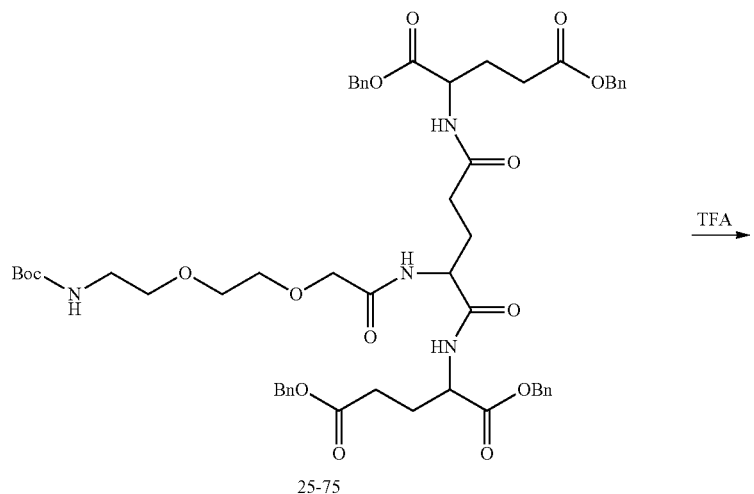
25-75
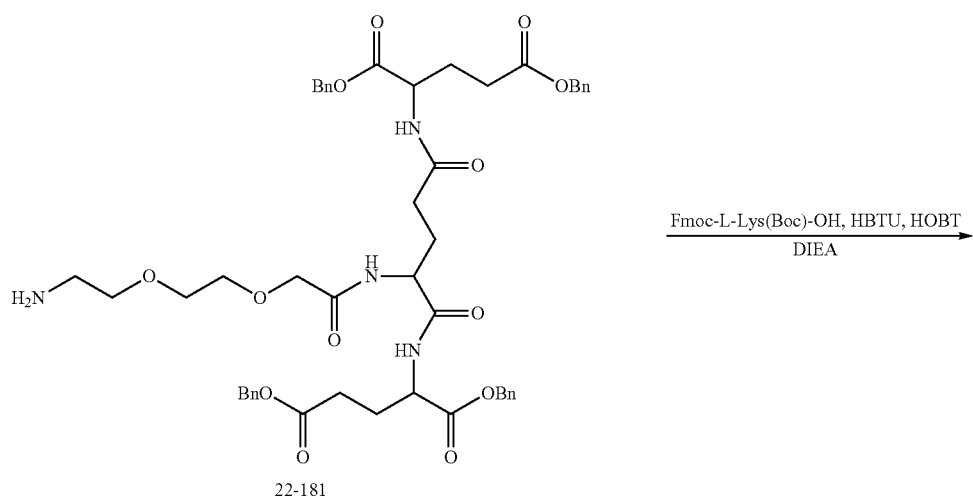
22-181

-continued
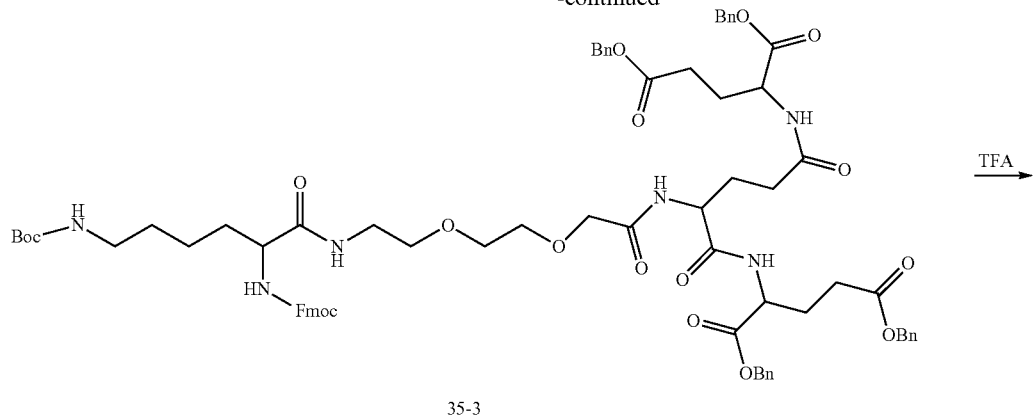
35-3
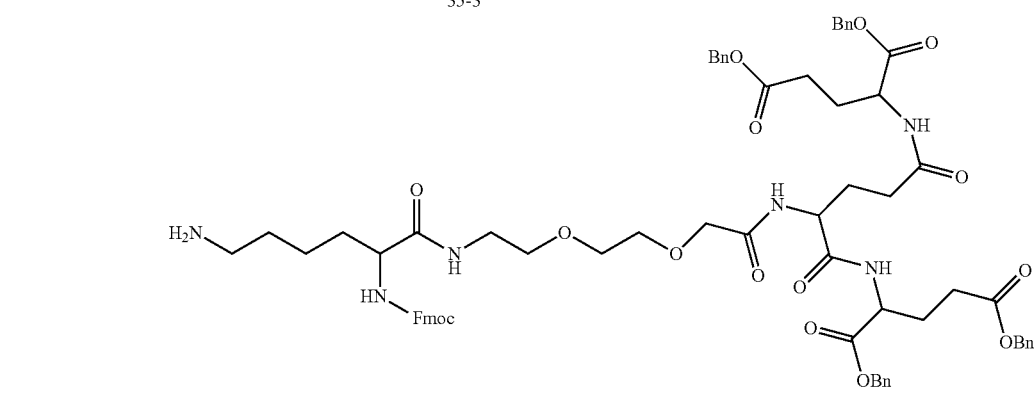
35-4
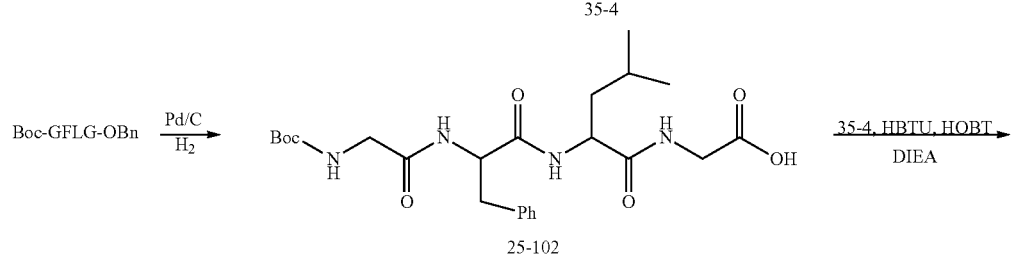
25-102
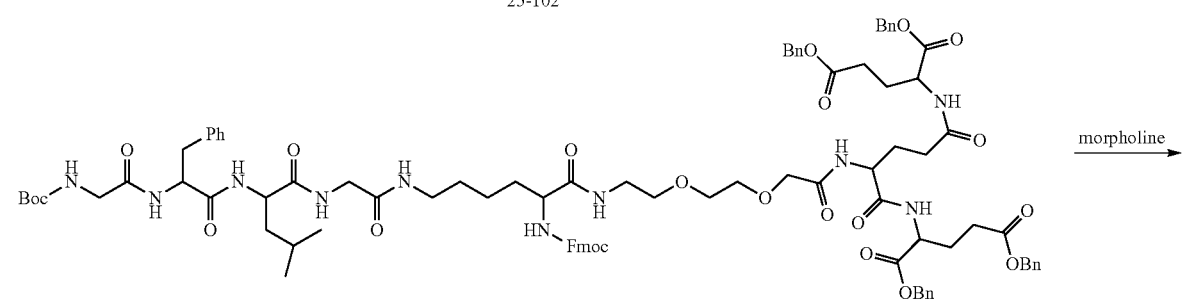
35-6
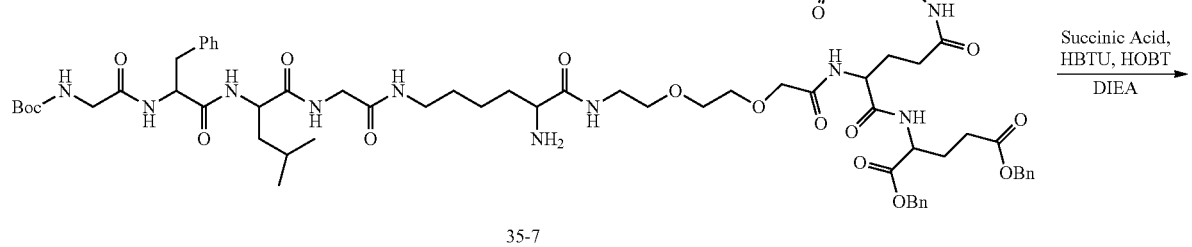
35-7

-continued
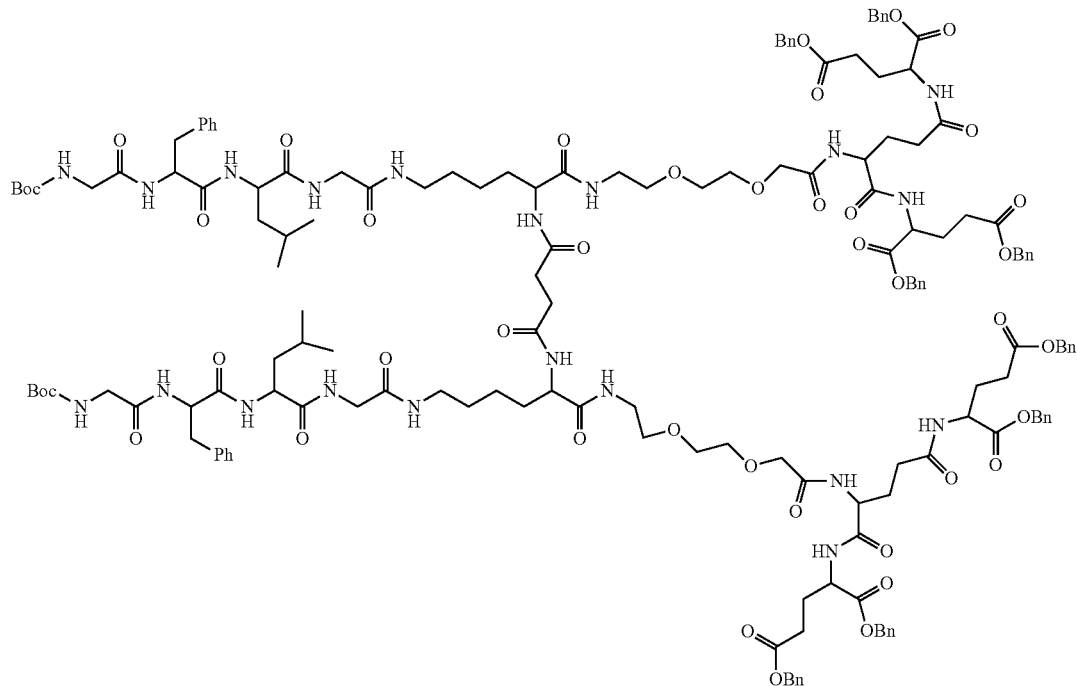
35-11
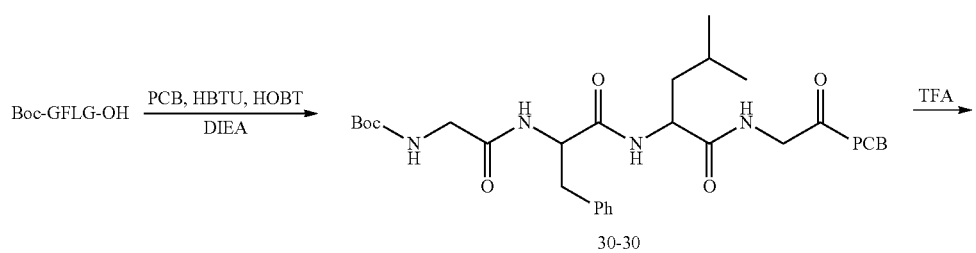
30-30
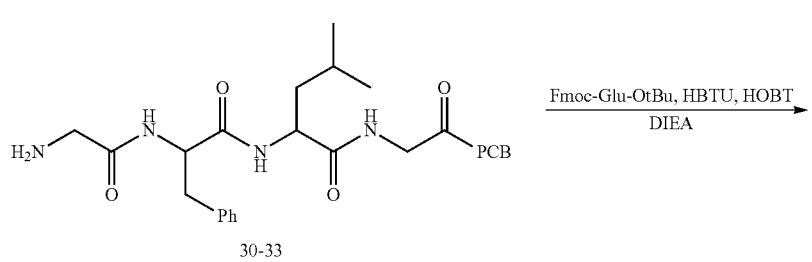
30-33
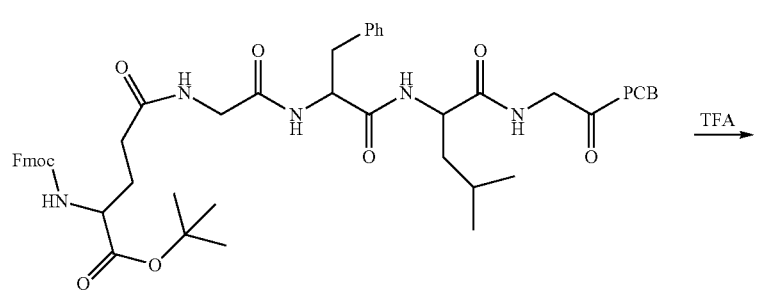
28-258

-continued
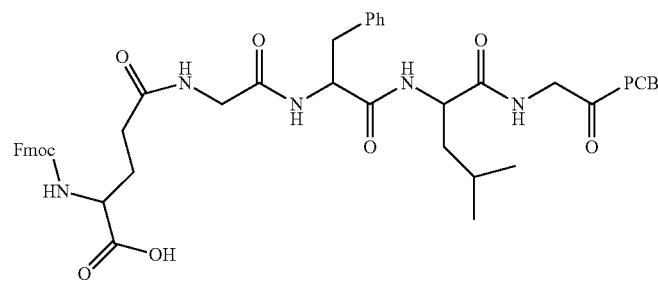
28-260
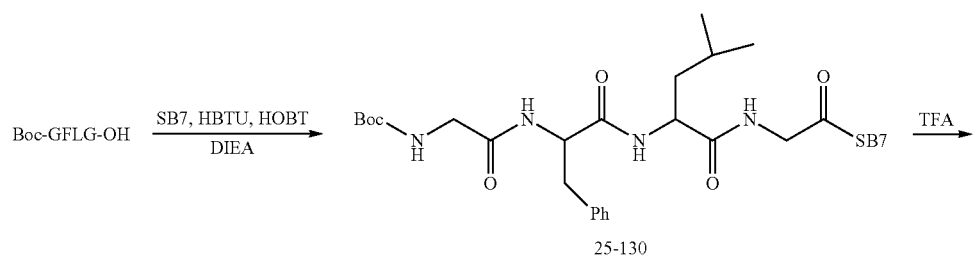
25-130
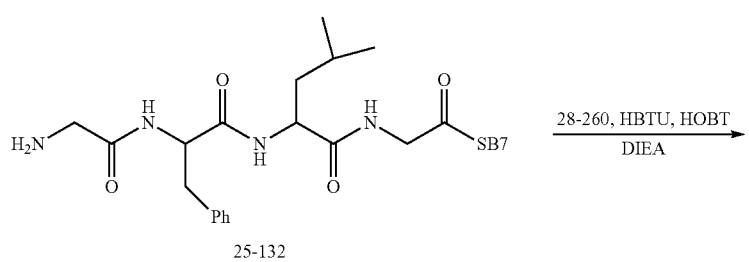
25-132
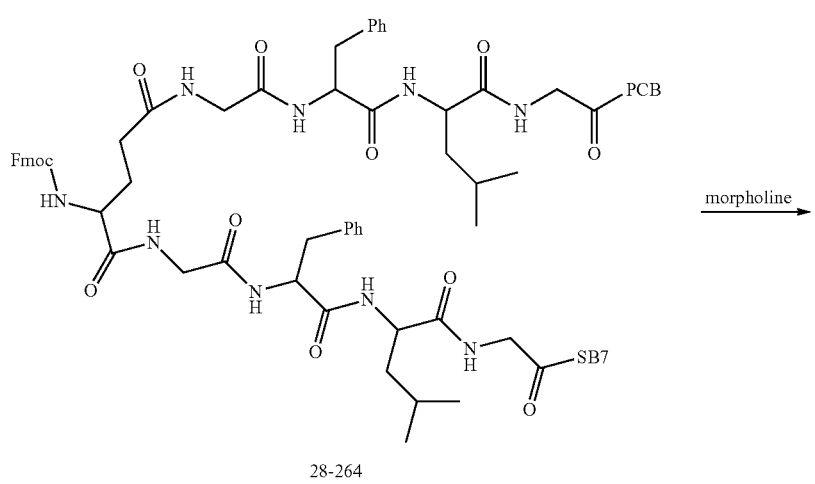
28-264

-continued
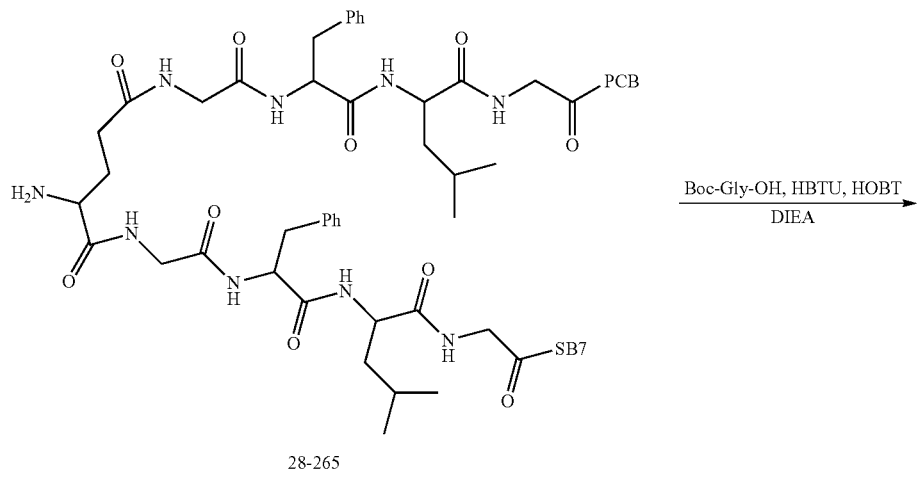
28-265
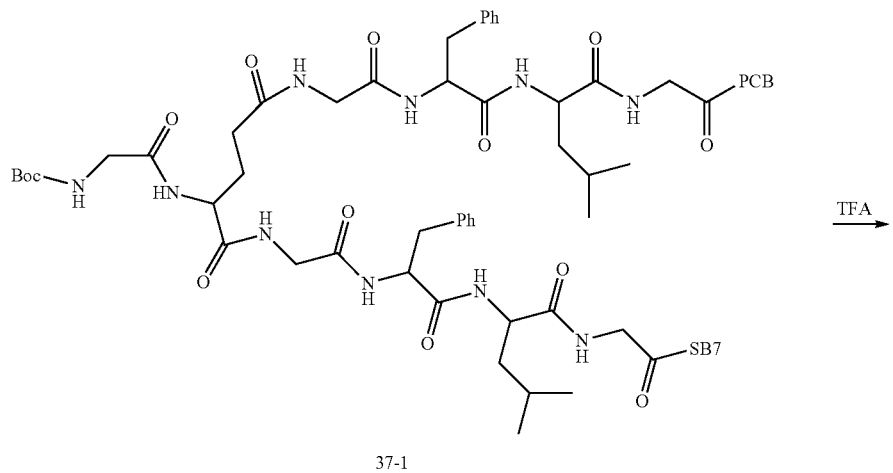
37-1
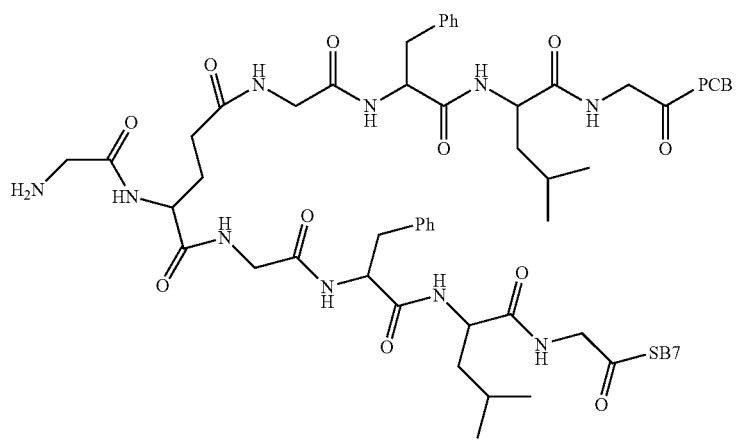
37-2

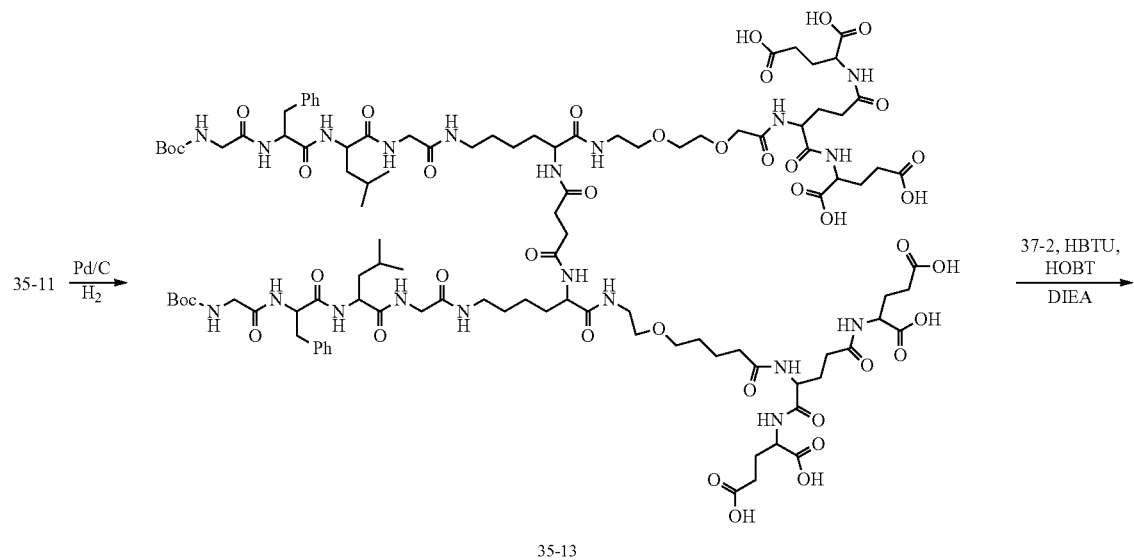
35-13

-continued
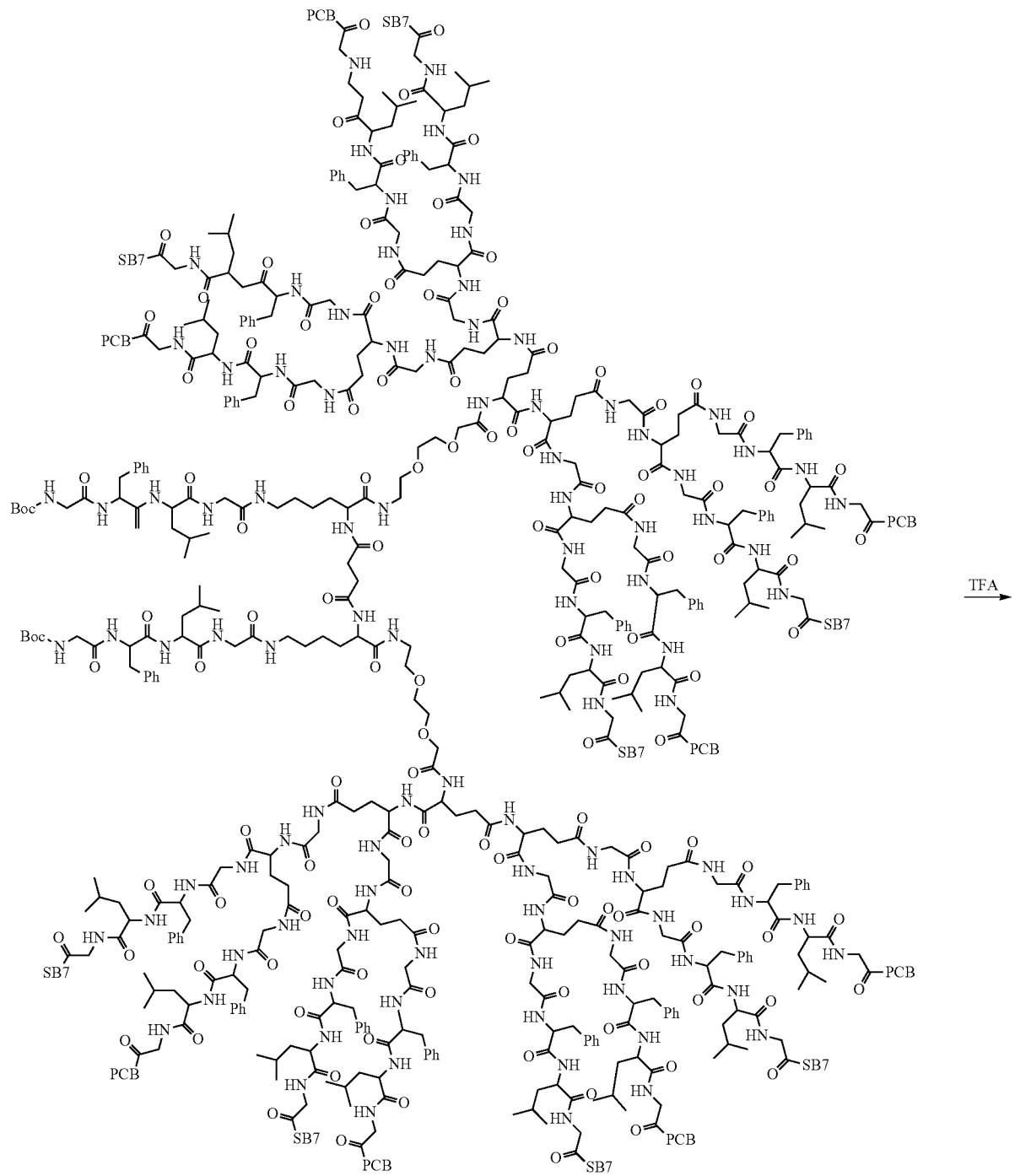
35-14
→ TFA

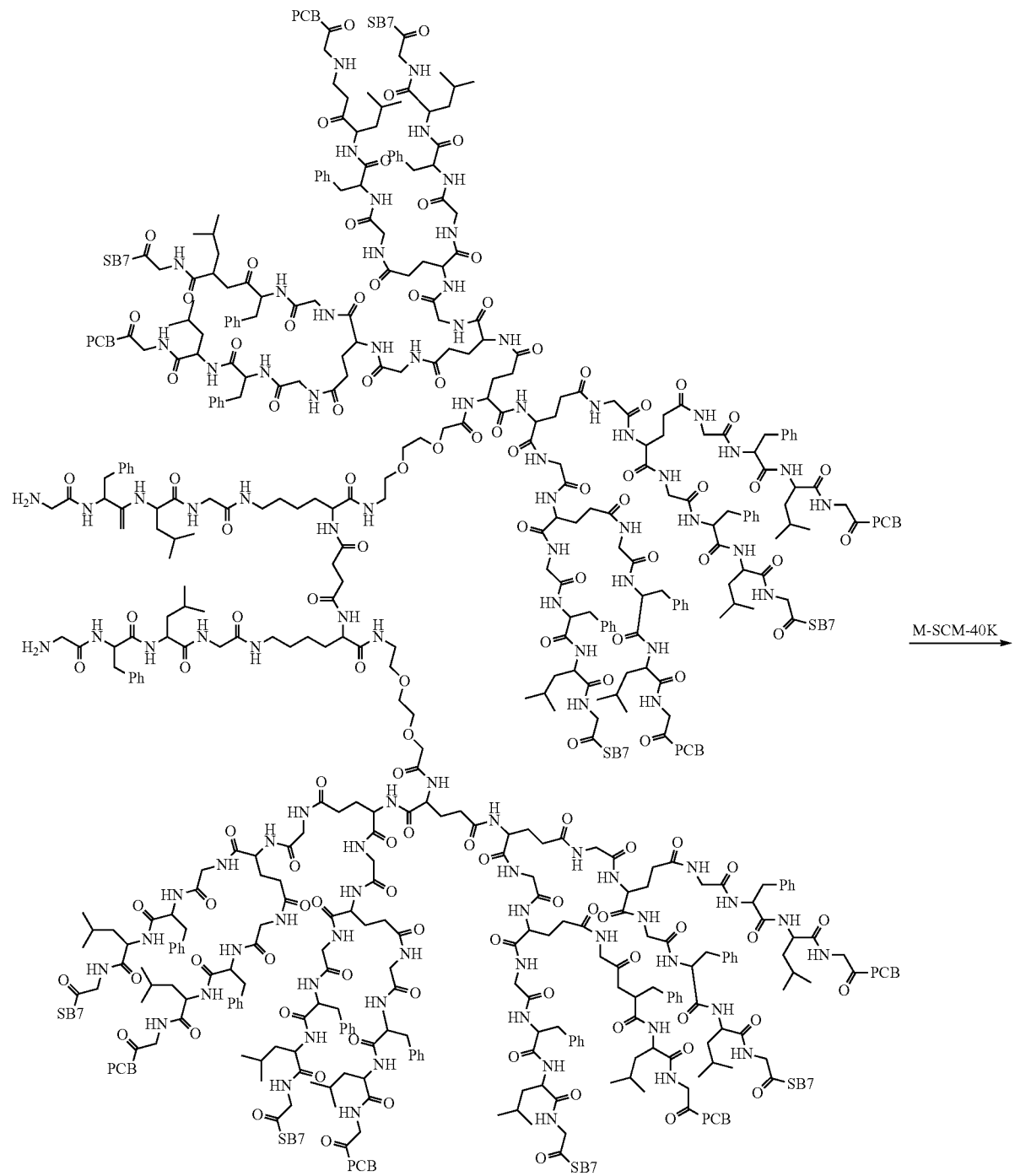
35-16
→ M-SCM-40K

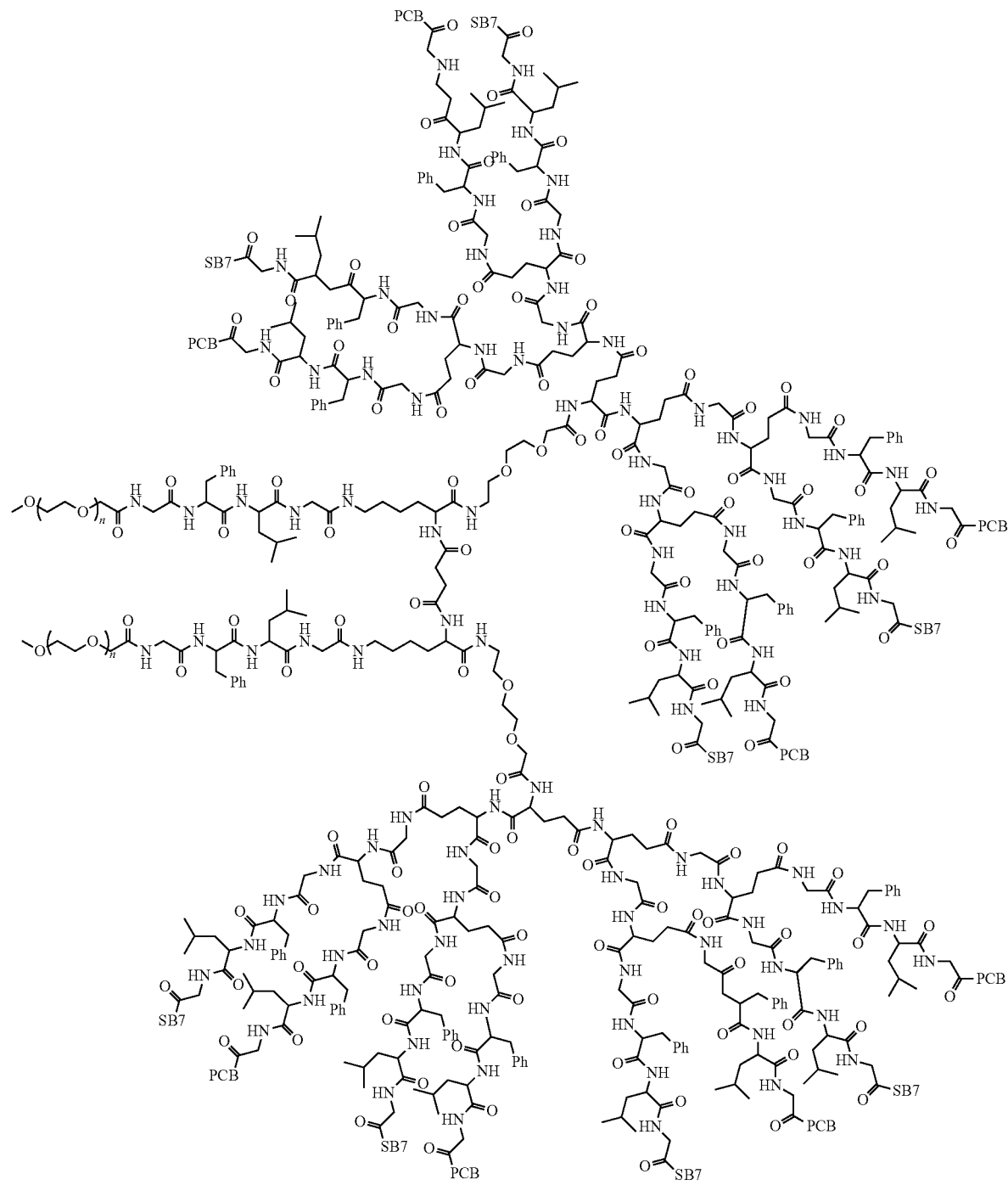
37-14

Details are given as follows:

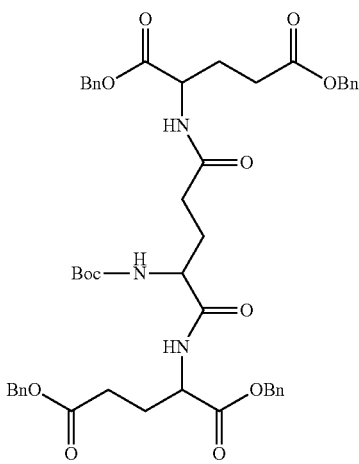

25-71

Boc-Glu-OH (purchased from Ark Pharm, 15.0 g, 60.6673 mmol), HBTU (purchased from Aladdin, 69.0225 g, 182.0022 mmol), HOBT (purchased from Innochem, 24.5921 g, 182.0022 mmol) and H-Glu (OBn)$_2$·TosOH (purchased from Ark Pharm, 63.6473 g, 127.4014 mmol) were added in a 1000 mL round-bottomed flask, and dissolved with DMF (300 mL), and the mixed solution was stirred to react at −5° C. for 30 minutes. Then DIEA (90.2 mL, 546.0066 mmol) was slowly added dropwise. At the end of the addition, the obtained solution continued to react with stirring at −5° C. for 1 hour, and then moved to room temperature and stirred to react overnight. At the end of the reaction, the reaction solution was transferred to a 2 L separatory funnel, saturated sodium bicarbonate solution (400 mL) and ethyl acetate (300 mL) were added to the separatory funnel, the obtained solution was shaken, and stood still for extraction, and then the organic phase was separated from the aqueous phase. Next, saturated sodium chloride solution (300 mL) was added to the organic phase, the obtained solution was shaken, and stood still for extraction, and then the organic phase was separated from the aqueous phase. Thereafter, saturated sodium chloride solution (300 mL) was further added to the organic phase, the obtained solution was shaken, and stood still for extraction, and then the organic phase was separated from the aqueous phase. Finally, the organic phase was concentrated, evaporated to dryness, and dried in an oven, thus obtaining the product 25-71: 67.9 g.

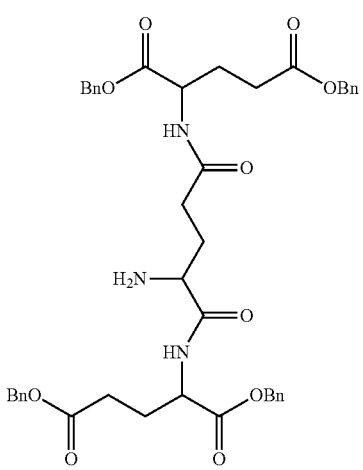

25-73

25-71 (52.5355 g, 60.6673 mmol) was added in a 500 mL round-bottomed flask, and dissolved with dichloromethane (10 mL), trifluoroacetic acid (TFA, 67.6 mL, 910.0101 mmol) was added with stirring, and then the mixed solution was stirred to react at room temperature overnight. At the end of the reaction, the reaction solution was first concentrated under reduced pressure and evaporated to remove the dichloromethane. The reaction solution was transferred to a 2 L separatory funnel, saturated sodium bicarbonate solution (400 mL) and ethyl acetate (300 mL) were added to the separatory funnel, the obtained solution was shaken, and stood still for extraction, and then the organic phase was separated from the aqueous phase. Next, saturated sodium bicarbonate solution (300 mL) was added to the organic phase, the obtained solution was shaken, and stood still for extraction, and then the organic phase was separated from the aqueous phase. Thereafter, deionized water (300 mL) was further added to the organic phase, the obtained solution was shaken, and stood still for extraction, and then the organic phase was separated from the aqueous phase. Finally, the organic phase was concentrated and evaporated to dryness. The obtained dry product was dissolved with a mixed solvent (100 mL) of 20% methanol/dichloromethane, 150 mL of silica gel powder was added, and the operations of evaporation, dry sample loading, column chromatography and elution with an elutent (60%-100% ethyl acetate: 40%-0% petroleum ether and 1%-4% methanol: 99%-96% ethyl acetate) were carried out. The elution product was then collected, concentrated, evaporated to dryness, and dried, thus obtaining the product 25-73: 44.4 g, yield: 95.56%.

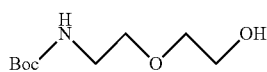

16-34

2-(2-aminoethoxy) ethanol (18.8680 g, 190.2226 mmol) was poured into a 500 mL round-bottomed flask, and diluted with dichloromethane (100 mL), then triethylamine (38.4972 mL, 380.4452 mmol) was added, (Boc) 20 (49.8261 g, 228.2671 mmol) was added slowly with stirring, and the mixed solution was stirred to react at room temperature. At the end of the reaction, the reaction solution was evaporated to dryness, then sodium bicarbonate powder was added, the obtained mixture was diluted with dichloromethane, silica gel powder was added, and the operations of evaporation, dry sample loading, column chromatography and elution with 50% ethyl acetate/petroleum ether were carried out, thus obtaining the product 27.3 g, yield 70%.

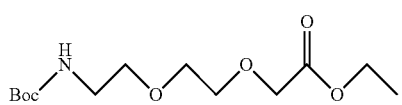

16-36

16-24 (27.3 g, 132.8144 mmol) was added in a 500 mL flask, nitrogen was introduced for protective purpose, the THF solution of potassium tert-butoxide was added, the mixed solution was placed at 0° C. to react, ethyl bromoacetate (17.6265 mL, 159.3773 mmol) was then added, and the obtained solution was first stirred for 3 hours, and then reacted at room temperature. At the end of the reaction, reaction solution was first evaporated to dryness, then deionized water and ethyl acetate were added for extraction, and the organic phase was separated. The aqueous phase was extracted with ethyl acetate until there was no product in the aqueous phase, and the obtained organic phases were combined. The organic phase was dried with anhydrous sodium sulfate powder, suction filtering was carried out, and the operations of dry sample loading, column chromatography and gradient elution with 30%-100% ethyl acetate/petroleum ether were carried out, thus obtaining the product 20 g, yield 52%.

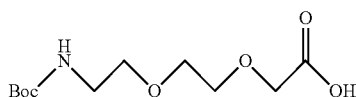

24-36

16-36 (17.9 g, 61.4402 mmol) was added in a 250 mL flask, 1,4-dioxane was added, lithium hydroxide (3.2386 g, 135.1685 mmol) was further added with stirring, and 30 min later, deionized water was added until the solution became clear. At the end of the reaction, the reaction solution was extracted three times (100 mL×3) with a mixed solvent of methyl tert-butyl ether and n-hexane (1:1). The aqueous phase was adjusted to pH=1 with concentrated hydrochloric acid, and then extracted three times with ethyl acetate (300 mL×3), the ethyl acetate phases were combined, the dissolution and washing with saturated sodium chloride was carried out three times (100 mL×3), and the obtained solution was concentrated. The operations of dry sample loading, column chromatography and elution with 40%400% ethyl acetate/petroleum ether were carried out, thus obtaining the product 10.1 g, yield 62%.

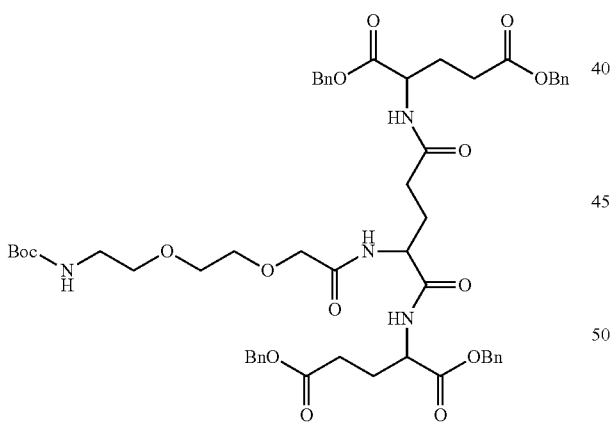

25-75

Boc-LC-OH (synthesized according to the method of synthesizing 24-36, 15.0236 g, 57.0608 mmol), HBTU (32.4596 g, 85.5912 mmol), HOBT (11.5651 g, 85.5912 mmol) and 25-73 (43.7 g, 57.0608 mmol) were added in a 500 mL round-bottomed flask, and dissolved with DMF (150 mL), and the mixed solution was stirred to react at −5° C. for 30 minutes. Then DIEA (61.5 mL, 342.3648 mmol) was slowly added dropwise. At the end of the addition, the obtained solution continued to react with stirring at −5° C. for 2 hours, and was then moved to room temperature and stirred to react overnight. At the end of the reaction, the reaction solution was first transferred to a 2 L separatory funnel, saturated sodium bicarbonate solution (400 mL) and ethyl acetate (300 mL) were added to the separatory funnel, the obtained solution was shaken, and stood still for extraction, and then the organic phase was separated from the aqueous phase. Next, saturated sodium chloride solution (300 mL) was added to the organic phase, the obtained solution was shaken, and stood still for extraction, and then the organic phase was separated from the aqueous phase. Thereafter, deionized water (300 mL) was further added to the organic phase, the obtained solution was shaken, and stood still for extraction, and then the organic phase was separated from the aqueous phase. Finally, the organic phase was concentrated and evaporated to dryness. The obtained dry product was dissolved with a mixed solvent (100 mL) of 20% methanol/dichloromethane, 150 mL of silica gel powder was added, and the operations of evaporation, dry sample loading, column chromatography and elution with an elutent (1% ammonia water: 1%-2% methanol: 98%-97% dichloromethane) were carried out. The elution product was then collected, concentrated and evaporated to dryness, thus obtaining the product 25-75: 42.1 g, yield: 72.97%.

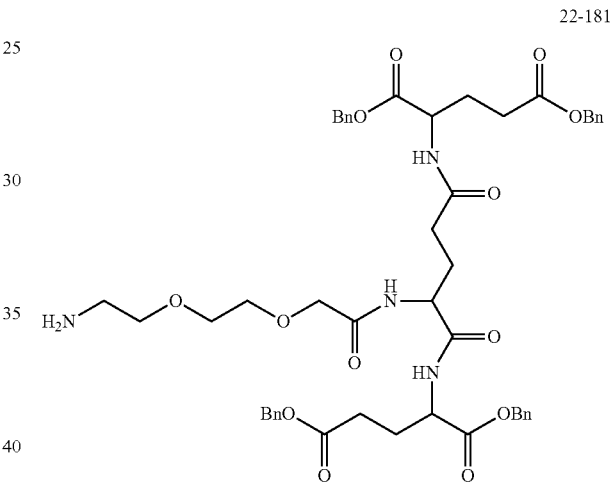

22-181

25-75 (26.7 g, 26.4064 mmol) was added in a 500 mL round-bottomed flask, and dissolved with dichloromethane (10 mL), trifluoroacetic acid (TFA, 19.6 mL, 264.064 mmol) was added with stirring, and then the mixed solution was stirred to react at room temperature overnight. At the end of the reaction, the reaction solution was first concentrated under reduced pressure and evaporated to remove the dichloromethane. Then, the reaction solution was first transferred to a 2 L separatory funnel, saturated sodium bicarbonate solution (400 mL) and ethyl acetate (300 mL) were added to the separatory funnel, the obtained solution was shaken, and stood still for extraction, and then the organic phase was separated from the aqueous phase. Next, saturated sodium chloride solution (300 mL) was added to the organic phase, the obtained solution was shaken, and stood still for extraction, and then the organic phase was separated from the aqueous phase. Thereafter, deionized water (300 mL) was further added to the organic phase, the obtained solution was shaken, and stood still for extraction, and then the organic phase was separated from the aqueous phase. Finally, the organic phase was concentrated, evaporated to dryness, and dried in an oven, thus obtaining the product 22-181: 20.3 g, yield: 84.2%.

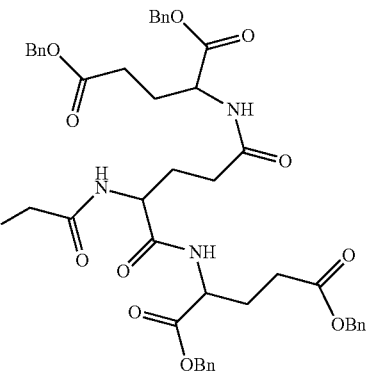

35-3

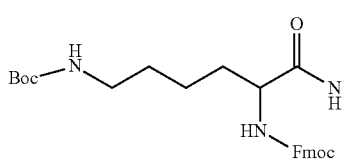

Fmoc-L-Lys (Boc)-OH (purchased from Accela, 1.39 g, 2.967 mmol), 22-181 (2.70 g, 2.967 mmol), HBTU (1.69 g, 4.4505 mmol), HOBT (0.6 g, 4.4505 mmol) were added in a 100 mL flask, and the mixed solution was stirred to react at −5° C. for 30 minutes. Then DIEA (2.21 mL, 13.3515 mmol) was slowly added dropwise. At the end of the addition, the obtained solution reacted at −5° C. for 1 hour, and was then moved to room temperature and stirred to react overnight. At the end of the reaction, the reaction solution was transferred to a 1 L separatory funnel and extracted with saturated saline solution (200 mL) and ethyl acetate (250 mL), and the organic phase was separated. The aqueous phase was washed with ethyl acetate (200 mL×1), and the obtained organic phases were combined. The organic phase was washed with saturated saline solution (200 mL×1), concentrated and evaporated to dryness, thus obtaining the product 35-3: 4.0 g.

solution. Such operations were repeated three times. Finally, a viscous oily product was obtained. The oily product was dried to give 35-4: 3.74 g.

25-102

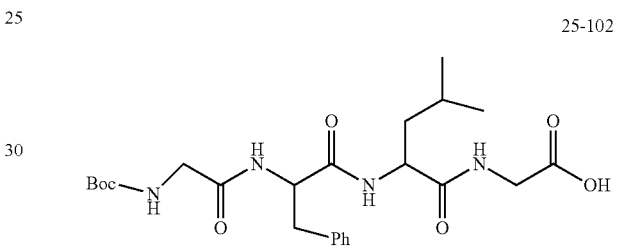

35-4

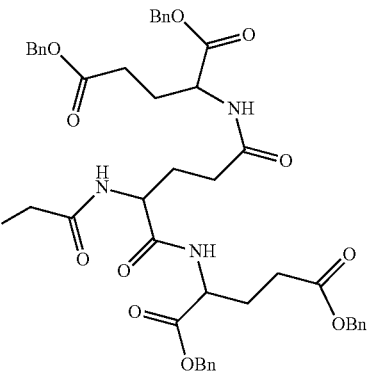

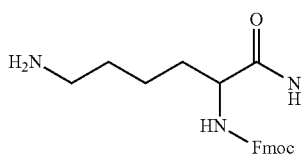

35-3 (4.04 g, 2.967 mmol) was added in a 250 mL round-bottomed flask, and dissolved with dichloromethane (10 mL), trifluoroacetic acid (3.31 mL, 44.505 mmol) was added with stirring, and then the mixed solution was stirred to react at room temperature overnight. At the end of the reaction, the reaction solution was first concentrated to a small amount. The operation of washing with stirring was carried out with the addition of n-hexane (120 mL) to remove the trifluoroacetic acid, the supernatant was discarded, and n-hexane (120 mL) was added to the lower oily Boc-GFLG-OBn (as synthesized in accordance with literature, 6.8282 g, 11.7184 mmol) and 10% Pd/C (50 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF (60 mL) until it did not contain any product, thus obtaining a reaction product solution.

35-6

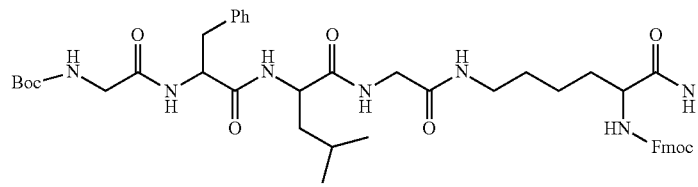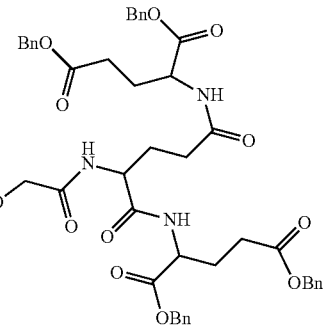

35-4 (3.74 g, 32.967 mmol), 25-102 (1.75 g, 3.560 mmol), HBTU (1.69 g, 4.451 mmol), HOBT (0.6 g, 4.451 mmol) were added in a 250 mL flask, and dissolved with DMF (30 mL), and the mixed solution was stirred to react at −5° C. for 30 minutes. Then DIEA (4.4 mL, 26.703 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×2), evaporated to dryness, and dried in an oven, thus obtaining the product 35-6: 5.1 g.

35-6 (5.1 g, 2.967 mmol) was added in a 250 mL flask, and dissolved with DMF (20 mL), morpholine (3.9 mL, 44.505 mmol) was added, and the mixed solution was stirred to react at room temperature for 1 hour. At the end of the reaction, the reaction solution was transferred to a 1 L separatory funnel, and extracted with saturated saline solution (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×1), and concentrated. Silica gel powder (30 g) was added, and the obtained mixture was then evaporated to dryness to obtain a powdery solid. The operations of dry sample loading, column chromatography and elution with a dichloromethane mixed solution containing 1% of ammonia water and 3%-5% of methanol were carried out. The elution product was then collected, concentrated, evaporated to dryness, and dried in an oven, thus obtaining the product 35-7: 3.4 g, yield 77%.

35-7

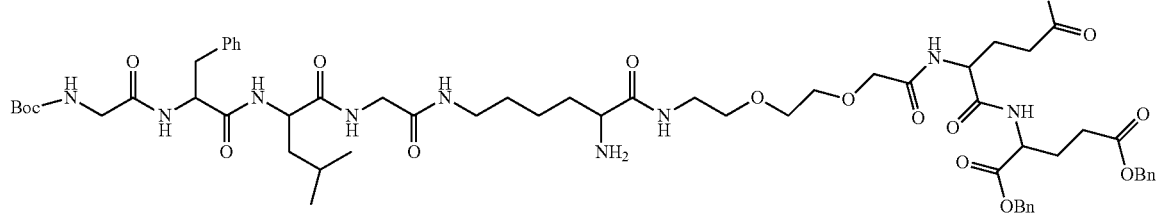

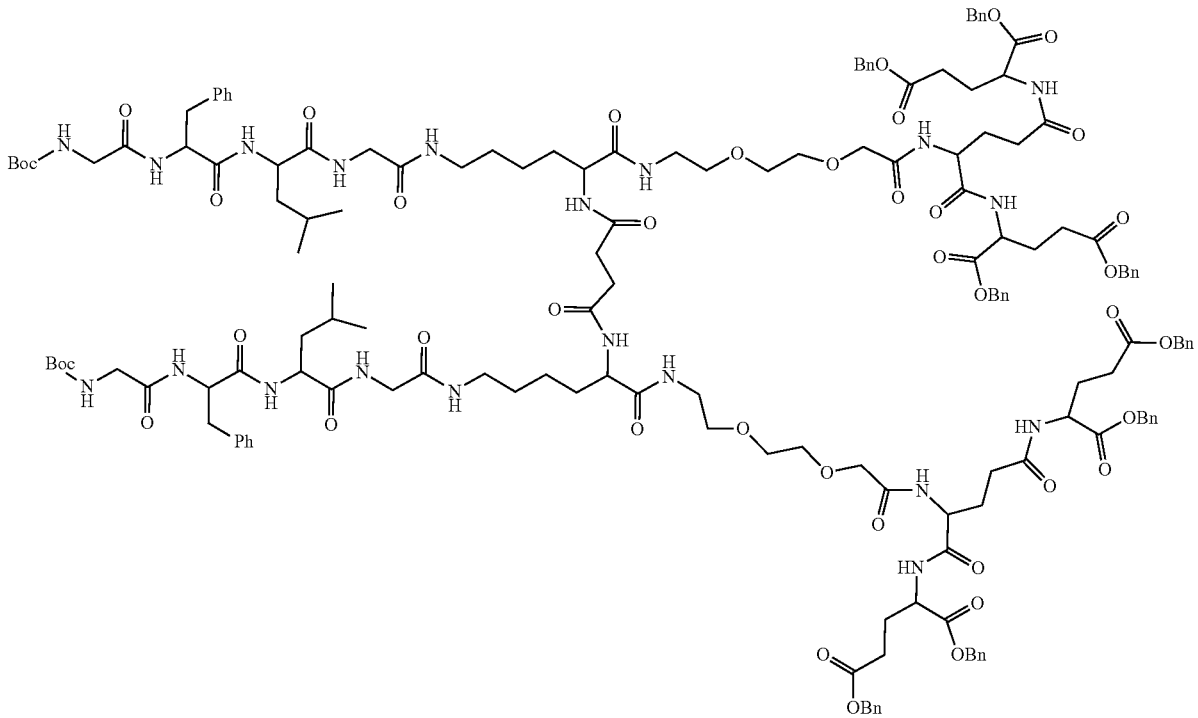

35-7 (3.4 g, 2.27 mmol), succinic acid (0.12 g, 1.03 mmol, purchased from InnoChem), HBTU (1.17 g, 3.09 mmol), HOBT (0.42 g, 3.09 mmol) were added in a 500 mL flask, and the mixed solution was stirred to react at −5° C. for about 30 minutes. Then DIEA (1.53 mL, 9.27 mmol) was slowly added dropwise. At the end of the addition, the obtained solution reacted at −5° C. for 1 hour, and was then moved to room temperature and stirred to react overnight. At the end of the reaction, the reaction solution was transferred to a 1 L separatory funnel, and extracted with saturated sodium bicarbonate solution (200 mL) and ethyl acetate (250 mL), and the organic phase was separated. The aqueous phase was washed with ethyl acetate (200 mL×3), and the obtained organic phases were combined. The organic phase was washed with saturated saline solution (200 mL×2), and concentrated. Silica gel powder (30 g) was added, and the obtained mixture was then evaporated to dryness to obtain a powdery solid. The operations of dry sample loading, column chromatography, and elution with a dichloromethane mixed solution containing 1% of ammonia water and 5% of methanol were carried out. The elution product was then collected, concentrated, evaporated to dryness, and dried in an oven, thus obtaining the product 35-11: 3.0 g, yield 96%.

$^1$H-NMR (400 MHz, DMSO-$d_6$) δ 8.59-8.43 (m, 1H), 8.36-8.26 (m, 2H), 8.20-8.14 (m, 1H), 8.01-7.87 (m, 6H), 7.78-7.61 (m, 3H), 7.38-7.11 (m, 55H), 6.93-6.95 (m, 2H), 5.21-4.97 (m, 15H), 4.53-4.52 (m, 1H), 4.42-4.22 (m, 7H), 4.15-4.13 (m, 1H), 3.89-3.87 (m, 3H), 3.76-3.43 (m, 19H), 3.18-3.16 (m, 5H), 2.31-2.98 (m, 7H), 2.84-2.64 (m, 6H), 2.44-2.38 (m, 8H), 2.37-2.28 (m, 8H), 2.21-2.10 (m, 5H), 2.08-1.81 (m, 11H), 1.81-1.68 (m, 3H), 1.51-1.40 (m, 4H), 1.50-1.41 (m, 7H), 1.29-1.16 (m, 18H), 1.28-1.16 (m, 12H), 0.93-0.75 (m, 12H).

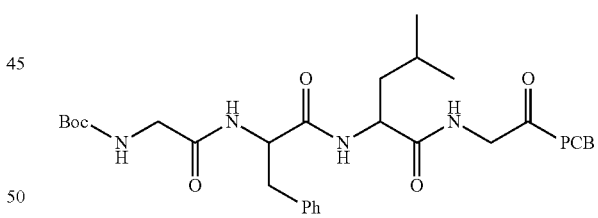

Boc-GFLG-OH (synthesized according to the method of synthesizing 25-102, 13.97 mmol), PCB (5 g, 11.17 mmol), HBTU (6.35 g, 16.76 mmol) and HOBT (2.26 g, 16.76 mmol) were added in a 500 mL round-bottomed flask, and dissolved with DMF (100 mL), and the mixed solution was stirred to react at −5° C. for 30 minutes. Then DIEA (8.31 mL, 50.28 mmol) was slowly added dropwise. At the end of the addition, the obtained solution reacted at the low temperature for 2 hours, and was then moved to room temperature and stirred to react overnight. At the end of the reaction, the filter cake was washed with deionized water (1000 mL), and a yellow solid was separated out by precipitation, and dried, thus obtaining the product 10.3 g.

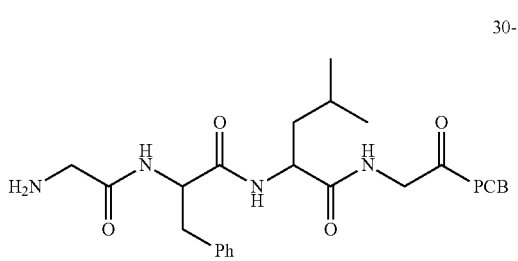

30-30 (10.3 g, 11.17 mmol) was added in a 500 mL round-bottomed flask, and dissolved with dichloromethane (50 mL), then TFA (12.45 mL, 167.55 mmol) was added, and the mixed solution was stirred to react at room temperature overnight. At the end of the reaction, the reaction solution was concentrated under reduced pressure, and then precipitated three times with n-hexane (50 mL) and methyl tert-butyl ether (400 mL). A solid product was obtained by filtration, and dissolved with dichloromethane and methanol. The operations of dry sample loading, column chromatography and elution with a dichloromethane mixed solution containing 5% methanol and 1% ammonia water were carried out. The elution product was then collected, concentrated, and dried, thus obtaining the product 8.6 g, yield 94%.

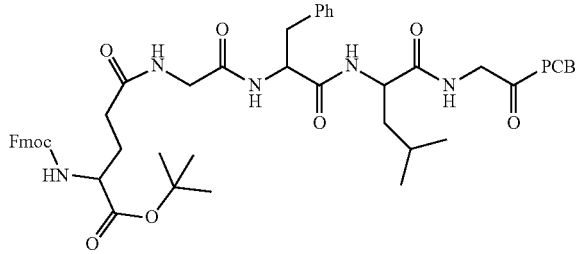

Fmoc-Glu-OtBu (3.223 g, 7.5915 mmol, purchased from Ark pharm), 30-33 (synthesized according to the method of synthesizing 30-33) (5.2 g, 6.3263 mmol), HBTU (3.5988 g, 9.4895 mmol), HOBT (1.282 g, 9.4895 mmol) were added in a 500 mL flask, and stirred for 10 minutes. Then DIEA (4.7 mL, 28.4684 mmol) was slowly added dropwise. At the end of the addition, the obtained solution was stirred to react at 0° C. overnight. At the end of the reaction, n-hexane (300 mL) and methyl tert-butyl ether (50 mL) were added for precipitation, the supernatant was discarded, and n-hexane (300 mL) and methyl tert-butyl ether (50 mL) were added to the lower oily liquid phase for further precipitation, and such operations were repeated five times, to obtain a viscous oily product. The oily product was then dried, thus obtaining the product 28-258: 7.78 g.

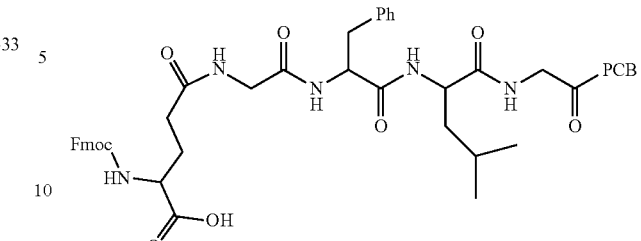

28-258 (7.78 g, 6.3263 mmol) was added in a 500 mL flask, and dissolved with dichloromethane (30 mL), TFA (9/396 mL, 126.52 mmol) was added with stirring, and the mixed solution was stirred to react at room temperature overnight. At the end of the reaction, the reaction solution was concentrated, methyl tert-butyl ether (300 mL) was added to the concentrated reaction solution to separate out a solid, and suction filtering was carried out. The filter cake was washed with methyl tert-butyl ether (80 mL×3), and dried, thus obtaining the product 28-260: 8.1 g.

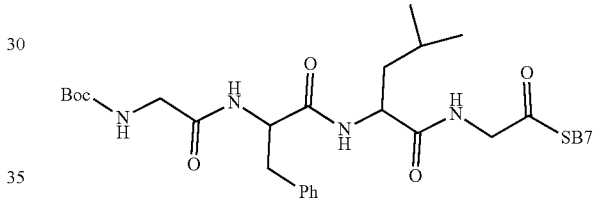

Boc-GFLG-OH (synthesized according to the method of synthesizing 25-102, 4.9738 g, 10.0977 mmol), HBTU (4.4186 g, 11.6513 mmol), HOBT (1.5743 g, 11.6513 mmol) and SB-743291 (4.0162 g, 7.7675 mmol) were added in a 500 mL round-bottomed flask, and dissolved with DMF (60 mL), and the mixed solution was stirred to react at −5° C. for 30 minutes. Then DIEA (5.8 mL, 34.9538 mmol) was slowly added dropwise. At the end of the addition, the obtained solution continued to react with stirring at −5° C. for 1 hour, and was then moved to room temperature and stirred to react overnight. At the end of the reaction, the reaction solution was first transferred to a 2 L separatory funnel, saturated sodium bicarbonate solution (400 mL) and ethyl acetate (300 mL) were added to the separatory funnel, the obtained solution was shaken, and stood still for extraction, and then the organic phase was separated from the aqueous phase. Next, saturated sodium chloride solution (300 mL) was added to the organic phase, the obtained solution was shaken, and stood still for extraction, and then the organic phase was separated from the aqueous phase. Thereafter, deionized water (300 mL) was further added to the organic phase, the obtained solution was shaken, and stood still for extraction, and then the organic phase was separated from the aqueous phase. Finally, the organic phase was concentrated, evaporated to dryness, and dried in an oven, thus obtaining the product 25-130: 7.7023 g.

25-132

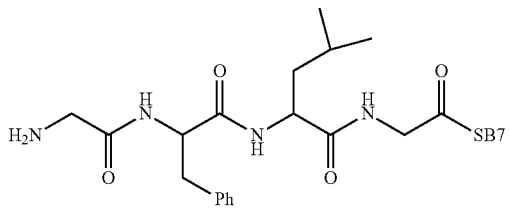

25-130 (7.7023 g, 7.7675 mmol) was added in a 500 mL round-bottomed flask, and dissolved with dichloromethane (5 mL), TFA (8.7 mL, 116.5125 mmol) was added with stirring, and the mixed solution was stirred to react at room temperature overnight. At the end of the reaction, the reaction solution was evaporated to remove the dichloromethane. Then, n-hexane (150 mL) and methyl tert-butyl ether (30 mL) were added to the obtained solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), methyl tert-butyl ether (150 mL) was added to the obtained solution for precipitation to separate out a powdery solid, and then a solid product was obtained by filtering. The solid product was dissolved with a mixed solvent (50 mL) of 20% methanol/dichloromethane, silica gel powder (80 mL) was added to the obtained solution, and the operations of evaporation, dry sample loading, column chromatography, and elution with an elutent (1% ammonia water: 3%-4% methanol: 96%-95% dichloromethane) were carried out. The elution product was then collected, concentrated and evaporated to dryness, thus obtaining the product 25-132: 5.4 g, yield: 77.98%.

28-264

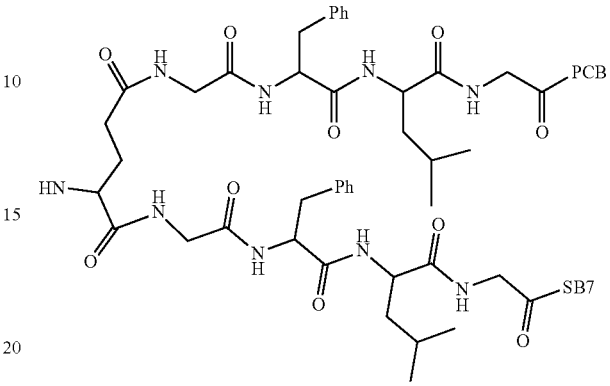

28-260 (7.4 g, 6.3263 mmol), 25-132 (5.9218 g, 6.6426 mmol), HBTU (3.5988 g, 9.4895 mmol), HOBT (1.2823 g, 9.4895 mmol) were added in a 500 mL flask, and dissolved with DMF (110 mL), and the mixed solution was stirred to react at 0° C. for 10 minutes. Then DIEA (4.7 mL, 28.4684 mmol) was slowly added dropwise. At the end of the addition, the obtained solution was stirred to react at 0° C. overnight. At the end of the reaction, n-hexane (300 mL) and methyl tert-butyl ether (50 mL) were added for precipitation, the supernatant was discarded, and n-hexane (300 mL) and methyl tert-butyl ether (50 mL) were added to the lower oily liquid phase for further precipitation, and such operations were repeated six times to obtain a viscous oily product. The oily product was dissolved with methanol (10 mL) and dichloromethane (40 mL), methyl tert-butyl ether (450 mL) was added to the obtained solution to separate out a solid, and then filtering was carried out. The filter cake was washed with methyl tert-butyl ether (100 mL×3), and dried, thus obtaining the product 28-264: 12.9 g.

28-265

28-264 (12.9 g, 6.3263 mmol) was added in a 500 mL flask, and dissolved with DMF (50 mL), morpholine (16.5 mL, 189.789 mmol) was added, and the mixed solution was stirred to react at room temperature for 1 hour. At the end of the reaction, n-hexane (300 mL) and methyl tert-butyl ether (50 mL) were added for precipitation to layer the reaction solution, the supernatant was discarded, and n-hexane (300 mL) and methyl tert-butyl ether (50 mL) were added to the lower oily liquid phase for further precipitation, and such operations were repeated five times, to obtain a viscous oily product. The oily product was dissolved with dichloromethane (20 mL) and methanol (80 mL), methyl tert-butyl ether (350 mL) was added to the obtained solution to separate out a solid, and then filtering was carried out. The filter cake was washed with methyl tert-butyl ether (120 mL×2), and dried, thus obtaining the product 28-265: 11.5 g.

37-1

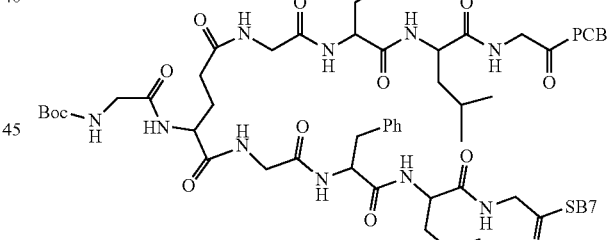

28-265 (11.54 g, 6.3263 mmol), Boc-Gly-OH (1.3299 g, 7.5916 mmol, purchased from Ark pharm), HBTU (3.5988 g, 9.4895 mmol), HOBT (1.2823 g, 9.4895 mmol) were added in a 250 mL flask, and dissolved with DMF (80 mL), and the mixed solution was stirred to react at −5° C. for 10 minutes. Then DIEA (4.7053 mL, 28.4684 mmol) was slowly added dropwise. At the end of the addition, the obtained solution continued to react at −5° C. for 30 minutes, and was then moved to room temperature and stirred to react overnight. At the end of the reaction, n-hexane (300 mL) and methyl tert-butyl ether (50 mL) were added for precipitation, the supernatant was discarded, and n-hexane (300 mL) and methyl tert-butyl ether (50 mL) were added to the lower oily liquid phase for further precipitation, and such operations were repeated four times, to obtain a viscous oily product. Then, dichloromethane (70 mL) and methyl tert-butyl ether (350 mL) were added to the oily product to separate out a solid, and filtering was carried out. The filter cake was washed with methyl tert-butyl ether (50 mL×3), and dried in a vacuum oven, thus obtaining the product 37-1: 12.5 g.

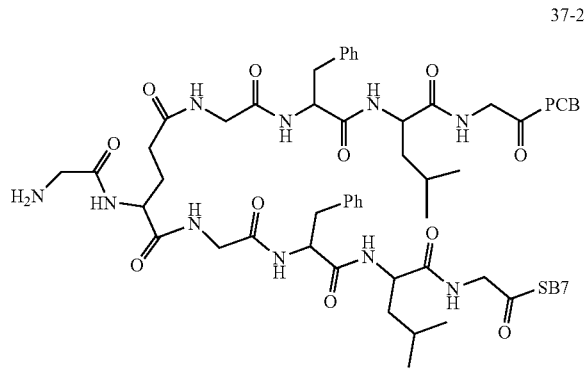

37-2

37-1 (12.537 g, 6.3263 mmol) was added in a 500 mL flask, and dissolved with dichloromethane (30 mL), TFA (14.09 mL, 189.789 mmol) was added, and the mixed solution was stirred to react at room temperature overnight. At the end of the reaction, methyl tert-butyl ether (250 mL) was added to the reaction solution to separate out a solid, and suction filtering was carried out. The filter cake was washed with methyl tert-butyl ether (100 mL×3), and dissolved with a mixed solvent of methanol (60 mL) and dichloromethane (240 mL), silica gel powder (25 g) was added, and the obtained mixture was then evaporated to dryness to obtain a powdery solid. The the operations of dry sample loading, column chromatography and elution with a dichloromethane mixed solution containing 15% ammonia water and 7%-8% methanol were carried out. The elution product was then collected, concentrated, evaporated to dryness, and dried in a vacuum oven, thus obtaining the product 37-2: 9.7 g, yield 82%.

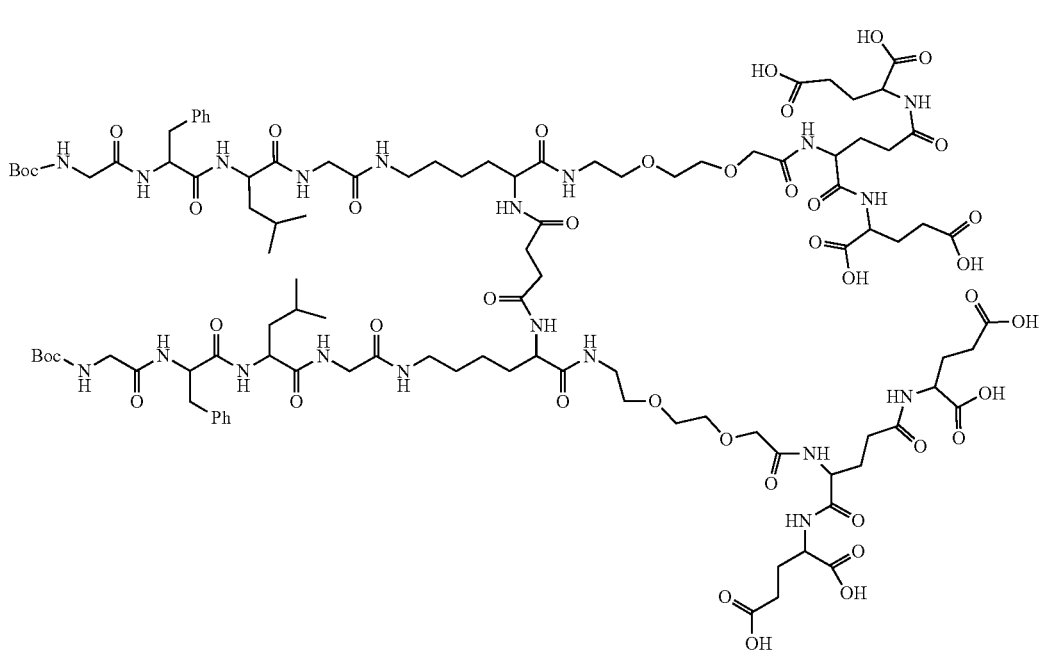

35-13

35-11 (0.38 g, 0.124 mmol) and Pd/C (0.0210 g) was added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was filtered with diatomaceous earth, and the diatomaceous earth was washed with DMF (20 mL×3), to obtain a DMF solution containing 35-13.

35-14

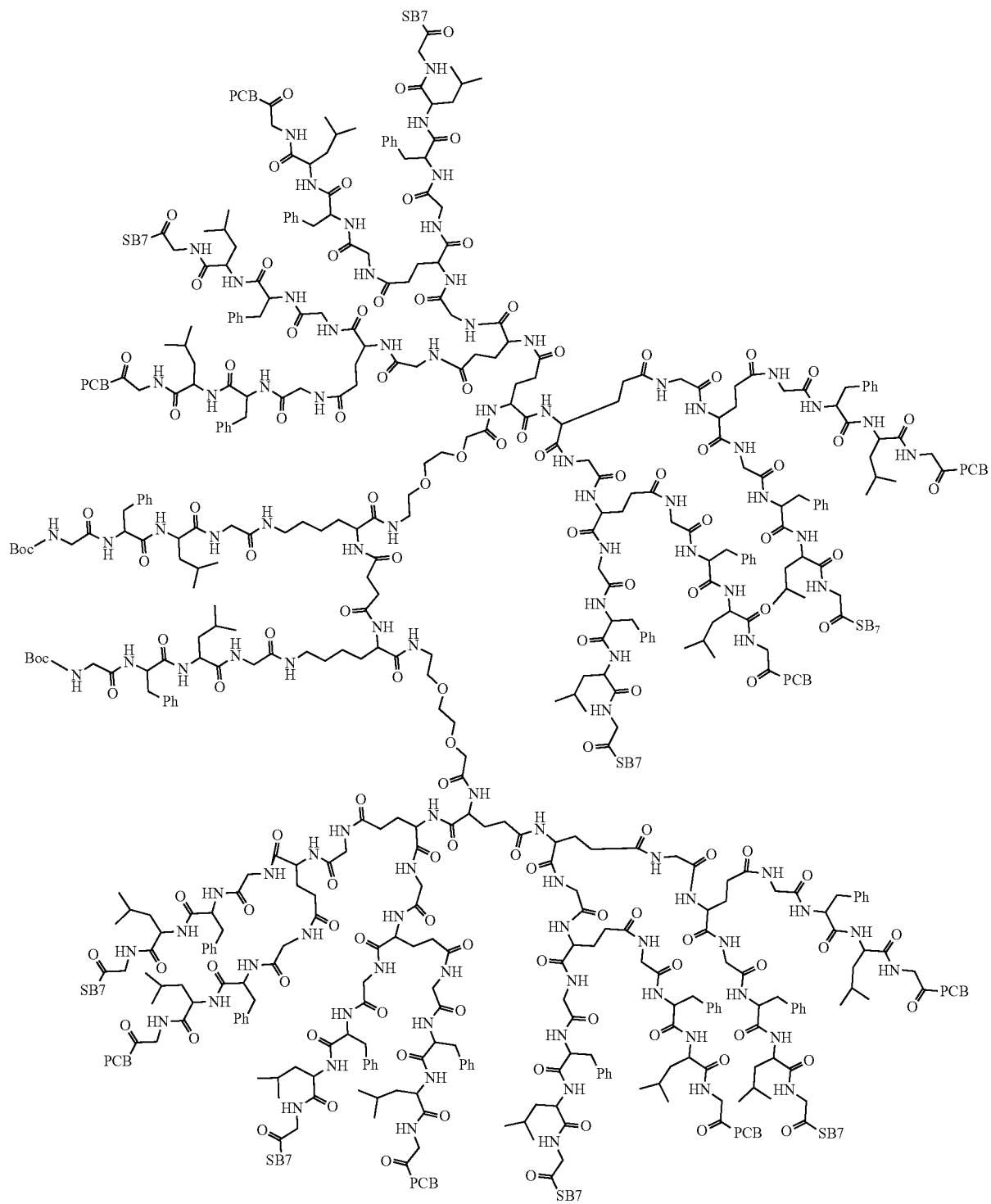

37-2 (2.0 g, 1.063 mmol), HBTU (0.56 g, 1.4832 mmol), HOBT (0.2 g, 1.4832 mmol) were added in a DMF (90 mL) solution containing 35-13 (0.364 g, 0.1236 mmol), and then the mixed solution was stirred to react at −5° C. for about 10 minutes. Then DIEA (0.74 mL, 4.4496 mmol) was slowly added dropwise. At the end of the addition, the obtained solution continued to react at −5° C. for 60 minutes, and was then moved to room temperature and stirred to react overnight. At the end of the reaction, n-hexane (100 mL) and methyl tert-butyl ether (30 mL) were added to the reaction solution, the obtained solution was shaken to be layered, the supernatant was discarded, and n-hexane (100 mL) and methyl tert-butyl ether (30 mL) were further added to the lower liquid, and such operations were repeated six times, to obtain a viscous oily product. Then, dichloromethane (30 mL) and methyl tert-butyl ether (250 mL) were added to the oily product to separate out a solid, and suction filtering was carried out. The filter cake was washed with methyl tert-butyl ether (100 mL×3), and dissolved with a mixed solvent of methanol (30 mL)/dichloromethane (120 mL), silica gel powder (15 g) was added, and the obtained mixture was then evaporated to dryness to obtain a powdery solid. The operations of column chromatography and elution with a dichloromethane mixed solution containing 1% ammonia water and 5%-7% methanol were carried out. The elution product was then collected, concentrated, evaporated to dryness, thus obtaining the product 35-14: 1.2 g, yield 56%.

35-16

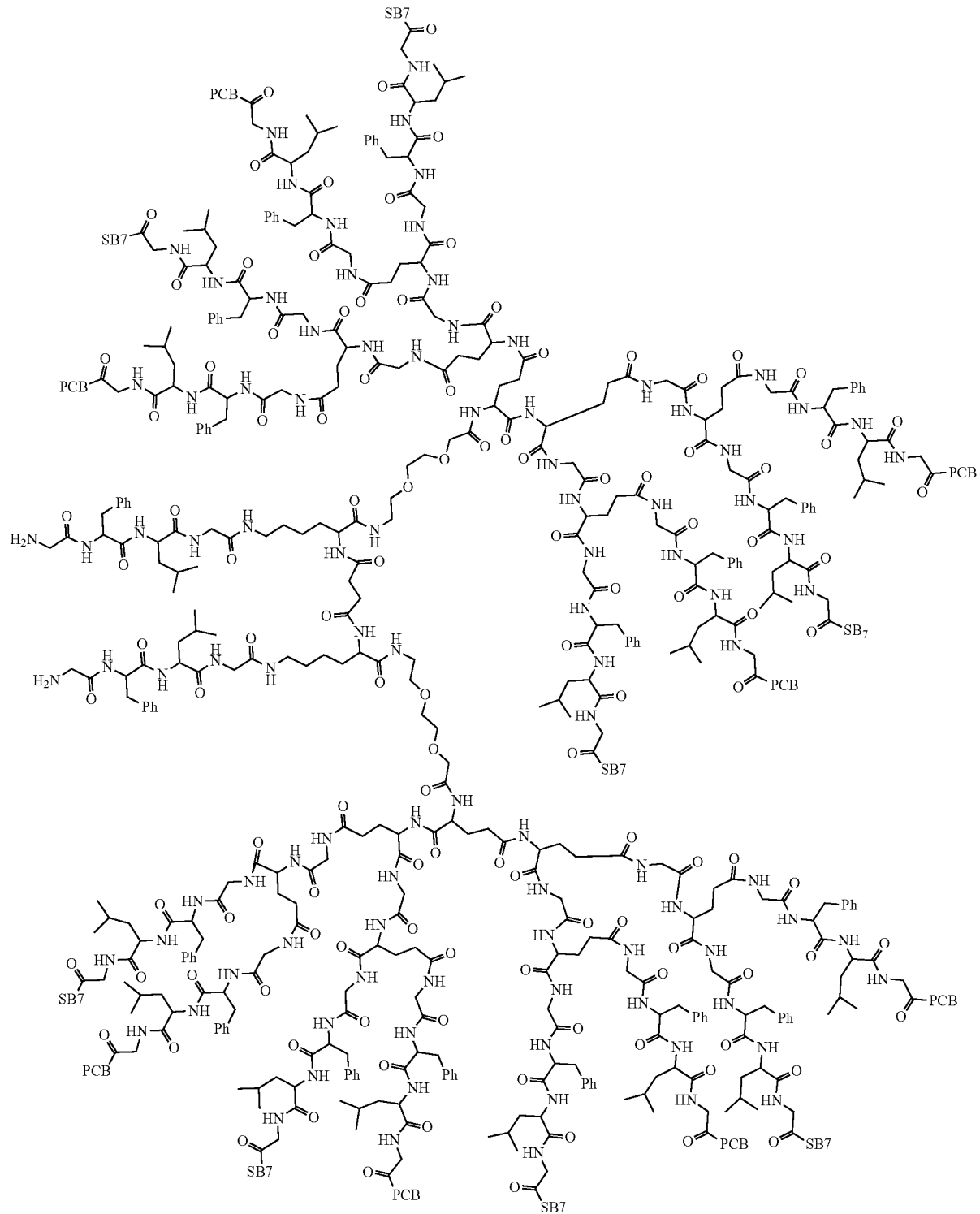

35-14 (1.2 g, 0.0695 mmol) was added in a 250 mL flask, and dissolved with dichloromethane (15 mL), TFA (1.0322 mL, 13.6 mmol) was added, and the mixed solution was stirred to react at room temperature overnight. At the end of the reaction, the reaction solution was concentrated to a small amount, methyl tert-butyl ether (100 mL) was added to the concentrated solution to separate out a powdery solid, and suction filtering was carried out. The filter cake was washed with methyl tert-butyl ether (50 mL×3), and dissolved with a mixed solvent of methanol (30 mL) and dichloromethane (120 mL), silica gel powder (10 g) was added, and the obtained mixture was then evaporated to dryness to obtain a powdery solid. The operations of dry sample loading, column chromatography and elution with a dichloromethane mixed solution containing 1% ammonia water: 6%-7% methanol were carried out. The elution product was then collected, concentrated and evaporated to dryness, thus obtaining the product 35-16: 0.74 g, yield 67%.

37-14

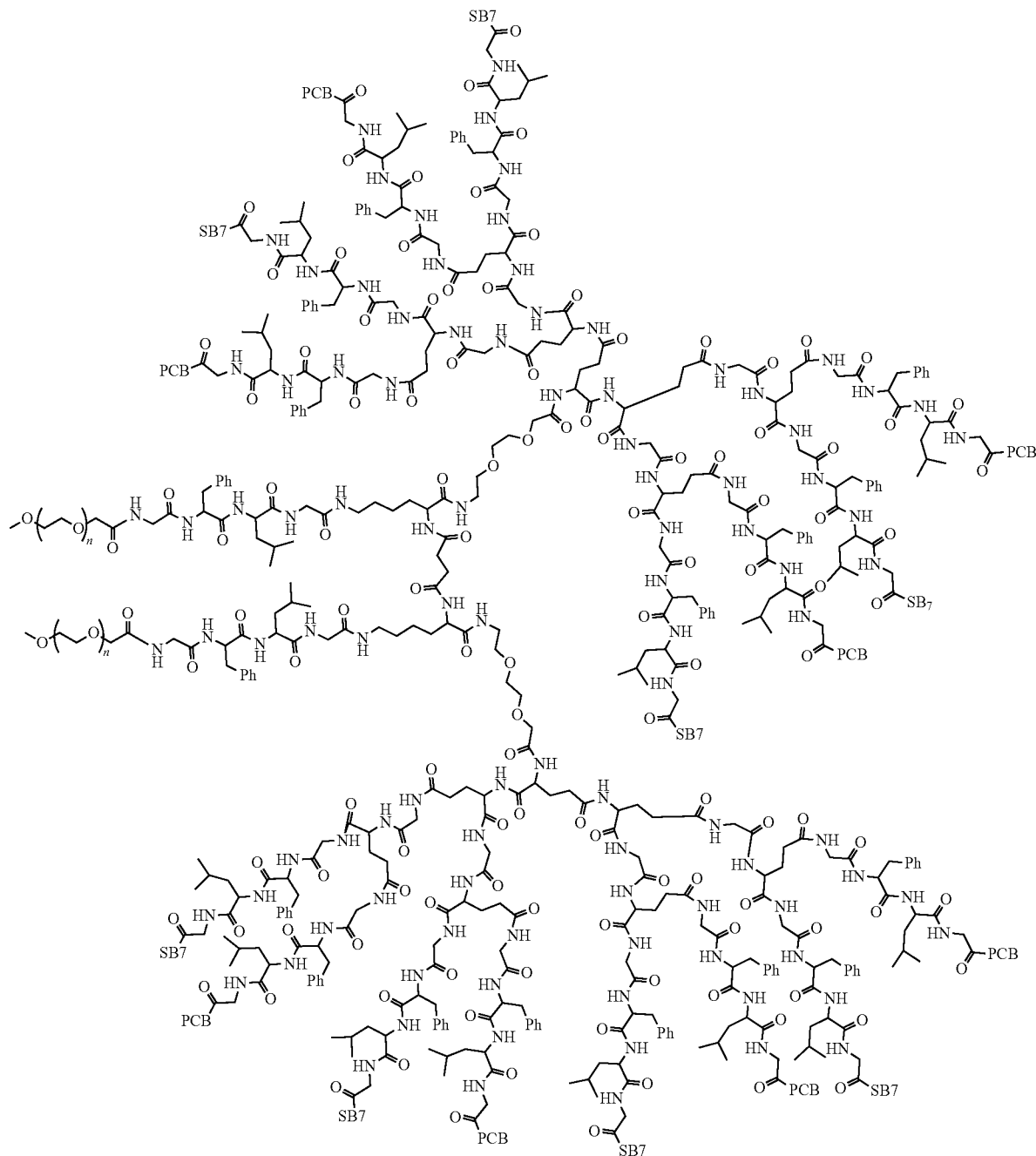

35-16 (0.3011 g, 0.01754 mmol) was added in a 250 mL flask, and dissolved with DMF (25 mL), M-SCM-40K (1.5227 g, 0.0369 mmol, purchased from JenKem) was added, and ultrasonic treatment was carried out to dissolve the reactants, the mixed solution reacted in the dark for 7 days at a low speed of stirring at room temperature. At the end of the reaction, n-hexane (120 mL) and methyl tert-butyl ether (40 mL) were added to the reaction solution, the supernatant was discarded, and n-hexane (120 mL) and methyl tert-butyl ether (40 mL) were added to the lower liquid. Such operations were repeated three times, to obtain a viscous oily product. Methyl tert-butyl ether (100 mL) was added to the oily product to separate out a solid, and filtering was carried out. The filter cake was washed with methyl tert-butyl ether (50 mL×3), and dissolved with a mixed solvent of methanol (30 mL) and dichloromethane (120 mL), silica gel powder (25 g) was added, and the obtained mixture was then evaporated to dryness to obtain a powdery solid. The operations of dry sample loading, column chromatography and elution with a dichloromethane mixed solution containing 1% ammonia water and 6%-7% methanol were carried out. The elution product was then collected, concentrated, evaporated to dryness, dried in a vacuum oven for 1 hour, and dissolved with anhydrous ethanol (5 mL) and dichloromethane (20 mL). Then, methyl tert-butyl ether (80 mL) was added to the obtained solution to separate out a solid, and filtering was carried out. The filter cake was washed with methyl tert-butyl ether (50 mL×2), and dried in a vacuum oven, thus obtaining the product 37-14: 0.98 g, yield: 58%.

$^1$H-NMR (600 MHz, DMSO-$d_6$) δ 10.18-10.11 (m, 4H), 9.21-8.97 (m, 4H), 8.24-7.89 (m, 61H), 7.58-7.43 (m, 12H), 7.30-7.08 (m, 99H), 5.91-5.77 (m, 4H), 4.64-4.68 (m, 23H), 4.38-4.14 (m, 57H), 4.07-3.89 (m, 81H), 3.60-3.45 (m, 7482H), 3.24-2.96 (m, 7H), 2.82-2.65 (m, 43H), 2.42-2.40 (m, 12H), 2.35-2.26 (m, 32H), 2.25-2.03 (m, 11H), 1.95-1.67 (m, 26H), 1.63-1.41 (m, 40H), 1.37-1.15 (m, 19H), 1.17-1.05 (m, 17H), 0.90-0.77 (m, 72H), 0.52-0.46 (m, 8H).

2. Synthesis of 10-109 (Compound No. 16)

Synthetic route is as follows:

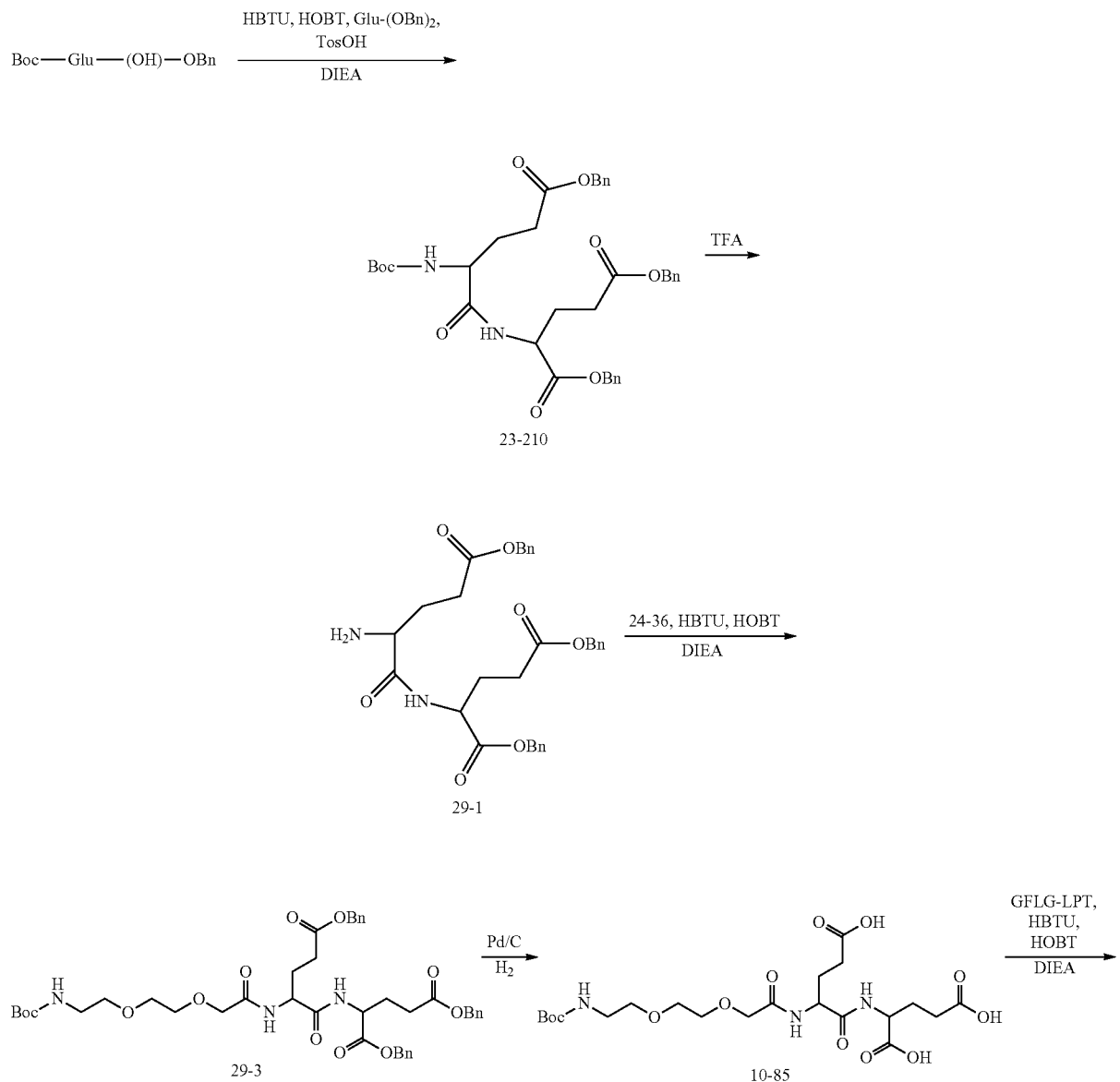

-continued
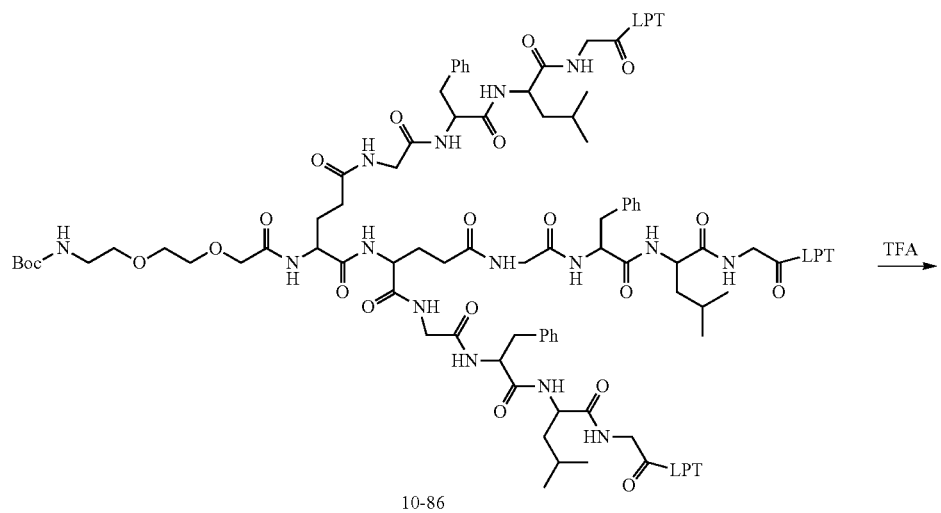
10-86
TFA →
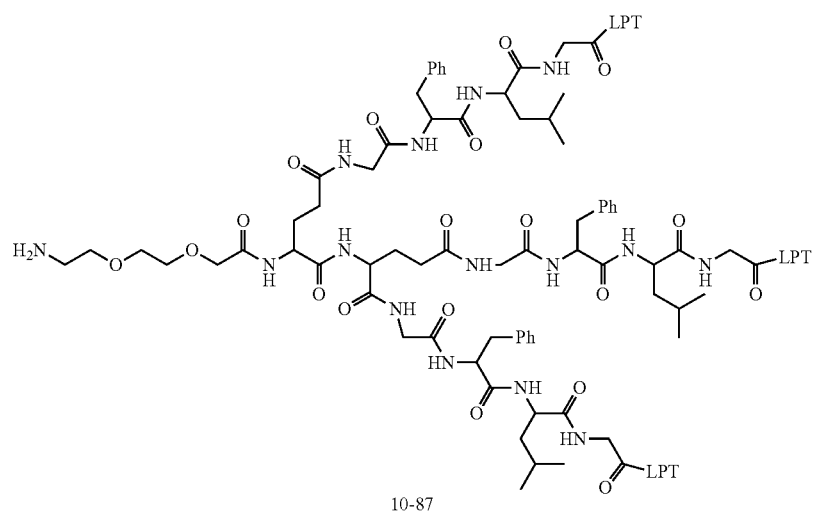
10-87
29-3 TFA →
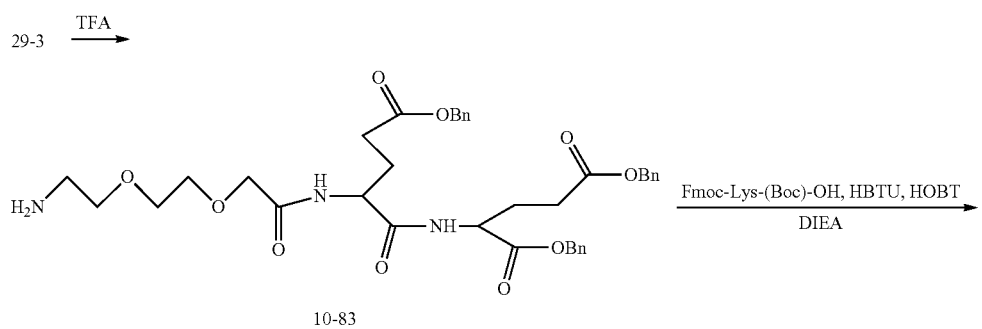
10-83
Fmoc-Lys-(Boc)-OH, HBTU, HOBT
―――――――――――――――――――
DIEA
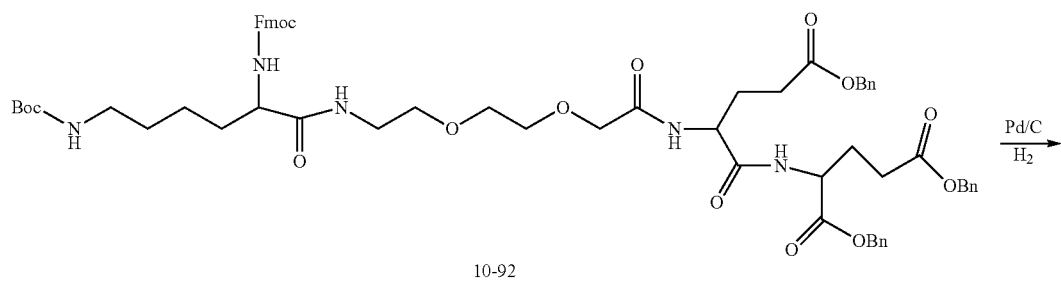
10-92
Pd/C
H₂ →

-continued
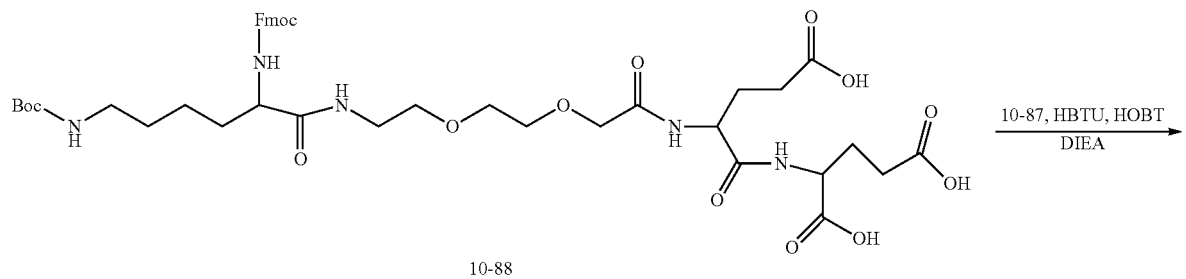
10-88
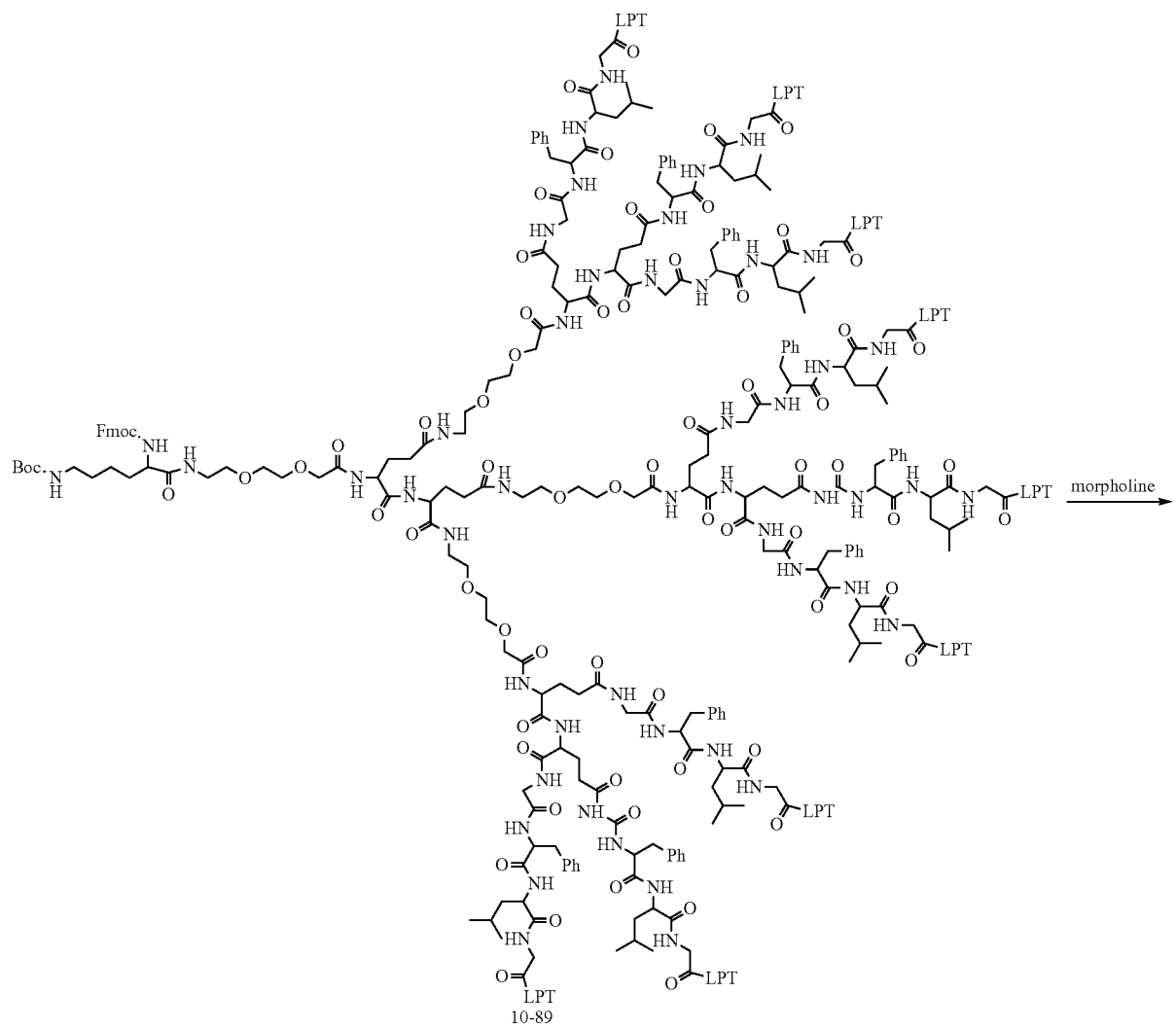
10-89

-continued
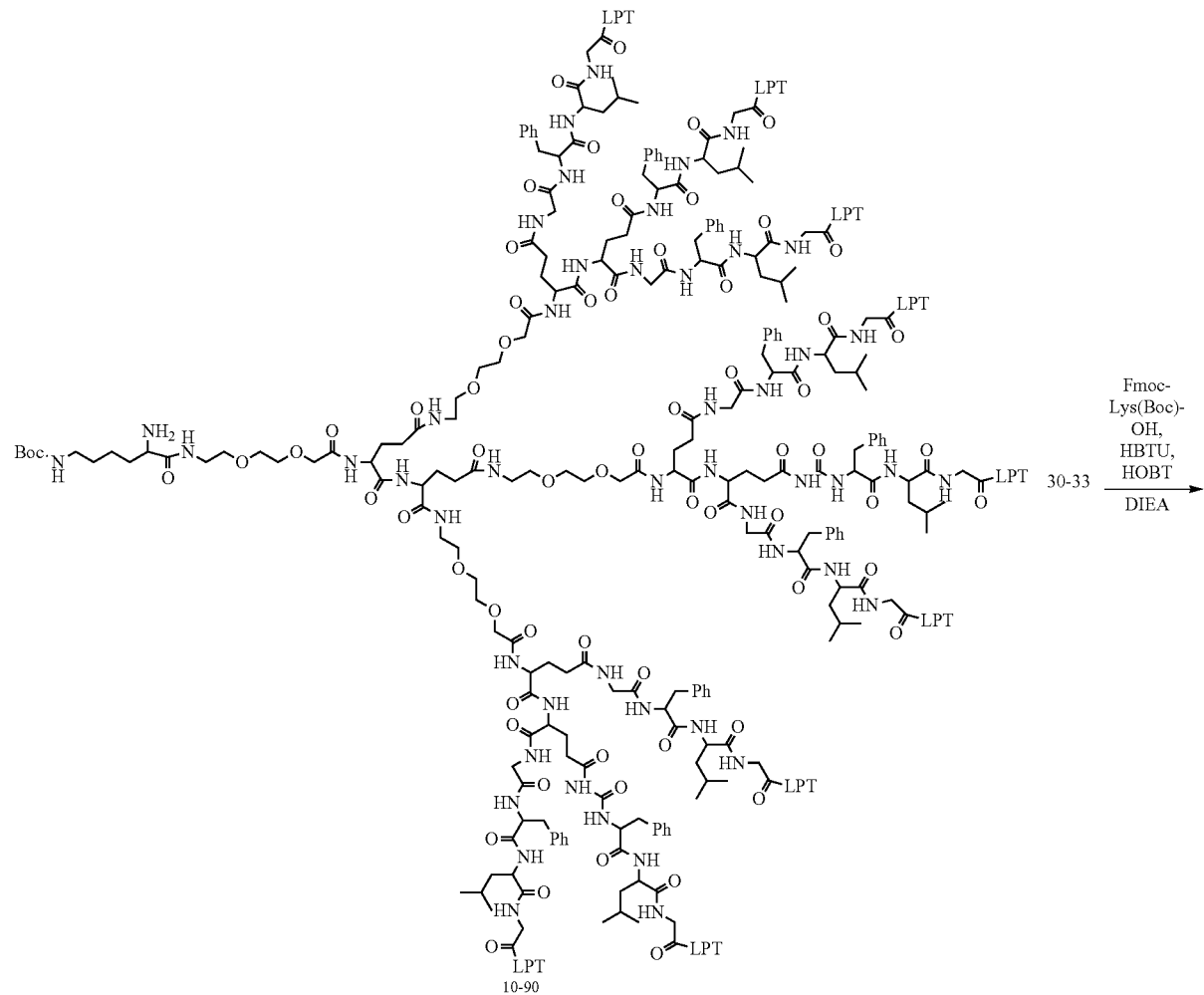
10-90
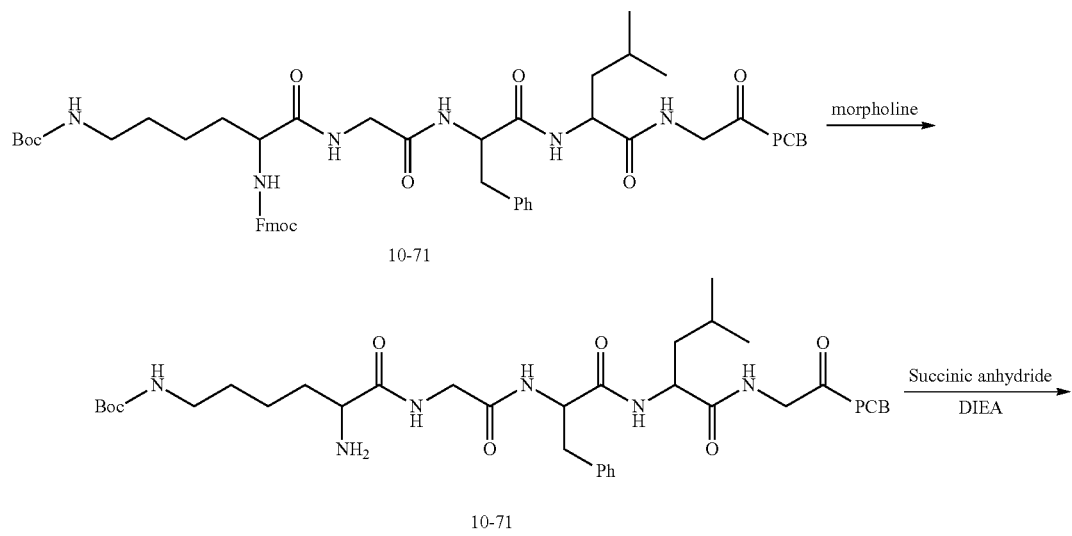
10-71

-continued
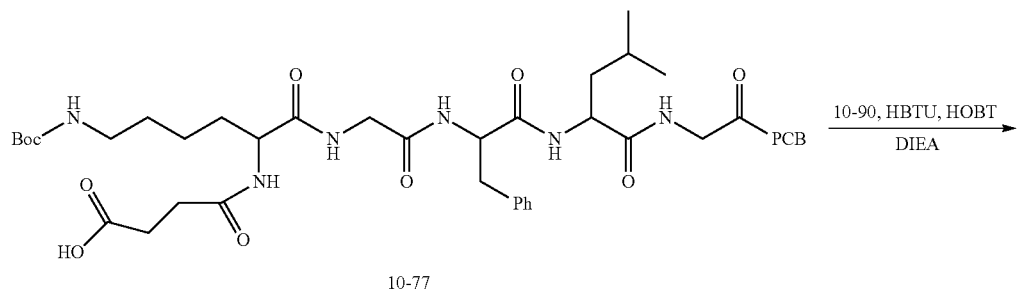
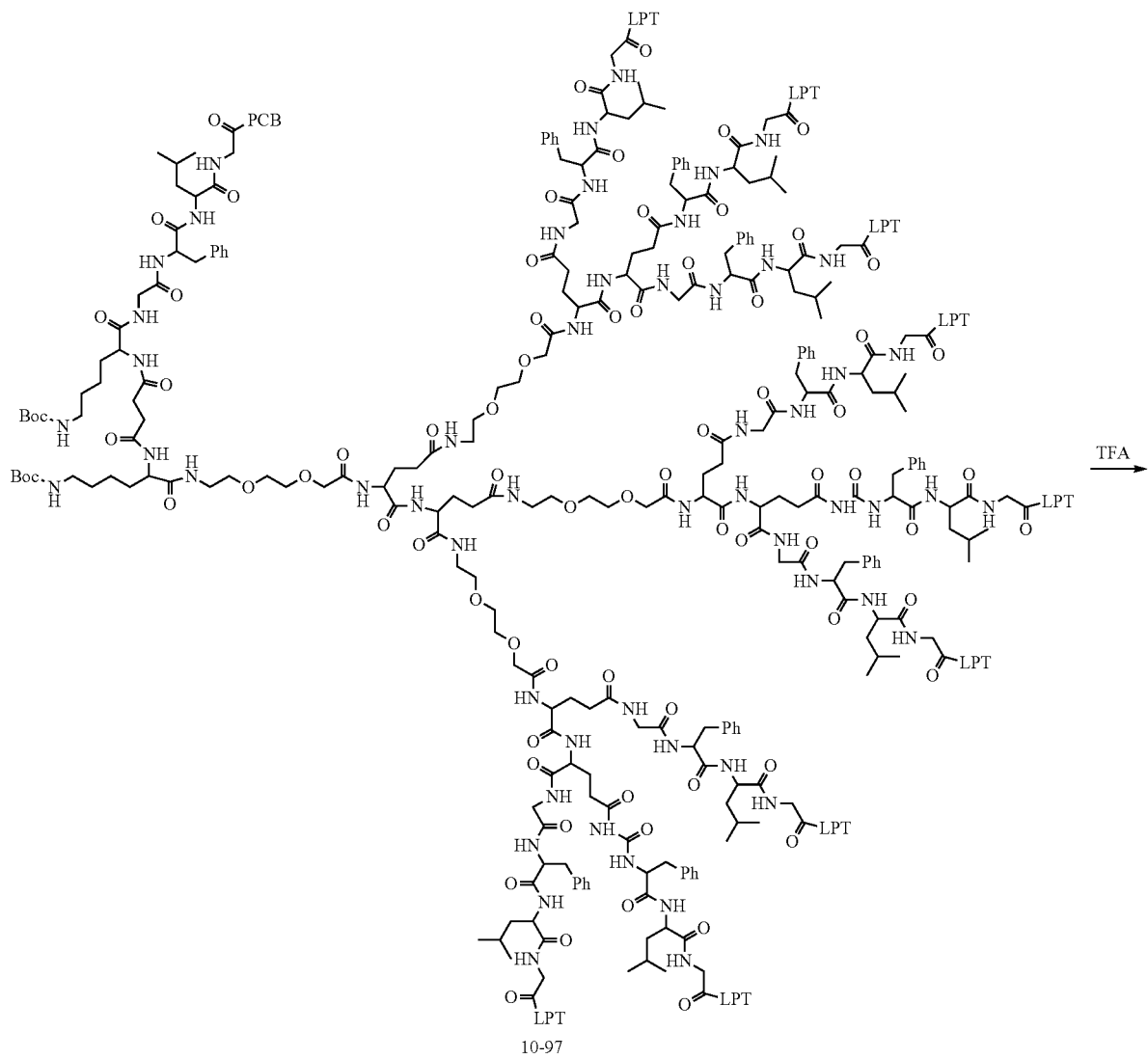

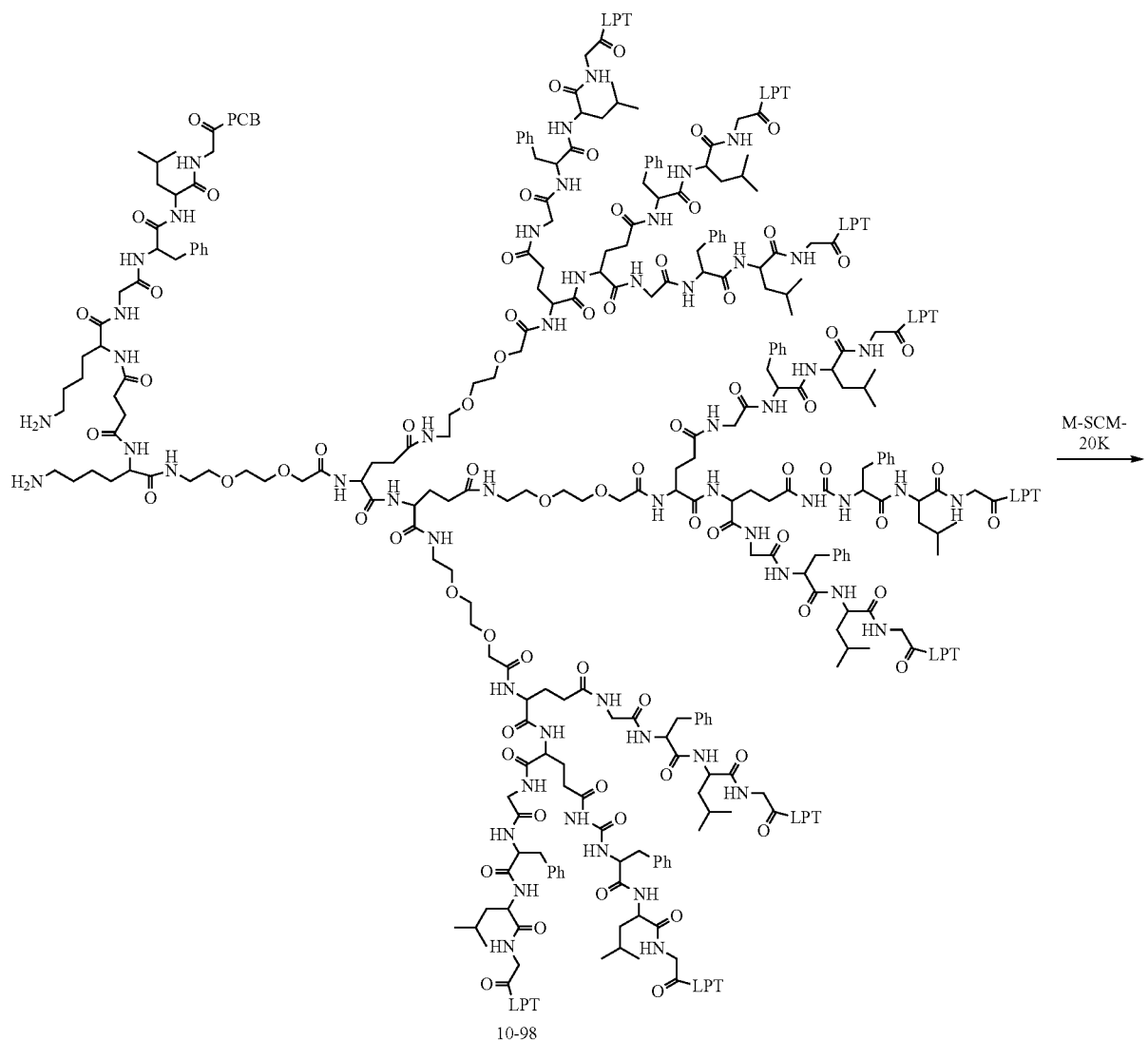
10-98

-continued

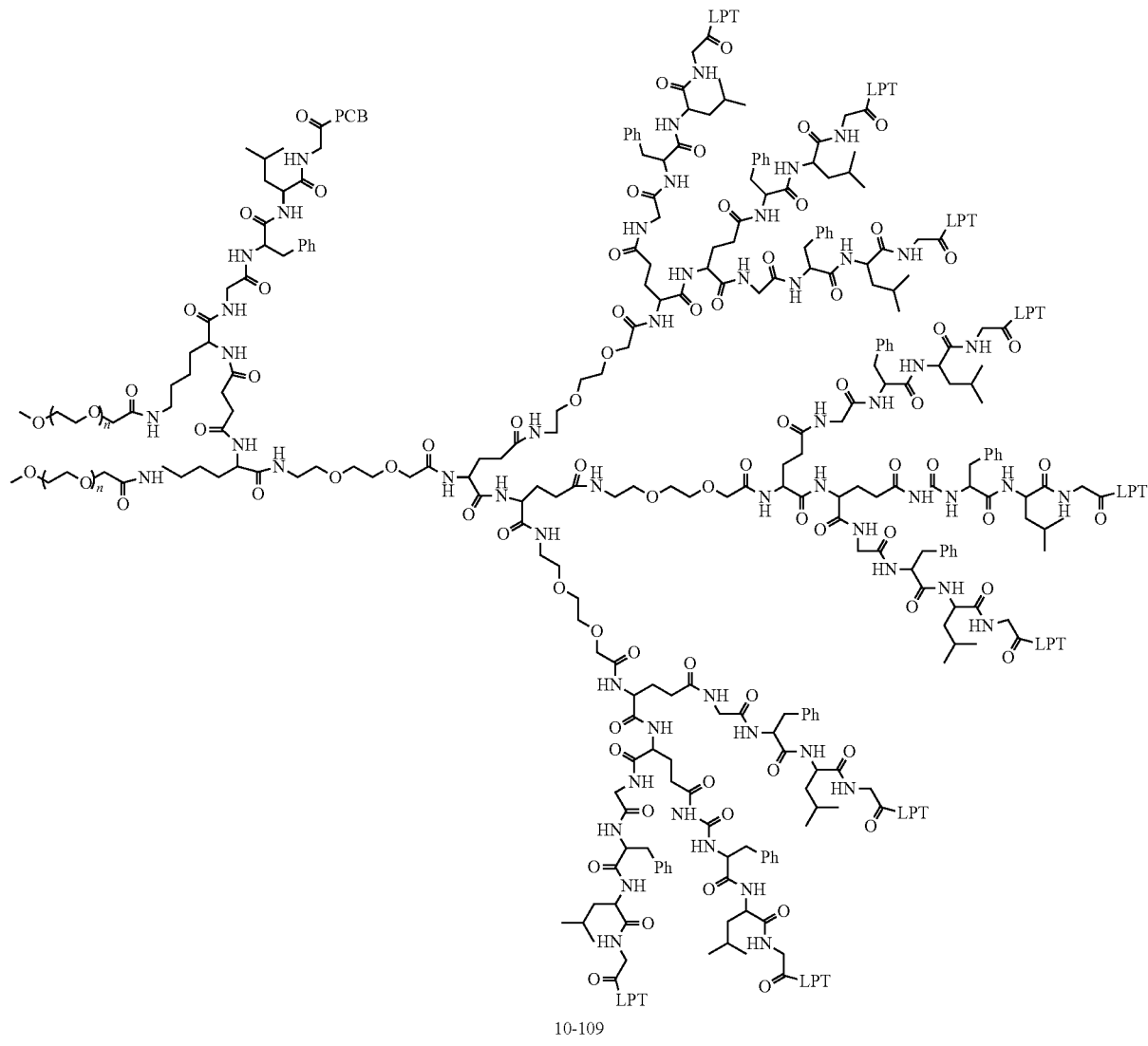

10-109

Details are given as follows

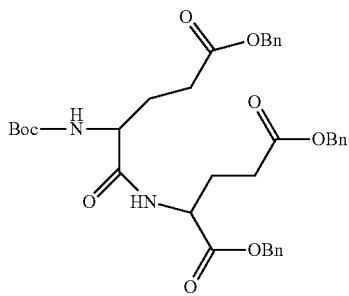

23-210

Boc-Glu-(OH) —OBn (purchased from Accela, 10 g, 29.64 mmol), Glu-(OBn)$_2$·TosOH (16.3 g, 32.61 mmol), HBTU (16.9 g, 44.46 mmol) and HOBT (6.1 g, 44.46 mmol) were added in a 500 mL round-bottomed flask, and dissolved with DMF (200 mL), and the mixed solution was stirred to react at −5° C. for 30 minutes. Then DIEA (22 mL, 133.4 mmol) was slowly added dropwise. At the end of the addition, the obtained solution reacted at the low temperature for 2 hours, and was then moved to room temperature and stirred to react overnight. At the end of the reaction, saturated sodium bicarbonate solution (200 mL) was added to the reaction solution, and then extraction with ethyl acetate (200 mL×3) was carried out three times, and the obtained organic phases were combined. Saturated sodium chloride solution (200 mL×2) was added to the organic phase, and then extraction with ethyl acetate (100 mL×2) was carried out twice. Finally, the organic phase was dried with anhydrous sodium sulfate, concentrated and evaporated to dryness, thus obtaining the product 31.4 g (weighed).

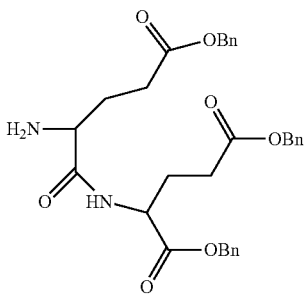

29-1

23-210 (31.4 g, 29.64 mmol) was added in a 500 mL round-bottomed flask, and dissolved with dichloromethane (100 mL), TFA (33 mL, 444.6 mmol) was added, and the mixed solution was stirred to react at room temperature overnight. At the end of the reaction, the reaction solution was concentrated and evaporated to dryness under reduced pressure. Saturated sodium bicarbonate solution (200 mL) was added to the reaction solution, and then extraction with ethyl acetate (200 mL×3) was carried out three times, and the obtained organic phases were combined. Saturated sodium chloride solution (200 mL) was added to the organic phase, and then extraction with ethyl acetate (100 mL×2) was carried out twice. Finally, the organic phase was dried with anhydrous sodium sulfate, and then evaporated to dryness for the next reaction.

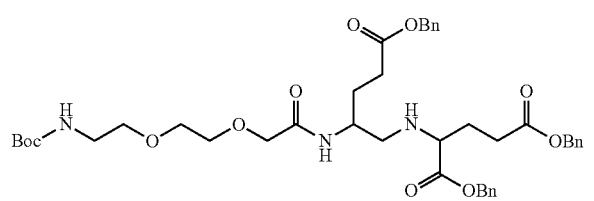

29-3

29-1 (16.2 g, 29.64 mmol), 10-102 (synthesized according to the method of synthesizing 24-36, 38.5 g, 38.5 mmol), HBTU (16.8 g, 44.4 mmol) and HOBT (6 g, 44.4 mmol) were added in a 500 mL round-bottomed flask, and dissolved with DMF (200 mL), and the mixed solution was stirred to react at −5° C. for 30 minutes. Then DIEA (22 mL, 133.2 mmol) was slowly added dropwise. At the end of the addition, the obtained solution reacted at the low temperature for 2 hours, and was then moved to room temperature and stirred to react overnight. At the end of the reaction, saturated sodium bicarbonate solution (200 mL) was added to the reaction solution, and then extraction with ethyl acetate three times (200 mL×3) was carried out three times, and the obtained organic phases were combined. Saturated sodium chloride solution (200 mL×2) was added to the organic phase, and then extraction with ethyl acetate (100 mL×2) was carried out twice. Finally, the organic phase was dried with anhydrous sodium sulfate, concentrated and evaporated to dryness, thus obtaining the product 34.1 g (weighed). The operations of dry sample loading, column chromatography and elution with 45% ethyl acetate were carried out. The elution product was then collected, concentrated, and evaporated to dryness. 11.1 g of pure product was collected and placed in a refrigerator for later use, and 10.7 g of crude product was collected and put into the next deprotection reaction.

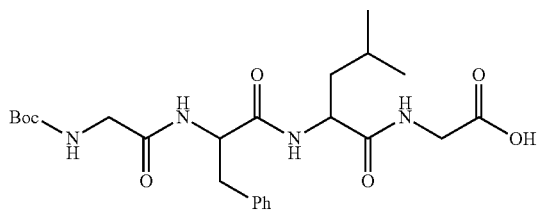

30-28

Boc-GFLG-OBn (as synthesized in accordance with literature, 19.0 g, 32.6 mmol), 10% Pd/C catalyst (300 mg) were added in a hydrogenation reactor, and dissolved with DMF (50 mL) where the level of the solvent was above a stirrer. The hydrogenation reactor was then sealed to perform the "three pumping and three charging" operation (i.e., pumping the air from the reaction system with a vacuum water pump for about 3 minutes—charging hydrogen—pumping hydrogen—charging hydrogen-pumping hydrogen—charging hydrogen) so that the pressure on the hydrogenation reactor was read as 18 Psi, and then the obtained solution reacted at room temperature overnight. On the second day, after the reaction was found to be completed from the monitoring of the TLC (thin-layer chromatography), workup procedures were performed. The reaction solution was taken out and evenly added dropwise to a suction funnel filled with compacted diatomaceous earth. The reactor was washed with DMF (90 mL) until the reactor did not contain any product, thus obtaining the reaction product.

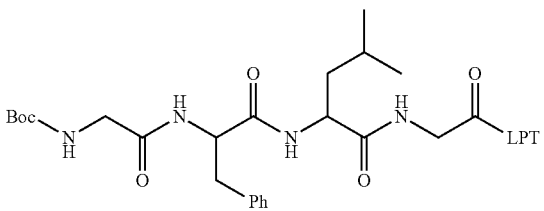

30-29

30-28 (17.9 mmol), LPT (8 g, 13.77 mmol), HBTU (7.83 g, 20.65 mmol) and HOBT (2.79 g, 20.65 mmol) were added in a 500 mL round-bottomed flask, and dissolved with DMF (100 mL), and the mixed solution was stirred to react at −5° C. for 30 minutes. Then DIEA (10.24 mL, 61.96 mmol) was slowly added dropwise. At the end of the addition, the obtained solution reacted at the low temperature for 2 hours, and was then moved to room temperature and stirred to react overnight. At the end of the reaction, deionized water (1000 mL) was added to wash DMF. A light yellow solid was separated out by precipitation, and dried, thus obtaining the product 14.53 g.

with anhydrous sodium sulfate, suction filtering was carried out, and the filtrate was concentrated, and dried. The operations of dry sample loading, column chromatography and elution with 5% methanol/0.5% ammonia water/dichloromethane were carried out. The elution product was then-collected, concentrated, thus obtaining a pure product 13.15 g.

14-128

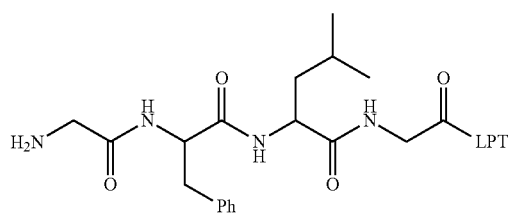

10-85

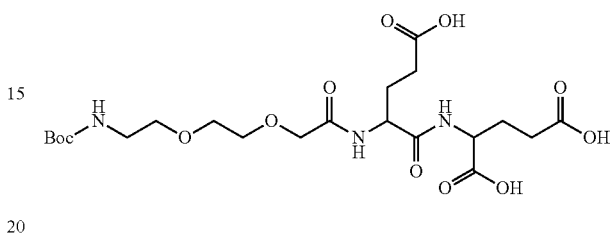

30-29 (14.53 g, 13.77 mmol) was added in a 500 mL round-bottomed flask, and dissolved with dichloromethane (150 mL), then TFA (15.34 mL, 206.55 mmol) was added, and the mixed solution was stirred to react at room temperature overnight. At the end of the reaction, the reaction solution was concentrated under reduced pressure, saturated sodium bicarbonate solution (200 mL) was added to neutralize TFA, the product in the aqueous phase was extracted three times with ethyl acetate (150 mL×3), and the obtained organic phases were combined. The organic phase was dried 29-3 (1.95 g, 2.46 mmol) and 10% Pd/C (0.1 g) were added in a hydrogenation reactor, and dissolved with DMF (30 mL). The hydrogenation reactor was then sealed to perform the "three pumping and three charging" operation, so that the pressure on the hydrogenation reactor was read as 0.18 MPa, and then the obtained solution reacted at room temperature overnight. At the end of the reaction, the reaction solution was filtered with diatomaceous earth. The filter cake was washed with DMF (20 mL×3), thus obtaining the product 10-85, yield 100%.

10-86

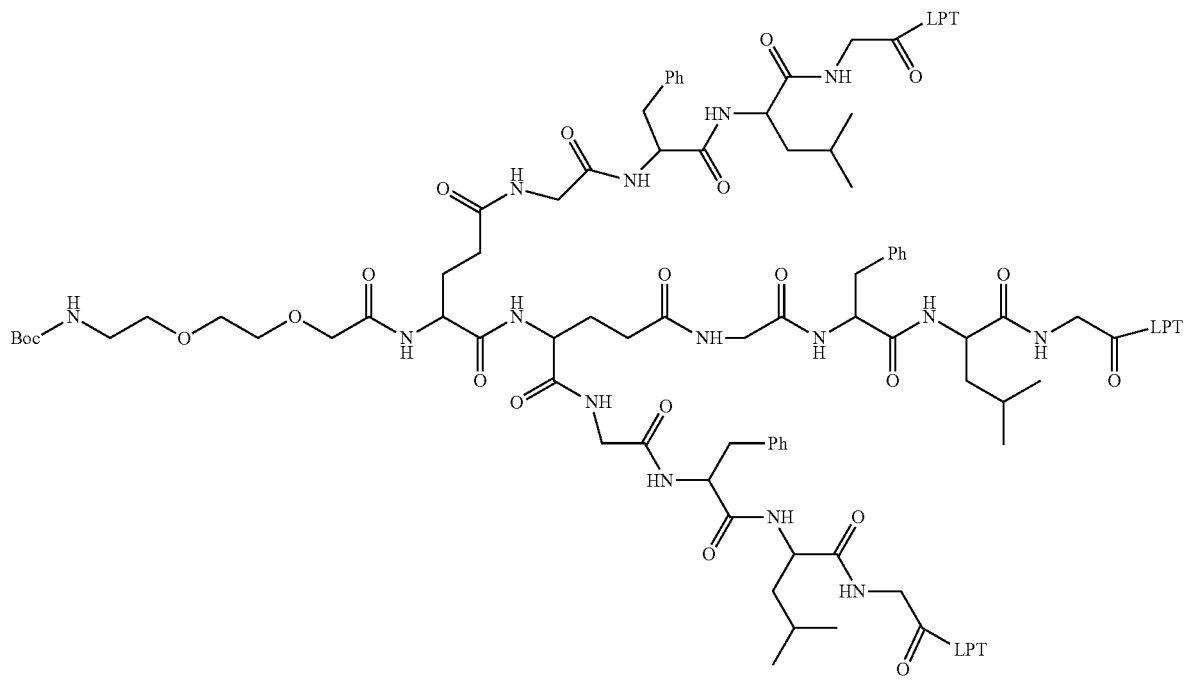

10-85 (1.28 g, 2.46 mmol), GFLG-LPT (synthesized according to the method of synthesizing 14-128, 8.0 g, 8.37 mmol), HBTU (4.20 g, 11.07 mmol), HOBT (1.49 g, 11.07 mmol) were added in a 500 mL flask, and dissolved with DMF (40 mL), and the mixed solution was stirred to react at 0° C. for 30 minutes. Then DIEA (5.69 mL, 34.44 mmol) was slowly added dropwise over 3 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), and the washed filter cakes were collected, and dried in a vacuum oven, thus obtaining the product 10-86: 8.2 g, yield 100%.

ammonia water and 4.5%-6% methanol were carried out. The elution product was then collected, concentrated, and dried in a vacuum oven, thus obtaining the product 18-87: 5.56 g, yield 70%.

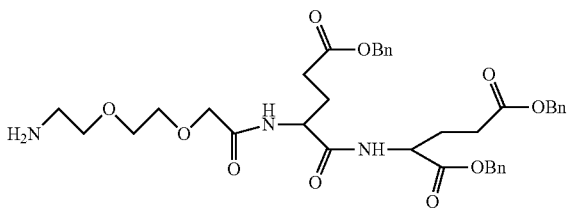

29-3 (9.9 g, 12.5019 mmol) was partially dissolved with dichloromethane (10 mL), and then TFA (18.5716 mL, 250.0379 mmol) was added, and ultrasonic treatment was

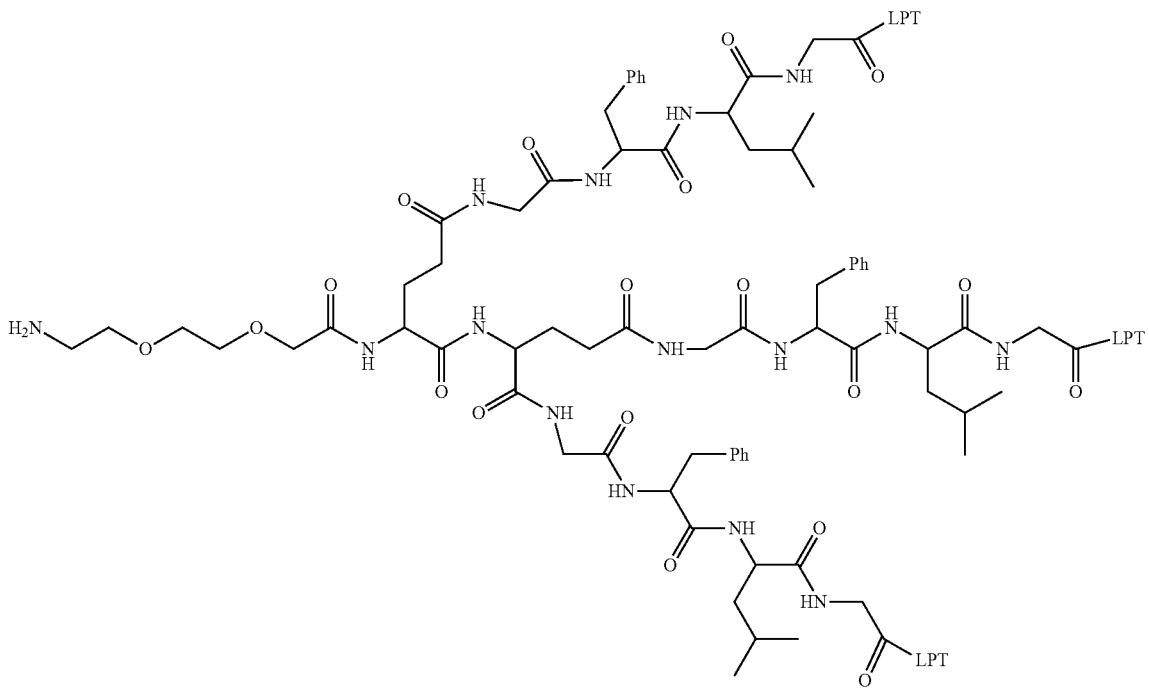

10-86 (8.2 g, 2.46 mmol) was added in a 250 mL flask, and dissolved with dichloromethane (8 mL), TFA (2.7 mL, 36.90 mmol), and the mixed solution was stirred to react at room temperature overnight. At the end of the reaction, the reaction solution was rotary evaporated to obtain a viscous oily product, and methyl tert-butyl ether (60 mL) was then added to the oily product. The powdery solid in the obtained solution was separated out by precipitation, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (40 g) was added, and the obtained mixture was then evaporated to dryness to obtain a powdery solid. The operations of dry sample loading, column chromatography and gradient elution with a dichloromethane mixed solution containing 1% carried out to completely dissolve the compound. A ground glass stopper was used, and the mixed solution was stirred at room temperature. After TLC detection and color development with phosphomolybdic acid, the reaction was completed. The reaction solution was evaporated to dryness, the dichloromethane was removed, and then the obtained solid was dissolved with ethyl acetate (200 mL). A saturated sodium bicarbonate solution was added until the aqueous phase became alkaline. Then, the organic phase was separated, and the aqueous phase was extracted with ethyl acetate until there was no product in the aqueous phase, and the obtained organic phases were combined. The organic phase was then washed with saturated saline solution three times (100 mL×3), concentrated and evaporated to dryness, thus obtaining the product 8.7 g, extra-quota 0.1 g.

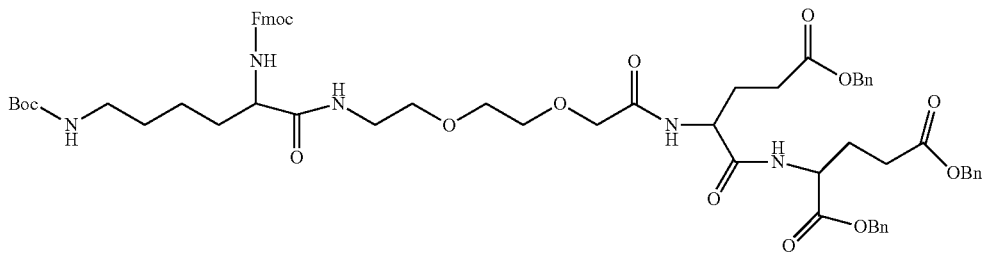

10-92

10-83 (1.6 g, 2.31 mmol), Fmoc-Lys (Boc)—OH (1.14 g, 2.43 mmol), HBTU (1.32 g, 3.47 mmol), HOBT (0.47 g, 3.47 mmol) were added in a 500 mL flask, and dissolved with a proper amount of DMF (40 mL), and the mixed solution was stirred to react at 0° C. for 30 minutes. Then DIEA (1.72 mL, 10.39 mmol) was slowly added dropwise over 3 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was collected, and dissolved with a mixed solvent (100 mL) of methanol/dichloromethane (1:4), Silica gel powder (30 g) was added, and the obtained mixture was then evaporated to dryness to obtain a powdery solid. The operations of dry sample loading, column chromatography and gradient elution with a dichloromethane mixed solution containing 1%-5% methanol were carried out. The elution product was then collected, concentrated, and dried in a vacuum oven, thus obtaining the product 10-92: 2.4 g, yield 92.3%.

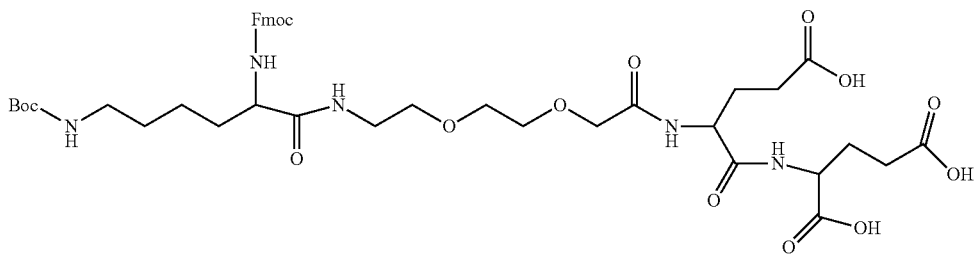

10-88

10-92 (0.57 g, 0.506 mmol) and 10% Pd/C (0.1 g) were added in a hydrogenation reactor, and dissolved with DMF (30 mL), The hydrogenation reactor was then sealed to perform the "three pumping and three charging" operation, so that the pressure on the hydrogenation reactor was read as 0.18 MPa, and then the obtained solution reacted at room temperature overnight. At the end of the reaction, the reaction solution was filtered with diatomaceous earth. The filter cake was washed with DMF (20 mL×3), thus obtaining the product 10-88: 0.434, yield 100%.

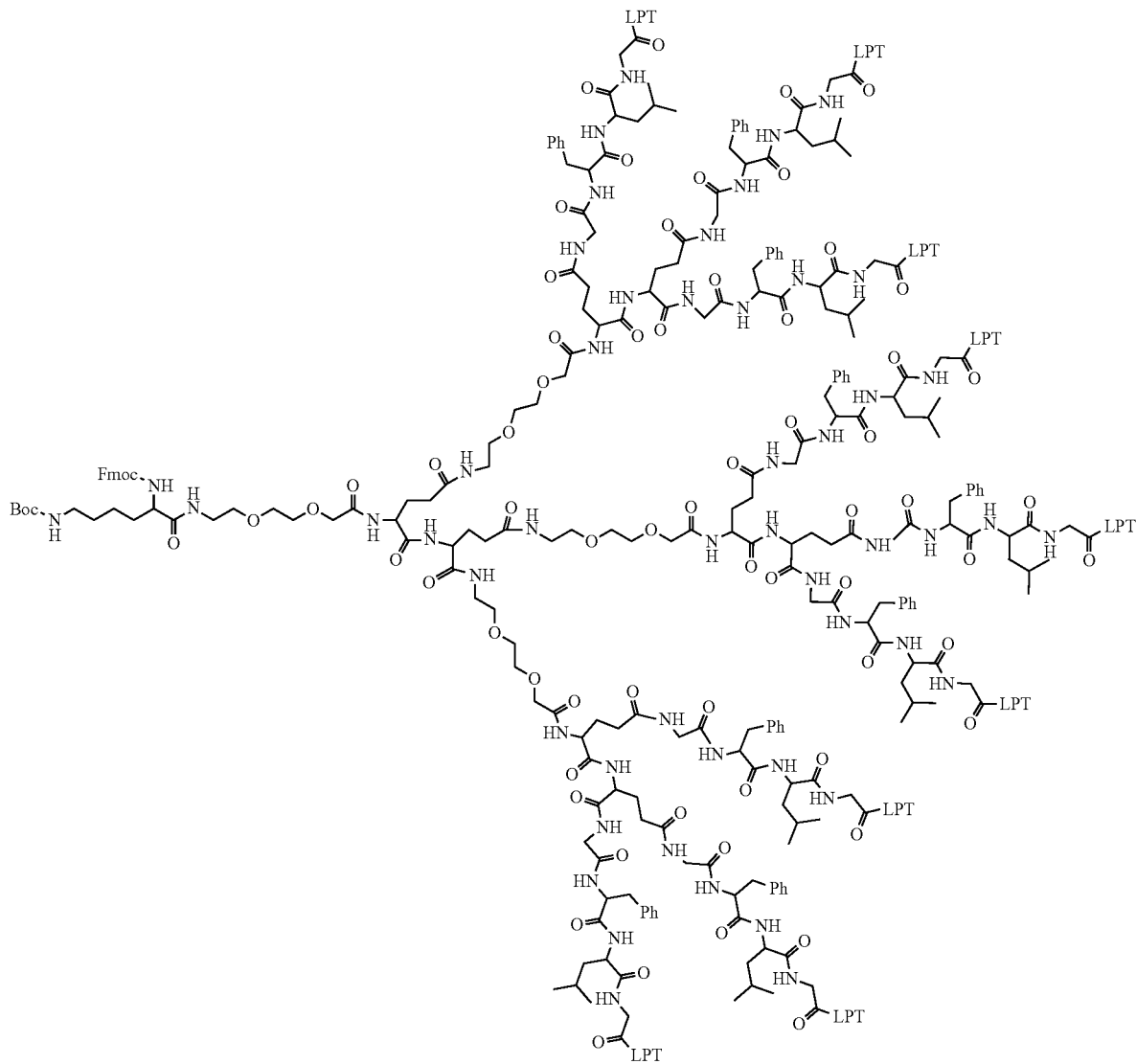

10-89

10-88 (0.434 g, 0.506 mmol), 10-87 (5.56 g, 1.722 mmol), HBTU (0.864 g, 2.277 mmol), HOBT (0.307 g, 2.277 mmol) were added in a 500 mL flask, and dissolved with a proper amount of DMF (40 mL), and the mixed solution was stirred to react at 0° C. for 30 minutes. Then DIEA (1.171 mL, 7.084 mmol) was slowly added dropwise over 30 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), and the washed filter cakes were collected, and dried in a vacuum oven, thus obtaining the product 10-89: 5.34 g, yield 100%.

10-90

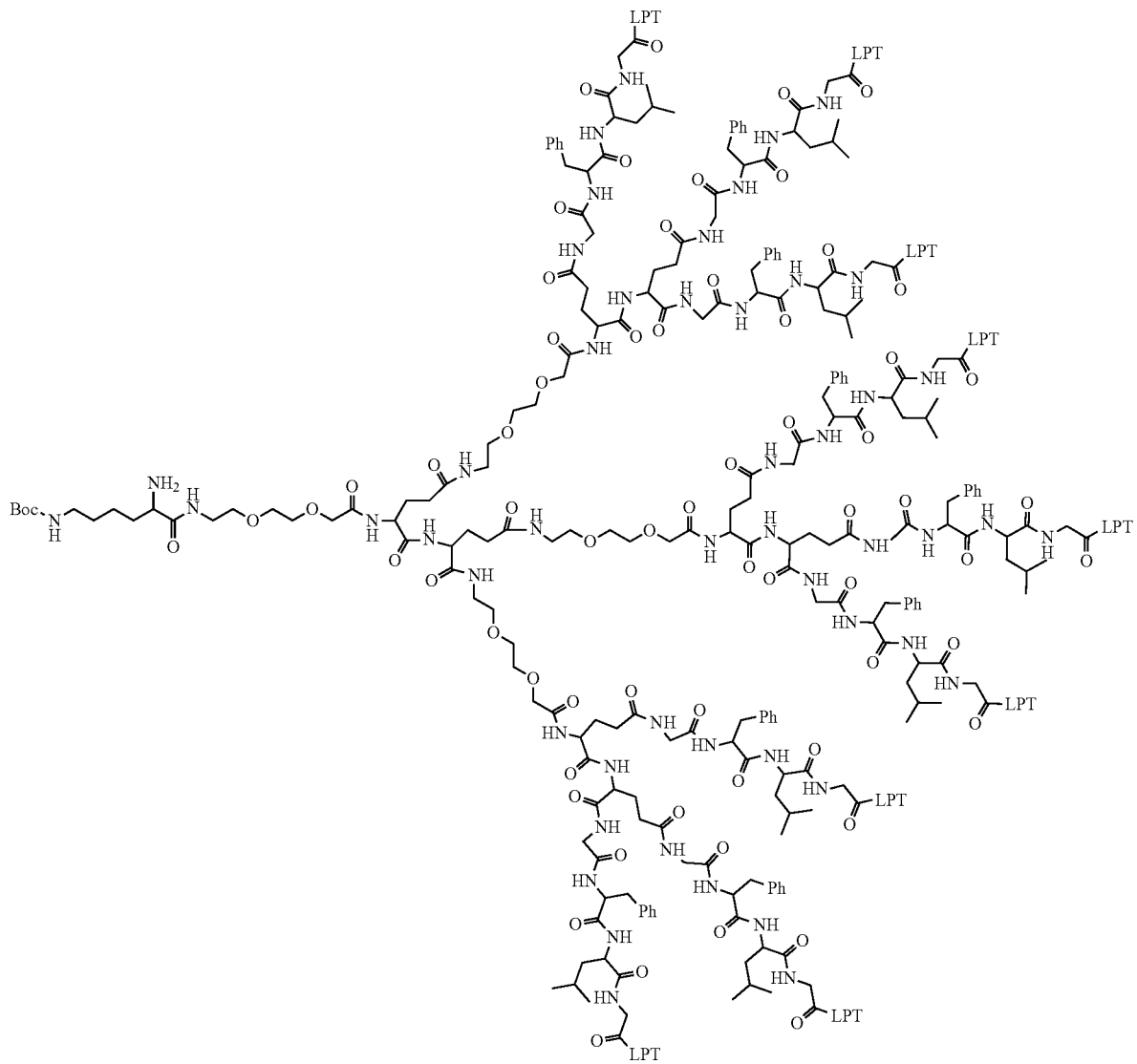

10-89 (5.34 g, 0.506 mmol) was added in a 250 mL flask, and dissolved with DMF (10 mL), morpholine (0.88 mL, 10.12 mmol) was added, and then the mixed solution was stirred to react at room temperature for 1 hour. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4). Silica gel powder (30 g) was added, and the obtained mixture was then evaporated to dryness to obtain a powdery solid. The operations of dry sample loading, column chromatography and gradient elution with a dichloromethane mixed solution containing 1% ammonia water and 3%-7% methanol were carried out. The elution product was then collected, concentrated, and dried in a vacuum oven, thus obtaining the product 10-90: 2.65 g, yield 51%.

10-71

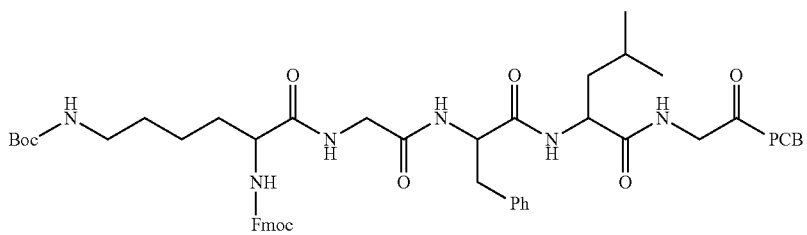

30-33 (3.5 g, 4.26 mmol), Fmoc-Lys (Boc) —OH (2.2 g, 4.69 mmol), HBTU (2.42 g, 6.39 mmol), HOBT (0.86 g, 6.39 mmol) were added in a 250 mL flask, and dissolved with a proper amount of DMF (40 mL), and the mixed solution was stirred to react at 0° C. for 30 minutes. Then DIEA (3.17 mL, 19.17 mmol) was slowly added dropwise over 30 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), and the washed filter cakes were collected, and dried in a vacuum oven, thus obtaining the product 10-71: 5.42 g, yield 100%.

10-76

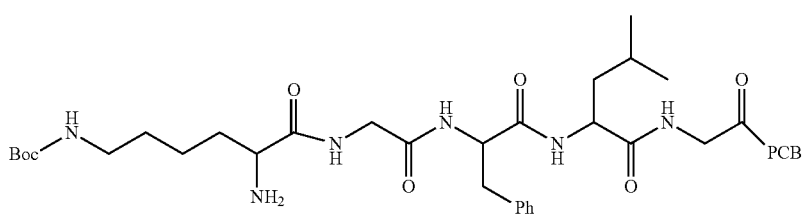

10-71 (5.42 g, 4.26 mmol) was added in a 250 mL flask, and dissolved with DMF (10 mL), morpholine (7.42 mL, 85.2 mmol) was added, and then the mixed solution was stirred to react at room temperature for 1 hour. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4). The obtained solution was concentrated, and dried in a vacuum oven, thus obtaining the product 10-76: 4.473 g, yield 100%.

10-77

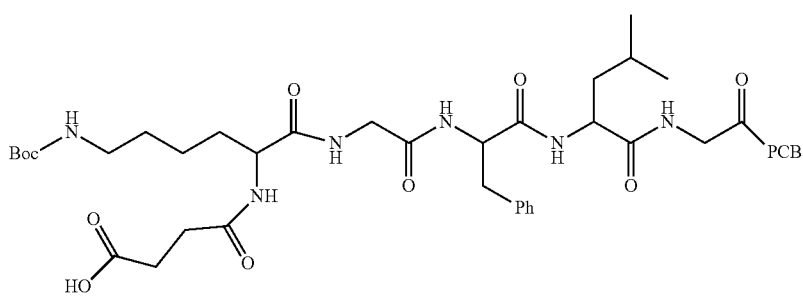

10-76 (4.473 g, 4.26 mmol), succinic anhydride (1.29 g, 12.89 mmol) were added in a 250 mL flask, and dissolved with a proper amount of DMF (40 mL), and the mixed solution was stirred to react at 0° C. for 30 minutes. Then DIEA (2.82 mL, 17.04 mmol) was slowly added dropwise over 30 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4). Silica gel powder (30 g) was added, and the obtained mixture was then evaporated to dryness to obtain a powdery solid. The operations of dry sample loading, column chromatography and gradient elution with a dichloromethane mixed solution containing 1% ammonia water and 5%-8% methanol were carried out. The elution product was then collected, concentrated, and dried in a vacuum oven, thus obtaining the product 10-77: 2.98 g, yield 61%.

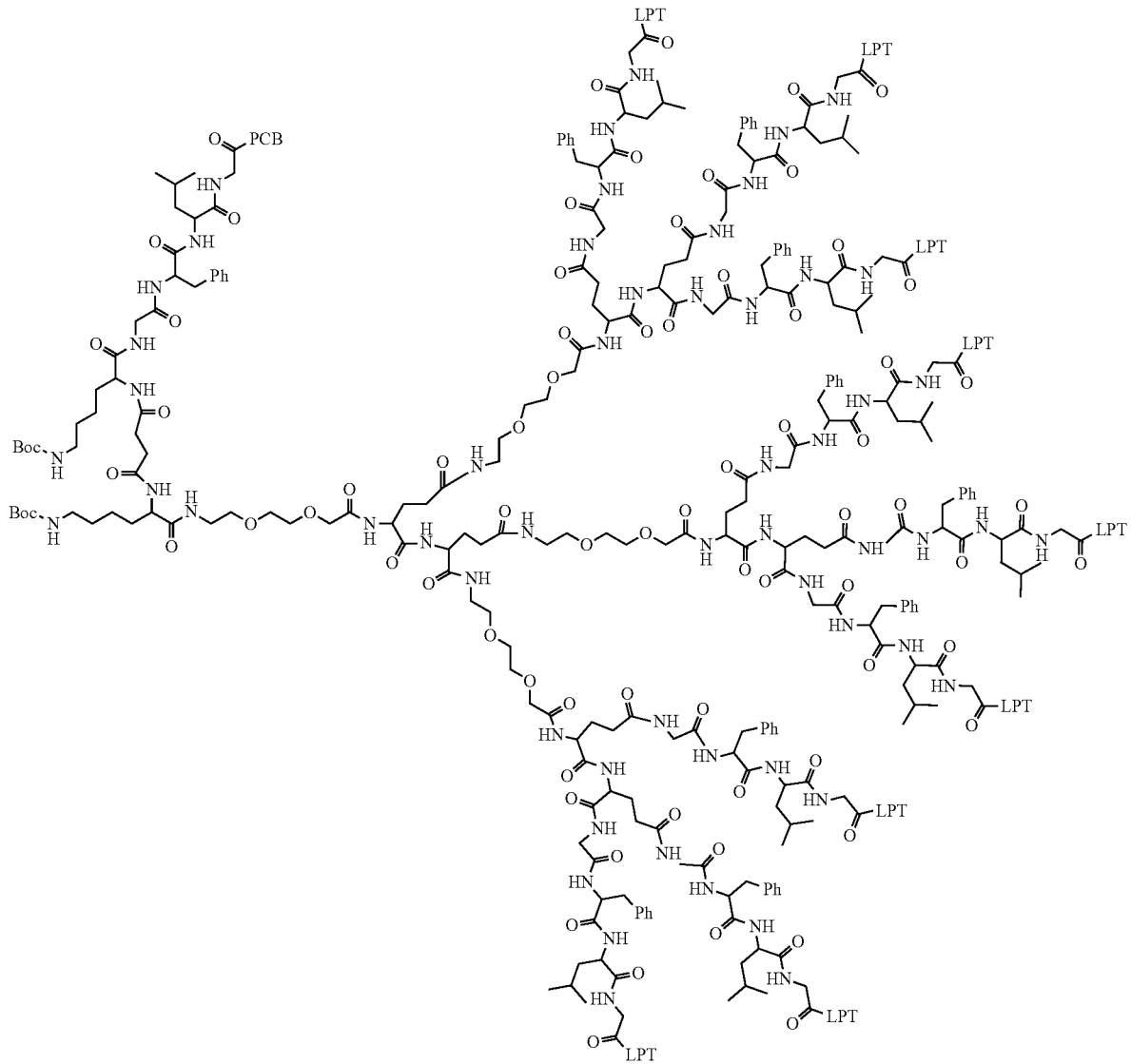

10-97

10-77 (0.28 g, 0.245 mmol), 10-90 (2.65 g, 0.62 mmol), HBTU (0.139 g, 0.368 mmol), HOBT (0.049 g, 0.368 mmol) were added in a 250 mL flask, and dissolved with a proper amount of DMF (40 mL), and the mixed solution was stirred to react at 0° C. for 30 minutes. Then DIEA (0.18 mL, 1.1 mmol) was slowly added dropwise over 30 minutes. At the end of the addition, the obtained solution continued to react with stirring at −5° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), and the washed filter cakes were collected, and dired in a vacuum oven, thus obtaining the product 10-97: 2.8 g, yield 100%.

obtained solution was separated out by precipitation, and suction filtering was carried out. The filter cake was washed with methyl tert-butyl ether (40 mL×3), the washed filter cakes were collected, and dissolved with a mixed solvent (100 mL) of methanol/dichloromethane (1:4). Silica gel powder (30 g) was added, and the obtained mixture was then evaporated to dryness to obtain a powdery solid. The opera-

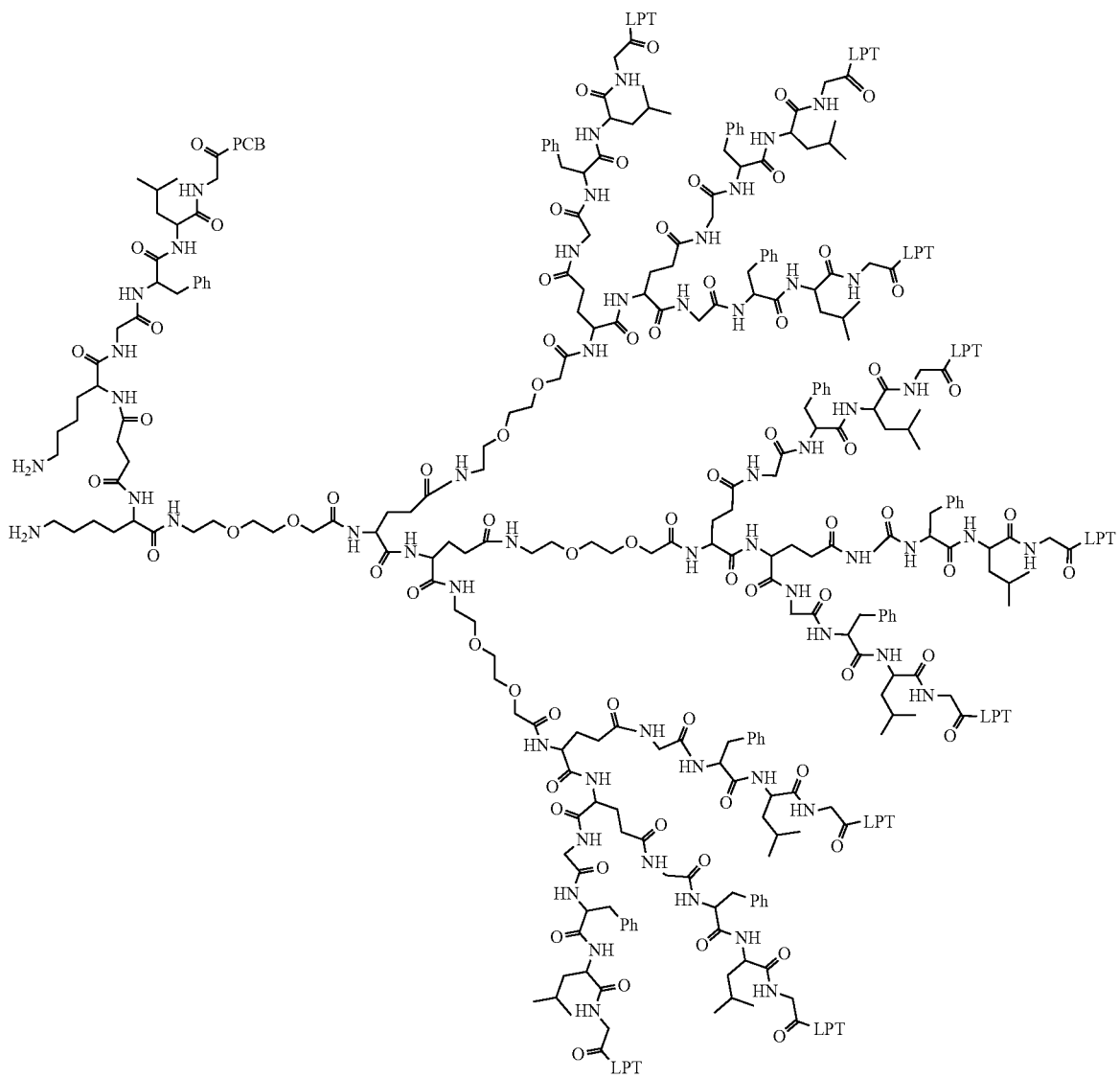

10-98

10-97 (2.8 g, 0.245 mmol) was added in a 250 mL flask, and dissolved with dichloromethane (8 mL), and TFA (0.546 mL, 7.35 mmol), and the mixed solution was stirred to react at room temperature overnight. At the end of the reaction, the reaction solution was rotary evaporated to obtain a viscous oily product, and methyl tert-butyl ether (60 mL) was then added to the oily product. The powdery solid in the tions of dry sample loading, column chromatography and gradient elution with a dichloromethane mixed solution containing 1% ammonia water and 5%-10% methanol were carried out. The elution product was then collected, concentrated, and dried in a vacuum oven, thus obtaining the product 10-98: 1.38 g, yield: 60%

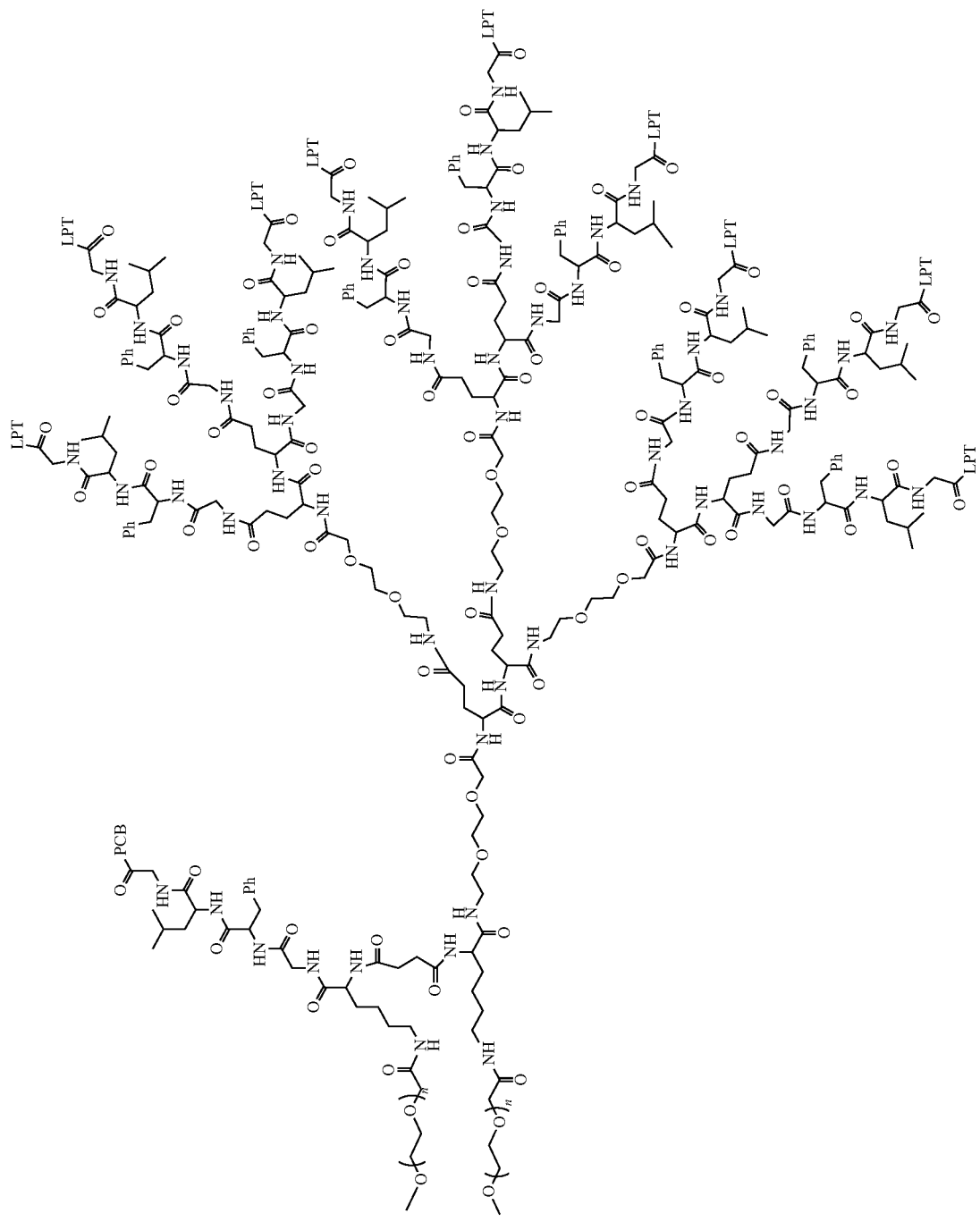

10-98 (1.29 g, 0.1134 mmol) was added in a 250 mL flask, and dissolved with DMF (10 mL), and M-SCM-20K (0.54 g, 0.054 mmol, purchased from JenKem) was added, the mixed solution reacted in the dark for one week at a low speed of stirring at room temperature. At the end of the reaction, methyl tert-butyl ether (40 mL) was added to the reaction solution to separate out a solid, and suction filtering was carried out. The filter cake was washed with methyl tert-butyl ether (40 mL×3), and dissolved with a mixed solvent (100 mL) of methanol/dichloromethane (1:4), silica gel powder (10 g) was added, and the obtained mixture was then evaporated to dryness to obtain a powdery solid. The operations of dry sample loading, column chromatography and gradient elution with a dichloromethane mixed solution containing 1% ammonia water and 6%-12% methanol were carried out. The elution product was then collected, concentrated, evaporated to dryness, and dried in a vacuum oven, thus obtaining the product 10-109: 0.7 g, yield 51%.

$^1$H-NMR (600 MHz, DMSO-$d_6$) δ 7.46-6.89 (m, 225H), 4.21-4.08 (m, 111H), 3.55-3.49 (m, 3882H), 3.08-2.64 (m, 209H), 2.45-2.40 (m, 10H), 2.34-2.28 (m, 28H), 0.88-0.83 (m, 60H).

3. Synthesis of 39-17 (Compound No. 14)

Synthetic route is as follows

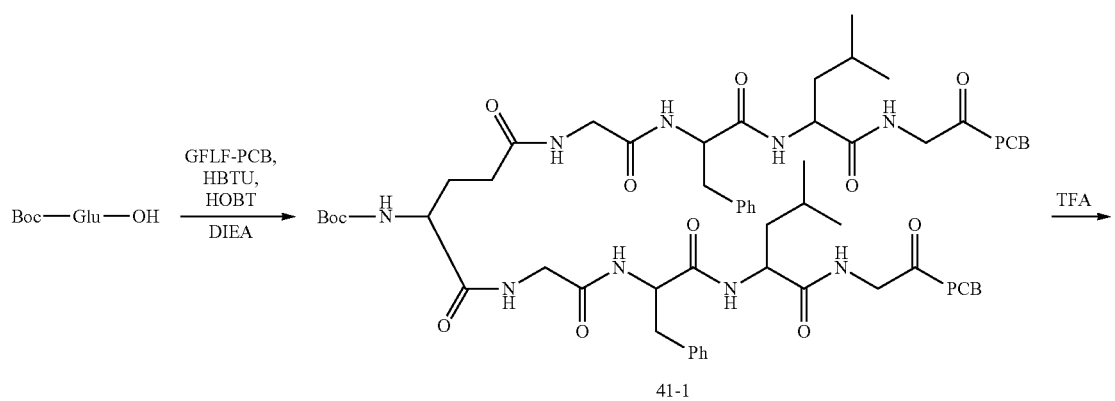

41-1

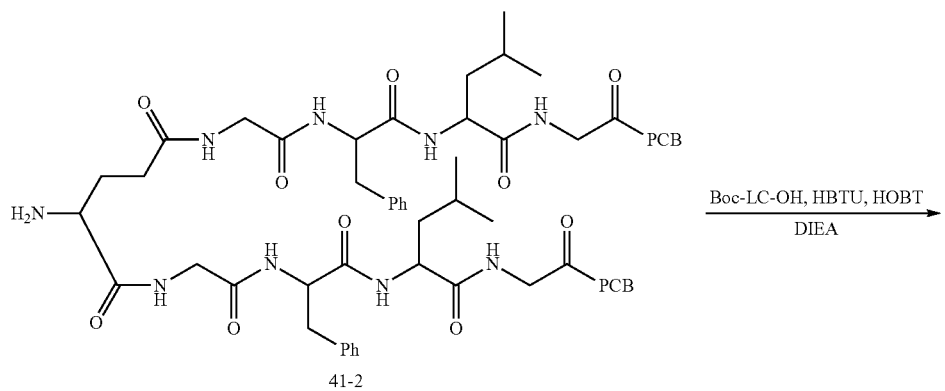

41-2

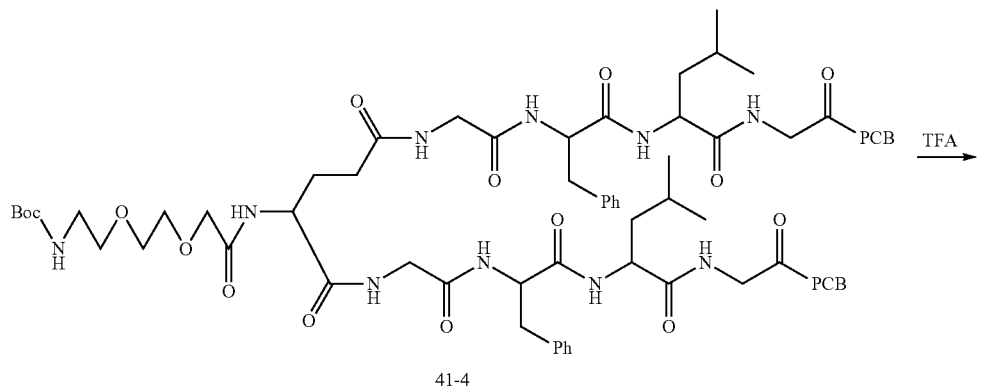

41-4

-continued
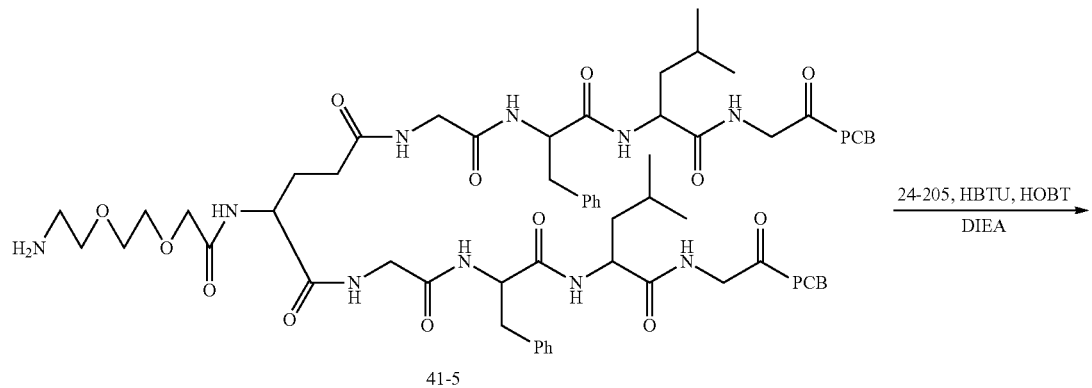
41-5
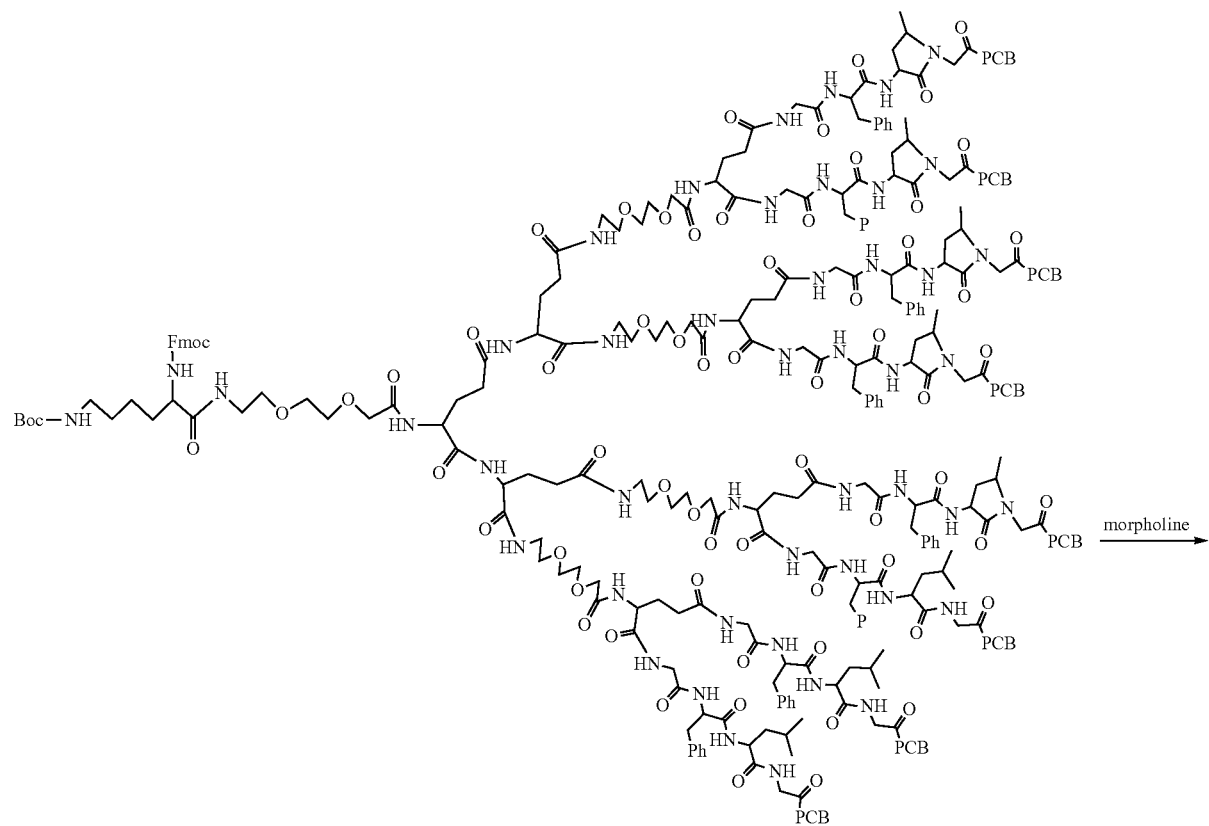
41-7

-continued
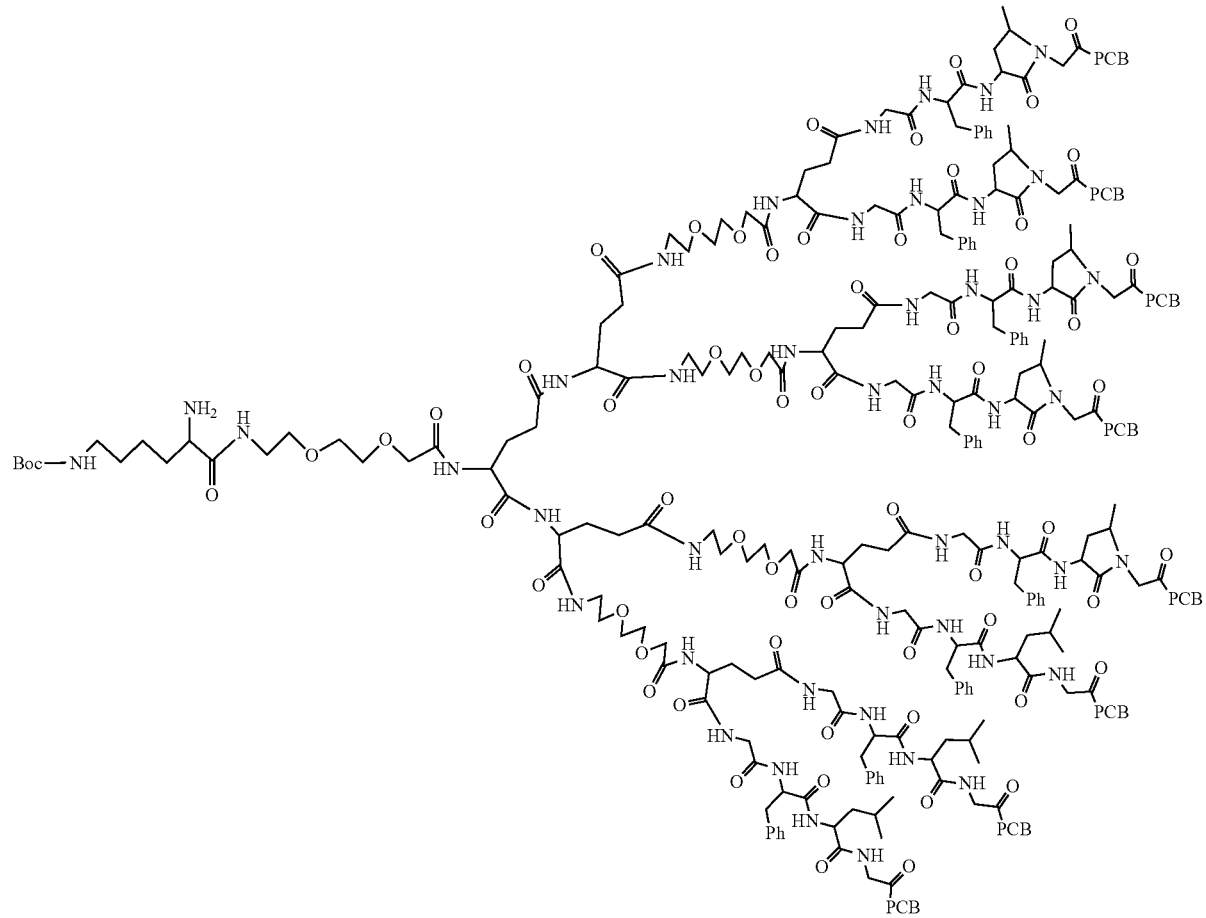
41-9
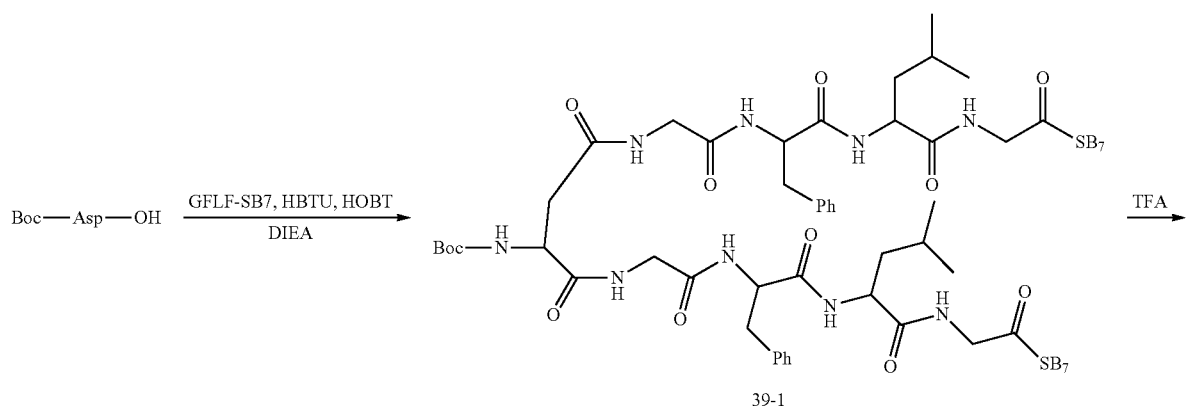

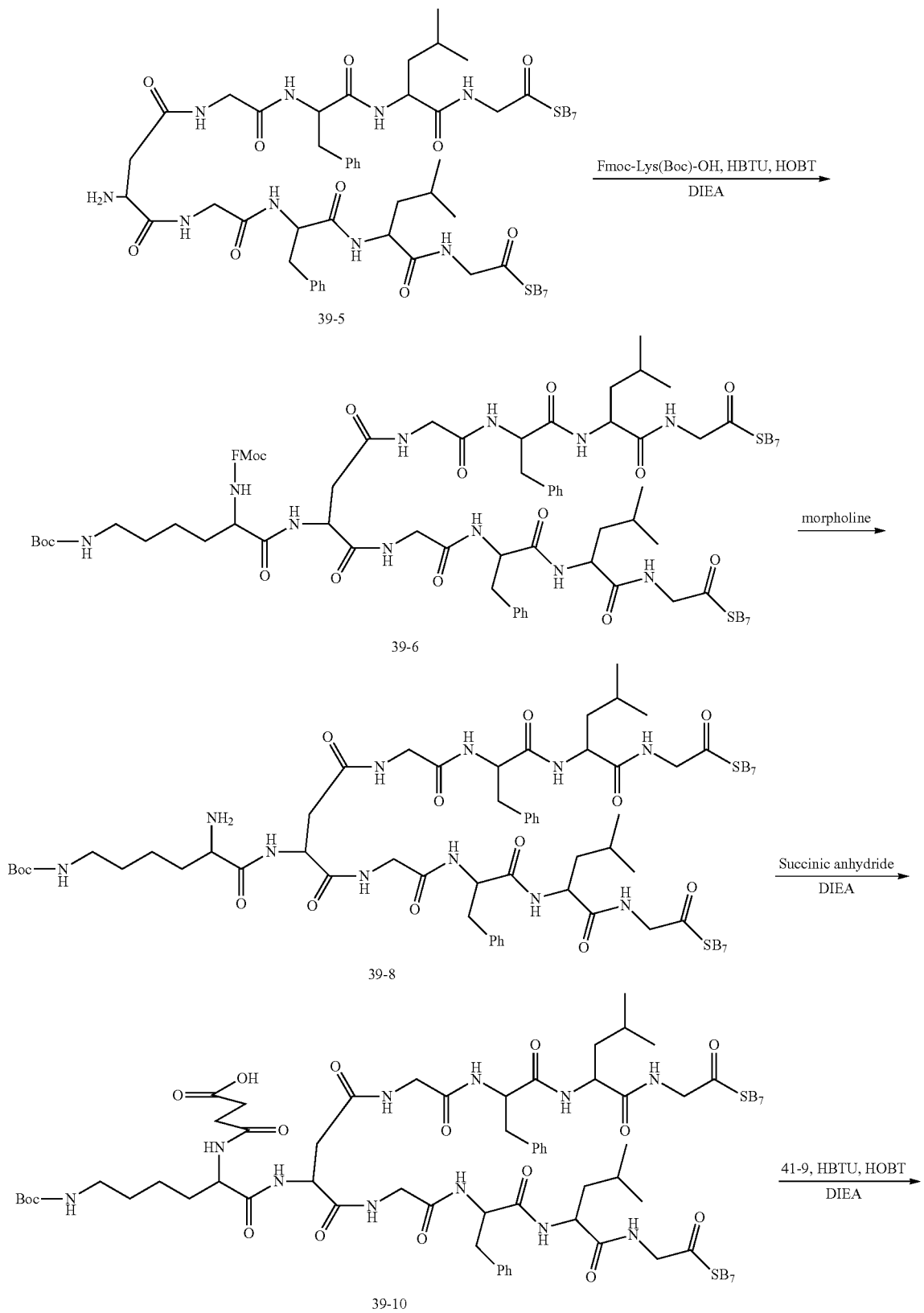

-continued
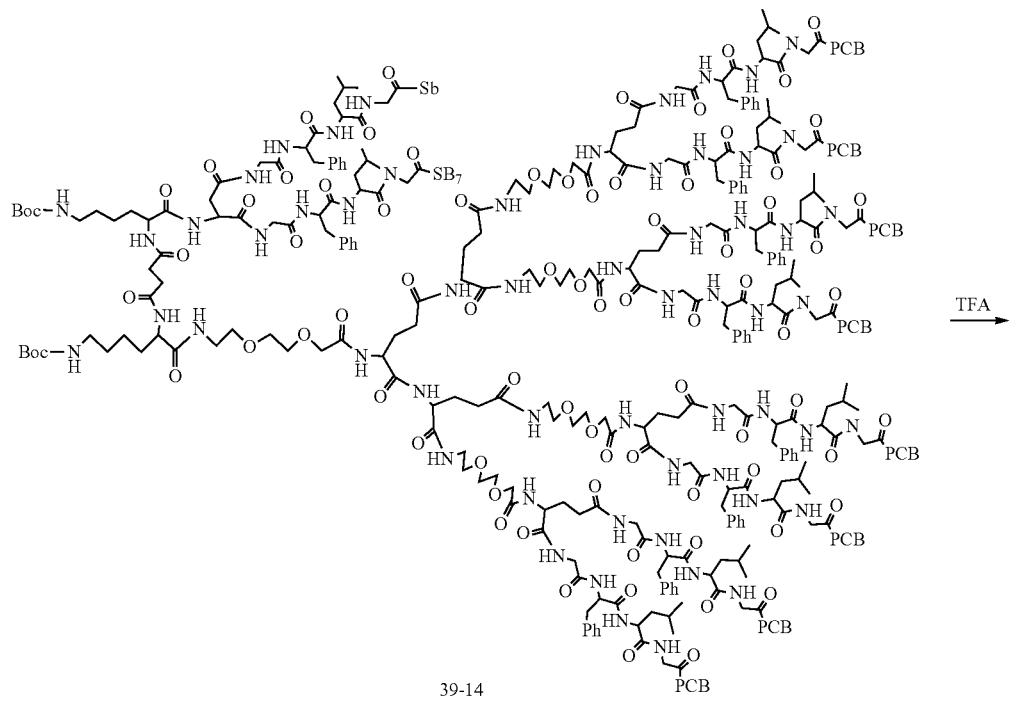
39-14
→ TFA
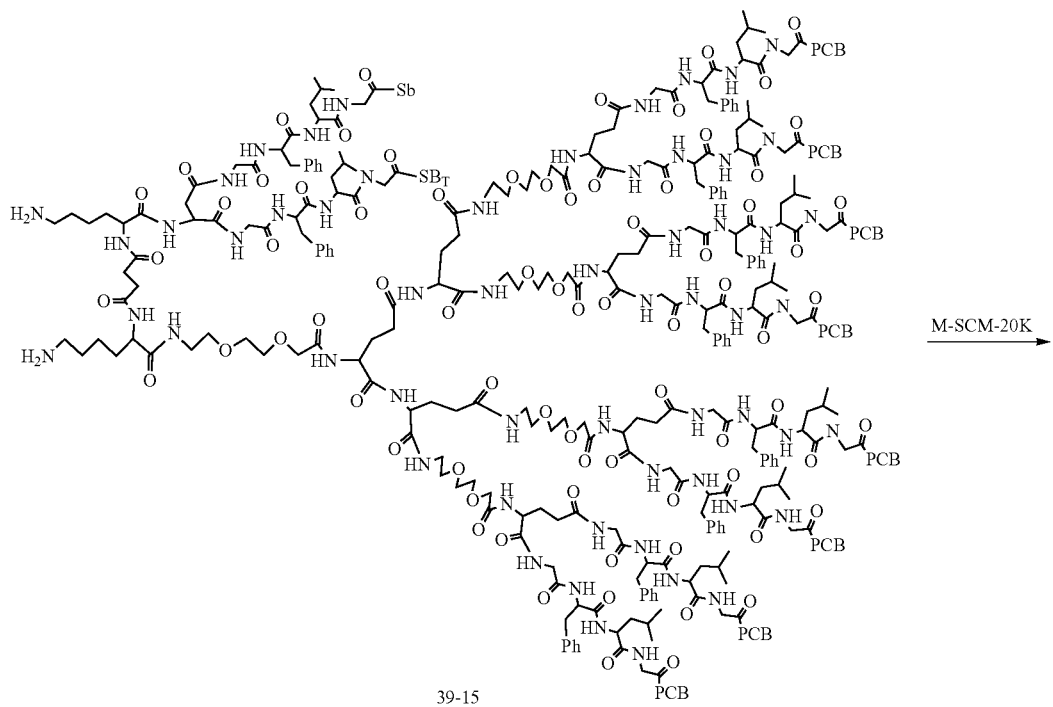
39-15
→ M-SCM-20K

-continued

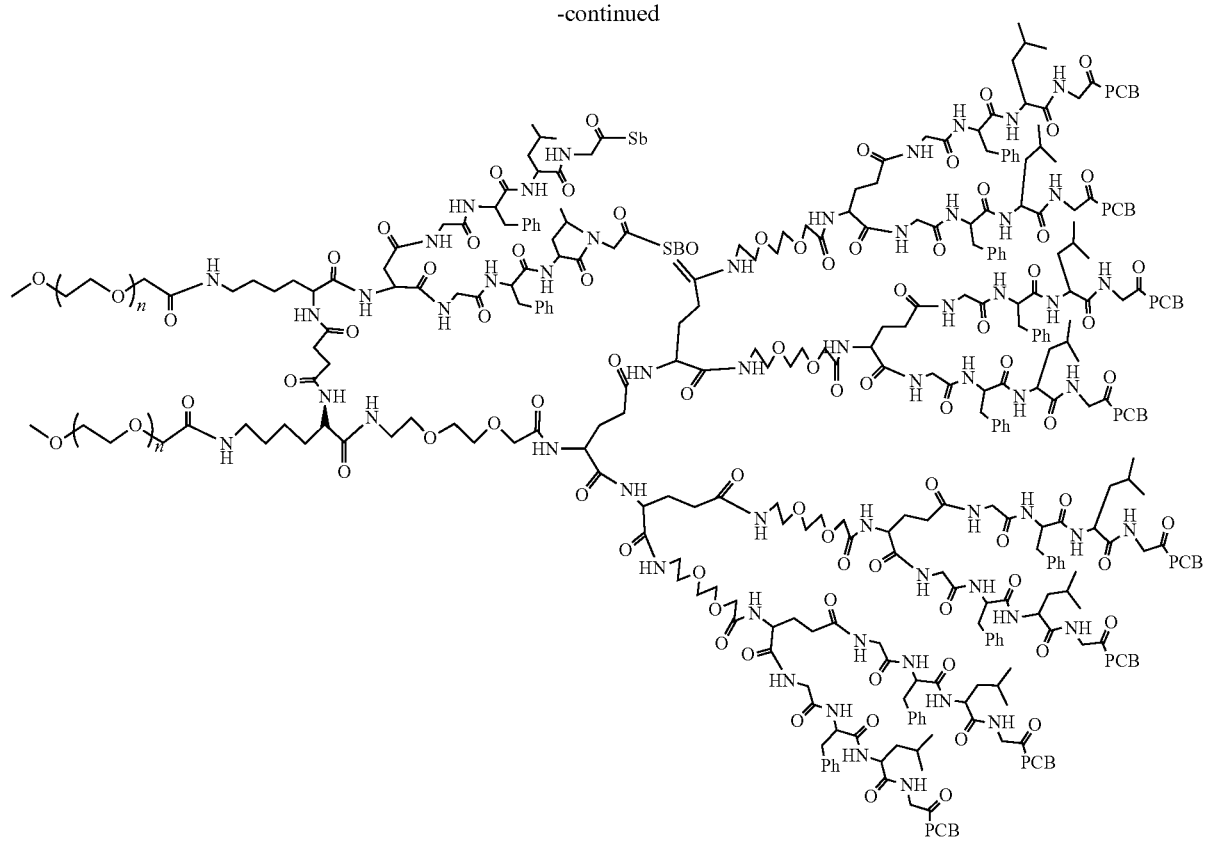

39-17

Details are given as follows:

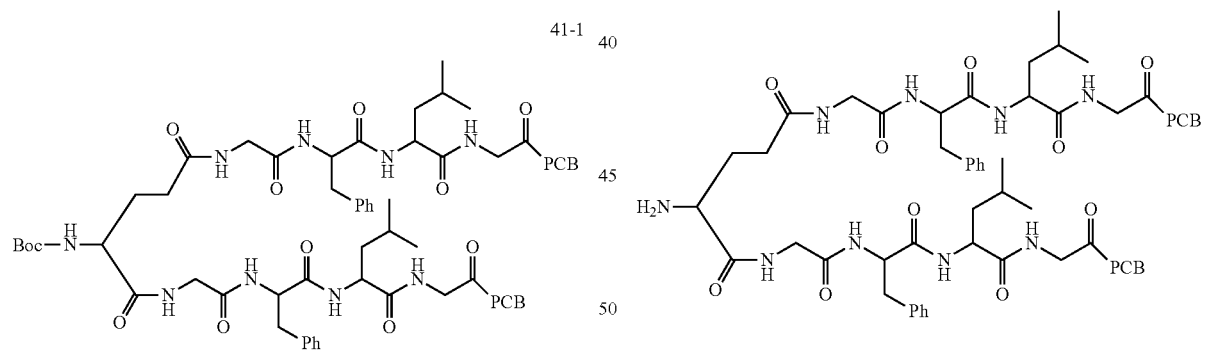

Boc-Glu-OH (1.2 g, 4.8 mmol), GFLF-PCB (synthesized according to the method of synthesizing 30-33, 8.2 g, 9.7 mmol), HBTU (5.5 g, 14.4 mmol) and HOBT (1.9 g, 14.4 mmol) were added in a 500 mL round-bottomed flask, and dissolved with DMF (50 mL), and the mixed solution was stirred to react at −5° C. for 30 minutes. Then DIEA (7.1 mL, 43.2 mmol) was slowly added dropwise, and the obtained solution continued to react for 2 hours, and was then moved to room temperature and stirred to react overnight. At the end of the reaction, deionized water (200 mL) was added to the reaction solution, a light yellow solid was separated out by precipitation, and suction filtering was carried out. The filter cake was dried, thus obtaining the product 22 g (weighed).

41-1 (22 g, 11.8 mmol) was added in a 500 mL round-bottomed flask, and dissolved with dichloromethane (10 mL), TFA (26.3 mL, 354 mmol) was added dropwise, and then the obtained solution was stirred to react at room temperature overnight. At the end of the reaction, the reaction solution was concentrated, and precipitated with n-hexane (100 mL) and methyl tert-butyl ether (300 mL), and then suction filtering was carried out. The filter cake was dissolved with dichloromethane (80 mL), methanol (20 mL), silica gel powder was added, and the operations of evaporation, dry sample loading, column chromatography and gradient elution with 1% ammonia water/3% methanol/dichloromethane-1% ammonia water/5% methanol/dichloromethane were carried out. The elution product was then collected, concentrated, thus obtaining the product 5.9 g, yield 70.2%.

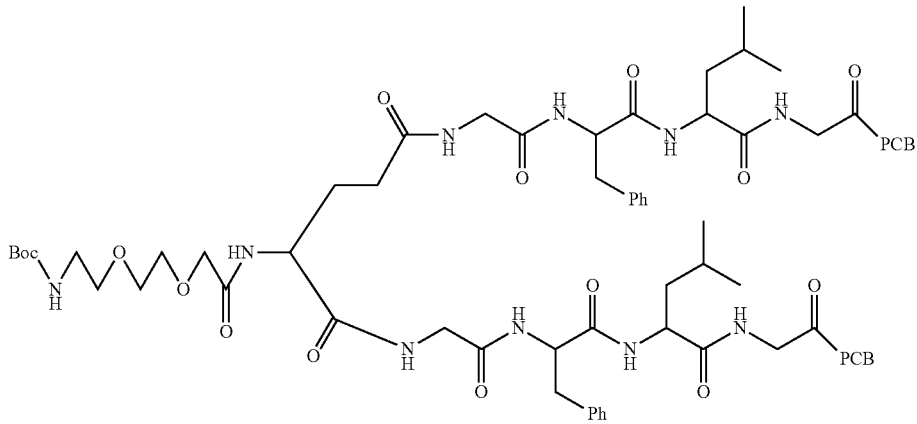

41-4

41-2 (5.9 g, 3.36 mmol), Boc-LC-OH (0.88 g, 3.36 mmol), HBTU (1.9 g, 5.04 mmol) and HOBT (0.68 g, 5.04 mmol) were added in a 250 mL round-bottomed flask, and dissolved with DMF (20 mL), and the mixed solution was stirred to react at −5° C. for 30 minutes. Then DIEA (2.5 mL, 15.12 mmol) was slowly added dropwise, and the obtained solution continued to react for 2 hours, and was then moved to room temperature and stirred to react overnight. At the end of the reaction, n-hexane (100 mL) and methyl tert-butyl ether (300 mL) were added to the obtained solution for precipitation to separate out a solid, and suction filtering was carried out. The filter cake was dried in vacuum.

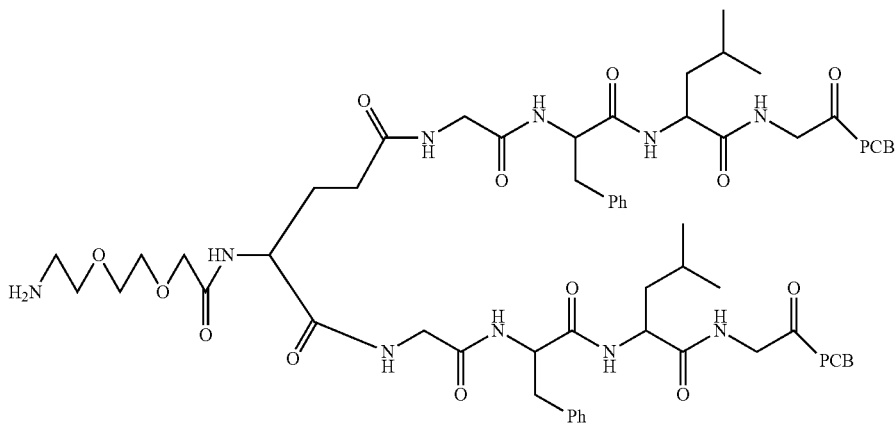

41-6

41-4 (7.9 g, 3.9 mmol) was added in a 250 mL round-bottomed flask, and dissolved with dichloromethane (10 mL), TFA (8.7 mL, 117 mmol) was added dropwise, and then the obtained solution was stirred to react at room temperature overnight. At the end of the reaction, the reaction solution was concentrated, precipitated with n-hexane (100 mL) and methyl tert-butyl ether (300 mL), suction filtering was carried out, and the solid product was separated out, and dried. The operations of dry sample loading, column chromatography and gradient elution with 1% ammonia water: 3% methanol/dichloromethane-1% ammonia water: 5% methanol/dichloromethane were carried out. The elution product was then collected, concentrated, thus obtaining the product.

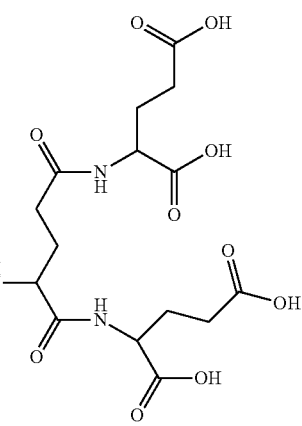

24-205

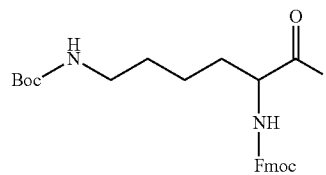

Reactants 15-91 (synthesized according to the method of synthesizing 35-3, 0.33 g, 0.1503 mmol) and 10% Pd/C (30 mg) were added in a micro-reactor, and dissolved with DMF (30 mL), $H_2$ (20 psi) was introduced, and then the mixed solution was stirred to react. At the end of the reaction, the reaction solution was filtered by suction with diatomaceous earth as a filter cake to remove the Pd/C, and then the diatomaceous earth was washed 4 times with DMF to obtain the DMF solution of 24-205 used for the next reaction.

41-7

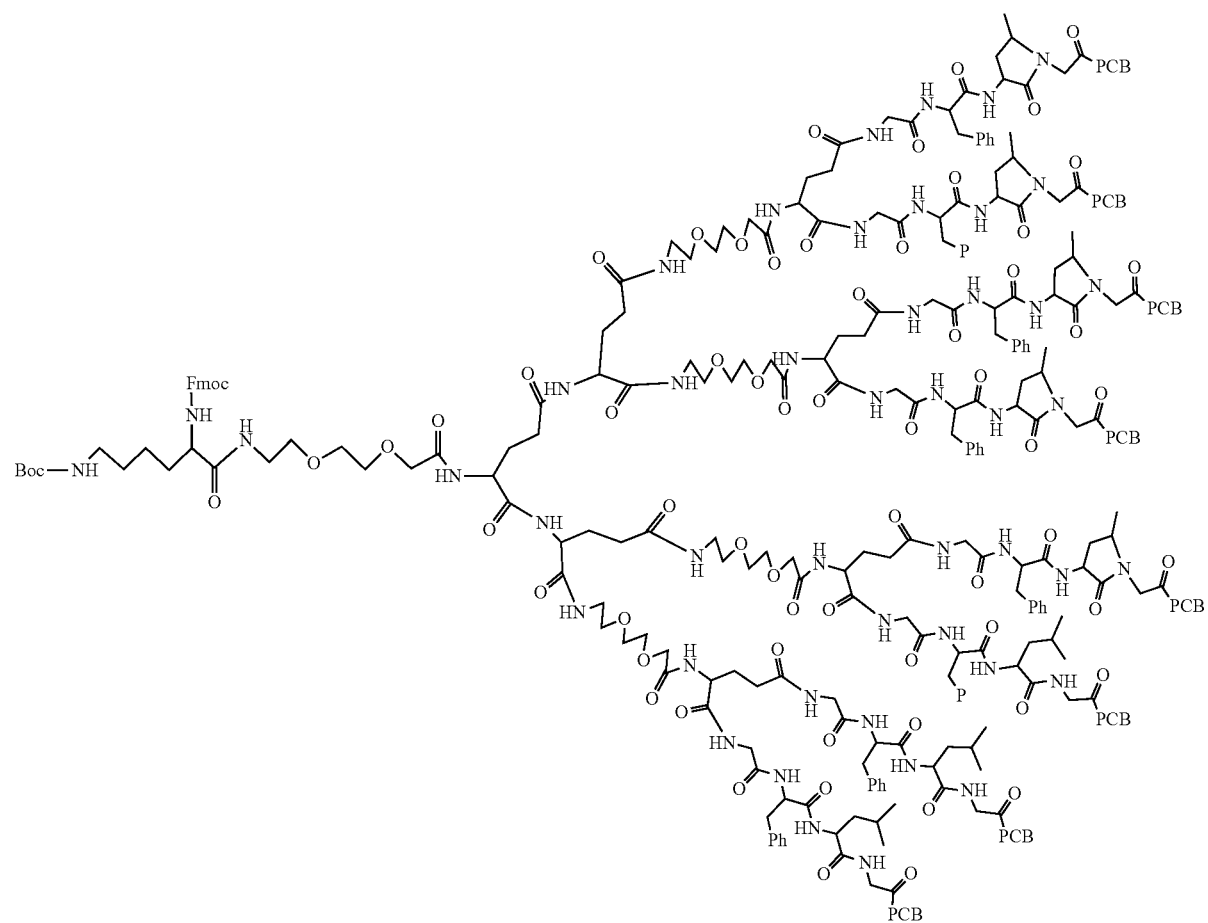

41-6 (0.84 g, 0.44 mmol), 24-247 (synthesized according to the method of synthesizing 24-205, 0.88 g, 0.091 mmol), HBTU (0.07 g, 0.546 mmol) and HOBT (0.2 g, 0.546 mmol) were added in a 250 mL round-bottomed flask, and dissolved with DMF (20 mL), and then the obtained solution was stirred at −5° C. for 30 minutes. Then DIEA (0.27 mL, 1.638 mmol) was slowly added dropwise, and the obtained solution continued to react for 2 hours, and was then moved to room temperature and stirred to react overnight. At the end of the reaction, the reaction solution was precipitated with n-hexane (100 mL) and methyl tert-butyl ether (300 mL) to separate out a solid, and suction filtering was carried out. The filter cake was dried in vacuum.

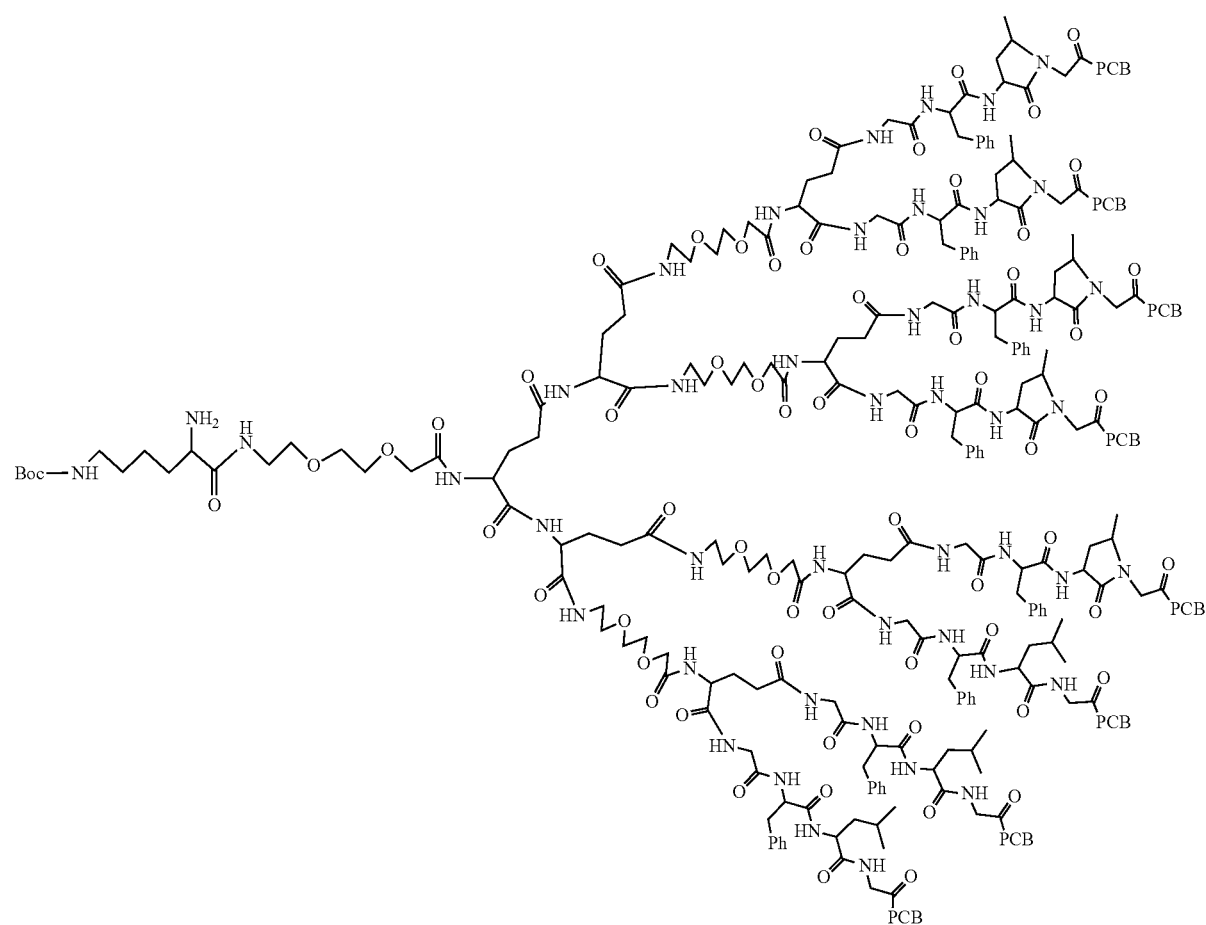

41-9

Reactant 41-7 (0.7 g, 0.082 mmol) was dissolved with DMF (30 mL), morpholine (0.214 mL, 2.46 mmol) was added, and then the mixed solution was stirred to react until the reaction ended. At the end of the reaction, methyl tert-butyl ether (100 mL) and n-hexane (200 mL) were added to the reaction solution for precipitation to obtain a powder product, and suction filtering was carried out. The operations of column chromatography, dry sample loading and gradient elution with 1% ammonia water: 5% methanol/dichloromethane—1% ammonia water: 12% methanol/dichloromethane were carried out, thus obtaining the product 0.5 g.

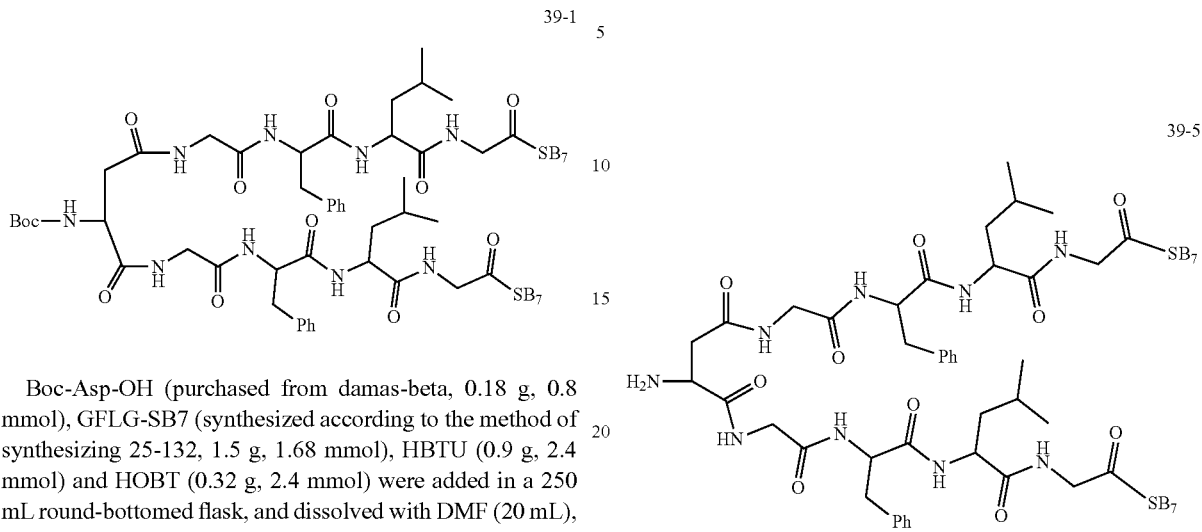

39-1

Boc-Asp-OH (purchased from damas-beta, 0.18 g, 0.8 mmol), GFLG-SB7 (synthesized according to the method of synthesizing 25-132, 1.5 g, 1.68 mmol), HBTU (0.9 g, 2.4 mmol) and HOBT (0.32 g, 2.4 mmol) were added in a 250 mL round-bottomed flask, and dissolved with DMF (20 mL), and the mixed solution was stirred to react at −5° C. for 30 minutes. Then DIEA (1.19 mL, 7.2 mmol) was slowly added dropwise, and the obtained solution continued to react for 2 hours, and was then moved to room temperature and stirred to react. At the end of the reaction, deionized water (200 mL) was added to the reaction solution, the obtained solution was extracted three times with ethyl acetate (100 mL×3), and the obtained organic phases were combined. The organic phase was washed two times with saturated sodium chloride solution (200 mL), concentrated and evaporated to dryness. The operations of dry sample loading, column chromatography and gradient elution with 1% ammonia water: 2% methanol/dichloromethane-1% ammonia water: 3% methanol/dichloromethane were carried out. The elution product was then collected, concentrated, and evaporated to dryness, obtaining the product used for the next reaction.

39-5

39-1 (1.5 g, 0.8 mmol) was added in a 250 mL round-bottomed flask and dissolved with dichloromethane (20 mL), TFA (1.78 mL, 24 mmol) was added, and then the mixed solution was stirred to react at room temperature overnight. At the end of the reaction, the reaction solution was concentrated, and extracted with saturated sodium bicarbonate solution (200 mL), ethyl acetate (100 mL), and the organic phase was separated. The aqueous phase was extracted three times with ethyl acetate (100 mL×3), and the obtained organic phases were combined. The organic phase was washed two times with saturated sodium chloride solution (200 mL), and evaporated to dryness, thus obtaining the product 1.1 g, yield 73.3%.

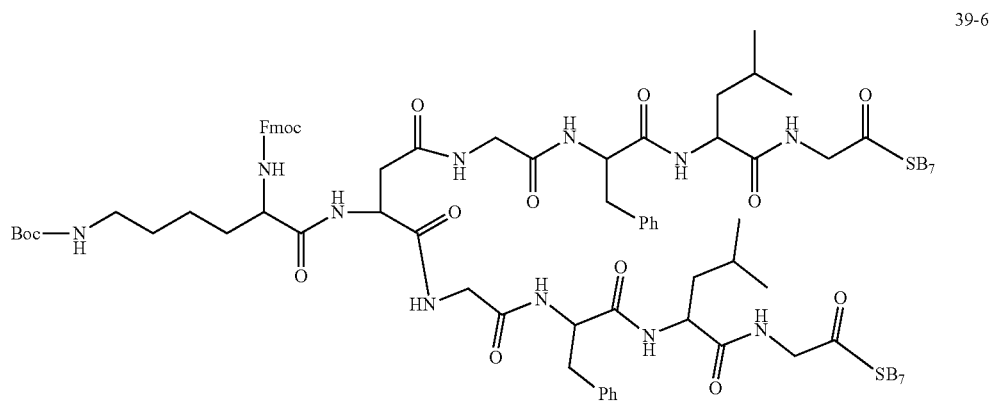

39-6

39-5 (1.1 g, 0.58 mmol), Fmoc-Lys (Boc) —OH (0.28 g, 0.609 mmol), HBTU (0.32 g, 0.87 mmol) and HOBT (0.11 g, 0.87 mmol) were added in a 250 mL round-bottomed flask, and dissolved with DMF (20 mL), and the mixed solution was stirred to react at −5° C. for 30 minutes. Then DIEA (0.43 mL, 2.61 mmol) was slowly added dropwise, and the obtained solution continued to react for 2 hours, and was then moved to room temperature and stirred to react. At the end of the reaction, the reaction solution was extracted with deionized water (200 mL), ethyl acetate (100 mL), and the organic phase was separated. The aqueous phase was extracted three times with ethyl acetate (100 mL×3), and the obtained organic phases were combined. The organic phase was washed two times with saturated sodium chloride solution (200 mL), concentrated and evaporated to dryness, thus obtaining the product 1.3 g.

39-8 (0.58 mmol) was added in a 250 mL round-bottomed flask, and dissolved with DMF (20 mL). Then, DIEA (0.38 ml, 2.32 mmol) was added, and then the mixed solution was stirred to react at room temperature for 30 minutes. Succinic anhydride (0.17 g, 2.32 mmol) was added, and the obtained solution continued to react. At the end of the reaction, the reaction solution was extracted with deionized water (200 mL), ethyl acetate (100 mL), and the organic phase was separated. The aqueous phase was extracted three times with ethyl acetate (100 mL×3), and the obtained organic phases were combined. The organic phase was washed two times with saturated sodium chloride solution (200 mL), concentrated and evaporated to dryness, and the obtained product was used for the next reaction.

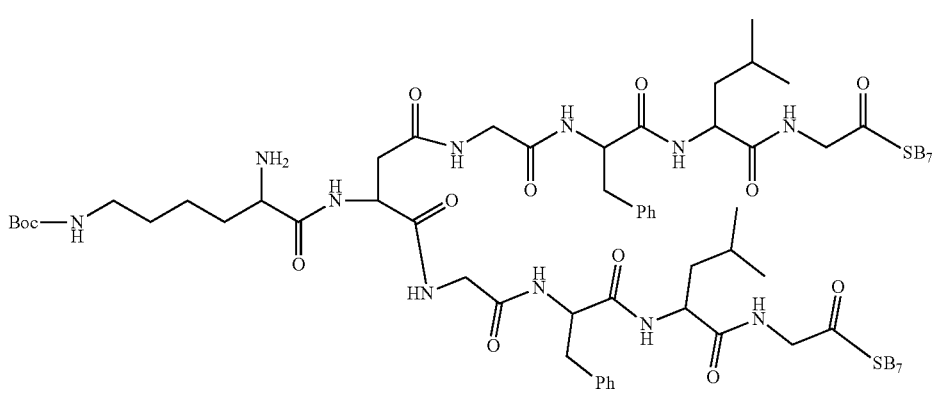

39-8

39-6 (1.5 g, 0.58 mmol) was added in a 250 mL round-bottomed flask, and dissolved with DMF (20 mL), morpholine (1.51 mL, 17.4 mmol) was added, and the mixed solution was stirred to react at room temperature for 1 hour. At the end of the reaction, the reaction solution was extracted with deionized water (200 mL), ethyl acetate (100 mL), and the organic phase was separated. The aqueous phase was extracted three times with ethyl acetate (100 mL×3), and the obtained organic phases were combined. The organic phase was washed two times with saturated sodium chloride solution (200 mL), concentrated and evaporated to dryness, and the obtained product was used for the next reaction.

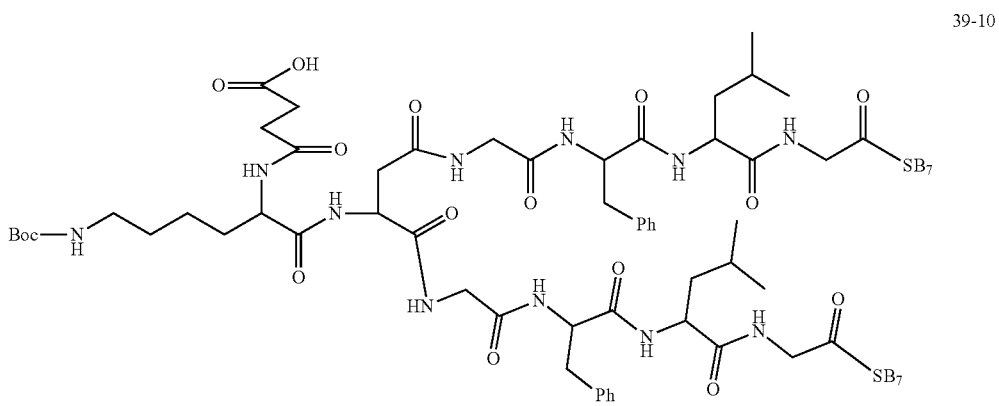

39-10

39-14

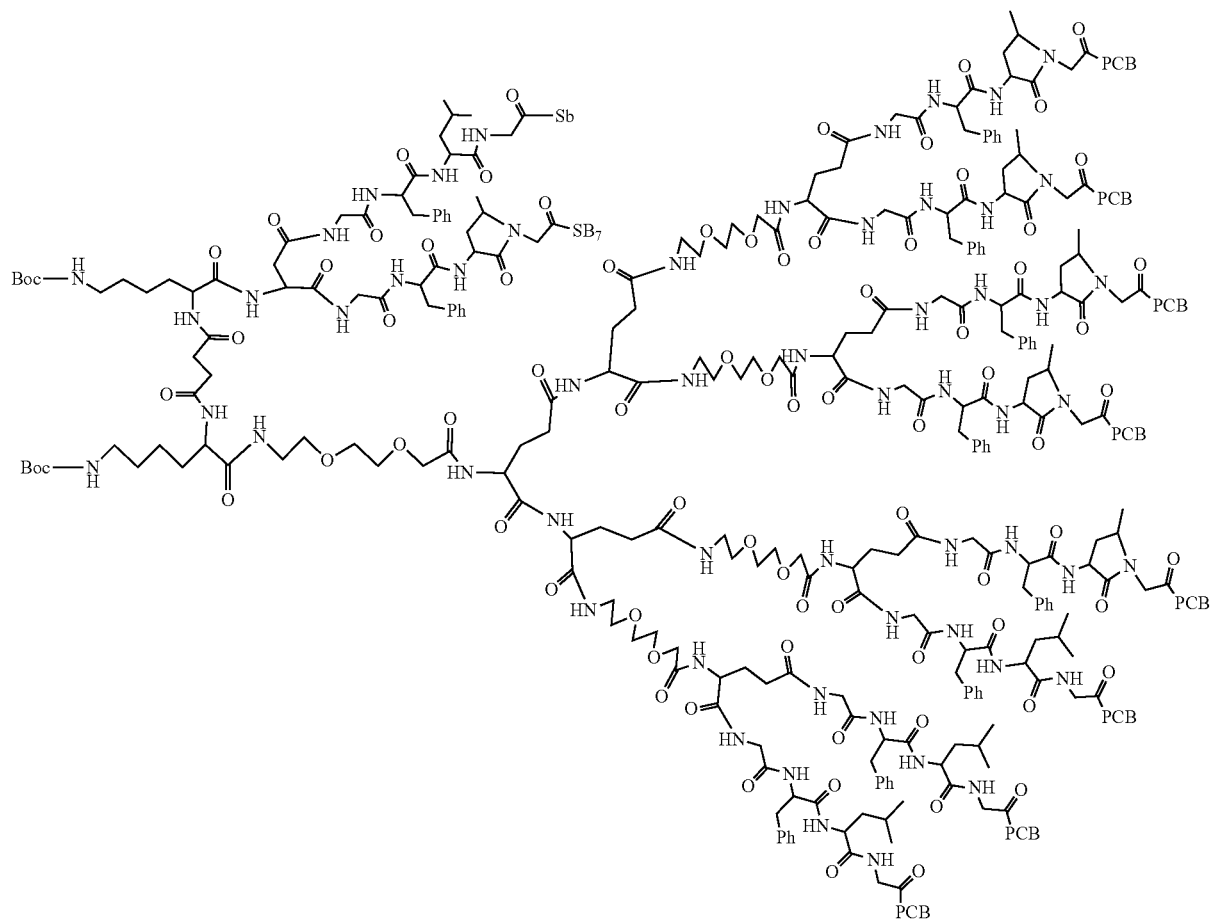

Reactants 41-9 (0.5 g, 0.06 mmoL), 39-10 (0.134 g, 0.060 mmoL), HBUT (0.034 g, 0.09 mmoL), HOBT (0.012 g, 0.09 mmoL) were added in a 250 mL flask, and dissolved with DMF (30 mL), and the mixed solution was stirred to react at −5° C. for 30 minutes. Then DIEA (0.044 mL, 0.27 mmoL) was slowly added dropwise, and, after 1 hour, the obtained solution was moved to room temperature and stirred to react. At the end of the reaction, methyl tert-butyl ether (100 mL) and n-hexane (200 mL) were added to the reaction solution for precipitation to obtain a powder product. The operations of column chromatography, dry sample loading and elution with 1% ammonia water: 4% methanol/dichloromethane—1% ammonia water: 10% methanol/dichloromethane were carried out. The elution product was evaporated to dryness, thus obtaining the product 0.5 g, yield 80%.

39-15

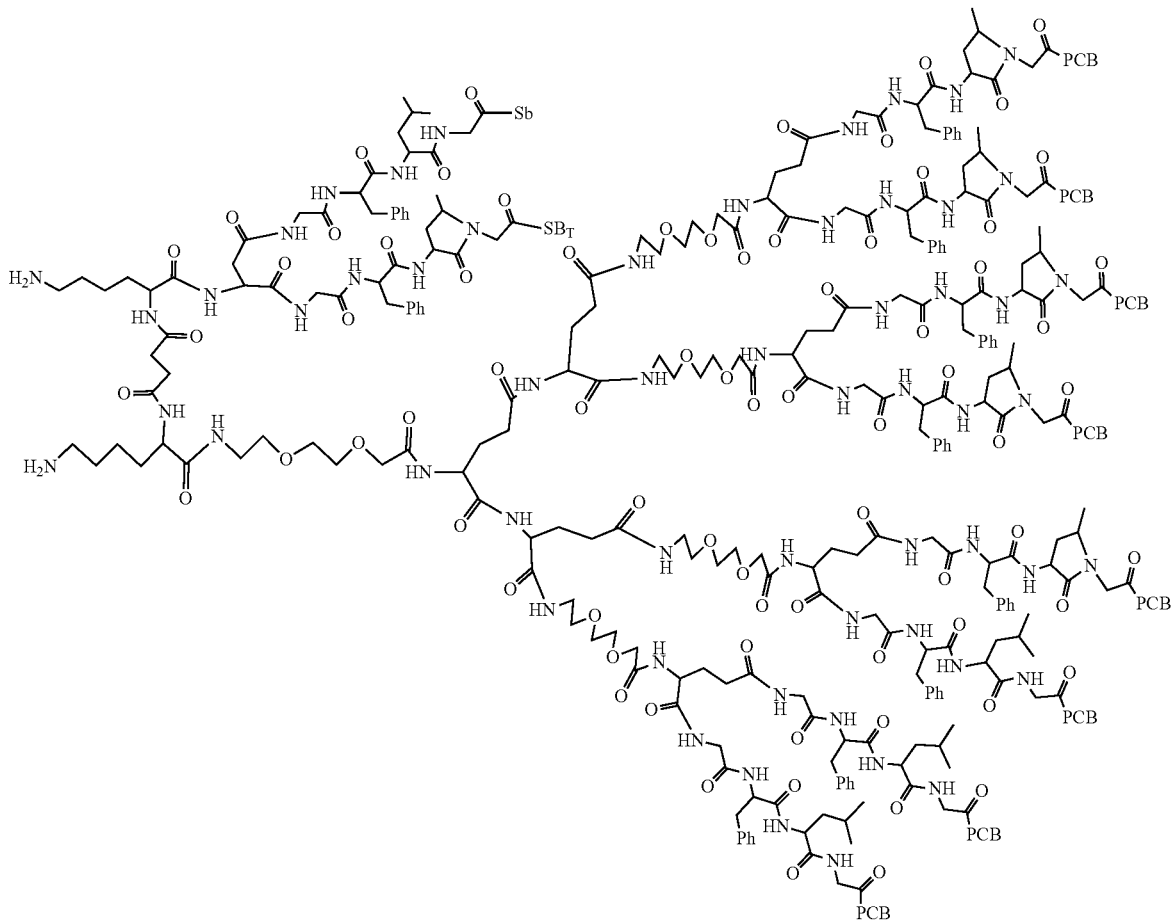

39-14 (0.5 g) was dissolved with dichloromethane (5 mL) and TFA (0.106 mL, 1.42 mmol) in a condition of ultrasonic, and then the mixed solution was stirred to react. At the end of the reaction, the reaction solution was concentrated, and methyl tert-butyl ether (100 mL) and n-hexane (200 mL) were added to the obtained solution for precipitation to obtain a powder product. The operations of column chromatography, dry sample loading and gradient elution with 1% ammonia water: 6% methanol/dichloromethane—1% ammonia water: 10% methanol/dichloromethane were carried out, thus obtaining the product 0.1 g.

$^1$H-NMR (600 MHz, DMSO-$d_6$) δ 10.19-10.15 (m, 7H), 9.11-8.89 (m, 7H), 8.36-8.00 (m, 37H), 7.94-7.85 (m, 13H), 7.54-7.47 (m, 11H), 7.30-7.11 (m, 89H), 6.74-6.63 (m, 2H), 5.87-5.78 (m, 6H), 4.66-3.37 (m, 118H), 3.29-2.53 (m, 123H), 2.45-2.39 (m, 24H), 2.34-2.18 (m, 59H), 2.14-1.42 (m, 107H), 0.94-0.76 (m, 72H).

39-17

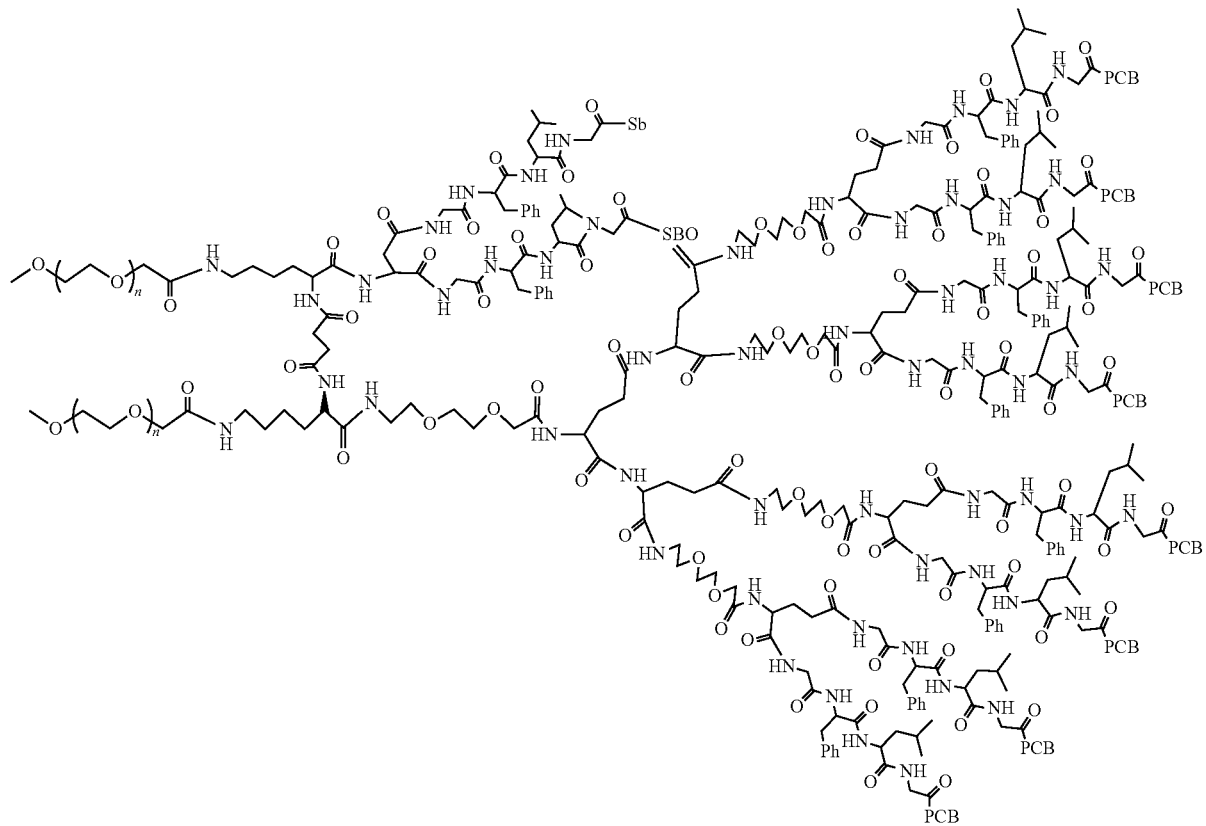

Reactant 39-15 (1 g) was dissolved with DMF solution (20 mL), M-SCM-20K (0.4 g) was added, and the obtained solution reacted at a low speed of stirring in the dark. At the end of the reaction, the reaction solution was precipitated with methyl tert-butyl ether (50 mL) and n-hexane (100 mL) to separate out a solid, and suction filtering was carried out. The filter cake was dissolved with dichloromethane (50 mL), silica gel powder was added to the obtained solution, and the operations of evaporation, column chromatography, dry sample loading and gradient elution with dichloromethane—1% ammonia water: 6% methanol/dichloromethane were carried out. The elution product was collected, evaporated to dryness, and then dissolved with anhydrous ethanol (10 mL), the obtained solution was treated by ultrasonic to obtain homogeneous phase, and then n-hexane (50 mL) was added for precipitation. Such precipitation operation was repeated three times. The precipitate was dried in vacuum, thus obtaining the product 0.15 g.

$^1$H-NMR (600 MHz, DMSO-$d_6$) δ 10.20-10.12 (m, 2H), 9.00-8.90 (m, 2H), 8.16-7.83 (m, 40H), 7.42-7.04 (m, 123H), 4.64-4.13 (m, 129H), 4.03-3.97 (m, 35H), 3.81-3.80 (m, 26H), 3.70-3.66 (m, 149H), 3.51-3.50 (m, 876H), 3.27-2.64 (m, 20H), 2.43-2.24 (m, 54H), 2.17-1.41 (m, 24H), 0.97-0.73 (m, 72H).

4. Synthesis of 43-27 (Compound No. 6)
Synthetic route is as follows

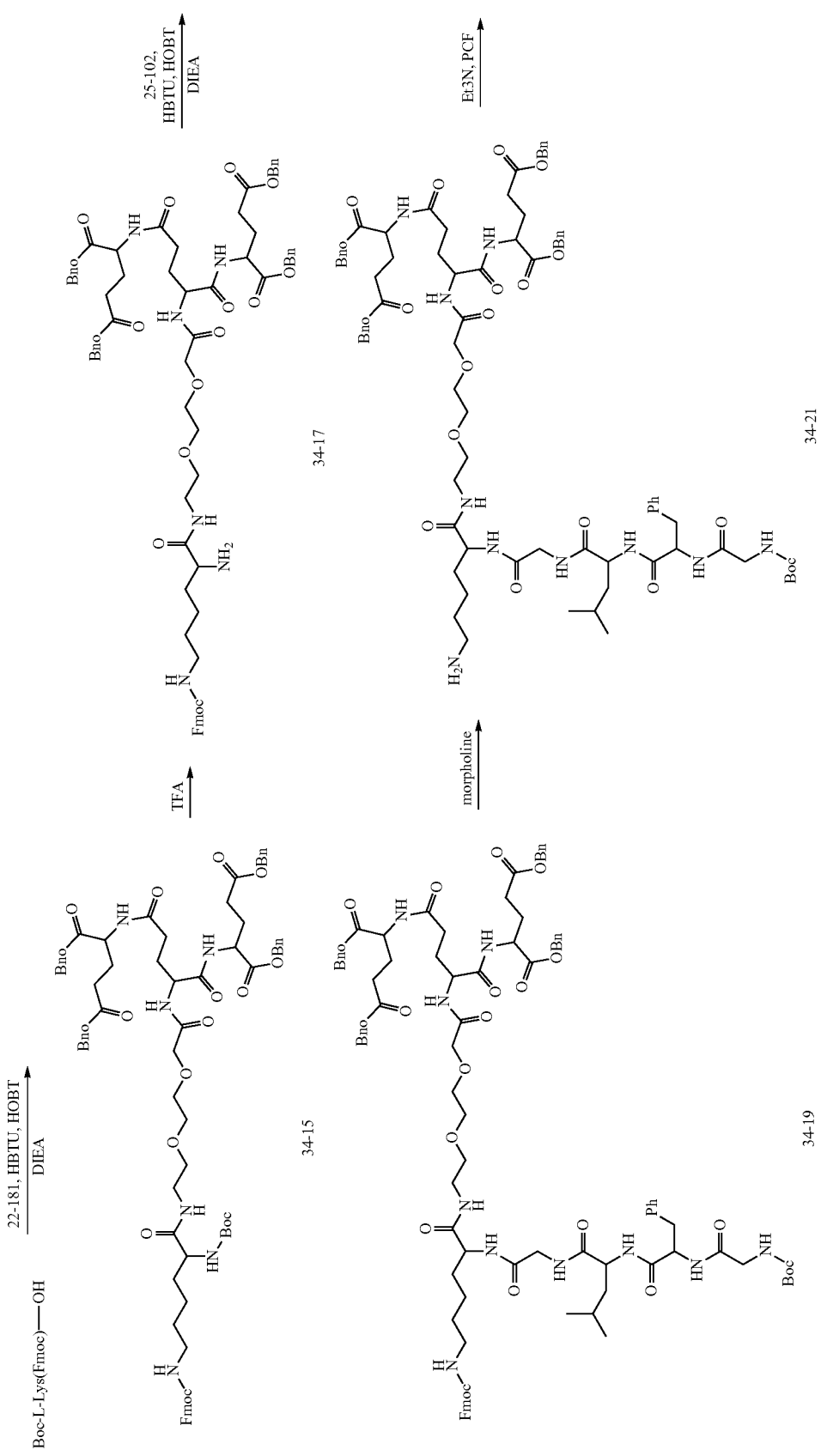

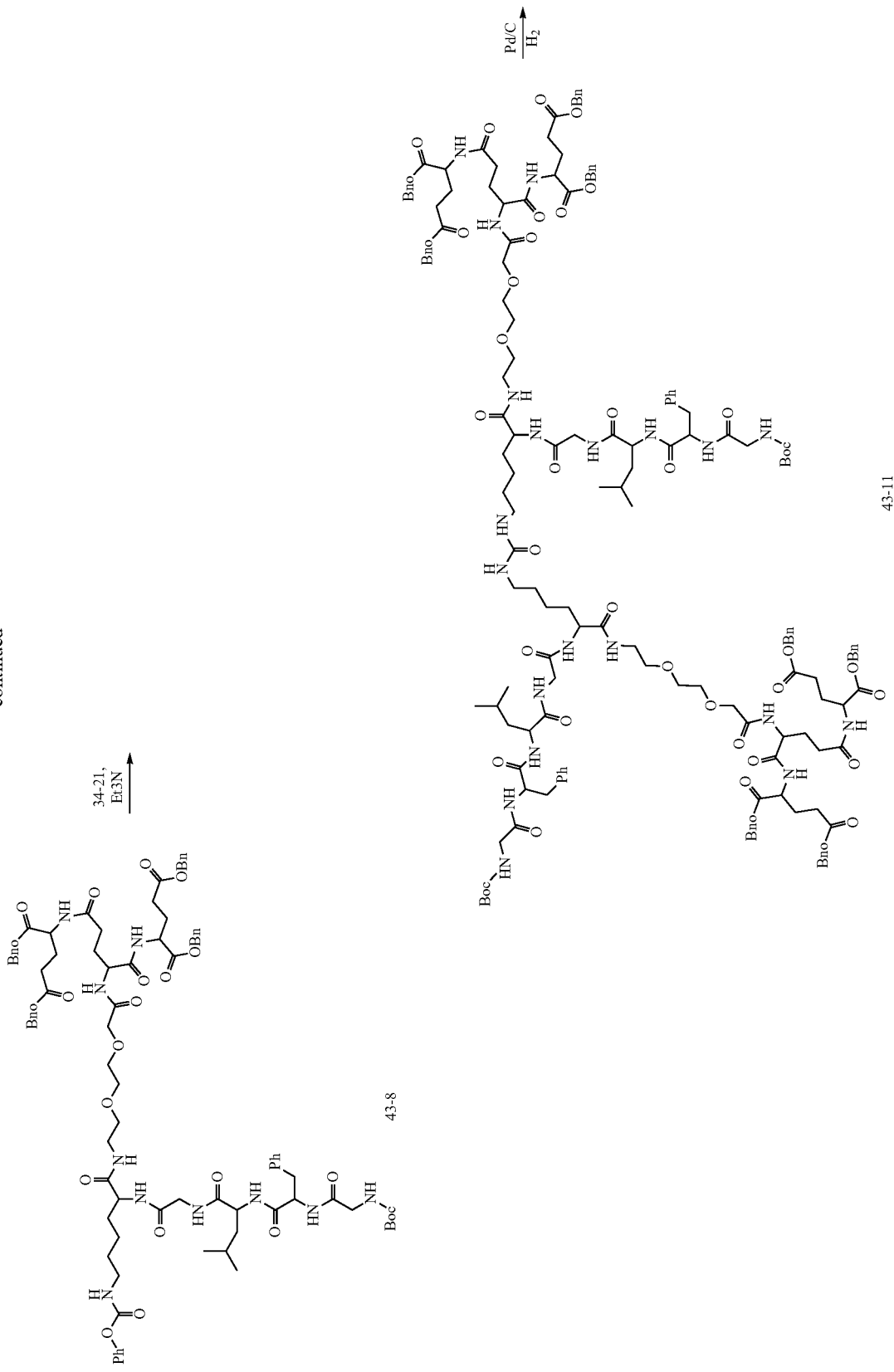

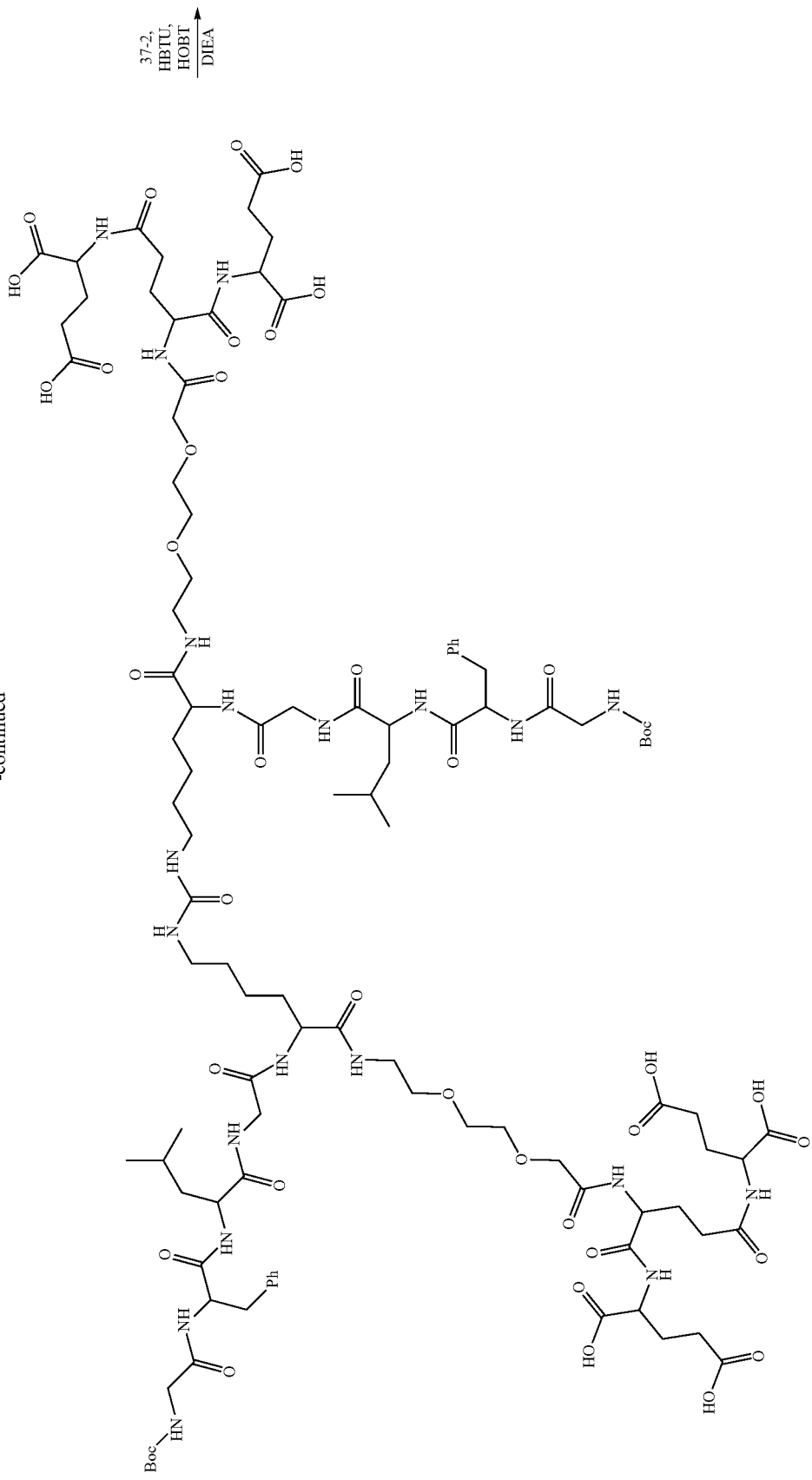

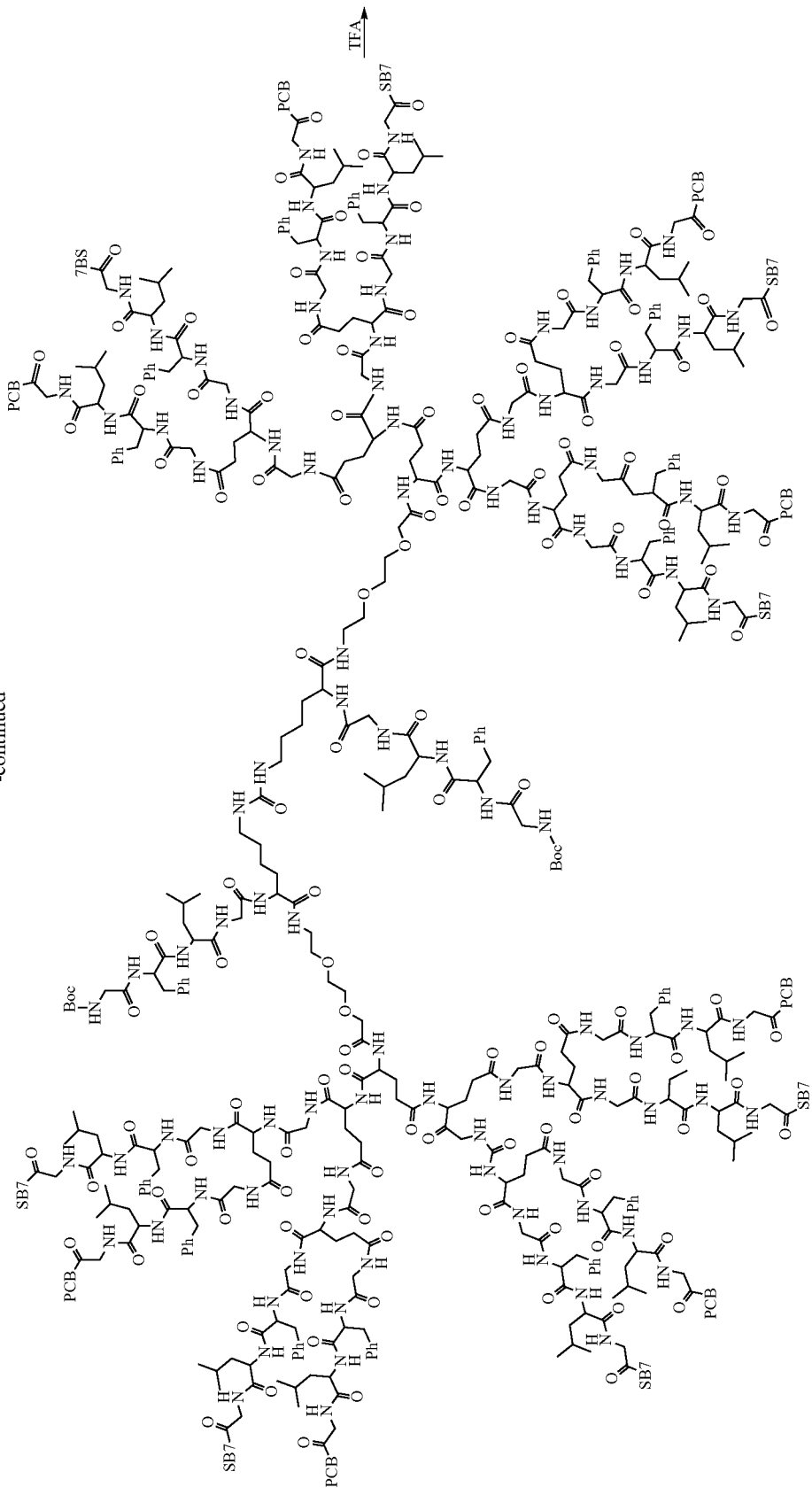

-continued
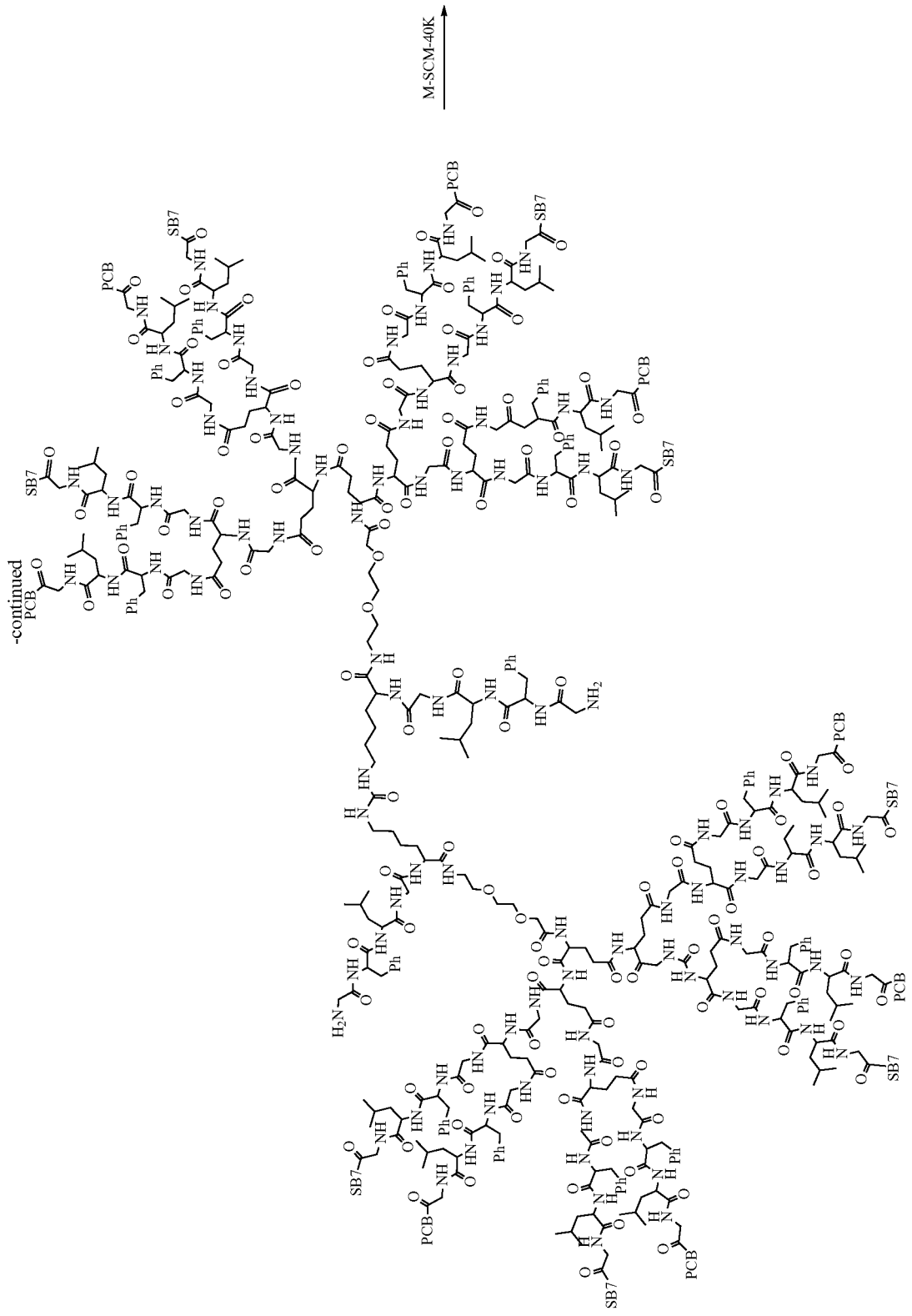
43-24

-continued
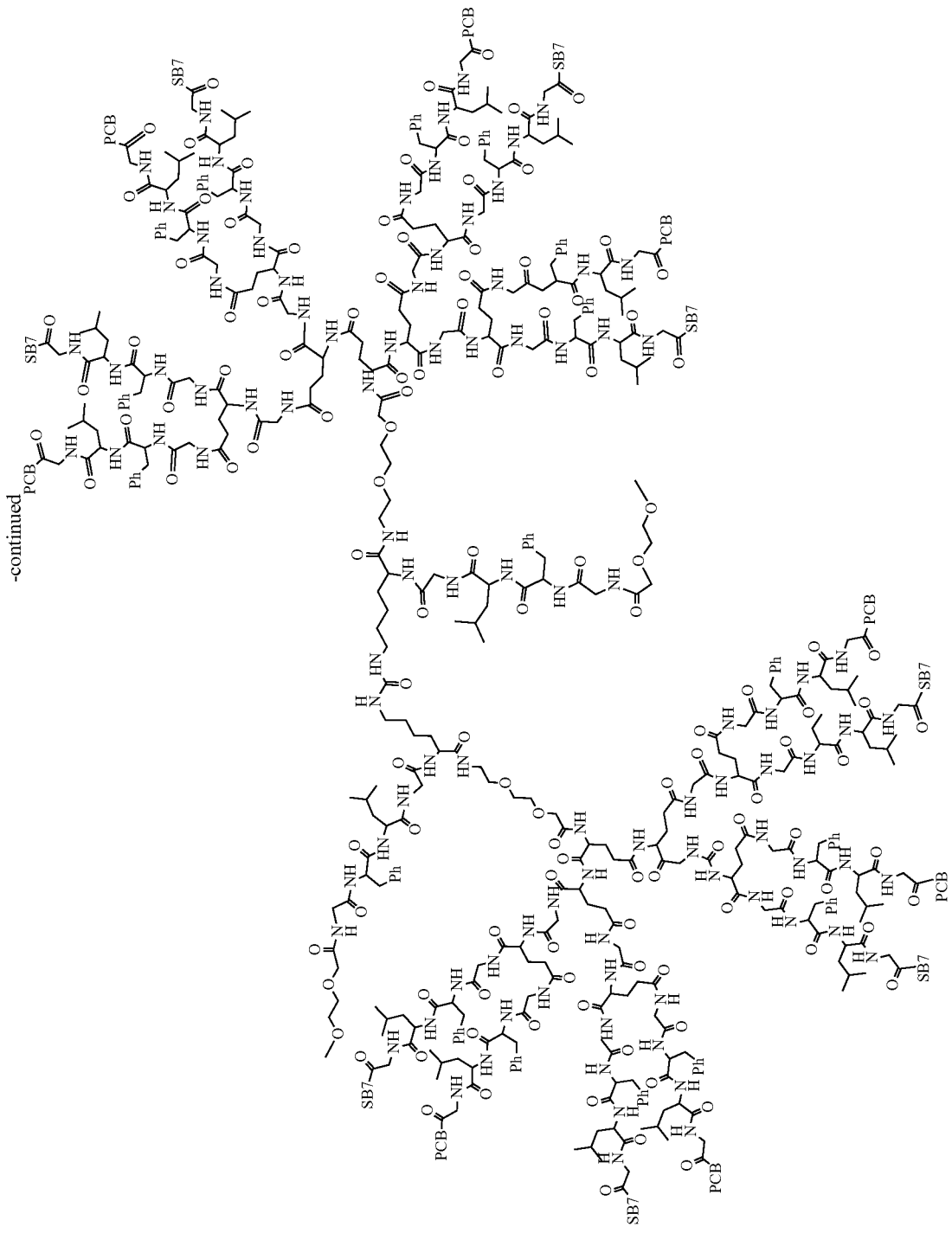
43-27

-continued
34-15
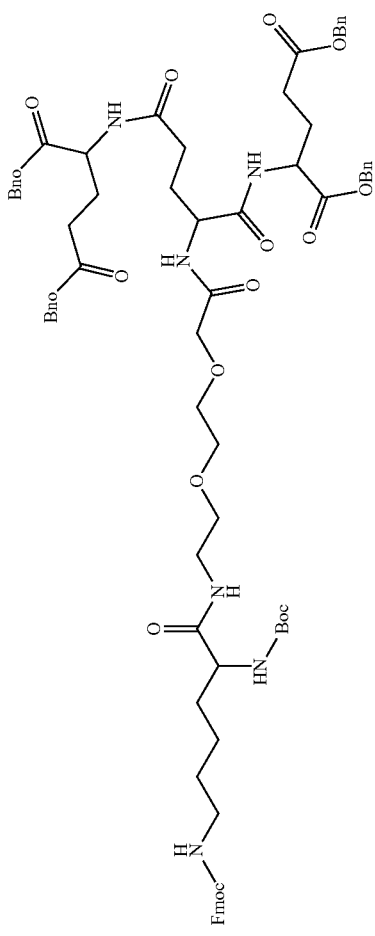

34-15

Boc-L-Lys (Fmoc)-OH (purchased from Aladdin, 2.78 g, 5.927 mmol), 22-181 (5.4 g, 5.927 mmol), HBTU (3.38 g, 8.891 mmol), HOBT (1.2 g, 8.891 mmol) were added in a 100 mL flask, and dissolved with DMF (50 mL), and then the obtained solution was stirred to react at −5° C. for about 30 minutes. Then DIEA (5.878 mL, 35.565 mmol) was slowly added dropwise. At the end of the addition, the obtained solution continued to react at −5° C. with stirring for 3 hours. At the end of the reaction, the reaction solution was transferred to a 1 L separatory funnel, deionized water (200 mL) and ethyl acetate (200 mL) were added, and the obtained solution was shaken for extraction. The aqueous phase was washed with ethyl acetate (150 mL×2), and the obtained organic phases were combined. The organic phase was washed with saturated saline solution (200 mL×1), concentrated, evaporated to dryness, and dried in a vacuum oven, thus obtaining the product 34-15: 8.07 g.

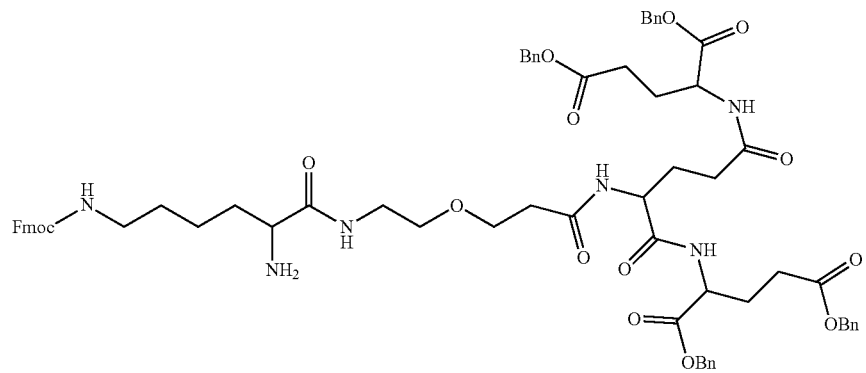

34-17

34-15 (8.0 g, 5.927 mmol) was added in a 500 mL flask, and dissolved with dichloromethane (15 mL), trifluoroacetic acid (4.4 mL, 59.271 mmol) was added, and the mixed solution was stirred to react at room temperature overnight. At the end of the reaction, the reaction solution was concentrated to a small amount, n-hexane (150 mL) was added to layer the obtained solution with shaking, the supernatant was discarded, and n-hexane (150 mL) was added to the lower oily product, and such operations were repeated six times. A viscous oily product was finally obtained, and dried, thus obtaining the product 34-17: 7.5 g.

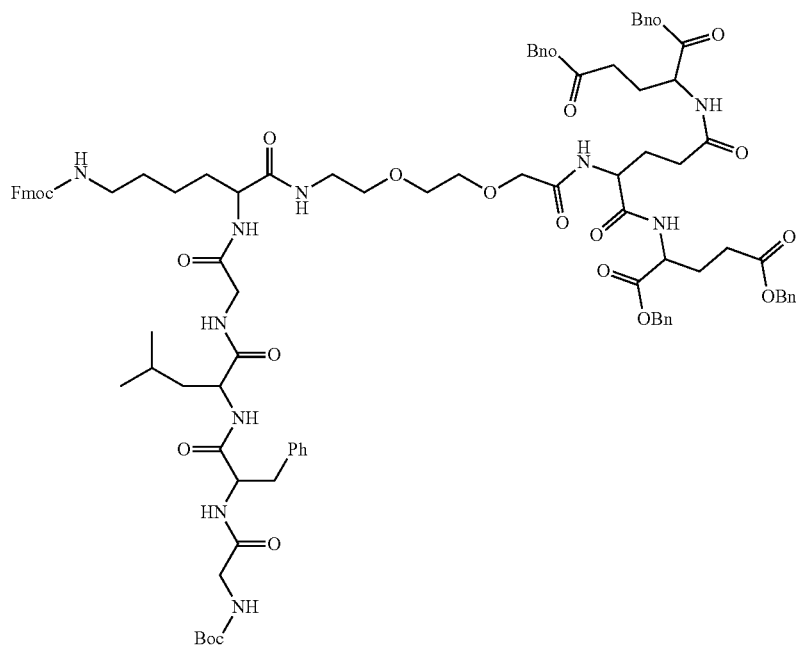

34-19

34-17 (7.5 g, 5.92 mmol), 34-18 (synthesized according to the method of synthesizing 25-102, 3.5 g, 7.11 mmol), HBTU (3.36 g, 8.88 mmol), HOBT (1.2 g, 8.88 mmol) were added in a 500 mL flask, and dissolved with DMF (50 mL), and then the obtained solution was stirred to react at −5° C. for about 30 minutes. Then DIEA (8.8 mL, 53.28 mmol) was slowly added dropwise. At the end of the addition, the obtained solution continued to react at −5° C. with stirring for 3 hours. At the end of the reaction, the reaction solution was transferred to a 1 L separatory funnel, deionized water (200 mL) and ethyl acetate (200 mL) were added, and the obtained solution was shaken for extraction. The aqueous phase was washed with ethyl acetate (150 mL×2), and the obtained organic phases were combined. The organic phase was washed with saturated saline solution (200 mL×1), concentrated, evaporated to dryness, and dried in a vacuum oven, thus obtaining the product 34-19: 10.3 g.

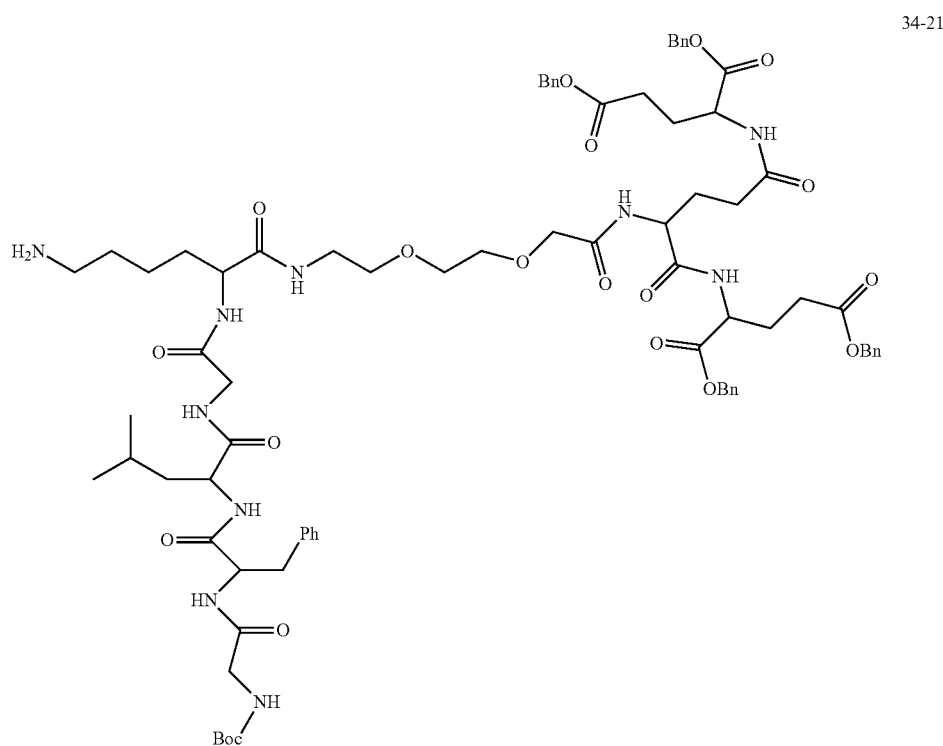 [SMILES: CC(C)CC(NC(=O)C(Cc1ccccc1)NC(=O)CNC(=O)OC(C)(C)C)C(=O)NCC(=O)NC(CCCCN)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

34-21

34-19 (10.3 g, 5.92 mmol) was added in a 500 mL flask, and dissolved with DMF (20 mL), morpholine (7.8 mL, 88.8 mmol) was added, and then the obtained solution reacted at room temperature for 1 hour. At the end of the reaction, the reaction solution was transferred to a 1 L separatory funnel, and extracted with saturated saline solution (150 mL) and ethyl acetate (250 mL), and the organic phase was separated. The aqueous phase was washed with ethyl acetate (200 mL×1), and the obtained organic phases were combined. The organic phase was washed with saturated saline solution (200 mL×2), concentrated and evaporated to dryness. The obtained dry product was then dissolved with methanol (30 mL) and dichloromethane (120 mL), silica gel powder (15 g) was added, and the obtained mixture was then evaporated to dryness to obtain a powdery solid. The operations of dry sample loading and column chromatography and elution with a dichloromethane mixed solution containing 3% methanol were carried out, thus obtaining the product 34-21: 5.37 g, yield 60%.

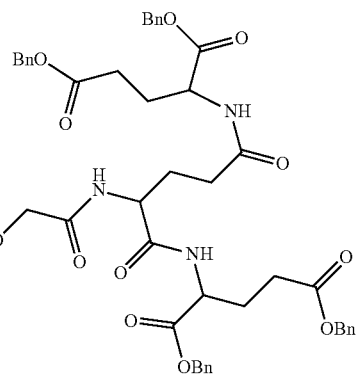
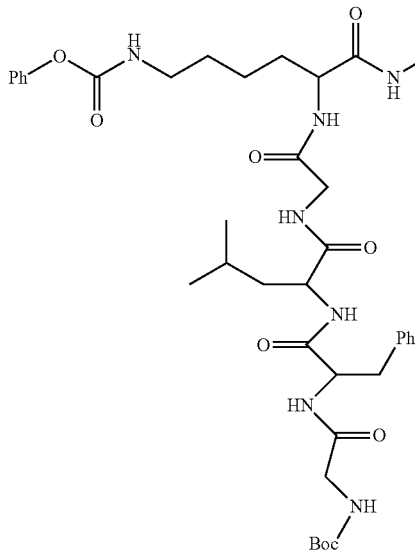

43-8

34-21 (1.6 g, 1.06 mmol) was added in a 250 mL flask, and dissolved with dichloromethane (30 mL), triethylamine (0.29 mL, 2.12 mmol) was added, and the obtained solution was stirred at 0° C. for 15 minutes, and then phenyl chloroformate (0.13 mL, 1.06 mmol) was added dropwise. At the end of the addition, the obtained solution continued to react at 0° C. with stirring overnight. At the end of the reaction, the reaction solution was transferred to a 1 L separatory funnel, and extracted with dichloromethane (250 mL) and saturated sodium chloride solution (200 mL), and the organic phase was separated. The aqueous phase was washed with dichloromethane (200 mL×1), and the obtained organic phases were combined. Silica gel powder (20 g) was added, and the obtained mixture was then evaporated to dryness to obtain a powdery solid. The operations of dry sample loading, column chromatography and elution with a dichloromethane mixed solution containing 4% methanol were carried out, thus obtaining the product 43-8: 0.9 g, yield 56%.

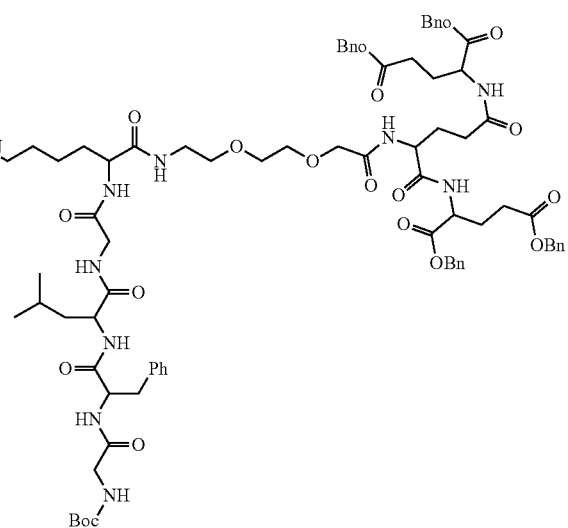
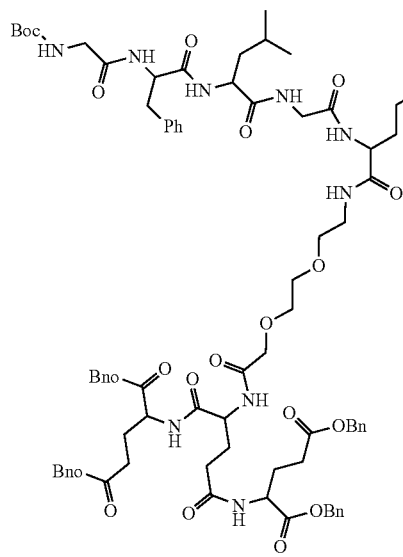

43-11

43-8 (0.9 g, 0.55 mmol), 34-21 (0.83 g, 0.55 mmol) were added in a 100 mL flask, and dissolved with DMF (20 mL), triethylamine (0.0771 mL, 0.55 mmol) was added, and the mixed solution was stirred to react at 80° C. overnight. At the end of the reaction, the reaction solution was transferred to a 1 L separatory funnel, and extracted with ethyl acetate (200 mL) and saturated saline solution (200 mL), and the organic phase was separated. The organic phase was washed with saturated saline solution (150 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 5%-36% methanol were carried out, thus obtaining the product 43-11: 0.95 g, yield 57%.

$^1$H-NMR (400 MHz, DMSO-$d_6$) δ 8.57-8.48 (m, 2H), 8.37-8.24 (m, 2H), 8.21-8.12 (m, 2H), 8.08-7.95 (m, 4H), 7.94-7.80 (m, 4H), 7.76-7.65 (m, 2H), 7.51 (s, 1H), 7.44-7.25 (m, 40H), 7.24-7.10 (m, 11H), 7.01-6.81 (m, 2H), 5.17-5.01 (m, 15H), 4.54 (d, J=4.4 Hz, 2H), 4.41-4.16 (m, 10H), 3.94-3.86 (m, 4H), 3.78-3.68 (d, J=4.4 Hz, 4H), 3.66-3.49 (m, 13H), 3.45 (d, J=6.0 Hz, 2H), 3.42-3.36 (m, 6H), 3.24-3.15 (d, J=5.5 Hz, 4H), 3.08-2.97 (m, 2H), 2.94-2.86 (m, 4H), 2.83-2.71 (m, 3H), 2.46-2.32 (m, 9H), 2.23-2.11 (m, 4H), 1.81-1.68 (m, 4H), 1.68-1.53 (m, 5H), 1.53-1.42 (m, 7H), 1.34 (d, J=5.9 Hz, 18H), 1.31-1.10 (m, 19H), 0.93-0.75 (m, 13H).

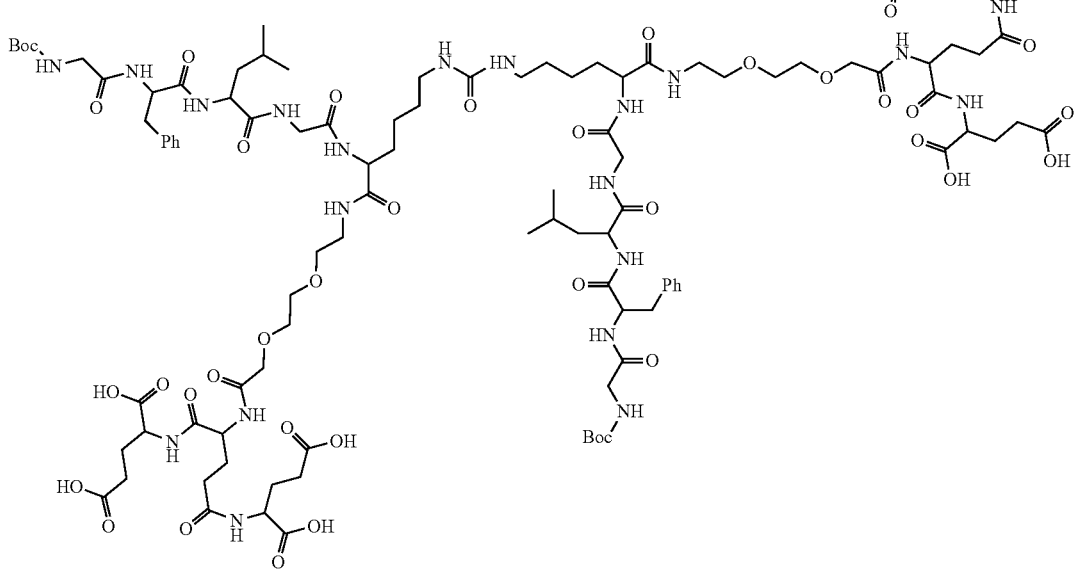

43-15

34-23 (synthesized according to the method of synthesizing 43-11, 0.377 g, 0.1236 mmol) and 10% Pd/C (0.0400 g) were added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was taken out, and filtered with diatomaceous earth, and the diatomaceous earth was washed with DMF (20 mL×3), as raw material for the next reaction.

43-21
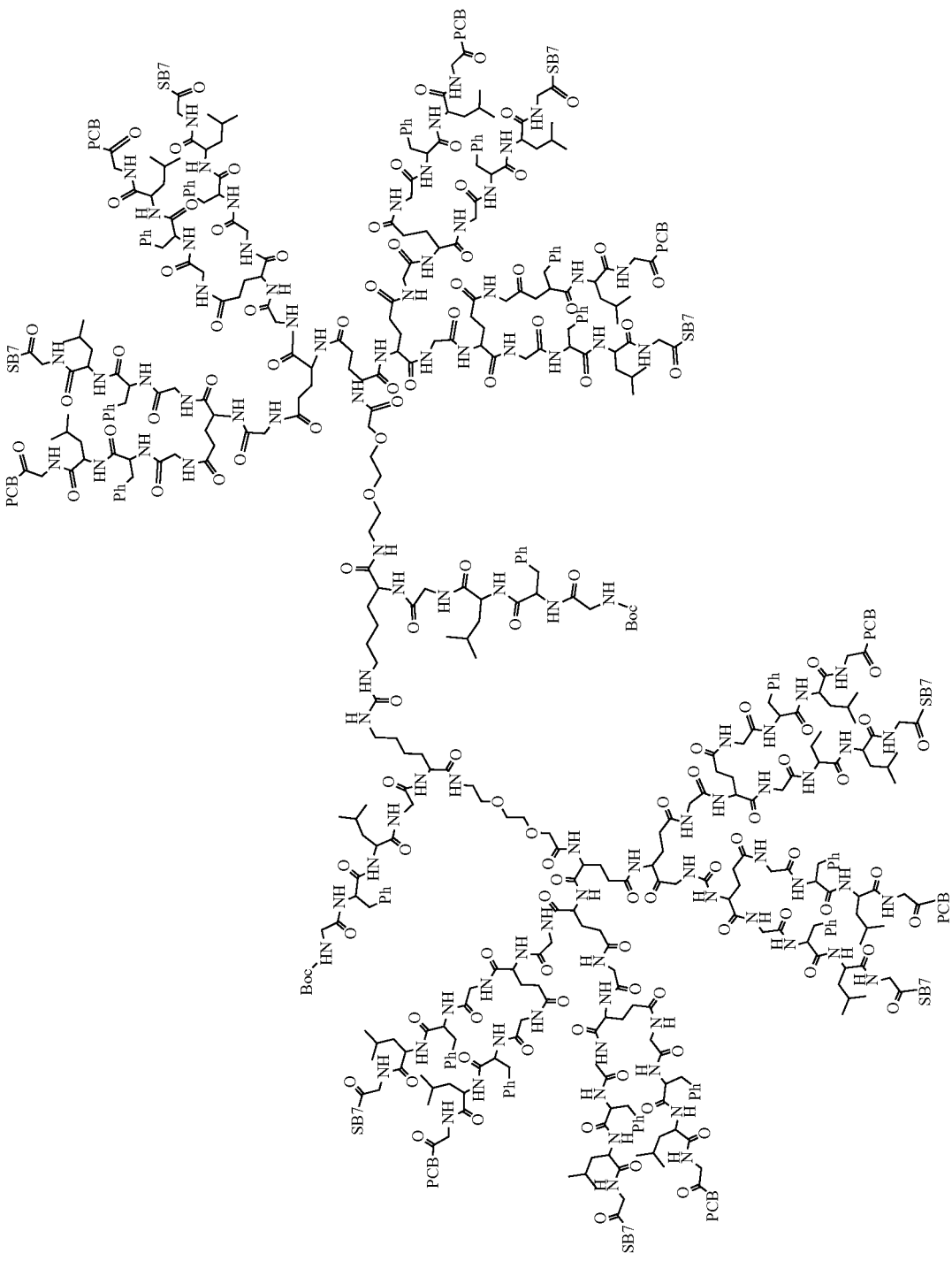

43-15 (0.288 g, 0.1236 mmol), 37-2 (2.0 g, 1.063 mmol), HBTU (0.56 g, 1.4832 mmol), HOBT (0.2 g, 1.4832 mmol) were added in a 250 mL flask, and dissolved with DMF (40 mL), and the mixed solution was stirred to react at −5° C. for 20 minutes. Then DIEA (0.74 mL, 4.4496 mmol) was slowly added dropwise. At the end of the addition, the obtained solution was stirred to react at −5° C. for 30 minutes, and then the mixed solution was stirred to react at room temperature overnight. At the end of the reaction, the reaction solution was precipitated three times with n-hexane (120 mL) and methyl tert-butyl ether (30 mL), and a viscous oily product was obtained. Then, methyl tert-butyl ether (250 mL) was added to the oily product to separate out a solid, and filtering was carried out. The filter cake was washed with methyl tert-butyl ether (50 mL×3), and dissolved with dichloromethane (150 mL) and methanol (30 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 5%-6% methanol were carried out. The elution product was then collected, concentrated and dried, thus obtaining the product 43-21: 1.6 g, yield 75%.

43-24
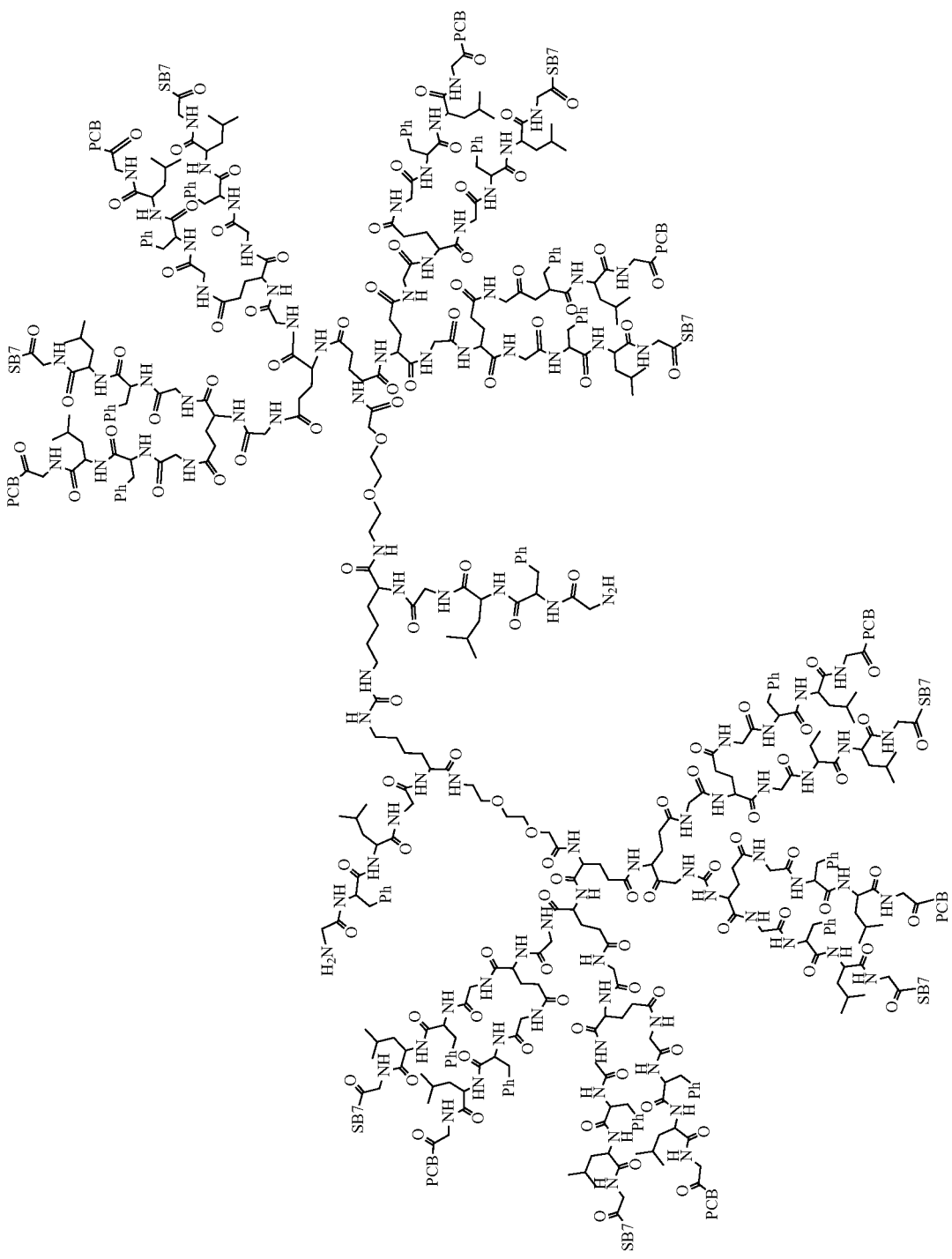

43-21 (1.6 g, 0.09 mmol) was added in a 250 mL flask, and dissolved with dichloromethane (10 mL), trifluoroacetic acid (1 mL, 13.47 mmol) was added, and the mixed solution was stirred to react at room temperature overnight. At the end of the reaction, the reaction solution was concentrated to a small amount, Methyl tert-butyl ether (150 mL) was added to the concentrated solution to separate out a solid, and suction filtering was carried out. The filter cake was washed with methyl tert-butyl ether (50 mL×3), and dissolved with a mixed solvent of methanol (30 mL) dichloromethane (120 mL), silica gel powder (20 g) was added, the obtained solution was evaporated to dryness to obtain a powdery solid. The operations of dry sample loading, column chromatography and elution with a dichloromethane mixed solution containing 1% ammonia water and 6%-8% methanol were carried out. The elution product was then collected, concentrated, evaporated to dryness, and dried in a vacuum oven, thus obtaining the product 43-24: 1.11 g, yield 73%.

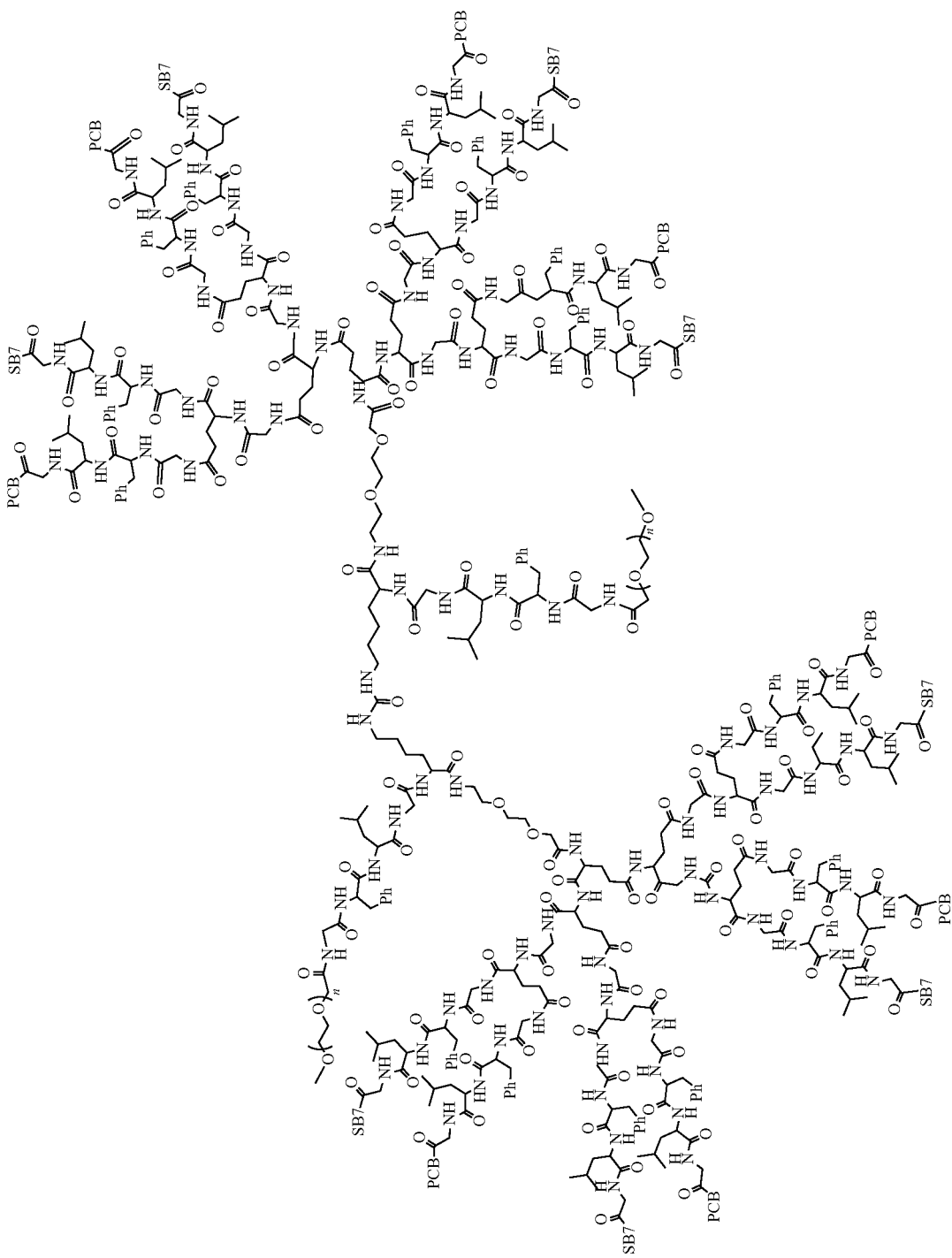

43-24 (0.4 g, 0.023 mmol) was added in a 250 mL flask, and dissolved with DMF (25 mL), M-SCM-40K (1.983 g, 0.048 mmol) was added, and ultrasonic treatment was carried out to dissolve the reactants, the mixed solution reacted in the dark for 7 days at a low speed of stirring at room temperature. At the end of the reaction, n-hexane (150 mL) and methyl tert-butyl ether (50 mL) were added to the reaction solution, the supernatant was discarded, and n-hexane (150 mL) and methyl tert-butyl ether (50 mL) were added to the lower liquid. Such operations were repeated three times, to obtain a viscous oily product. Then, methyl tert-butyl ether (120 mL) was added to the oily product to separate out a solid, and filtering was carried out. The filter cake was washed with methyl tert-butyl ether (50 mL×3), and dissolved with a mixed solvent of methanol (30 mL) and dichloromethane (120 mL), silica gel powder (15 g) was added, and the obtained mixture was then evaporated to dryness to obtain a powdery solid. The operations of dry sample loading, column chromatography and elution with a dichloromethane mixed solution containing 1% ammonia water and 5%-6% methanol were carried out. The elution product was then collected, concentrated, and evaporated to dryness to obtain a solid. The solid was dried in a vacuum oven for 1 hour, and dissolved with anhydrous ethanol (5 mL) and dichloromethane (20 mL). Then, methyl tert-butyl ether (80 mL) was added to the obtained solution to separate out a solid, and filtering was carried out. The filter cake was washed with methyl tert-butyl ether (50 mL×2), and dried in a vacuum oven, thus obtaining the product 43-27: 0.9 g, yield: 38%.

$^1$H-NMR (600 MHz, DMSO-d$_6$) δ 10.16-10.13 (m, 5H), 8.99-8.93 (m, 6H), 8.29-7.95 (m, 84H), 7.92-7.85 (m, 14H), 7.59-7.44 (d, J=3.3 Hz, 70H), 7.33-7.03 (m, 154H), 4.53-4.41 (m, 55H), 3.72-3.41 (m, 7336H), 3.20-3.03 (m, 123H), 2.42-2.38 (m, 25H), 2.36-2.15 (48, 71H), 1.94-1.69 (m, 48H), 1.65-1.39 (m, 71H), 1.36-1.08 (m, 235H), 0.99-0.68 (m, 124H), 0.56-0.39 (m, 16H).

5. Synthesis of 27-134 (Compound No. 18)

Synthetic route is as follows

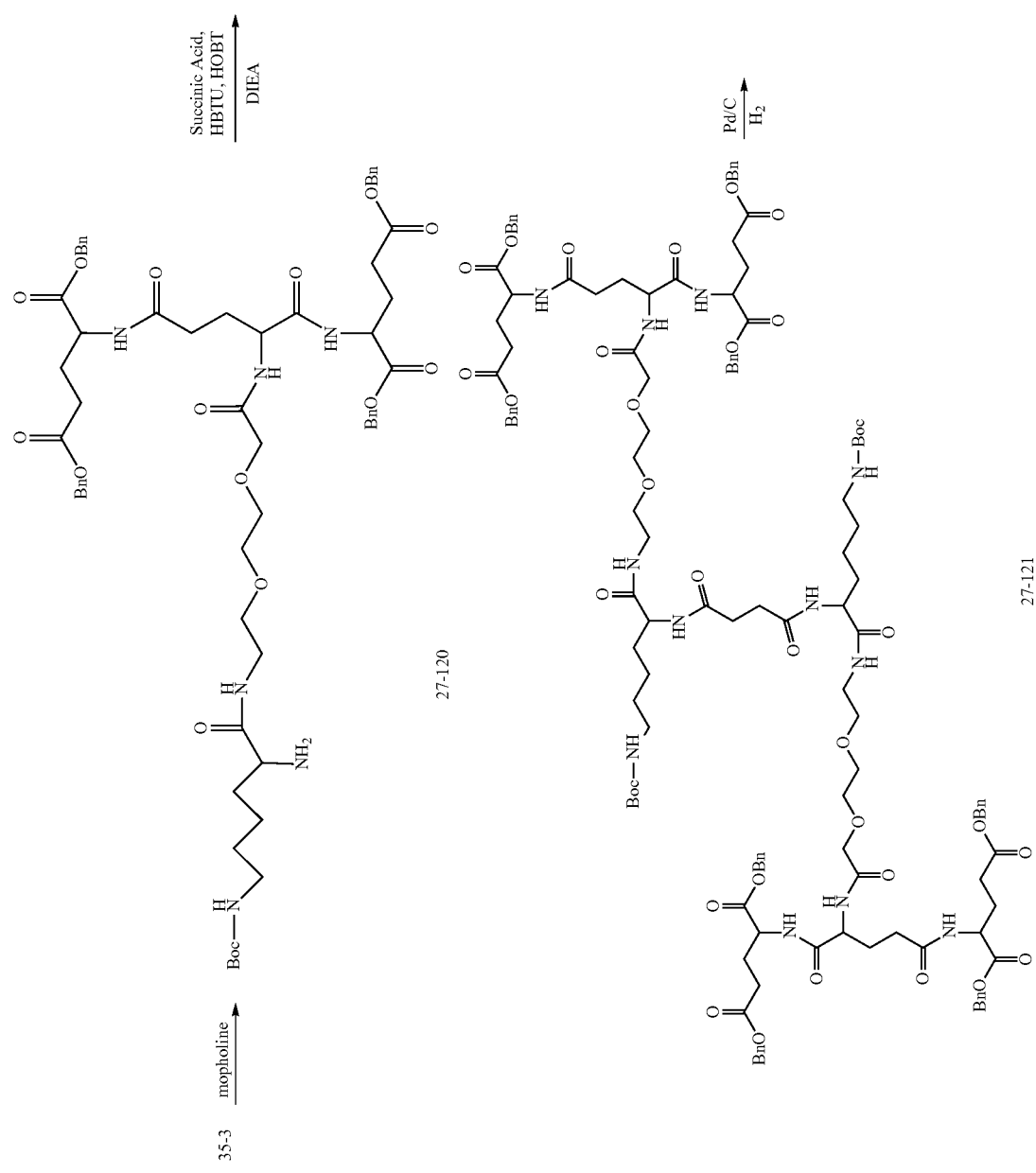

-continued
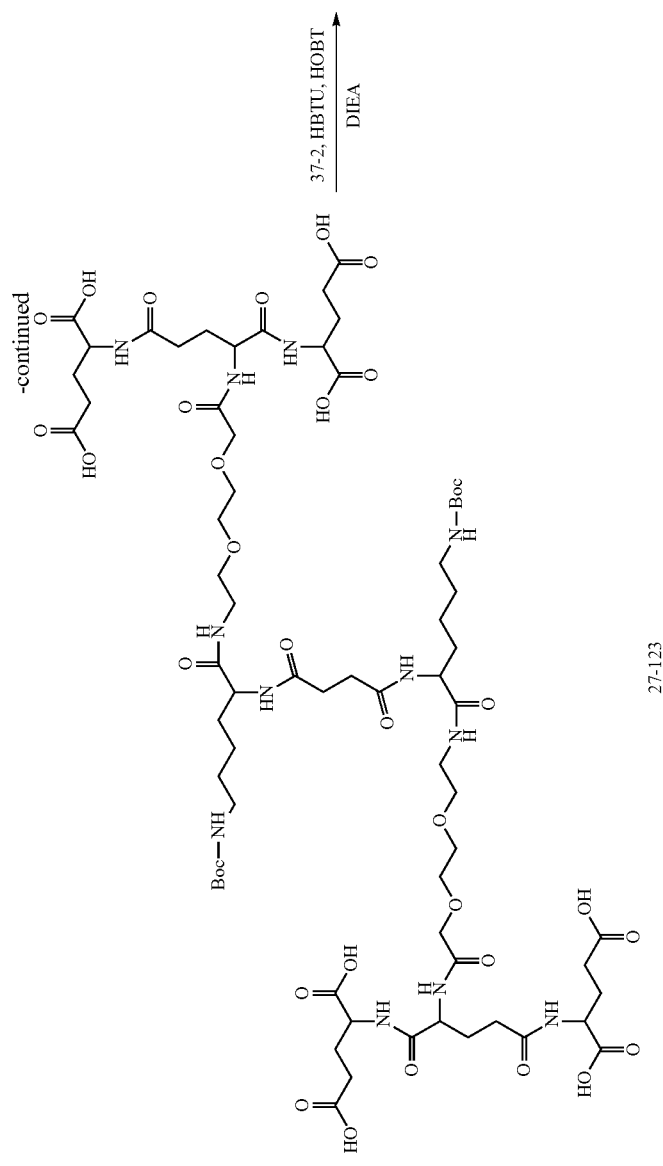
27-123

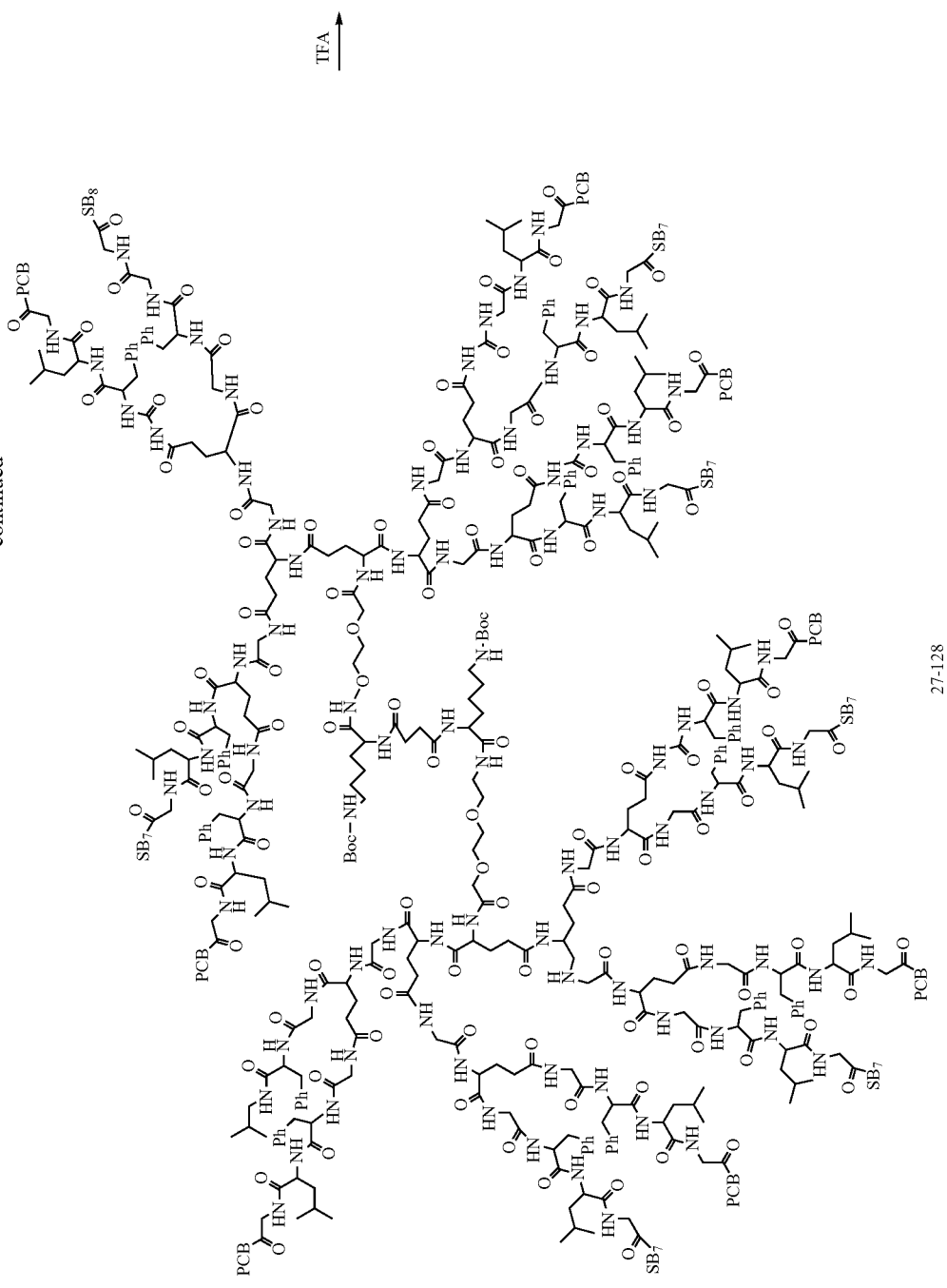

-continued
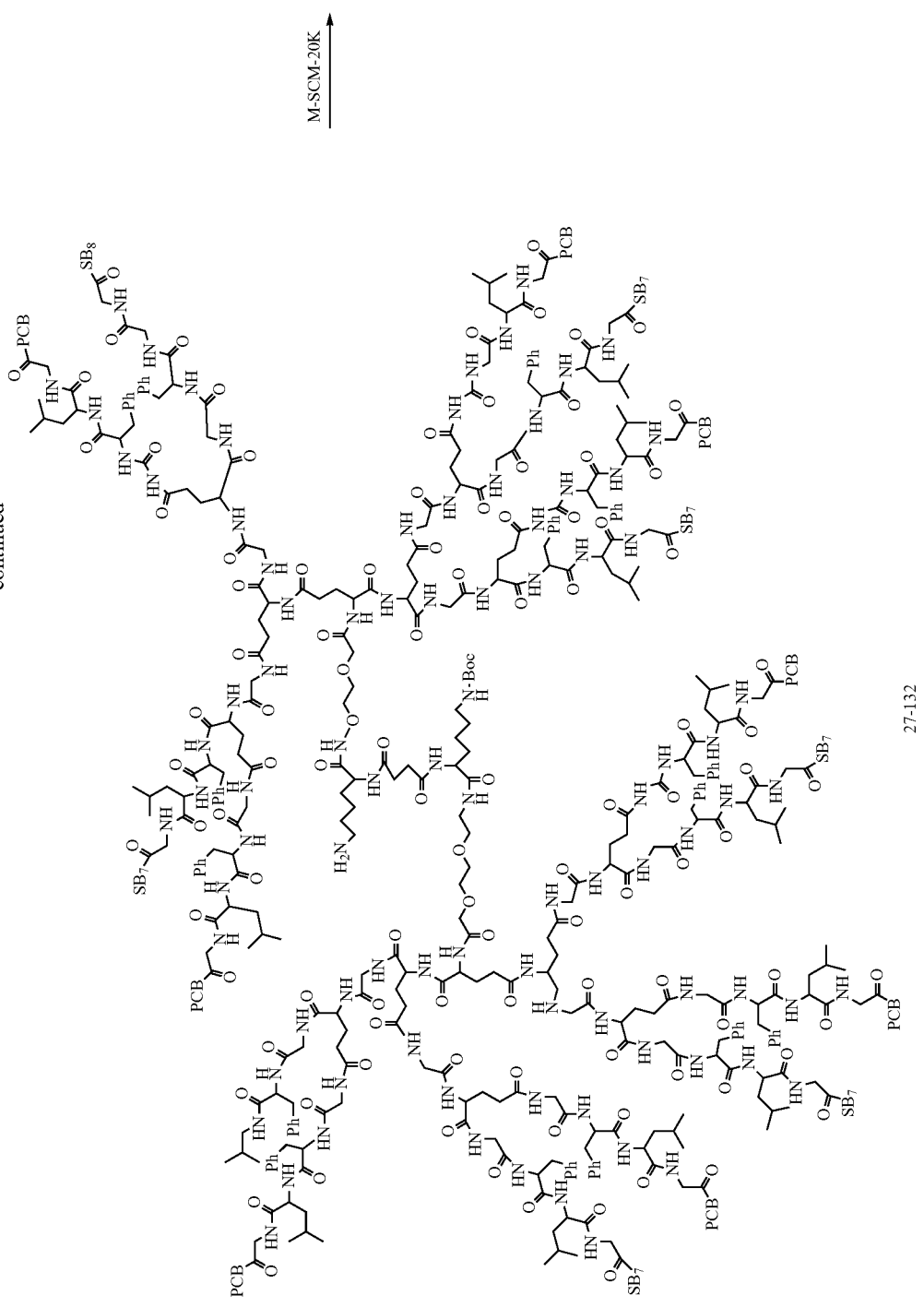
27-132

-continued
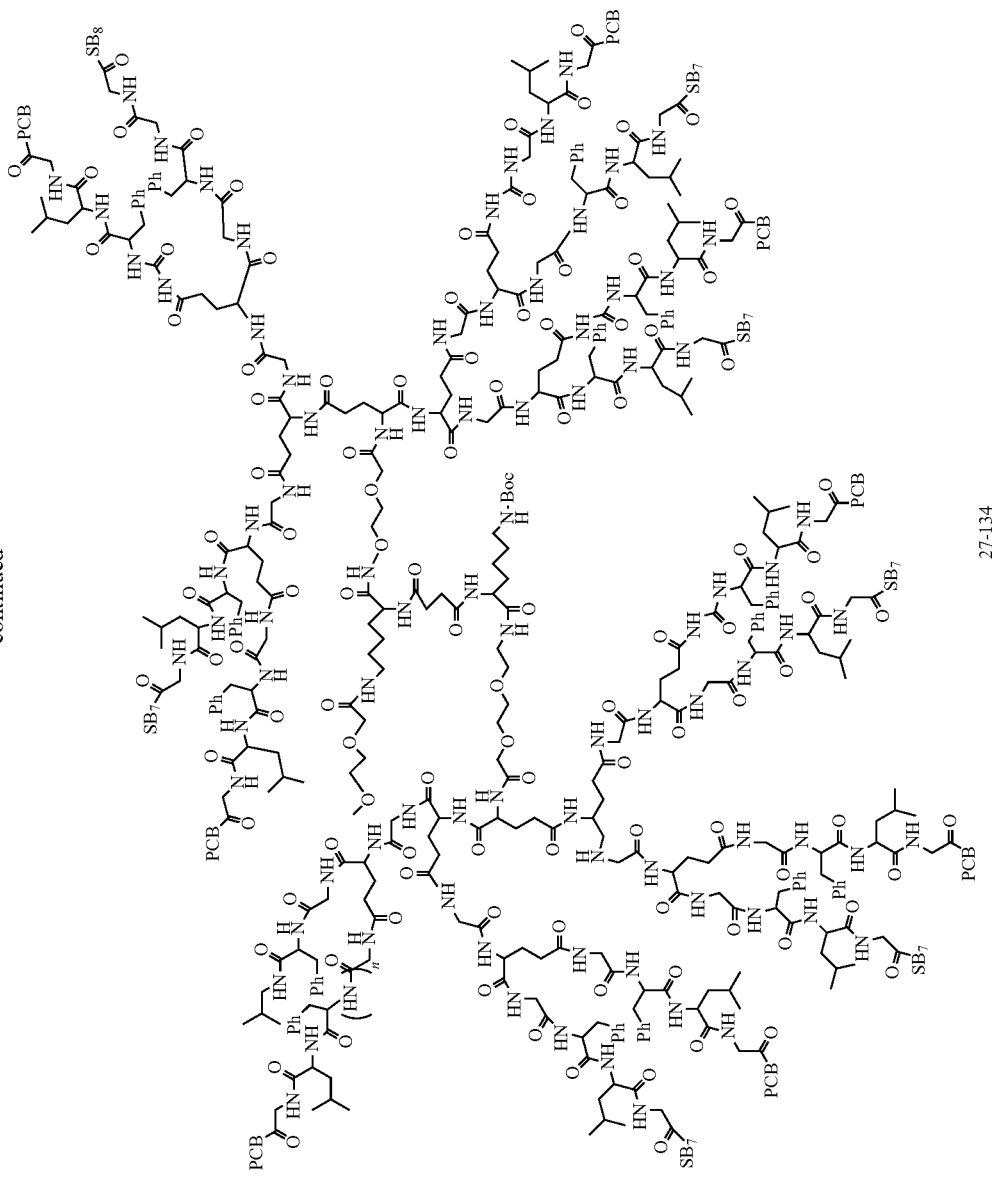
27-134

27-120
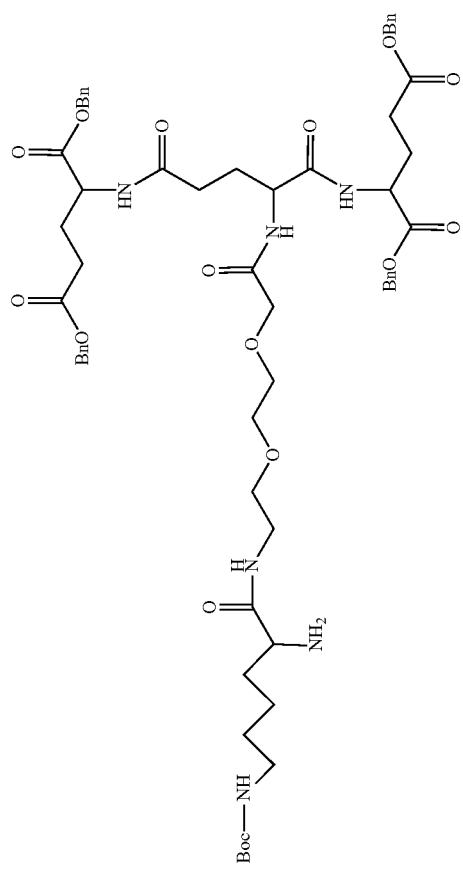

DMF (10 mL) was added in a flask loaded with 27-119 (synthesized according to the method of synthesizing 35-3, 1 g, 0.7345 mmol), ultrasonic vibration was carried out to completely dissolve the compound, morpholine (0.64 mL, 7.345 mmol) was added, and the mixed solution was stirred to react at room temperature for 2 h. At the end of the reaction, the reaction solution was extracted with saturated sodium bicarbonate solution (100 mL) and ethyl acetate (200 mL), and stood still to be layered, and the organic phase was separated. The aqueous phase was then washed with ethyl acetate (200 mL*3), and the obtained organic phases were combined. The organic phase was evaporated to dryness and concentrated to about 50 mL, and then washed with saturated sodium chloride solution (100 mL*3). The obtained organic phases were combined. The organic phase was concentrated, evaporated to dryness, and dried in a vacuum oven, thus obtaining the product 27-120 (1.4317 g, 100%)

mmol) was slowly added dropwise. At the end of the addition, the obtained solution reacted for half an hour, and was then moved to room temperature and stirred to react overnight. At the end of the reaction, an excess amount of a saturated sodium bicarbonate solution was added until the solution became alkaline, the obtained solution was extracted with ethyl acetate (200 mL), and stood still to be layered, and the organic phase was separated. The aqueous phase was then washed with ethyl acetate (200 mL*3), and the obtained organic phases were combined. The organic phase was evaporated to dryness and concentrated to about 100 mL. The concentrated solution was taken out, washed with saturated sodium chloride solution (100 mL*3), and the obtained organic phases were combined. The organic phase was evaporated to dryness, and dissolved with a mixed solvent (100 mL) of methanol/dichloromethane (1:4), silica gel powder (50 mL) was added, and the operations of evaporation to dryness, dry sample loading, column chro-

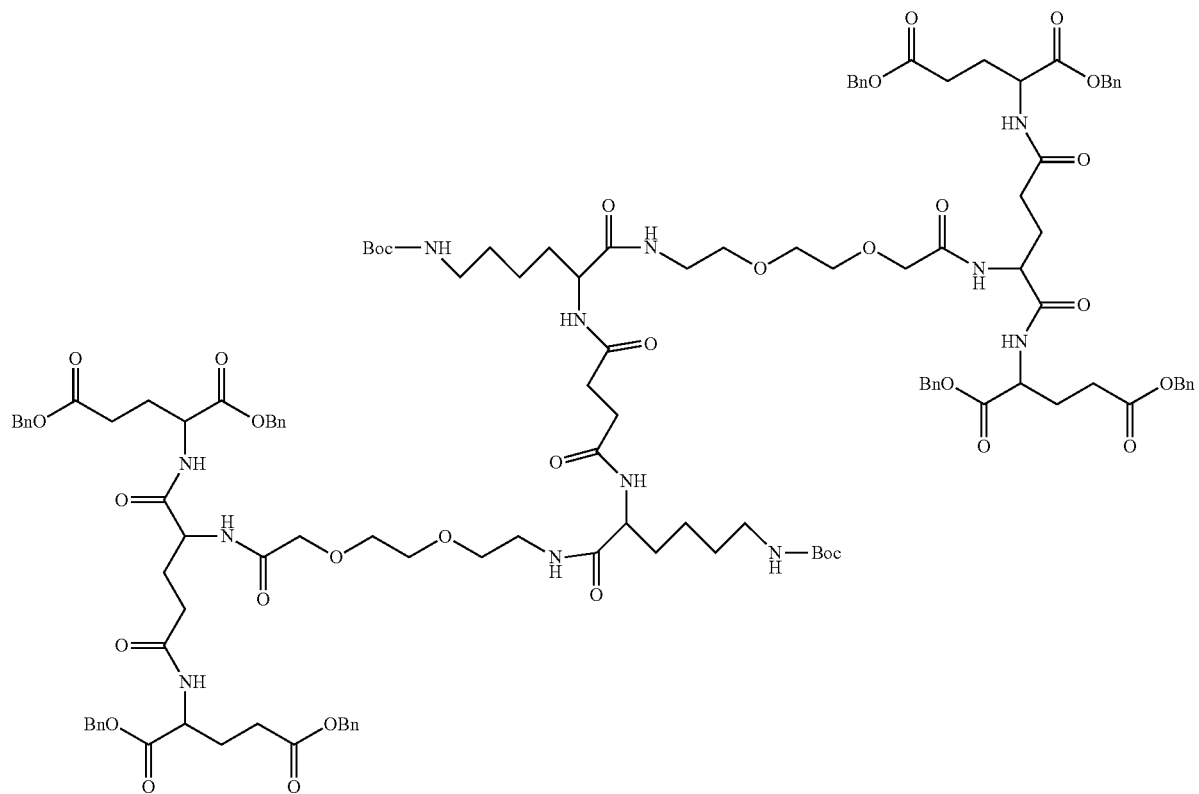

27-121

Succinic acid (0.039 g, 0.3339 mmol), HBTU (0.3798 g, 1.0017 mmol), HOBT (0.1354 g, 1.0017 mmol) were added in a flask loaded with 27-120 (0.8368 g, 0.7345 mmol), and dissolved with a proper amount of DMF, then the obtained solution was placed at −5° C., and DIEA (0.50 mL, 3.0051 matography and elution with a dichloromethane mixed solution containing 1% ammonia water and 6% methanol were carried out. The elution product was then collected, concentrated, evaporated to dryness, and dried in a vacuum oven, thus obtaining the product 27-121 (0.5811 g, 73.72%)

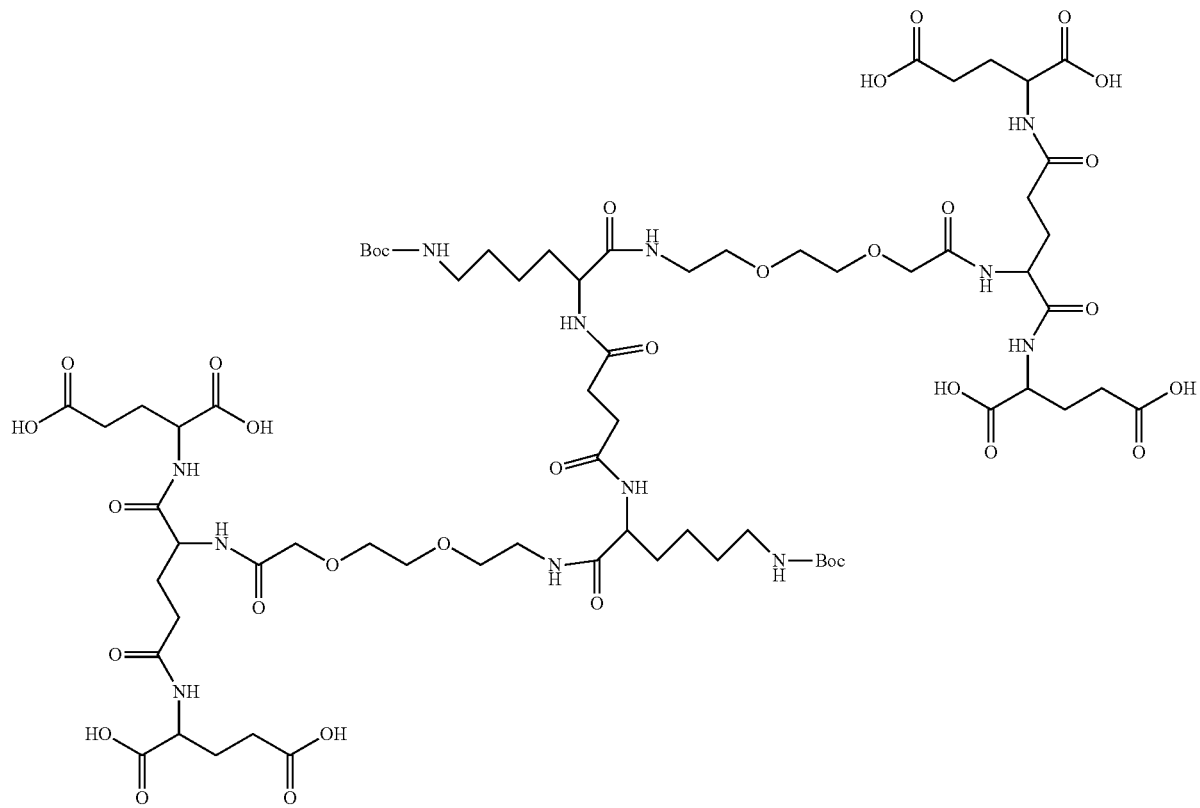

27-121 (0.5811 g, 0.2462 mmol) was added in a hydrogenation reactor, Pd/C (0.1 g) and DMF (20 mL) were added, hydrogen was introduced to a pressure of 1.4 MPa, and then the mixed solution was stirred to react at room temperature overnight. At the end of the reaction, the reaction solution was filtered with diatomaceous earth. The filter cake was washed with DMF (15 mL×3), and the filtrate was put into a 250 mL round-bottomed flask, obtaining 27-123 as the raw material for the next reaction.

27-128

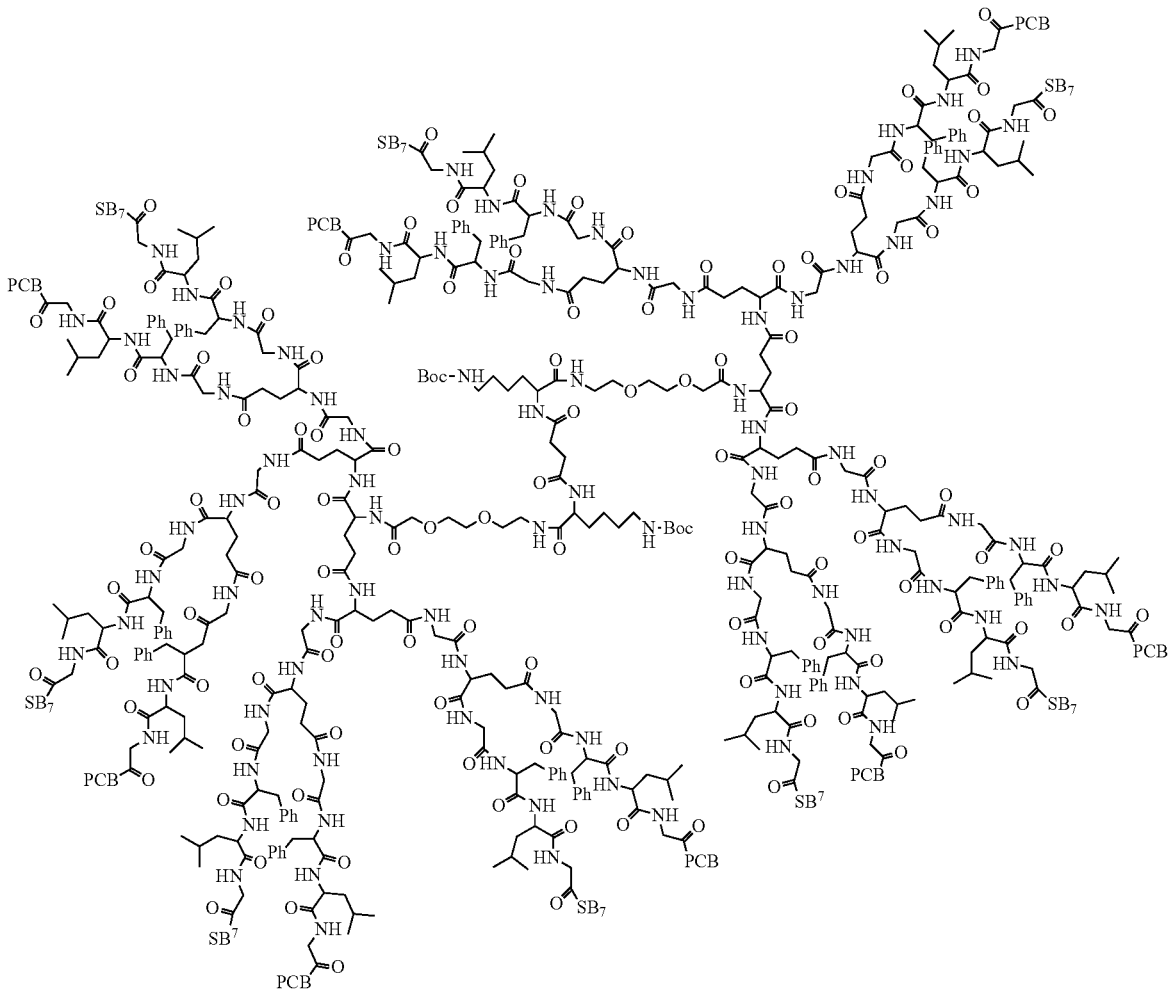

35-12 (synthesized according to the method of synthesizing 37-2, 1.8 g, 0.9566 mmol), HBTU (0.54 g, 1.4348 mmol), HOBT (0.19 g, 1.4348 mmol) were added in a flask loaded with 27-123 (0.1782 g, 0.1087 mmol), and dissolved with a proper amount of DMF, then the obtained solution was placed at −5° C., and DIEA (0.23 mL, 4.3045 mmol) was slowly added dropwise. At the end of the addition, the obtained solution reacted for half an hour, and was then moved to room temperature and stirred to react overnight. At the end of the reaction, a mixed solution (250 mL) of methyl tert-butyl ether:n-hexane=1:5 was added to the reaction solution, the obtained solution was shaken, and stood still, the supernatant was discarded, and the above operations were repeated three times. Then, methyl tert-butyl ether (200 mL) was added to the obtained solution to separate out a solid, and suction filtering was carried out. The filter cake was then dissolved with a mixed solvent (100 mL) of methanol/dichloromethane (1:4), silica gel powder (40 mL) was added, the obtained solution was evaporated to dryness to obtain a powdery solid. The operations of dry sample loading. column chromatography and elution with a dichloromethane mixed solution containing 1% ammonia water and 3-5% methanol were carried out. The elution product was then collected, concentrated, and dried in a vacuum oven, thus obtaining the product 27-128 (0.8 g, 44.69%)

27-132

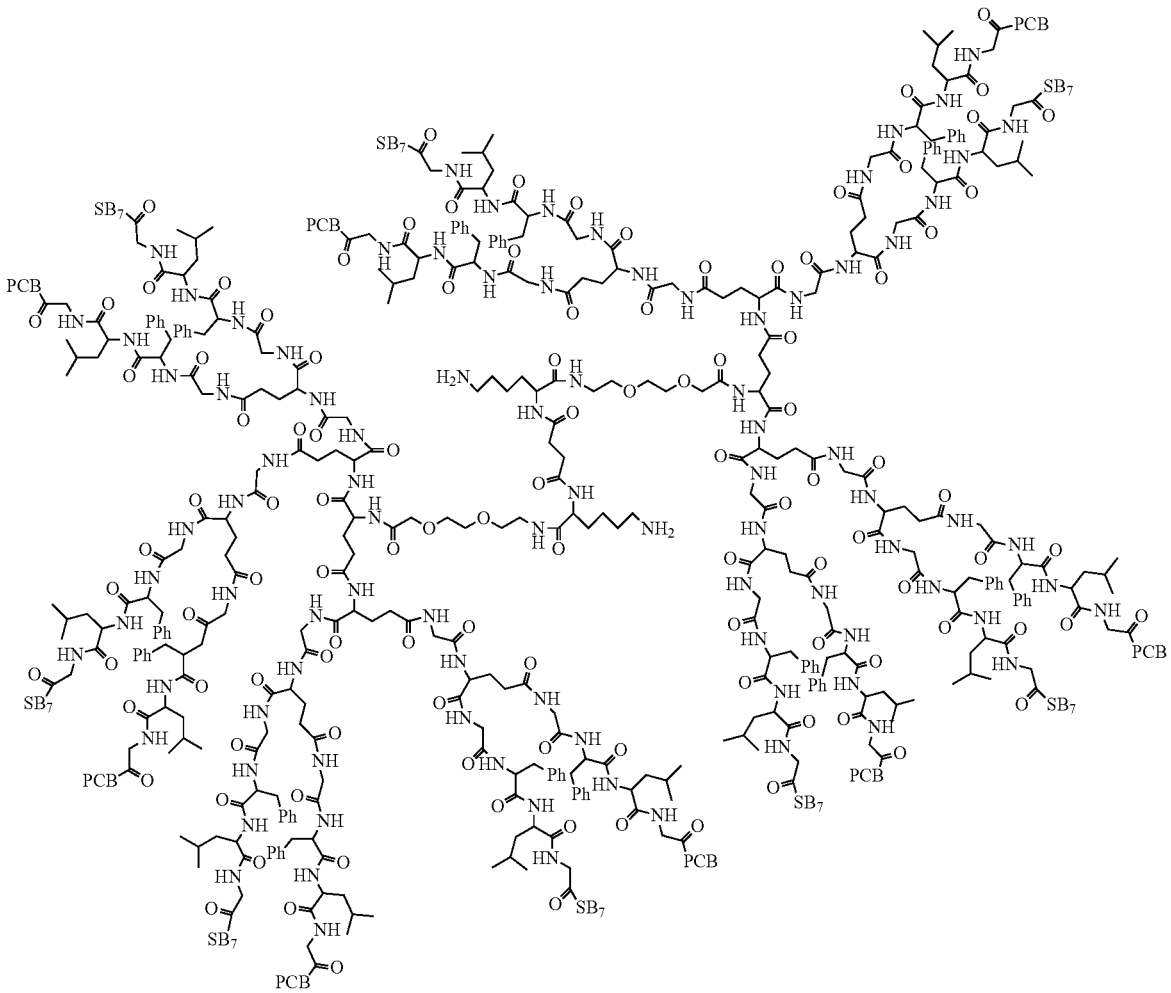

Dichloromethane was added in a flask loaded with 27-128 (0.8 g, 0.0483 mmol), ultrasonic vibration was carried out to completely dissolve the compound, then TFA (0.107 mL, 1.4503 mmol) was added, and the mixed solution was stirred to react at room temperature overnight. At the end of the reaction, the dichloromethane in the reaction solution was evaporated, methyl tert-butyl ether (100 mL) was added, and the obtained solution was shakn to separate out a solid, and suction filtering was carried out. The filter cake was dissolved with a mixed solvent (100 mL) of methanol/dichloromethane (1:4), silica gel powder (40 mL) was added, and the operations of evaporation, dry sample loading, column chromatography and elution with a dichloromethane mixed solution containing 1% ammonia water and 7-10% methanol were carried out. The elution product was then collected, concentrated, and dried in a vacuum oven, thus obtaining the product 27-132 (0.5633 g, 71.34%).

$^1$H-NMR (600 MHz, DMSO-d$_6$) δ 10.21-10.17 (m, 4H), 9.15-8.87 (m, 8H), 8.47-7.69 (m, 91H), 7.60-6.88 (m, 202H), 6.78-6.62 (m, 4H), 5.93-5.60 (m, 13H), 5.35-5.29 (m, 1H), 4.57-4.53 (m, 9H), 4.27 (m, 23H), 4.07-3.22 (m, 166H), 3.21-2.85 (m, 40H), 2.85-2.53 (m, 28H), 2.44-2.04 (m, 87H), 2.04-1.95 (m, 7H), 1.83-1.79 (m, 41H), 1.55-1.49 (m, 55H), 1.38-0.99 (m, 92H), 0.86-0.82 (m, 103H), 0.52-0.47 (m, 39H).

27-134

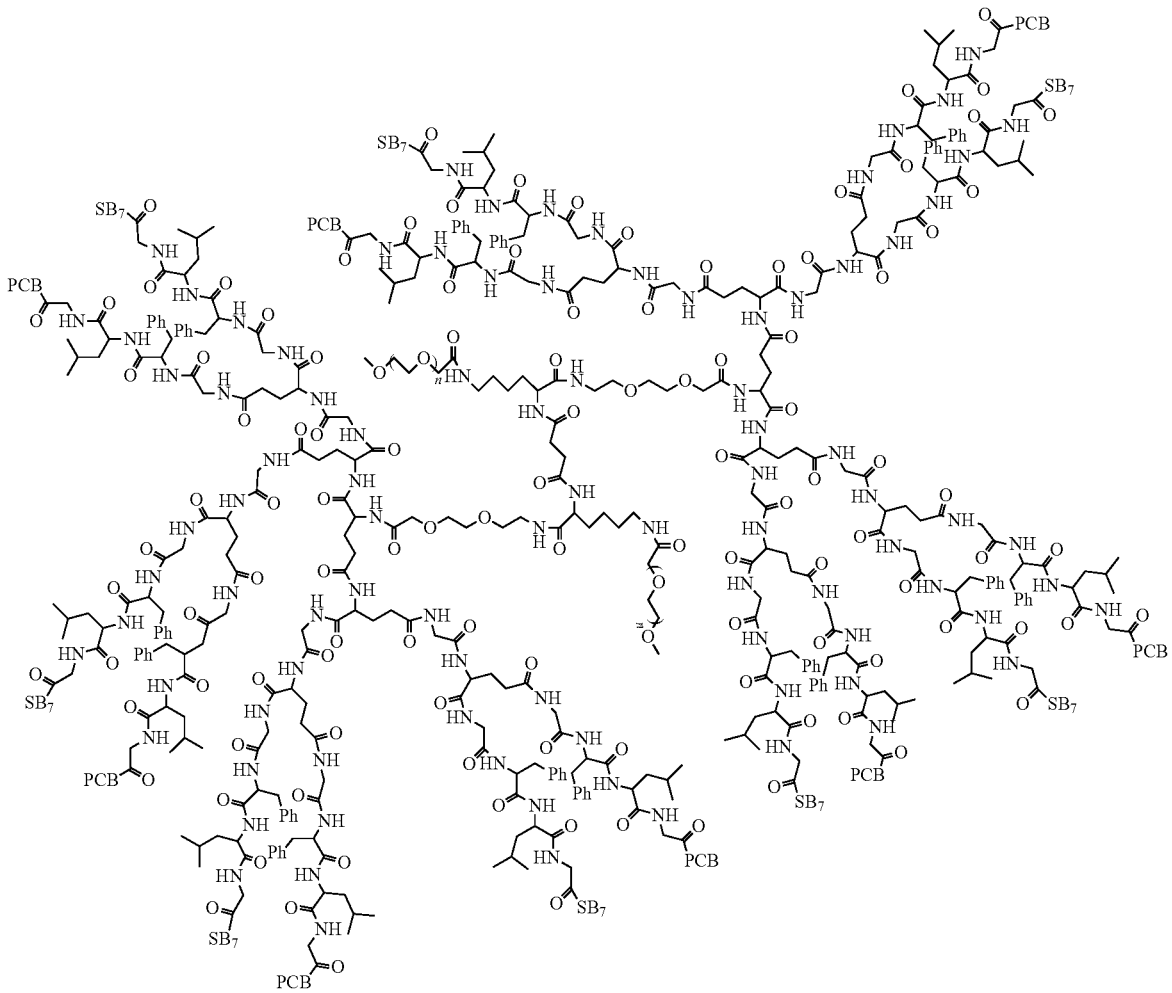

27-132 (0.2633 g, 0.01610 mmol) was added in a 250 mL flask, and dissolved with DMF (20 mL), M-SCM-20K (0.7955 g, 0.03703 mmol, purchased from JenKem) was added, ultrasonic vibration was carried out to dissolve the compound, and then the mixed solution reacted in the dark for one week at a low speed of stirring at room temperature. At the end of the reaction, methyl tert-butyl ether (200 mL) and n-hexane (70 mL) was added to the reaction solution to separate out a solid, and suction filtering was carried out. The filter cake was washed with methyl tert-butyl ether (40 mL×3), and dissolved with a mixed solvent (100 mL) of methanol/dichloromethane (1:4), silica gel powder (50 mL) was added, the obtained solution was evaporated to dryness to obtain a powdery solid. The operations of dry sample loading, column chromatography and elution with a dichloromethane mixed solution containing 1% ammonia water and 7% methanol were carried out. The elution product was then collected, concentrated, and dried in a vacuum oven, thus obtaining the product 27-134 (0.5876 g, 61.85%).

$^1$H-NMR (600 MHz, DMSO-$d_5$) δ 9.06-9.02 (m, 19H), 8.98-8.92 (m, 11H), 8.28-7.93 (m, 69H), 7.87-7.82 (m, 25H), 7.55-7.49 (m, 32H), 7.44-6.95 (m, 116H), 6.92-6.88 (m, 10H), 6.76-6.63 (m, 26H), 5.40-5.25 (m, 29H), 4.62-4.43 (m, 38H), 4.39-4.07 (m, 64H), 3.72-3.68 (m, 3897H), 3.19-3.10 (m, 20H), 2.91-2.86 (m, 19H), 2.83-2.57 (m, 62H), 2.36-2.06 (m, 66H), 2.05-1.89 (m, 38H), 1.51-1.45 (m, 50H), 1.39-0.97 (m, 242H), 0.95-0.64 (m, 87H).

6. Synthesis of 44-2 (Compound No. 3)

Synthetic route is as follows

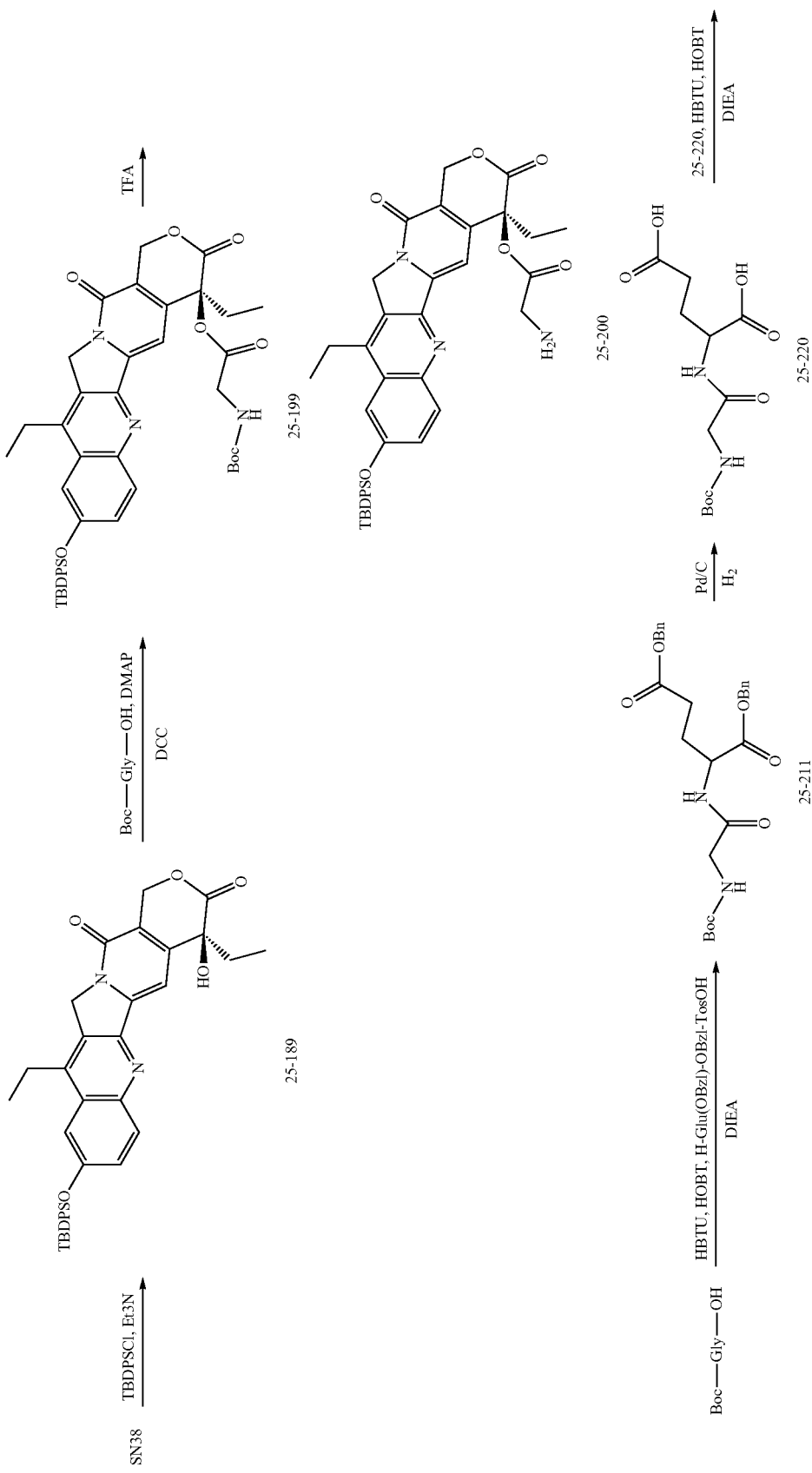

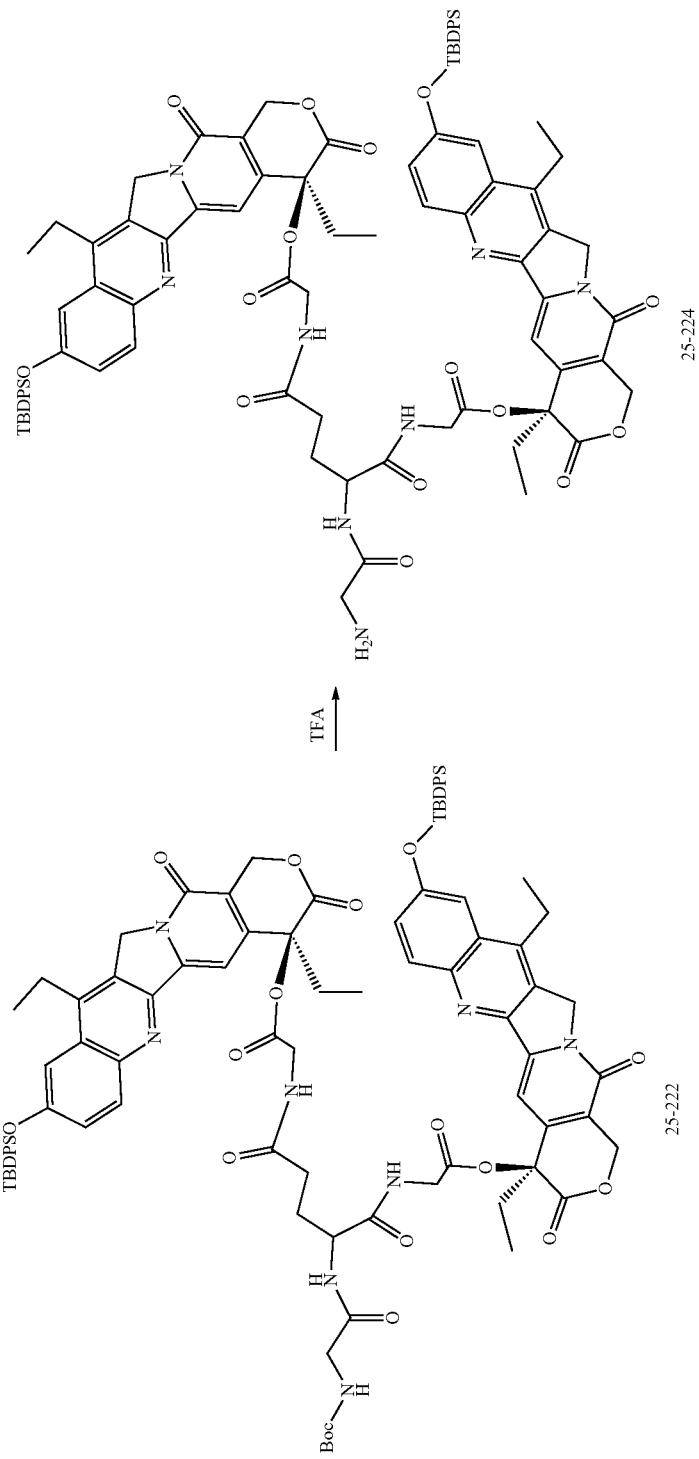

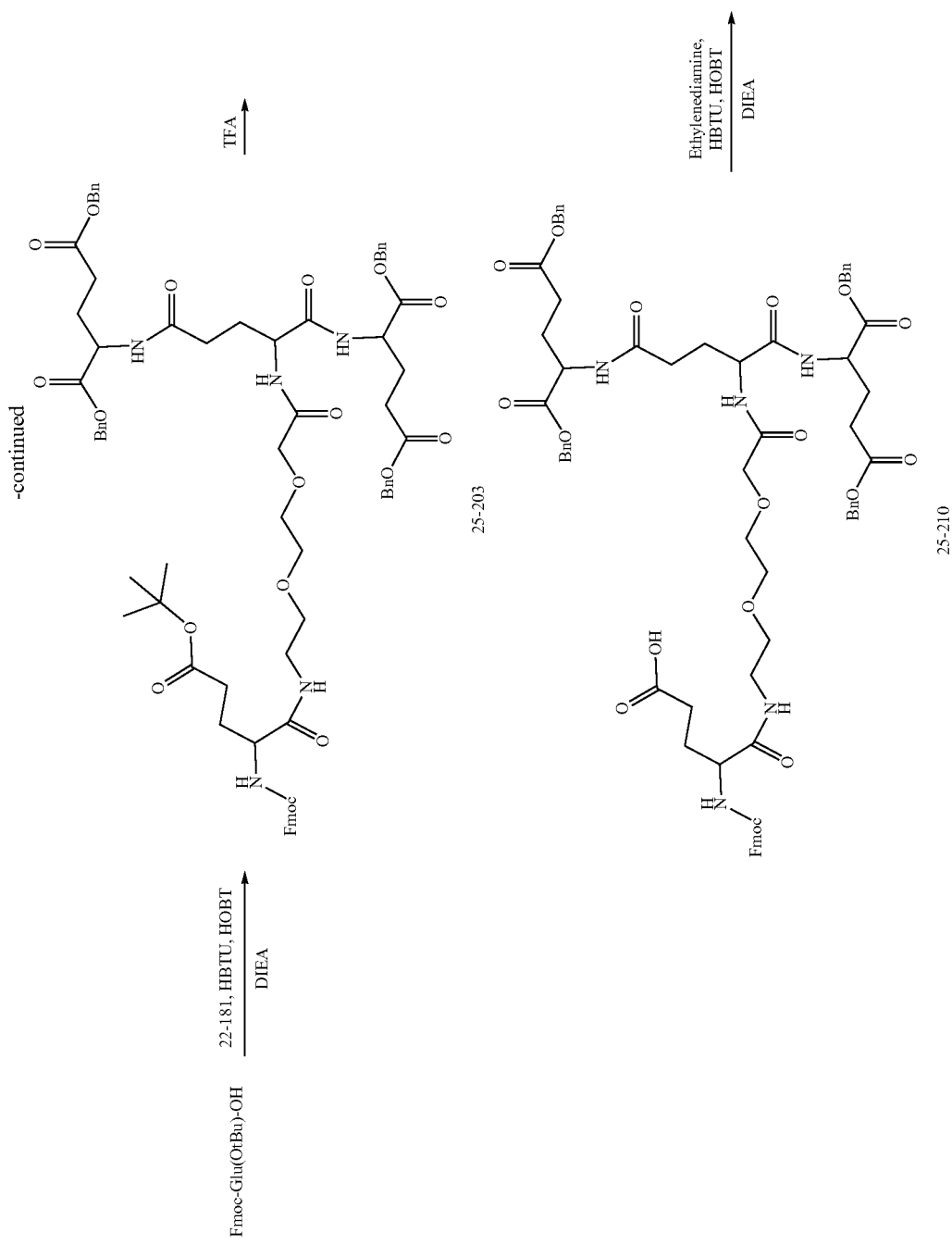

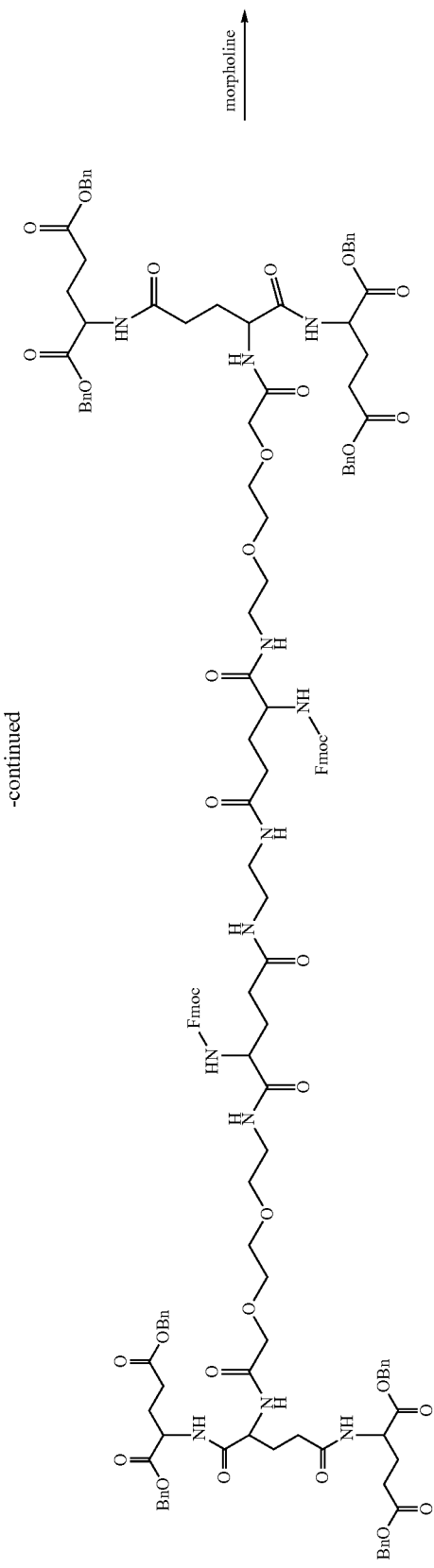
25-221
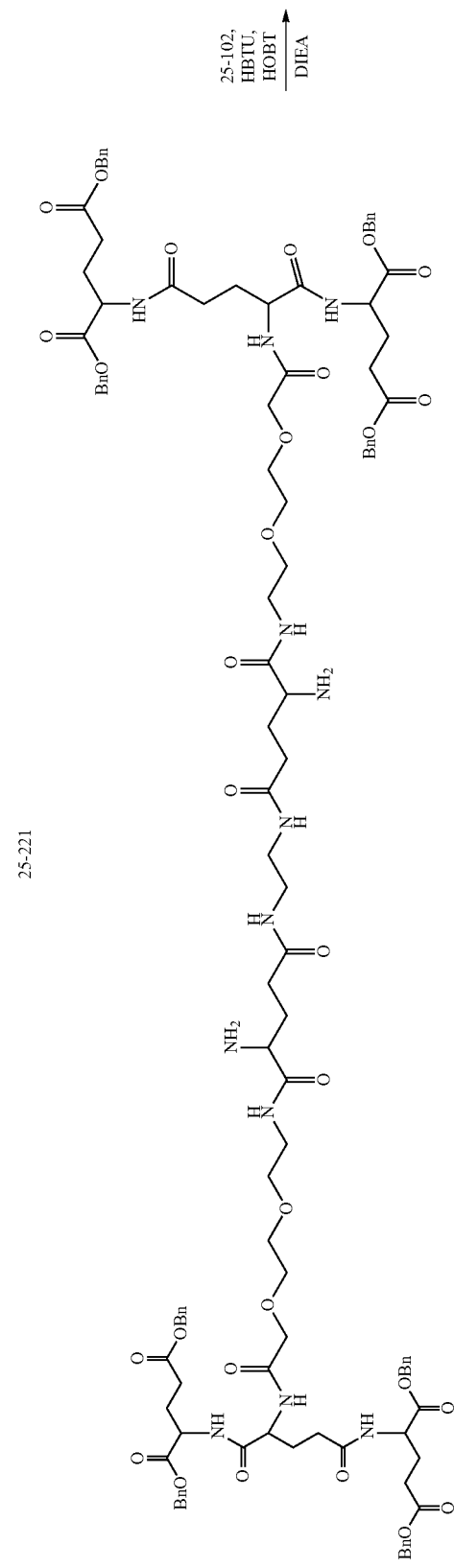
25-226

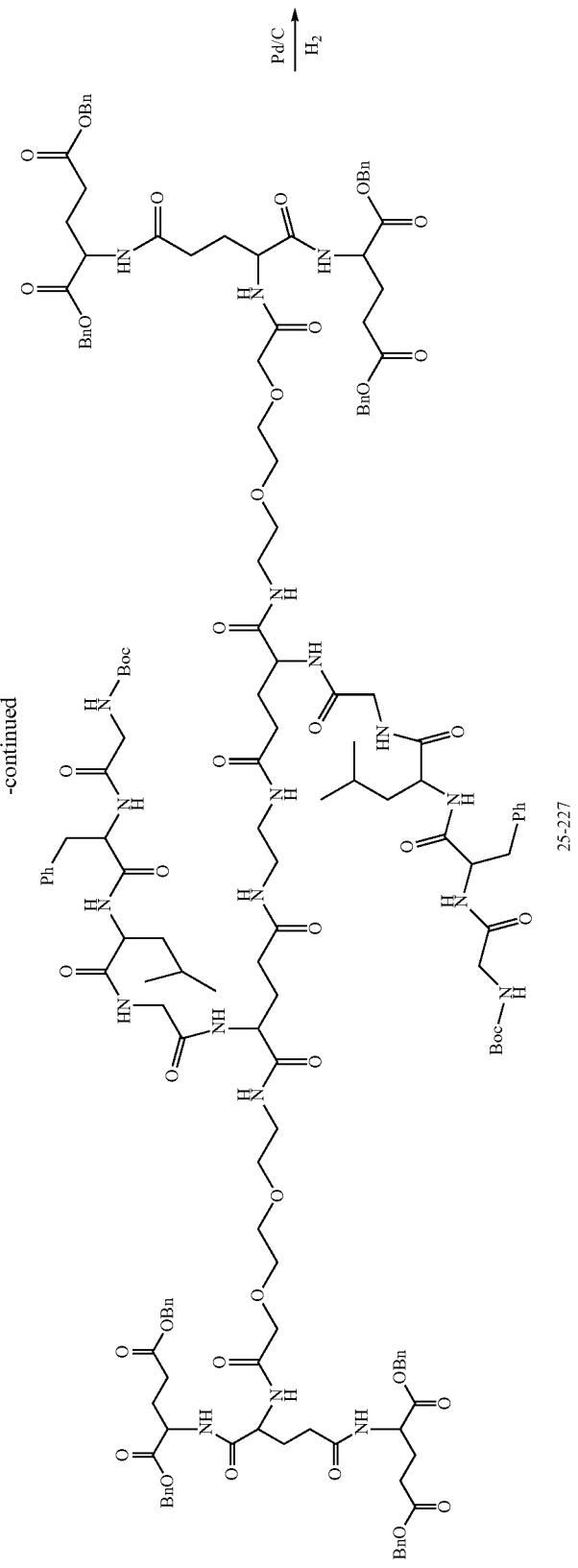

-continued
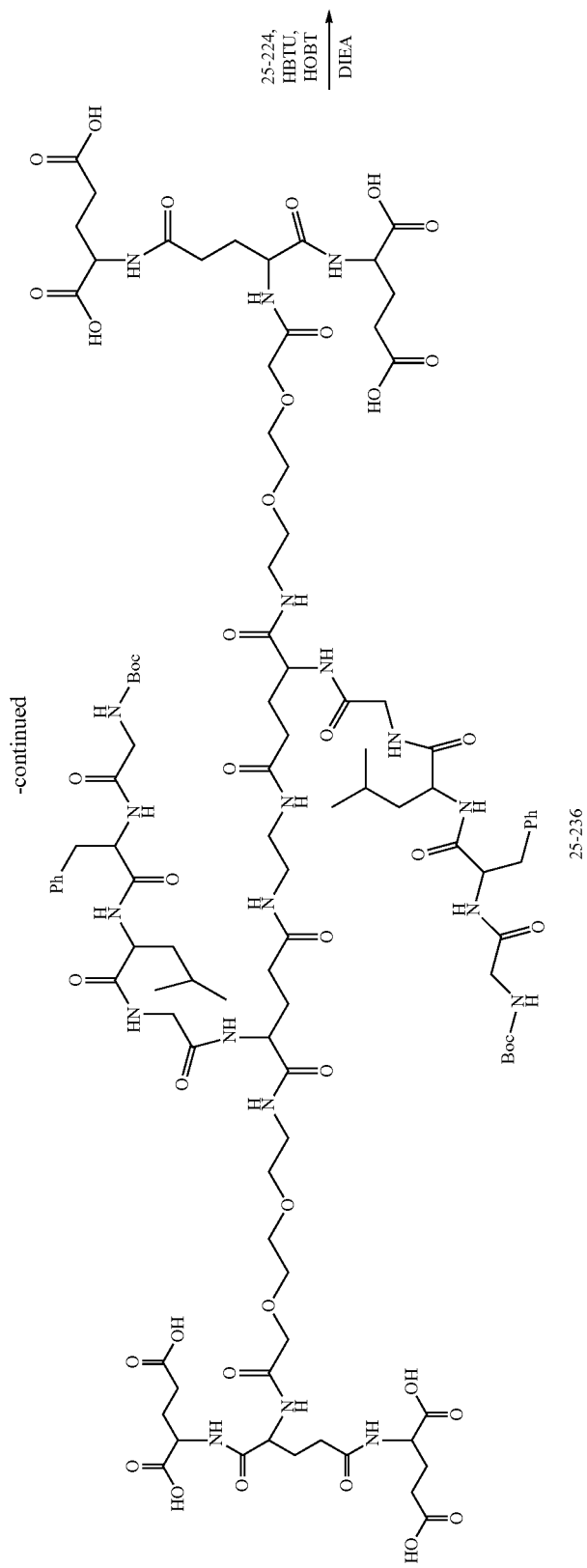

-continued
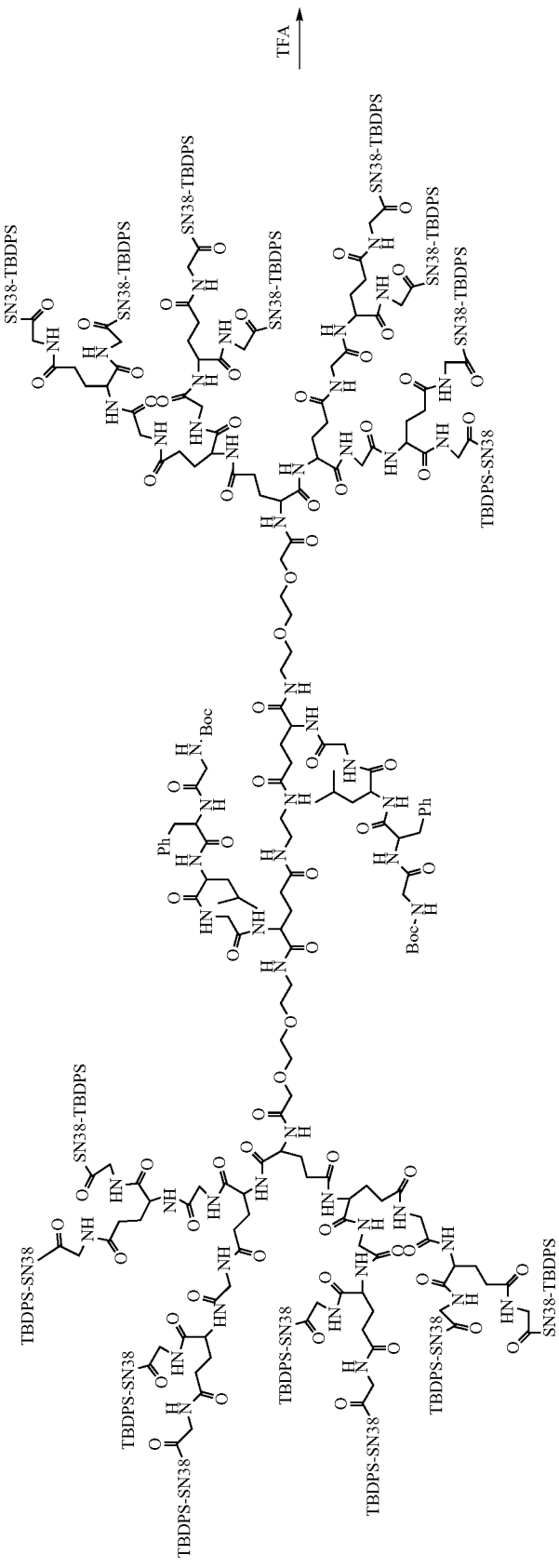

-continued
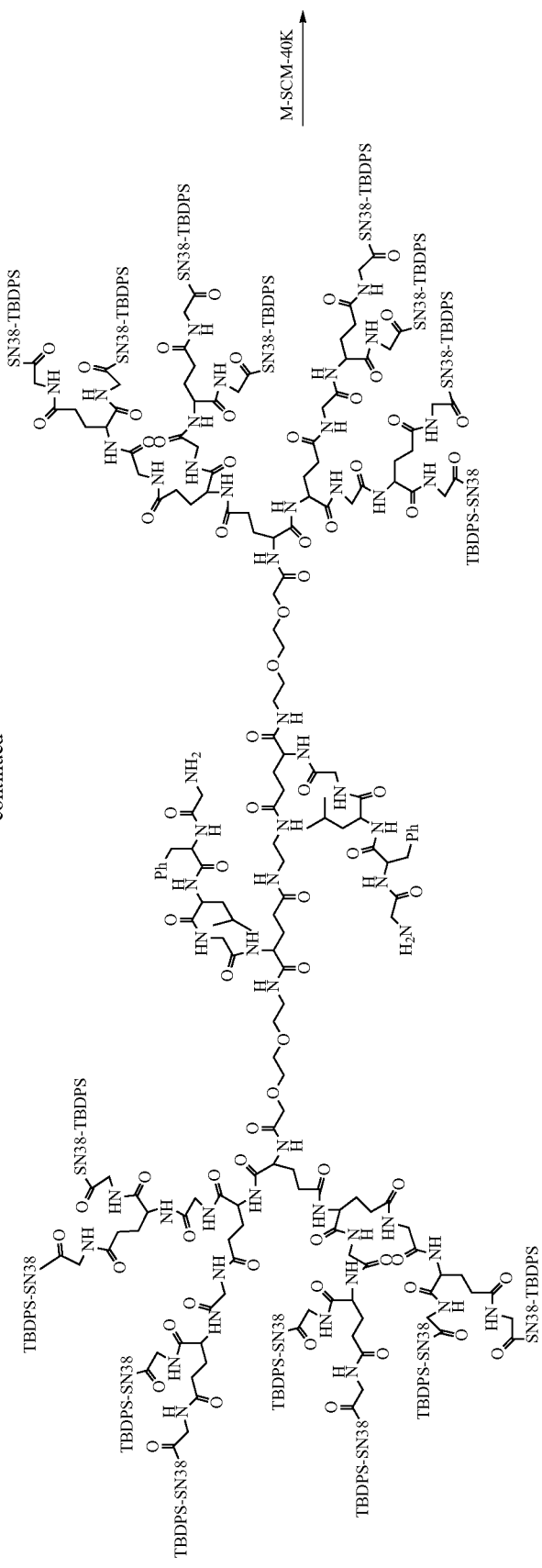
25-243

-continued
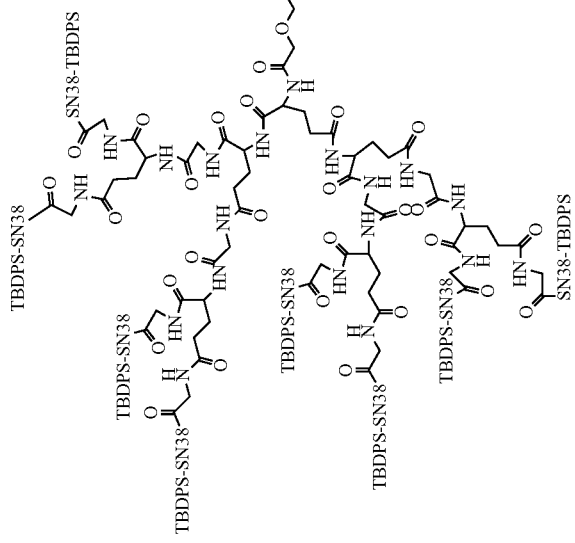
25-260

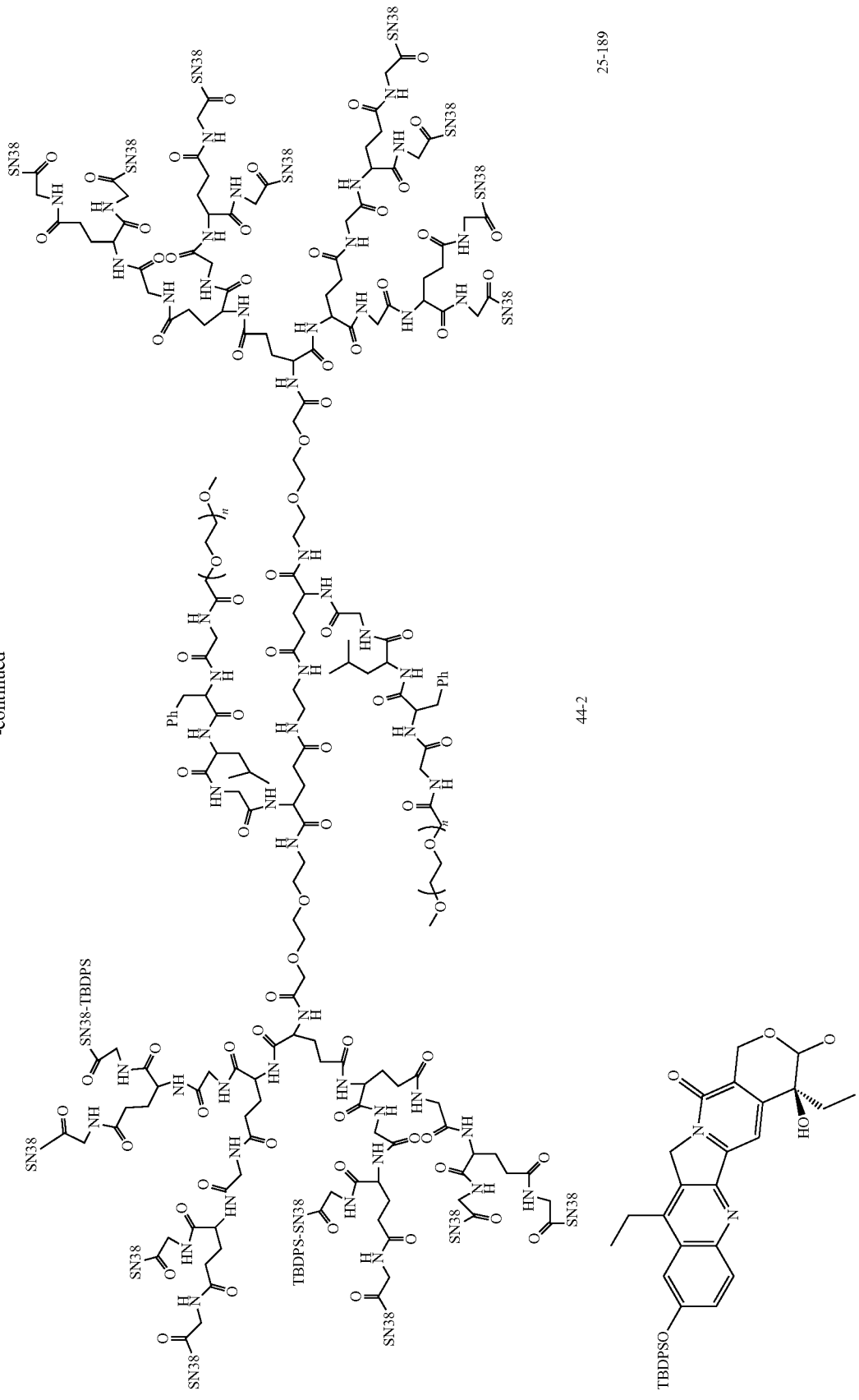

7-ethyl-10-hydroxycamptothecin (also referred to as SN38, 20 g, 50.9684 mmol) and tert-butyl diphenylchlorosilane (purchased from Innochem, TBDPSC1, 79.5 mL, 305.8104 mmol) were added in a 1 L round-bottomed flask, and dissolved with dichloromethane (250 mL) and triethylamine (Et₃N, 42.5 mL, 305.8104 mmol), and then the obtained solution was placed in an oil bath at 37° C. and stirred to react overnight. At the end of the reaction, the reaction solution was concentrated and evaporated to dryness under reduced pressure to remove the dichloromethane, the obtained solid was dissolved with dichloromethane (20 mL), the obtained solution was precipitated with n-hexane (200 mL) to separate out a solid product, and filtering was carried out. The filter cake was washed with n-hexane (100 mL), the filtrate was kept in a refrigerator at 2° C.-8° C. for 30 minutes, taken out and filtered, and the filter cake was washed with n-hexane (100 mL). Such operations were repeated five times, to obtain a solid product. The solid product was dried in an oven, thus obtaining the product 25-189: 23.9 g, yield: 74.34%.

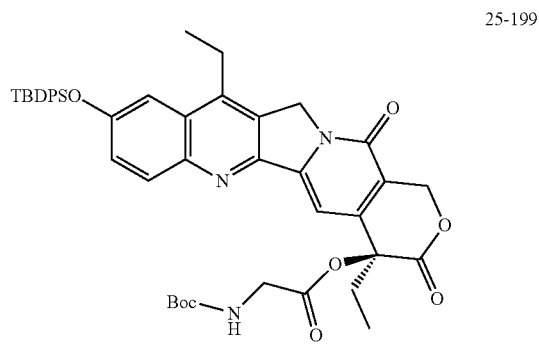

25-199

Boc-glycine (Boc-Gly-OH, 7.9647 g, 45.4661 mmol), 25-189 (23.9 g, 37.8884 mmol) and DMAP (0.9258 g, 7.5777 mmol) were added in a 500 mL round-bottomed flask, and dissolved with dichloromethane (100 mL), the mixed solution was stirred at 0° C. for about 30 minutes, then dicyclohexylcarbodiimide (DCC, 15.6350 g, 75.7767 mmol) was added, and the obtained solution was stirred to react at 0° C. for 3 hours. At the end of the reaction, the reaction solution was first filtered to remove the DCC, the filter cake was washed with dichloromethane (60 mL), and the filtrate was collected, evaporated to dryness, and dried, thus obtaining the product 25-199: 29.8549 g.

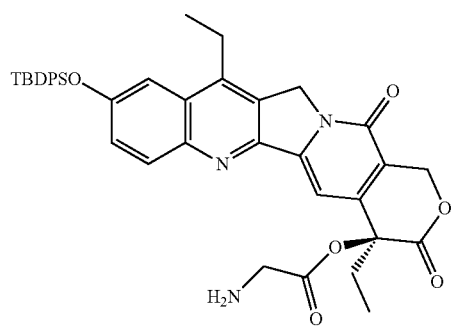

25-200

25-199 (29.8549 g, 37.8884 mmol) was added in a 100 mL round-bottomed flask, and dissolved with dichloromethane (20 mL), TFA (42.2 mL, 568.326 mmol) was added with stirring, and the mixed solution was stirred to react at room temperature overnight. At the end of the reaction, the reaction solution was first concentrated under reduced pressure and evaporated to remove the dichloromethane, the obtained solution was precipitated with n-hexane (150 mL), the supernatant was discarded, and then the lower oily solution was precipitated with n-hexane (150 mL). Such operations were repeated three times to obtain an oily solid. The oily solid was dissolved with dichloromethane (20 mL), silica gel powder (100 mL) was added to the obtained solution, and the operations of evaporation, dry sample loading, column chromatography, and elution with an elutent (1%-4% methanol: 99%-96% dichloromethane) were carried out. The elution product was then collected, concentrated, evaporated to dryness, and dried, thus obtaining the product 25-200: 23.4557 g, yield: 90.04%.

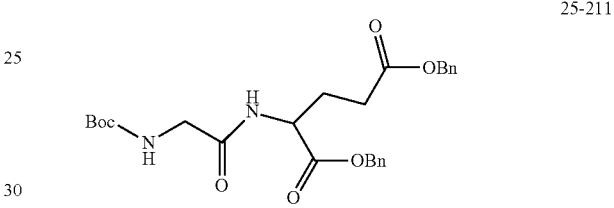

25-211

Boc-Gly-OH (purchased from Aladdin, 3.0 g, 17.1252 mmol), HBTU (9.7418 g, 25.6878 mmol), HOBT (3.4709 g, 25.6878 mmol) and H-Glu (OBzl)-OBzl·TosOH (8.5554 g, 17.1252 mmol) were added in a 500 mL round-bottomed flask, and dissolved with DMF (50 mL), and the mixed solution was stirred to react at −5° C. for 30 minutes. Then DIEA (12.7 mL, 77.0634 mmol) was slowly added dropwise. At the end of the addition, the obtained solution continued to react with stirring at −5° C. for 1 hour, and then moved to room temperature and stirred to react for 2 hours. At the end of the reaction, the reaction solution was transferred to a 2 L separatory funnel, saturated sodium bicarbonate solution (400 mL) and ethyl acetate (300 mL) were added, the obtained solution was shaken for extraction, and then the organic phase was separated from the aqueous phase. Then, saturated sodium chloride solution (300 mL) was further added to the organic phase, the obtained solution was shaken for extraction, and then the organic phase was separated from the aqueous phase. Next, saturated sodium chloride solution (300 mL) was added to the organic phase, the obtained solution was shaken for extraction, and then the organic phase was separated from the aqueous phase. The organic phase was concentrated and evaporated to dryness, the obtained solid was dissolved with a mixed solvent (50 mL) of 20% methanol/dichloromethane, silica gel powder (50 mL) was added to the obtained solution, and the operations of evaporation, dry sample loading, column chromatography, and elution with an elutent (1%-2% methanol: 99%-98% ethyl acetate) were carried out. The elution product was then collected, concentrated, evaporated to dryness, and dried, thus obtaining the product 25-211: 6.9213 g, yield: 83.41%.

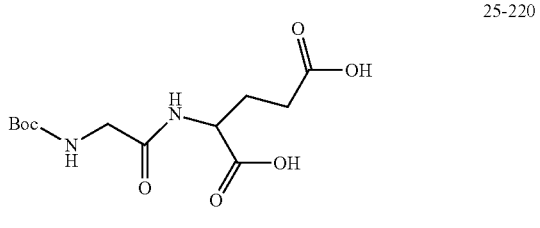 [SMILES: CC(C)(C)OC(=O)NCC(=O)NC(CCC(=O)O)C(=O)O]

25-220

25-211 (2.6890 g, 5.5382 mmol) and 10% Pd/C (50 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF (60 mL) until it did not contain any product, thus obtaining a reaction product solution.

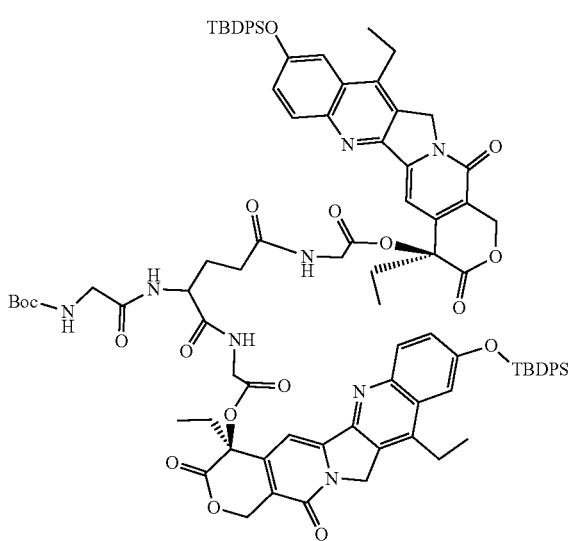

25-222

25-220 (1.6853 g, 5.5382 mmol), HBTU (6.3009 g, 16.6146 mmol), HOBT (2.2450 g, 16.6146 mmol) and 25-200 (8.3810 g, 12.1841 mmol) were added in a 500 mL round-bottomed flask, and dissolved with DMF (50 mL), and the mixed solution was stirred at −5° C. for 30 minutes. Then DIEA (8.2 mL, 49.8438 mmol) was slowly added dropwise. At the end of the addition, the obtained solution continued to react with stirring at −5° C. for 1 hour, and then moved to room temperature and stirred to react for 2 hours. At the end of the reaction, the reaction solution was first transferred to a 1 L separatory funnel, saturated sodium chloride solution (300 mL) and ethyl acetate (200 mL) were added, the obtained solution was shaken for extraction, and then the organic phase was separated from the aqueous phase. Then, saturated sodium chloride solution (300 mL) was added to the organic phase, the obtained solution was shaken for extraction, and then the organic phase was separated from the aqueous phase. Next, deionized water (300 mL) was added to the organic phase, the obtained solution was shaken for extraction. Finally, the organic phase was concentrated, evaporated to dryness, and dried in a vacuum oven, thus obtaining the product 25-222: 9.0 g, yield: 98.85%.

MALDI-TOF MS: [M−H$^+$]1641.76.

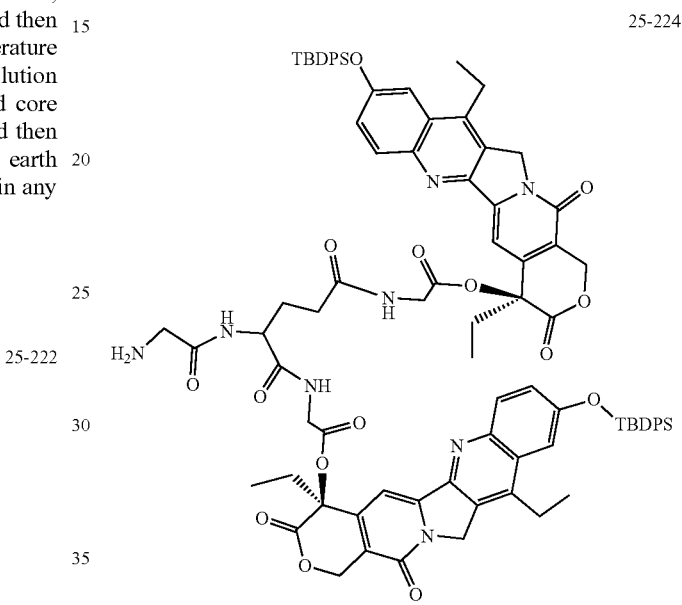

25-224

25-222 (9.0 g, 5.4745 mmol) was added in a 100 mL round-bottomed flask, and dissolved with dichloromethane (10 mL), TFA (6.1 mL, 82.1178 mmol) was added with stirring, and the mixed solution was stirred to react at room temperature overnight. At the end of the reaction, the reaction solution was first concentrated under reduced pressure and evaporated to remove the dichloromethane, then the reaction solution was transferred to a 2 L separatory funnel, saturated sodium chloride solution (400 mL) and ethyl acetate (200 mL) were added, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. The organic phase was concentrated and evaporated to dryness, the obtained solid was dissolved with a mixed solvent (70 mL) of 20% methanol/dichloromethane, silica gel powder (50 mL) was added, and the operations of evaporation, dry sample loading, column chromatography, and elution with an elutent (2%-7% methanol: 98%-93% ethyl acetate) were carried out. The elution product was then collected, concentrated, evaporated to dryness, and dried, thus obtaining the product 25-224: 6.0 g, yield: 70.99%.

MALDI-TOF MS: [M+Na$^+$]1565.64.

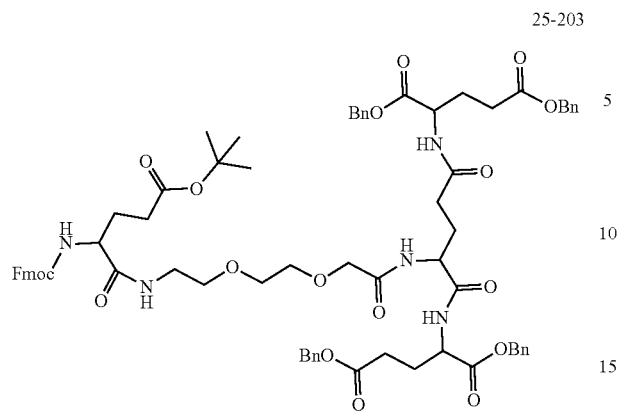

25-203

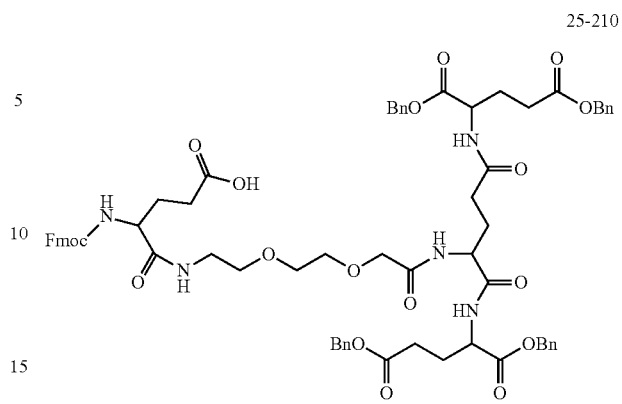

25-210

Fmoc-Glu (OtBu)-OH (purchased from Ark Pharm, 4.0646 g, 9.5134 mmol), HBTU (5.4118 g, 14.2701 mmol), HOBT (1.9282 g, 14.2701 mmol) and 25-201 (synthesized according to the method of synthesizing 22-181, 9.1 g, 9.9890 mmol) were added in a 500 mL round-bottomed flask, and dissolved with DMF (60 mL), and then the mixed solution was stirred to react at −5° C. for 30 minutes. Then DIEA (7.1 mL, 42.8103 mmol) was slowly added dropwise. At the end of the addition, the obtained solution continued to react with stirring at −5° C. for 2 hours, and then moved to room temperature and stirred to react overnight. At the end of the reaction, the reaction solution was first transferred to a 2 L separatory funnel, saturated sodium chloride solution (300 mL) and ethyl acetate (200 mL) were added, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried in a vacuum oven, thus obtaining the product 25-203: 12.5430 g.

25-203 (12.5430 g, 9.5134 mmol) was added in a 100 mL round-bottomed flask, and dissolved with dichloromethane (10 mL), trifluoroacetic acid (TFA, 10.6 mL, 142.701 mmol) was added with stirring, and then the mixed solution was stirred to react at room temperature overnight. At the end of the reaction, the reaction solution was first concentrated under reduced pressure and evaporated to remove the dichloromethane. Then, the reaction solution was transferred to a 1 L separatory funnel, saturated sodium chloride solution (300 mL) and ethyl acetate (300 mL) were added, the obtained solution was shaken for extraction, and the aqueous phase was separated. Then, saturated sodium chloride solution (300 mL) was added to the organic phase, the obtained solution was shaken for extraction, and the aqueous phase was separated. Next, deionized water (300 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (50 mL) was added to the obtained solution, and the operations of evaporation, dry sample loading, column chromatography, and elution with an elutent (1%-5% methanol: 99%-95% dichloromethane) were carried out. The elution product was then collected, concentrated, evaporated to dryness, and dried, thus obtaining the product 25-210: 9.0 g, yield: 74.94%.

MALDI-TOF MS: [M+Na$^+$]1284.24.

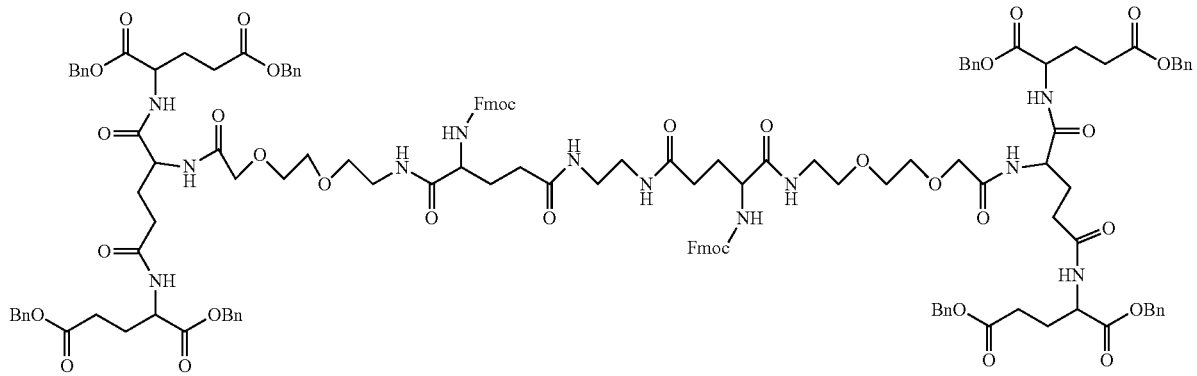

25-221

25-210 (9.0 g, 7.1295 mmol), HBTU (3.9376 g, 10.3828 mmol), HOBT (1.4029 g, 10.3828 mmol) and ethylenediamine monohydrate (purchased from TCI, 0.2 mL, 3.4609 mmol) were added in a 500 mL round-bottomed flask, and dissolved with DMF (60 mL), and then the obtained solution was stirred to react at −5° C. for about 30 minutes. Then DIEA (5.1 mL, 31.1483 mmol) was slowly added dropwise. At the end of the addition, the obtained solution continued to react with stirring at −5° C. for 2 hours, and was then moved to room temperature and stirred to react overnight. At the end of the reaction, the reaction solution was first transferred to a 1 L separatory funnel, saturated sodium chloride solution (300 mL) and ethyl acetate (300 mL) were added, the obtained solution was shaken for extraction, and the aqueous phase was separated. Then, saturated sodium chloride solution (300 mL) was added to the organic phase, the obtained solution was shaken for extraction, and the aqueous phase was separated. Next, deionized water (300 mL) was added to the organic phase, the obtained solution was shaken for extraction, and the aqueous phase was separated. Finally, the organic phase was concentrated, evaporated to dryness, and dried in a vacuum oven, thus obtaining the product 25-221: 8.8211 g.

MALDI-TOF MS: [M+Na$^+$]2570.22.

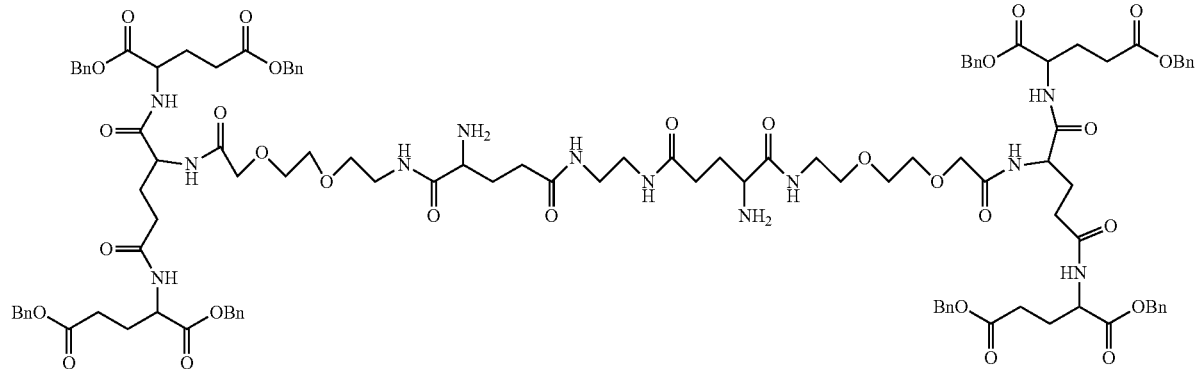

25-226

25-221 (8.8211 g, 3.4609 mmol) was added in a 500 mL round-bottomed flask, and dissolved with DMF (10 mL), morpholine (4.5 mL, 51.9135 mmol) was added with stirring, and then the mixed solution was stirred to react at room temperature for 2 hours. At the end of the reaction, the reaction solution was first transferred to a 1 L separatory funnel, saturated sodium chloride solution (300 mL) and ethyl acetate (300 mL) were added, the obtained solution was shaken for extraction, and the aqueous phase was separated. Then, saturated sodium chloride solution (300 mL) was added to the organic phase, the obtained solution was shaken for extraction, and the aqueous phase was separated. Next, deionized water (300 mL) was added to the organic phase, the obtained solution was shaken for extraction, and the aqueous phase was separated. Finally, the organic phase was concentrated, evaporated to dryness, and dried in a vacuum oven, thus obtaining the product 25-226: 7.2828 g.

MALDI-TOF MS: [M+Na$^+$]2125.39.

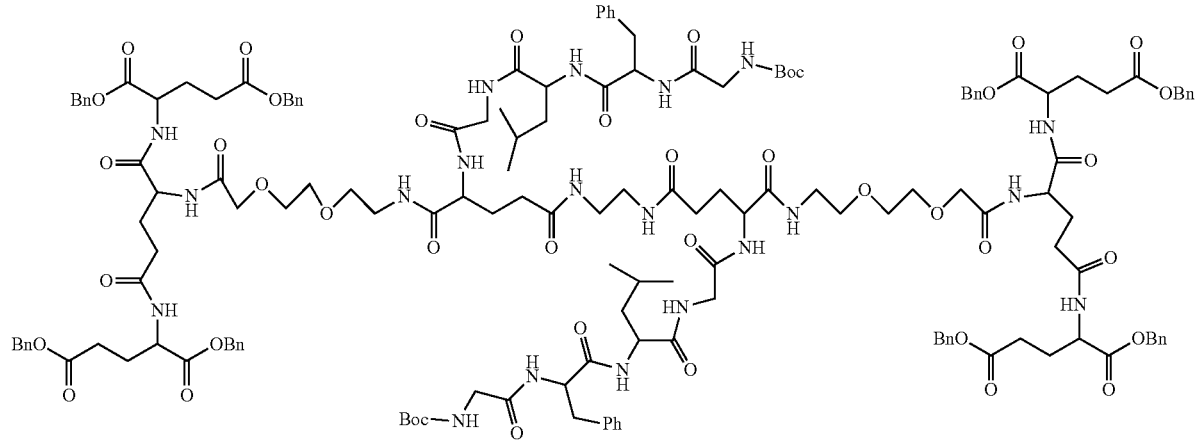

25-227

25-226 (3.2368 g, 1.5382 mmol), HBTU (1.7500 g, 4.6146 mmol), HOBT (0.6235 g, 4.6146 mmol) and 25-207 (synthesized according to the method of synthesizing 25-102) (1.7426 g, 3.5379 mmol) were added in a 500 mL round-bottomed flask, and dissolved with DMF (60 mL), and then the mixed solution was stirred to react at −5° C. for 30 minutes. Then DIEA (2.3 mL, 13.8438 mmol) was slowly added dropwise. At the end of the addition, the obtained solution continued to react with stirring at −5° C. for 1 hour, and then moved to room temperature and stirred to react for 2 hours. At the end of the reaction, the reaction solution was first transferred to a 2 L separatory funnel, saturated sodium bicarbonate solution (300 mL) and ethyl acetate (200 mL) were added, the obtained solution was shaken for extraction, and the aqueous phase was separated. Then, saturated sodium chloride solution (300 mL) was added to the organic phase, the obtained solution was shaken for extraction, and the aqueous phase was separated. Next, deionized water (300 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (50 mL) was added to the obtained solution, and the operations of evaporation, dry sample loading, column chromatography, and elution with an elutent (1% ammonia water: 2%-6% methanol: 97%-93% dichloromethane) were carried out. The elution product was then collected, concentrated, evaporated to dryness, and dried, thus obtaining the product 25-227: 2.0618 g, yield: 43.9%.

MALDI-TOF MS: [M+Na$^+$]3076.43.

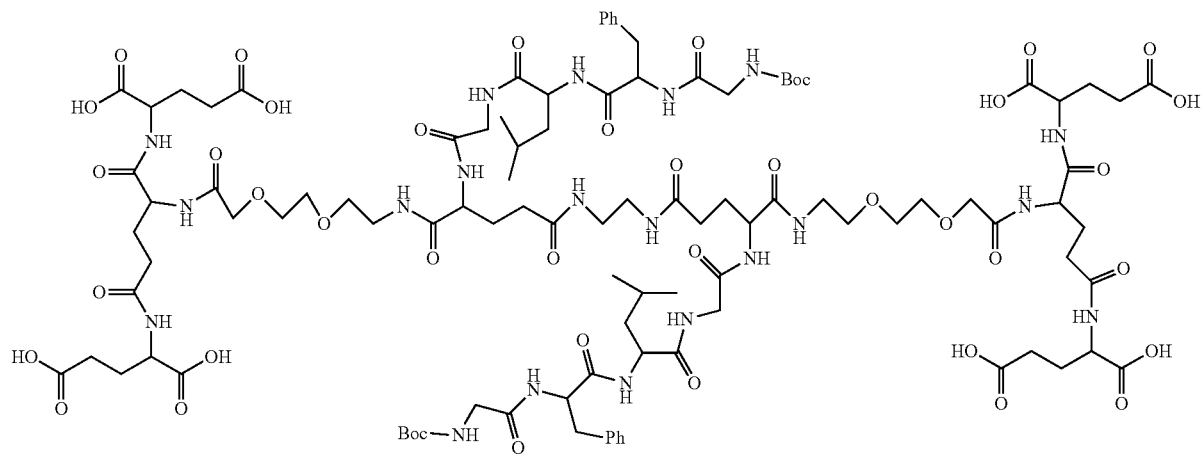

25-236

25-227 (0.6519 g, 0.2135 mmol) and 10% Pd/C (50 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF (50 mL) until it did not contain any product, thus obtaining a reaction product solution.

25-238

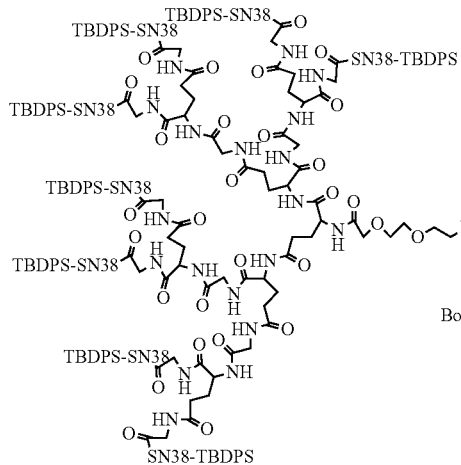
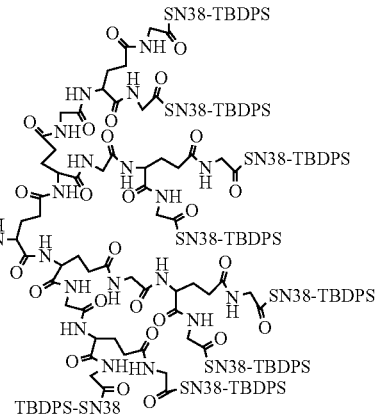

The solution of 25-236 (0.4980 g, 0.2135 mmol), HBTU (0.9716 g, 2.5620 mmol), HOBT (0.3462 g, 2.5620 mmol) and 25-224 (2.9 g, 1.8784 mmol) were added in a 500 mL round-bottomed flask, and dissolved with DMF (30 mL), and then the mixed solution was stirred to react at −5° C. for 30 minutes. Then DIEA (1.3 mL, 7.6860 mmol) was slowly added dropwise. At the end of the addition, the obtained solution continued to react at −5° C. with stirring for 3 hours. At the end of the reaction, the reaction solution was first transferred to a 1 L separatory funnel, saturated sodium chloride solution (300 mL) and ethyl acetate (200 mL) were added, the obtained solution was shaken for extraction, and the aqueous phase was separated. Then, deionized water (300 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (30 ml) was added to the obtained solution, and the operations of evaporation, dry sample loading, column chromatography, and elution with an elutent (3%-10% methanol: 97%-90% dichloromethane) were carried out. The elution product was then collected, concentrated, evaporated to dryness, and dried, thus obtaining the product 25-238: 1.9233 g, yield: 61.96%.

25-243
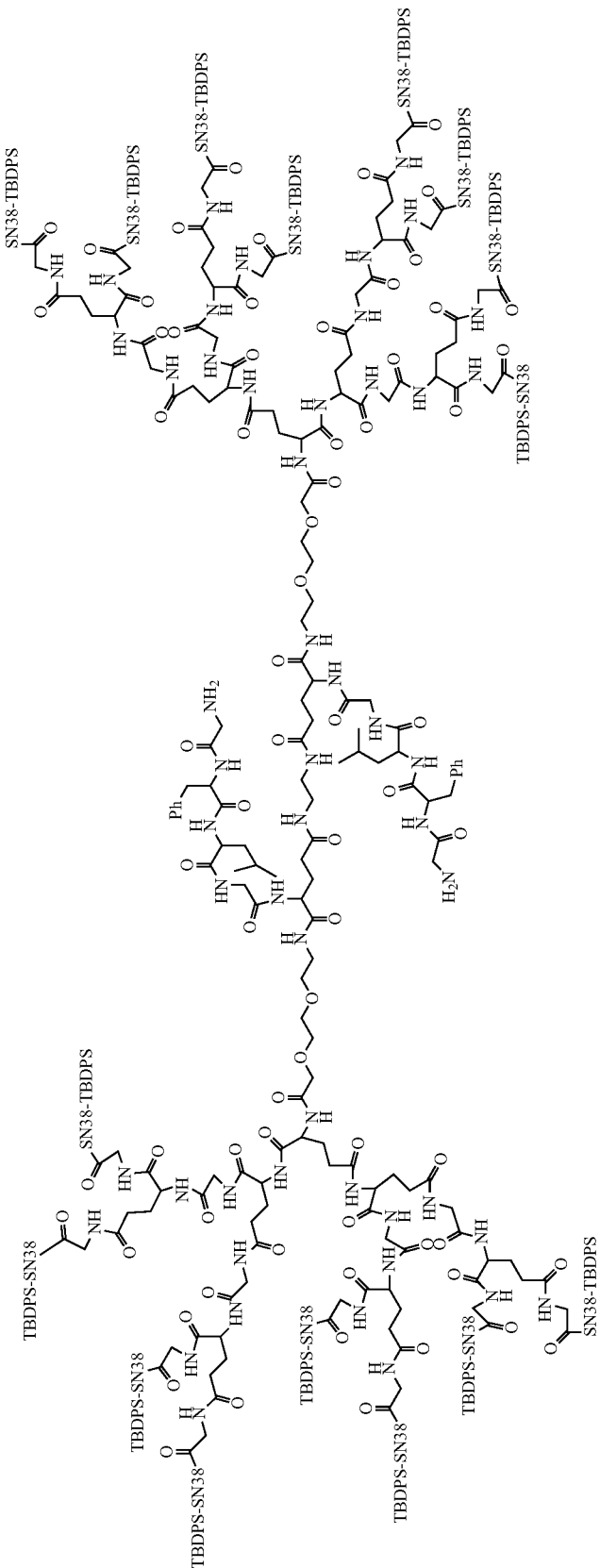

25-238 (1.9233 g, 0.1323 mmol) was added in a 100 mL round-bottomed flask, and dissolved with dichloromethane (5 mL), trifluoroacetic acid (TFA, 0.2 mL, 1.9843 mmol) was added with stirring, and then the mixed solution was stirred to react at room temperature overnight. At the end of the reaction, the reaction solution was evaporated to remove the dichloromethane. Then, the reaction solution was transferred to a 1 L separatory funnel, saturated sodium chloride solution (300 mL) and ethyl acetate (300 mL) were added, the obtained solution was shaken for extraction, and the aqueous phase was separated. Then, saturated sodium chloride solution (300 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (30 mL) was added to the obtained solution, and the operations of evaporation, dry sample loading, column chromatography, and elution with an elutent (1%-5% methanol: 99%-95% dichloromethane) were carried out. The elution product was then collected, concentrated, evaporated to dryness, and dried, thus obtaining the product 25-243: 0.7924 g, yield: 71.01%.

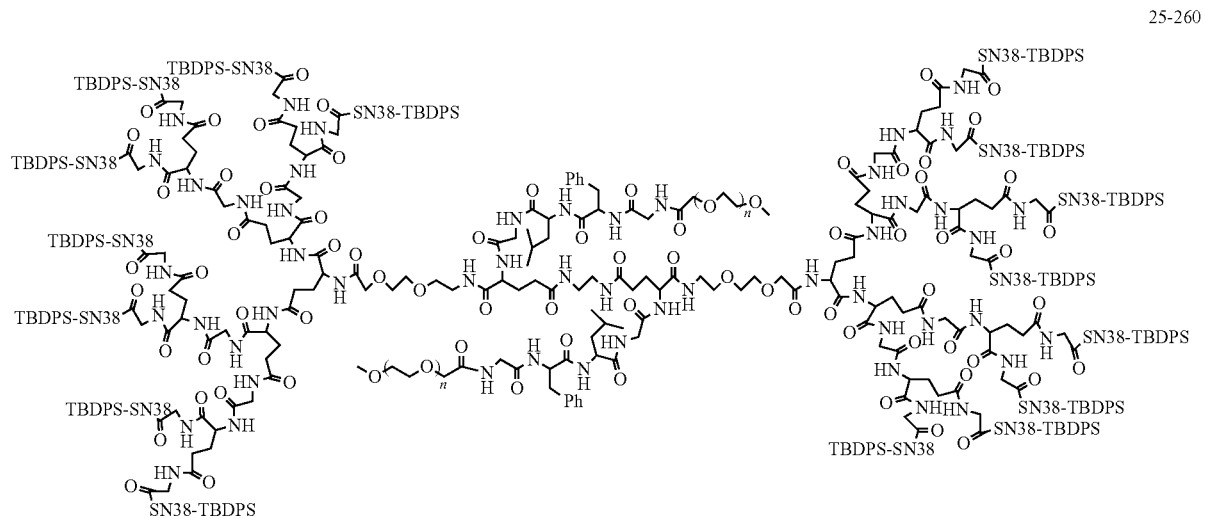

25-243 (0.4738 g, 0.033 mmol) and M-SCM-40K (purchased from Jenkem Technology, 3.0 g, 0.0727 mmol) were added in a 500 mL round-bottomed flask, and dissolved with DMF (20 mL), and then the mixed solution reacted at room temperature in the dark for one week. At the end of the reaction, n-hexane (100 mL) and methyl tert-butyl ether (10 mL) were added for precipitation to layer the reaction solution, the supernatant was discarded, and n-hexane (300 mL) and methyl tert-butyl ether (50 mL) were added to the lower oily liquid phase for further precipitation. Such operations were repeated three times, to finally obtain a viscous oily product. Then, dichloromethane (5 mL) was added to the viscous oily product, the obtained solution was precipitated with methyl tert-butyl ether (60 mL) to obtain a powdery solid, and filtering was carried out. The filter cake was washed with methyl tert-butyl ether (60 mL), to obtain a solid product. The solid product was dissolved with a mixed solvent (50 mL) of 20% methanol/dichloromethane, silica gel powder (40 ml) was added to the obtained solution, and the operations of evaporation, dry sample loading, column chromatography, and elution with an elutent (4%-12% methanol: 96%-88% dichloromethane) were carried out. The elution product was then collected, concentrated, evaporated to dryness, and dried, thus obtaining the product 25-260: 1.6 g, yield: 50.17%.

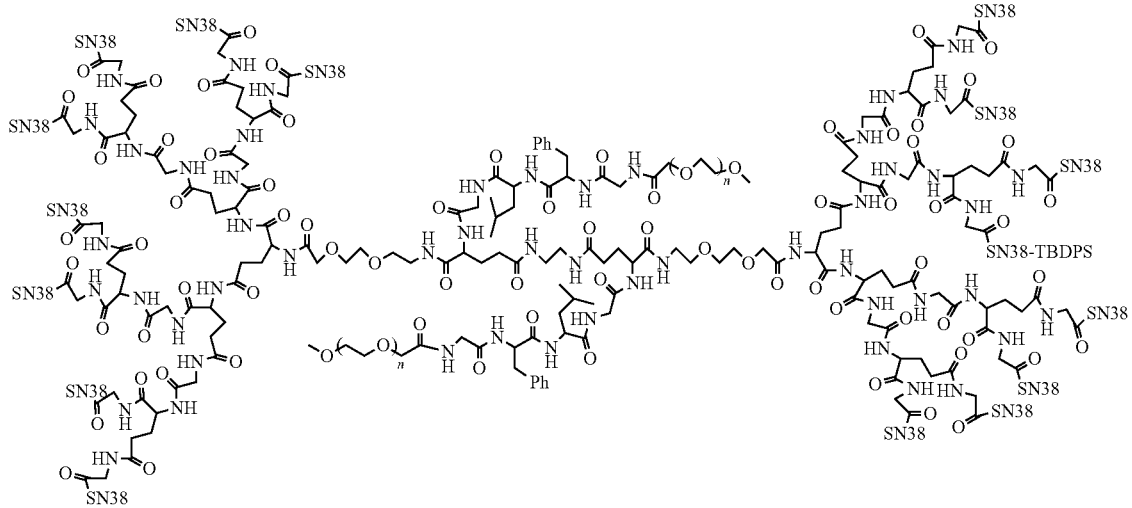

44-2

25-260 (0.8233 g, 0.0085 mmol) was dissolved with THF (20 mL); TBAF·3H$_2$O (0.0860 g, 0.2726 mmol) was dissolved with THF (10 mL); the THF solution of TBAF was added to the THF solution of 25-260, a certain amount of diluted hydrochloric acid solution (30 mL, 0.05 mol/L) was added, and then the mixed solution was stirred to react at room temperature in the dark overnight. At the end of the reaction, the reaction solution was first evaporated to dryness, anhydrous ethanol (20 mL) was added, the obtained solution was concentrated under reduced pressure and evaporated to dryness. Such operations were repeated three times. The obtained solid was dissolved with DMF (1.0 mL), isopropanol (50 mL) was added to the obtained solution for precipitation, to obtain a powdery solid, and filtering was carried out. The filter cake was further dissolved with DMF (3.0 mL), isopropanol (50 mL) was added to the obtained solution for precipitation, to obtain a powdery solid, and filtering was carried out. The filter cake was washed with isopropanol (30 mL). The solid obtained in the second step was dissolved with dichloromethane (2.0 mL), methyl tert-butyl ether (50 mL) was added for precipitation, to obtain a powdery solid, and filtering was carried out. The filter cake was then dissolved with dichloromethane (2.0 mL), methyl tert-butyl ether (50 mL) was added for precipitation, to obtain a powdery solid, and filtering was carried out. The filter cake was washed with methyl tert-butyl ether (30 mL), and dried, thus obtaining the product 44-2: 0.5519 g, yield: 69.79%.

$^1$H-NMR (600 MHz, DMSO-d$_6$) δ9.45-9.29 (m, 80H), 9.09-7.93 (m, 103H), 7.65-7.56 (m, 20H), 7.30-7.19 (m, 81H), 6.97-6.95 (s, 40H), 5.46-5.42 (m, 59H), 5.15-5.12 (m, 87H), 4.05-3.54 (m, 6944H), 2.93-2.89 (m, 97H), 2.74-2.66 (m, 39H), 2.34-2.31 (m, 20H), 2.09-2.06 (m, 106H), 1.90-1.72 (m, 104H), 1.48-1.45 (m, 31H), 1.31-1.21 (m, 119H), 0.95-0.84 (m, 96H).

7. Synthesis of 42-52 (Compound No. 1)

Synthetic route is as follows

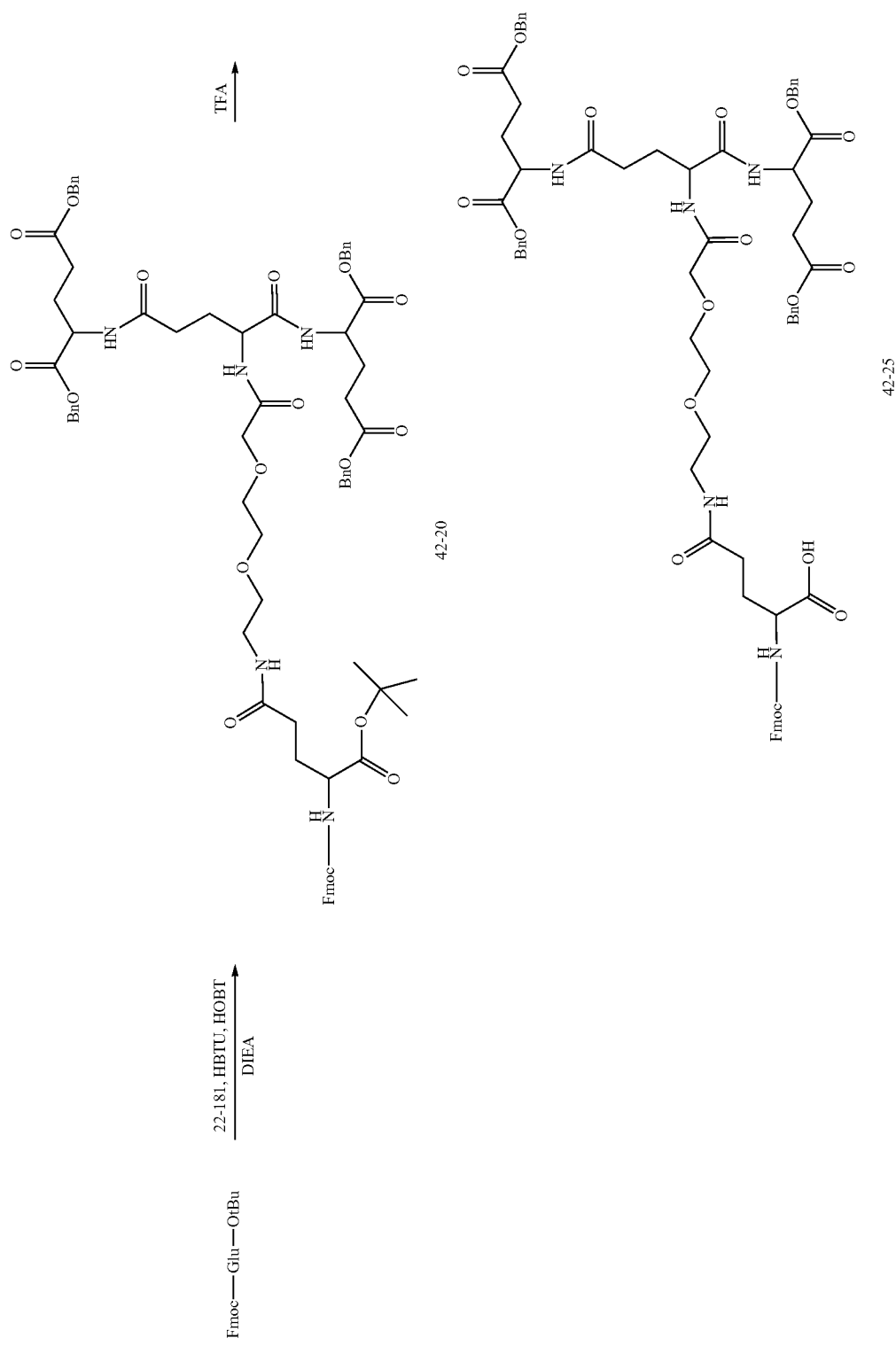

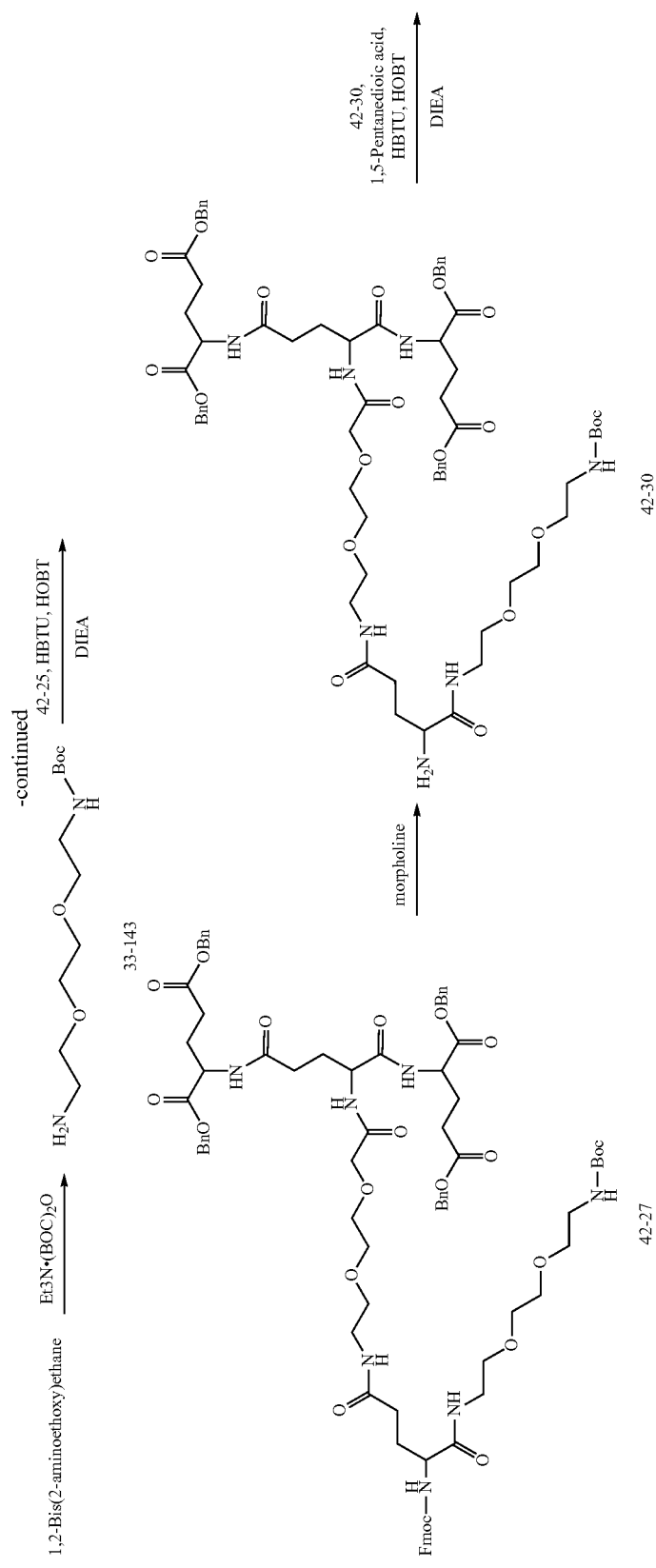

-continued
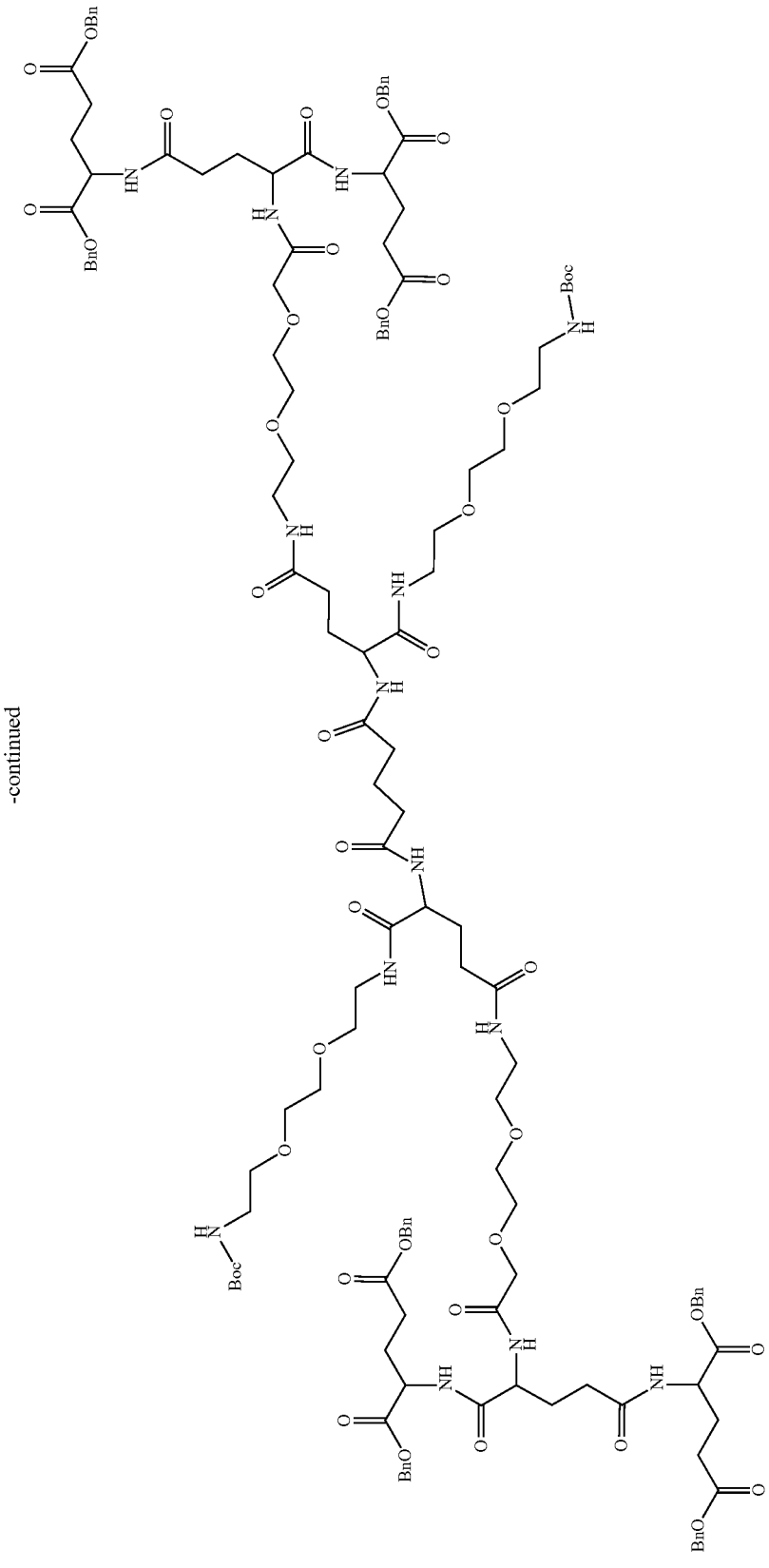
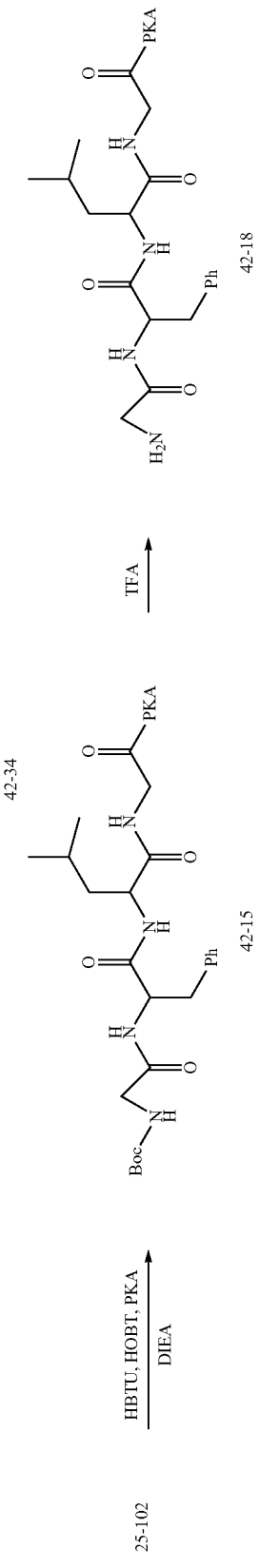

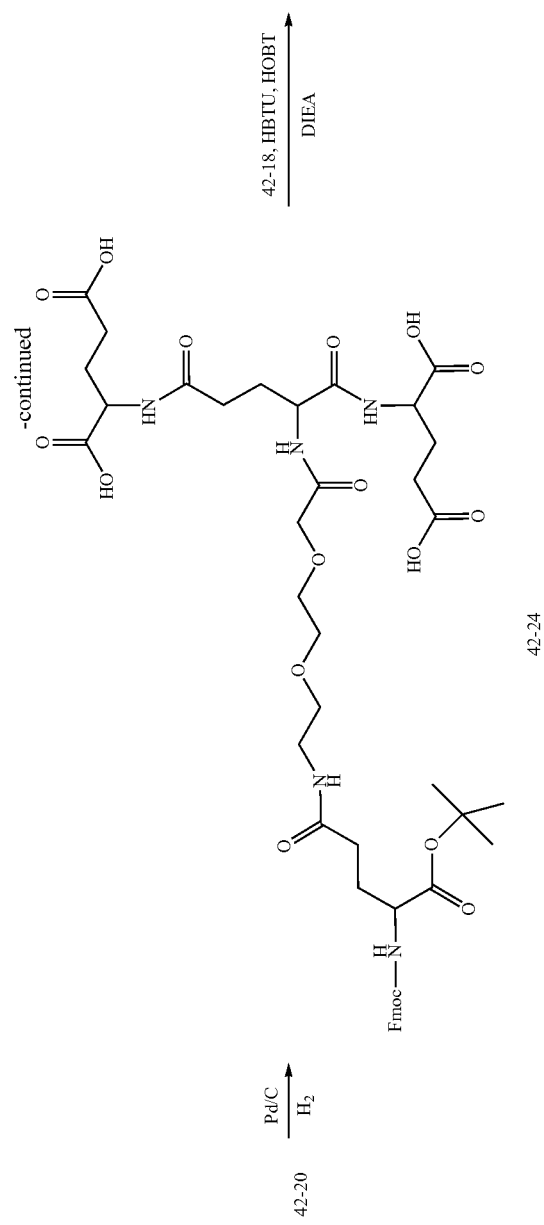

-continued
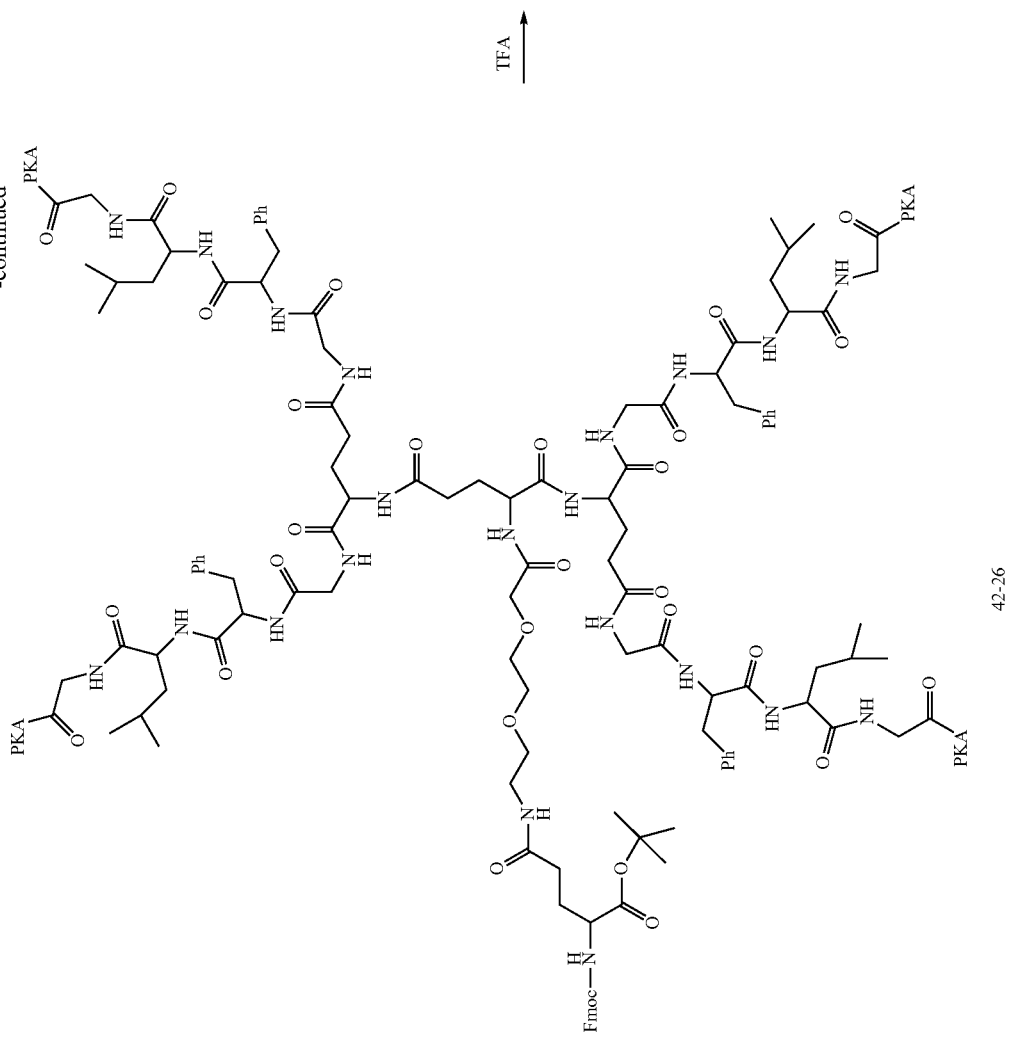
42-26

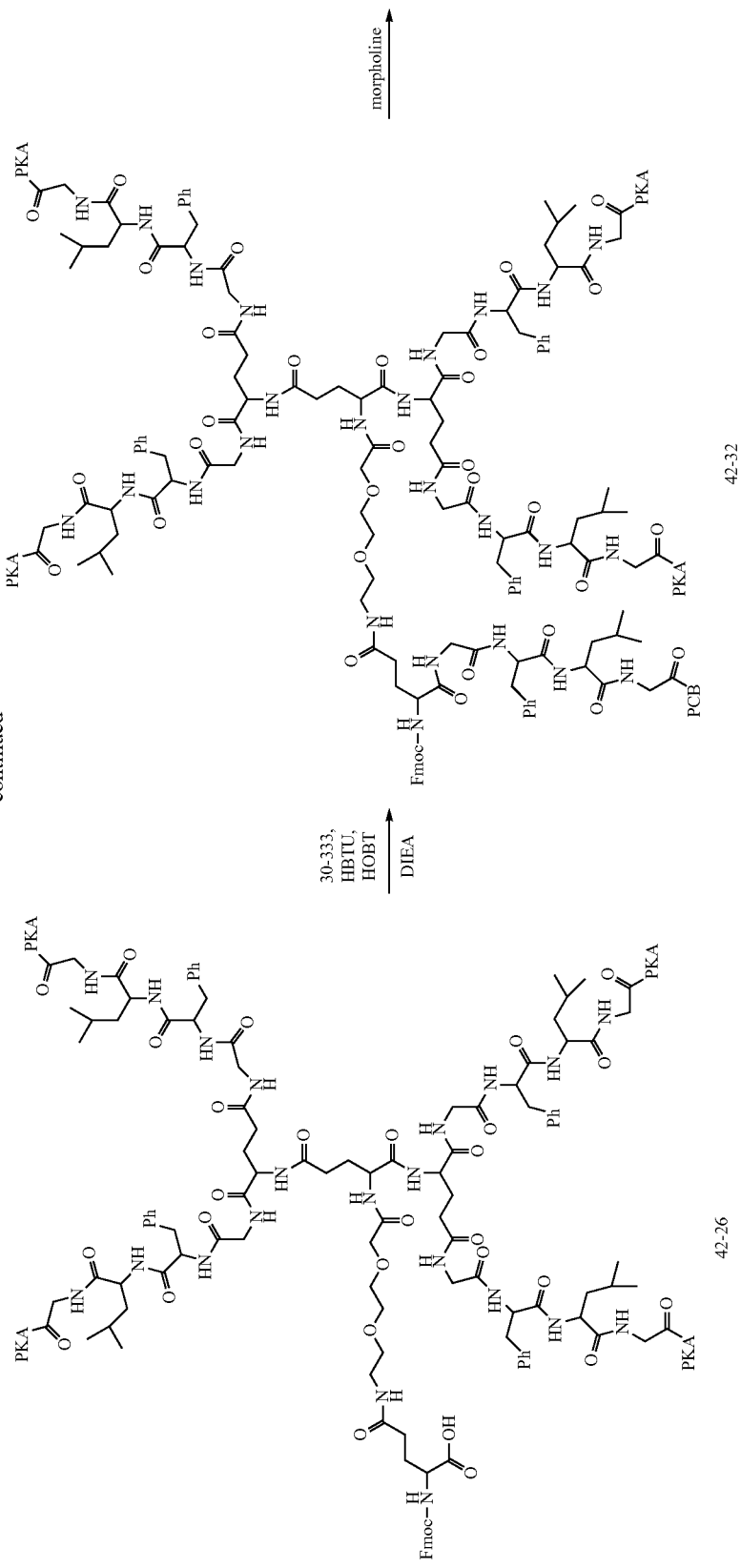

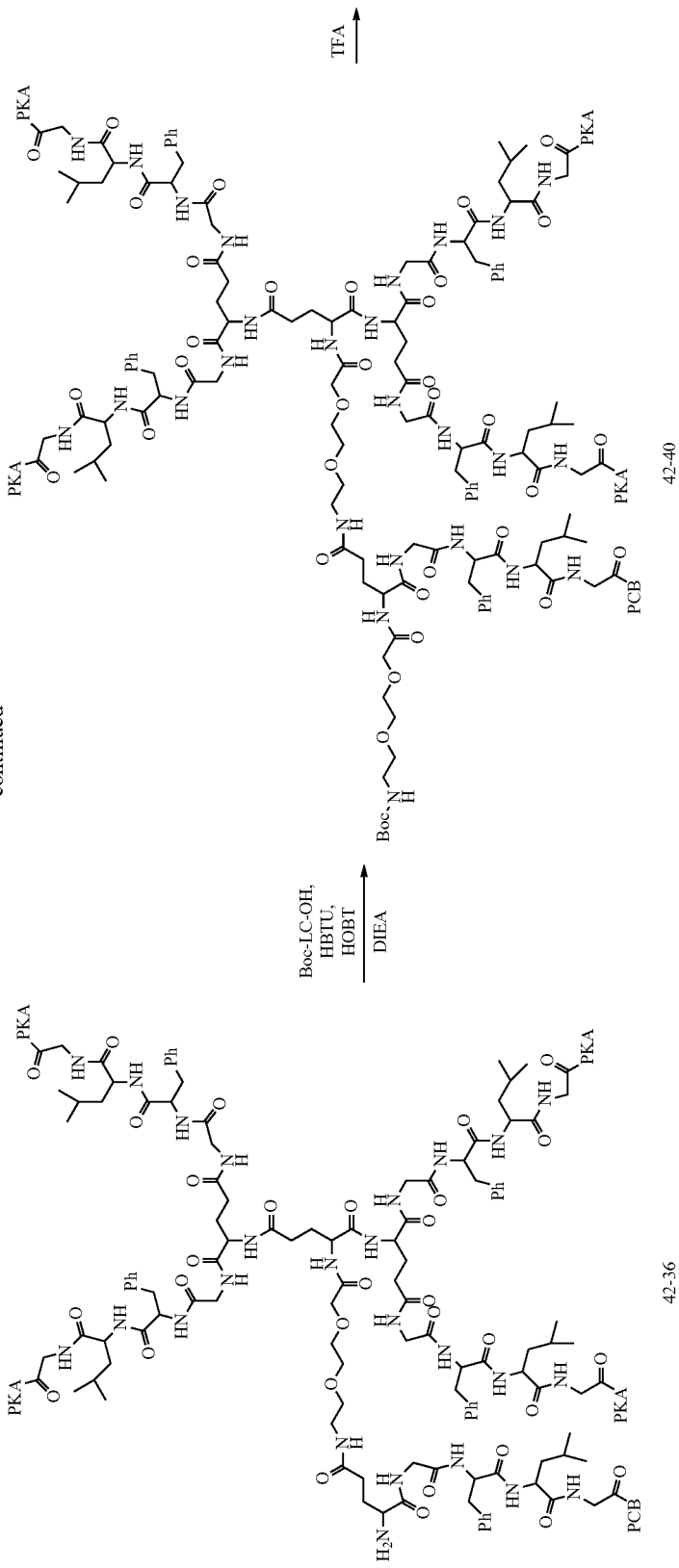

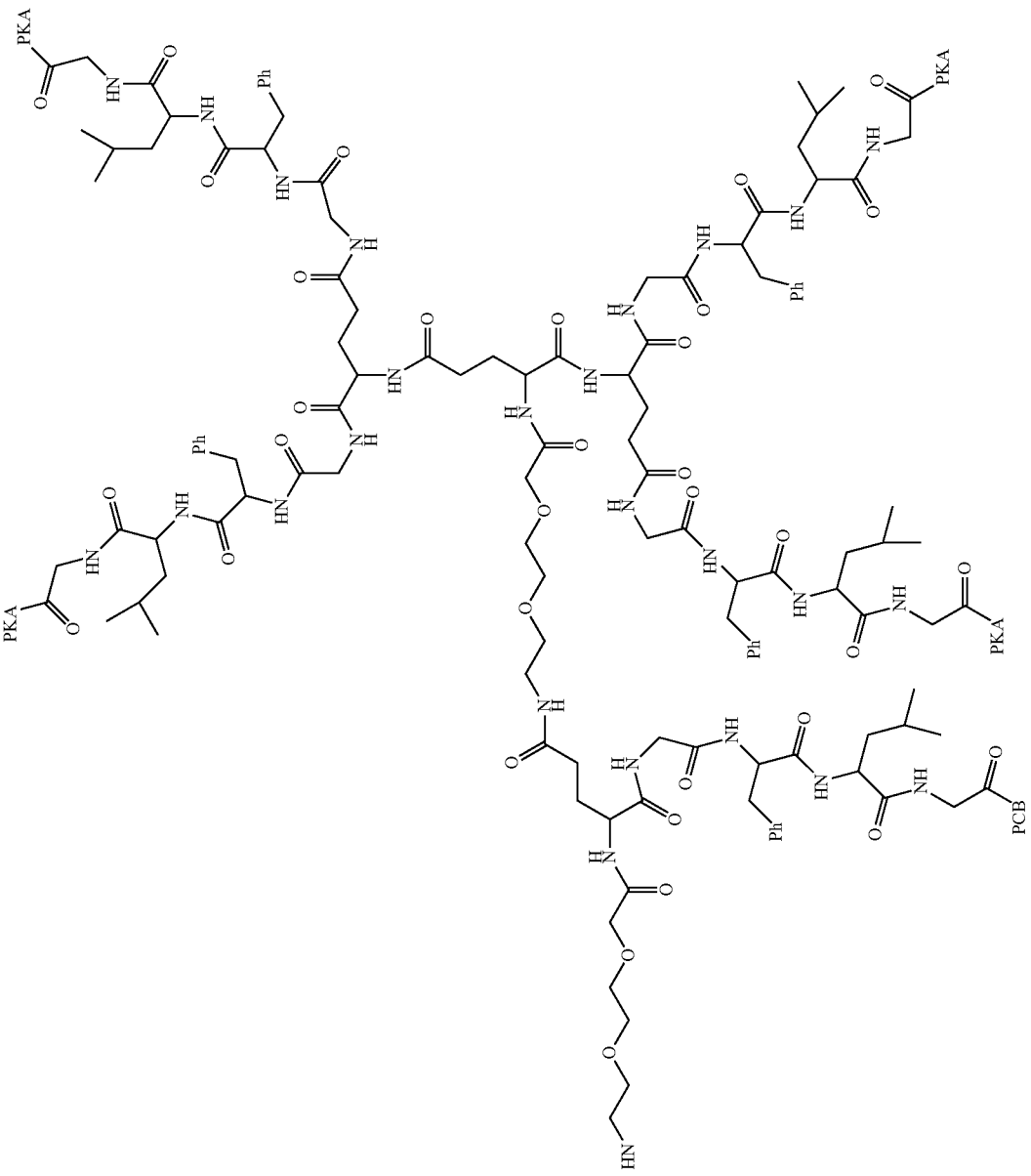

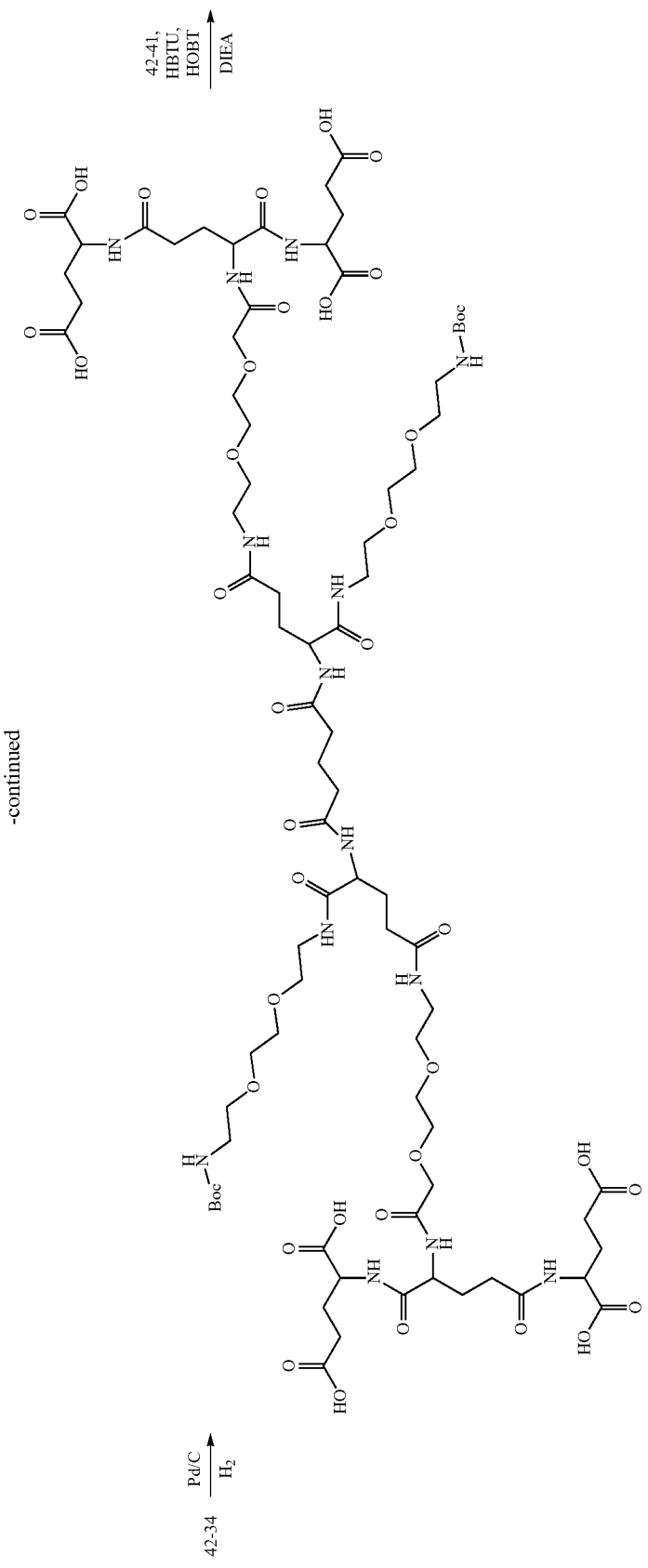

-continued
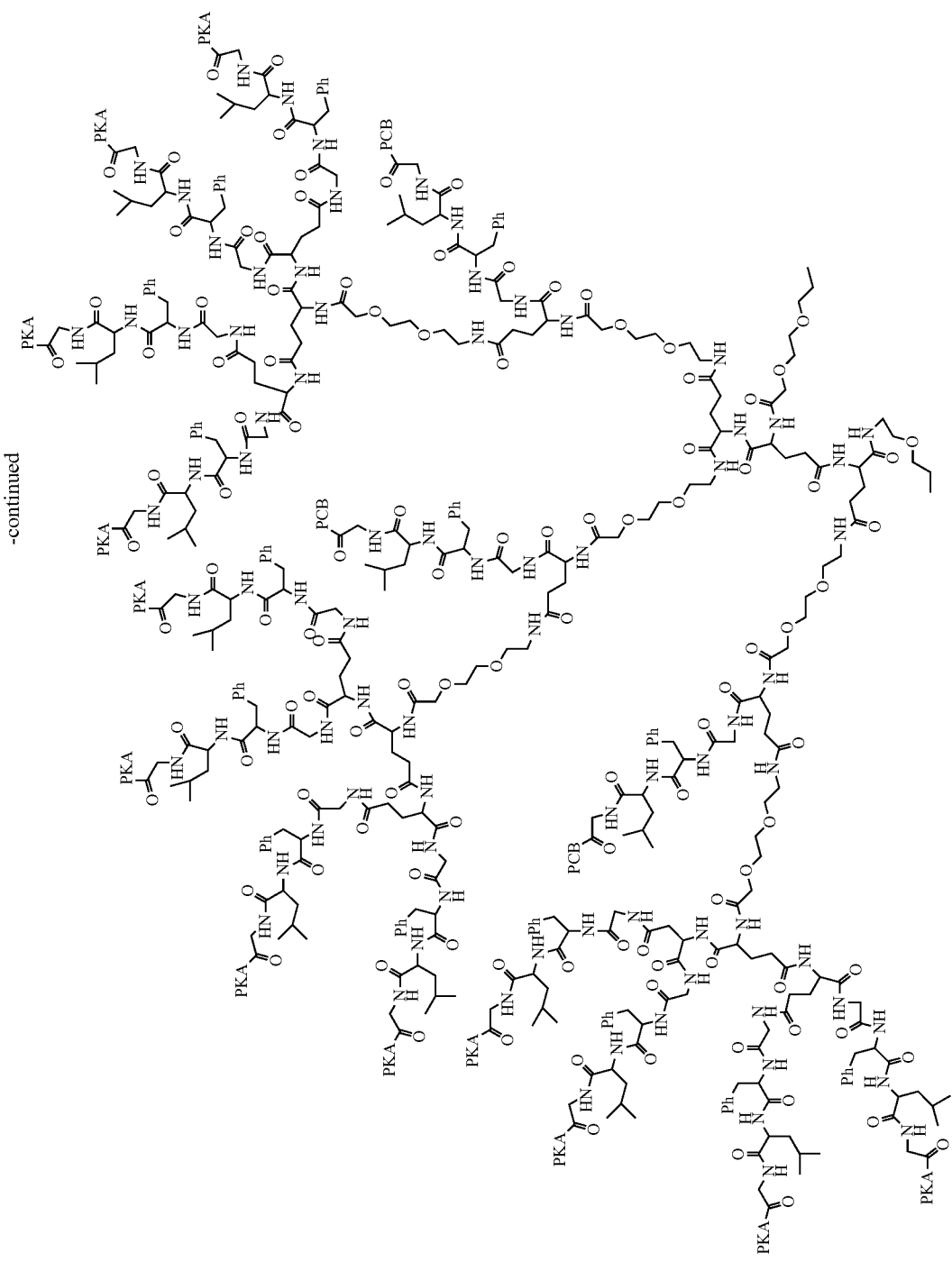

-continued
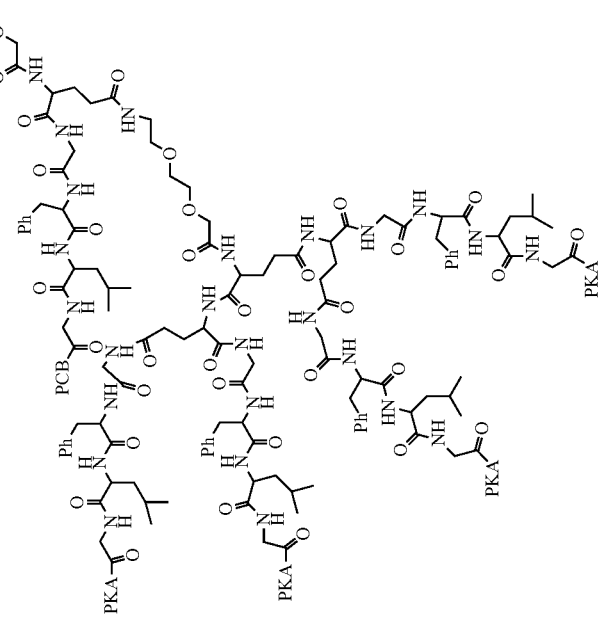

-continued
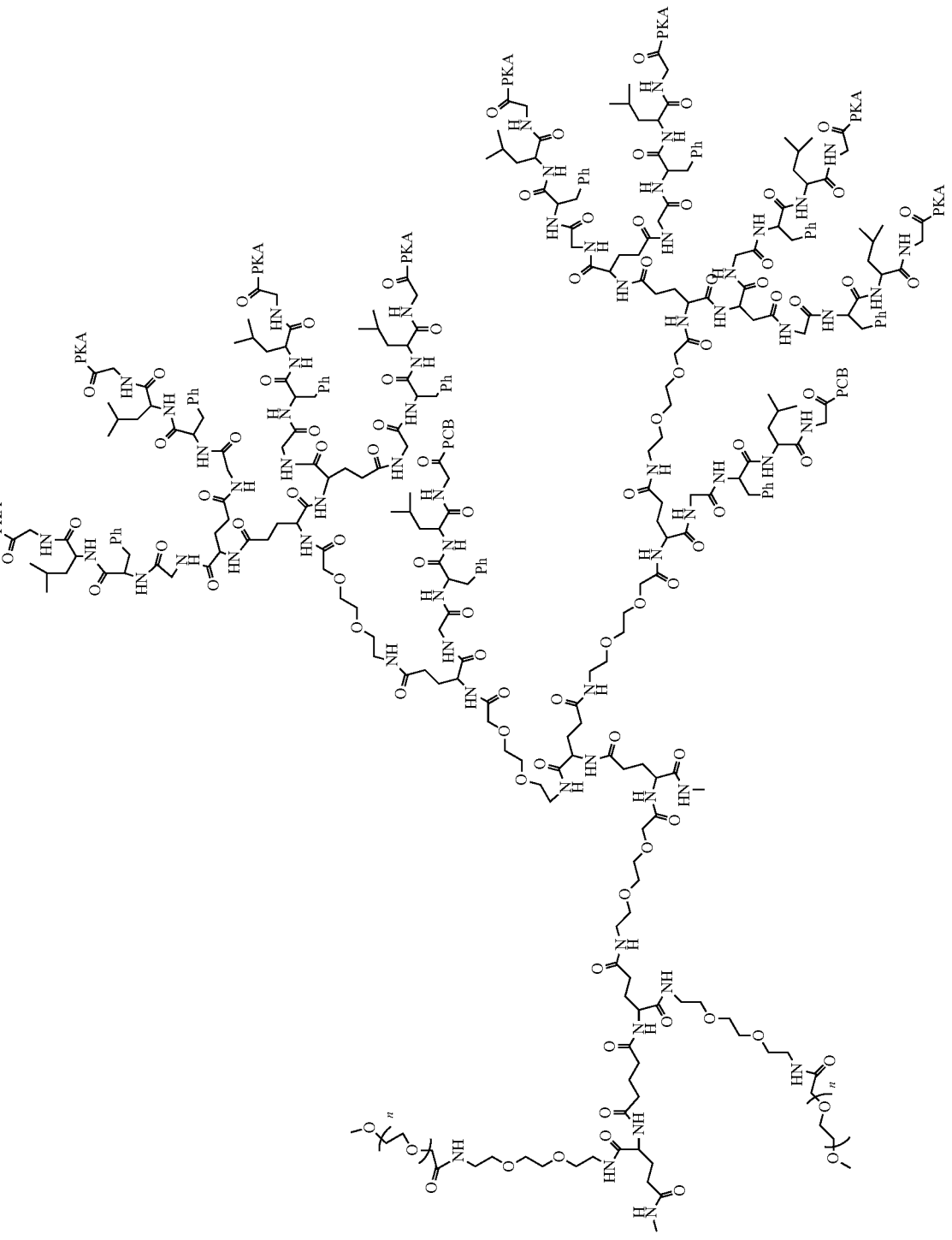

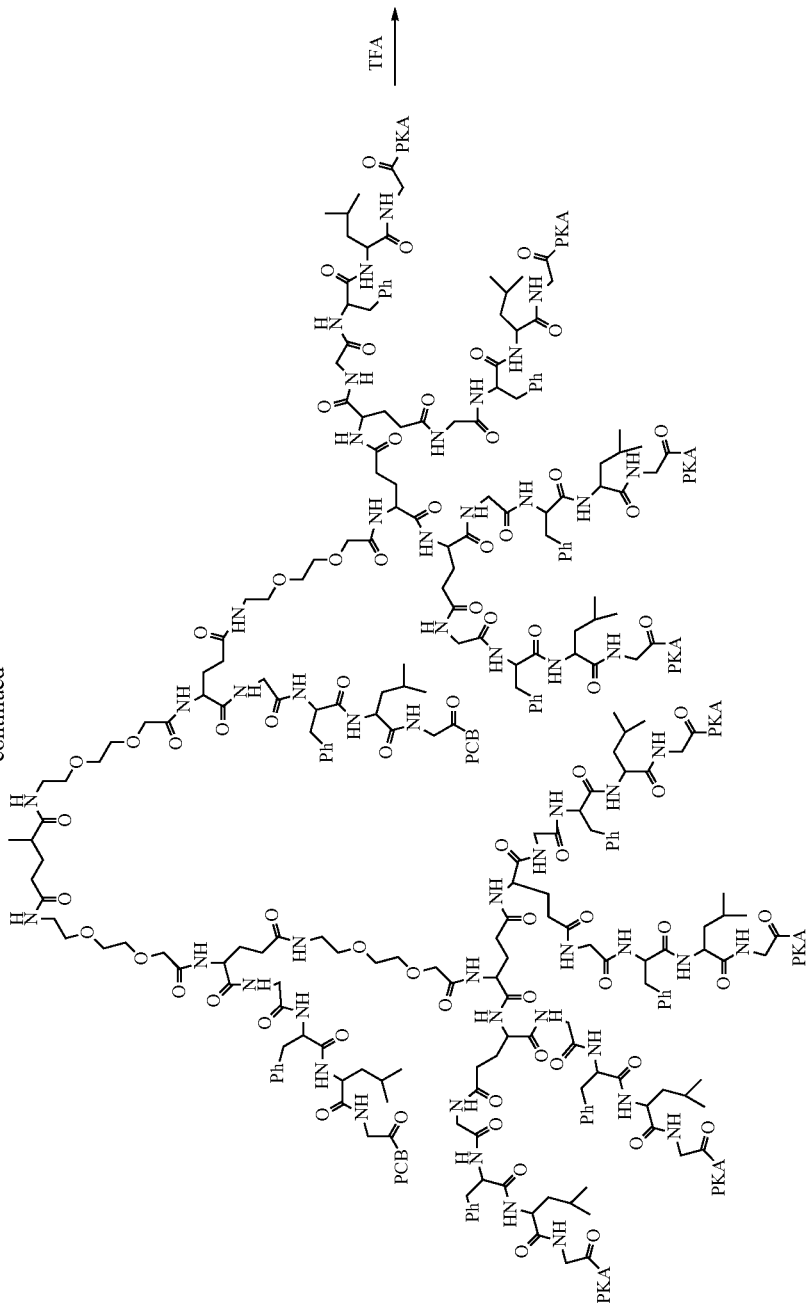
42-43

-continued
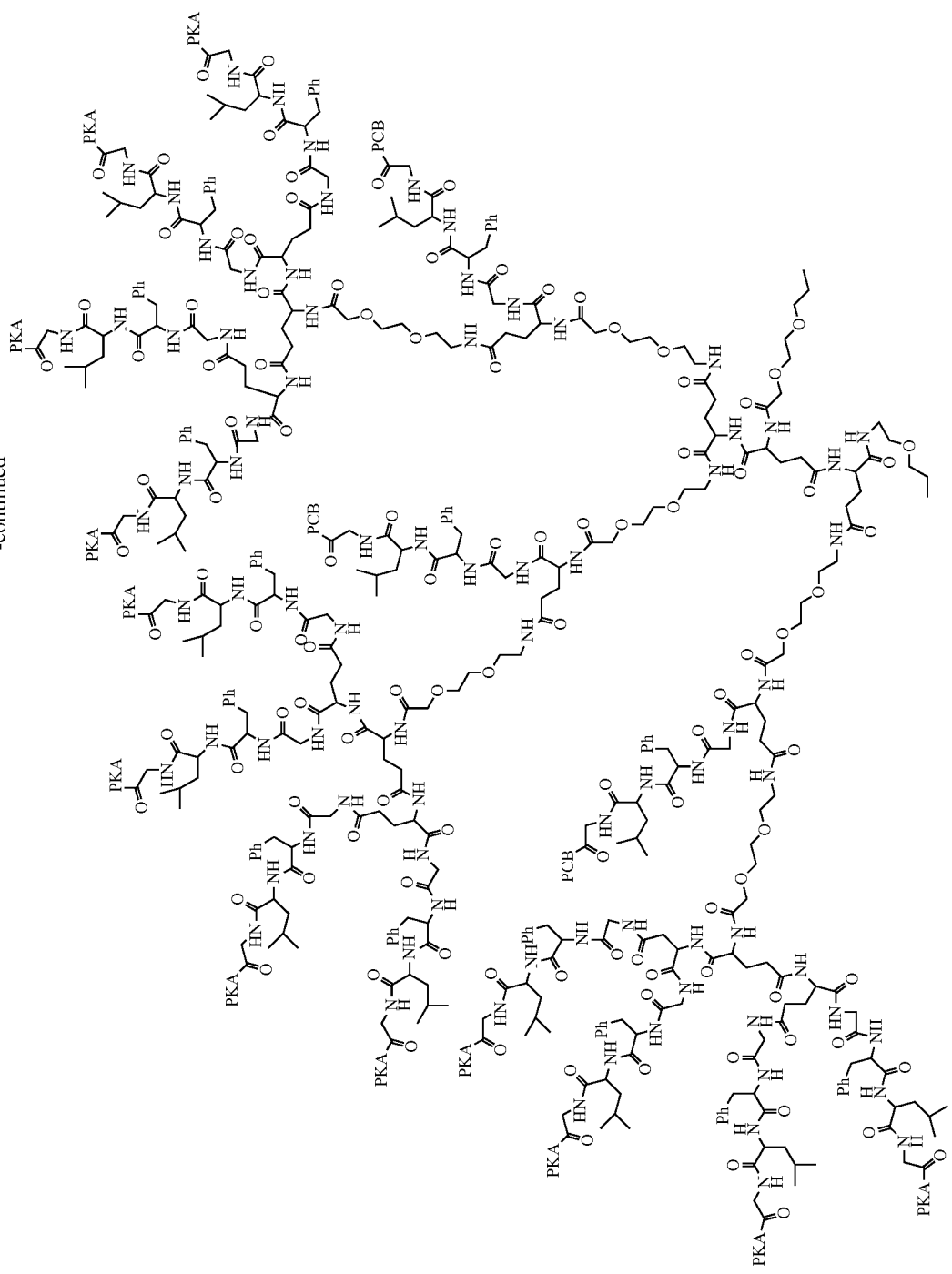

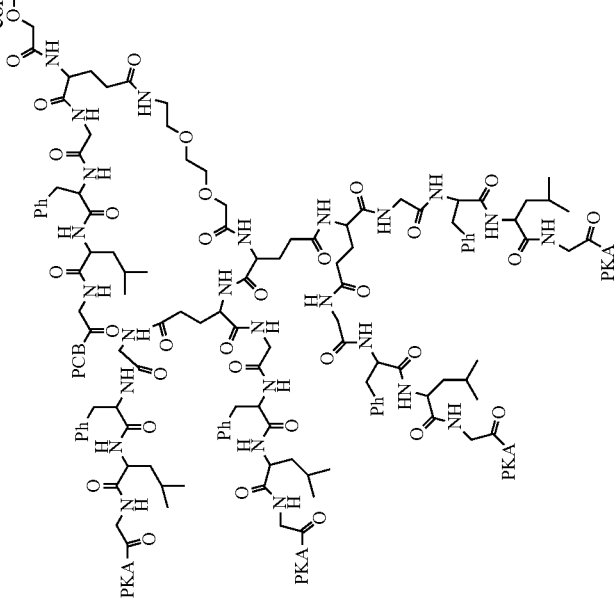

-continued
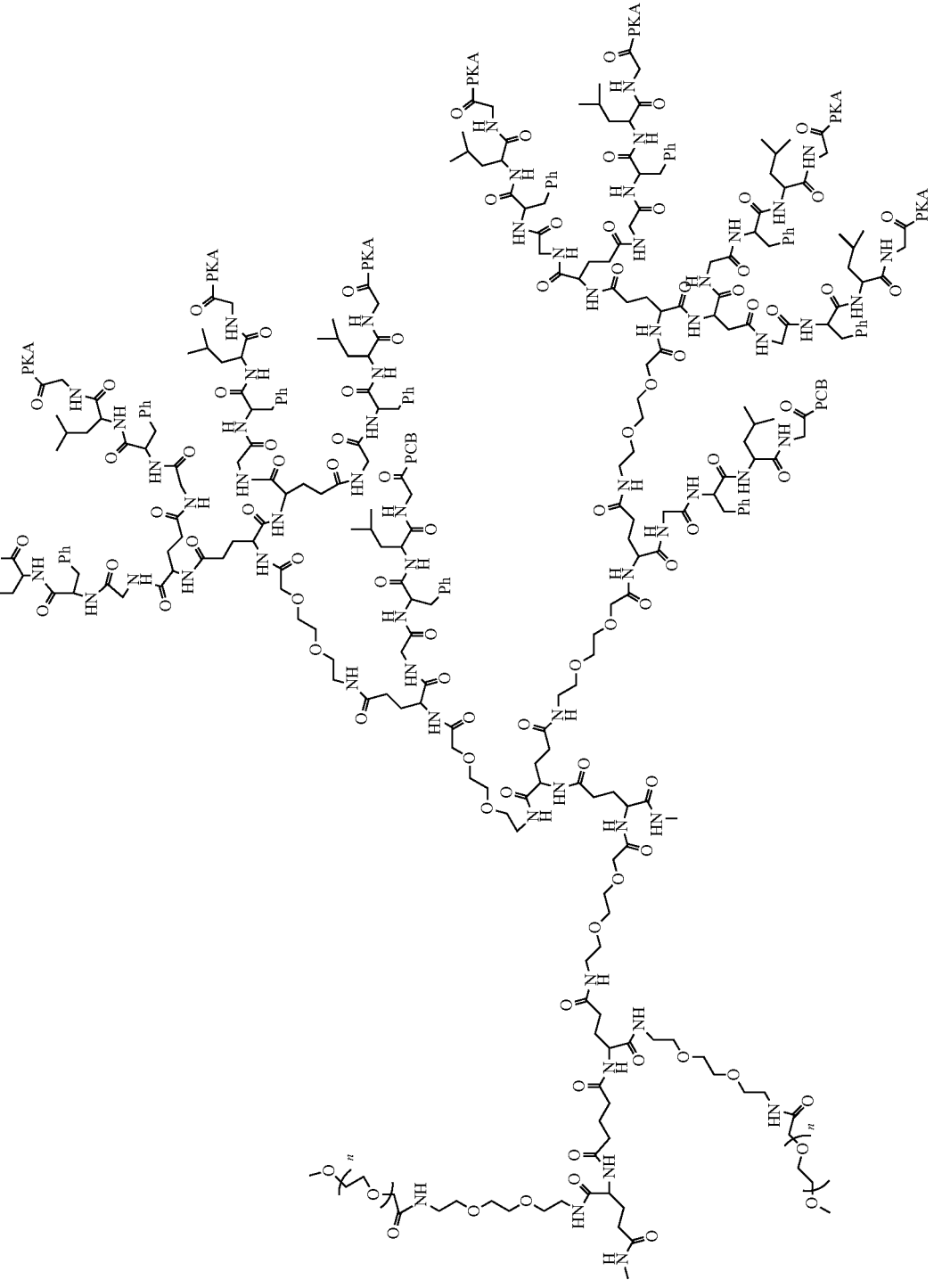

-continued
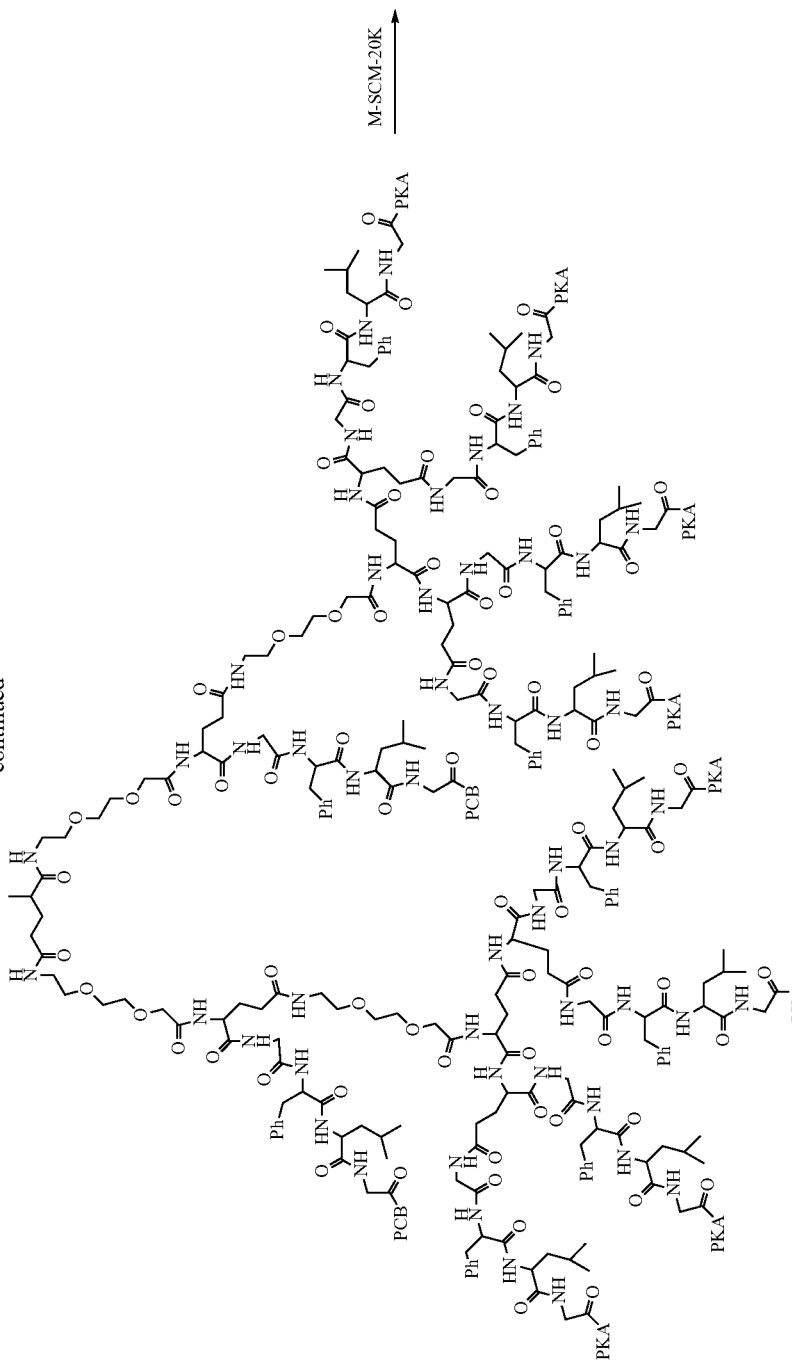
42-50

-continued
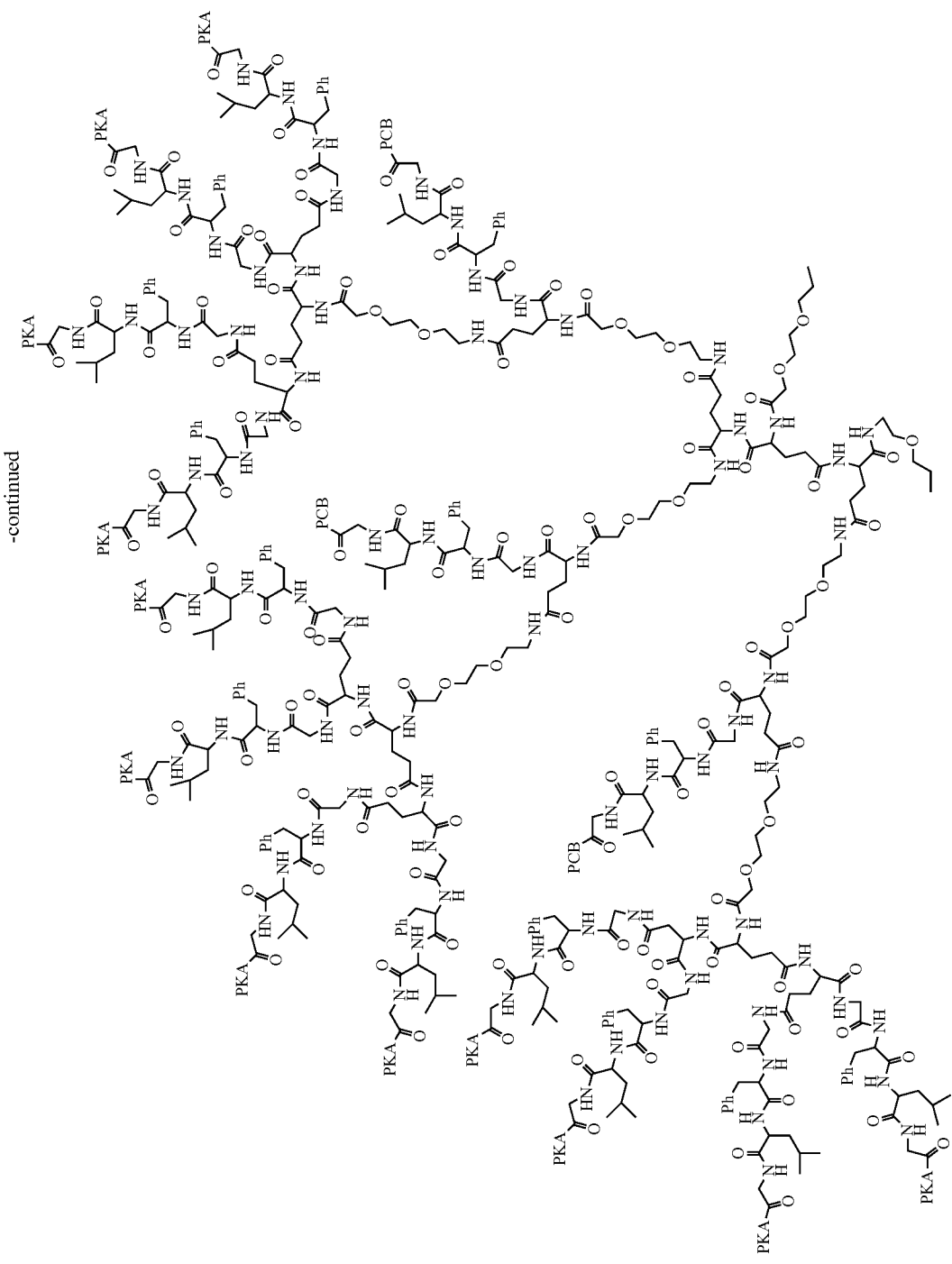

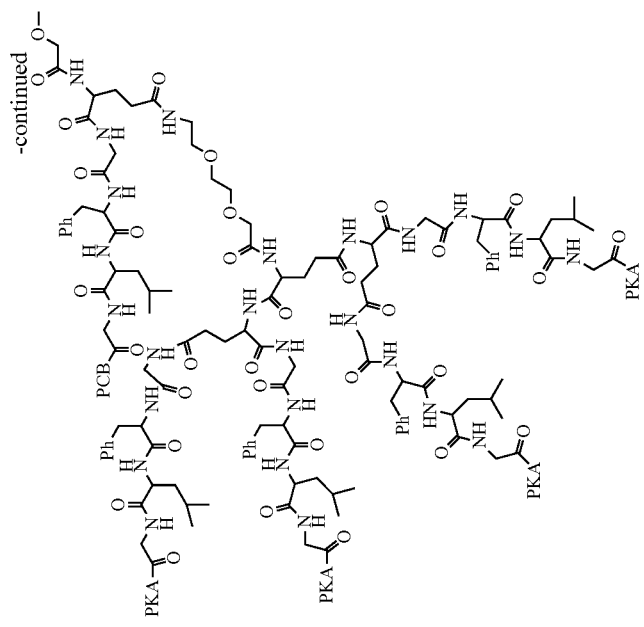

-continued
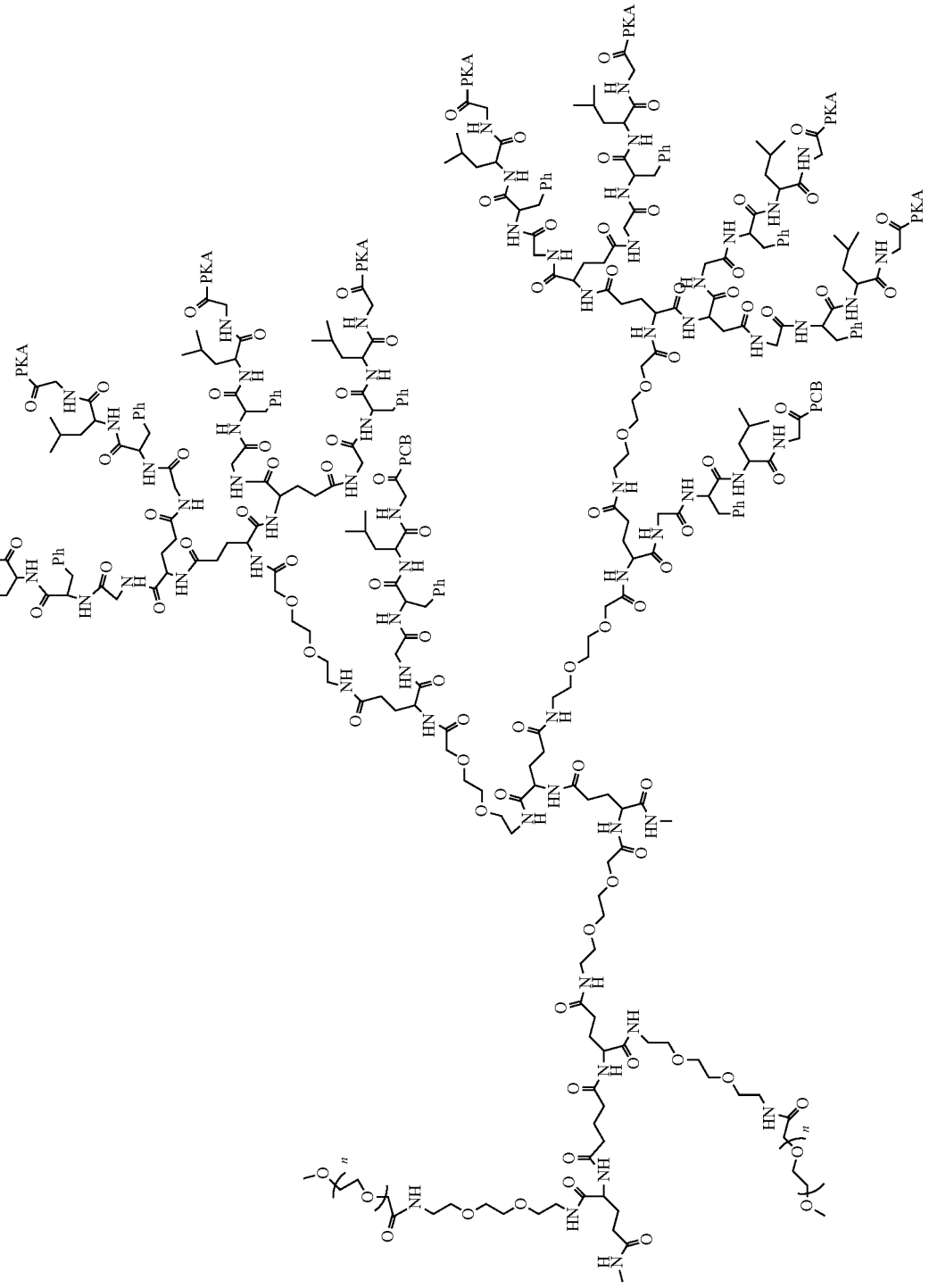

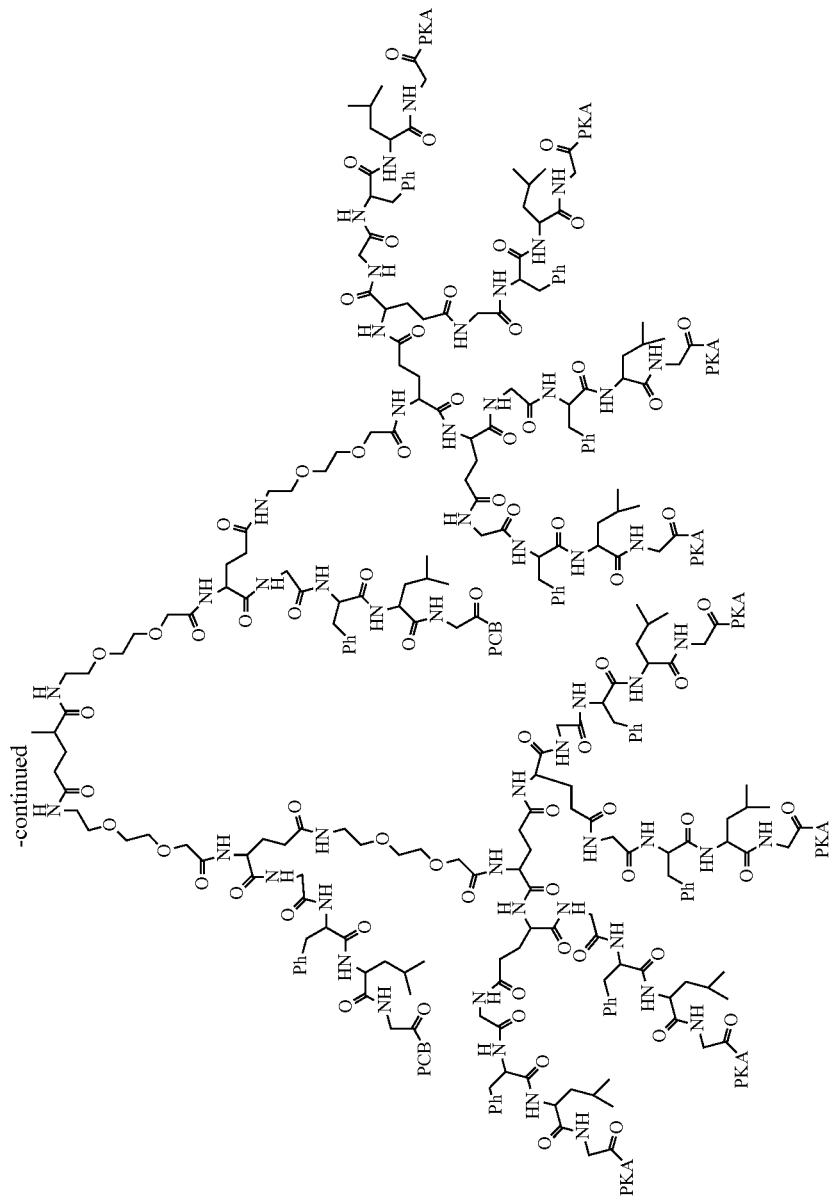
42-52

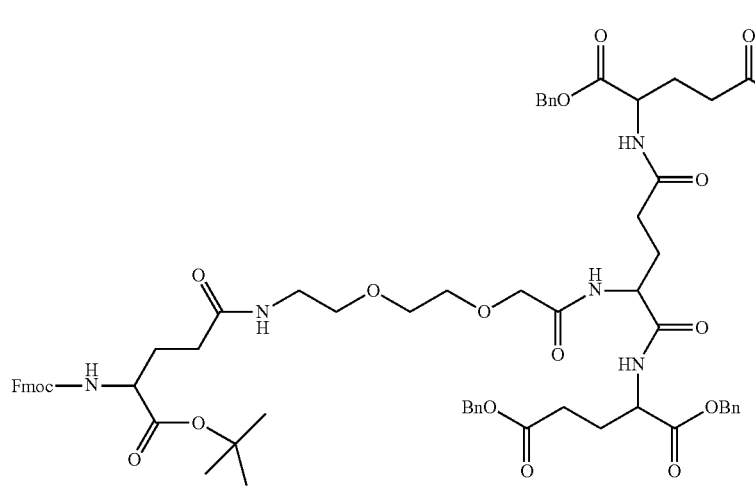

Fmoc-Glu-OtBu (purchased from Accela, 3.2226 g, 7.5741 mmol), HBTU (4.3086 g, 11.3612 mmol), HOBT (1.5351 g, 11.3612 mmol) and 44-19 (synthesized according to the method of synthesizing 22-181, 6.9 g, 7.5741 mmol) were added in a 500 mL round-bottomed flask, and dissolved with DMF (60 mL), and then the mixed solution was stirred to react at −5° C. for 30 minutes. Then DIEA (7.5 mL, 45.4460 mmol) was slowly added dropwise. At the end of the addition, the obtained solution was stirred to react at −5° C. for 2 hours. At the end of the reaction, the reaction solution was first transferred to a 2 L separatory funnel, saturated sodium chloride solution (300 mL) and ethyl acetate (200 mL) were added, the obtained solution was shaken for extraction, and the aqueous phase was separated. Then, saturated sodium chloride solution (200 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (80 mL) was added to the obtained solution, and the operations of evaporation, dry sample loading, column chromatography, and elution with an elutent (4%-12% methanol: 96%-88% dichloromethane) were carried out. The elution product was then collected, concentrated, evaporated to dryness, and dried, thus obtaining the product 42-20: 6.9 g, yield: 69.10%.

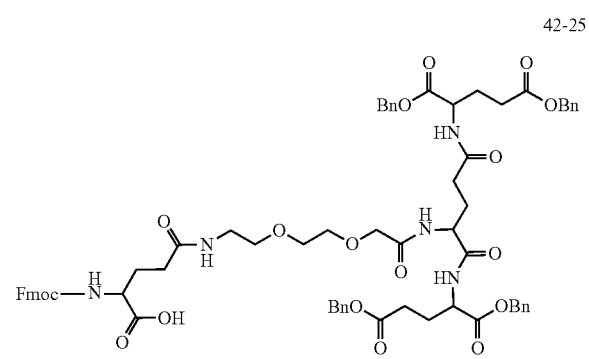

42-20 (5.0 g, 3.7923 mmol) was added in a 500 mL round-bottomed flask, and dissolved with dichloromethane (10 mL), TFA (4.2 mL, 56.8845 mmol) was added with stirring, and then the mixed solution was stirred to react at room temperature overnight. At the end of the reaction, the reaction solution was first concentrated under reduced pressure and evaporated to remove the dichloromethane, the obtained solution was then transferred to a 2 L separatory funnel, saturated sodium chloride solution (300 mL) and ethyl acetate (200 mL) were added, the obtained solution was shaken for extraction, and the aqueous phase was separated. Then, saturated sodium chloride solution (200 mL) was added to the organic phase, the obtained solution was shaken for extraction, and the aqueous phase was separated. Next, deionized water (300 mL) was added to the organic phase, the obtained solution was shaken for extraction, and the aqueous phase was separated. The organic phase was concentrated, evaporated to dryness, and dried in a vacuum oven, thus obtaining the product 42-25: 4.7872 g.

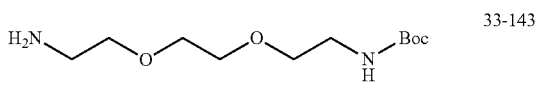 [SMILES: CC(C)(C)OC(=O)NCCOCCOCCN]

1,2-bis (2-aminoethoxy) ethane (purchased from TCl, 50 mL, 340.7327 mmol) was added in a 500 mL flask, and dissolved with dichloromethane (150 mL), triethylamine (94.8928 mL, 681.4654 mmol) was added, and then di-tert-butyl dicarbonate (purchased from Innochem, 74.3751 g, 340.7321 mmol) was slowly added dropwise with stirring at room temperature. At the end of the addition, the obtained solution was stirred to react at room temperature overnight. At the end of the reaction, silica gel powder was added, and the obtained mixture was then evaporated to dryness to obtain a powdery solid. The operations of dry sample loading, column chromatography and elution with a dichloromethane mixed solution containing 1% ammonia water and 2%-3% methanol were carried out. The elution product was then collected, concentrated, and dried, thus obtaining the product 33-143, yield 10%.

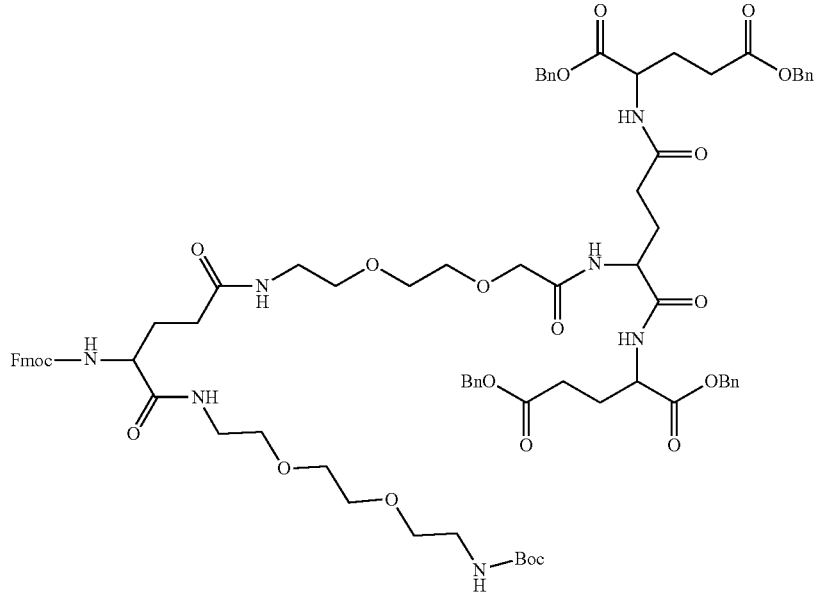

42-27

42-25 (4.7872 g, 3.7923 mmol), HBTU (2.1573 g, 5.6885 mmol), HOBT (0.7686 g, 5.6885 mmol) and 33-143 (0.9888 g, 3.9819 mmol) were added in a 500 mL round-bottomed flask, and dissolved with DMF (60 mL), and then the mixed solution was stirred to react at −5° C. for 30 minutes. Then DIEA (2.8 mL, 17.0654 mmol) was slowly added dropwise. At the end of the addition, the obtained solution continued to react at −5° C. with stirring for 2 hours. At the end of the reaction, the reaction solution was first transferred to a 2 L separatory funnel, saturated sodium chloride solution (300 mL) and ethyl acetate (200 mL) were added, the obtained solution was shaken for extraction, and the aqueous phase was separated. Then, saturated sodium chloride solution (200 mL) was added to the organic phase, the obtained solution was shaken for extraction, and the aqueous phase was separated. Finally, the organic phase was concentrated, evaporated to dryness, and dried in a vacuum oven, thus obtaining the product 42-27: 5.4 g, yield: 95.40%.

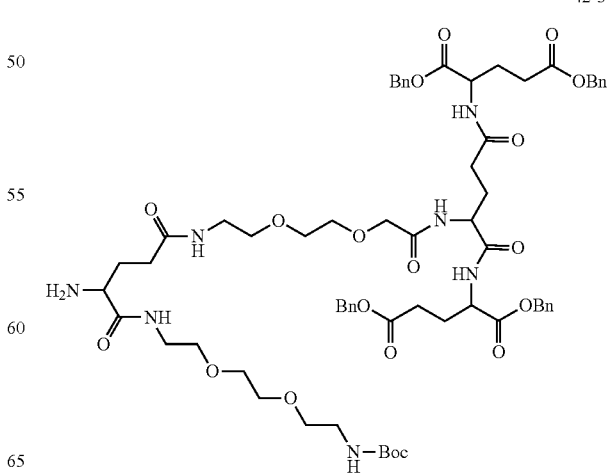

42-30

42-27 (5.4 g, 3.6177 mmol) was added in a 500 mL round-bottomed flask, and dissolved with DMF (10 mL), morpholine (4.7 mL, 54.2635 mmol) was added with stirring, and then the mixed solution was stirred to react at room temperature for 2 hours. At the end of the reaction, the reaction solution was first transferred to a 2 L separatory funnel, saturated sodium chloride solution (300 mL) and ethyl acetate (200 mL) were added, the obtained solution was shaken for extraction, and the aqueous phase was separated. Then, saturated sodium chloride solution (200 mL) was added to the organic phase, the obtained solution was shaken for extraction, and the aqueous phase was separated. Finally, the organic phase was concentrated and evaporated to dryness, the obtained solid was dissolved with a mixed solvent (50 mL) of 20% methanol/dichloromethane, silica gel powder (80 mL) was added, and the operations of evaporation, dry sample loading, column chromatography, and elution with an elutent (1% ammonia water: 1%-6% methanol: 98%-93% dichloromethane) were carried out. The elution product was then collected, concentrated, evaporated to dryness, and dried, thus obtaining the product 42-30: 3.0140 g, yield: 65.58%.

extraction, and the aqueous phase was separated. Finally, the organic phase was concentrated and evaporated to dryness, the obtained solid was dissolved with a mixed solvent (50 mL) of 20% methanol/dichloromethane, silica gel powder (50 mL) was added to the obtained solution, and the operations of evaporation, dry sample loading, column chromatography, and elution with an elutent (1% ammonia water: 2%-5% methanol: 97%-94% dichloromethane) were carried out. The elution product was then collected, concentrated, evaporated to dryness, and dried, thus obtaining the product 42-34: 2.8437 g, yield: 100%.

$^1$H-NMR (400 MHz, DMSO-d$_6$) δ8.60-8.22 (m, 5H), 8.19-7.63 (m, 11H), 7.55-7.11 (m, 40H), 5.10-5.07 (m, 16H), 3.56-3.47 (m, 20H), 3.19-3.17 (m, 8H), 3.09-3.01 (m, 4H), 2.99-2.65 (m, 16H), 2.43-2.42 (m, 8H), 2.17-2.09 (m, 32H), 1.36-1.34 (m, 18H).

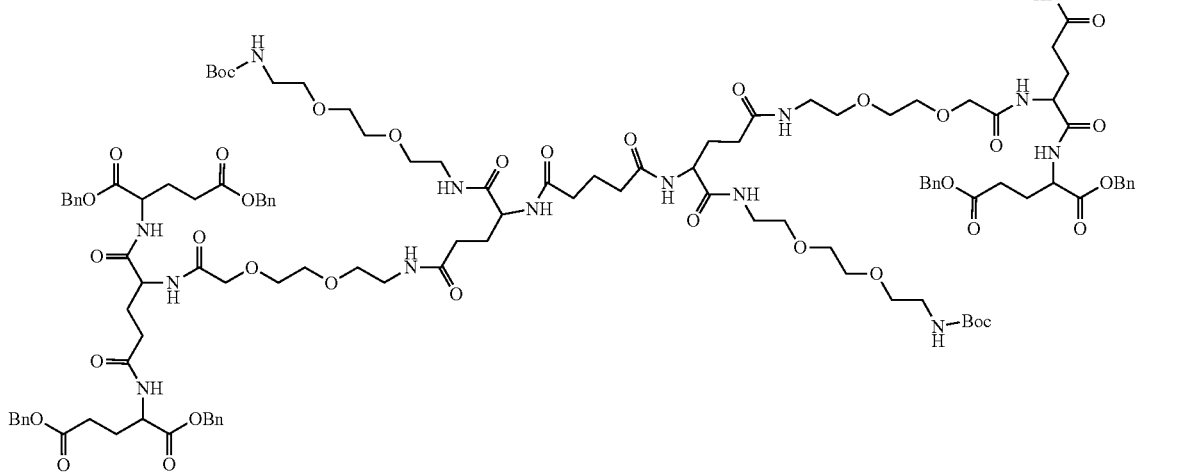

42-34

42-30 (3.0140 g, 2.3724 mmol), HBTU (1.2269 g, 3.2352 mmol), HOBT (0.4371 g, 3.2352 mmol) and glutaric acid (0.1425 g, 1.0784 mmol) were added in a 500 mL round-bottomed flask, and dissolved with DMF (50 mL), and then the mixed solution was stirred to react at −5° C. for 30 minutes. Then DIEA (1.6 mL, 9.7056 mmol) was slowly added dropwise. At the end of the addition, the obtained solution continued to react at −5° C. with stirring for 2 hours, and was then moved to room temperature and stirred to react overnight. At the end of the reaction, the reaction solution was first transferred to a 2 L separatory funnel, saturated sodium bicarbonate solution (300 mL) and ethyl acetate (200 mL) were added, the obtained solution was shaken for extraction, and the aqueous phase was separated. Then, saturated sodium chloride solution (200 mL) was added to the organic phase, the obtained solution was shaken for

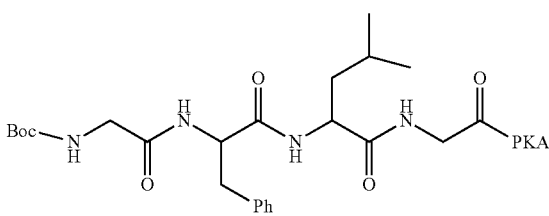

42-15

The solution of 42-14 (synthesized according to the method of synthesizing 25-102, 5.5320 g, 11.2308 mmol), HBTU (5.8080 g, 15.3147 mmol), HOBT (2.0693 g, 15.3147 mmol) and PKA (PKA is a de-terminated dimethyl derivative of clinical novel drug PKI-587, 6.0 g, 10.2098 mmol) were added in a 500 mL round-bottomed flask, and dissolved with DMF (80 mL), and then the mixed solution was stirred to react at −5° C. for 30 minutes. Then DIEA (7.6 mL, 45.9441 mmol) was slowly added dropwise. At the end of the addition, the obtained solution continued to react with stirring at −5° C. for 1 hour, and then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added to the obtained solution for precipitation, to obtain a powdery solid, and filtering was carried out. The filter cake was washed with methyl tert-butyl ether (60 mL), and dried in a vacuum oven, thus obtaining the product 42-15: 10.8450 g.

42-18

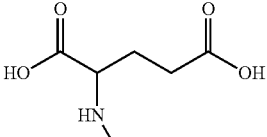

42-15 (10.8450 g, 10.2098 mmol) was added in a 500 mL round-bottomed flask, and dissolved with dichloromethane (5 mL), TFA (11.4 mL, 153.1470 mmol) was added with stirring, and then the mixed solution was stirred to react at room temperature overnight. At the end of the reaction, the reaction solution was first concentrated under reduced pressure and evaporated to remove the dichloromethane, methyl tert-butyl ether (150 mL) was then added to the obtained solution for precipitation, to obtain a powdery solid, and filtering was carried out. The filter cake was washed with methyl tert-butyl ether (60 mL), and dried in an oven, thus obtaining the product 42-18: 9.8230 g, yield: 100%.

42-24

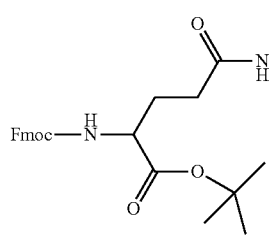 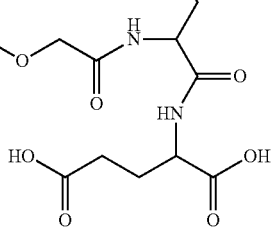

42-20 (1.8683 g, 1.4170 mmol) and 10% Pd/C (50 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF (60 mL) until it did not contain any product, thus obtaining a reaction product solution.

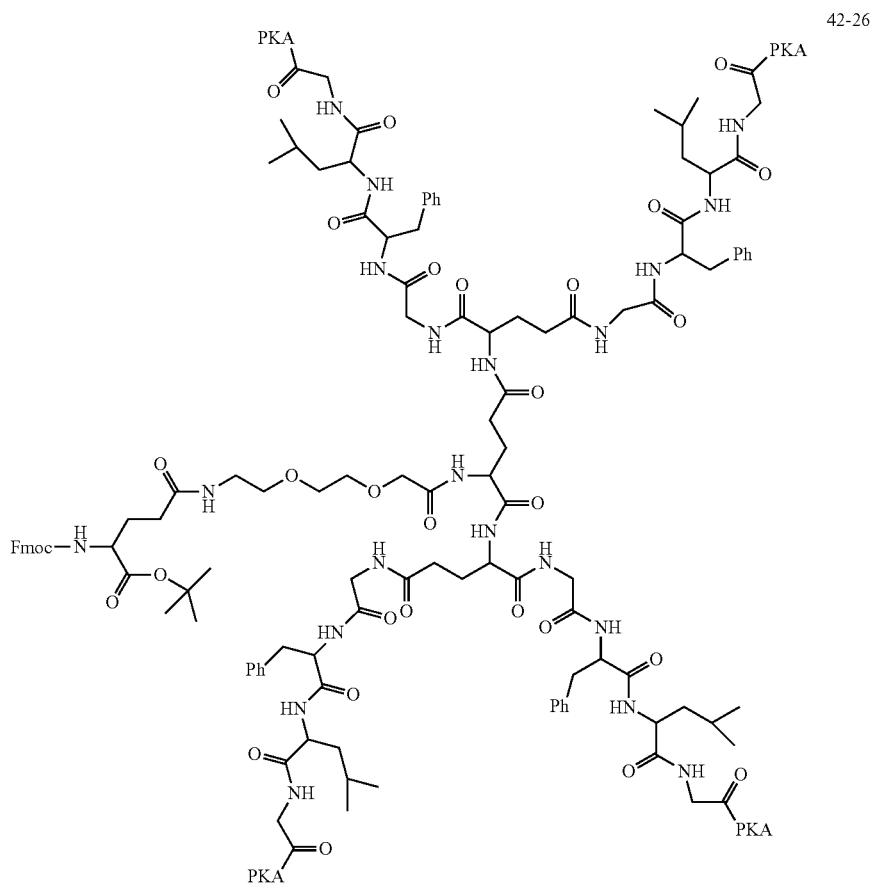

42-26

The solution of 42-24 (1.3574 g, 1.4170 mmol), HBTU (3.2243 g, 8.5020 mmol), HOBT (1.1488 g, 8.5020 mmol) and 42-18 (8.0 g, 6.2350 mmol) were added in a 500 mL round-bottomed flask, and dissolved with DMF (80 mL), and then the mixed solution was stirred to react at −5° C. for 30 minutes. Then DIEA (4.2 mL, 25.5060 mmol) was slowly added dropwise. At the end of the addition, the obtained solution continued to react with stirring at −5° C. for 3 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dried in a vacuum oven, thus obtaining the product 42-26: 6.7086 g.

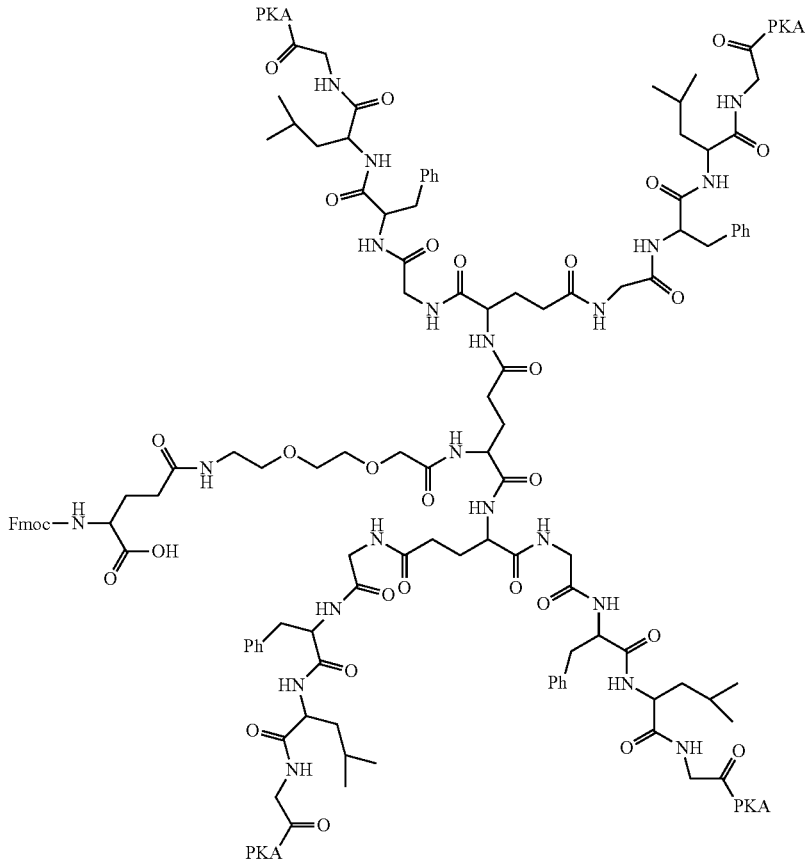

42-26 (6.7086 g, 1.4170 mmol) was added in a 100 mL round-bottomed flask, and dissolved with dichloromethane (10 mL), TFA (1.6 mL, 21.2550 mmol) was added with stirring, and then the mixed solution was stirred to react at room temperature overnight. At the end of the reaction, the reaction solution was first concentrated under reduced pressure and evaporated to remove the dichloromethane, methyl tert-butyl ether (150 mL) was added to the obtained solution for precipitation, to obtain a powdery solid, and filtering was carried out. The filter cake was washed with methyl tert-butyl ether (60 mL), and dissolved with 20% methanol/dichloromethane solution (60 mL), silica gel powder (70 ml) was added to the obtained solution, and the operations of evaporation, dry sample loading, column chromatography, and elution with an elutent (2%-11% methanol: 98%-89% dichloromethane) were carried out. The elution product was then collected, concentrated, evaporated to dryness, and dried, thus obtaining the product 42-28: 5.4 g, yield: 81.46%.

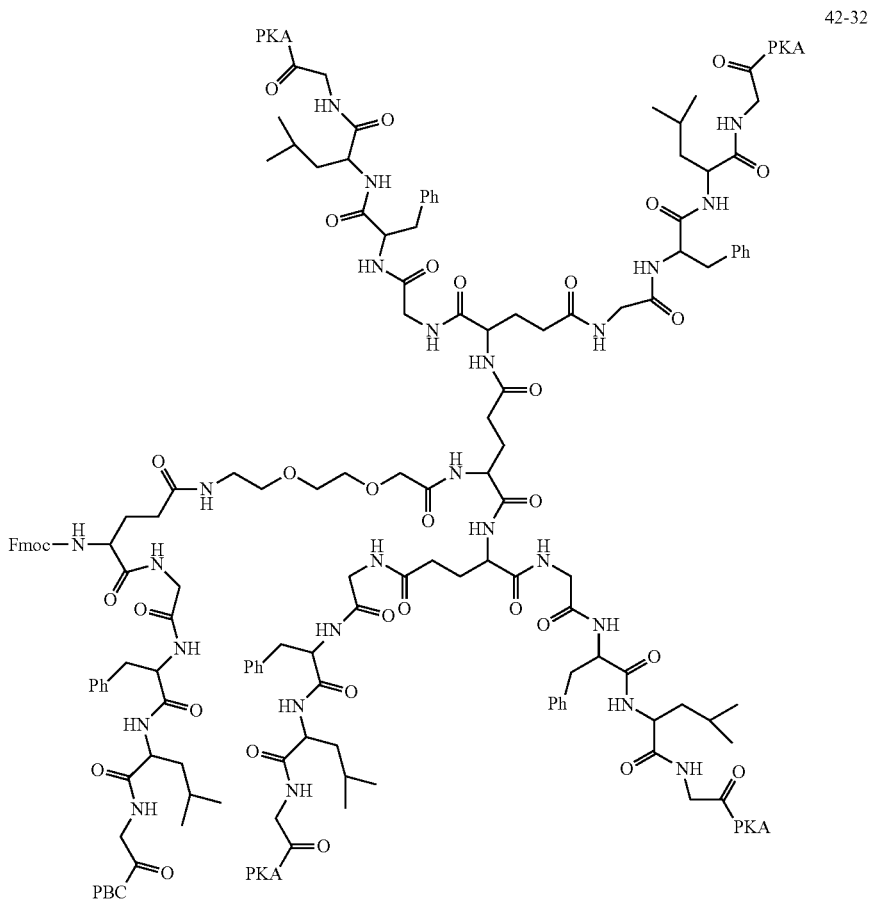

42-28 (4.4 g, 0.9405 mmol), HBTU (0.5350 g, 1.4108 mmol), HOBT (0.1906 g, 1.4108 mmol) and 25-254 (synthesized according to the method of synthesizing 30-33) (0.8504 g, 1.0346 mmol) were added in a 500 mL round-bottomed flask, and dissolved with DMF (60 mL), and the mixed solution was stirred to react at −5° C. for 30 minutes. Then DIEA (0.7 mL, 4.2324 mmol) was slowly added dropwise. At the end of the addition, the obtained solution continued to react with stirring at −5° C. for 3 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dissolved with 20% methanol/dichloromethane solution (60 mL), silica gel powder (50 mL) was added to the obtained solution, and the operations of evaporation, dry sample loading, column chromatography, and elution with an elutent (3%-15% methanol: 97%-85% dichloromethane) were carried out. The elution product was then collected, concentrated, evaporated to dryness, and dried, thus obtaining the product 42-32: 3.6 g, yield: 69.82%.

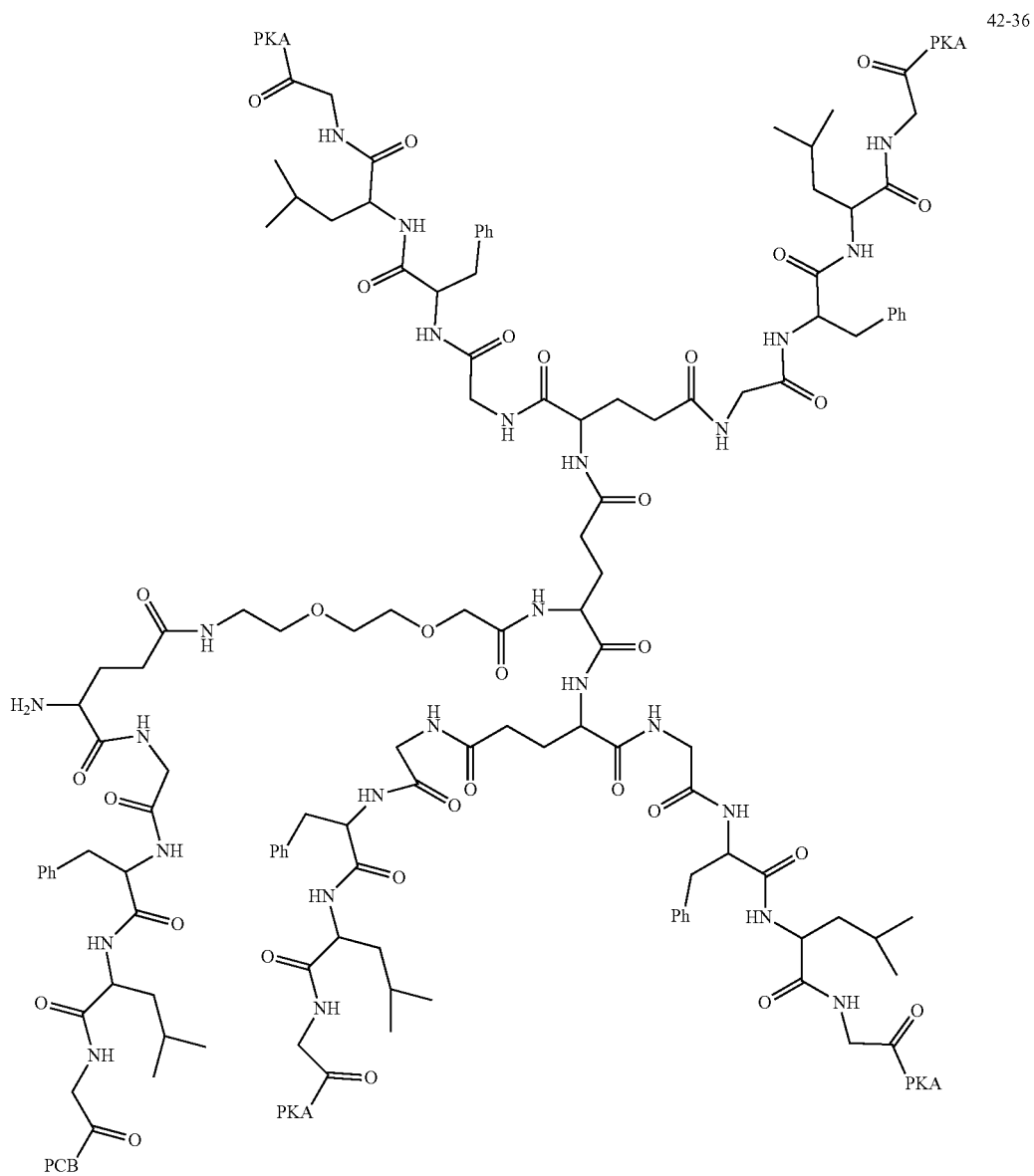

42-32 (3.6 g, 0.6567 mmol) was added in a 500 mL round-bottomed flask, and dissolved with DMF (30 mL) morpholine (0.9 mL, 9.8505 mmol) was added with stirring, and then the mixed solution was stirred to react at room temperature for 2 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dissolved with 20% methanol/dichloromethane solution (60 mL), silica gel powder (30 ml) was added to the obtained solution, and the operations of evaporation, dry sample loading, column chromatography, and elution with an elutent (1% ammonia water: 2%-7% methanol: 97%-92% dichloromethane) were carried out. The elution product was then collected, concentrated, evaporated to dryness, and dried, thus obtaining the product 42-36: 3.2 g, yield: 92.64%.

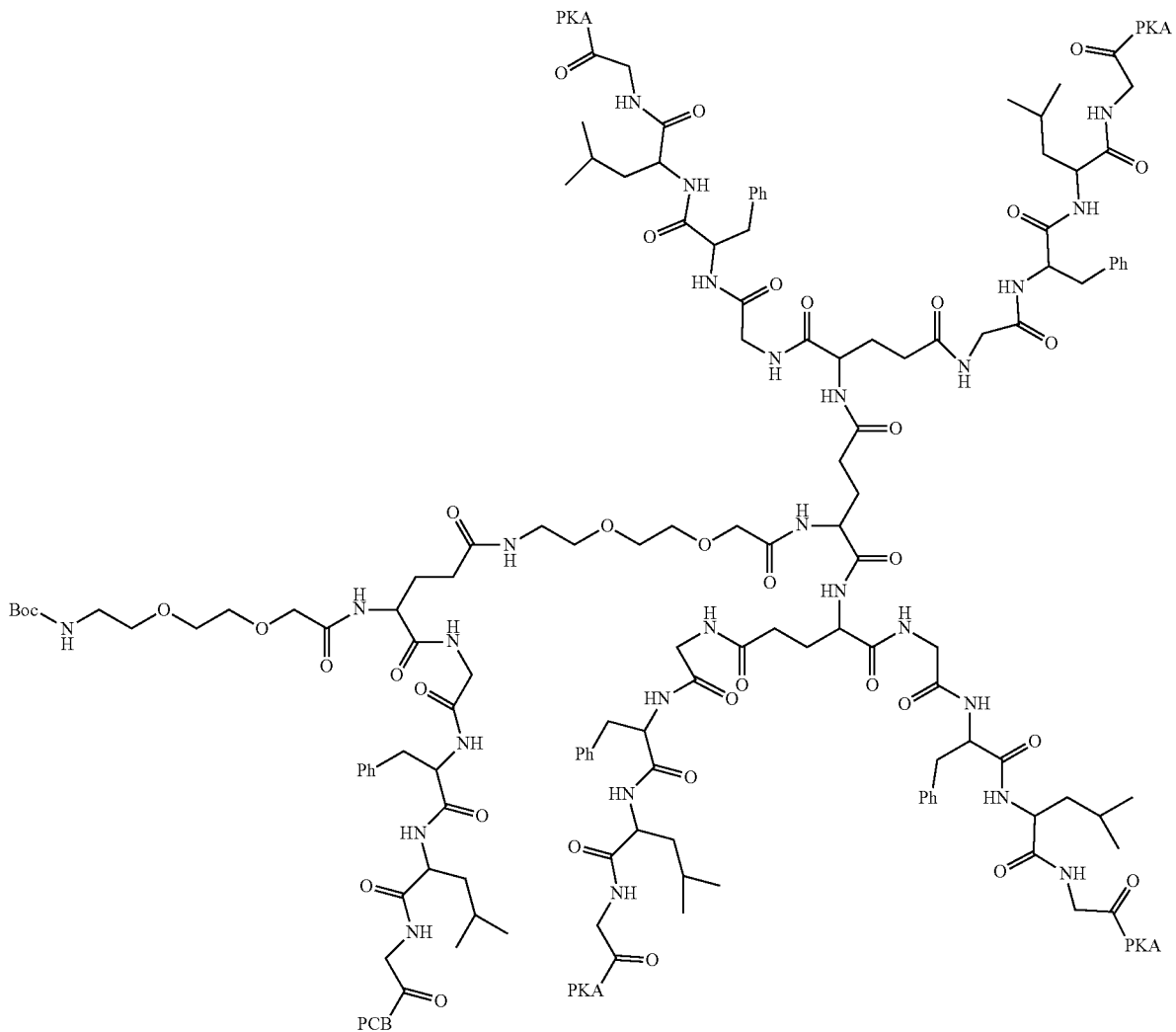

42-36 (3.2 g, 0.6084 mmol), HBTU (0.3461 g, 0.9126 mmol), HOBT (0.1233 g, 0.9126 mmol) and Boc-LC-OH (synthesized according to the method of synthesizing 24-36, 0.1762 g, 0.6692 mmol) were added in a 500 mL round-bottomed flask, and dissolved with DMF (60 mL), and then the mixed solution was stirred to react at −5° C. for 30 minutes. Then DIEA (0.5 mL, 2.7378 mmol) was slowly added dropwise. At the end of the addition, the obtained solution continued to react with stirring at −5° C. for 1 hour, and was then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dried in a vacuum oven, thus obtaining the product 42-40: 3.3473 g.

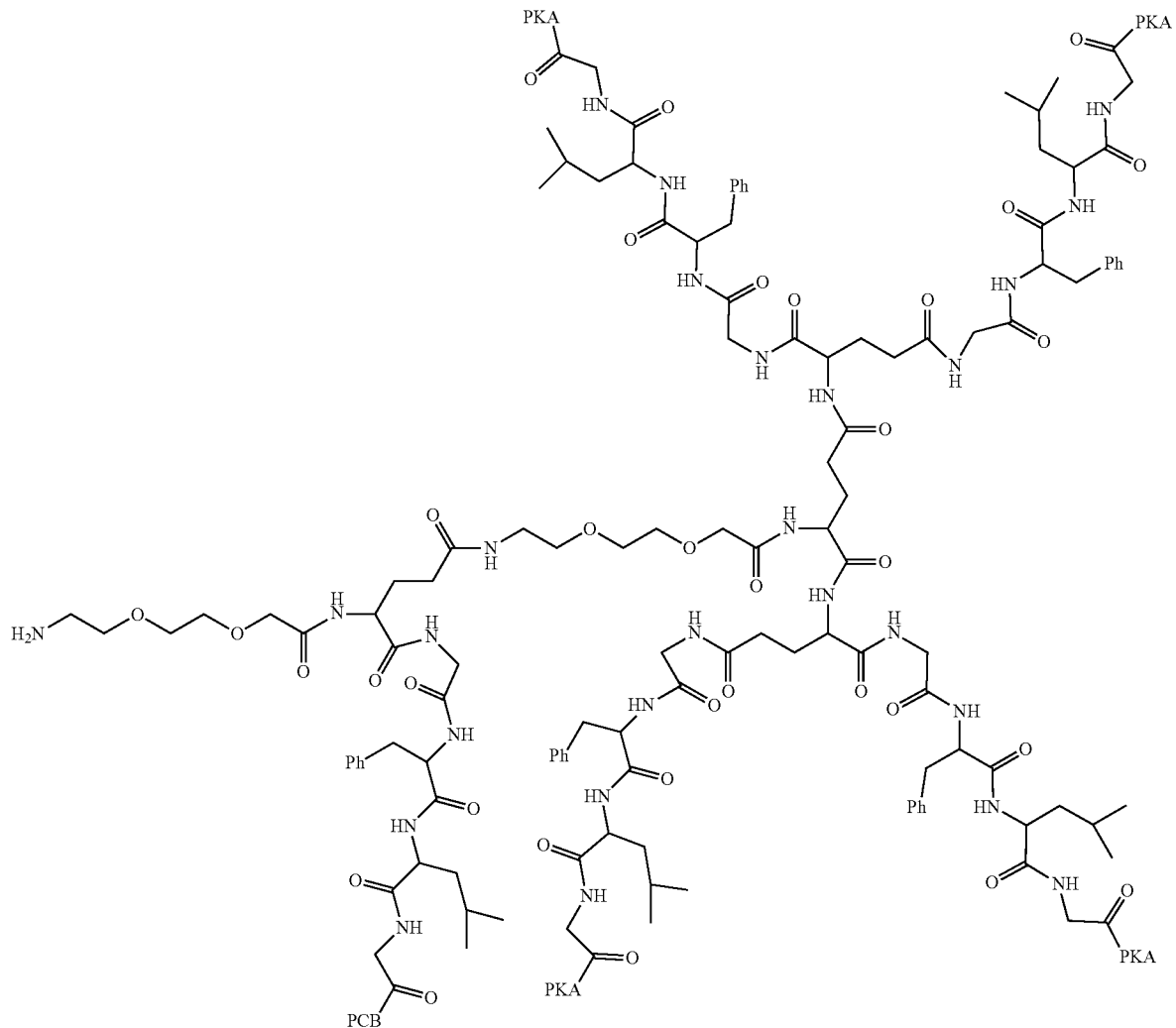

42-40 (3.3473 g, 0.6084 mmol) was added in a 100 mL round-bottomed flask, and dissolved with dichloromethane (10 mL), TFA (0.7 mL, 9.1260 mmol) was added with stirring, and then the mixed solution was stirred to react at room temperature overnight. At the end of the reaction, the reaction solution was first concentrated under reduced pressure and evaporated to remove the dichloromethane, methyl tert-butyl ether (100 mL) was added to the obtained solution for precipitation, to obtain a powdery solid, and filtering was carried out. The filter cake was washed with methyl tert-butyl ether (60 mL), and dissolved with 20% methanol/dichloromethane solution (60 mL), silica gel powder (40 ml) was added to the obtained solution, and the operations of evaporation, dry sample loading, column chromatography, and elution with an elutent (1% ammonia water: 3%-10% methanol: 96%-89% dichloromethane) were carried out. The elution product was then collected, concentrated, evaporated to dryness, and dried, thus obtaining the product 42-41: 2.1 g, yield: 63.86%.

42-37

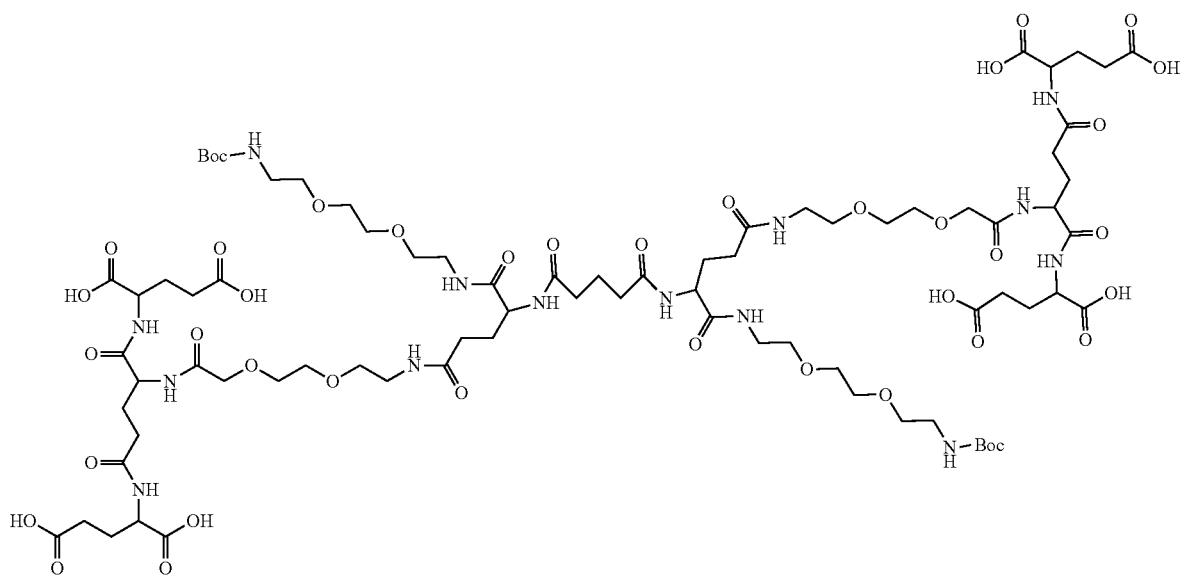

42-34 (1.0 g, 0.3792 mmol) and 10% Pd/C (40 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF (60 mL) until it did not contain any product, thus obtaining a reaction product solution.

42-43
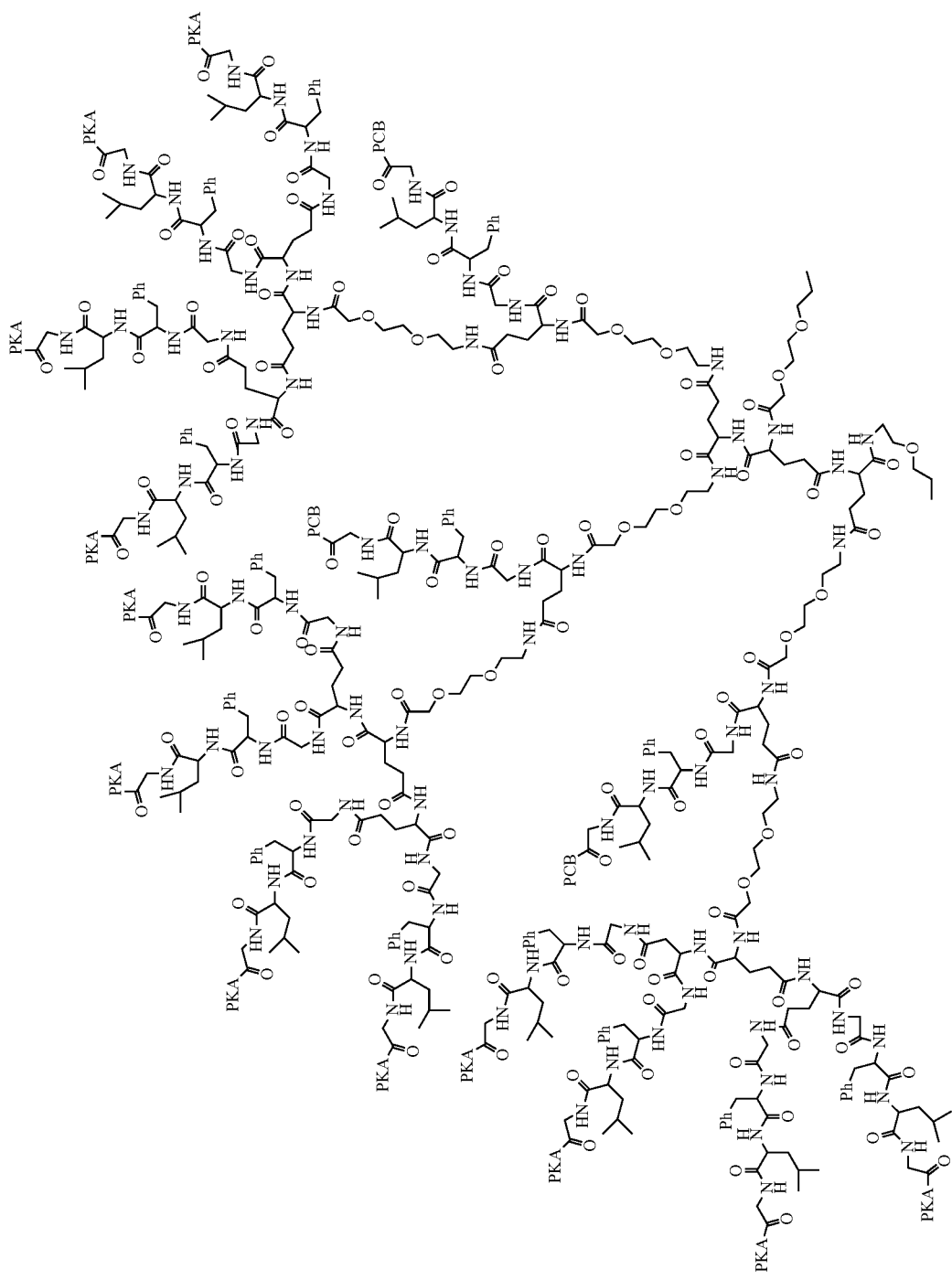

-continued
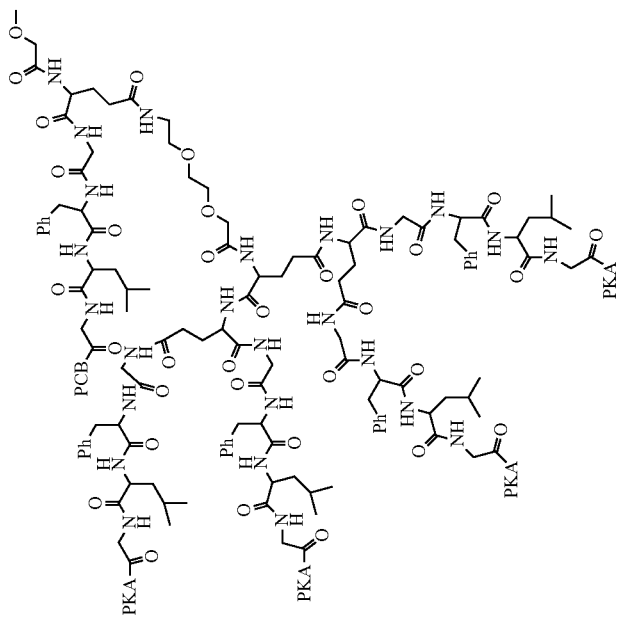

-continued
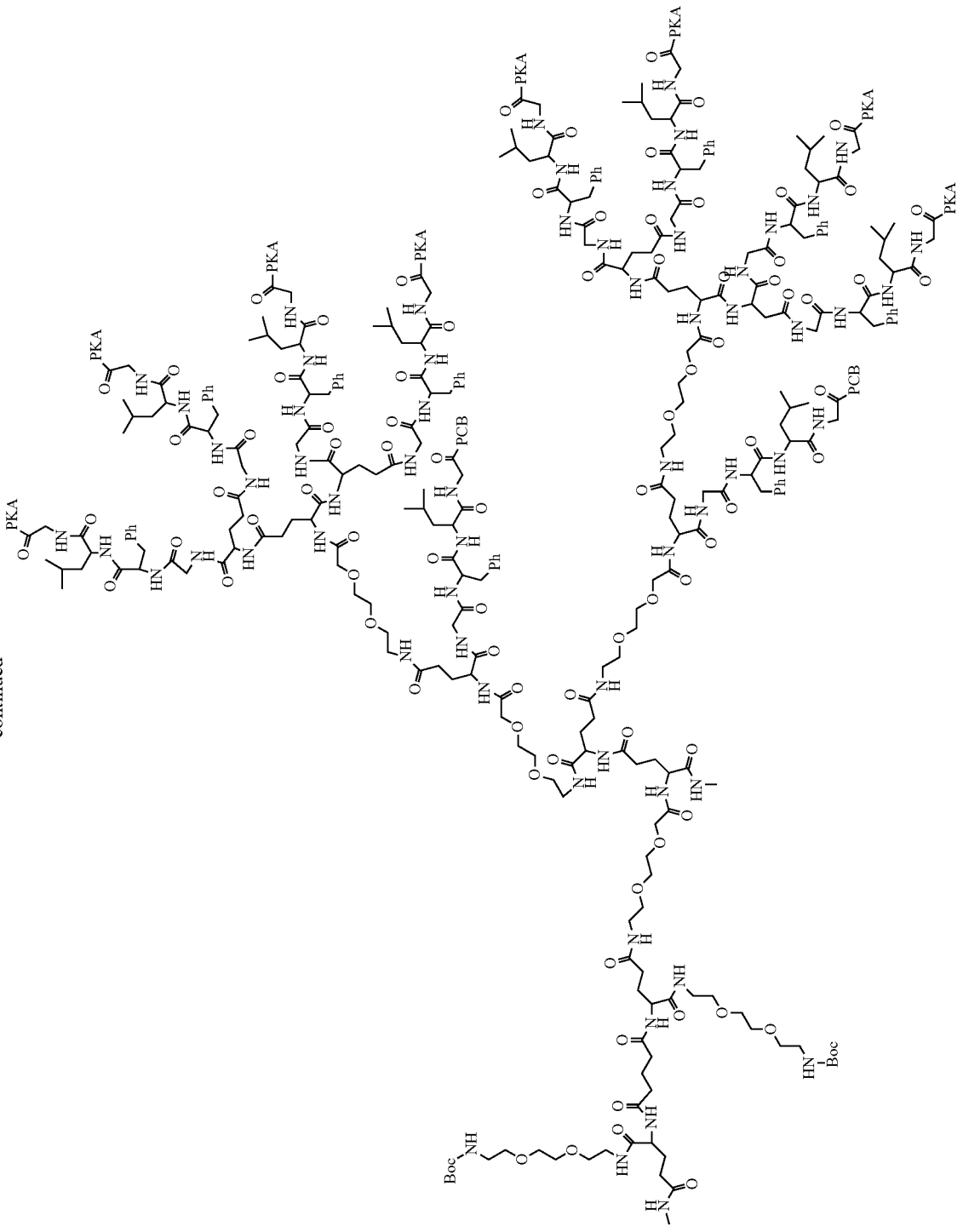

-continued
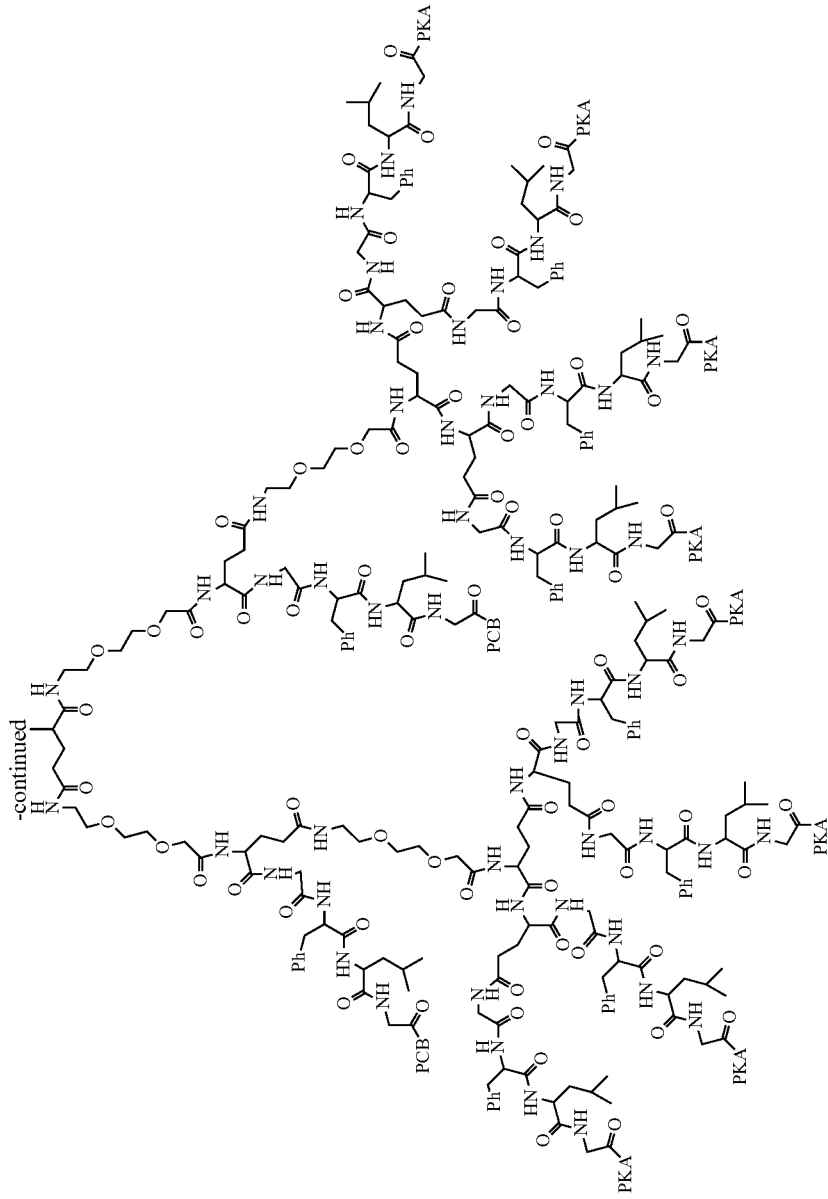

42-41 (2.1 g, 0.3885 mmol), HBTU (0.2007 g, 0.5292 mmol), HOBT (0.0715 g, 0.5292 mmol) and 42-37 solution (0.0845 g, 0.0441 mmol) were added in a 500 mL round-bottomed flask, and dissolved with DMF (50 mL), and then the mixed solution was stirred to react at −5° C. for 30 minutes. Then DIEA (0.3 mL, 1.5876 mmol) was slowly added dropwise. At the end of the addition, the obtained solution continued to react with stirring at −5° C. for 1 hour, and was then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded, and such operations were repeated five times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dissolved with a mixed solvent (80 mL) of 20% methanol/dichloromethane, silica gel powder (30 ml) was added to the obtained solution, and the operations of evaporation, dry sample loading, column chromatography, and elution with an elutent (1% ammonia water: 4%-8% methanol: 95%-91% dichloromethane) were carried out. The elution product was then collected, concentrated, evaporated to dryness, and dried, thus obtaining the product 42-43: 1.0 g, yield: 50.38%.

$^1$H-NMR (600 MHz, DMSO-d$_6$) δ 10.31-10.27 (m, 52H), 8.53-7.91 (m, 88H), 7.80-7.71 (m, 28H), 7.62-7.26 (m, 55H), 7.04-6.98 (m, 32H), 5.76 (s, 48H), 5.44-5.22 (m, 80H), 4.78-4.27 (m, 76H), 4.07-4.02 (m, 61H), 3.92-3.20 (m, 2292H), 3.17-3.03 (m, 53H), 2.67-2.59 (m, 118H), 2.33-2.09 (m, 98H), 1.78-1.61 (m, 54H), 1.41-0.70 (m, 127H).

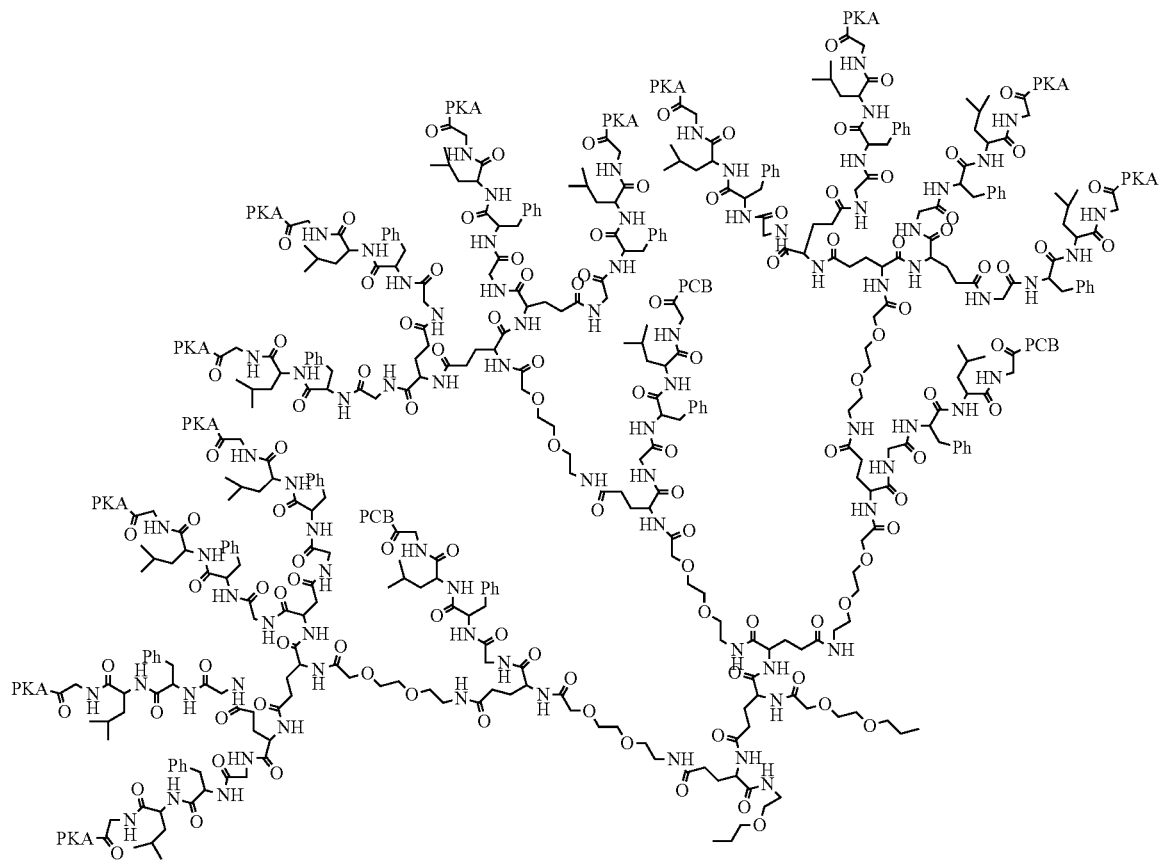

42-50

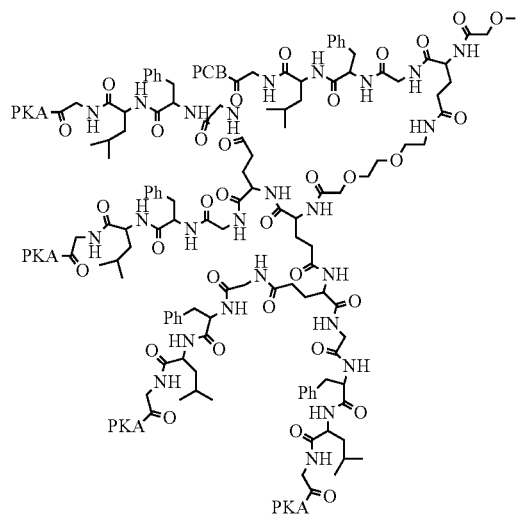
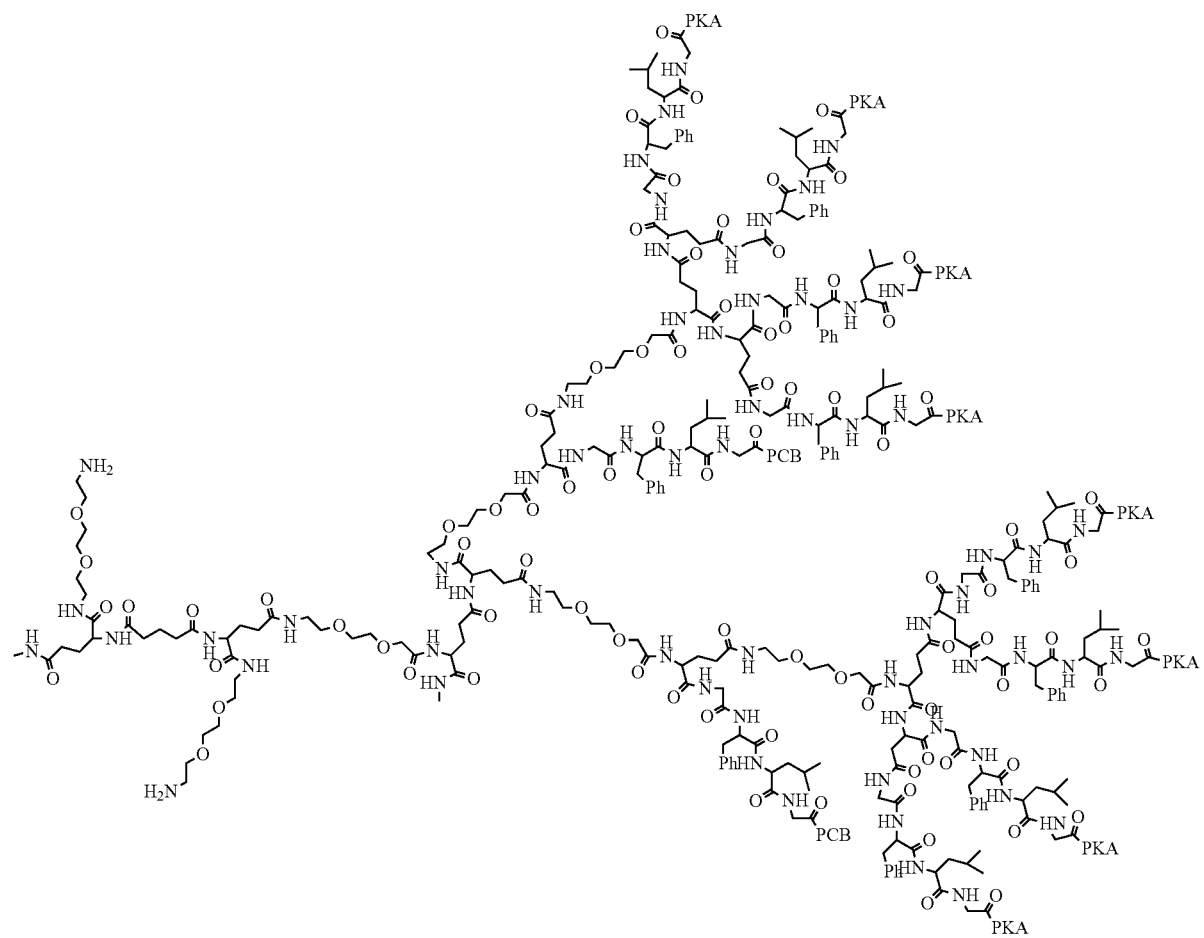

-continued

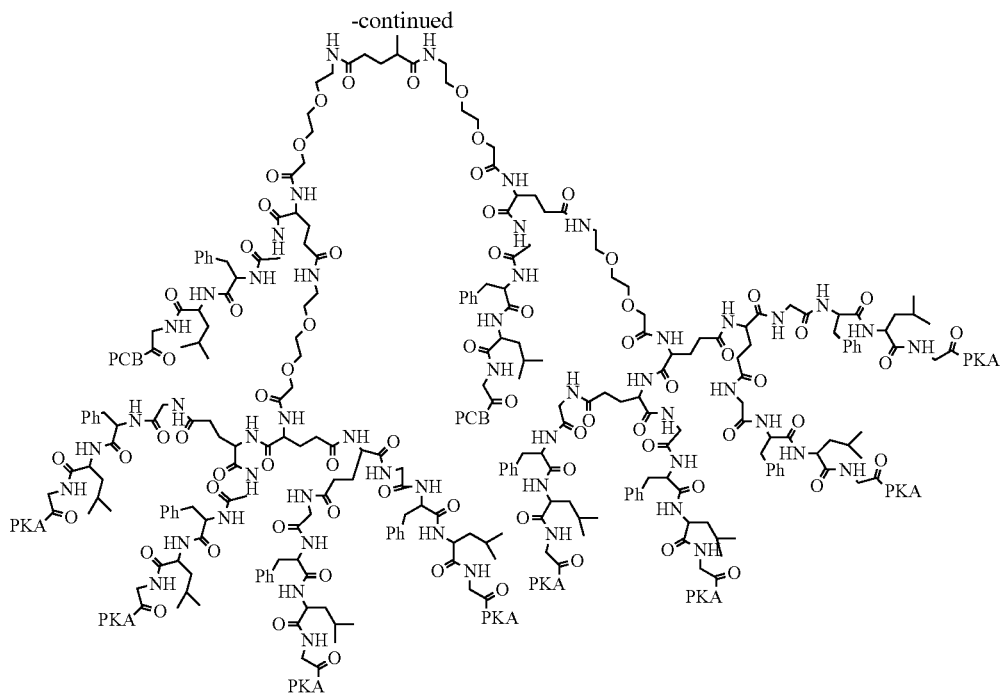

42-43 (1.0 g, 0.0222 mmol) was added in a 250 mL round-bottomed flask, and dissolved with dichloromethane (5 mL), TFA (0.1 mL, 0.6615 mmol) was added with stirring, and then the mixed solution was stirred to react at room temperature overnight. At the end of the reaction, the reaction solution was evaporated to remove the dichloromethane, methyl tert-butyl ether (150 mL) was added to the obtained solution for precipitation, to obtain a powdery solid, and filtering was carried out. The filter cake was washed with methyl tert-butyl ether (60 mL), and dissolved with 20% methanol/dichloromethane solution (50 mL), silica gel powder (30 ml) was added to the obtained solution, and the operations of evaporation, dry sample loading, column chromatography, and elution with an elutent (1% ammonia water: 4%-10% methanol: 95%-89% dichloromethane) were carried out. The elution product was then collected, concentrated and evaporated to dryness, thus obtaining the product 42-50: 0.4772 g, yield: 47.97%.

42-52
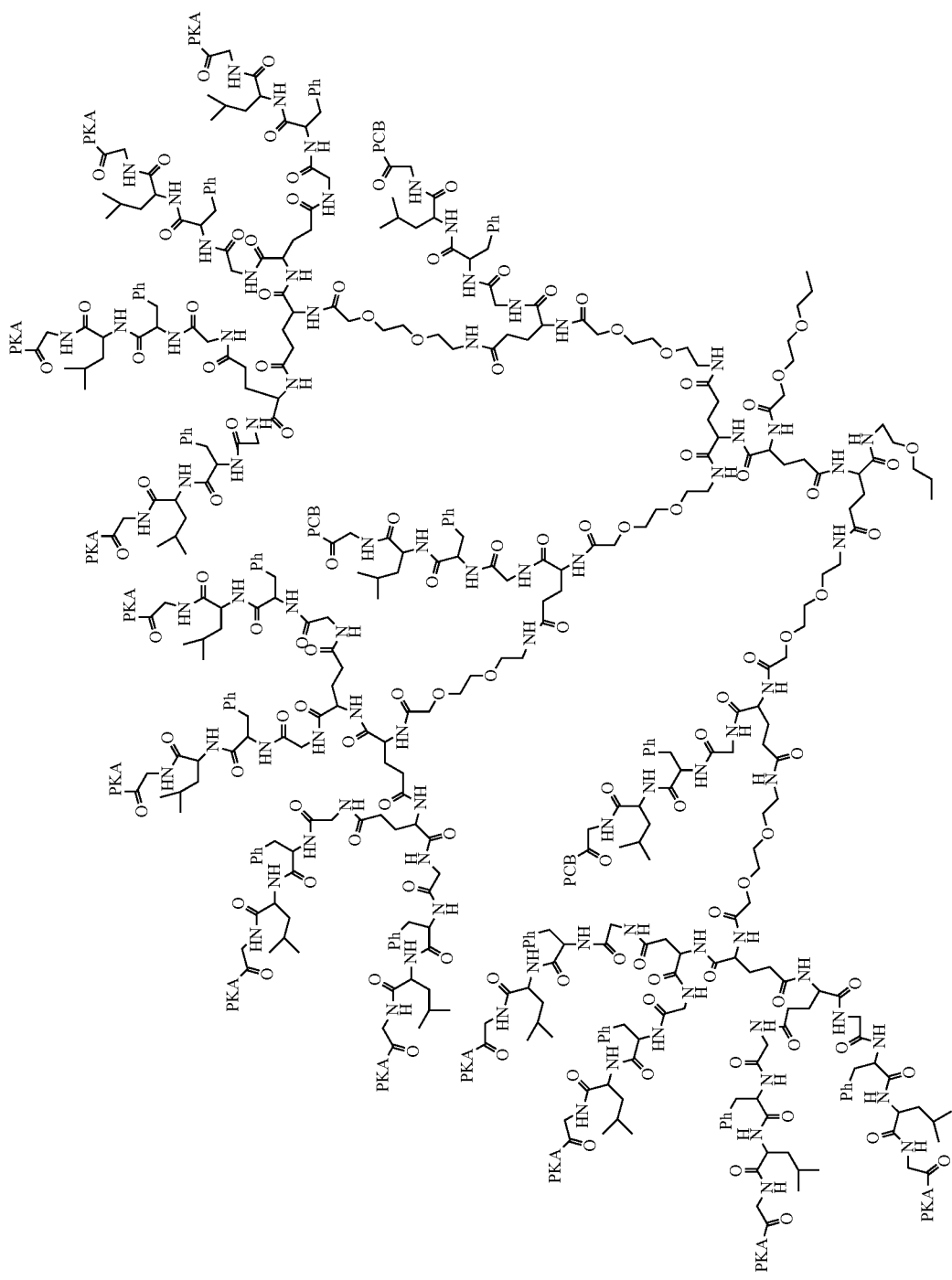

-continued
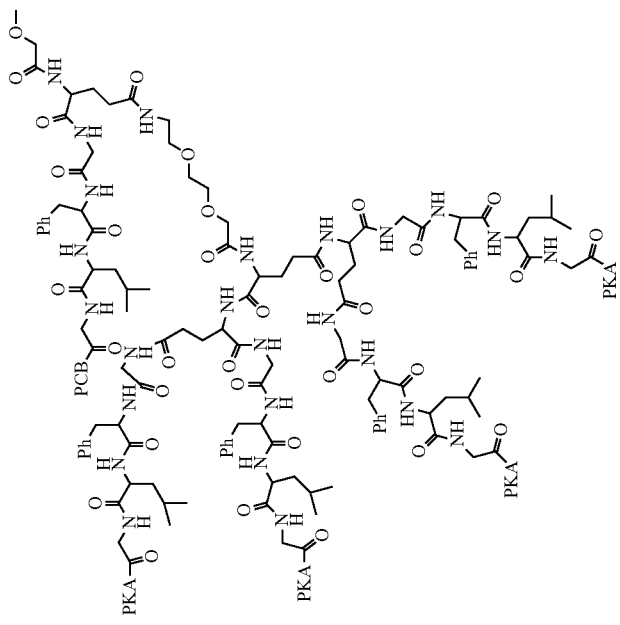

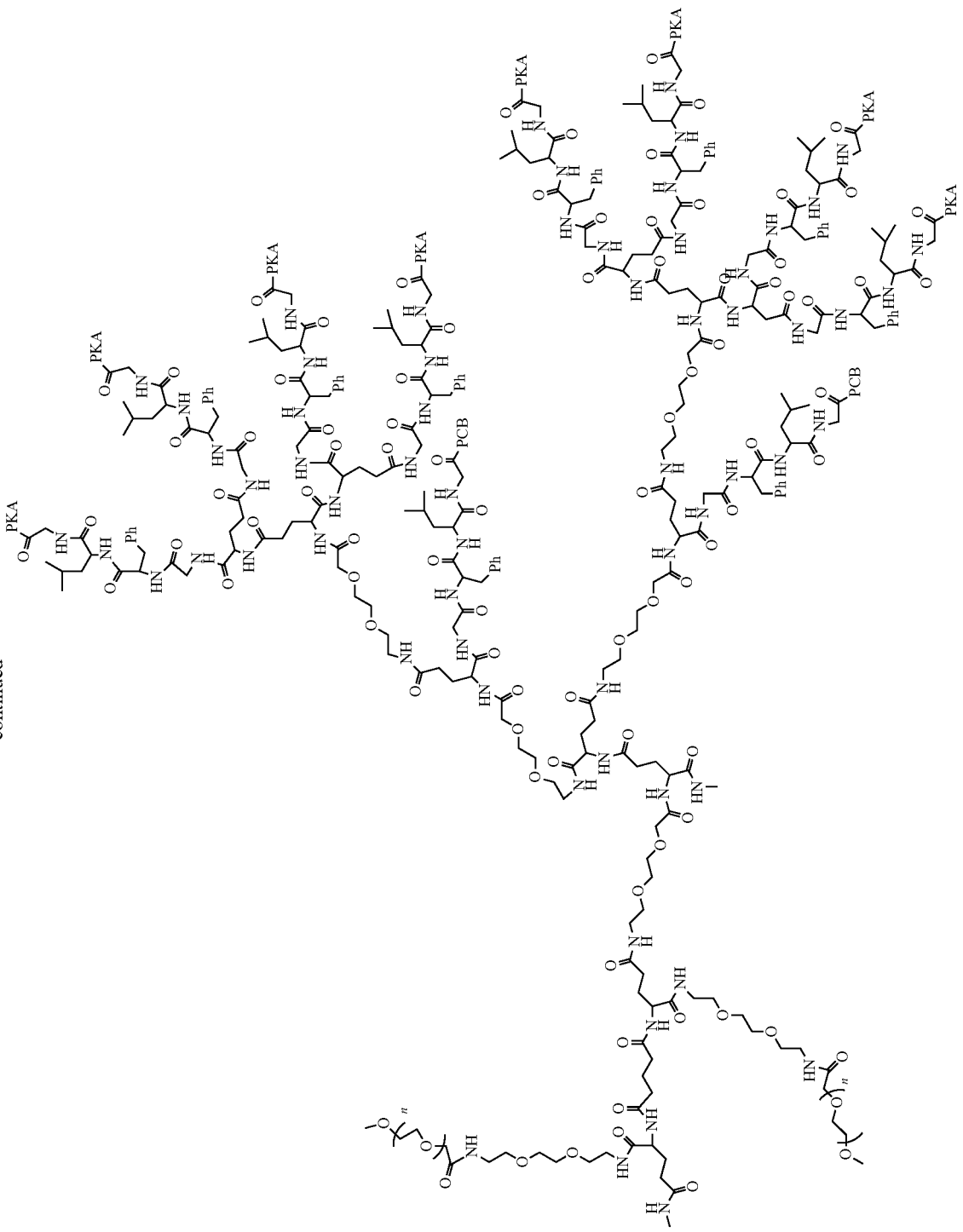

-continued
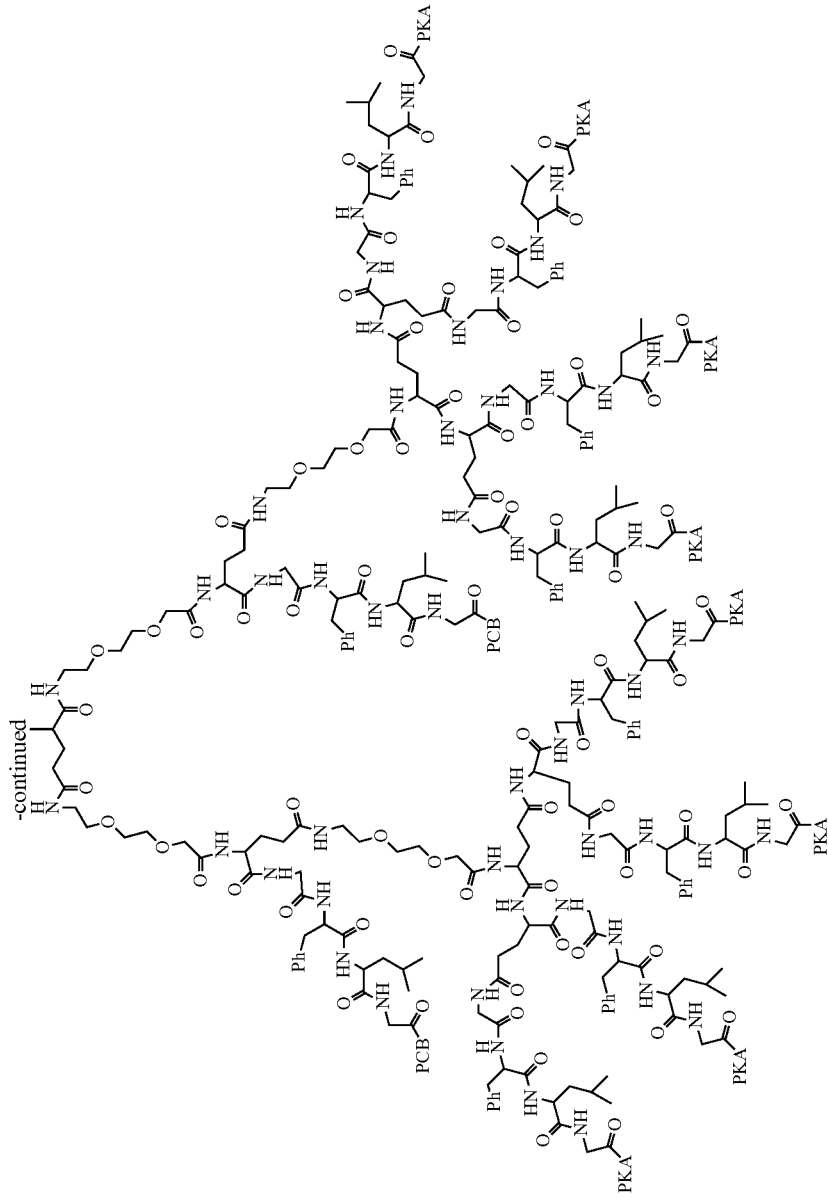

42-50 (0.4472 g, 0.0106 mmol) and M-SCM-20K (0.5004 g, 0.0233 mmol) were added in a 500 mL round-bottomed flask, and dissolved with DMF (30 mL), and then the mixed solution reacted in the dark at room temperature for 7 days. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were added to the lower liquid for precipitation, the supernatant was discarded. Such operations were repeated three times, to obtain a viscous product. Then, the viscous product was dissolved with dichloromethane (5 mL), methyl tert-butyl ether (100 mL) was added for precipitation, to obtain a powdery solid, and filtering was carried out. The filter cake was washed with methyl tert-butyl ether (60 mL), and dissolved with a mixed solvent (80 mL) of 20% methanol/dichloromethane, silica gel powder (40 ml) was added to the obtained solution, and the operations of evaporation, dry sample loading, column chromatography and elution with an elutent (1% ammonia water: 4%-10% methanol: 95%-89% dichloromethane) were carried out. The elution product was then collected, concentrated, evaporated to dryness, and dried, thus obtaining the product 42-52: 0.547 g, yield: 58.96%.

$^1$H-NMR (600 MHz, DMSO-d$_6$) δ 9.36-8.90 (m, 144H), 8.53-7.94 (m, 349H), 7.94-7.48 (m, 250H), 7.32-7.22 (m, 231H), 7.15-7.09 (m, 27H), 7.03-6.96 (m, 16H), 4.54-4.23 (m, 380H), 4.10-3.36 (m, 3418H), 3.19-3.03 (m, 106H), 2.90-2.73 (m, 50H), 2.63-2.59 (m, 380H), 2.41-2.30 (m, 61H), 2.22-2.12 (m, 95H), 1.98-1.49 (m, 288H), 1.40-1.35 (m, 59H), 1.15-1.03 (m, 75H), 0.91-0.85 (m, 240H).

8. Synthesis of 37-200 (Compound No. 2)

Synthetic route is as follows

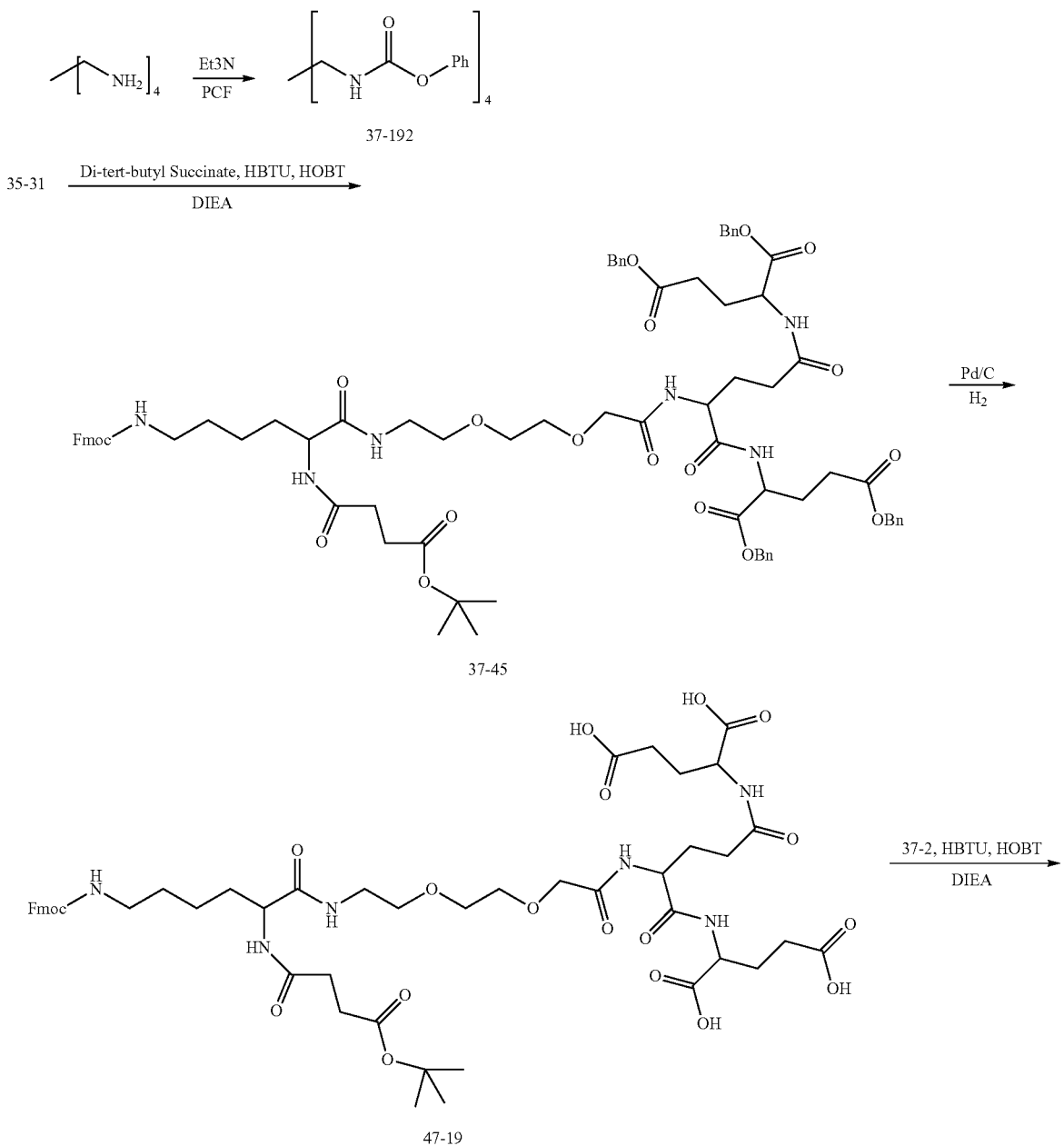

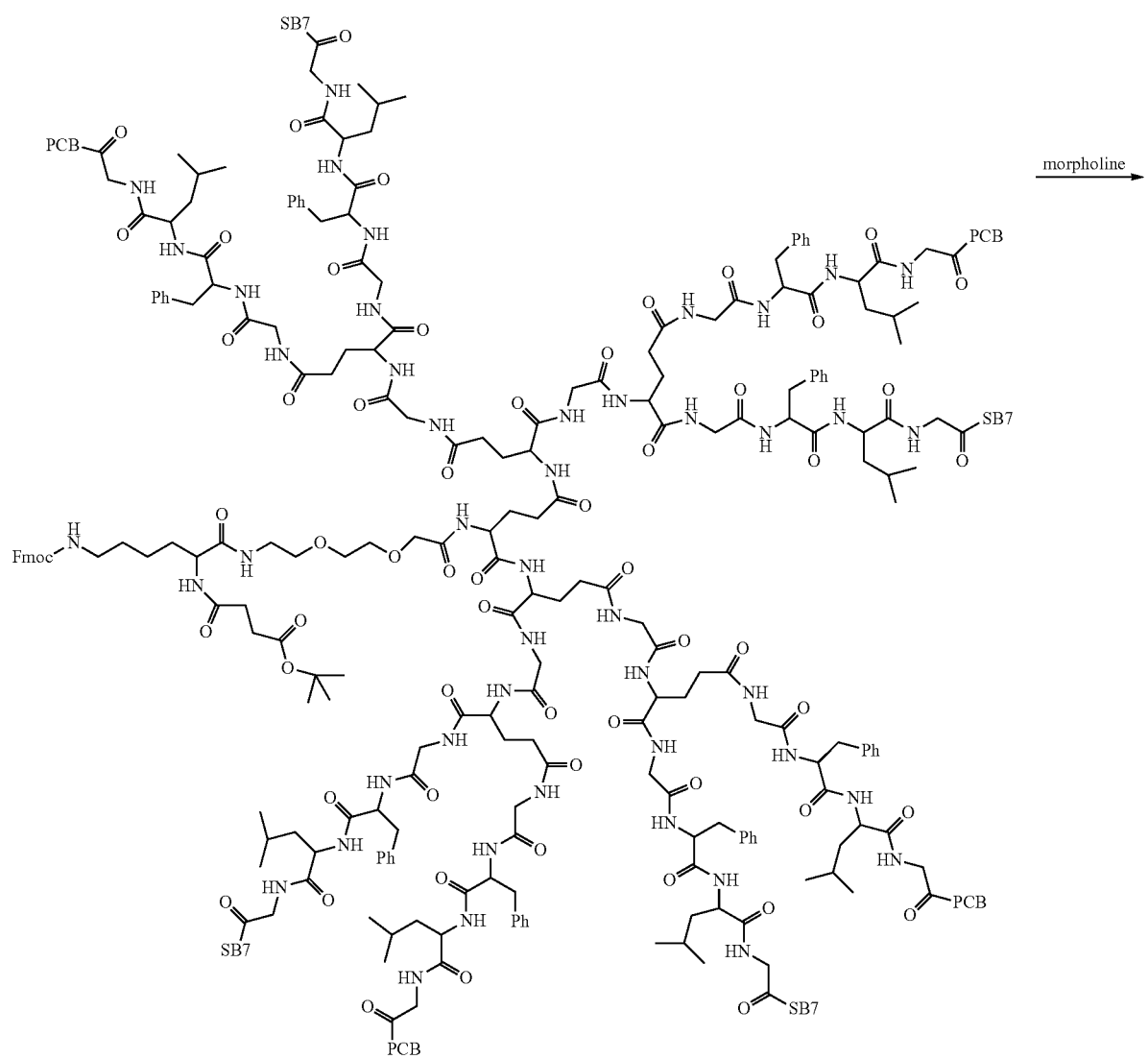
47-21

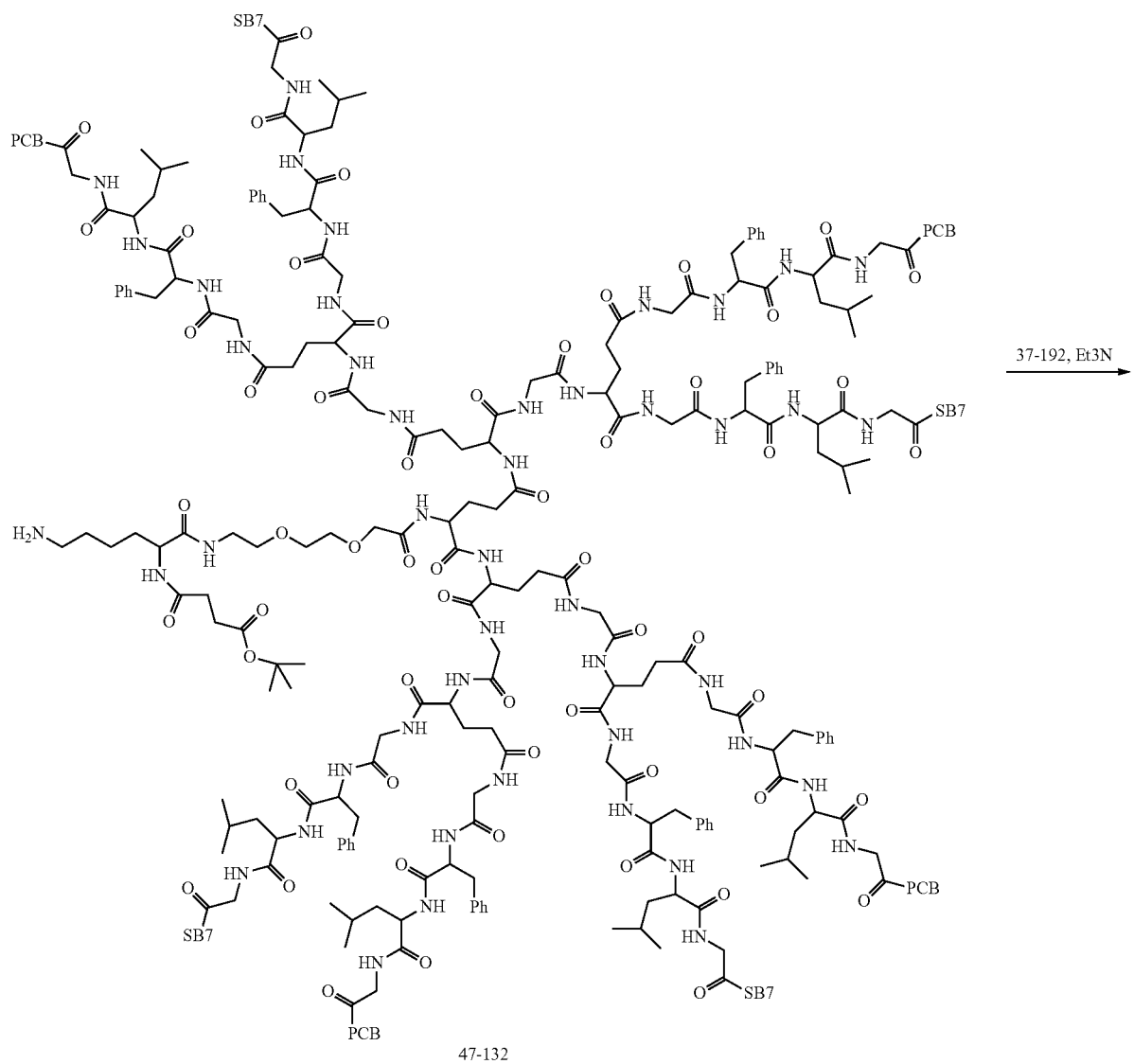
47-132

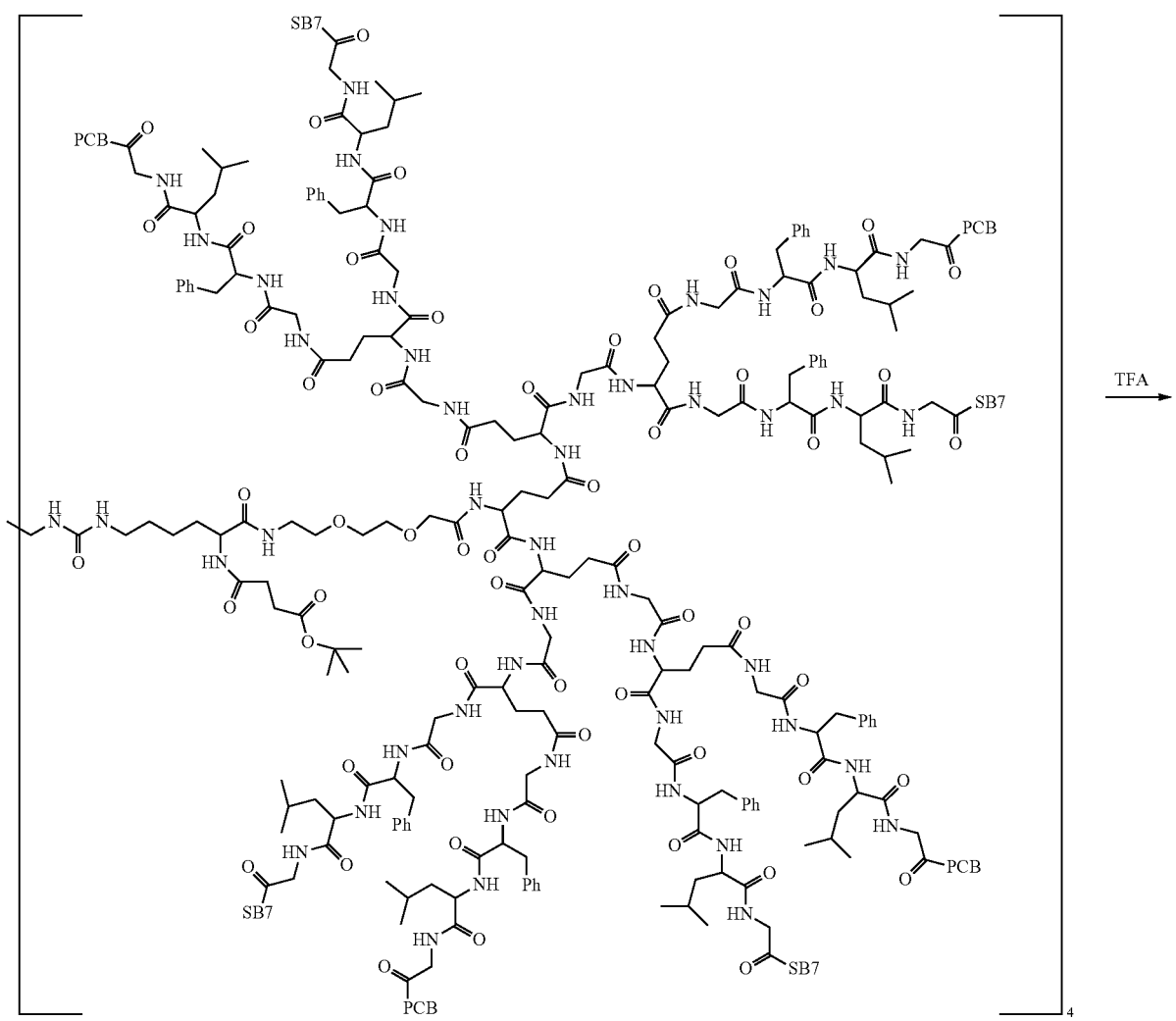
37-195

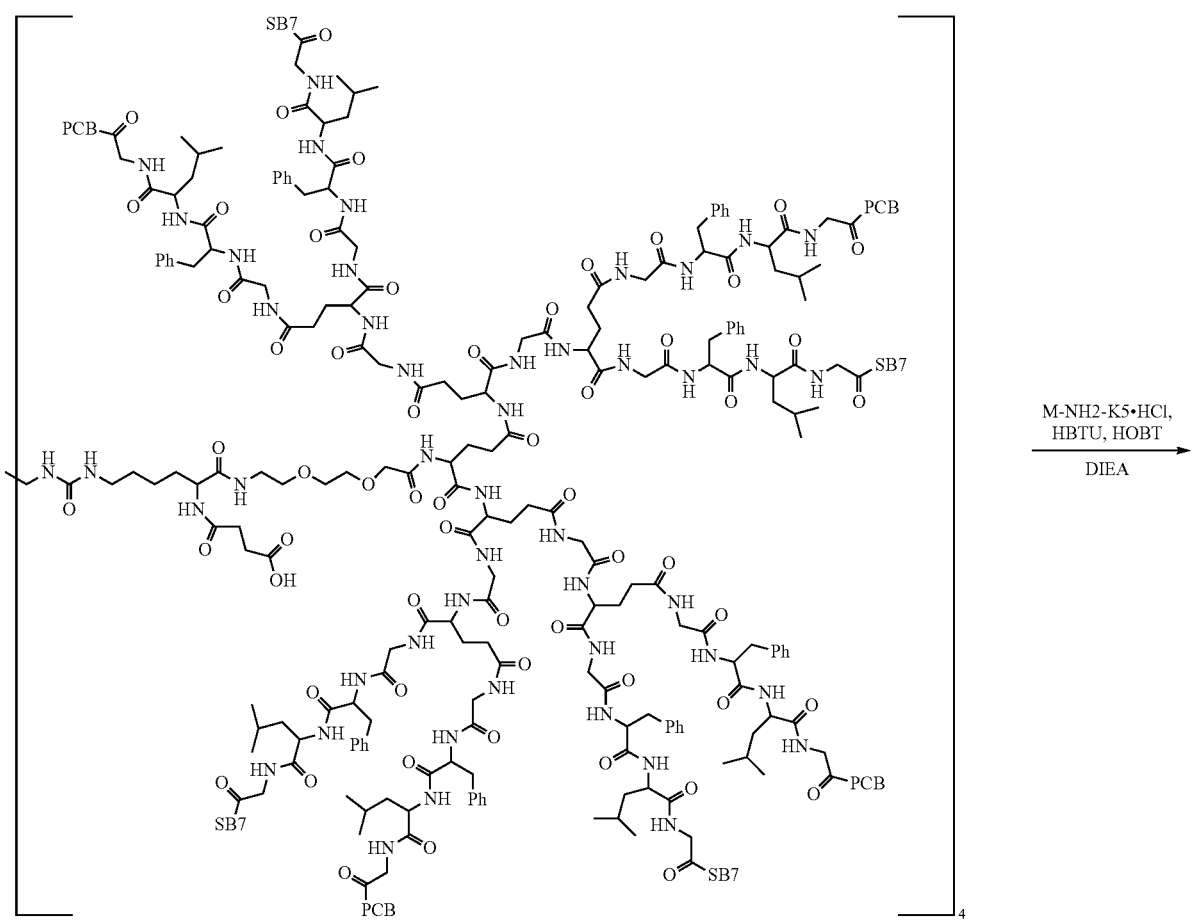
37-199

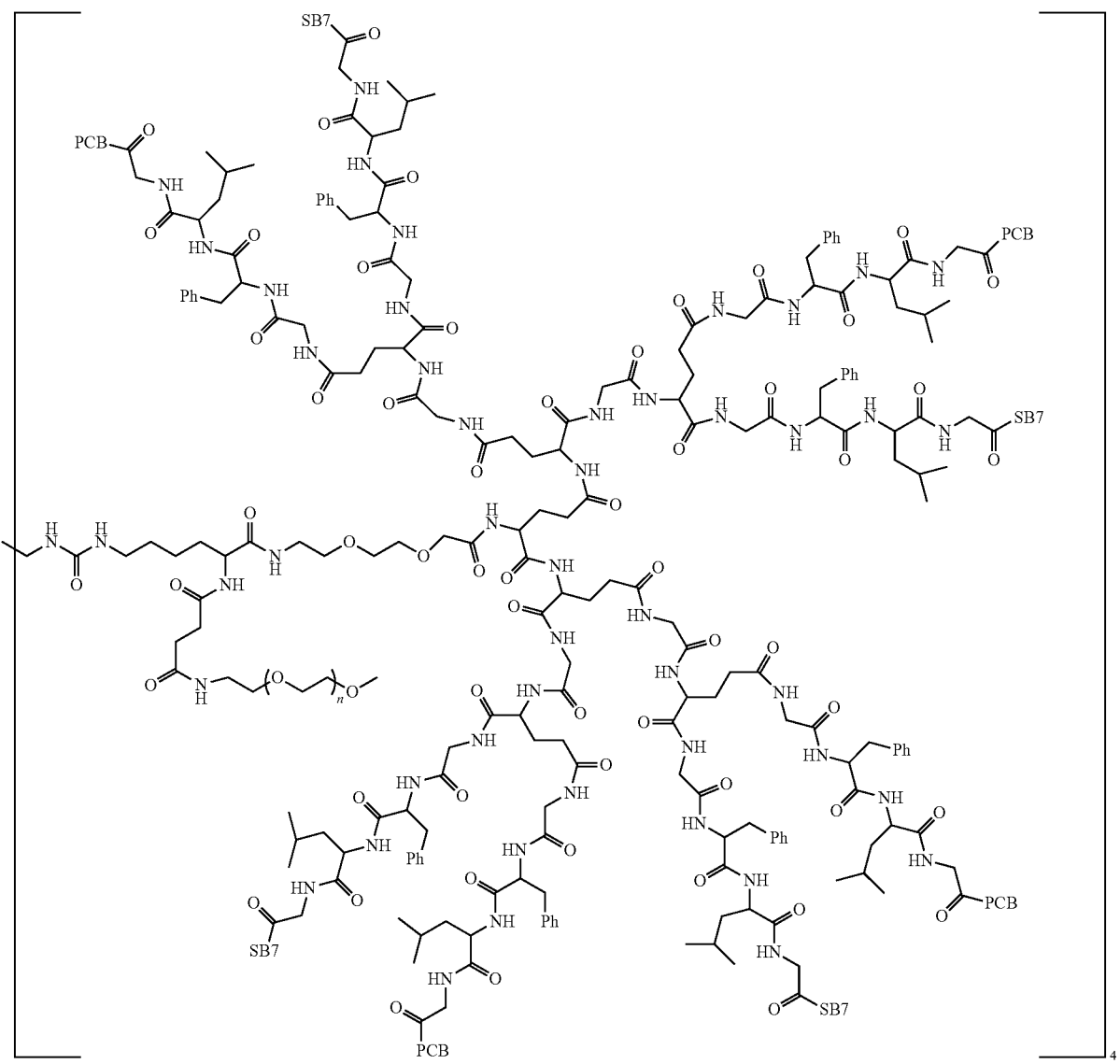

37-200

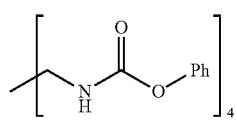

37-192

Pentatetramine disulfate (4.33 g, 13.20 mmol, purchased from Pharmaron) was added in a 500 mL flask, and dissolved with dichloromethane (30 mL), triethylamine (14.8 mL, 105.6 mmol) was added, and then the mixed solution was stirred to react at 0° C. for 30 minutes. Phenyl chloroformate (9.95 mL, 79.2 mmol) was then slowly added dropwise, and the mixed solution was stirred to react at room temperature overnight. At the end of the reaction, the reaction solution was transferred to a 1 L reparatory funnel, extracted with dichloromethane (200 mL) and deionized water (200 mL), and the organic phase was separated. The aqueous phase was washed with dichloromethane (200 mL×1), and the obtained organic phases were combined, silica gel powder (15 g) was added, and the obtained mixture was then evaporated to dryness to obtain a powdery solid. The operations of dry sample loading, column chromatography and elution with a dichloromethane mixed solution containing 5% methanol were carried out, thus obtaining the product 37-192: 3.3 g, yield 42%.

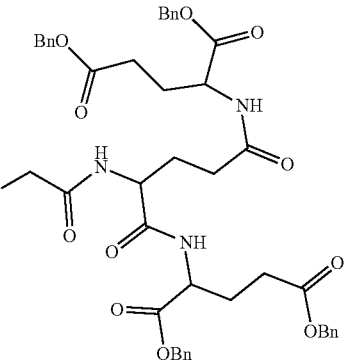
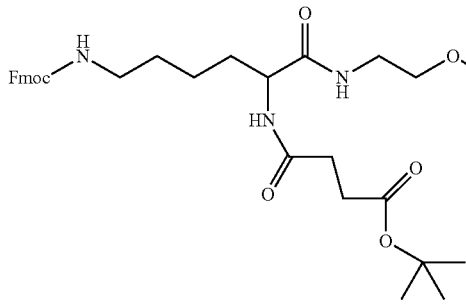

37-45

35-31 (2.73 g, 2.196 mmol, synthesized according to the method of synthesizing 34-17), tert-butyl succinate (0.459 g, 2.635 mmol, purchased from InnoChem), HBTU (1.249 g, 3.294 mmol), HOBT (0.445 g, 3.294 mmol) were added in a 500 mL flask, and dissolved with DMF (70 mL), and then the mixed solution was stirred to react at −5° C. for about 30 minutes. Then DIEA (1.633 mL, 9.882 mmol) was slowly added dropwise. At the end of the addition, the obtained solution continued to react at −5° C. with stirring for 3 hours. At the end of the reaction, the reaction solution was transferred to a 1 L separatory funnel, deionized water (200 mL) and ethyl acetate (200 mL) were added, and the obtained solution was shaken for extraction. The aqueous phase was washed with ethyl acetate (150 mL×2), and the obtained organic phases were combined. The organic phase was washed with saturated saline solution (200 mL×1), concentrated, evaporated to dryness, and dried in a vacuum oven, thus obtaining the product 37-45: 3.1 g.

$^1$H-NMR (400 MHz, DMSO-d$_6$) δ 8.52 (d, J=7.3 Hz, 1H), 8.30 (d, J=7.4 Hz, 1H), 7.99-7.93 (m, 4H), 7.88 (d, J=7.3 Hz, 2H), 7.68 (t, J=7.2 Hz, 3H), 7.51 (t, J=7.6 Hz, 1H), 7.43-7.18 (m, 22H), 5.16-5.01 (m, 7H), 4.45-4.07 (m, 7H), 3.70-3.46 (m, 4H), 3.43-3.29 (m, 10H), 3.24-3.12 (m, 4H), 2.46-2.28 (m, 7H), 2.17 (t, J=7.9 Hz, 2H), 1.39-1.24 (m, 9H).

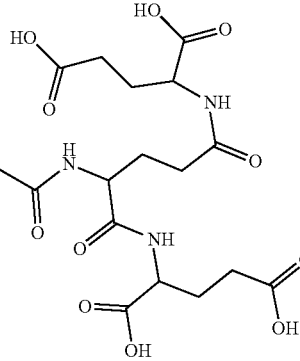
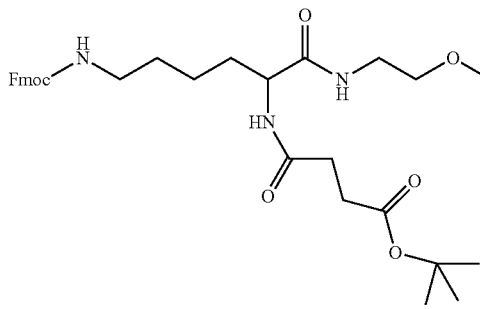

47-19

37-45 (0.5137 g, 0.3624 mmol) and Pd/C (0.010 g) were added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was taken out, and filtered with diatomaceous earth. The diatomaceous earth was then washed with DMF (20 mL×3), and the DMF solutions were combined as raw material for the next reaction.

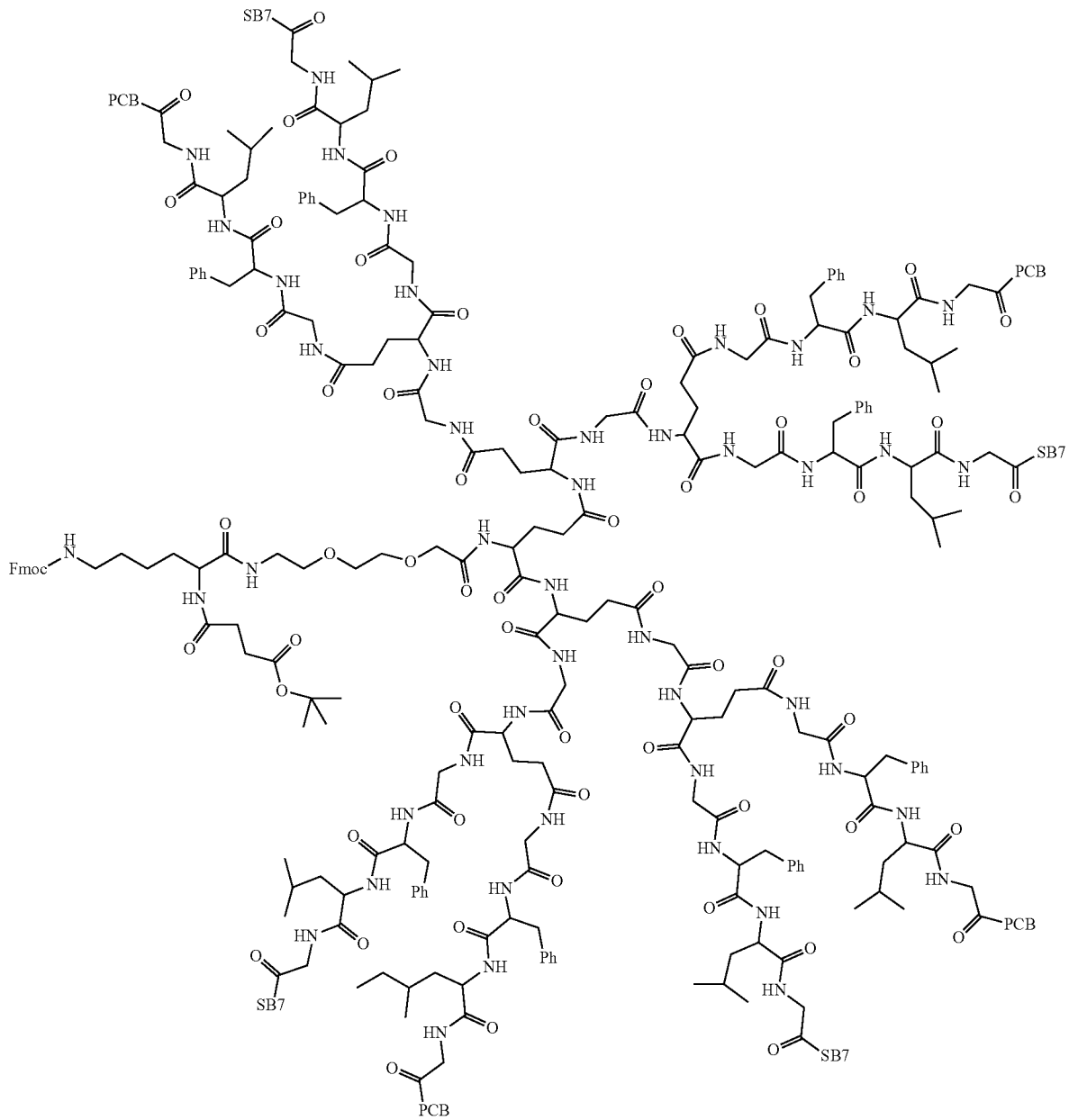

47-21

47-19 (0.38 g, 0.3624 mmol), 37-2 (3 g, 1.5944 mmol), HBTU (0.8246 g, 2.1744 mmol), HOBT (0.2938 g, 2.1744 mmol) were added in a 250 mL flask, and dissolved with DMF (95 mL), and then the mixed solution was stirred to react at −5° C. for 20 minutes. Then. Then, DIEA (1.078 mL, 6.523 mmol) was slowly added dropwise. At the end of the addition, the obtained solution was stirred to react at −5° C. for 30 minutes, and was then moved to room temperature and stirred to react overnight. At the end of the reaction, the reaction solution was precipitated three times with n-hexane (120 mL) and methyl tert-butyl ether (30 mL), and a viscous oily product was obtained. Then, methyl tert-butyl ether (250 mL) was added to the oily product to separate out a solid, and filtering was carried out. The filter cake was washed with methyl tert-butyl ether (50 mL×3), and dissolved with dichloromethane (150 mL) and methanol (30 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 4%-8% methanol were carried out. The elution product was then collected, concentrated and dried, thus obtaining the product 47-21: 2.5 g, yield 83%.

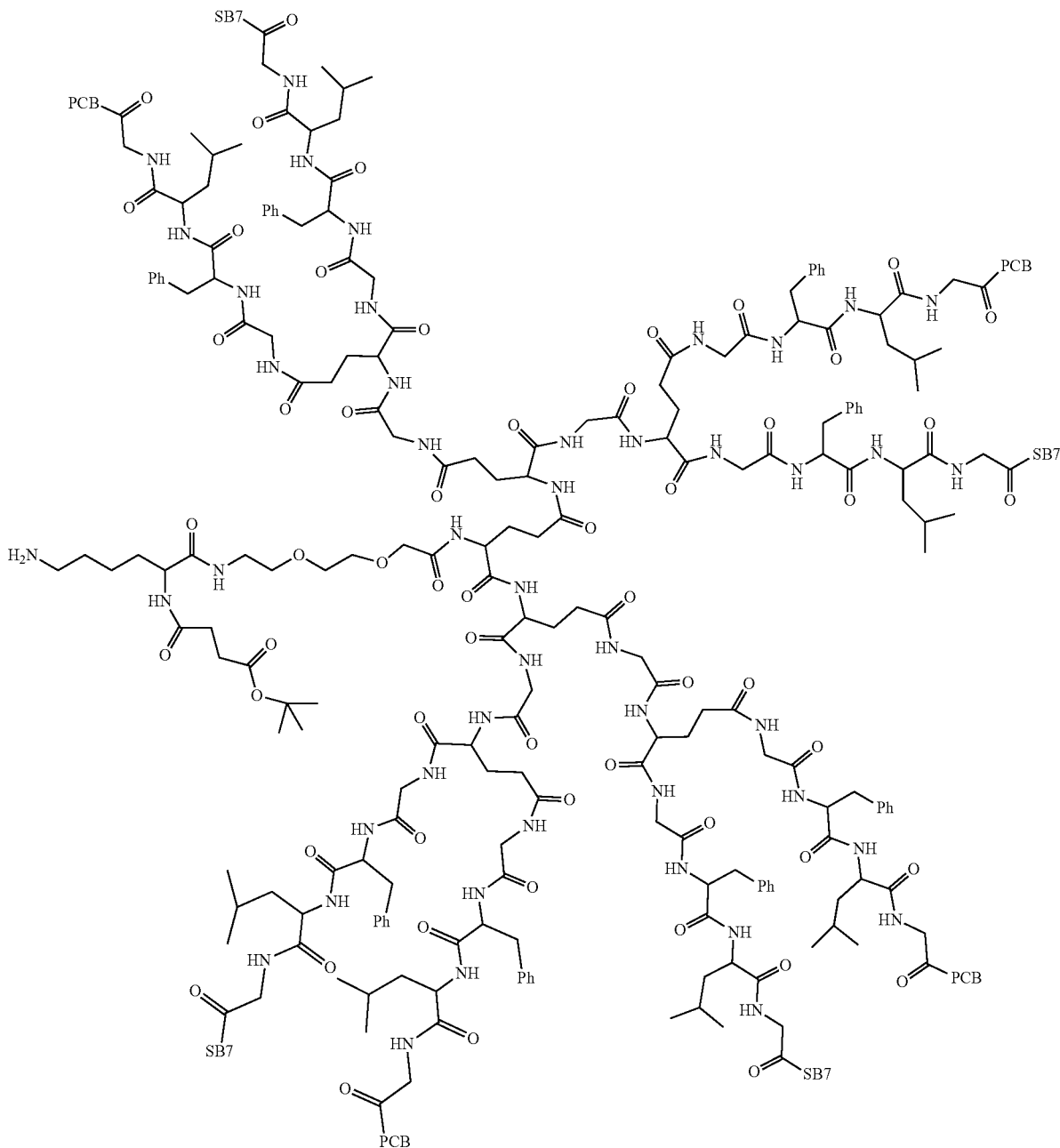

47-21 (2.5 g, 0.2938 mmol) was added in a 250 mL flask, and dissolved with DMF (30 mL), morpholine (7.67 mL, 88.14 mmol) was added, and then the mixed solution was stirred to react at room temperature for 1 hour. At the end of the reaction, n-hexane (100 mL) and methyl tert-butyl ether (20 mL) were added for precipitation to layer the reaction solution, the supernatant was discarded, and n-hexane (100 mL) and methyl tert-butyl ether (20 mL) were added to the lower oily liquid phase for further precipitation. Such operations were repeated three times, to obtain a viscous oily product. Methyl tert-butyl ether (150 mL) was added to the oily product to separate out a solid, and then filtering was carried out. The filter cake was washed with methyl tert-butyl ether (40 mL×2), and dissolved with dichloromethane (20 mL) and methanol (80 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 6%-10% methanol were carried out, thus obtaining the product 43-123: 1.85 g, yield 77%.

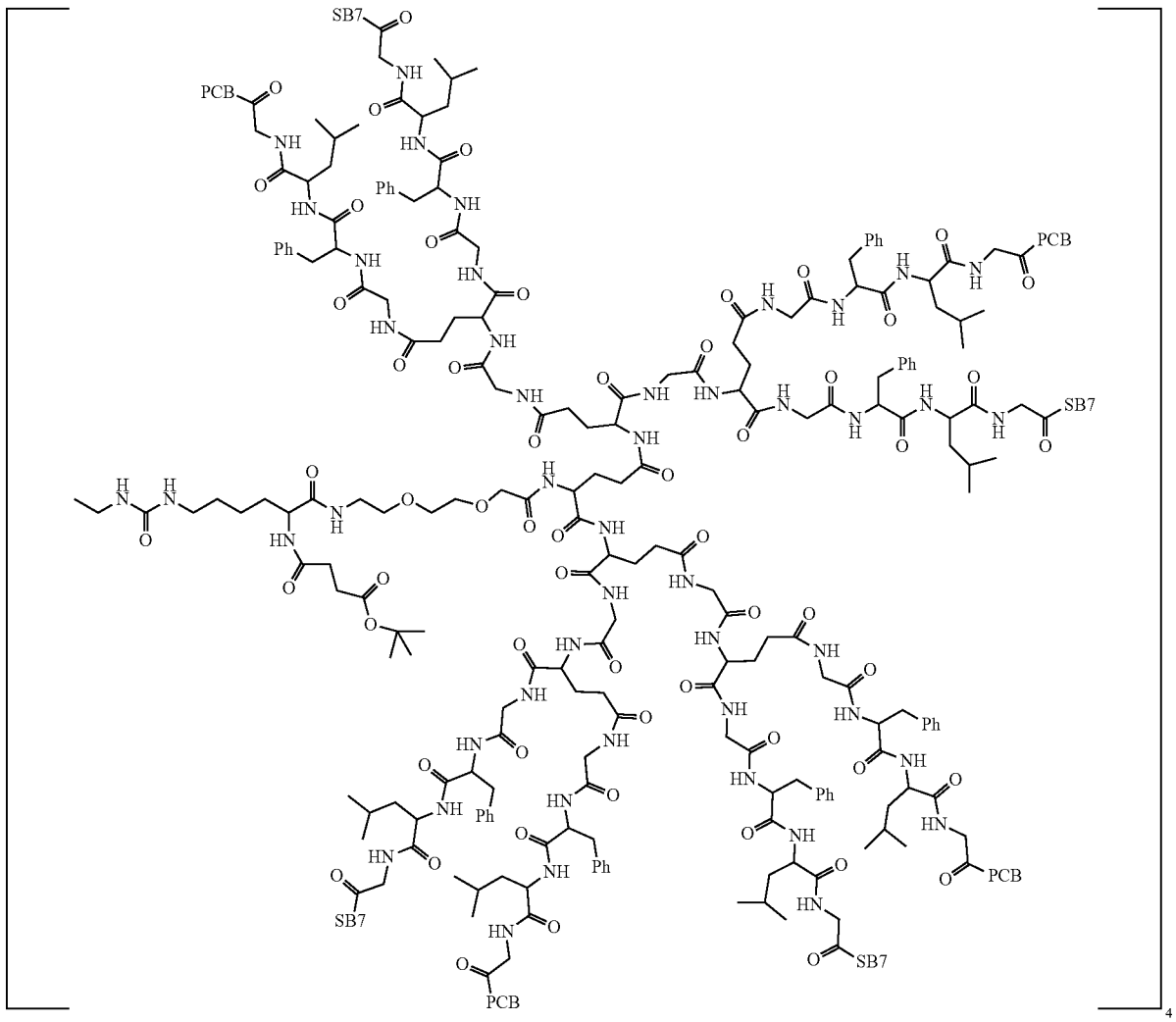

43-123 (1.85 g, 0.2628 mmol), 37-192 (0.0326 g, 0.0531 mmol) was added in a 250 mL flask, and dissolved with DMF (30 mL) triethylamine (0.0336 mL, 0.239 mmol) was added, the obtained solution was stirred to react at 80° C. overnight. At the end of the reaction, n-hexane (100 mL) and methyl tert-butyl ether (20 mL) were added for precipitation to layer the reaction solution, the supernatant was discarded, and n-hexane (100 mL) and methyl tert-butyl ether (20 mL) were added to the lower oily liquid phase for further precipitation. Such operations were repeated three times, to obtain a viscous oily product. Methyl tert-butyl ether (150 mL) was added to the oily product to separate out a solid, and then filtering was carried out. The filter cake was washed with methyl tert-butyl ether (40 mL×2), and dissolved with dichloromethane (20 mL) and methanol (80 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 6%-7% methanol were carried out, thus obtaining the product 37-195: 0.7 g, yield 40%.

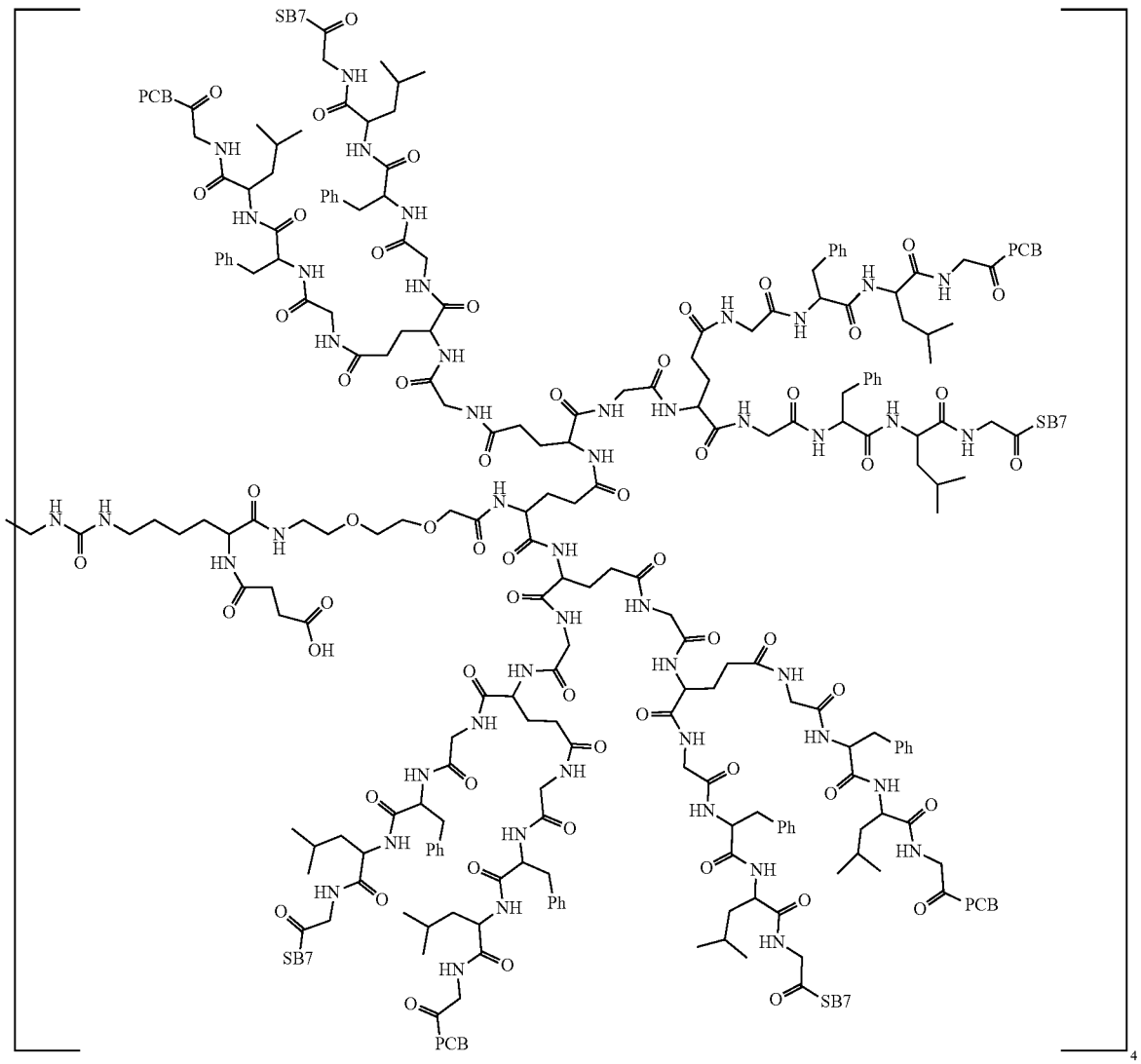

37-195 (0.7 g, 0.021 mmol) was added in a 100 mL flask, and dissolved with dichloromethane (10 mL), TFA (4.67 mL, 6.29 mmol) was added, and then the mixed solution was stirred to react at room temperature overnight. At the end of the reaction, methyl tert-butyl ether (100 mL) was added to the reaction solution to separate out a solid, and suction filtering was carried out. The filter cake was washed with methyl tert-butyl ether (100 mL×3), and dissolved with a mixed solvent of methanol (20 mL) and dichloromethane (80 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 6%-8% methanol were carried out. The elution product was then collected, concentrated, evaporated to dryness, and dried in a vacuum oven, thus obtaining the product 37-199: 0.697 g, yield 43%.

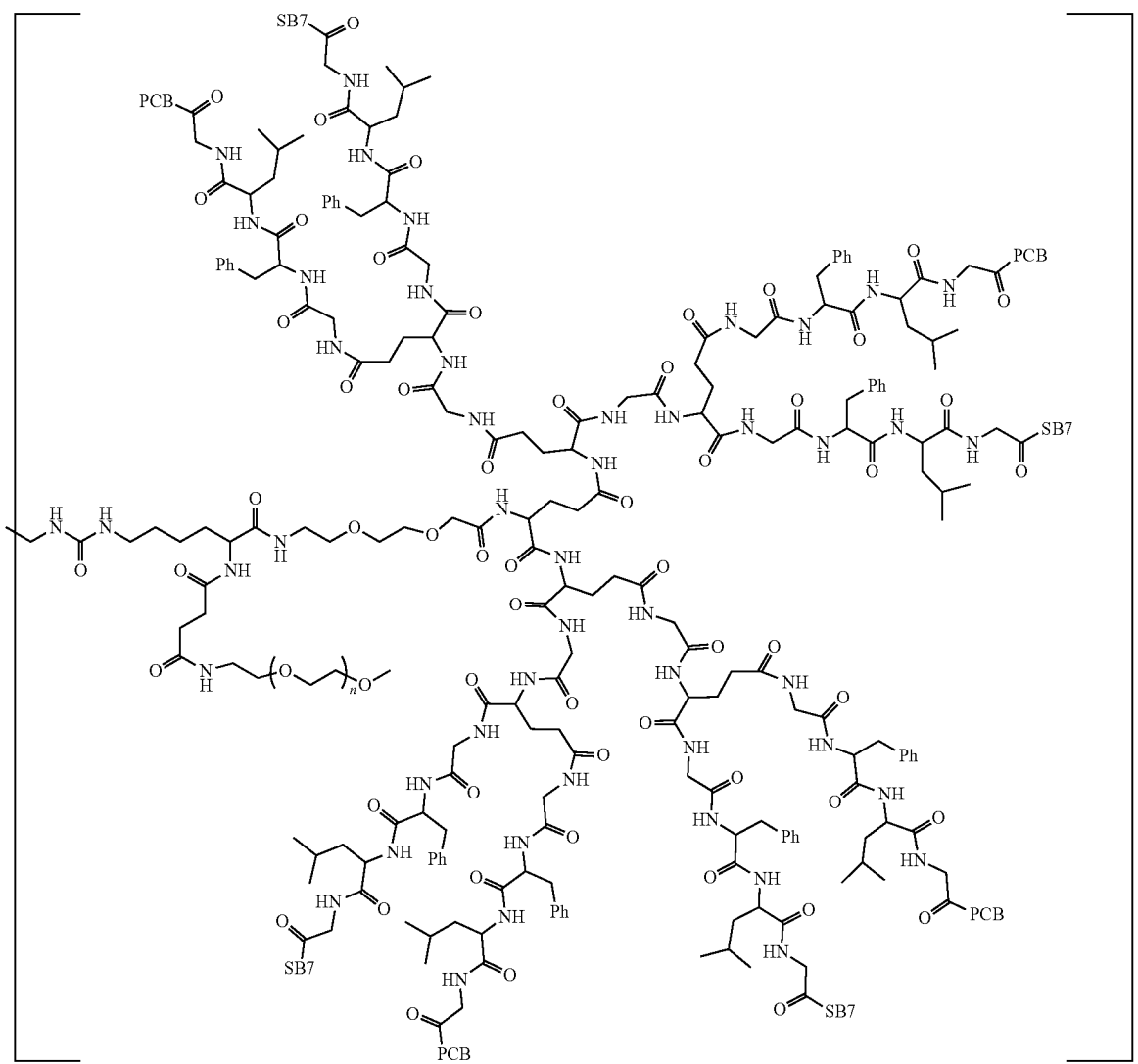

37-200

37-199 (0.3 g, 0.009 mmol) was added in a 100 mL flask, and dissolved with DMF (40 mL), M-NH$_2$-5K·HCl (0.2772 g, 0.0543 mmol, purchased from JenKem), HBTU (0.21 g, 0.543 mmol), HOBT (0.073 g, 0.543 mmol) were added, and then the mixed solution was stirred to react at −5° C. at a low speed for about 10 min. Then. Then, DIEA (0.7 mL, 4.32 mmol) was slowly added dropwise, and the obtained solution continued to react at −5° C. for 20 minutes, and was then moved to room temperature and stirred to react in the dark for 7 days at a low speed. At the end of the reaction, n-hexane (100 mL) and methyl tert-butyl ether (30 mL) were added to the reaction solution for precipitation, the supernatant was discarded, and n-hexane (100 mL) and methyl tert-butyl ether (30 mL) were added to the lower liquid. Such operations were repeated three times, to obtain a viscous oily product. Methyl tert-butyl ether (100 mL) was added to the oily product to separate out a solid, and filtering was carried out. The filter cake was washed with methyl tert-butyl ether (30 mL×3), and dissolved with a mixed solvent of methanol (40 mL) and dichloromethane (160 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 4%-7% methanol were carried out. The elution product was then collected, concentrated, evaporated to dryness, dried in a vacuum oven for 1 hour, and dissolved with anhydrous ethanol (2 mL) and dichloromethane (30 mL). Then, methyl tert-butyl ether (200 mL) was added to the obtained solution to separate out a solid, and filtering was carried out. The filter cake was washed with methyl tert-butyl ether (50 mL×2), and dried in a vacuum oven, thus obtaining the product 37-200: 0.27 g, yield: 56%.

$^1$H-NMR (600 MHz, DMSO-d$_6$) δ 10.19-10.05 (m, 16H), 9.06-8.84 (m, 15H), 8.32-7.77 (m, 251H), 7.59-7.46 (m, 45H), 7.31-7.05 (m, 313H), 5.92-5.66 (m, 25H), 4.61-4.49 (m, 25H), 4.43-4.29 (m, 14H), 4.26-4.16 (m, 40H), 4.05-3.84 (m, 31H), 3.70-3.61 (m, 113H), 3.58-3.41 (m, 1856H), 3.26-3.24 (m, 28H), 3.20-3.17 (m, 44H), 3.14-3.11 (m, 32H), 3.07-2.87 (m, 99H), 2.81-2.69 (m, 75H), 2.67-2.60 (m, 35H), 2.45-2.37 (m, 87H), 2.36-2.28 (m, 118H), 2.27-2.08 (m, 116H), 1.94-1.69 (m, 145H), 1.62-1.42 (m, 151H), 1.30-1.16 (m, 44H), 0.94-0.75 (m, 247H), 0.53-0.46 (m, 35H).

9. Synthesis of 35-78 (Compound No. 4)
Synthetic route is as follows
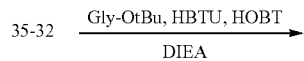
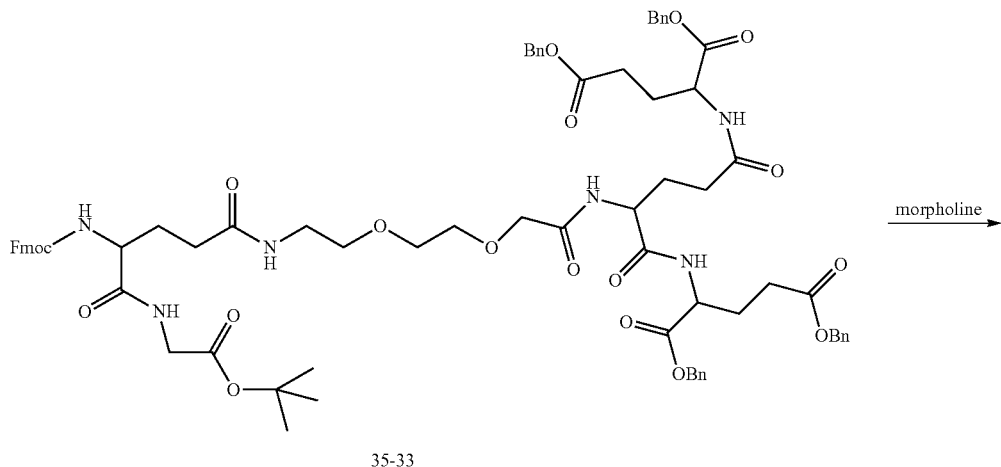
35-33
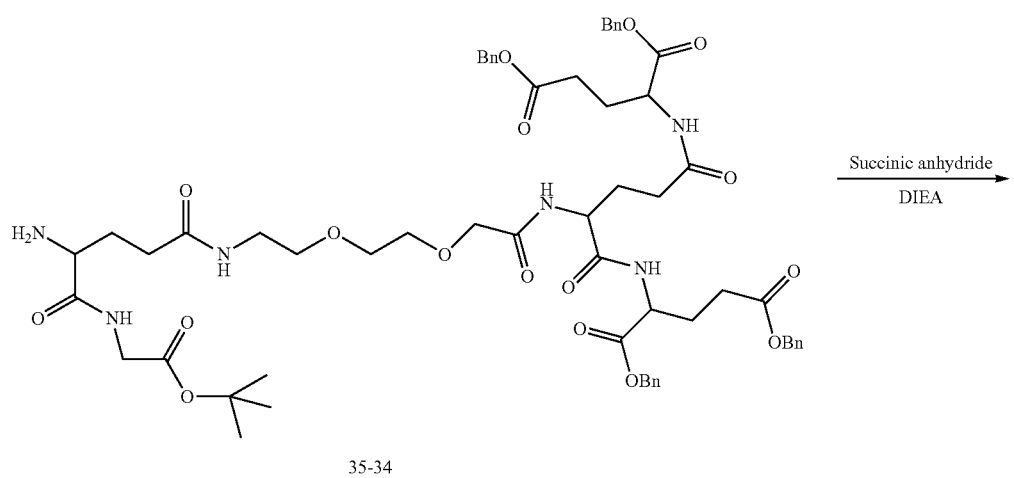
35-34
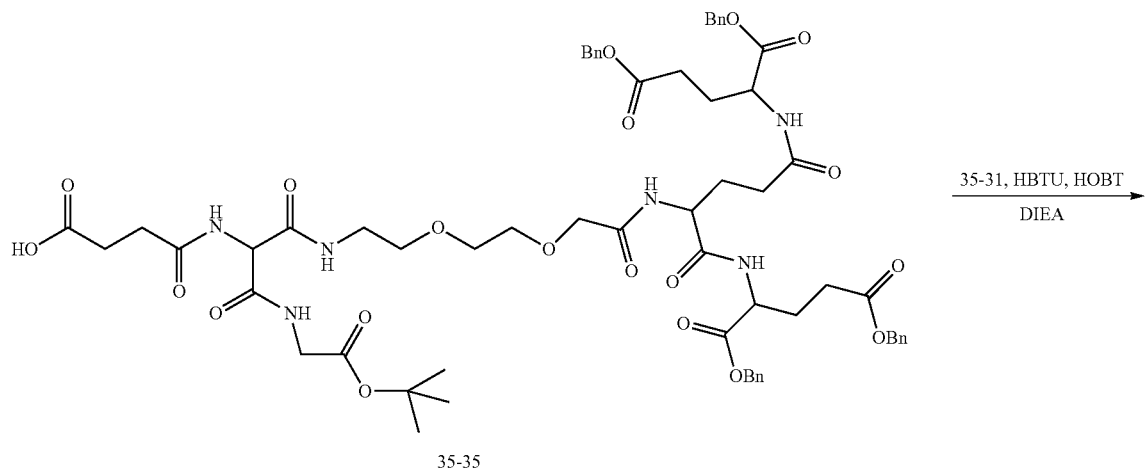
35-35

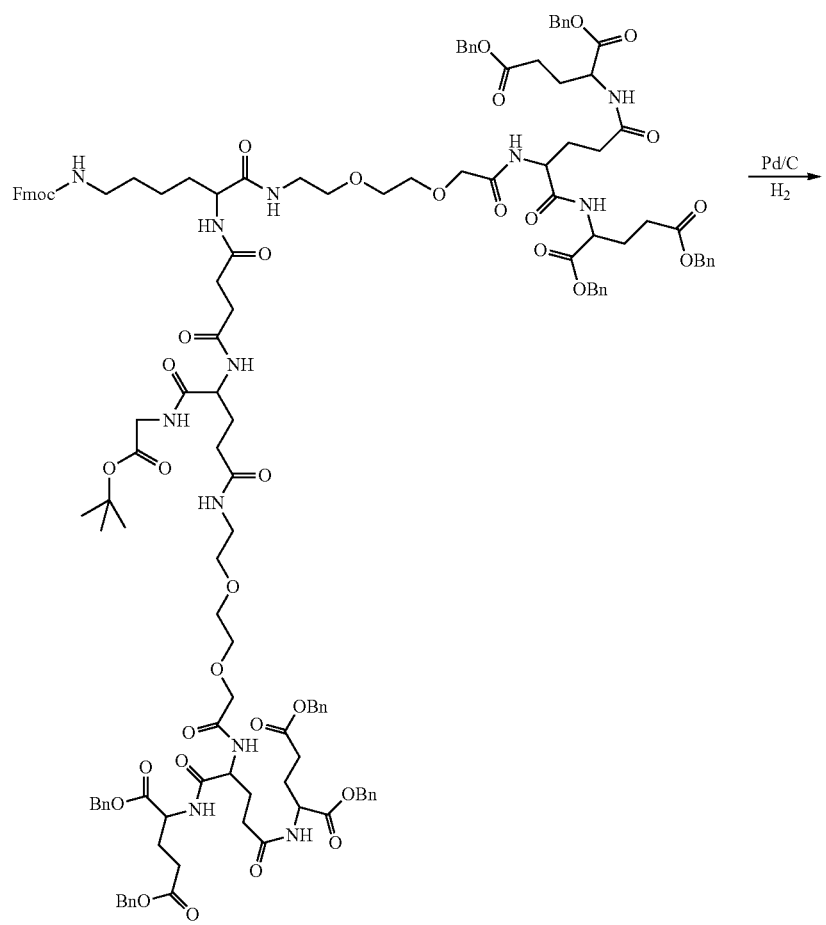
35-36

-continued
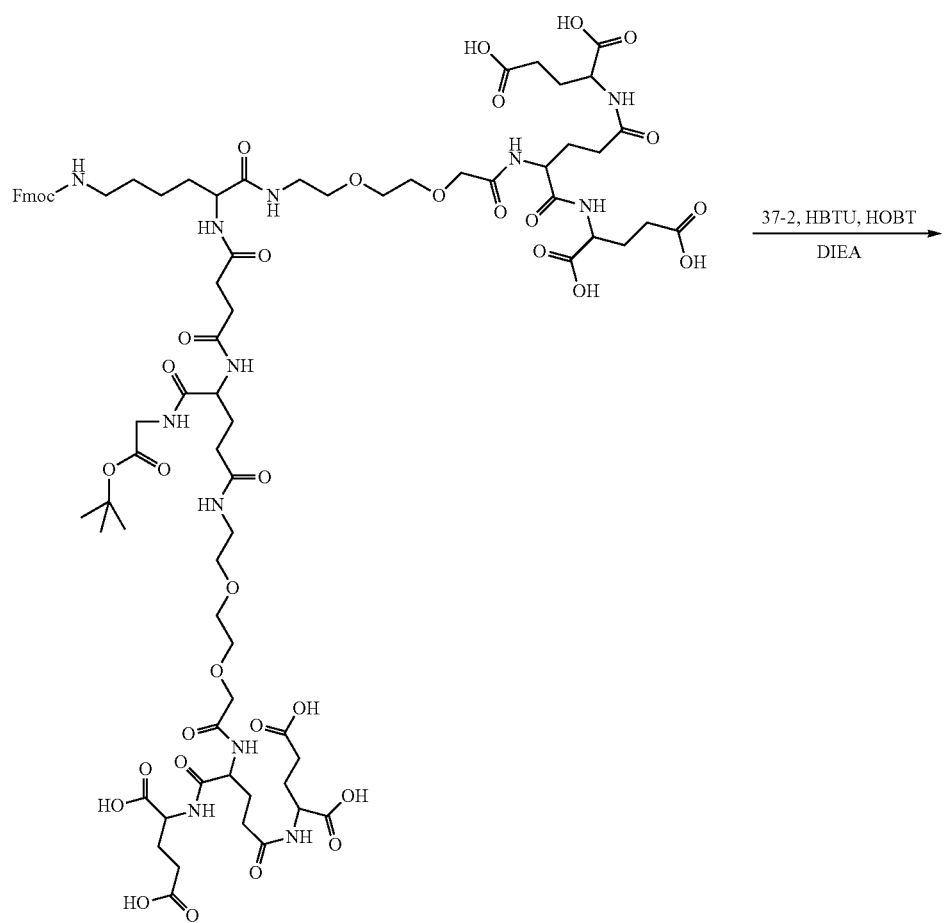
35-48

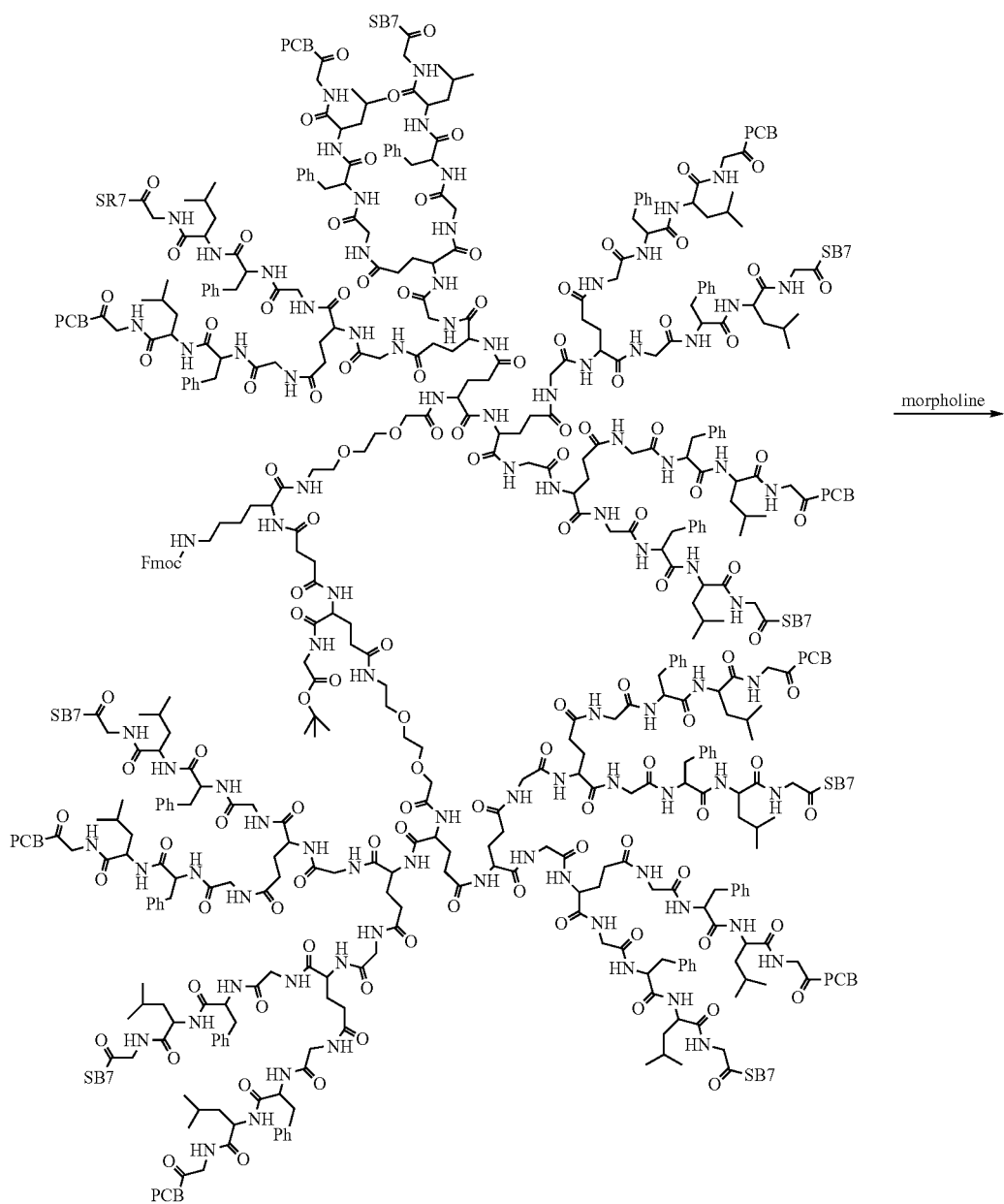
35-49

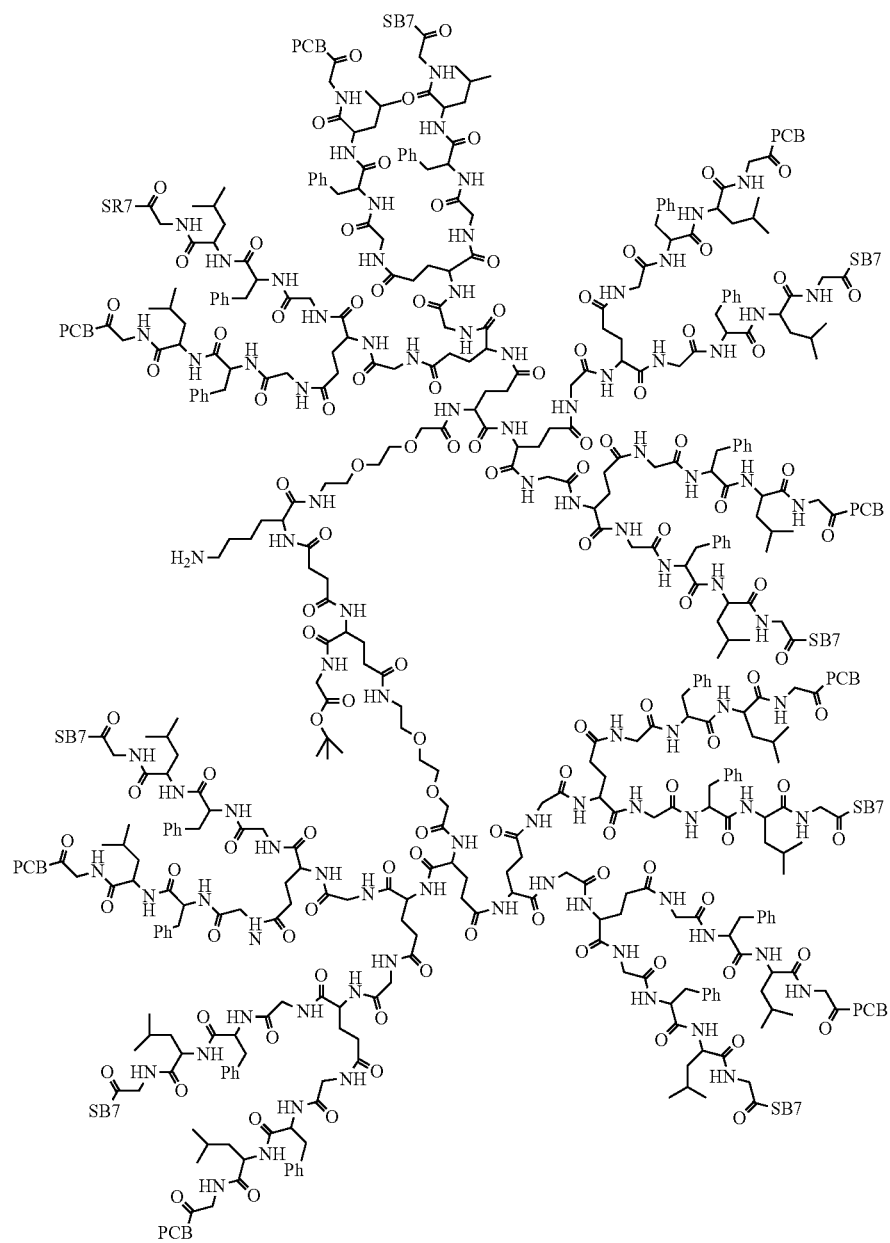
35-73
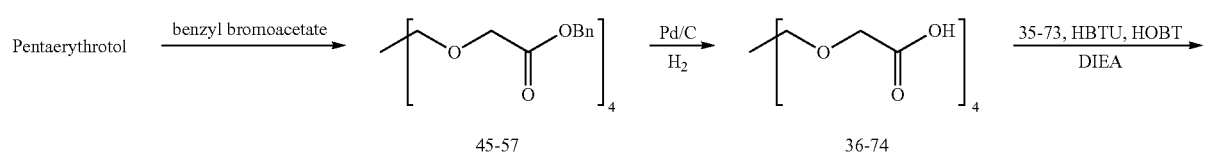

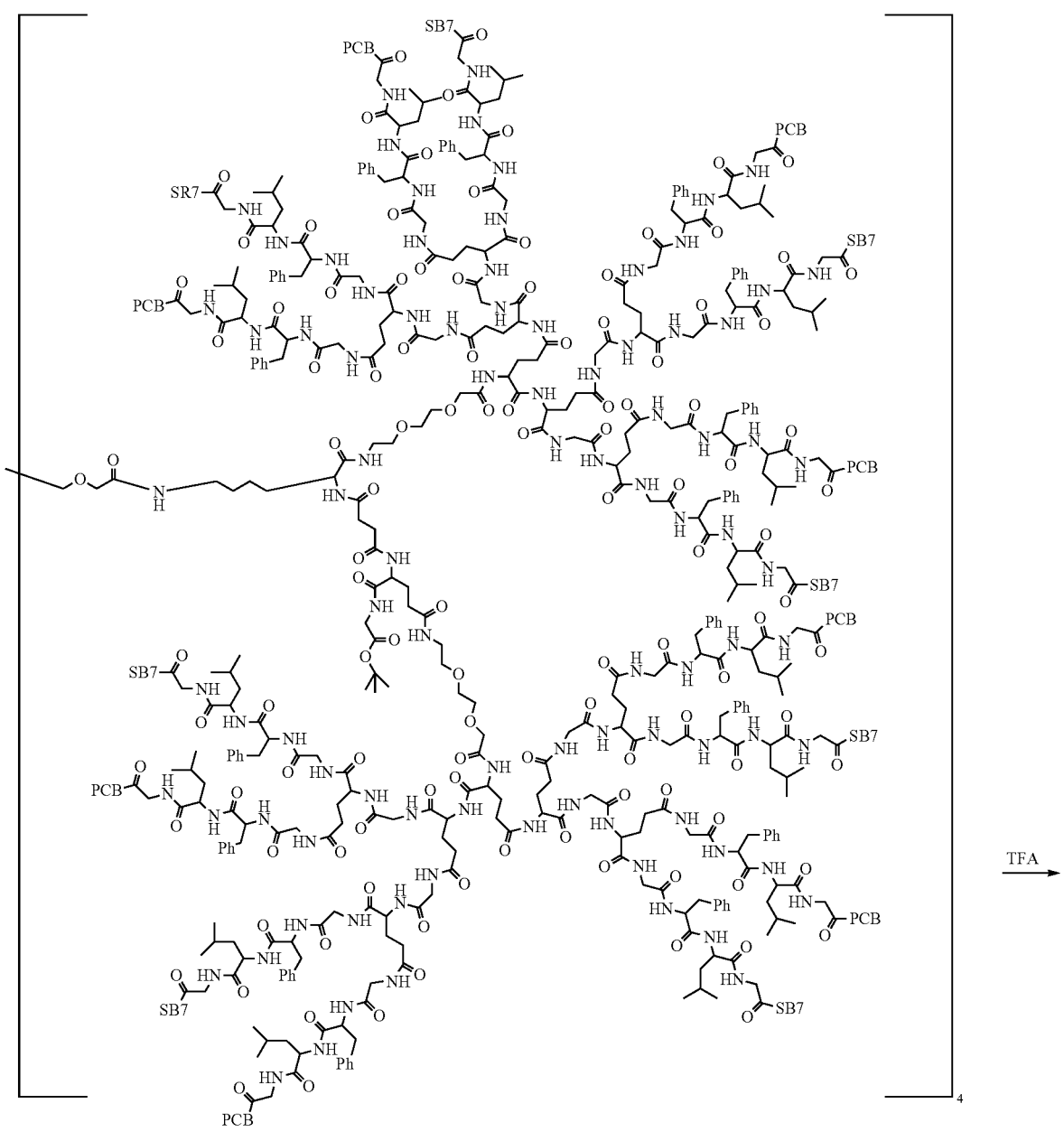
35-75

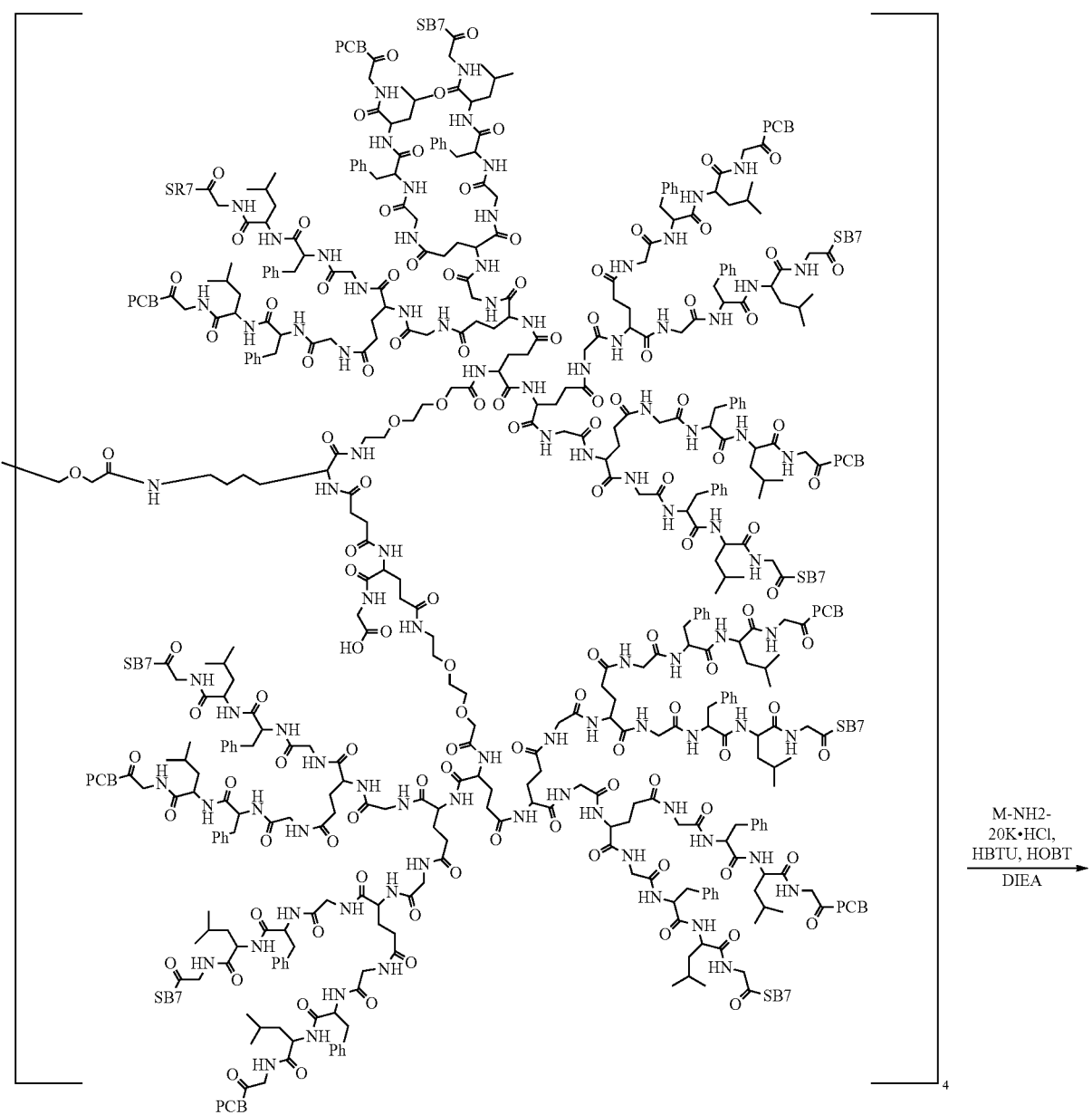
35-77
M-NH2-
20K•HCl,
HBTU, HOBT
DIEA

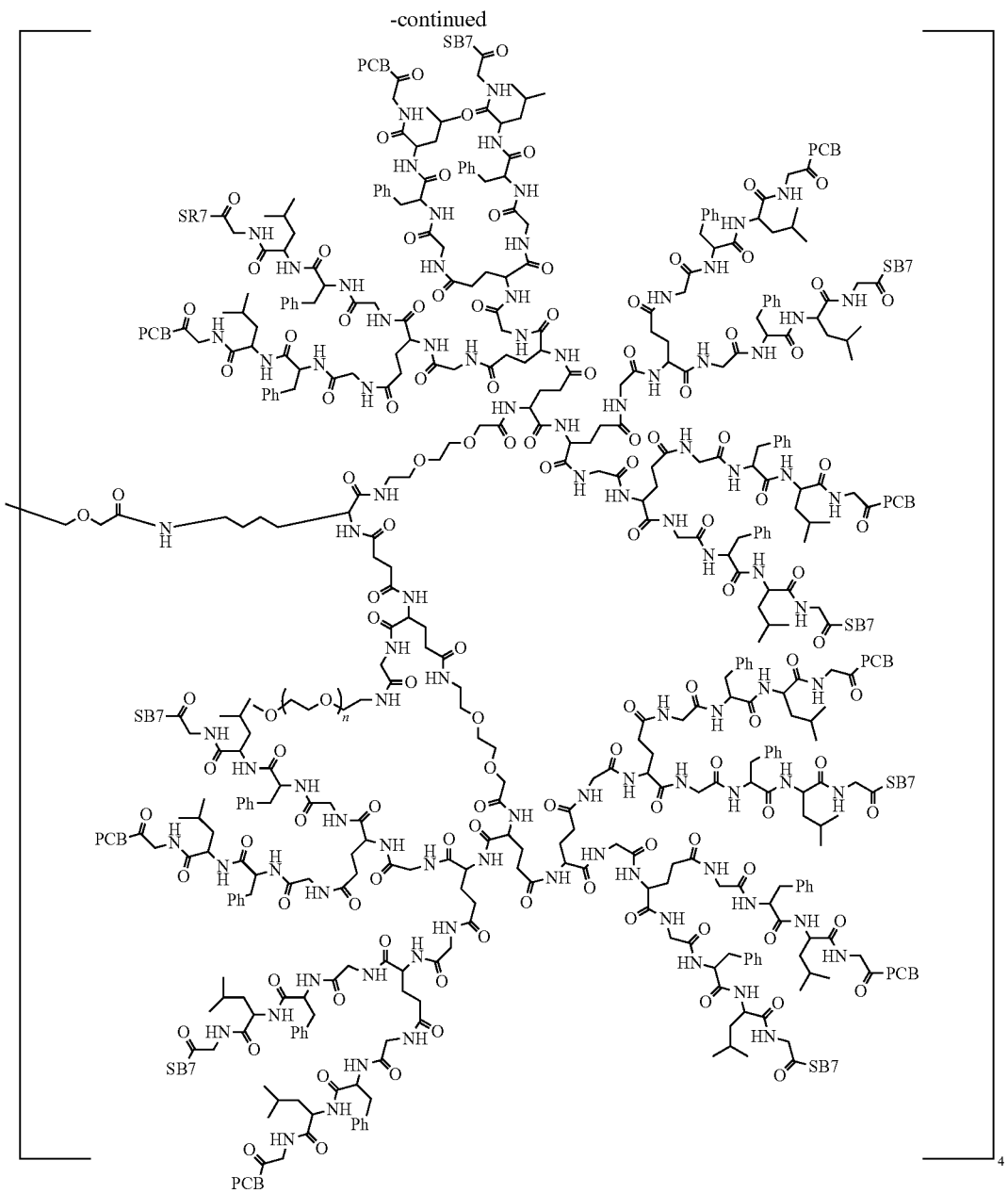

35-78

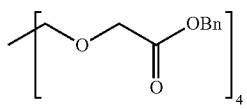

45-57

Pentaerythritol (5 g, 36.7242 mmol, purchased from Aladdin) was added in a 500 mL flask, the THF solution of potassium tert-butoxide (146.8968 mL, 146.8968 mmol) was added, and then the mixed solution was stirred to react at 0° C. for 20 minutes. Then benzyl bromoacetate (24.5129 mL, 161.5865 mmol) was slowly added dropwise. At the end of the addition, the obtained solution continued to react at 0° C. with stirring for 2 hours, and was then moved to room temperature and react overnight. At the end of the reaction, the reaction solution was transferred to a 2 L separatory funnel, deionized water (300 mL) and ethyl acetate (300 mL) were added, and the obtained solution was shaken for extraction. The aqueous phase was washed with ethyl acetate (250 mL×2), and the obtained organic phases were combined. The organic phase was washed with saturated saline solution (200 mL×1), concentrated and evaporated to dryness, the obtained solid was dissolved with dichloromethane (300 mL), silica gel powder (55 g) was added, and the obtained mixture was then evaporated to dryness to obtain a powdery solid. The operations of dry sample loading, column chromatography and elution with a petroleum ether mixed solution containing 20% ethyl acetate were carried out. The elution product was then collected, concentrated, evaporated to dryness, and dried in a vacuum oven, thus obtaining the product 45-57: 12.3 g, yield 46%.

water and 3% methanol were carried out. The elution product was then collected, concentrated, evaporated to dryness, and dried in an oven, thus obtaining the product 35-34: 5.2 g, yield 61%.

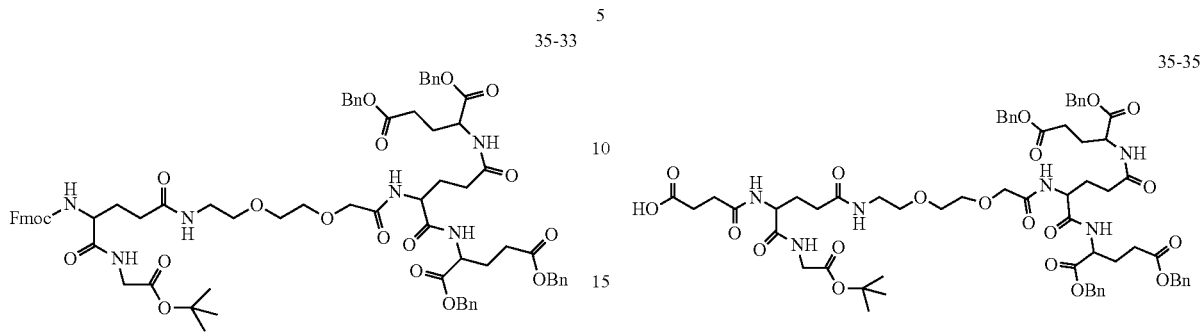

35-32 (synthesized according to the method of synthesizing 42-25, 9.364 g, 7.418 mmol), Gly-OtBu·HCl (1.243 g, 7.418 mmol, purchased from InnoChem), HBTU (4.219 g, 11.126 mmol), HOBT (1.503 g, 11.126 mmol) were added in a 250 mL flask, and dissolved with DMF (30 mL), and then the mixed solution was stirred to react at −5° C. for 30 minutes. Then DIEA (11.034 mL, 66.758 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×2), evaporated to dryness, and dried in an oven, thus obtaining the product 35-33: 10.2 g.

35-34 (5.2 g, 4.509 mmol), succinic anhydride (1.35 g, 13.527 mmol, purchased from InnoChem), were added in a 250 mL flask, and dissolved with DMF (30 mL), and then the mixed solution was stirred to react at −5° C. for 30 minutes. Then DIEA (4.47 mL, 27.053 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×2), evaporated to dryness, and dried in an oven, thus obtaining the product 35-35: 4.7 g, yield: 83%.

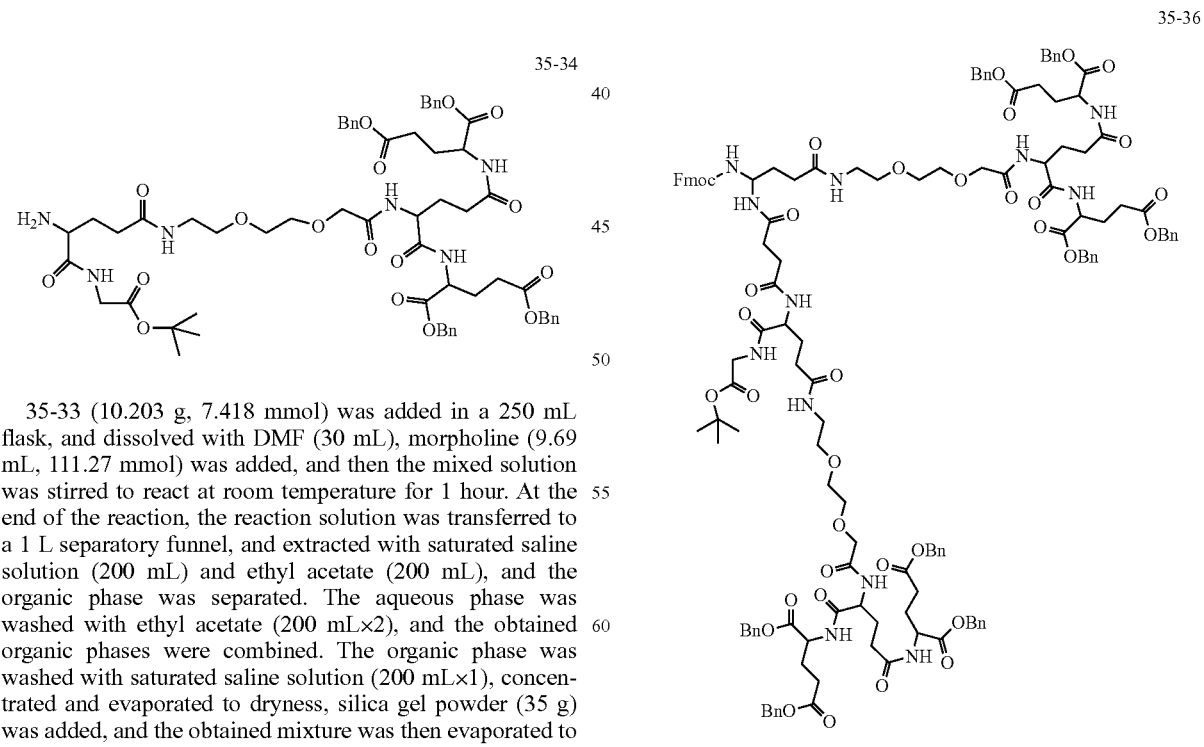

35-33 (10.203 g, 7.418 mmol) was added in a 250 mL flask, and dissolved with DMF (30 mL), morpholine (9.69 mL, 111.27 mmol) was added, and then the mixed solution was stirred to react at room temperature for 1 hour. At the end of the reaction, the reaction solution was transferred to a 1 L separatory funnel, and extracted with saturated saline solution (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×1), concentrated and evaporated to dryness, silica gel powder (35 g) was added, and the obtained mixture was then evaporated to dryness to obtain a powdery solid. The operations of dry sample loading, column chromatography and elution with a dichloromethane mixed solution containing 0.5% ammonia 35-35 (4.7 g, 3.75 mmol), 35-31 (synthesized according to the method of synthesizing 34-17, 5.203 g, 4.125 mmol), HBTU (2.133 g, 5.625 mmol), HOBT (0.76 g, 5.625 mmol) were added in a 250 mL flask, and dissolved with DMF (30 mL), and then the mixed solution was stirred to react at −5° C. for 30 minutes. Then DIEA (2.789 mL, 16.875 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, and extracted with saturated sodium chloride solution (270 mL) and ethyl acetate (240 mL), and the organic phase was separated. The aqueous phase was washed with ethyl acetate (200 mL×2), and the obtained organic phases were combined. The organic phase was washed with saturated saline solution (200 mL×2), and evaporated to dryness, silica gel powder (15 g) was added, and the obtained mixture was then evaporated to dryness to obtain a powdery solid. The operations of dry sample loading, column chromatography and elution with a dichloromethane mixed solution containing 4%-6% methanol were carried out. The elution product was then collected, concentrated and evaporated to dryness, dried in a vacuum oven, thus obtaining the product 35-36: 6.3 g, yield: 67%.

$^1$H-NMR (400 MHz, DMSO-d$_6$) δ 8.52 (d, J=6.8 Hz, 2H), 8.31 (d, J=6.8 Hz, 3H), 8.20 (s, 1H), 8.08 (s, 1H), 7.96 (m, 2H), 7.86 (m, 3H), 7.78-7.54 (m, 4H), 7.54-7.46 (m, 2H), 7.39-7.26 (m, 42H), 4.26-4.16 (m, 11H), 4.12-3.84 (m, 3H), 3.72-3.47 (m, 15H), 3.25-3.10 (m, 10H), 2.99-2.84 (m, 3H), 2.81-2.67 (m, 2H), 2.45-2.34 (m, 13H), 2.23-2.11 (m, 6H), 1.42-1.34 (m, 9H), 1.29-1.24 (d, J=6.6 Hz, 28H).

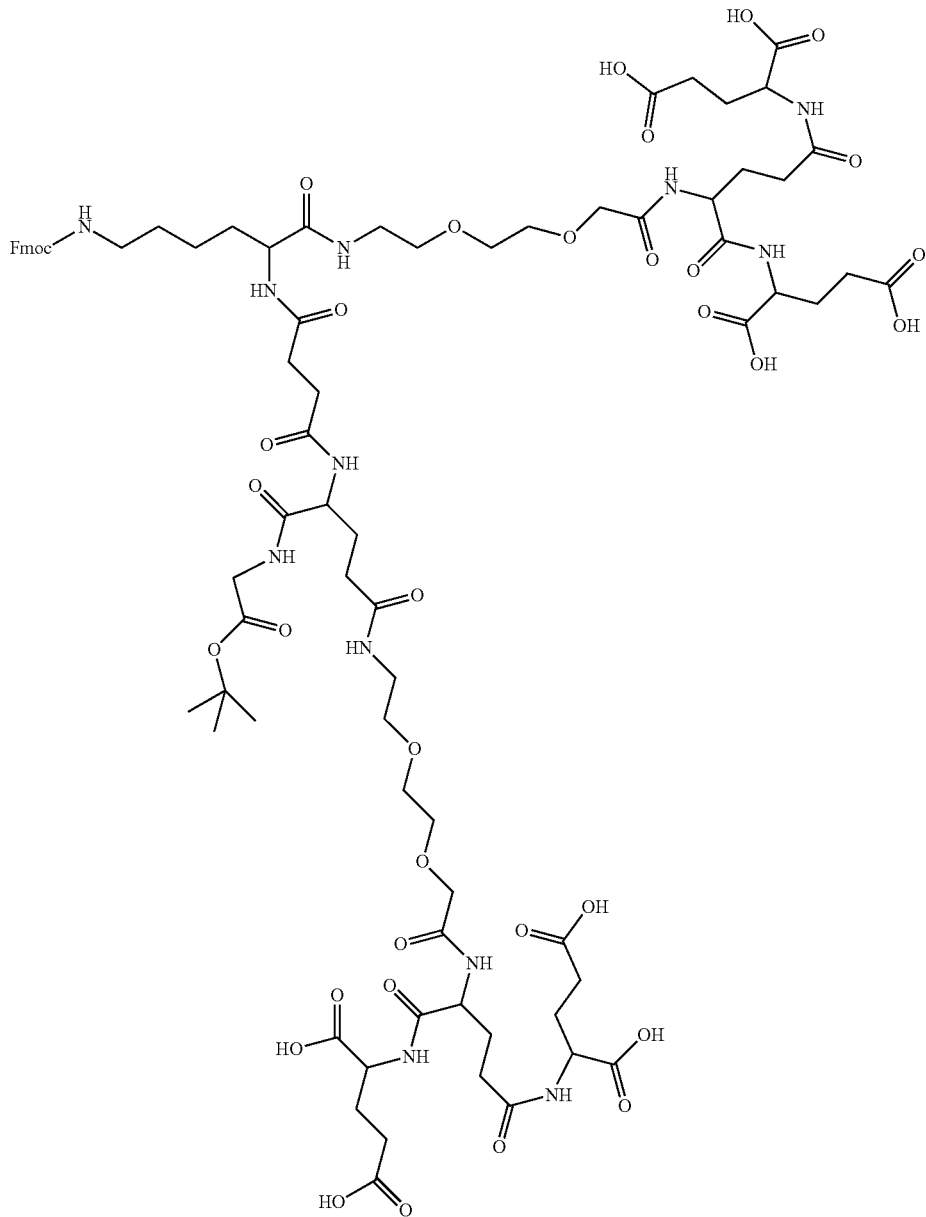

35-48

35-36 (0.463 g, 0.185 mmol) and Pd/C (0.030 g) were added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was taken out, and filtered with diatomaceous earth. The diatomaceous earth was then washed with DMF (20 mL×3), thus obtaining a DMF solution containing C₇.

reaction solution was precipitated three times with n-hexane (150 mL) and methyl tert-butyl ether (40 mL), to obtain a viscous oily product. Then, methyl tert-butyl ether (250 mL) was added to the oily product to separate out a solid, and filtering was carried out. The filter cake was washed with methyl tert-butyl ether (50 mL×3), and dissolved with

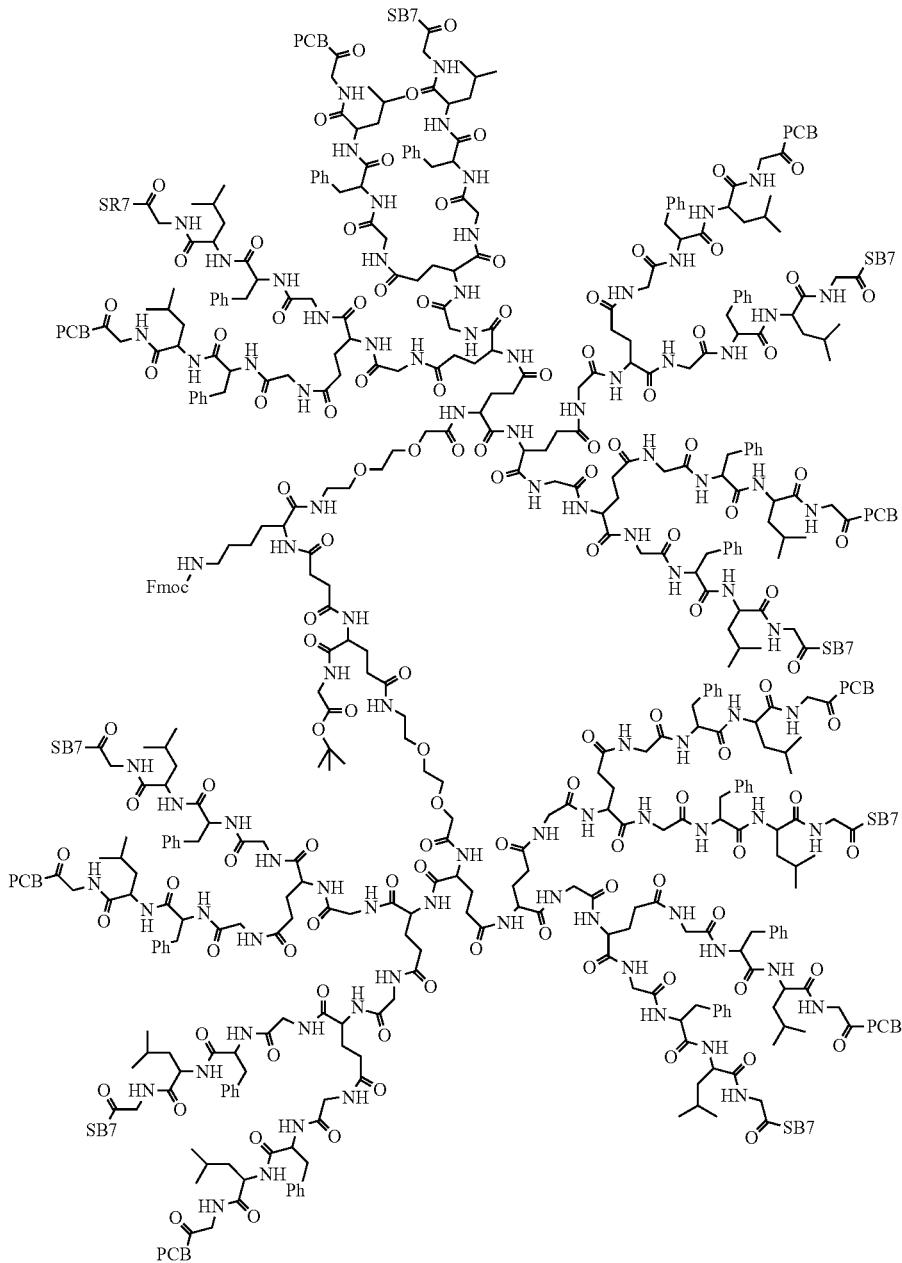

35-49

35-48 (0.329 g, 0.185 mmol), 37-2 (synthesized according to the method of synthesizing 37-2, 3.0 g, 1.594 mmol), HBTU (0.842 g, 2.22 mmol), HOBT (0.3 g, 2.22 mmol) were added in a 250 mL flask, and dissolved with DMF (90 mL), and then the mixed solution was stirred to react at −5° C. for 20 minutes. Then DIEA (1.1 mL, 6.66 mmol) was slowly added dropwise. At the end of the addition, the obtained solution was stirred to react at −5° C. for 30 minutes, and was then moved to room temperature and stirred to react overnight. At the end of the reaction, the dichloromethane (130 mL) and methanol (25 mL), silica gel powder (15 g) was added, and the obtained mixture was then evaporated to dryness to obtain a powdery solid. The operations of dry sample loading, column chromatography and elution with a dichloromethane mixed solution containing 0.5% ammonia water and 5%-12% methanol were carried out. The elution product was then collected, concentrated and dried, thus obtaining the product 35-49: 2.7 g, yield 87%.

35-73

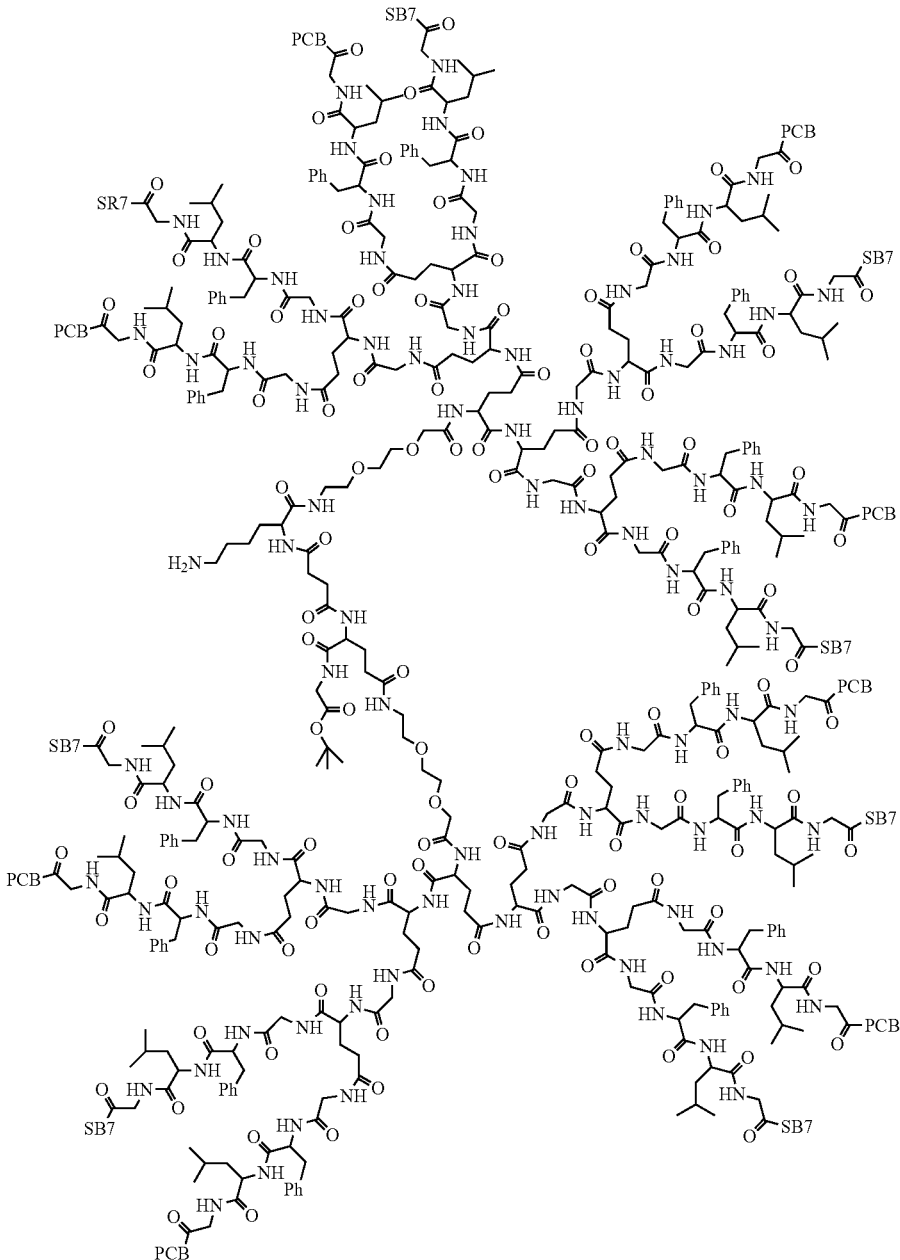

35-49 (2.7 g, 0.1615 mmol) was added in a 250 mL flask, and dissolved with DMF (30 mL) piperidine (0.479 mL, 4.8443 mmol) was added, and then the mixed solution was stirred to react at room temperature for 1 hour. At the end of the reaction, n-hexane (100 mL) and methyl tert-butyl ether (20 mL) were added for precipitation to layer the reaction solution, the supernatant was discarded, and n-hexane (100 mL) and methyl tert-butyl ether (20 mL) were added to the lower oily liquid phase for further precipitation. Such operations were repeated three times, to obtain a viscous oily product. Methyl tert-butyl ether (150 mL) was added to the oily product to separate out a solid, and then filtering was carried out. The filter cake was washed with methyl tert-butyl ether (40 mL×2), and dissolved with dichloromethane (20 mL) and methanol (80 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 5%-7% methanol were carried out, thus obtaining the product 35-73: 1.2 g, yield 45%.

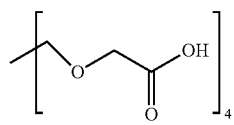

35-74

45-57 (0.118 g, 0.1655 mmol) and Pd/C (0.01 g) were added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was taken out, and filtered with diatomaceous earth. The diatomaceous earth was then washed with DMF (20 mL×3), obtaining a DMF solution containing 35-74.

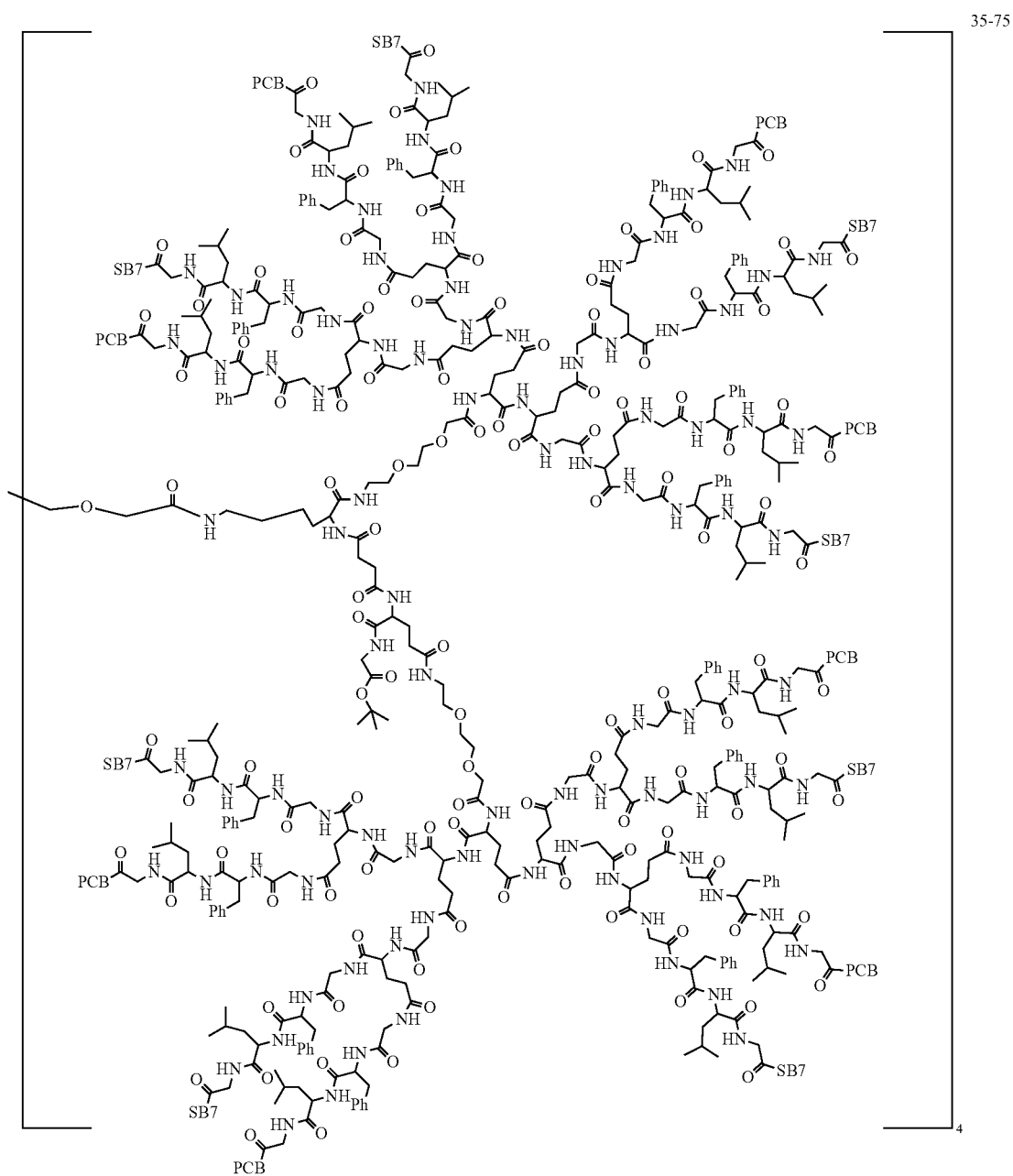

35-75

35-73 (1.2 g, 0.0727 mmol), 35-74 (0.375 g, 0.0165 mmol), HBTU (0.375 g, 0.99 mmol), HOBT (0.134 g, 0.99 mmol) were added in a 250 mL flask, and dissolved with DMF (30 mL), and then the mixed solution was stirred to react at −5° C. for 20 minutes. Then DIEA (0.492 mL, 2.975 mmol) was slowly added dropwise. At the end of the addition, the obtained solution was stirred to react at −5° C. for 30 minutes, and was then moved to room temperature and stirred to react overnight. At the end of the reaction, the reaction solution was precipitated three times with n-hexane (150 mL) and methyl tert-butyl ether (40 mL), to obtain a viscous oily product. Then, methyl tert-butyl ether (250 mL) was added to the oily product to separate out a solid, and filtering was carried out. The filter cake was washed with methyl tert-butyl ether (50 mL×3), and dissolved with dichloromethane (130 mL) and methanol (25 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 6%-9% methanol were carried out. The elution product was then collected, concentrated and dried, thus obtaining the product 35-75: 0.8 g, yield 73%.

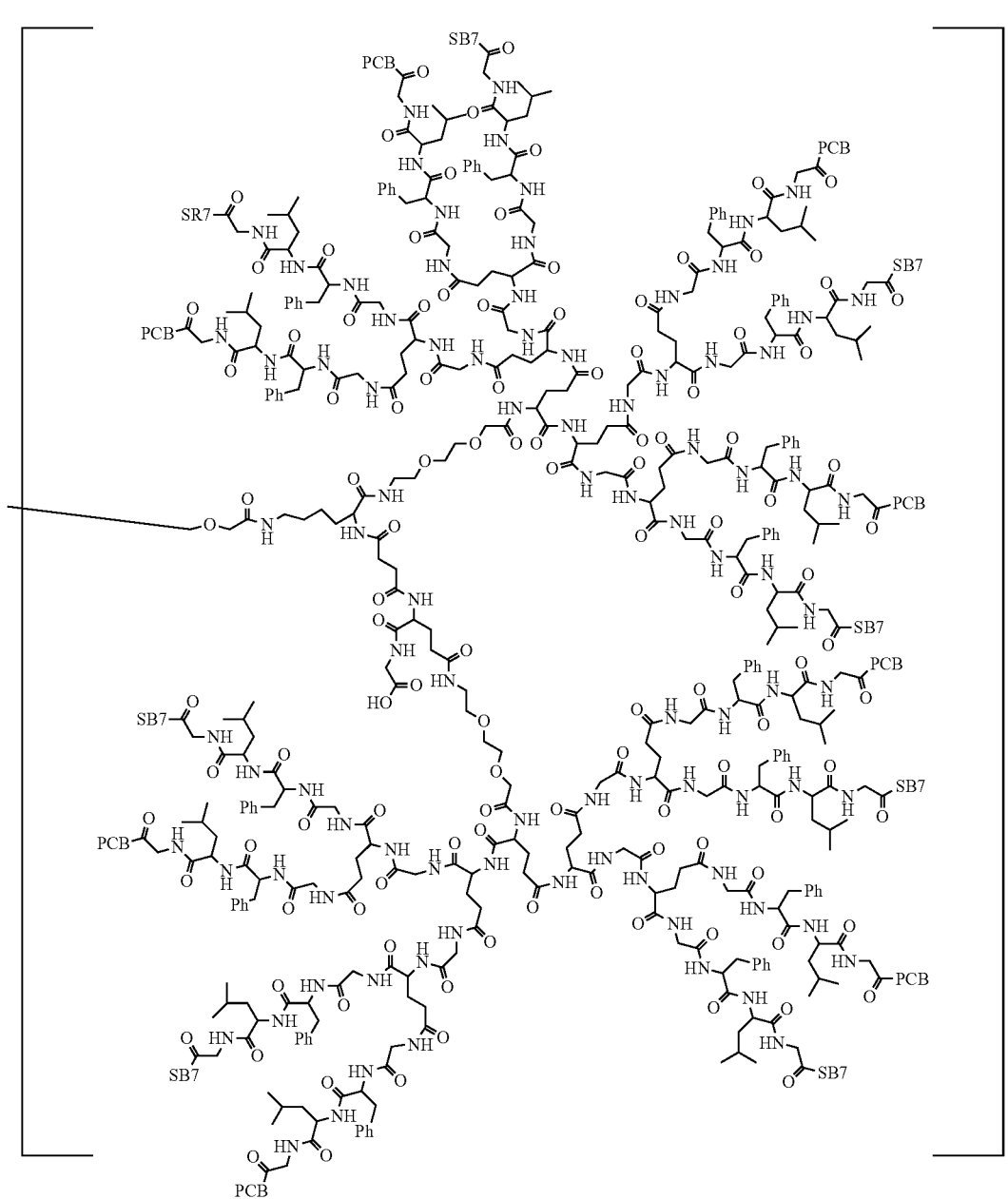

35-75 (0.8 g, 0.012 mmol) was added in a 100 mL flask, and dissolved with dichloromethane (10 mL), TFA (10 mL, 134.65 mmol) was added, and then the mixed solution was stirred to react at room temperature overnight. At the end of the reaction, methyl tert-butyl ether (70 mL) was added to the reaction solution to separate out a solid, and suction filtering was carried out. The filter cake was washed with methyl tert-butyl ether (40 mL×3), and dissolved with a mixed solvent of methanol (20 mL) and dichloromethane (80 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 4%-8% methanol were carried out. The elution product was then collected, concentrated, evaporated to dryness, and dried in a vacuum oven, thus obtaining the product 35-77: 0.4 g, yield 51%.

then the mixed solution was stirred to react at −5° C. at a low speed for about 10 min. Then DIEA (0.1313 mL, 0.7945 mmol) was slowly added dropwise, and the obtained solution continued to react at −5° C. for 20 minutes, and was then moved to room temperature and stirred to react in the dark for 7 days at a low speed. At the end of the reaction, n-hexane (100 mL) and methyl tert-butyl ether (30 mL) were added to the reaction solution for precipitation, the supernatant was discarded, and n-hexane (100 mL) and methyl tert-butyl ether (30 mL) were added to the lower liquid for precipitation. Such operations were repeated three times, to

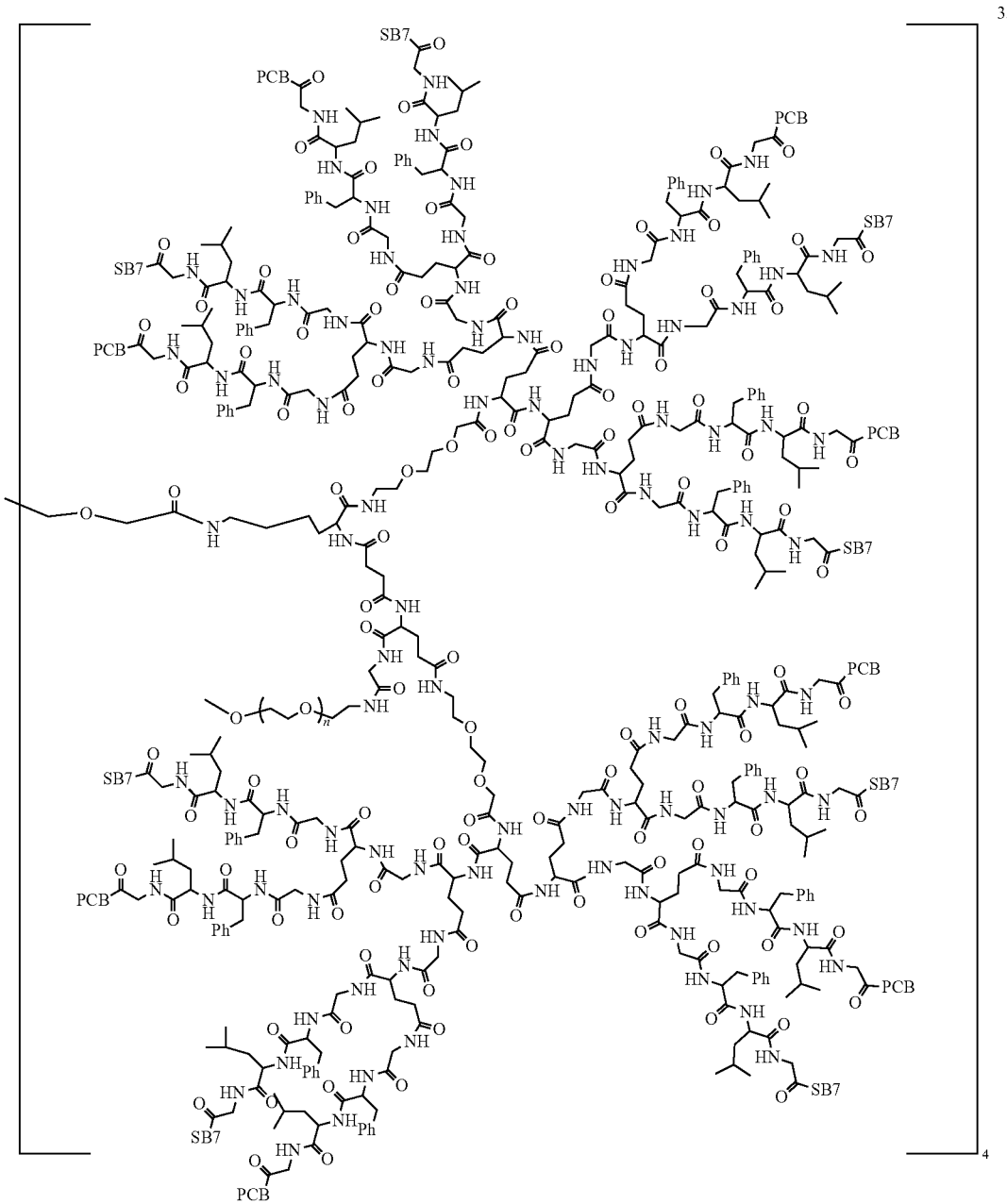

35-78

35-77 (0.4 g, 0.0061 mmol) was added in a 250 mL flask, and dissolved with DMF (25 mL), M-NH₂-20K·HCl (0.379 g, 0.036 mmol, purchased from JenKem), HBTU (0.137 g, 0.36 mmol), HOBT (0.049 g, 0.36 mmol) were added, and obtain a viscous oily product. Methyl tert-butyl ether (100 mL) was added to the oily product to separate out a solid, and filtering was carried out. The filter cake was washed with methyl tert-butyl ether (30 mL×3), and dissolved with a mixed solvent of methanol (40 mL) and dichloromethane (160 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 4%-7% methanol were carried out. The elution product was then collected, concentrated, evaporated to dryness, dried in a vacuum oven for 1 hour, and dissolved with anhydrous ethanol (2 mL) and dichloromethane (30 mL). Then, methyl tert-butyl ether (140 mL) was added to the obtained solution to separate out a solid, and filtering was carried out. The filter cake was washed with methyl tert-butyl ether (50 mL×2), and dried in a vacuum oven, thus obtaining the product 35-78: 0.46 g, yield: 70%.

$^1$H-NMR (600 MHz, DMSO-$d_6$) δ 10.23-9.98 (m, 34H), 9.12-8.76 (m, 32H), 8.25-8.13 (m, 116H), 8.12-7.95 (m, 240H), 7.84-7.64 (m, 95H), 7.57-7.31 (m, 99H), 7.21-6.91 (m, 630H), 5.88-5.63 (m, 56H), 4.76-4.48 (m, 64H), 4.33-4.26 (m, 154H), 4.05-3.83 (m, 116H), 3.71-3.62 (m, 241H), 3.59-3.41 (m, 3840H), 3.42-3.37 (m, 91H), 3.27-3.21 (m, 393H), 3.19-3.11 (m, 149H), 3.09-3.93 (m, 72H), 2.85-2.73 (m, 102H), 2.52-2.42 (m, 116H), 2.34-2.07 (m, 369H), 1.91-1.84 (m, 120H), 1.78-1.63 (m, 123H), 1.61-1.52 (m, 265H), 1.29-0.92 (m, 89H), 0.85-0.63 (m, 461H), 0.60-0.47 (m, 81H).

10. Synthesis of 33-200 (Compound No. 5)

Synthetic route is as follows

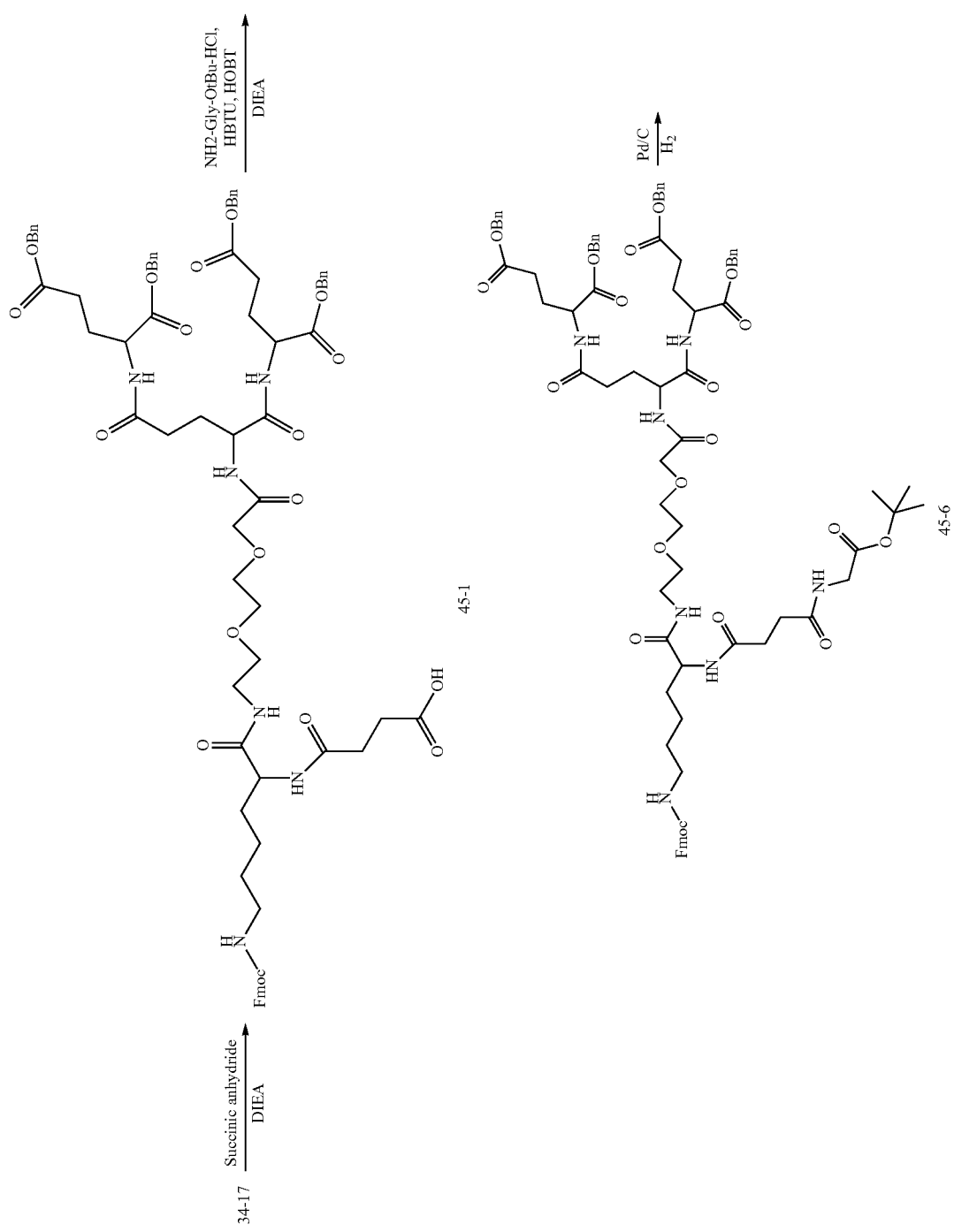

-continued
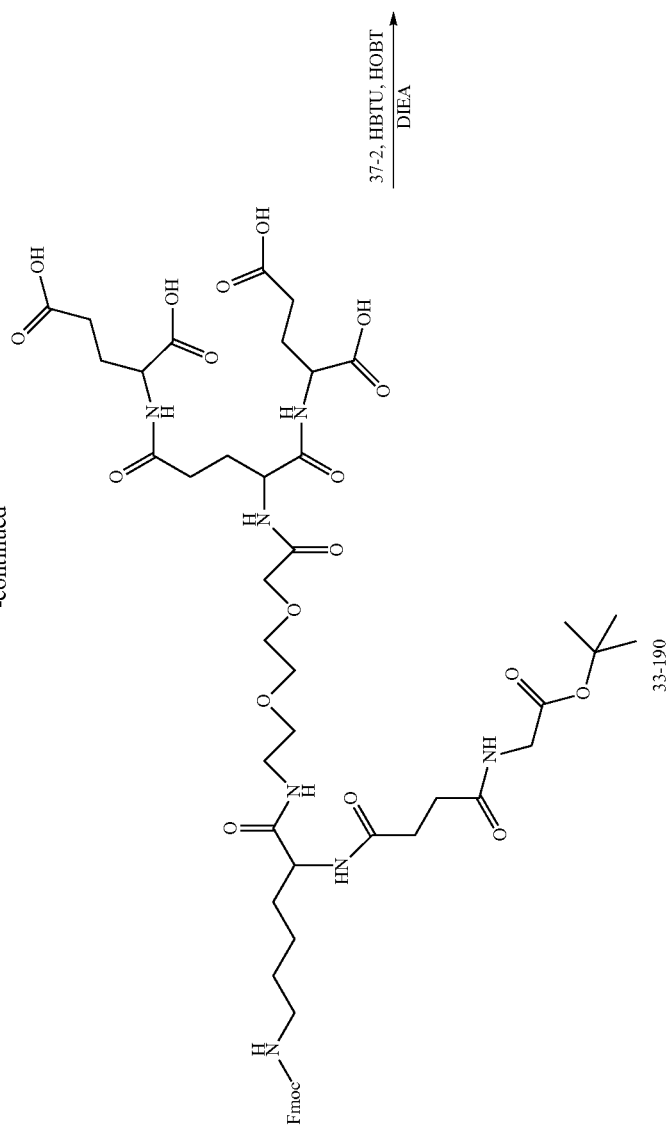

-continued
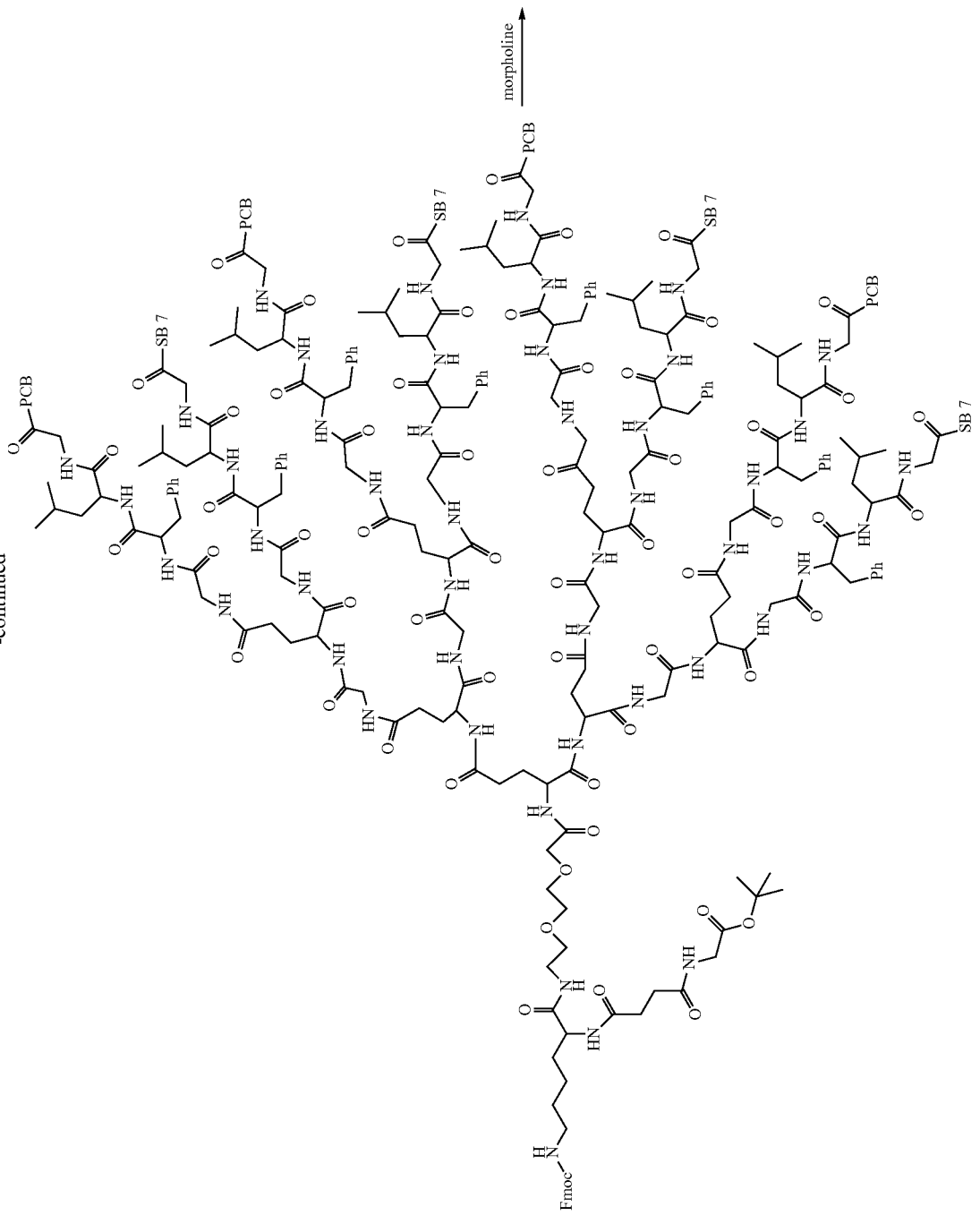

-continued
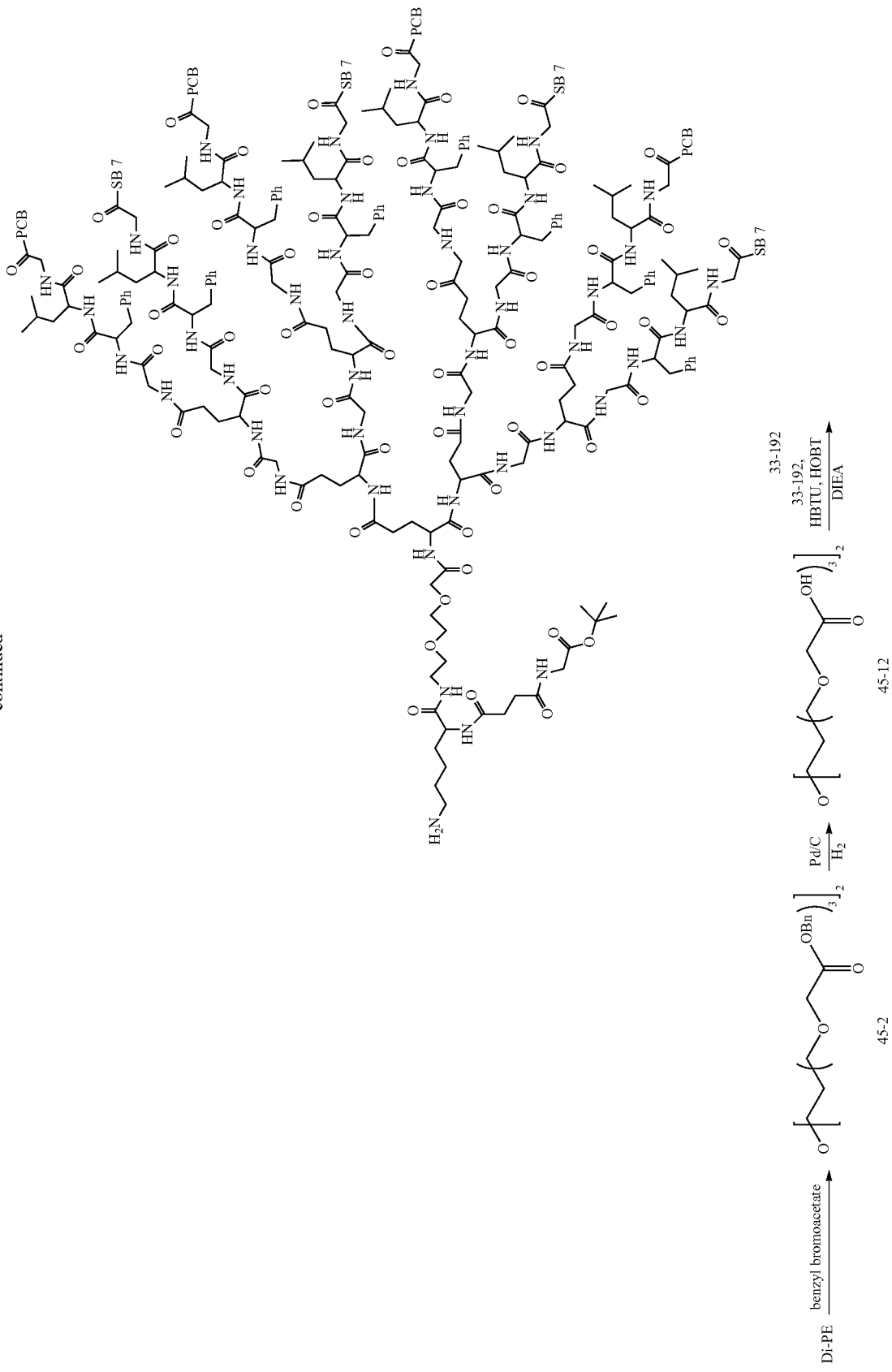

-continued
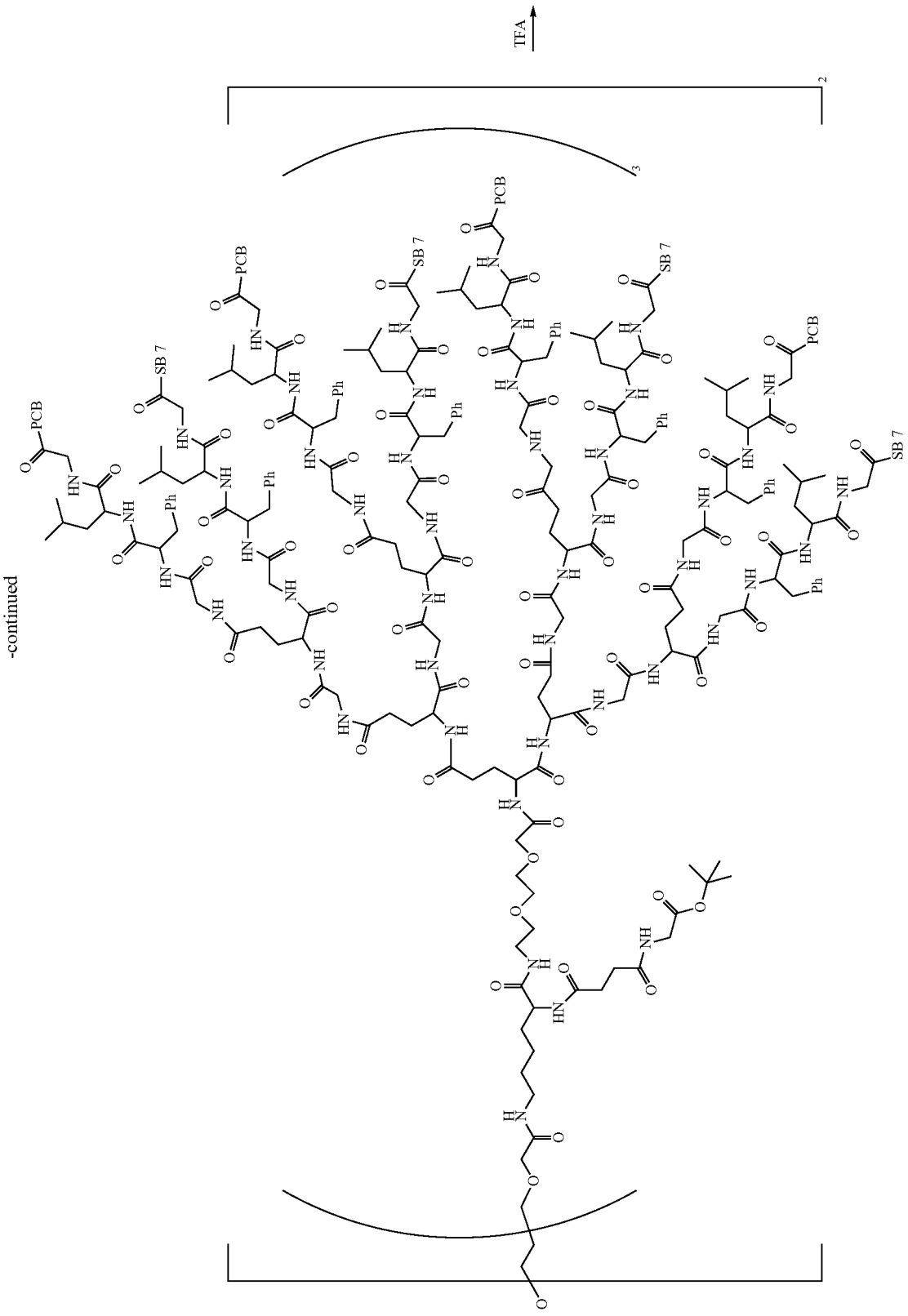

-continued
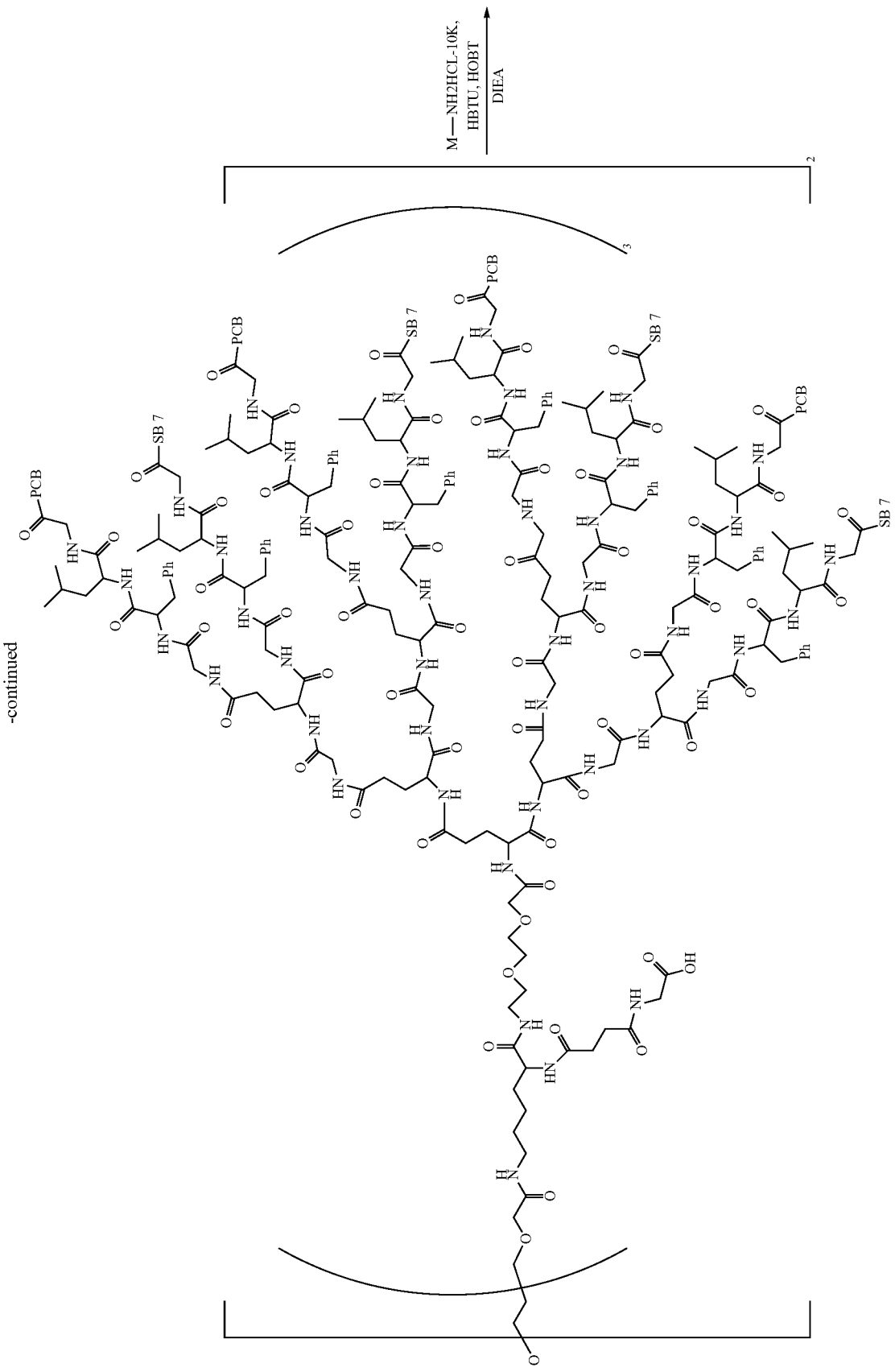

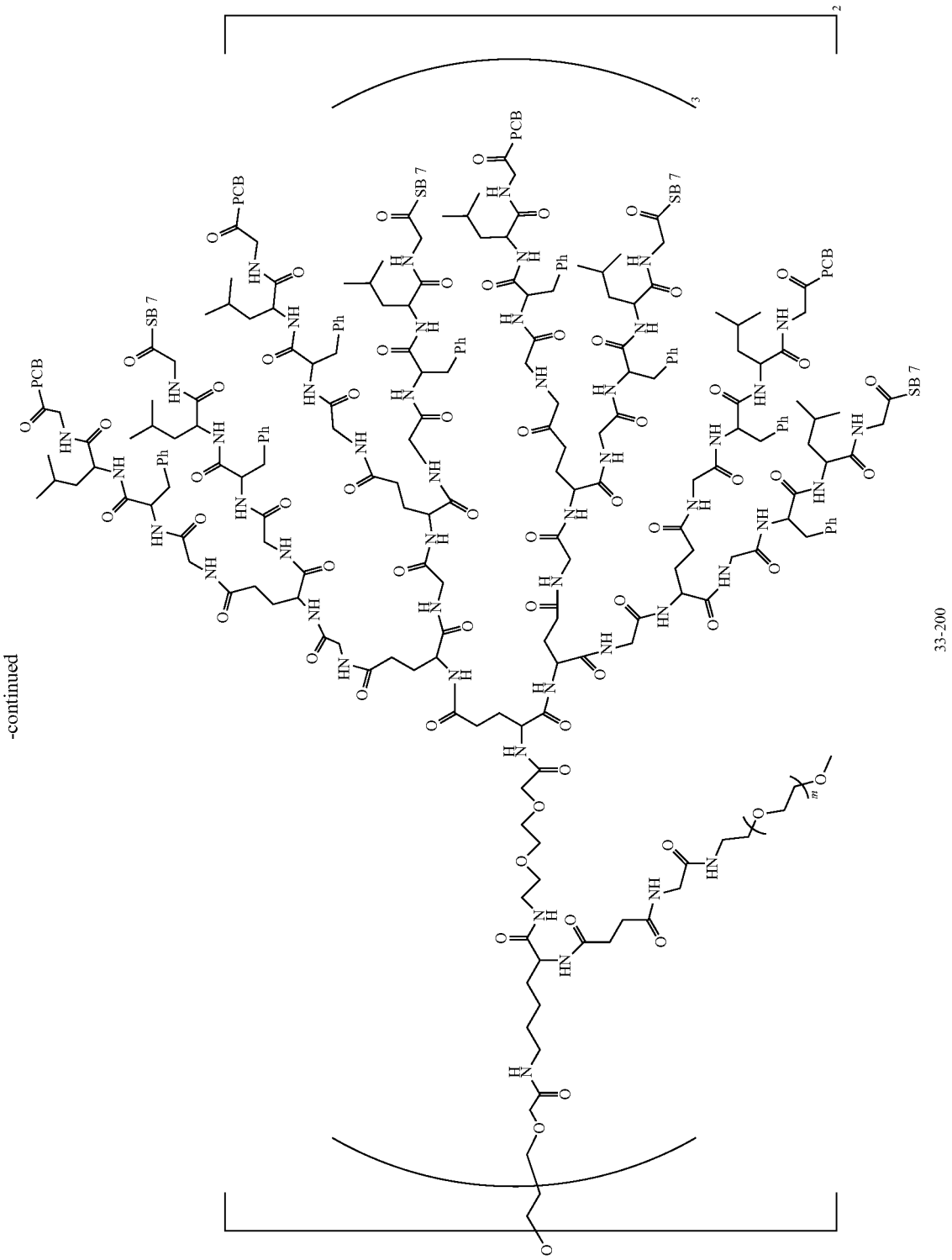

-continued
45-1
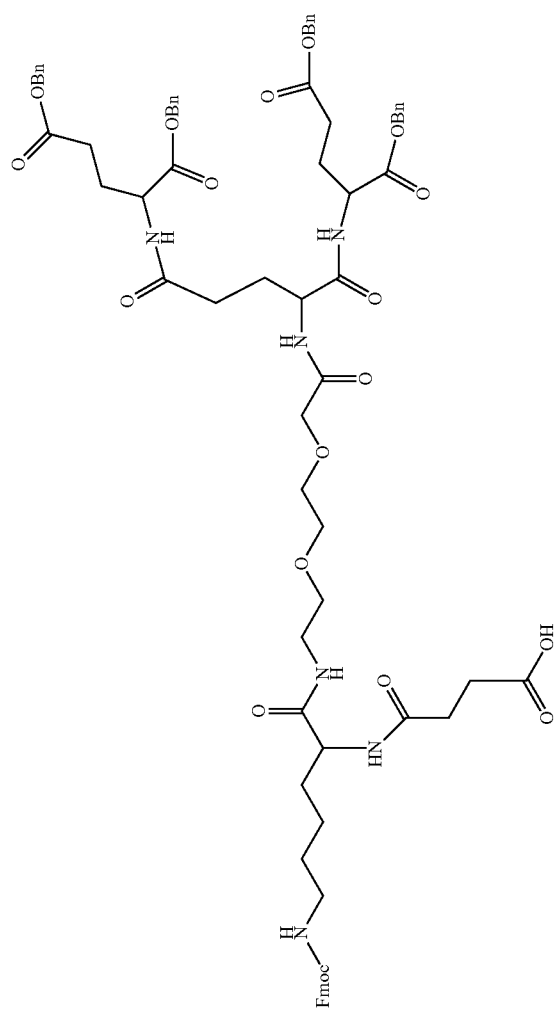

24-143 (synthesized according to the method of synthesizing 34-17, 5 g, 3.6723 mmol) was added in a 250 mL round-bottomed flask, and dissolved with DMF (20 mL), the obtained solution was placed in a low-temperature and constant temperature bath at −5° C. Then, DIEA (2.5390 mL, 18.3615 mmol) was added, and then the mixed solution was stirred to react at room temperature for 30 minutes. Succinic anhydride (1.1025 g, 11.0170 mmol) was added, and, after 1 hour, the obtained solution reacted at room temperature. At the end of the reaction, the reaction solution was transferred to a 1 L separatory funnel, ethyl acetate (200 mL) and deionized water (150 mL) were added for extraction, and the organic phase was separated. The aqueous phase was extracted two times with ethyl acetate (100 mL×2) until there was no product in the aqueous phase, and the obtained organic phases were combined. The organic phase was washed one time with saturated saline solution (100 mL), concentrated, and evaporated to dryness, thus obtaining the product 5 g, extra-quota 0.1 g, yield 100%.

phase was separated. The aqueous phase was extracted two times with ethyl acetate (100 mL×2) until there was no product in the aqueous phase, and the obtained organic phases were combined. The organic phase was washed one time with saturated saline solution (100 mL), and concentrated, silica gel powder was added, and the operations of evaporation, column chromatography and elution with 50%-100% ethyl acetate/petroleum ether were carried out, thus obtaining the product 3.5 g, yield 66%.

$^1$H-NMR (400 MHz, DMSO-d$_6$) δ 8.34-8.18 (m, 2H), 8.01-7.85 (m, 4H), 7.72-7.64 (m, 3H), 7.43-7.22 (m, 26H), 5.14-5.03 (m, 8H), 4.41-4.06 (m, 8H), 3.94-3.86 (m, 2H), 3.71-3.66 (m, 2H), 3.58-3.49 (m, 4H), 3.42-3.36 (m, 2H), 3.22-3.13 (m, 3H), 2.98-2.88 (m, 2H), 2.47-1.81 (m, 17H), 1.39-1.37 (m, 9H), 1.28-1.20 (m, 3H).

MALDI-TOF MS: [M+H$^+$]1474.70, [M+Na$^+$]1496.70.

45-6

33-190

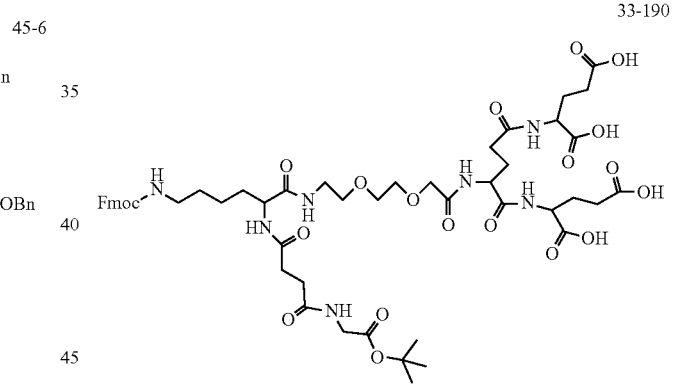

Reactants 45-1 (4.9 g, 3.5990 mmol), NH$_2$-Gly-OtBuHCl (purchased from Accela, 0.4721 g, 3.5990 mmol), HBTU (2.0473 g, 5.3985 mmol), HOBT (0.7294 g, 5.3985 mmol) were added in a 250 mL flask, and dissolved with DMF (30 mL), and then the mixed solution was stirred to react at −5° C. for 30 minutes. Then DIEA (4 mL, 24.2933 mmol) was slowly added dropwise, and the obtained solution reacted at the low temperature until the reaction ended. At the end of the reaction, the reaction solution was transferred to a 1 L separatory funnel, ethyl acetate (200 mL) and deionized water (150 mL) were added for extraction, and the organic Reactants 45-6 (0.4702 g, 0.3189 mmol) and 10% Pd/C (50 mg) were added in a micro-reactor, and dissolved with DMF (30 mL), H$_2$ (20 psi) was introduced, and then the mixed solution was stirred to react. At the end of the reaction, the reaction solution was filtered by suction with diatomaceous earth as a filter cake to remove the Pd/C, and then the diatomaceous earth was washed 3-4 times with DMF to obtain the DMF solution of the product for the next reaction.

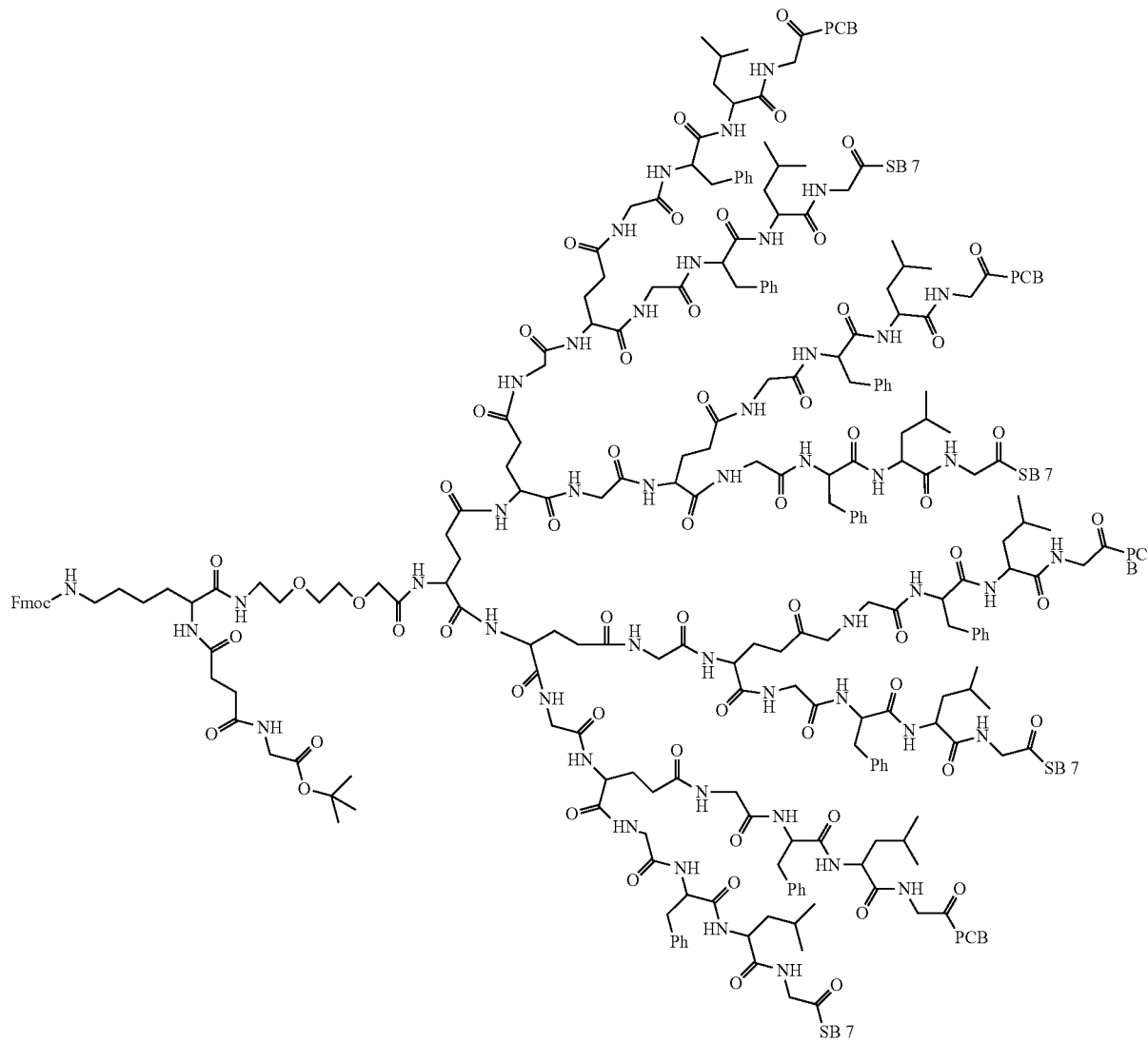

33-162 (synthesized according to the method of synthesizing 37-2, 3 g, 1.5944 mmol), HBTU (0.7256 g, 1.9134 mmol), HOBT (0.2585 g, 1.9134 mmol) were added in a 250 mL flask, and dissolved with a DMF solution of 33-190, and ultrasonic treatment was carried out to completely dissolve the reactants, and then the obtained solution was stirred at −5° C. for 30 minutes. Then DIEA (0.9487 mL, 5.7402 mmol) was slowly added dropwise, and the obtained solution reacted at the low temperature until the reaction ended. At the end of the reaction, methyl tert-butyl ether (100 mL), n-hexane (150 mL) were added to the reaction solution, ultrasonic treatment was carried out for 5 minutes, the obtained solution was placed in a refrigerator, stood still for 20 minutes, the supernatant was discarded, ethyl acetate (20 mL) was added to the lower liquid, ultrasonic treatment was carried out for 2 minutes, n-hexane (100 mL) was added to the obtained solution, and suction filtering was carried out. The filter cake was dissolved with 20% methanol/dichloromethane (70 mL), silica gel powder was added, and the operations of evaporation, column chromatography and gradient elution with 1% ammonia water: 5% methanol/dichloromethane-1% ammonia water: 10% methanol/dichloromethane were carried out, thus obtaining the product 1.9 g, yield 70%.

33-192

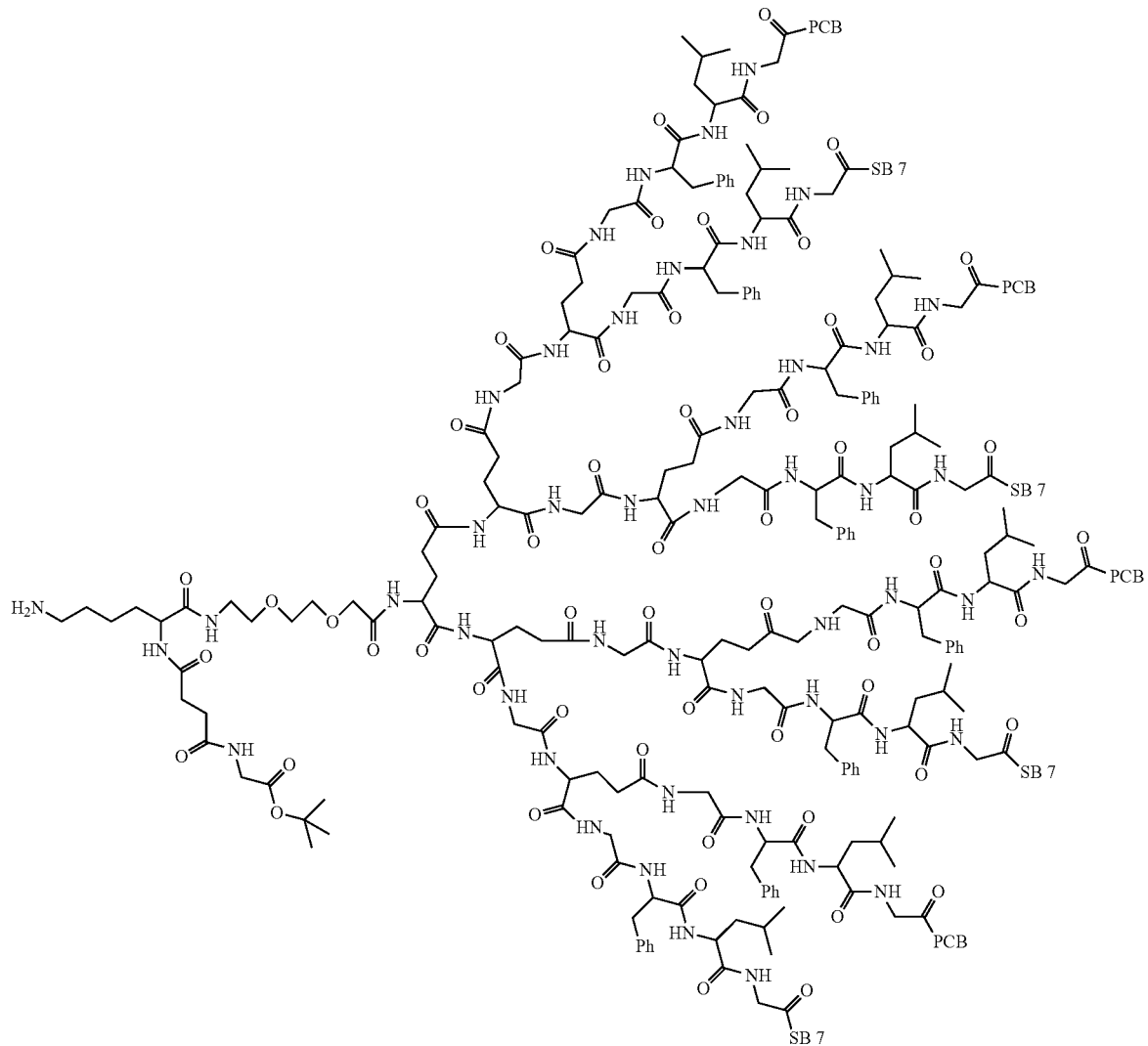

33-191 (1.9 g, 0.2218 mmol) was added in a 250 mL round-bottomed flask, and dissolved with DMF (20 mL), morpholine (0.5796 mL, 6.6540 mmol) was added, and then the mixed solution was stirred to react at room temperature. At the end of the reaction, methyl tert-butyl ether (150 mL), n-hexane (100 mL) were added to the reaction solution, ultrasonic treatment was carried out for 5 minutes, and suction filtering was carried out. The filter cake was dissolved with 20% methanol/dichloromethane (50 mL), silica gel powder was added to the obtained solution, and the operations of evaporation, column chromatography and elution with 1% ammonia water: 7%/dichloromethane-1% ammonia water: 15% methanol/dichloromethane were carried out, thus obtaining the product 1.3 g, yield 72%.

45-2

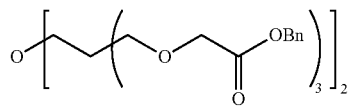

Dipentaerythritol (purchased from ACROS, 5 g, 19.6634 mmol) was added in a 500 mL flask, nitrogen was introduced for protective purpose, the THF solution of potassium tert-butoxide (141.57 mL, 141.5762 mmol) was added, and the obtained solution was stirred at 0° C. for 1 hour. phenyl bromoacetate (30.4445 g, 141.5762 mmol) was added, and then the obtained solution was stirred to react for 3 hours, and then reacted at room temperature. At the end of the reaction, the reaction solution was first evaporated to dryness, then deionized water and ethyl acetate were added for extraction, and the organic phase was separated. The aqueous phase was extracted with ethyl acetate until there was no product in the aqueous phase, and the obtained organic phases were combined. The organic phase was dried with anhydrous sodium sulfate powder, suction filtering was carried out, and the operations of dry sample loading, column chromatography and gradient elution with 3%-5% ethyl acetate/petroleum ether were carried out, thus obtaining the product 13.9 g, yield 62%.

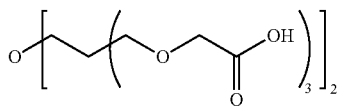

45-12

Reactants 45-2 (0.2541 g, 0.0223 mmol) and 10% Pd/C (50 mg) were added in a micro-reactor, and dissolved with DMF (30 mL), H$_2$ (20 psi) was introduced, and then the mixed solution was stirred to react. At the end of the reaction, the reaction solution was filtered by suction with diatomaceous earth as a filter cake to remove the Pd/C, and then the diatomaceous earth was washed 3-4 times with DMF to obtain the DMF solution of the product for the next reaction.

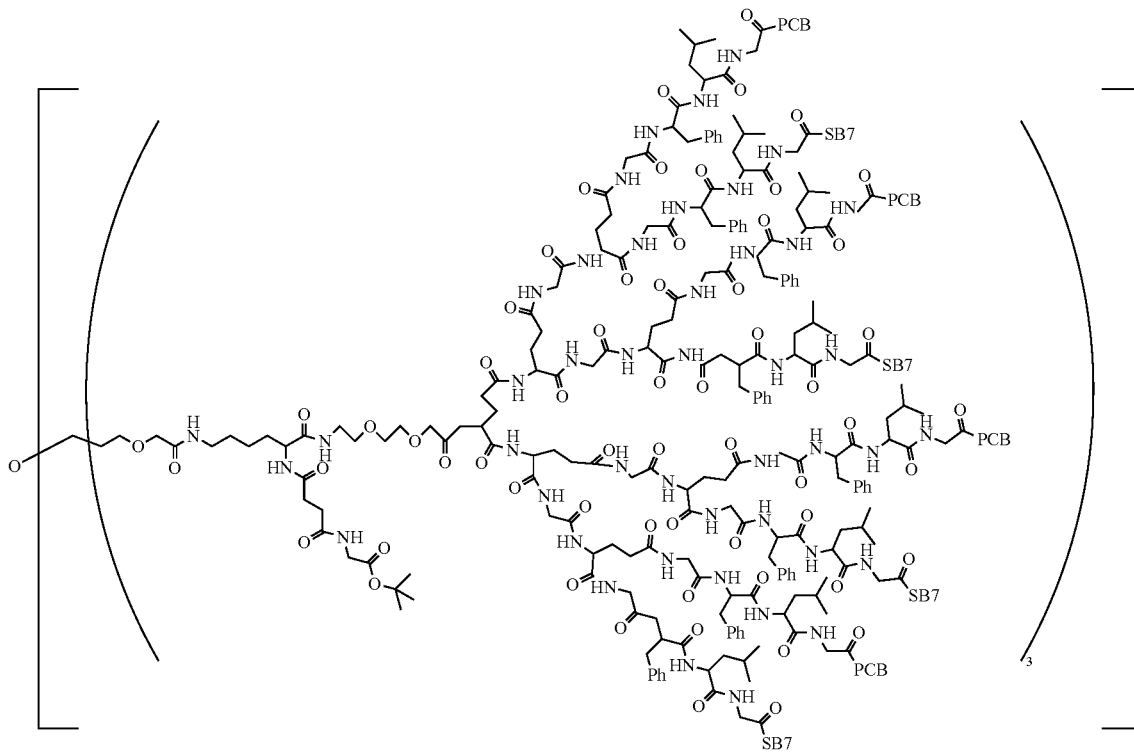

33-195

33-192 (1.3 g, 0.1558 mmol), HBTU (0.0761 g, 0.2007 mmol), HOBT (0.0271 g, 0.2007 mmol) were added in a 250 mL flask, and dissolved with a DMF solution of 45-12, and ultrasonic treatment was carried out to completely dissolve the reactants, and then the obtained solution was stirred at −5° C. for 30 minutes. Then DIEA (0.0995 mL, 0.6021 mmol) was slowly added dropwise, and the obtained solution reacted at the low temperature until the reaction ended. At the end of the reaction, methyl tert-butyl ether (100 mL), n-hexane (150 mL) were added to the reaction solution, ultrasonic treatment was carried out for 5 minutes, the obtained solution was placed in a refrigerator, stood still for 20 minutes, the supernatant was discarded, ethyl acetate (20 mL) was added to the lower liquid, ultrasonic treatment was carried out for 2 minutes, n-hexane (100 mL) was added to the obtained solution, and suction filtering was carried out. The filter cake was dissolved with 20% methanol/dichloromethane (70 mL), silica gel powder was added to the obtained solution, and the operations of evaporation, column chromatography and gradient elution with 1% ammonia water: 5% methanol/dichloromethane-1% ammonia water: 15% methanol/dichloromethane were carried out, thus obtaining the product 0.8 g, yield 53%.

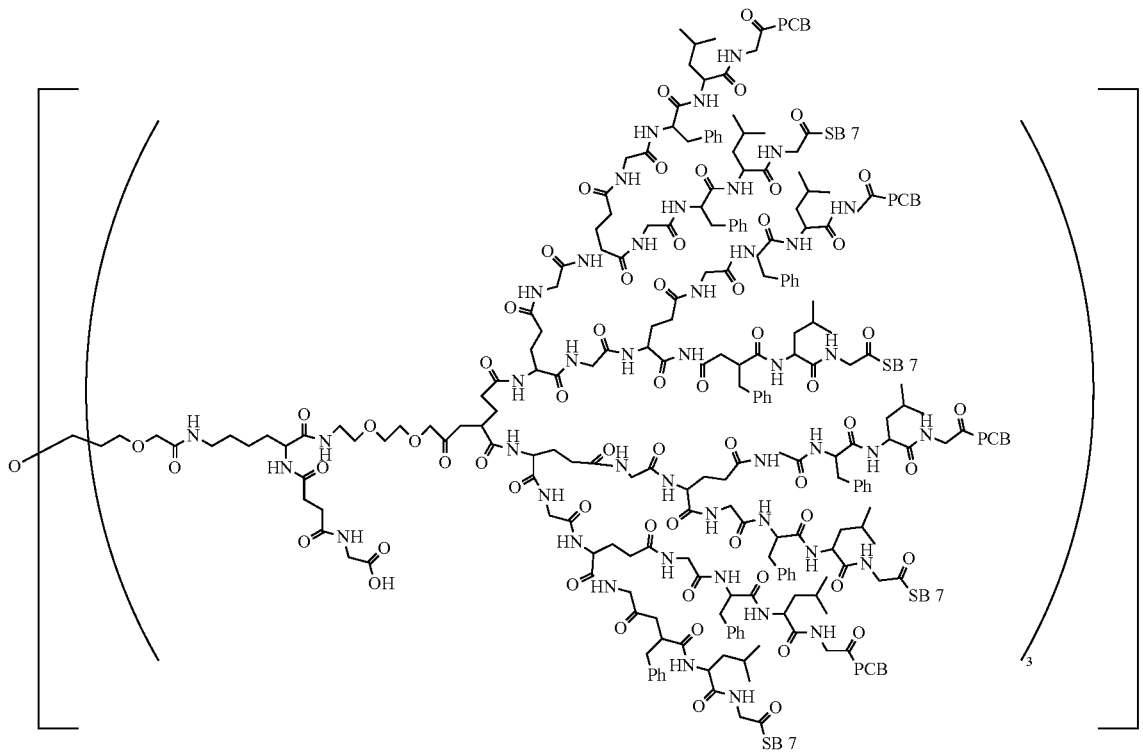

33-197

33-195 (0.8 g, 0.0158 mmol) was dissolved with dichloromethane (10 mL), TFA (0.03572 mL, 0.4749 mmol) was added, and ultrasonic treatment was carried out to completely dissolve the compound. A ground glass stopper was used, and the mixed solution was stirred to react at room temperature. At the end of the reaction, methyl tert-butyl ether (150 mL) and n-hexane (100 mL) were directly added to the reaction solution, and suction filtering was carried out. The filter cake was dried in vacuum, thus obtaining the product 0.6 g, yield 75%.

33-200

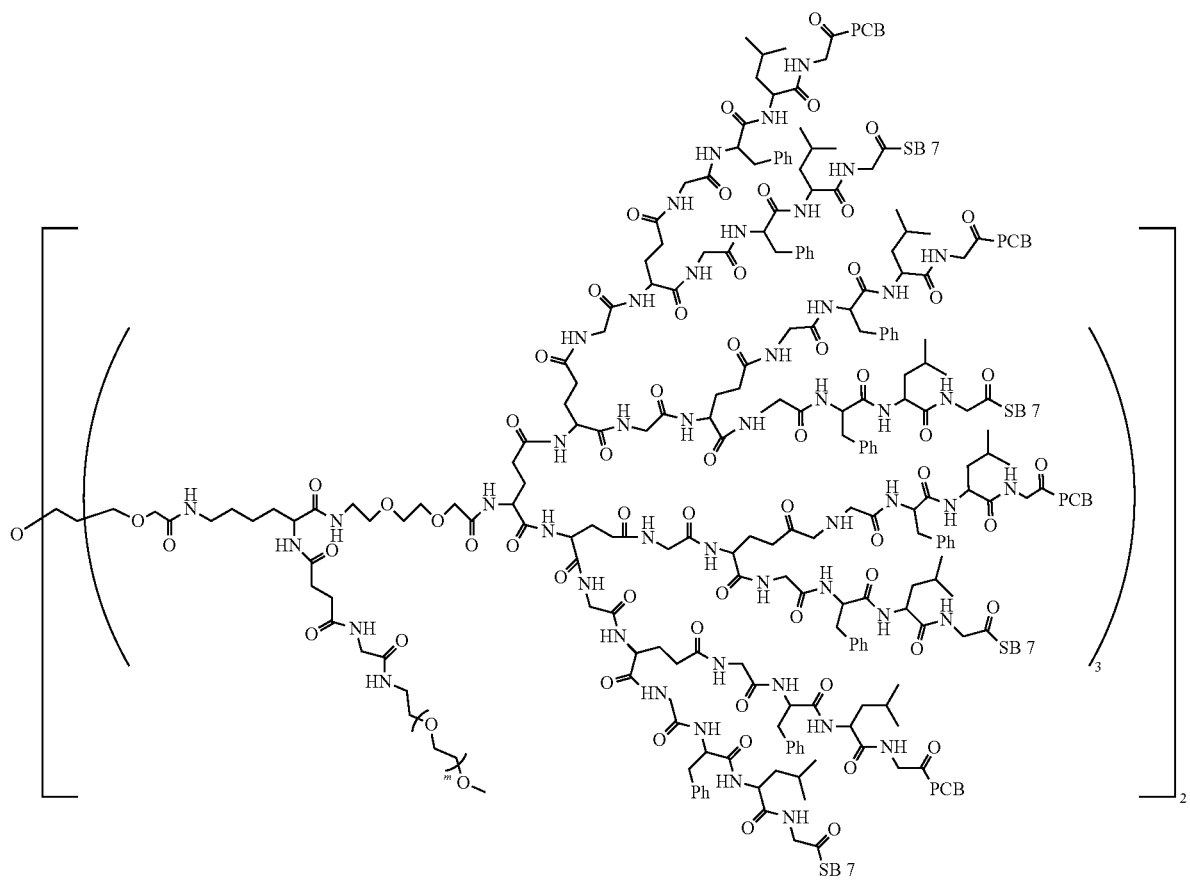

Reactants 33-197 (0.6 g, 0.0119 mmoL), M-NH$_2$HCL-10K (0.1 g, 0.0099 mmoL), HBTU (0.0056 g, 0.0149 mmoL), HOBT (0.0020 g, 0.0149 mmoL) were added in a 250 mL flask, and dissolved with DMF (15 mL) in a condition of ultrasonic, and then the obtained solution was stirred at −5° C. for 30 minutes. Then DIEA (0.0073 mL, 0.0446 mmoL) was slowly added dropwise, the obtained solution was stirred for 1 hour, and then reacted at room temperature in the dark at a low speed. At the end of the reaction, methyl tert-butyl ether (200 mL) was added to the reaction solution for precipitation, and suction filtering was carried out to obtain a powder product. The powder product was dissolved with a mixed solvent of 20% methanol/dichloromethane, and silica gel powder (3 g) was added to the obtained solution. The operations of evaporation, dry sample loading, column chromatography and gradient elution with 6% methanol/dichloromethane-1% ammonia water: 10% methanol/dichloromethane were carried out. The elution product was then collected and evaporated to dryness, the obtained solid was dissolved with dichloromethane (5 mL) in a condition of ultrasonic, methyl tert-butyl ether (150 mL), n-hexane (50 mL) were added to the obtained solution, and suction filtering was carried out. The filter cake was further dissolved with dichloromethane, methyl tert-butyl ether and n-hexane were added for precipitation, and The process of dissolution and precipitation was repeated three times, thus obtaining the product 0.5 g, yield 71%.

$^1$H-NMR (600 MHz, DMSO-d$_6$) δ 10.17-10.13 (m, 18H), 8.97-8.93 (m, 32H), 8.25-7.88 (m, 412H), 7.59-7.48 (m, 93H), 7.32-7.16 (m, 459H), 5.92-5.67 (m, 58H), 4.40-3.99 (m, 672H), 3.51-3.50 (m, 3560H), 3.29-2.99 (m, 344H), 2.94-2.64 (m, 264H), 2.45-2.05 (m, 133H), 1.93-1.06 (m, 301H), 0.99-0.74 (m, 432H).

11. Synthesis of 40-123 (Compound No. 7)

Synthetic route is as follows

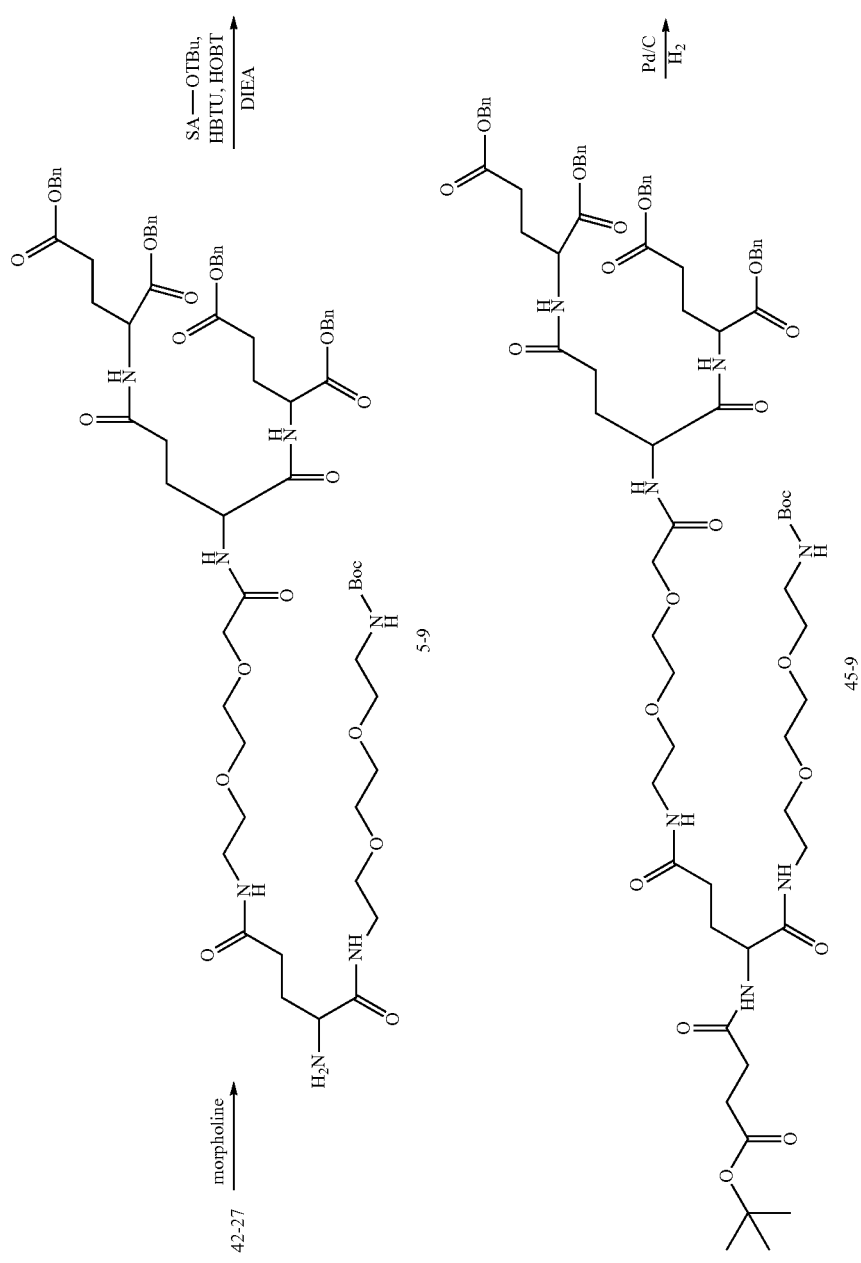

-continued
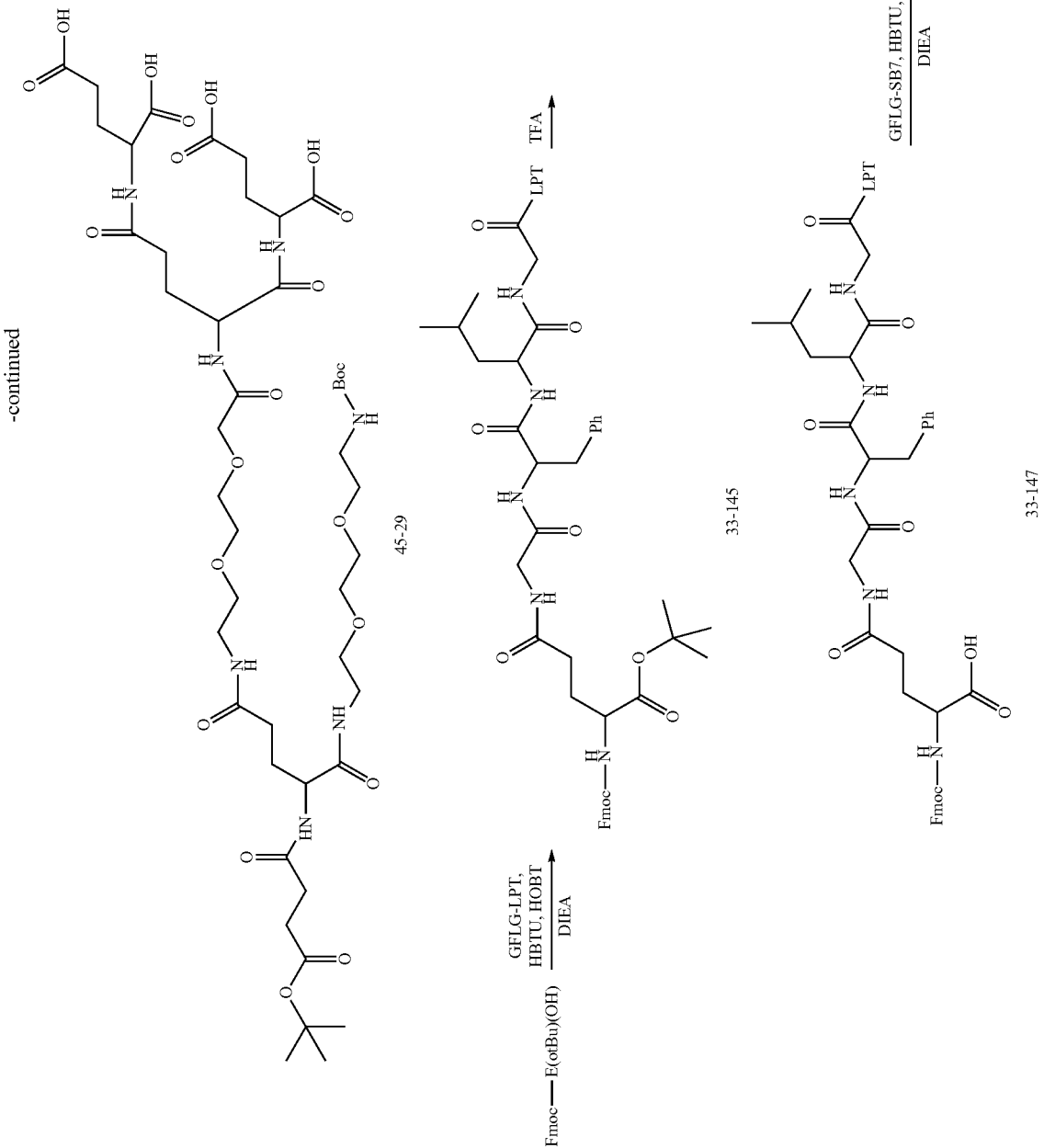

-continued
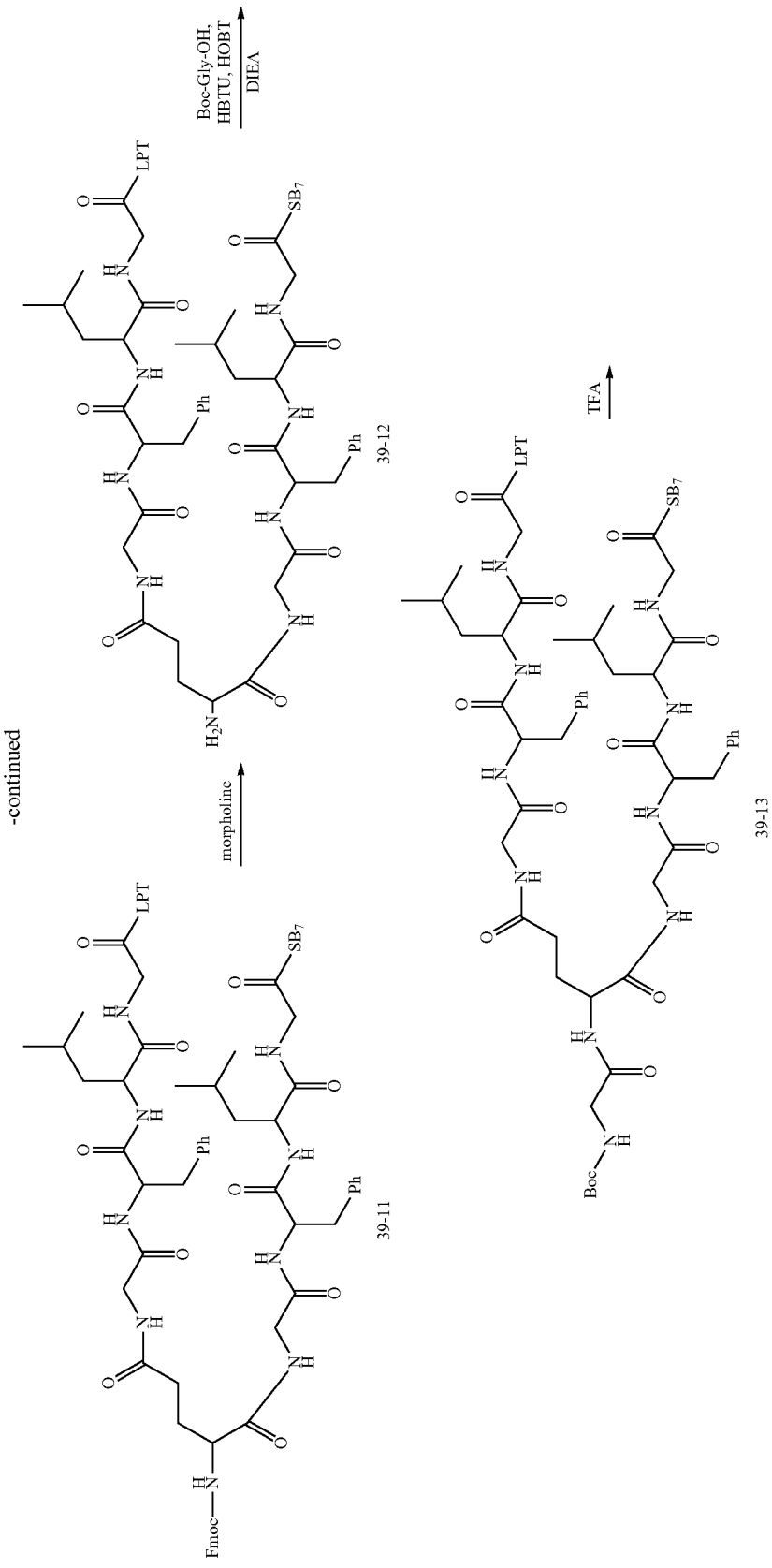

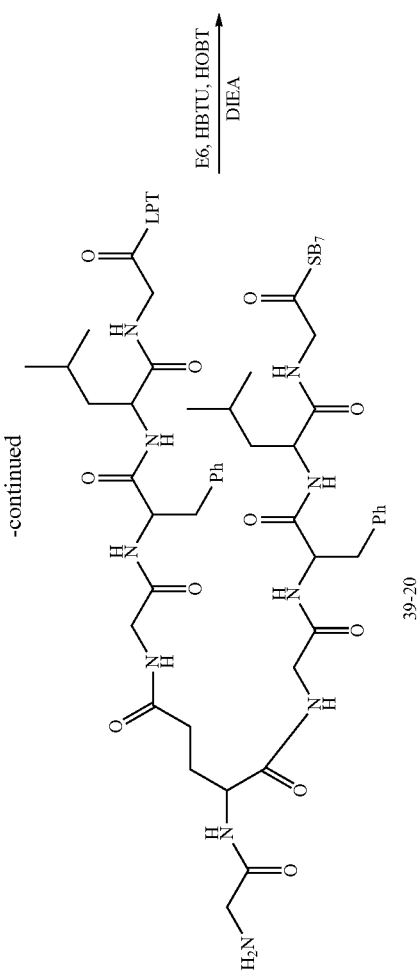

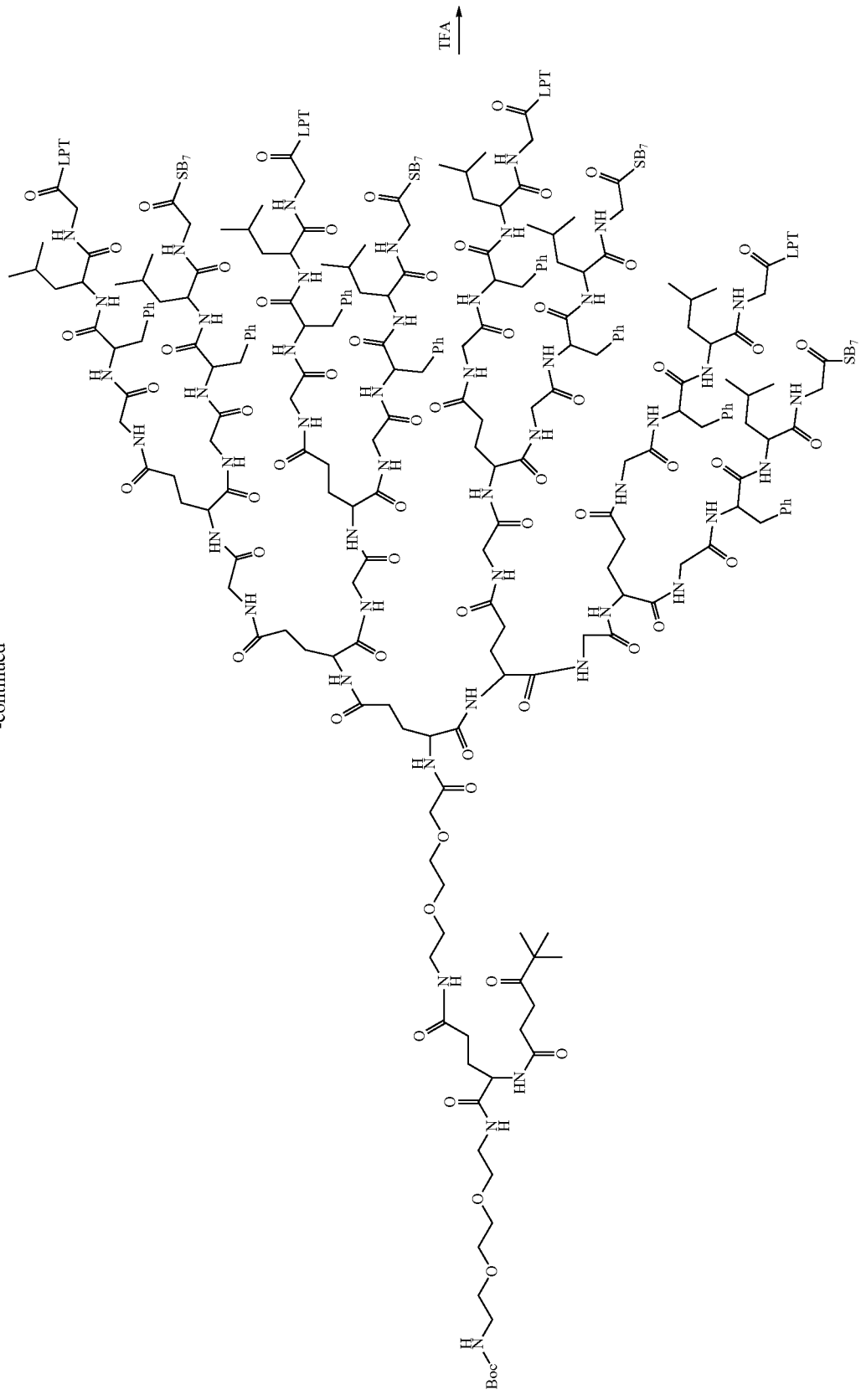

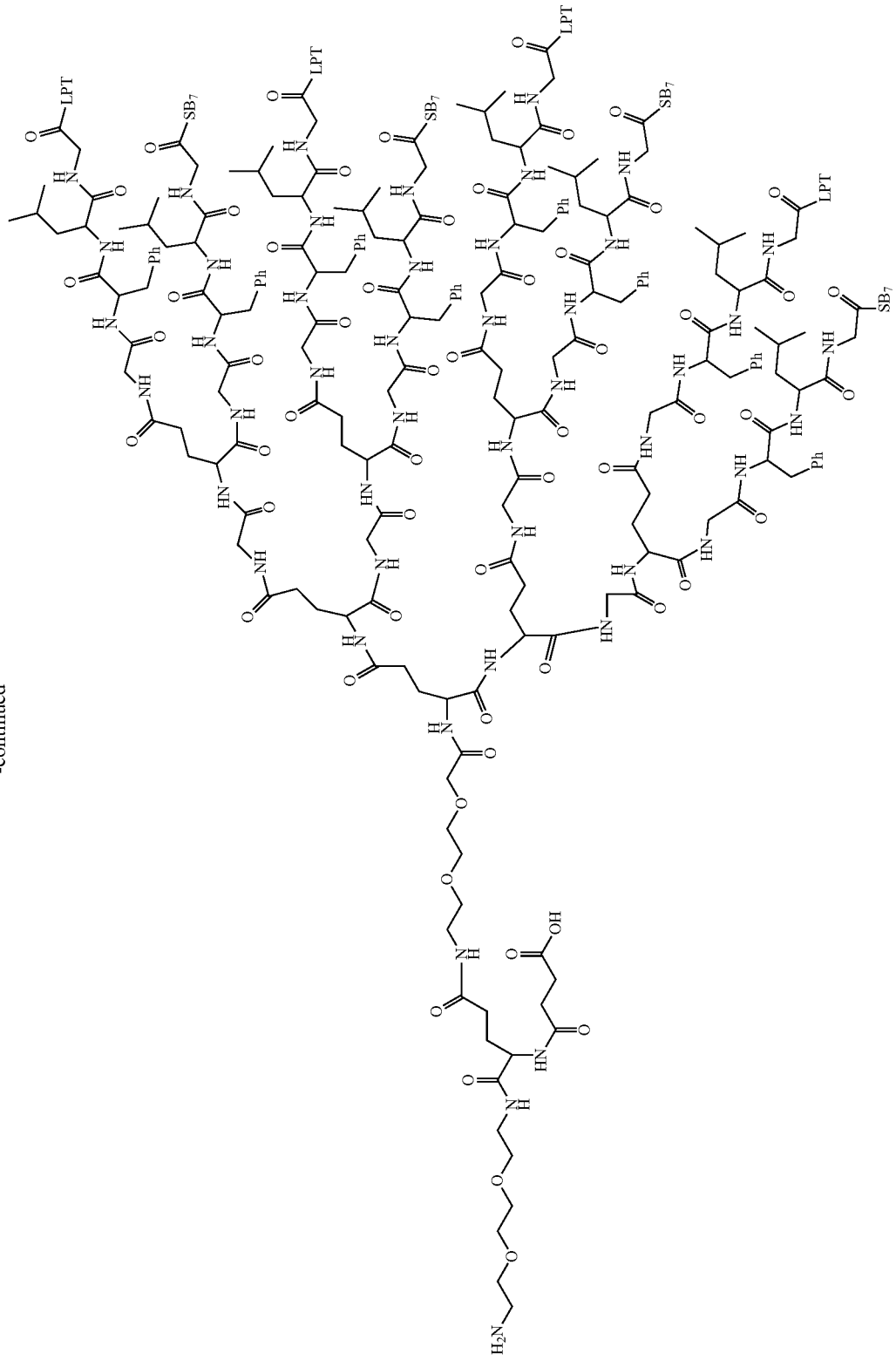
45-35

-continued
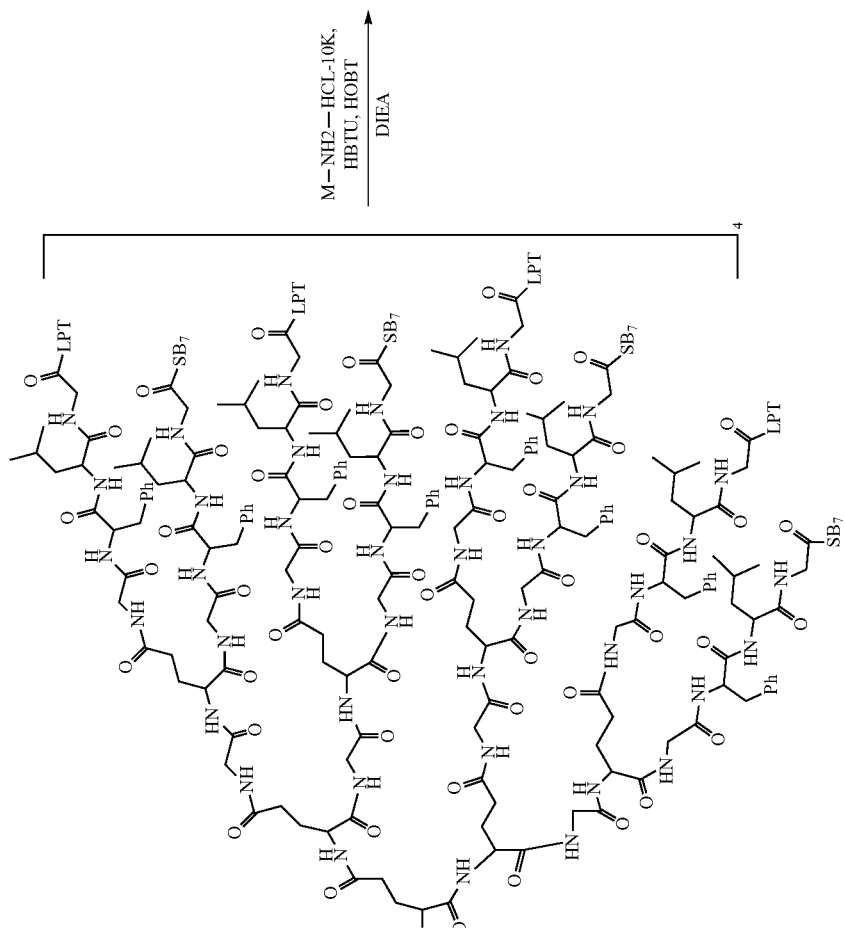
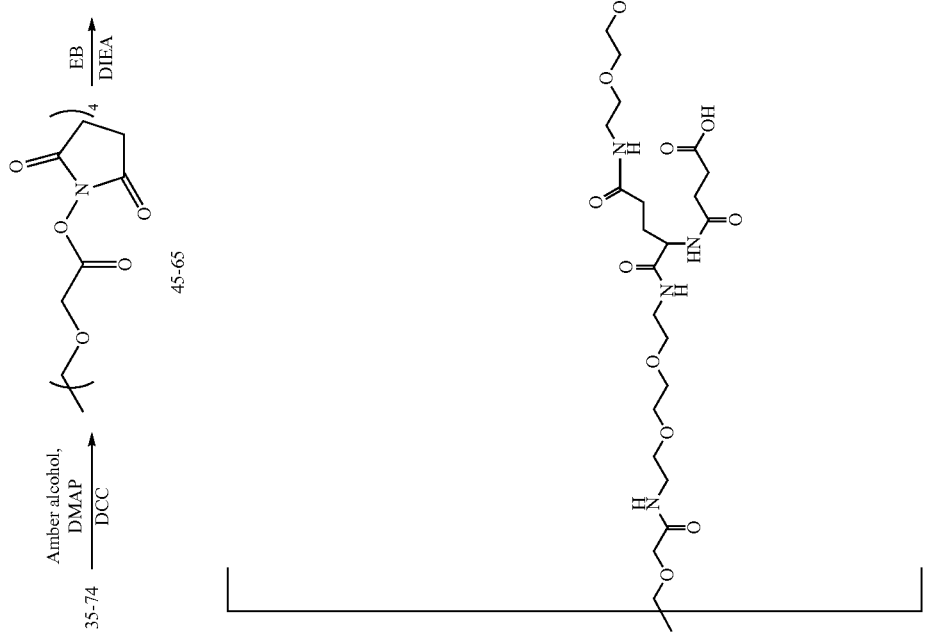

-continued
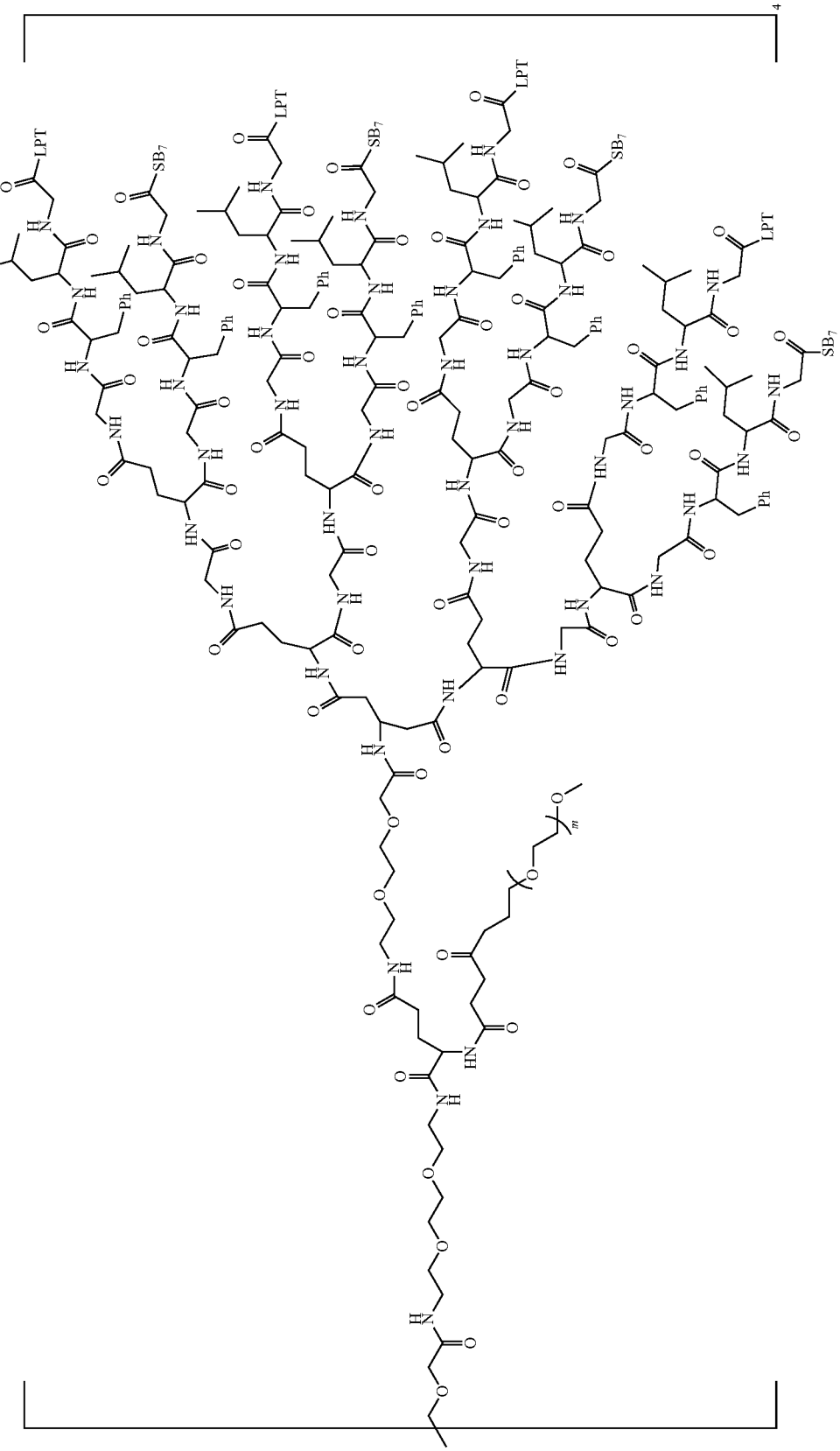
40-123

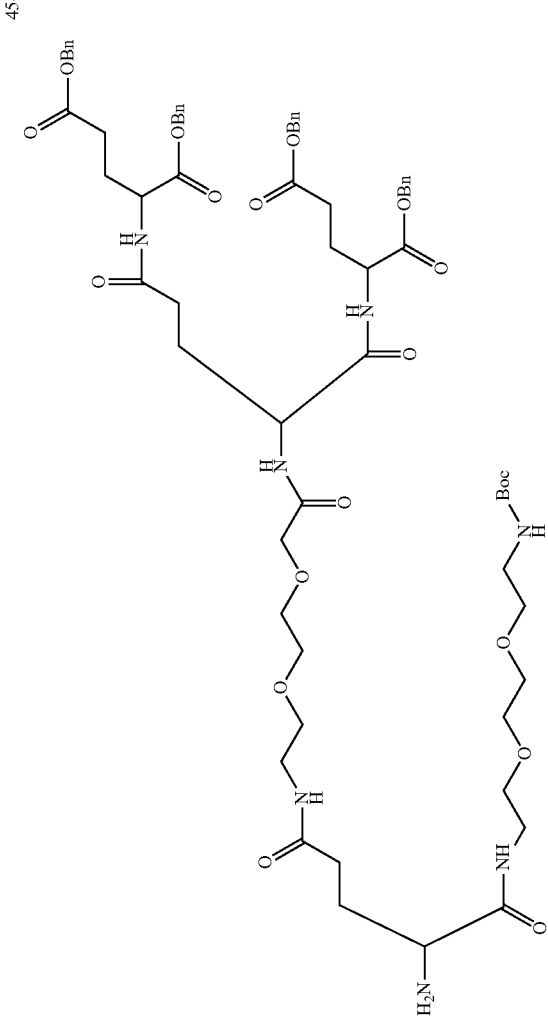
45-8

Reactant 42-27 was added in a 250 mL flask, and dissolved with DMF (20 mL), morpholine (7.2 mL, 83.4 mmoL) was added, and then the mixed solution was stirred to react at room temperature for 3 hours. At the end of the reaction, methyl tert-butyl ether (100 mL) and n-hexane (200 mL) were added to the reaction solution for precipitation to obtain a powder product. The operations of column chromatography, dry sample loading and gradient elution with 1% ammonia water: 2% methanol/dichloromethane—1% ammonia water 6% methanol/dichloromethane were carried out, thus obtaining the product 4 g.

Reactants Fmoc-E (OtBu) (OH) (1.39 g, 3.29 mmoL), GFLG-LPT (synthesized according to the method of synthesizing 14-128, 3 g, 3.13 mmoL), HBUT (1.78 g, 4.7 mmoL), HOBT (0.63 g, 4.7 mmoL) were added in a 250 mL flask, and dissolved with DMF (30 mL), and the obtained solution was stirred at −5° C. for 0.5 hour. Then, DIEA (2.34 mL, 14.2 mmoL) was slowly added dropwise, and, after 1 hour, the obtained solution was moved to room temperature and stirred to react. At the end of the reaction, deionized water (100 mL) and ethyl acetate (100 mL) were added to the reaction solution for extraction, and the organic phase

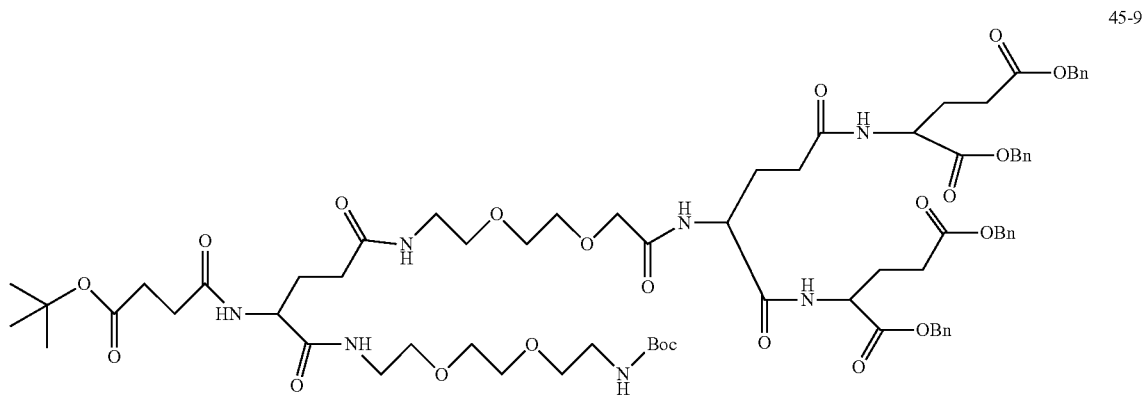 [SMILES: CC(C)(C)OC(=O)CCC(=O)NC(CCC(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1)C(=O)NCCOCCOCCNC(=O)OC(C)(C)C]

45-9

Reactants E4 (4 g, 3.14 mmoL), SA-OtBu ((purchased from Accela, 0.54, 3.14 mmoL), HBUT (1.78 g, 4.71 mmoL), HOBT (0.63 g, 4.71 mmoL) were added in a 250 mL flask, and dissolved with DMF (40 mL), and the obtained solution was stirred at 0° C. for 0.5 hour. Then, DIEA (2.3 mL, 14.13 mmoL) was slowly added dropwise, and then the obtained solution was stirred to react. At the end of the reaction, deionized water (100 mL) and ethyl acetate (100 mL) were added to the reaction solution for extraction, and the organic phase was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness, thus obtaining the product 3.5 g, yield 79%.

$^1$H-NMR (400 MHz, DMSO-$d_6$) δ 8.58-8.43 (m, 1H), 8.35-8.23 (m, 1H), 8.06-7.76 (m, 4H), 7.74-7.65 (m, 1H), 7.37-7.27 (m, 20H), 5.13-5.02 (m, 8H), 4.41-4.13 (m, 4H), 3.95-3.85 (m, 2H), 3.53-3.46 (m, 9H), 3.25-2.99 (m, 8H), 2.89-2.87 (m, 1H), 2.73-2.71 (m, 1H), 2.46-2.30 (m, 9H), 2.21-1.79 (m, 12H), 1.37-1.34 (m, 18H).

MALDI-TOF MS: [M+H$^+$]1426.75, [M+Na$^+$]1448.75.

was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness. Yield 100%.

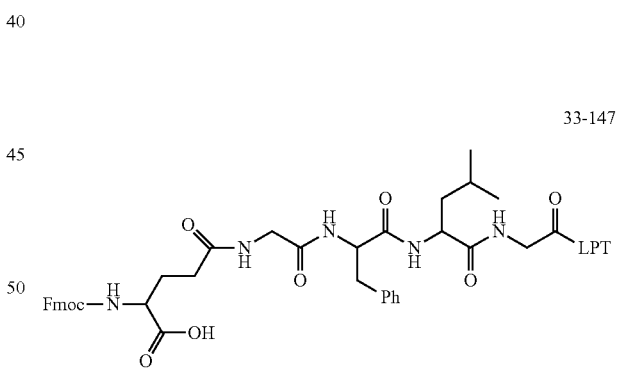

33-147

33-145 (3.13 mmol) was dissolved with dichloromethane (5 mL) and TFA (6.63 mL, 89.4 mmol) in a condition of ultrasonic, and then the mixed solution was stirred to react. At the end of the reaction, the reaction solution was concentrated, methyl tert-butyl ether (100 mL) and n-hexane (200 mL) were added to the obtained solution for precipitation to obtain a powder product. The operations of column chromatography, dry sample loading, and elution with 2% methanol/dichloromethane—6% methanol/dichloromethane were carried out, thus obtaining the product 2.8 g, yield 70%.

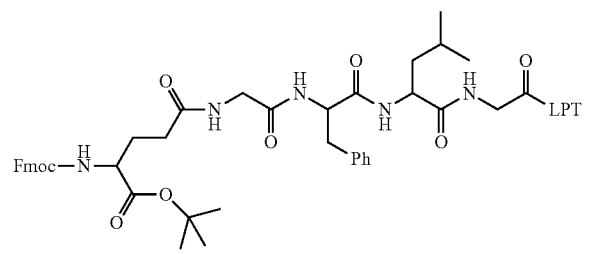

33-145

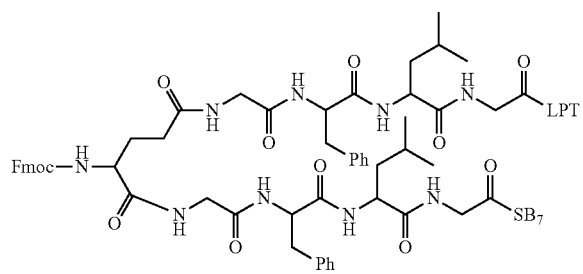

39-11

Reactant 39-11 (2.14 mmol) was added in a 250 mL flask, and dissolved with DMF (20 mL), morpholine (5.59 mL, 64.2 mmoL) was added, and the mixed solution was stirred to react at room temperature for 3 hours. At the end of the reaction, deionized water (300 mL) and ethyl acetate (150 mL) were added to the reaction solution for extraction, and the organic phase was separated. The aqueous phase was extracted three times with ethyl acetate (50 mL×3) until there was no product in the aqueous phase, and the obtained organic phases were combined. Yield 100%.

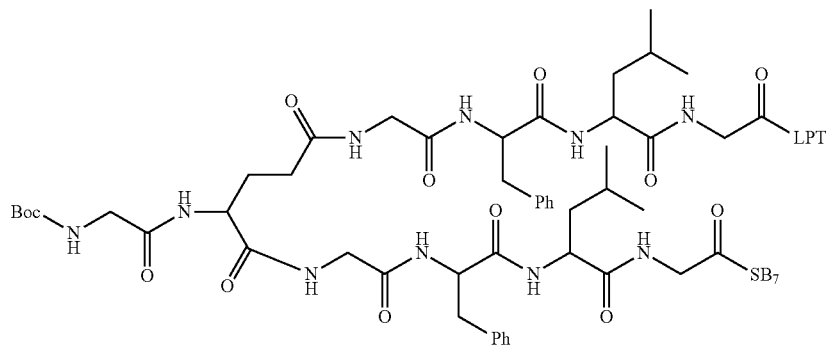

39-13

Reactants 33-147 (2.8 g, 2.14 mmoL), GFLG-SB7 (synthesized according to the method of synthesizing 25-132, 2 g, 2.247 mmoL), HBUT (1.21 g, 3.21 mmoL), HOBT (0.43 g, 3.21 mmoL) were added in a 250 mL flask, and dissolved with DMF (30 mL), and the obtained solution was stirred at −5° C. for 0.5 hour. Then, DIEA (1.59 mL, 9.63 mmoL) was slowly added dropwise, and, after 1 hour, the obtained solution was moved to room temperature and stirred to react. At the end of the reaction, deionized water (100 mL) and ethyl acetate (100 mL) were added to the reaction solution for extraction, and the organic phase was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness, thus obtaining the product 4.6 g. Yield 100%.

Reactants 39-12 (2.14 mmoL), Boc-Gly-OH (0.39, 2.247 mmoL), HBUT (1.21 g, 3.21 mmoL), HOBT (0.43 g, 3.21 mmoL) were added in a 250 mL flask, and dissolved with DMF (50 mL), and the obtained solution was stirred at −5° C. for 0.5 hour. Then, DIEA (1.59 mL, 9.63 mmoL) was slowly added dropwise, and, after 1 hour, the obtained solution was moved to room temperature and stirred to react. At the end of the reaction, deionized water (300 mL) and ethyl acetate (150 mL) were added to the reaction solution for extraction, and the organic phase was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness, yield 100%.

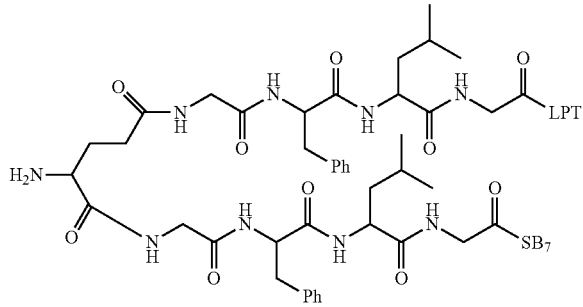

39-12

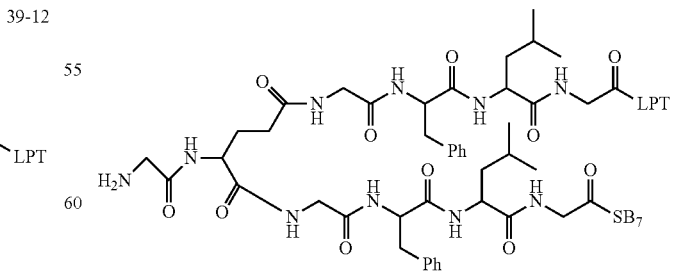

39-20

39-13 (2.14 mmol) was dissolved with dichloromethane (5 mL) and TFA (4.7 mL, 64.2 mmol), in a condition of ultrasonic, and then the mixed solution was stirred to react.

At the end of the reaction, the reaction solution was concentrated, methyl tert-butyl ether (100 mL) and n-hexane (200 mL) were added to the obtained solution for precipitation to obtain a powder product. The operations of column chromatography, dry sample loading, and elution with 1% ammonia water: 3% methanol/dichloromethane—1% ammonia water: 6% methanol/dichloromethane were carried out, thus obtaining the product 3 g, yield 69%.

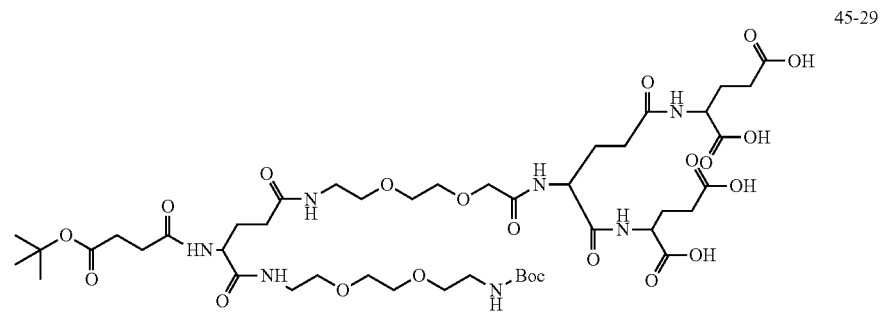 [SMILES: CC(C)(C)OC(=O)CCC(=O)NC(CCC(=O)NCCOCCOCC(=O)NC(CCC(=O)NC(CCC(=O)O)C(=O)O)C(=O)NC(CCC(=O)O)C(=O)O)C(=O)NCCOCCOCCNC(=O)OC(C)(C)C]

45-29

Reactant 45-9 (0.22 g, 0.1551 mmoL) was added in a hydrogenation reactor, DMF was added dropwise along the inner wall to dissolve the reactant, 10% Pd/C (0.05 g) was added, hydrogen was introduced, and the obtained solution was stirred to react overnight. At the end of the reaction, the reaction solution was filtered by suction through a sand core funnel filled with compacted diatomaceous earth to remove the Pd/C, and then the diatomaceous earth was washed 3-4 times with DMF (40 ml), thus obtaining a product solution for the next reaction.

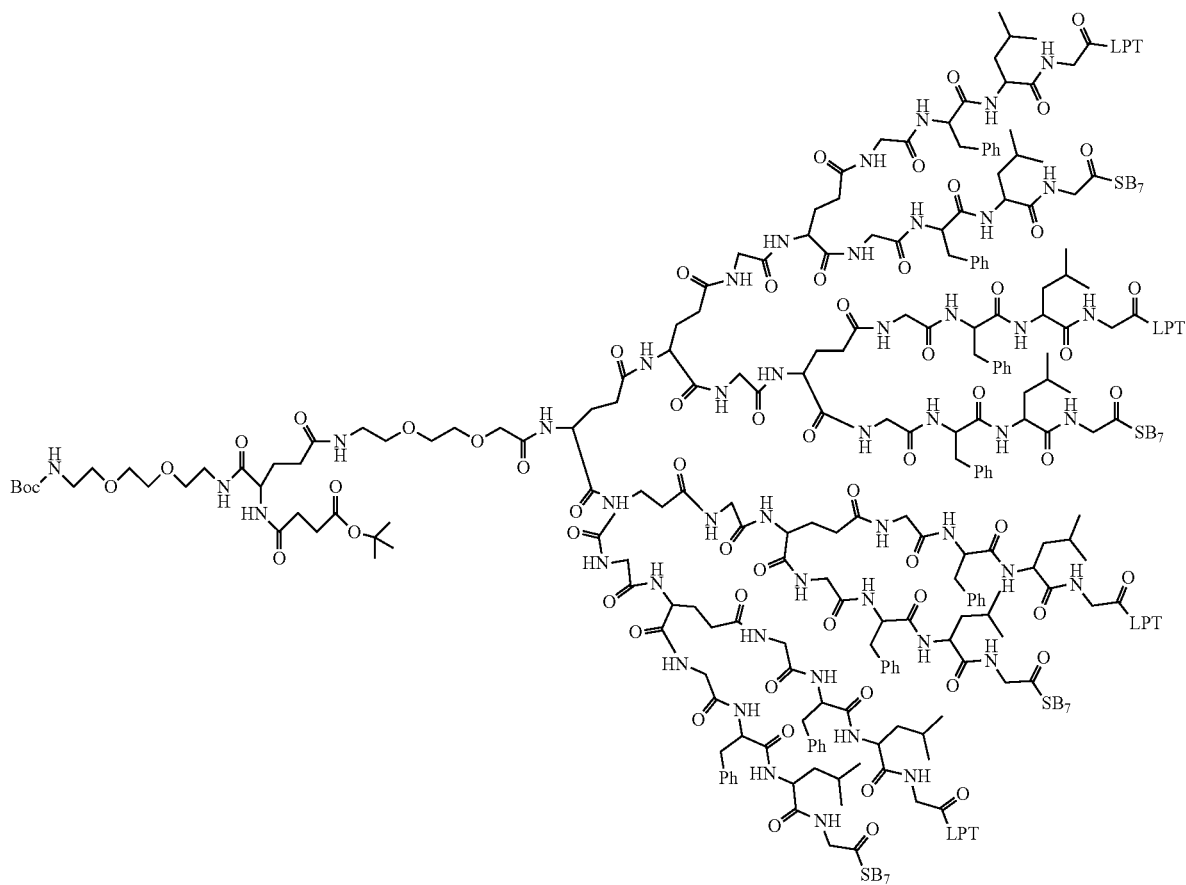

45-30

Reactants 39-20 (1.5 g, 0.7445 mmoL), 45-29 (0.10551 mmoL), HBUT (0.3529 g, 0.9306 mmoL), HOBT (0.1257 g, 0.9306 mmoL) were added in a 250 mL flask, and dissolved with DMF (50 mL), and the obtained solution was stirred at −5° C. for 0.5 hour. Then, DIEA (0.4614 mL, 2.7918 mmoL) was slowly added dropwise, and, after 1 hour, the obtained solution was moved to room temperature and stirred to react. At the end of the reaction, methyl tert-butyl ether (100 mL) and n-hexane (200 mL) were added to the reaction solution for precipitation to obtain a powder product. The operations of column chromatography, dry sample loading, and elution with 1% ammonia water: 4% methanol/dichloromethane—1% ammonia water: 10% methanol/dichloromethane were carried out. The elution product was evaporated to dryness, thus obtaining the product 1.4 g, yield 40%.

ammonia water: 10% methanol/dichloromethane were carried out, thus obtaining the product 1.2 g, yield 80%.

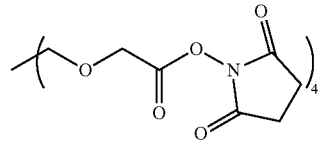

45-65

Reactants 35-74 (2 g, 5.4 mmol), succinyl alcohol (5.5082 g, 47.86 mmol), DMAP (0.2922 g, 2.392) were added in a 250 mL round-bottomed flask, and dissolved with dichlo-

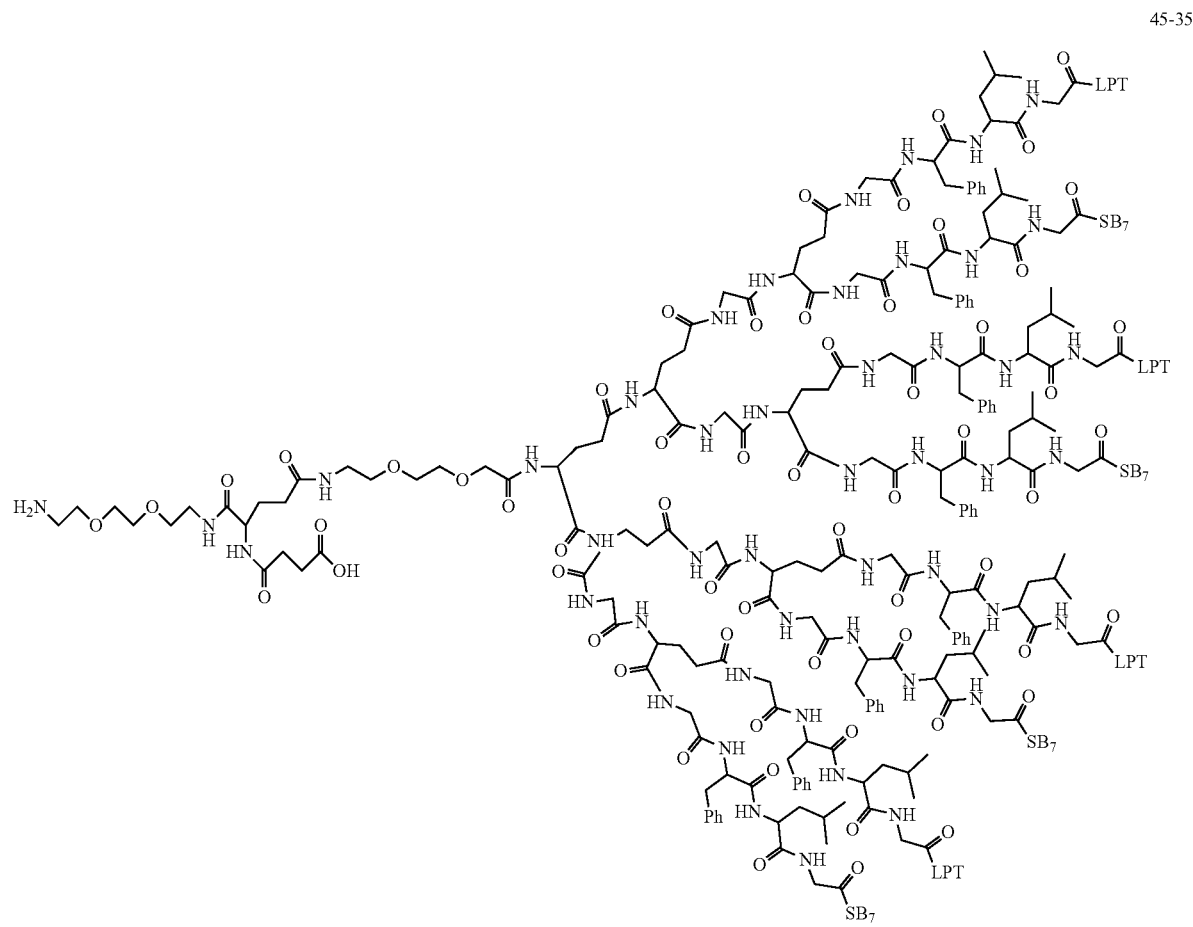

45-35

45-35 (1.4 g) was dissolved with dichloromethane (5 mL) and TFA (0.5741 mL, 7.73 mmol) in a condition of ultrasonic, and then the mixed solution was stirred to react. At the end of the reaction, the reaction solution was concentrated, methyl tert-butyl ether (100 mL) and n-hexane (200 mL) were added to the obtained solution for precipitation to obtain a powder product. The operations of column chromatography, dry sample loading, and elution with 1% ammonia water: 5% methanol/dichloromethane—1% romethane (50 mL), and the obtained solution was stirred at −5° C., and DCC (9.8750 g, 47.86 mmol) was quickly added in batches. The obtained solution was stirred to react at room temperature. At the end of the reaction, the reaction solution was filtered, and the filtrate was evaporated to dryness. The operations of column chromatography, dry sample loading and gradient elution with 10% ethyl acetate/petroleum ether-ethyl acetate were carried out, thus obtaining the product 3 g, yield 81%.

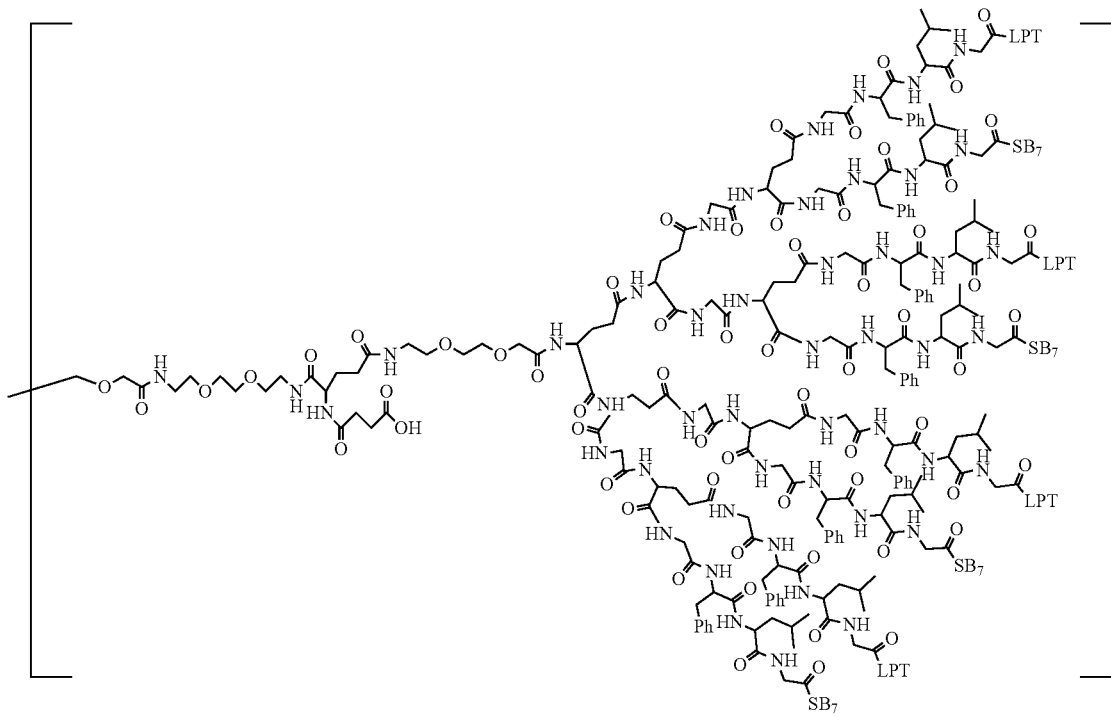

40-121

Reactant 45-35 (1.2 g, 0.101 mmol) was added in a 250 mL flask, and dissolved with DMF (20 mL), the obtained solution was placed in a low-temperature and constant temperature bath (−5° C.) and stirred for 30 minutes, and DIEA (0.1 mL) was added dropwise. Then, 45-65 (0.015 g, 0.021 mmoL) was added. After dissolution, the obtained solution reacted at room temperature in the dark at a low speed of stirring. At the end of the reaction, methyl tert-butyl ether (150 mL) was added in a conical flask, the reaction solution was poured into the conical flask, then n-hexane (200 mL) was added, to separate out a product, and suction filtering was carried out. The operations of column chromatography (column height: 5 cm) and gradient elution with 7% methanol/dichloromethane—1% ammonia water: 10% methanol/dichloromethane were carried out, thus obtaining the product 0.7 g.

$^1$H-NMR (600 MHz, DMSO-$d_6$)δ 10.14-10.12 (m, 12H), 9.02-9.00 (m, 4H), 8.95-8.94 (m, 14H), 8.18-8.16 (m, 41H), 8.13-8.05 (m, 90H), 7.86-7.83 (m, 30H), 7.55-7.47 (m, 41H), 7.26-7.17 (m, 274H), 7.11-7.08 (m, 65H), 7.02-7.00 (m, 44H), 6.73-6.64 (m, 6H), 4.39-4.13 (m, 71H), 4.03-3.45 (m, 268H), 3.22-2.66 (m, 207H), 2.41-2.38 (m 59H), 2.31-2.28 (m, 99H), 2.26-1.97 (m, 127H), 1.88-1.47 (m, 281H), 0.97-0.73 (m, 288H).

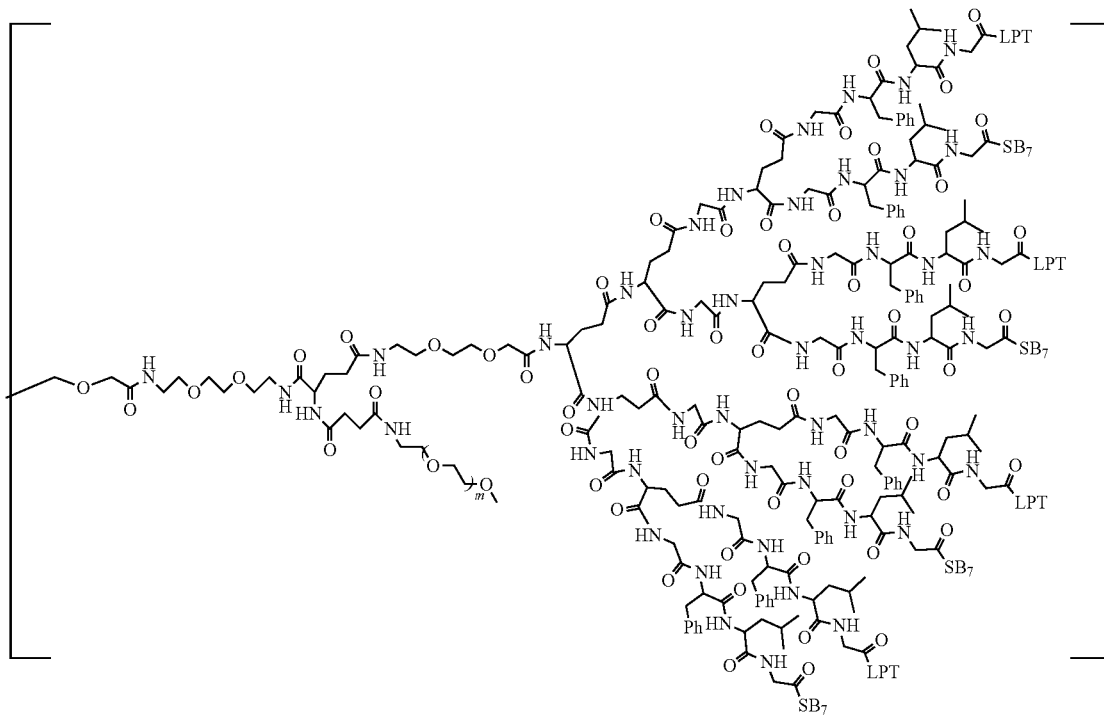

40-123

M-NH$_2$·HCL −10K (0.0528 g, 0.05 mmoL), 40-121 (0.37 g, 0.012 mmoL), HOBT (0.009 g, 0.072 mmoL), HBTU (0.027 g, 0.072 mmoL) were added in a 250 mL flask, and dissolved with DMF solution (20 mL), the obtained solution was placed in a low-temperature and constant temperature bath, after 30 minutes. Then, DIEA (0.035 mL, 0.216 mmol) was added dropwise, after 1 hour, the obtained solution was moved to room temperature and stirred to react in the dark at a low speed. At the end of the reaction, methyl tert-butyl ether (50 mL) and n-hexane (150 mL) were added to the reaction solution for precipitation, and suction filtering was carried out. The filter cake was dissolved with 20% methanol: 80% dichloromethane (50 mL). The operations of dry sample loading, column chromatography (column height: 5 cm) and gradient elution with 1% ammonia water: 5-10% methanol/dichloromethane were carried out. The elution product was evaporated to dryness, and dissolved with anhydrous ethanol (5 mL) and dichloromethane (2 mL), the obtained solution was treated by ultrasonic to obtain homogeneous phase, n-hexane (100 mL) was added, and suction filtering was carried out. The process of dissolution and precipitation was repeated three times. The precipitate was dried in vacuum, thus obtaining the product 0.45 g.

$^1$H-NMR (600 MHz, DMSO-d$_6$) δ 10.12-10.10 (m, 16H), 8.93-8.91 (m, 16H), 8.19-8.06 (m, 172H), 7.84-7.67 (m, 65H), 7.21-7.11 (m, 354H), 4.54-3.89 (m, 134H), 3.48-3.46 (m, 3578H), 3.21-3.11 (m, 175H), 2.89-2.87 (m, 28H), 2.79-2.66 (m, 80H), 2.43-2.07 (m, 353H), 1.93-1.43 (m, 340H), 0.96-0.74 (m, 288H).

12. Synthesis of 41-40 (Compound No. 13) Synthetic route is as follows

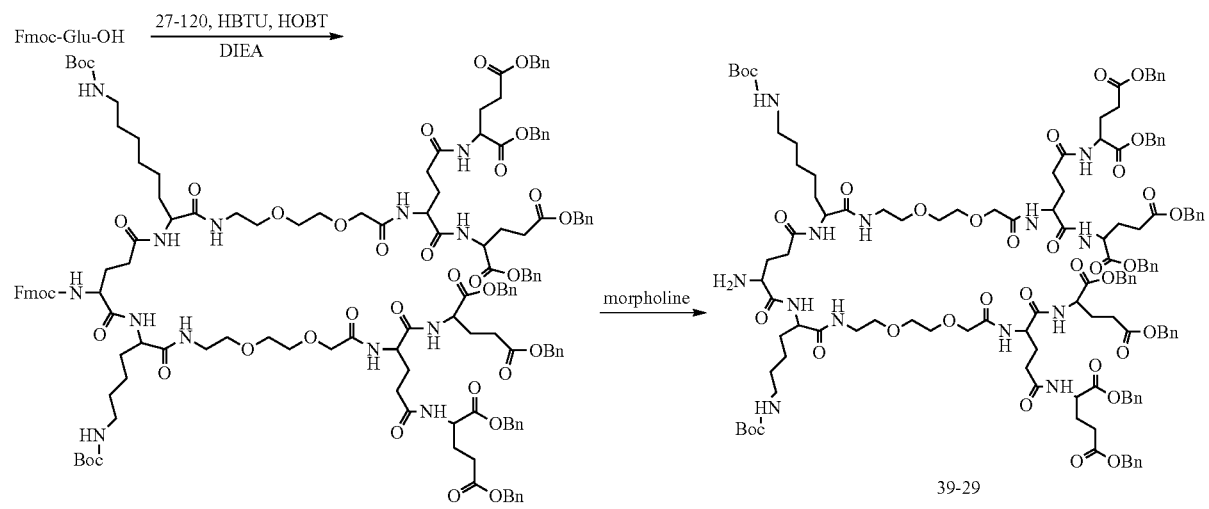

-continued
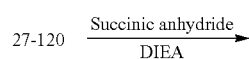
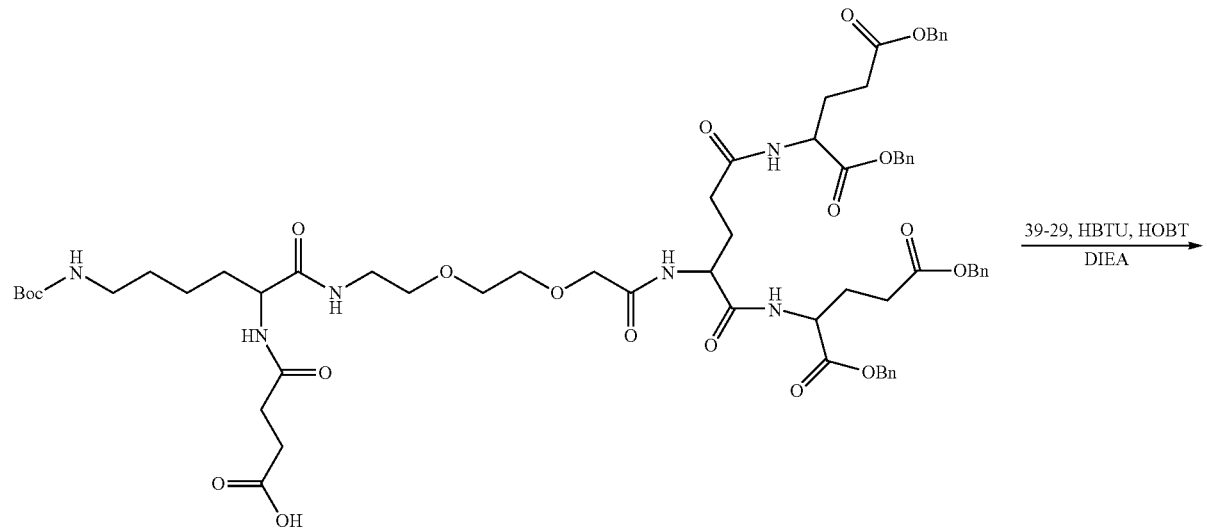
41-26
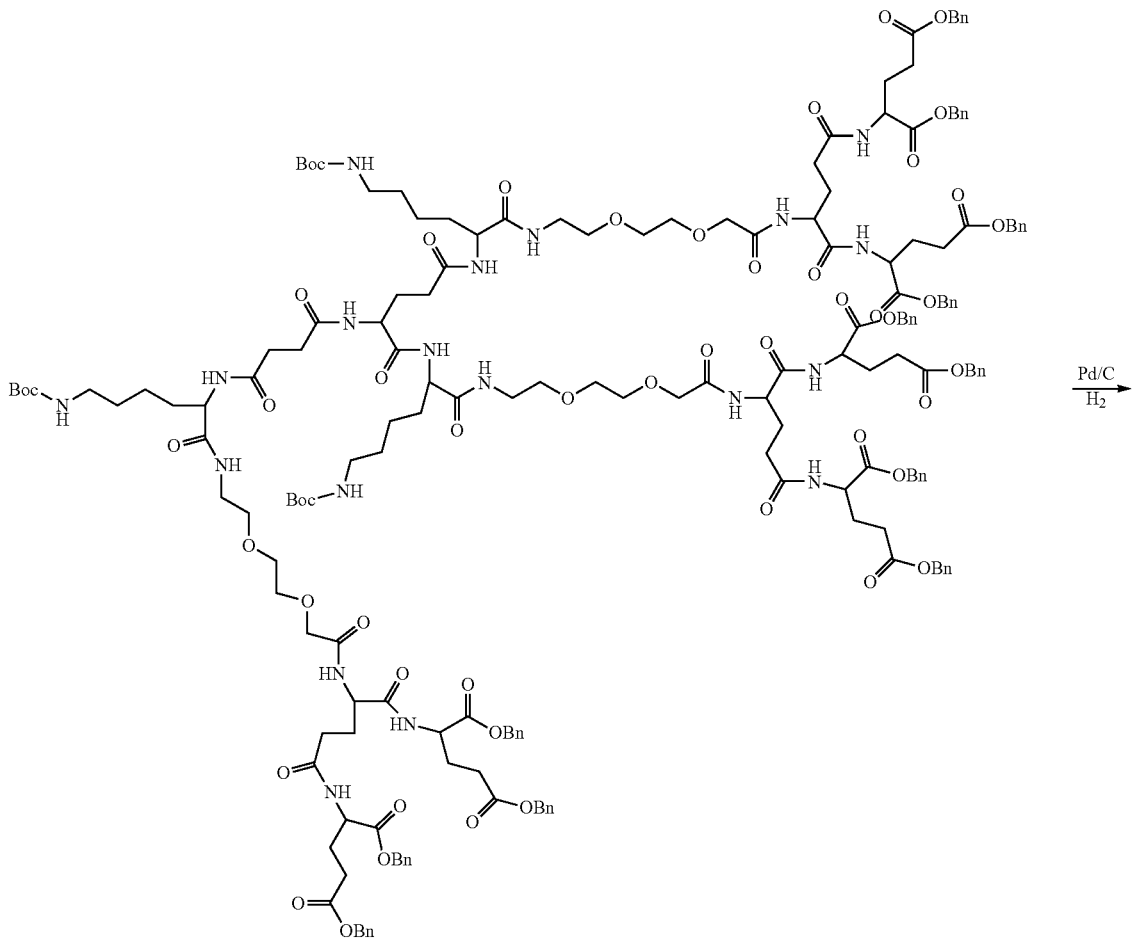
41-27

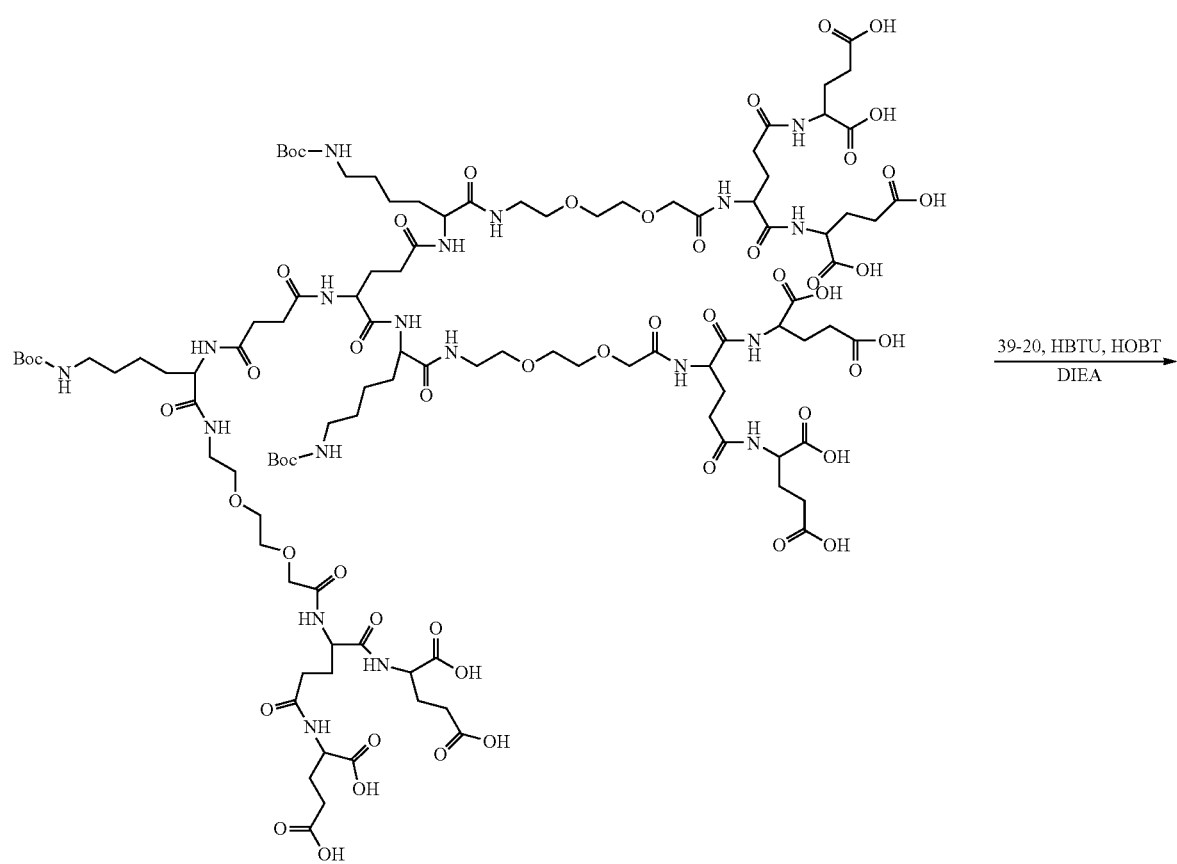
41-33

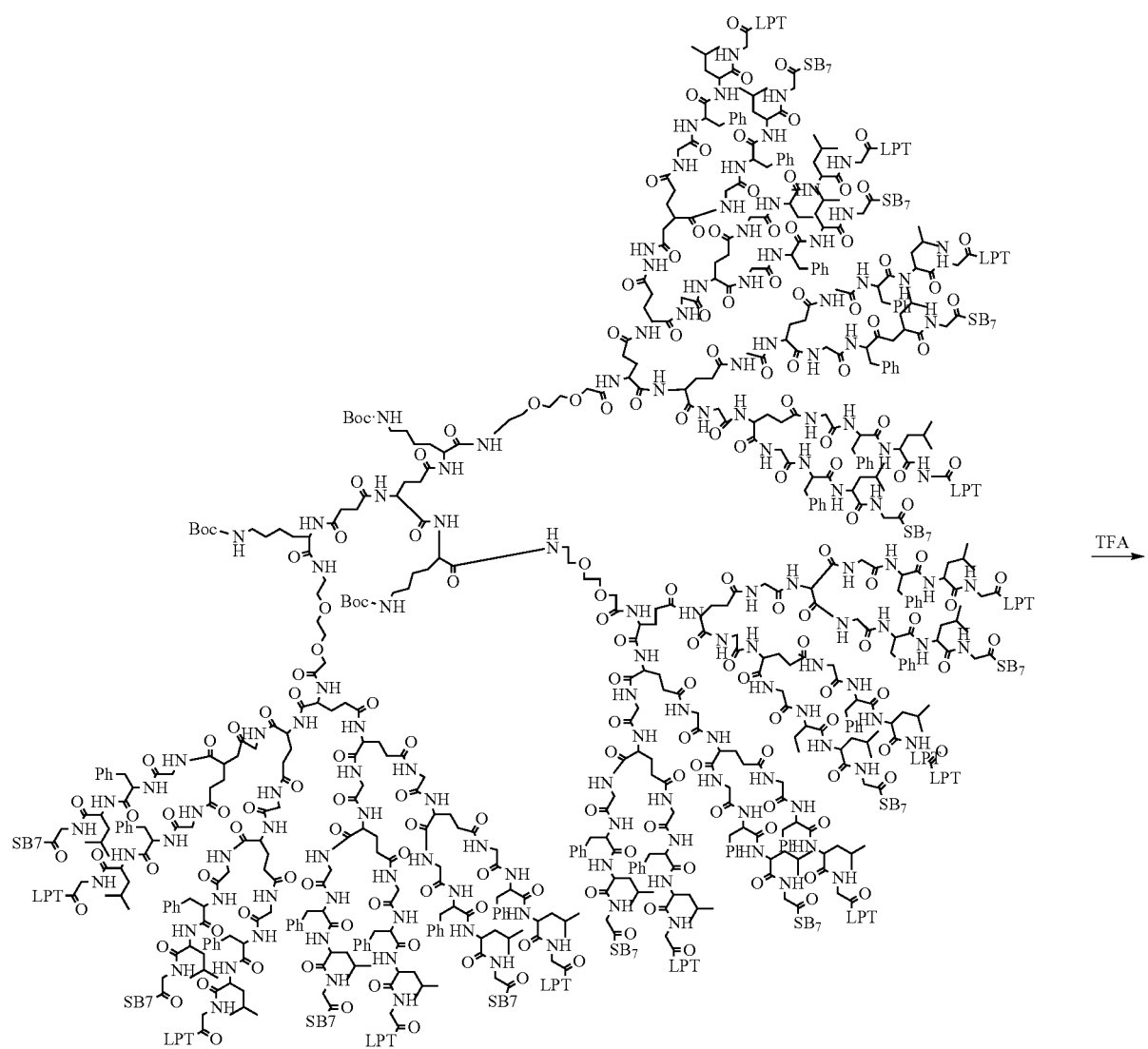

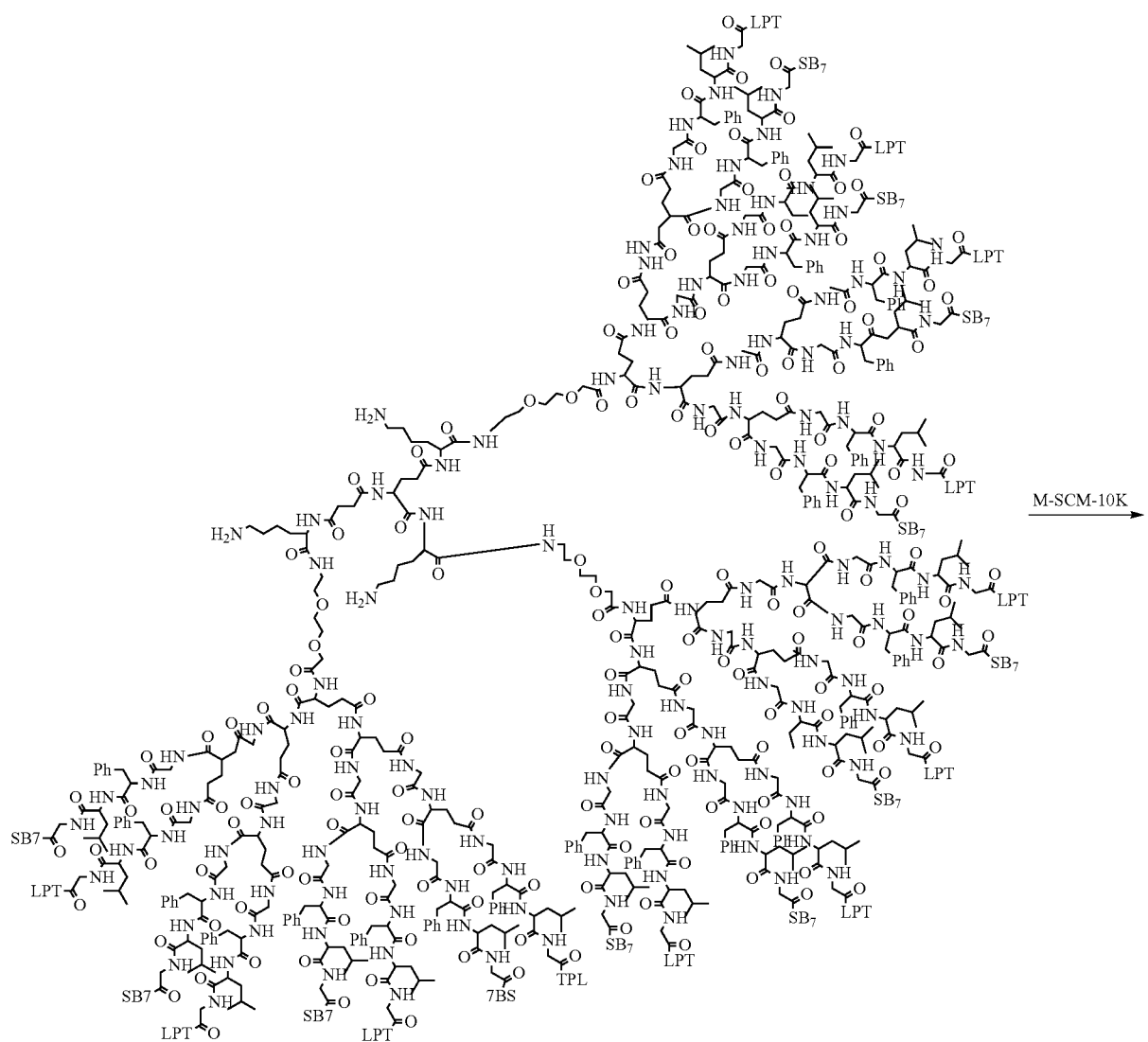
41-35

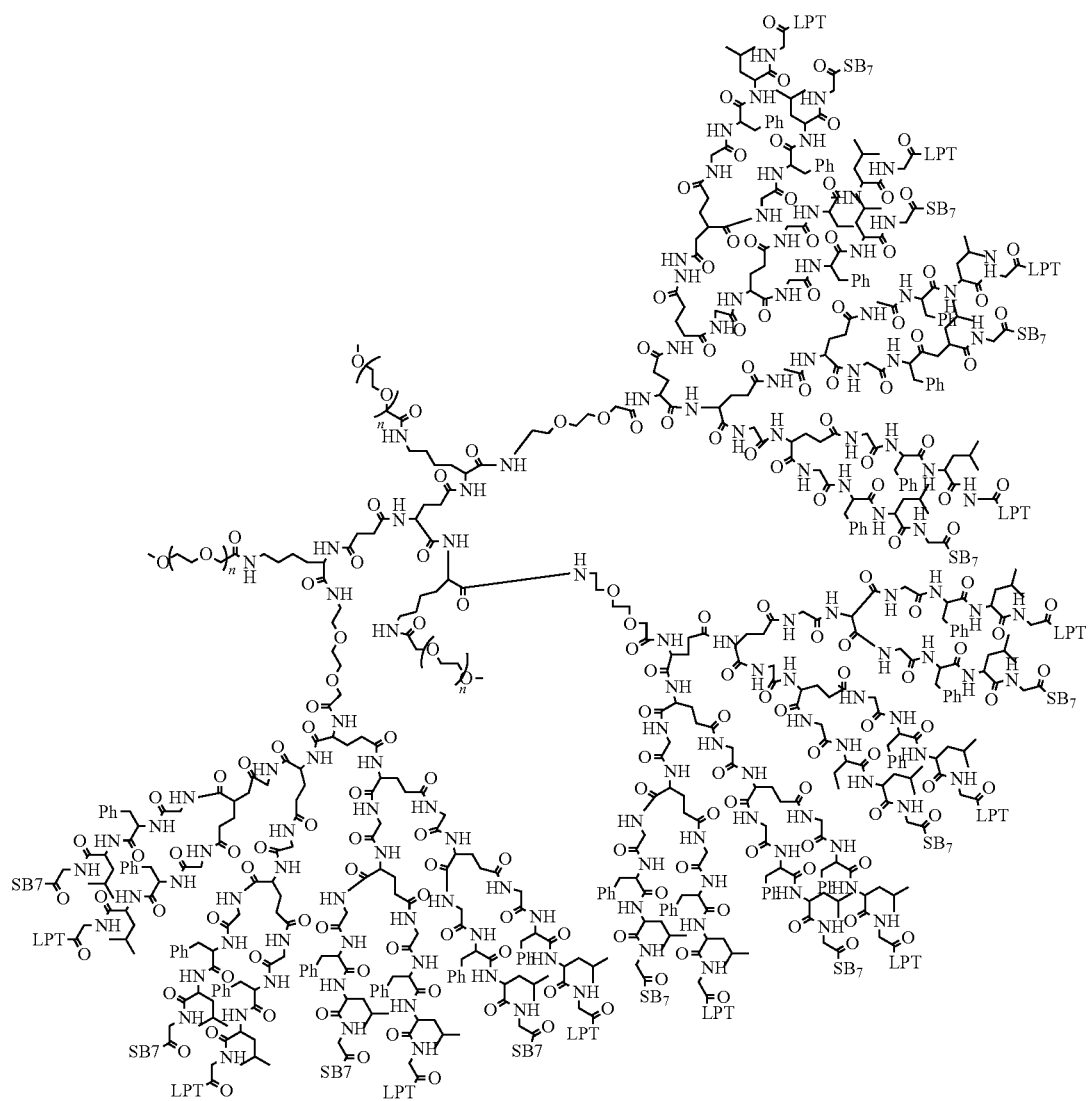
41-40

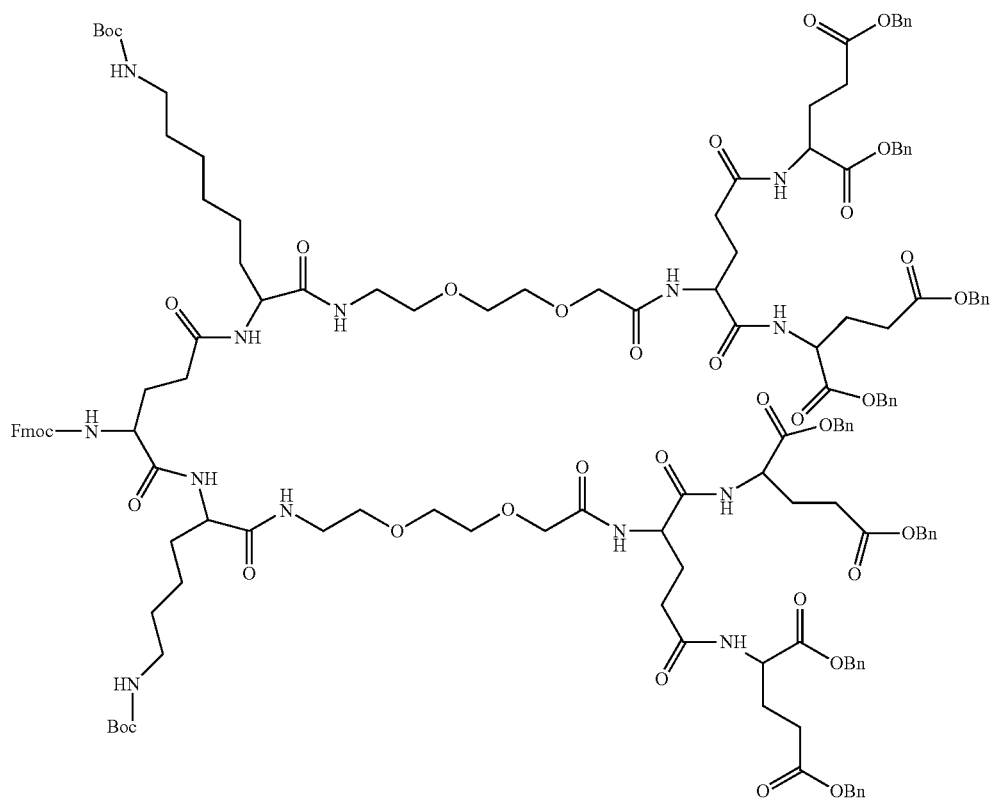

39-27

Reactants Fmoc-Glu-OH (purchased from Aladdin, 0.7719 g, 2.0899 mmol), 31-155 (synthesized according to the method of synthesizing 27-120, 5 g, 4.3887 mmol), HBUT (2.3777 g, 6.2697 mmol), HOBT (0.8472 g, 6.2697 mmol) were added in a 250 mL flask, and dissolved with DMF (40 mL), and the obtained solution was stirred at −5° C. for 30 minutes. Then, DIEA (3.1208 mL, 18.8091 mmol) was slowly added dropwise, the obtained solution reacted at the low temperature for 2 hours, and then reacted at room temperature. At the end of the reaction, the reaction solution was transferred to a 1 L separatory funnel, deionized water (200 mL) and ethyl acetate (300 mL) were added for extraction, and the organic phase was separated. The aqueous phase was extracted three times with ethyl acetate (100 mL×3), and the obtained organic phases were combined. The organic phase was washed two times with saturated saline solution (150 mL×2), concentrated, and evaporated to dryness, thus obtaining the product 5.5 g, yield 100%.

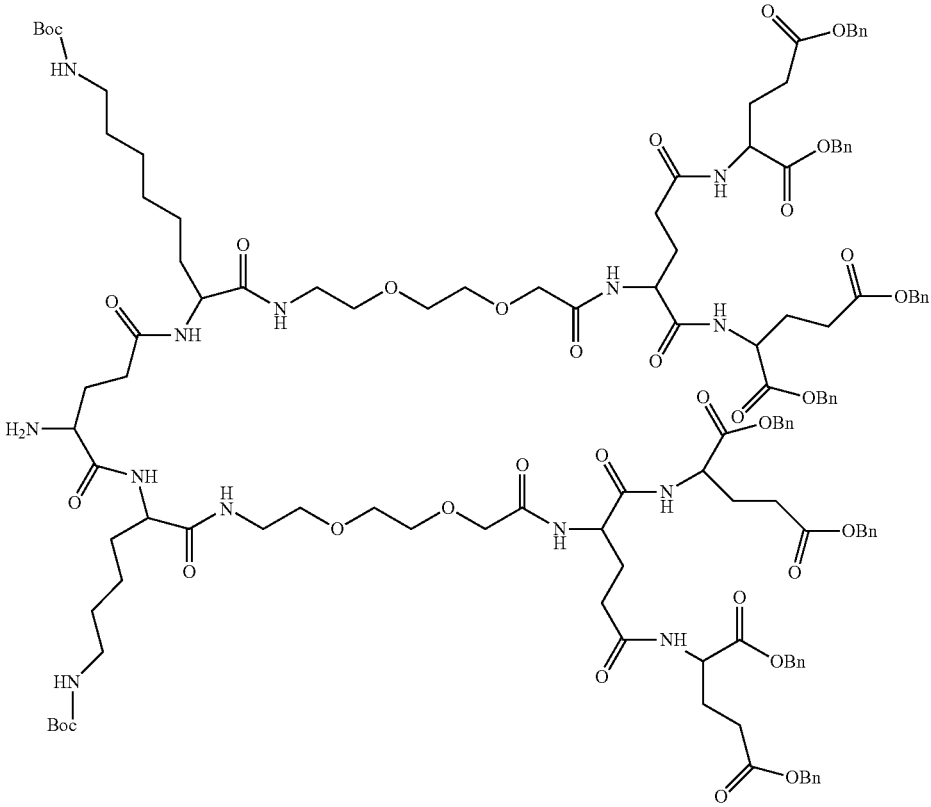

39-29

Reactant 39-27 (5.4 g, 2.0899 mmol) was added in a 250 mL round-bottomed flask, and dissolved with DMF (20 mL), and then the mixed solution was stirred at room temperature. Then morpholine (4.5544 mL, 52.2475 mmol) was added dropwise. At the end of the addition, the obtained solution reacted at room temperature for 2 hours. At the end of the reaction, the reaction solution was transferred to a 1 L separatory funnel, deionized water (200 mL) and ethyl acetate (300 mL) were added for extraction, and the organic phase was separated. The aqueous phase was extracted three times with ethyl acetate (100 mL×3), and the obtained organic phases were combined. The organic phase was washed two times with saturated saline solution (150 mL×2), concentrated to 100 mL, and silica gel powder (15 g) was added. The operations of evaporation, column chromatography and gradient elution with 1% ammonia water: 0.5% methanol/dichloromethane-1% ammonia water: 2% methanol/dichloromethane were carried out, thus obtaining the product 3.9848 g, yield 73%.

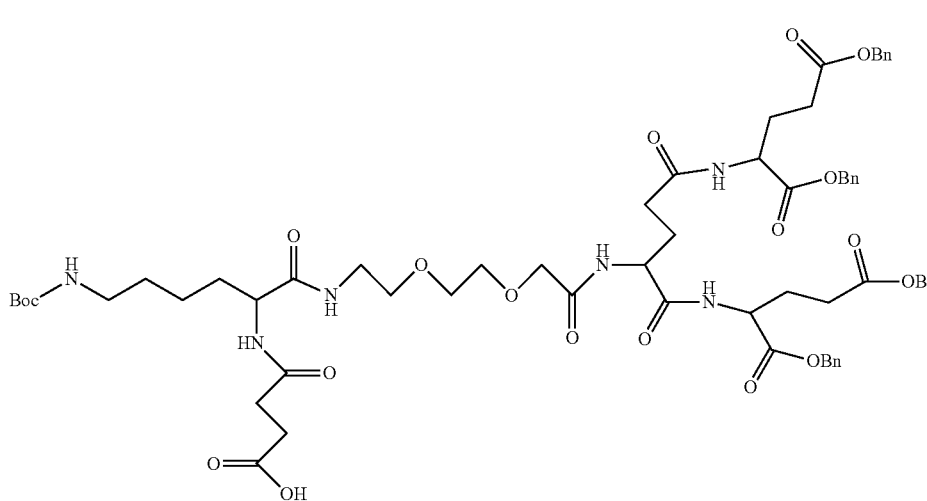

41-26

Reactant 31-155 (synthesized according to the method of synthesizing 27-120, 1 g, 0.87 mmol) was dissolved with DMF (20 mL), and the obtained solution was stirred at 0° C., and DIEA (0.58 mL, 3.51 mmol) was added dropwise. After 30 minutes, succinic anhydride (0.26 g, 2.16 mmol) was added. At the end of the reaction, the reaction solution was transferred to a 1 L separatory funnel, deionized water (100 mL) and ethyl acetate (100 mL) were added for extraction, and the organic phase was separated. The aqueous phase was extracted three times with ethyl acetate (50 mL×3) until there was no product in the aqueous phase, and the obtained organic phases were combined. The organic phase was evaporated to dryness, yield 100%.

the low temperature until the reaction ended. At the end of the reaction, the reaction solution was transferred to a 1 L separatory funnel, ethyl acetate (200 mL) and deionized water (150 mL) were added for extraction, and the organic phase was separated. The aqueous phase was extracted two times with ethyl acetate (100 mL×2), and the obtained organic phases were combined. The organic phase was washed one time with saturated saline solution (100 mL), and concentrated, silica gel powder was added, and the operations of evaporation, column chromatography, and elution with 50%-100% ethyl acetate/petroleum ether were carried out, thus obtaining the product 1.8 g, yield 60%.

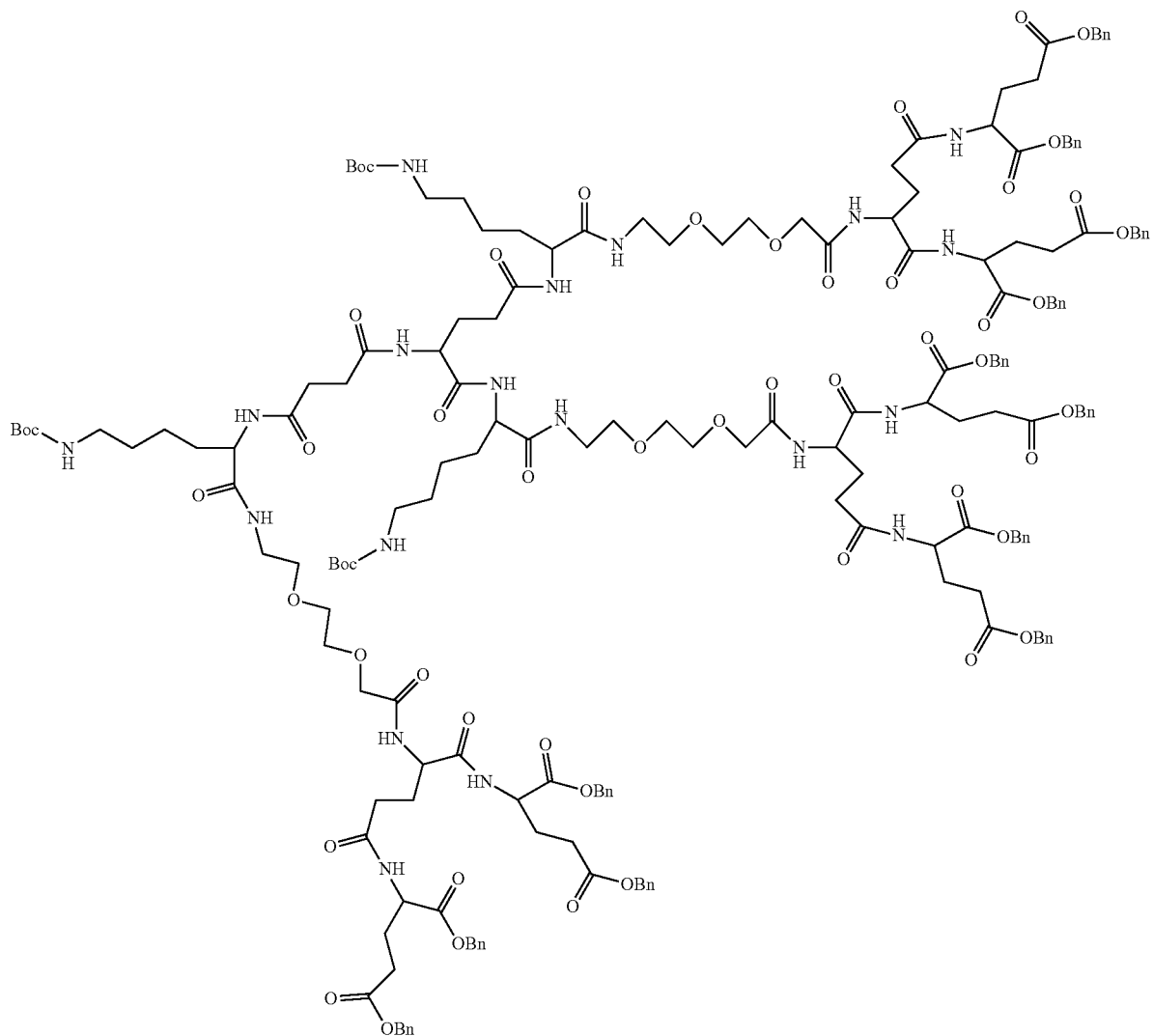

41-27

Reactants 39-29 (2.0 g, 0.87 mmol), 41-26 (0.4721 g, 0.87 mmol), HBTU (0.49 g, 1.30 mmol), HOBT (0.17 g, 1.30 mmol) were added in a 250 mL flask, and dissolved with DMF (30 mL), and the obtained solution was stirred at −5° C. for 30 minutes. Then, DIEA (0.64 mL, 3.91 mmol) was slowly added dropwise, and the obtained solution reacted at $^1$H-NMR (400 MHz, DMSO-$d_6$) δ8.57-8.47 (m, 3H), 8.35-7.88 (m, 10H), 7.75-7.65 (m, 3H), 7.39-7.27 (m, 60H), 6.76-6.61 (m, 3H), 5.15-5.02 (m, 24H), 4.42-4.29 (m, 9H), 3.93-3.87 (m, 5H), 3.61-3.47 (m, 13H), 3.42-3.36 (m, 7H), 2.90-2.80 (m, 6H), 2.47-2.39 (m, 12H), 2.23-1.68 (m, 31H), 1.38-1.14 (m, 55H).

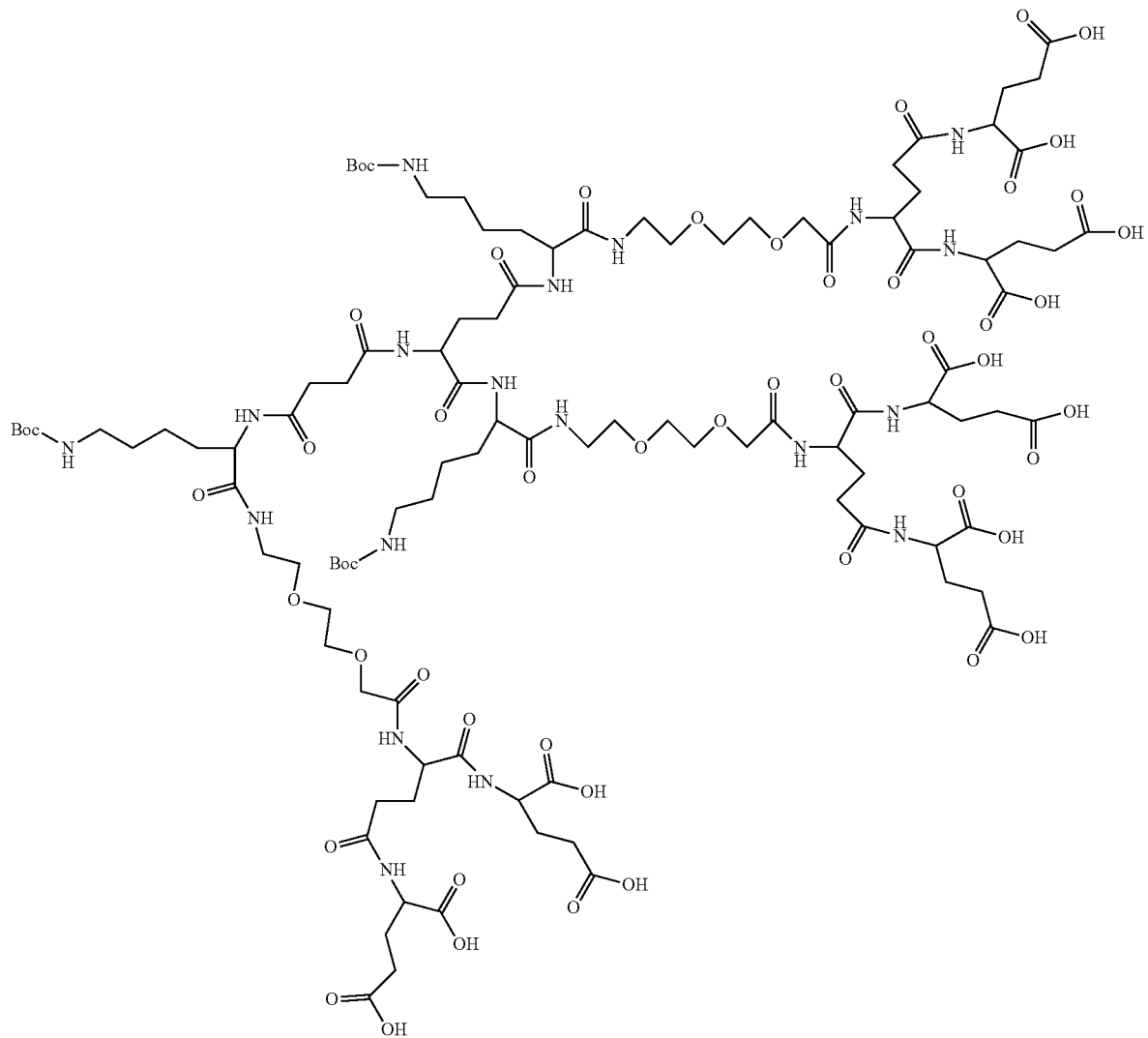

41-33

Reactants 41-27 (0.41 g, 0.113 mmol) and 10% Pd/C (0.166 g) were dissolved with DMF (30 mL), and added in a hydrogenation reactor, the device was set ready, hydrogen was introduced to a pressure of 18 Ps, and then the mixed solution was stirred to react. At the end of the reaction, the reaction solution was filtered by suction with diatomaceous earth as a filter cake to remove the Pd/C, and then the diatomaceous earth was washed four times with DMF (25 mL×4), thus obtaining the product solution.

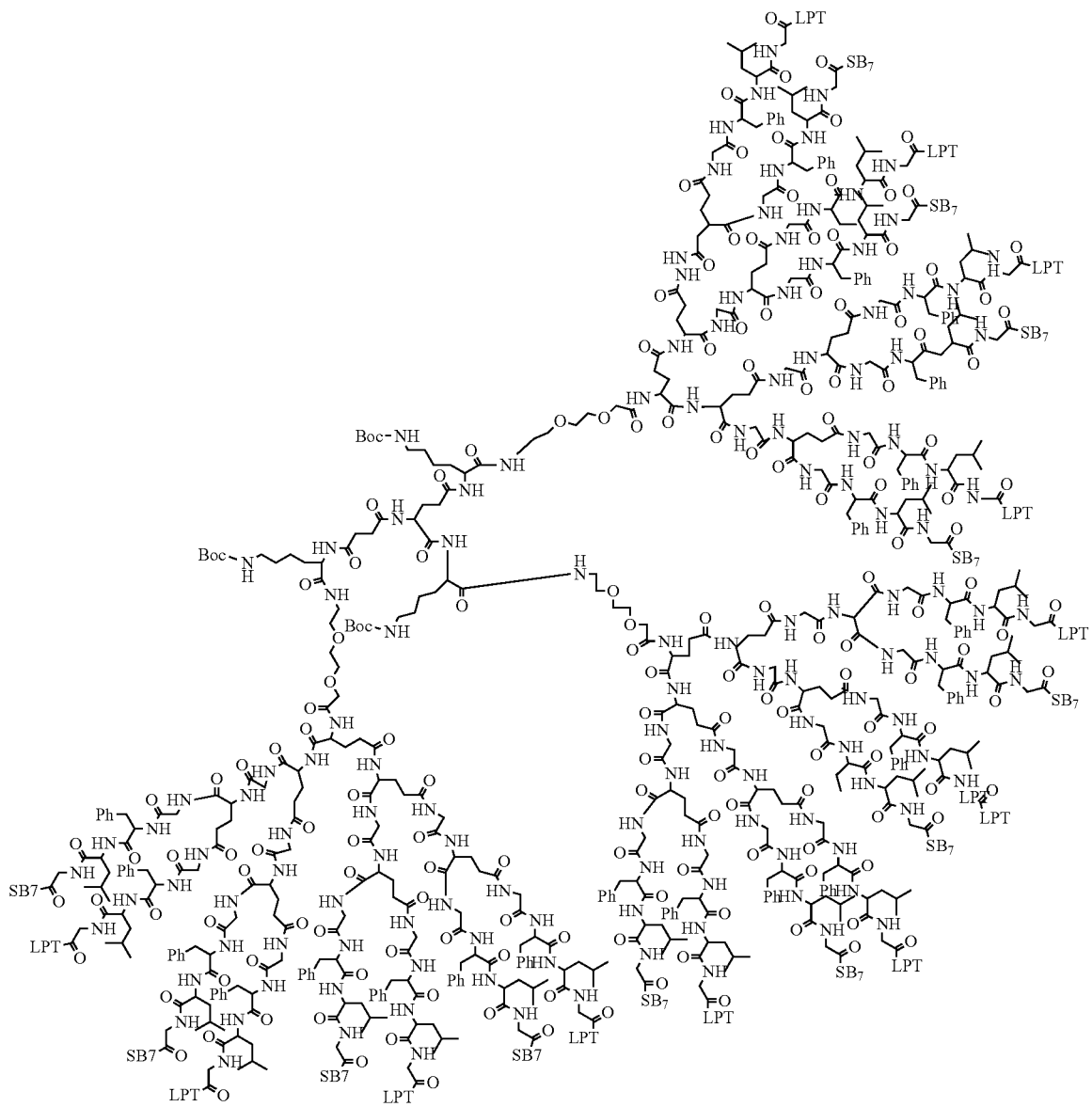

41-34

Reactants 39-20 (3.0 g, 1.48 mmol), 41-33 (0.2858 g, 0.113 mmol), HBTU (0.77 g, 2.034 mmol), HOBT (0.27 g, 2.034 mmol) were added in a 250 mL flask, and dissolved with DMF (30 mL), and the obtained solution was stirred at −5° C. for 30 minutes. Then, DIEA (1.0 mL, 6.102 mmol) was slowly added dropwise, and the obtained solution reacted at the low temperature until the reaction ended. At the end of the reaction, methyl tert-butyl ether (100 mL) and n-hexane (200 mL) were added to the reaction solution for precipitation to obtain a powder product. The operations of column chromatography, dry sample loading, and elution with 1% ammonia water: 2% methanol/dichloromethane—1% ammonia water: 10% methanol/dichloromethane were carried out, thus obtaining the product 1.64 g, yield 55%.

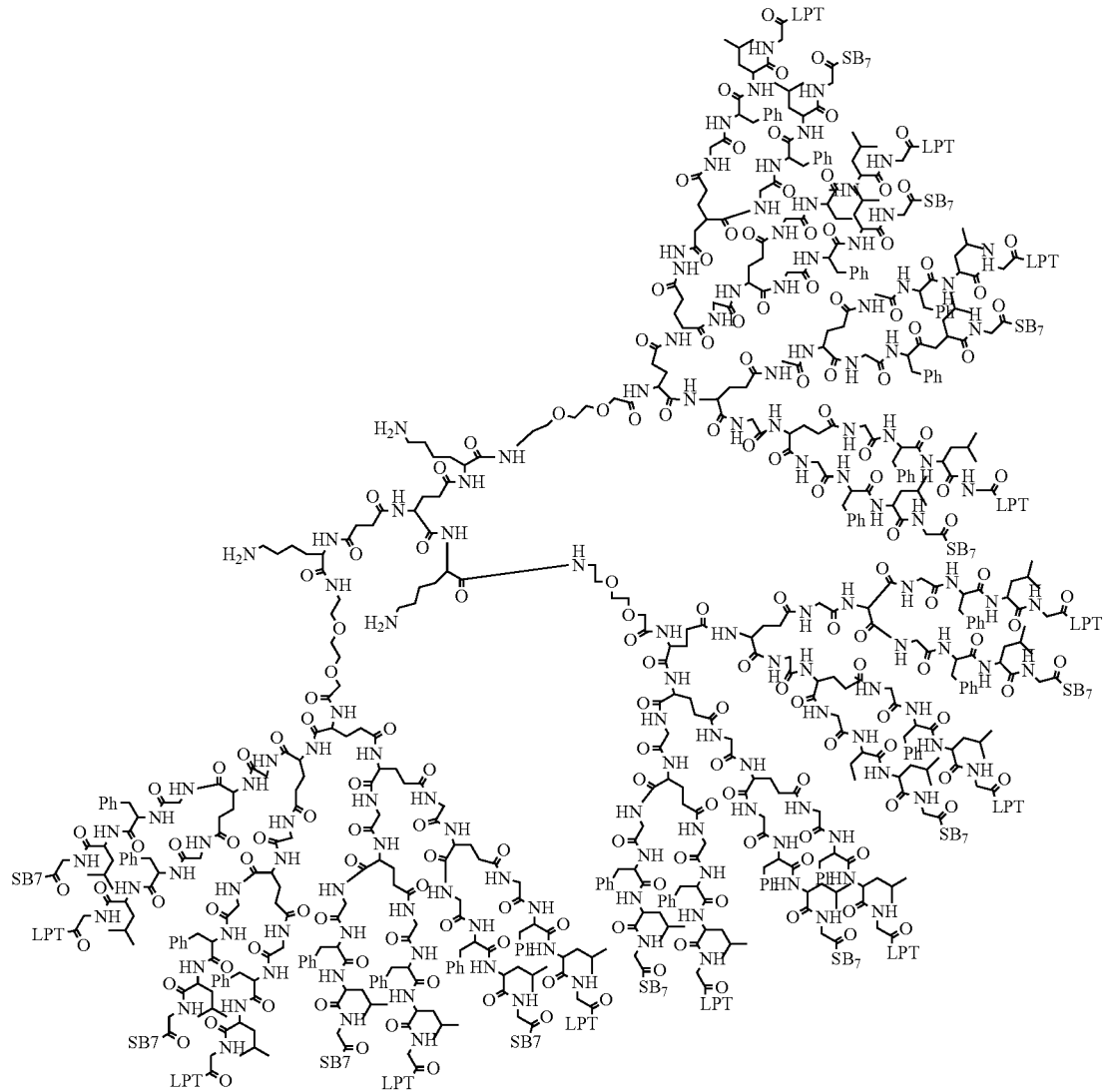

41-35

41-34 (1.64 g, 0.06215 mmol) was dissolved with dichloromethane (5 mL) and TFA (0.41 mL, 5.5935 mmol) in a condition of ultrasonic, and then the mixed solution was stirred to react. At the end of the reaction, the reaction solution was concentrated, methyl tert-butyl ether (100 mL) and n-hexane (200 mL) were added to the obtained solution for precipitation to obtain a powder product. The operations of column chromatography, dry sample loading, and elution with 1% ammonia water: 5% methanol/dichloromethane—1% ammonia water: 10% methanol/dichloromethane were carried out, thus obtaining the product 1.13 g, yield 70%.

41-40

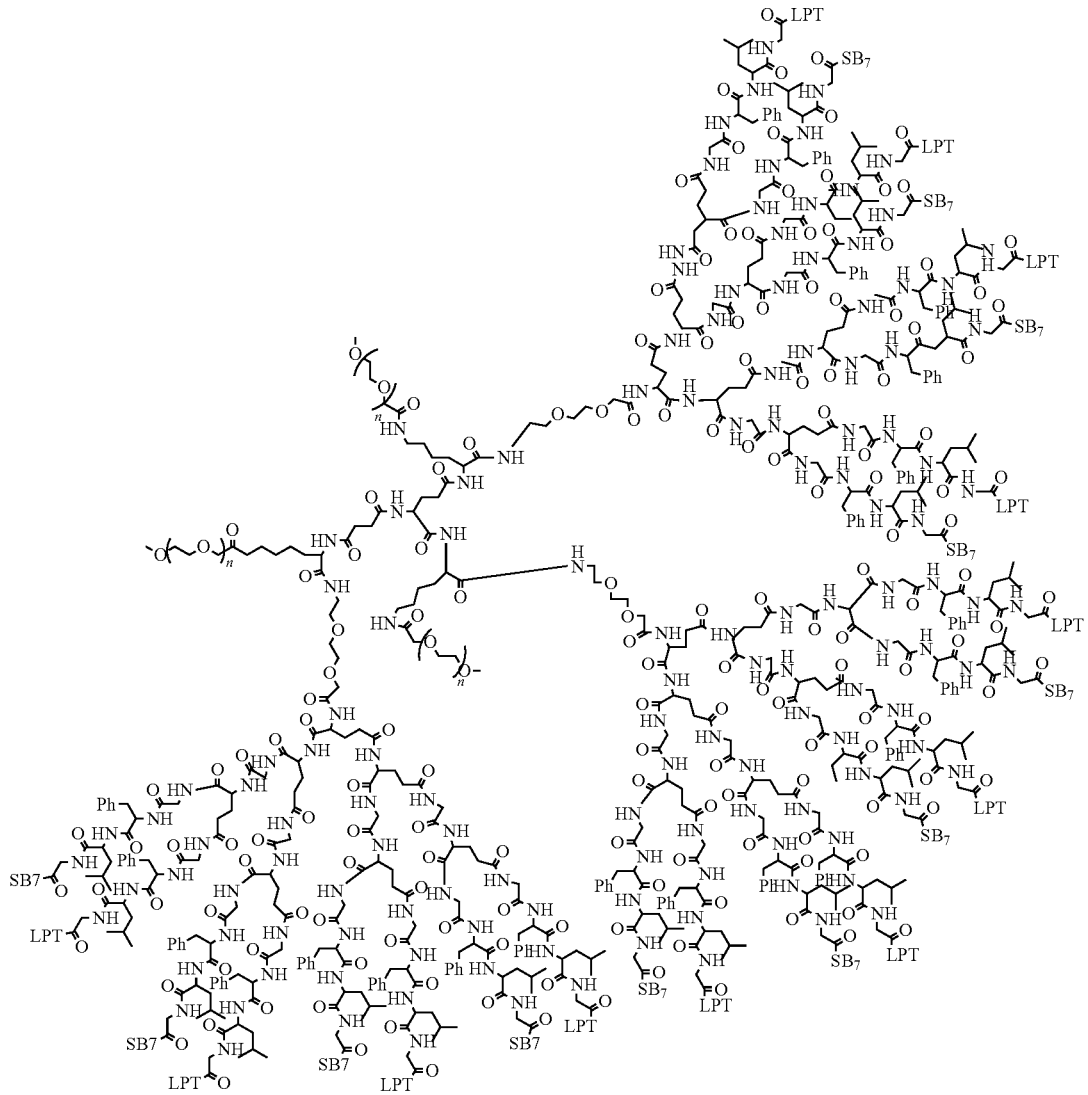

Reactants 41-35 (1.1 g, 0.04350 mmol) and M-SCM-10K (1.43 g, 0.14355 mmol) were dissolved with DMF solution (20 mL), and the obtained solution reacted at a low speed of stirring in the dark. At the end of the reaction, the reaction solution was precipitated with methyl tert-butyl ether (50 mL) and n-hexane (100 mL), and suction filtering was carried out. The operations of column chromatography, dry sample loading and gradient elution with dichloromethane—1% ammonia water: 8% methanol/dichloromethane were carried out. The elution product was then evaporated to dryness, and dissolved with anhydrous ethanol (10 mL), the obtained solution was treated by ultrasonic to obtain homogeneous phase, and then n-hexane (50 mL) was added for precipitation. Such precipitation operation was repeated three times. The precipitate was dried in vacuum, thus obtaining the product 1 g. Yield 41%.

$^1$H-NMR (600 MHz, DMSO-$d_6$) δ8.58-8.53 (m, 5H), 8.13-7.92 (m, 111H), 7.72-7.65 (m, 34H), 7.58-7.46 (m, 51H), 7.41-7.33 (m, 88H), 7.30-7.16 (m, 241H), 5.29-5.23 (m, 12H), 5.16-5.08 (s, 19H), 4.15-4.12 (m, 48H), 4.05-3.97 (m, 75H), 3.51-3.50 (m, 3285H), 3.25-3.23 (m, 173H), 3.16-2.98 (m, 242H), 2.93-2.85 (m, 54H), 2.76-2.72 (m, 50H), 2.68-2.65 (m, 55H), 2.36-2.27 (m, 74H), 0.94-0.75 (m, 216H).

13. Synthesis of 39-55 (Compound No. 12)

Synthetic route is as follows

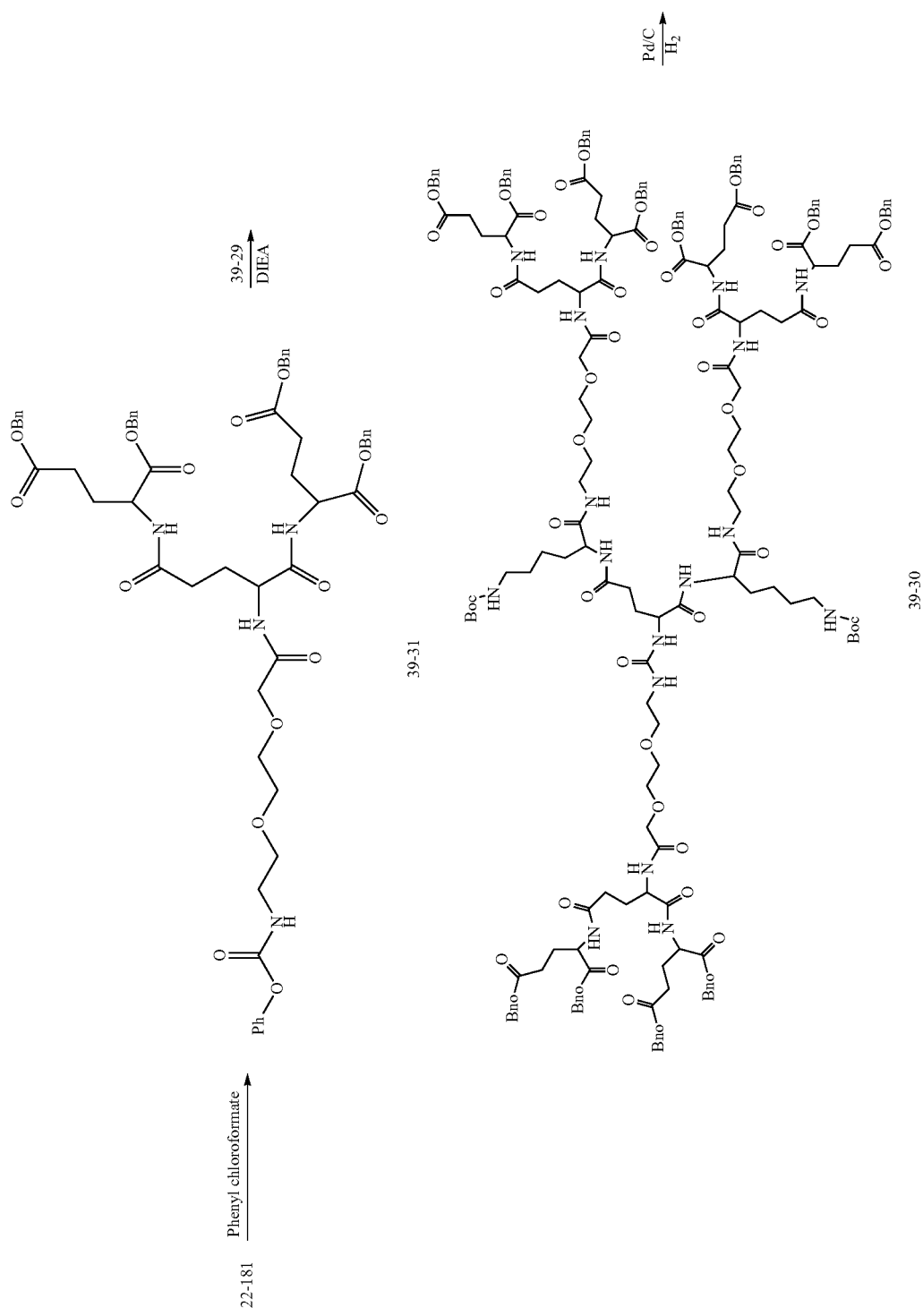

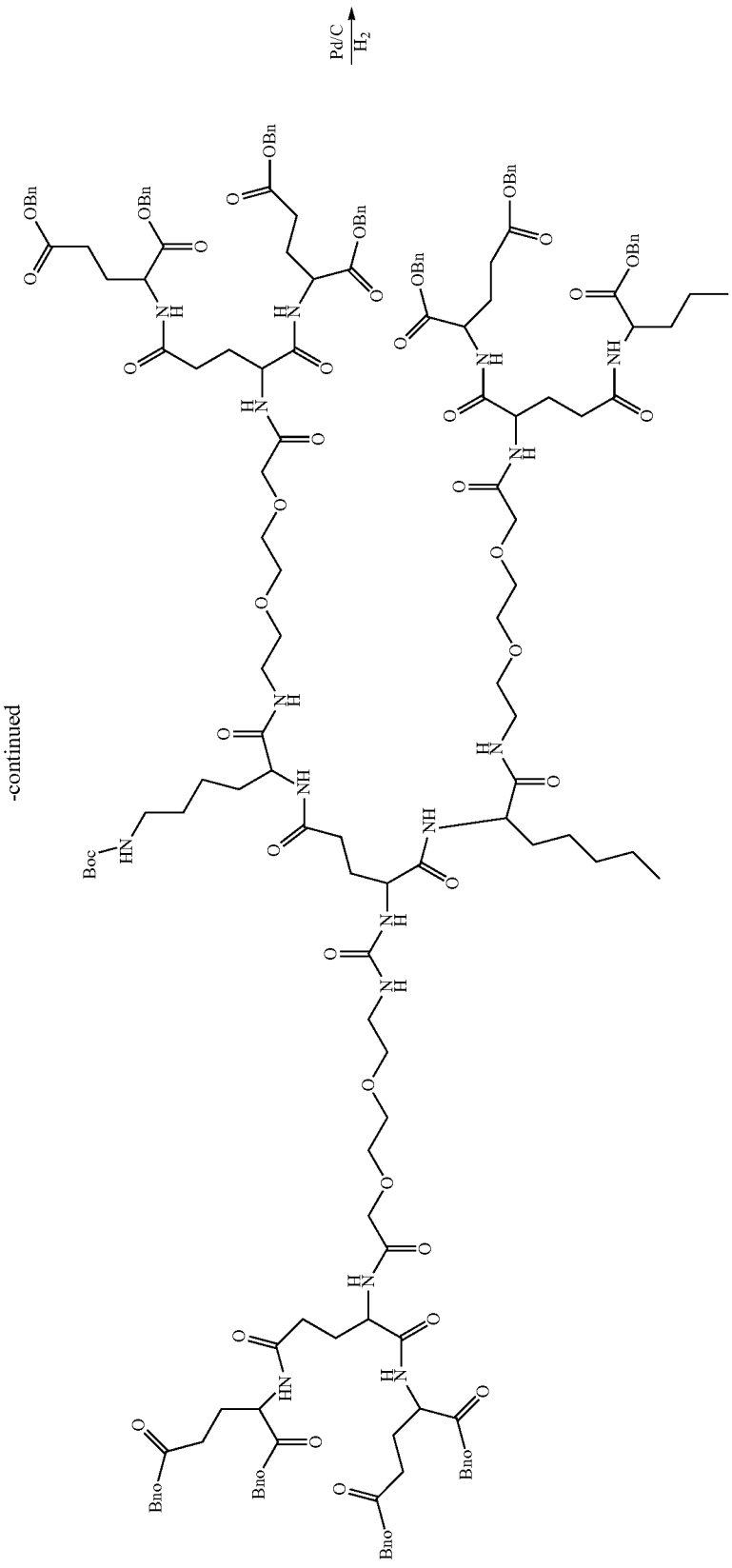

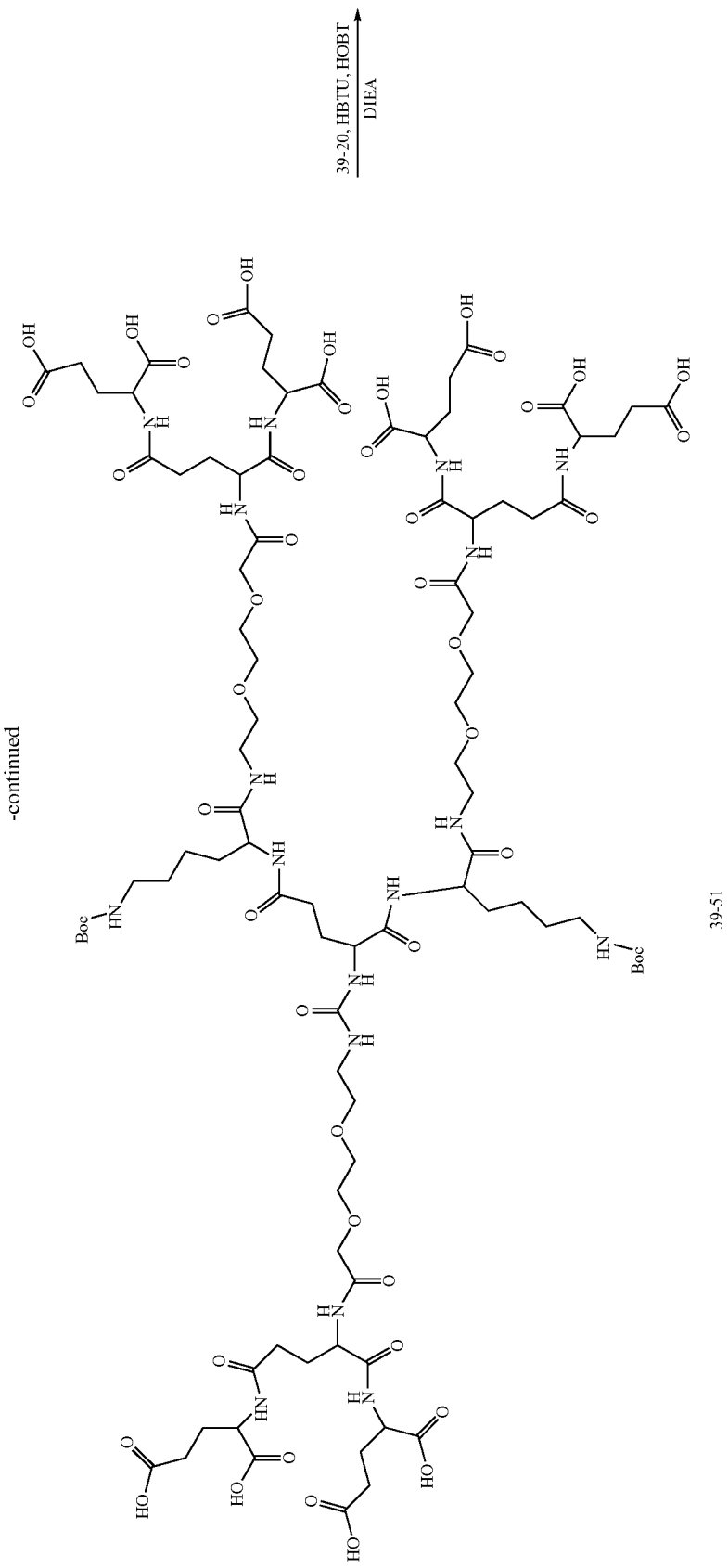

-continued
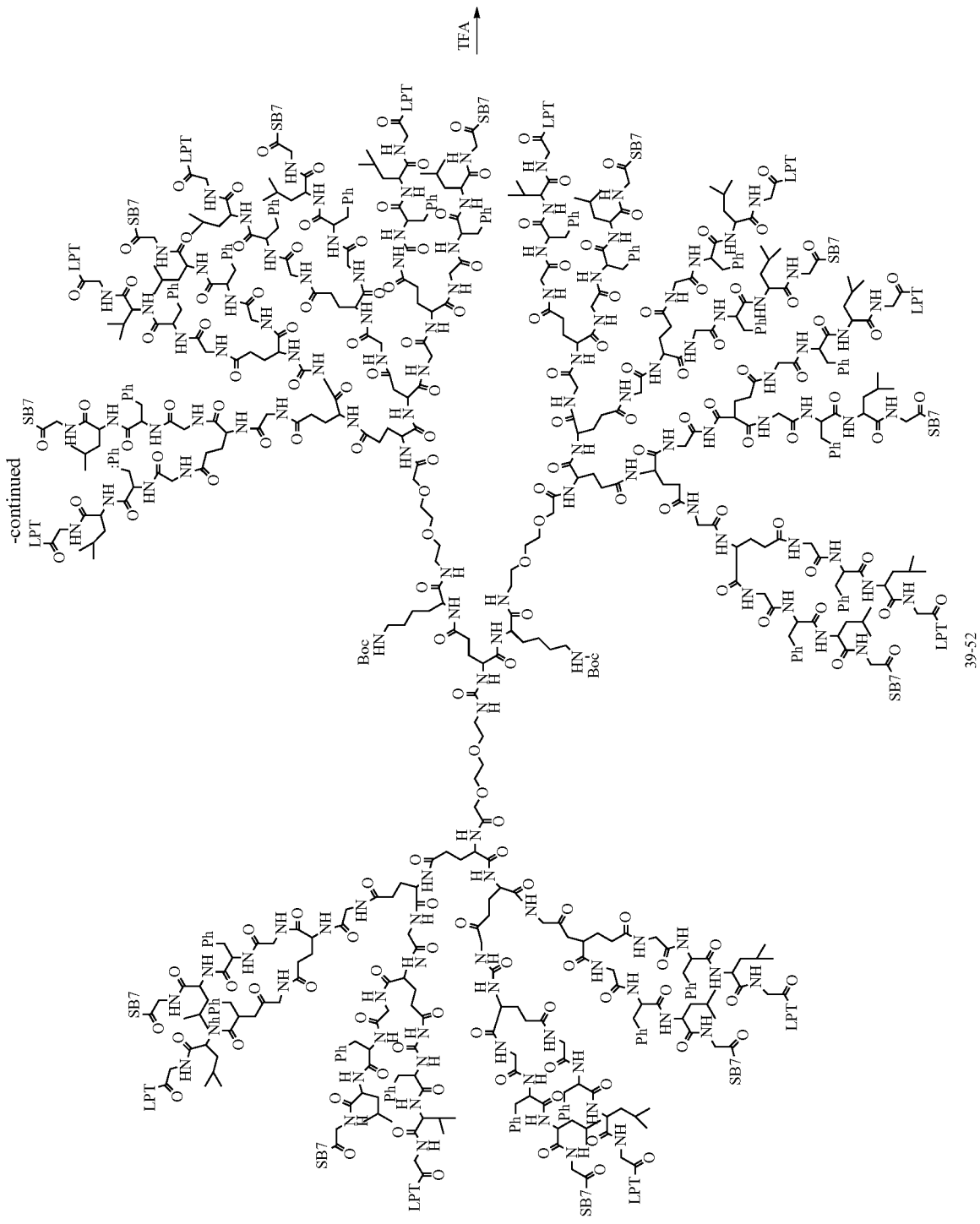
39-52

-continued
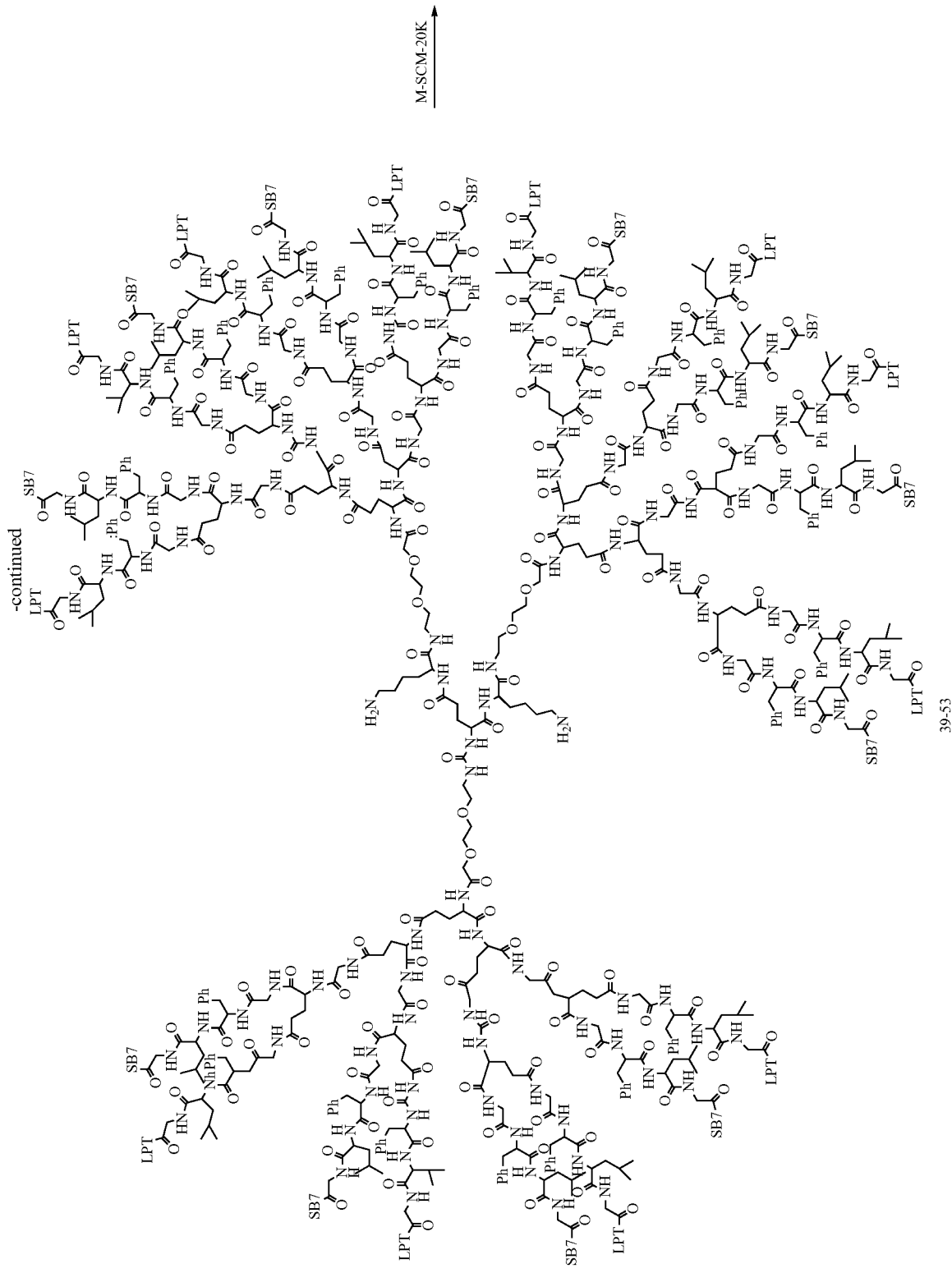
39-53

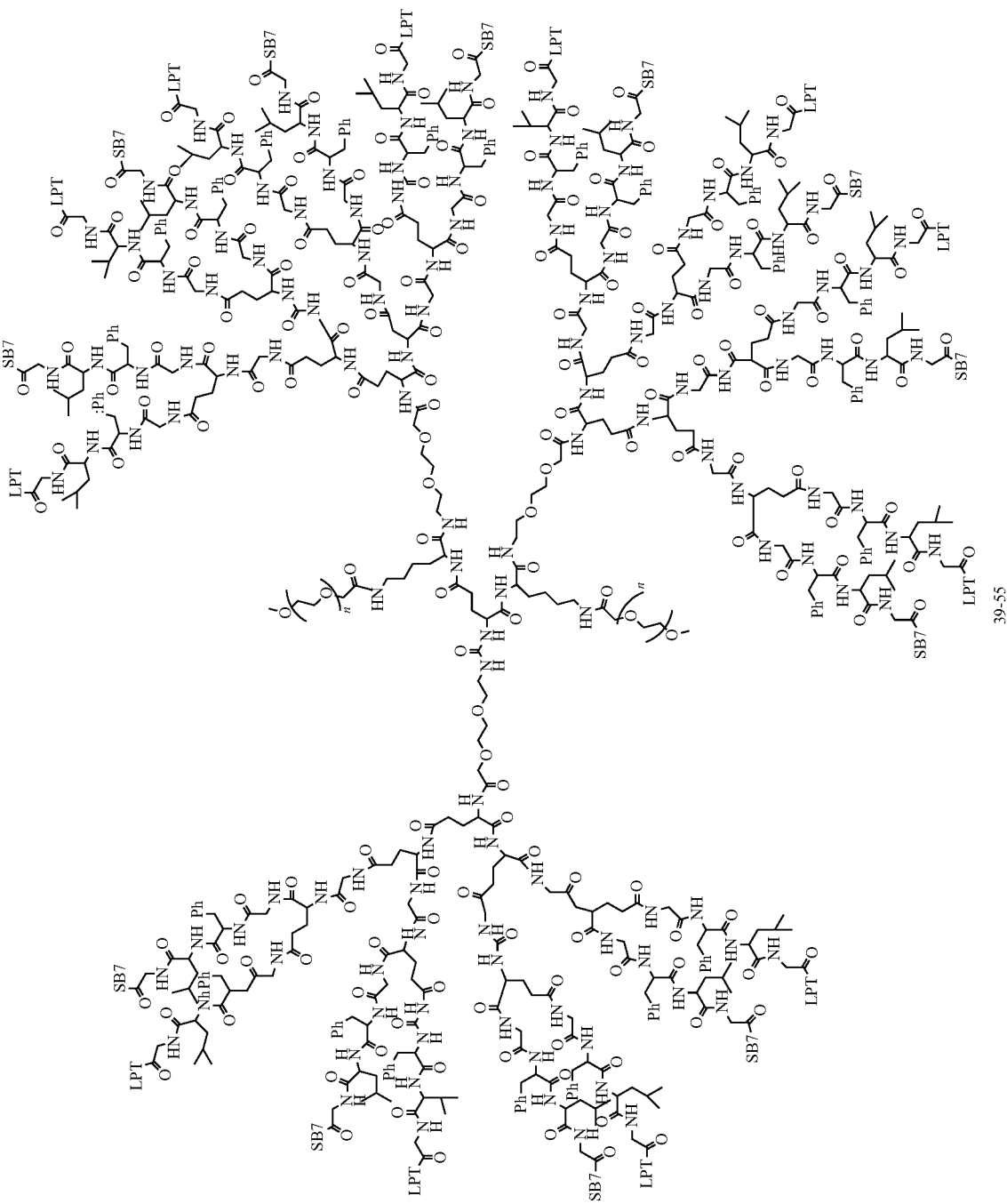
39-55

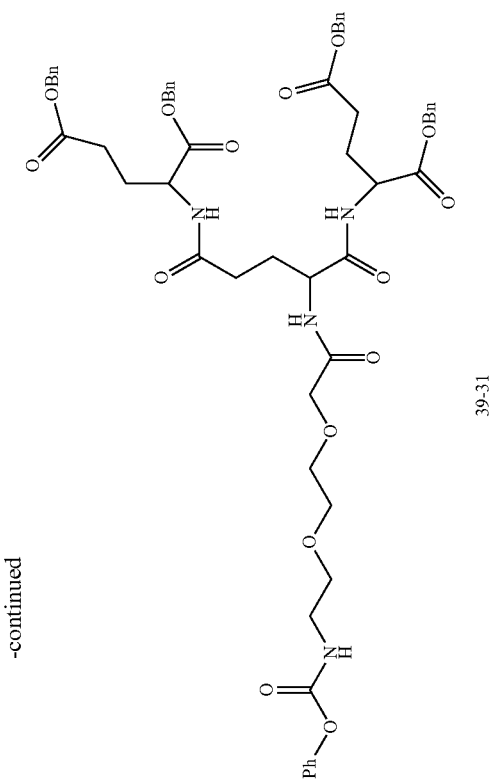
39-31

33-22 (synthesized according to the method of synthesizing 22-181, 0.5 g, 0.54 mmol) was added in a 100 mL round-bottomed flask, and dissolved with dichloromethane (10 mL) in a condition of ultrasonic. Phenyl chloroformate (0.3 mL, 2.19 mmol) was added, and the obtained solution was stirred to react at 0° C. for 30 minutes. Then phenyl chloroformate (0.13 mL, 1.09 mmol) was slowly added dropwise, and the obtained solution reacted at the low temperature for 2 hours. At the end of the reaction, deionized water (200 mL) and ethyl acetate (300 mL) were added for extraction, and the organic phase was separated. The aqueous phase was extracted three times with ethyl acetate (100 mL×3), and the obtained organic phases were combined. The organic phase was washed two times with saturated saline solution (150 mL×2), and evaporated to dryness, thus obtaining the product 0.5 g.

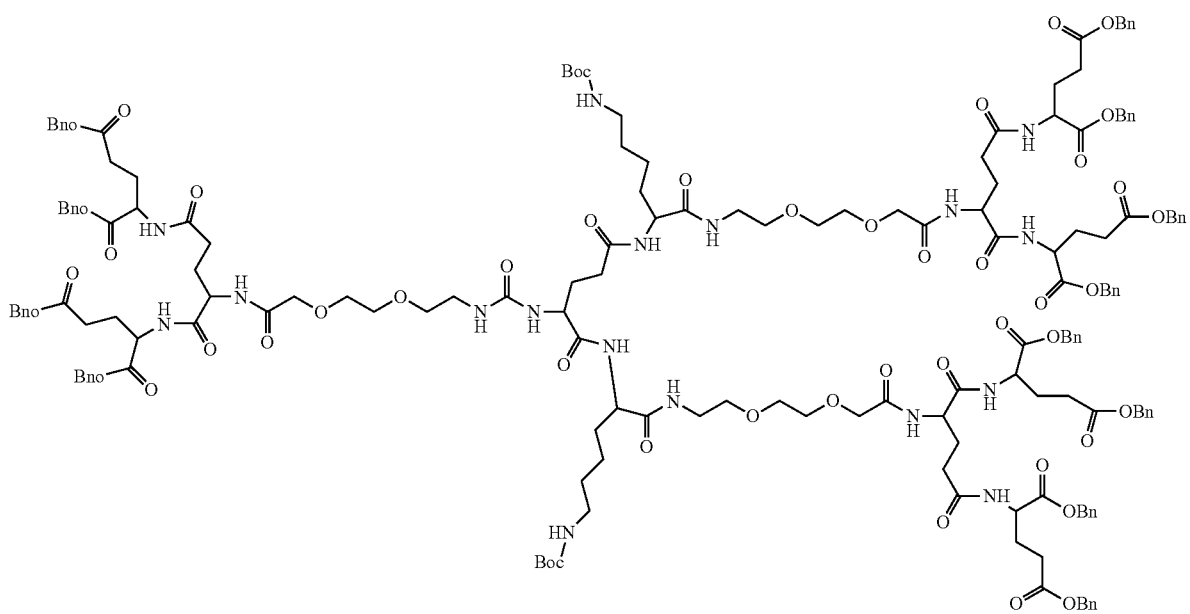

39-30

39-29 (1.4 g, 0.59 mmol), 39-31 (0.5 g, 0.54 mmol) were added in a 250 mL flask, and dissolved with DMF (30 mL). Then, DIEA (0.1 mL) was added, and then the mixed solution was stirred to react at 80° C. until the reaction ended. At the end of the reaction, the reaction solution was transferred to a 1 L separatory funnel, deionized water (100 mL) and ethyl acetate (150 mL) were added for extraction, and the organic phase was separated. The aqueous phase was extracted three times with ethyl acetate (50 mL×3), and the obtained organic phases were combined. The organic phase was washed two times with saturated saline solution (100 mL×2), and concentrated to 50 mL, silica gel powder (6 g) was added, and the operations of evaporation, column chromatography and gradient elution with 2% methanol/dichloromethane-3% methanol/dichloromethane were carried out, thus obtaining the product 1.3 g, yield 65.38%.

$^1$H-NMR (400 MHz, DMSO-d$_6$) δ8.57-8.47 (m, 3H), 8.40-8.06 (m, 6H), 8.01-7.65 (m, 4H), 7.38-7.28 (s, 60H), 7.22-7.11 (m, 1H), 5.14-5.03 (m, 24H), 4.42-4.31 (m, 8H), 3.94-3.86 (m, 5H), 3.60-3.48 (m, 13H), 2.88-2.81 (m, 4H), 2.47-2.37 (m, 11H), 2.22-2.13 (m, 6H), 2.10-1.72 (m, 23H), 1.37-1.31 (m, 29H), 1.26-1.21 (m, 18H), 0.88-0.82 (m, 2H).

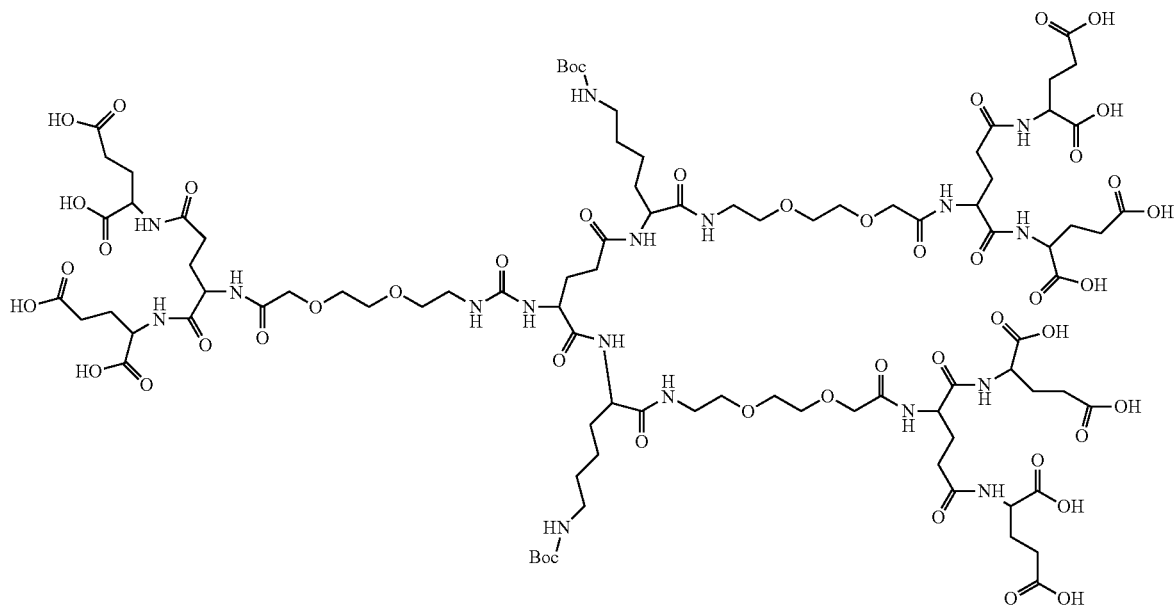

39-51

39-30 (0.16 g, 0.048 mmol) and 10% Pd/C (70 mg) were dissolved with DMF (30 mL), and added in a hydrogenation reactor, the device was set ready, hydrogen was introduced to a pressure of 18 Ps, and then the mixed solution was stirred to react. At the end of the reaction, the reaction solution was filtered by suction with diatomaceous earth as a filter cake to remove the Pd/C, and then the diatomaceous earth was washed four times with DMF (25 mL×4), thus obtaining the product solution.

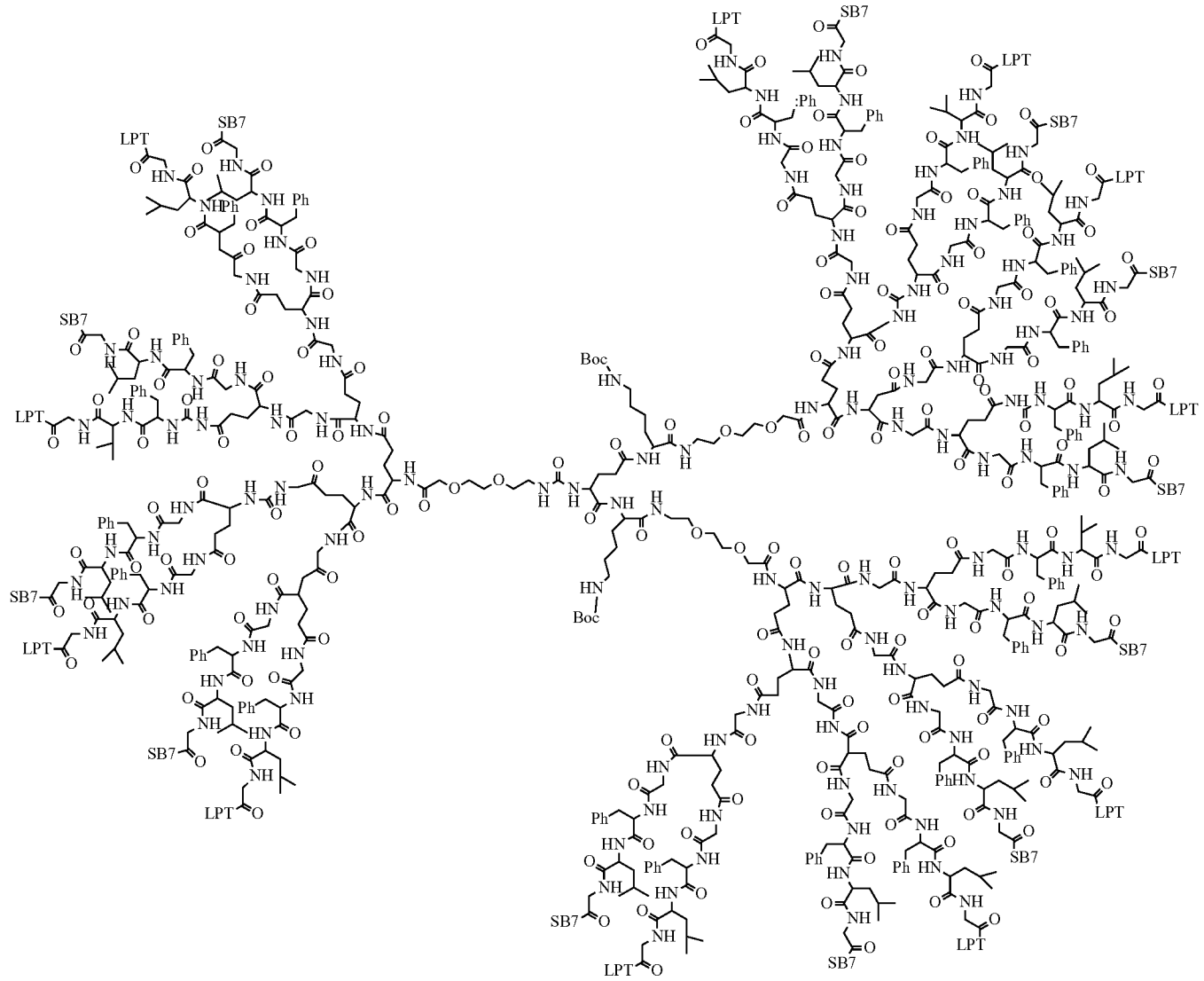

39-20 (1.25 g, 0.625 mmol), 39-51 (0.048 mmol), HBTU (0.32 g, 0.864 mmol), HOBT (0.11 g, 0.864 mmol) were added in a 250 mL flask, and dissolved with DMF (30 mL), and ultrasonic treatment was carried out to completely dissolve the reactants, and the obtained solution was stirred at −5° C. for 30 minutes. Then, DIEA (0.42 mL, 2.59 mmol) was slowly added dropwise, and the obtained solution was stirred at the low temperature for 2 hours, and then reacted at room temperature until the reaction ended. At the end of the reaction, methyl tert-butyl ether (250 mL) was added to the reaction solution, ultrasonic treatment was carried out for 5 minutes, the supernatant was discarded, ethyl acetate (20 mL) was added to the lower liquid, ultrasonic treatment was carried out for 3 minutes, methyl tert-butyl ether (150 mL) and n-hexane (100 mL) were added to separate out a solid, and suction filtering was carried out. The filter cake was dissolved with 20% methanol/dichloromethane (20 mL), silica gel powder (10 g) was added, the operations of evaporation, column chromatography and gradient elution with 1% ammonia water: 6% methanol/dichloromethane-1% ammonia water: 15% methanol/dichloromethane were carried out, thus obtaining the product 0.6 g.

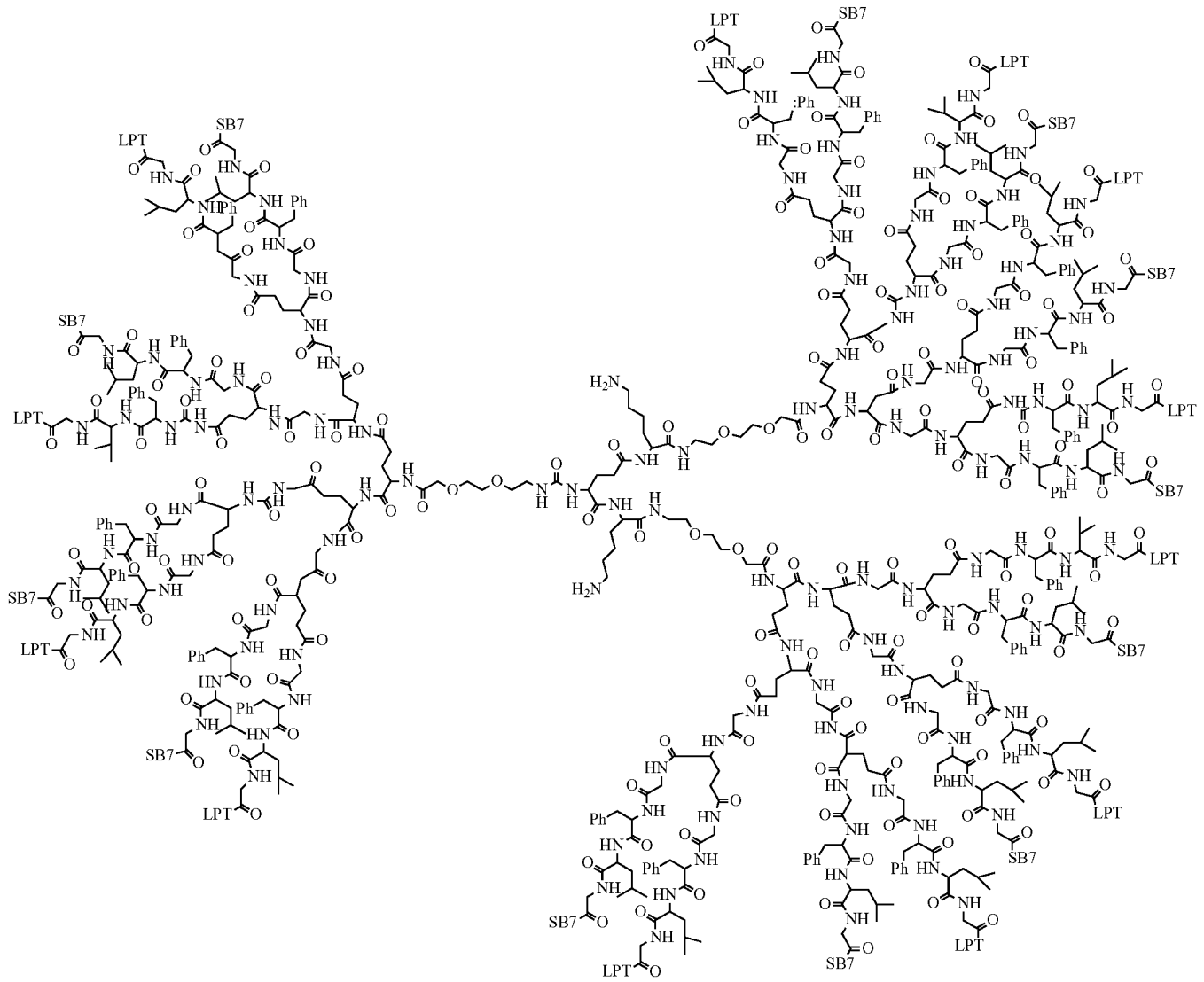

39-52 (0.6 g) was dissolved with dichloromethane (15 mL) and TFA (0.2267 mL, 3.0521 mmol), and ultrasonic treatment was carried out to completely dissolve the compound. A ground glass stopper was used, and the mixed solution was stirred to react at room temperature. At the end of the reaction, the reaction solution was evaporated to remove the dichloromethane, ethyl acetate (20 mL) was added, ultrasonic treatment was carried out for 2 minutes, methyl tert-butyl ether (150 mL) and n-hexane (70 mL) were added, and suction filtering was carried out. The filter cake was dissolved with 20% methanol/dichloromethane in a condition of ultrasonic, silica gel powder (6 g) was added, and the operations of evaporation with a rotary evaporator, column chromatography and gradient elution with 1% ammonia water: 6% methanol/dichloromethane-1% ammonia water: 15% methanol/dichloromethane were carried out, thus obtaining the product 0.3 g.

39-55
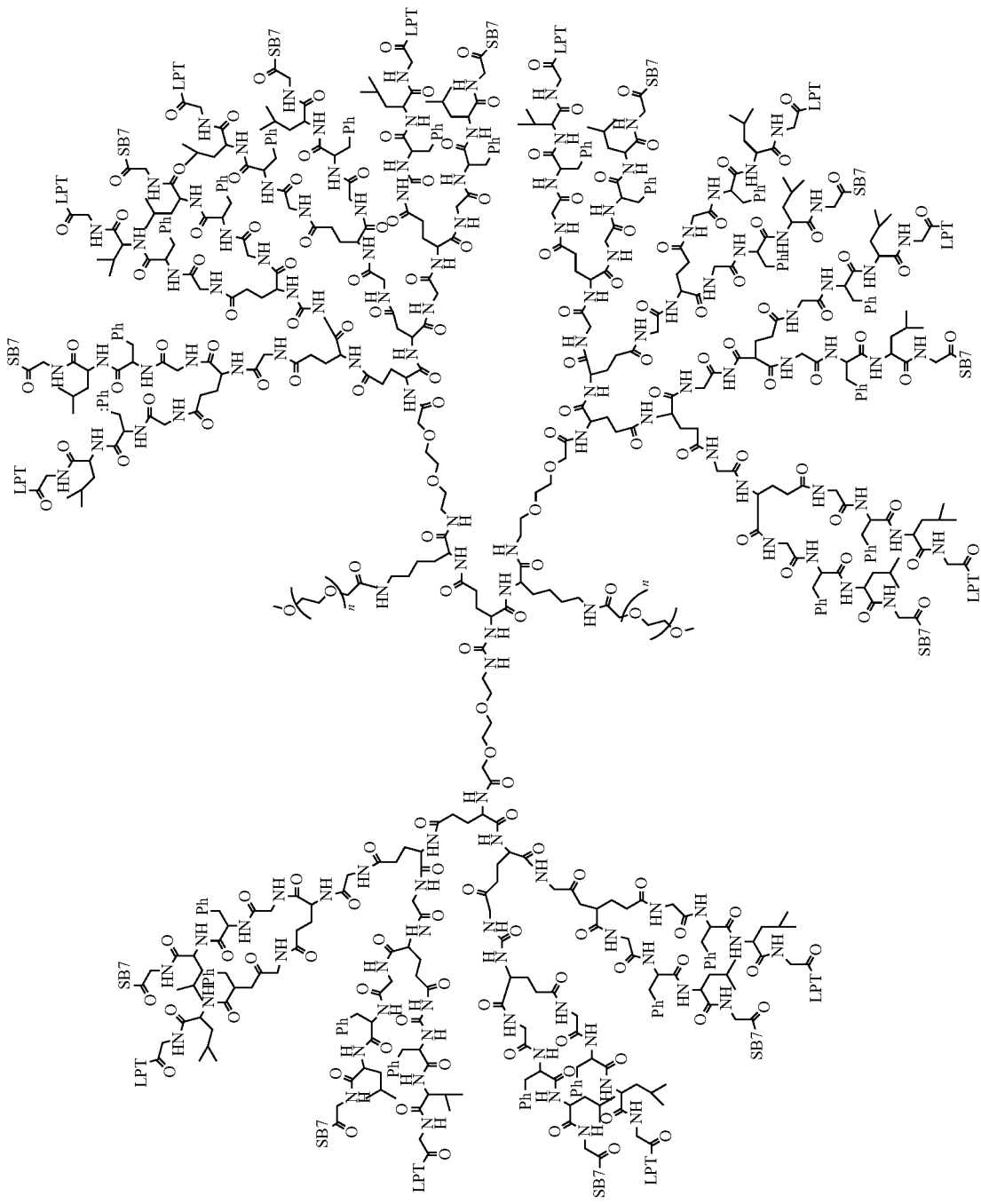

39-53 (0.6 g) was dissolved with DMF (20 mL), M-SCM-20K (0.9378 g) was added, ultrasonic treatment was carried out to dissolve the reactants, and then the obtained solution reacted in the dark at a low speed. At the end of the reaction, methyl tert-butyl ether (150 mL), n-hexane (70 mL) were added to the reaction solution to separate out a solid, and suction filtering was carried out. The filter cake was dissolved with 20% methanol/dichloromethane, silica gel powder (10 g) was added, and the operations of evaporation, column chromatography and gradient elution with dichloromethane-1% ammonia water: 15% methanol/dichloromethane were carried out. The elution product was collected, evaporated to dryness, and then dissolved with anhydrous ethanol (3 mL), and the obtained solution was treated by ultrasonic to obtain homogeneous phase. Then, methyl tert-butyl ether (150 mL), n-hexane (50 mL) were added, and suction filtering was carried out. The filter cake was further dissolved with anhydrous ethanol (3 mL), methyl tert-butyl ether and n-hexane were added for precipitation. The process of dissolution and precipitation was repeated three times. Suction filtering was carried out, and the filter cake was dried, thus obtaining the product 0.8 g.

$^1$H-NMR (600 MHz, DMSO-$d_6$) δ9.93-9.81 (m, 7H), 9.09-9.01 (m, 14H), 8.79-7.94 (m, 163H), 7.87-6.50 (m, 404H), 5.79-5.70 (m, 5H), 5.29-5.23 (m, 18H), 4.81-4.00 (m, 138H), 3.51-3.50 (m, 2227H), 3.25-2.64 (m, 177H), 2.36-1.91 (m, 101H), 1.55-1.32 (m, 293H), 0.88-0.72 (m, 216H).

14. Synthesis of 29-235 (Compound No. 15)

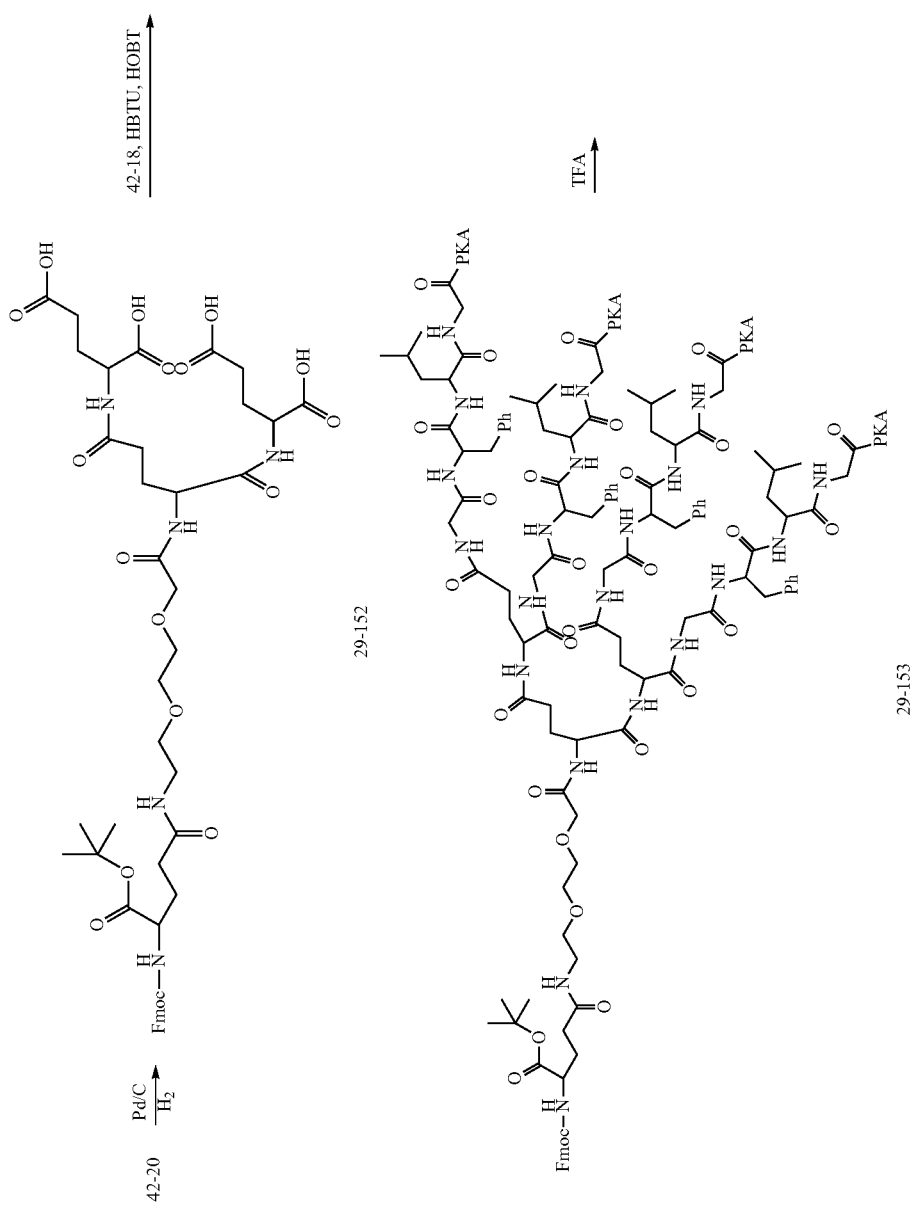

-continued
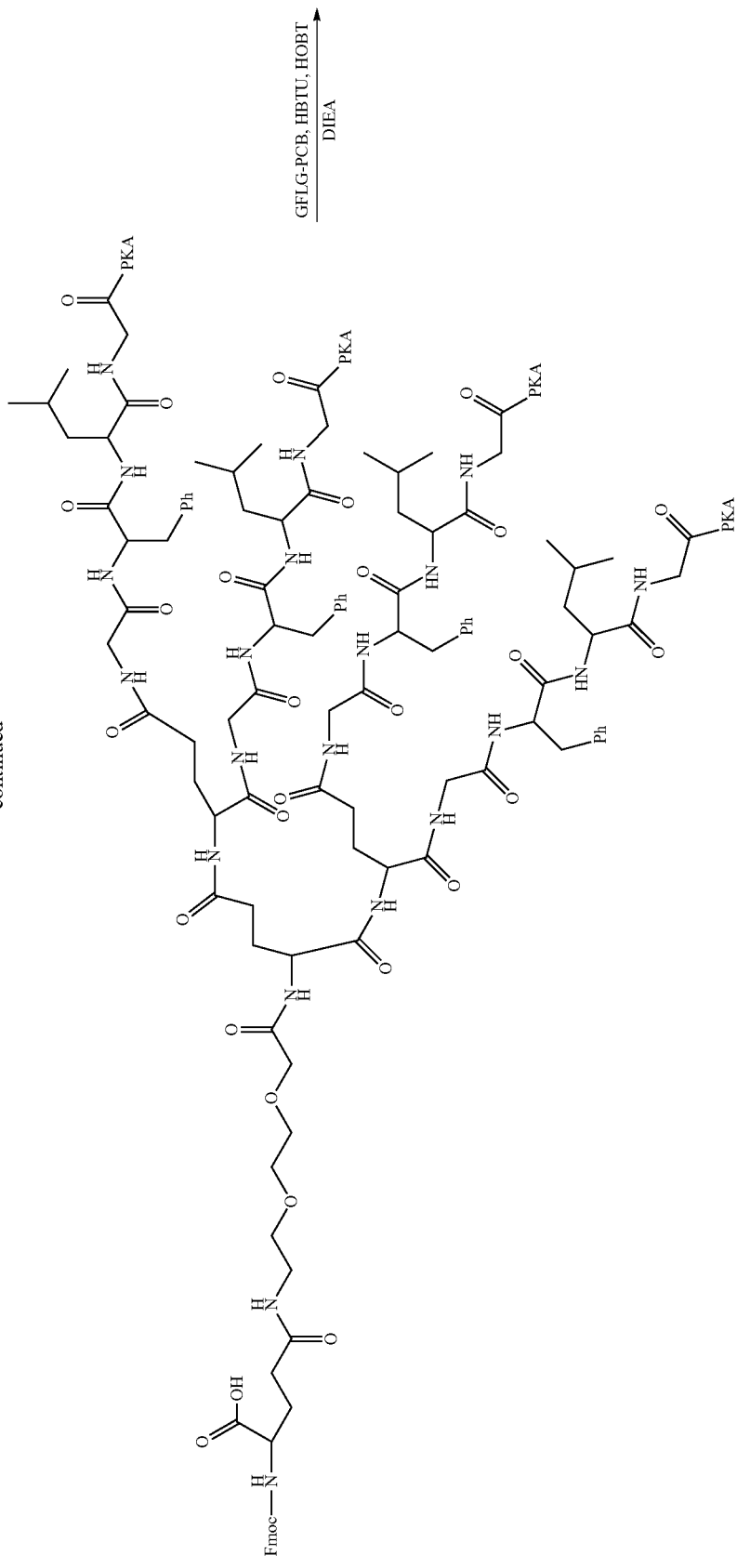
29-157

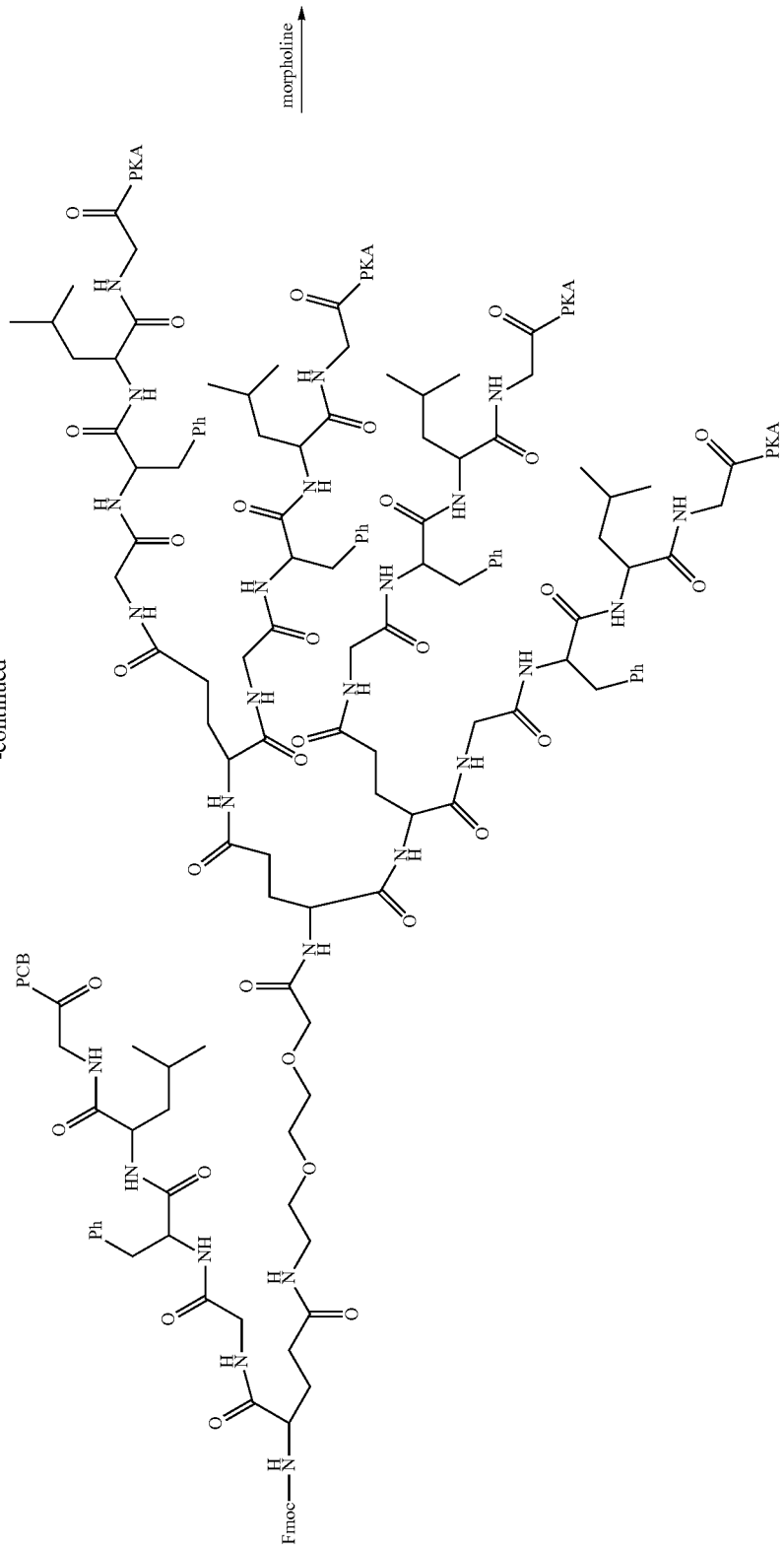

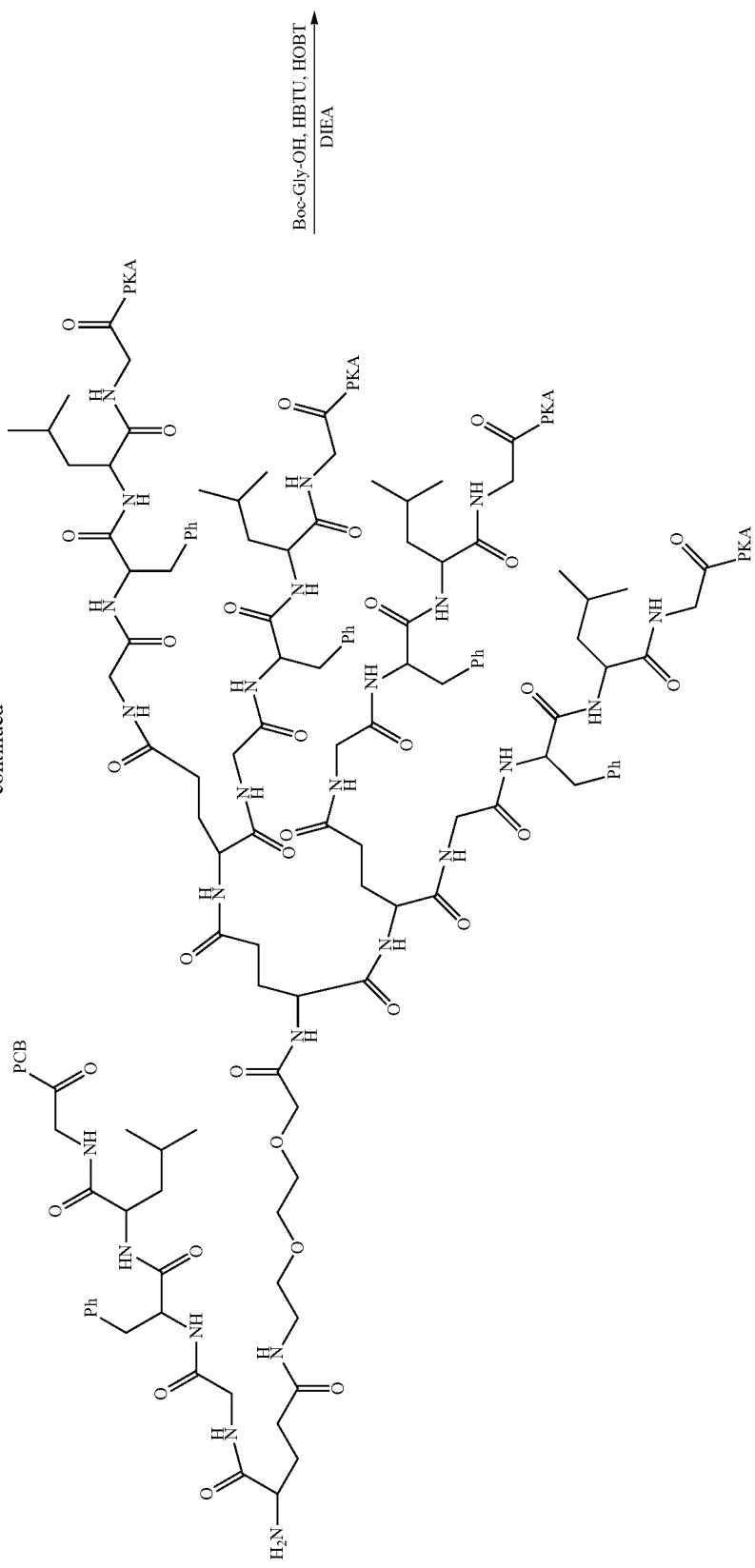

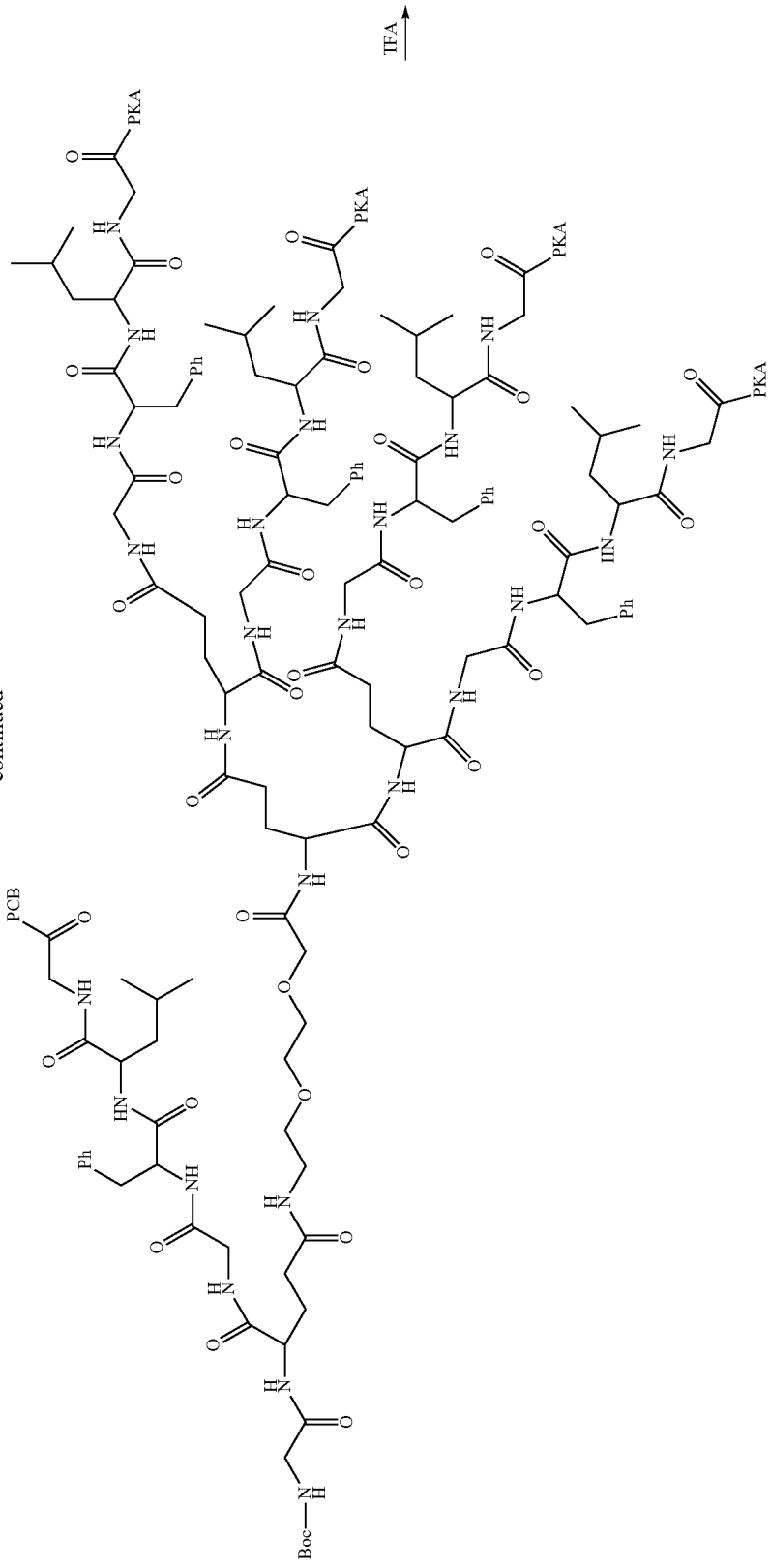

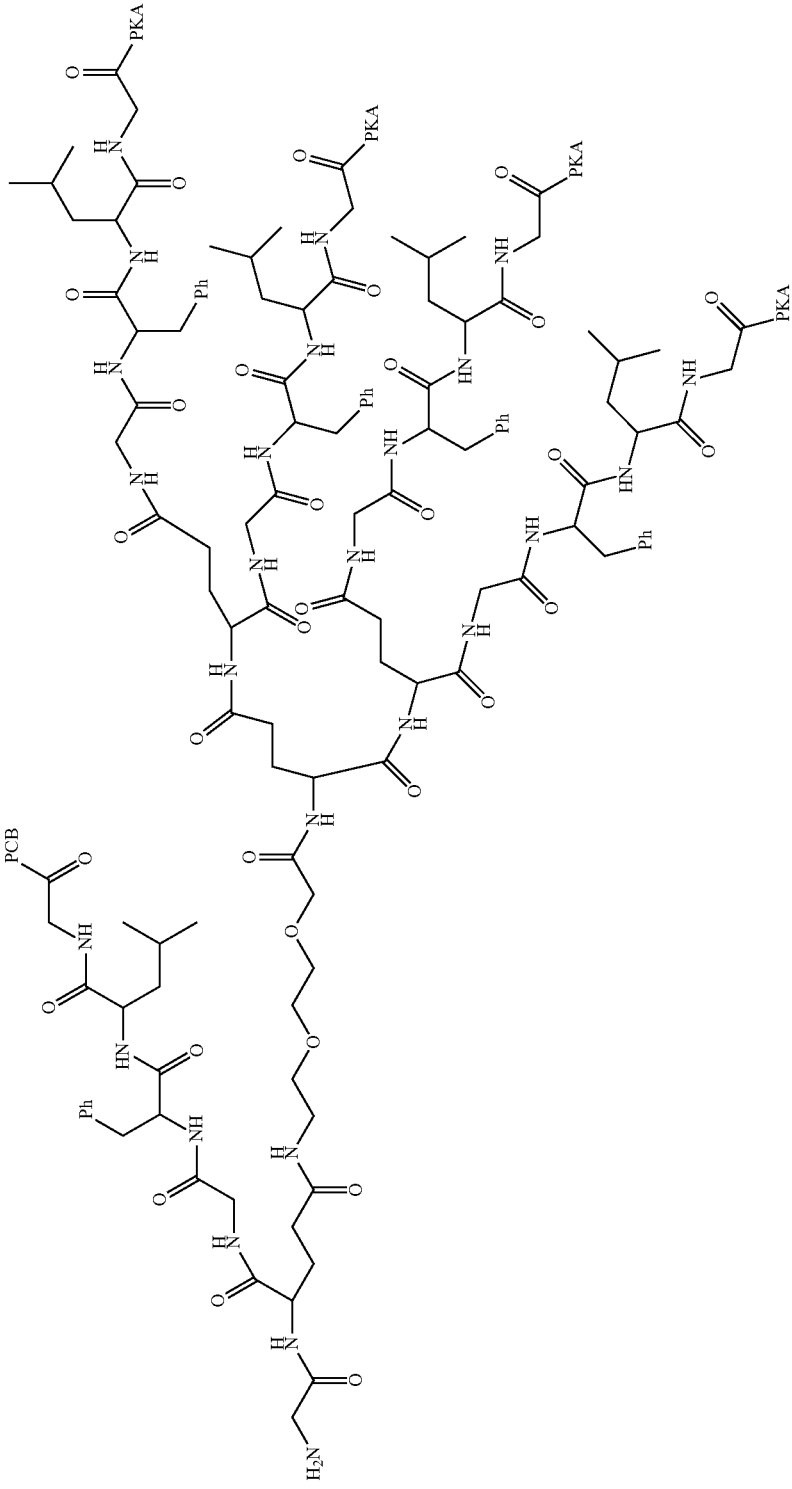
29-194

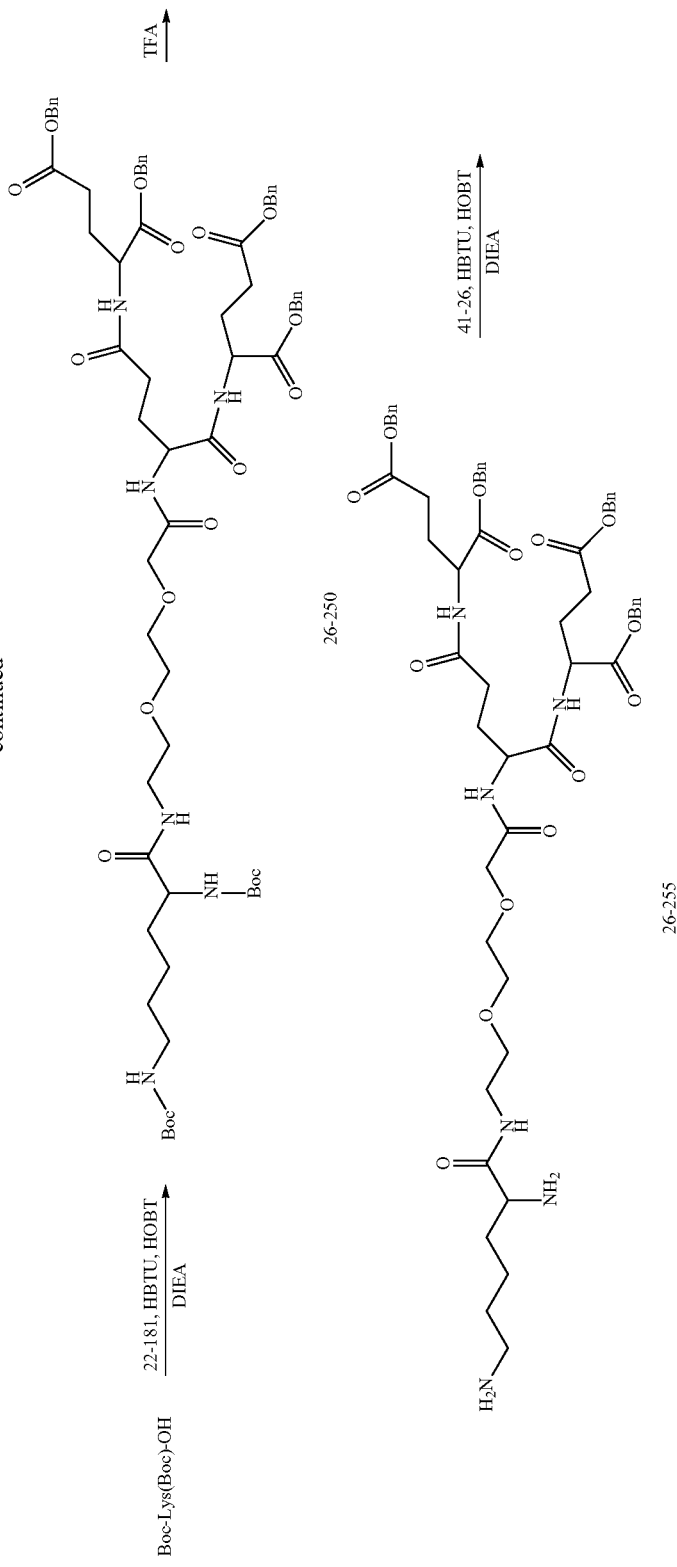

-continued
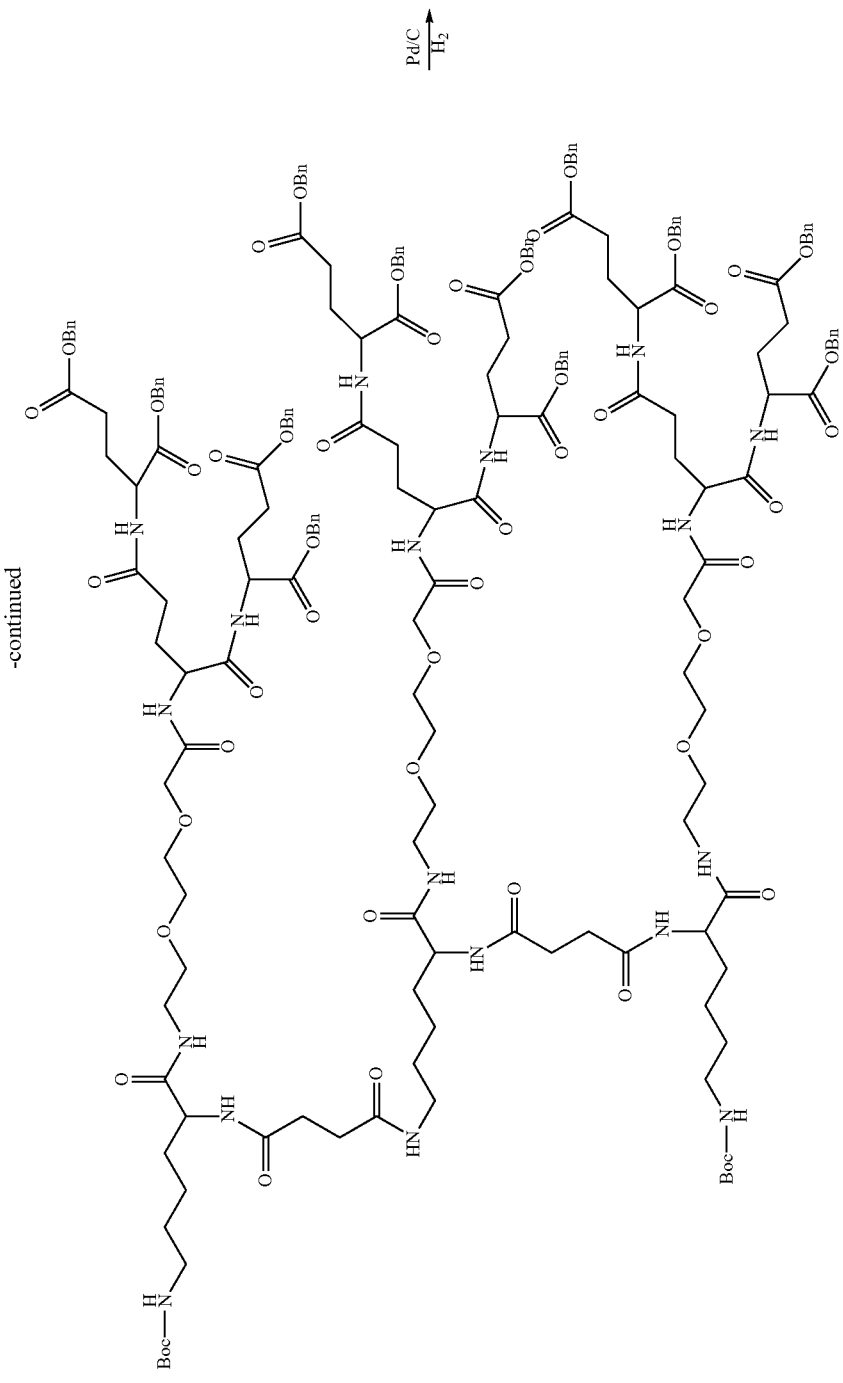
26-258

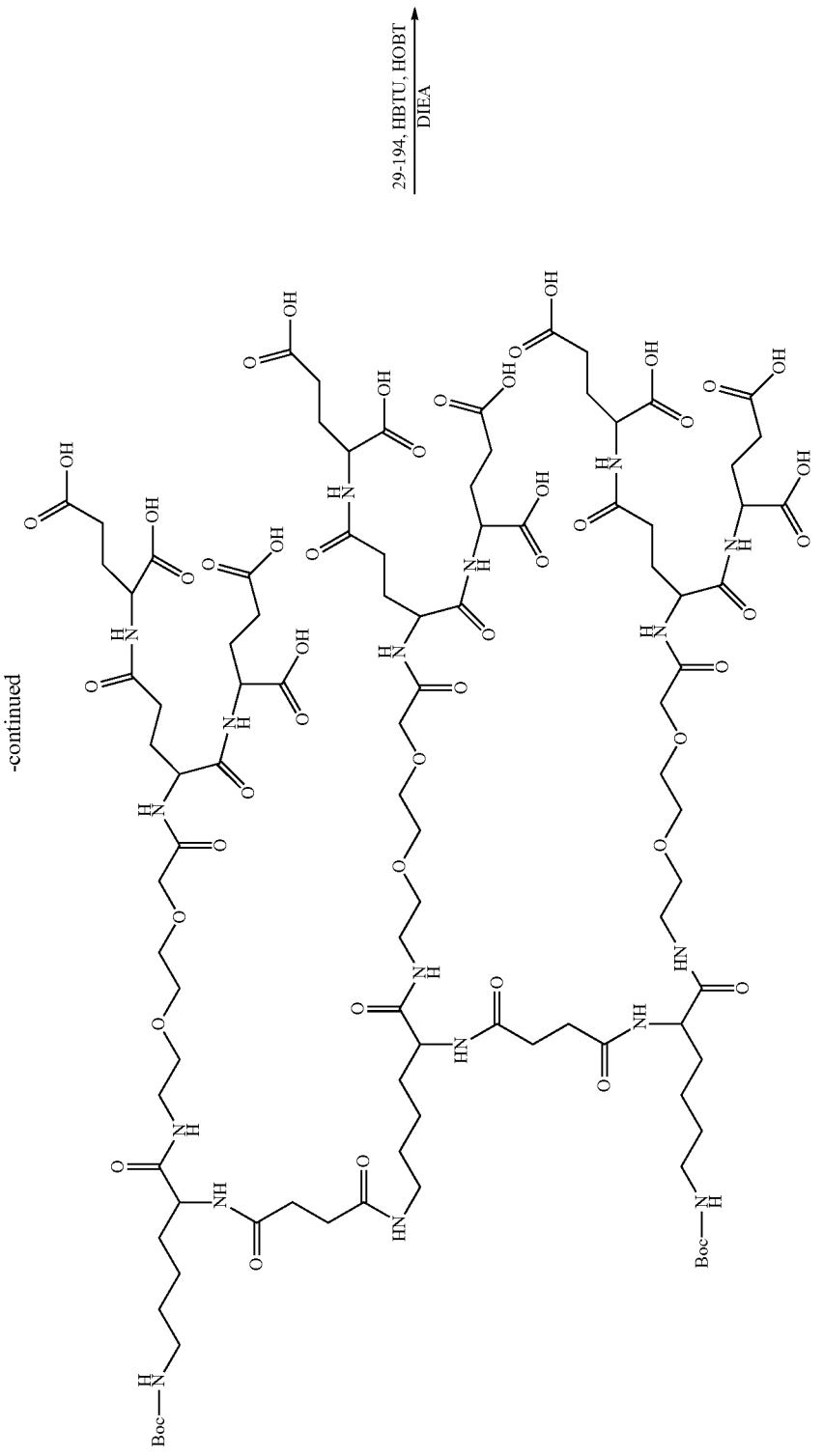

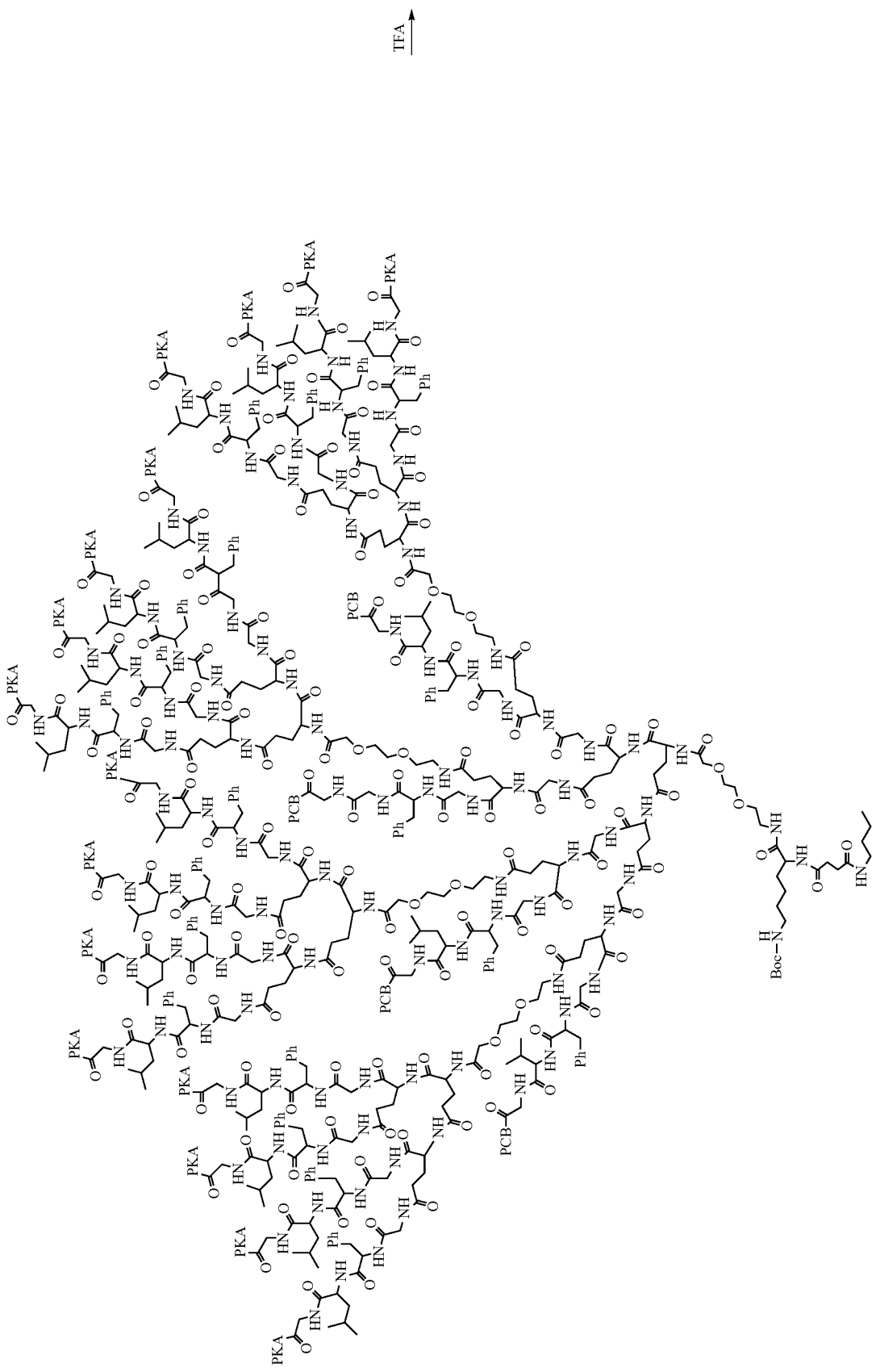

-continued
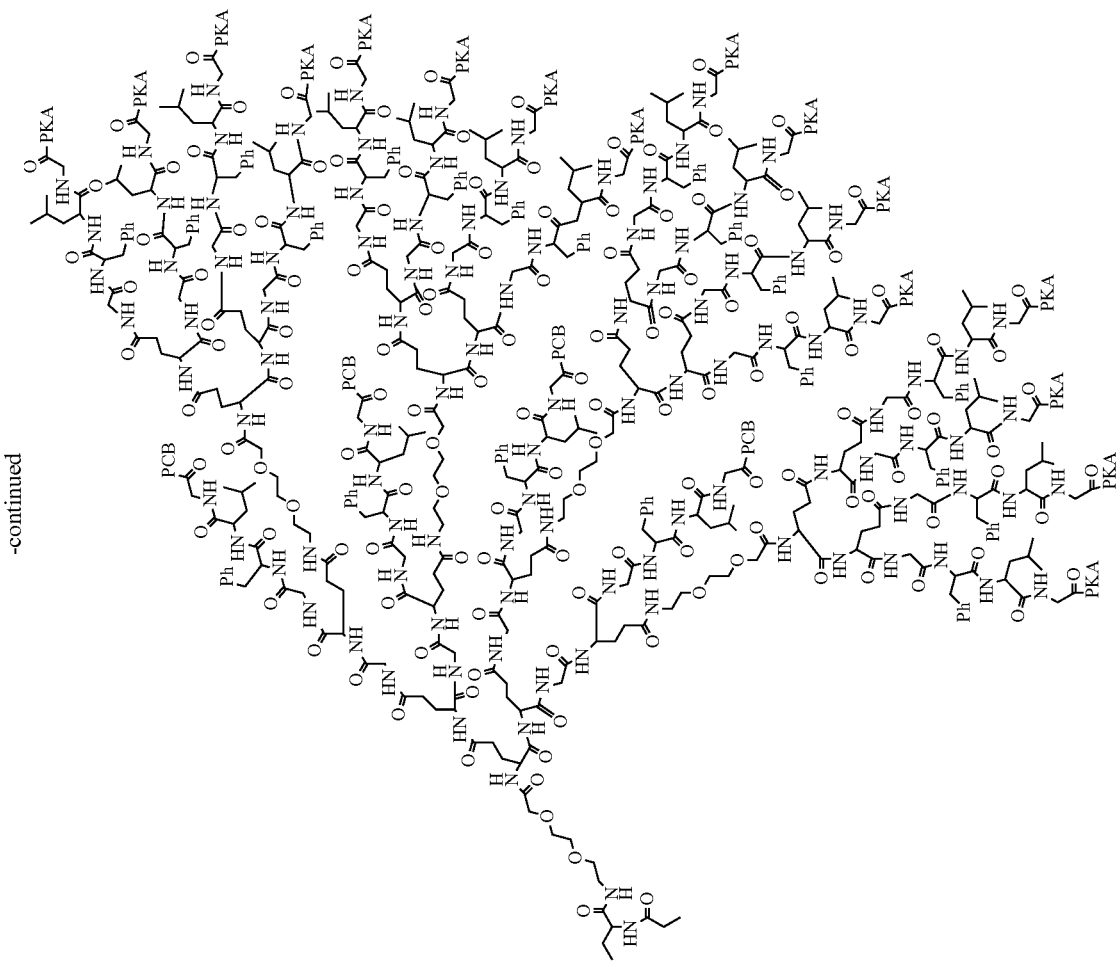

-continued
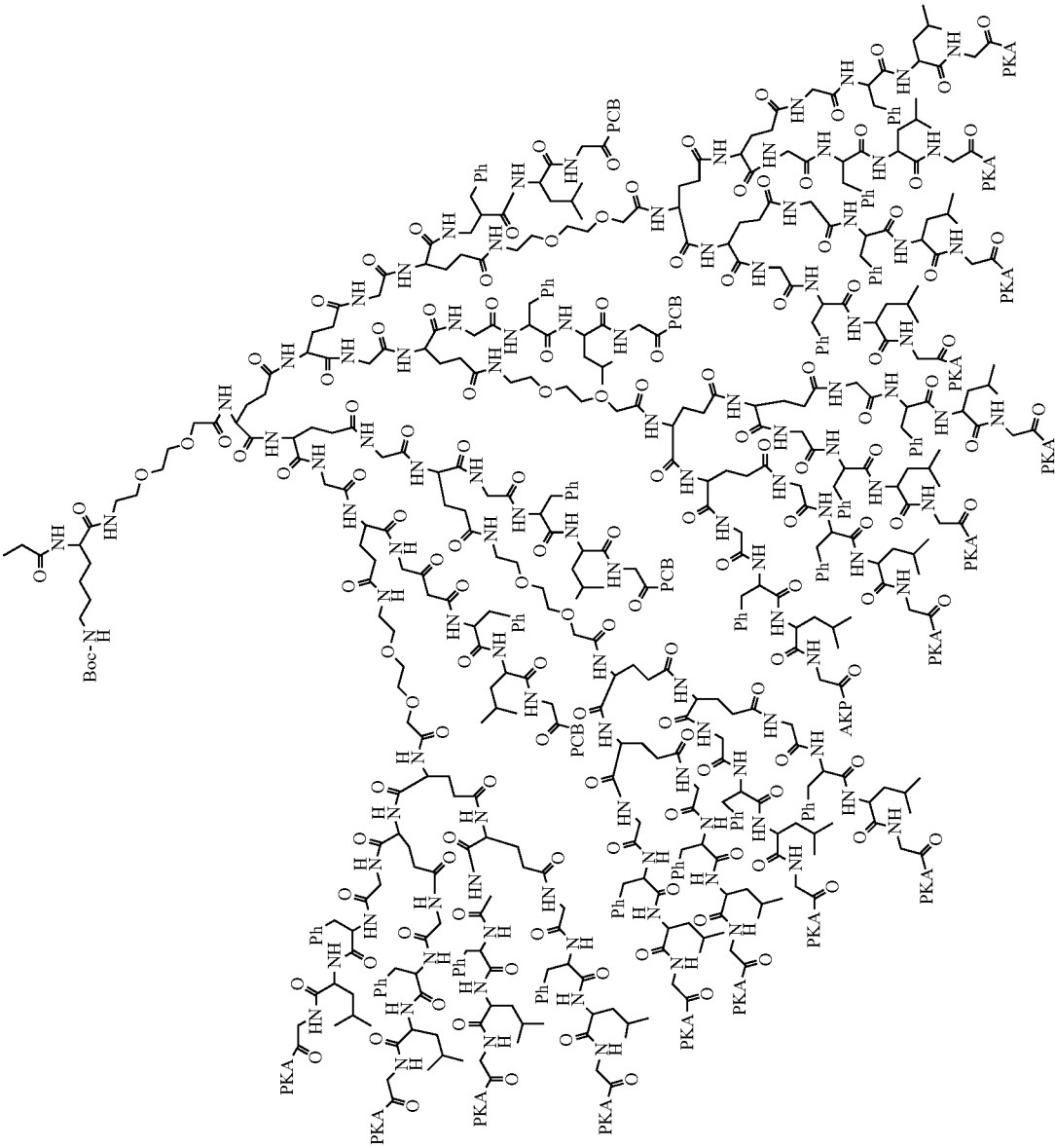

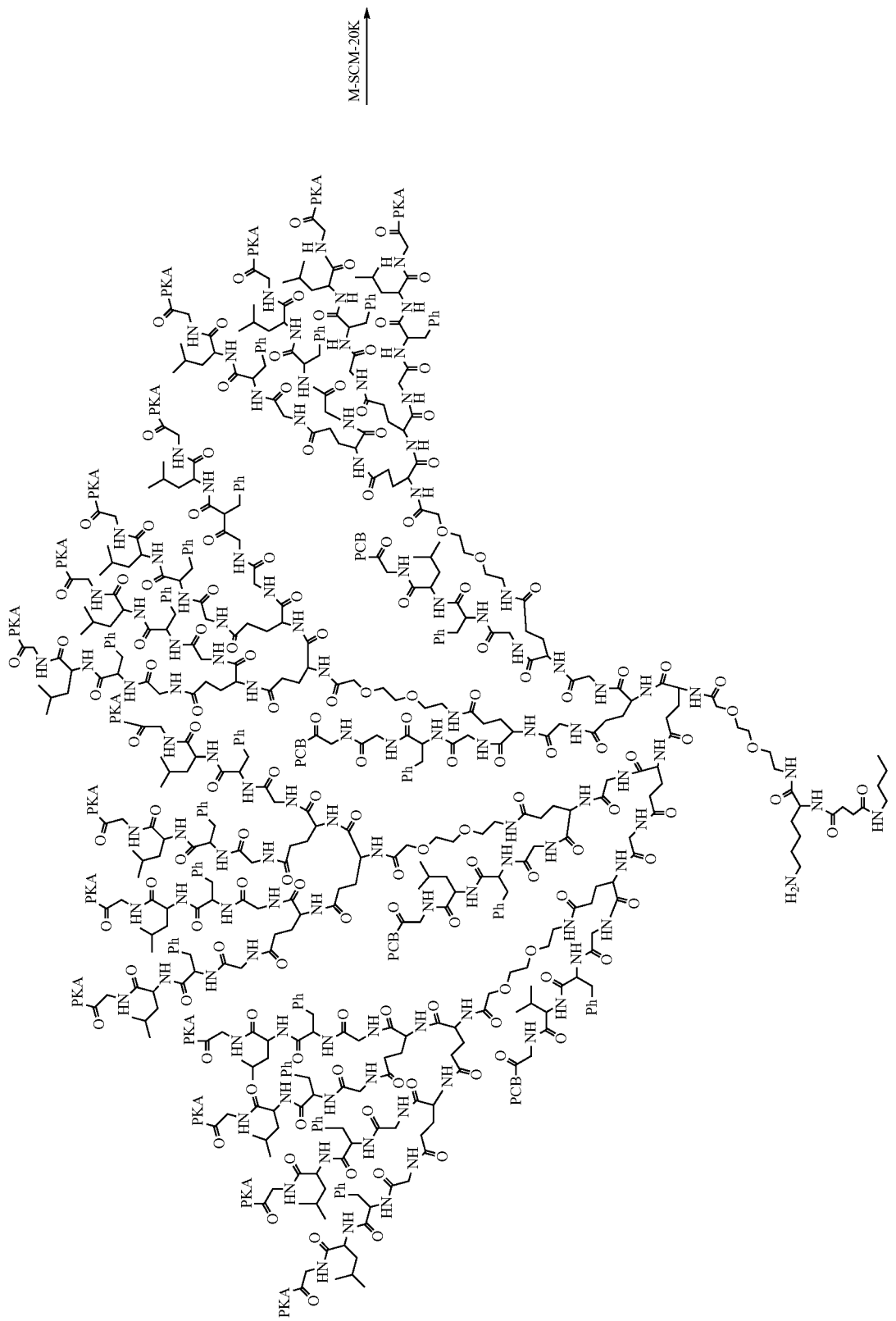

-continued
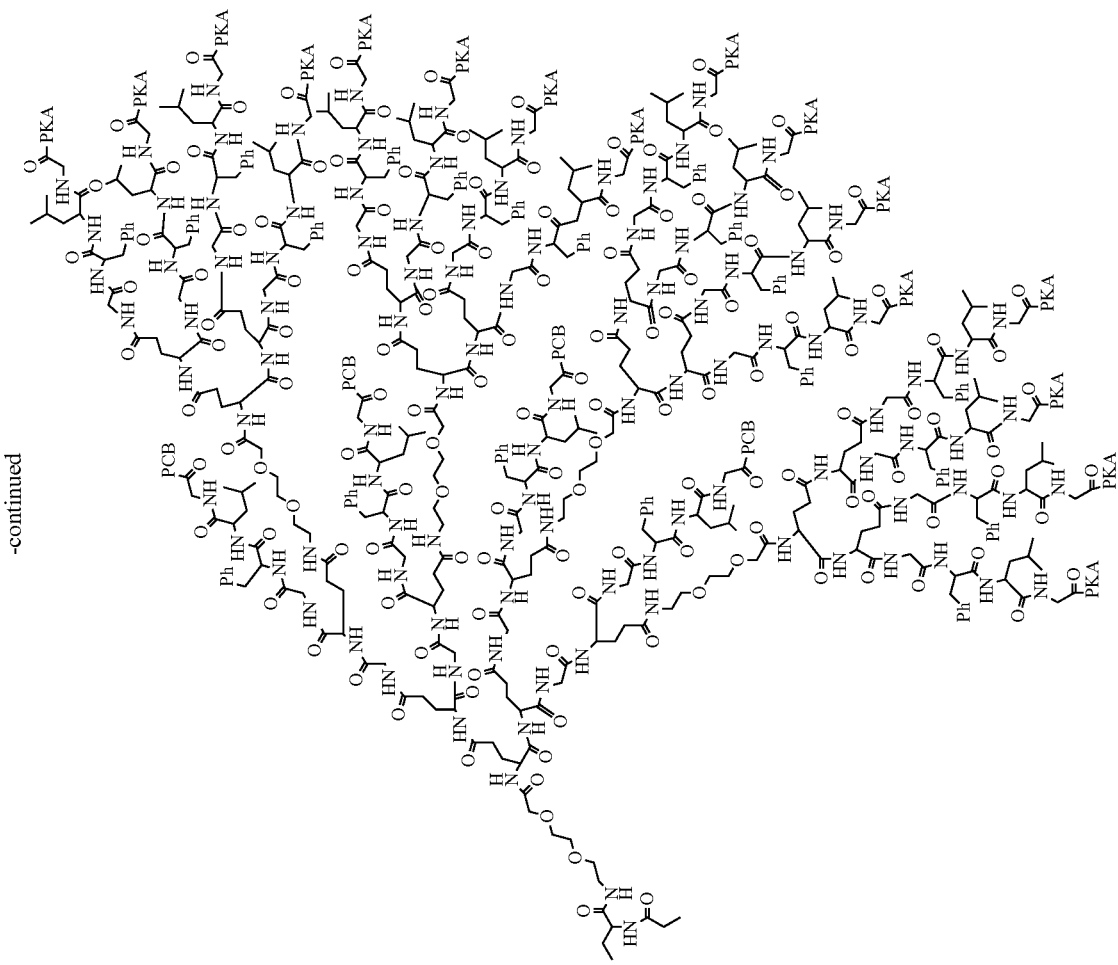

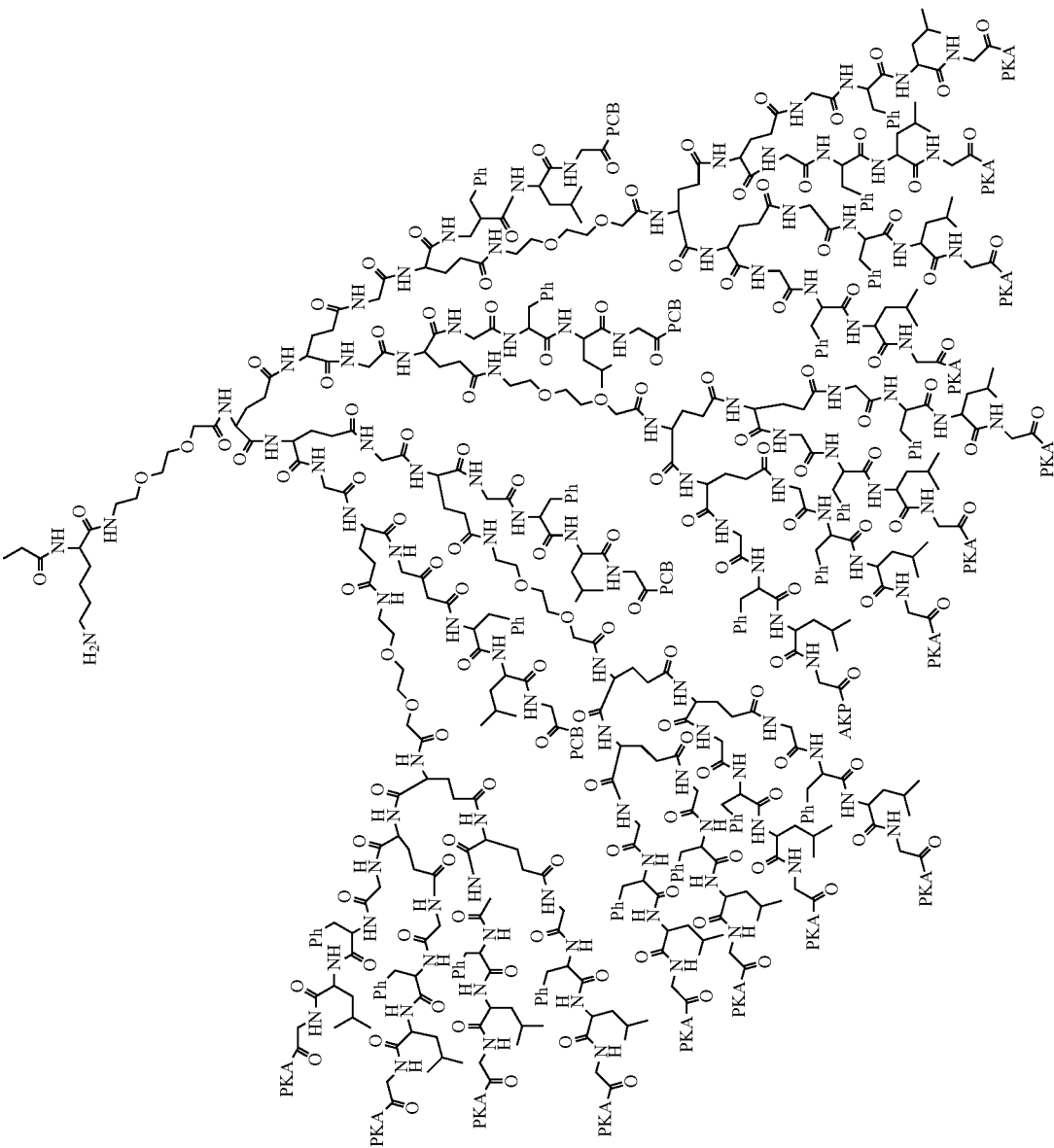

29-235
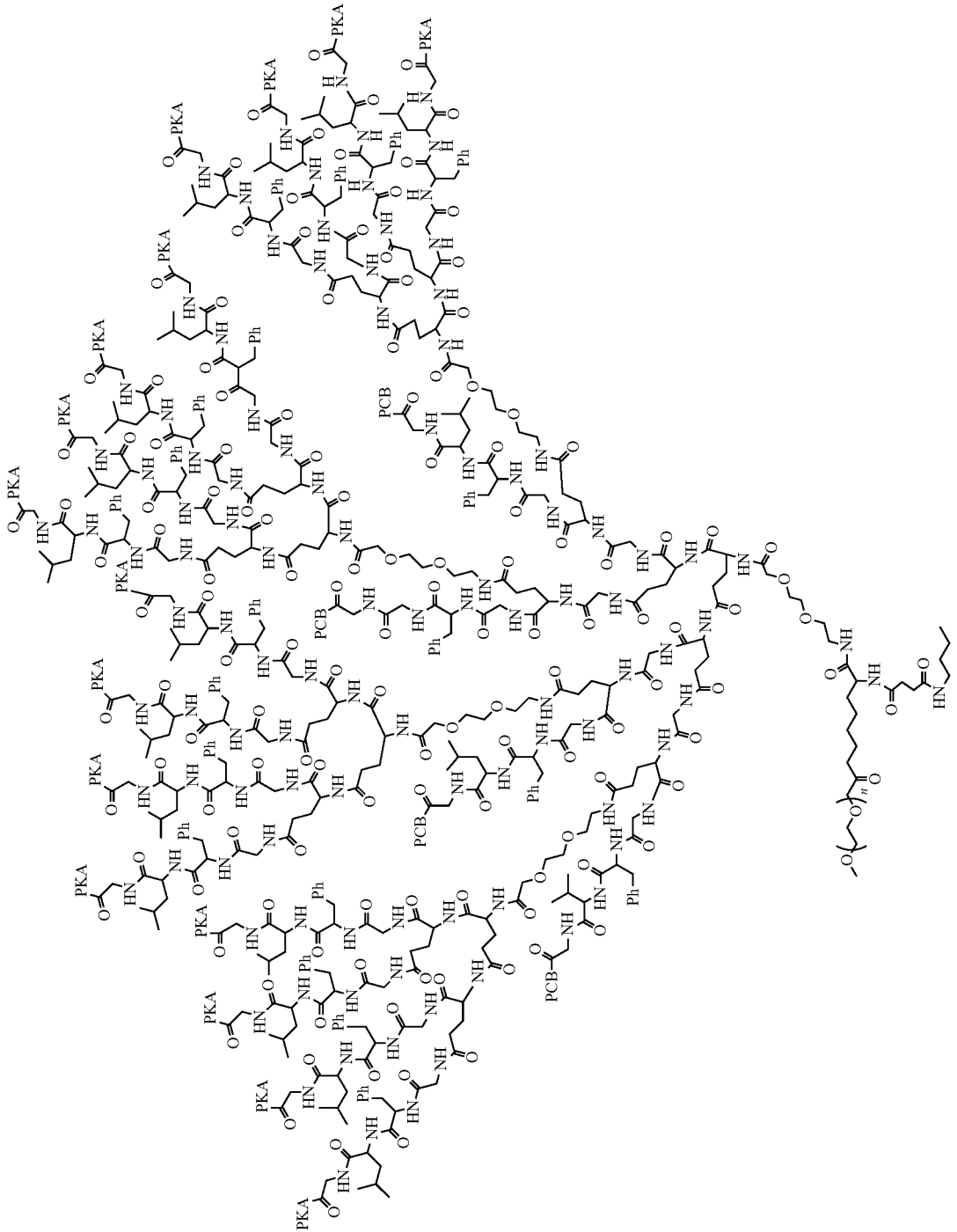

-continued
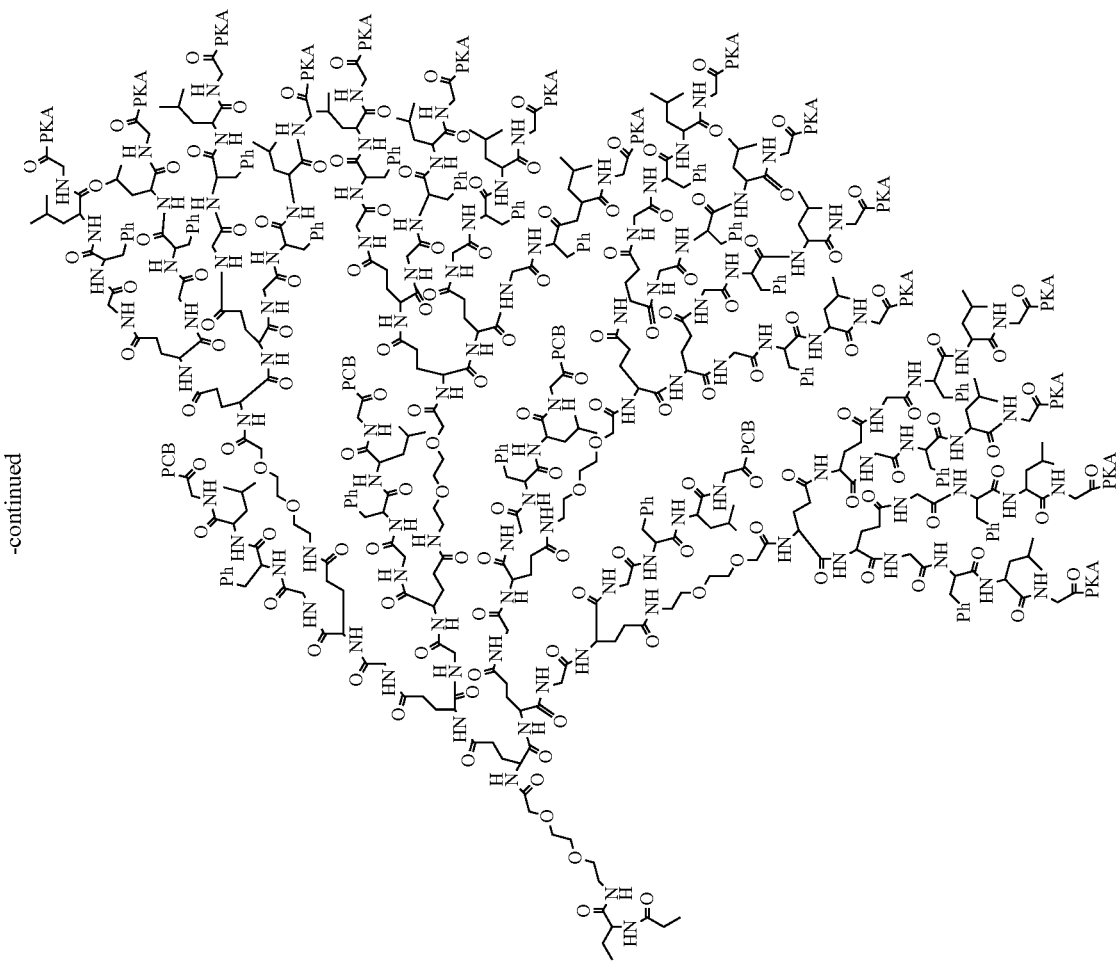

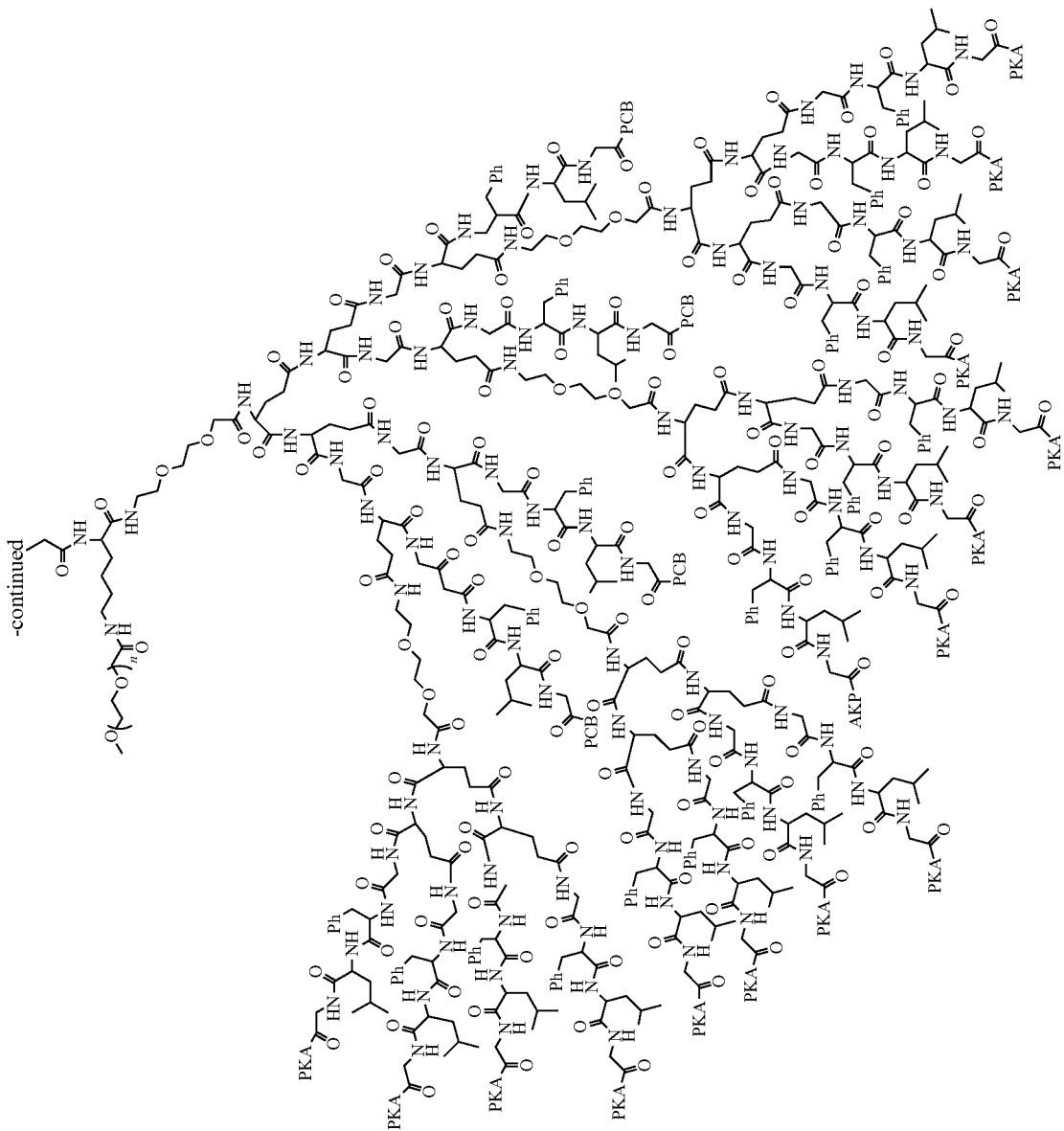

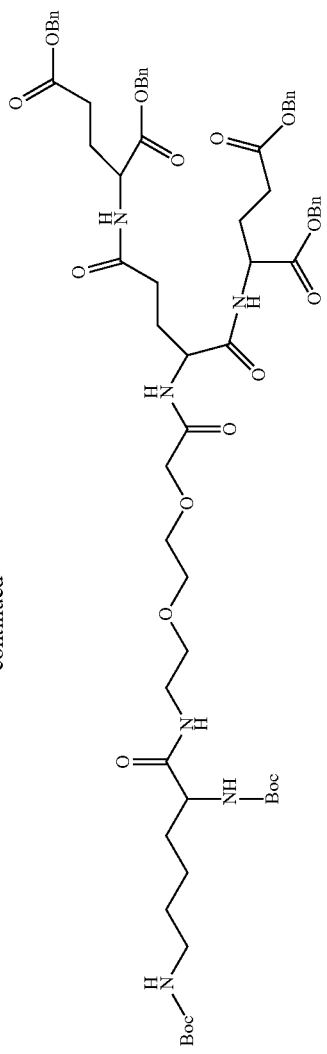
26-250

Boc-Lys (Boc)-OH (purchased from Arm Pharm, 0.3769 g, 1.0879 mmol), 26-232 (synthesized according to the method of synthesizing 22-181, 0.989 mmol), HBTU (0.5627 g, 1.4835 mmol), HOBT (0.2005 g, 1.4835 mmol) were added in a 250 mL flask, and dissolved with DMF (40 mL), and the obtained solution was stirred at −5° C. for 30 minutes. Then DIEA (0.7356 mL, 4.4505 mmol) was slowly added dropwise over 3 minutes. At the end of the addition, the obtained solution continued to react at −5° C. with stirring for 1 hour, and was then moved to room temperature and stirred to react overnight. At the end of the reaction, the reaction solution was transferred to a 1 L reparatory funnel, pure water (120 mL) and ethyl acetate (80 mL) were added for extraction, and the organic phase was separated. The aqueous phase was extracted three times with ethyl acetate (80 mL×3), and the obtained organic phases were combined. The organic phase was washed with saturated sodium chloride solution (80 mL×3), concentrated, evaporated to dryness, and dried in a vacuum oven, thus obtaining a crude product 26-250: yield 100%.

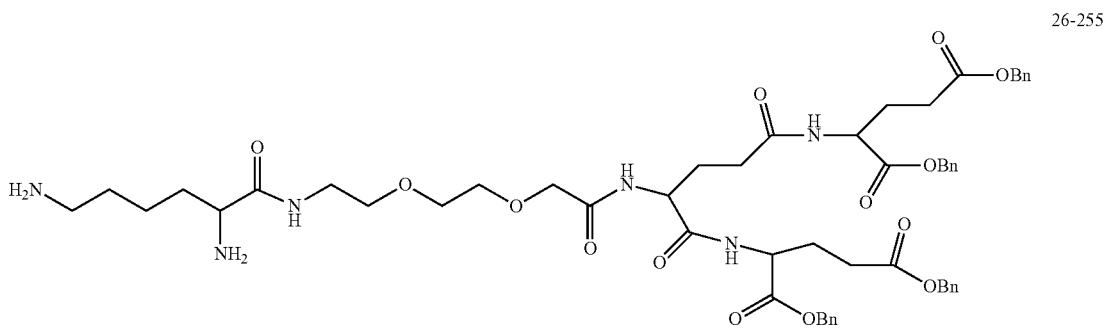 [SMILES: NCCCCC(N)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

26-255

26-250 (0.989 mmol) was added in a 250 mL flask, and dissolved with dichloromethane (10 mL), TFA (2.2182 mL, 29.87 mmol) was added, and then the mixed solution was stirred to react at room temperature overnight. At the end of the reaction, the reaction solution was evaporated to dryness to obtain an oily product. The residue was dissolved with ethyl acetate (50 mL), an excess amount of solid sodium bicarbonate was added to the obtained solution for neutralization until there was no bubble, and filtering was carried out. Silica gel powder (15 g) was added to the filtrate, and the obtained solution was then evaporated to dryness to obtain a powdery solid. The operations of dry sample loading, column chromatography and gradient elution with a dichloromethane mixed solution containing 1% ammonia water and 3%-6% methanol were carried out. The elution product was then collected, concentrated, and dried in a vacuum oven, thus obtaining the product 26-255: 0.8 g, yield 81%.

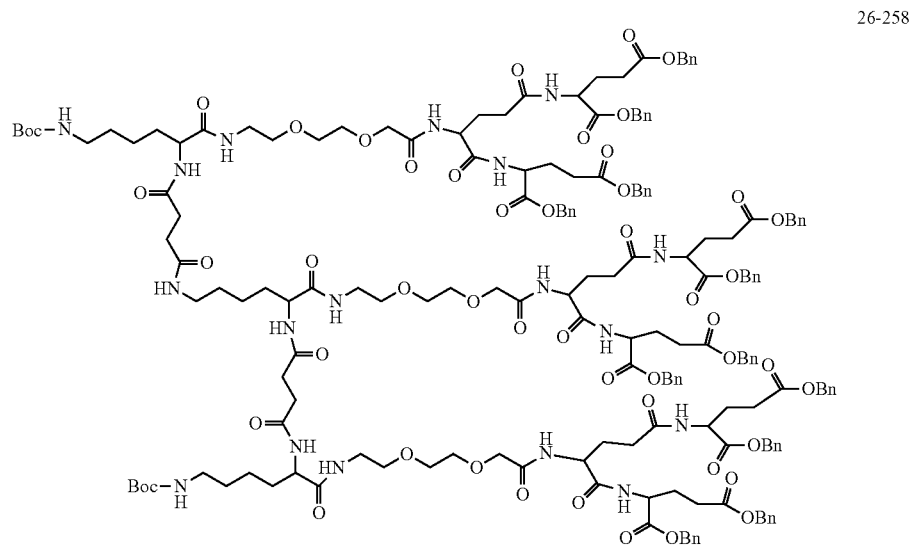 [SMILES: CC(C)(C)OC(=O)NCCCCC(NC(=O)CCC(=O)NCCCCC(NC(=O)CCC(=O)NC(CCCCNC(=O)OC(C)(C)C)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

26-258

26-255 (0.8 g, 0.7698 mmol), 41-26 (2.0990 g, 1.6936 mmol), HBTU (0.8761 g, 2.3095 mmol), HOBT (0.3121 g, 2.3095 mmol) were added in a 250 mL flask, and dissolved with DMF (30 mL), and then the mixed solution was stirred to react at −5° C. for 30 minutes. Then DIEA (1.1458 mL, 6.9285 mmol) was slowly added dropwise over 3 minutes. At the end of the addition, the obtained solution continued to react at −5° C. with stirring for 1 hour, and was then moved to room temperature and stirred to react overnight. At the end of the reaction, the reaction solution was transferred to a 1 L separatory funnel, pure water (120 mL) and ethyl acetate (80 mL) were added for extraction, and the organic phase was separated. The aqueous phase was extracted with ethyl acetate (80 mL×3), and the obtained organic phases were combined. The organic phase was washed with saturated sodium chloride solution (80 mL×3), concentrated and evaporated to dryness. The obtained solid was dissolved with methanol/dichloromethane (1:4) solution (200 mL), silica gel powder (15 g) was added, and the obtained mixture was then evaporated to dryness to obtain a powdery solid. The operations of dry sample loading, column chromatography and gradient elution with a dichloromethane mixed solution containing 3%-5% methanol were carried out. The elution product was then collected, concentrated, evaporated to dryness, and dried in a vacuum oven, thus obtaining the product 26-258: 1.6884 g, yield 63%.

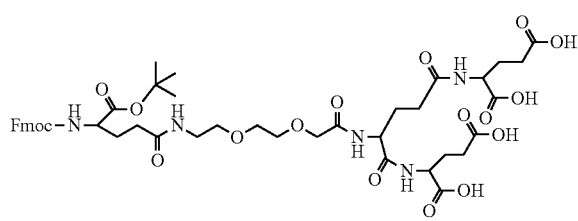

29-152

29-147 (synthesized according to the method of synthesizing 42-20, 1.7952 g, 1.3616 mmol) and 10% Pd/C (0.03 g) were added in a hydrogenation reactor, and dissolved with DMF (30 mL), The hydrogenation reactor was then sealed to perform the "three pumping and three charging" operation, so that the pressure on the hydrogenation reactor was read as 0.18 MPa, and then the obtained solution reacted at room temperature overnight. At the end of the reaction, the reaction solution was filtered with diatomaceous earth. The filter cake was washed with DMF (20 mL×3), thus obtaining the product 29-152, yield 100%.

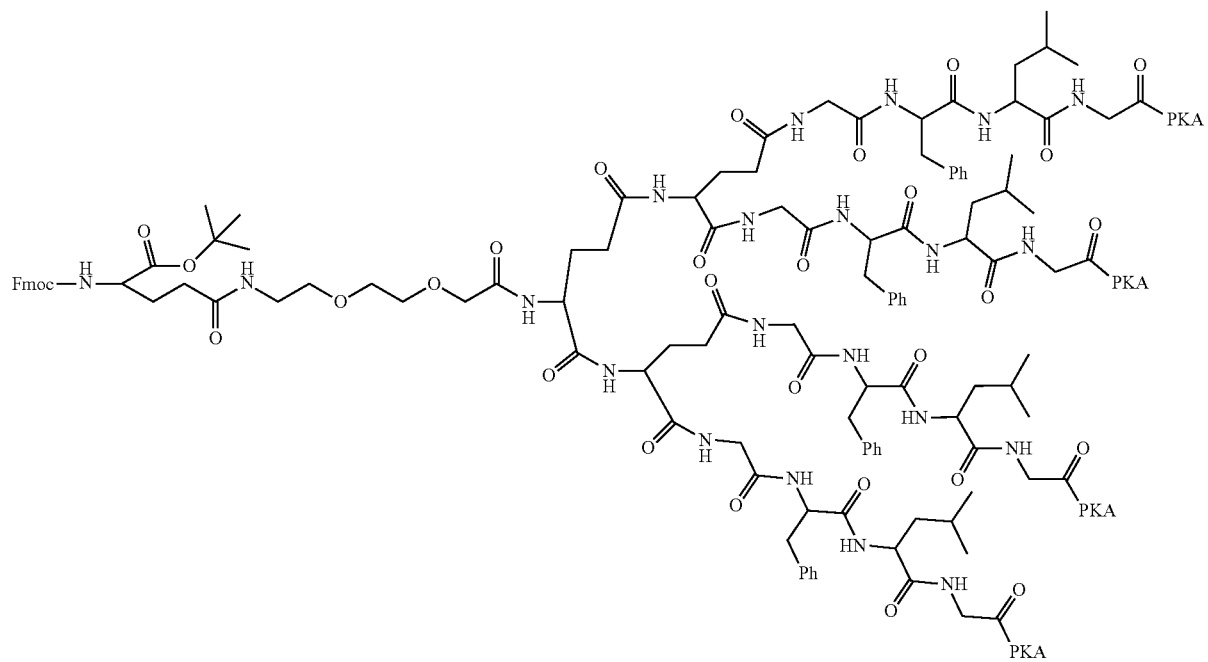

29-153

29-152 (1.3616 mmol), 42-18 (6.0 g, 6.2632 mmol), HBTU (3.0990 g, 8.1696 mmol), HOBT (1.1040 g, 8.1696 mmol) were added in a 500 mL flask, and dissolved with DMF (60 mL), and then the mixed solution was stirred to react at 0° C. for 30 minutes. Then DIEA (4.0532 mL, 24.5088 mmol) was slowly added dropwise over 7 minutes, and the obtained solution continued to react with stirring at 0° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4). Silica gel powder (30 g) was added, and the obtained mixture was then evaporated to dryness to obtain a powdery solid. The operations of dry sample loading, column chromatography and gradient elution with a dichloromethane mixed solution containing 1% ammonia water and 5%-8% methanol were carried out. The elution product was then collected, concentrated, and dried in a vacuum oven, thus obtaining the product 29-153: 3.6 g, yield 47%.

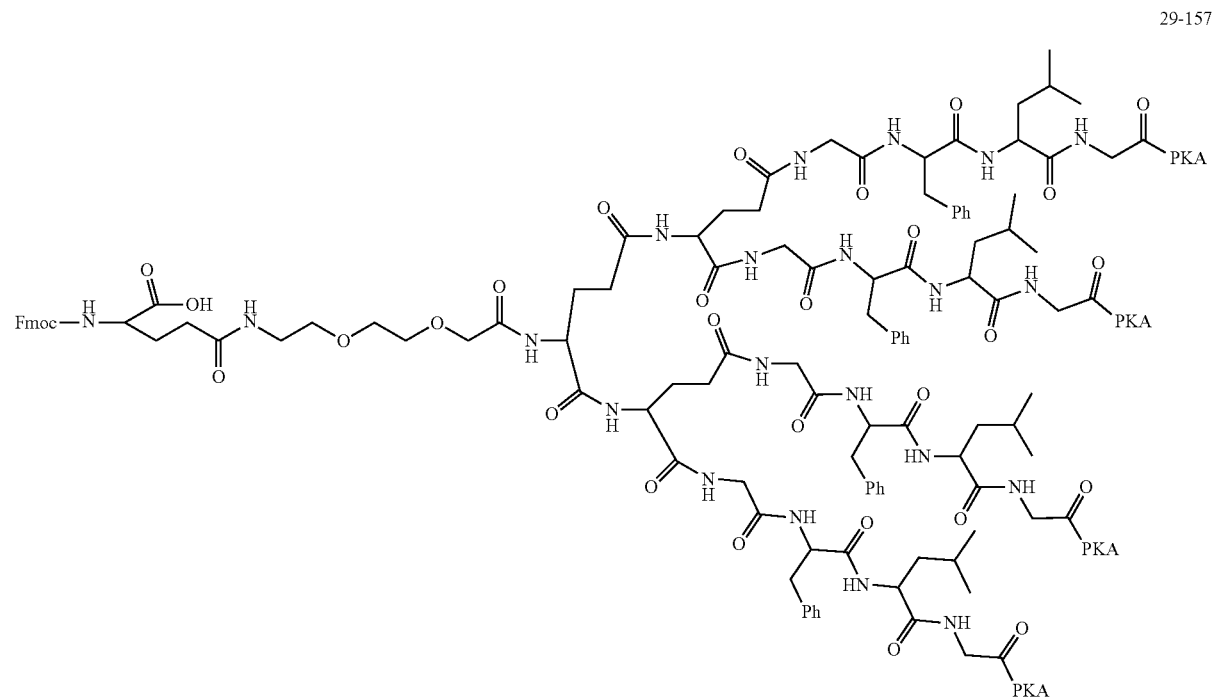

29-157

29-153 (3.6 g, 1.3493 mmol) was added in a 250 mL flask, and dissolved with dichloromethane (10 mL), then TFA (1.5031 mL, 20.2401 mmol) was added, and the mixed solution was stirred to react at room temperature overnight. At the end of the reaction, the reaction solution was evaporated to dryness to obtain an oily product. Then, methyl tert-butyl ether (40 mL) was added to separate out a powdery solid, and suction filtering was carried out. The filter cake was washed with methyl tert-butyl ether (40 mL×3), and the washed filter cakes were collected, and dried in a vacuum oven, thus obtaining the product 29-157, yield 100%.

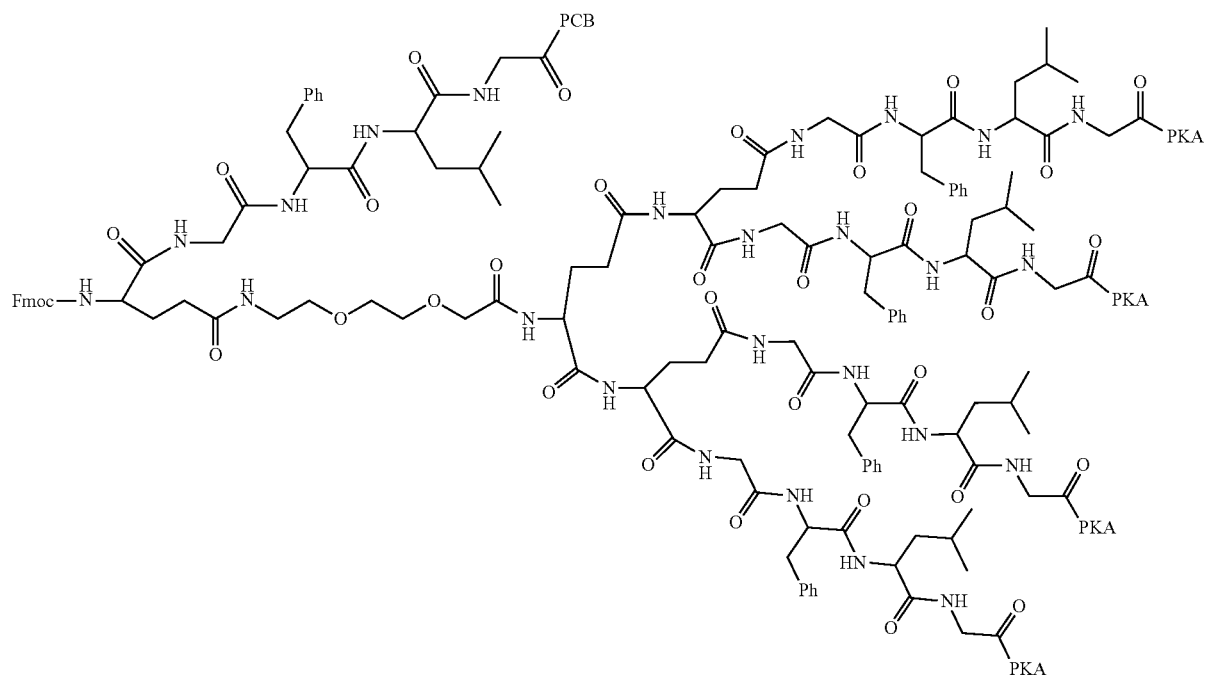

29-157 (1.3493 mmol), GFLG-PCB (synthesized according to the method of synthesizing 30-33, 1.220 g, 1.4842 mmol), HBTU (0.7676 g, 2.0240 mmol), HOBT (0.2735 g, 2.0240 mmol) were added in a 250 mL flask, and dissolved with DMF (60 mL), and then the mixed solution was stirred to react at 0° C. for 30 minutes. Then DIEA (1.0 mL, 6.0719 mmol) was slowly added dropwise over 3 minutes. At the end of the addition, the obtained solution continued to react with stirring at 0° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), and the washed filter cakes were collected, and dried in a vacuum oven, thus obtaining the product 29-162: yield 100%.

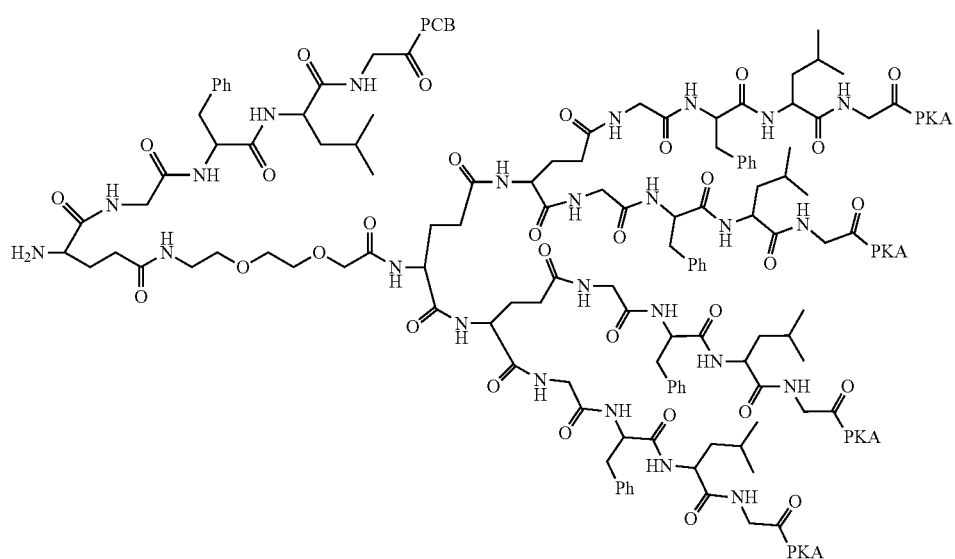

29-162 (1.3493 mmol) was added in a 250 mL flask, and dissolved with DMF (15 mL), morpholine (1.2 mL, 13.493 mmol) was added, and then the mixed solution was stirred to react at room temperature for 1 hour. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (15 g) was added, and the obtained mixture was then evaporated to dryness to obtain a powdery solid. The operations of dry sample loading, column chromatography and gradient elution with a dichloromethane mixed solution containing 1% ammonia water and 5%-9% methanol were carried out. The elution product was then collected, concentrated, and dried in a vacuum oven, thus obtaining the product 29-164: 4.1 g, yield 59%.

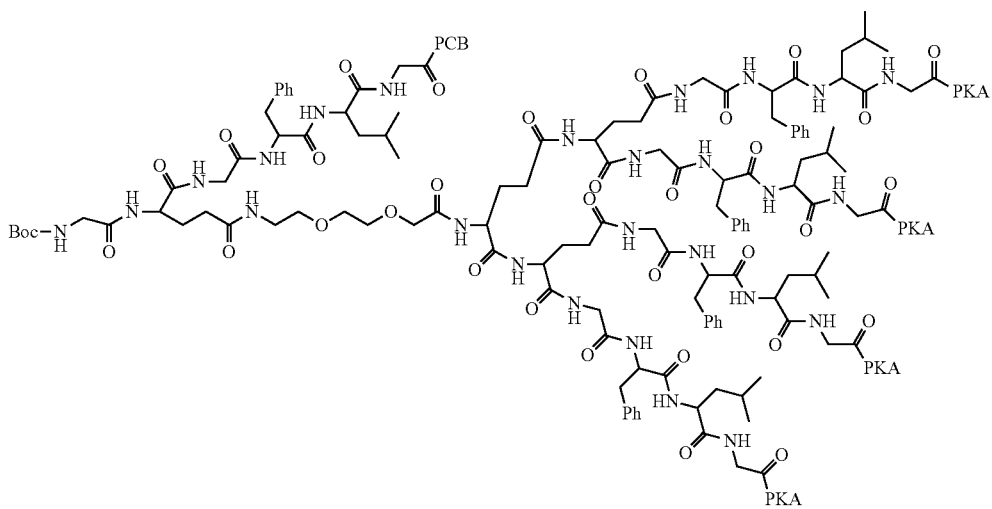

29-167

29-164 (4.1 g, 0.7795 mmol), Boc-Gly-OH (0.1502 g, 8574 mmol), HBTU (0.4434 g, 1.1692 mmol), HOBT (0.1578 g, 0.1.1692 mmol) were added in a 250 mL flask, and dissolved with DMF (40 mL), and then the mixed solution was stirred to react at −5° C. for 30 minutes. Then DIEA (0.5797 mL, 3.5076 mmol) was slowly added dropwise, and the obtained solution continued to react with stirring at −5° C. for 1 hour, and was then moved to room temperature and stirred to react overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dried in a vacuum oven, thus obtaining the product, yield 100%.

29-194

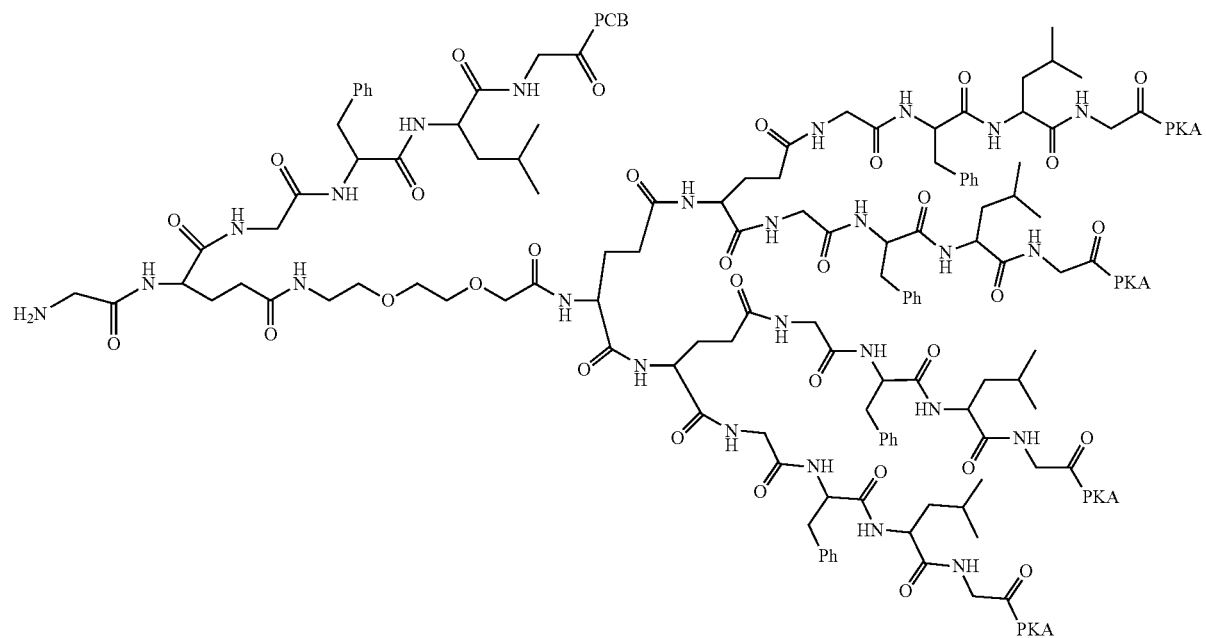

29-167 (0.7795 mmol) was added in a 250 mL flask, and dissolved with dichloromethane (5 mL), TFA (0.8683 mL, 11.6921 mmol) was added, and then the mixed solution was stirred to react at room temperature overnight. At the end of the reaction, the reaction solution was evaporated to dryness to obtain an oily product. Then, methyl tert-butyl ether (250 mL) was added to separate out a solid, and suction filtering was carried out. The filter cake was washed with methyl tert-butyl ether (100 mL×3), and dissolved with methanol (60 mL)/dichloromethane (240 mL) solution, silica gel powder (15 g) was added, and the obtained mixture was then evaporated to dryness to obtain a powdery solid. The operations of dry sample loading, column chromatography and elution with a dichloromethane mixed solution containing 1% ammonia water and 3%-8% methanol were carried out. The elution product was then collected, concentrated, evaporated to dryness, and dried in a vacuum oven, thus obtaining the product: 3.2 g, yield 76%.

29-196

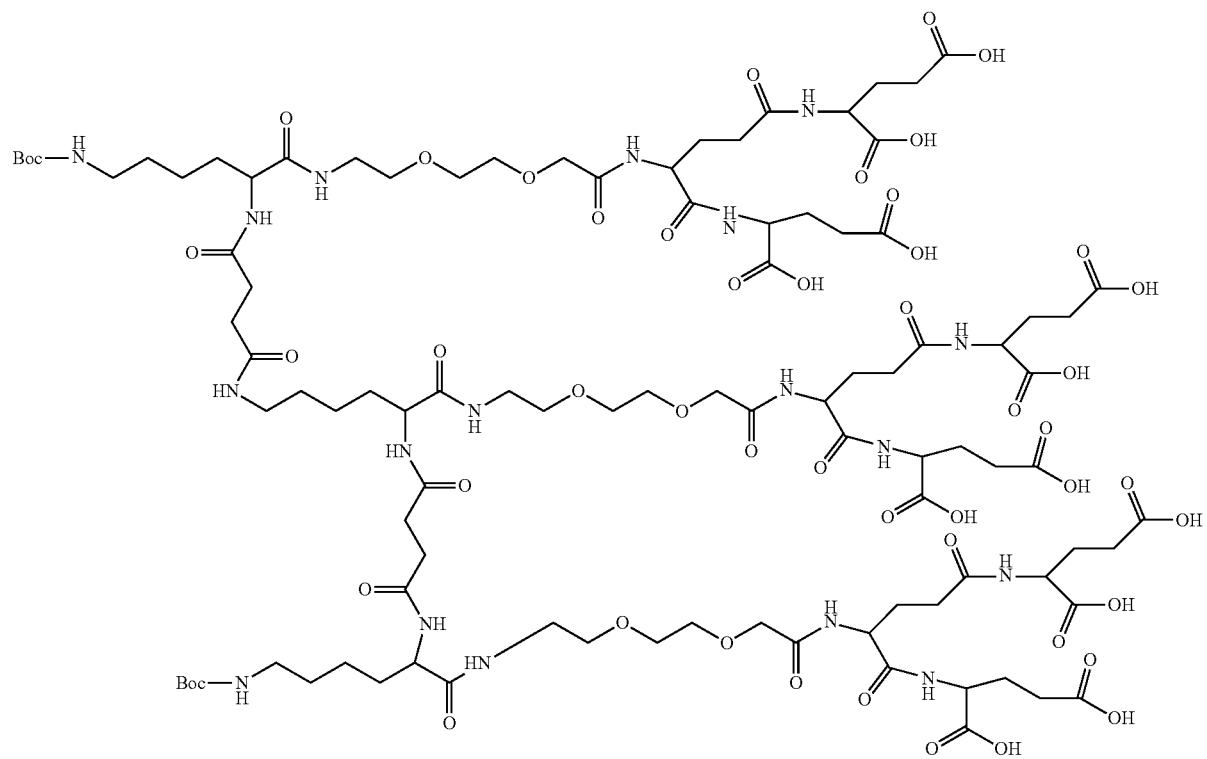

Reactants 26-258 (0.2545 g, 0.073 mmol), 10% Pd/C (40 mg) were added in a hydrogenation reactor, and dissolved with DMF (30 mL), then hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

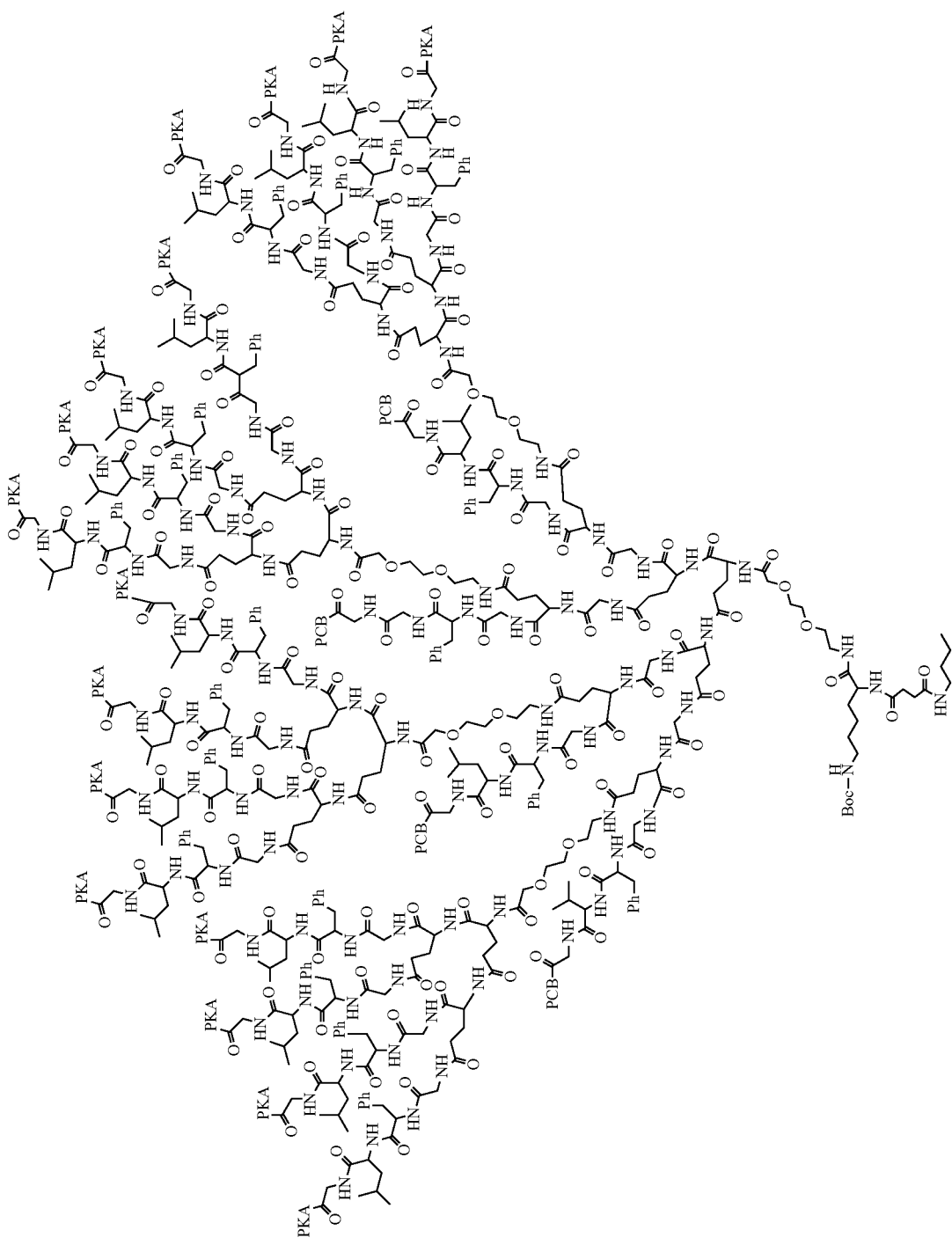

-continued
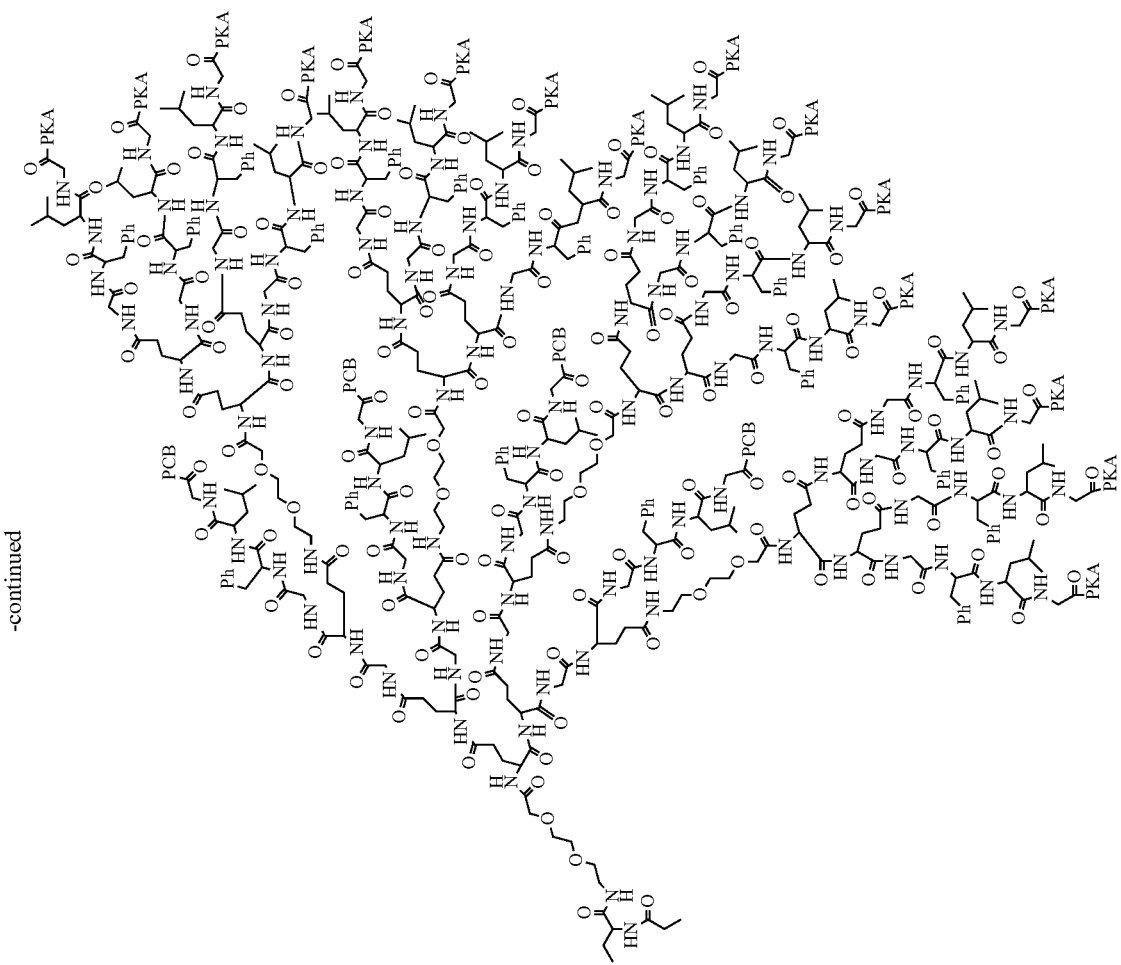

-continued
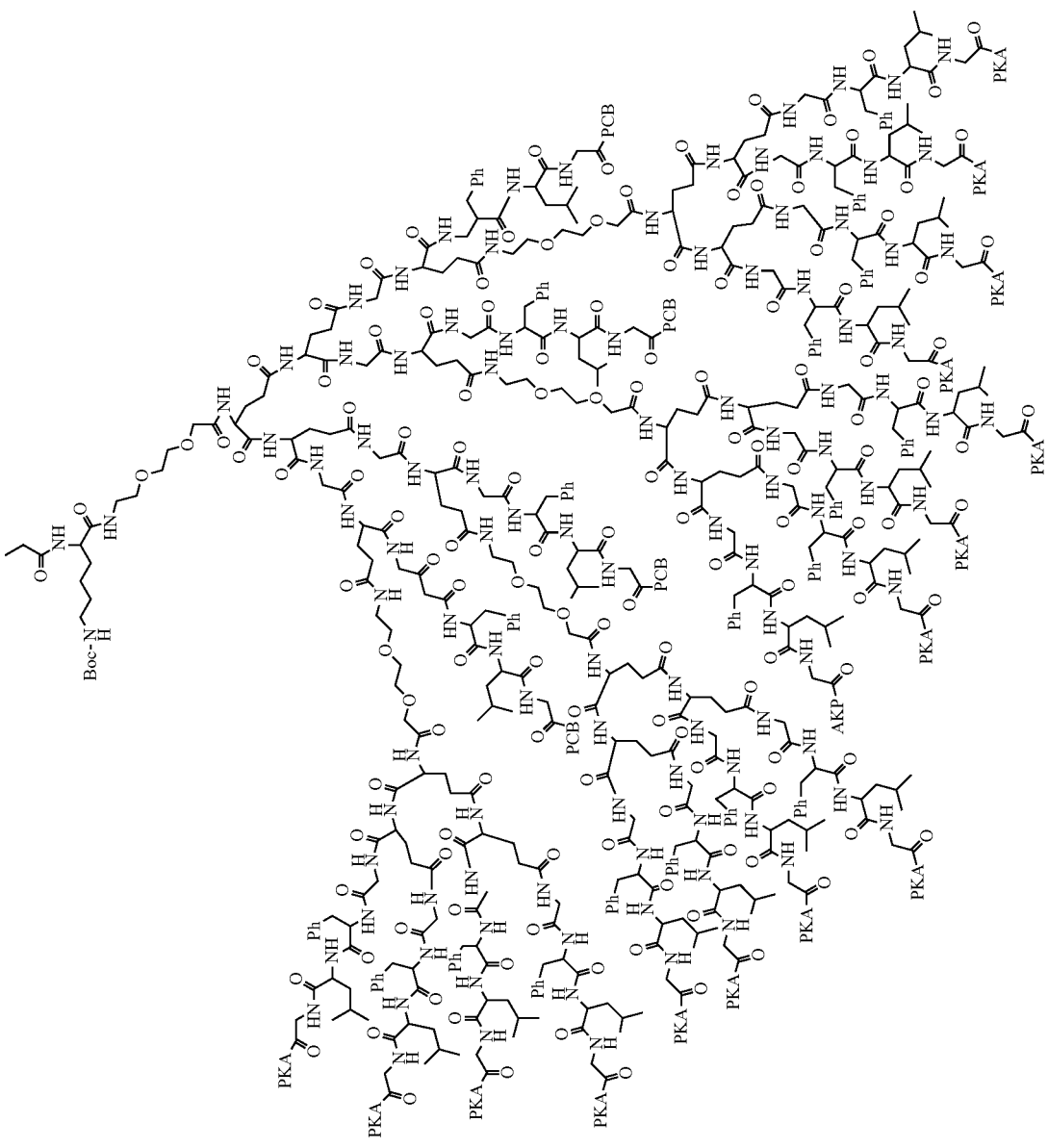

Reactants 29-194 (3.2 g, 0.9211 mmol), 29-196 (0.073 mmol), HBTU (0.5 g, 1.3159 mmol), HOBT (0.1778 g, 1.3159 mmol) were added in a 250 mL flask, and dissolved with DMF (30 mL), and the obtained solution was stirred at −5° C. for 30 minutes. Then, DIEA (0.6525 mL, 3.9477 mmol) was slowly added dropwise, and the obtained solution was stirred to react at −5° C. for 1 hour, and then moved to room temperature and stirred to react overnight. At the end of the reaction, methyl tert-butyl ether (100 mL) was added to the reaction solution, the obtained solution was placed in a refrigerator and taken out after 30 minutes, a solid was separated out, and suction filtering was carried out. The filter cake was collected, and dissolved with a mixed solvent (100 mL) of methanol/dichloromethane (1:4), silica gel powder (15 g) was added, and the obtained mixture was then evaporated to dryness to obtain a powdery solid. The operations of thy sample loading, column chromatography and elution with 1% ammonia water: 3% methanol/dichloromethane—1% ammonia water: 10% methanol/dichloromethane were carried out, thus obtaining the product 2.2 g, yield 67%.

$^1$H-NMR (600 MHz, DMSO-$d_6$) δ 10.17-10.13 (m, 10H), 9.10-8.84 (m, 88H), 8.35-7.43 (m, 676H), 7.37-6.69 (m, 420H), 5.87-5.73 (m, 12H), 4.60-4.09 (m, 217H), 3.96-3.43 (m, 1173H), 3.21-2.65 (m, 524H), 2.30-1.66 (m, 440H), 1.59-1.08 (m, 541H), 0.92-0.75 (m, 360H).

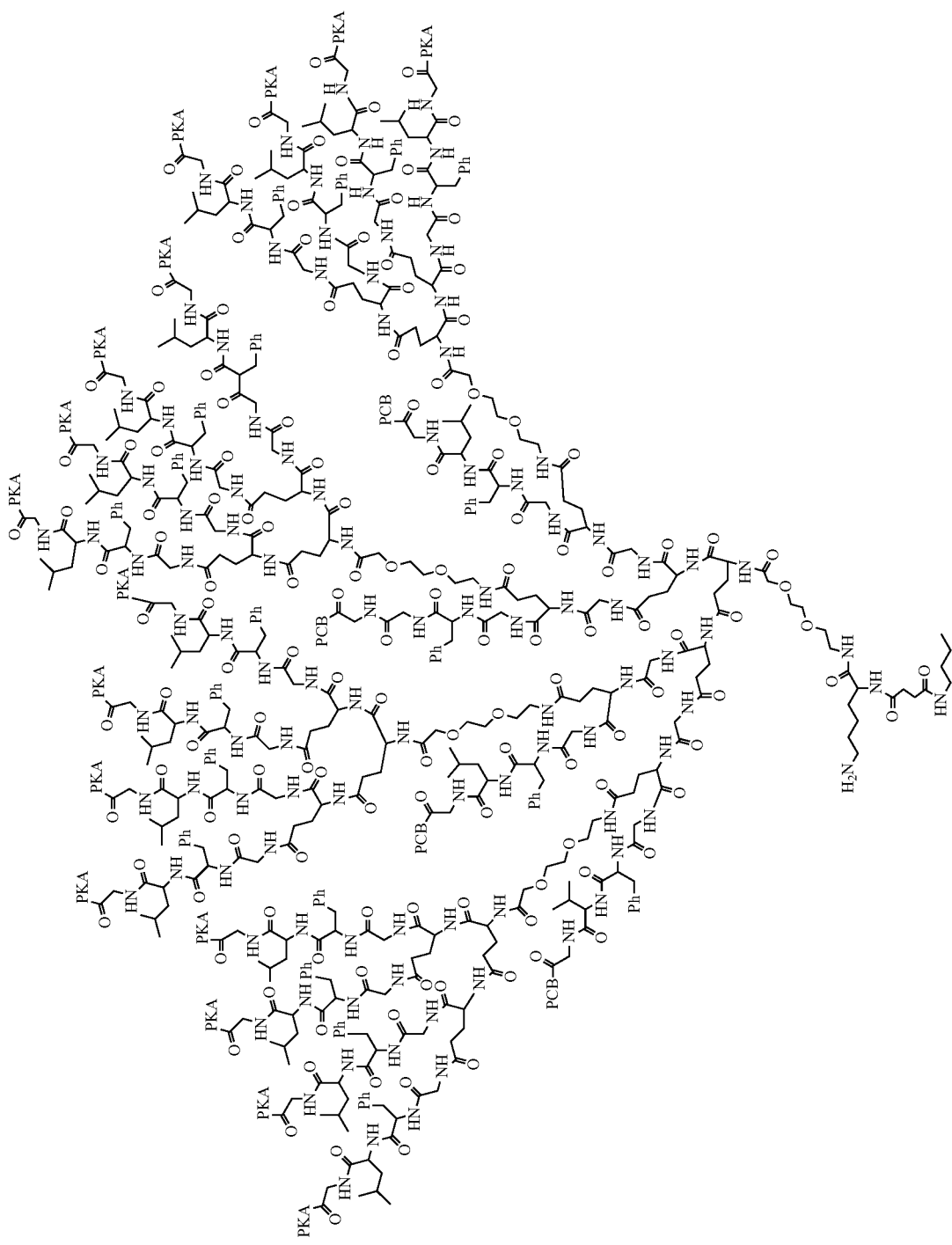

-continued
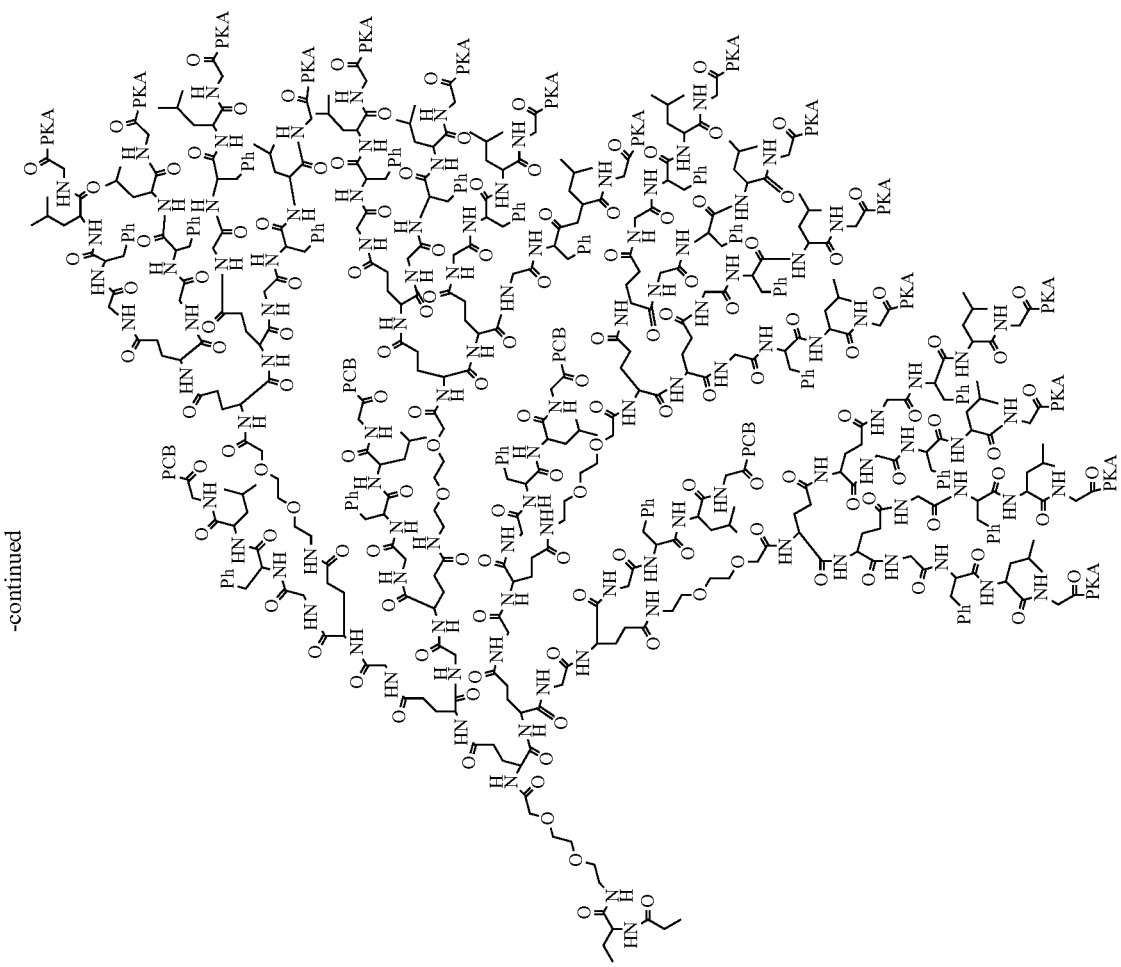

-continued
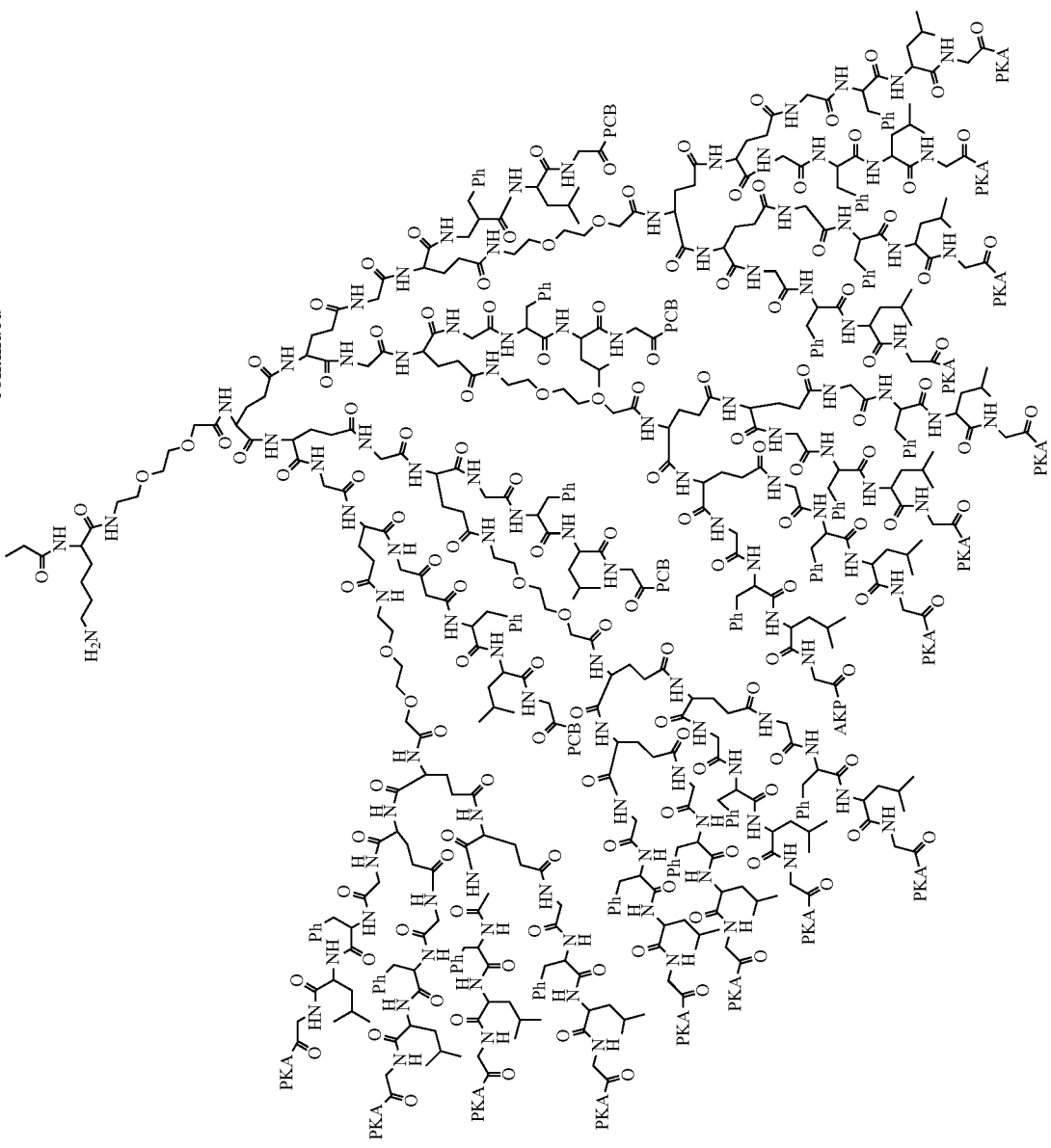

29-197 (2.2 g) was dissolved with dichloromethane (10 mL) and TFA (4 mL) in a condition of ultrasonic, and then the mixed solution was stirred to react. At the end of the reaction, the reaction solution was evaporated to dryness to obtain an oily product. Methyl tert-butyl ether (100 mL) was added to separate out a solid, and suction filtering was carried out. The filter cake was collected, and dissolved with a mixed solvent (100 mL) of methanol/dichloromethane (1:4), silica gel powder (15 g) was added, and the obtained mixture was then evaporated to dryness to obtain a powdery solid. The operations of column chromatography, dry sample loading, and elution with 1% ammonia water: 4% methanol/dichloromethane—1% ammonia water: 10% methanol/dichloromethane were carried out, thus obtaining the product 1.4 g, yield 52%.

$^1$H-NMR (600 MHz, DMSO-$d_6$)δ 10.13-10.07 (m, 10H), 9.37-9.29 (m, 63H), 9.09-8.84 (m, 51H), 8.55-8.49 (m, 20H), 8.03-7.38 m, 560H), 7.12-7.06 (m, 376H), 6.74-6.64 (m, 13H), 5.36-5.28 (m, 12H), 4.57-4.19 (m, 153H), 3.85-3.60 (m, 803H), 3.16-3.01 (m, 317H), 2.30-2.10 (m, 150H), 1.91-1.72 (m, 143H), 1.54-1.44 (m, 127H), 1.34-1.15 (m, 940H), 0.93-0.76 (m, 360H).

29-235
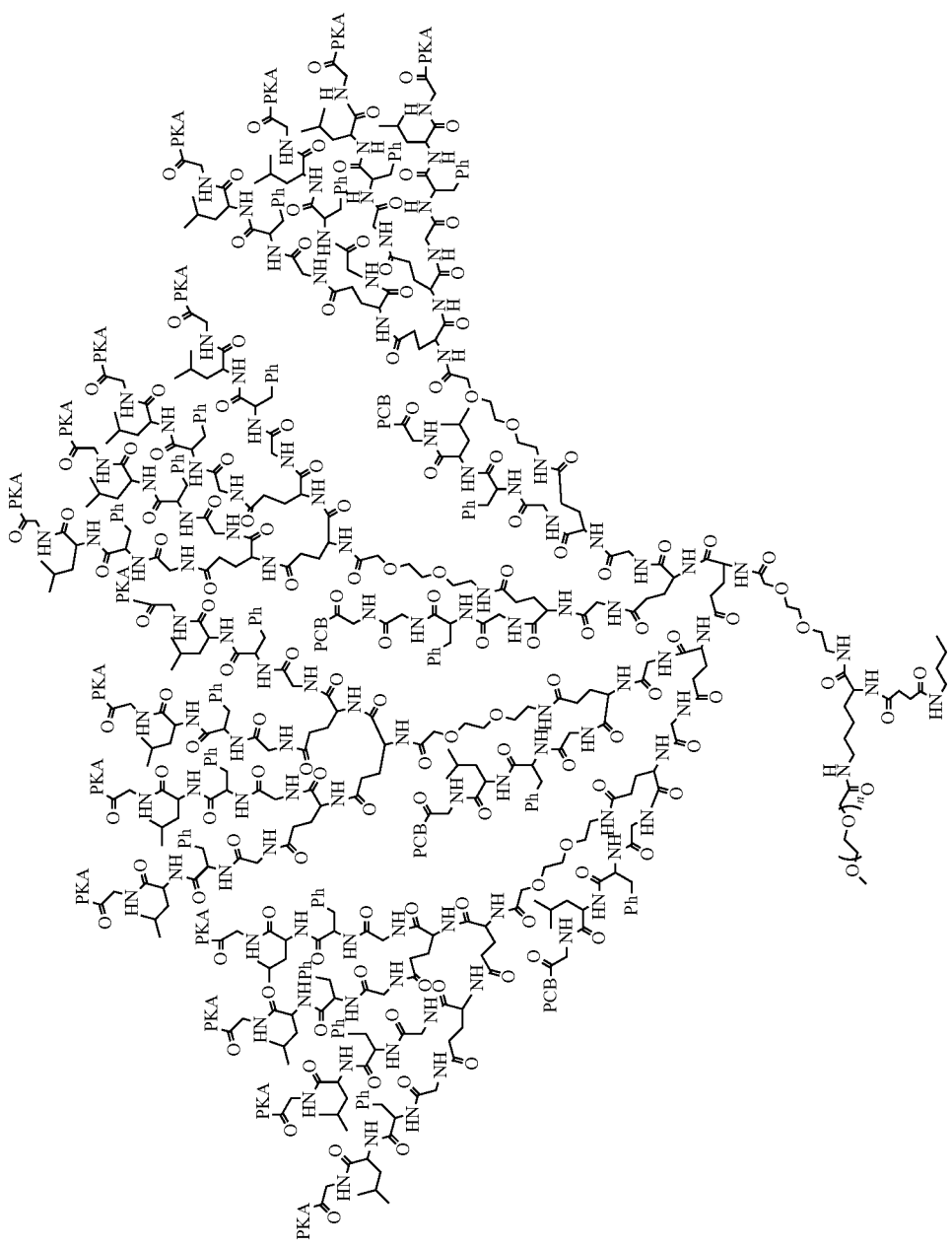

-continued
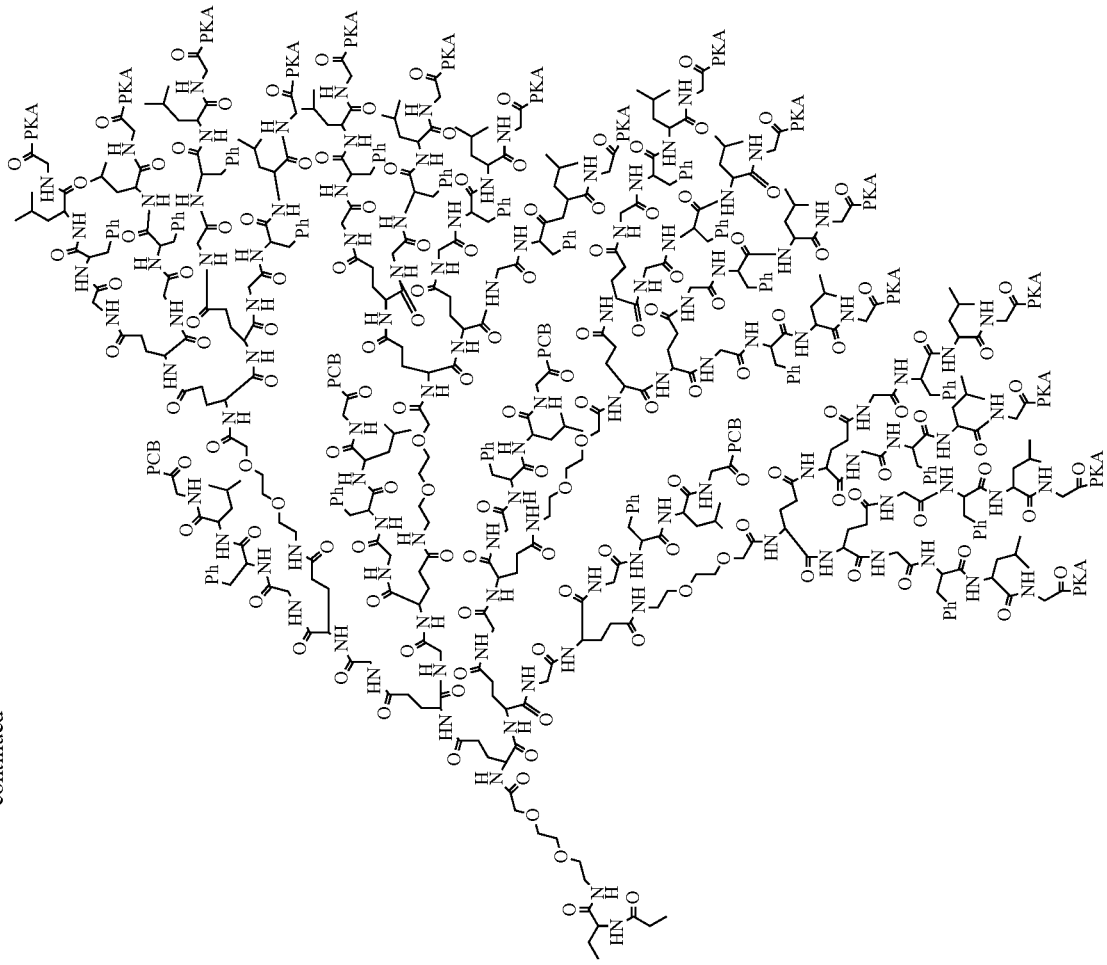

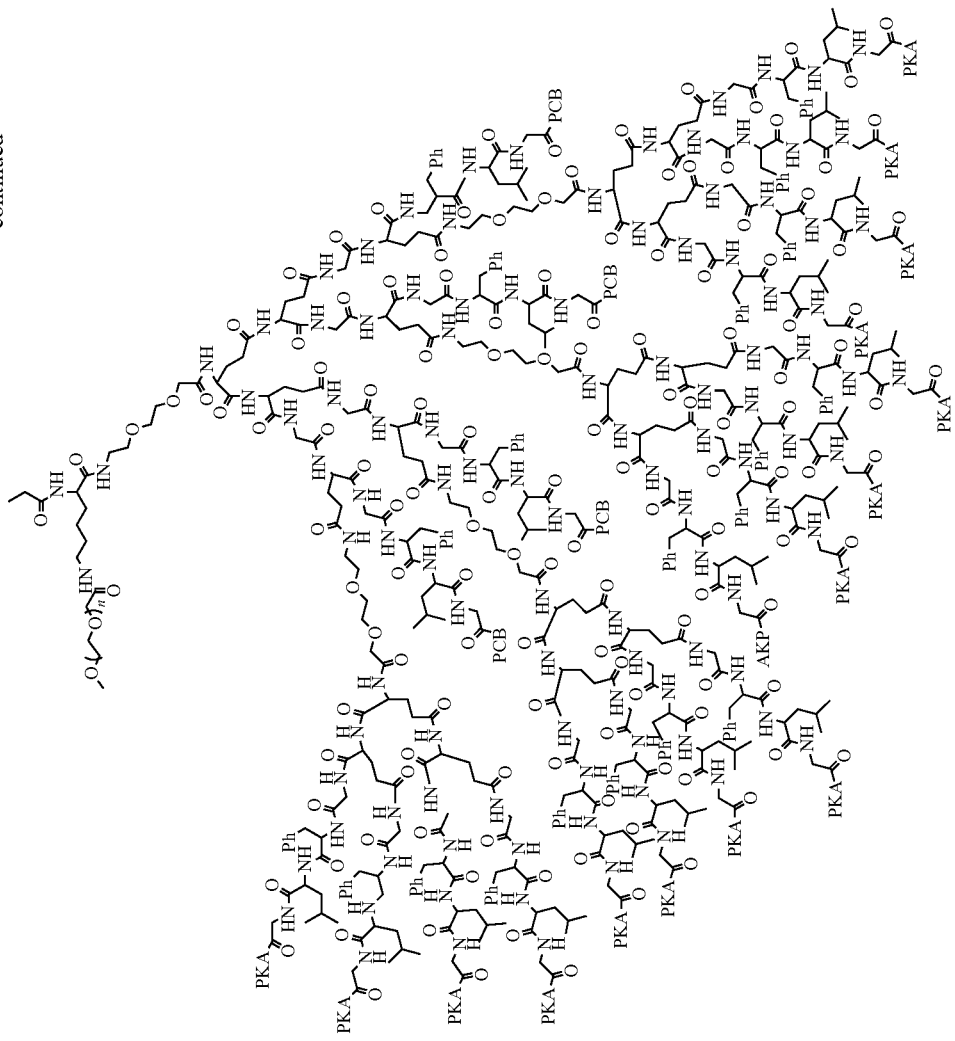

Reactants 29-201 (1.0 g) and M-SCM-20K (1.2163 g, 0.0589 mmol) were dissolved with DMF solution (20 mL), and the obtained solution reacted at a low speed of stirring in the dark for one week. At the end of the reaction, methyl tert-butyl ether (100 mL) was added to the reaction solution, the obtained solution was placed in a refrigerator and taken out after 30 minutes, a solid was separated out, and suction filtering was carried out. The filter cake was collected, and dissolved with a mixed solvent (100 mL) of methanol/dichloromethane (1:4), silica gel powder (15 g) was added, and the obtained mixture was then evaporated to dryness to obtain a powdery solid. The operations of column chromatography, dry sample loading and gradient elution with 1% ammonia water: 3% methanol/dichloromethane—1% ammonia water: 8% methanol/dichloromethane were carried out. The elution product was then evaporated to dryness, and dissolved with anhydrous ethanol (10 mL), the obtained solution was treated by ultrasonic to obtain homogeneous phase, and then n-hexane (50 mL) was added for precipitation. Such precipitation operation was repeated three times. The precipitate was dried in vacuum, thus obtaining the product 1.3 g. Yield 61%.

$^1$H-NMR (600 MHz, DMSO-$d_6$) δ 10.05-9.88 (m, 10H), 9.41-9.30 (m, 62H), 9.11-8.89 (m, 50H), 8.58-8.51 (m, 20H), 8.11-7.40 m, 562H), 7.15-7.08 (m, 378H), 6.78-6.66 (m, 13H), 5.38-5.31 (m, 15H), 4.58-4.21 (m, 151H), 3.95-3.65 (m, 796H), 3.52-3.43 (m, 370614), 3.19-3.07 (m, 321H), 2.32-2.13 (m, 148H), 1.93-1.76 (m, 146H), 1.58-1.46 (m, 125H), 1.36-1.16 (m, 935H), 0.98-0.74 (m, 366H).

15. Synthesis of 37-108 (Compound No. 17)

Synthetic route is as follows

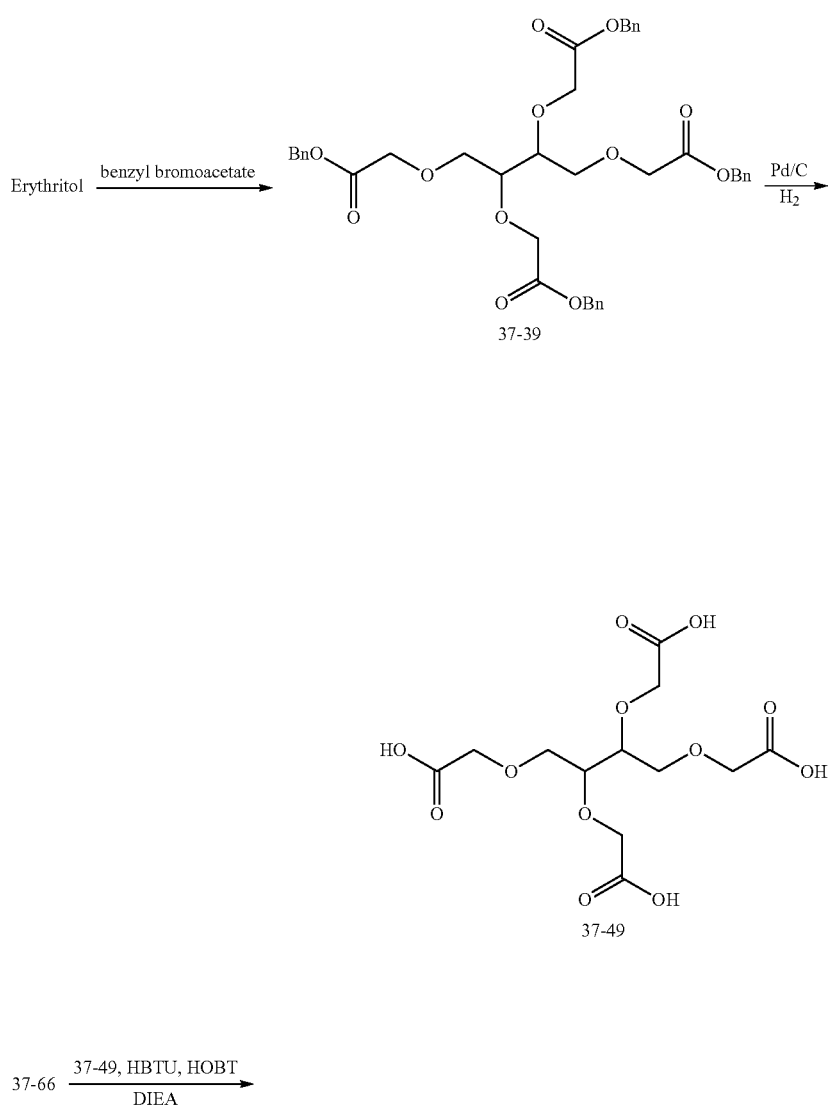

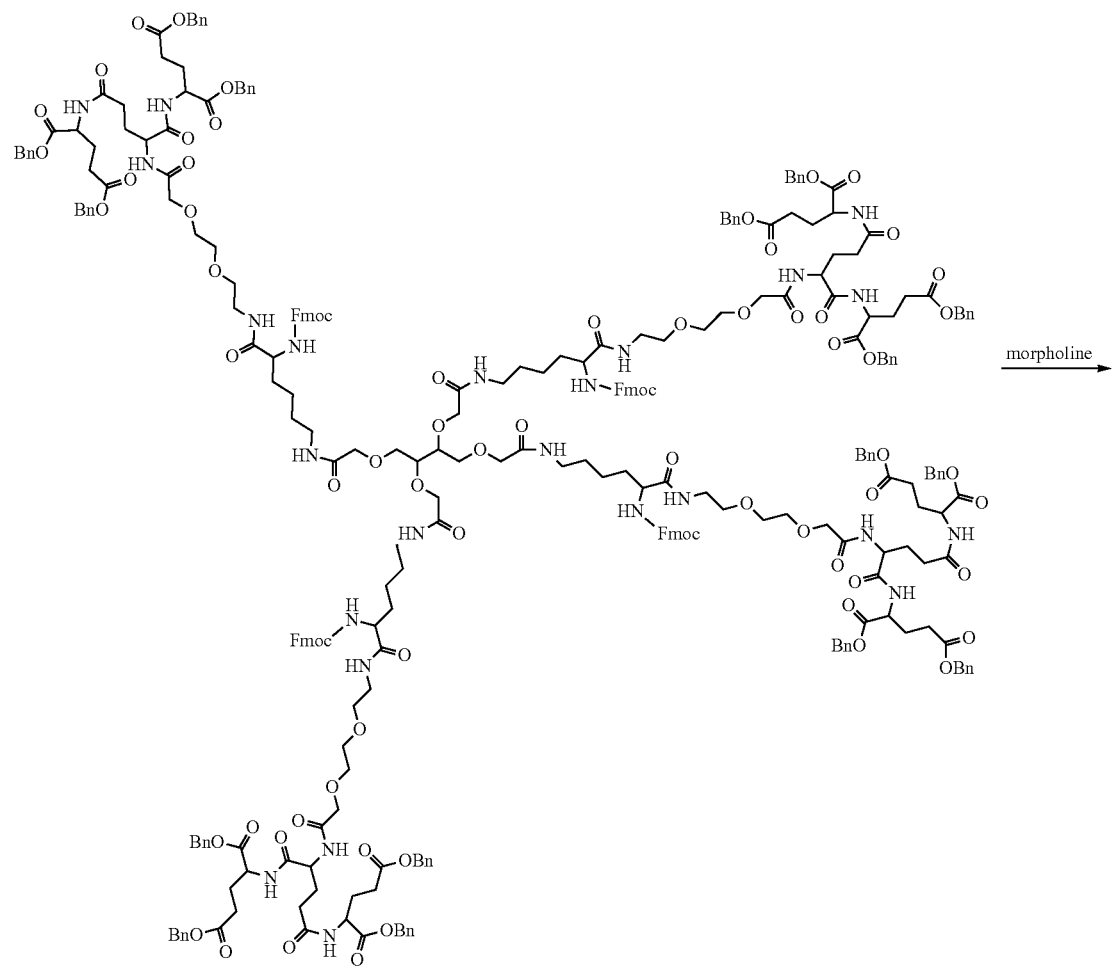
37-67

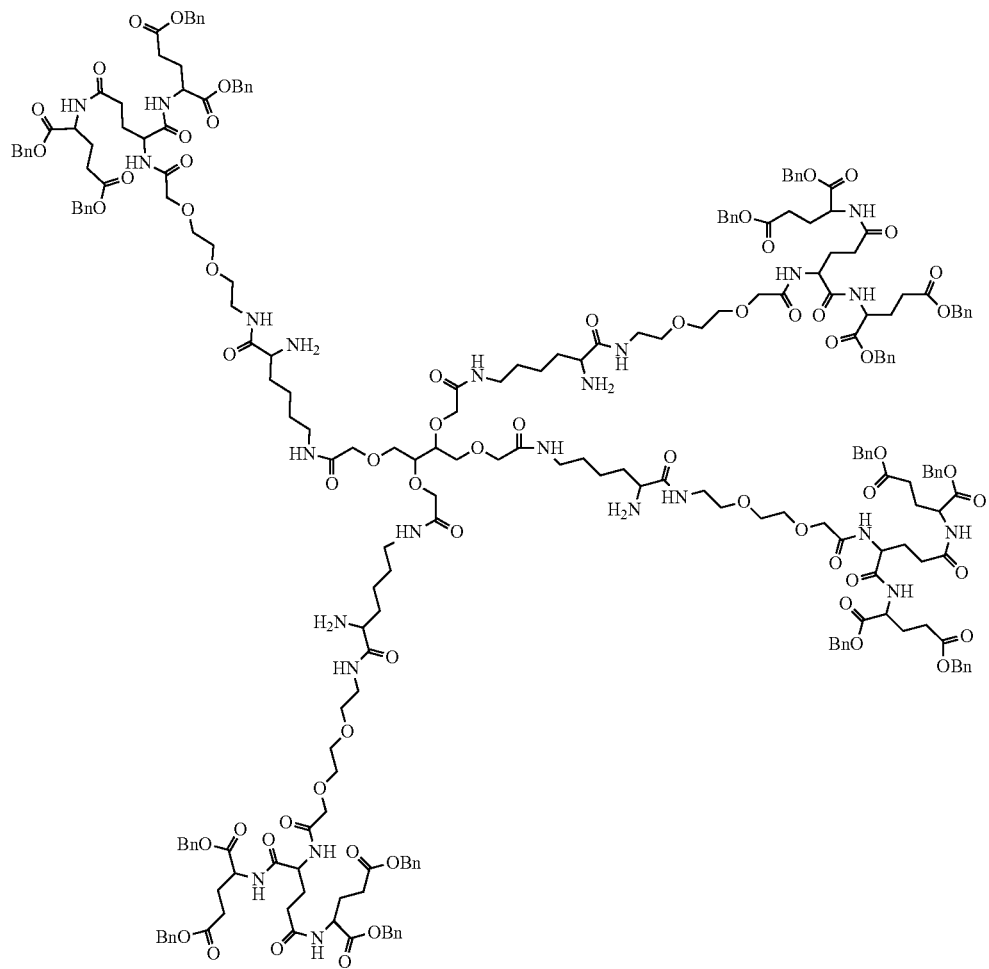
37-68
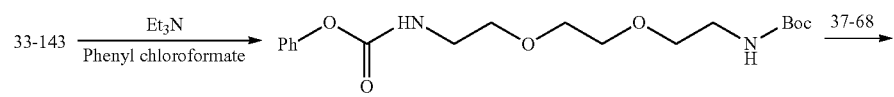
37-79

-continued
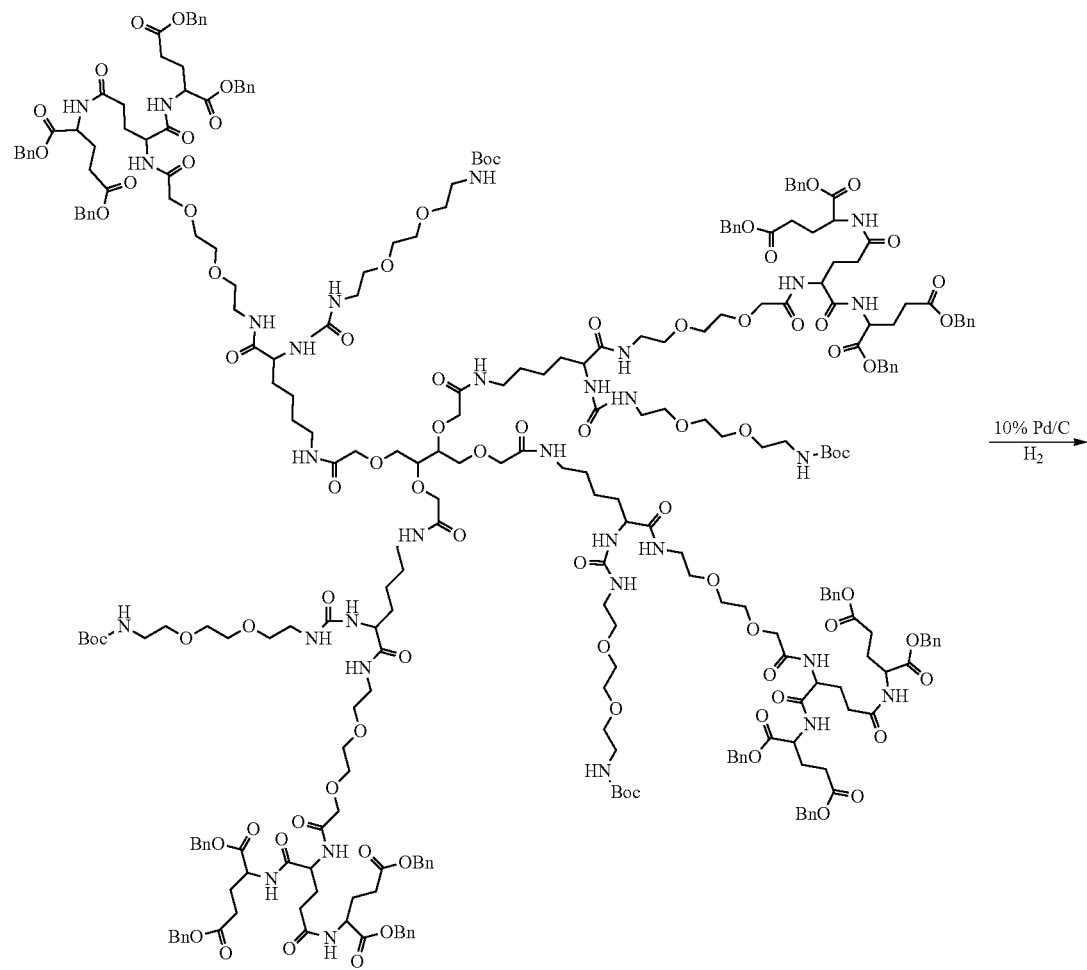
37-81

-continued
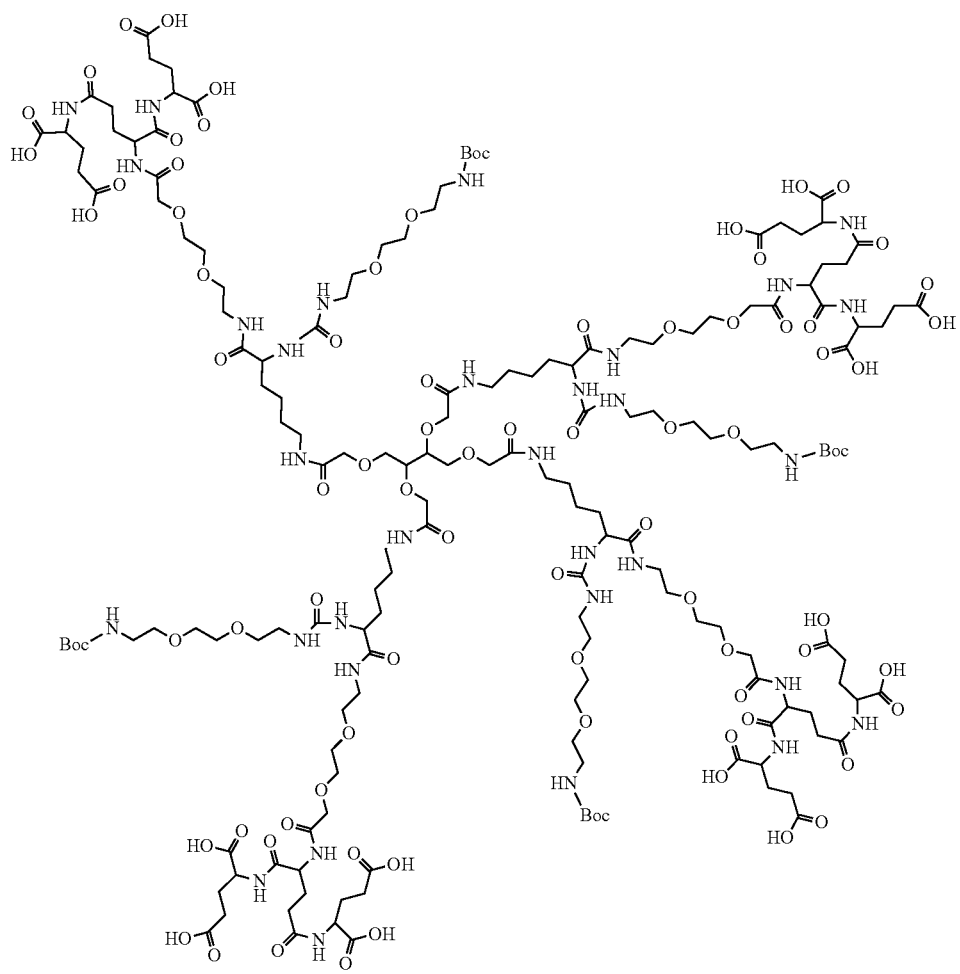
37-89
39-20 →(37-89, HBTU, HOBT / DIEA)

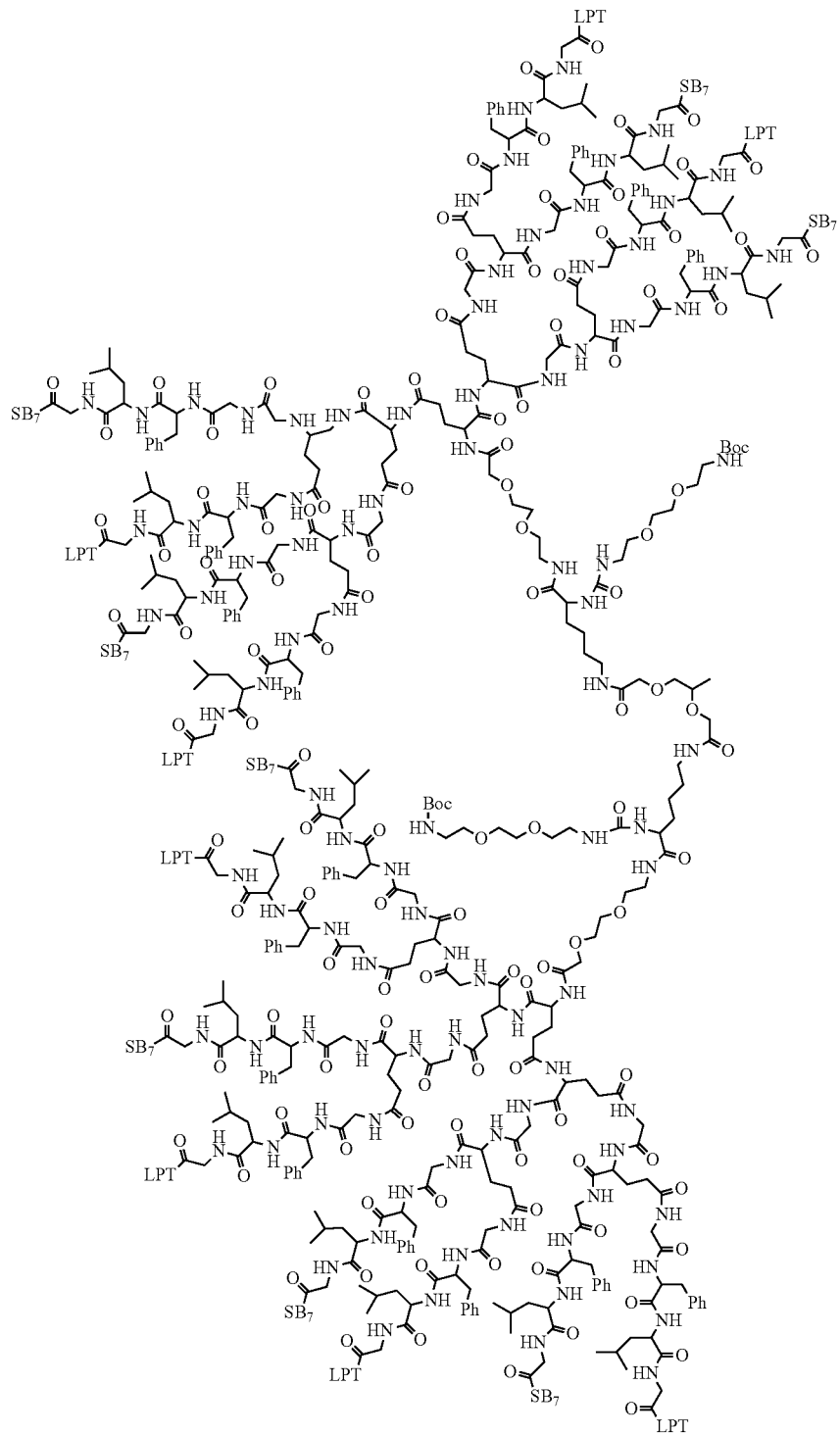

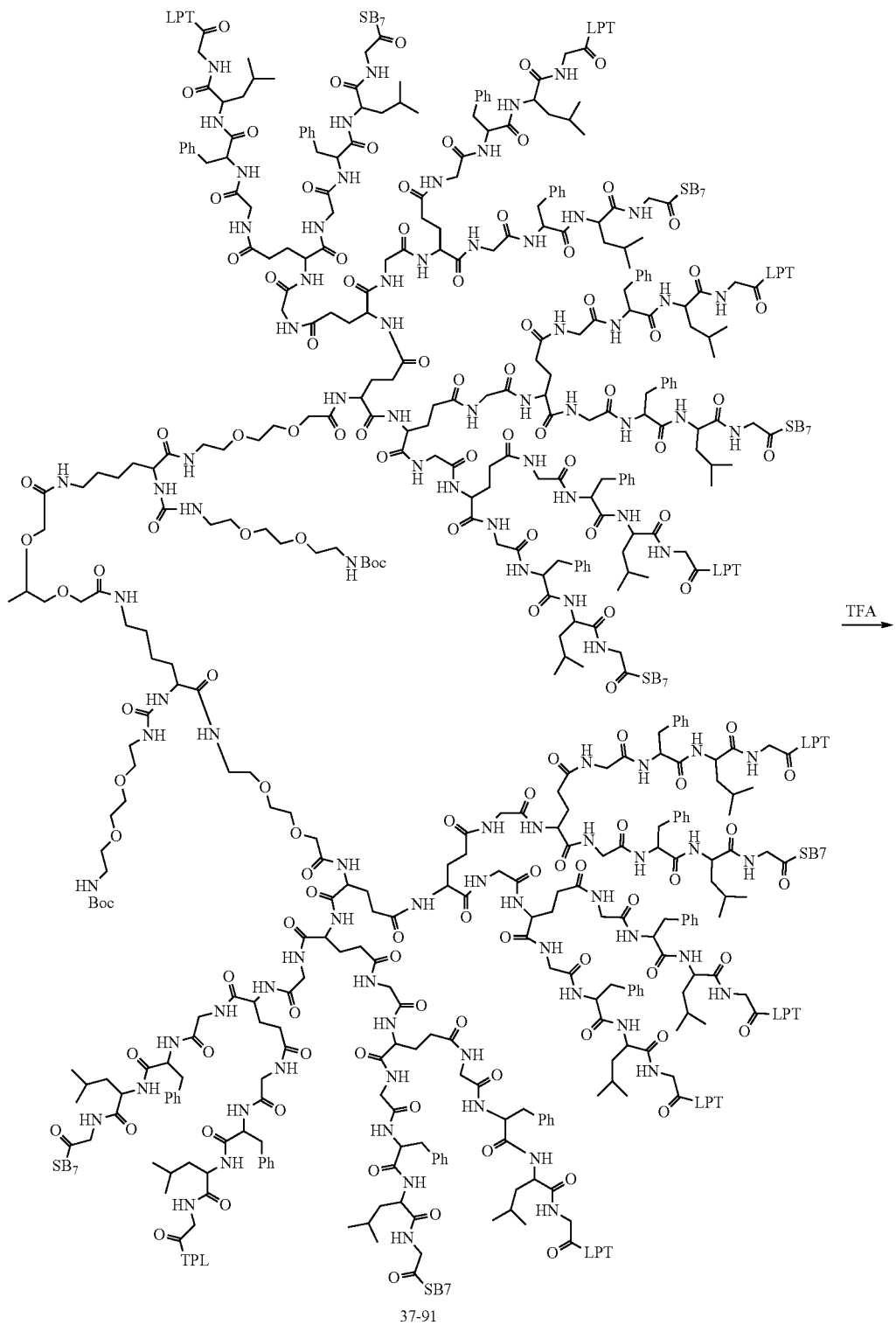
37-91

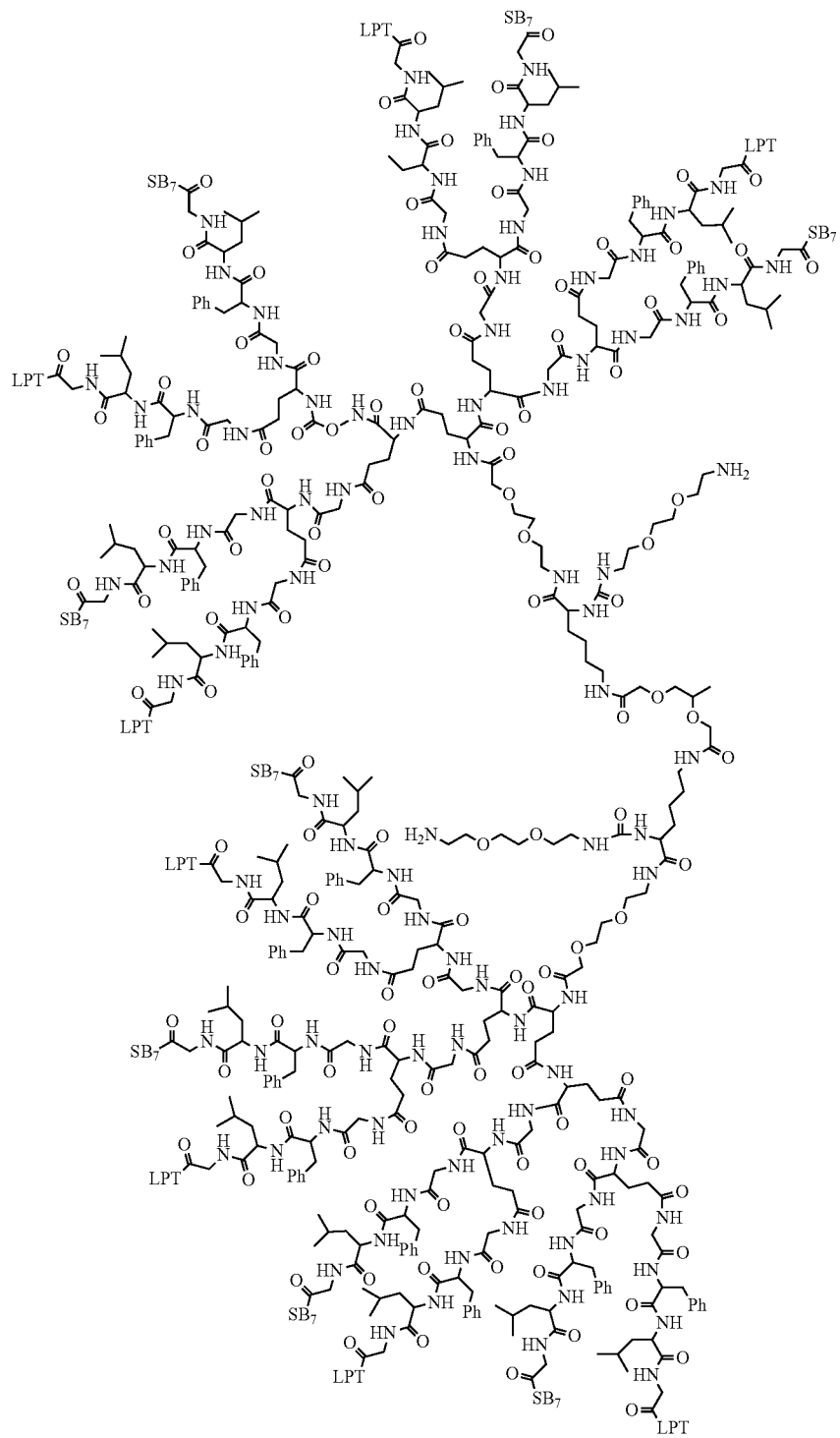

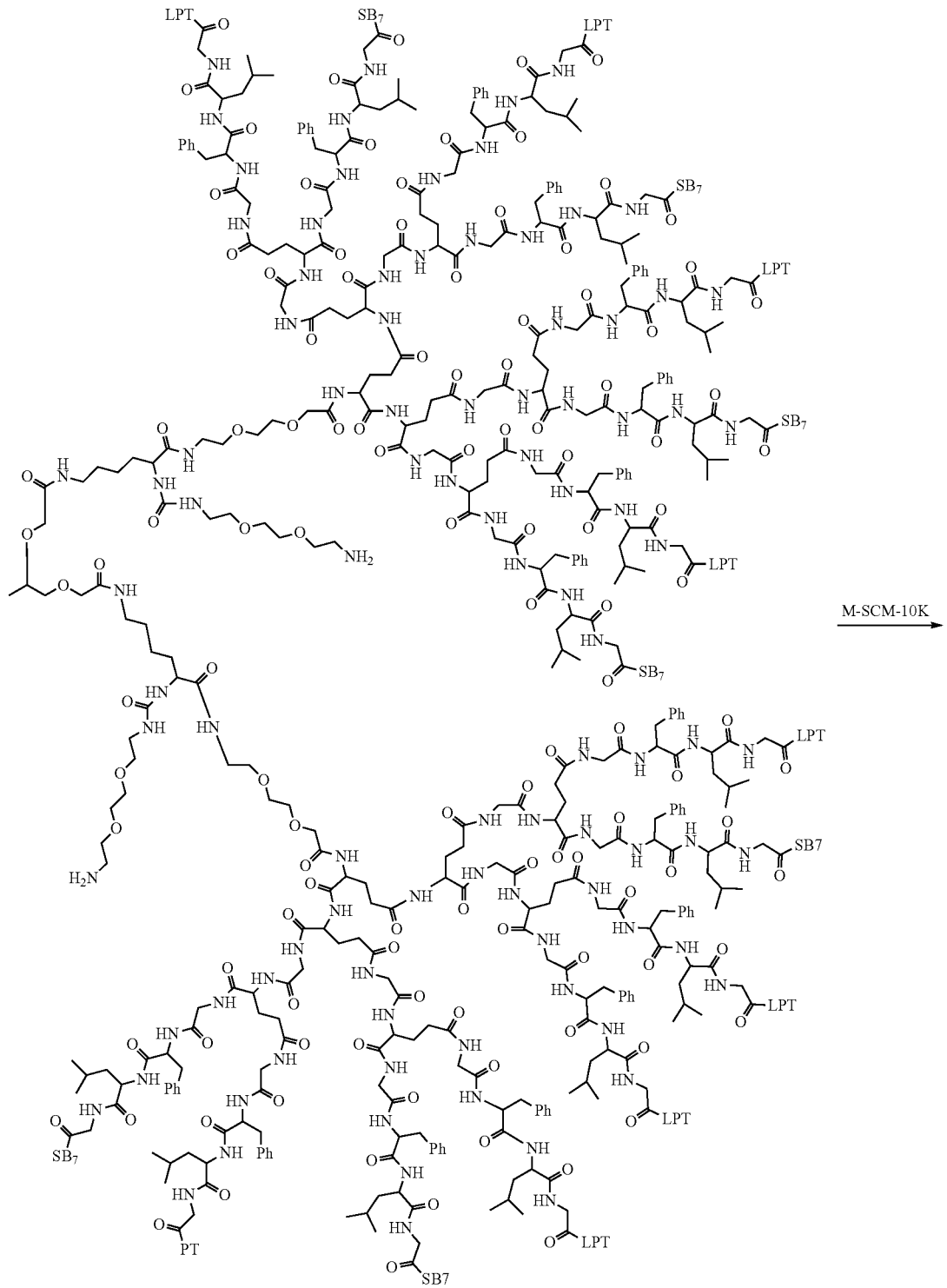
37-101

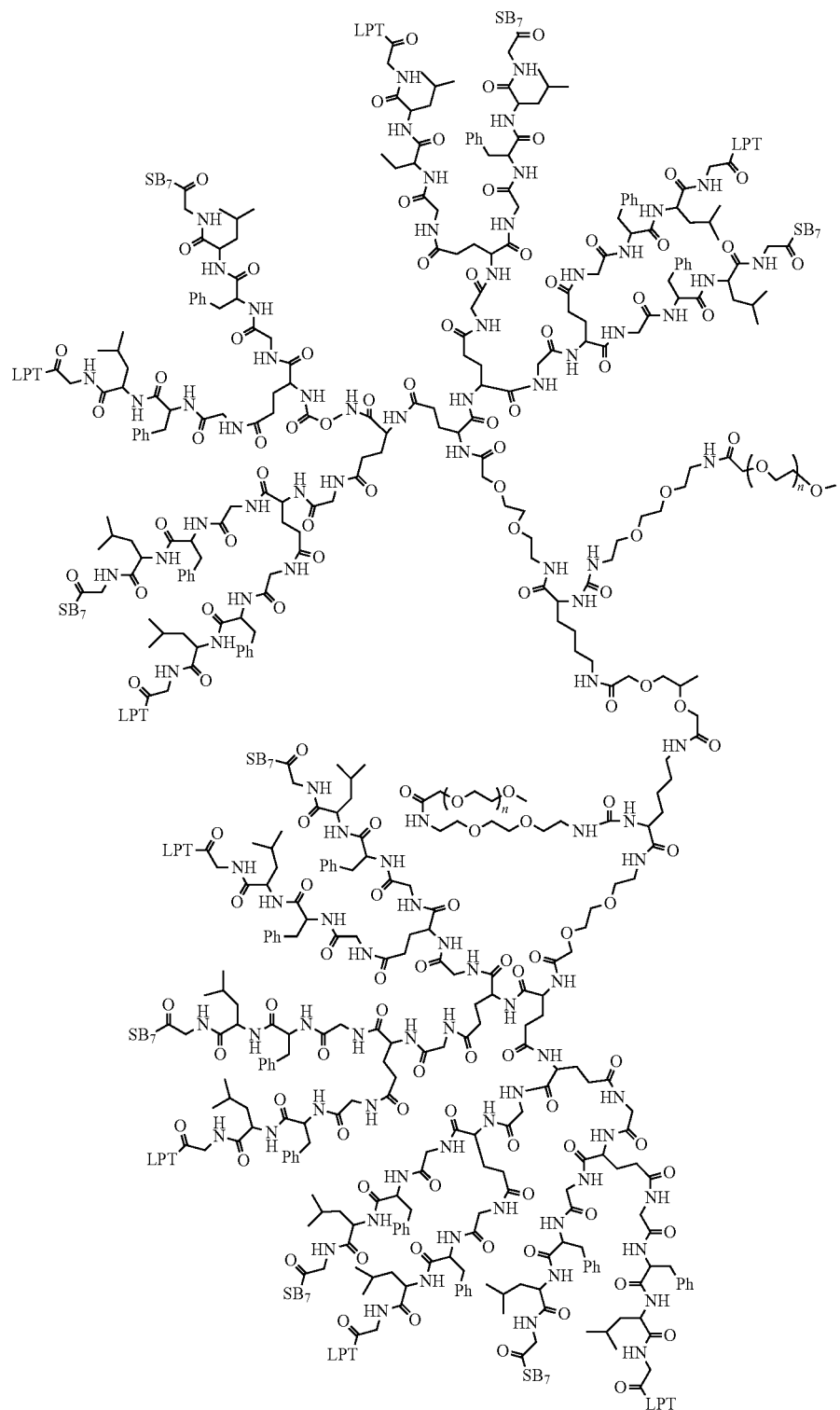

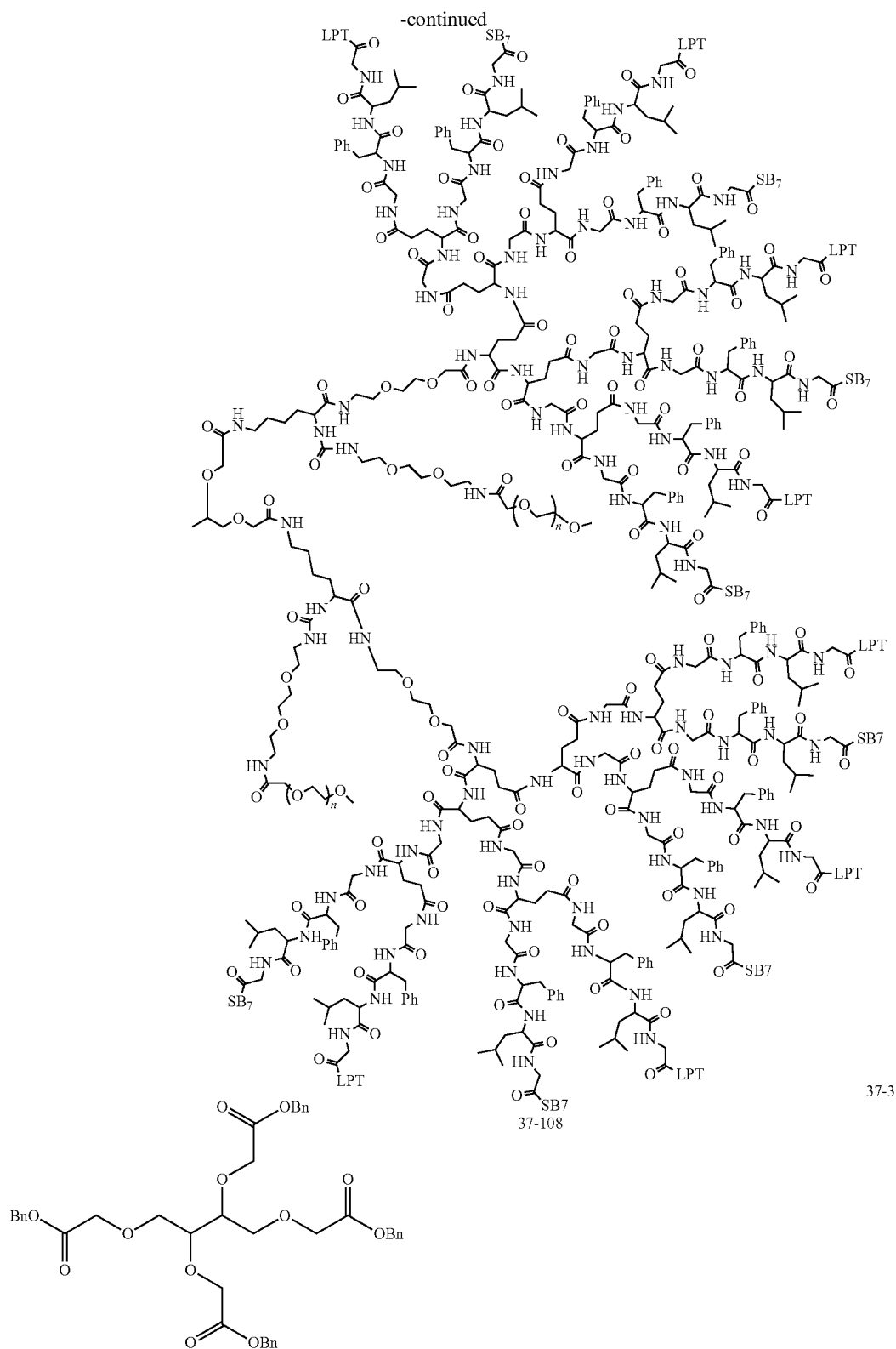

37-39

37-108

Erythritol (purchased from Aladdin, 2.5 g, 20.4717 mmol) was added in a 500 mL flask, and dissolved with THF (130 mL), and then the obtained solution reacted at 0° C. Under the protection of nitrogen gas, the THF solution of potassium tert-butoxide (1 mol/L) (98.2642 mL, 98.2642 mmol) was slowly added dropwise. At the end of the addition, the obtained solution continued to react with stirring for 5 hours. Then benzyl bromoacetate (14.5937 mL, 92.1225 mmol) was slowly added dropwise. At the end of the addition, the obtained solution continued to react with stirring for 2 hours, and was then moved to room temperature and stirred to react overnight. At the end of the reaction, the reaction solution was transferred to a 1 L separatory funnel, saturated sodium bicarbonate solution (200 mL) and ethyl acetate (250 mL) were added, and the obtained solution was shaken for extraction. The aqueous phase was washed with ethyl acetate (200 mL×2), and the obtained organic phases were combined. The organic phase was washed with saturated saline solution (200 mL×2), concentrated and evaporated to dryness. The obtained dry product was dissolved with dichloromethane, silica gel powder (50 g) was added, and the obtained mixture was then evaporated to dryness to obtain a powdery solid. The operations of dry sample loading, column chromatography and elution with a petroleum ether mixed solution containing 1.5%-5% ethyl acetate were carried out. The elution product was then collected, concentrated, evaporated to dryness, and dried in a vacuum oven, thus obtaining the product 37-39: 4.8 g, yield 33%.

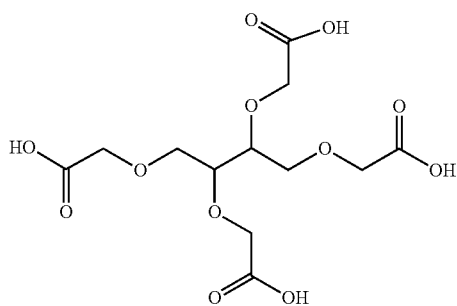

37-49

37-39 (1.03 g, 1.441 mmol) and 10% Pd/C (0.040 g) were added in a hydrogenation reactor, and dissolved with DMF (30 mL), then hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

37-67

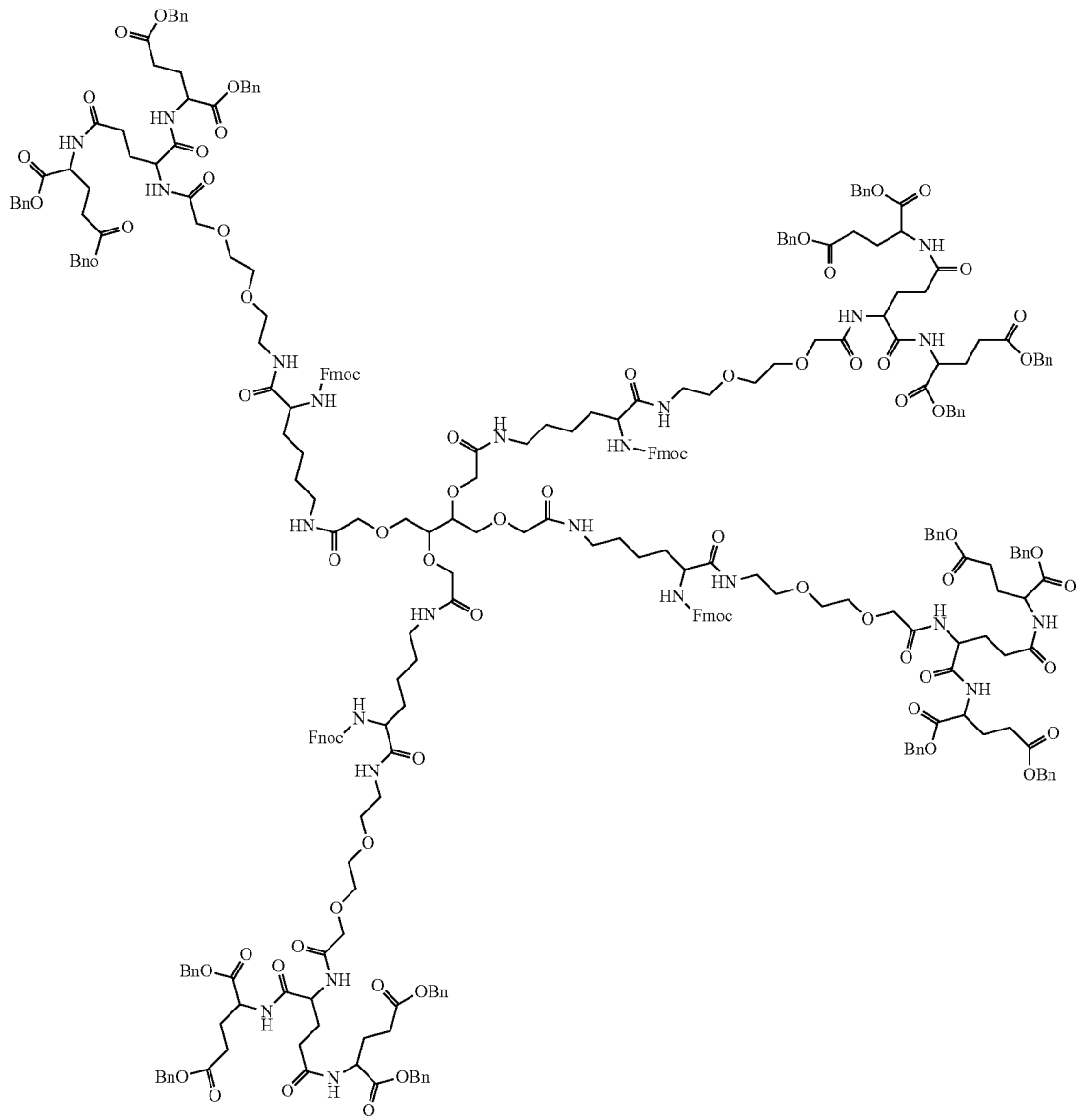

37-49 (0.14 g, 0.3013 mmol), 37-66 (synthesized according to the method of synthesizing 35-4, 1.9 g, 1.506 mmol), HBTU (1.537 g, 4.0528 mmol), HOBT (0.5473 g, 4.0528 mmol) were added in a 250 mL flask, and dissolved with DMF (30 mL), and then the mixed solution was stirred to react at −5° C. for 30 minutes. Then DIEA (2.01 mL, 12.1585 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×2), evaporated to dryness, and dried in an oven, thus obtaining the product 37-67: 1.61 g.

37-67 (1.6053 g, 0.3013 mmol) was added in a 250 mL flask, and dissolved with DMF (30 mL), morpholine (2.6245 mL, 30.125 mmol) was added, and the mixed solution was stirred to react at room temperature for 1 hour. At the end of the reaction, the reaction solution was transferred to a 1 L separatory funnel, and extracted with saturated saline solution (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×1), concentrated and evaporated to dryness, silica gel powder (20 g) was added, and the obtained mixture was then evaporated to dryness to obtain a powdery solid. The operations of dry sample loading, column chromatography and elution with a dichloromethane mixed solution containing 0.5% ammonia water and 5%-8% methanol were carried out. The elution product was then 37-68

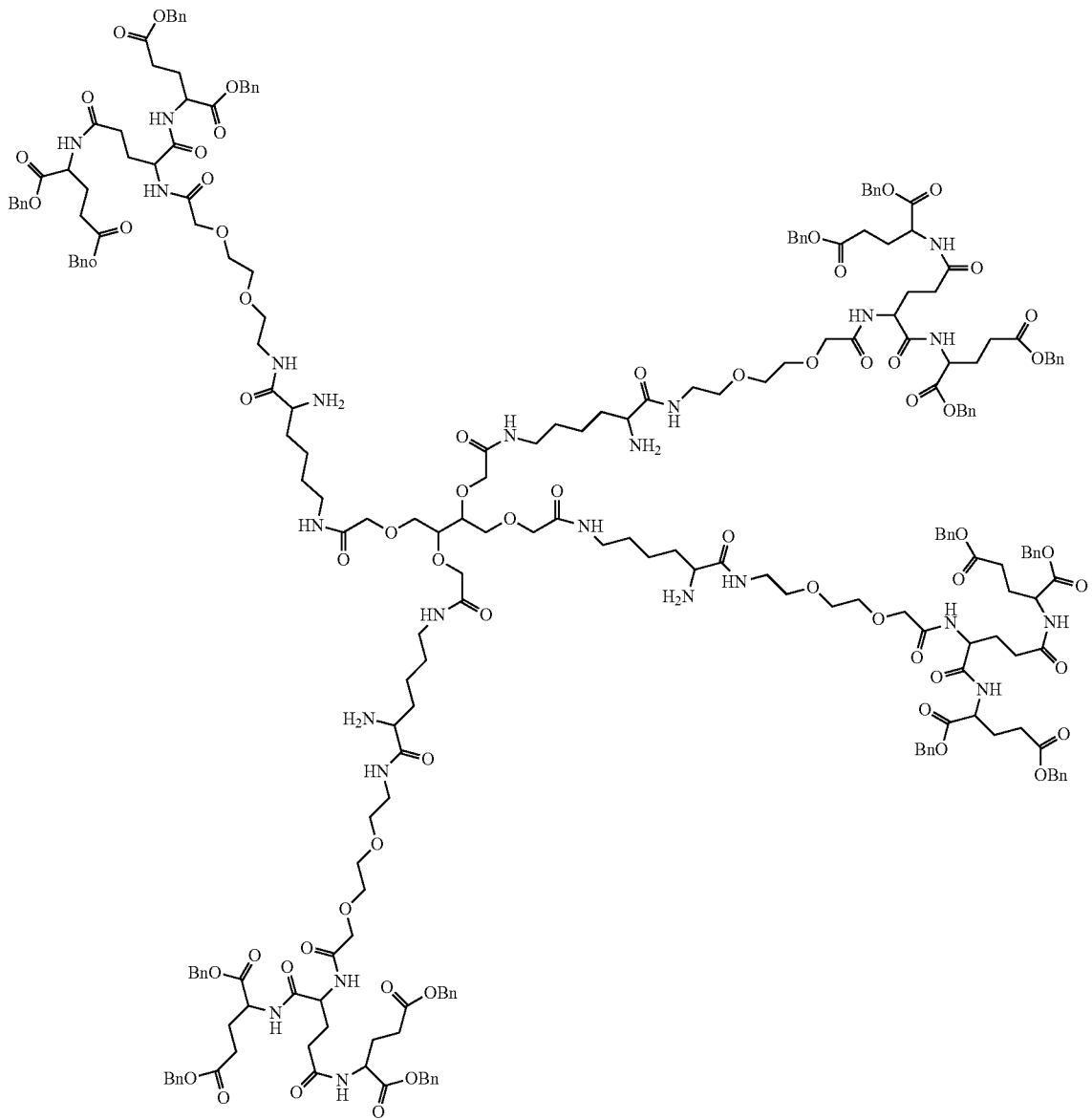

collected, concentrated, evaporated to dryness, and dried in an oven, thus obtaining the product 37-68: 0.59 g, yield 45%.

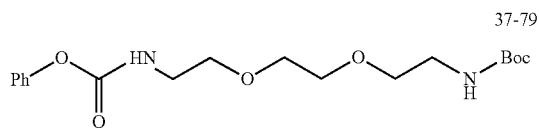 [SMILES: CC(C)(C)OC(=O)NCCOCCOCCNC(=O)Oc1ccccc1]

37-79

33-143 (3.7248 g, 15.0 mmol) was added in a 250 mL flask, and dissolved with dichloromethane (30 mL), triethylamine (2.598 mL, 18.4912 mmol) was added, and then the obtained solution was stirred to react at 0° C. for 30 minutes. Phenyl chloroformate (1.39 mL, 11.0947 mmol) was slowly added dropwise, and then the obtained solution was stirred to react at room temperature overnight. At the end of the reaction, the reaction solution was transferred to a 1 L separatory funnel, and extracted with dichloromethane (200 mL) and deionized water (200 mL), and the organic phase was separated. The aqueous phase was washed with dichloromethane (200 mL×1), and the obtained organic phases were combined, silica gel powder (10 g) was added, and the obtained mixture was then evaporated to dryness to obtain a powdery solid. The operations of dry sample loading, column chromatography and elution with a dichloromethane mixed solution containing 3% methanol were carried out, thus obtaining the product 37-79: 2.34 g, yield 69%.

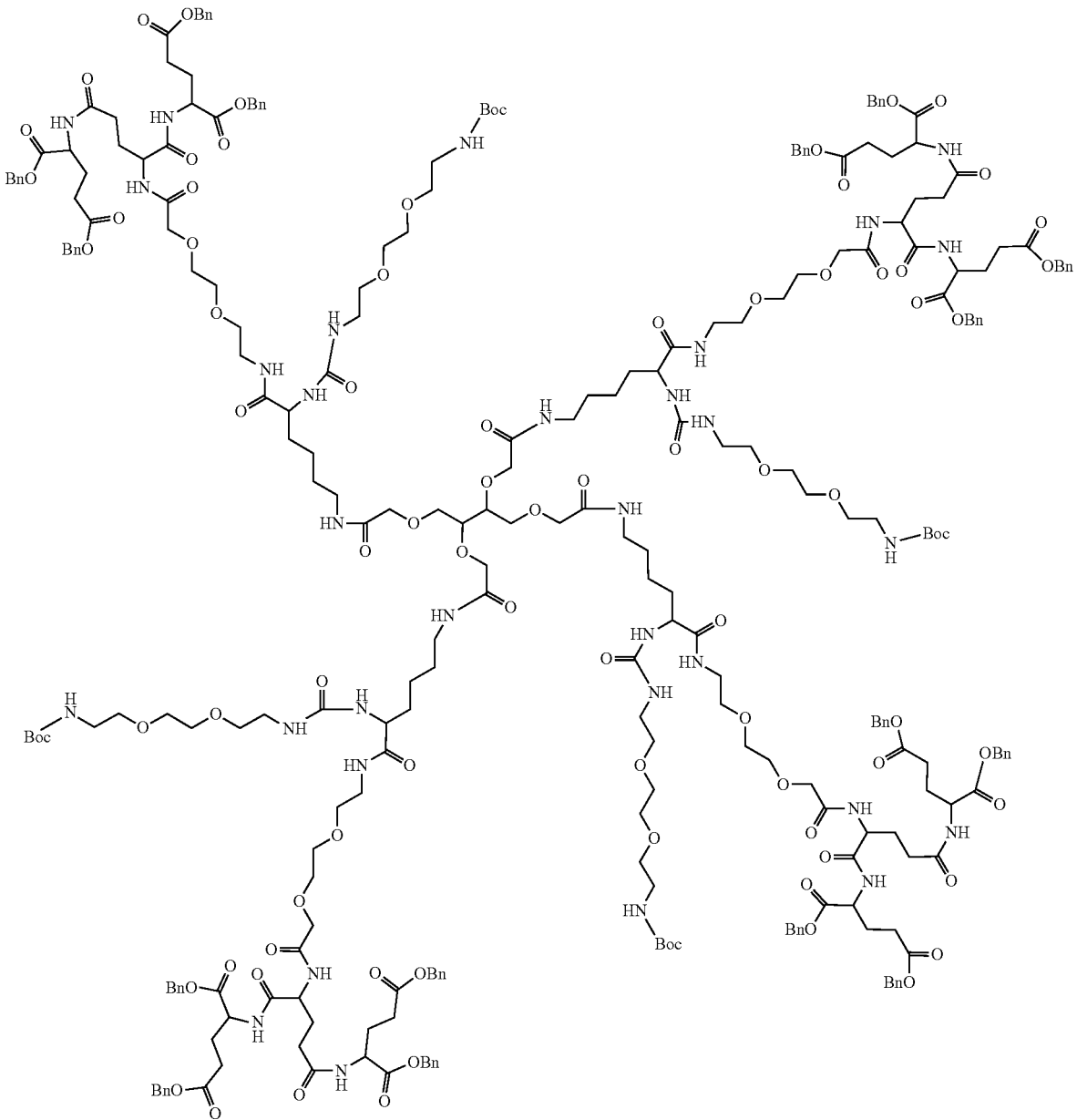

37-81

37-68 (0.59 g, 0.1329 mmol), 37-79 (0.2938 g, 0.7975 mmol) were added in a 250 mL flask, and dissolved with DMF (40 mL), and then the mixed solution was stirred to react at 80° C. overnight. At the end of the reaction, the reaction solution was transferred to a 1 L separatory funnel, and extracted with ethyl acetate (200 mL) and saturated saline solution (200 mL), and the organic phase was separated. The organic phase was washed with saturated saline solution (150 mL), silica gel powder (15 g) was added, and the obtained mixture was then evaporated to dryness to obtain a powdery solid. The operations of dry sample loading, column chromatography and elution with a dichloromethane mixed solution containing 6%-8% methanol were carried out, thus obtaining the product 37-81: 0.27 g, yield 39%.

$^1$H-NMR (400 MHz, DMSO-$d_6$) δ 8.32-8.14 (m, 20H), 7.41-7.38 (m, 80H), 7.26-7.10 (m, 4H), 6.21-5.93 (m, 8H), 5.34-5.20 (m, 32H), 4.51-4.45 (m, 16H), 3.96-3.81 (m, 24H), 3.63-3.04 (m, 32H), 2.21-2.05 (m, 64H), 1.84-1.55 (m, 16H), 1.48-1.33 (m, 36H), 1.25 (m, 9H).

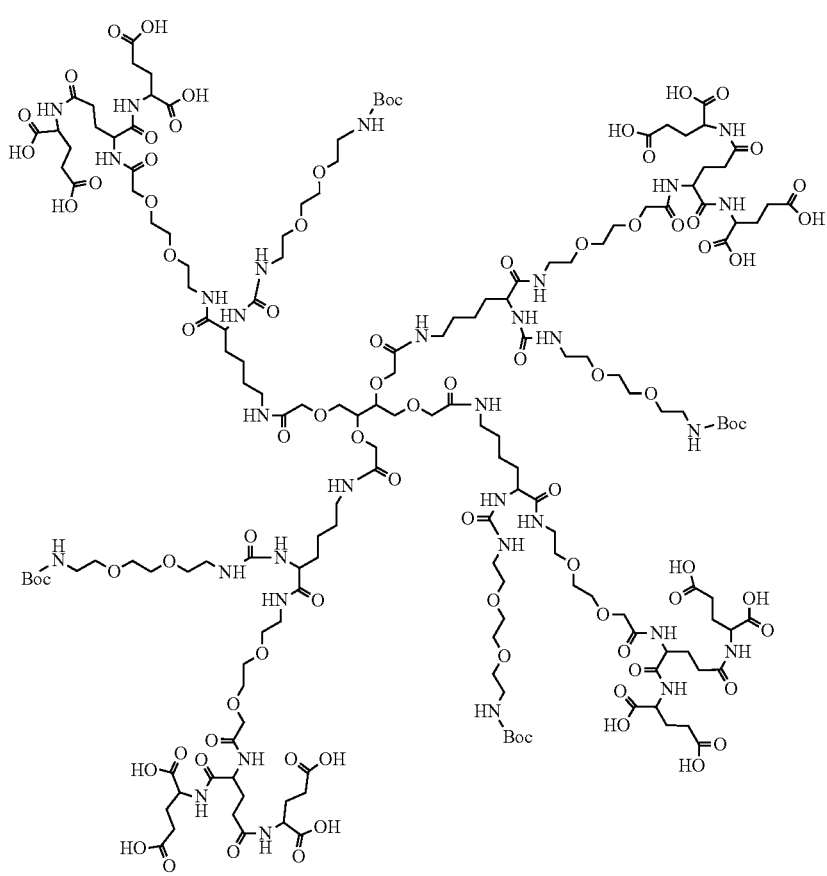

37-89

37-81 (0.27 g, 0.0488 mmol) and 10% Pd/C (0.070 g) were added in a hydrogenation reactor, and dissolved in DMF (30 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

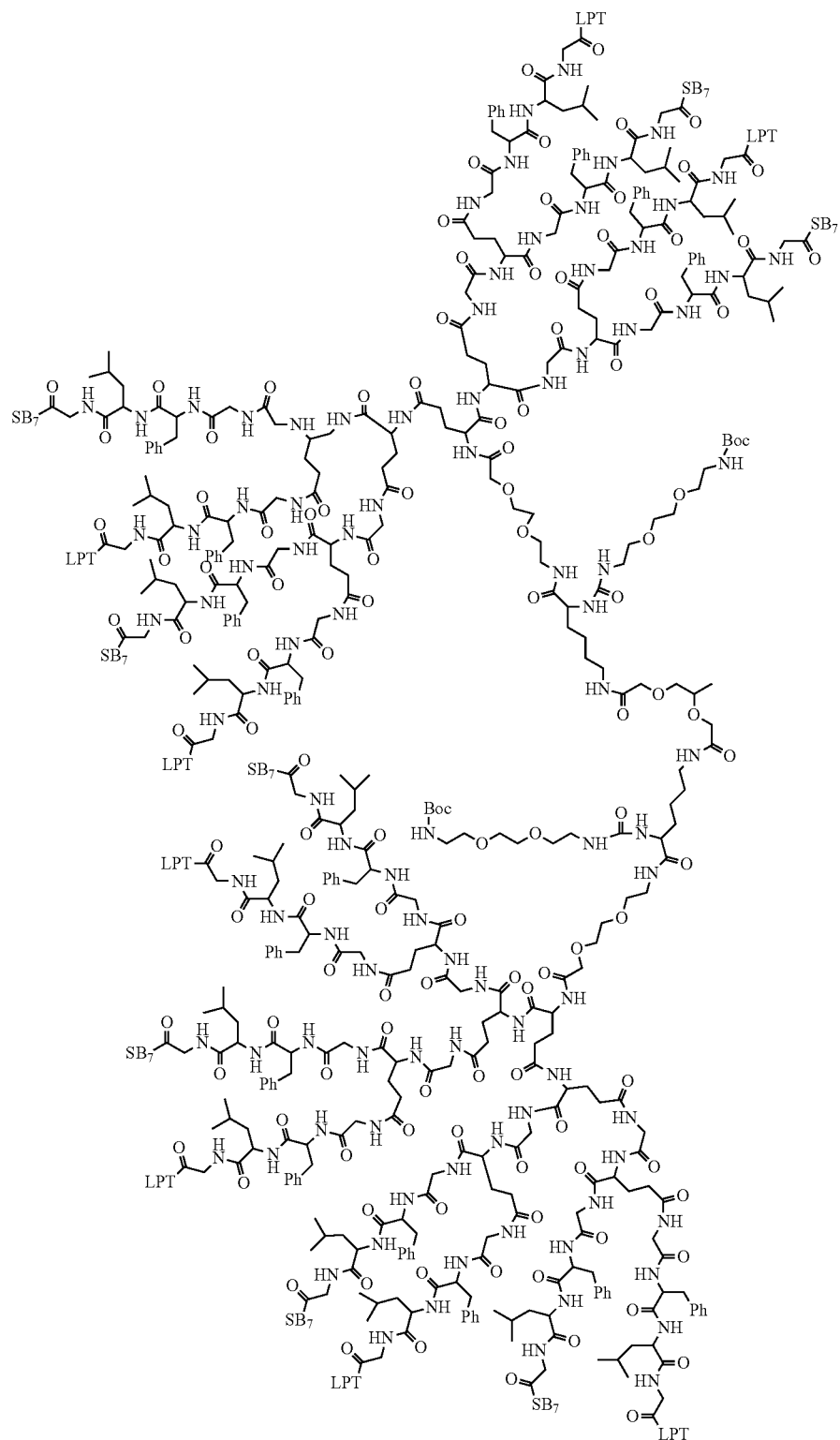
37-91

-continued

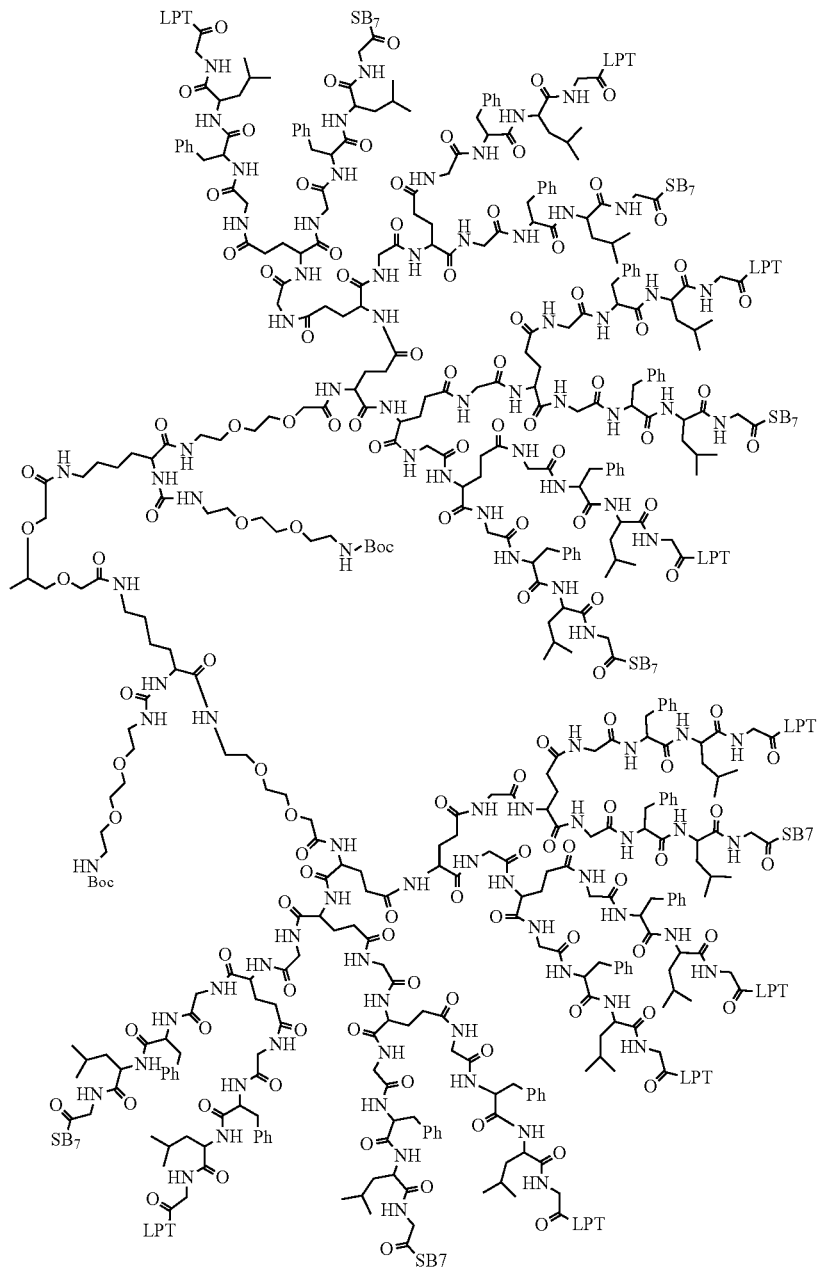

37-89 (0.1998 g, 0.0488 mmol), 37-38 (synthesized according to the method of synthesizing 39-20, 1.769 g, 0.87796 mmol), HBTU (0.4442 g, 1.1712 mmol), HOBT (0.1583 g, 1.1712 mmol) were added in a 250 mL flask, and dissolved with DMF (30 mL), and then the mixed solution was stirred to react at −5° C. for 30 minutes. Then DIEA (0.58 mL, 3.5136 mmol) was slowly added dropwise. At the end of the addition, the obtained solution continued to react for 1 hour, and was then moved to room temperature and stirred to react overnight. At the end of the reaction, n-hexane (250 mL) and methyl tert-butyl ether (40 mL) were added to layer the reaction solution, the supernatant was discarded, and n-hexane (250 mL) and methyl tert-butyl ether (40 mL) were added to the lower oily liquid phase for further precipitation, and such operations were repeated four times, to obtain a viscous oily product. Methyl tert-butyl ether (150 mL) was added to the oily product to separate out a solid, and then filtering was carried out, silica gel powder (15 g) was added, and the obtained mixture was then evaporated to dryness to obtain a powdery solid. The operations of dry sample loading, column chromatography and elution with a dichloromethane mixed solution containing 1% ammonia water and 8%-10% methanol were carried out. The elution product was then collected, concentrated, evaporated to dryness, and dried in an oven, thus obtaining the product 37-91: 1.2 g, yield: 68%.

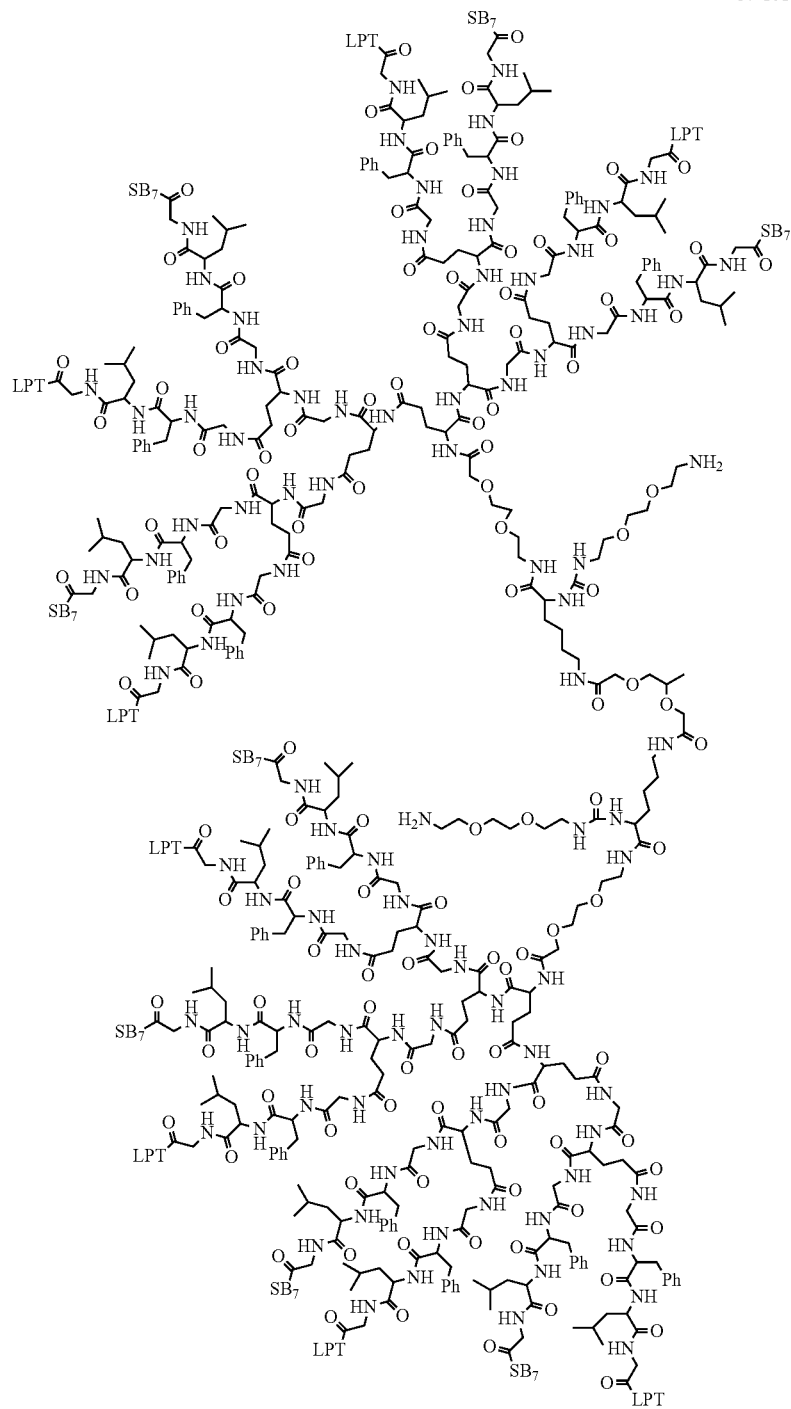
37-101

-continued

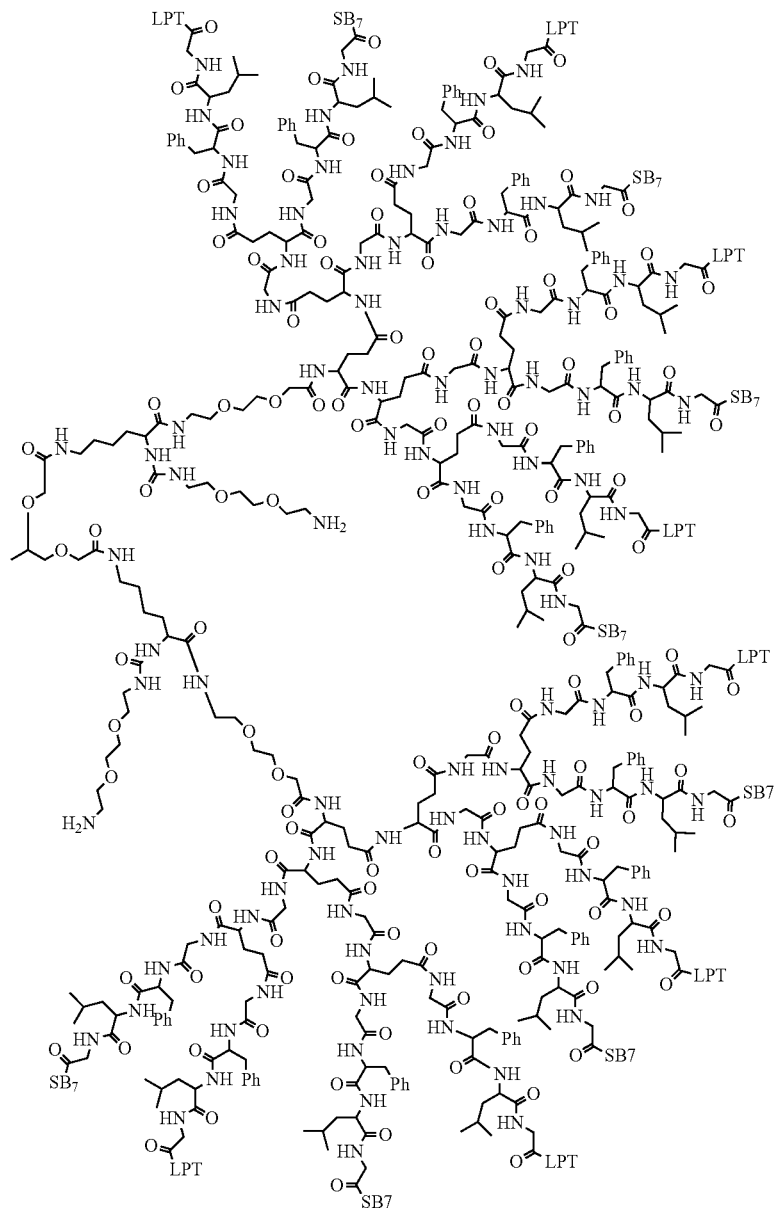

37-91 (1.2 g, 0.0488 mmol) was added in a 250 mL flask, and dissolved with dichloromethane (20 mL), trifluoroacetic acid (0.7248 mL, 9.76 mmol), and then the mixed solution was stirred to react at room temperature overnight. At the end of the reaction, methyl tert-butyl ether (100 mL) was added to the reaction solution to separate out a solid, and suction filtering was carried out. The filter cake was washed with methyl tert-butyl ether (40 mL×3), and dissolved with a mixed solvent of methanol (20 mL) dichloromethane (80 mL), silica gel powder (15 g) was added, and the obtained mixture was then evaporated to dryness to obtain a powdery solid. The operations of dry sample loading, column chromatography and elution with a dichloromethane mixed solution containing 1% ammonia water and 8%-12% methanol were carried out. The elution product was then collected, concentrated, evaporated to dryness, and dried in a vacuum oven, thus obtaining the product 37-101: 0.69 g, yield 40%.

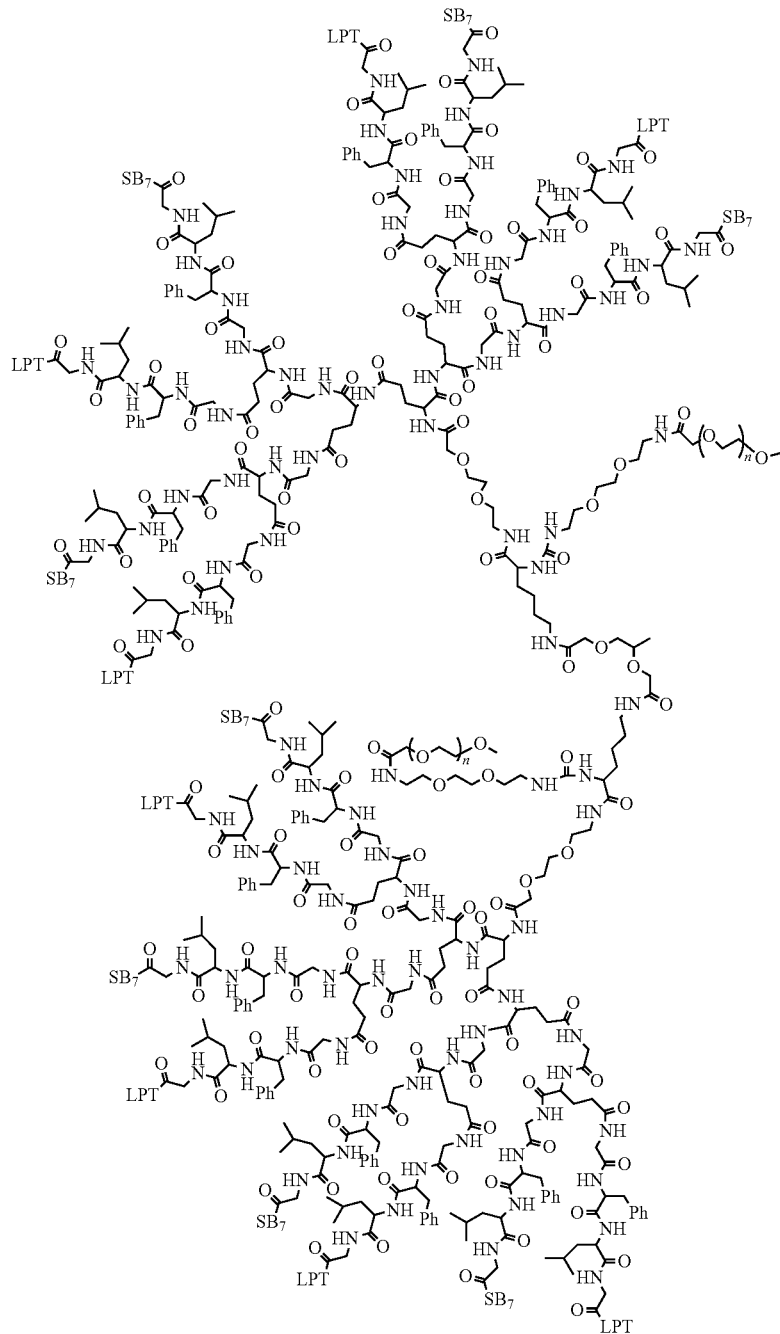
37-108

-continued

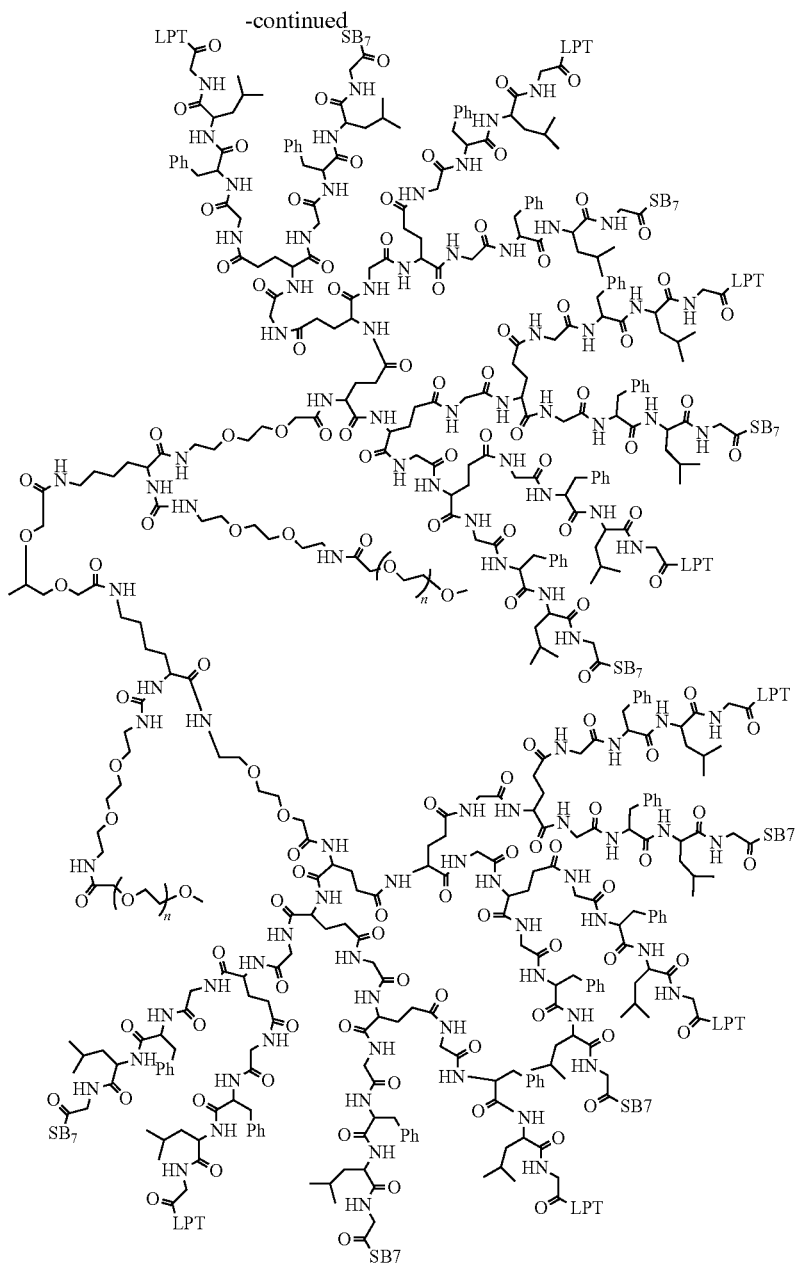

37-101 (0.3 g, 0.0084 mmol) was added in a 250 mL flask, and dissolved with DMF (35 mL), M-SCM-10K (0.5348 g, 0.0505 mmol, purchased from JenKem) was added, and ultrasonic treatment was carried out to dissolve the reactants, and then the mixed solution reacted in the dark for 7 days at a low speed of stirring at room temperature. At the end of the reaction, n-hexane (150 mL) and methyl tert-butyl ether (30 mL) were added to the reaction solution for precipitation, the supernatant was discarded, and n-hexane (130 mL) and methyl tert-butyl ether (30 mL) were added to the lower liquid. Such operations were repeated three times, to obtain a viscous oily product. Methyl tert-butyl ether (100 mL) was added to the oily product to separate out a solid, and filtering was carried out. The filter cake was washed with methyl tert-butyl ether (50 mL×3), and dissolved with a mixed solvent of methanol (30 mL) and dichloromethane (120 mL), silica gel powder (15 g) was added, and the obtained mixture was then evaporated to dryness to obtain a powdery solid. The operations of dry sample loading, column chromatography and elution with a dichloromethane mixed solution containing 1% ammonia water and 6%-9% methanol were carried out. The elution product was then collected, concentrated, evaporated to dryness, and dried in a vacuum oven for 1 hour. The obtained dry product was dissolved with anhydrous ethanol (7 mL) and dichloromethane (20 mL), then methyl tert-butyl ether (100 mL) was added to the obtained solution to separate out a solid, and filtering was carried out. The filter cake was washed with methyl tert-butyl ether (50 mL×2), and dried in a vacuum oven, thus obtaining the product 37-108: 0.3 g, yield: 52%.

$^1$H-NMR (600 MHz, DMSO-$d_6$) δ8.49-8.22 (m, 49H), 8.12-8.03 (m, 212H), 7.91-7.66 (m, 48H), 7.36-7.01 (m, 388H), 6.97-6.85 (m, 16H), 6.70-6.01 (m, 40H), 5.34-5.16 (m, 64H), 4.92-4.26 (m, 144H), 4.09-4.03 (m, 152H), 3.76-3.54 (m, 86H), 3.51-3.41 (m, 3722H), 3.44-3.19 (m, 160H), 2.93-2.72 (m, 48H), 2.46-2.05 (m, 192H), 1.84-1.55 (m, 144H), 1.25-0.91 (m, 297H).

16. Synthesis of 29-226 (Compound No. 8)
Synthetic route is as follows
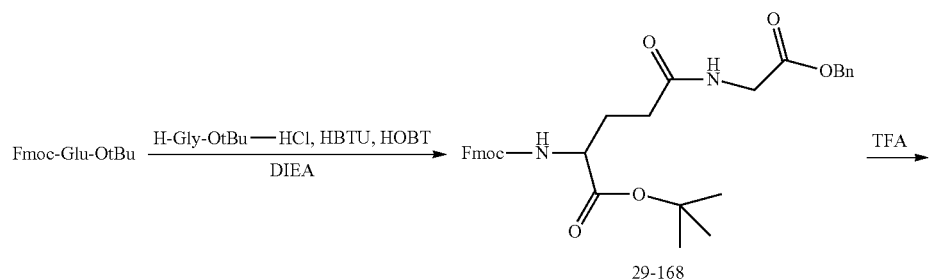
29-168
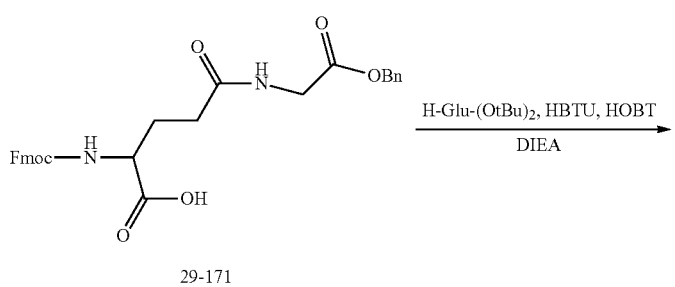
29-171
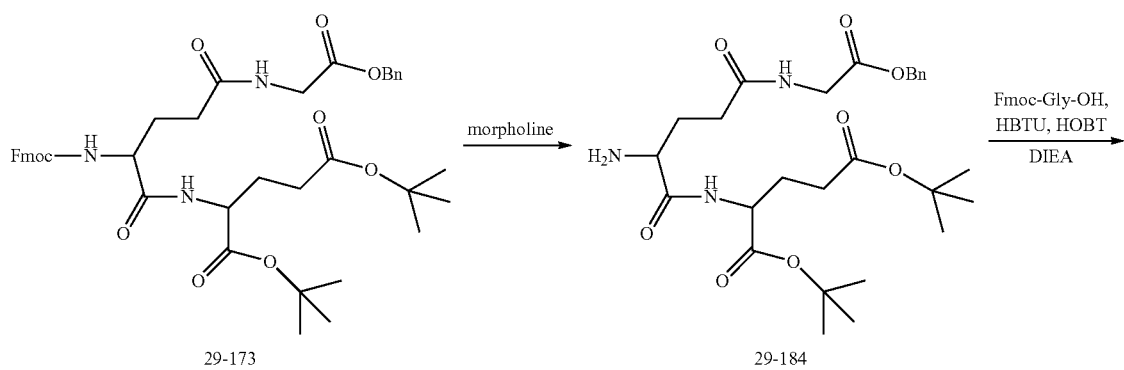
29-173     29-184
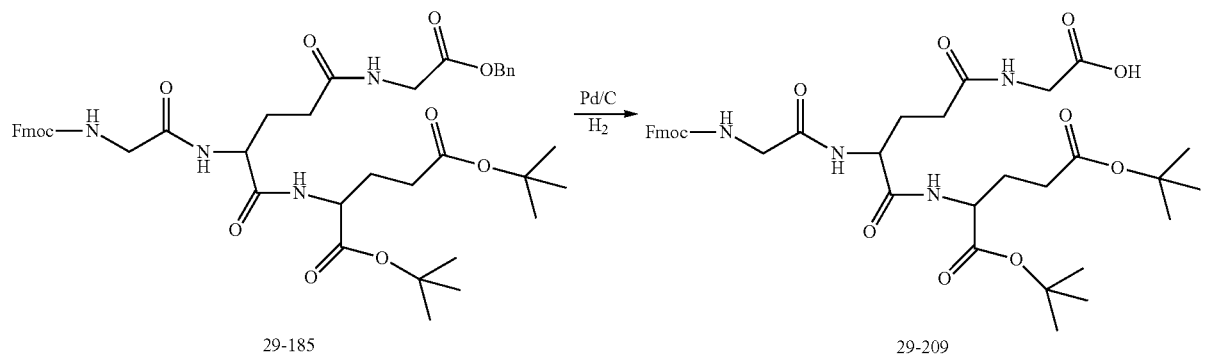
29-185     29-209

-continued
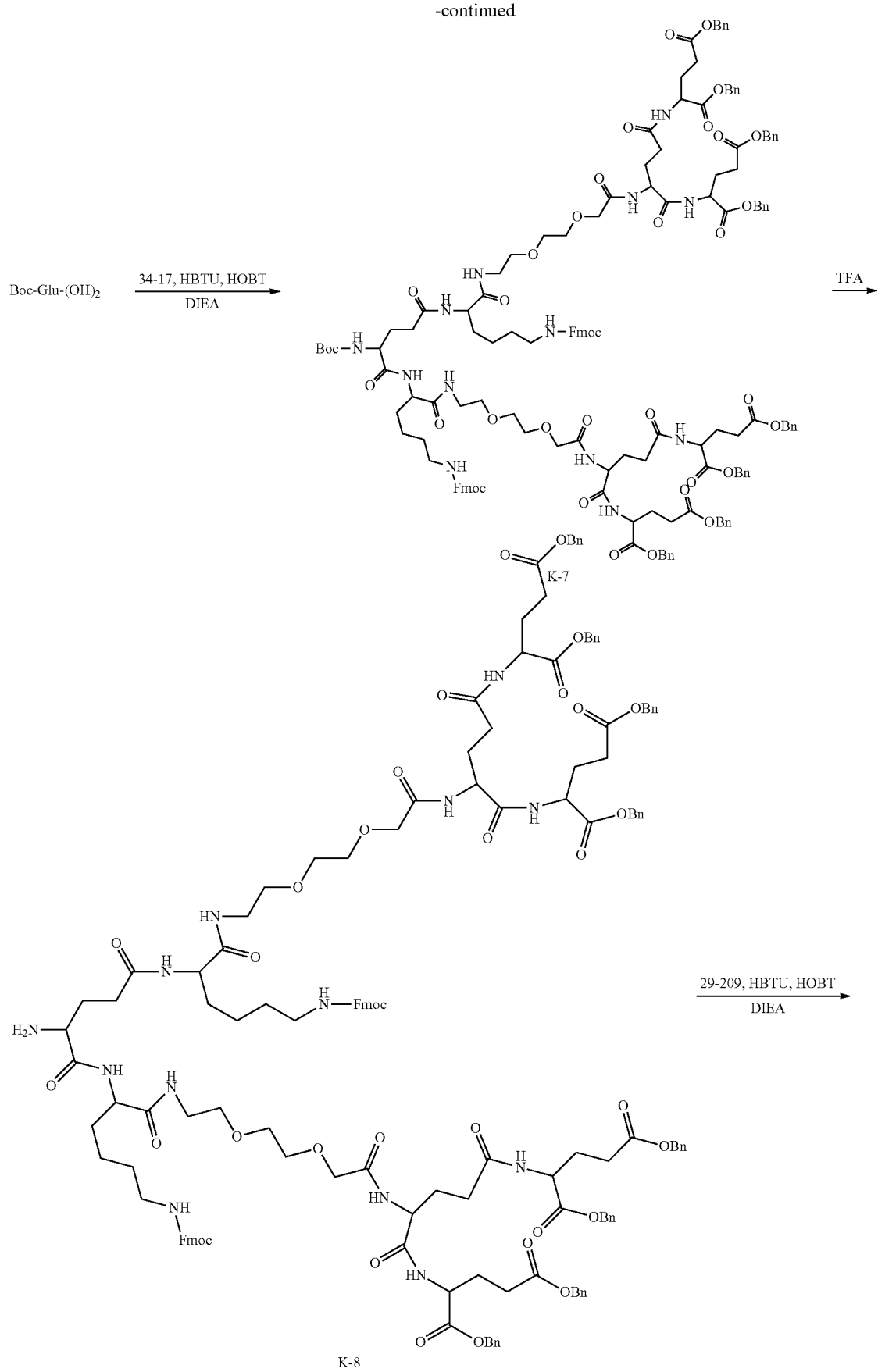

-continued
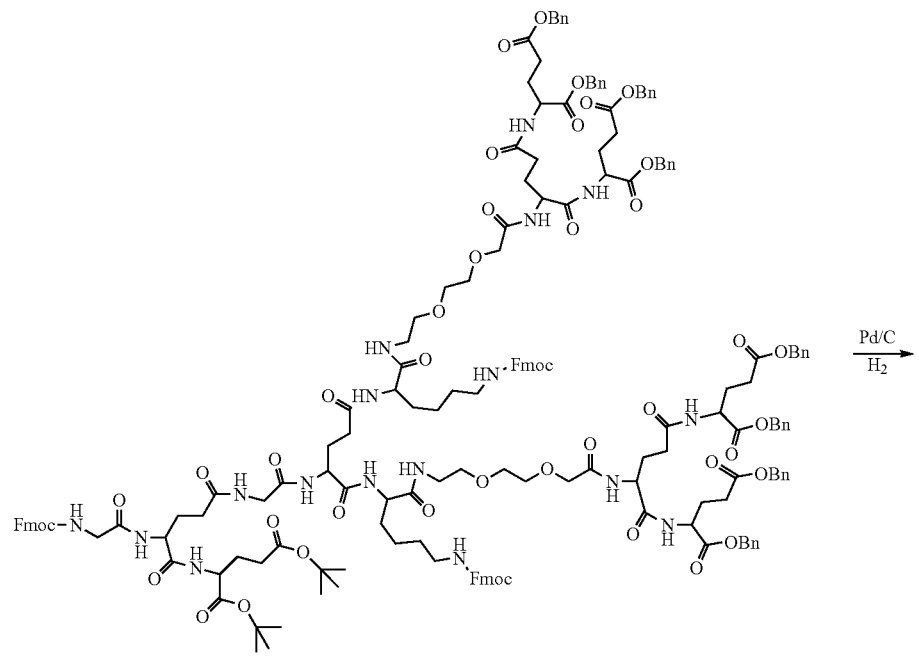
29-210
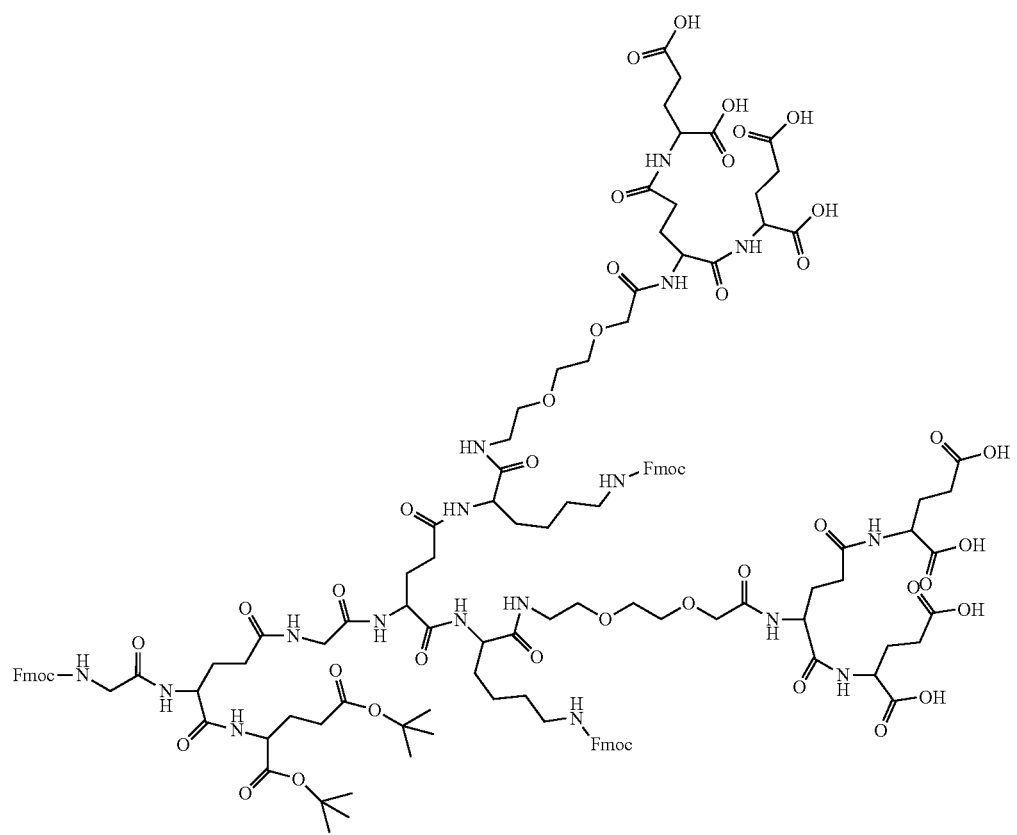
29-212

-continued
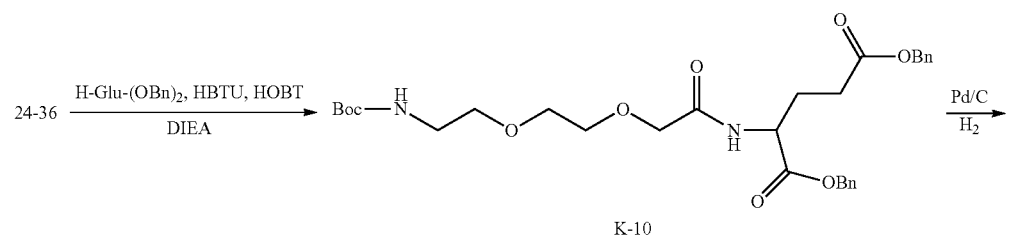
K-10
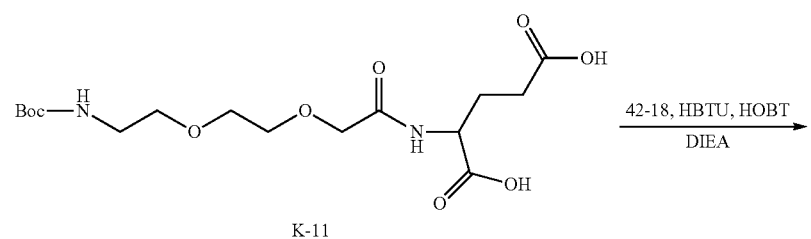
K-11
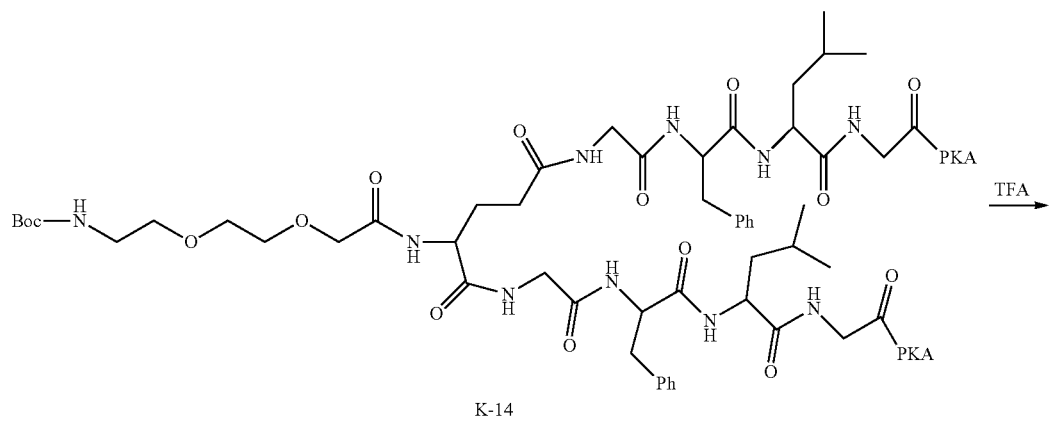
K-14
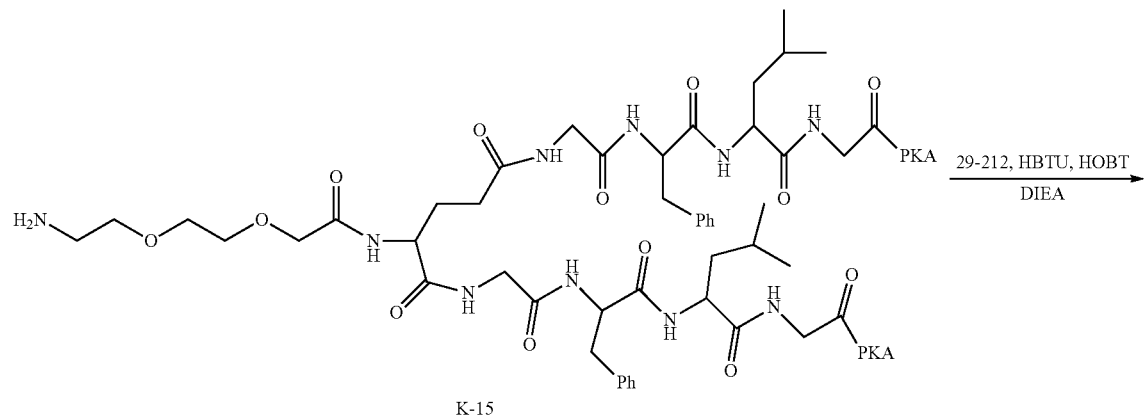
K-15

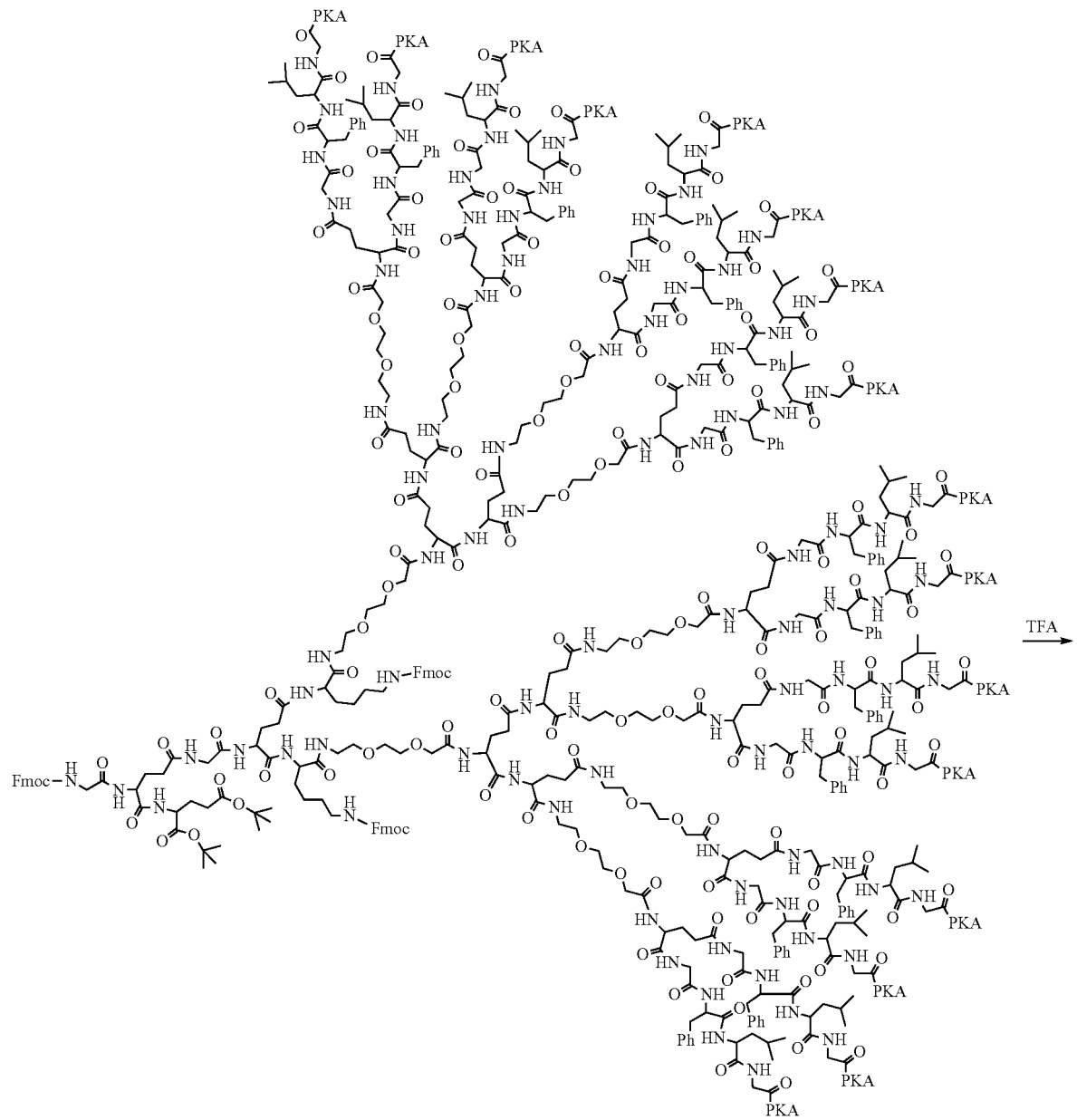
29-213

-continued
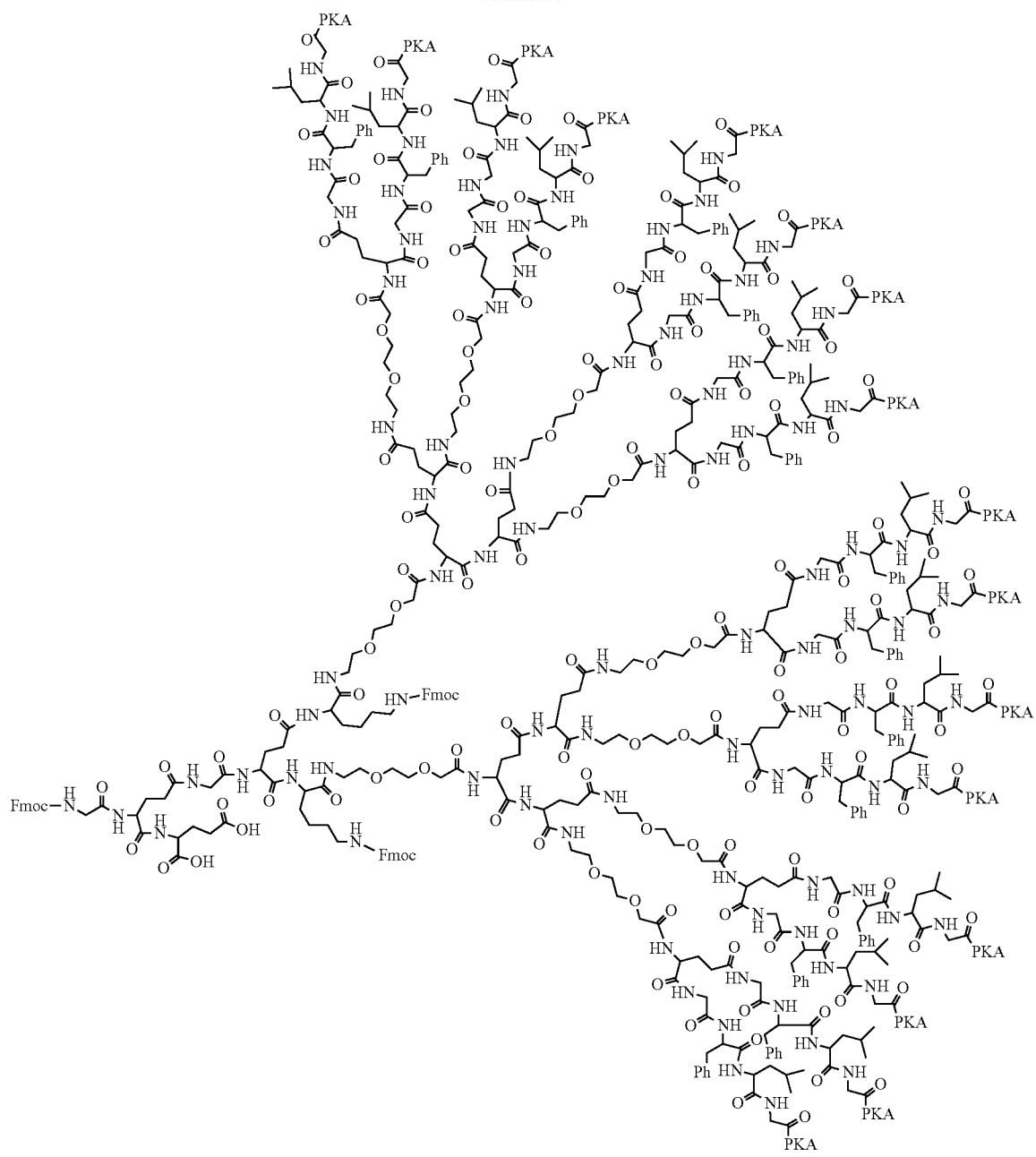
29-214
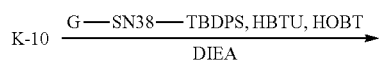
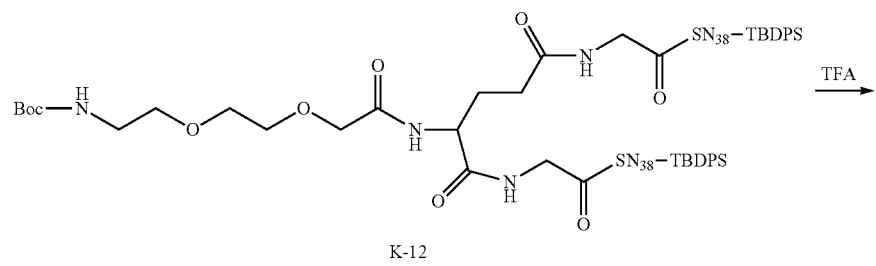

-continued
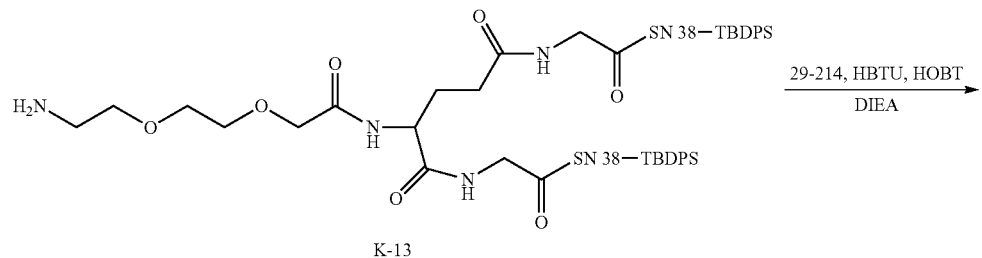
K-13
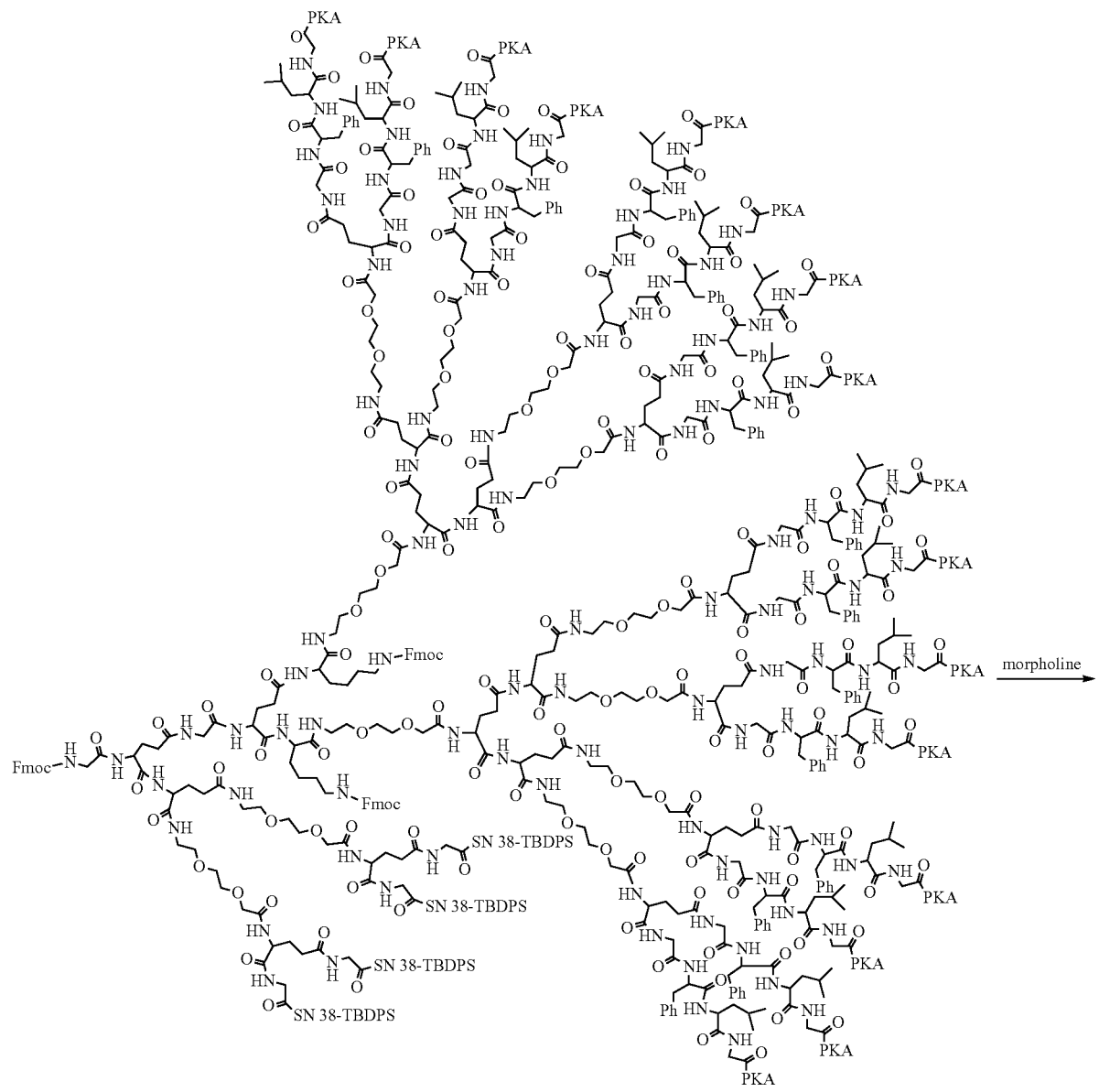
29-216

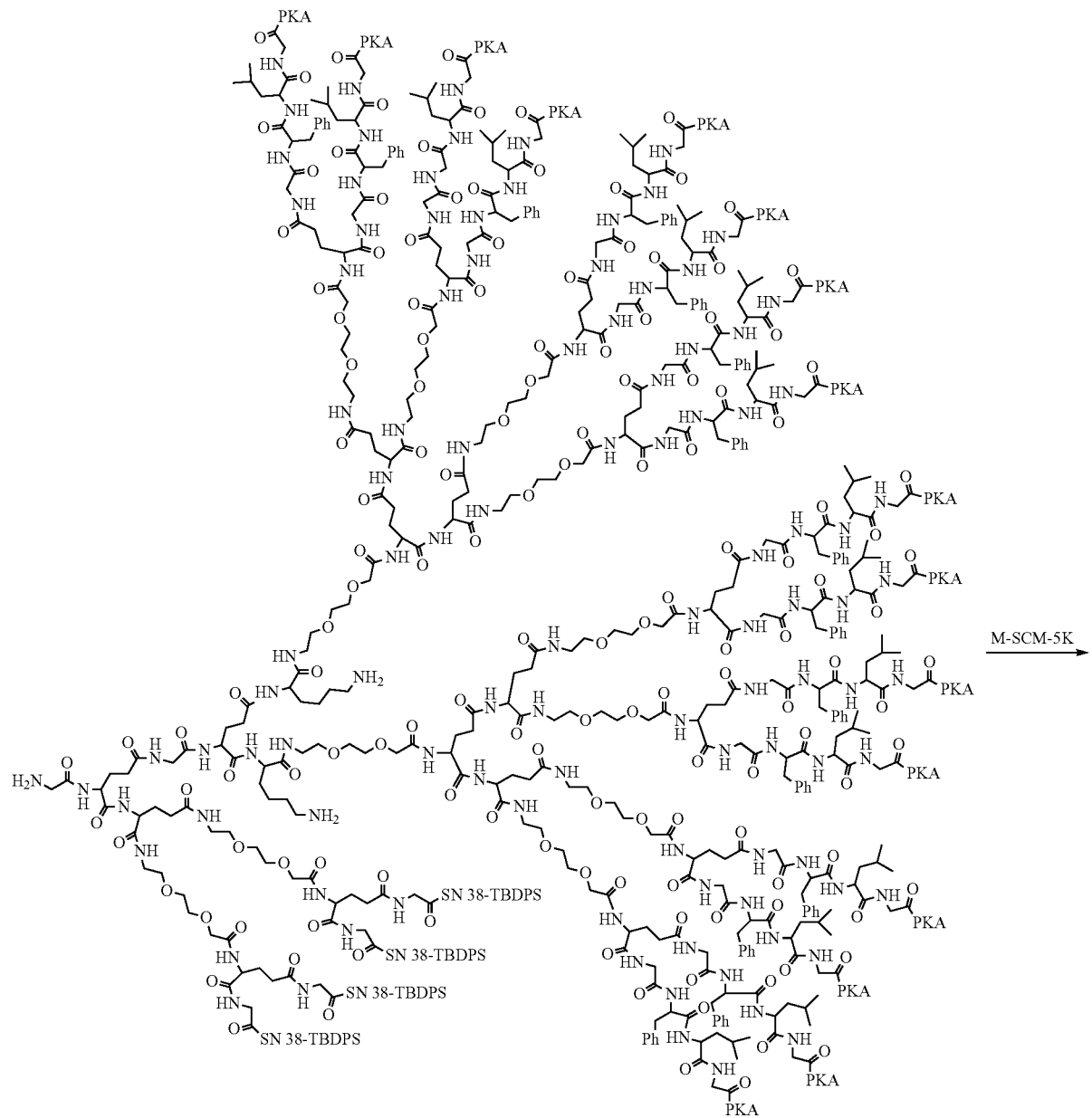
29-220
M-SCM-5K →

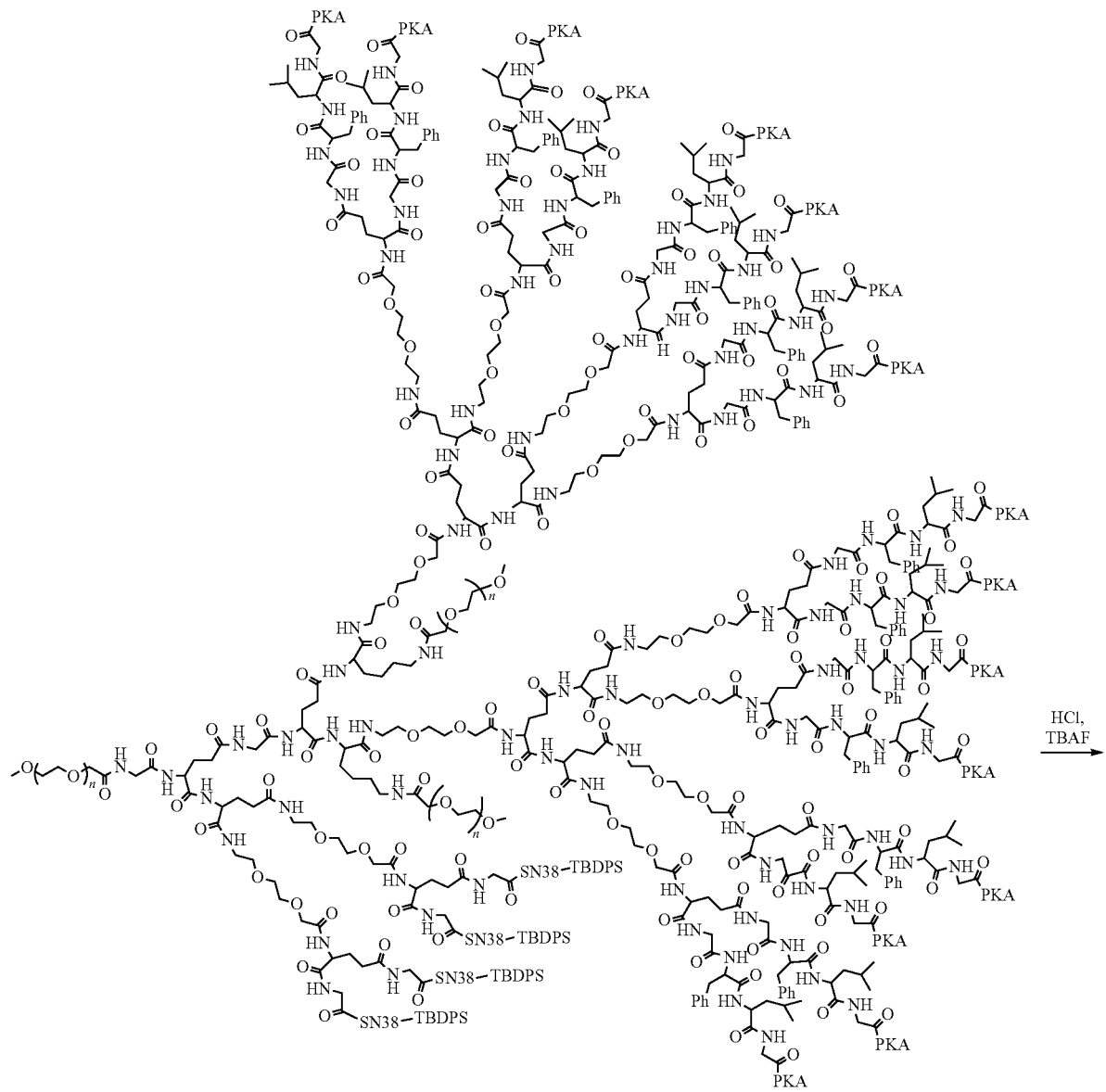
29-221

-continued

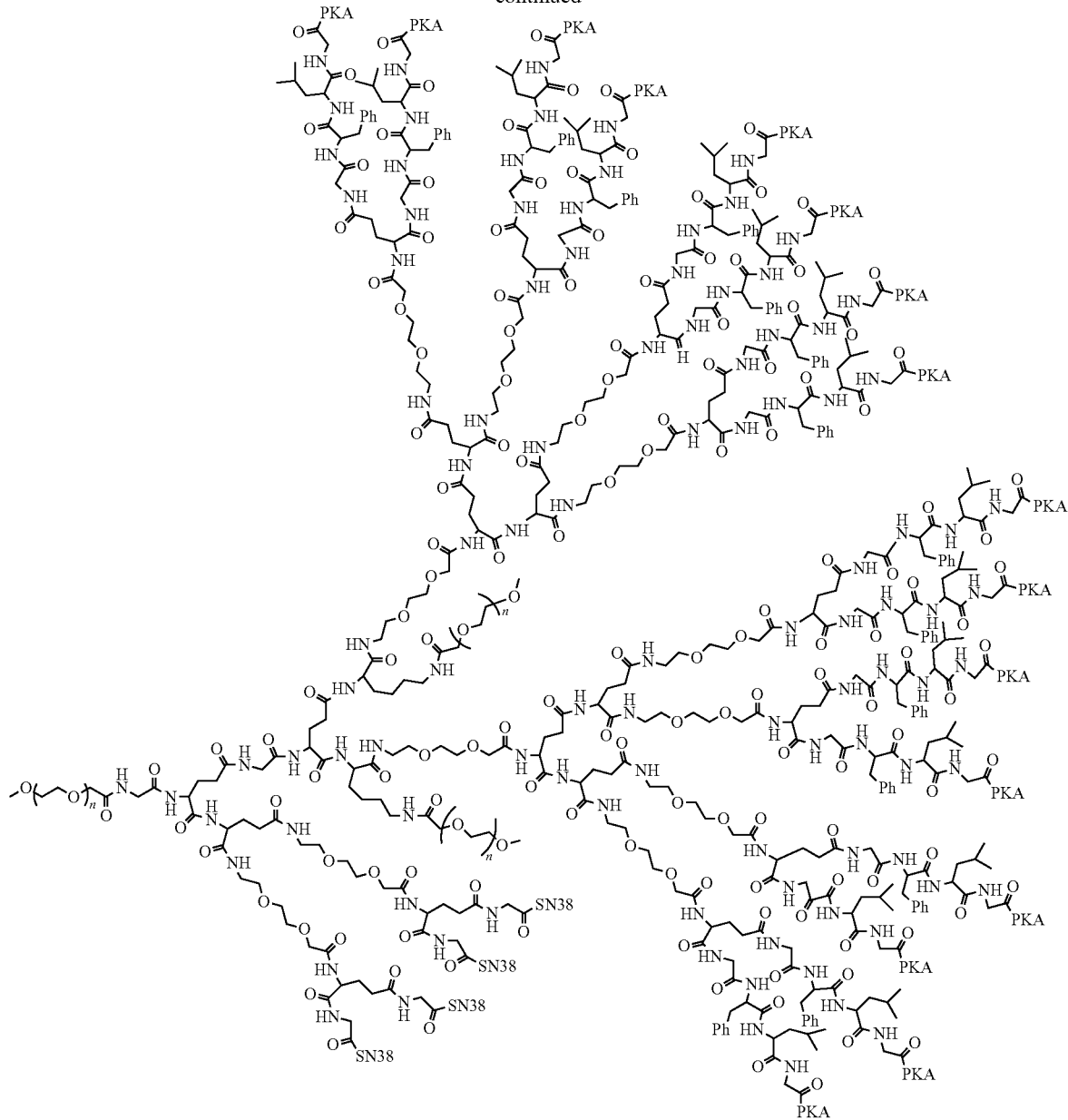

29-226

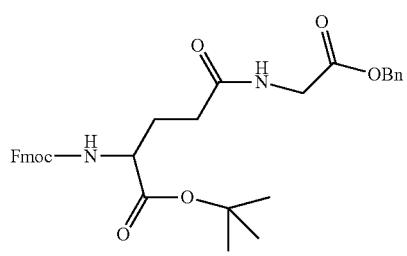

29-168

Fmoc-Glu-OtBu (4 g, 9.401 mmol, purchased from Inno-Chem), H-Gly-OtBu·HCl (1.7 g, 10.3415 mmol, purchased from InnoChem), HBTU (5.3 g, 14.1021 mmol) and HOBT (1.9 g, 14.1021 mmol) were added in a 500 mL round-bottomed flask, and dissolved with DMF (70 mL), and then the mixed solution was stirred at 0° C. for 30 minutes. Then DIEA (7.0 mL, 42.3061 mmol) was slowly added dropwise. At the end of the addition, the obtained solution was stirred to react at 0° C. overnight. At the end of the reaction, the reaction solution was transferred to a 1 L separatory funnel, and extracted with pure water (100 mL) and ethyl acetate (80 mL), and the organic phase was separated. The aqueous phase was extracted with ethyl acetate (80 mL×2), and the obtained organic phases were combined. The organic phase was then extracted with saturated sodium chloride solution (150 mL×3), concentrated, evaporated to dryness, and dried, thus obtaining a crude product.

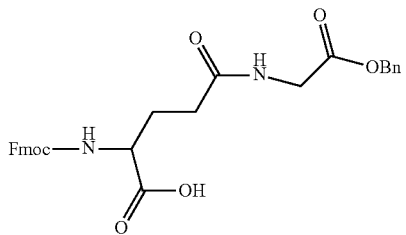

29-171

29-168 (9.401 mmol) was added in a 500 mL flask, and dissolved with dichloromethane (10 mL), and TFA (7.0 mL, 94.01 mmol), and then the mixed solution wag stirred to react at room temperature overnight. At the end of the reaction, the reaction solution was subjected to rotary evaporation to obtain an oily product, the oily product was then transferred to a 1 L separatory funnel, saturated sodium bicarbonate solution (100 mL) was added to adjust the pH to alkaline, ethyl acetate (80 mL) was then added for extraction, and the organic phase was separated. The aqueous phase was extracted with ethyl acetate (80 mL×2), and the obtained organic phases were combined. The organic phase was then extracted with saturated sodium chloride solution (100 mL×3), concentrated, evaporated to dryness, and dried in a vacuum oven, thus obtaining a crude product, yield 100%.

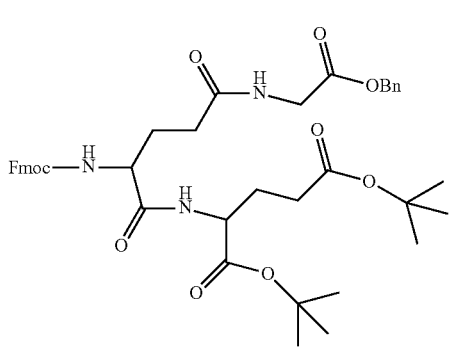

29-173

29-171 (9.401 mmol), H-Glu-(OtBu)$_2$ (2.6789 g, 10.3415 mmol), HBTU (5.3 g, 14.1021 mmol) and HOBT (1.9 g, 14.1021 mmol) were added in a 500 mL round-bottomed flask, and dissolved with DMF (70 mL), and then the mixed solution was stirred at 0° C. for 30 minutes. Then DIEA (7.0 mL, 42.3061 mmol) was slowly added dropwise. At the end of the addition, the obtained solution was stirred to react at 0° C. overnight. At the end of the reaction, the reaction solution was transferred to a 1 L separatory funnel, and extracted with pure water (100 mL) and ethyl acetate (80 mL), and the organic phase was separated. The aqueous phase was extracted with ethyl acetate (80 mL×2), and the obtained organic phases were combined. The organic phase was extracted with saturated sodium chloride solution (150 mL×3), concentrated, evaporated to dryness, and dried, thus obtaining a crude product.

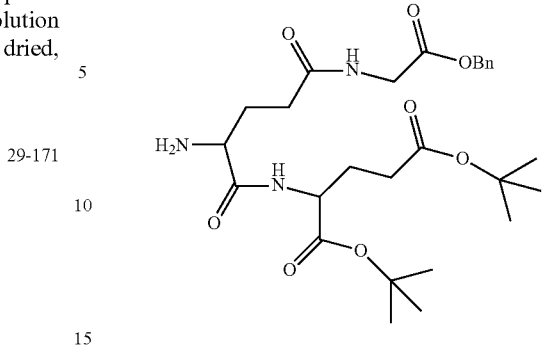

29-184

29-173 (9.401 mmol) was added in a 250 mL flask, and dissolved with DMF (10 mL), morpholine (8.2 mL, 94.01 mmol) was added, and then the mixed solution was stirred to react at room temperature for 1 hour. At the end of the reaction, the reaction solution was transferred to a 1 L separatory funnel, and extracted with pure water (100 mL) and ethyl acetate (80 mL), and the organic phase was separated. The aqueous phase was extracted with ethyl acetate (80 mL×2), and the obtained organic phases were combined. The organic phase was extracted with saturated sodium chloride solution (150 mL×3), and concentrated, silica gel powder (20 g) was added, and the obtained mixture was then evaporated to dryness to obtain a powdery solid. The operations of dry sample loading, column chromatography and gradient elution with a dichloromethane mixed solution containing 1% ammonia water and 4%-8% methanol were carried out. The elution product was then collected, concentrated, and dried in a vacuum oven, thus obtaining the product 3.7 g, yield 74%.

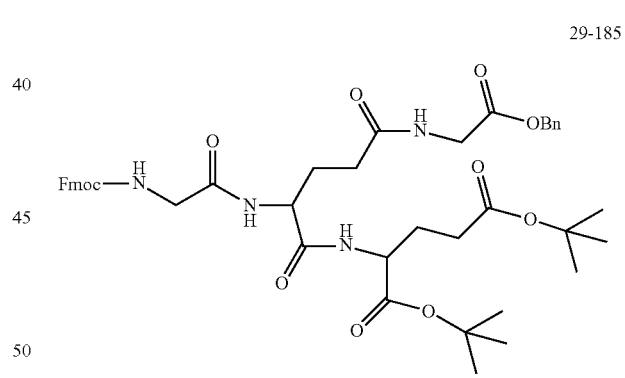

29-185

Fmoc-Gly-OH (2.2 g, 7.5985 mmol, purchased from InnoChem), 29-184 (3.7 g, 6.9078 mmol), HBTU (3.9 g, 10.3616 mmol), HOBT (1.400 g, 10.3616 mmol) were added in a 500 mL round-bottomed flask, and dissolved with DMF (70 mL), and then the mixed solution was stirred at 0° C. for 30 minutes. Then DIEA (5.1 mL, 31.0849 mmol) was slowly added dropwise. At the end of the addition, the obtained solution was stirred to react at 0° C. overnight. At the end of the reaction, the reaction solution was transferred to a 1 L separatory funnel, and extracted with pure water (100 mL) and ethyl acetate (80 mL), and the organic phase was separated. The aqueous phase was extracted with ethyl acetate (80 mL×2), and the obtained organic phases were combined. The organic phase was extracted with saturated sodium chloride solution (150 mL×3), and concentrated, silica gel powder (25 g) was added, and the obtained mixture was then evaporated to dryness to obtain a powdery solid. The operations of dry sample loading, column chromatography and gradient elution with a dichloromethane mixed solution containing 3%-7% methanol were carried out. The elution product was then collected, concentrated, and dried in a vacuum oven, thus obtaining the product 4.5 g, yield 77%.

29-209

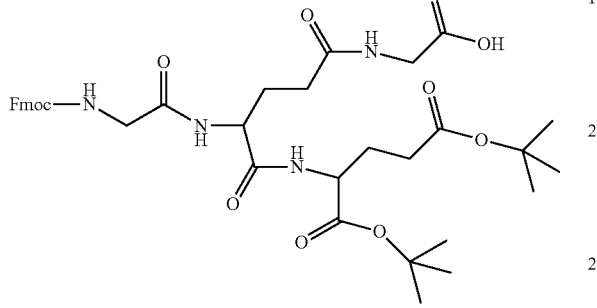

29-185 (0.9281 g, 1.0354 mmol) and 10% Pd/C catalyst (30 mg) were added in a hydrogenation reactor, and dissolved with DMF (30 mL), the hydrogenation reactor was then sealed, hydrogen was introduced so that the pressure on the hydrogenation reactor was read as 18 psi, and then the mixed solution was stirred to react at room temperature overnight. At the end of the reaction, the reaction solution was taken out and evenly added dropwise to a suction funnel filled with compacted diatomaceous earth. The reaction device and diatomaceous earth were washed with DMF (30 mL×3), and the filtrate was collected, thus obtaining the reaction product.

K-7

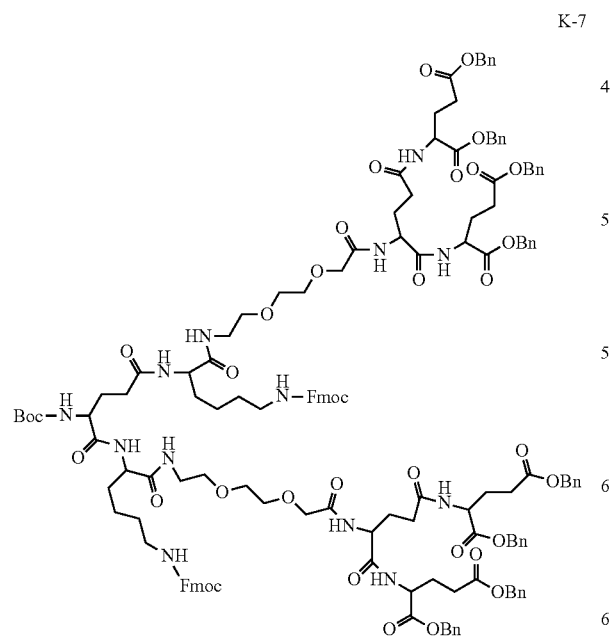

Boc-Glu-(OH)$_2$ (0.39 g, 1.5738 mmol, purchased from InnoChem), 34-17 (4.5 g, 3.3051 mmol), HBTU (1.8 g, 4.7216 mmol) and HOBT (0.6380 g, 4.7216 mmol) were added in a 250 mL round-bottomed flask, and dissolved with DMF (50 mL), and then the mixed solution was stirred at 0° C. for 30 minutes. Then DIEA (2.3 mL, 14.1647 mmol) was slowly added dropwise. At the end of the addition, the obtained solution was stirred to react at 0° C. overnight. At the end of the reaction, the reaction solution was transferred to a 1 L separatory funnel, and extracted with pure water (100 mL) and ethyl acetate (80 mL), and the organic phase was separated. The aqueous phase was extracted with ethyl acetate (80 mL×2), and the obtained organic phases were combined. The organic phase was extracted with saturated sodium chloride solution (150 mL×3), concentrated, evaporated to dryness, and dried, thus obtaining a crude product.

K-8

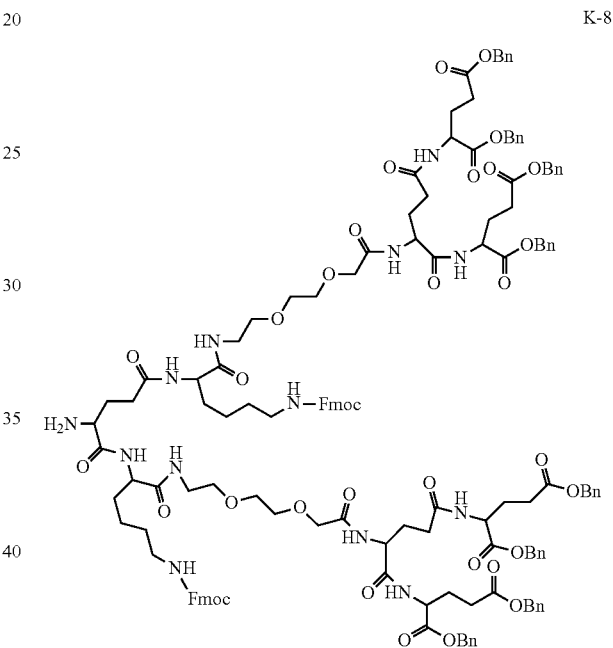

K-7 (1.5738 mmol) was added in a 500 mL flask, and dissolved with dichloromethane (10 mL), TFA (1.7531 mL, 15.738 mmol), and then the mixed solution was stirred to react at room temperature overnight. At the end of the reaction, the reaction solution was evaporated to dryness to obtain an oily product. The oily product was transferred to a 1 L separatory funnel, saturated sodium bicarbonate solution (100 mL) was added to adjust the pH to alkaline, ethyl acetate (80 mL) was then added for extraction, and the organic phase was separated, The aqueous phase was extracted with ethyl acetate (80 mL×2), and the obtained organic phases were combined. The organic phase was extracted with saturated sodium chloride solution (100 mL×3), and concentrated, silica gel powder (20 g) was added, and the obtained mixture was then evaporated to dryness to obtain a powdery solid. The operations of dry sample loading, column chromatography and gradient elution with a dichloromethane mixed solution containing 3%-8% methanol were carried out. The elution product was then collected, concentrated, and dried in a vacuum oven, thus obtaining the product 3.2 g, yield 77%.

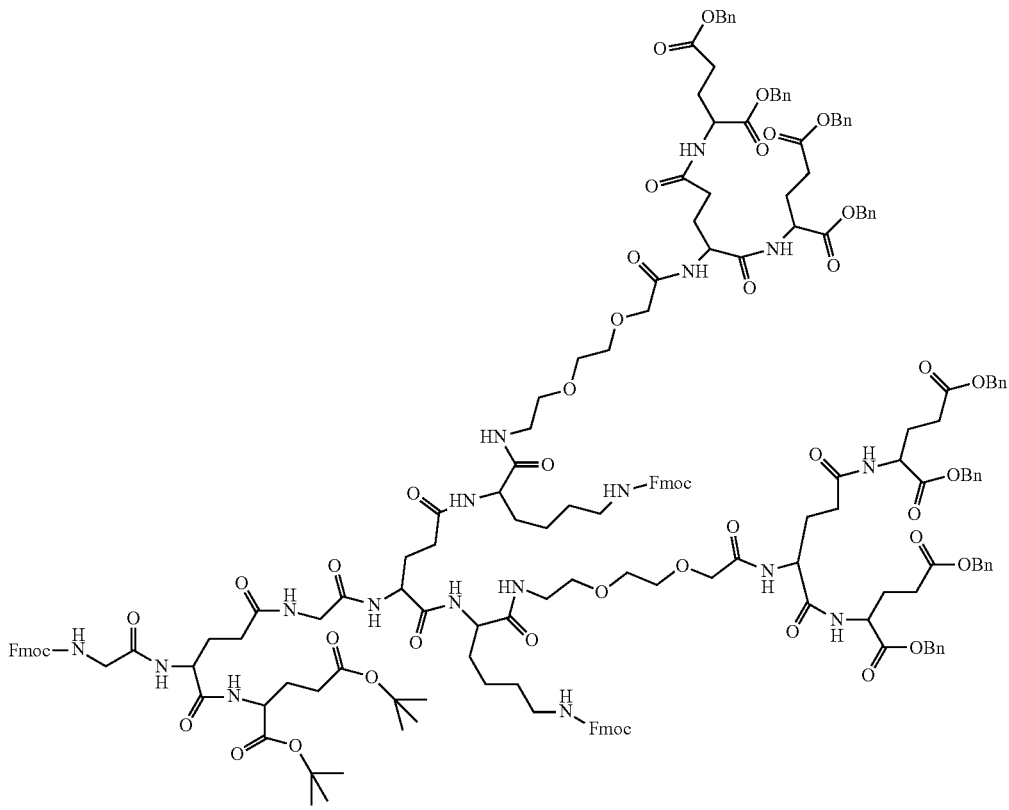

29-210

K-8 (3.0 g, 1.1389 mmol), 29-209 (1.0354 mmol), HBTU (0.5891 g, 1.5531 mmol) and HOBT (0.2099 g, 1.5531 mmol) were added in a 250 mL round-bottomed flask, and dissolved with DMF (50 mL), and then the mixed solution was stirred at 0° C. for 30 minutes. Then DIEA (0.7701 mL, 4.6595 mmol) was slowly added dropwise. At the end of the addition, the obtained solution was stirred to react at 0° C. overnight. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (10 g) was added, and the obtained mixture was then evaporated to dryness to obtain a powdery solid. The operations of dry sample loading, column chromatography and gradient elution with a dichloromethane mixed solution containing 3%-8% methanol were carried out. The elution product was then collected, concentrated, and dried in a vacuum oven, thus obtaining the product 2.7 g, yield 79%.

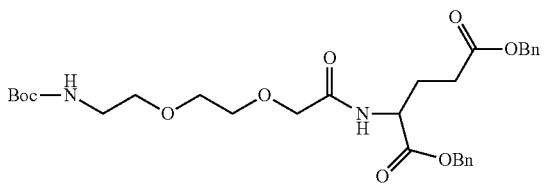

K-10

24-36 (4 g, 15.1924 mmol), H-Glu-(OBn)$_2$ (6.9 g, 13.8112 mmol, purchased from InnoChem), HBTU (7.8567 g, 20.7169 mmol), HOBT (2.8 g, 20.7169 mmol) were added in a 500 mL round-bottomed flask, and dissolved with DMF (70 mL), and then the mixed solution was stirred at −5° C. for 30 minutes. Then DIEA (10.2723 mL, 62.1506 mmol) was slowly added dropwise. At the end of the addition, the obtained solution was stirred at −5° C. for 1 hour, and then moved to room temperature and stirred to react overnight. At the end of the reaction, the reaction solution was transferred to a 1 L separatory funnel, and extracted with saturated sodium bicarbonate solution (100 mL) and ethyl acetate (80 mL), and the organic phase was separated. The aqueous phase was extracted with ethyl acetate (80 mL×2), and the obtained organic phases were combined. The organic phase was extracted with saturated sodium chloride solution (150 mL×3), and concentrated, silica gel powder (20 g) was added, and the obtained mixture was then evaporated to dryness to obtain a powdery solid. The operations of dry sample loading, column chromatography and gradient elution with a dichloromethane mixed solution containing 1%-3% methanol were carried out. The elution product was then collected, concentrated, and dried in a vacuum oven, thus obtaining the product 8.7 g, yield 62%.

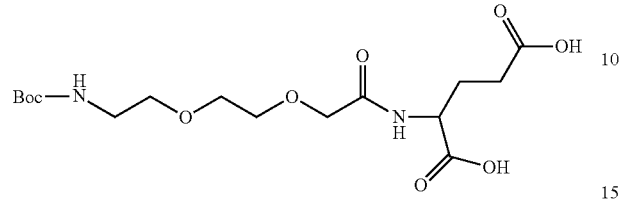

K-11

K-10 (2.7 g, 4.7469 mmol) and 10% Pd/C catalyst (30 mg) were added in a hydrogenation reactor, and dissolved with DMF (30 mL), the hydrogenation reactor was then sealed, hydrogen was introduced so that the pressure on the hydrogenation reactor was read as 18 psi, and then the mixed solution was stirred to react at room temperature overnight. At the end of the reaction, the reaction solution was taken out and evenly added dropwise to a suction funnel filled with compacted diatomaceous earth. The reaction device and diatomaceous earth were washed with DMF (30 mL×3), and the filtrate was collected, thus obtaining the reaction product.

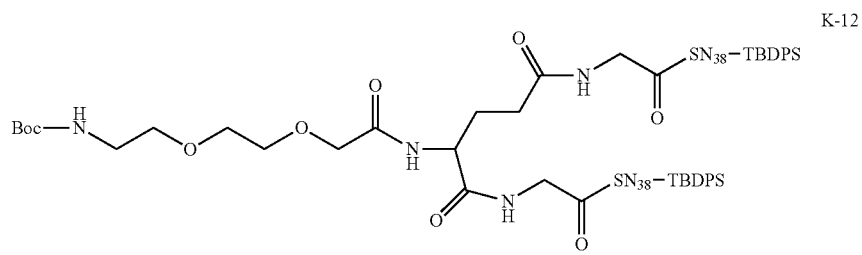

K-12

K-11 (2.1484 mmol), G-SN38-TBDPS (synthesized according to the method of synthesizing 25-200, 3.0 g, 4.3614 mmol), HBTU (2.4443 g, 6.4453 mmol) and HOBT (0.8710 g, 6.4453 mmol) were added in a 500 mL round-bottomed flask, and dissolved with DMF (50 mL), and then the mixed solution was stirred to react at −5° C. for 30 minutes. Then DIEA (3.1959 mL, 19.3360 mmol) was slowly added dropwise. At the end of the addition, the obtained solution was stirred at −5° C. for 1 hour, and then moved to room temperature and stirred to react overnight. At the end of the reaction, methyl tert-butyl ether (80 mL) was added to the reaction solution, the reaction flask was placed in a refrigerator and taken out after 30 minutes, a solid was separated out, and suction filtering was carried out. The filter cake was washed with methyl tert-butyl ether (30 mL×3), the washed filter cakes were collected and dried, thus obtaining a crude product.

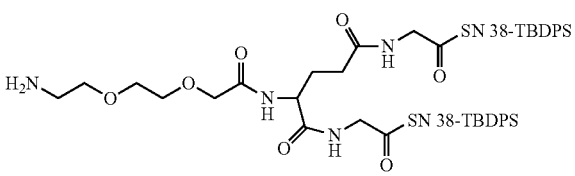

K-13

K-12 (2.1484 mmol) was added in a 500 mL flask, and dissolved with dichloromethane (5 mL), and TFA (2.3932 mL, 32.226 mmol), and then the obtained solution was stirred to react at room temperature overnight. At the end of the reaction, the reaction solution was evaporated to dryness to obtain an oily product, methyl tert-butyl ether (60 mL) was added to the oily product to separate out a solid, and suction filtering was carried out. The filter cake was washed with methyl tert-butyl ether (30 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 3%-8% methanol were carried out. The elution product was then collected, concentrated, and dried in a vacuum oven, thus obtaining the product 2.7 g, yield 72%.

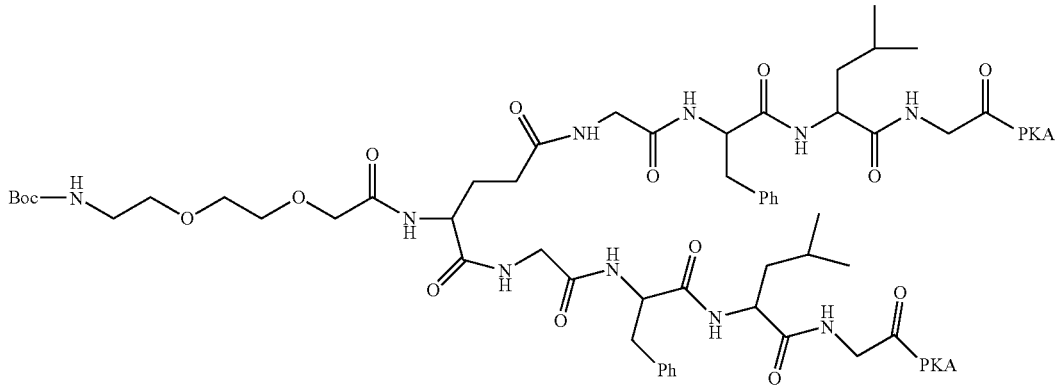

K-14

K-11 (2.5985 mmol), 42-18 (6.0 g, 6.2363 mmol), HBTU (2.9563 g, 7.7953 mmol) and HOBT (1.0534 g, 7.7953 mmol) were added in a 500 mL round-bottomed flask, and dissolved with DMF (50 mL), and then the mixed solution was stirred at −5° C. for 30 minutes. Then DIEA (3.8653 mL, 23.360 mmol) was slowly added dropwise. At the end of the addition, the obtained solution was stirred at −5° C. for 1 hour, and then moved to room temperature and stirred to react overnight. At the end of the reaction, methyl tert-butyl ether (80 mL) was added to the reaction solution, the reaction flask was placed in a refrigerator and taken out after 30 minutes, a solid was separated out, and suction filtering was carried out. The filter cake was washed with methyl tert-butyl ether (30 mL×3), the washed filter cakes were collected and dried, thus obtaining a crude product.

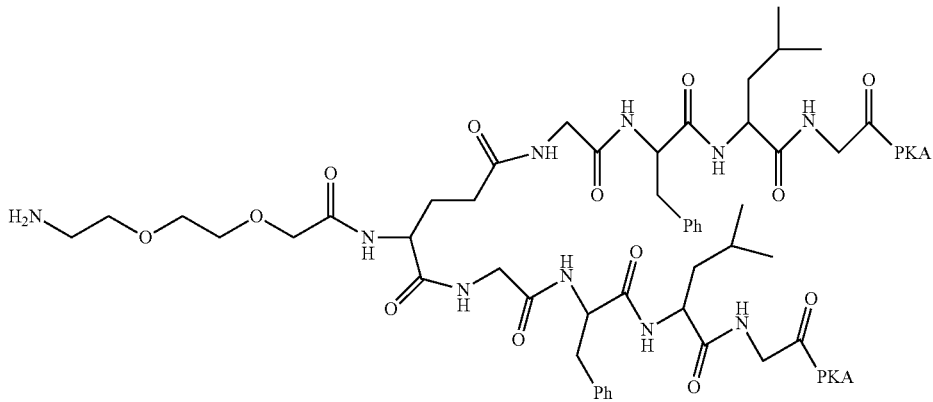

K-15

K-14 (2.5985 mmol) was added in a 500 mL flask, and dissolved with dichloromethane (5 mL), and TFA (2.8946 mL, 38.9775 mmol), and then the mixed solution was stirred to react at room temperature overnight. At the end of the reaction, the reaction solution was evaporated to dryness to obtain an oily product, methyl tert-butyl ether (60 mL) was added to the oily product to separate out a solid, and suction filtering was carried out. The filter cake was washed with methyl tert-butyl ether (30 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 1% ammonia water and 3%-8% methanol were carried out. The elution product was then collected, concentrated, and dried in a vacuum oven, thus obtaining the product 3.3 g, yield 61%.

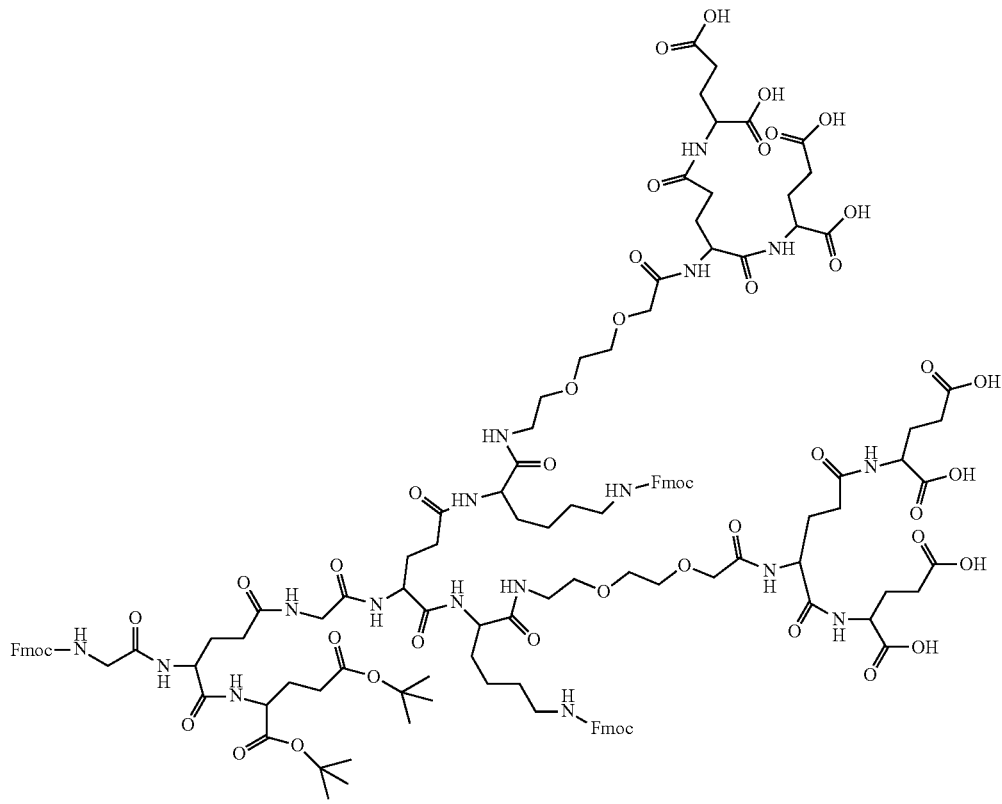

29-212

29-210 (0.6579 g, 0.1972 mmol) and 10% Pd/C catalyst (30 mg) were added in a hydrogenation reactor, and dissolved with DMF (30 mL), the hydrogenation reactor was then sealed, hydrogen was introduced so that the pressure on the hydrogenation reactor was read as 18 psi, and then the mixed solution was stirred to react at room temperature overnight. At the end of the reaction, the reaction solution was taken out and evenly added dropwise to a suction funnel filled with compacted diatomaceous earth. The reaction device and diatomaceous earth were washed with DMF (30 mL×3), and the filtrate was collected, thus obtaining the reaction product.

29-213

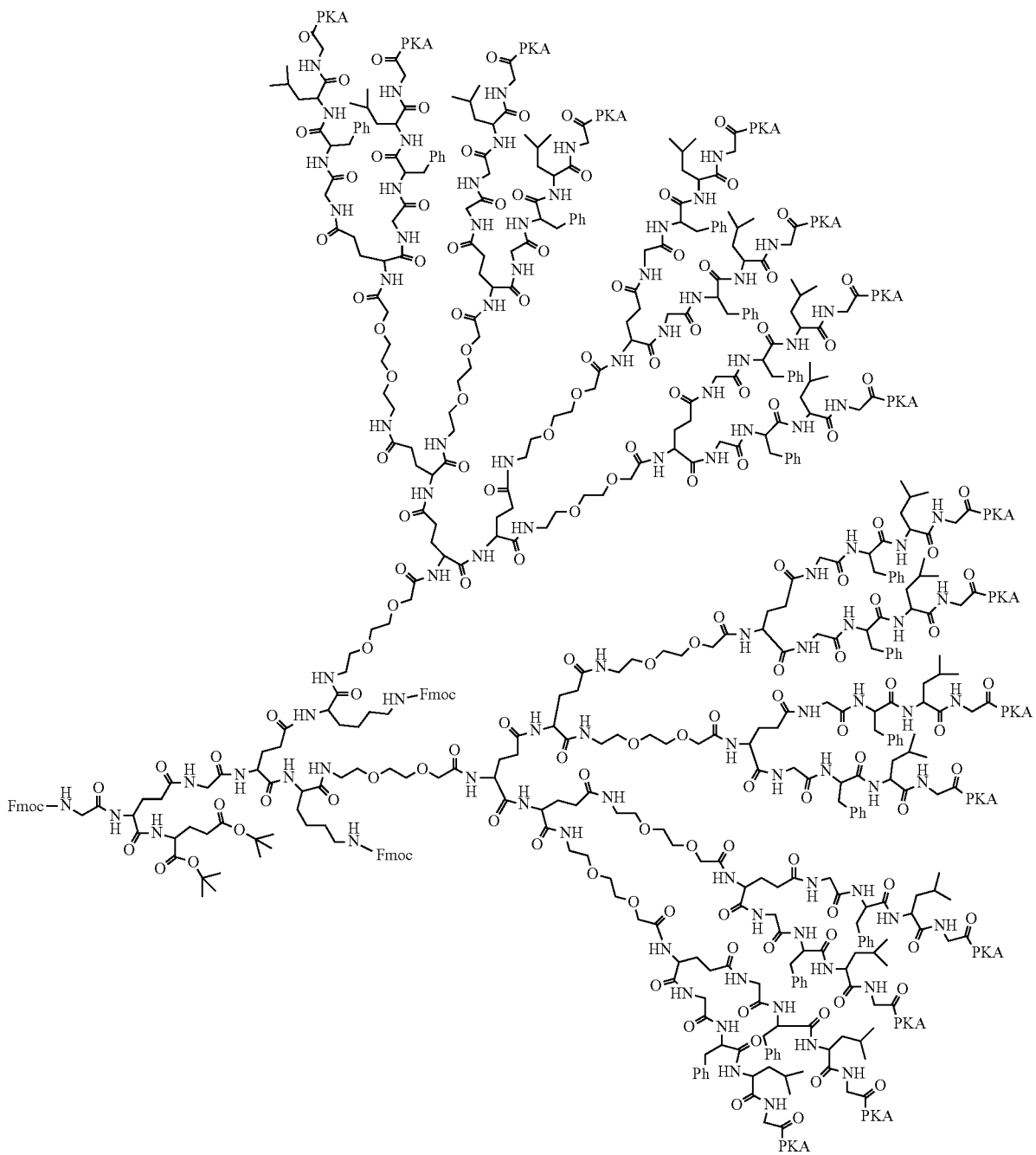

K-15 (3.3 g, 1.6566 mmol), 29-212 (0.5391 g, 0.1972 mmol), HBTU (0.8975 g, 2.3667 mmol) and HOBT (0.3198 g, 2.3667 mmol) were added in a 500 mL round-bottomed flask, and dissolved with DMF (50 mL), and then the mixed solution was stirred at 0° C. for 30 minutes. Then DIEA (1.1735 mL, 7.1 mmol) was slowly added dropwise. At the end of the addition, the obtained solution was stirred to react at 0° C. overnight. At the end of the reaction, methyl tert-butyl ether (80 mL) was added to the reaction solution, the reaction flask was placed in a refrigerator and taken out after 30 minutes, a solid was separated out, and suction filtering was carried out. The filter cake was washed with methyl tert-butyl ether (30 mL×3), the washed filter cakes were collected and dried, thus obtaining a crude product.

29-214

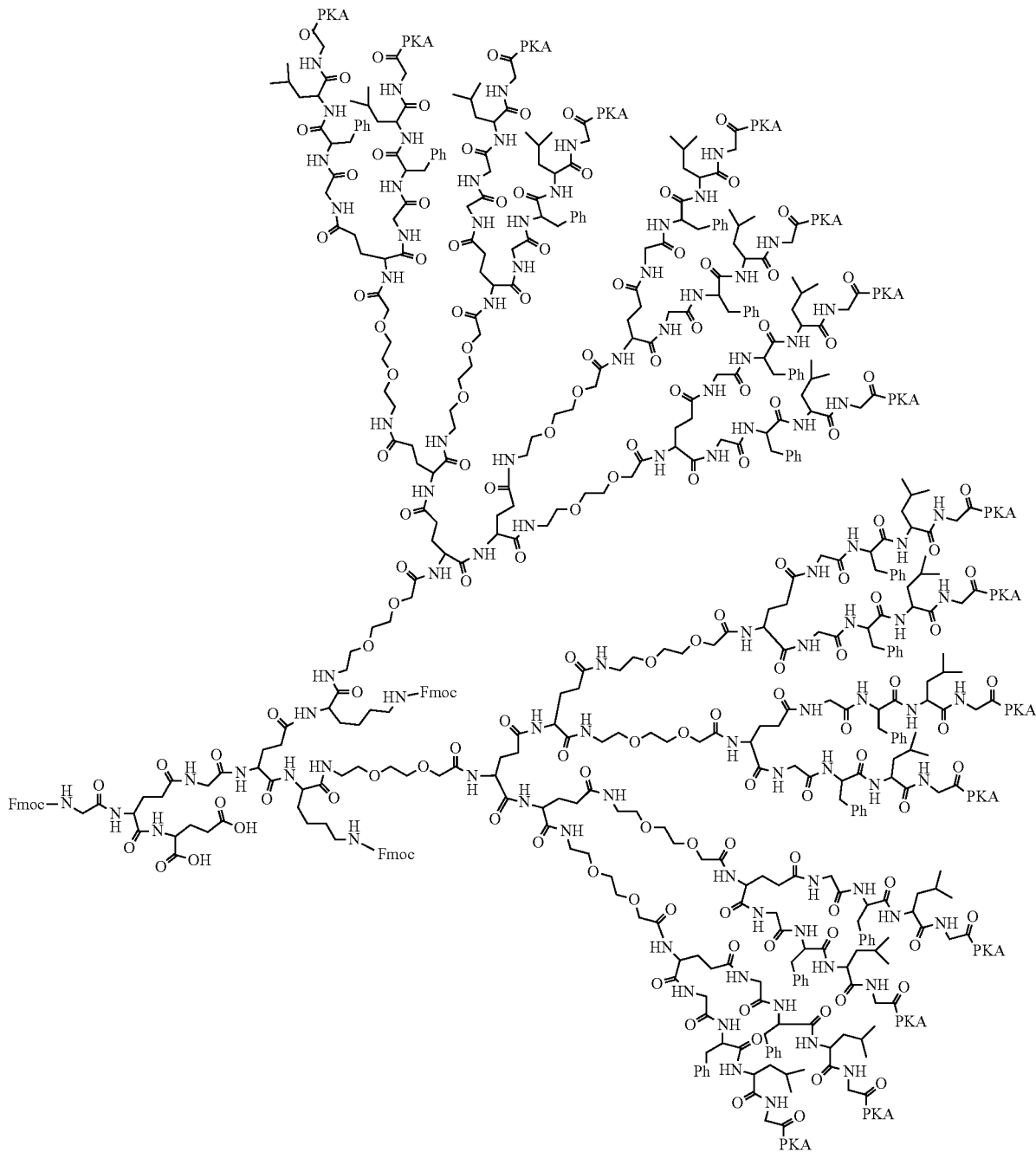

29-213 (0.1972 mmol) was added in a 500 mL flask, and dissolved with dichloromethane (5 mL), and TFA (0.22 mL, 2.958 mmol), and then the mixed solution was stirred to react at room temperature overnight. At the end of the reaction, the reaction solution was evaporated to dryness to obtain an oily product, methyl tert-butyl ether (60 mL) was added to the oily product to separate out a solid, and suction filtering was carried out. The filter cake was washed with methyl tert-butyl ether (30 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 3%-9% methanol were carried out. The elution product was then collected, concentrated, and dried in a vacuum oven, thus obtaining the product 2.7 g, yield 69%.

29-216

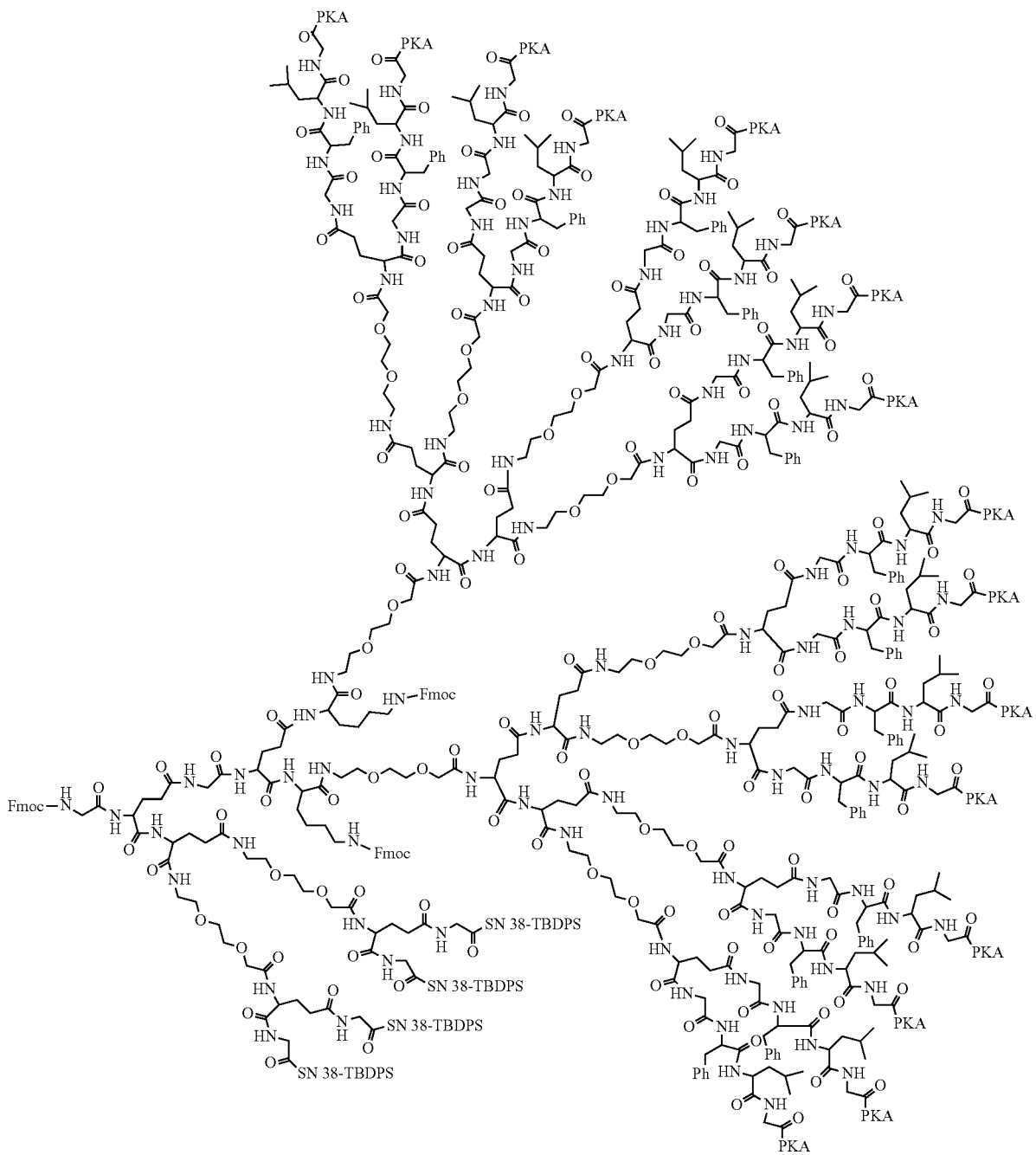

29-214 (2.7 g, 0.1405 mmol), K-13 (0.5117 g, 0.2951 mmol), HBTU (0.1599 g, 0.4215 mmol), HOBT (0.057 g, 0.4215 mmol) were added in a 500 mL round-bottomed flask, and dissolved with DMF, and then the mixed solution was stirred at 0° C. for 30 minutes. DIEA (0.2090 g, 1.2645 mmol) was then added, and the obtained solution continued to react at 0° C. with stirring overnight. At the end of the reaction, methyl tert-butyl ether (80 mL) was added, the reaction flask was placed in a refrigerator and taken out after 30 minutes, a solid was separated out, and suction filtering was carried out. The filter cake was washed with methyl tert-butyl ether (30 mL×3), the washed filter cakes were collected and dried, thus obtaining a crude product.

29-220

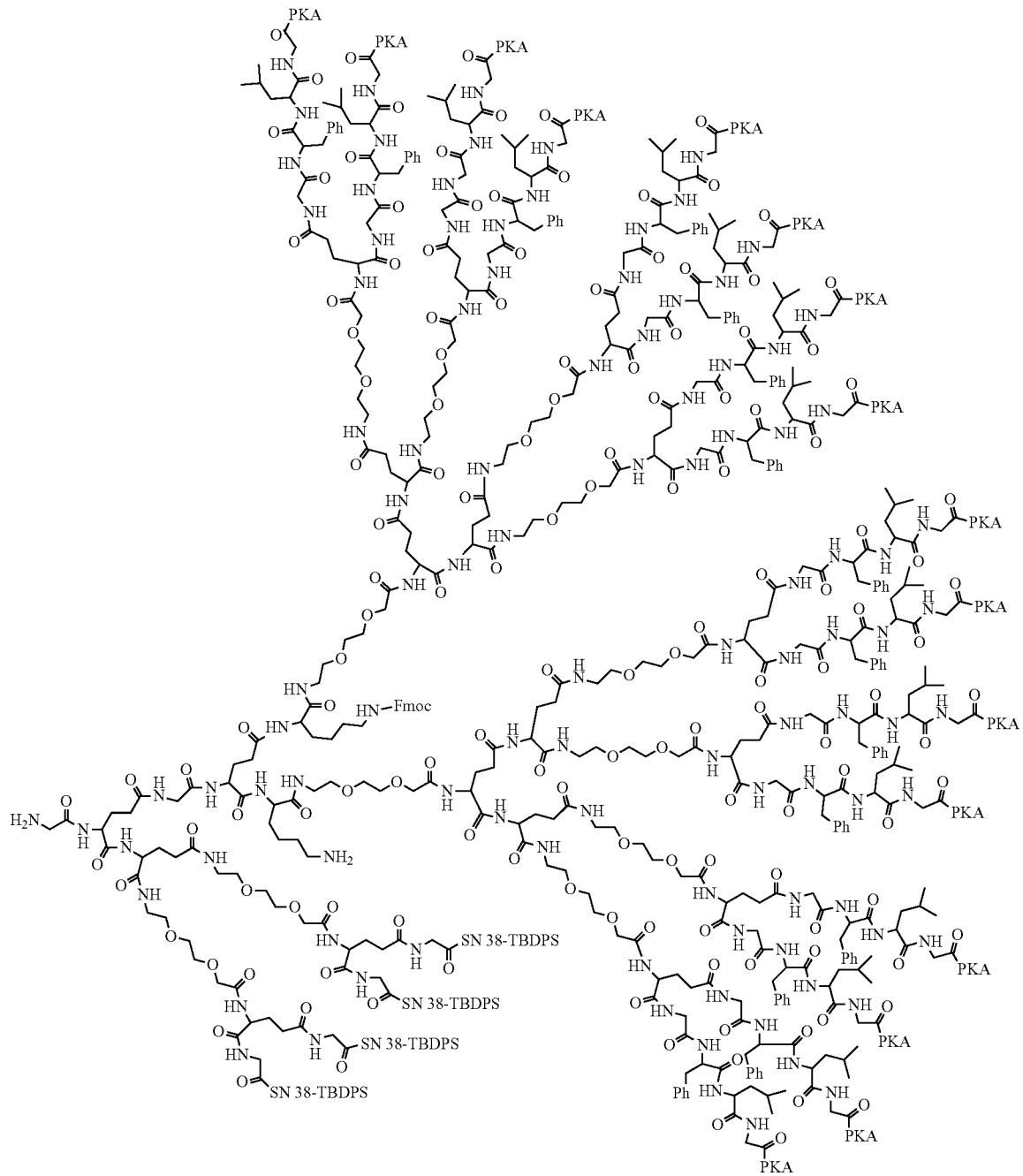

29-216 (0.1405 mmol) was added in a 250 mL flask, and dissolved with DMF (8 mL), morpholine (0.3378 mL, 3.8778 mmol) was added, and then the mixed solution was stirred to react at room temperature for 1 hour. At the end of the reaction, the reaction solution was shaken with n-hexane (100 mL), and the supernatant was discarded. The above operations were repeated three times. Methyl tert-butyl ether (80 mL) and a small amount of n-hexane (10 mL) were then added, the obtained solution was shaken, and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, dissolved with methanol/dichloromethane (1:4) solution (10 mL), and the obtained solution was precipitated with methyl tert-butyl ether. Such operations were repeated three times, thus obtaining a crude product.

29-221

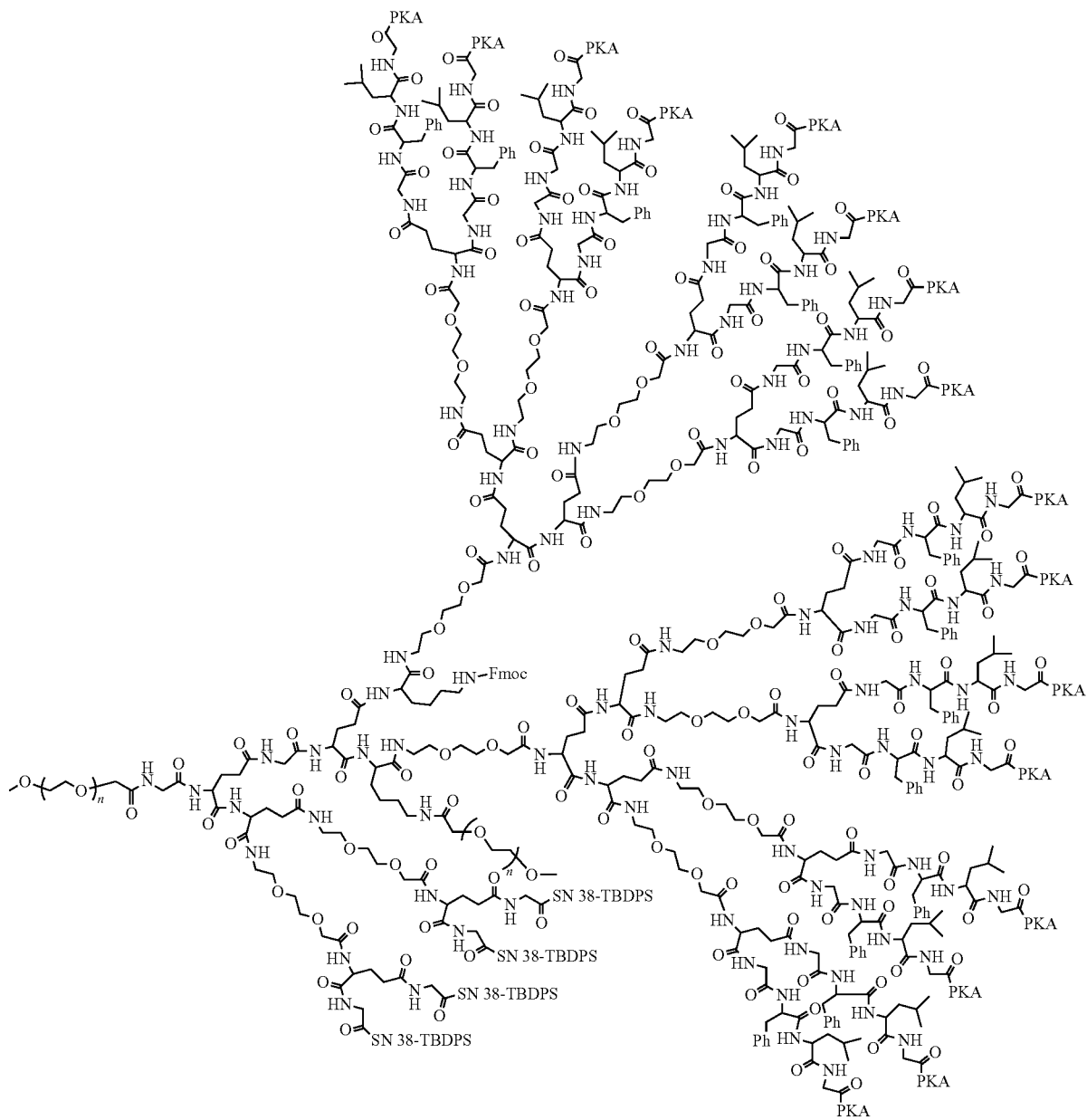

M-SCM-5K (0.8773 g, 0.1667 mmol, purchased from JenKem) was added in a 250 mL round-bottomed flask, and dissolved with DMF (20 mL). Then, DIEA (0.3443 mL, 2.0833 mmol) was added, the obtained solution was stirred at 0° C. for 10 minutes, then the DMF (20 mL) solution of 29-220 (1.0 g, 0.0416 mmol) was slowly added dropwise with a drop funnel over about 2 hours. At the end of the addition, the obtained solution was stirred at 0° C. for 15 minutes, and then moved to room temperature and stirred to react in the dark for one week at a low speed. At the end of the reaction, methyl tert-butyl ether (80 mL) was added to the reaction solution, the reaction flask was placed in a refrigerator and taken out after 30 minutes, a solid was separated out, and suction filtering was carried out. The filter cake was washed with methyl tert-butyl ether (30 mL×3), the washed filter cakes were collected, and dissolved with a mixed solvent (100 mL) of methanol/dichloromethane (1:4), silica gel powder (10 g) was added, and the obtained mixture was then evaporated to dryness to obtain a powdery solid. The operations of dry sample loading, column chromatography and gradient elution with a dichloromethane mixed solution containing 4%-15% methanol were carried out. The elution product was then collected, concentrated, and dried in a vacuum oven, thus obtaining the product 1.6 g, yield 58%.

$^1$H-NMR (600 MHz, DMSO-$d_6$) δ 9.27-9.02 (m, 62H), 8.36-7.95 (m, 171H), 7.77-7.51 (m, 115H), 7.34-7.12 (m, 157H), 6.69-6.65 (m, 13H), 4.57-4.50 (m, 34H), 4.31-4.17 (m, 71H), 3.91-3.80 (m, 207H), 3.55-3.45 (m, 1430H), 3.26-3.20 (m, 12H), 3.12-3.05 (m, 71H), 2.93-2.88 (m, 12H), 2.81-2.65 (m, 50H), 2.25-2.19 (m, 61H), 1.89-1.19 (m, 298H), 0.85-0.79 (m, 96H).

29-226

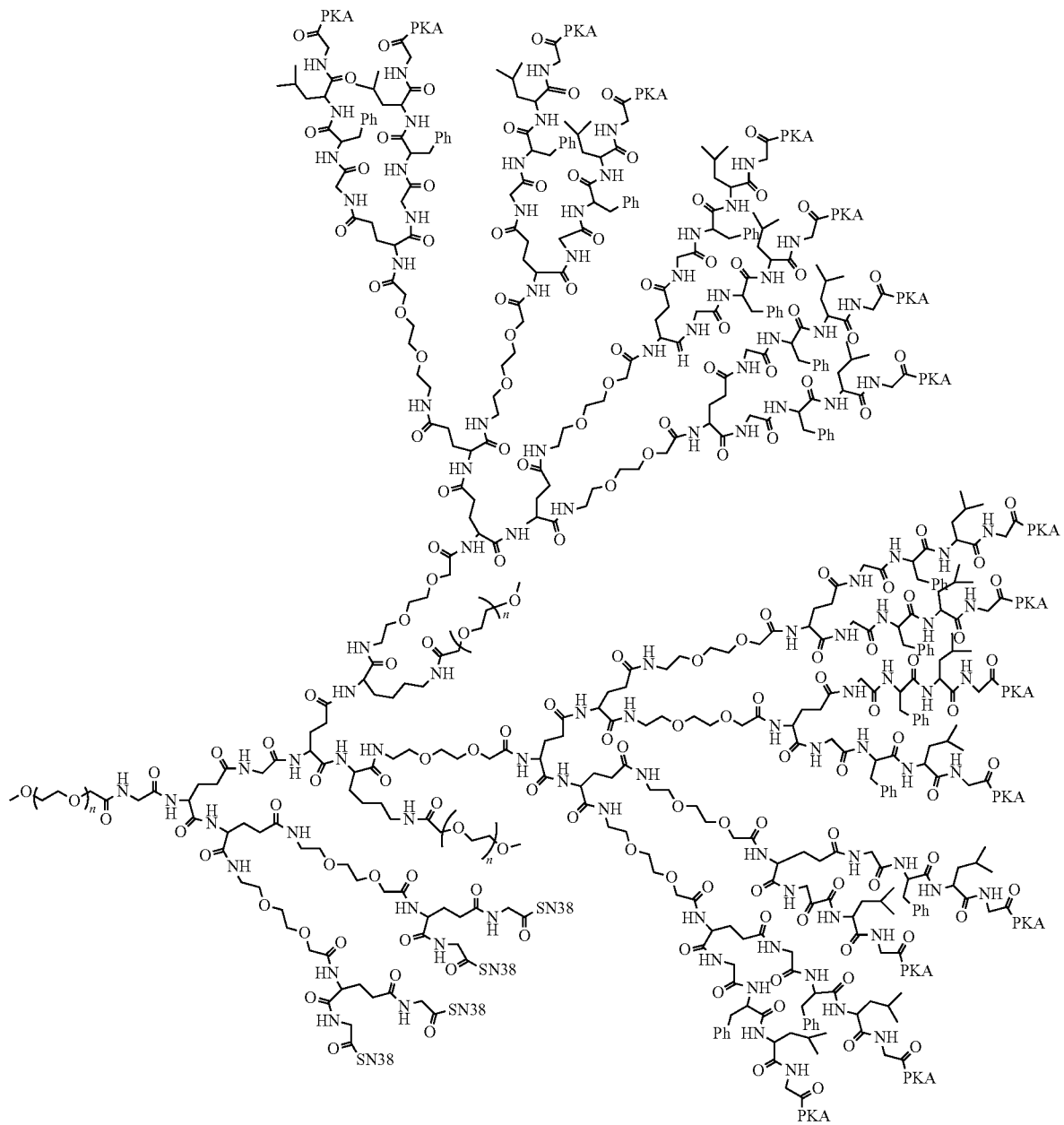

29-221 in a 250 mL flask was dissolved first with THF (10 mL), and then with diluted hydrochloric acid (10 mL, 0.05 mol/L), TBAF (67 mg, 0.256 mmol) was added, and then the obtained solution was stirred to react at room temperature for 3 hours. At the end of the reaction, the reaction solution was first evaporated to obtain an oily product, then anhydrous ethanol was added to the oily product to remove water, and the obtained solution was evaporated to dryness. Such operations were repeated three times, and a solid product was obtained. The solid product was dissolved with DMF (20 mL), and then precipitated with isopropanol (30 mL). Such operations were repeated three times. The obtained solid product was dissolved with dichloromethane and a small amount of anhydrous ethanol, and then precipitated with methyl tert-butyl ether. Such operations were repeated three times. The precipitate was dried, thus obtaining the product 1.1 g, yield 72%

$^1$H-NMR (600 MHz, DMSO-$d_6$) δ 9.06-9.00 (m, 40H), 8.29-8.22 (m, 50H), 8.15-7.95 (m, 96H), 7.73-7.47 (m, 121H), 7.29-7.08 (m, 170H), 4.59-4.11 (m, 99H), 3.95-3.73 (m, 240H), 3.53-3.48 (m, 1434.3H), 3.24-3.00 (m, 110H), 2.92-2.87 (m, 9H), 2.80-5.65 (m, 45H), 2.14-2.08 (m, 45H), 1.91-1.28 (m, 244H), 0.85-0.81 (m, 96H)

17. Synthesis of 27-253 (Compound No. 9)

Synthetic route is as follows

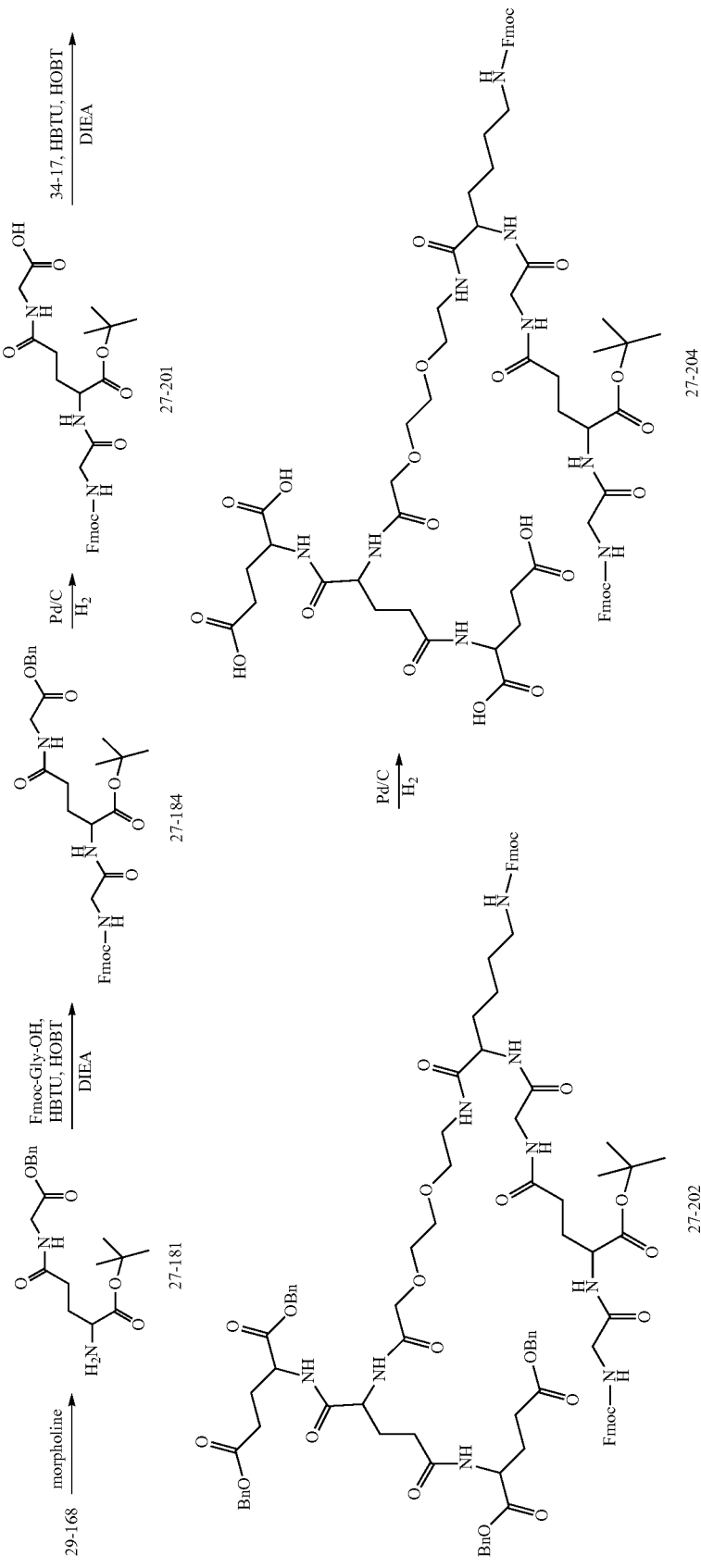

-continued
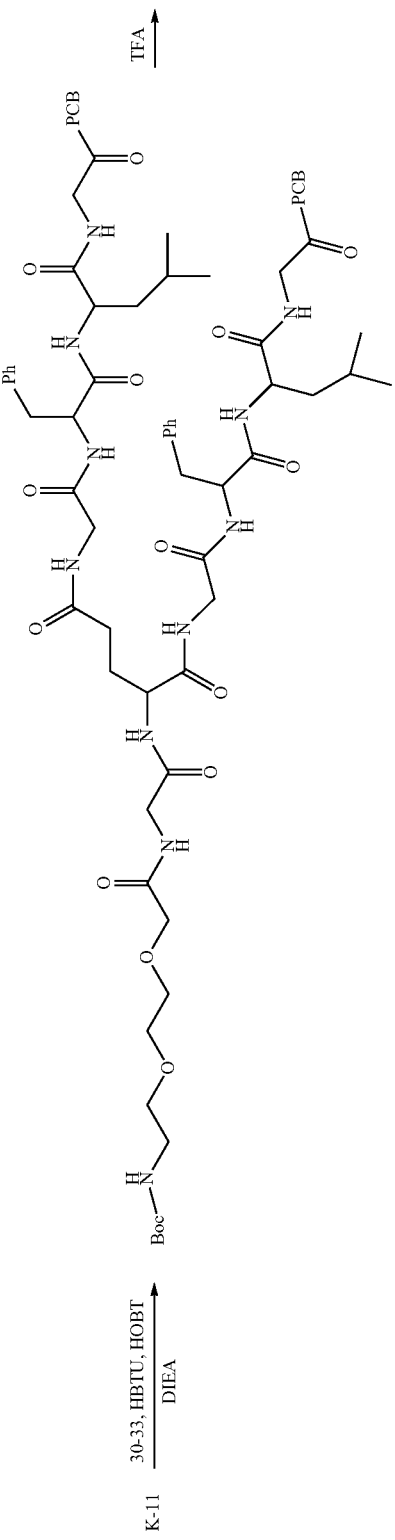
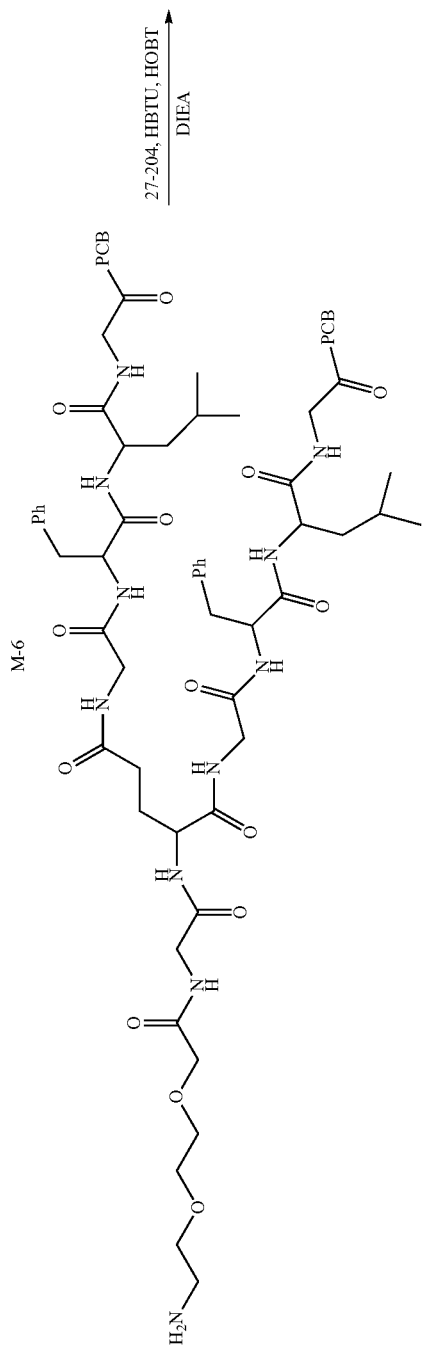

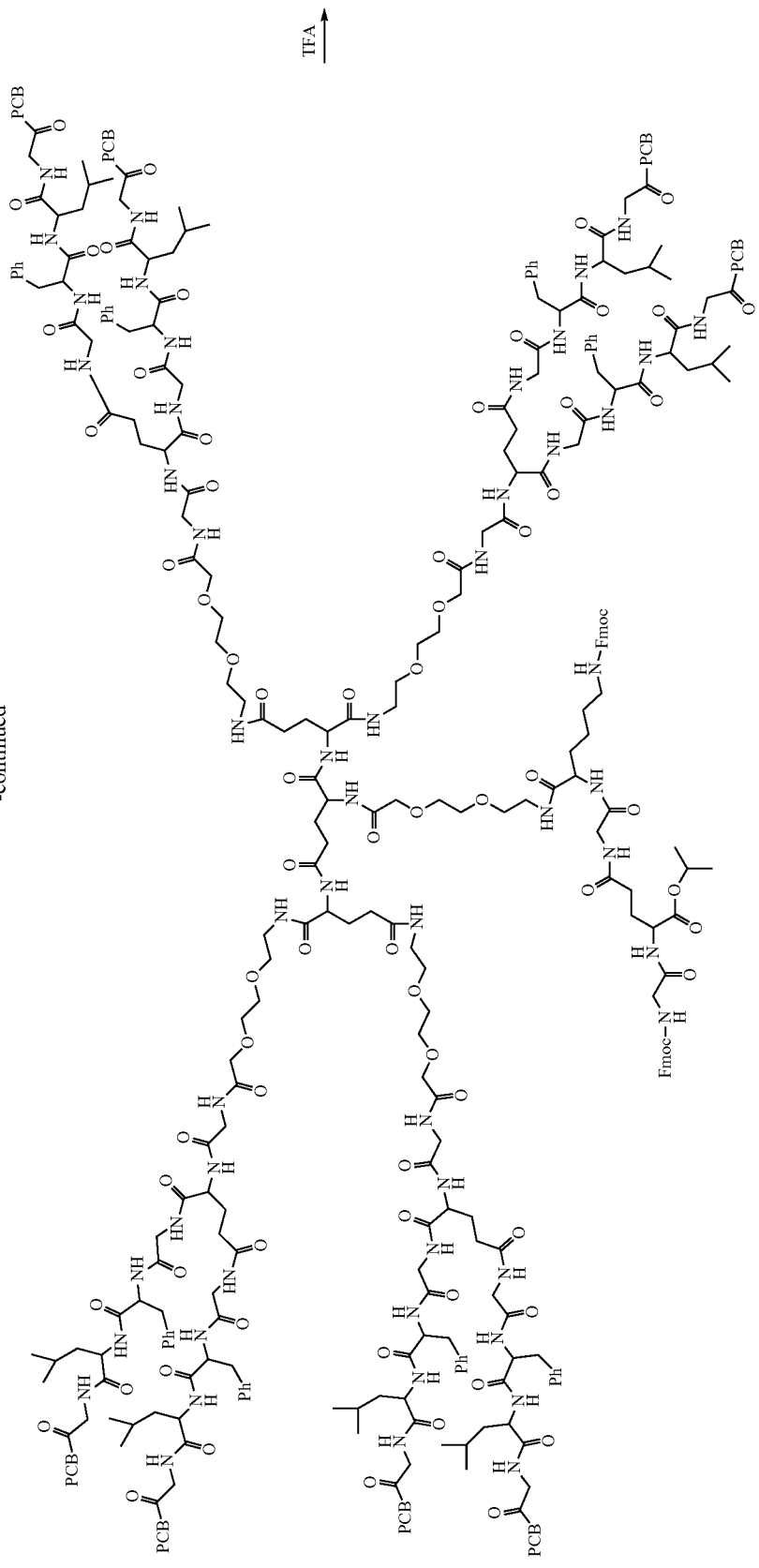

-continued
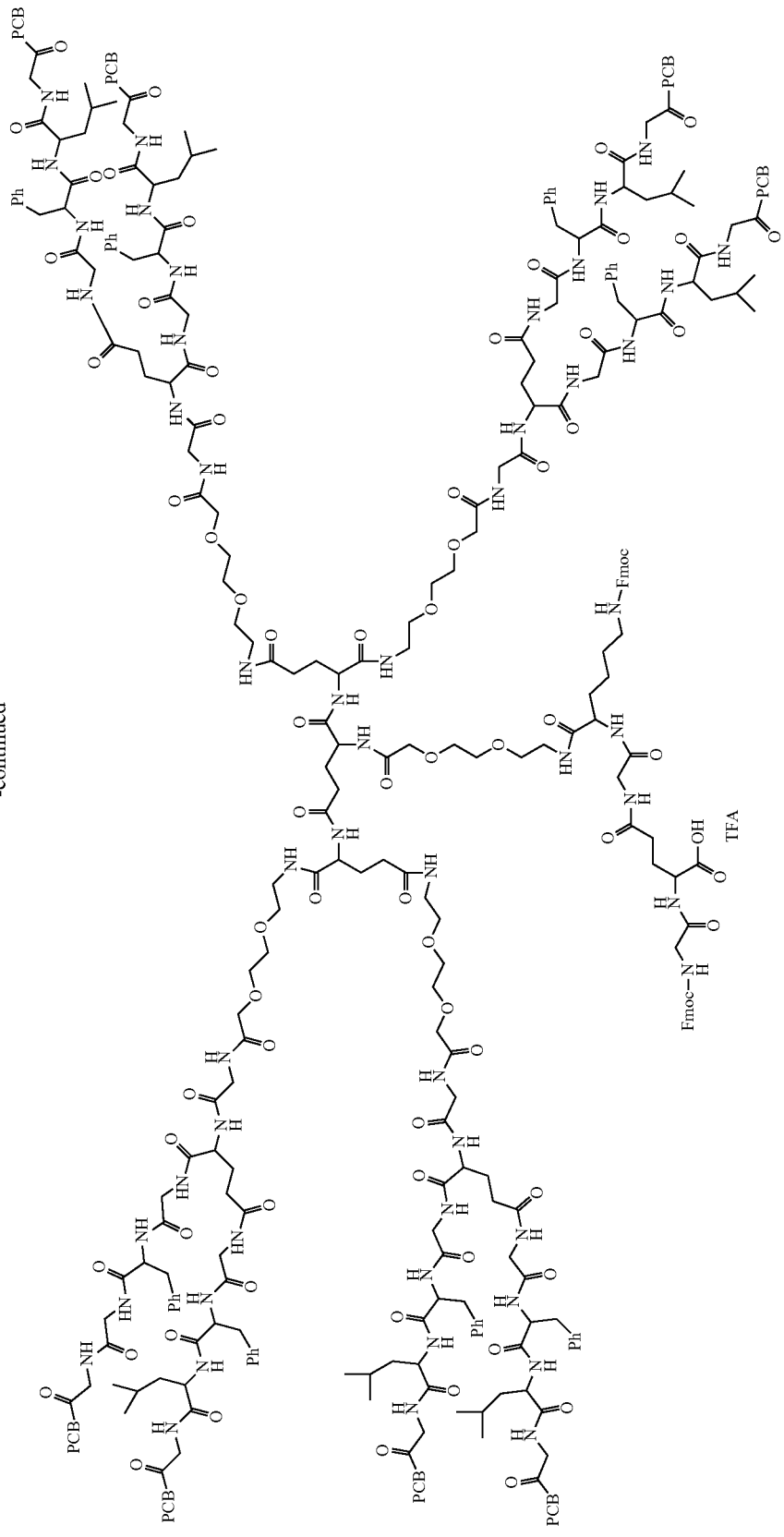
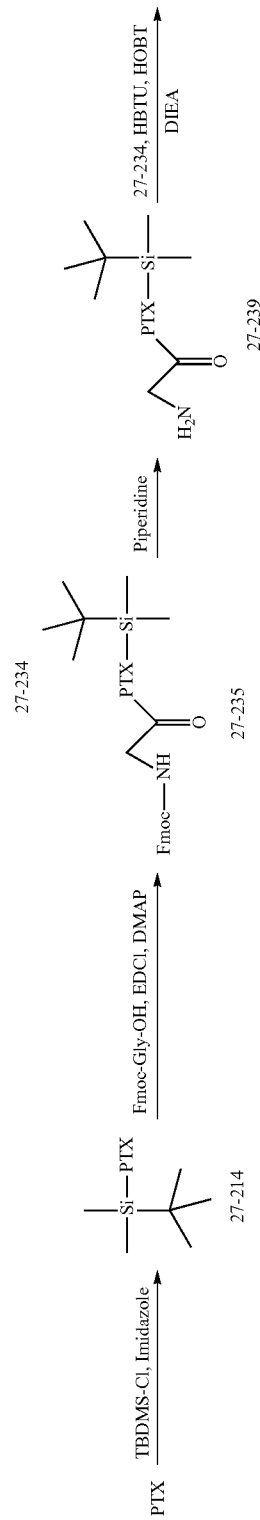

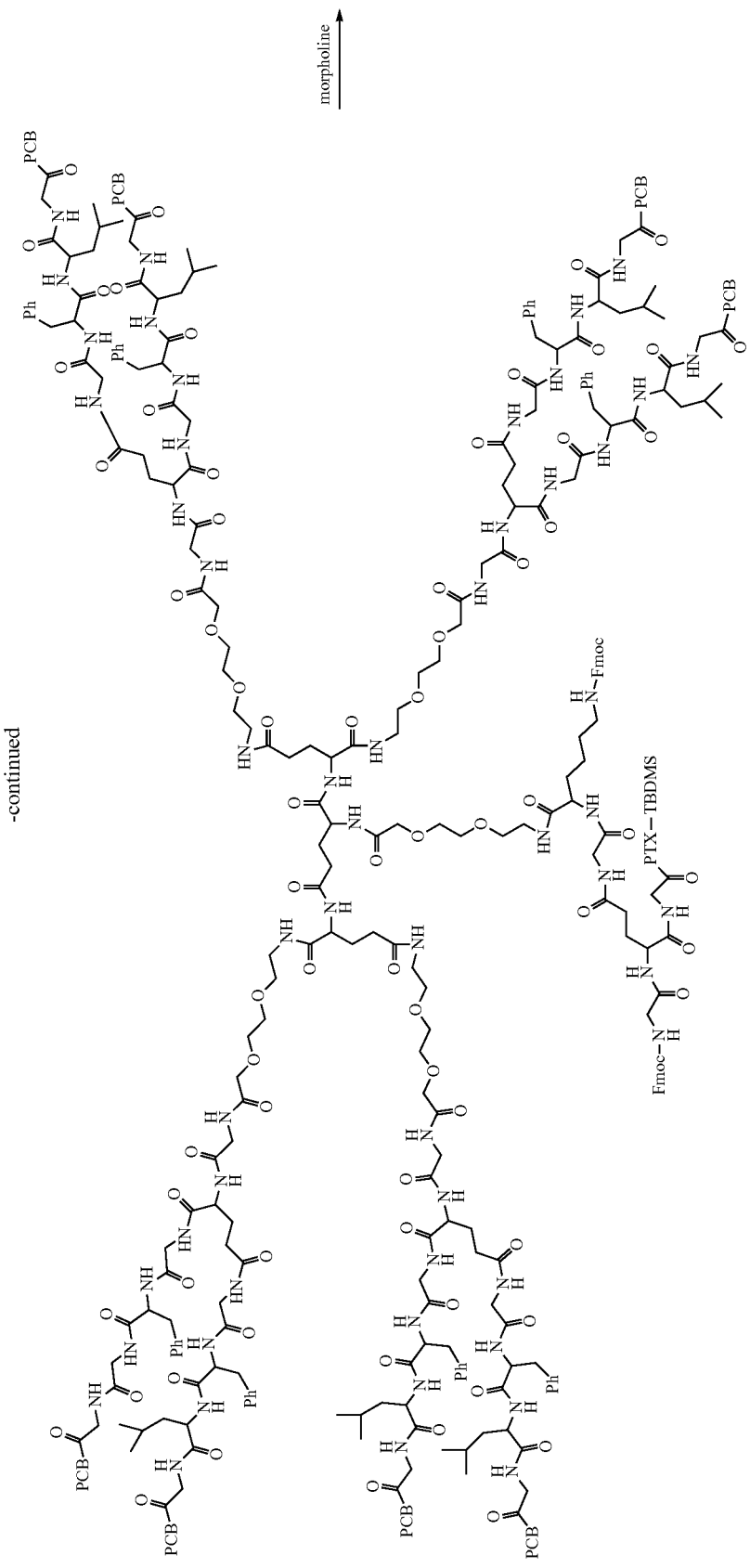

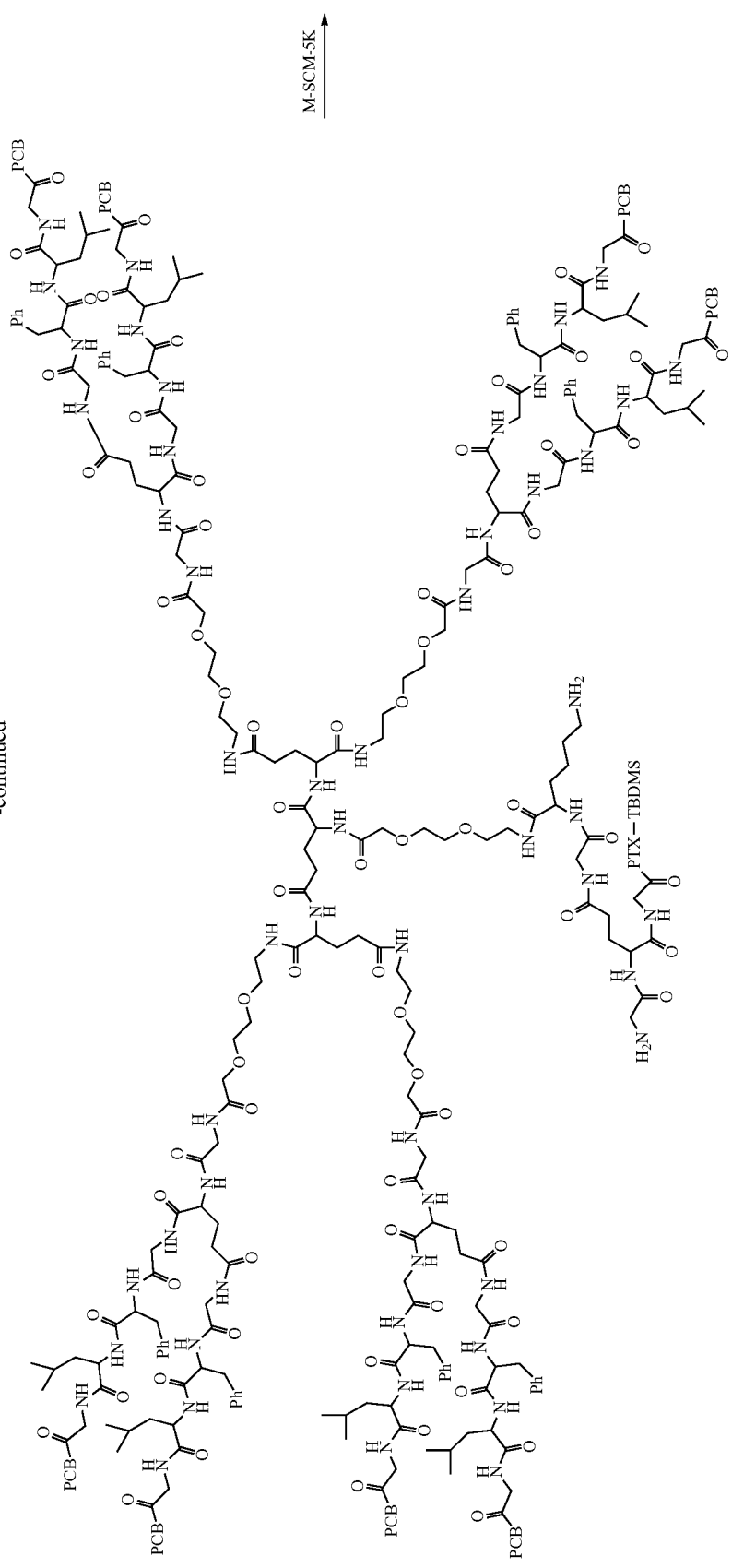
27-243

-continued
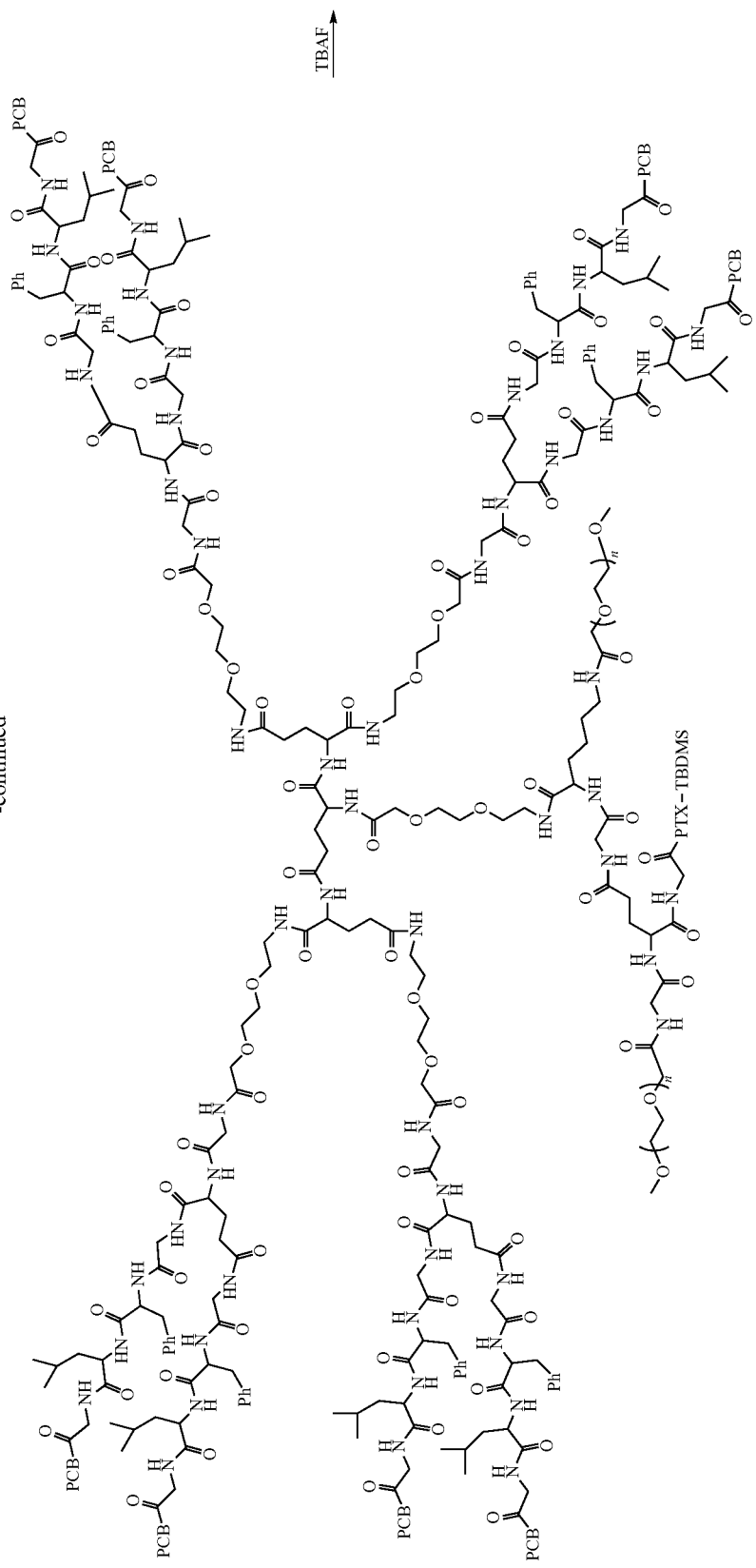
27-247

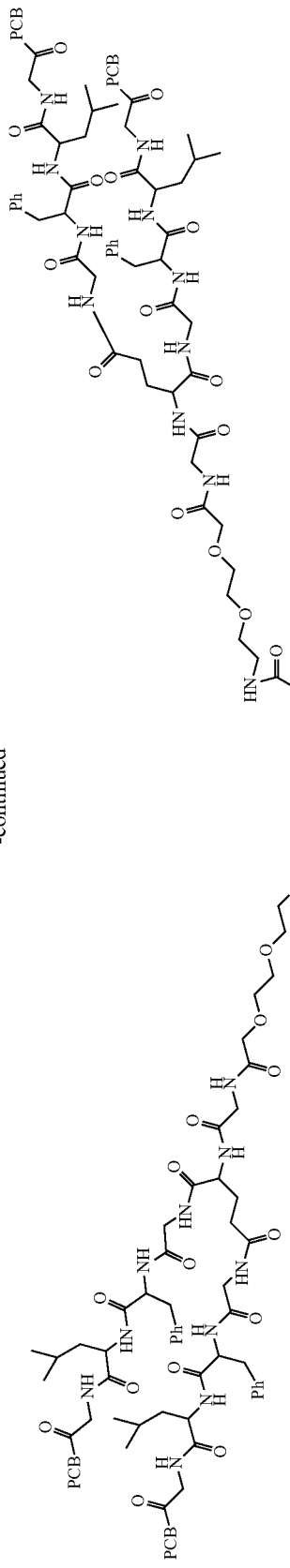
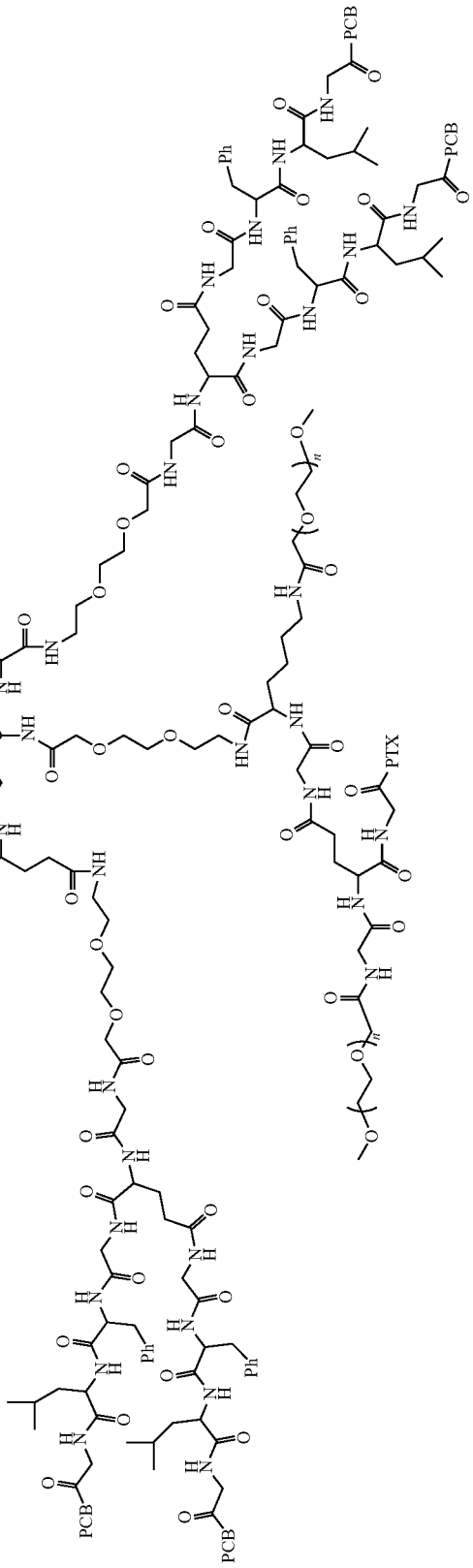
27-253

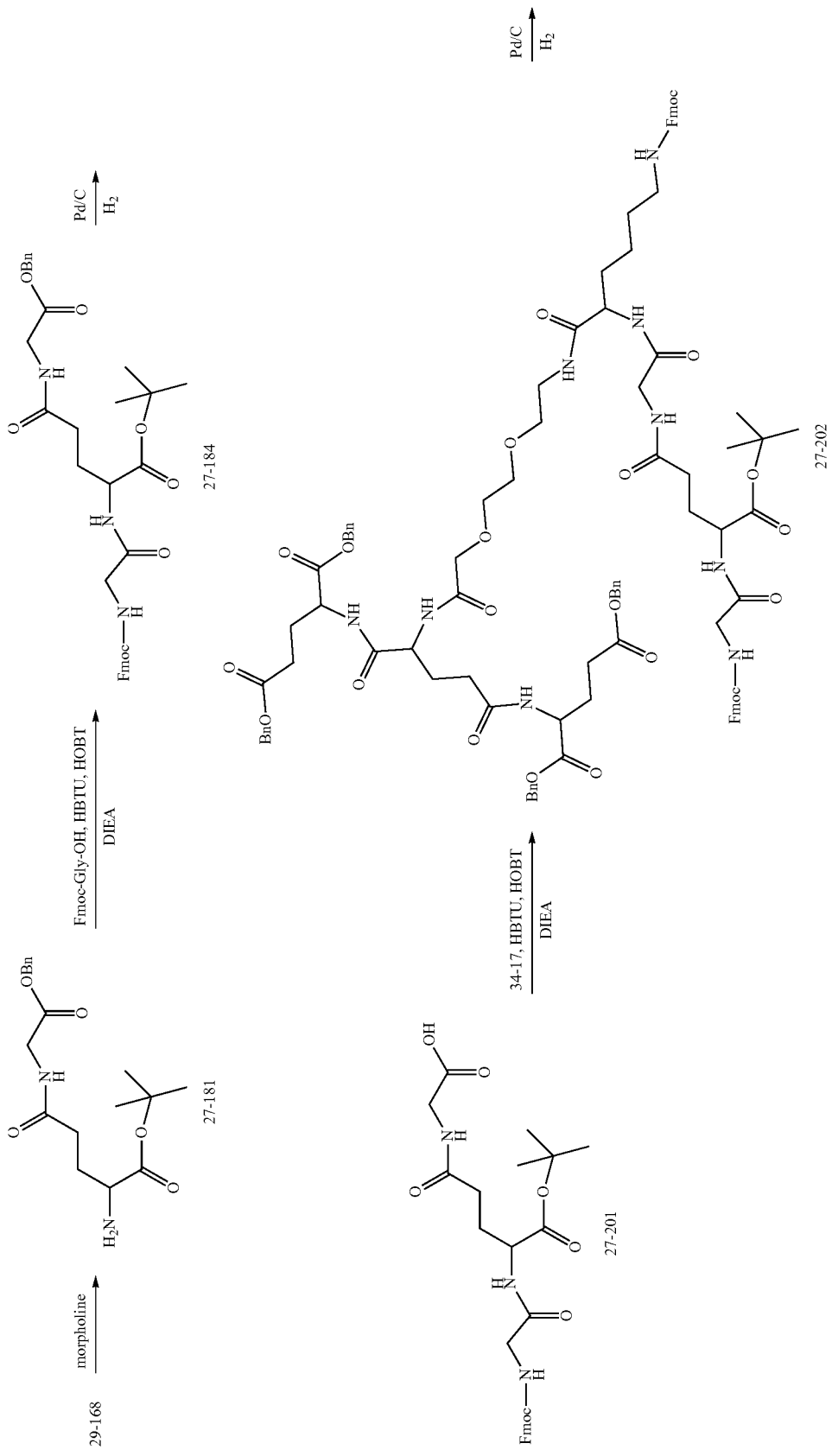

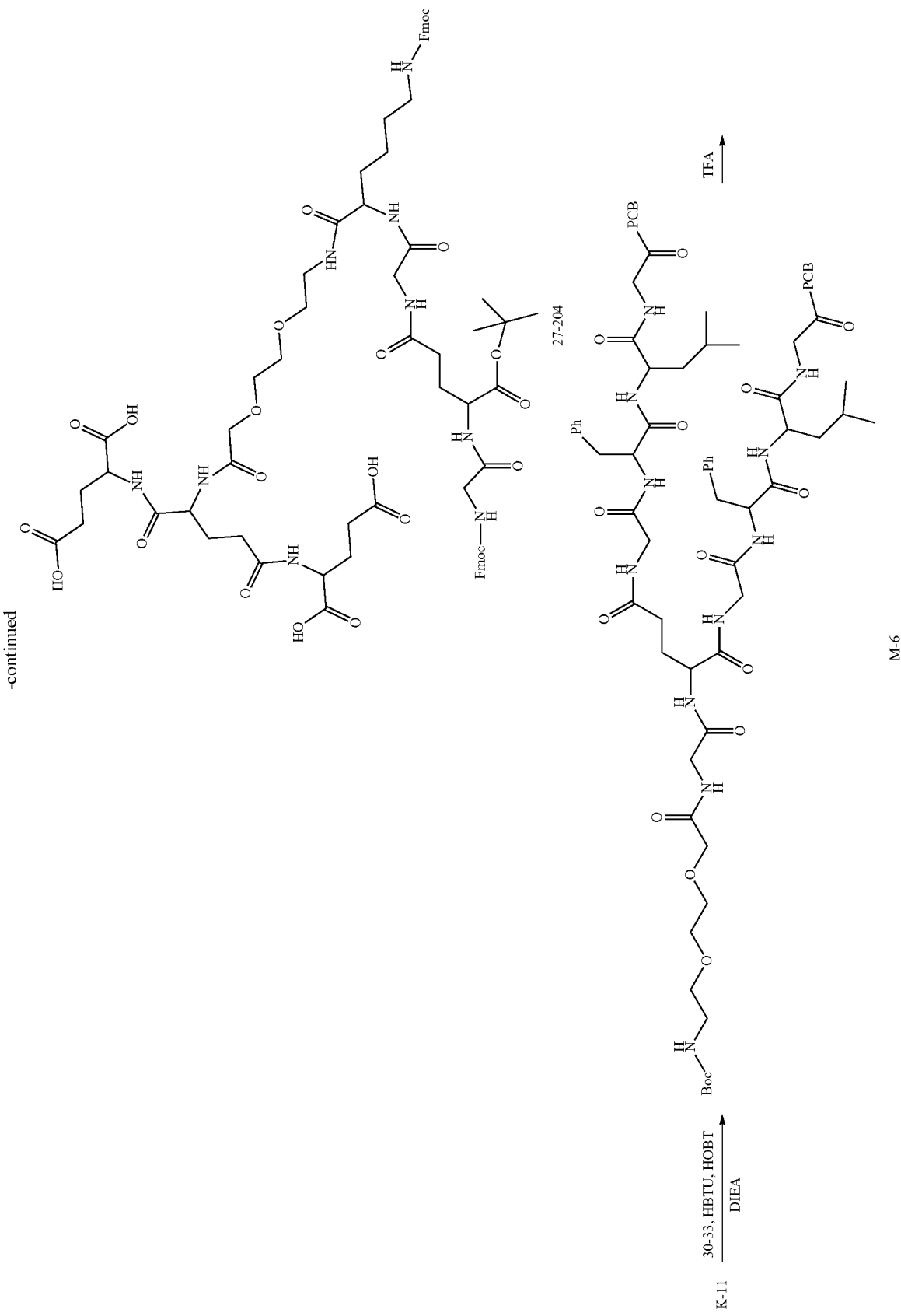

-continued
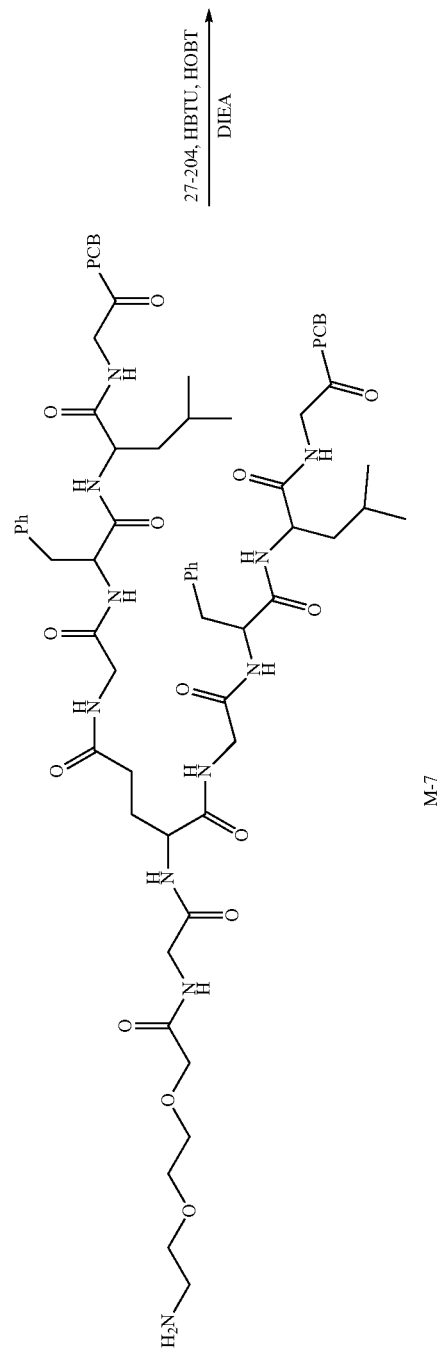
M-7
$\xrightarrow{\text{27-204, HBTU, HOBT}}_{\text{DIEA}}$

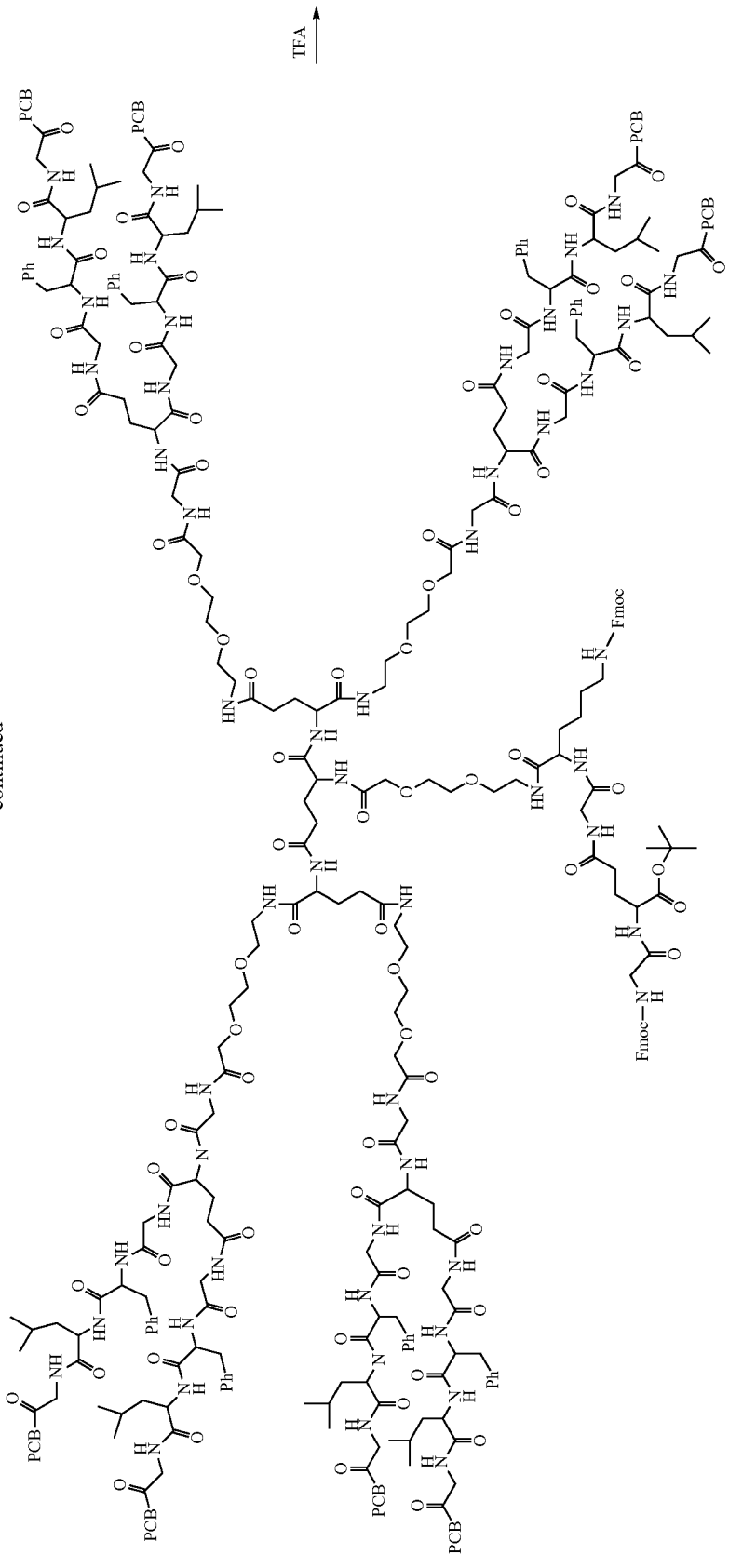
-continued

901
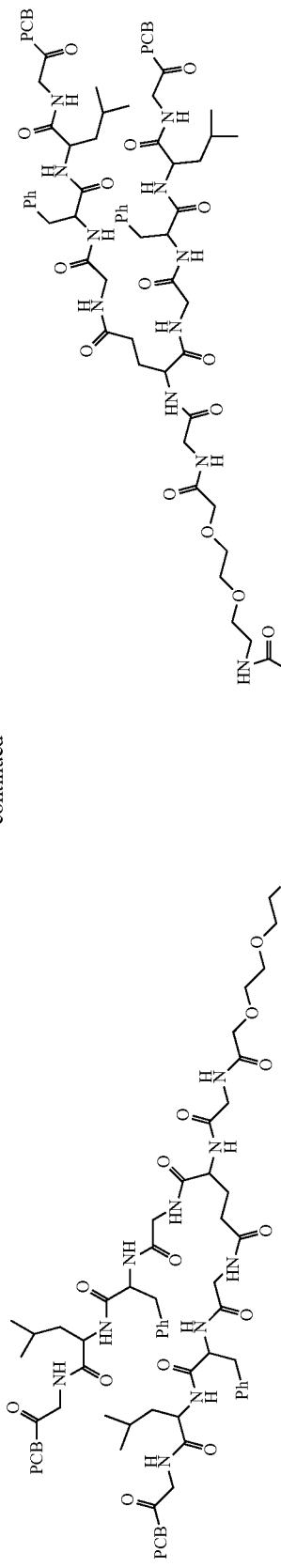
902
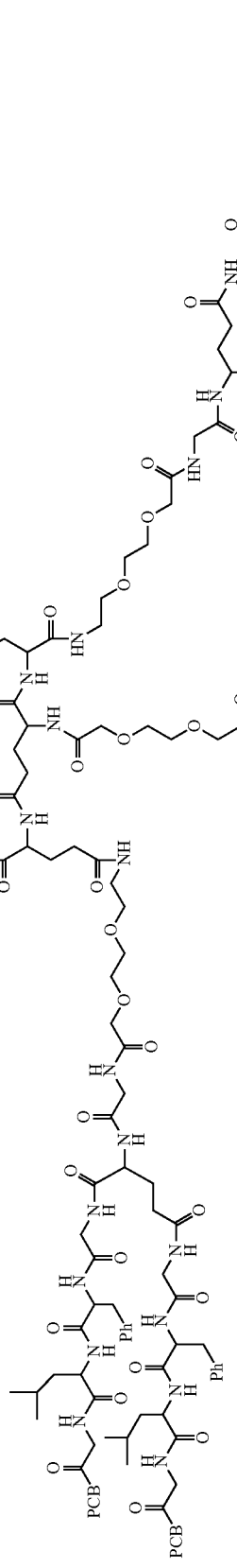 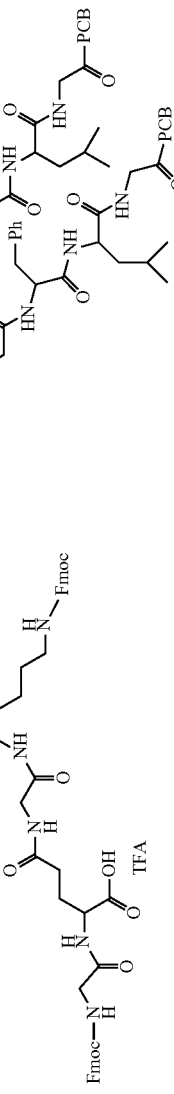 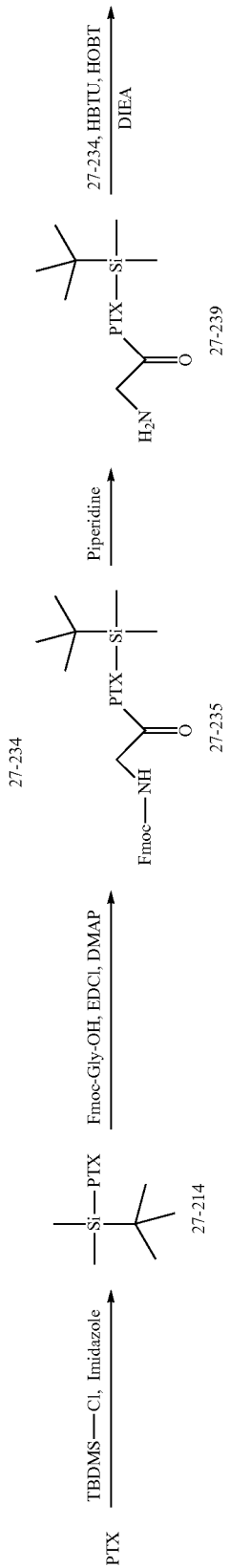

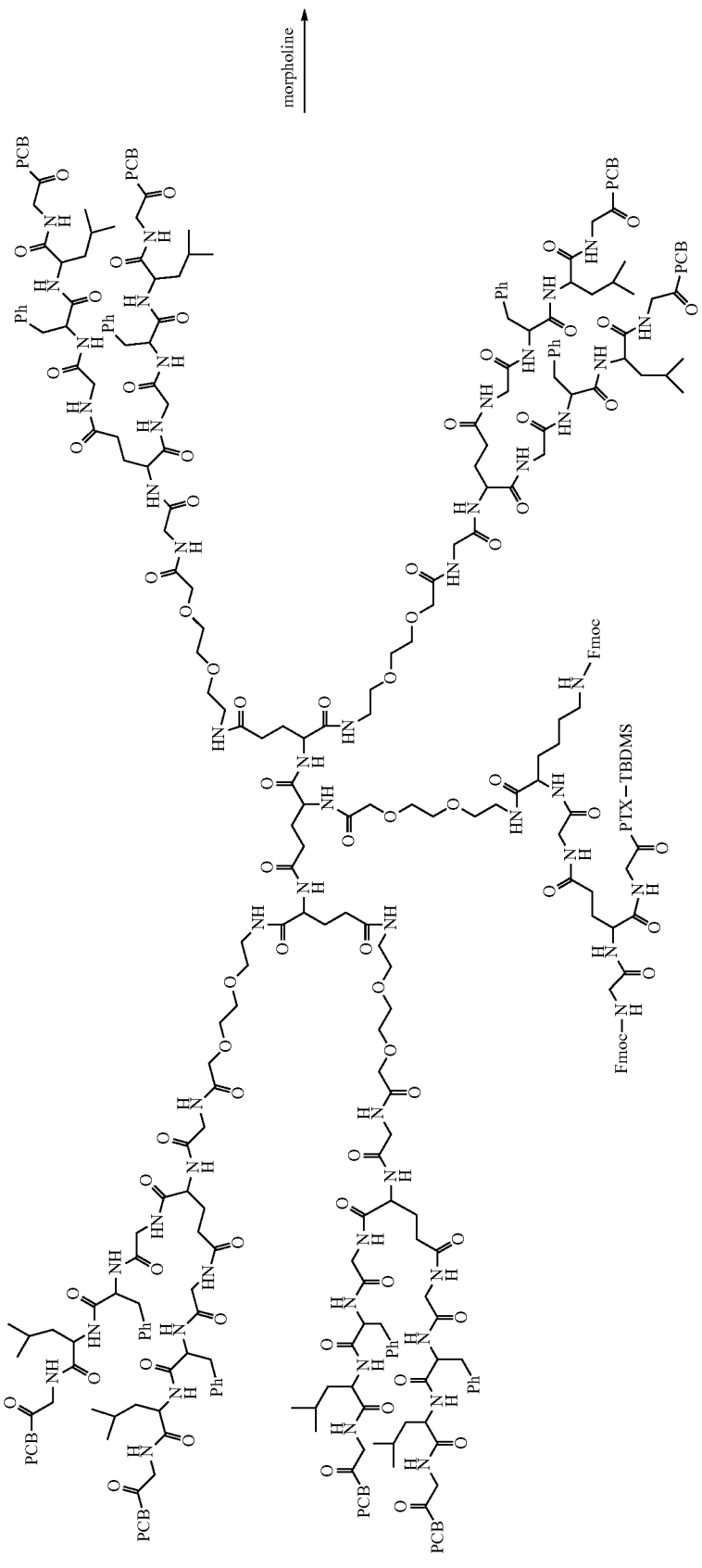

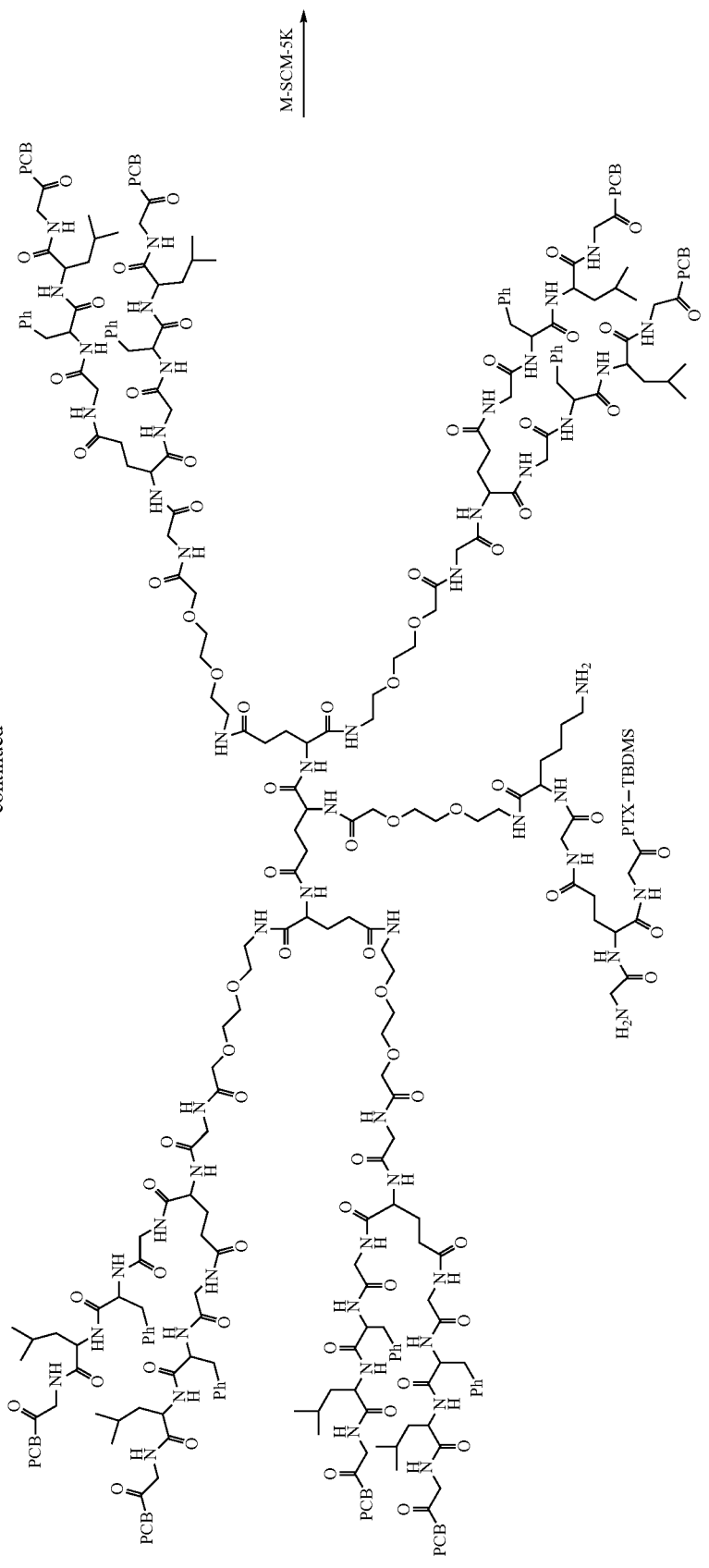

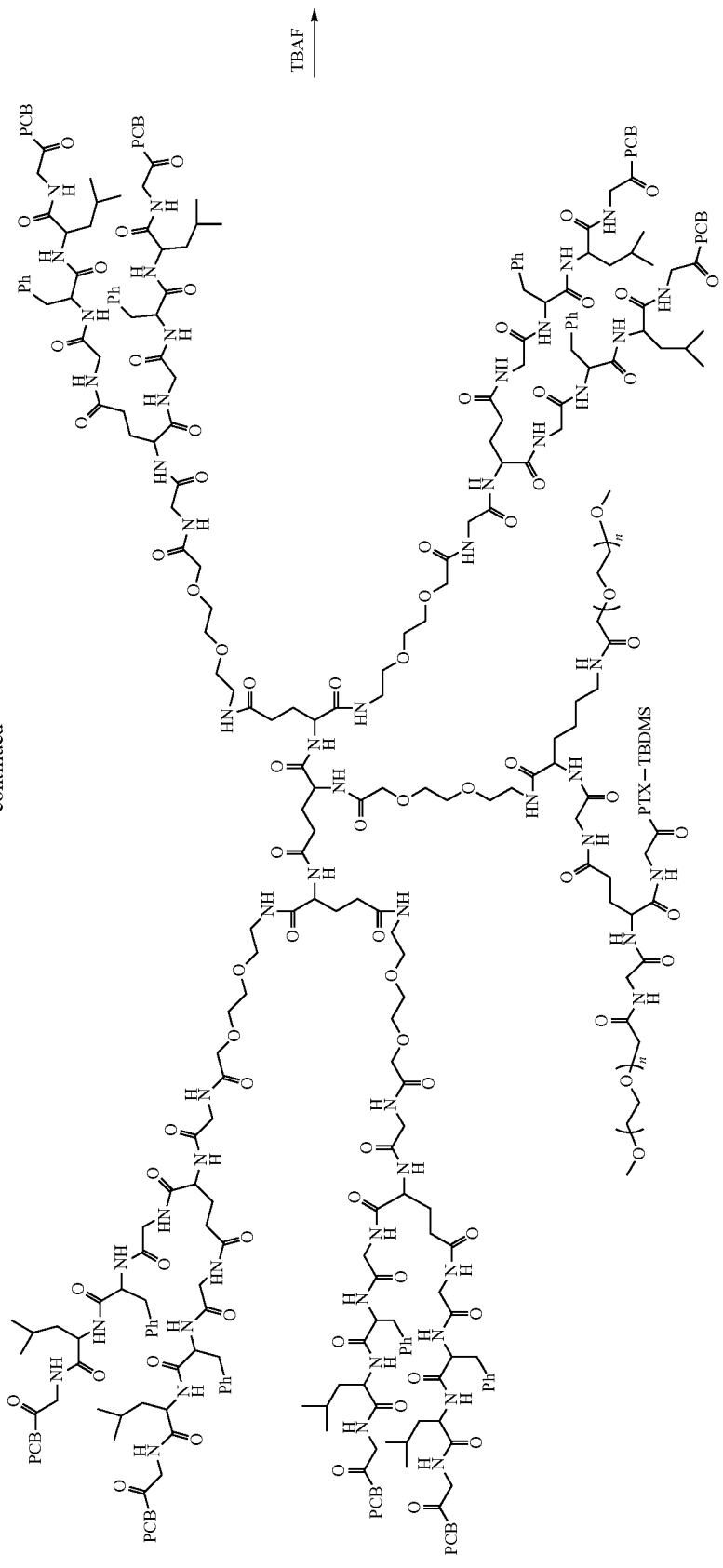

-continued
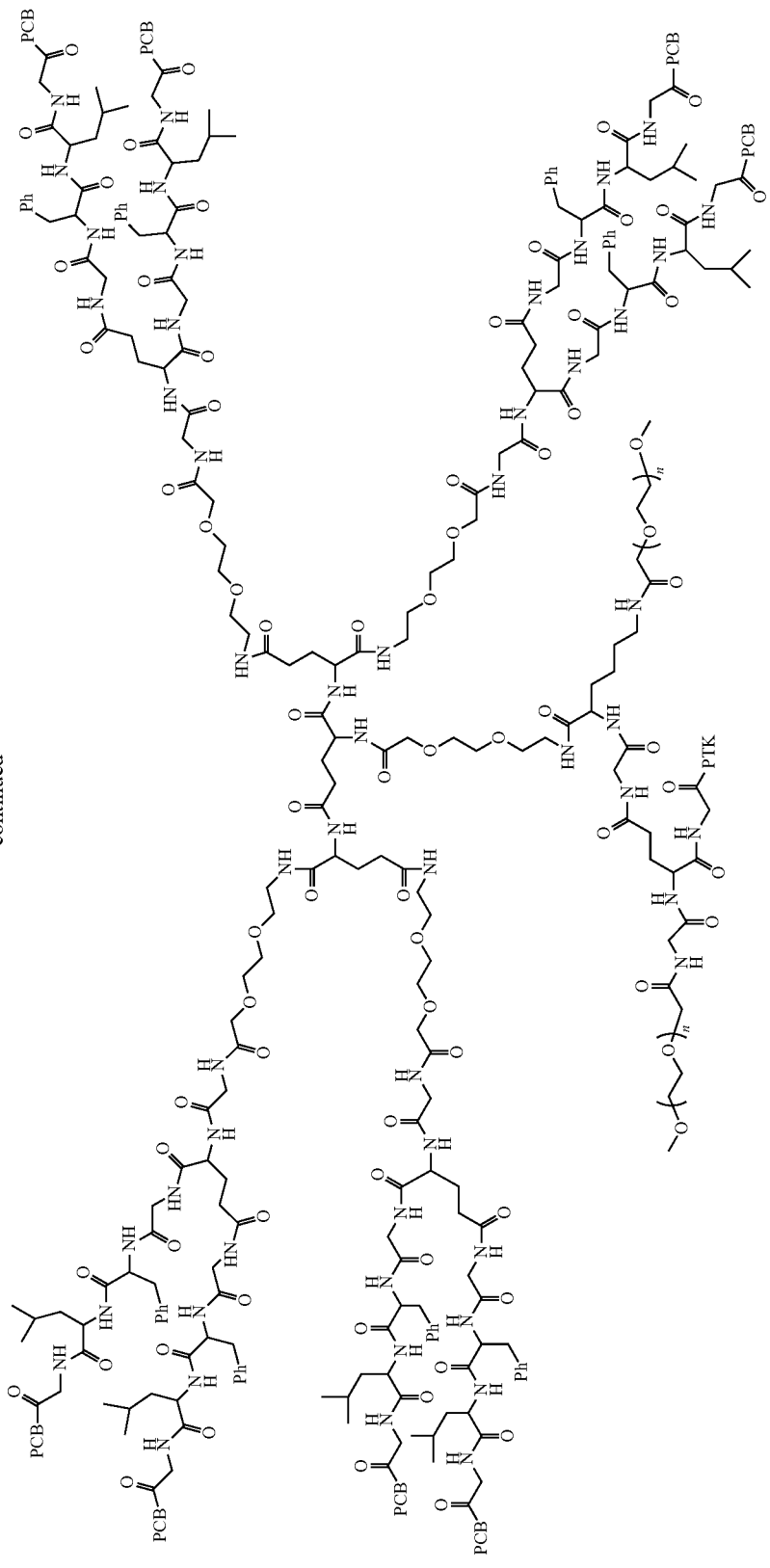
27-181
27-253
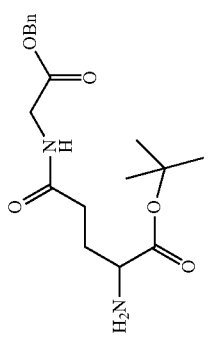

29-168 (3.33 g, 5.8079 mmol) was added in a 500 mL round-bottomed flask, and dissolved with DMF (20 mL), ultrasonic treatment was carried out to completely dissolve the compound, morpholine (5.06 mL, 58.079 mmol) was added, and then the mixed solution was stirred to react at room temperature for 2 hours. At the end of the reaction, the reaction solution was extracted with saturated sodium chloride solution (200 mL) and ethyl acetate (200 mL), and the organic phase was separated. The aqueous phase was then extracted with ethyl acetate (200 mL×3), and the obtained organic phases were combined. The organic phase was concentrated under reduced pressure, and dried, thus obtaining the product 4.2 g, overweight.

27-184

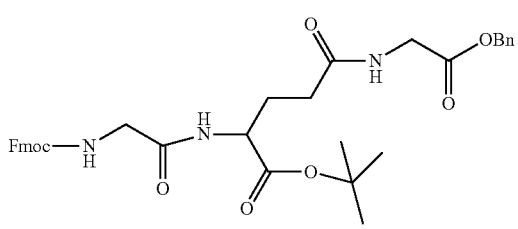

27-181 (2.03 g, 5.8079 mmol), Fmoc-Gly-OH (1.72 g, 5.8079 mmol, purchased from InnoChem), HBTU (3.3 g, 8.7119 mmol) and HOBT (1.13 g, 8.7119 mmol) were added in a 500 mL round-bottomed flask, and dissolved with DMF (100 mL), and then the mixed solution was stirred at −5° C. for 30 minutes. Then DIEA (4.32 mL, 26.1356 mmol) was slowly added dropwise. At the end of the addition, the obtained solution reacted at −5° C. for 2 hours, and was then moved to room temperature and stirred to react overnight. At the end of the reaction, the reaction solution was extracted with saturated sodium chloride solution (200 mL) and ethyl acetate (200 mL), and the organic phase was separated. The aqueous phase was then extracted with ethyl acetate (200 mL×3), and the obtained organic phases were combined. The organic phase was concentrated under reduced pressure, silica gel powder (60 ml) was added, and the operations of evaporation, dry sample loading, column chromatography and elution with an elutent (2%-3% methanol: 97%-98% dichloromethane) were carried out. The elution product was then collected, concentrated under reduced pressure, and dried, thus obtaining the product 2.68 g, yield: 73.42%.

27-201

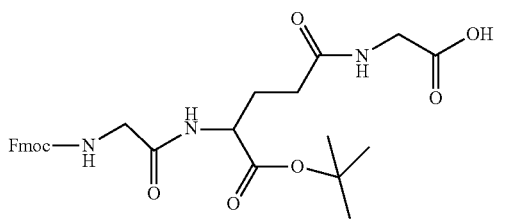

27-184 (2.68 g, 4.9669 mmol) and 10% Pd/C catalyst (100 mg) were added in a hydrogenation reactor, and dissolved with DMF (50 mL), the hydrogenation reactor was then sealed, hydrogen was introduced to a pressure of 18 psi, and then the mixed solution was stirred to react at room temperature overnight. After the reaction was found to be completed from the monitoring of the TLC, the reaction solution was taken out and evenly added dropwise to a sand core funnel filled with compacted diatomaceous earth, and then suction filtering was carried out. The diatomaceous earth was washed with DMF (30 mL×3), thus obtaining a reaction product solution.

27-202

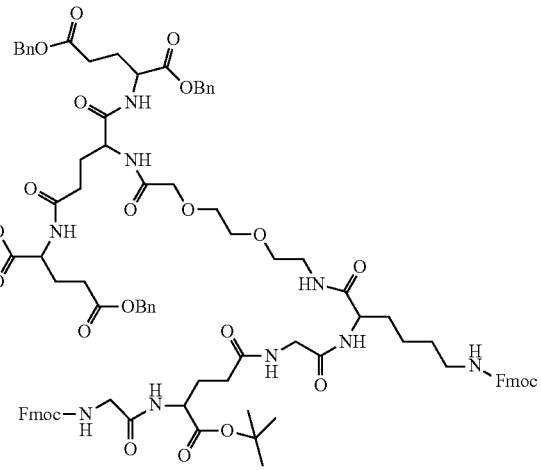

27-201 (1.57 g, 2.9123 mmol), 34-17 (3.34 g, 2.6475 mmol), HBTU (1.50 g, 3.9713 mmol) and HOBT (0.54 g, 3.9713 mmol) were added in a 500 mL round-bottomed flask, and dissolved with DMF (100 mL), and then the mixed solution was stirred at −5° C. for 30 minutes. Then DIEA (1.97 mL, 11.9138 mmol) was slowly added dropwise. At the end of the addition, the obtained solution reacted at −5° C. for 2 hours, and was then moved to room temperature and stirred to react overnight. At the end of the reaction, saturated sodium chloride solution (200 mL) and ethyl acetate (200 mL) were added to the reaction solution for extraction, and the organic phase was separated. The aqueous phase was then extracted with ethyl acetate (200 mL×3), and the obtained organic phases were combined. The organic phase was concentrated under reduced pressure, silica gel powder (60 ml) was added, and the operations of evaporation, dry sample loading, column chromatography and elution with an elutent (3% methanol: 97% dichloromethane) were carried out. The elution product was then collected, concentrated under reduced pressure, and dried, thus obtaining the product 3.58 g, yield: 75.84%.

27-204

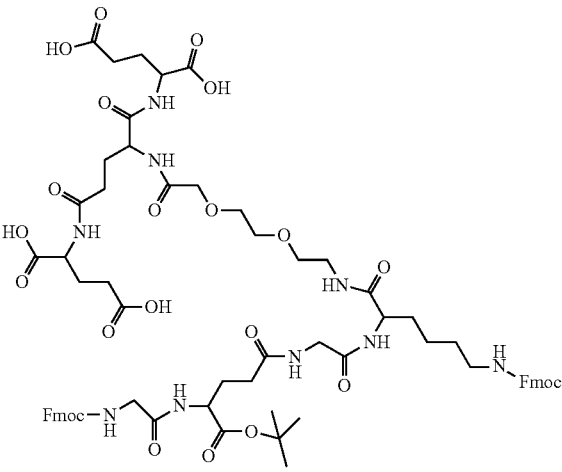

27-202 (3.58 g, 1.9456 mmol) and 10% Pd/C catalyst (100 mg) were added in a hydrogenation reactor, and dissolved with DMF (50 mL), the hydrogenation reactor was then sealed, hydrogen was introduced to a pressure of 18 psi, and then the mixed solution was stirred to react at room temperature overnight. After the reaction was found to be completed from the monitoring of the TLC, the reaction solution was taken out and evenly added dropwise to a sand core funnel filled with compacted diatomaceous earth, and then suction filtering was carried out. The diatomaceous earth was washed with DMF (30 mL×3), thus obtaining a reaction product solution.

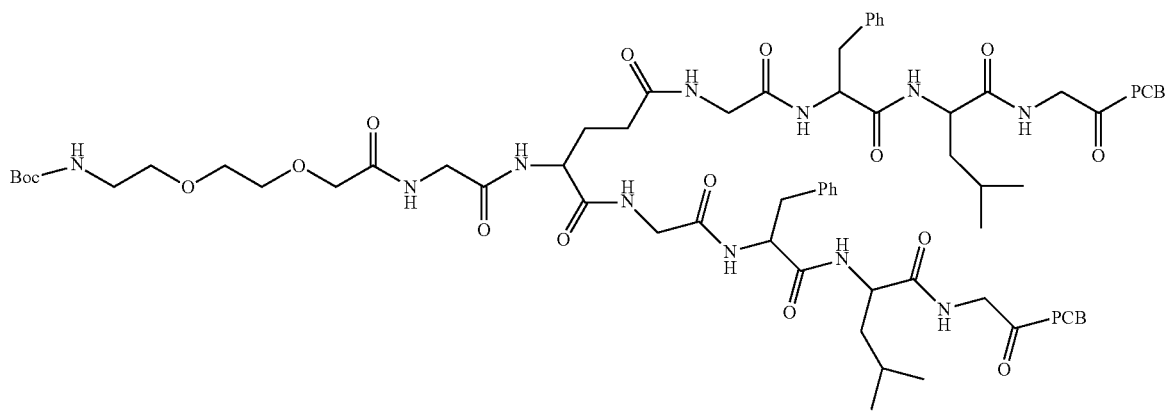

M-6

K-11 (0.65 g, 1.6590 mmol), 30-33 (3 g, 3.6498 mmol), HBTU (0.94 g, 2.4885 mmol) and HOBT (0.34 g, 2.4885 mmol) were added in a 500 mL round-bottomed flask, and dissolved with DMF (100 mL), and then the mixed solution was stirred at −5° C. for 30 minutes. Then DIEA (1.23 mL, 7.4655 mmol) was slowly added dropwise. At the end of the addition, the obtained solution reacted at −5° C. for 2 hours, and was then moved to room temperature and stirred to react overnight. At the end of the reaction, n-hexane (50 mL) and methyl tert-butyl ether (400 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dried, thus obtaining the product 5.9 g, overweight.

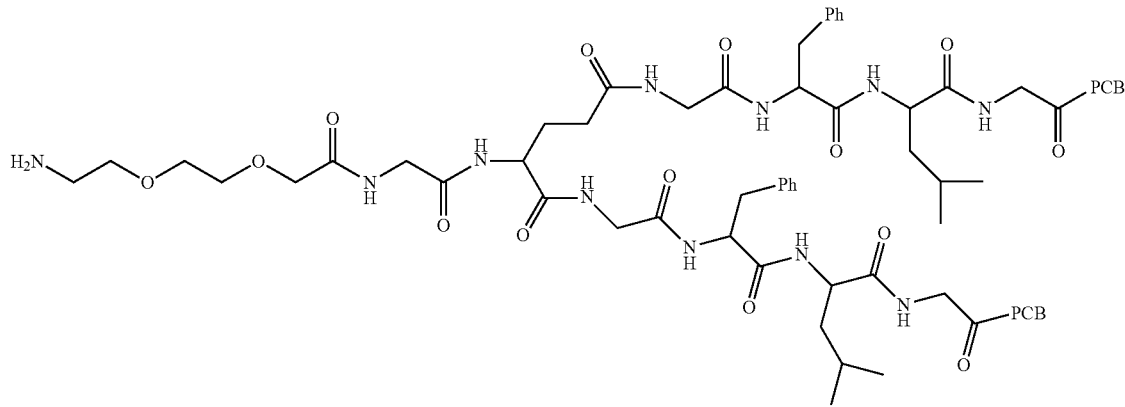

M-7

M-6 (3.32 g, 1.6590 mmol) was added in a 500 mL round-bottomed flask, and dissolved with dichloromethane (50 mL), TFA (2.35 mL, 16.590 mmol) was added, and then the mixed solution was stirred to react at room temperature overnight, At the end of the reaction, the reaction solution was concentrated under reduced pressure, n-hexane (50 mL) and methyl tert-butyl ether (400 mL) were added to the obtained solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 7% methanol/1% ammonia water/dichloromethane were carried out. The elution product was then collected, concentrated, and dried, thus obtaining the product 2.5 g, yield 79.36%.

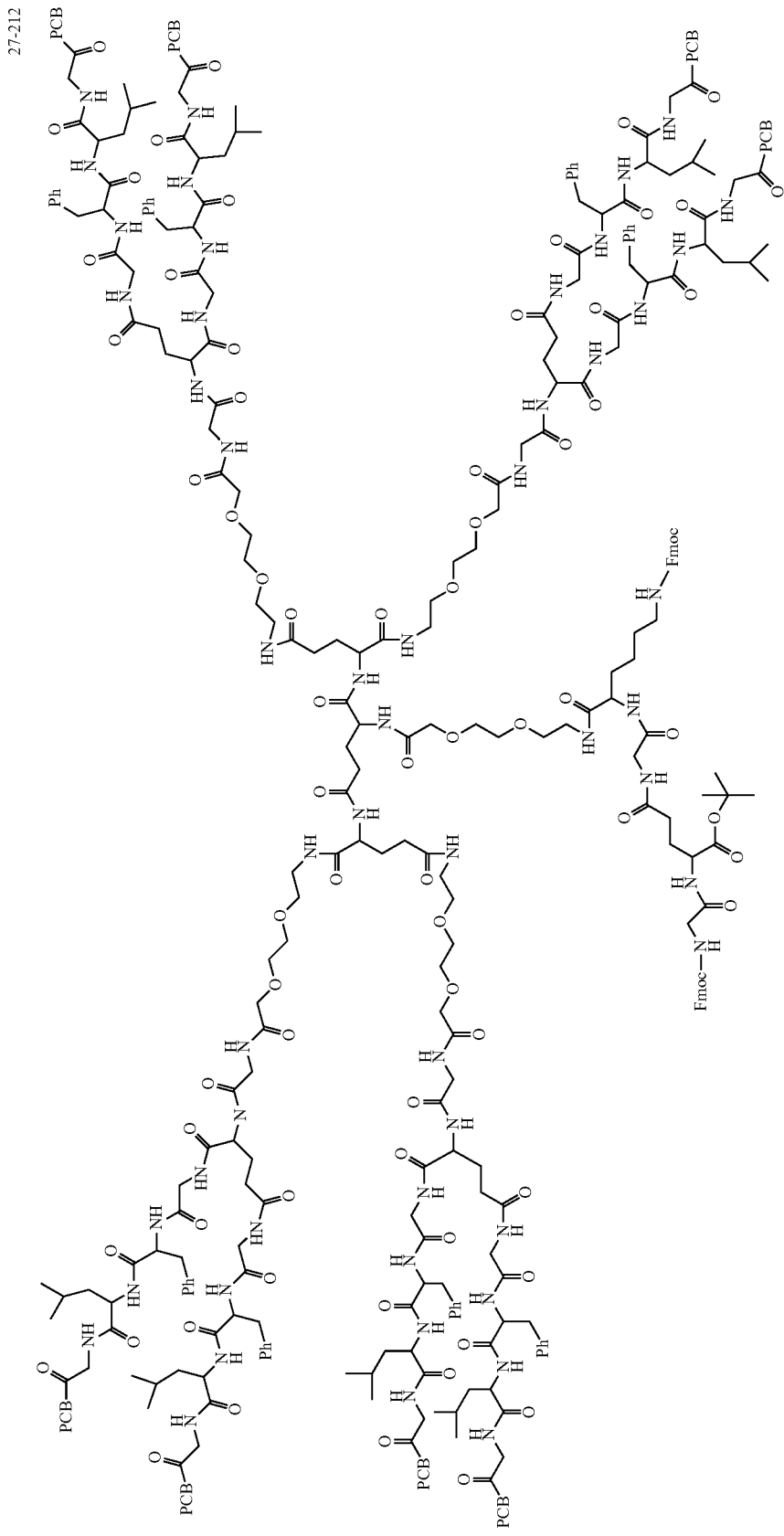

M-7 (2.5 g, 1.3244 mmol), 27-204 (0.43 g, 0.3010 mmol), HBTU (0.69 g, 1.806 mmol) and HOBT (0.24 g, 1.806 mmol) were added in a 500 mL round-bottomed flask, and dissolved with DMF (100 mL), and then the mixed solution was stirred at −5° C. for 30 minutes. Then DIEA (0.90 mL, 5.418 mmol) was slowly added dropwise. At the end of the addition, the obtained solution reacted at −5° C. for 2 hours, and was then moved to room temperature and stirred to react overnight. At the end of the reaction, n-hexane (50 mL) and methyl tert-butyl ether (400 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dried, thus obtaining the product 4.5 g, overweight.

921 922
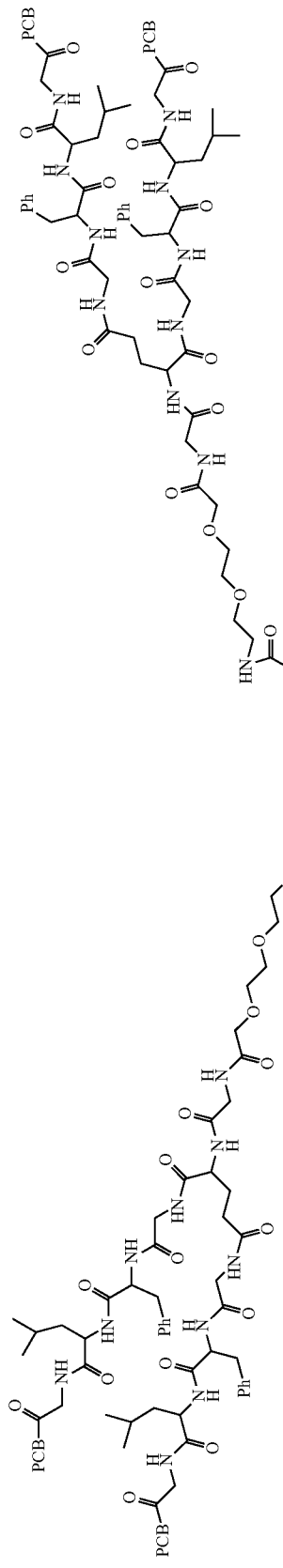
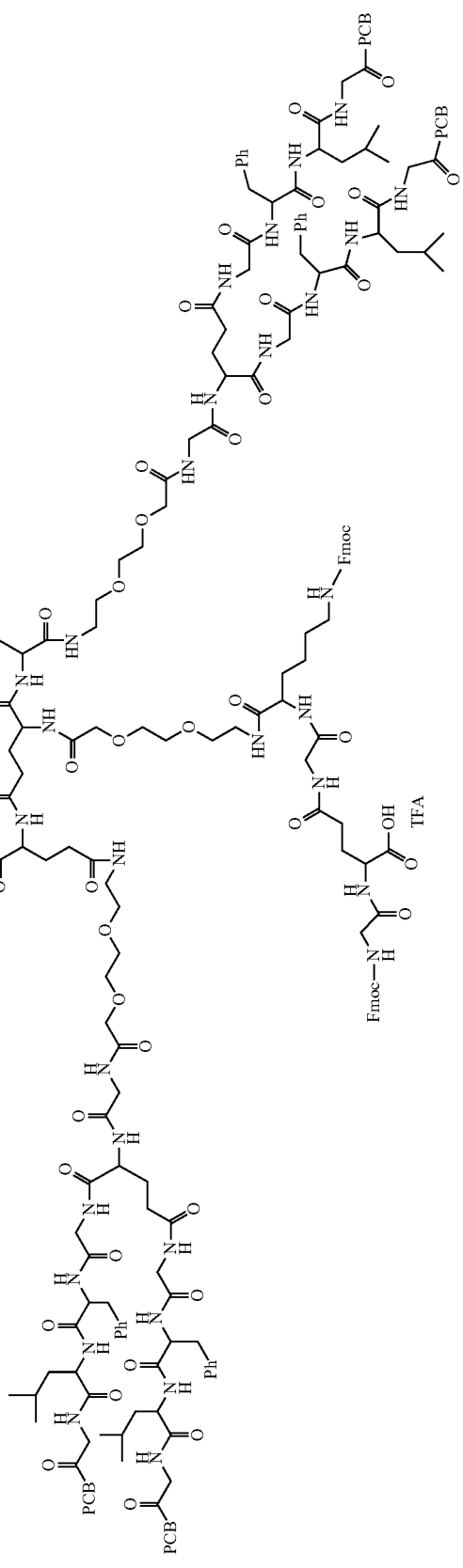

27-212 (2.69 g, 0.3010 mmol) was added in a 500 mL round-bottomed flask, and dissolved with dichloromethane (50 mL), TFA (0.22 mL, 3.010 mmol) was added, and then the mixed solution was stirred to react at room temperature overnight, At the end of the reaction, the reaction solution was concentrated under reduced pressure, n-hexane (50 mL) and methyl tert-butyl ether (400 mL) were added to the obtained solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 8% methanol/dichloromethane were carried out. The elution product was then collected, concentrated, and dried, thus obtaining the product 1.9 g, yield 71.76%.

$^1$H-NMR (600 MHz, DMSO-$d_6$) δ10.17-10.13 (m, 8H), 8.99-8.91 (m, 8H), 8.34-8.14 (m, 16H), 8.14-7.94 (m, 24H), 7.88-7.67 (m, 30H), 7.45-7.05 (m, 49H), 5.83-5.77 (m, 10H), 5.35-5.28 (m, 5H), 4.56-3.98 (m, 51H), 3.74-3.49 (m, 60H), 3.15-2.99 (m, 48H), 2.81-2.66 (m, 19H), 2.41-2.03 (m, 68H), 1.89-1.85 (m, 50H), 1.57-1.51 (m, 43H), 1.34-1.23 (m, 18H), 0.98-0.77 (m, 72H).

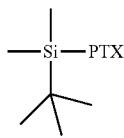

27-214

Paclitaxel (also referred to as PTX, 0.5 g, 0.5855 mmol), TBDMS-Cl (purchased from Innochem, 0.53 g, 3.5310 mmol), imidazole (0.2 g, 2.9425 mmol) were added in a 500 mL round-bottomed flask, and dissolved with anhydrous DMF (20 mL), and then the mixed solution was stirred to react at room temperature overnight. At the end of the reaction, the reaction solution was diluted with dichloromethane (200 mL), washed in turn with saturated NH$_4$Cl (50 mL), deionized water (50 mL), and saturated sodium chloride solution (100 mL), and the obtained organic phase was dried with anhydrous sodium sulfate. The operations of dry sample loading, column chromatography and elution with petroleum ether:ethyl acetate=1:1 were carried out. The elution product was then collected, concentrated, and dried, thus obtaining the product 0.35 g, yield 62.5%, wherein hydroxy in position 2' of paclitaxel was protected by TBDMS.

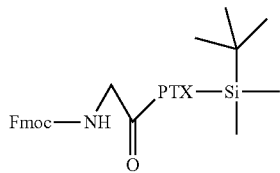

27-235

Fmoc-Gly-OH (0.44 g, 1.4476 mmol), EDCI (0.28 g, 1.4476 mmol), DMAP (0.02 g, 0.1810 mmol) were added in a 500 mL round-bottomed flask, and dissolved with anhydrous dichloromethane (50 mL) and anhydrous DMF (25 mL), and then the mixed solution was stirred to react at room temperature for 15 min. Then 27-214 (0.35 g, 0.3619 mmol) was added, and the obtained solution reacted at room temperature overnight. At the end of the reaction, the reaction solution was diluted with dichloromethane (200 mL), washed in turn with saturated NH$_4$Cl (100 mL), deionized water (50 mL), and saturated sodium chloride solution (100 mL), and the obtained organic phase was dried with anhydrous sodium sulfate. The operations of dry sample loading, column chromatography and elution with 3% methanol/dichloromethane were carried out. The elution product was then collected, concentrated, and dried, thus obtaining the product 0.31 g, yield 68.89%, wherein the esterification occurred at hydroxy in position 7.

$^1$H-NMR (400 MHz, DMSO-$d_6$) δ 8.83 (m, 1H), 7.99 (m, 2H), 7.92-7.81 (m, 4H), 7.76-7.59 (m, 6H), 7.57-7.27 (m, 12H), 7.21 (m, 1H), 5.99 (s, 1H), 5.86 (m, 1H), 5.56-5.40 (m, 3H), 5.01 (m, 1H), 4.80 (s, 2H), 4.26 (s, 3H), 3.66 (m, 3H), 2.45 (s, 3H), 1.99 (s, 6H), 1.65 (s, 5H), 1.55 (s, 3H), 1.00 (m, 6H), 0.80 (s, 9H), 0.05 (m, 6H).

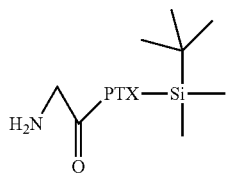

27-239

27-235 (0.31 g, 0.2487 mmol) was added in a 500 mL round-bottomed flask, piperidine (0.25 ml, 2.487 mmol) and DMF (5 mL) were added, and then the mixed solution was stirred to react at room temperature for 2 h. At the end of the reaction, the reaction solution was concentrated under reduced pressure to remove the piperidine, thus obtaining the DMF solution of the reaction product.

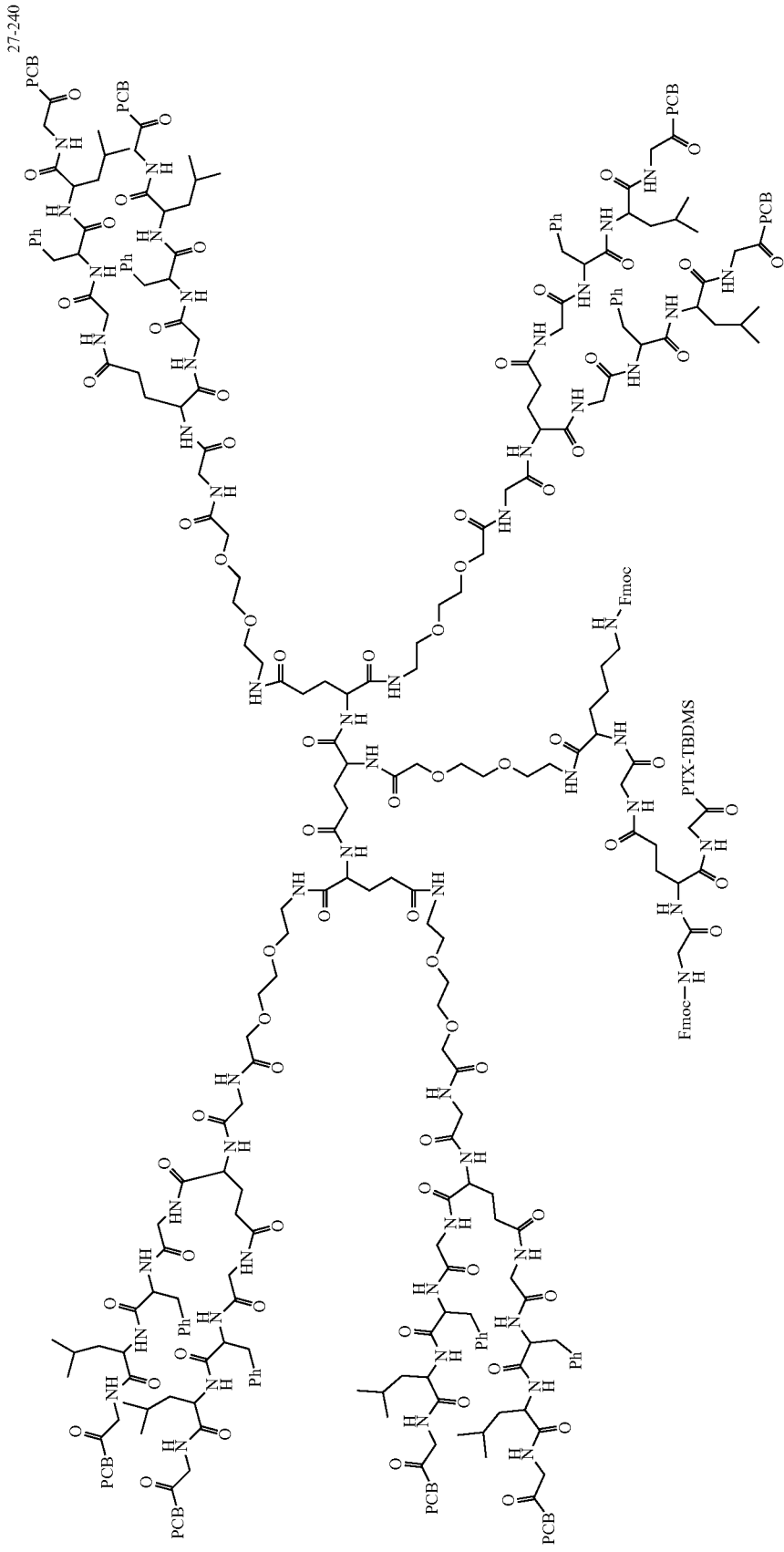

27-234 (1.9 g, 0.2135 mmol), 27-239 (0.2487 mmol), HBTU (0.12 g, 0.3203 mmol) and HOBT (0.04 g, 0.3203 mmol) were added in a 500 mL round-bottomed flask, and dissolved with DMF (30 mL), and then the mixed solution was stirred at −5° C. for 30 minutes. Then DIEA (0.17 mL, 0.9608 mmol) was slowly added dropwise. At the end of the addition, the obtained solution reacted at −5° C. for 2 hours, and was then moved to room temperature and stirred to react overnight. At the end of the reaction, n-hexane (50 mL) and methyl tert-butyl ether (400 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with a small amount of a mixed solvent of methanol and dichloromethane, n-hexane (50 mL) and methyl tert-butyl ether (400 mL) were then added to the obtained solution for precipitation, and suction filtering was carried out. The process of dissolution and precipitation was repeated three times, thus obtaining the product 1.6 g, yield 75.82%.

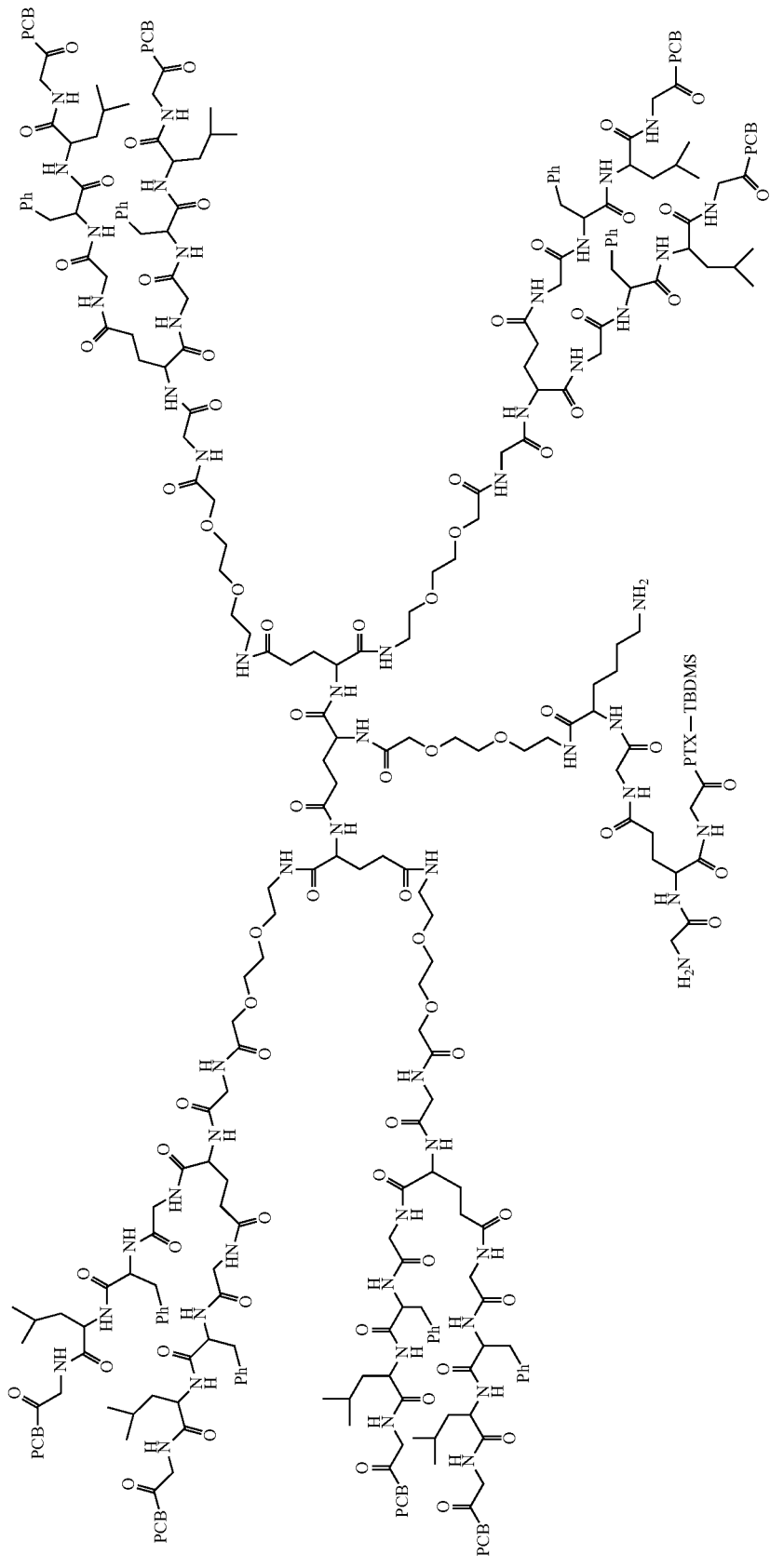

27-240 (1.6 g, 0.1615 mmol) was added in a 500 mL round-bottomed flask, and dissolved with DMF (10 mL), ultrasonic treatment was carried out to completely dissolve the compound, morpholine (0.14 mL, 1.615 mmol) was added, and then the mixed solution was stirred to react at room temperature for 2 hours. At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 7% methanol/dichloromethane were carried out. The elution product was then collected, concentrated, and dried, thus obtaining the product 1.2 g, yield 78.43%.

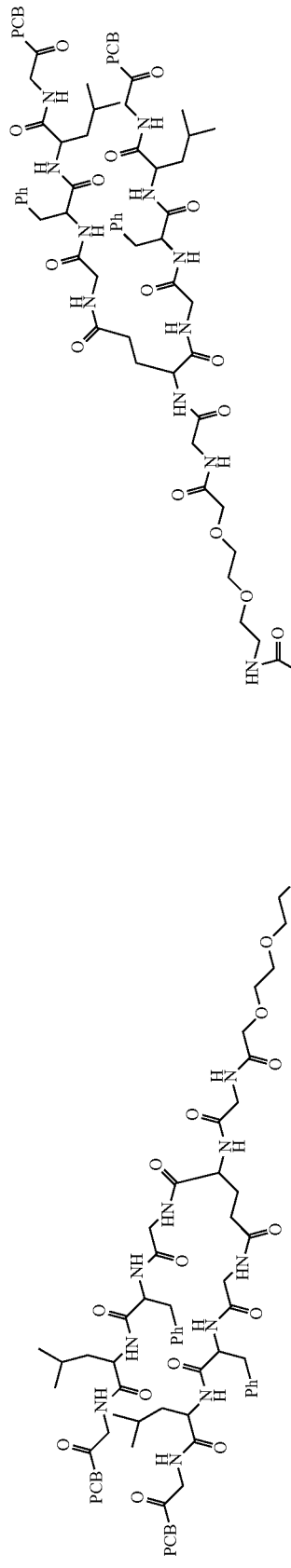
933
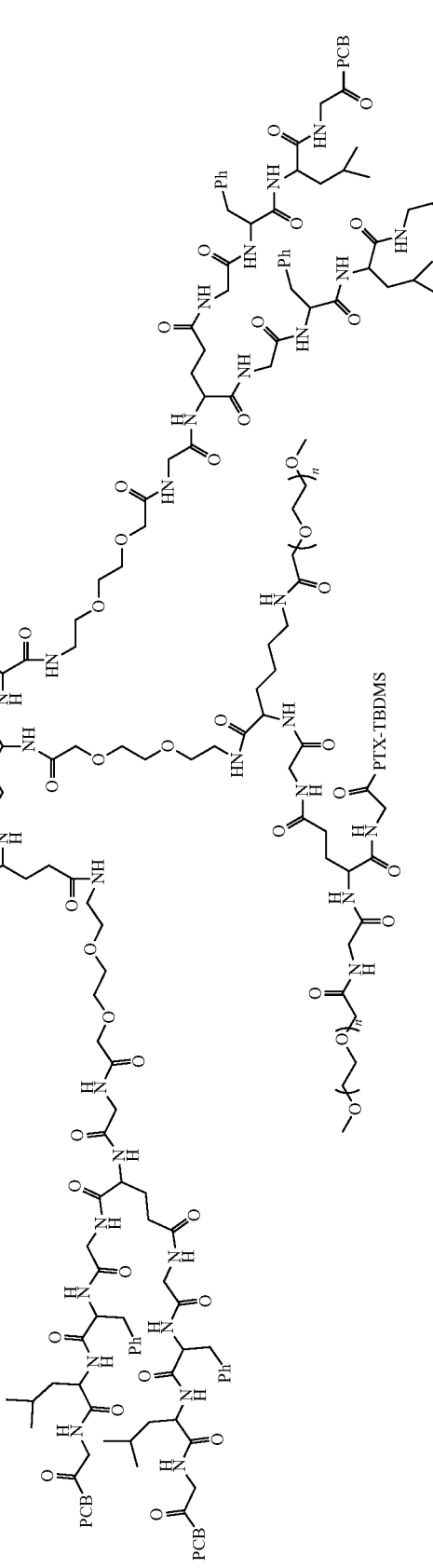
934

27-243 (1.2 g, 0.1268 mmol) was added in a 250 mL flask, and dissolved with DMF (20 mL), 加λM-SCM-5K (1.45 g, 0.2790 mmol, purchased from JenKem), ultrasonic vibration was carried out to dissolve the compound, the mixed solution reacted in the dark for one week at a low of speed stirring at room temperature. At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 9% methanol/dichloromethane were carried out. The elution product was then collected, concentrated, and dried, thus obtaining the product 1.9 g, yield 75.70%.

$^1$H-NMR (600 MHz, DMSO-$d_6$) δ10.16-10.12 (m, 8H), 9.02-8.98 (m, 11H), 8.08-7.98 (m, 55H), 7.72-7.64 (m, 14H), 7.56-7.09 (m, 49H), 7.05-6.98 (m, 2H), 6.69-6.65 (m, 3H), 5.80-5.37 (m, 21H), 5.14-4.75 (m, 20H), 4.56-4.30 (m, 35H), 4.03-4.38 (m, 45H), 3.51 (s, 1120H), 3.44-3.04 (m, 65H), 2.77-2.68 (m, 13H), 2.41-2.04 (m, 55H), 2.02-1.69 (m, 39H), 1.68-1.26 (m, 66H), 1.18-1.12 (m, 5H), 1.06-0.69 (m, 45H), 0.09-0.06 (m, 3H).

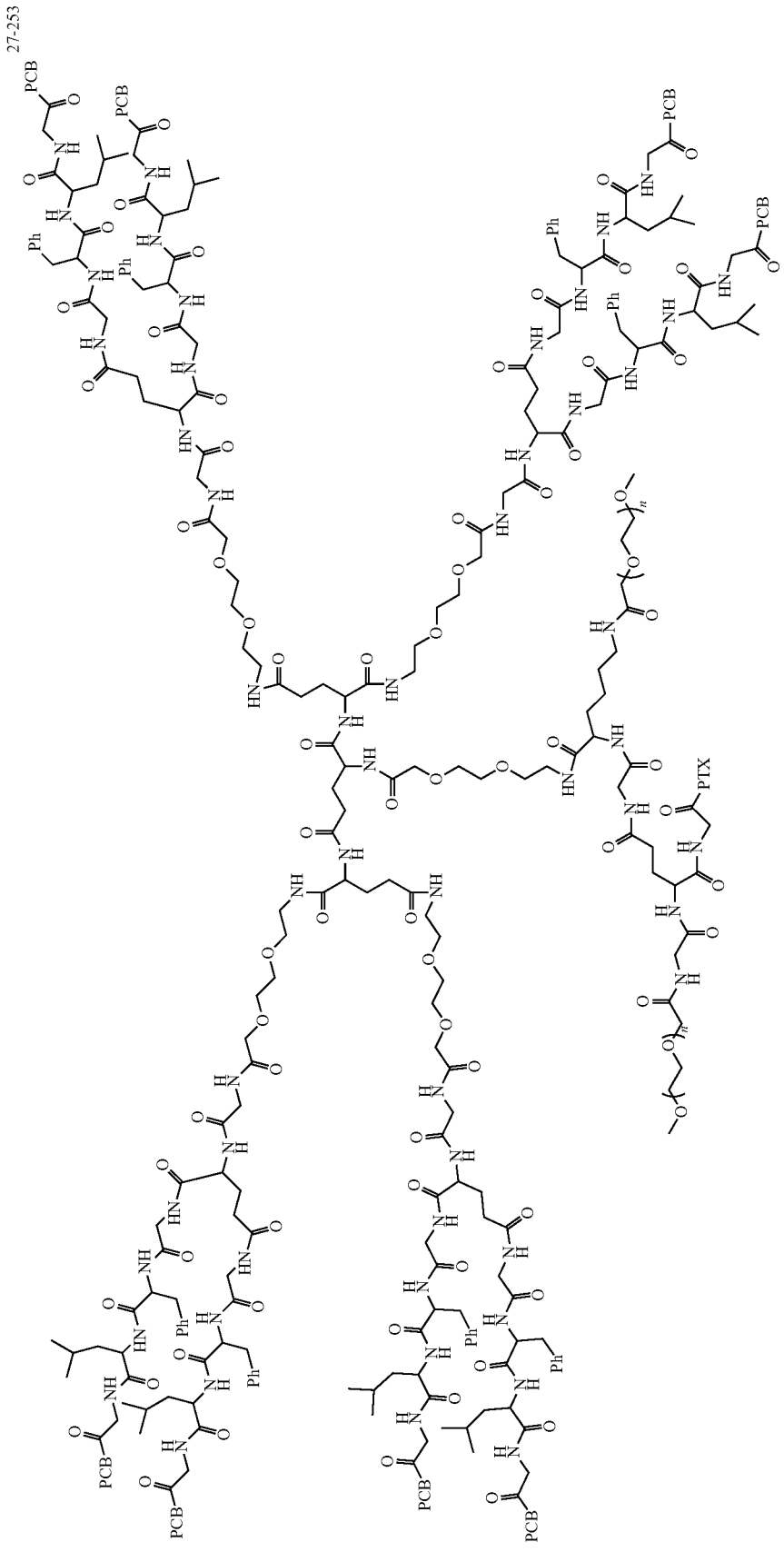

27-247 (1.9 g, 0.0958 mmol), TBAF (0.06 g, 0.1916 mmol) were added in a 500 mL round-bottomed flask, and dissolved with THF (20 mL), and then the mixed solution was stirred to react at room temperature for 1.5 h. At the end of the reaction, the reaction solution was concentrated under reduced pressure to obtain a solid product, the solid product was dissolved with DMF (5 mL), isopropanol was added to the obtained solution for precipitation. Such operations were repeated three times. A solid product was obtained by filtering. The obtained solid product was dissolved with dichloromethane (10 mL), and the obtained solution was precipitated with methyl tert-butyl ether. Such operations were repeated three times. The obtained solid product was dried, thus obtaining the product 0.75 g, yield 62.5%.

$^1$H-NMR (400 MHz, DMSO-$d_6$) δ 10.16-10.10 (m, 8H), 9.02-8.97 (m, 11H), 8.55-7.81 (m, 58H), 7.70-7.62 (m, 9H), 7.21-6.99 (m, 53H), 6.71-6.66 (m, 5H), 5.88-5.84 (m, 10H), 5.37-4.96 (m, 10H), 4.59-4.28 (m, 27H), 4.14-3.81 (m, 32H), 3.57-3.48 (s, 1101H), 3.19-3.15 (m, 61H), 2.81-2.76 (m, 7H), 2.44-2.27 (s, 68H), 1.82-1.43 (m, 89H), 1.36-1.32 (m, 36H), 0.90-0.79 (m, 40H).

18. Synthesis of 49-5(Compound No. 11)

Synthetic route is as follows

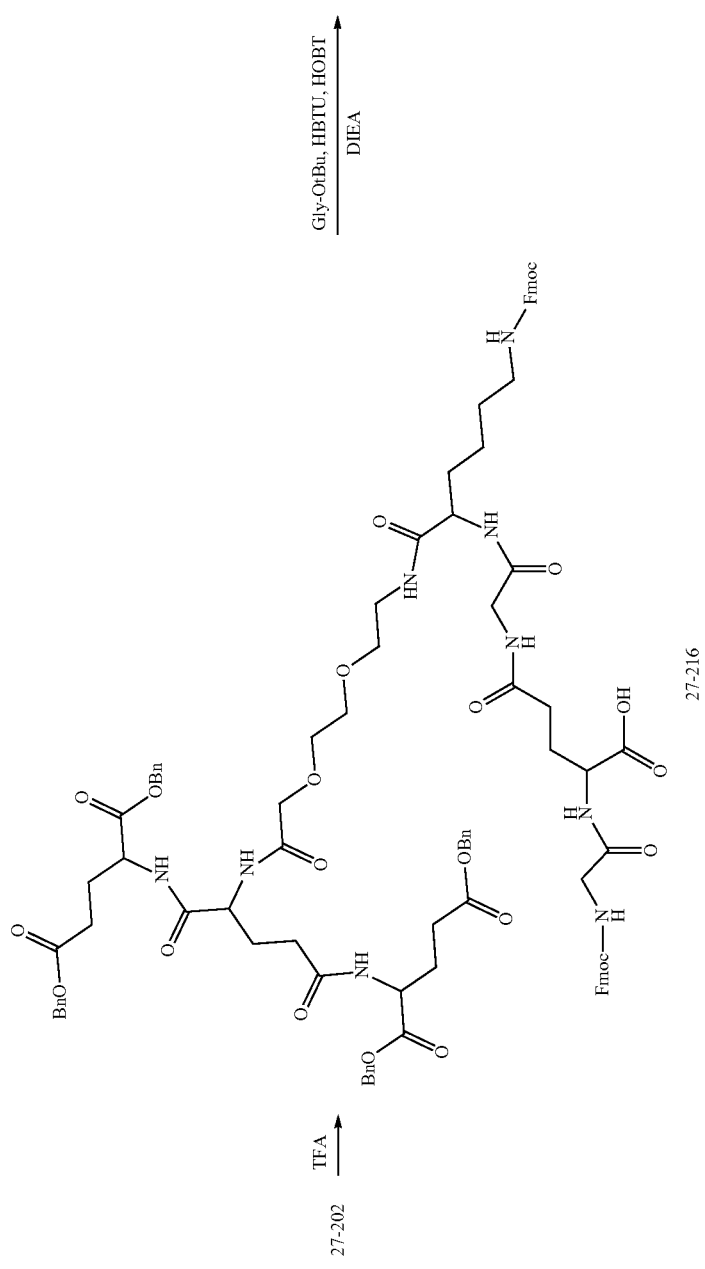

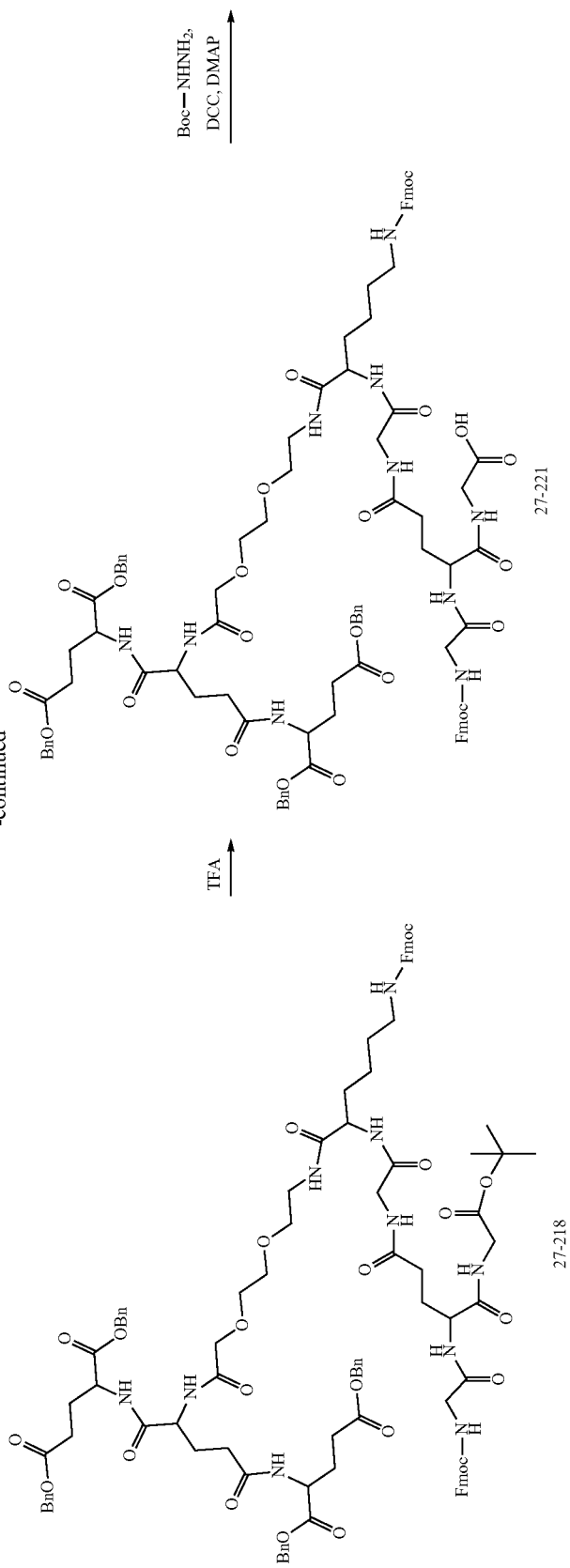

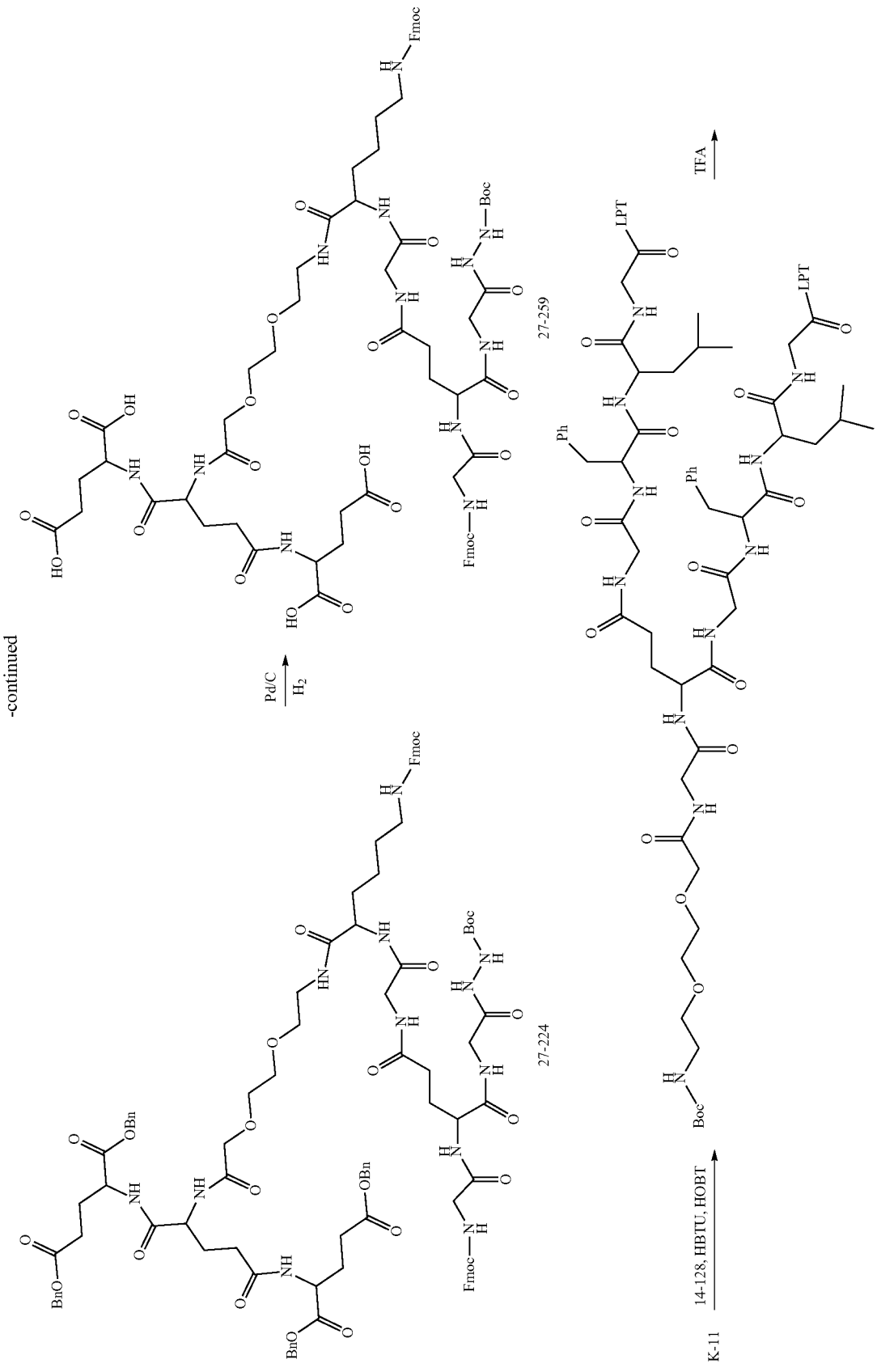

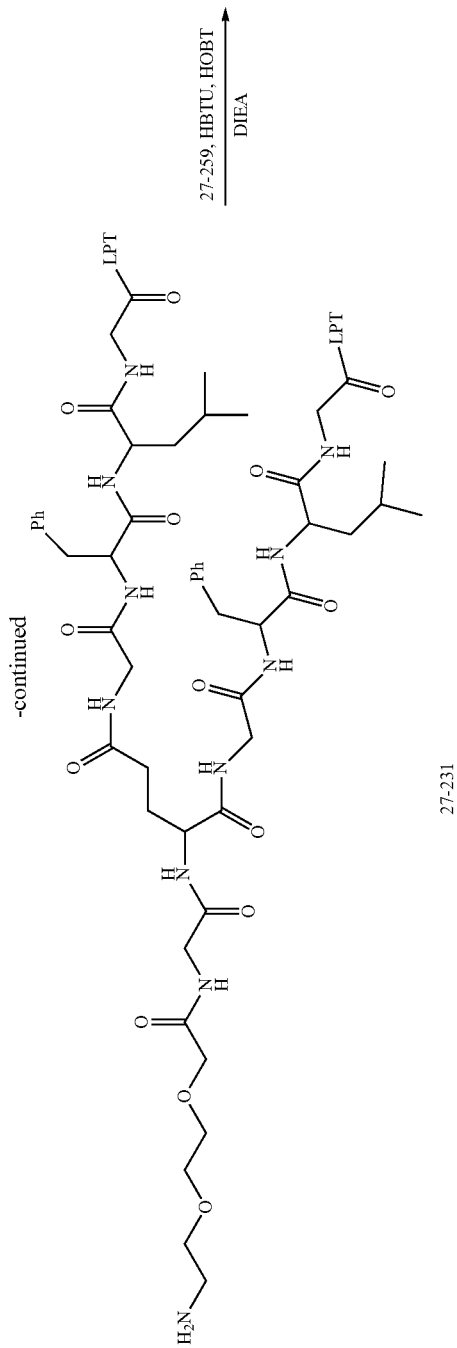

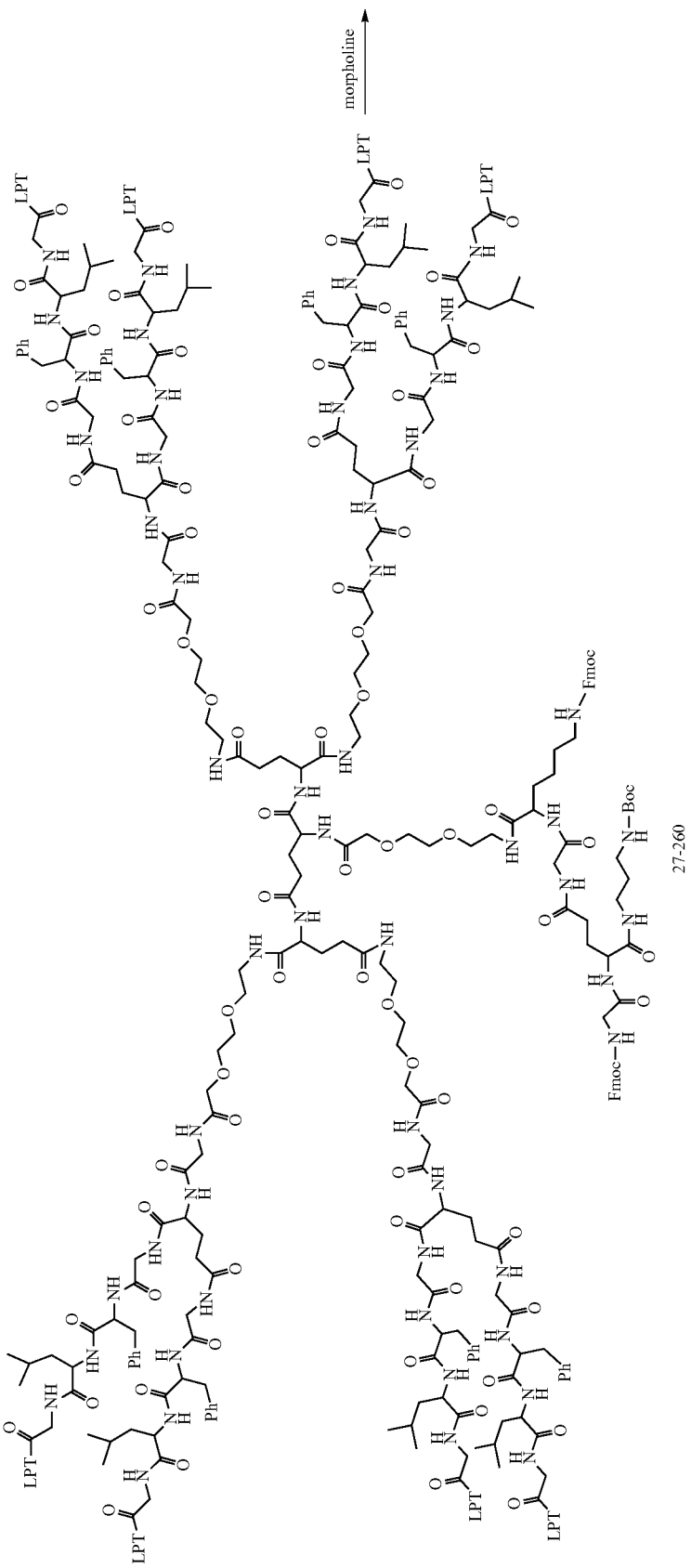

-continued
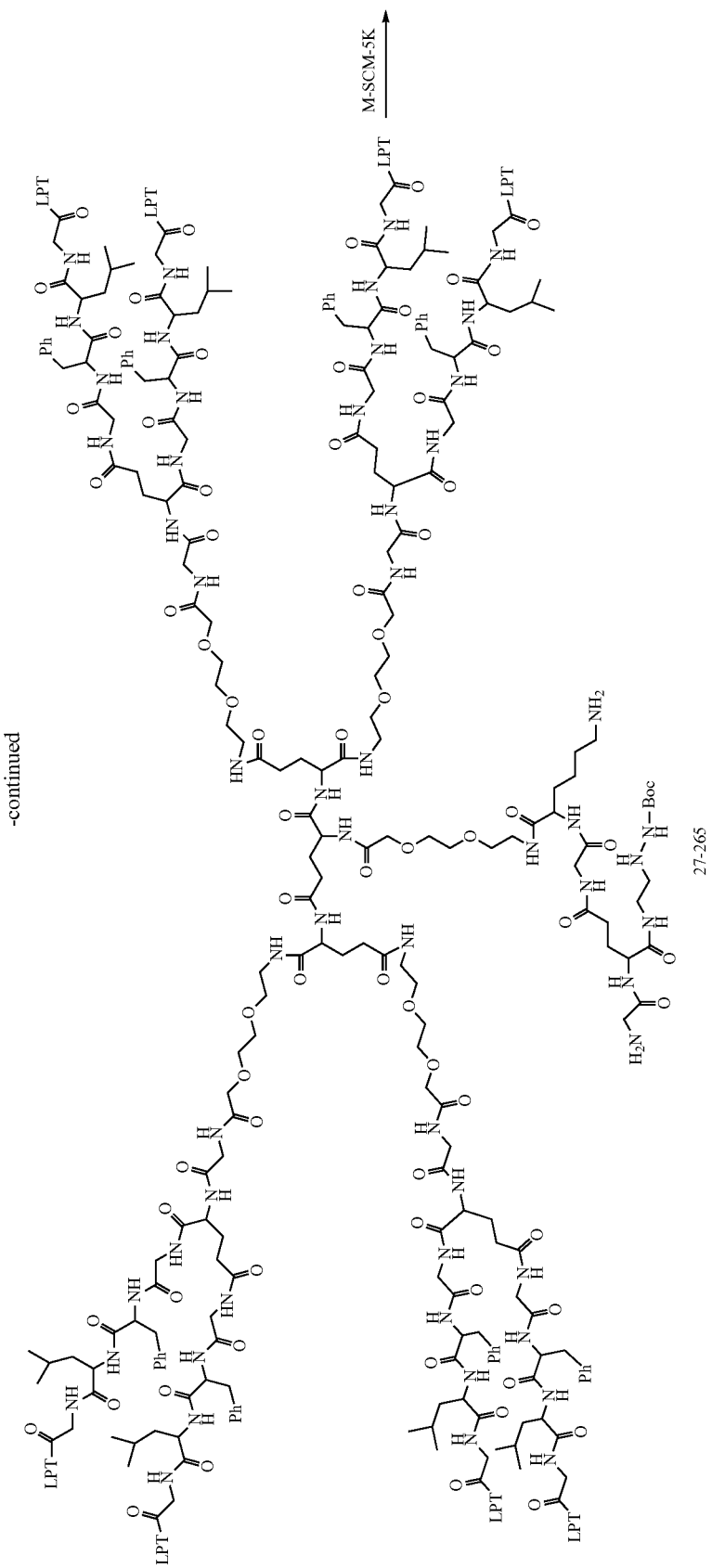
27-265

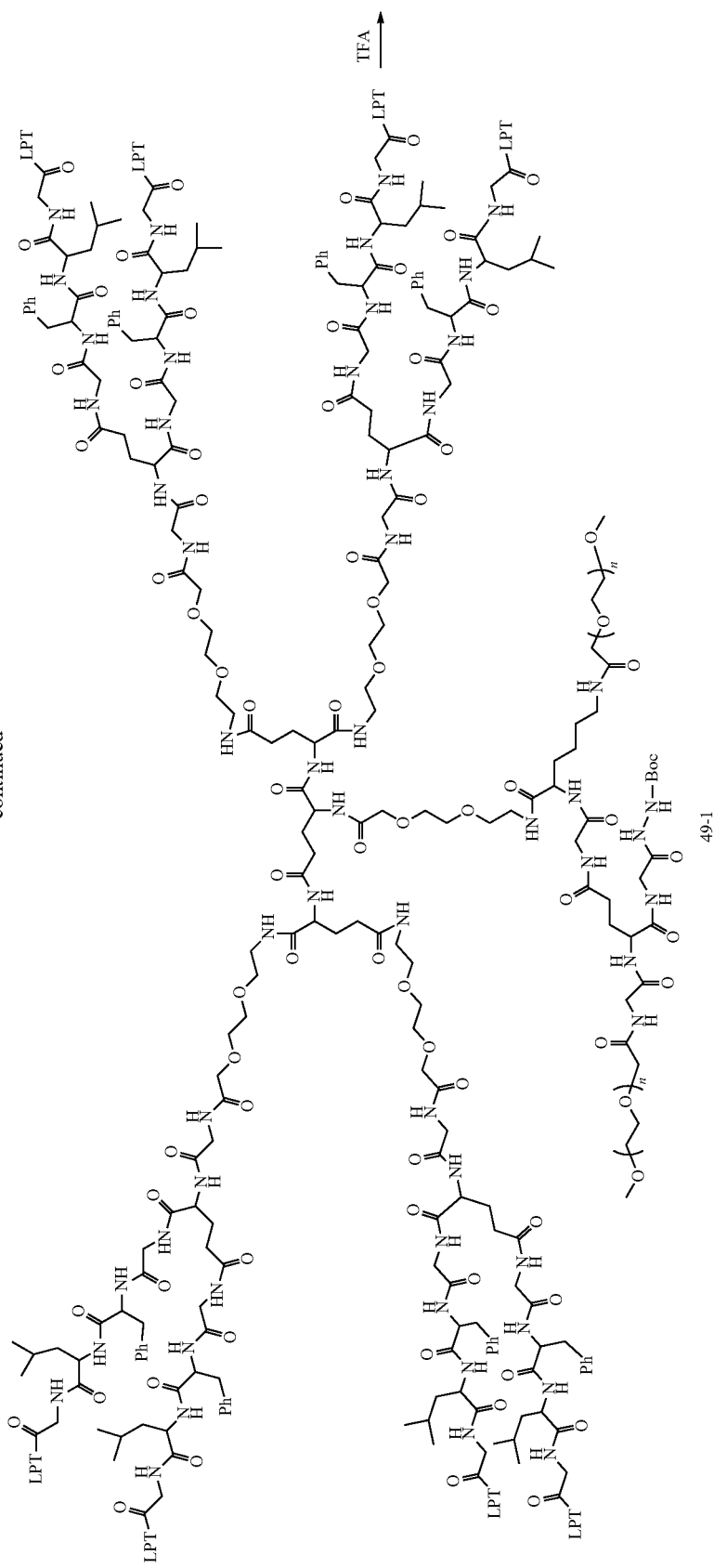

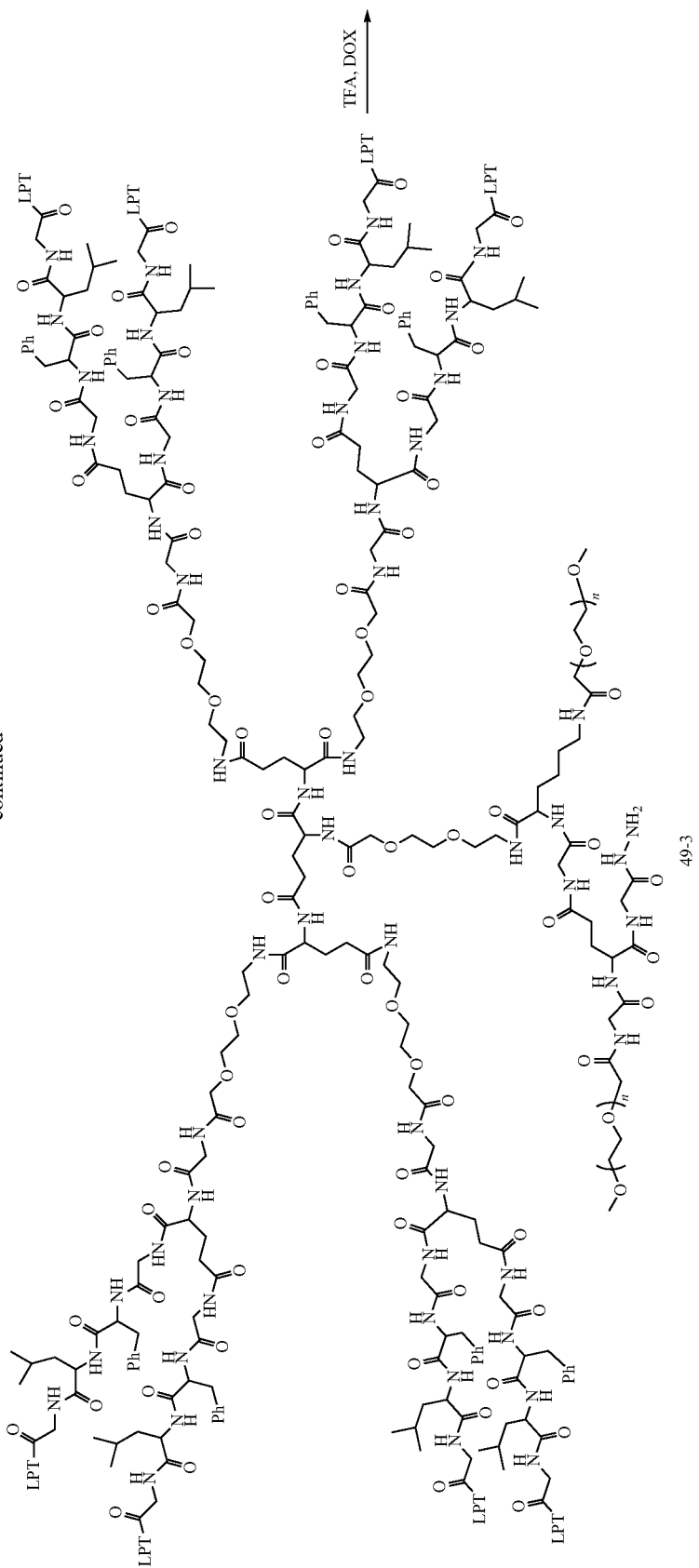

-continued
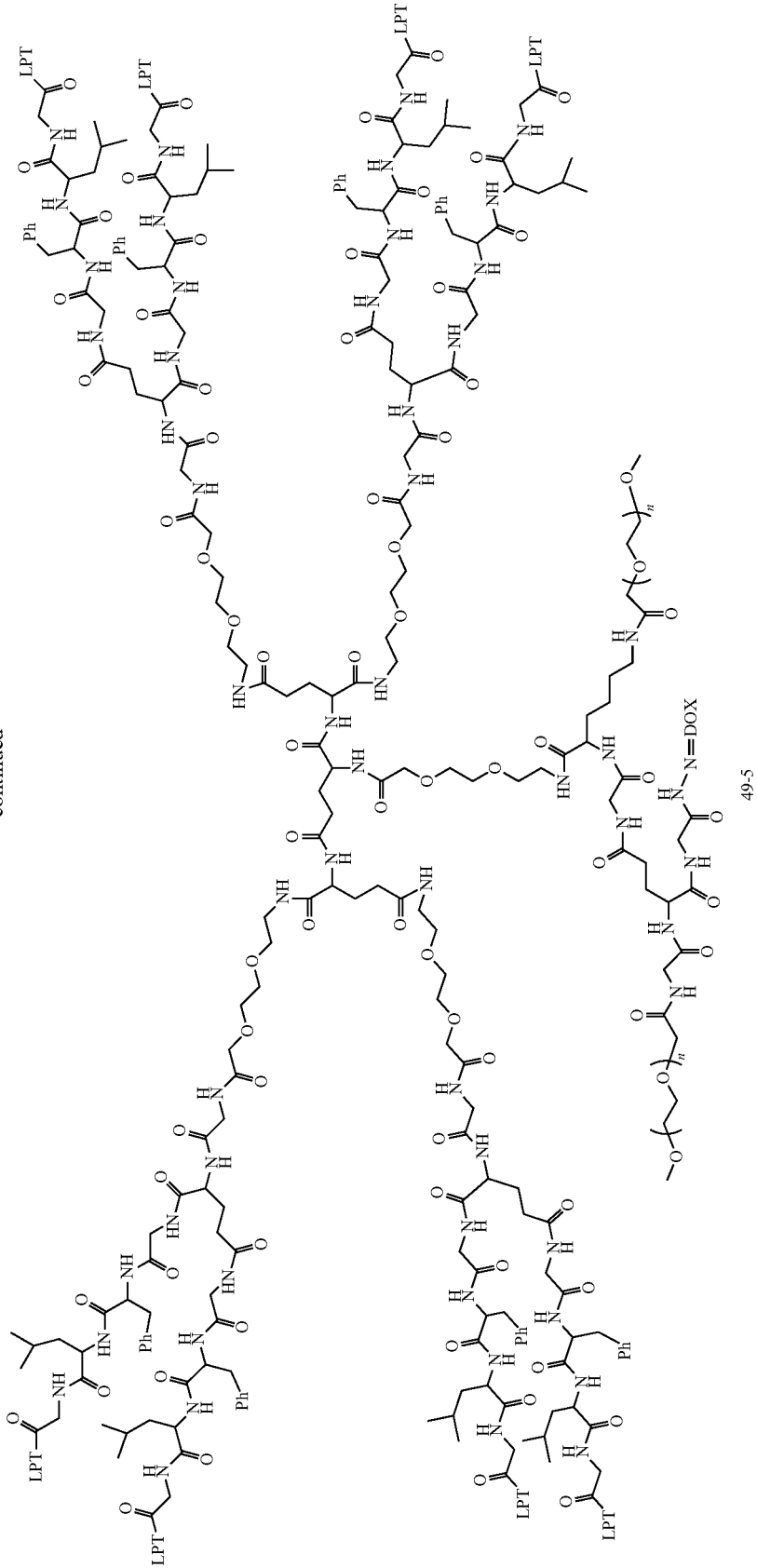
49-5

27-216
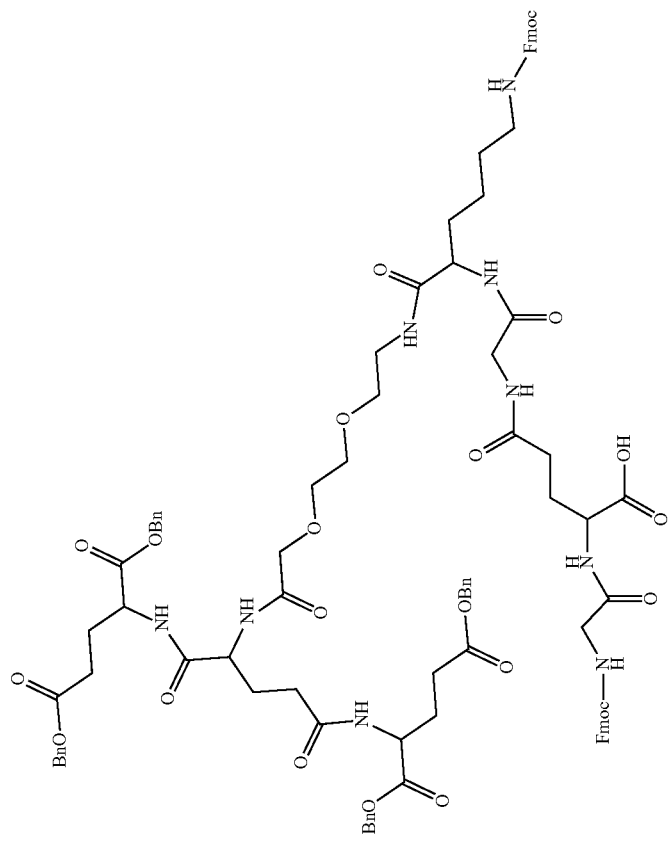

27-202 (3 g, 1.6826 mmol) was added in a 500 mL round-bottomed flask, and dissolved with dichloromethane (50 mL), TFA (1.25 mL, 16.826 mmol) was added, and then the mixed solution was stirred to react at room temperature overnight, At the end of the reaction, the reaction solution was concentrated under reduced pressure, saturated sodium chloride solution (200 mL) and ethyl acetate (200 mL) were added to the obtained solution for extraction, and the organic phase was separated. The aqueous phase was then extracted with ethyl acetate (200 mL×3), and the obtained organic phases were combined. The organic phase was concentrated under reduced pressure, and dried, thus obtaining the product 4.3 g, overweight.

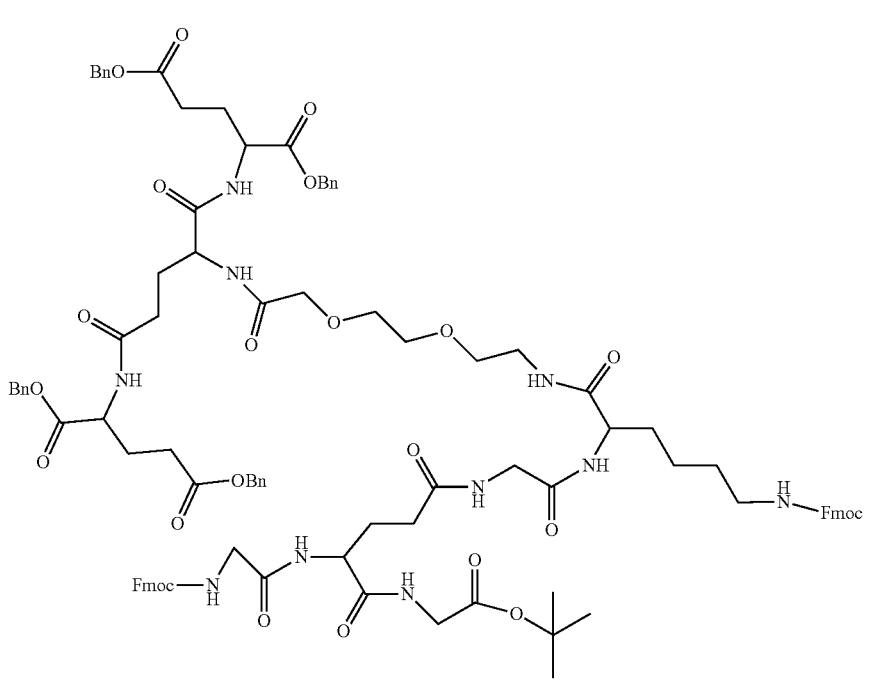

27-218

27-216 (2.90 g, 1.6826 mmol), Gly-OtBu (0.24 g, 1.8509 mmol, purchased from InnoChem), HBTU (0.96 g, 2.5239 mmol) and HOBT (0.34 g, 2.5239 mmol) were added in a 500 mL round-bottomed flask, and dissolved with DMF (100 mL), and then the mixed solution was stirred at −5° C. for 30 minutes. Then DIEA (1.25 mL, 7.5717 mmol) was slowly added dropwise. At the end of the addition, the obtained solution reacted at −5° C. for 2 hours, and was then moved to room temperature and stirred to react overnight. At the end of the reaction, saturated sodium chloride solution (200 mL) and ethyl acetate (200 mL) were added to the reaction solution for extraction, and the organic phase was separated. The aqueous phase was then extracted with ethyl acetate (200 mL×3), and the obtained organic phases were combined. The organic phase was concentrated under reduced pressure, and dried in vacuum, thus obtaining the product 6.6 g, overweight.

27-221

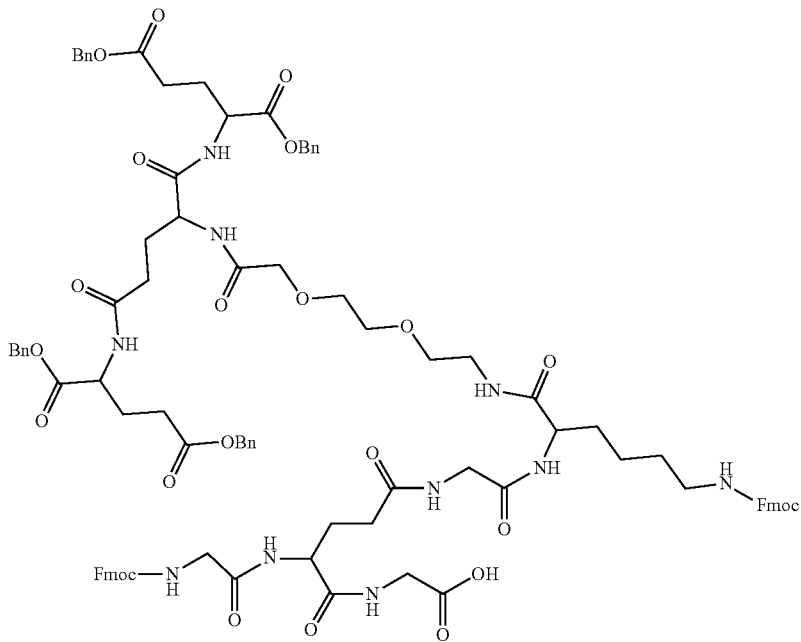

27-218 (2 g, 1.0867 mmol) was added in a 500 mL round-bottomed flask, and dissolved with dichloromethane (50 mL), TFA (0.81 mL, 10.867 mmol) was added, and then the mixed solution was stirred to react at room temperature overnight, At the end of the reaction, the reaction solution was concentrated under reduced pressure, saturated sodium chloride solution (200 mL) and ethyl acetate (200 mL) were added to the reaction solution for extraction, and the organic phase was separated. The aqueous phase was then extracted with ethyl acetate (200 mL×3), and the obtained organic phases were combined. The organic phase was concentrated under reduced pressure, and dried, thus obtaining the product 4.3 g, overweight.

27-224

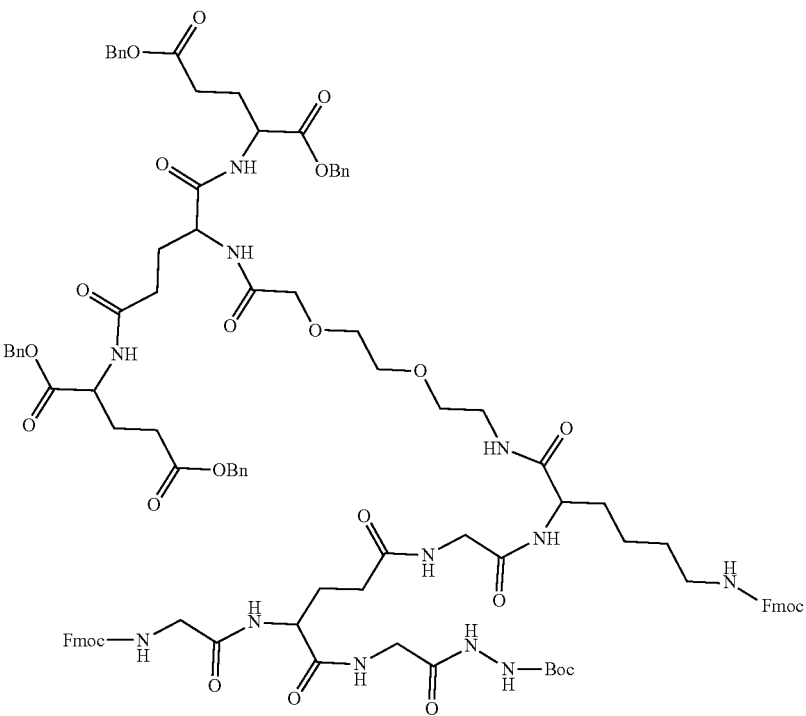

27-221 (1.94 g, 1.0867 mmol) was added in a 500 mL round-bottomed flask, and dissolved with dichloromethane (20 mL) by ultrasonic, Boc-NHNH$_2$ (0.16 g, 1.1954 mmol), DCC (0.67 g, 3.2601 mmol) and DMAP (0.026 g, 0.2173 mmol) were added to the flask, and then the mixed solution was stirred to react at room temperature overnight. At the end of the reaction, saturated saline solution (200 mL) and ethyl acetate (200 mL) were added to the reaction solution for extraction, and the organic phase was separated. The aqueous phase was then extracted with ethyl acetate (200 mL×3), and the obtained organic phases were combined. The organic phase was concentrated under reduced pressure, and the operations of dry sample loading, column chromatography and elution with 3% methanol/dichloromethane were carried out. The elution product was then collected, concentrated, and dried, thus obtaining the product 1.62 g, yield 78.64%.

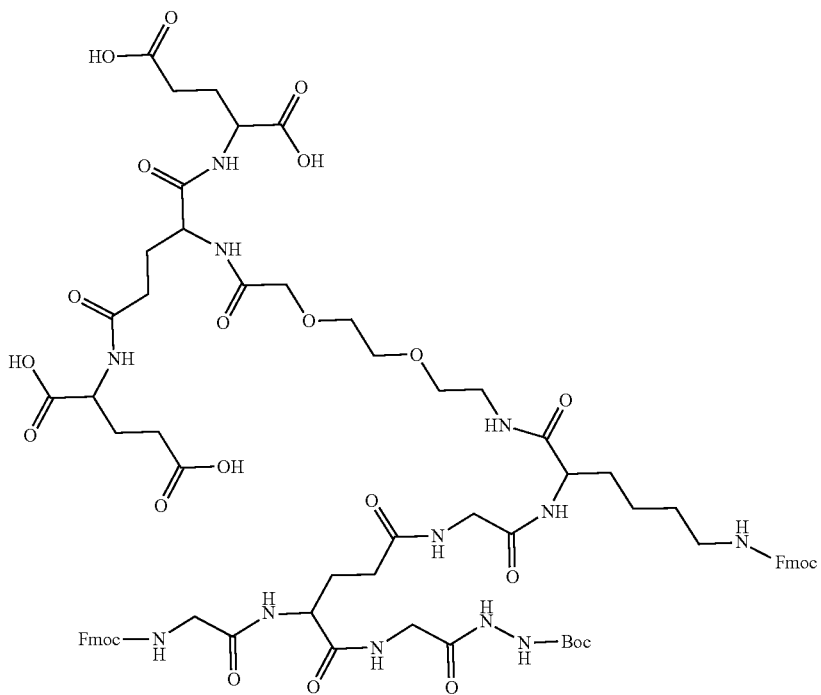

27-259

27-224 (1.62 g, 0.8535 mmol), and 10% Pd/C catalyst (100 mg) were added in a hydrogenation reactor, and dissolved with DMF (30 mL), the hydrogenation reactor was then sealed, hydrogen was introduced to a pressure of 18 psi, and then the mixed solution was stirred to react at room temperature overnight. After the reaction was found to be completed from the monitoring of the TLC, the reaction solution was taken out and evenly added dropwise to a sand core funnel filled with compacted diatomaceous earth, and then suction filtering was carried out. The diatomaceous earth was washed with DMF (30 mL×3), thus obtaining a reaction product solution.

27-205

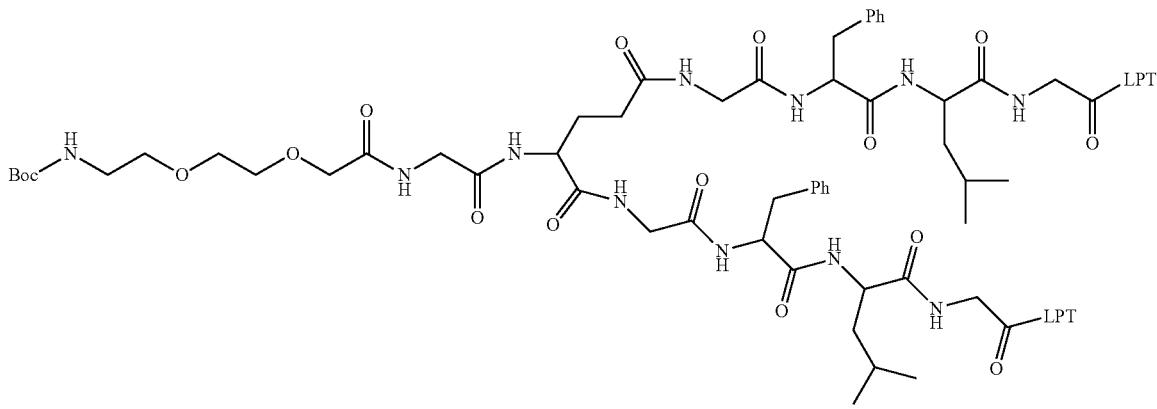

K-11 (0.69 g, 1.4272 mmol), 14-128 (3 g, 3.1398 mmol), HBTU (1.62 g, 4.2816 mmol) and HOBT (0.58 g, 4.2816 mmol) were added in a 500 mL round-bottomed flask, and dissolved with DMF (50 mL), and then the mixed solution was stirred at −5° C. for 30 minutes. Then DIEA (2.12 mL, 12.8448 mmol) was slowly added dropwise. At the end of the addition, the obtained solution reacted at −5° C. for 2 hours, and was then moved to room temperature and stirred to react overnight. At the end of the reaction, n-hexane (50 mL) and methyl tert-butyl ether (400 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dried, thus obtaining the product 5.1 g, weighed.

27-205 (3.03 g, 1.4272 mmol) was added in a 500 mL round-bottomed flask, and dissolved with dichloromethane (50 mL), TFA (1.06 mL, 14.272 mmol) was added, and then the mixed solution was stirred to react at room temperature overnight, At the end of the reaction, the reaction solution was concentrated under reduced pressure, n-hexane (50 mL) and methyl tert-butyl ether (400 mL) were added to the obtained solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 8% methanol/1% ammonia water/dichloromethane were carried out. The elution product was then collected, concentrated, and dried, thus obtaining the product 2 g, yield 69.20%.

27-231

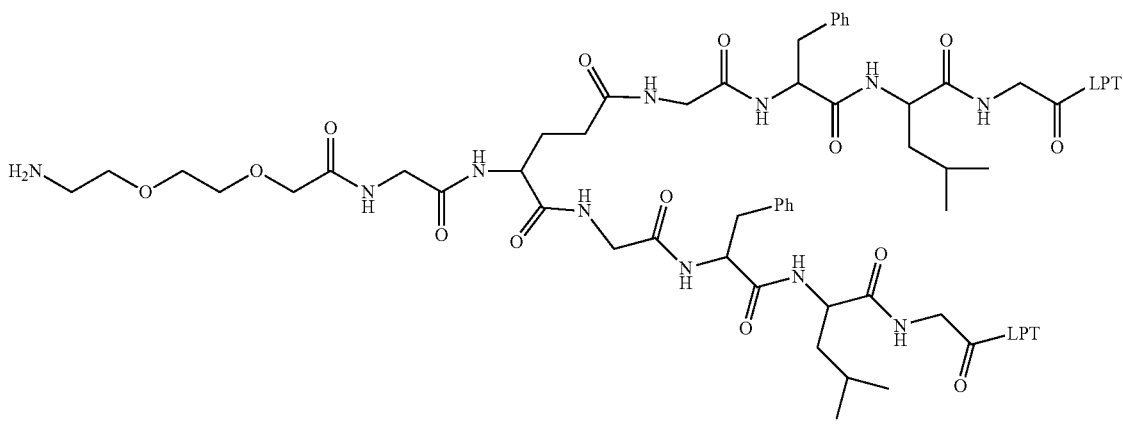

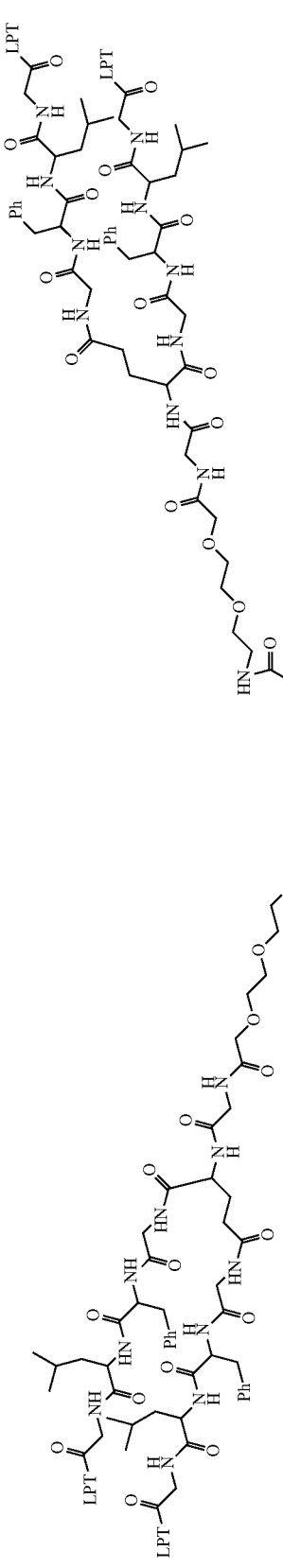
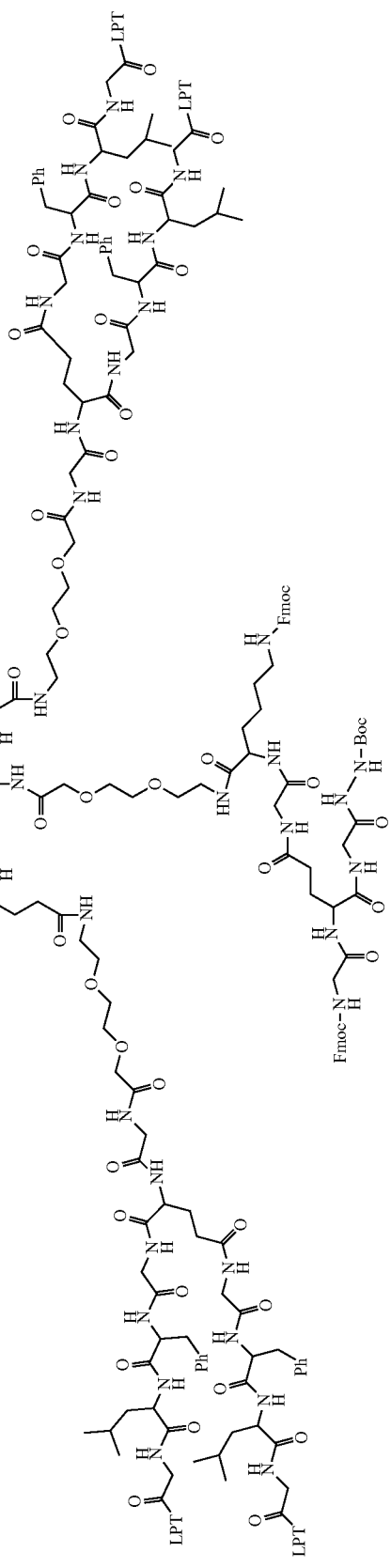

27-259 (0.35 g, 0.2248 mmol), 27-231 (2 g, 0.9891 mmol), HBTU (0.51 g, 1.3488 mmol) and HOBT (0.18 g, 1.3488 mmol) were added in a 500 mL round-bottomed flask, and dissolved with DMF (100 mL), and then the mixed solution was stirred at −5° C. for 30 minutes. Then DIEA (0.67 mL, 4.0464 mmol) was slowly added dropwise. At the end of the addition, the obtained solution reacted at −5° C. for 2 hours, and was then moved to room temperature and stirred to react overnight. At the end of the reaction, n-hexane (50 mL) and methyl tert-butyl ether (400 mL) were added to the reaction solution for precipitation, the supernatant was discarded, and then n-hexane and methyl tert-butyl ether were added to the obtained solution for precipitation. Such operations were repeated three times. The obtained solid product was dissolved with dichloromethane and methanol, and the operations of dry sample loading, column chromatography and elution with 6% methanol/dichloromethane were carried out. The elution product was then collected, concentrated, and dried, thus obtaining the product 1.3 g, yield 60.46%.

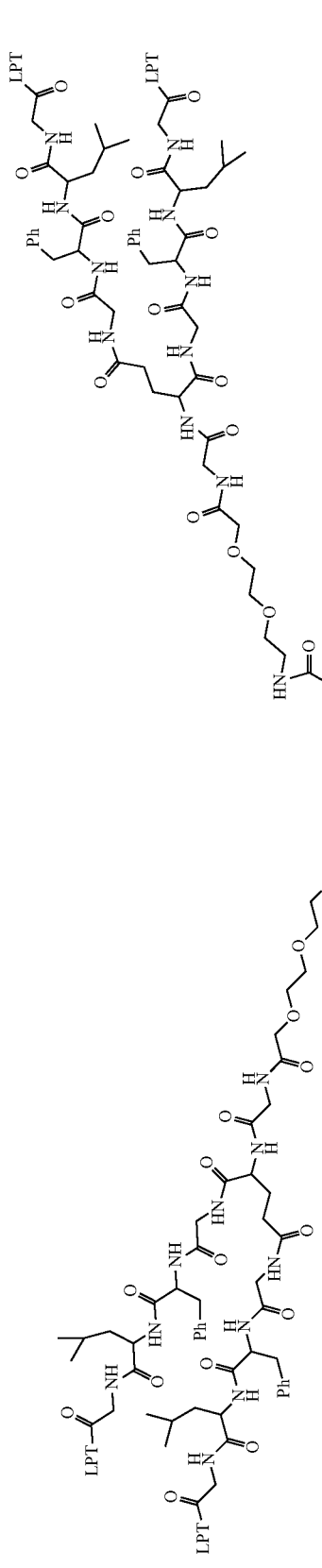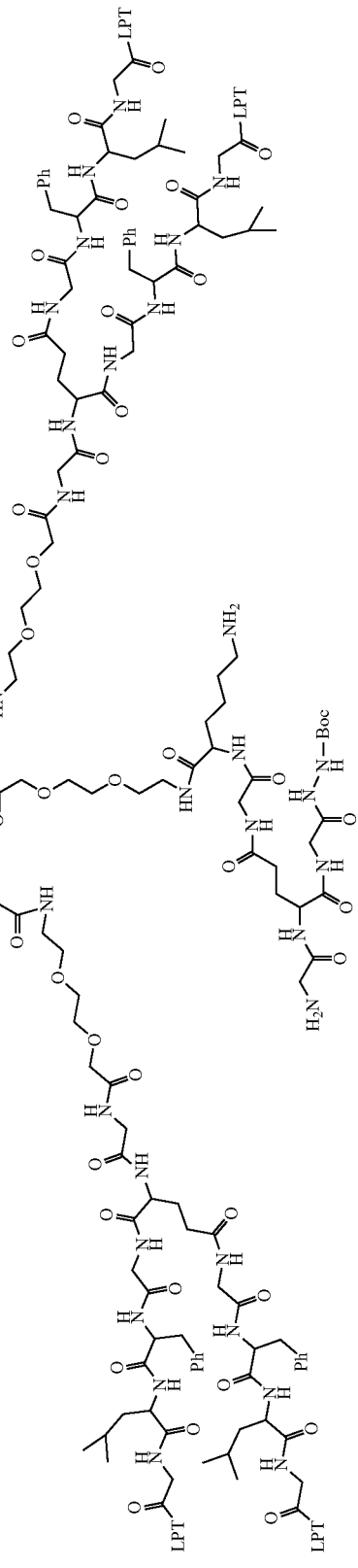

27-260 (1.3 g, 0.1361 mmol) was added in a 500 mL round-bottomed flask, and dissolved with DMF (10 mL), ultrasonic treatment was carried out to completely dissolve the compound, morpholine (0.12 mL, 1.361 mmol) was added, and then the mixed solution was stirred to react at room temperature for 2 hours. At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 6% methanol/dichloromethane were carried out. The elution product was then collected, concentrated, and dried, thus obtaining the product 0.91 g, yield 73.39%.

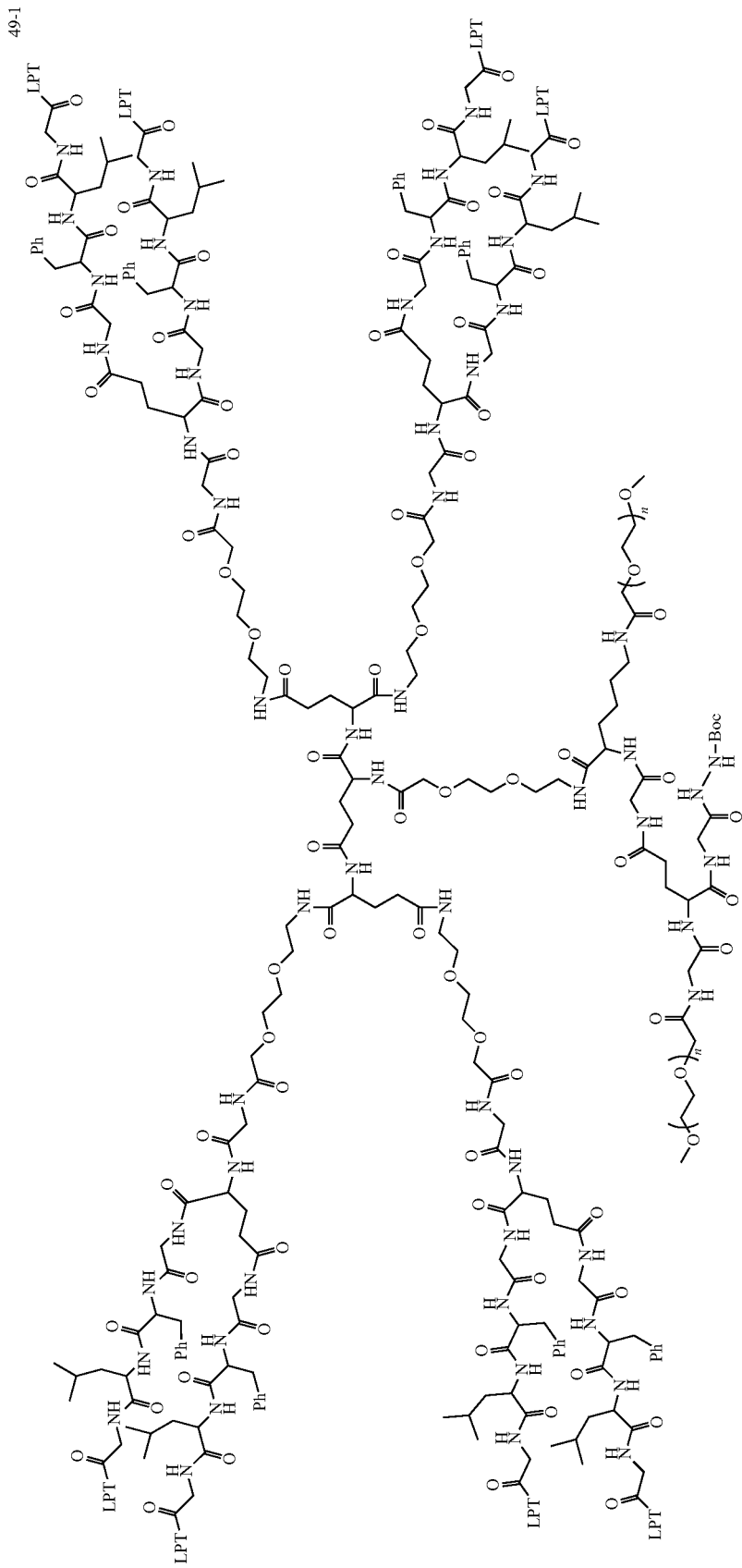

49-265 (0.91 g, 0.0999 mmol) was added in a 250 mL flask, and dissolved with DMF (20 mL), M-SCM-5K (1.14 g, 0.2198 mmol, purchased from JenKem) was added, ultrasonic vibration was carried out to dissolve the compound, and then the mixed solution reacted in the dark for one week at a low speed of stirring at room temperature. At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 9% methanol/dichloromethane were carried out. The elution product was then collected, concentrated, and dried, thus obtaining the product 1.23 g, yield 63.07%.

$^1$H-NMR (600 MHz, DMSO-$d_6$) δ9.85-9.79 (m, 6H), 8.77-8.71 (m, 7H), 8.55-7.91 (m, 63H), 7.89-7.63 (m, 23H), 7.47-6.98 (m, 93H), 6.69-6.54 (s, 7H), 5.27-5.21 (m, 14H), 4.72-4.57 (m, 20H), 4.41-4.12 (m, 32H), 3.85-3.79 (m, 43H), 3.55-3.48 (m, 1115H), 3.27-3.12 (m, 19H), 3.09-2.95 (m, 32H), 2.90-2.60 (m, 32H), 2.14-1.70 (m, 31H), 1.54-1.14 (m, 95H), 0.86-0.79 (m, 51H).

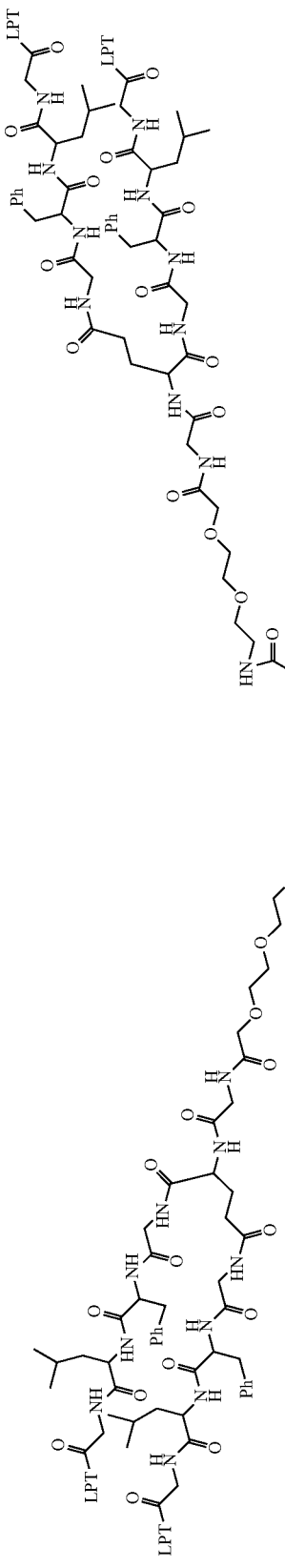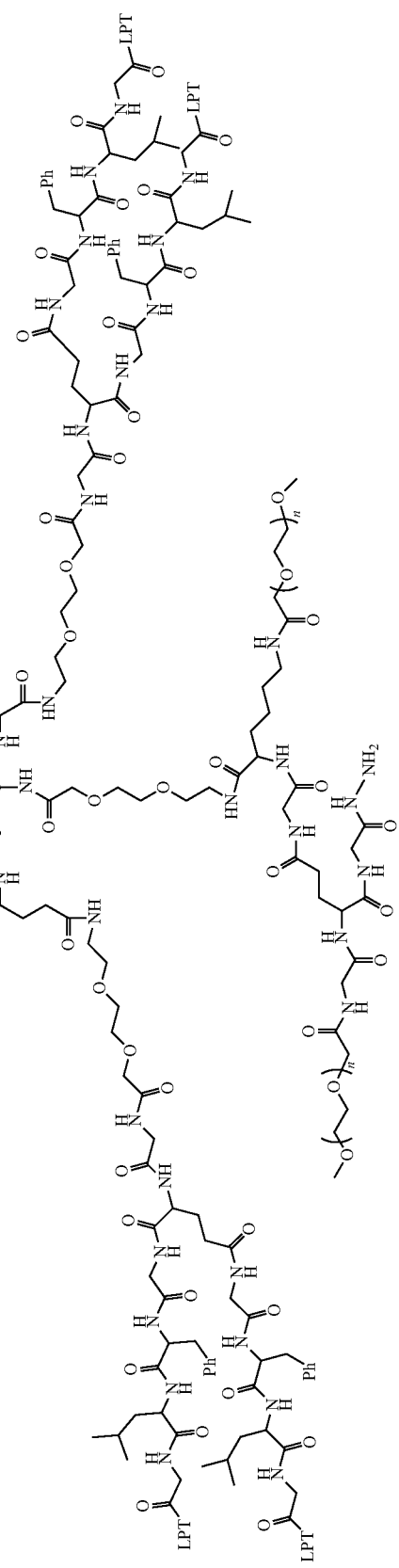

49-1 (1.23 g, 0.0632 mmol) was added in a 500 mL round-bottomed flask, and dissolved with dichloromethane (20 mL), TFA (0.094 mL, 1.264 mmol) was added, and then the mixed solution was stirred to react at room temperature overnight, At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 9% methanol/dichloromethane were carried out. The elution product was then collected, concentrated, and dried, thus obtaining the product 0.98 g, yield 80.33%.

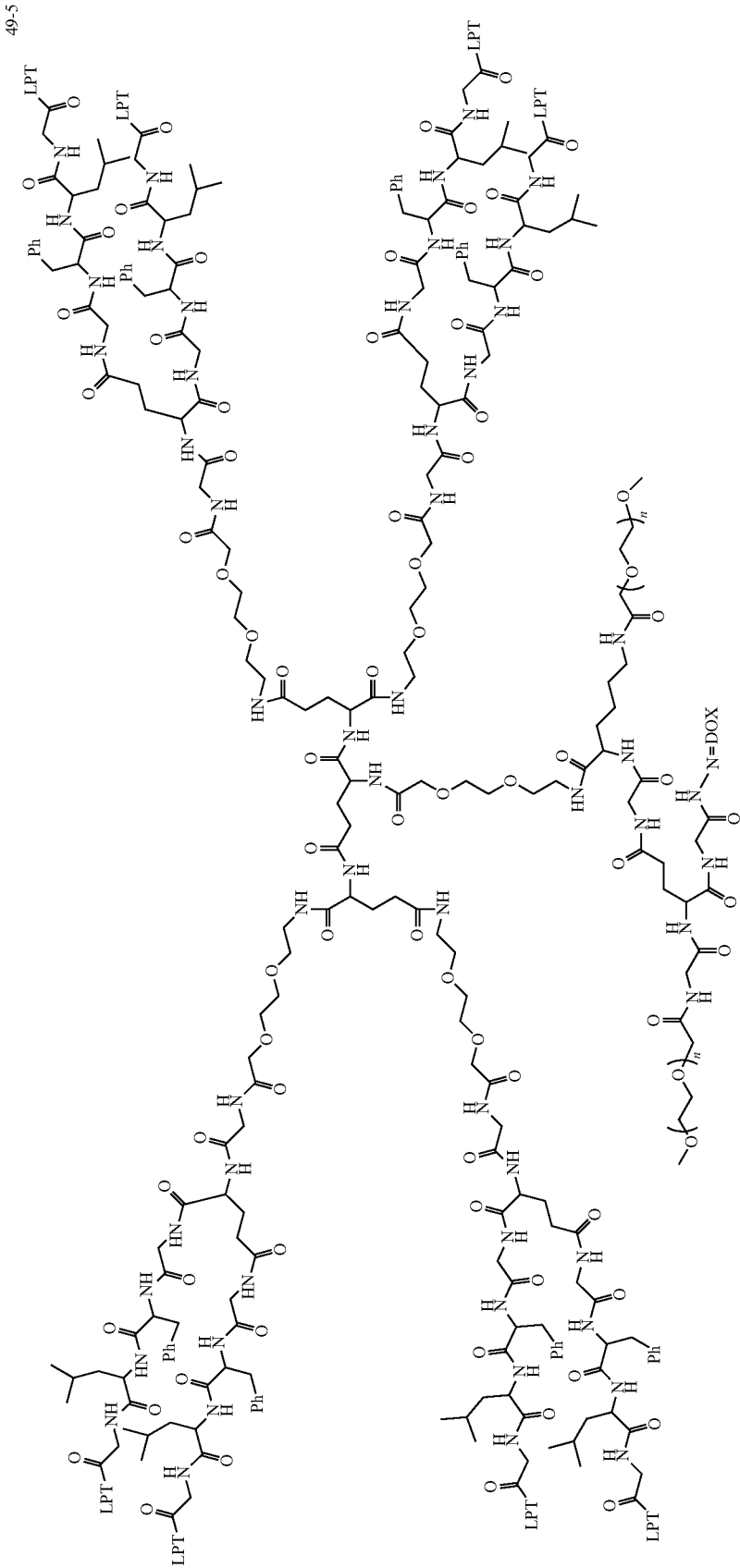

49-3 (0.98 g, 0.0506 mmol) was added in a 500 mL dried round-bottomed flask, and dissolved with anhydrous methanol (10 mL), TFA (0.018 mL, 0.253 mmol) and adriamycin (also referred to as DOX, 0.028 g, 0.0506 mmol) were added, and then the mixed solution was stirred to react at room temperature overnight, At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. A solid product was obtained by suction filtering, and dissolved with dichloromethane and methanol. The operations of dry sample loading, column chromatography and elution with 9% methanol/dichloromethane were carried out. The elution product was then collected, concentrated, and dried. The obtained dry product was dissolved with anhydrous alcohol (5 mL) and dichloromethane (1 mL), and the obtained solution was precipitated with methyl tert-butyl ether (40 mL). Such operations were repeated three times. Filtering was carried out, and the filter cake was dried, thus obtaining the product 0.65 g, yield 65%, wherein the formation of hydrazone bond occurred at carbonyl in position 13 of adriamycin.

$^1$H-NMR (600 MHz, DMSO-$d_6$) δ 10.28 (s, 5H), 8.98-8.94 (m, 8H), 8.58-8.51 (m, 8H), 8.34-7.92 (m, 79H), 7.49-7.45 (m, 10H), 7.46-7.10 (m, 82H), 6.68 (s, 5H), 6.54 (s, 3H), 5.26 (s, 20H), 4.80-4.71 (m, 16H), 4.56 (s, 10H), 4.41-4.06 (m, 42H), 3.95-3.74 (m, 45H), 3.52-3.50 m, 1289H), 3.11-2.97 (m, 57H), 2.78-2.74 (m, 26H), 2.11 (s, 26H), 1.60-1.52 (m, 40H), 1.00-0.61 (m, 72H).

19. Synthesis of 39-42 (Compound No. 19)

Synthetic route is as follows

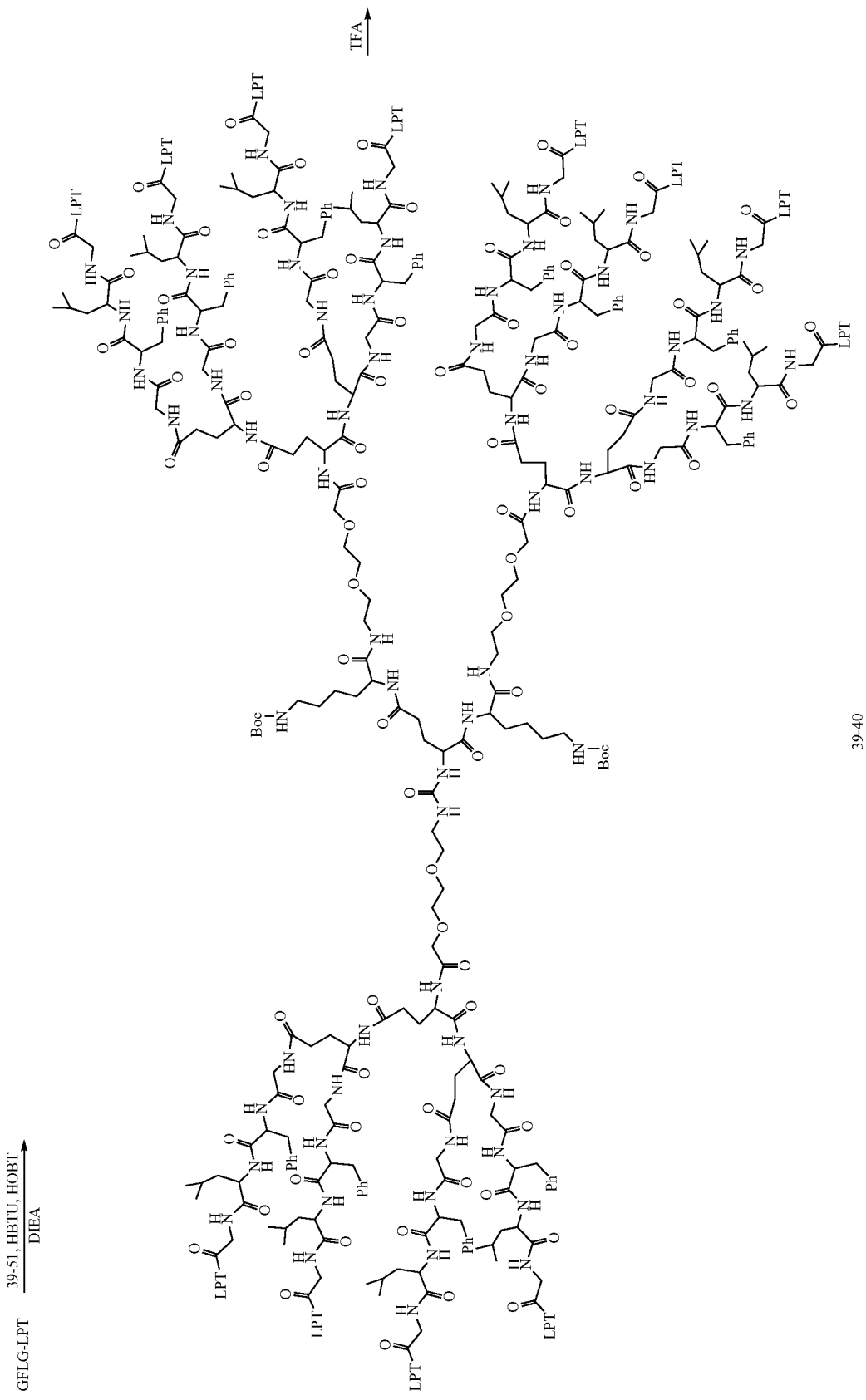

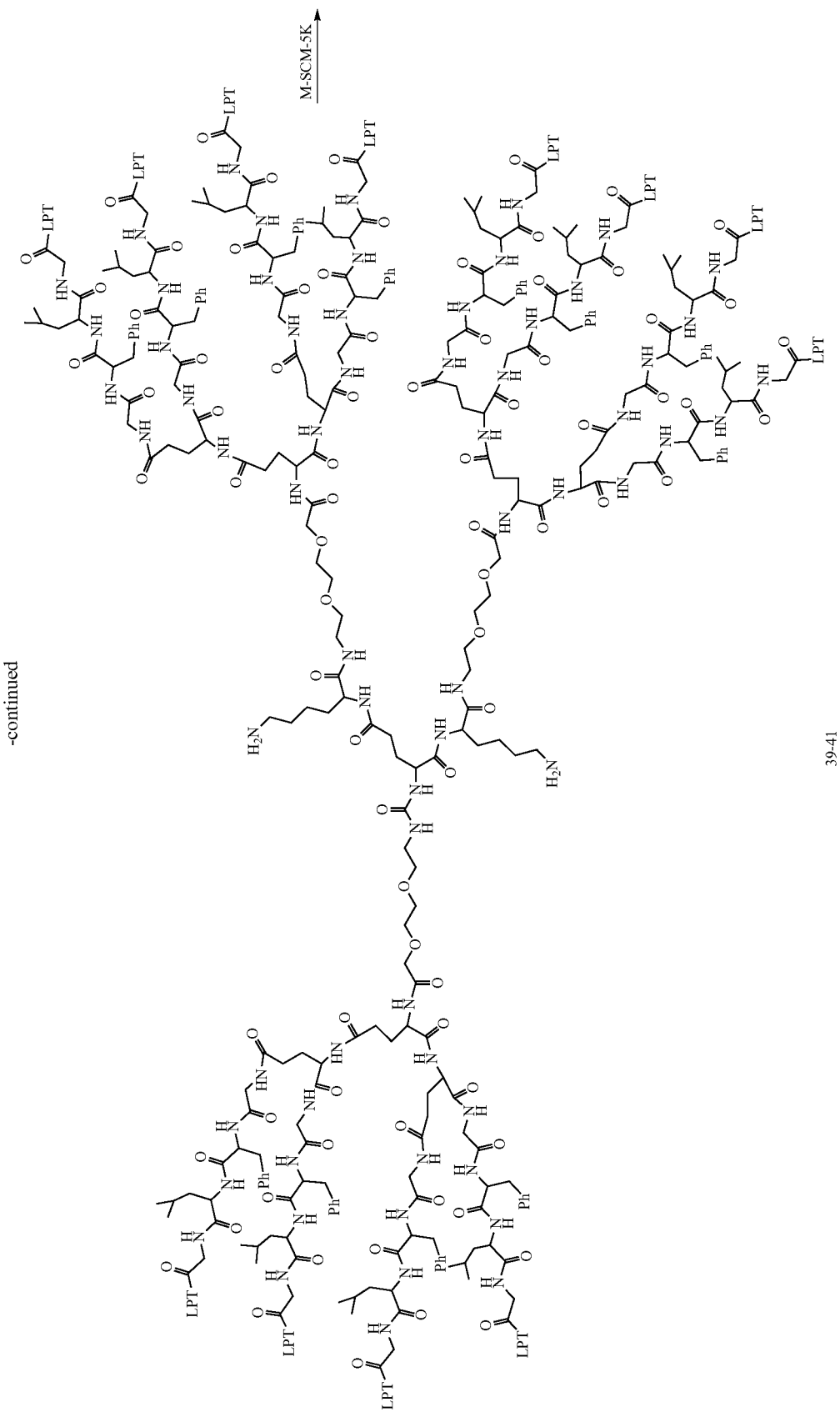
39-41

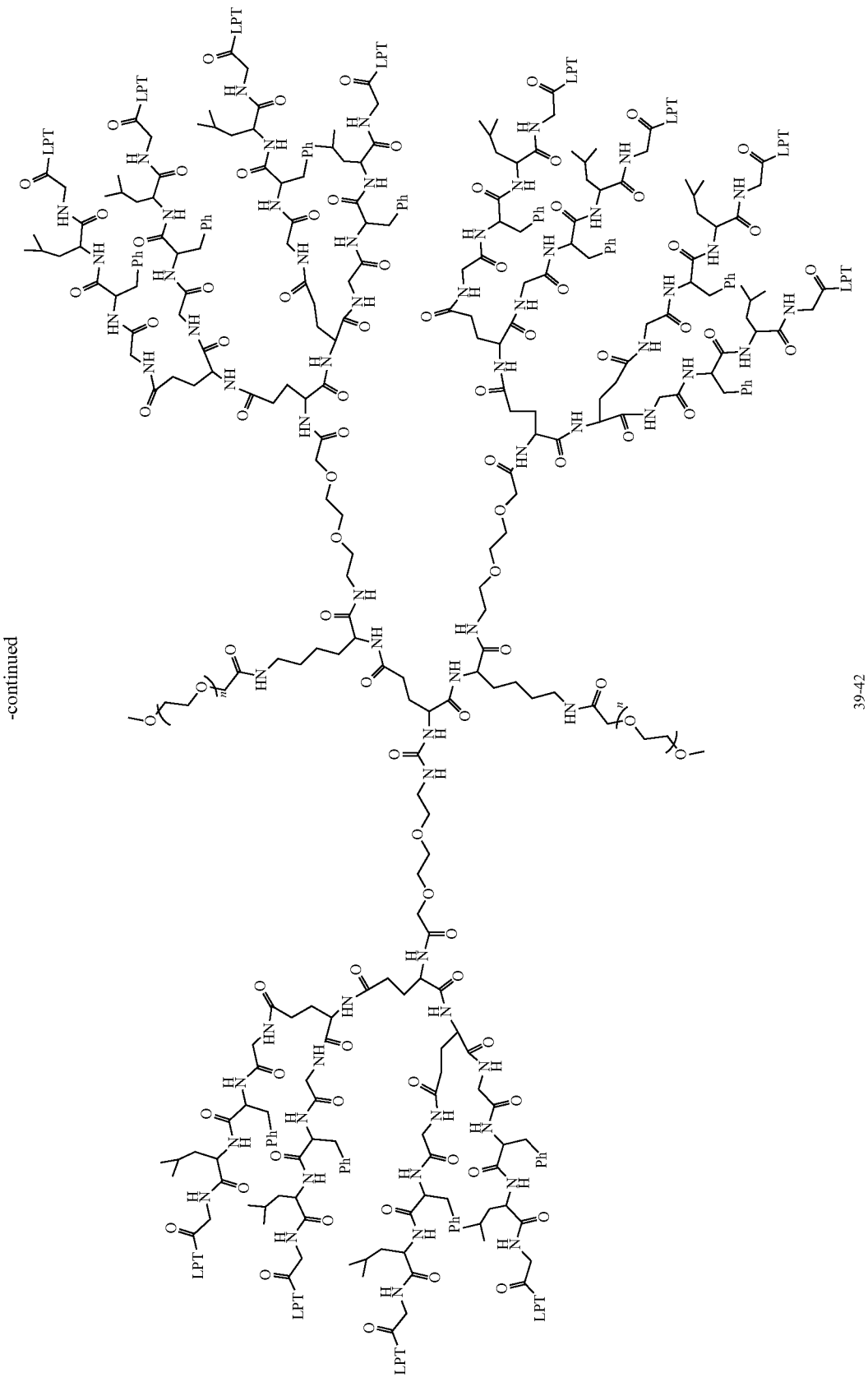

39-40
-continued
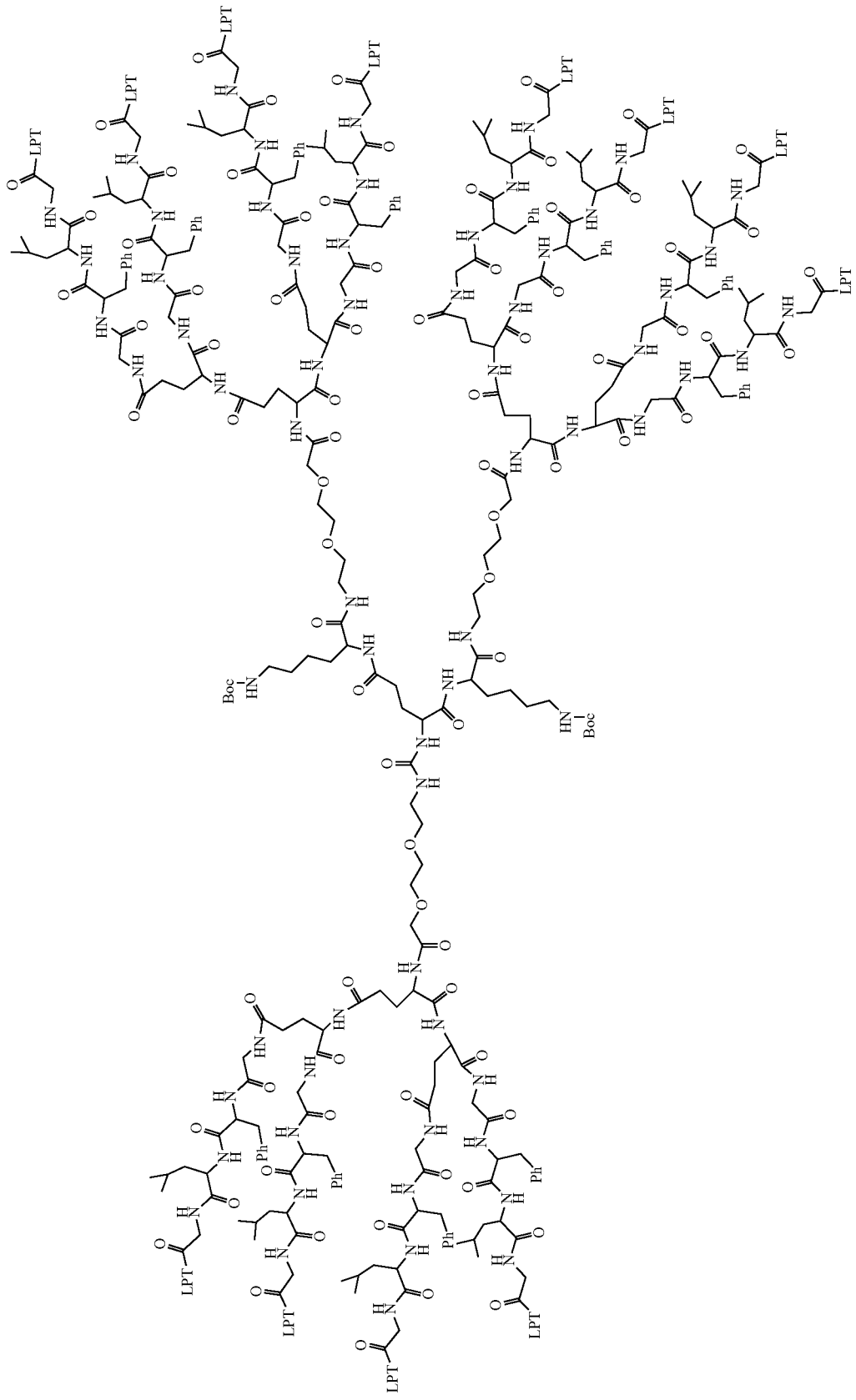

GFLG-LPT (1.0 g, 1.04 mmol, synthesized according to the method of synthesizing 14-128), 39-51 (0.08 mmol), HBTU (0.54 g, 1.44 mmol), HOBT (0.19 g, 1.44 mmol) were added in a 250 mL flask, and dissolved with DMF (30 mL), and ultrasonic treatment was carried out to completely dissolve the reactants, and then the mixed solution was stirred at −5° C. for 30 minutes. Then DIEA (0.71 mL, 4.32 mmol) was slowly added dropwise, and the obtained solution was stirred at the low temperature for 2 hours, and then reacted at room temperature until the reaction ended. At the end of the reaction, methyl tert-butyl ether (250 mL) was added to the reaction solution, ultrasonic treatment was carried out for 5 minutes, the supernatant was discarded, ethyl acetate (20 mL) was added to the lower liquid, ultrasonic treatment was carried out for 3 minutes, methyl tert-butyl ether (150 mL) and n-hexane (100 mL) were added to separate out a solid, and suction filtering was carried out. The filter cake was dissolved with 20% methanol/dichloromethane (20 mL), silica gel powder (10 g) was added, and the operations of evaporation, column chromatography and gradient elution with 3% methanol/dichloromethane-10% methanol/dichloromethane were carried out, thus obtaining the product 0.2 g.

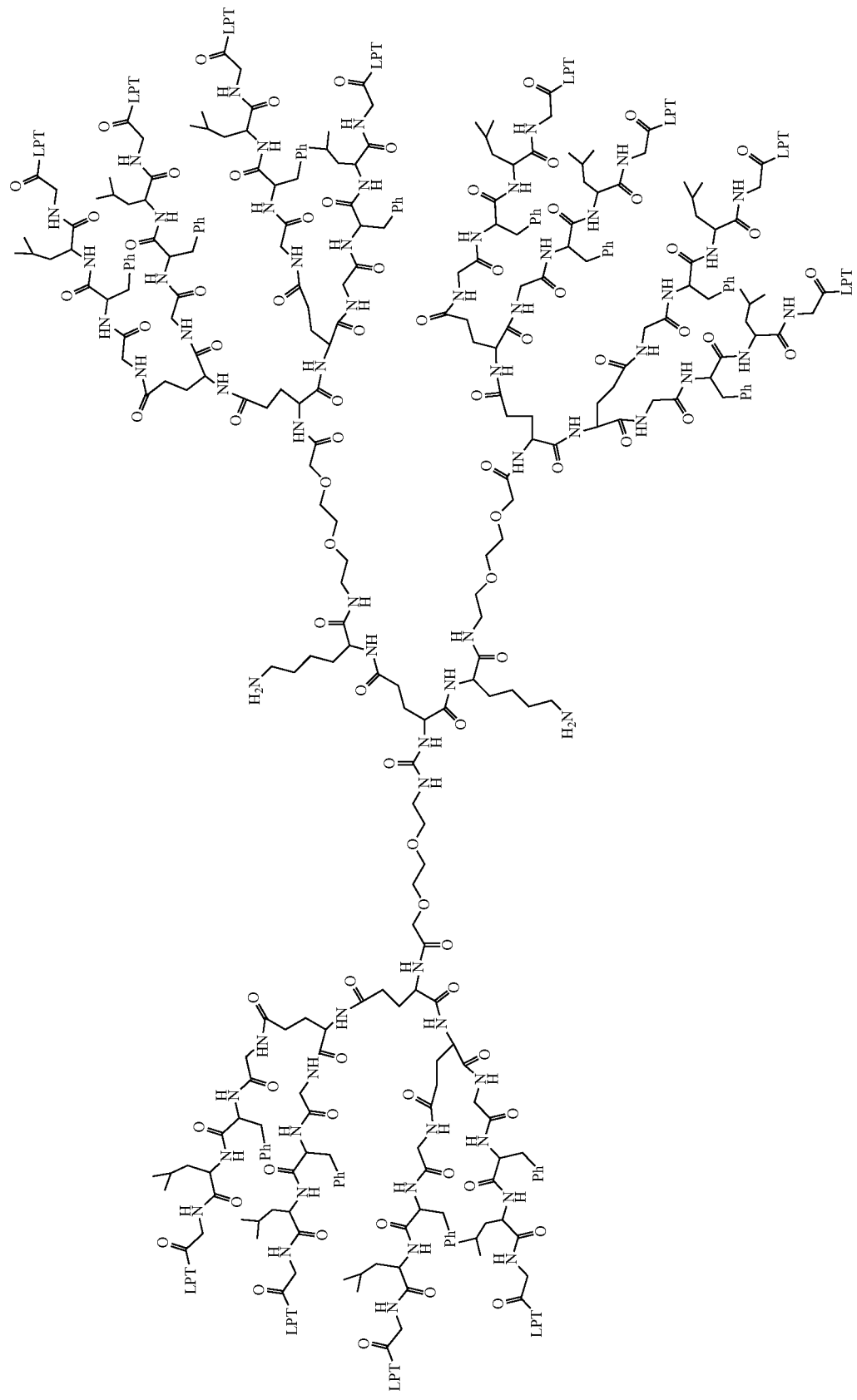

39-40 (0.2 g) was dissolved with dichloromethane (15 mL), and TFA (0.033 mL, 0.444 mmol), and ultrasonic treatment was carried out to completely dissolve the compound. A ground glass stopper was used, and the mixed solution was stirred to react at room temperature. At the end of the reaction, the reaction solution was evaporated to remove the dichloromethane, ethyl acetate (20 mL) was added, ultrasonic treatment was carried out for 2 minutes, and then methyl tert-butyl ether (150 mL) and n-hexane (70 mL) were added for precipitation to separate out a solid. Suction filtering was carried out, and the filter cake was dried in vacuum, thus obtaining the product 0.2 g.

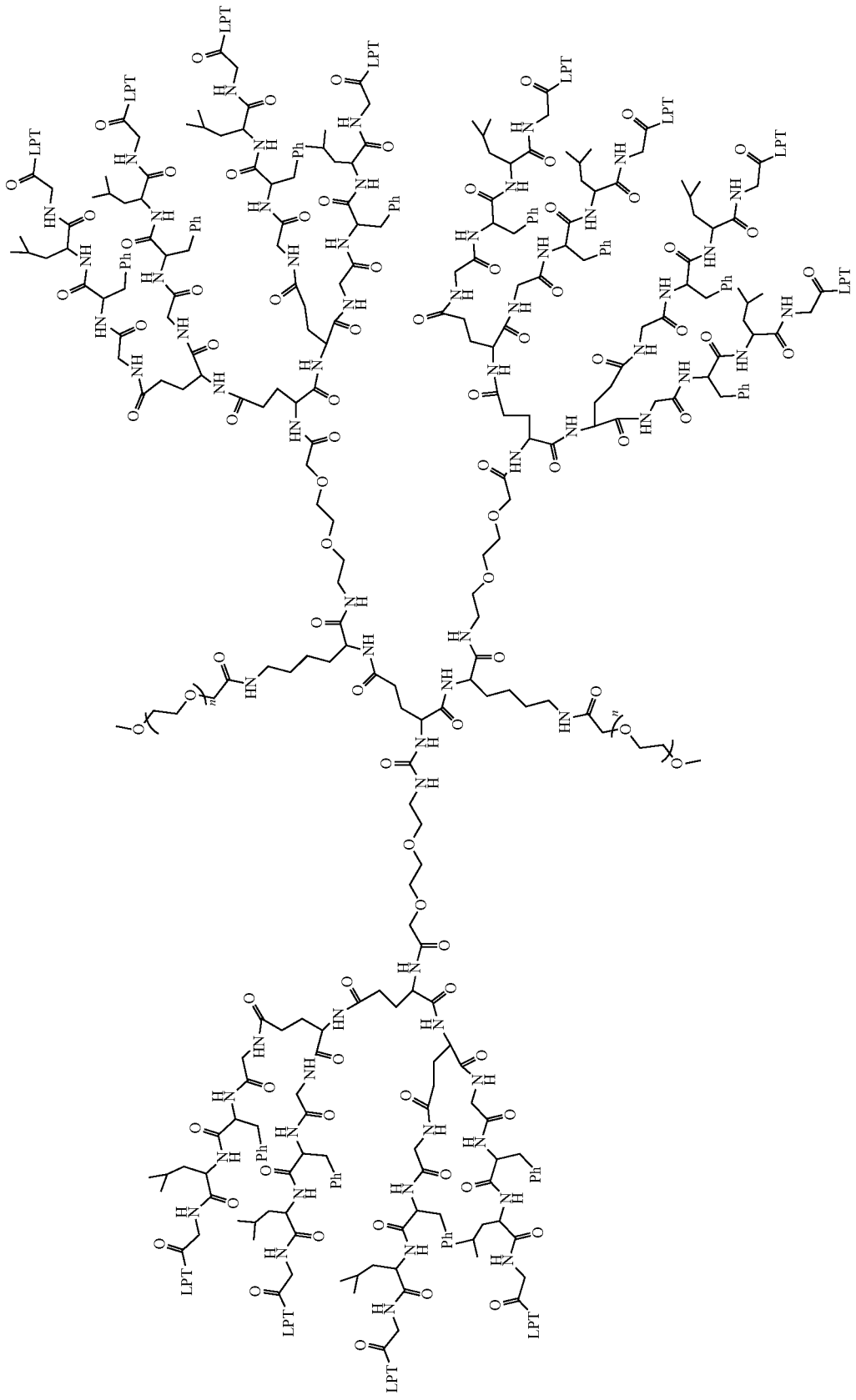

39-41 (0.6 g) was dissolved with DMF (20 mL) and M-SCM-5K (0.9378 g) was added, and ultrasonic treatment was carried out to dissolve the reactants, and then the obtained solution reacted in the dark at a low speed. At the end of the reaction, methyl tert-butyl ether (150 mL), n-hexane (70 mL) were added to the reaction solution to separate out a solid, and suction filtering was carried out. The filter cake was dissolved with 20% methanol/dichloromethane, silica gel powder (10 g) was added, the operations of evaporation, column chromatography and gradient elution with 1% ammonia water: 4% methanol dichloromethane-1% ammonia water: 8% methanol/dichloromethane were carried out. The elution product was collected, evaporated to dryness, and dissolved with anhydrous ethanol (3 mL), and the obtained solution was then treated by ultrasonic to obtain homogeneous phase. Then, methyl tert-butyl ether (150 mL), n-hexane (50 mL) were added to the obtained solution, and suction filtering was carried out. The filter cake was further dissolved with anhydrous ethanol (3 mL), and precipitated with methyl tert-butyl ether and n-hexane. The process of dissolution and precipitation was repeated three times. Suction filtering was carried out, and the filter cake was dried, thus obtaining the product 0.15 g.

$^1$H-NMR (400 MHz, DMSO-$d_6$) δ10.06-9.84 (m, 3H), 8.84-8.36 (m, 4H), 8.29-7.65 (m, 85H), 7.57-6.79 (m, 187H), 6.73-6.51 (m, 15H), 4.83-4.07 (m, 86H), 3.50-3.49 (m, 512H), 3.08-2.99 (m, 81H), 1.70-1.17 (m, 125H), 0.90-0.80 (m, 72H).

20. Synthesis of 41-32 (Compound No. 20)

Synthetic route is as follows

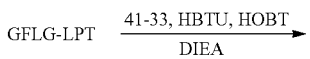

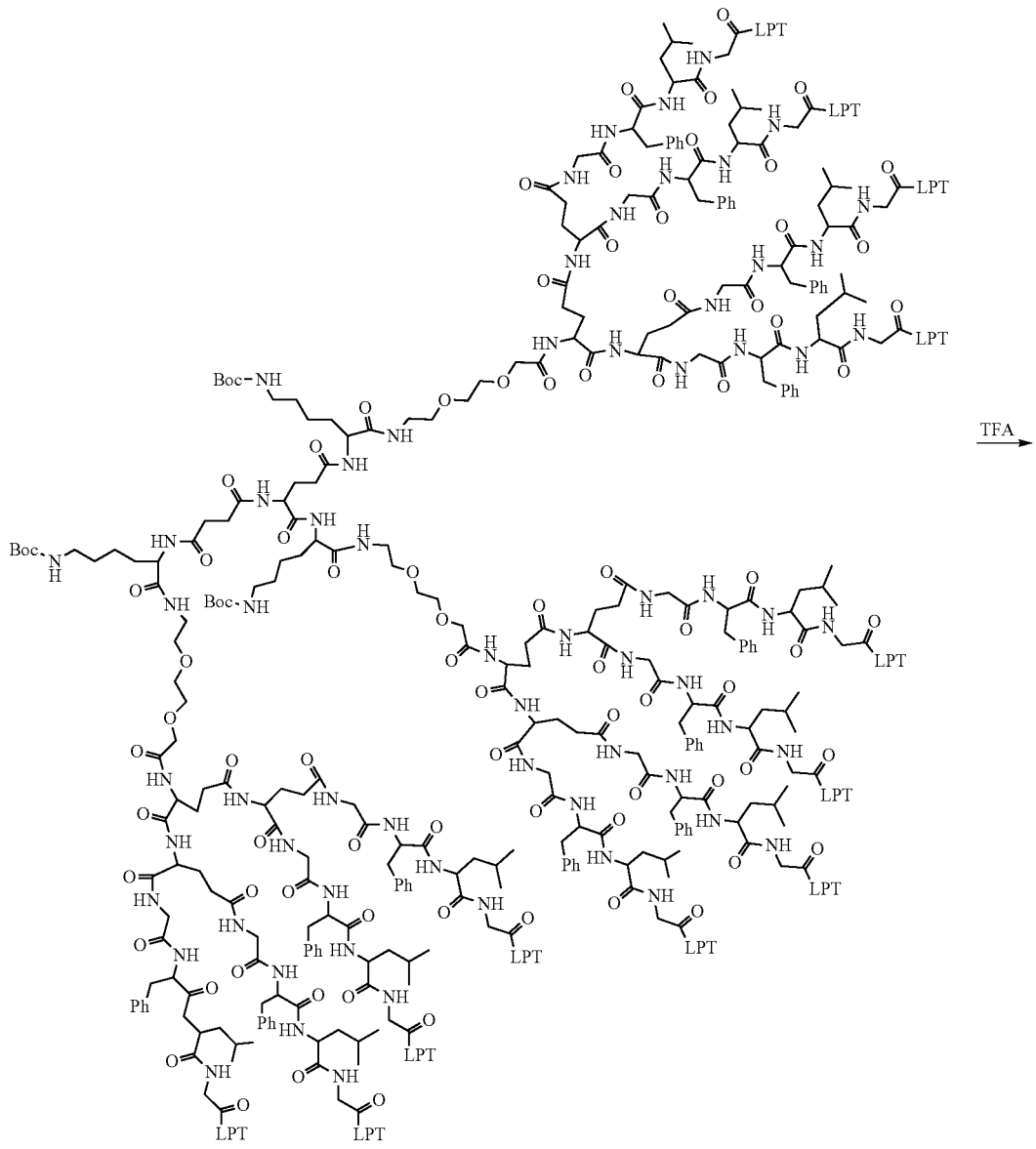

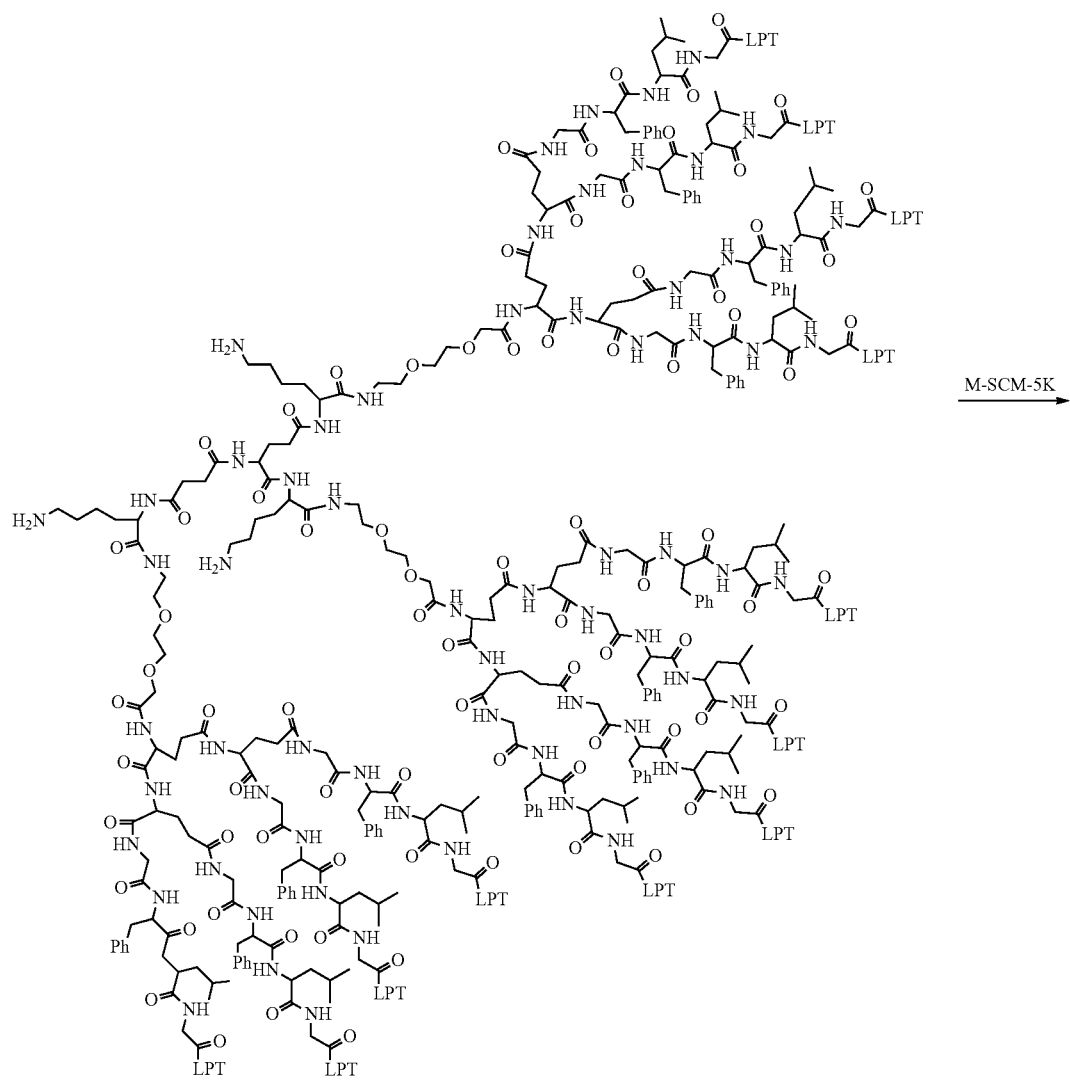
41-31

-continued
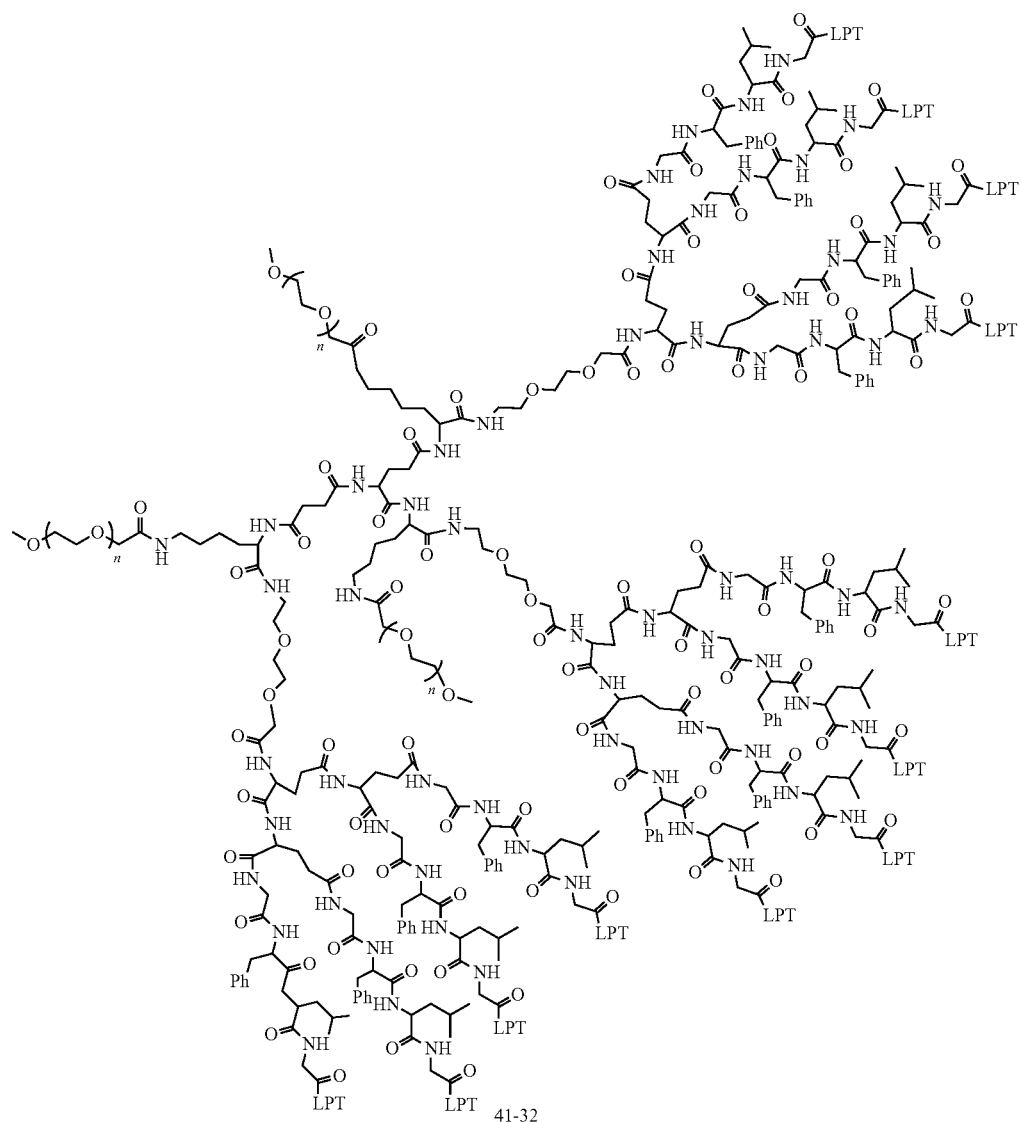
41-32

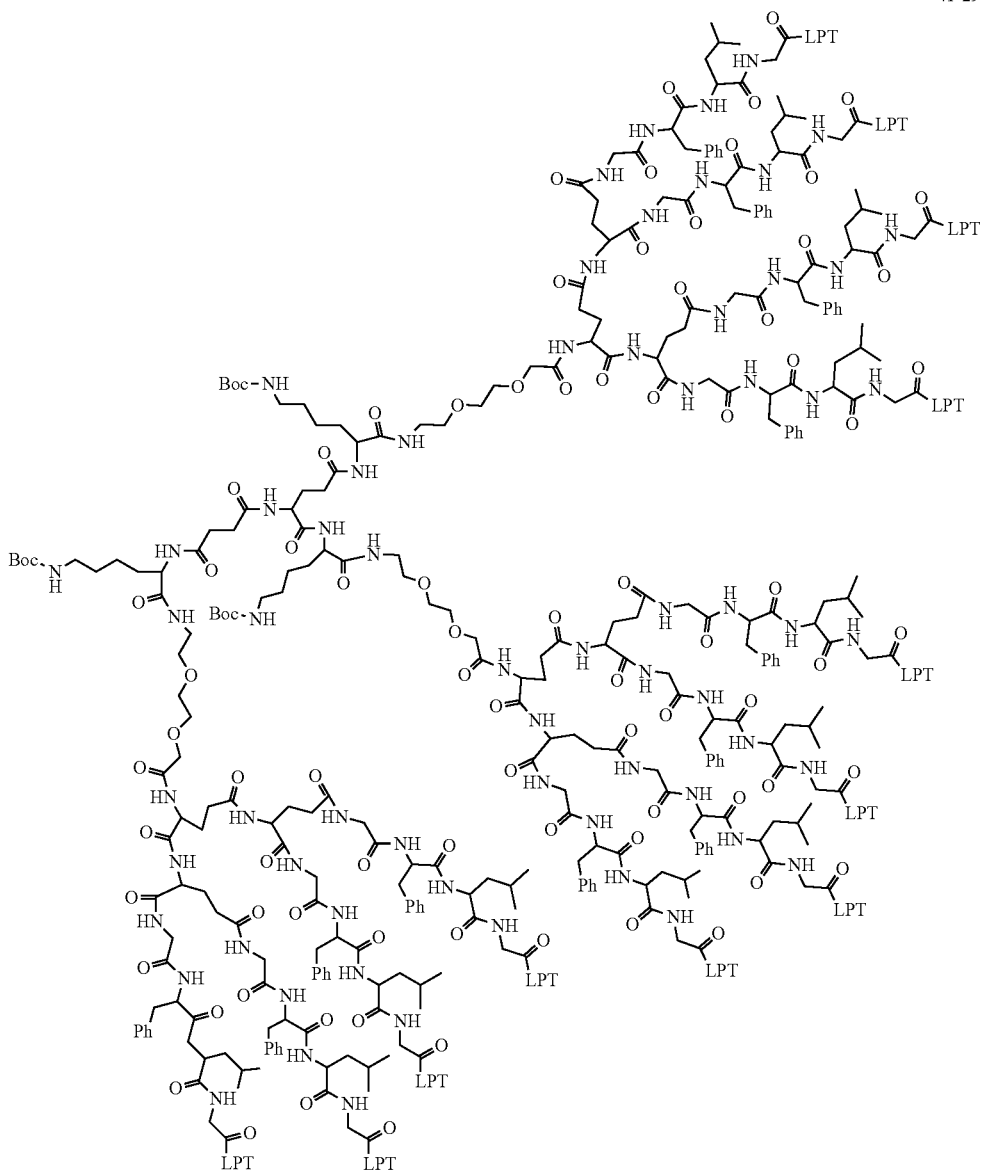

41-29

Reactants GFLG-LPT (1.0 g, 1.48 mmol, synthesized according to the method of synthesizing 14-128), 41-33 (0.077 mmol), HBTU (0.35 g, 0.924 mmol), HOBT (0.1 g, 0.924 mmol) were added in a 250 mL flask, and dissolved with DMF (30 mL), and then the mixed solution was stirred at −5° C. for 30 minutes. Then DIEA (0.45 mL, 2.772 mmol) was slowly added dropwise, and the obtained solution reacted at the low temperature until the reaction ended. At the end of the reaction, methyl tert-butyl ether (100 mL) and n-hexane (200 mL) were added to the reaction solution for precipitation to obtain a powder product. The operations of column chromatography, dry sample loading, and elution with 1% ammonia water: 2% methanol/dichloromethane— 1% ammonia water: 10% methanol/dichloromethane were carried out, thus obtaining the product 0.6 g.

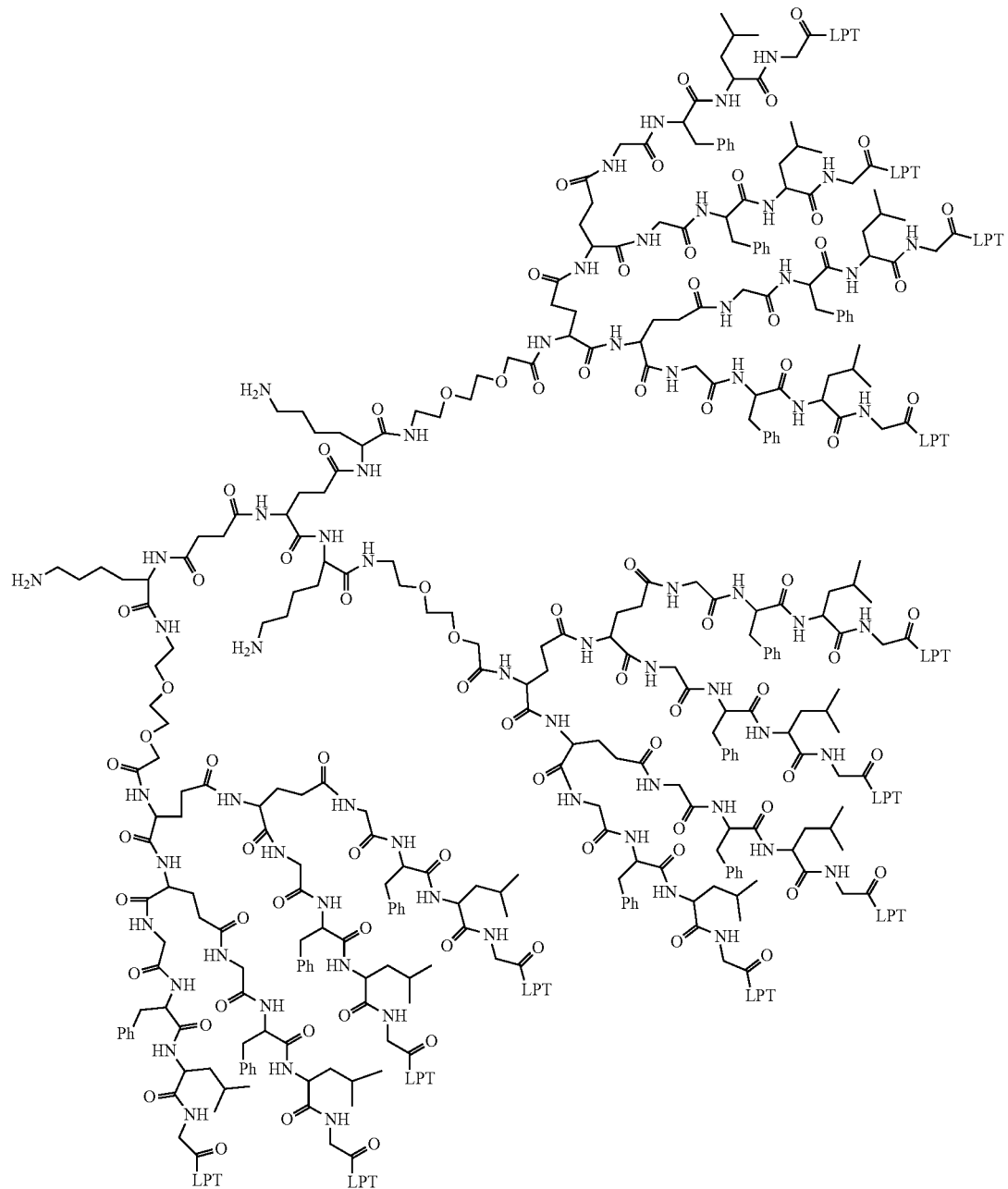

41-31

41-29 (0.6 g) was dissolved with dichloromethane (5 mL) and TFA (0.17 mL, 2.31 mmol) in a condition of ultrasonic, and then the mixed solution was stirred to react. At the end of the reaction, the reaction solution was concentrated, methyl tert-butyl ether (100 mL) and n-hexane (200 mL) were added to the obtained solution for precipitation to obtain a powder. The powder was dried in vacuum, thus obtaining the product 0.6 g.

41-32

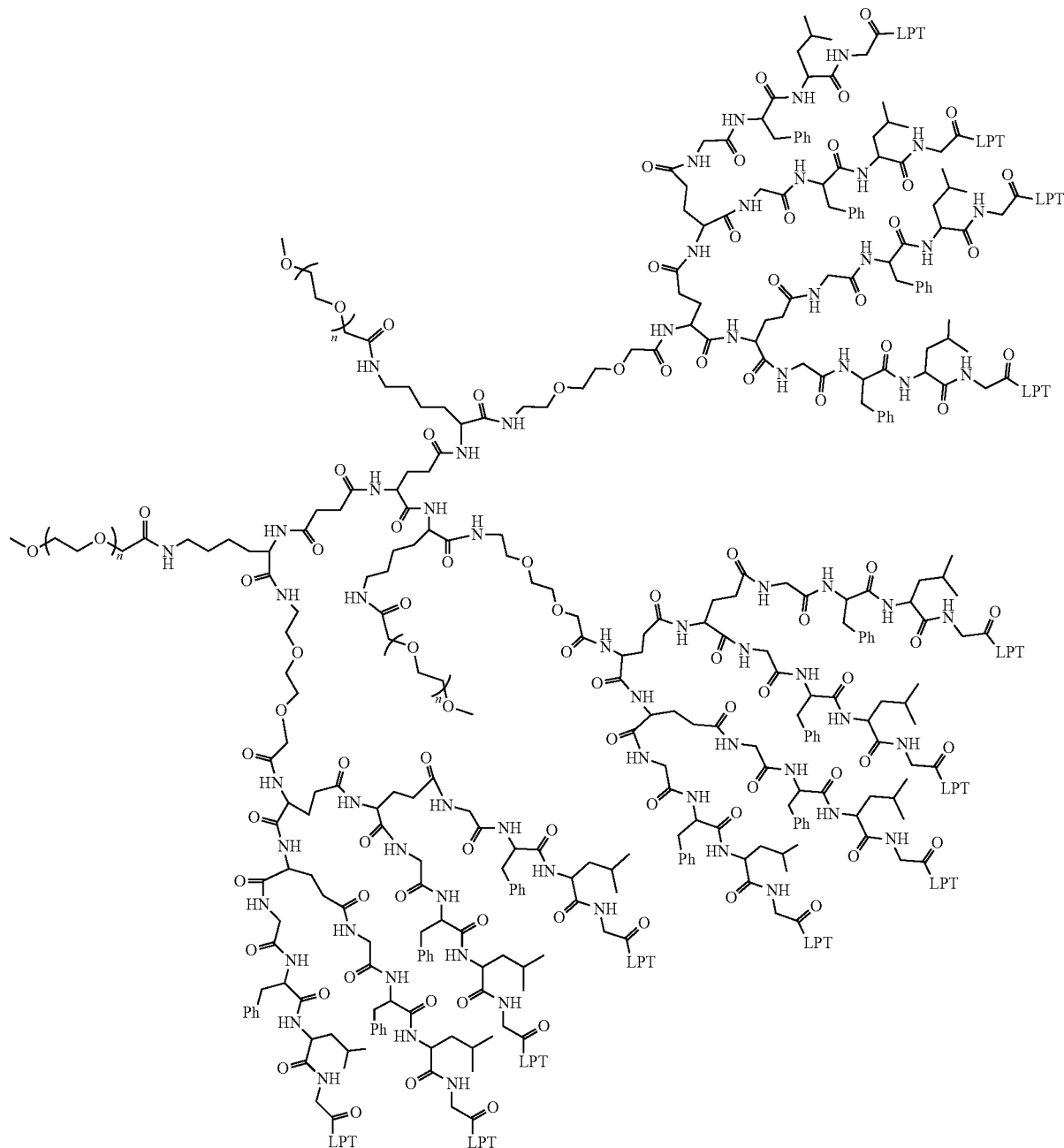

Reactants 41-31 (0.6 g, 0.044 mmol) and M-SCM-5K (1.6 g, 0.30 mmol) were dissolved with DMF solution (20 mL), and then the mixed solution reacted at a low speed of stirring in the dark. At the end of the reaction, the reaction solution was precipitated with methyl tert-butyl ether (50 mL) and n-hexane (100 mL), and suction filtering was carried out. The operations of column chromatography, dry sample loading and gradient elution with dichloromethane—1% ammonia water: 8% methanol/dichloromethane were carried out. The elution product was then evaporated to dryness, and dissolved with anhydrous ethanol (10 mL), the obtained solution was treated by ultrasonic to obtain homogeneous phase, and then n-hexane (50 mL) was added for precipitation. Such precipitation operation was repeated three times. The precipitate was dried in vacuum, thus obtaining the product 0.4 g.

$^1$H-NMR (600 MHz, DMSO-d$_6$) δ 9.91-9.83 (m, 8H), 8.80-8.72 (m, 10H), 8.58-8.50 (m, 10H), 8.27-7.96 (m, 82H), 7.63-7.49 (m, 128H), 7.24-7.14 (m, 51H), 6.71-6.50 (m, 7H), 5.29-5.21 (m, 22H), 4.52-4.40 (m, 82H), 4.04-3.98 (m, 54H), 3.51-3.50 (m, 600H), 3.17-3.14 (m, 83H), 3.03-2.97 (m, 122H), 2.88-2.86 (m, 15H), 0.91-0.70 (m, 72H).

21. Synthesis of 33-207 (Compound No. 21)

Synthetic route is as follows

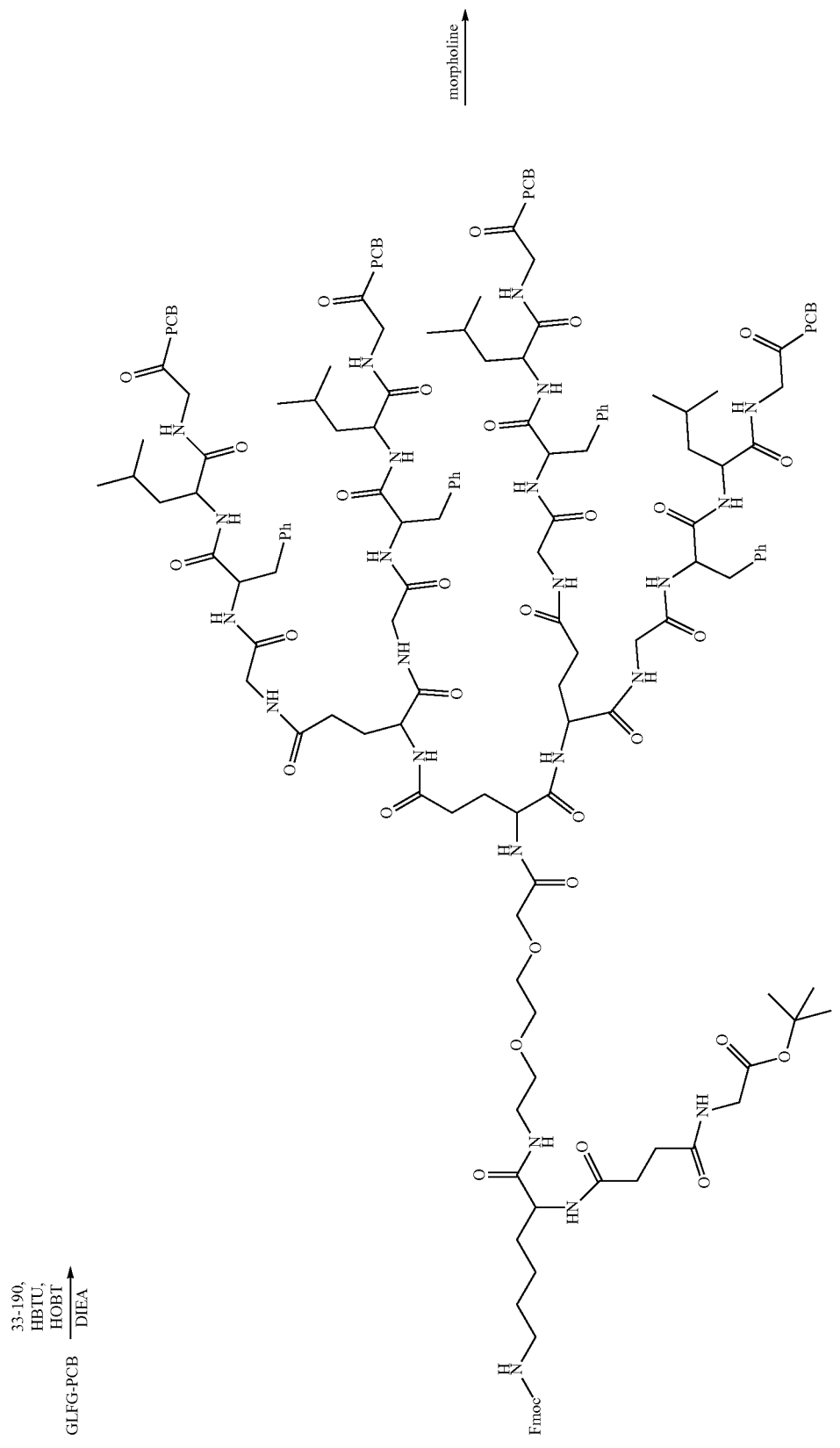

-continued
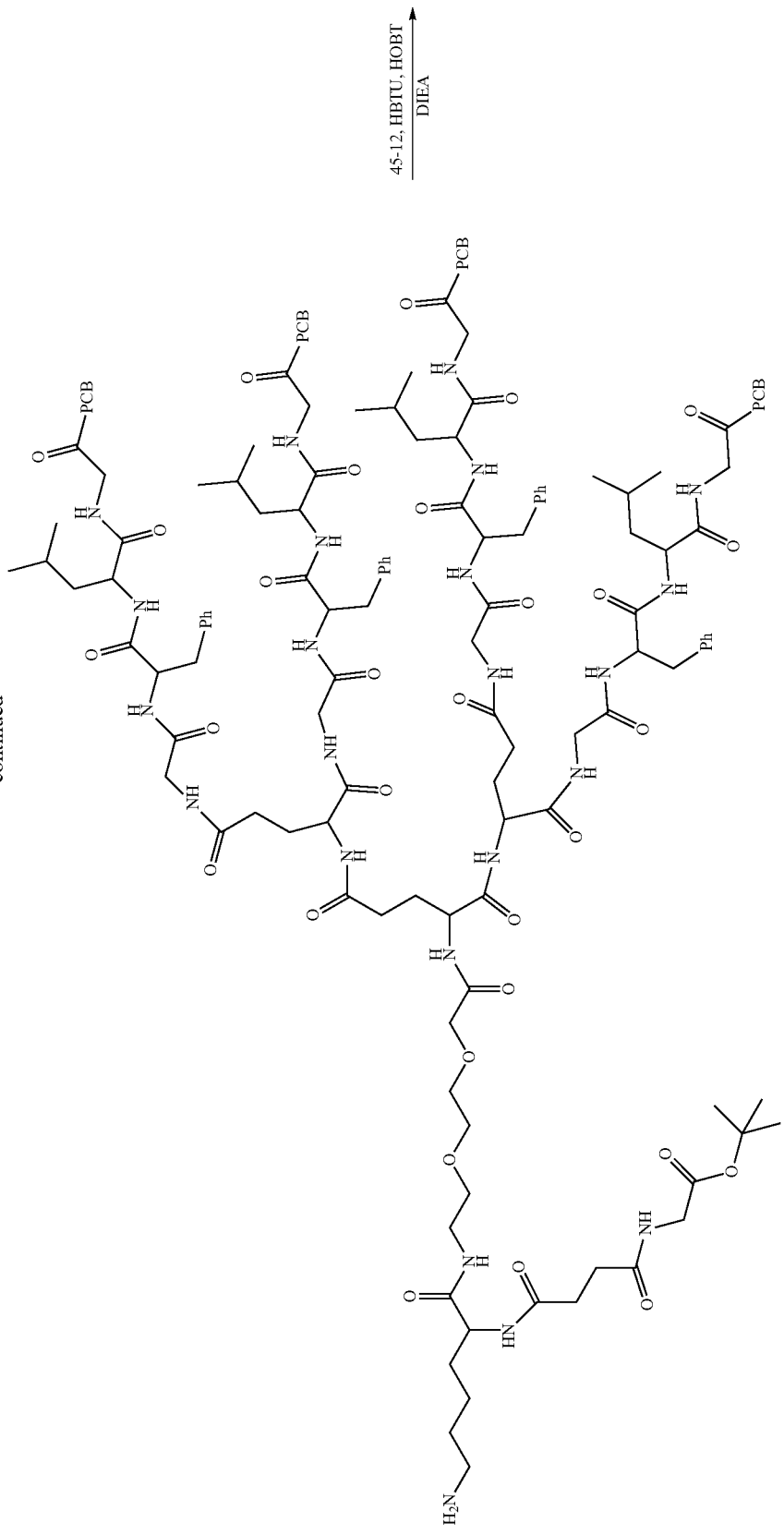
33-196

-continued
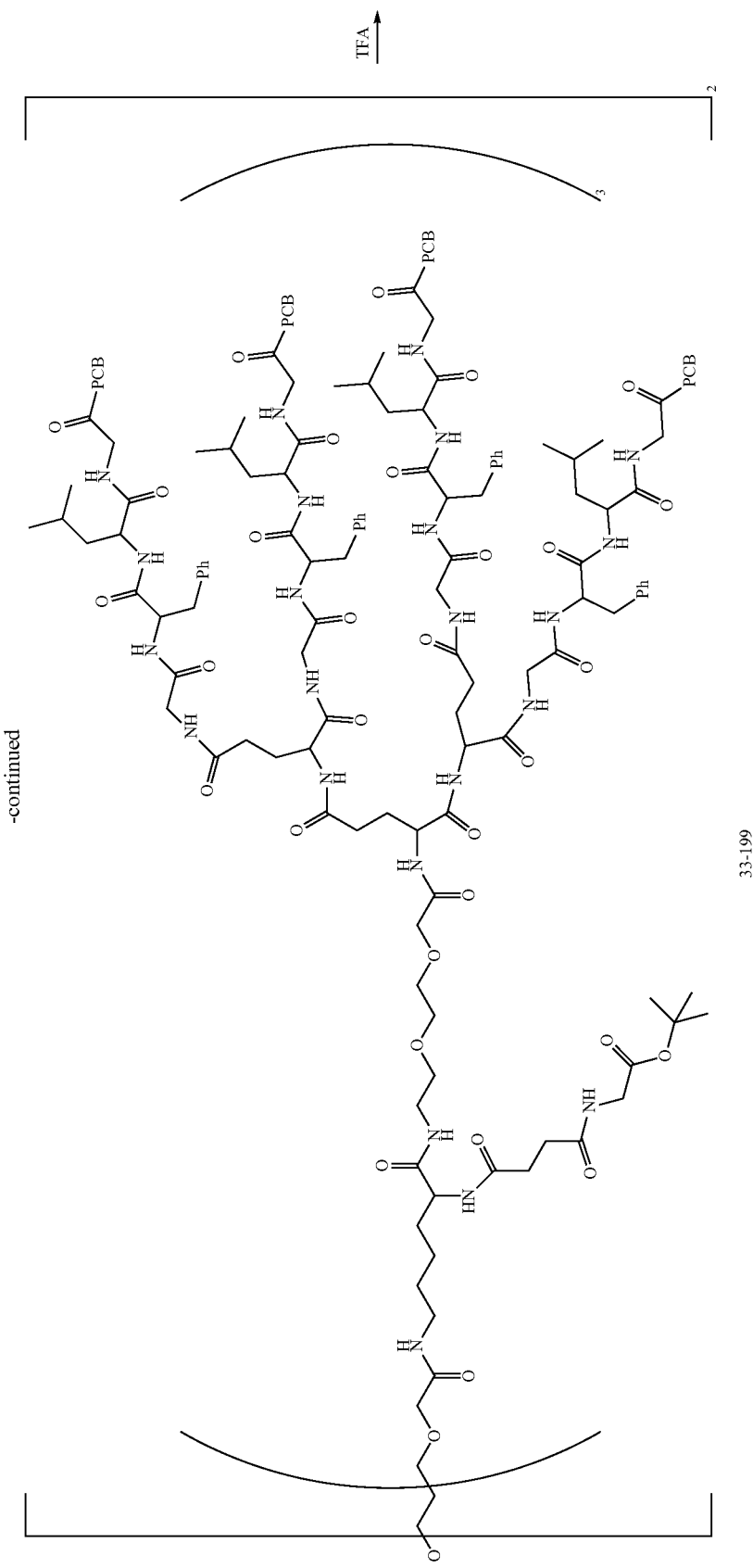

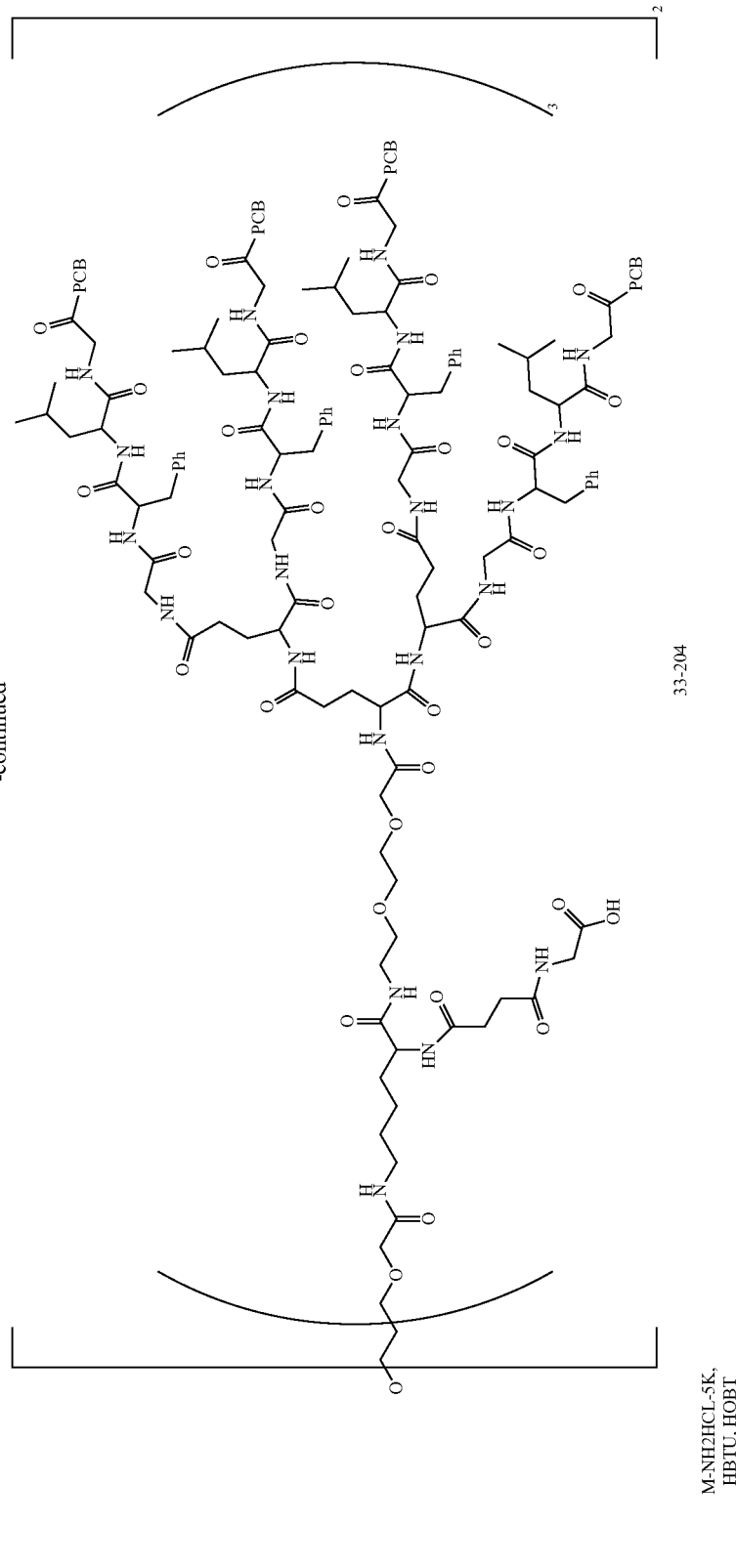

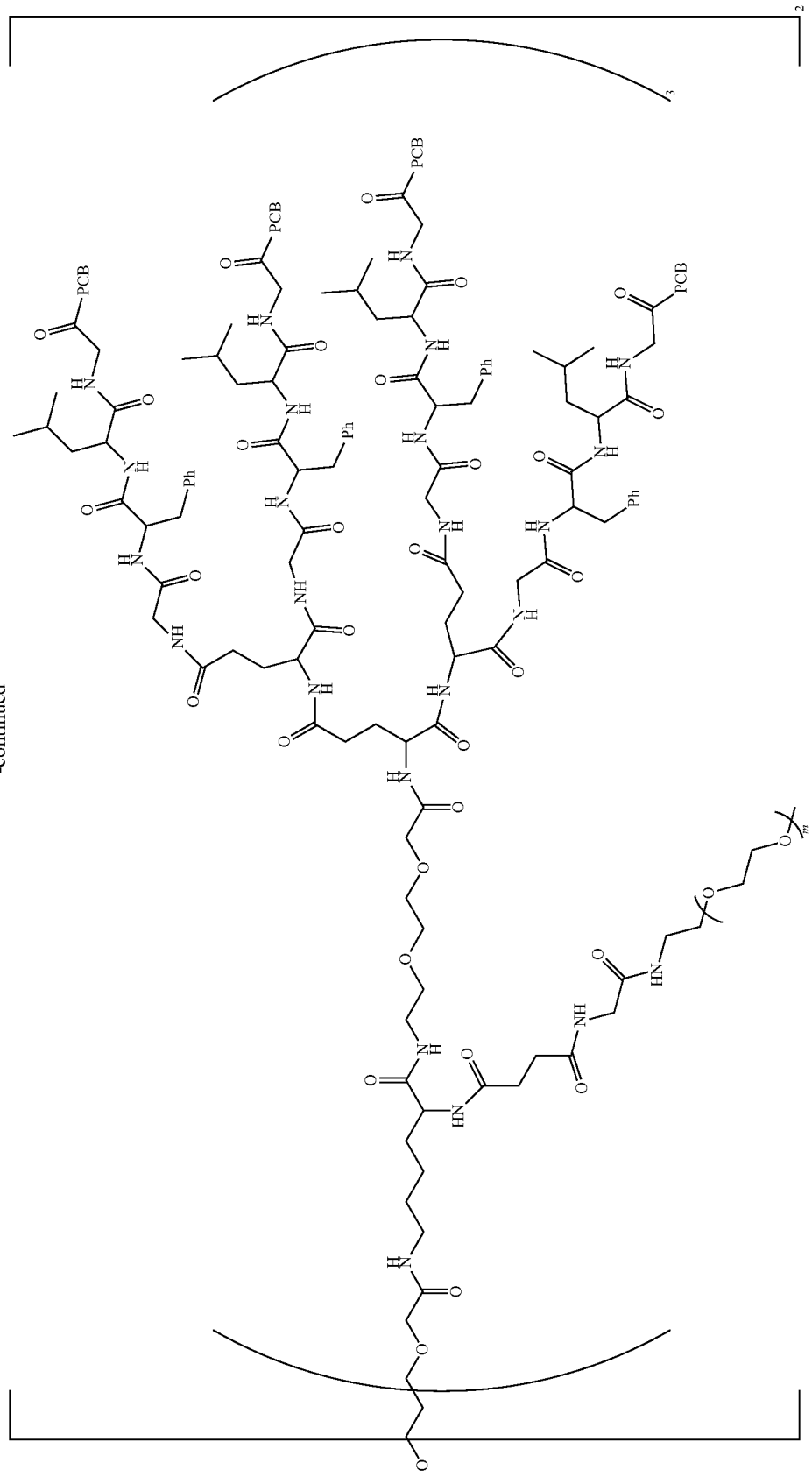

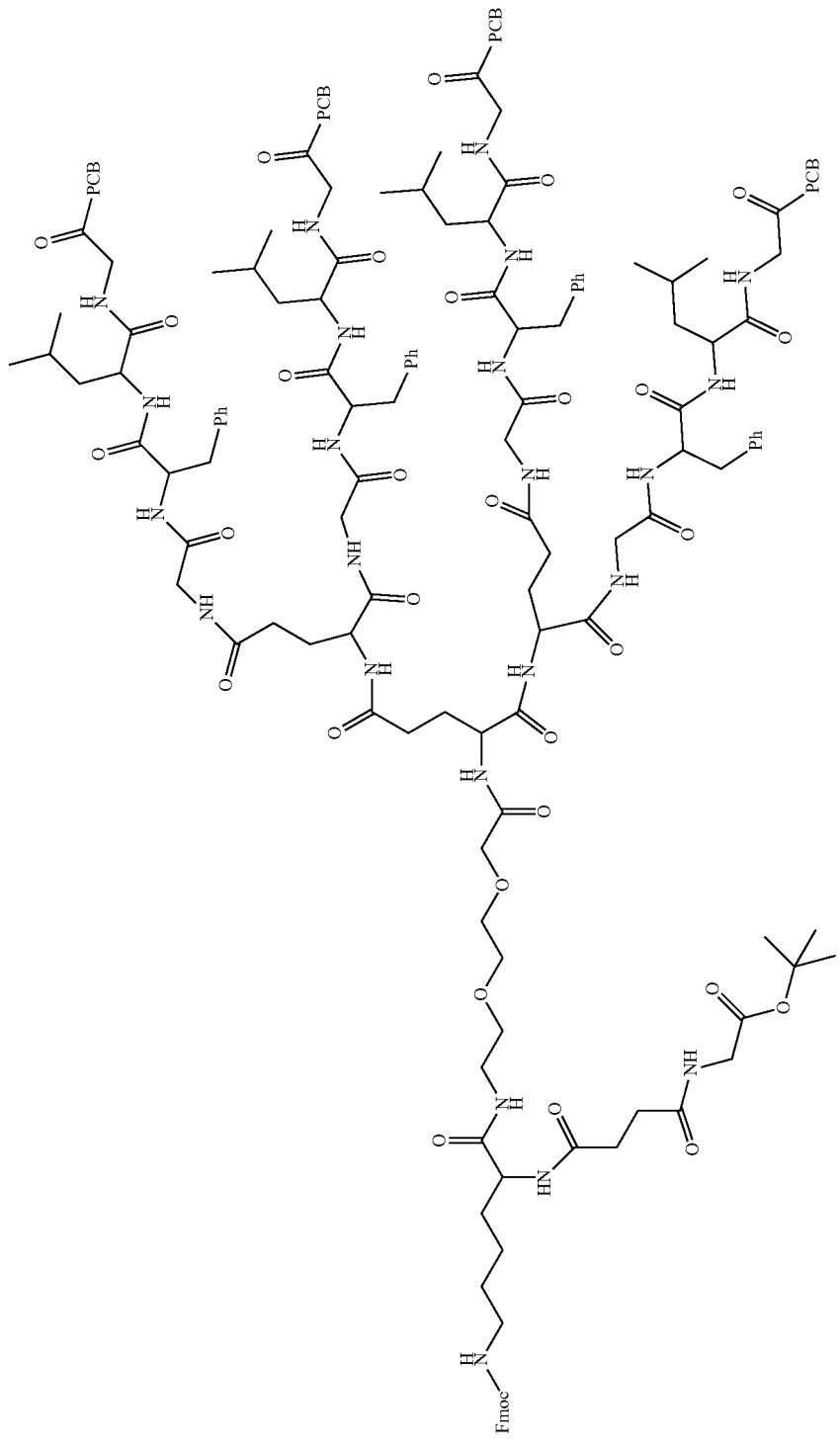

GFLG-PCB (synthesized according to the method of synthesizing 30-33, 2 g, 2.43 mmol), HBTU (1.15 g, 3.03 mmol), HOBT (0.41 g, 3.03 mmol) were added in a 250 mL flask, and dissolved with a DMF solution of 33-190, and ultrasonic treatment was carried out to completely dissolve the reactants, and then the obtained solution was stirred at −5° C. for 30 minutes. Then DIEA (1.5 mL, 9.108 mmol) was slowly added dropwise, and the obtained solution reacted at the low temperature until the reaction ended. At the end of the reaction, methyl tert-butyl ether (100 mL), n-hexane (150 mL) were added to the reaction solution, ultrasonic treatment was carried out for 5 minutes, the obtained solution was placed in a refrigerator, and stood still for 20 minutes, the supernatant was discarded, ethyl acetate (20 mL) was added to the lower liquid, ultrasonic treatment was carried out for 2 minutes, n-hexane (100 mL) was added, and suction filtering was carried out. The filter cake was dried in vacuum, thus obtaining the product 1.4 g.

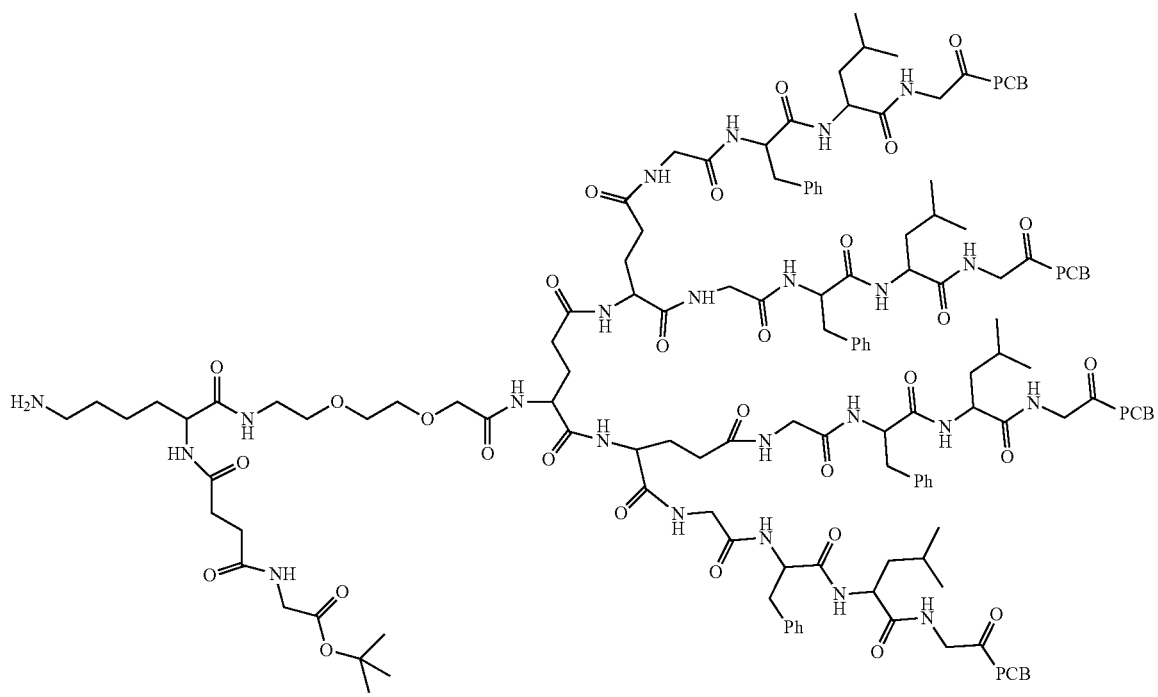

33-196

33-194 (1.4 g, 0.32 mmol) was added in a 250 mL round-bottomed flask, and dissolved with DMF (70 mL), morpholine (0.84 mL, 9.6 mmol) was added, and then the mixed solution was stirred to react at room temperature. At the end of the reaction, methyl tert-butyl ether (150 mL), n-hexane (100 mL) were added to the reaction solution, and ultrasonic treatment was carried out for 5 minutes to separate out a solid. Suction filtering was carried out, and the filter cake was dried in vacuum, thus obtaining the product 1.3 g.

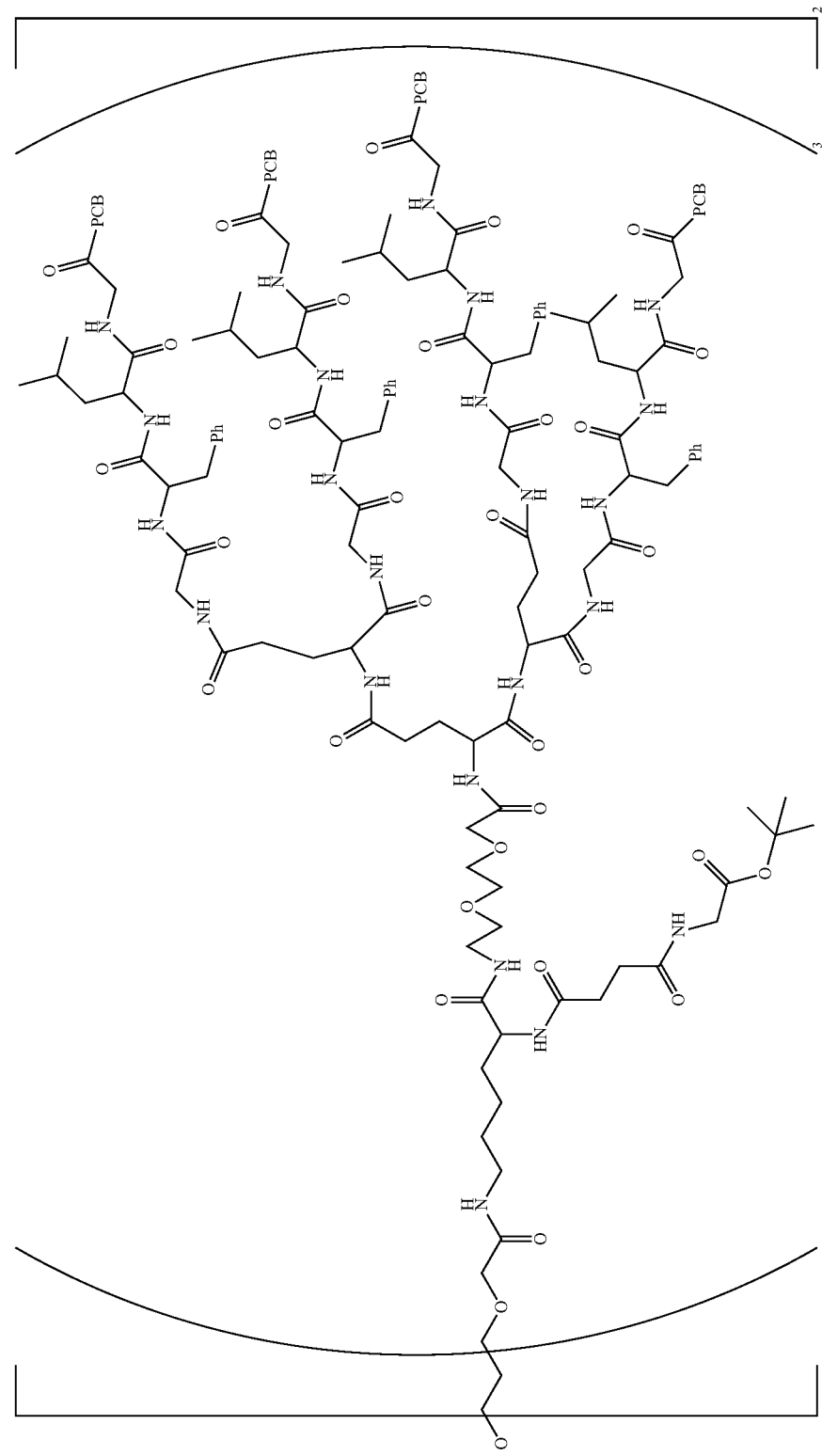

33-196 (1.3 g, 0.316 mmol), HBTU (0.153 g, 0.406 mmol), HOBT (0.0541 g, 0.406 mmol) were added in a 250 mL flask, and dissolved with a DMF solution of 45-12 (19 mL, 0.0452 mmol), DMSO (80 mL) was added, and ultrasonic treatment was carried out to completely dissolve the reactants, and then the mixed solution was stirred at −5° C. for 30 minutes. Then DIEA (0.2 mL, 1.22 mmol) was slowly added dropwise, and, after 1 hour, the obtained solution reacted with stirring at room temperature. At the end of the reaction, deionized water (100 mL) was added to the reaction solution to separate out a solid, and suction filtering was carried out. The filter cake was dried in vacuum, thus obtaining the product 1.3 g.

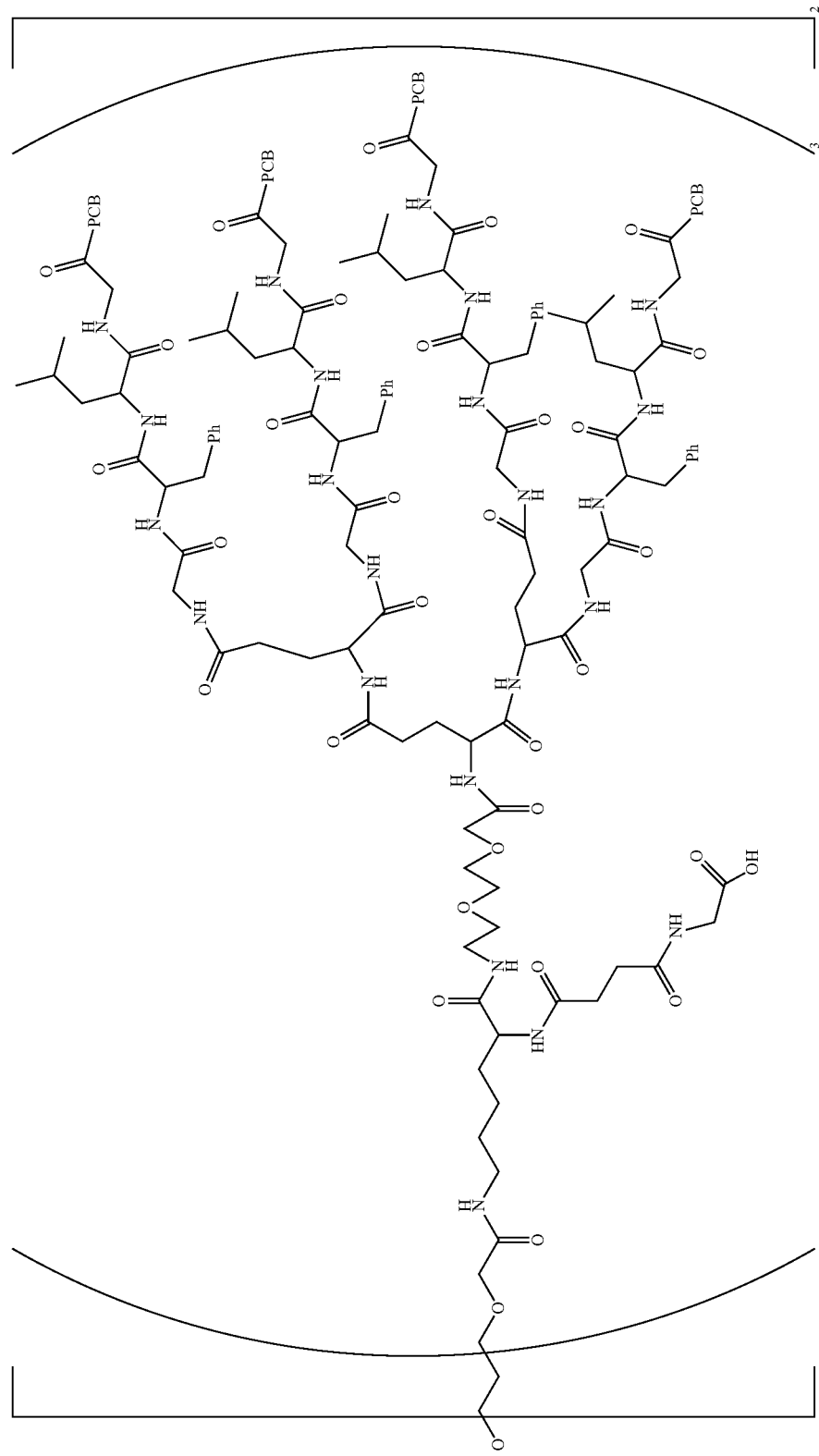

33-199 (1.3 g, 0.316 mmol) was dissolved with dichloromethane (10 mL), TFA (0.7 mL, 9.48 mmol) was added, and ultrasonic treatment was carried out to completely dissolve the compound. A ground glass stopper was used, and the mixed solution was stirred to react at room temperature. At the end of the reaction, methyl tert-butyl ether (150 mL) and n-hexane (100 mL) were directly added to the reaction solution, and suction filtering was carried out. The filter cake was dried in vacuum, thus obtaining the product 1.2 g.

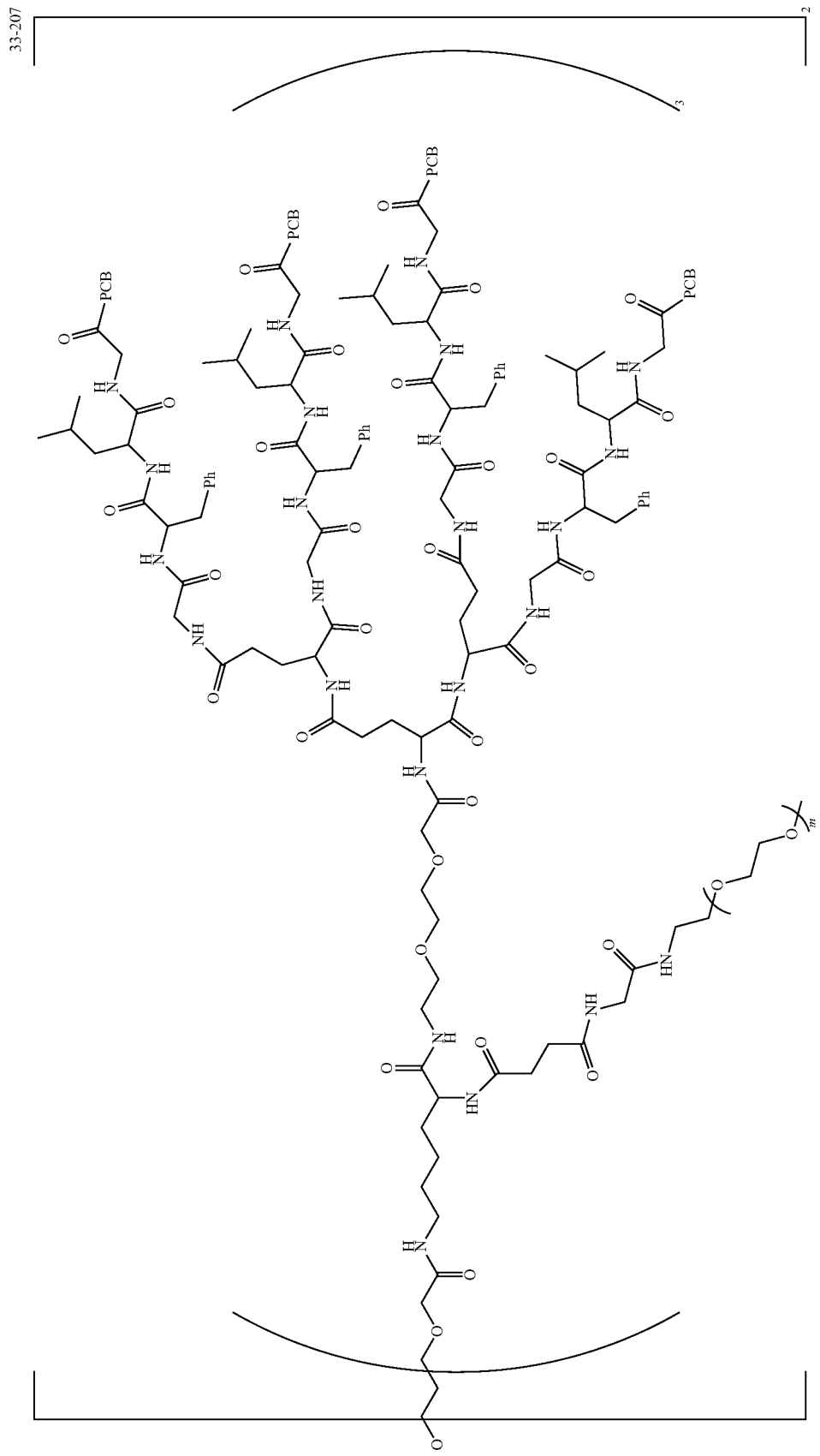

Reactants 33-199 (1.20 g, 0.048 mmoL), M-NH$_2$HCL-5K (2.0 g, 0.38 mmoL), HBTU (0.21 g, 0.576 mmoL), HOBT (0.077 g, 0.576 mmoL) were added in a 250 mL flask, and dissolved with DMF (75 mL) in a condition of ultrasonic, and then the mixed solution was stirred at −5° C. for 30 minutes. Then DIEA (0.0073 mL, 0.0446 mmoL) was slowly added dropwise, and the obtained solution was stirred for 1 hour, and then reacted at room temperature in the dark at a low speed. At the end of the reaction, methyl tert-butyl ether (200 mL) was added to the reaction solution for precipitation, and suction filtering was carried out to obtain a powder product. The powder product was dissolved with a mixed solvent of 20% methanol/dichloromethane, and silica gel (6 g) was added. The operations of evaporation, dry sample loading, column chromatography and gradient elution with 6% methanol/dichloromethane—1% ammonia water: 10% methanol/dichloromethane were carried out. The elution product was then collected and evaporated to dryness, the obtained solid was dissolved with dichloromethane (5 mL) in a condition of ultrasonic, methyl tert-butyl ether (150 mL) and n-hexane (50 mL) were added, and suction filtering was carried out. The filter cake was then dissolved with dichloromethane, and the obtained solution was precipitated with methyl tert-butyl ether and n-hexane. The process of dissolution and precipitation was repeated three times, thus obtaining the product 0.5 g.

$^1$H-NMR (400 MHz, DMSO-d$_6$) δ10.58-10.39 (m, 14H), 9.05-8.89 (m, 13H), 8.23-7.66 (m, 169H), 7.26-6.91 (m, 165H), 3.51-3.50 (m, 1957H), 3.26-3.22 (m, 148H), 2.97-2.83 (m, 232H), 2.34-2.28 (m, 86H), 1.94-1.45 (m, 282H), 0.94-0.75 (m, 144H).

22. Synthesis of 29-160 (Compound No. 22)

Synthetic route is as follows

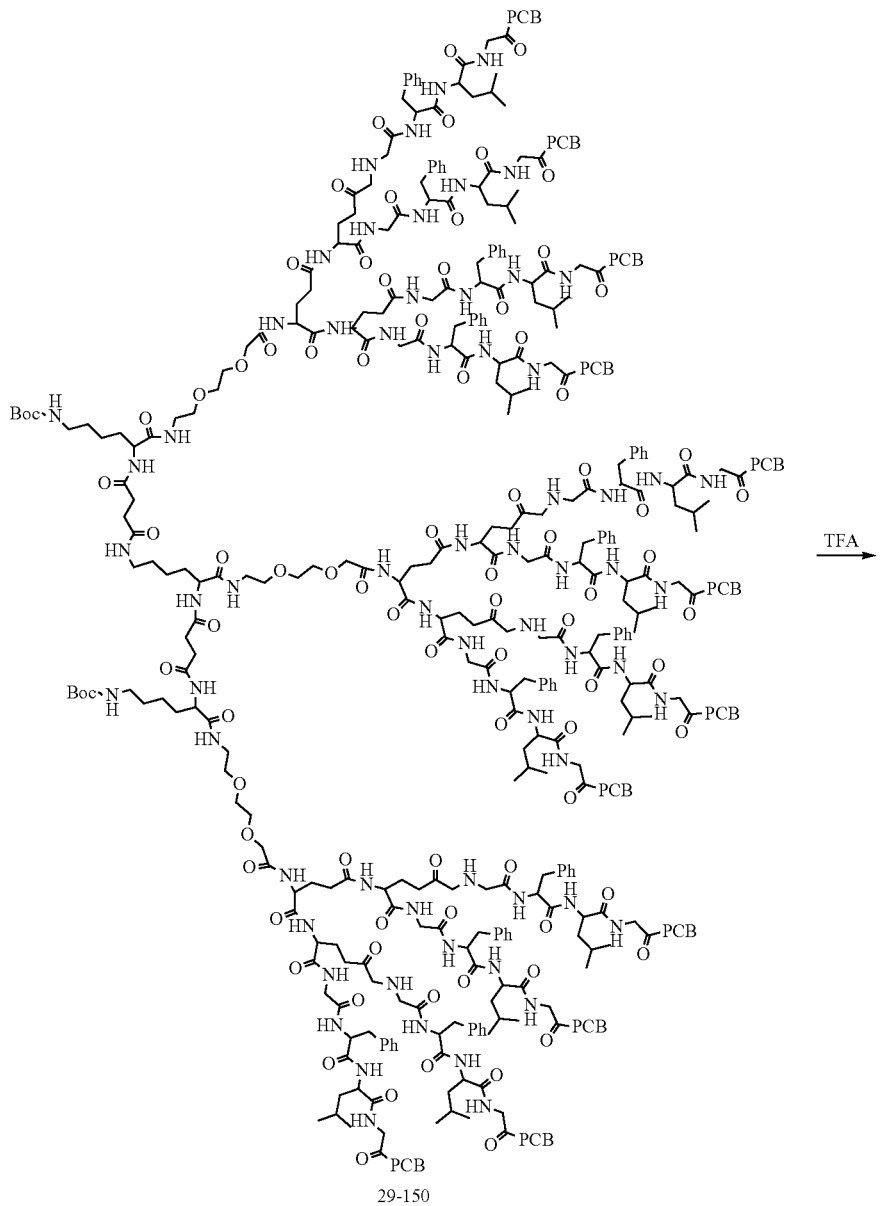

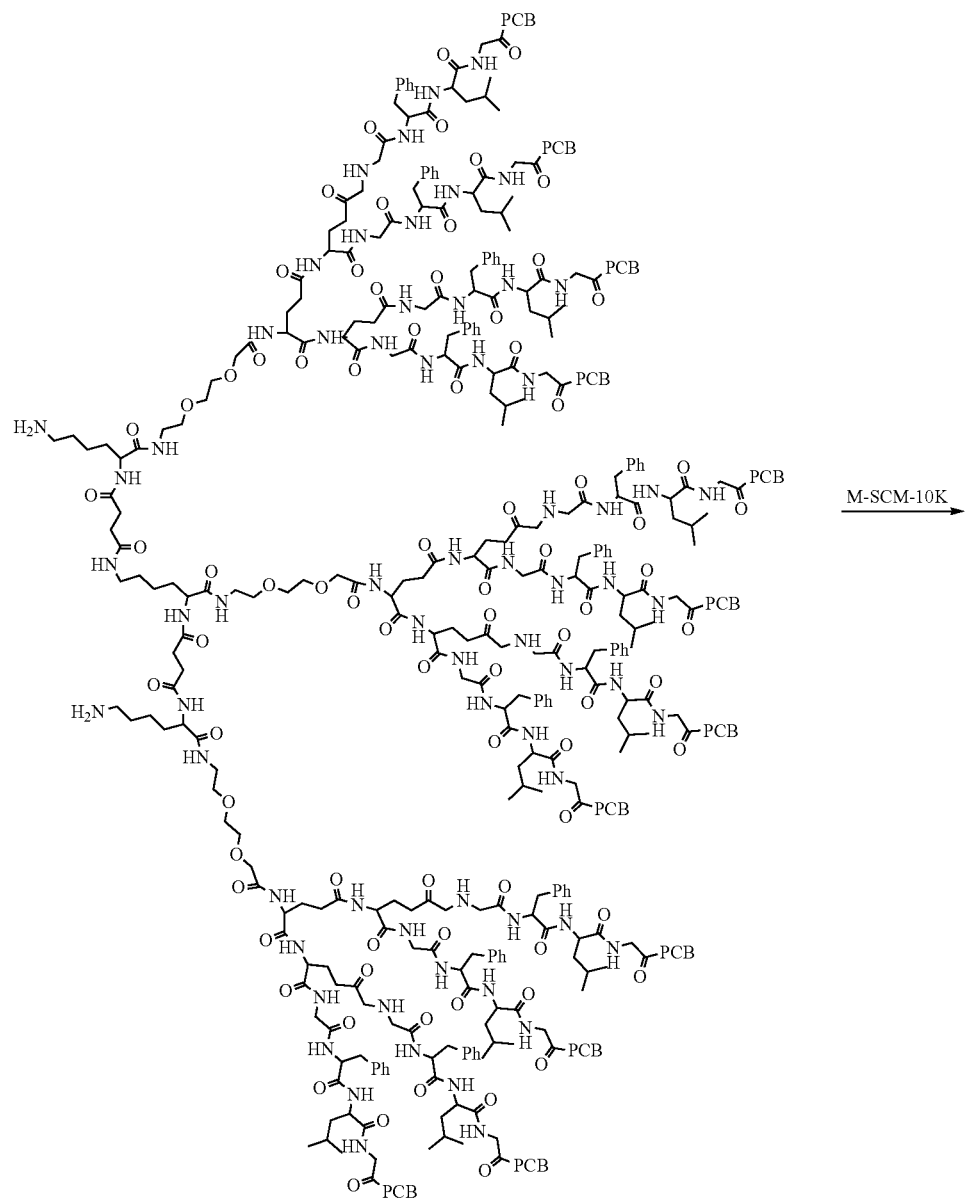
29-154

-continued
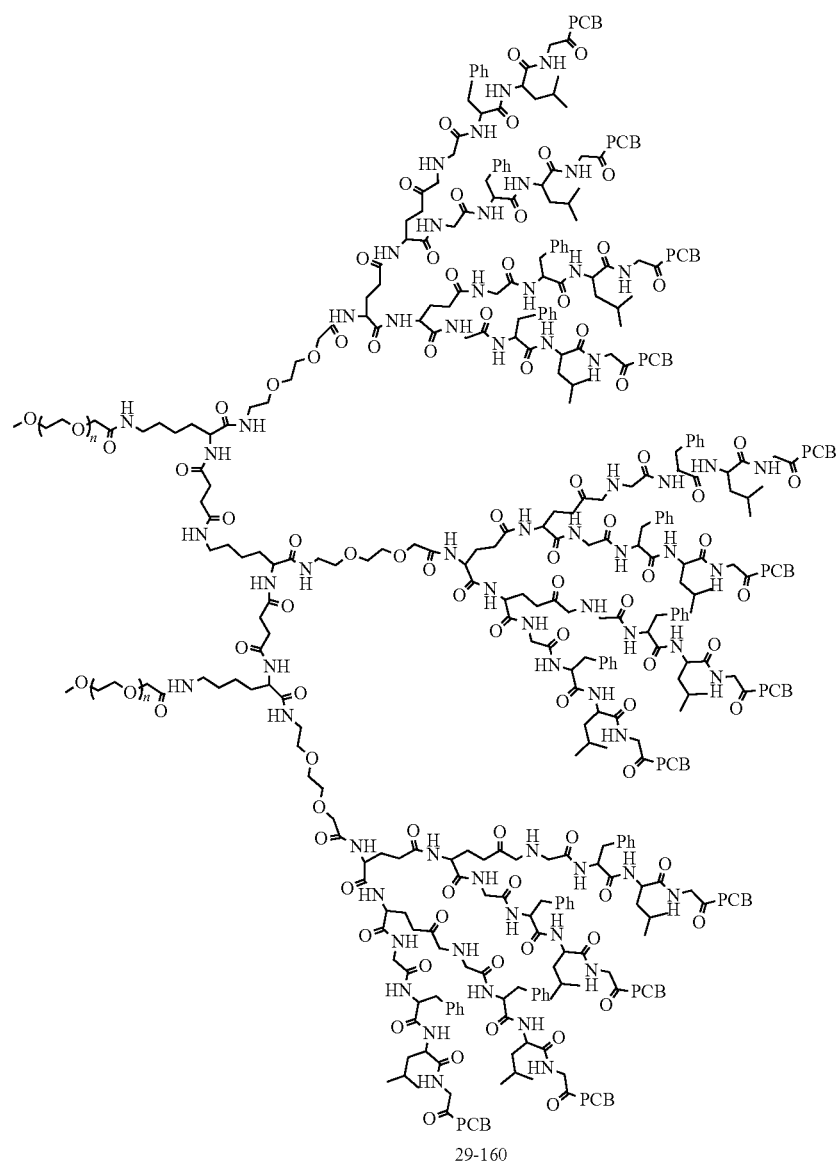
29-160

29-150

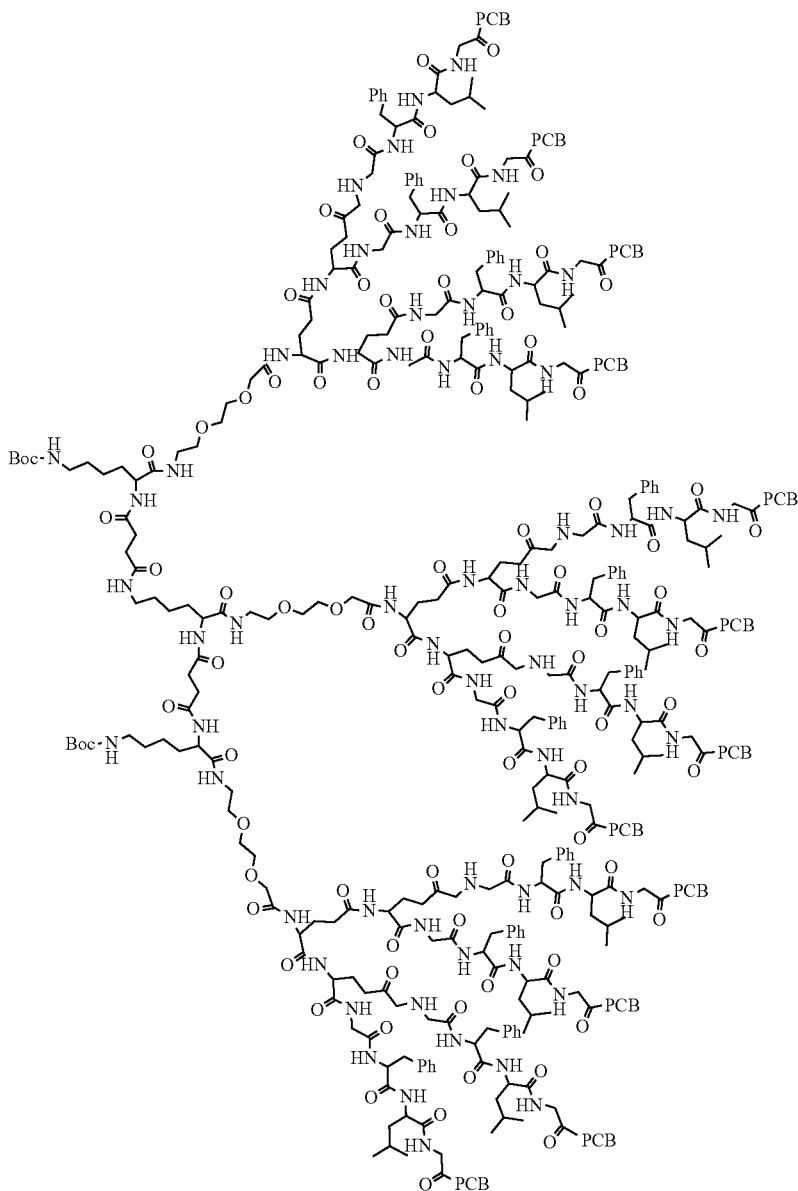

Reactants 30-33 (3.5 g, 4.2581 mmol), 29-149 (synthesized according to the method of synthesizing W3, 0.3275 mmol), HBTU (2.2359 g, 5.8958 mmol), HOBT (0.7967 g, 5.8958 mmol) were added in a 250 mL flask, and dissolved with DMF (50 mL), and then the mixed solution was stirred at −5° C. for 30 minutes. Then DIEA (2.9 mL, 17.6873 mmol) was slowly added dropwise, the obtained solution was stirred at −5° C. for 1 hour, and then moved to room temperature and stirred to react overnight. At the end of the reaction, methyl tert-butyl ether (100 mL) was added to the reaction solution, the obtained solution was placed in a refrigerator and taken out after 30 minutes, a solid was separated out, and suction filtering was carried out. The filter cake was collected, and dried, thus obtaining a crude product.

29-154

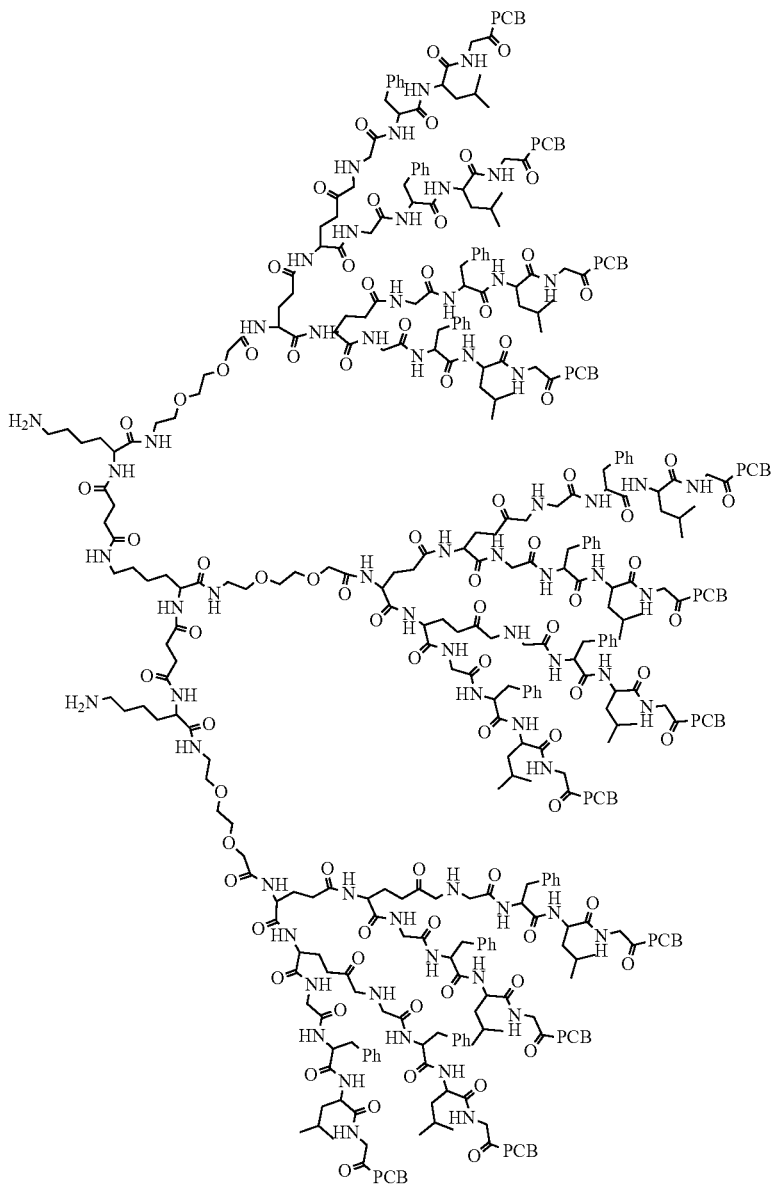

29-150 (0.3275 mmol) was dissolved with dichloromethane (10 mL) and TFA (0.3648 mL) in a condition of ultrasonic, and then the mixed solution was stirred to react. At the end of the reaction, the reaction solution was evaporated to dryness to obtain an oily product. Methyl tert-butyl ether (100 mL) was added to the oily product to separate out a solid, and suction filtering was carried out. The filter cake was collected, and dissolved with a mixed solvent (100 mL) of methanol/dichloromethane (1:4), silica gel powder (15 g) was added, and the obtained mixture was then evaporated to dryness to obtain a powdery solid. The operations of column chromatography, dry sample loading, and elution with 1% ammonia water: 4% methanol/dichloromethane—1% ammonia water: 10% methanol/dichloromethane were carried out, thus obtaining the product 1.0 g, yield 30%.

29-160

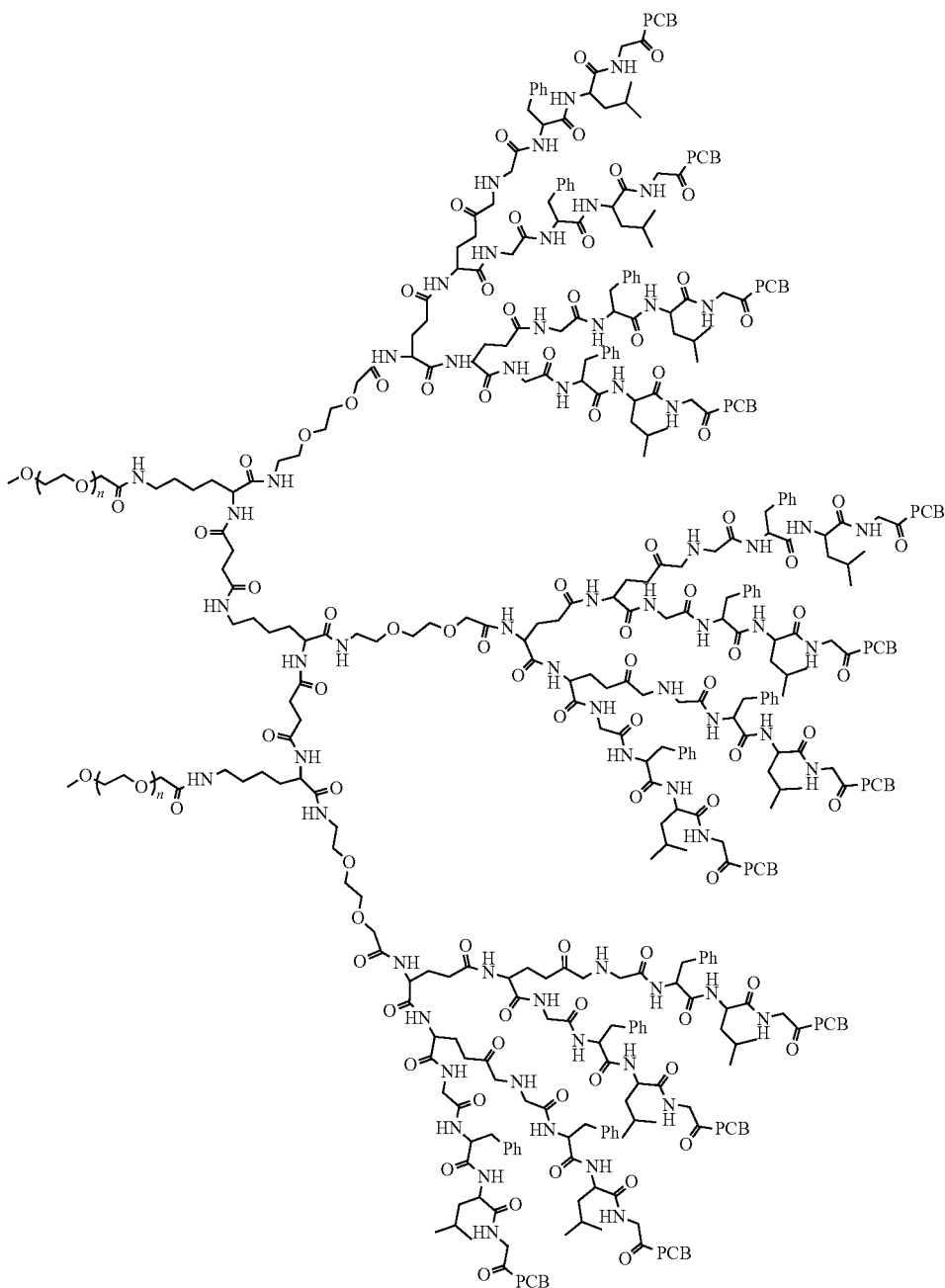

Reactants 29-154 (0.4 g) and M-SCM-10K (0.75 g, 0.07 mmol) were dissolved with DMF solution (20 mL), and then the obtained solution reacted at a low speed of stirring in the dark for one week. At the end of the reaction, methyl tert-butyl ether (100 mL) was added to the reaction solution, the obtained solution was placed in a refrigerator and taken out after 30 minutes, a solid was separated out, and suction filtering was carried out. The filter cake was collected, and dissolved with a mixed solvent (100 mL) of methanol/dichloromethane (1:4), silica gel powder (15 g) was added, and the obtained mixture was then evaporated to dryness to obtain a powdery solid. The operations of column chromatography, dry sample loading and gradient elution with 1% ammonia water: 3% methanol/dichloromethane—1% ammonia water: 8% methanol/dichloromethane were carried out. The elution product was evaporated to dryness, and dissolved with anhydrous ethanol (8 mL) and a small amount of dichloromethane, and the obtained solution was precipitated with methyl tert-butyl ether (50 mL). Such precipitation operation was repeated three times. The precipitate was dried in vacuum, thus obtaining the product 0.6 g. Yield 55%.

$^1$H-NMR (600 MHz, DMSO-$d_6$) δ 10.18-10.09 (m, 8H), 9.12-8.90 (m, 17H), 8.25-7.82 (m, 72H), 7.503-7.44 (m, 13H), 7.19-7.15 (m, 41H), 7.05-6.97 (m, 11H), 6.90-6.81 (m, 7H), 6.69-6.64 (m, 5H), 5.36-5.26 (m, 9H), 4.59-4.32 (m, 27H), 4.05-3.84 (m, 31H), 3.52-3.48 (m, 1925H), 2.32-2.85 (m, 28H), 2.76-2.69 (m, 39H), 2.43-2.38 (m, 23H), 2.33-2.22 (m, 50H), 1.99-1.74 (m, 85H), 1.60-1.45 (m, 59H), 1.37-1.32 (m, 48H), 1.25-1.18 (m, 40H), 0.89-0.78 (m, 72H).

23. Synthesis of 35-98 (Compound No. 23)
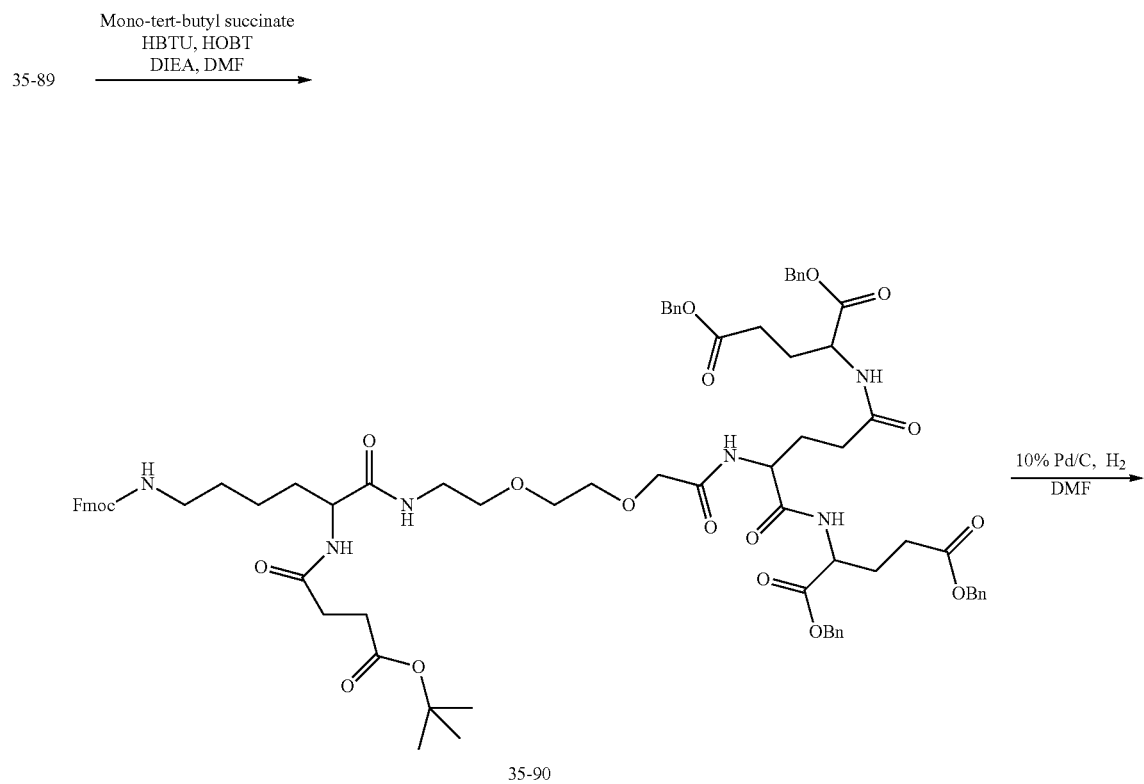
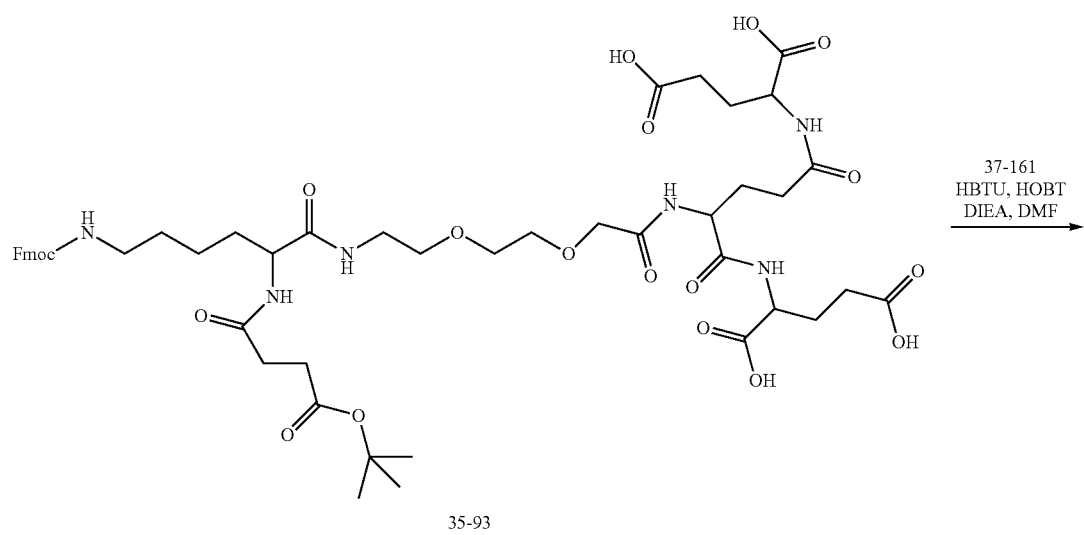

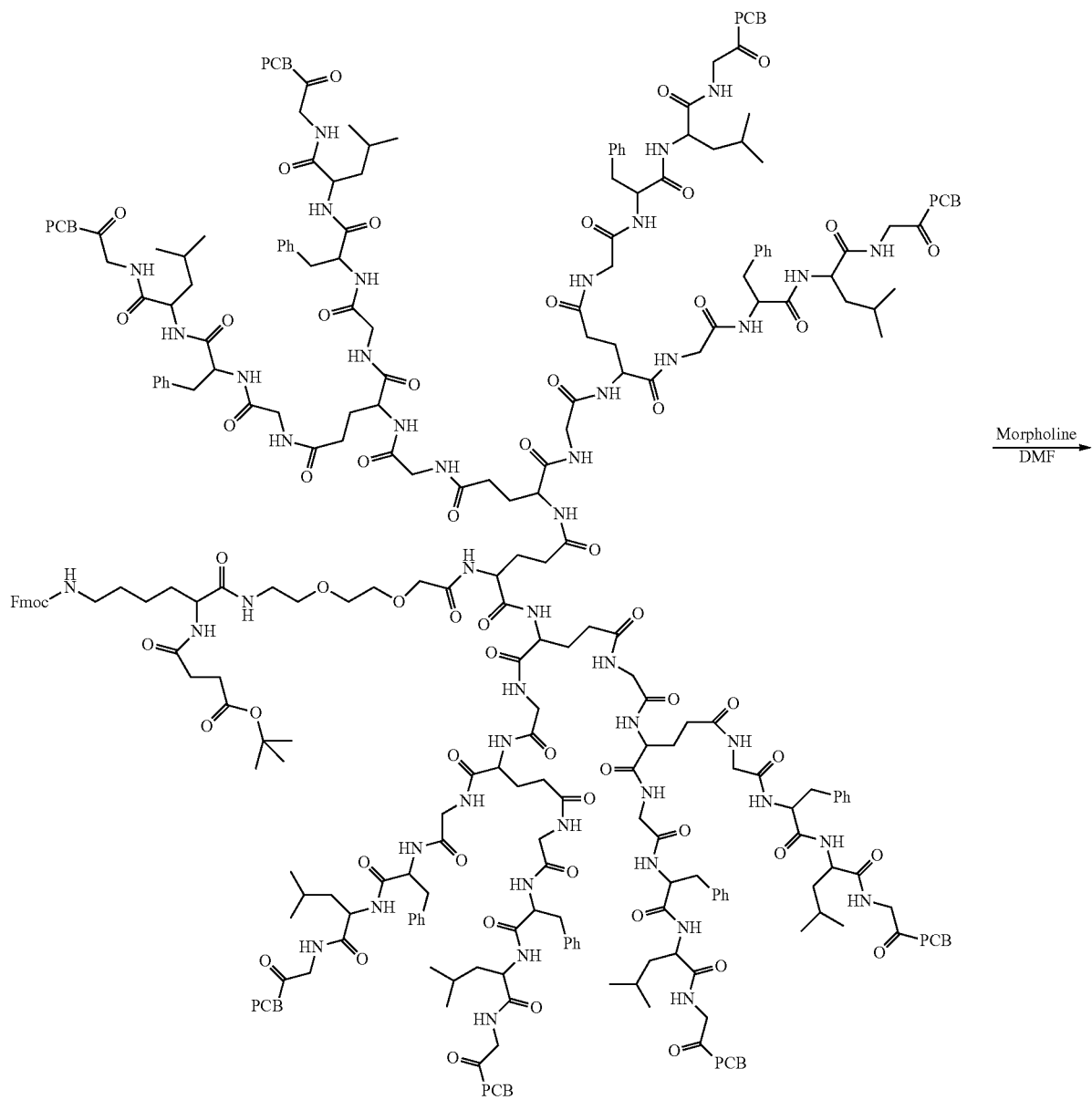
35-94

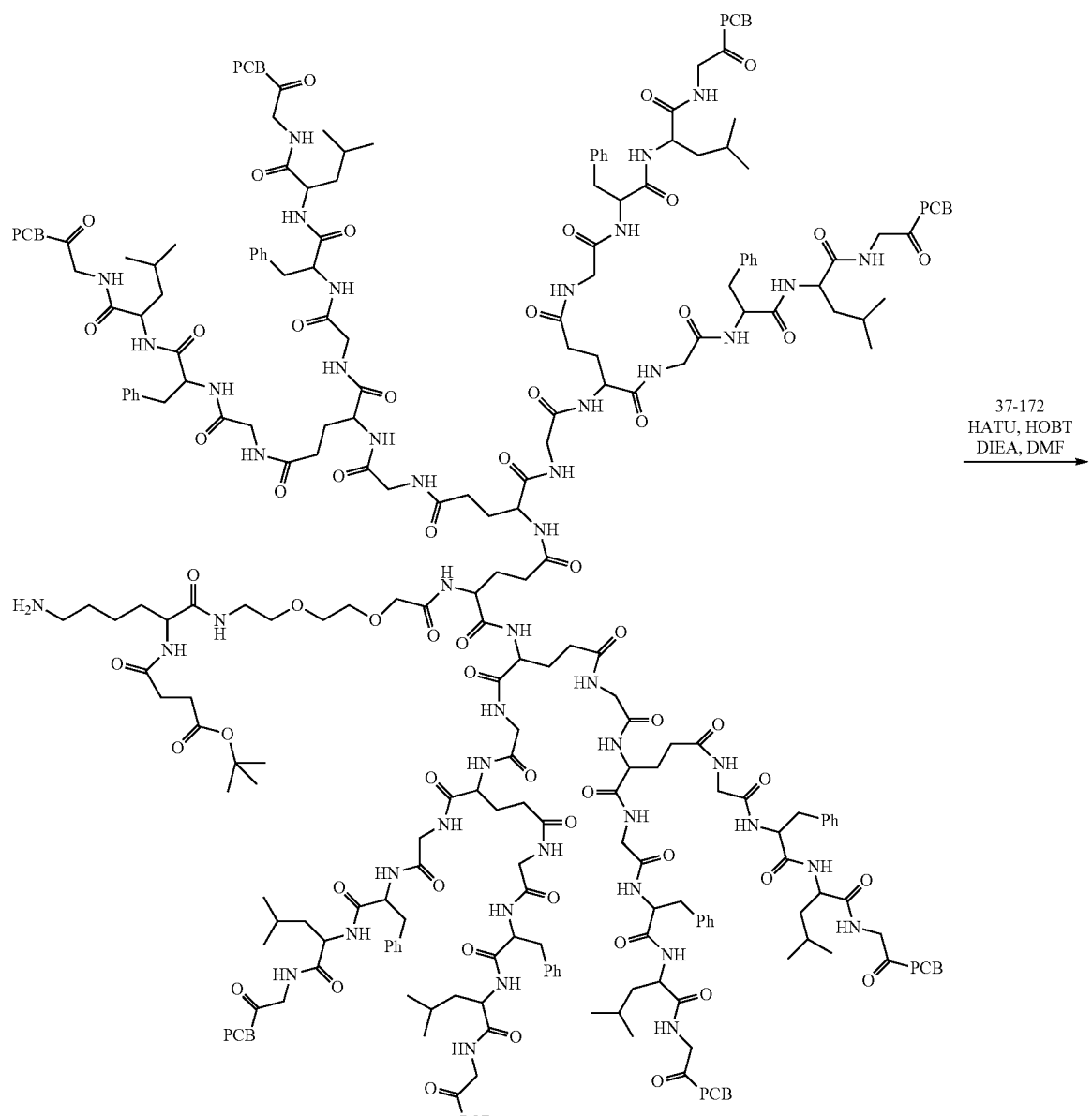

-continued
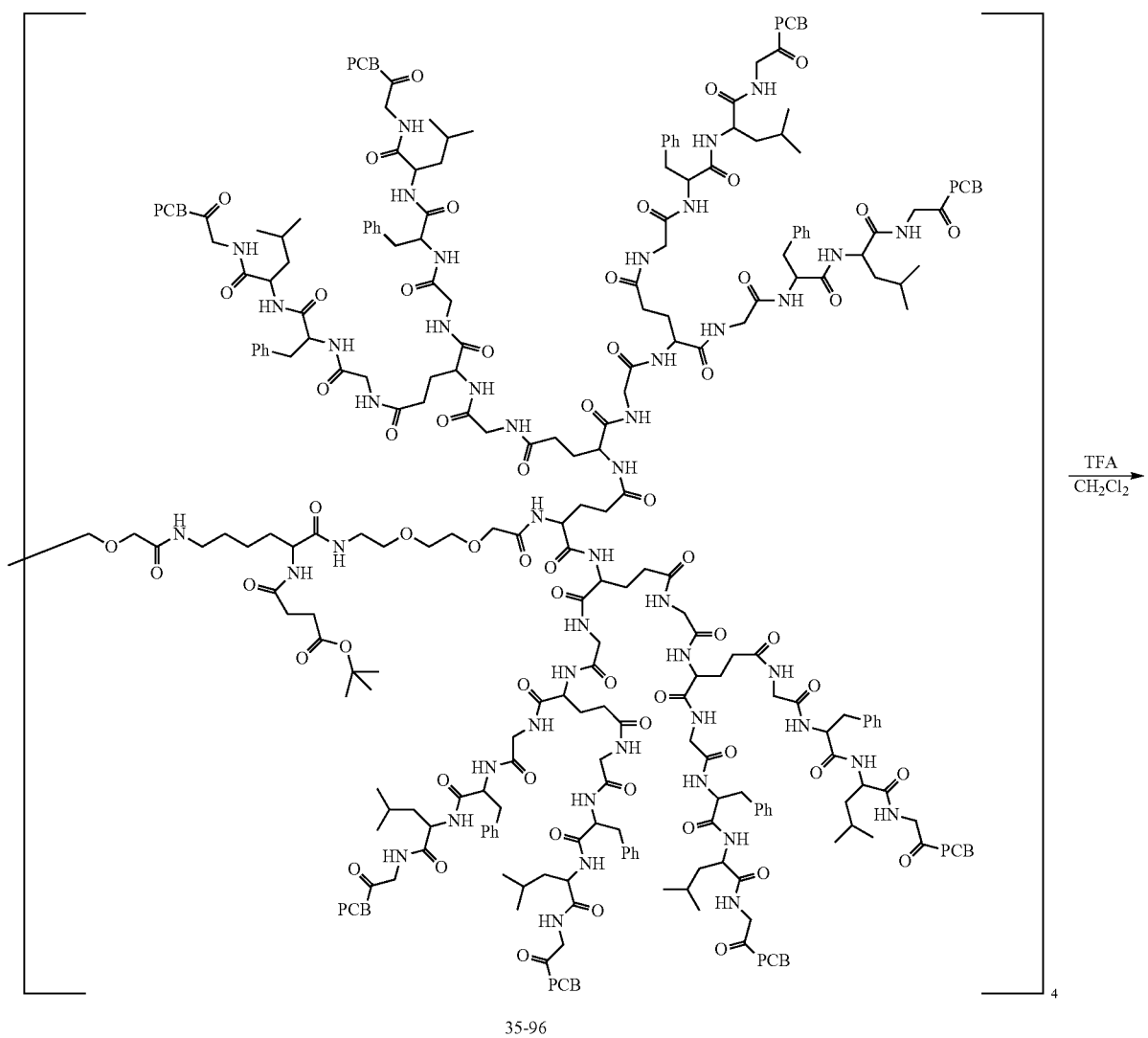
35-96

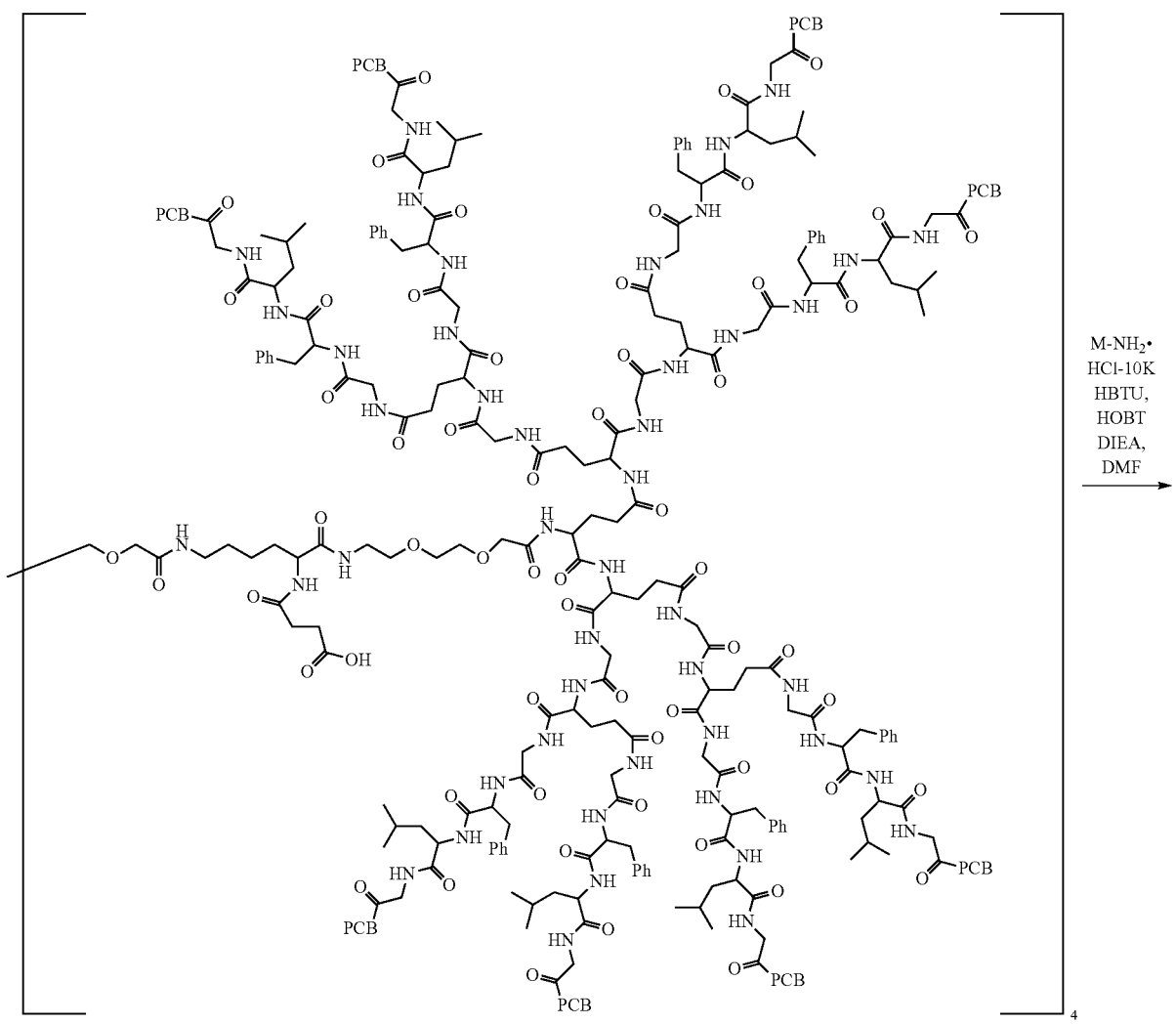
35-97

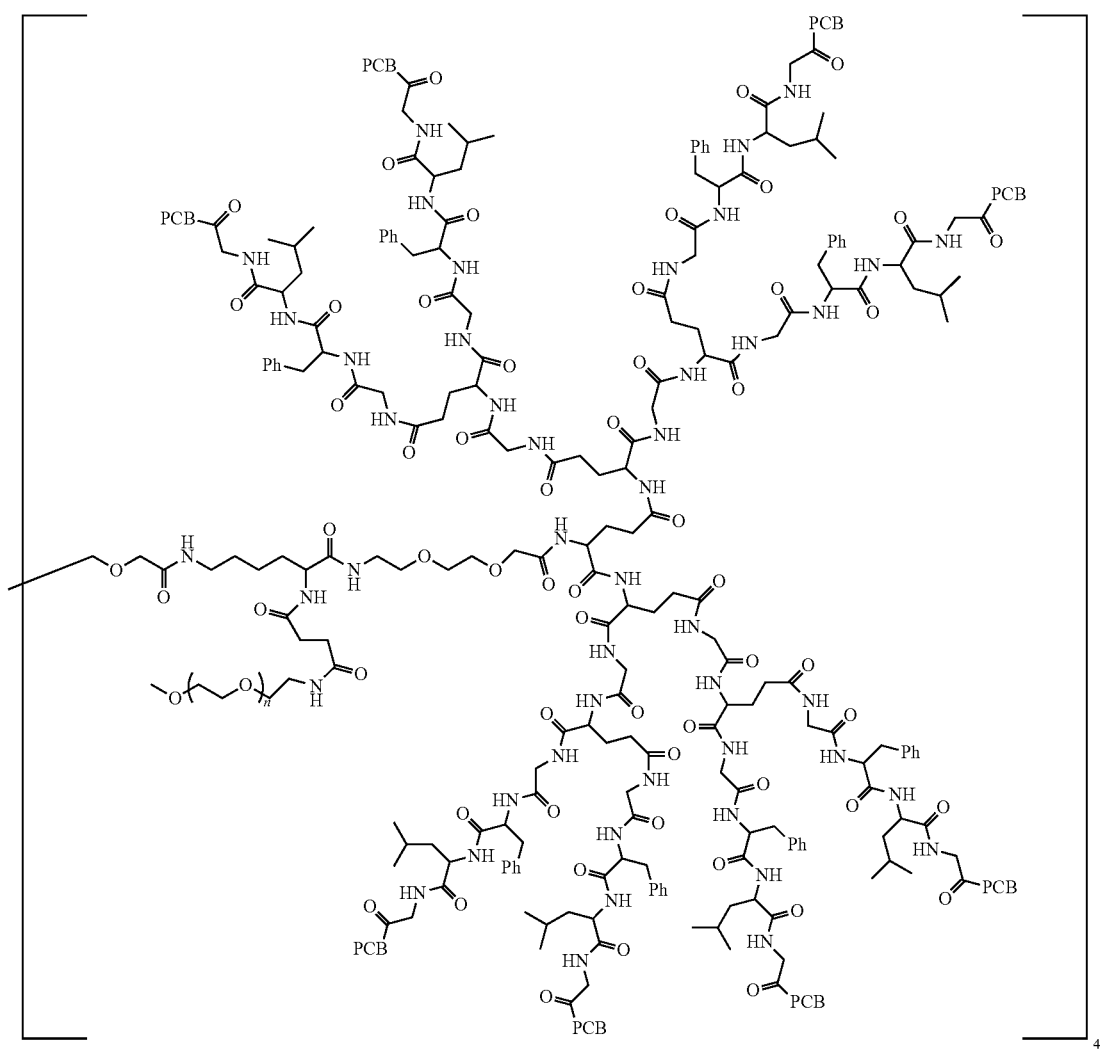

35-96

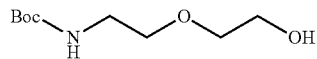

50

Diglycolamine (25.84 mL, 260.59 mmol, purchased from TCI) was added in a 1 L flask, and dissolved with dichloromethane (50 mL), triethylamine (72.64 mL, 521.18 mmol) was added, and then the obtained solution was stirred at 0° C. for 1 hour. Tert-butyl dicarbonate was dissolved with dichloromethane, and slowly added dropwise to the flask. At the end of the addition, the obtained solution continued to react at 0° C. with stirring overnight. At the end of the reaction, the reaction solution was concentrated to a small amount, silica gel powder (50 g) was added, and the obtained mixture was then evaporated to dryness to obtain a powdery solid. The operations of dry sample loading, column chromatography and elution with a petroleum ether mixed solution containing 50%-60% ethyl acetate were carried out, thus obtaining the product 37-88: 53.4861 g.

37-88

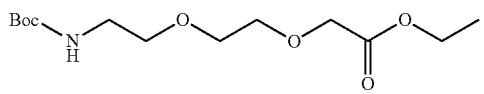

37-148

37-88 (53.4861 g, 260.59 mmol) was added in a 1 L flask, stirred to react at 0° C. for 30 minutes, and the THF solution of potassium tert-butoxide (286.64 mL, 1 mol/L, 286.64 mmol) was slowly added dropwise. At the end of the addition, the obtained solution was further stirred for 1 hour. Then ethyl bromoacetate (28.82 mL, 260.59 mmol) was slowly added dropwise. At the end of the addition, the obtained solution was further stirred at 0° C. for 30 minutes, and then moved to room temperature and stirred to react overnight. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×1), and the obtained organic phases were combined. The organic phase was concentrated and evaporated to dryness. The obtained dry product was then dissolved with methanol (30 mL) and dichloromethane (120 mL), silica gel powder (100 g) was added, and the obtained mixture was then evaporated to dryness to obtain a powdery solid. The operations of dry sample loading, column chromatography and elution with a petroleum ether mixed solution containing 20% ethyl acetate were carried out, thus obtaining the product 37-148: 52.1 g, yield 68.6%.

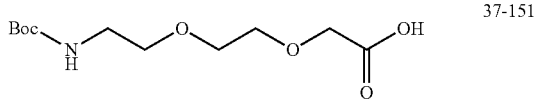 [SMILES: CC(C)(C)OC(=O)NCCOCCOCC(=O)O]

37-151

37-148 (52.1 g, 178.8 mmol) was added in a 1 L flask, and dissolved with 1,4-dioxane (100 mL), lithium hydroxide (9.4 g, 393.4 mmol) was added, and then the mixed solution was stirred to react at room temperature for 30 minutes, pure water (200 mL) was then added, and the obtained solution continued to react with stirring for 2 hours. At the end of the reaction, the reaction solution was transferred to a 1 L separatory funnel, and extracted with n-hexane (125 mL) and methyl tert-butyl ether (125 mL). The aqueous phase was adjusted to pH=2 with concentrated hydrochloric acid, and then extracted with ethyl acetate (200 mL×2), and the obtained organic phases were combined. Silica gel powder was added, and the operations of evaporation, dry sample loading, column chromatography and elution with a petroleum ether mixed solution containing 50%-60% ethyl acetate were carried out, thus obtaining the product 37-151: 45.1 g, yield: 96%.

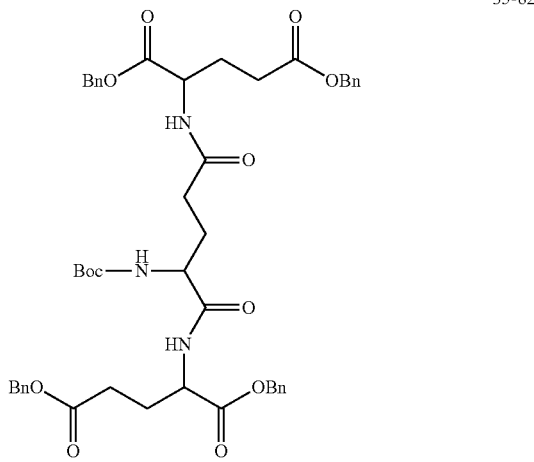

35-82

Boc-Glu-OH (20.0 g, 80.89 mmol, purchased from Ark Pharm), HBTU (92.02 g, 242.66 mmol), HOBT (32.8 g, 242.66 mmol) and H-Glu (OBn)$_2$·TsOH (84.861 g, 161.8 mmol, purchased from Ark Pharm) were added in a 1000 mL flask, and dissolved with DMF (200 mL), and then the mixed solution was stirred at −5° C. for 30 minutes. Then DIEA (120.32 mL, 728 mmol) was slowly added dropwise. At the end of the addition, the obtained solution continued to react at −5° C. with stirring for 1 hour, and was then moved to room temperature and stirred to react overnight. At the end of the reaction, the reaction solution was transferred to a 2 L separatory funnel, and extracted with saturated sodium bicarbonate solution (600 mL) and ethyl acetate (300 mL), the aqueous phase was washed with ethyl acetate (200 mL×1), and the obtained organic phases were combined. The organic phase was washed with saturated saline solution (200 mL×2), concentrated and evaporated to dryness, thus obtaining the product 35-82: 70 g.

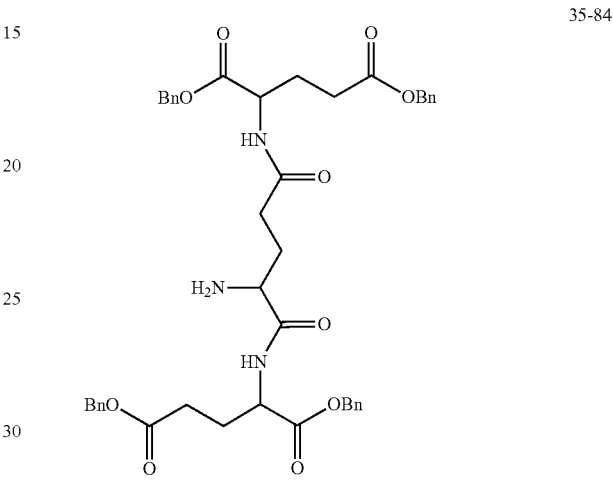

35-84

35-82 (70 g, 80.89 mmol) was added in a 1000 mL round-bottomed flask, and dissolved with dichloromethane (50 mL), trifluoroacetic acid (300 mL, 4044.5 mmol) was added with stirring, and then the mixed solution was stirred to react at room temperature overnight. At the end of the reaction, the reaction solution was concentrated, ethyl acetate (300 mL) and saturated sodium bicarbonate solution (300 mL) were added, a lot of bubbles were generated, a sodium bicarbonate solid was further added till a pH of greater than 7, and then the extraction was carried out. The aqueous phase was washed with ethyl acetate (200 mL×1), and the obtained organic phases were combined. The organic phase was evaporated to dryness, thus obtaining 35-84: 62 g.

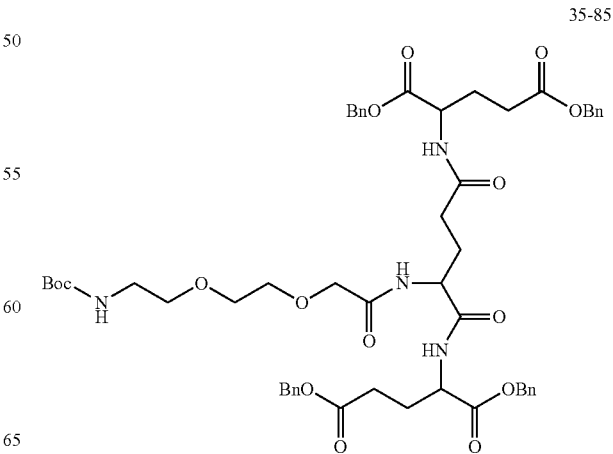

35-85

37-151 (19.36 g, 73.5364 mmol), HBTU (41.83 g, 110.3045 mmol), HOBT (14.91 g, 110.3045 mmol) and 35-84 (61.95 g, 80.89 mmol) were added in a 1000 mL round-bottomed flask, and dissolved with DMF (200 mL), and then the mixed solution was stirred to react at −5° C. for about 30 minutes. Then DIEA (54.69 mL, 330.9136 mmol) was slowly added dropwise. At the end of the addition, the obtained solution continued to react at −5° C. with stirring for 1 hour, and was then moved to room temperature and stirred to react overnight. At the end of the reaction, the reaction solution was first transferred to a 2 L separatory funnel, saturated sodium bicarbonate solution (500 mL) and ethyl acetate (300 mL) were added, the obtained solution was shaken for extraction, and the organic phase was separated. The aqueous phase was washed with ethyl acetate (200 mL×1), and the obtained organic phases were combined. The organic phase was concentrated to a small amount, silica gel powder was added, and the operations of evaporation, dry sample loading, column chromatography and elution with a petroleum ether mixed solution containing 50%-70% ethyl acetate were carried out, thus obtaining the product 35-85: 51 g, yield: 69%.

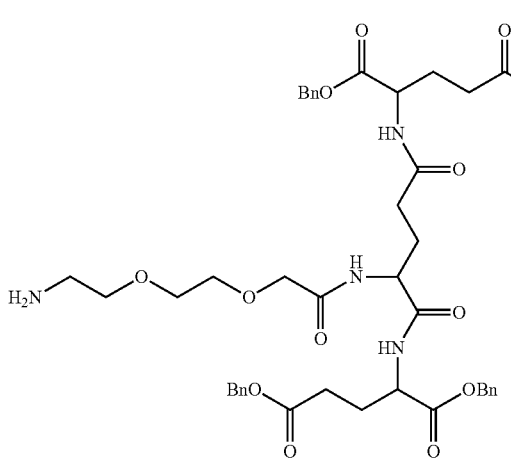

35-86

35-85 (23.4 g, 23.14 mmol) was added in a 500 mL round-bottomed flask, and dissolved with dichloromethane (30 mL), trifluoroacetic acid (85.93 mL, 1157.13 mmol) was added with stirring, and then the mixed solution was stirred to react at room temperature overnight. At the end of the reaction, the reaction solution was concentrated, ethyl acetate (300 mL) and saturated sodium bicarbonate solution (300 mL) were added, a lot of bubbles were generated, a sodium bicarbonate solid was further added till a pH of greater than 7, and then the extraction was carried out. The aqueous phase was washed with ethyl acetate (200 mL×1), and the obtained organic phases were combined. The organic phase was evaporated to dryness, thus obtaining 35-86: 18.2 g, yield: 86%.

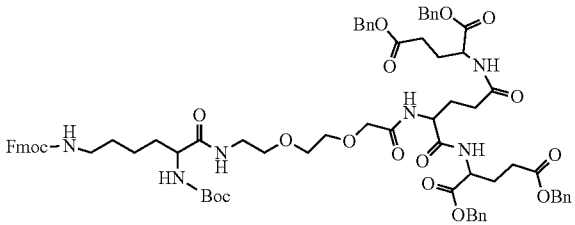

35-88

35-86 (18.2 g, 19.98 mmol), HBTU (11.36 g, 29.97 mmol), HOBT (4.05 g, 29.97 mmol) and Boc-Lys (Fmoc)—OH (8.5 g, 18.16 mmol, purchased from Accela) were added in a 500 mL round-bottomed flask, and dissolved with DMF (100 mL), and then the mixed solution was stirred at 0° C. for 30 minutes. Then DIEA (14.86 mL, 89.90 mmol) was slowly added dropwise. At the end of the addition, the obtained solution continued to react with stirring at 0° C. overnight. At the end of the reaction, the reaction solution was first transferred to a 1 L separatory funnel, saturated sodium bicarbonate solution (300 mL) and ethyl acetate (200 mL) were added, the obtained solution was shaken for extraction, and the organic phase was separated. The aqueous phase was washed with ethyl acetate (200 mL×1), and the obtained organic phases were combined. The organic phase was concentrated to a small amount, silica gel powder was added, and the operations of evaporation, dry sample loading, column chromatography and elution with a petroleum ether mixed solution containing 80%-100% ethyl acetate were carried out, thus obtaining the product 35-88: 19.6 g, yield: 79%.

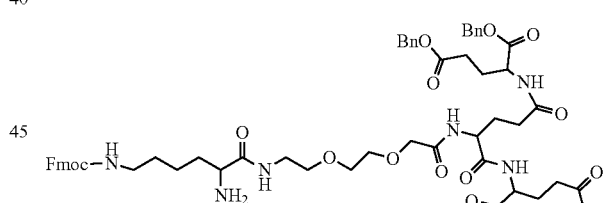

35-89

35-88 (7.0 g, 5.1413 mmol) was added in a 250 mL flask, and dissolved with dichloromethane (20 mL), trifluoroacetic acid (5.7270 mL, 77.1191 mmol) was added with stirring, and then the mixed solution was stirred to react at room temperature overnight. At the end of the reaction, the reaction solution was concentrated, the reaction solution was transferred to a 1 L separatory funnel, saturated sodium bicarbonate solution (300 mL) and ethyl acetate (200 mL) were added, the obtained solution was shaken for extraction, and the organic phase was separated. The aqueous phase was washed with ethyl acetate (150 mL×2), and the obtained organic phases were combined. The organic phase was washed with saturated saline solution (200 mL×2), concentrated and evaporated to dryness, thus obtaining the product 35-89: 6.4853 g.

35-90

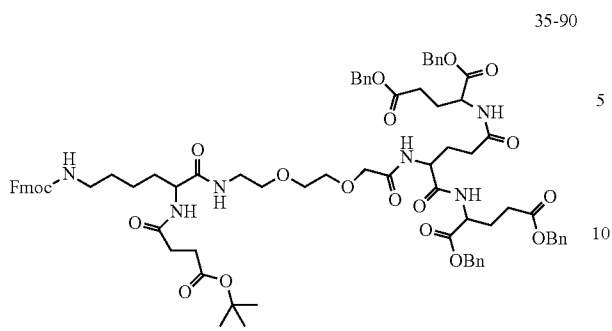

35-89 (4.2 g, 3.33 mmol), HBTU (1.72 g, 4.54 mmol), HOBT (0.61 g, 4.54 mmol) and mono-tert-butyl succinate (0.53 g, 3.03 mmol) were added in a 250 mL flask, and dissolved with DMF (40 mL), and then the mixed solution was stirred to react at 0° C. for 30 minutes. Then DIEA (2.25 mL, 13.62 mmol) was slowly added dropwise. At the end of the addition, the obtained solution continued to react with stirring at 0° C. overnight. At the end of the reaction, the reaction solution was transferred to a 1 L reparatory funnel, deionized water (300 mL) and ethyl acetate (200 mL) were added, the obtained solution was shaken for extraction, and the organic phase was separated. The aqueous phase was washed with ethyl acetate (200 mL×1), and the obtained organic phases were combined. The organic phase was concentrated to a small amount, silica gel powder was added, and the operations of evaporation, dry sample loading, column chromatography and elution with a dichloromethane mixed solution containing 3% methanol were carried out, thus obtaining the product 35-90: 4.3 g.

$^1$H-NMR (600 MHz, DMSO-d$_6$) δ 8.62-8.53 (m, 1H), 8.40-8.24 (d, J=7.4 Hz, 1H), 7.95-7.81 (m, 1H), 7.88-7.82 (d, J=7.5 Hz, 3H), 7.77-7.64 (m, 3H), 7.51-7.43 (m, 2H), 7.38-7.29 (m, 22H), 7.24-7.12 (t, J=5.6 Hz, 1H), 5.15-5.01 (m, 9H), 4.46-4.15 (m, 8H), 3.92-3.82 (m, 2H), 3.64-3.50 (m, 4H), 3.38-3.27 (m, 2H), 3.20-3.13 (d, J=5.0 Hz, 2H), 3.01-2.89 (m, 3H), 2.48-2.32 (m, 10H), 2.18-2.10 (t, J=8.0 Hz, 2H), 2.05-1.71 (m, 7H), 1.56-1.46 (d, J=5.9 Hz, 1H), 1.40-1.37 (m, 2H), 1.36-1.21 (m, 10H).

35-93

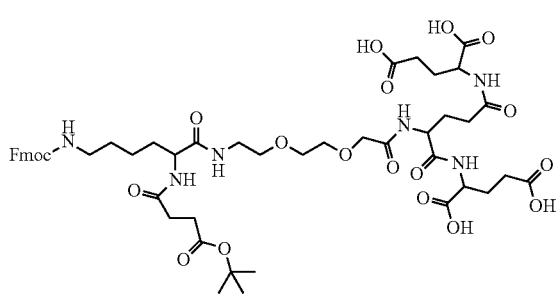

35-90 (0.622 g, 0.4390 mmol) and Pd/C (0.0300 g) were added in a hydrogenation reactor, and dissolved with DMF (30 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

37-53

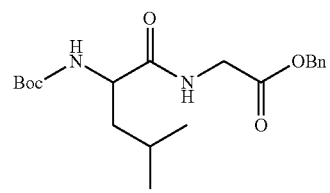

Boc-Leu-OH·H$_2$O (40 g, 160.44 mmol, purchased from InnoChem), Gly-OBn·TsOH (56.837 g, 168.462 mmol, purchased from Ark pharm), HBTU (66.93 g, 176.48 mmol), HOBT (23.85 g, 176.48 mmol) were added in a 1000 mL flask, and dissolved with DMF (250 mL), and then the mixed solution was stirred at −5° C. for 20 minutes. Then DIEA (145.85 mL, 882.4356 mmol) was slowly added dropwise. At the end of the addition, the obtained solution was further stirred at −5° C. for 1 hour, and then moved to room temperature and stirred to react overnight. At the end of the reaction, the reaction solution was transferred to a 2 L separatory funnel, saturated sodium bicarbonate solution (250 mL) and ethyl acetate (300 mL) were added for extraction, and the organic phase was separated. The aqueous phase was washed with ethyl acetate (200 mL×3), and the obtained organic phases were combined. The organic phase was washed with saturated saline solution (200 mL×2), concentrated and evaporated to dryness. The operations of dry sample loading, column chromatography and elution with a petroleum ether mixed solution containing 30%-40% EA were carried out, thus obtaining the product 37-53: 60.7 g.

37-54

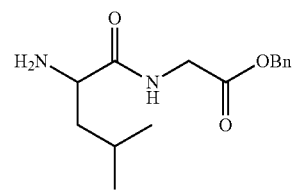

37-53 (60.7 g, 160.44 mmol) was added in a 1000 mL flask, and dissolved with dichloromethane (40 mL), TFA (95 mL, 1283.52.9 mmol) was added, and then the mixed solution was stirred to react at room temperature overnight. At the end of the reaction, the reaction solution was transferred to a 2 L separatory funnel, saturated sodium bicarbonate solution (350 mL) and ethyl acetate (300 mL) were added for extraction, and the organic phase was separated. The aqueous phase was washed with ethyl acetate (1500 mL×2), and the obtained organic phases were combined. The organic phase was concentrated and evaporated to dryness, thus obtaining the product 37-54: 45 g.

37-56

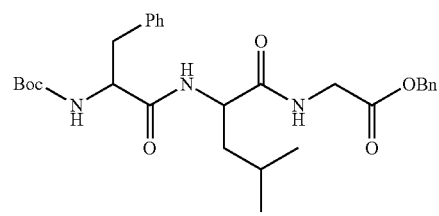

37-54 (45 g, 160.44 mmol), Boc-Phe-OH (40.438 g, 152.42 mmol, purchased from aladdin), HBTU (66.93 g, 1276.48 mmol), HOBT (23.85 g, 176.48 mmol) were added in a 1000 mL flask, and dissolved with DMF (250 mL), and the mixed solution was stirred to react at −5° C. for 20 minutes. Then DIEA (119.85 mL, 722 mmol) was slowly added dropwise. At the end of the addition, the obtained solution was further stirred at −5° C. for 1 hour, and then moved to room temperature and stirred to react overnight. At the end of the reaction, the reaction solution was transferred to a 2 L separatory funnel, saturated sodium bicarbonate solution (350 mL) and ethyl acetate (300 mL) were added for extraction, and the organic phase was separated. The aqueous phase was washed with ethyl acetate (200 mL×3), and the obtained organic phases were combined. The organic phase was washed with saturated saline solution (250 mL×2), concentrated and evaporated to dryness, thus obtaining the product 37-56: 84 g.

37-59

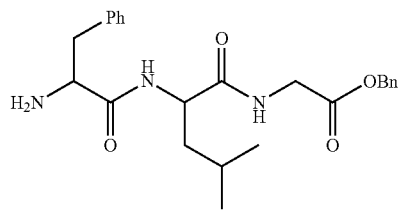

37-56 (84 g, 160.44 mmol) was added in a 1000 mL flask, and dissolved with dichloromethane (40 mL), TFA (95 mL, 1283.52.9 mmol) was added, and then the mixed solution was stirred to react at room temperature overnight. At the end of the reaction, the reaction solution was transferred to a 2 L conical flask, saturated sodium bicarbonate solution (350 mL) was added, a lot of bubbles were generated, a sodium bicarbonate solid was slowly added till a pH of greater than 7, to separate out a solid, and filtering was carried out. The filter cake was washed with pure water (100 mL×2), and dried, thus obtaining the product 37-59: 68 g.

37-62

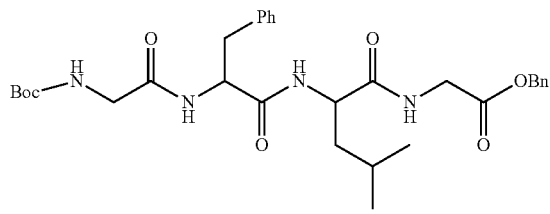

37-59 (68.27 g, 152.42 mmol), Boc-Gly-OH (25.37 g, 144.799 mmol, purchased from aladdin), HBTU (63.58 g, 167.66 mmol), HOBT (63.58 g, 167.66 mmol) were added in a 1000 mL flask, and dissolved with DMF (250 mL), and then the mixed solution was stirred at −5° C. for 20 minutes. Then DIEA (113.3 mL, 685.89 mmol) was slowly added dropwise. At the end of the addition, the obtained solution was further stirred at −5° C. for 1 hour, and then moved to room temperature and stirred to react overnight. At the end of the reaction, the reaction solution was transferred to a 2 L separatory funnel, saturated sodium bicarbonate solution (300 mL) and ethyl acetate (350 mL) were added for extraction, and the organic phase was separated. The aqueous phase was washed with ethyl acetate (200 mL×3), and the obtained organic phases were combined. The organic phase was washed with saturated saline solution (250 mL×2), and stood still at room temperature for 1.5 hours, to separate out a solid, and filtering was carried out. The filter cake was washed with ethyl acetate:petroleum ether (3:7) (150 mL×5), thus obtaining the product 37-62: 72.8 g.

37-149

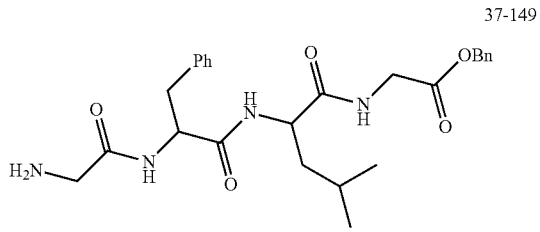 [SMILES: CC(C)CC(NC(=O)C(Cc1ccccc1)NC(=O)CN)C(=O)NCC(=O)OCc1ccccc1]

37-62 (30 g, 51.4871 mmol) was added in a 250 mL flask, and dissolved with dichloromethane (20 mL), trifluoroacetic acid (30.6 mL, 411.9 mmol) was added with stirring, and then the mixed solution was stirred to react at room temperature overnight. At the end of the reaction, the reaction solution was concentrated, saturated sodium bicarbonate solution (200 mL) was added, a lot of bubbles were generated, then a sodium bicarbonate solid was slowly added till a pH of greater than 7, to separate out a solid, and filtering was carried out. The filter cake was washed with deionized water (150 mL×4), and dried, thus obtaining the product 37-149: 24.85 g.

37-152

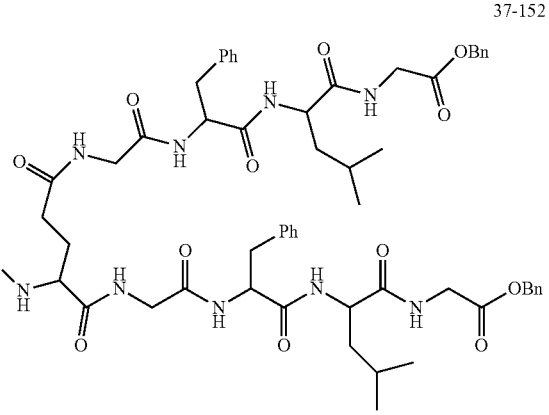

Boc-Glu-OH (5.7864 g, 23.4032 mmol, purchased from Ark pharm), 37-149 (24.85 g, 51.4871 mmol), HBTU (26.626 g, 70.2096 mmol), HOBT (9.4874 g, 70.2096 mmol) were added in a 500 mL flask, and dissolved with DMF (150 mL), and then the mixed solution was stirred to react at −5° C. for about 10 minutes. Then DIEA (34.8 mL, 210.628 mmol) was slowly added dropwise. At the end of the addition, the obtained solution was further stirred at −5° C. for 1 hour, and then moved to room temperature and stirred to react overnight. At the end of the reaction, the reaction solution was transferred to a 1 L separatory funnel, saturated sodium bicarbonate solution (200 mL) and ethyl acetate (300 mL) were added, and the obtained solution was shaken for extraction. The aqueous phase was washed with ethyl acetate (150 mL×1), and the obtained organic phases were combined. The organic phase was concentrated and evaporated to dryness. The dry product was dissolved with methanol (20 mL) and dichloromethane (100 mL), silica gel powder (50 g) was added, and the obtained mixture was then evaporated to dryness to obtain a powdery solid. The operations of dry sample loading, column chromatography and elution with a dichloromethane mixed solution containing 4%-8% methanol were carried out. The elution product was then collected, and dried in a vacuum oven, thus obtaining the product 37-152: 19.2 g, yield: 69.8%.

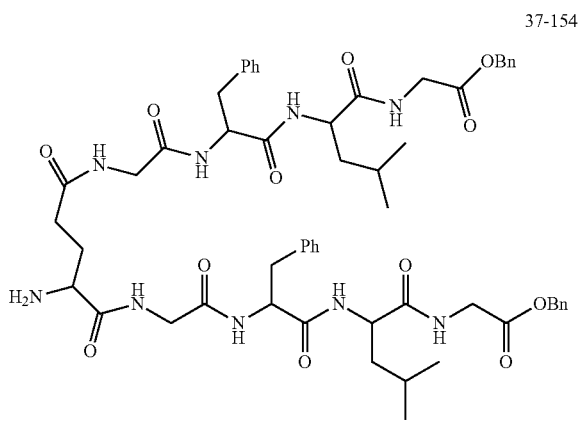 [SMILES: CC(C)CC(NC(=O)C(Cc1ccccc1)NC(=O)CNC(=O)CCC(N)C(=O)NCC(=O)NC(Cc1ccccc1)C(=O)NC(CC(C)C)C(=O)NCC(=O)OCc1ccccc1)C(=O)NCC(=O)OCc1ccccc1]

37-154

37-152 (19.2 g, 16.3215 mmol) was added in a 1000 mL flask, and dissolved with dichloromethane (30 mL), trifluoroacetic acid (9.6966 mL, 130.5722 mmol) was added, and then the mixed solution was stirred to react at room temperature overnight. At the end of the reaction, the reaction solution was concentrated to a small amount, methyl tert-butyl ether (200 mL) was added to the concentrated solution to separate out a solid, and suction filtering was carried out. The filter cake was washed with methyl tert-butyl ether (100 mL×3), and dried, thus obtaining the product 37-154: 17.5 g.

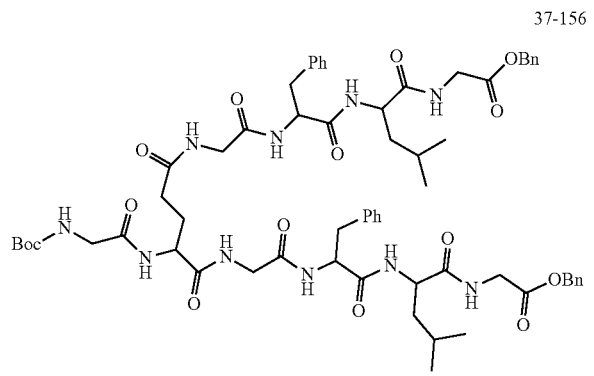 [SMILES: CC(C)CC(NC(=O)C(Cc1ccccc1)NC(=O)CNC(=O)CCC(NC(=O)CNC(=O)OC(C)(C)C)C(=O)NCC(=O)NC(Cc1ccccc1)C(=O)NC(CC(C)C)C(=O)NCC(=O)OCc1ccccc1)C(=O)NCC(=O)OCc1ccccc1]

37-156

Boc-Gly-OH (3.4310 g, 19.5858 mmol, purchased from Ark Pharm), 37-154 (17.5 g, 16.3215 mmol), HBTU (9.2847 g, 24.4823 mmol), HOBT (3.3083 g, 24.4823 mmol) were added in a 1000 mL flask, and dissolved with DMF (150 mL), and then the mixed solution was stirred to react at −5° C. for about 10 minutes. Then DIEA (12.14 mL, 73.4468 mmol) was slowly added dropwise. At the end of the addition, the obtained solution was further stirred at −5° C. for 1 hour, and then moved to room temperature and stirred to react overnight. At the end of the reaction, ethyl acetate (200 mL), methyl tert-butyl ether (200 mL), n-hexane (300 mL) were added to the reaction solution to separate out a solid, and suction filtering was carried out. The filter cake was washed with methyl tert-butyl ether (100 mL×3), and dried, thus obtaining the product 37-156: 19.2 g.

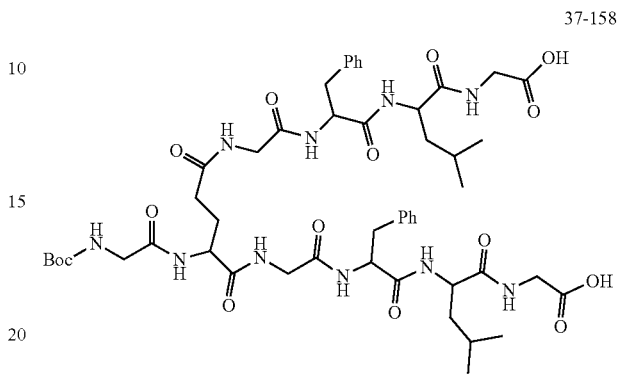

37-158

37-156 (10.499 g, 8.5125 mmol) and 10% Pd/C (0.10 g) were added in a hydrogenation reactor, and dissolved with DMF (50 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the obtained DMF solutions were combined, as raw material for the next reaction.

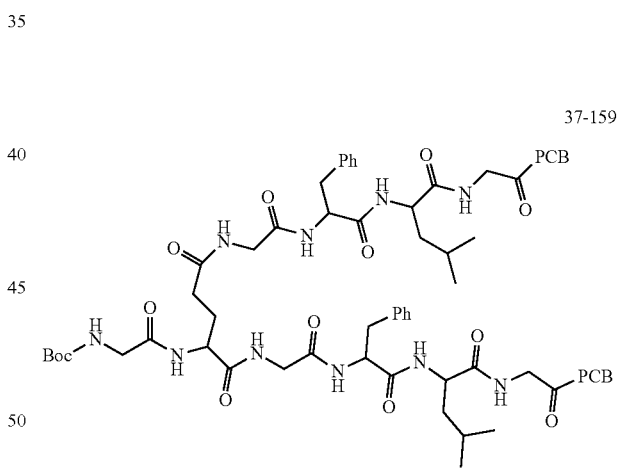

37-159

37-158 (8.965 g, 0.4390 mmol), Palbociclib (8 g, 17.8763 mmol, also referred to as PCB), HBTU (9.6848 g, 25.5375 mmol), HOBT (3.4509 g, 25.5375 mmol) were added in a 500 mL flask, and dissolved with DMF (130 mL), and then the mixed solution was stirred at −5° C. for 20 minutes. Then DIEA (12.6626 mL, 76.6125 mmol) was slowly added dropwise. At the end of the addition, the obtained solution was stirred at −5° C. for 1 hour, and then moved to room temperature and stirred to react overnight. At the end of the reaction, n-hexane (150 mL) and methyl tert-butyl ether (100 mL) were added to the reaction solution to separate out a solid, and filtering was carried out. The filter cake was washed with methyl tert-butyl ether (100 mL×3), and dried, thus obtaining the product 37-159: 16.3 g.

37-161

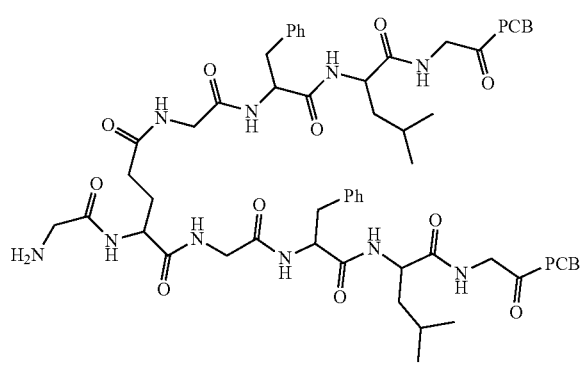

37-159 (16.3 g, 8.5125 mmol) was added in a 500 mL flask, and dissolved with dichloromethane (30 mL), trifluoroacetic acid (18.964 mL, 255.375 mmol) was added, and then the mixed solution was stirred to react at room temperature overnight. At the end of the reaction, methyl tert-butyl ether (250 mL) was added to the reaction solution to separate out a solid, and filtering was carried out. The filter cake was washed with methyl tert-butyl ether (50 mL×3), and dissolved with dichloromethane (240 mL) and methanol (60 mL), silica gel powder (50 g) was added, and the obtained mixture was then evaporated to dryness to obtain a powdery solid. The operations of dry sample loading, column chromatography and elution with a dichloromethane mixed solution containing 1% ammonia water and 5%-7% methanol were carried out. The elution product was then collected, concentrated and dried, thus obtaining the product 37-161: 11.2 g, yield 73%.

35-94

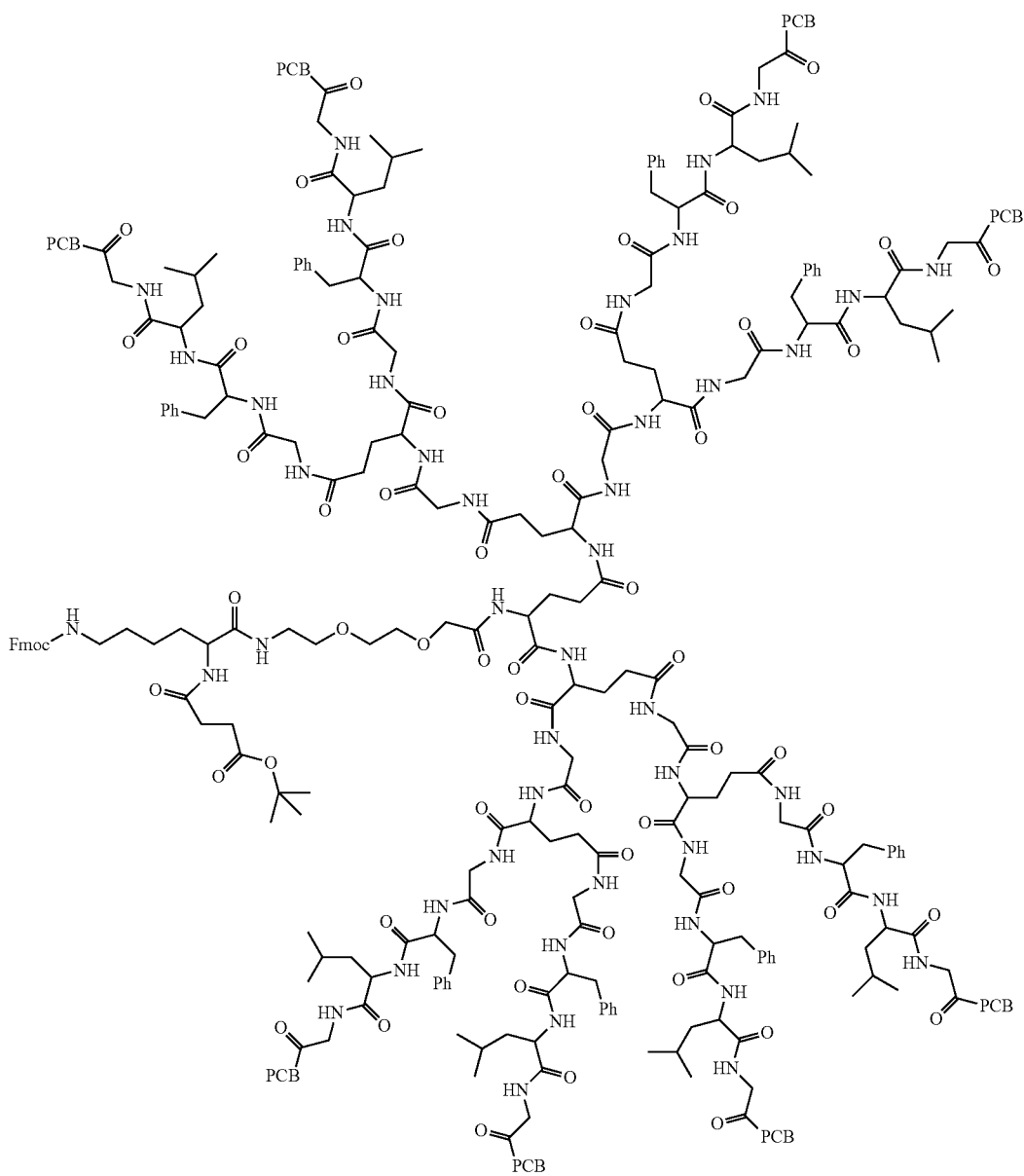

35-93 (0.464 g, 0.4390 mmol), 37-161 (3.5 g, 1.9315 mmol), HBTU (0.9988 g, 2.6338 mmol), HOBT (0.3559 g, 2.6338 mmol) were added in a 250 mL flask, and dissolved with DMF (50 mL), and then the mixed solution was stirred at −5° C. for 20 minutes. Then DIEA (1.306 mL, 7.9015 mmol) was slowly added dropwise. At the end of the addition, the obtained solution was stirred at −5° C. for 40 minutes, and then moved to room temperature and stirred to react overnight. At the end of the reaction, the reaction solution was precipitated two times with n-hexane (100 mL) and methyl tert-butyl ether (60 mL), to obtain a viscous oily product. Methyl tert-butyl ether (100 mL) was added to the oily product to separate out a solid, and filtering was carried out. The filter cake was washed with methyl tert-butyl ether (50 mL×2), and dried, thus obtaining the product 35-94: 3.614 g.

35-94 (3.614 g, 0.4390 mmol) was added in a 250 mL flask, and dissolved with DMF (25 mL), morpholine (1.7 mL, 19.7507 mmol) was added, and then the mixed solution was stirred to react at room temperature for 1 hour. At the end of the reaction, methyl tert-butyl ether (150 mL) was added to the reaction product to separate out a solid, and then filtering was carried out. The filter cake was washed with methyl tert-butyl ether (50 mL×3), and dissolved with dichloromethane (200 mL) and methanol (50 mL), silica gel powder (20 g) was added, and the obtained mixture was then evaporated to dryness to obtain a powdery solid. The operations of dry sample loading, column chromatography and elution with a dichloromethane mixed solution containing 1% ammonia water and 5%-9% methanol were carried out. The elution product was then collected, concentrated and dried, thus obtaining the product 35-95: 0.7 g, yield 20%.

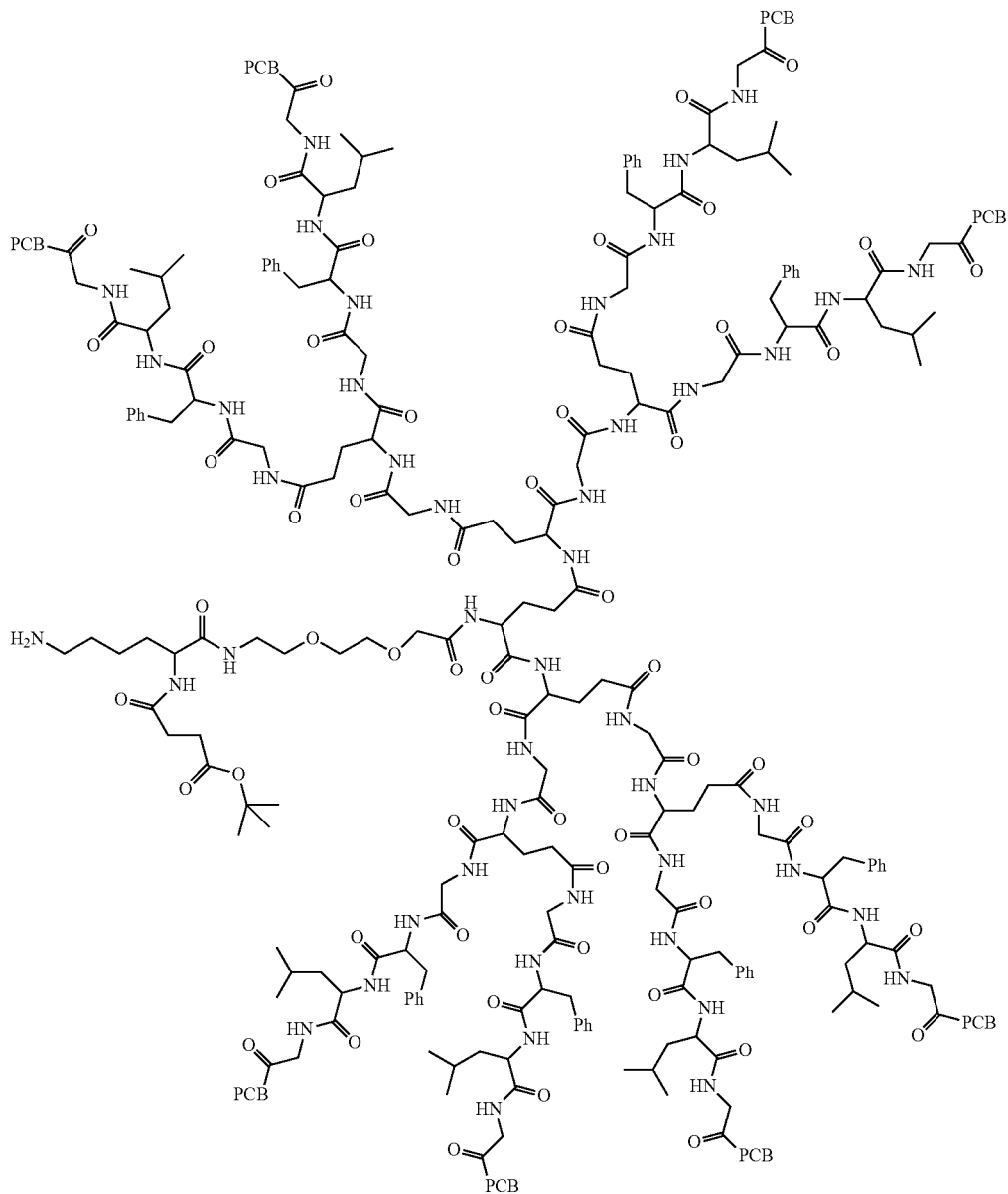

35-95

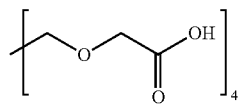
37-172

45-57 (0.0412 g, 0.0565 mmol) and 10% Pd/C (0.10 g) were added in a hydrogenation reactor, and dissolved with DMF (50 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

37-172 (0.007 g, 0.0199 mmol), 35-95 (0.7 g, 0.0874 mmol), HBTU (0.45 g, 1.192 mmol), HOBT (0.16 g, 1.192 mmol) were added in a 250 mL flask, and dissolved with DMF (35 mL), and then the mixed solution was stirred at −5° C. for 20 minutes. Then DIEA (0.59 mL, 3.575 mmol) was slowly added dropwise. At the end of the addition, the obtained solution was stirred at −5° C. for 20 minutes, and then moved to room temperature and stirred to react overnight. At the end of the reaction, the reaction solution was precipitated one time with n-hexane (150 mL) and methyl tert-butyl ether (60 mL), to obtain a viscous oily product. Methyl tert-butyl ether (100 mL) was added to the oily product to separate out a solid, and filtering was carried out. The filter cake was washed with methyl tert-butyl ether (50 mL×2), and dried, thus obtaining the product 35-96: 0.6434 g.

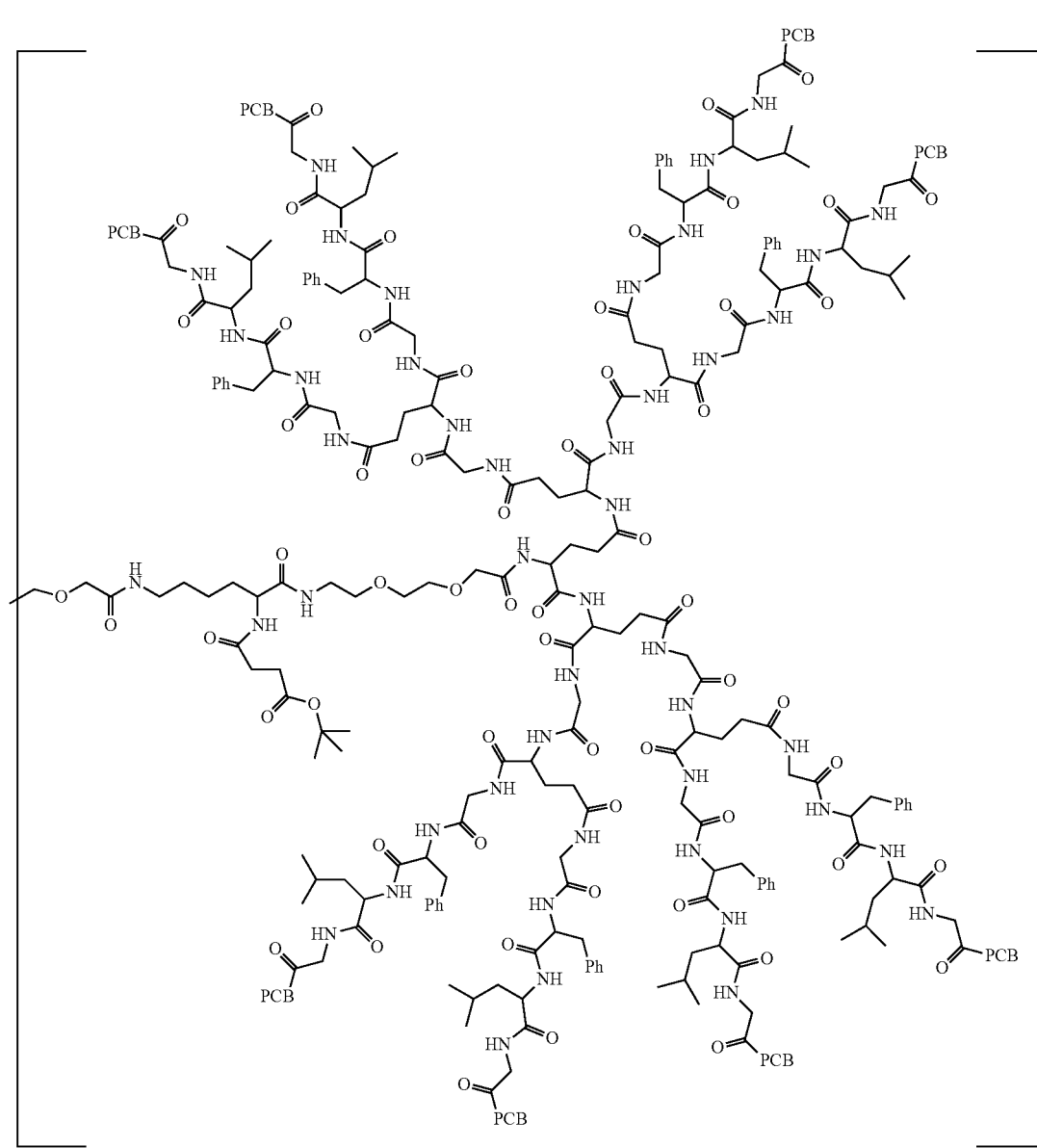
35-96

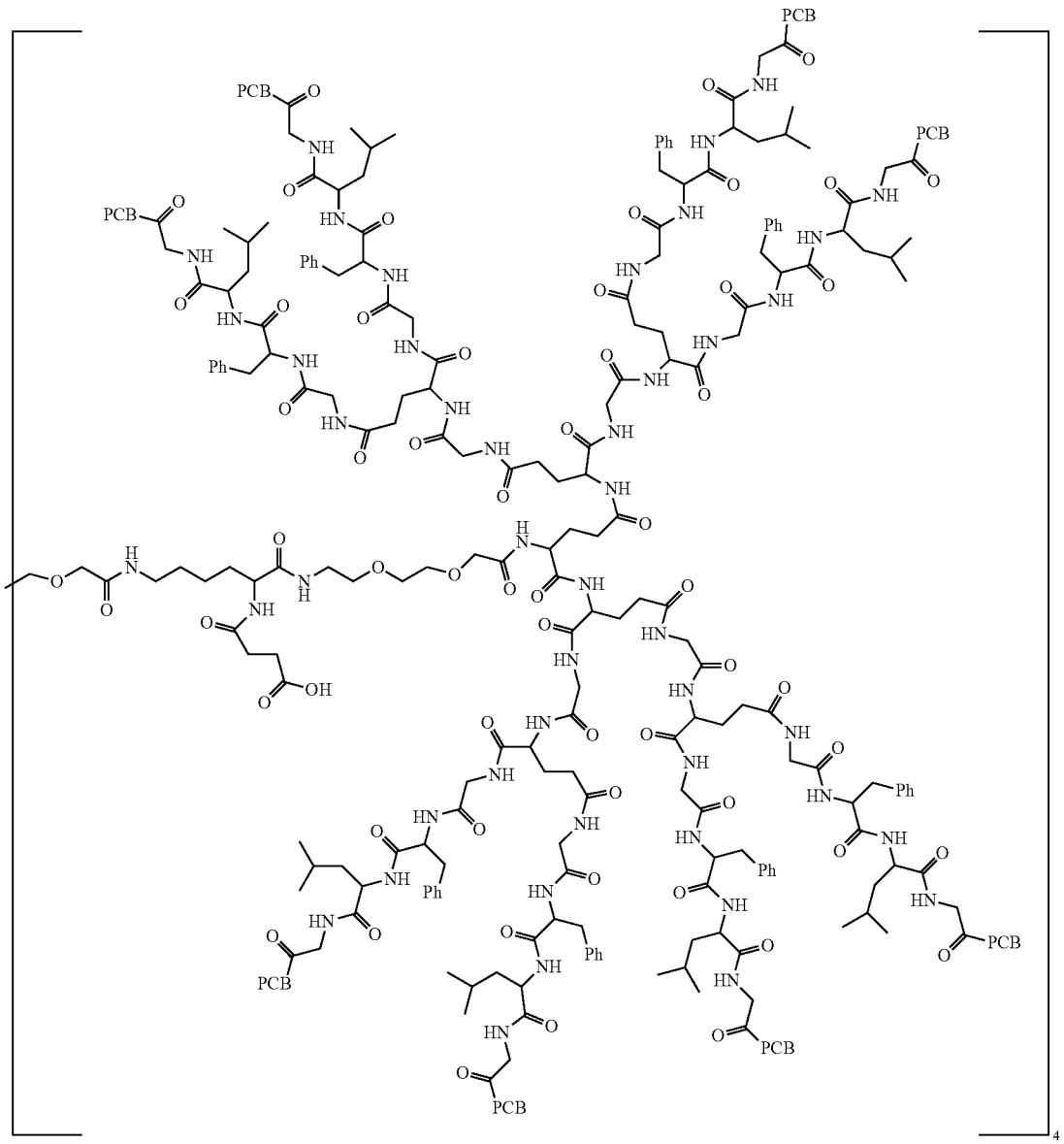

35-97

35-96 (0.6436 g, 0.0199 mmol) was added in a 250 mL flask, and dissolved with dichloromethane (25 mL), trifluoroacetic acid (2.073 mL, 27.92 mmol) was added, and then the mixed solution was stirred to react at room temperature overnight. At the end of the reaction, the reaction solution was concentrated to a small amount, methyl tert-butyl ether (150 mL) was added to the concentrated solution to separate out a solid, and suction filtering was carried out. The filter cake was washed with methyl tert-butyl ether (50 mL×3), and dissolved with a mixed solvent of methanol (30 mL) and dichloromethane (120 mL), silica gel powder (10 g) was added, and the obtained mixture was then evaporated to dryness to obtain a powdery solid. The operations of dry sample loading, column chromatography and elution with a dichloromethane mixed solution containing 1% ammonia water and 5%-8% methanol were carried out. The elution product was then collected, concentrated, evaporated to dryness, thus obtaining the product 35-97: 0.23 g, yield 36%.

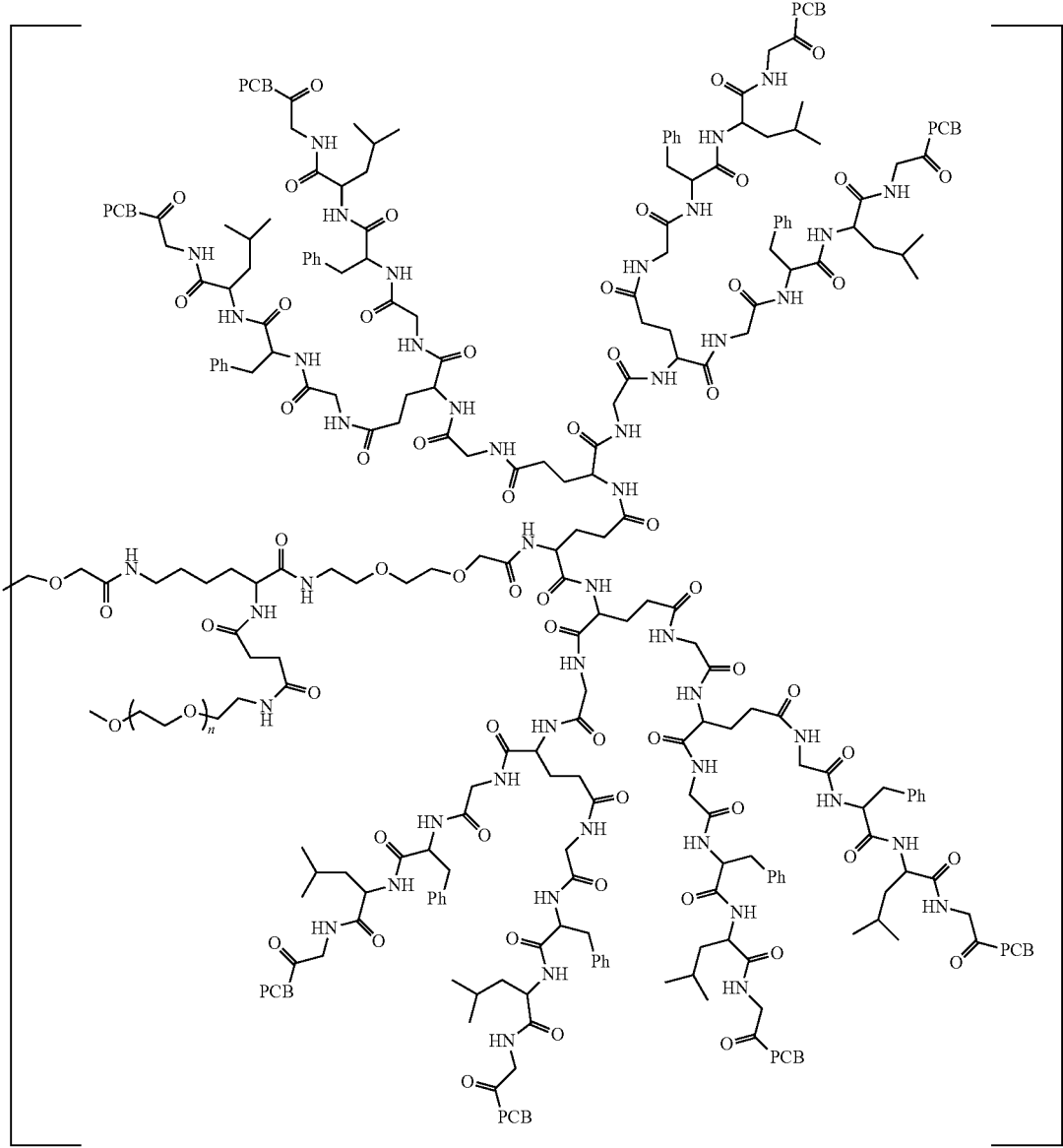

35-98

35-97 (0.23 g, 0.0072 mmol) was added in a 250 mL flask, and dissolved with DMF (10 mL), M-NH$_2$·HCl-10K (0.452 g, 0.043 mmol, purchased from JenKem), HBTU (0.163 g, 0.43 mmol), HOBT (0.058 g, 0.43 mmol) were added, and then the mixed solution was stirred at −5° C. for about 15 minutes at a low speed. Then DIEA (0.1226 mL, 0.7415 mmol) was slowly added dropwise, and the obtained solution continued to react at −5° C. for 20 minutes, and was then moved to room temperature and stirred to react in the dark for 7 days at a low speed. At the end of the reaction, n-hexane (150 mL) and methyl tert-butyl ether (40 mL) were added to the reaction solution, the supernatant was discarded, and n-hexane (150 mL) and methyl tert-butyl ether (40 mL) were added to the lower liquid. Such operations were repeated two times, and a viscous oily product was obtained. Methyl tert-butyl ether (100 mL) was added to obtain a viscous product. The viscous product was dissolved with a mixed solvent of methanol (30 mL) and dichloromethane (120 mL), silica gel powder (15 g) was added, and the obtained mixture was then evaporated to dryness to obtain a powdery solid. The operations of dry sample loading, column chromatography and elution with a dichloromethane mixed solution containing 1% ammonia water and 8%-11% methanol were carried out. The elution product was then collected, concentrated, evaporated to dryness, dried in a vacuum oven, and dissolved with anhydrous ethanol (10 mL) and dichloromethane (15 mL). Then, methyl tert-butyl ether (200 mL) was added to the obtained solution to separate out a solid, and filtering was carried out. The filter cake was washed with methyl tert-butyl ether (50 mL×3), and dried in a vacuum oven, thus obtaining the product 35-98: 0.3 g, yield 57%.

$^1$H-NMR (600 MHz, DMSO-d$_6$) δ 9.24-9.10 (m, 5H), 8.53-8.13 (m, 134H), 7.96-7.82 (m, 85H), 7.86-7.64 (m, 68H), 7.59-7.42 (m, 68H), 7.41-7.34 (m, 71H), 7.30-7.21 (m, 69H), 7.17-7.04 (m, 28H), 6.99-6.73 (m, 5H), 6.68-6.53

(m, 5H), 4.45-4.23 (m, 8H), 4.14-4.01 (m, 21H), 3.79-3.54 (m, 304H), 3.51-3.42 (m, 3763H), 3.14-3.03 (m, 205H), 2.98-2.73 (m, 298H), 2.79-2.70 (m, 270H), 2.62-2.51 (m, 17H), 2.40-2.35 (m, 26H), 2.31-2.24 (m, 22H), 2.12-1.90 (m, 21H), 1.84-1.62 (m, 17H), 1.44-1.29 (m, 221H), 1.25-1.16 (m, 173H).
24. Synthesis of 44-172 (Compound No. 24)
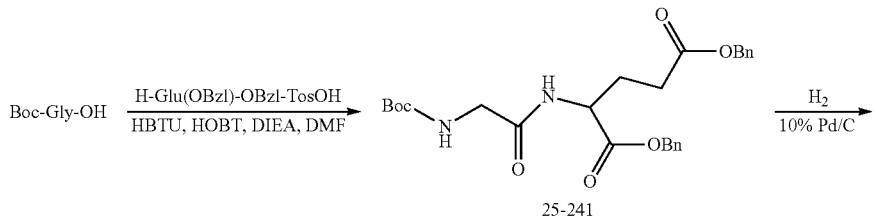
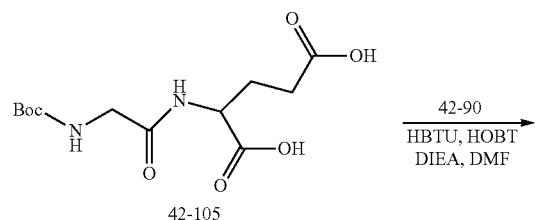
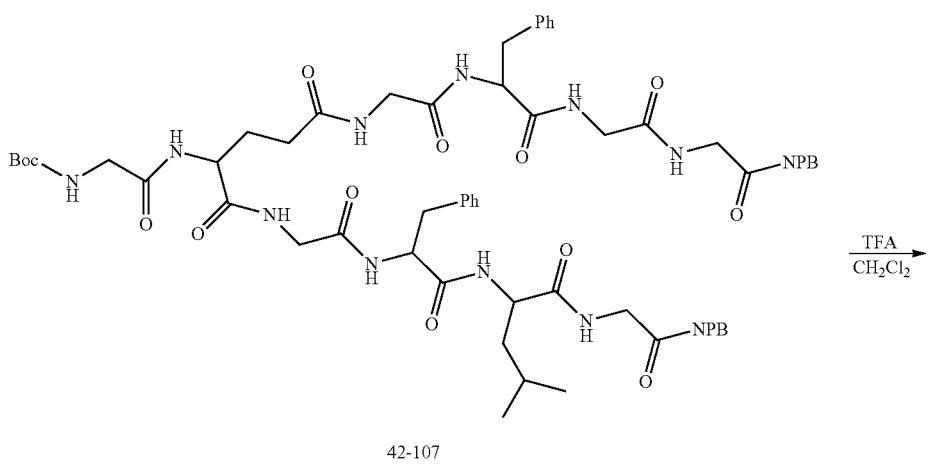
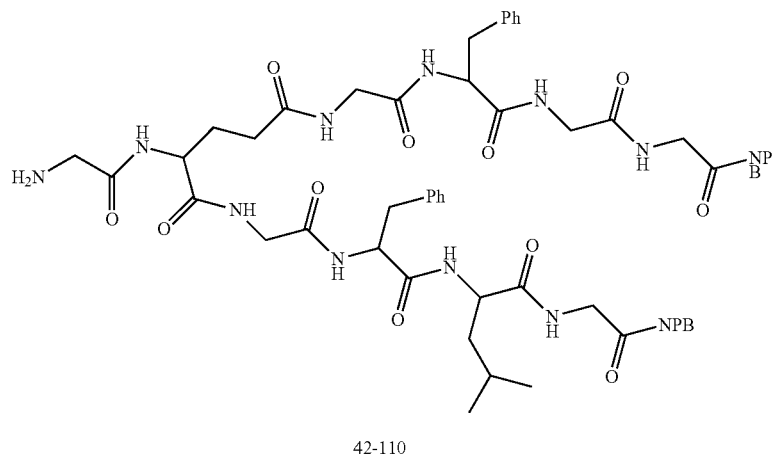

-continued
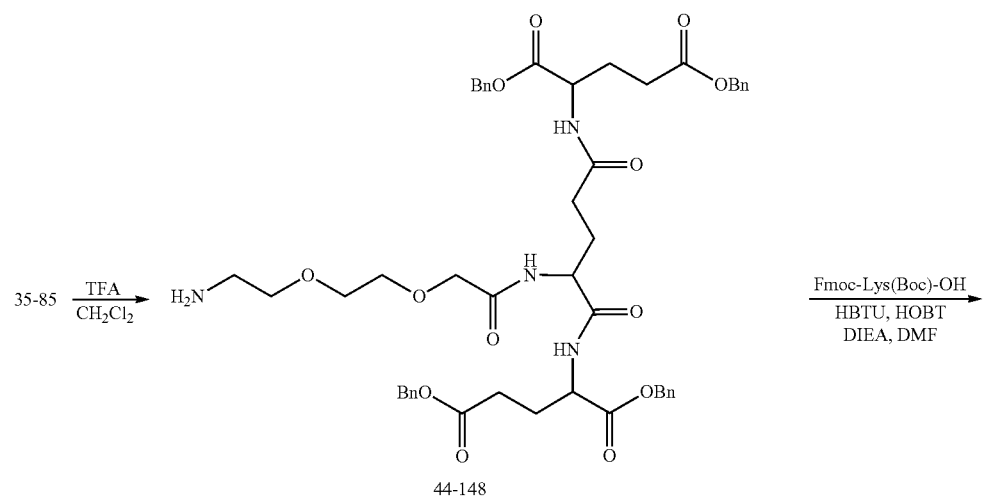
44-148
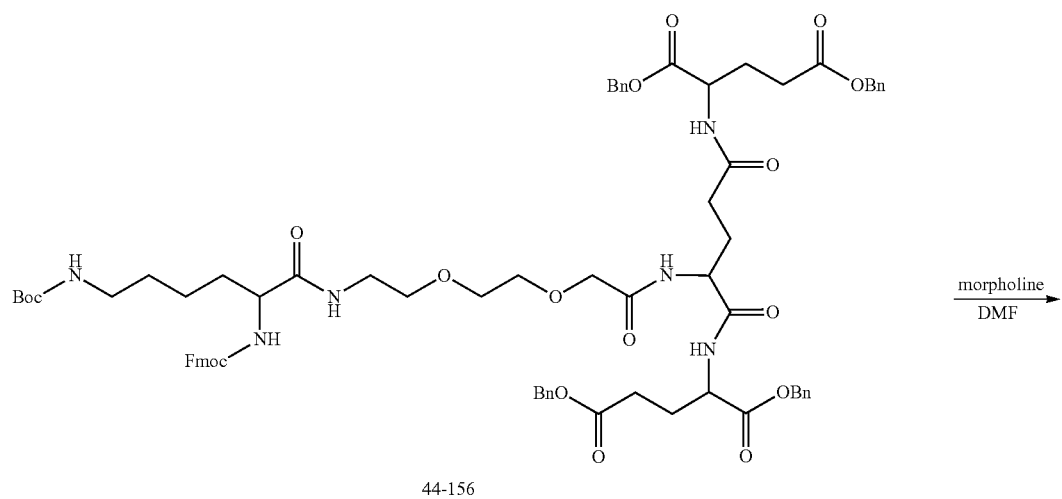
44-156
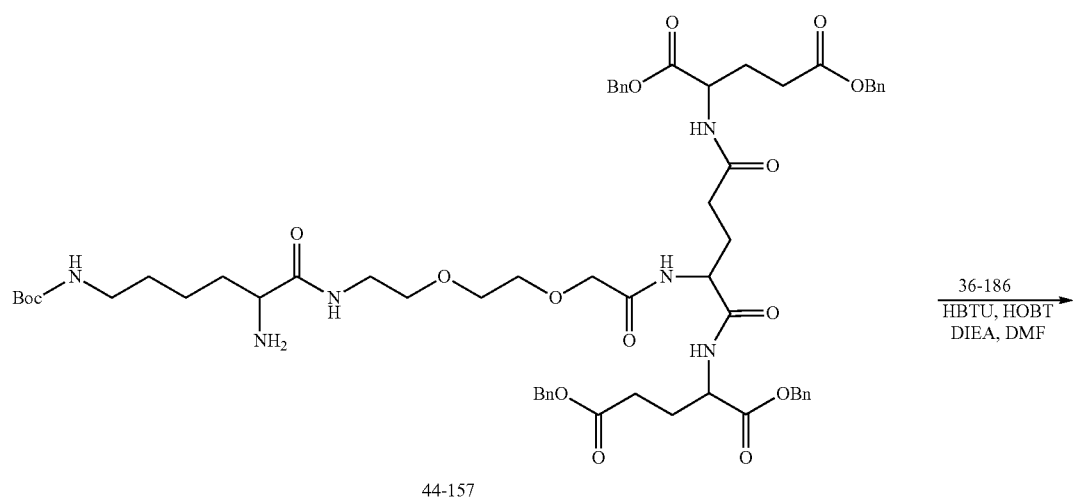
44-157

-continued
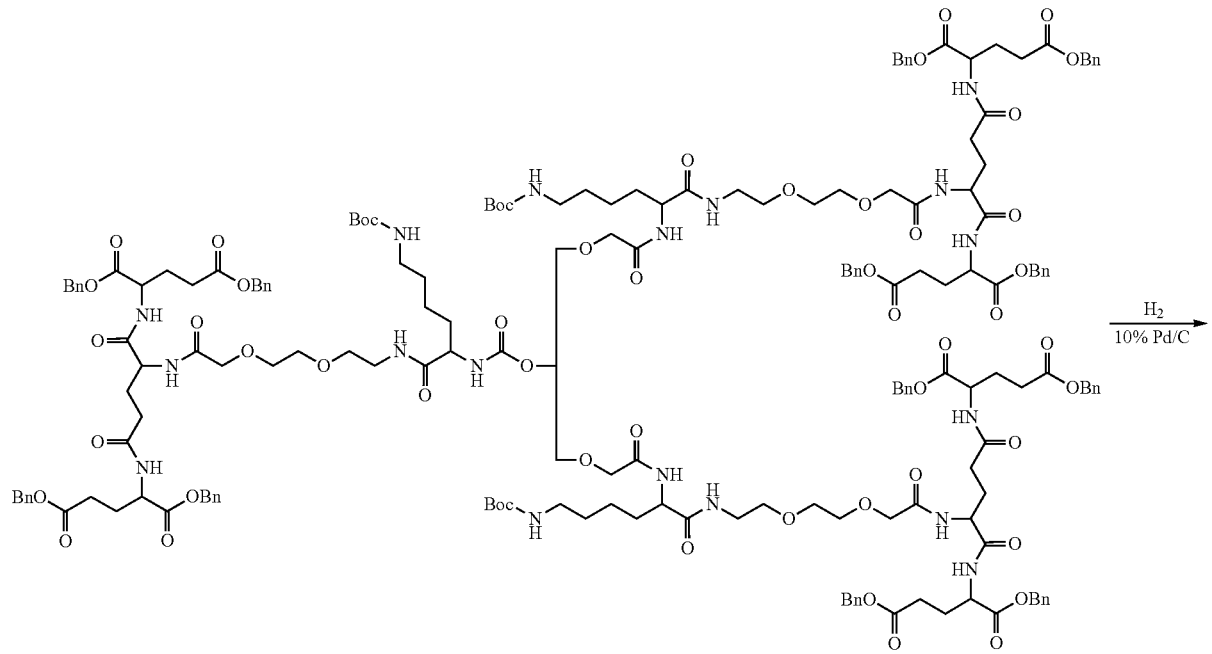
44-161
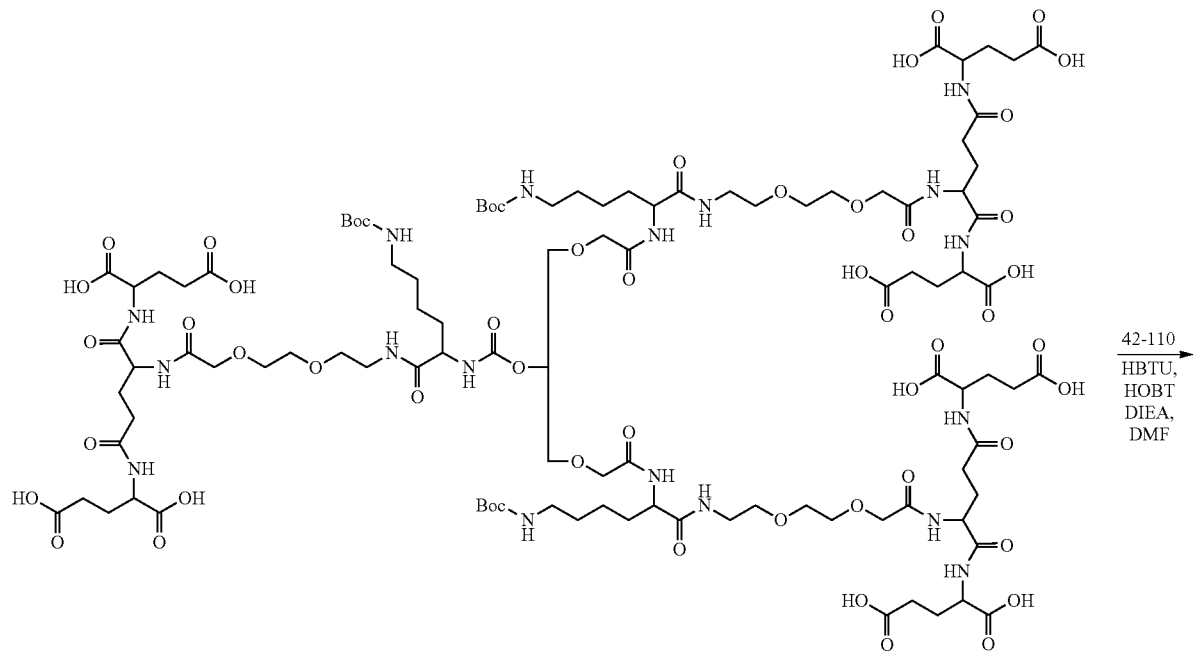
44-166

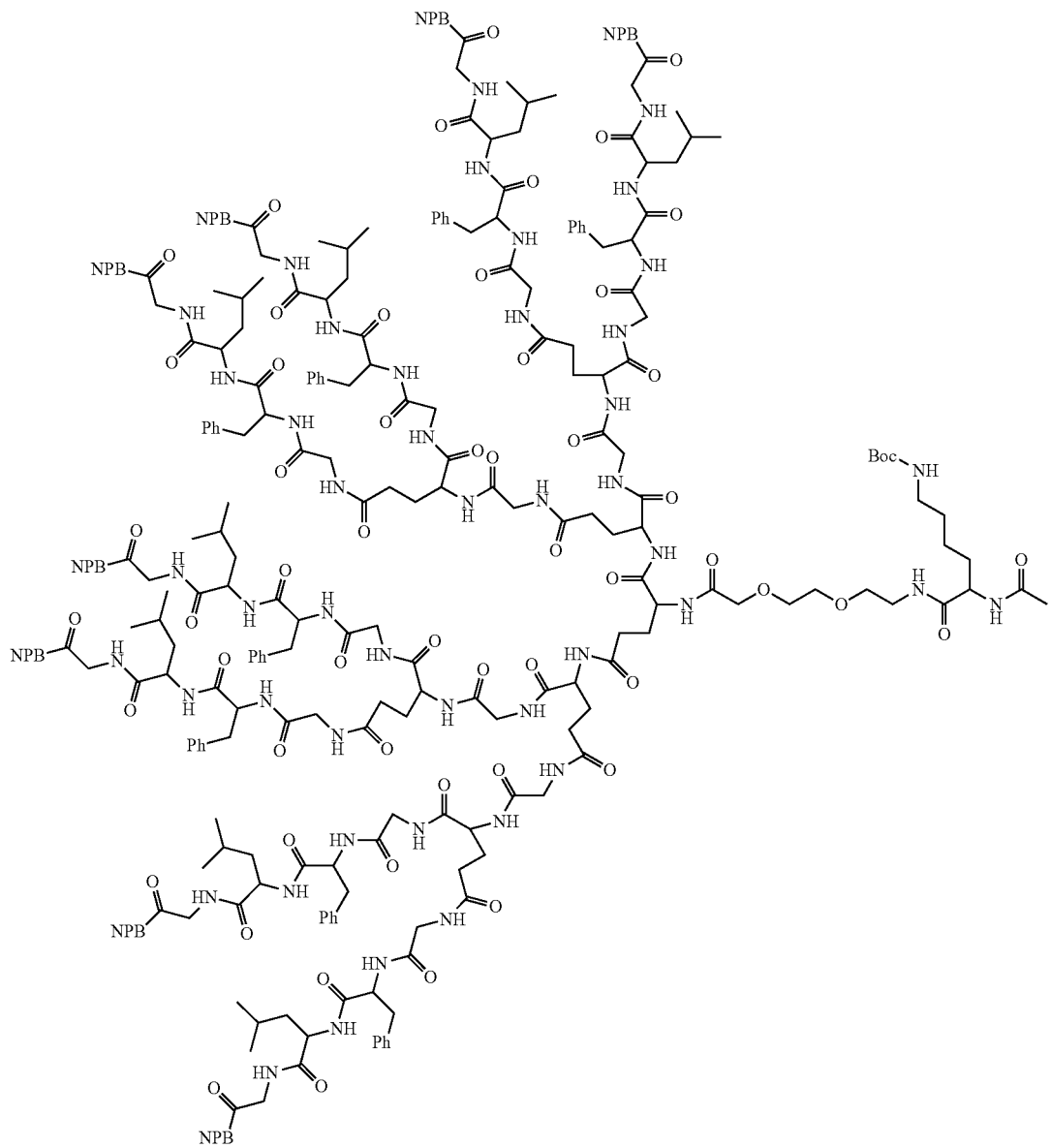

-continued
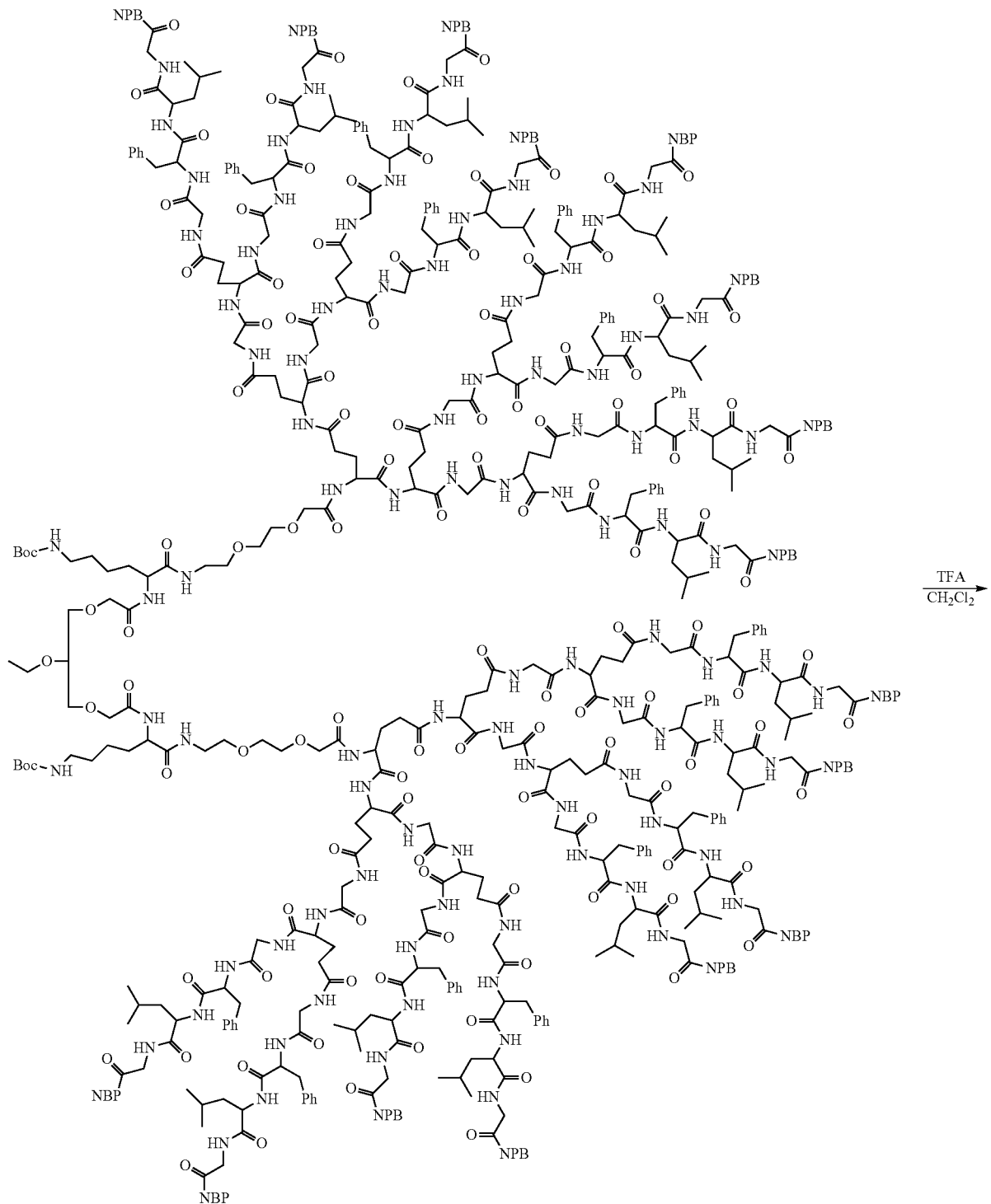
$\xrightarrow{\text{TFA}}{\text{CH}_2\text{Cl}_2}$

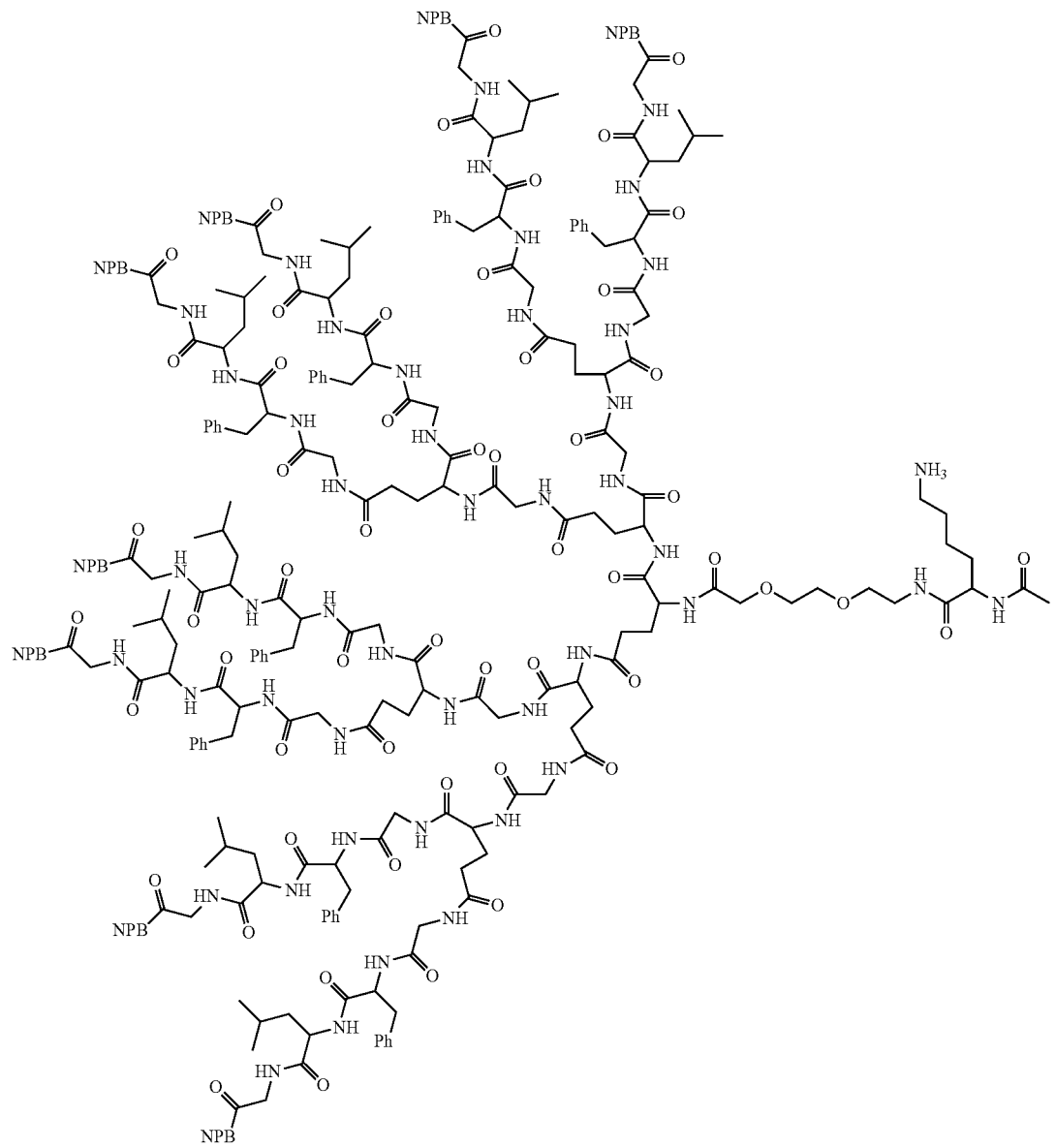

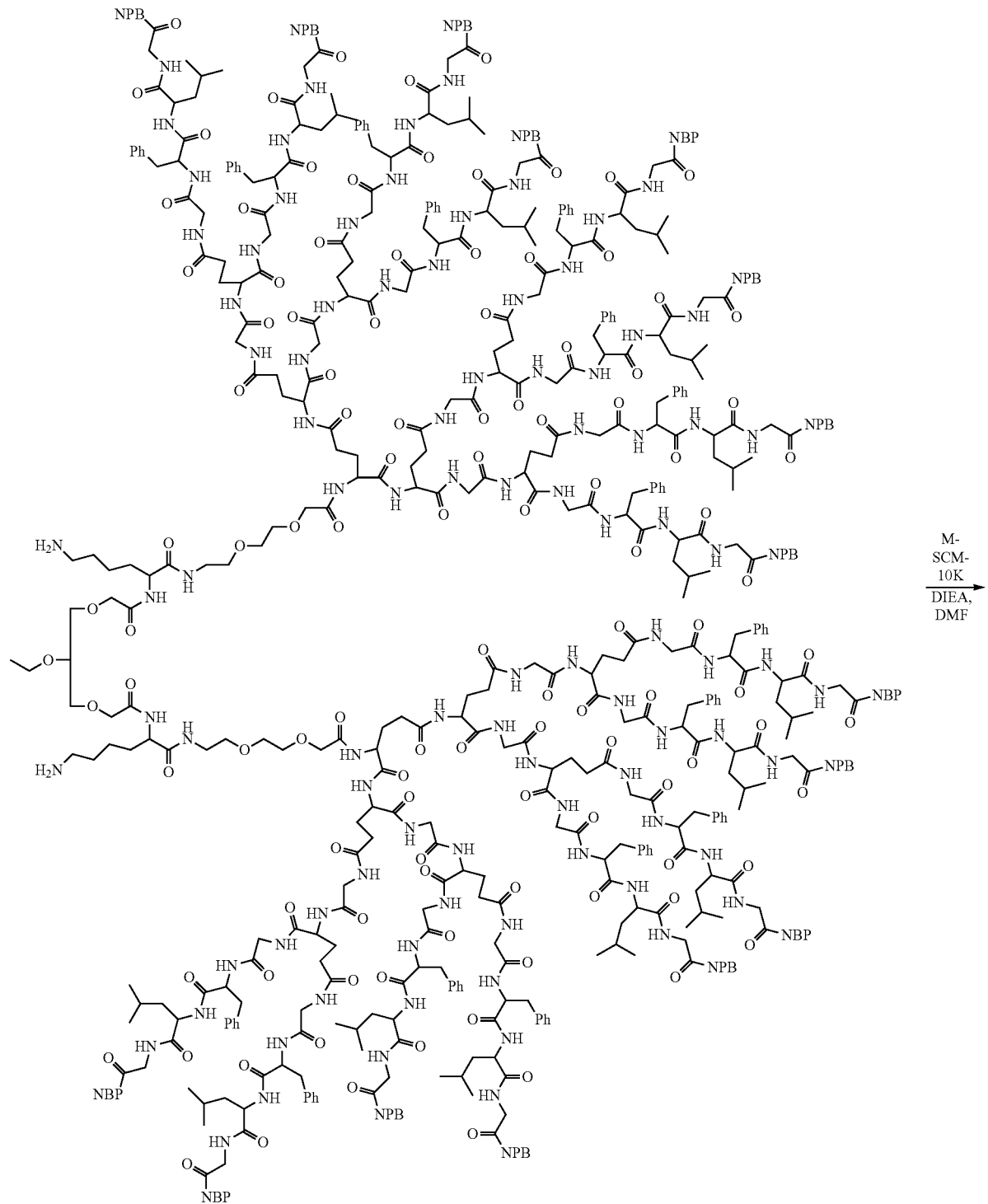
44-168

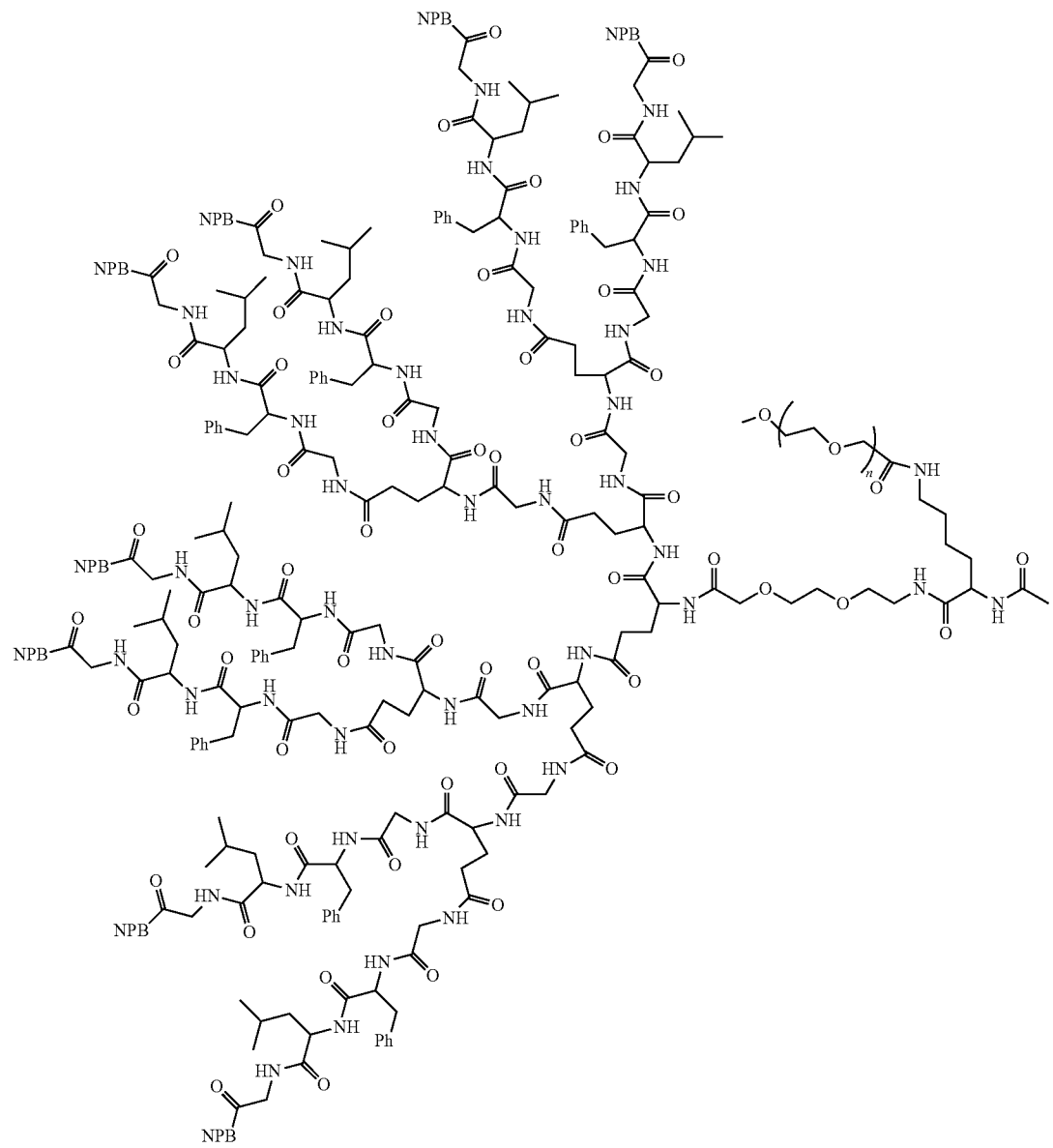

1101 1102
-continued
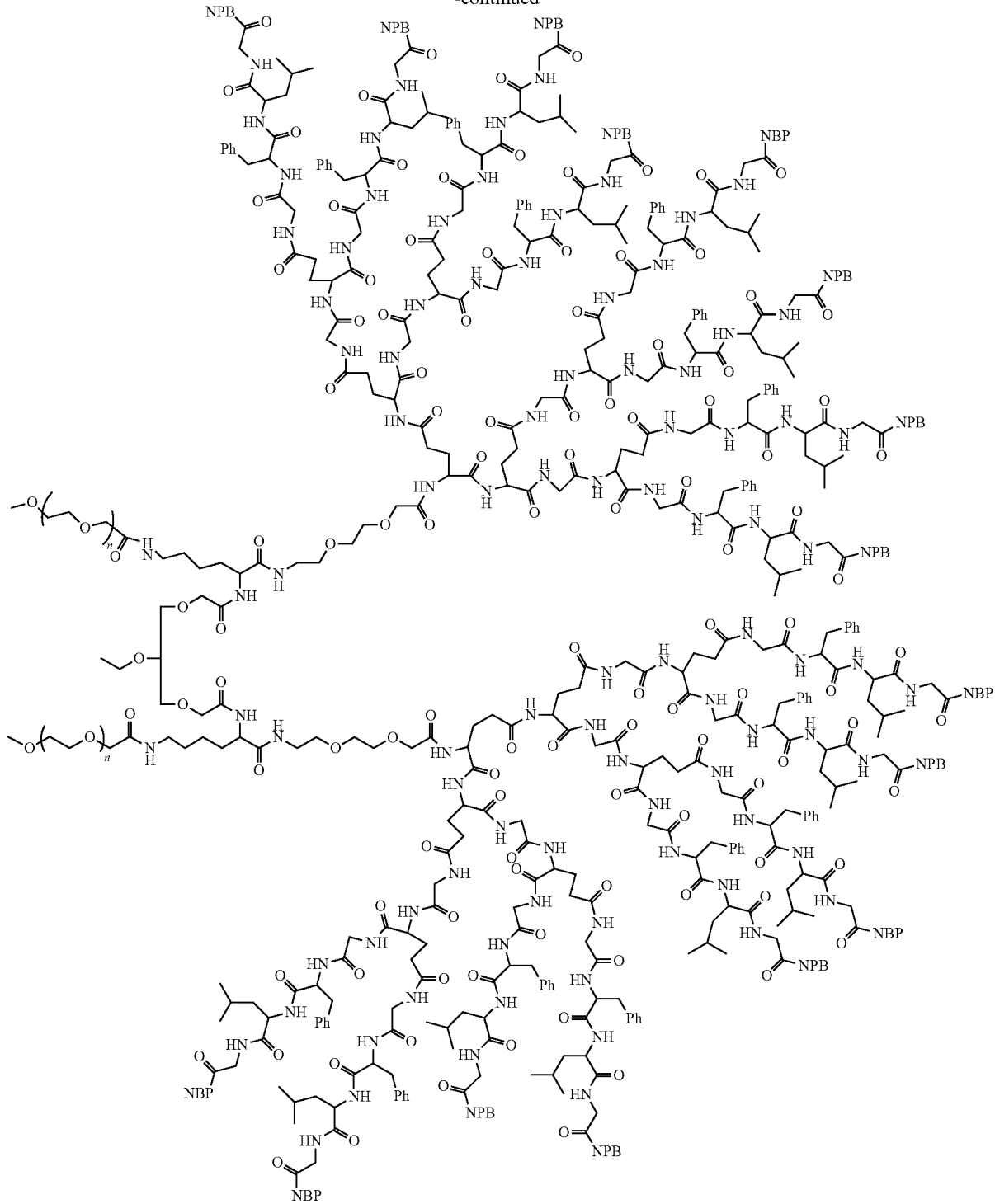
44-172
25-241
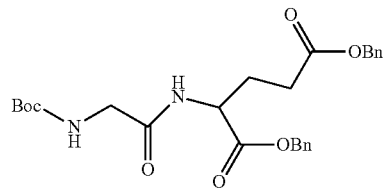

Boc-Gly-OH (3.0 g, 17.1252 mmol, purchased from Ark Pharm), HBTU (9.7418 g, 25.6878 mmol), HOBT (3.4709 g, 25.6878 mmol) and H-Glu (OBzl)-OBzl·TosOH (8.5554 g, 17.1252 mmol, purchased from Ark Pharm) were added in a 500 mL round-bottomed flask, and dissolved with DMF (50 mL), and then the mixed solution was stirred at −5° C. for about 30 minutes. Then DIEA (12.7 mL, 77.0634 mmol) was slowly added dropwise. At the end of the addition, the obtained solution continued to react with stirring at −5° C. for 1 hour, and was then moved to room temperature and stirred to react for 2 hours. At the end of the reaction, the reaction solution was transferred to a 2 L separatory funnel, saturated sodium bicarbonate solution (400 mL) and ethyl acetate (300 mL) were added, the obtained solution was shaken for extraction, and then the organic phase was separated from the aqueous phase. Then, saturated sodium chloride solution (300 mL) was added to the organic phase, the obtained solution was shaken for extraction, and then the organic phase was separated from the aqueous phase. And, saturated sodium chloride solution (300 mL) was further added to the organic phase, the obtained solution was shaken for extraction, and then the organic phase was separated from the aqueous phase. Finally, the organic phase was concentrated and evaporated to dryness. The obtained solid product was dissolved with a mixed solvent (50 mL) of 20% methanol/dichloromethane, silica gel powder (50 mL) was added to the obtained solution, and the operations of evaporation, dry sample loading, column chromatography, and elution with an elutent (1%-2% methanol: 99%-98% dichloromethane) were carried out. The elution product was then collected, concentrated, evaporated to dryness, and dried, thus obtaining the product 25-241: 6.9213 g, yield: 83.41%.

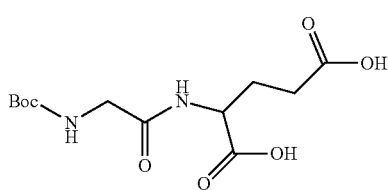
42-105

25-241 (2.0 g, 4.1276 mmol) and 10% Pd/C (100 mg) were added in a hydrogenation reactor, and dissolved with DMF (30 mL). The hydrogenation reactor was sealed, hydrogen was introduced to a pressure of 2.0 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF until it did not contain any product, thus obtaining a reaction product solution.

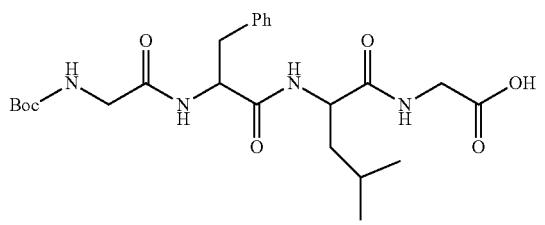
43-116

Boc-GFLG-OBn (9.9 g, 17 mmol, synthesized according to the method of synthesizing 37-62) and 10% Pd/C (0.025 g) were added in a hydrogenation reactor, and dissolved with DMF (40 mL), hydrogen was introduced to a pressure of 2.1 MPa, and then the mixed solution was stirred to react at room temperature overnight. At the end of the reaction, the reaction solution was filtered with diatomaceous earth. The diatomaceous earth was then washed three times with DMF (20 mL×3), and the filtrate was put into a 500 mL round-bottomed flask, as raw material for the next reaction.

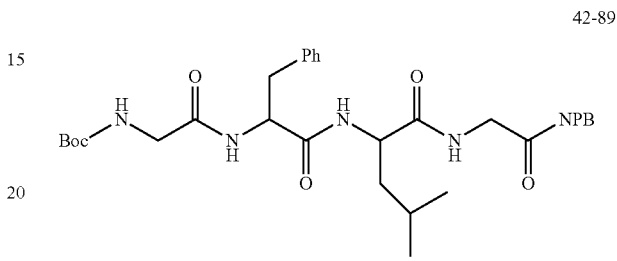
42-89

The DMF solution of 43-116 (8.4534 g, 17.1618 mmol), Niraparib (4.5821 g, 14.3015 mmol, also referred to as NPB), HBTU (8.1356 g, 21.4523 mmol) and HOBT (2.8986 g, 21.4523 mmol) were added in a 250 mL round-bottomed flask, and dissolved with DMF (60 mL), and then the mixed solution was stirred at −5° C. for about 30 minutes. Then DIEA (10.6 mL, 64.3568 mmol) was slowly added dropwise. At the end of the addition, the obtained solution continued to react with stirring at −5° C. for 1 hour, and was then moved to room temperature and stirred to react overnight. At the end of the reaction, the reaction solution was transferred to a 1 L separatory funnel, saturated sodium chloride aqueous solution (300 mL) and ethyl acetate (200 mL) were added, the obtained solution was shaken for extraction, and the aqueous phase was separated. Then, ethyl acetate (200 mL) was added to the aqueous phase, the obtained solution was shaken for extraction, and the aqueous phase was separated. The obtained organic phases were combined, saturated sodium chloride aqueous solution (300 mL) was then added to the organic phase, the obtained solution was shaken for extraction, and the aqueous phase was separated. Then, deionized water (300 mL) was added to the organic phase, the obtained solution was shaken for extraction, and the aqueous phase was separated. Finally, the organic phase was concentrated and evaporated to dryness, and then dried in an oven, thus obtaining the product 42-89: 11.3695 g.

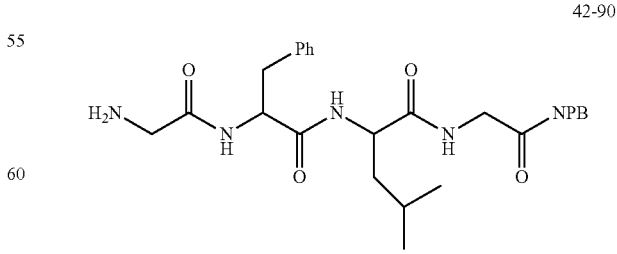
42-90

42-89 (11.3695 g, 14.3015 mmol) was added in a 250 mL round-bottomed flask, and dissolved with dichloromethane (30 mL), TFA (15.9 mL, 214.5225 mmol) was added with stirring, and then the mixed solution was stirred to react at room temperature overnight. At the end of the reaction, the reaction solution was evaporated to remove the dichloromethane, and then precipitated with methyl tert-butyl ether (150 mL) to obtain a powdery solid, and filtering was carried out. The filter cake was washed with methyl tert-butyl ether (60 mL), and dissolved with a mixed solvent (60 mL) of 20% methanol/dichloromethane, silica gel powder (65 mL) was added, and the operations of evaporation, dry sample loading, column chromatography, and elution with an elutent (0%-2% methanol: 100%-98% dichloromethane) were carried out. The elution product was then collected, concentrated, evaporated to dryness, and dried, thus obtaining the product 42-90: 8.6 g, yield: 86.6%.

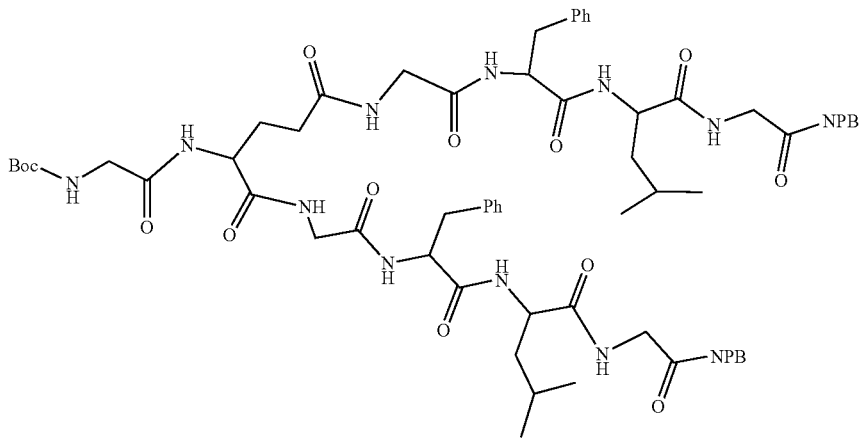

42-107

The solution of 42-105 (1.2560 g, 4.1276 mmol), 42-90 (6.3095 g, 9.0807 mmol), HBTU (4.6961 g, 12.3828 mmol) and HOBT (1.6732 g, 12.3828 mmol) were added in a 500 mL round-bottomed flask, and dissolved with DMF (60 mL), and then the mixed solution was stirred at −5° C. for about 30 minutes. Then DIEA (6.1 mL, 37.1484 mmol) was slowly added dropwise. At the end of the addition, the obtained solution continued to react with stirring at −5° C. for 1 hour, and was then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 42-107: 6.8432 g.

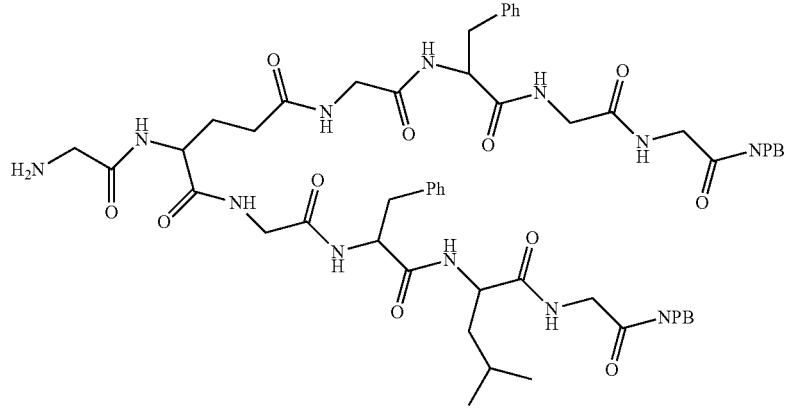

42-110

42-107 (6.4832 g, 4.1276 mmol) was added in a 250 mL round-bottomed flask, and dissolved with dichloromethane (15 mL), TFA (4.6 mL, 61.9140 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), and dissolved with a mixed solvent (100 mL) of 20% methanol/dichloromethane, silica gel powder (70 ml) was added to the obtained solution, and the operations of evaporation, dry sample loading, column chromatography, and elution with an elutent (0.5% ammonia water: 2%-10% methanol: 97.5%-89.5% dichloromethane) were carried out. The elution product was then collected, concentrated, evaporated to dryness, and dried, thus obtaining the product 42-110: 2.9609 g, yield: 46.05%.

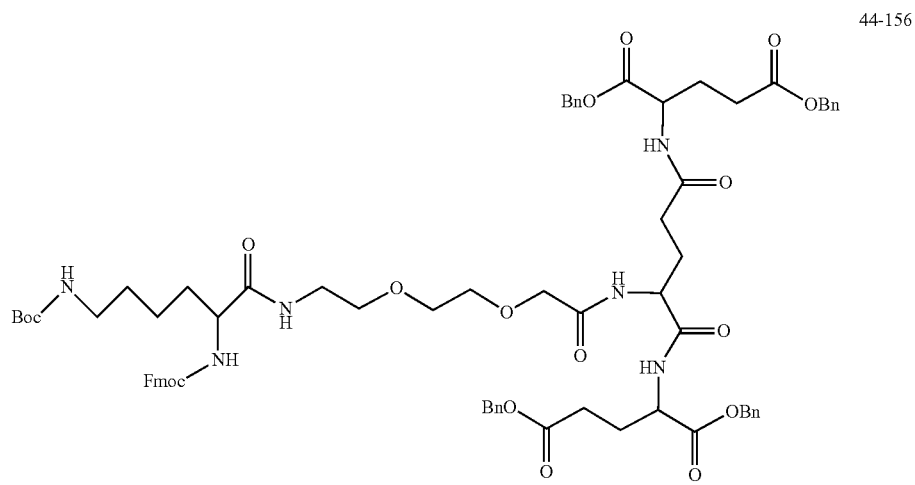

44-156

Fmoc-Lys (Boc)-OH (3.6002 g, 7.6839 mmol, purchased from Accela), 35-86 (9.1 g, 9.9890 mmol), HBTU (4.3710 g, 11.5258 mmol) and HOBT (1.5574 g, 11.5258 mmol) were added in a 500 mL round-bottomed flask, and dissolved with DMF (80 mL), and then the mixed solution was stirred at −5° C. for about 30 minutes. Then DIEA (7.6 mL, 46.4032 mmol) was slowly added dropwise. At the end of the addition, the obtained solution was stirred to react at −5° C. for 1 hour, and then moved to room temperature and stirred to react for 3 hours. At the end of the reaction, the reaction solution was transferred to a 1 L separatory funnel, saturated sodium chloride aqueous solution (300 mL) and ethyl acetate (200 mL) were added, the obtained solution was shaken for extraction, and then the organic phase was separated from the aqueous phase. Ethyl acetate (100 mL) was added to the aqueous phase, the obtained solution was shaken for extraction, and then the organic phase was separated from the aqueous phase. Then, the obtained organic phases were combined, saturated sodium chloride aqueous solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 44-148: 10.4619 g.

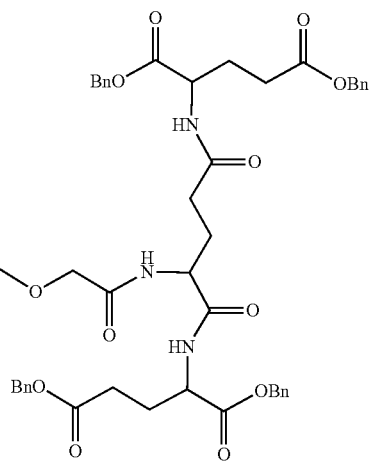

44-157

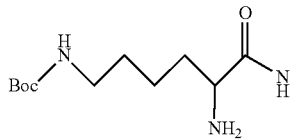

44-156 (10.4619 g, 7.6839 mmol) was added in a 500 mL round-bottomed flask, and dissolved with DMF (10 mL), morpholine (10.0 mL, 115.2583 mmol) was added with stirring, and then the mixed solution was stirred to react at room temperature for 2 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated five times, and a viscous solid was obtained. The viscous solid was dissolved with a mixed solvent (60 mL) of 20% methanol/dichloromethane, silica gel powder (50 mL) was added to the obtained solution, and the operations of evaporation, dry sample loading, column chromatography, and elution with an elutent (1%-5% methanol: 99%-95% dichloromethane) were carried out. The elution product was then collected, concentrated, evaporated to dryness, and dried, thus obtaining the product 44-157: 8.7542 g, yield: 100%.

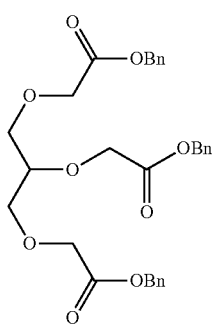

45-91

Glycerin (5 g, 54.295 mmol, purchased from Innochem) was added in a 500 mL flask, nitrogen was introduced for protective purpose, the THF solution of potassium tert-butoxide (211 mL, 211.7505 mmol) was added, the obtained solution was stirred at 0° C. for 3 hours, benzyl bromoacetate (30.964 g, 195.46 mmol) was added, and the obtained solution was stirred for 2 hours, and then reacted at room temperature. At the end of the reaction, the reaction solution was first evaporated to dryness, then deionized water and ethyl acetate were added for extraction, and the organic phase was separated. The aqueous phase was extracted with ethyl acetate until there was no product in the aqueous phase, and the obtained organic phases were combined. The organic phase was dried with anhydrous sodium sulfate powder, suction filtering was carried out, and the filtrate was subjected to dry sample loading, column chromatography and gradient elution with 1%-2% ethyl acetate/petroleum ether, thus obtaining the product 9 g, yield 31%.

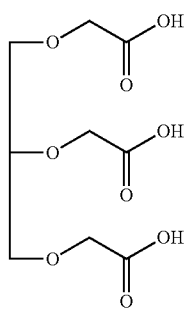

36-186

45-91 (0.5 g, 0.9318 mmol) and 10% Pd/C (0.0200 g) were added in a reactor, and dissolved with DMF (30 mL). The air in the reactor was then pumped out to reach a vacuum state by a water pump, hydrogen was introduced to a pressure of 0.16 MPa, hydrogen was then discharged, the reactor was pumped to reach a vacuum state by the water pump, and hydrogen was then introduced again. Such operations were repeated three times. Finally. hydrogen was introduced again, and the mixed solution was stirred to react at room temperature overnight. At the end of the reaction, the reaction solution was filtered with diatomaceous earth. The filter cake was washed with DMF (20 mL×3), and the DMF solutions were combined as the raw material for the next step.

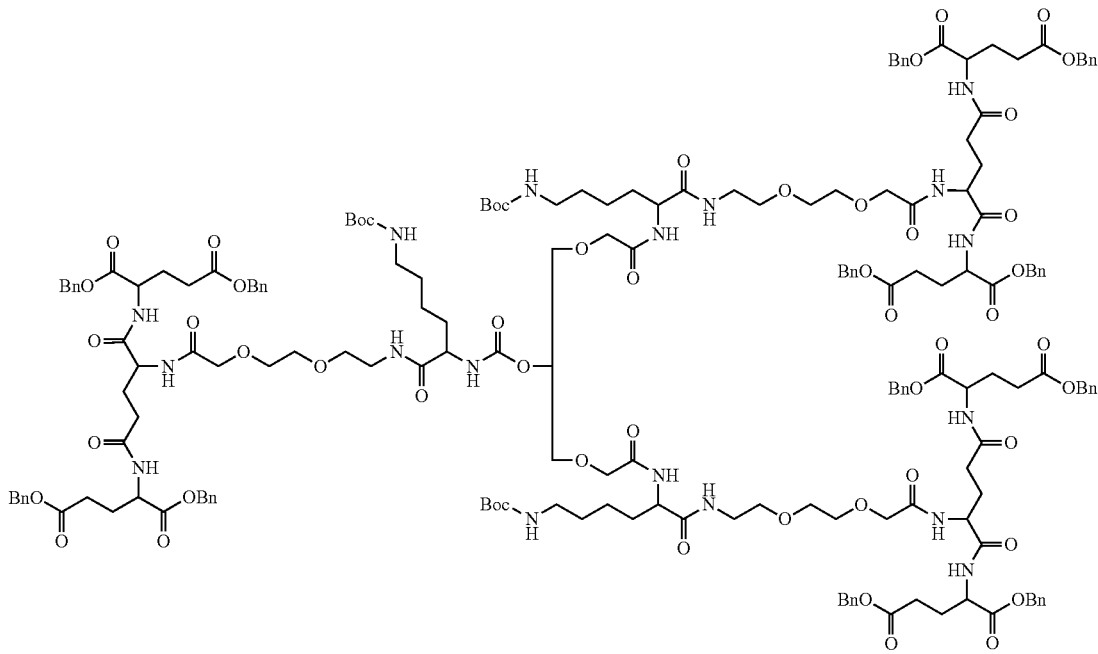

44-161

36-186 solution (0.5021 g, 1.8862 mmol), 44-157 (8.5957 g, 7.5448 mmol), HBTU (3.2190 g, 8.4879 mmol) and HOBT (1.1469 g, 8.4879 mmol) were added in a 250 mL round-bottomed flask, and dissolved with DMF (80 mL), and then the mixed solution was stirred at −5° C. for about 30 minutes. Then DIEA (4.2 mL, 25.4637 mmol) was slowly added dropwise. At the end of the addition, the obtained solution was stirred to react at −5° C. for 1 hour, and then moved to room temperature and stirred to react for 3 hours. At the end of the reaction, the reaction solution was transferred to a 1 L separatory funnel, saturated sodium bicarbonate solution (400 mL) and ethyl acetate (300 mL) were added, the obtained solution was shaken for extraction, and then the organic phase was separated from the aqueous phase. Ethyl acetate (200 mL) was added to the aqueous phase, the obtained solution was shaken for extraction, and then the organic phase was separated from the aqueous phase. Then, the obtained organic phases were combined, deionized water (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, and evaporated to dryness. The obtained solid product was dissolved with a mixed solvent (60 mL) of 20% methanol/dichloromethane, silica gel powder (50 mL) was added to the obtained solution, and the operations of evaporation, dry sample loading, column chromatography, and elution with an elutent (2%-8% methanol: 98%-92% dichloromethane) were carried out. The elution product was then collected, concentrated, evaporated to dryness, and dried, thus obtaining the product 44-161: 3.2551 g, yield: 47.54%.

$^1$H-NMR (600 MHz, DMSO-$d_6$) δ 8.33-8.02 (m, 18H), 7.50-7.17 (m, 60H), 5.36-4.94 (m, 24H), 4.55-4.50 (m, 12H), 3.95-3.87 (m, 6H), 3.67-3.47 (m, 25H), 3.39-3.16 (m, 16H), 2.47-2.38 (m, 24H), 2.25-1.94 (m, 12H), 1.94-1.79 (m, 6H), 1.57-1.46 (m, 6H), 1.38 (s, 27H), 1.26-1.23 (m, 6H).

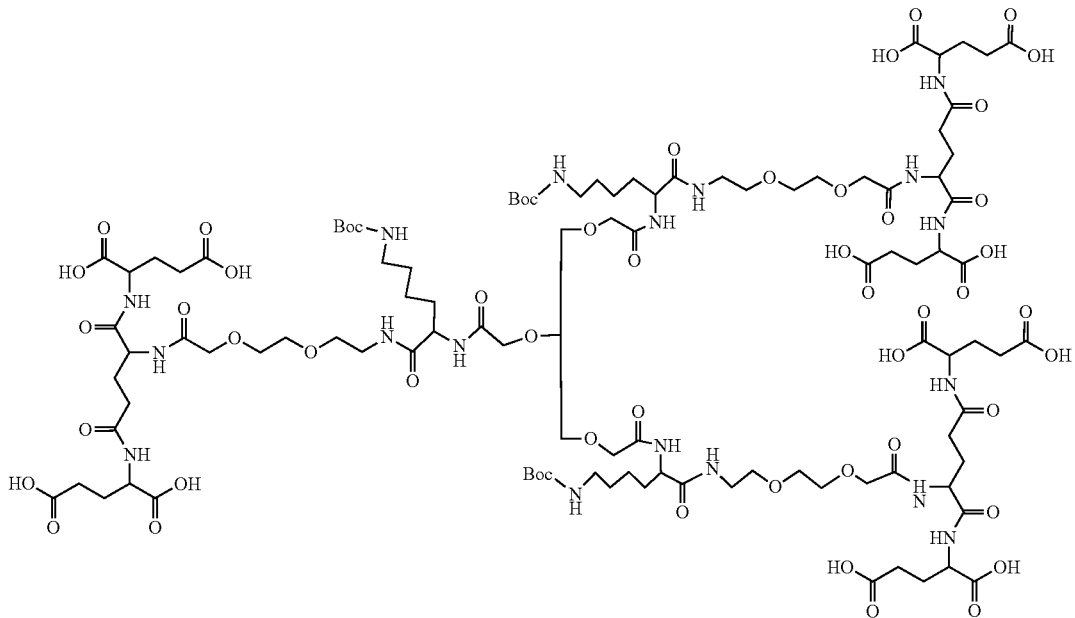

44-166

44-161 (1.0 g, 0.2755 mmol, home-made) and 10% Pd/C (50 mg) were added in a hydrogenation reactor, and dissolved with DMF (30 mL). The hydrogenation reactor was sealed, hydrogen was introduced to a pressure of 1.6 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF until it did not contain any product, thus obtaining a reaction product solution.

1115  1116
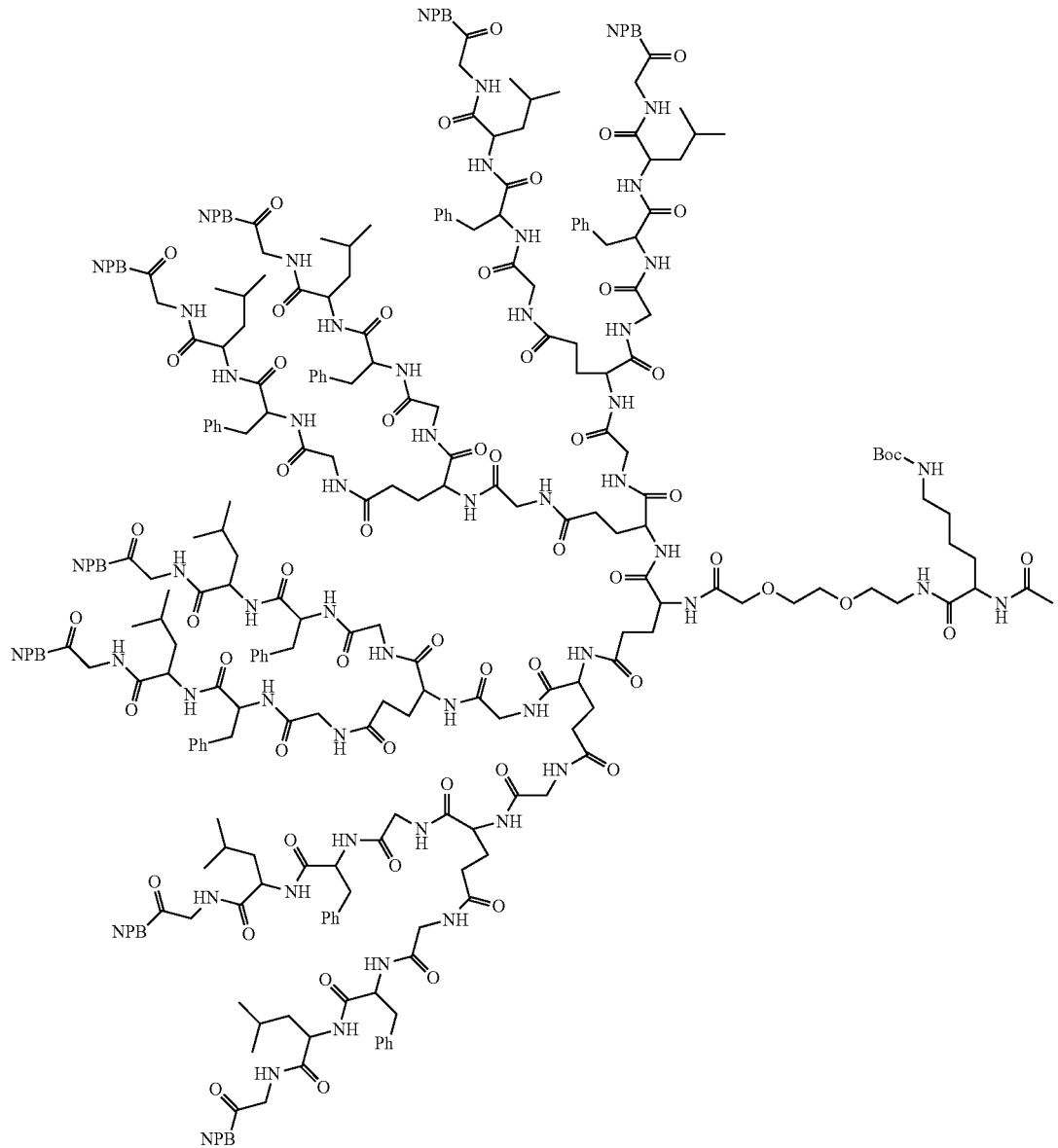
44-167

-continued

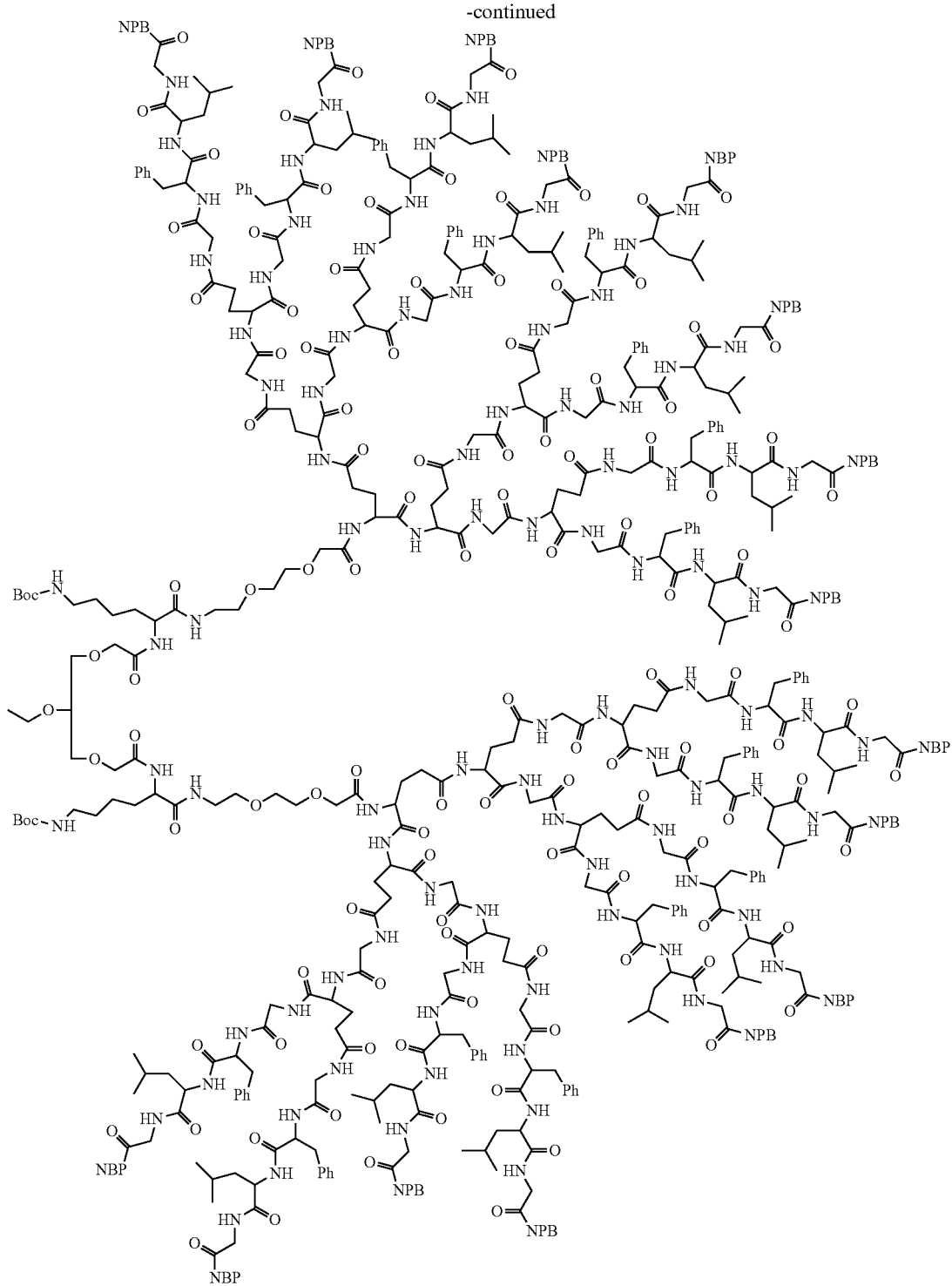

The solution of 44-166 (0.3181 g, 0.1248 mmol), 42-110 (2.8 g, 1.7974 mmol), HBTU (0.8519 g, 2.2464 mmol) and HOBT (0.3035 g, 2.2464 mmol) were added in a 250 mL round-bottomed flask, and dissolved with DMF (30 mL), and then the mixed solution was stirred at −5° C. for about 30 minutes. Then DIEA (1.1 mL, 6.7392 mmol) was slowly added dropwise. At the end of the addition, the obtained solution was stirred to react at −5° C. for 1 hour, and then moved to room temperature and stirred to react. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 44-167: 2.4242 g.

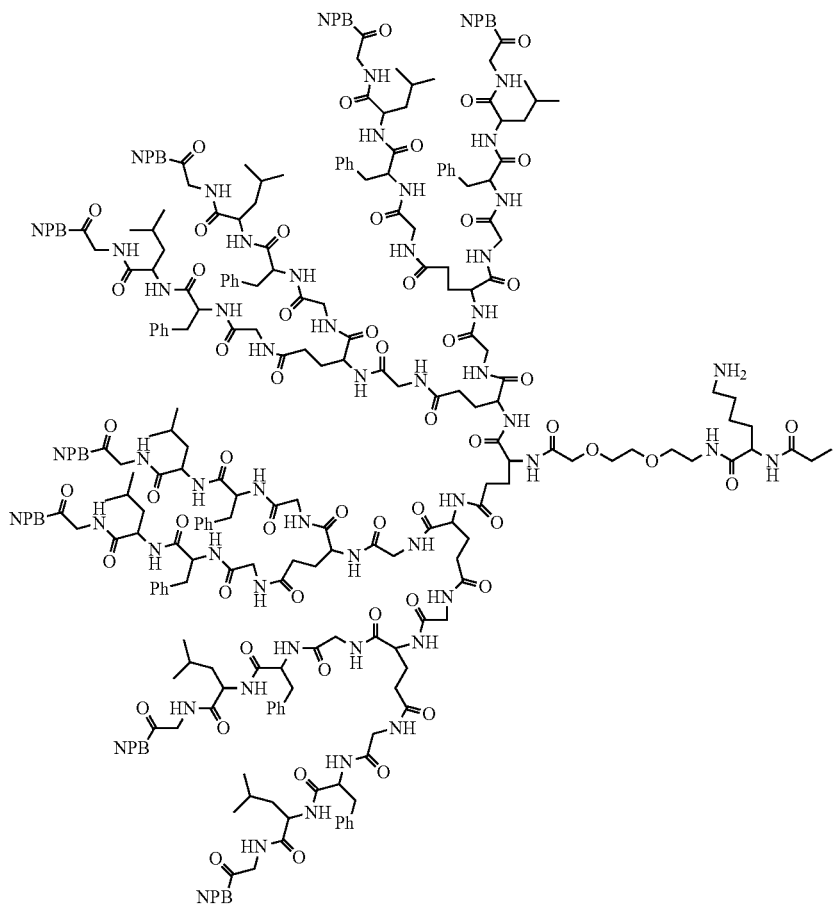
44-168

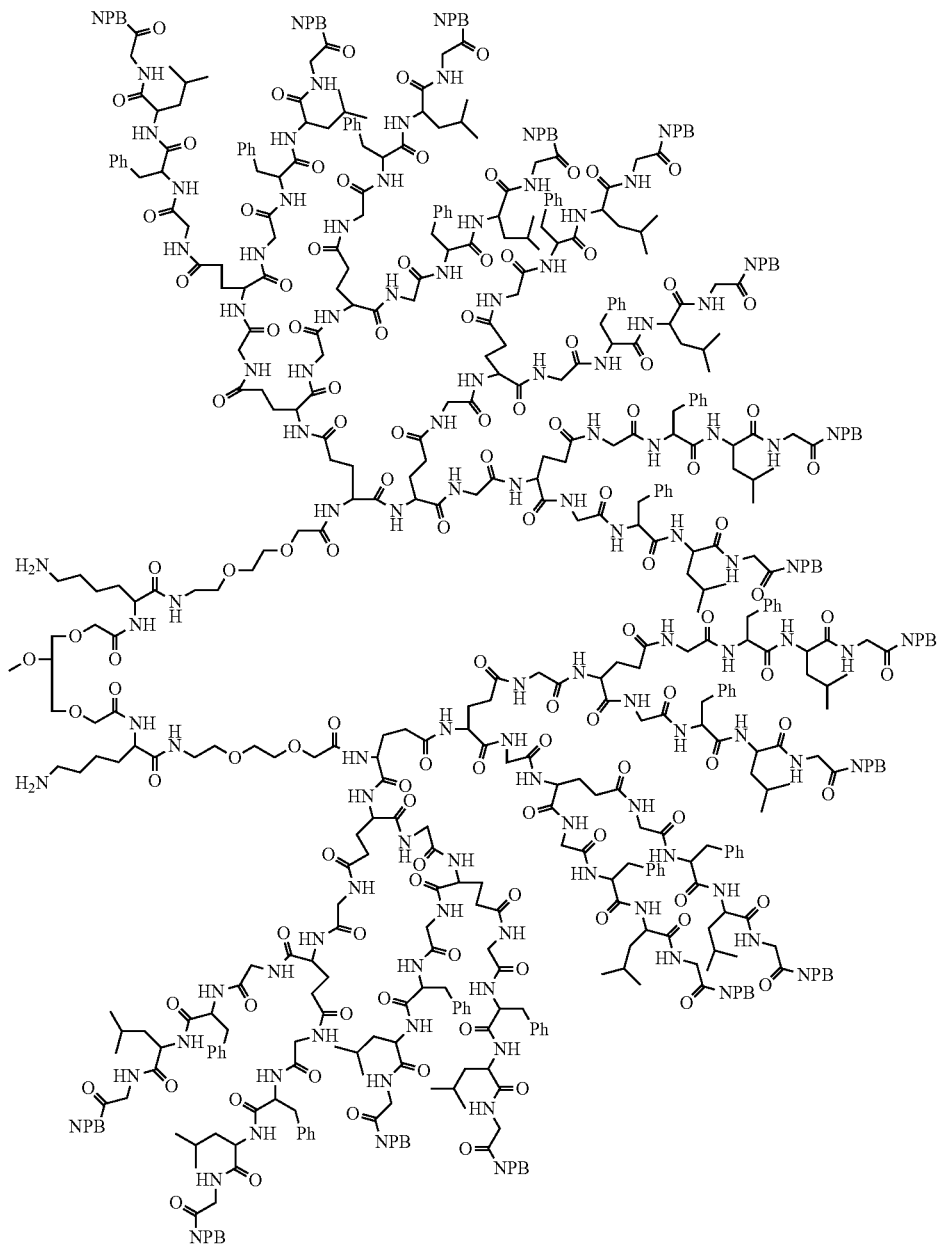

44-167 (1.7663 g, 0.0840 mmol) was added in a 250 mL round-bottomed flask, and dissolved with dichloromethane (20 mL), TFA (1.0 mL, 12.6010 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The filter cake was washed with methyl tert-butyl ether (60 mL), and dissolved with a mixed solvent (100 mL) of 20% methanol/dichloromethane, silica gel powder (50 mL) was added to the obtained solution, and the operations of evaporation, dry sample loading, column chromatography, and elution with an elutent (1% ammonia water: 3%-10% methanol: 96%-89% dichloromethane) were carried out. The elution product was then collected, concentrated, evaporated to dryness, and dried, thus obtaining the product 44-168: 0.9538 g, yield: 54.79%.

$^1$H-NMR (600 MHz, DMSO-$d_6$) δ 8.61-8.57 (m, 20H), 8.46-7.80 (m, 196H), 7.77-7.44 (m, 53H), 7.44-7.04 (m, 166H), 5.33-5.31 (m, 3H), 4.67-4.18 (m, 77H), 4.11-3.92 (m, 46H), 3.86-3.84 (m, 40H), 3.79-3.57 (m, 44H), 3.19-3.04 (m, 45H), 2.94-2.89 (m, 52H), 2.88-2.71 (m, 102H), 2.17-1.90 (m, 60H), 1.61-1.51 (m, 96H), 1.28-1.21 (m, 178H), 0.96-0.78 (m, 144H).

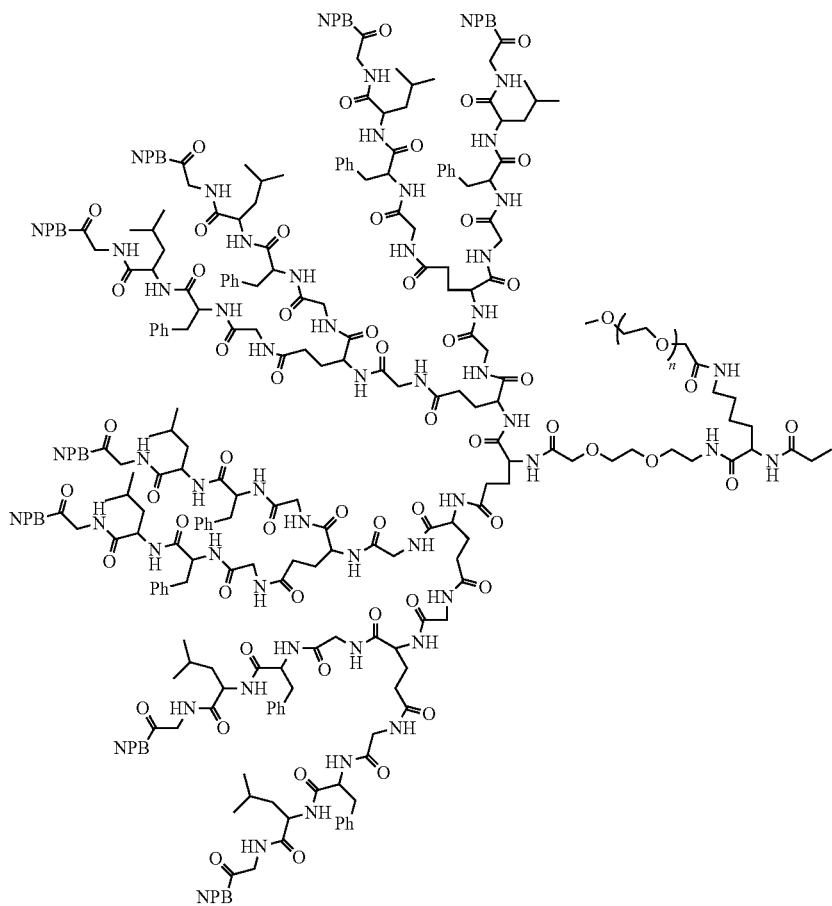
44-172

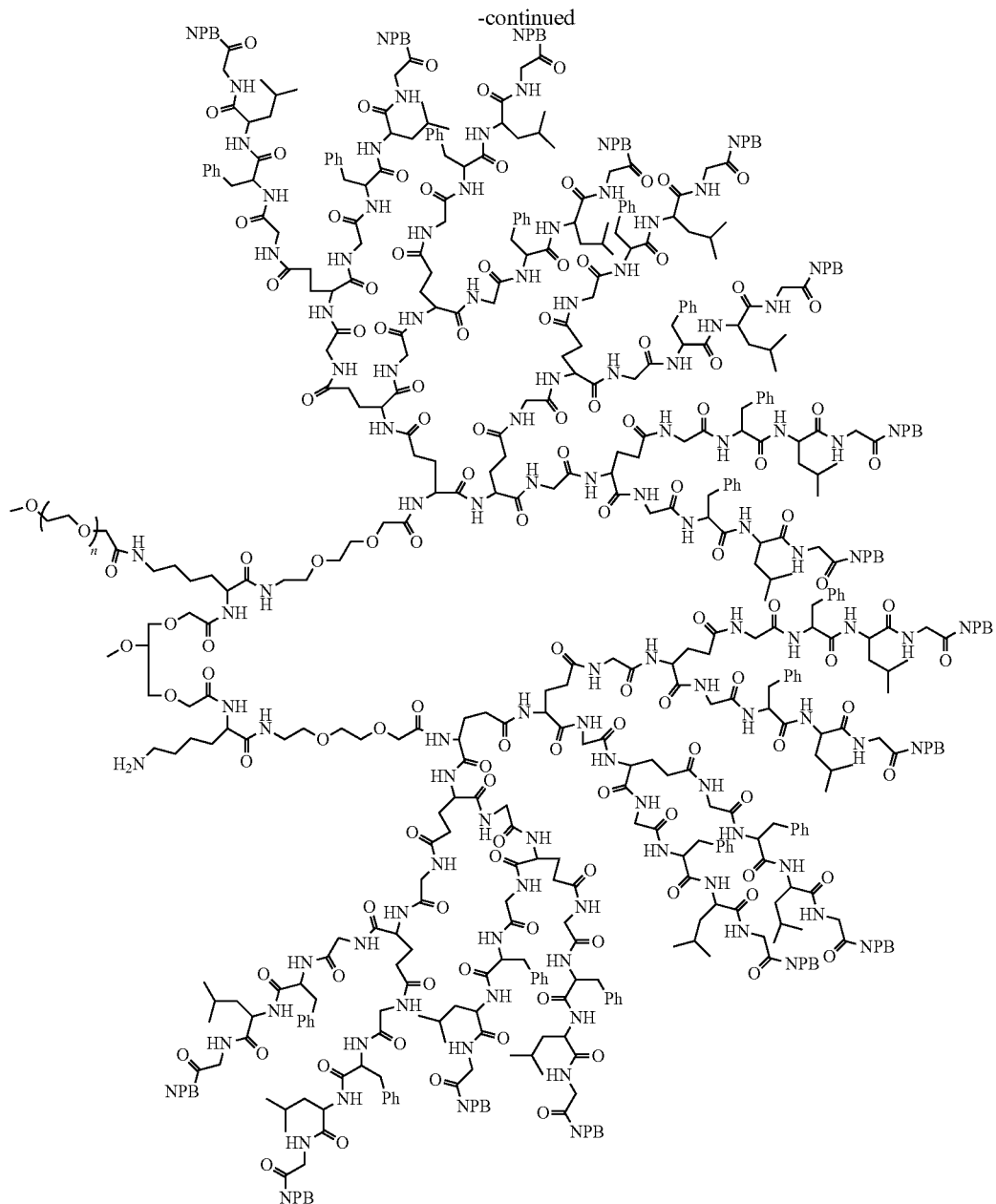

44-168 (0.8105 g, 0.0420 mmol) and M-SCM-10K (2.0019 g, 0.1890 mmol, purchased from JenKem) were added in a 500 mL round-bottomed flask, and dissolved with DMF (10 mL), and then the mixed solution was stirred at −5° C. for about 30 minutes. Then DIEA (0.7 mL, 4.2 mmol) was slowly added dropwise. At the end of the addition, the obtained solution continued to react with stirring at −5° C. for 10 minutes, and then reacted at room temperature for one week. At the end of the reaction, n-hexane (150 mL) and methyl tert-butyl ether (20 mL) were added to the reaction solution for precipitation, the supernatant was discarded, and n-hexane (150 mL) and methyl tert-butyl ether (30 mL) were then added to the lower oily solution for precipitation. Such operations were repeated five times, to obtain an oily solid. The oily solid was dissolved with dichloromethane (10 mL), and precipitated with methyl tert-butyl ether (60 mL) to separate out a powdery solid, and then a solid product was obtained by filtering. The filter cake was dissolved with a mixed solvent (100 mL) of 20% methanol/dichloromethane, silica gel powder (50 mL) was added, and the operations of evaporation, dry sample loading, column chromatography, and elution with an elutent (1% ammonia water: 2%-10% methanol: 97%-89% dichloromethane) were carried out. The elution product was then collected, concentrated, evaporated to dryness, and dried, thus obtaining the product 44-172: 0.6468 g, yield: 29.53%.

$^1$H-NMR (600 MHz, DMSO-$d_6$) δ 8.61-8.57 (m, 20H), 8.46-7.80 (m, 196H), 7.77-7.44 (m, 53H), 7.44-7.04 (m, 166H), 5.33-5.31 (m, 3H), 4.67-4.18 (m, 77H), 4.11-3.92 (m, 46H), 3.86-3.84 (m, 40H), 3.79-3.57 (m, 44H), 3.58-3.44 (m, 2853H), 3.24-3.04 (m, 45H), 2.94-2.89 (m, 52H), 2.88-2.71 (m, 102H), 2.17-1.90 (m, 60H), 1.61-1.51 (m, 96H), 1.28-1.21 (m, 178H), 0.94-0.77 (m, 144H).

25. Synthesis of 41-126 (Compound No. 25)
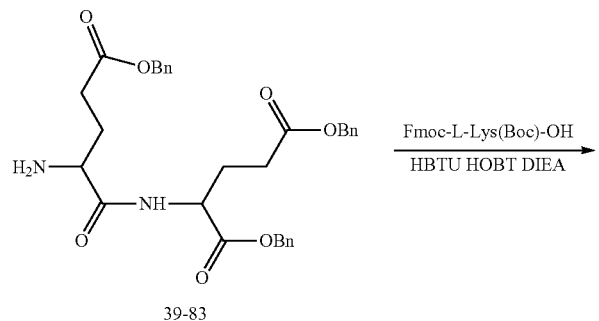
39-83
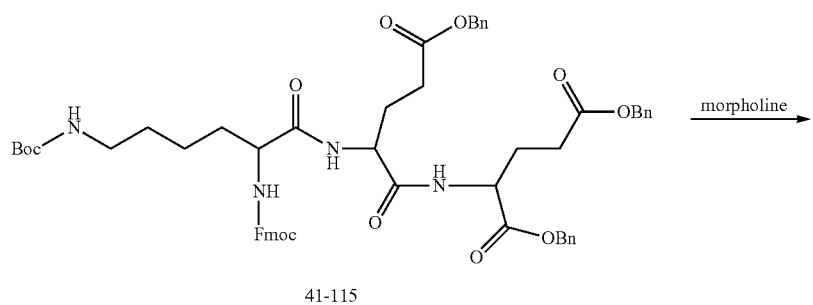
41-115
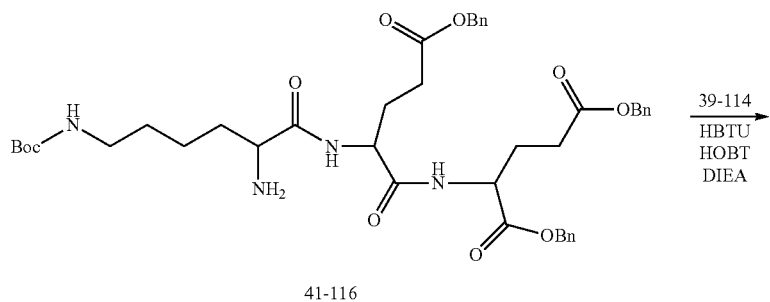
41-116
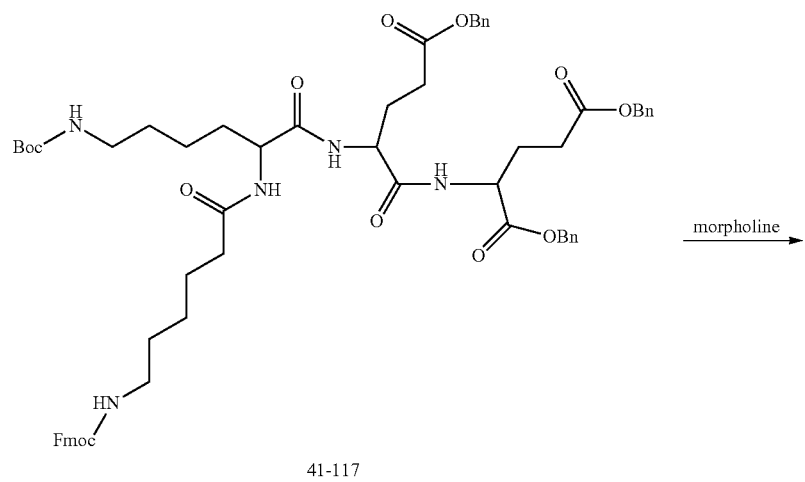
41-117

-continued
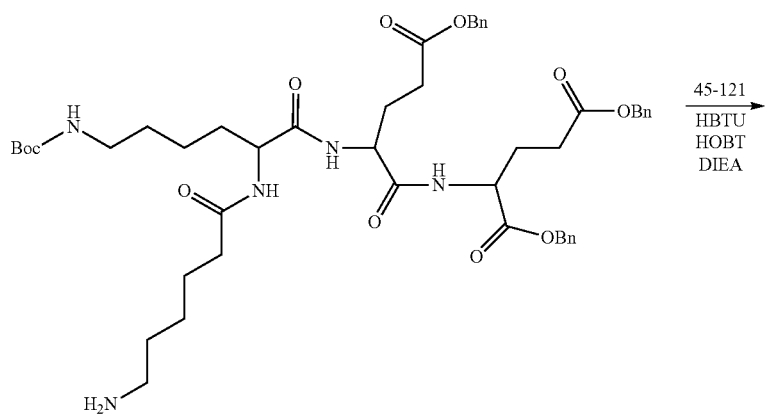
41-118
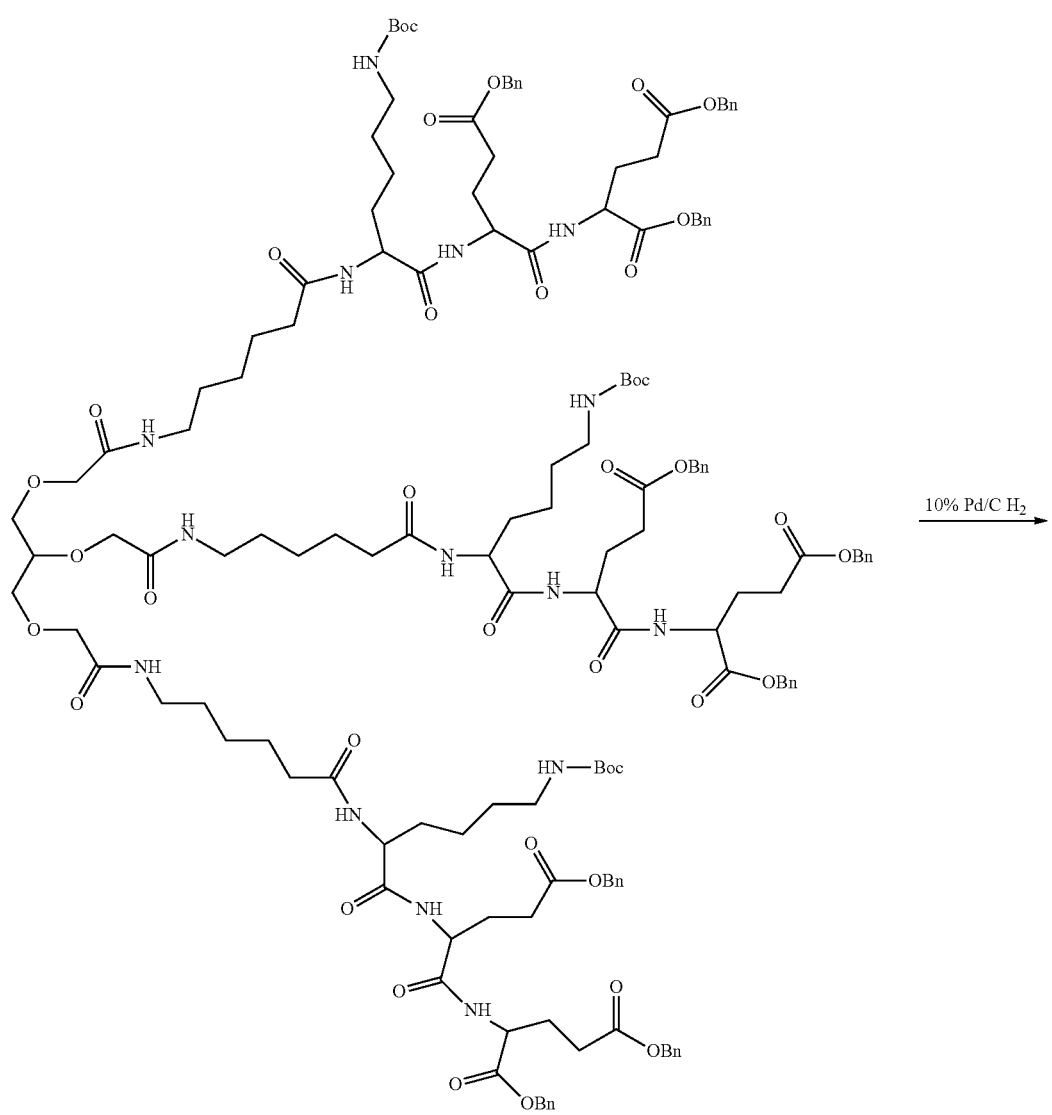
41-119

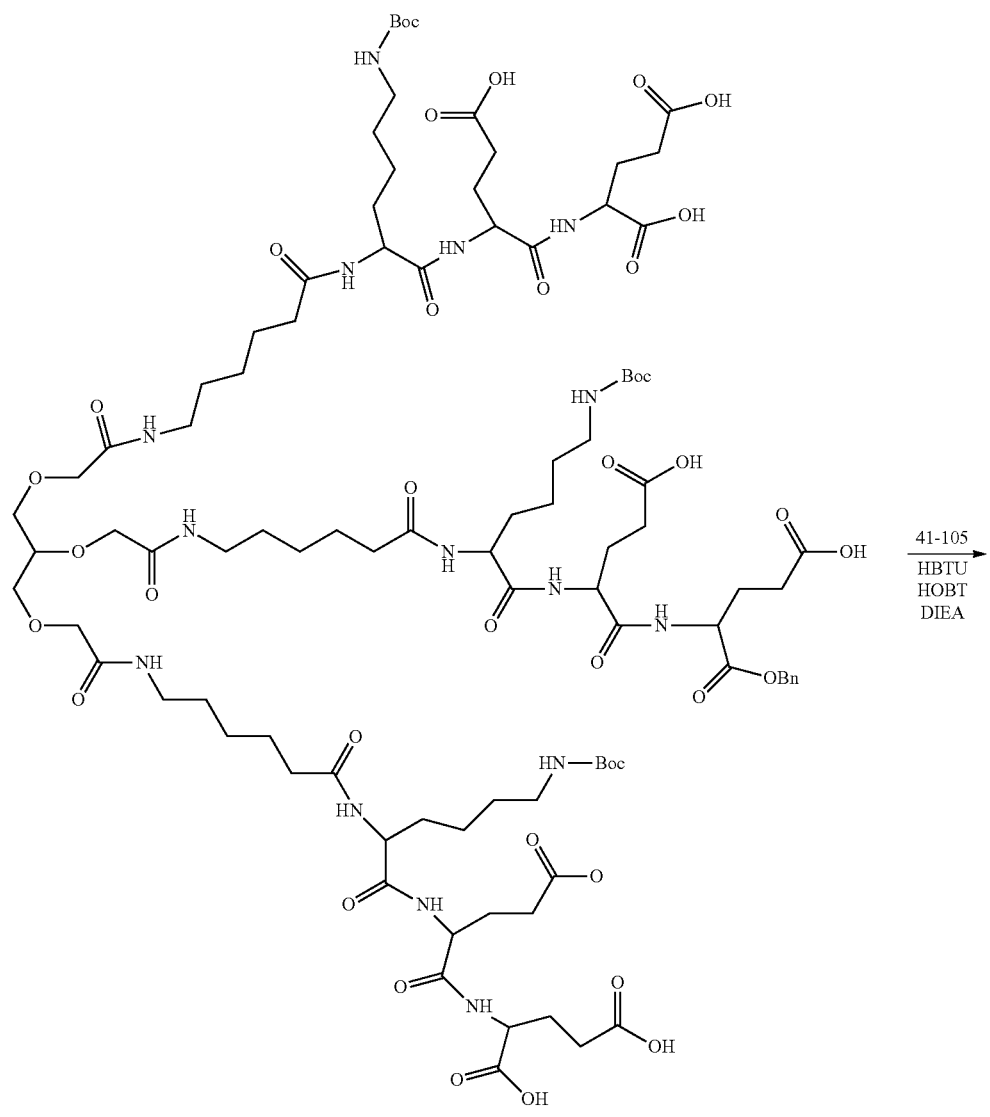

1133
1134
-continued
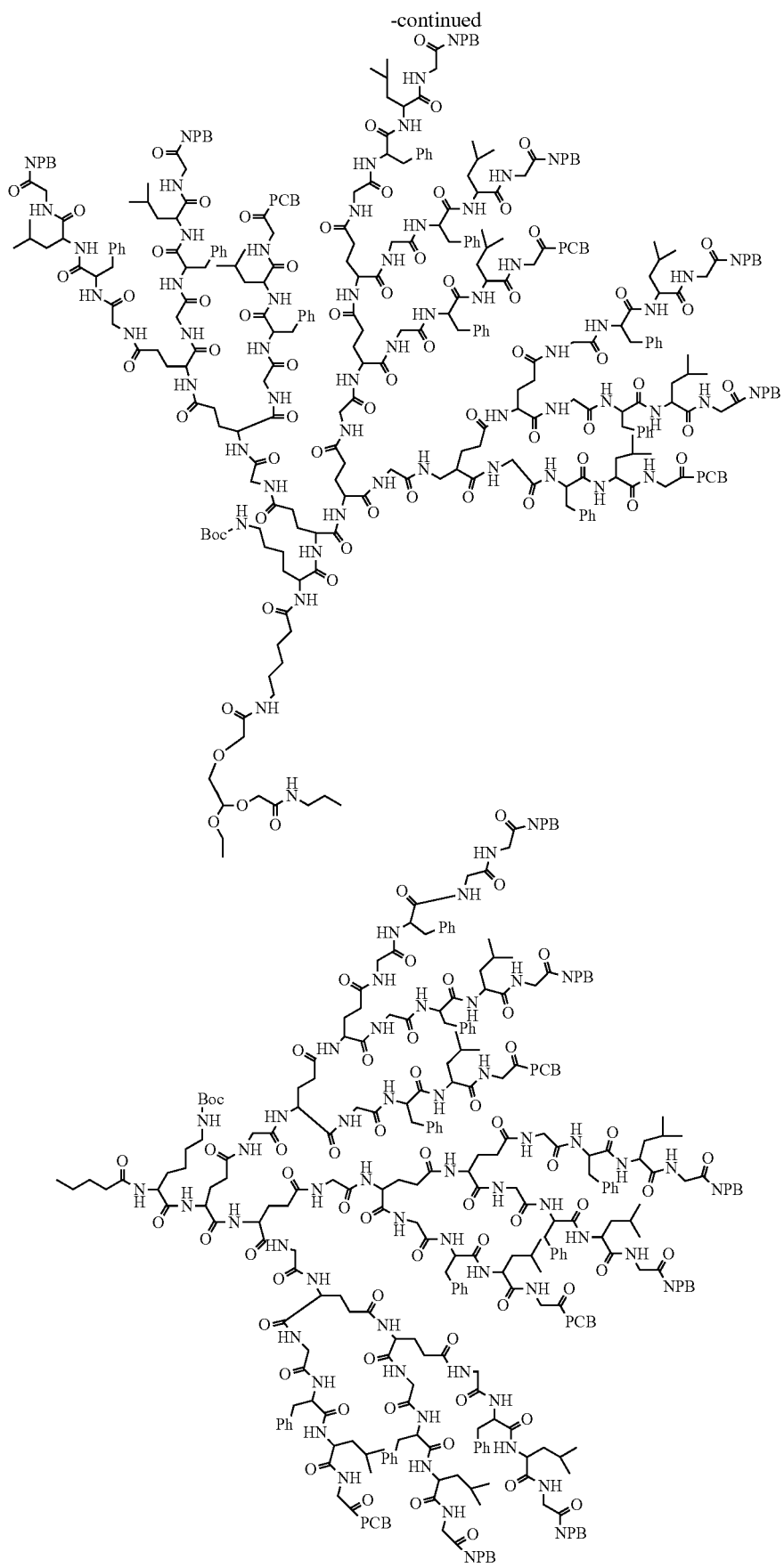

-continued
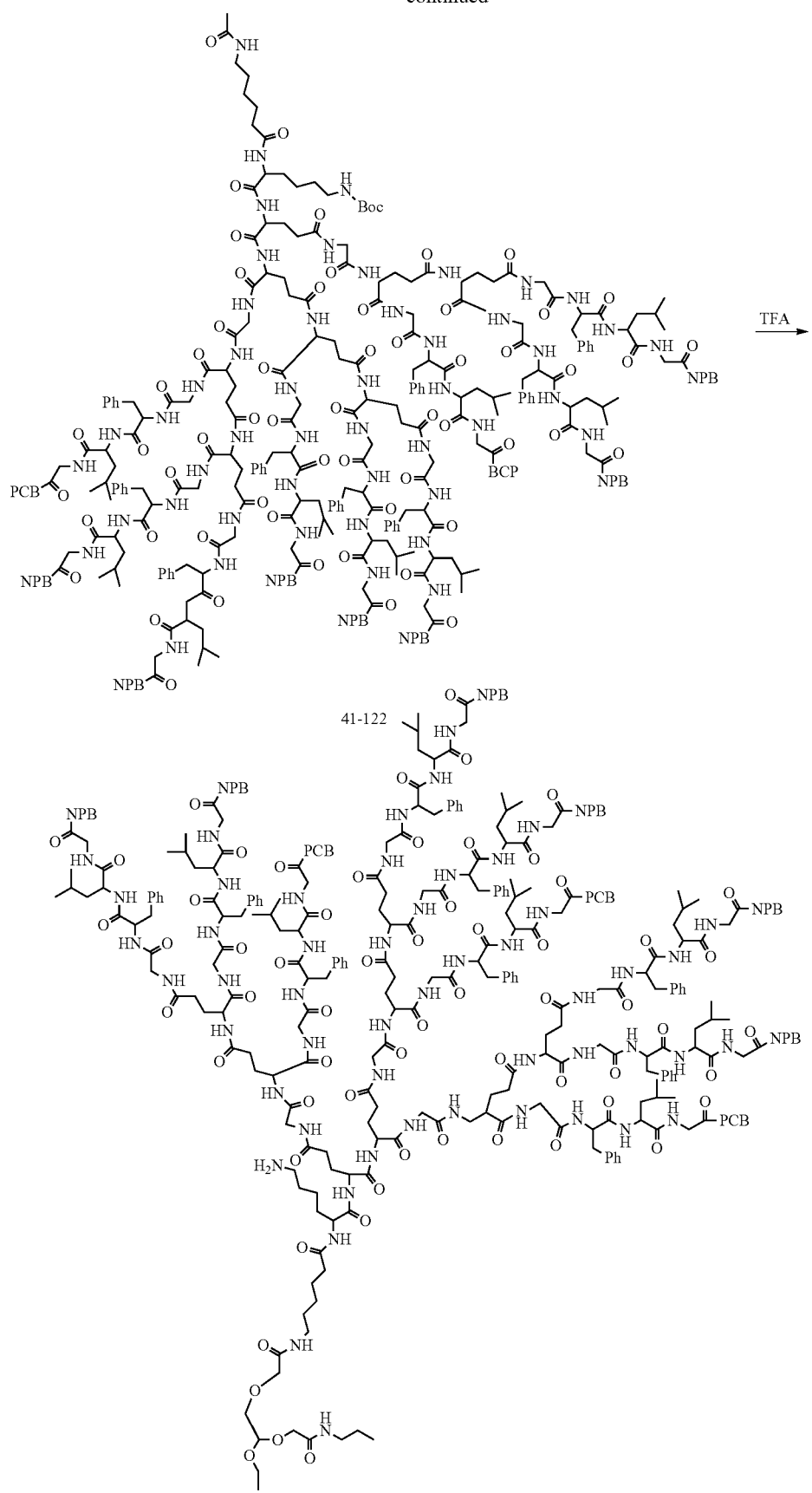

-continued
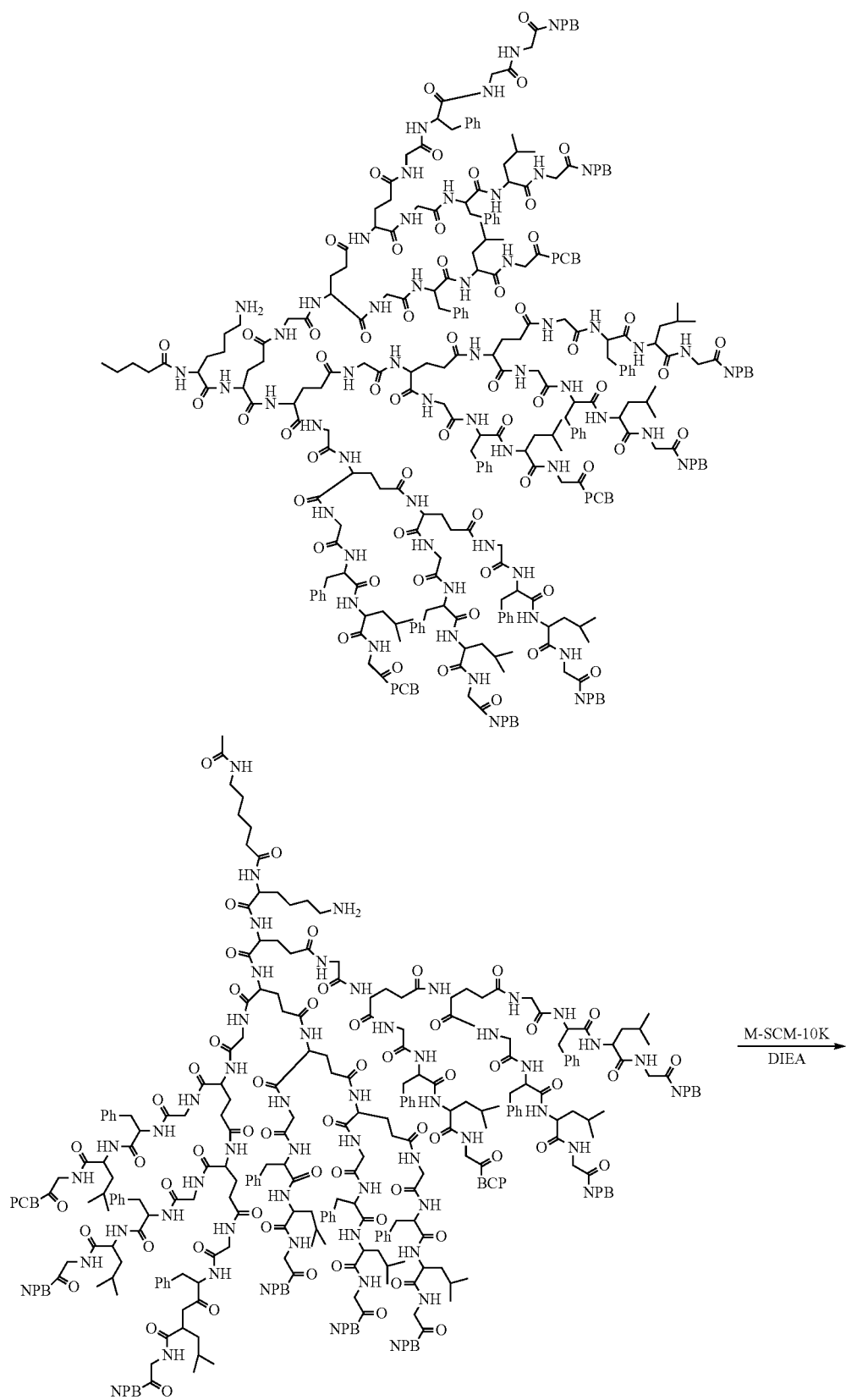
41-125

-continued
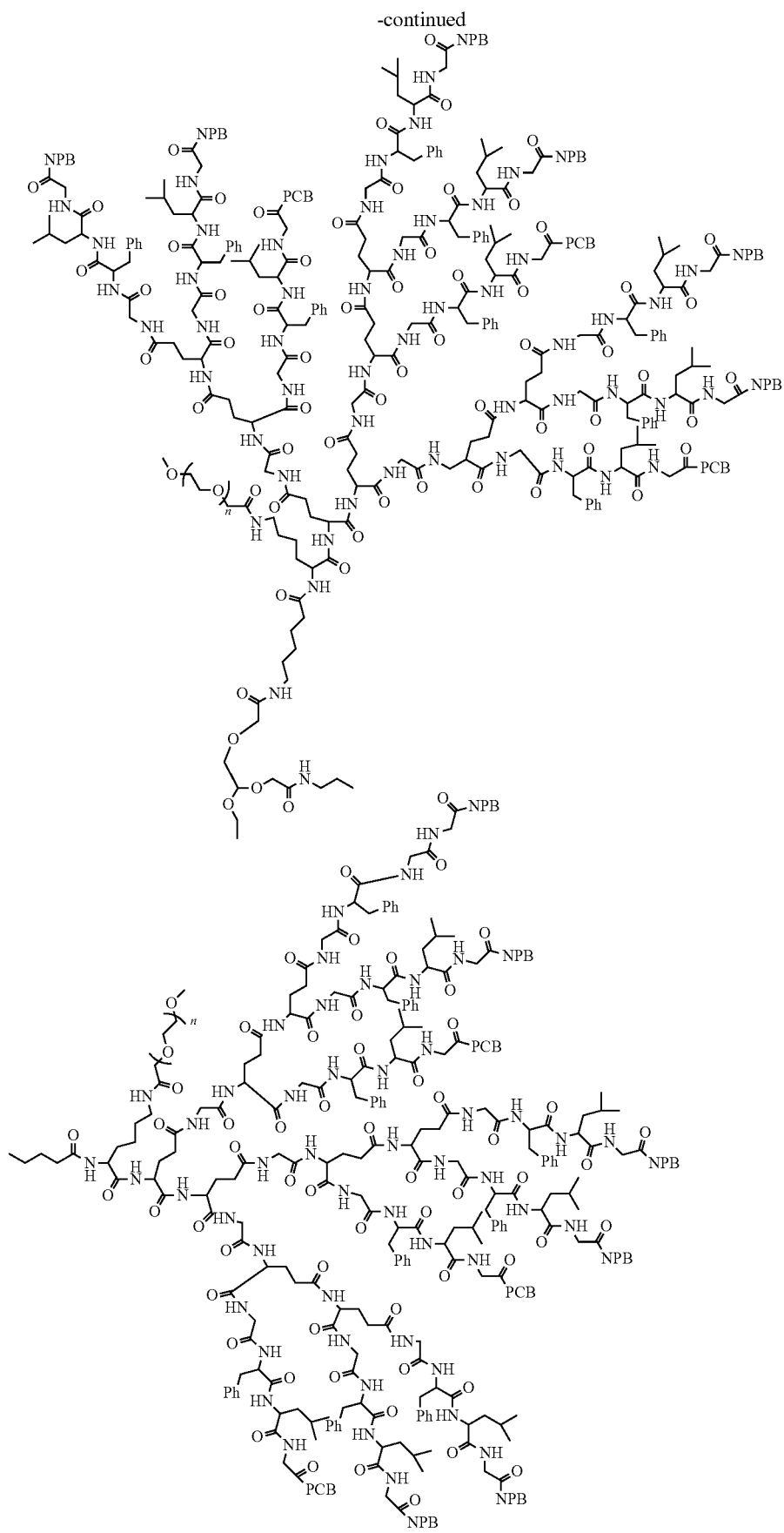

-continued

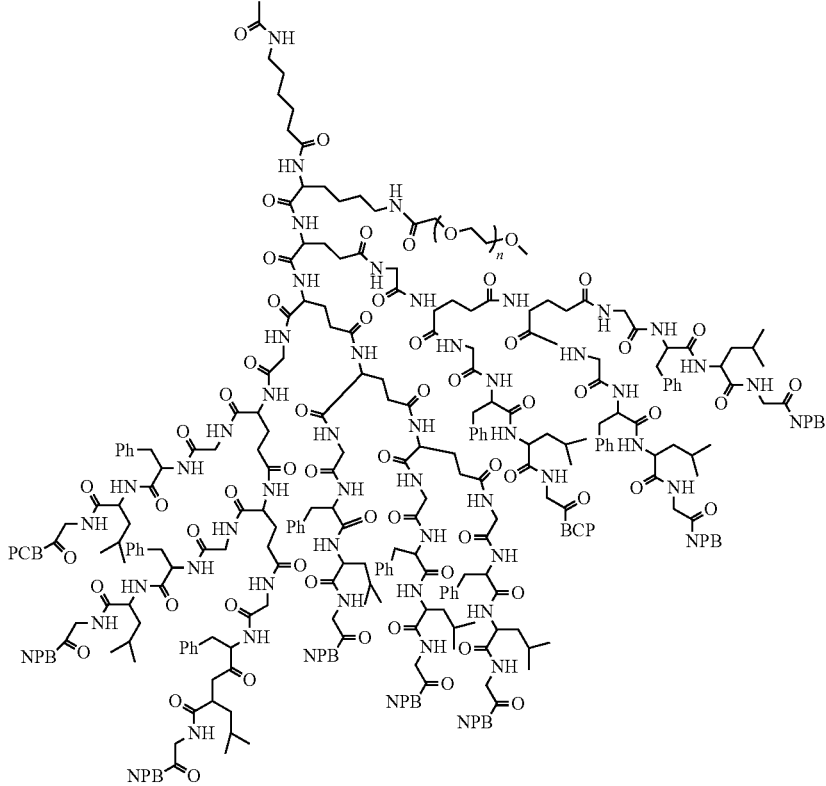

41-126

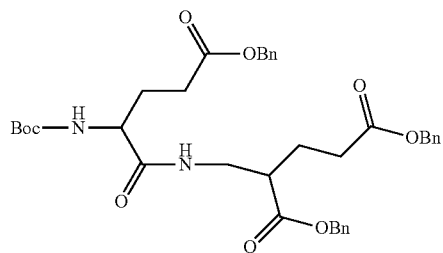

39-81

N-Boc-L-glutamic acid 5-benzyl ester (10 g, 29.6 mmoL, purchased from Aladdin), H-Glu (Obzl)-Obzl·TsOH (16.2 g, 32.6 mmol, purchased from Ark Pharm), HOBT (6 g, 44.4 mmoL), HBTU (16.8 g, 44.4 mmoL) were added in a 250 mL flask, and dissolved with DMF (80 mL), and ultrasonic treatment was carried out to completely dissolve the reactants, and then the obtained solution was stirred at −5° C. for 30 minutes. Then DIEA (22 mL, 133.4 mmoL) was slowly added dropwise, and the obtained solution reacted under this condition until the reaction ended. At the end of the reaction, deionized water (100 mL) was added to the reaction solution, the obtained solution was extracted three times with ethyl acetate (100 mL×3), and the obtained organic phases were combined. The organic phase was washed two times with saturated sodium chloride solution (100 mL×2), concentrated and evaporated to dryness. The operations of dry sample loading, column chromatography and elution with 30% ethyl acetate/petroleum ether were carried out. The elution product was then collected, concentrated, and evaporated to dryness, thus obtaining the product.

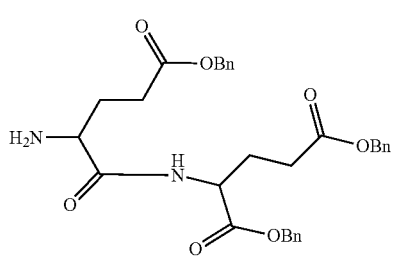

39-83

39-81 (29.6 mmol) was dissolved with dichloromethane (5 mL), TFA (22 mL, 296 mmol) was added, and ultrasonic treatment was carried out to completely dissolve the compound. A ground glass stopper was used, and the mixed solution was stirred to react at room temperature. At the end of the reaction, saturated sodium bicarbonate solution (300 mL) was added to the reaction solution, the obtained solution was extracted three times with ethyl acetate (100 mL×3), and the obtained organic phases were combined.

The organic phase was washed two times with saturated sodium chloride solution (100 mL), concentrated and evaporated to dryness.

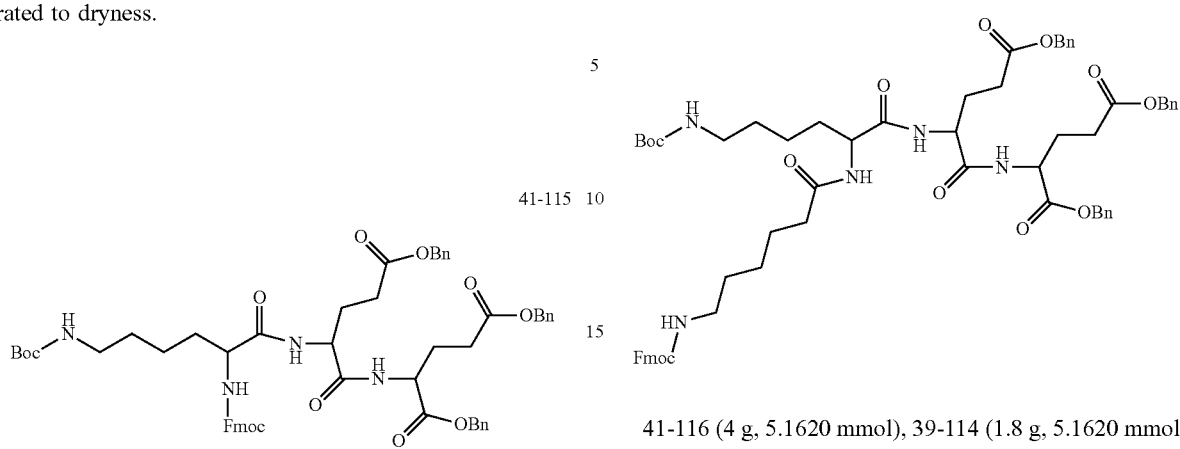

41-115

Fmoc-L-Lys(Boc)-OH (5.1430 g, 10.9767 mmol, purchased from Accela), 39-83 (6 g, 10.9767 mmol), HBTU (6.2442 g, 16.4651 mmol), HOBT (1.8257 g, 16.4651 mmol) were added in a 250 mL flask, and dissolved with DMF (50 mL), and then the mixed solution was stirred at −5° C. for 30 minutes. DIEA (8.2 mL, 19.3954 mmol) was slowly added dropwise, and then the obtained solution reacted at −5° C. overnight. At the end of the reaction, the reaction solution was extracted with pure water and ethyl acetate, and the organic phase was concentrated, thus obtaining the product 4.6 g.

41-116

Reactant 41-115 (4.6 g, 4.6132 mmol) was added in a 250 mL flask, and dissolved with DMF (30 mL), morpholine (8 mL, 92.2639 mmoL) was added, and then the mixed solution was stirred to react at room temperature for 3 hours. At the end of the reaction, saturated saline solution (150 mL) and ethyl acetate (200 mL) were added to the reaction solution, and the organic phase was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness, thus obtaining the product 4 g.

41-117

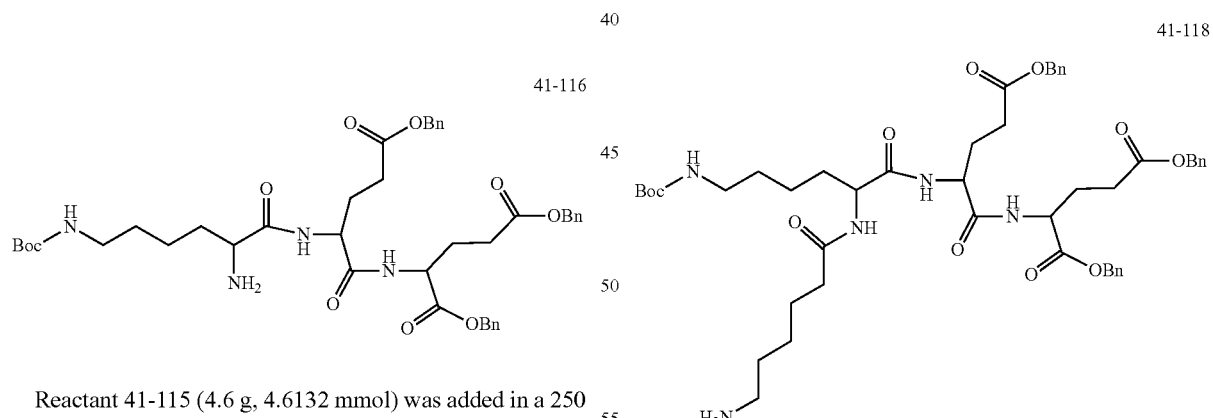

41-116 (4 g, 5.1620 mmol), 39-114 (1.8 g, 5.1620 mmol), HBTU (2.9364 g, 7.7429 mmol), HOBT (1.0462 g, 7.7429 mmol) were added in a 250 mL flask, and dissolved with DMF (40 mL), and then the mixed solution was stirred at −5° C. for 30 minutes. DIEA (8.45 mL, 50.9319 mmol) was slowly added dropwise, and then the obtained solution reacted at −5° C. overnight. At the end of the reaction, the reaction solution was precipitated with petroleum ether, the lower liquid was collected, pure water was then added, and suction filtering was carried out. The above operations were repeated three times. The obtained solid was collected, and dried, thus obtaining the product 5 g, yield 87%.

41-118

Reactant 41-117 (5 g, 5.6303 mmol) was added in a 250 mL flask, and dissolved with DMF (30 mL), morpholine (9 mL, 103.24 mmoL) was added, and then the mixed solution was stirred to react at room temperature. At the end of the reaction, the reaction solution was precipitated with petroleum ether, the lower liquid was collected, pure water was then added, and suction filtering was carried out. The obtained solid was collected, and dried, thus obtaining the product 2.6 g, yield 58%.

41-119

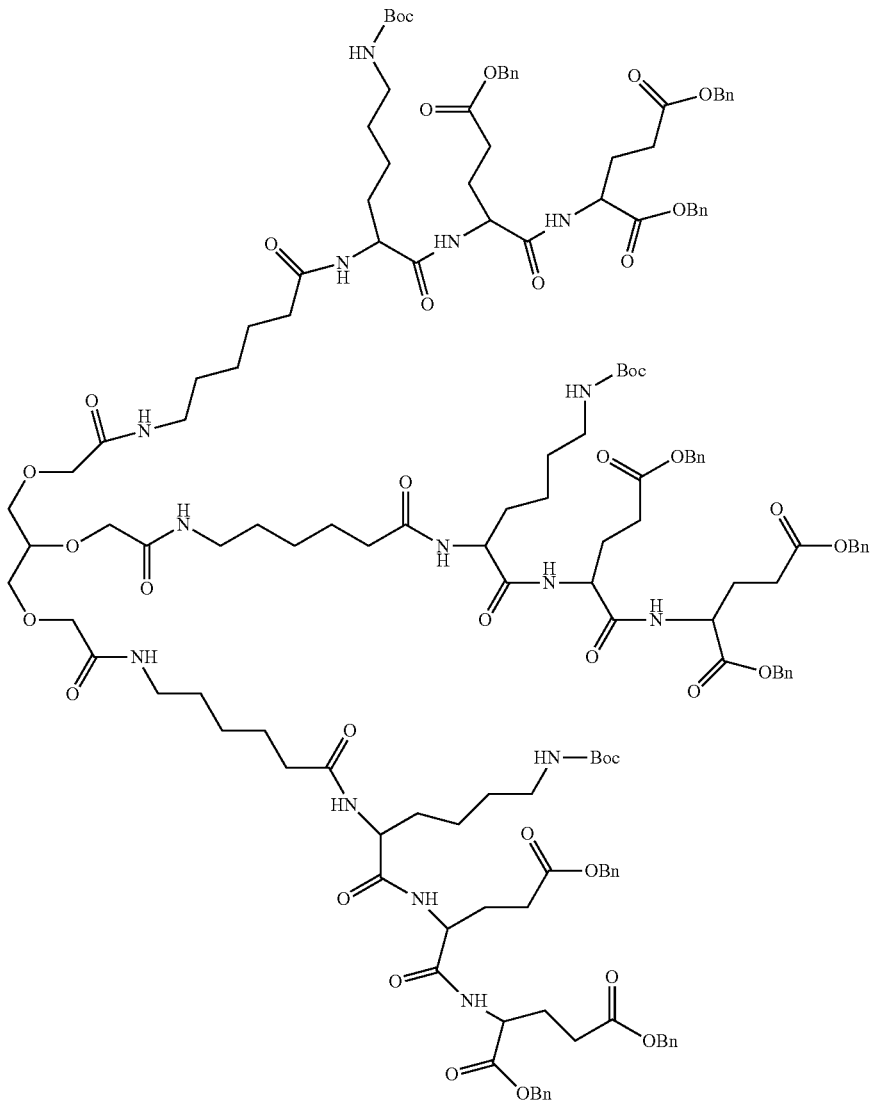

41-118 (2.6 g, 2.9353 mmol), HBTU (1.4312 g, 3.7740 mmol), HOBT (0.5099 g, 3.7740 mmol) were added in a 250 mL flask, and dissolved with the DMF solution of 45-121 (that is, 36-186, 0.8387 mmol), and then the mixed solution was stirred at −5° C. for about 30 minutes. DIEA (2.1 mL, 12.852 mmol) was slowly added dropwise, and then the obtained solution reacted at −5° C. overnight. At the end of the reaction, saturated saline solution (150 mL) and ethyl acetate (200 mL) were added to the reaction solution, and the organic phase was separated. The aqueous phase was extracted three times with ethyl acetate (50 mL×3) until there was no product in the aqueous phase, and the obtained organic phases were combined. The organic phase was washed two times with saturated saline solution (50 mL×2), and evaporated to dryness. The operations of dry sample loading, column chromatography and elution with 1%-7% methanol/dichloromethane were carried out, thus obtaining the product 0.5 g, yield 55.6%.

1147

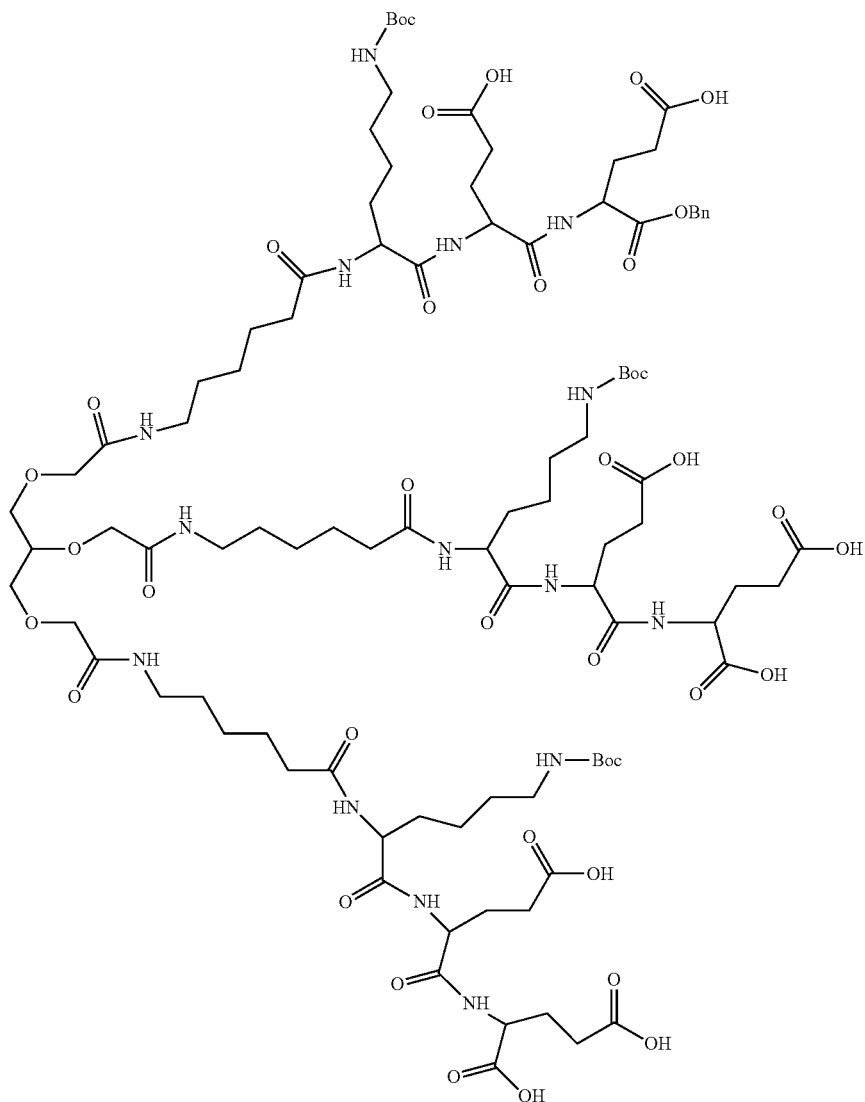

41-119 (0.1 g, 0.0348 mmol) and 10% Pd/C (150 mg) were added in a hydrogenation reactor, and dissolved with stirring with DMF (35 mL) that was added slowly, hydrogen was introduced to a pressure of 300 psi, and then the mixed solution was stirred to react at room temperature overnight. Next day, the reaction solution was filtered by suction through a sand core funnel filled with diatomaceous earth to remove the Pd/C, thus obtaining the DMF solution of the product, directly used for next reaction.

41-93

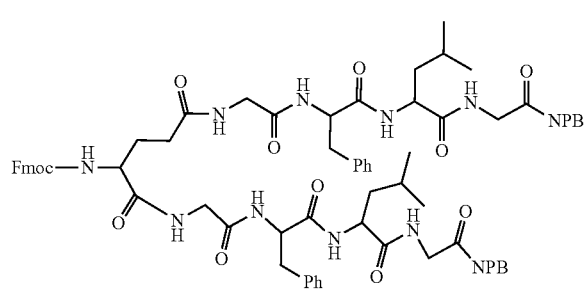

1148

41-120

Fmoc-Glu-OH (1.6433 g, 4.4485 mmol, purchased from Aladdin), GFLG-NPB (synthesized according to the method of synthesizing 42-90, 6.8 g, 9.7867 mmol), HBTU (5.0615 g, 13.3455 mmol), HOBT (1.8032 g, 13.3455 mmol) were added in a 250 mL flask, and dissolved with DMF (50 mL), and then the obtained solution was stirred to react under low-temperature and constant temperature condition of −5° C. for 30 minutes. Then DIEA (6.6 mL, 40.0365 mmol) was slowly added dropwise, and the obtained solution continued to react under this condition for 3 hours. At the end of the reaction, methyl tert-butyl ether (30 mL) and n-hexane (200 mL) were added to the reaction solution for precipitation, and suction filtering was carried out. The obtained solid powder was transferred to a 500 mL round-bottomed flask, and evaporated to dryness, thus obtaining the product 10.2 g, yield 100%.

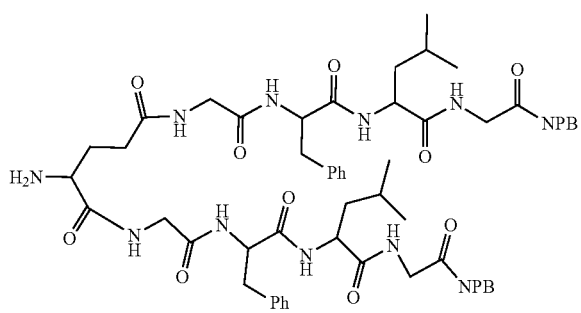

41-95

41-93 (7.6 g, 4.4485 mmol) was dissolved with DMF (40 mL), morpholine (7.8 mL, 88.97 mmol) was added, and then the mixed solution was stirred to react at room temperature for 1 hour. At the end of the reaction, ethyl acetate (100 mL) and n-hexane (200 mL) were added to the reaction solution for precipitation, and suction filtering was carried out. The obtained solid powder was transferred to a 500 mL round-bottomed flask, silica gel powder was added, and the operations of evaporation, column chromatography and elution with 3% methanol/dichloromethane were carried out, thus obtaining the product 4.4 g, yield 65.7%.

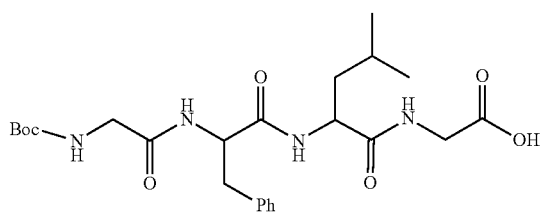

36-81

37-62 (14.95 g, 25.654 mmol and 10% Pd/C (0.300 g) were added in a reactor, and dissolved with DMF (40 mL). The air in the reactor was then pumped out to reach a vacuum state by a water pump, hydrogen was introduced to a pressure of 0.16 MPa, hydrogen was then discharged, the reactor was pumped to reach a vacuum state by the water pump, and hydrogen was then introduced again. Such operations were repeated three times. Finally, hydrogen was introduced again, and the mixed solution was stirred to react at room temperature overnight. At the end of the reaction, the reaction solution was filtered with diatomaceous earth. The filter cake was washed with DMF (20 mL×3), and the DMF solutions were combined as the raw material for the next step.

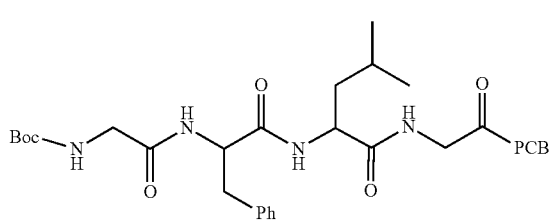

36-84

36-81 (5.3 g, 10.7255 mmol), Palbociclib (4 g, 8.9380 mmol, also referred to as PCB), HBTU (5 g, 13.4069 mmol), HOBT (1.8 g, 13.4069 mmol) were added in a 500 mL flask, and stirred at −5° C. for about 20 minutes. Then DIEA (6.6 mL, 40.2208 mmol) was slowly added dropwise, and the obtained solution continued to react at −5° C. for 1 hour, and was then moved to room temperature and stirred to react overnight. At the end of the reaction, n-hexane (150 mL) and methyl tert-butyl ether (30 mL) were added for precipitation, the supernatant was discarded, and n-hexane (150 mL) and methyl tert-butyl ether (50 mL) were then added to the lower oily product. Such operations were repeated three times, to obtain an oily product. Methyl tert-butyl ether (200 mL) was added to the oily product to separate out a solid, and then suction filtering was carried out. The filter cake was dried, thus obtaining 36-84: 15.9 g.

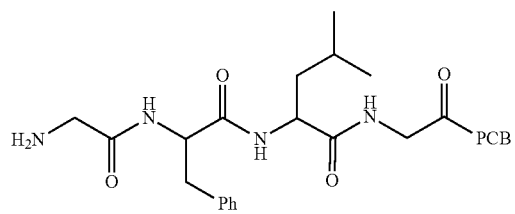

36-98

36-84 (15.9 g, 8.938 mmol) was added in a 500 mL flask, and dissolved with dichloromethane (10 mL), and TFA (6.6 mL, 89.38 mmol), and then the mixed solution was stirred to react at room temperature overnight. At the end of the reaction, the reaction solution was concentrated to 10 mL, methyl tert-butyl ether (200 mL) was added to the obtained solution to separate out a powder product, and suction filtering was carried out. The filter cake was washed with methyl tert-butyl ether (50 mL×3), and dissolved with a mixed solvent (200 mL) of 20% methanol: 80% dichloromethane solution, silica gel power (60 ml) was added, and the obtained mixture was then evaporated to dryness to obtain a powder solid. The operations of dry sample loading, column chromatography and elution with a dichloromethane mixed solution containing 0.5% ammonia water: 2%-5% methanol were carried out. The elution product was then collected, concentrated and evaporated to dryness, thus obtaining the product 36-98: 8.5 g, yield: 91.4%.

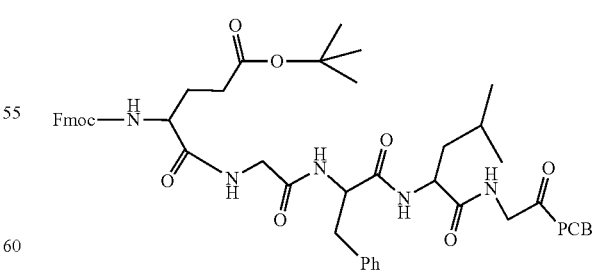

41-92

Fmoc-Glu (OtBu)-OH (3.3522 g, 7.7879 mmol, purchased from Ark Pharm), 36-98 (6.8 g, 8.2728 mmol), HBTU (4.7061 g, 12.4092 mmol), HOBT (1.6767 g, 12.4092 mmol) were added in a 250 mL flask, and dissolved with DMF (20 mL), and then the obtained solution was stirred to react under low-temperature and constant temperature condition of −5° C. for 0.5 hour. DIEA (6.2 mL, 37.2276 mmol) was then slowly added dropwise, and the obtained solution continued to react under this condition for 3 hours. At the end of the reaction, methyl tert-butyl ether (30 mL) and n-hexane (200 mL) were added to the reaction solution for precipitation, and suction filtering was carried out. The obtained solid powder was transferred to a 500 mL round-bottomed flask, and dissolved with 20% methanol/dichloromethane, silica gel powder was added, and the operations of evaporation, column chromatography, and elution with 2% methanol/dichloromethane were carried out, thus obtaining the product 8.9 g, yield 100%.

41-95 (4.4 g, 2.9319 mmol), 41-97 (3.6121 g, 3.0785 mmol), HBTU (1.6679 g, 4.3979 mmol), HOBT (0.5492 g, 4.3979 mmol) were added in a 250 mL flask, and dissolved with DMF (20 mL), and then the obtained solution was stirred to react under low-temperature and constant temperature condition of 0° C. for 30 minutes. Then DIEA (2.2 mL, 13.1936 mmol) was slowly added dropwise, and the obtained solution continued to react under this condition for 3 hours. At the end of the reaction, methyl tert-butyl ether (30 mL) and n-hexane (200 mL) were added to the reaction solution for precipitation, and suction filtering was carried out. The obtained solid powder was transferred to a 2 L round-bottomed flask, and evaporated to dryness, thus obtaining the product 7.7873 g.

41-97

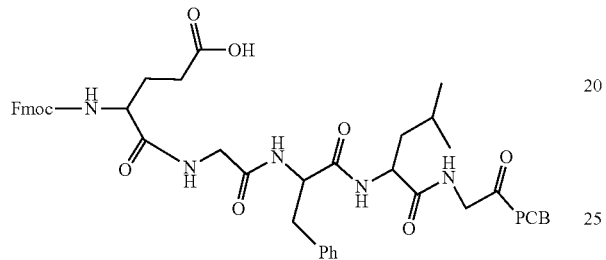

41-92 (8.9 g, 7.2447 mmol) was added in a reaction flask, and dissolved with dichloromethane (20 mL), and TFA (8 mL, 108.6709 mmol), and then the mixed solution was stirred to react at room temperature for 3 hours. At the end of the reaction, the reaction solution was evaporated to remove the dichloromethane, methyl tert-butyl ether (30 mL) and n-hexane (200 mL) were added for precipitation, and suction filtering was carried out. The obtained solid powder was transferred to a 500 mL round-bottomed flask, and evaporated to dryness, thus obtaining the product 8.5 g, yield 100%.

41-103

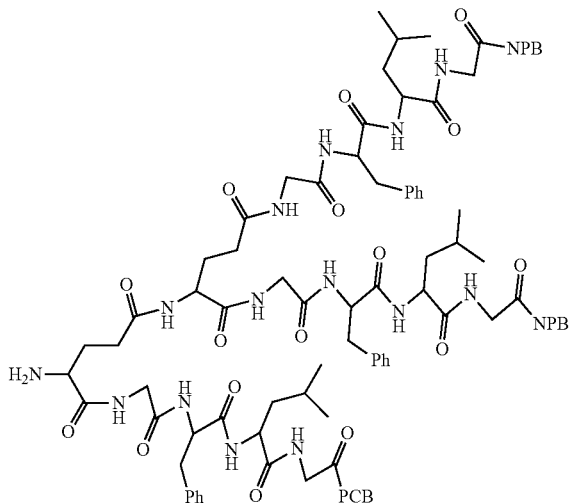

41-98

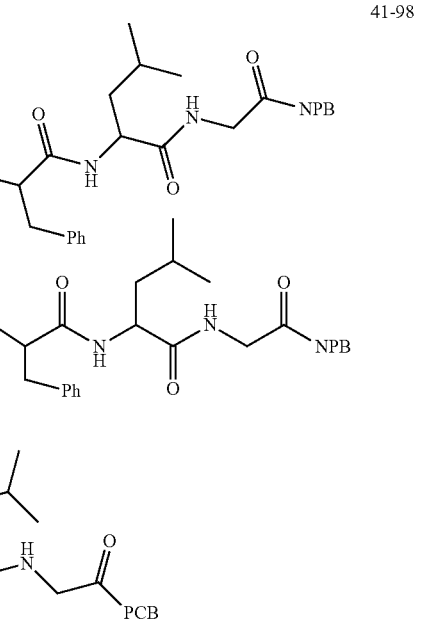

41-98 (6.2 g, 2.3343) was dissolved with DMF (20 mL), morpholine (6 mL, 70.0298 mmol) was added, and then the mixed solution was stirred to react at room temperature for 1 hour. At the end of the reaction, methyl tert-butyl ether (100 mL) and n-hexane (200 mL) were added to the reaction solution for precipitation, and suction filtering was carried out. The obtained solid powder was transferred to a 500 mL round-bottomed flask, and evaporated to dryness, thus obtaining the product 5.68 g.

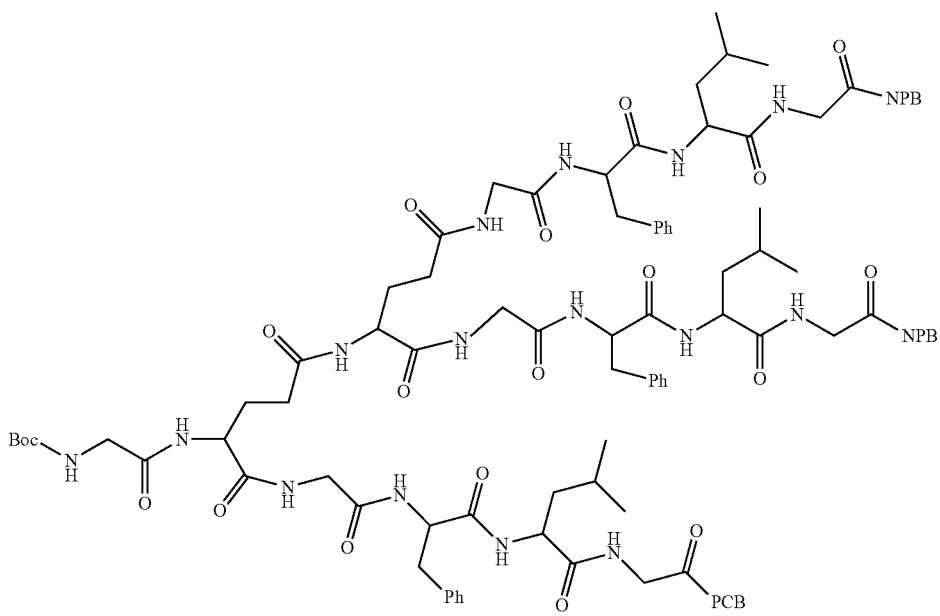

41-104

41-103 (5.5 g, 2.2598 mmol), Boc-Gly-OH (0.4157 g, 2.3728 mmol, purchased from Aladdin), HBTU (1.2855 g, 3.3897 mmol), HOBT (0.4580 g, 3.3897 mmol) were added in a 250 mL flask, and dissolved with DMF (20 mL), and then the obtained solution was stirred to react under low-temperature and constant temperature condition of −5° C. for 30 minutes. Then DIEA (1.7 mL, 10.1692 mmol) was slowly added dropwise, and the obtained solution continued to react under this condition for 3 hours. At the end of the reaction, ethyl acetate (30 mL) and n-hexane (200 mL) were added to the reaction solution for precipitation, and suction filtering was carried out many times. The obtained solid powder was transferred to a 2 L round-bottomed flask, and evaporated to dryness, for the next reaction.

41-105

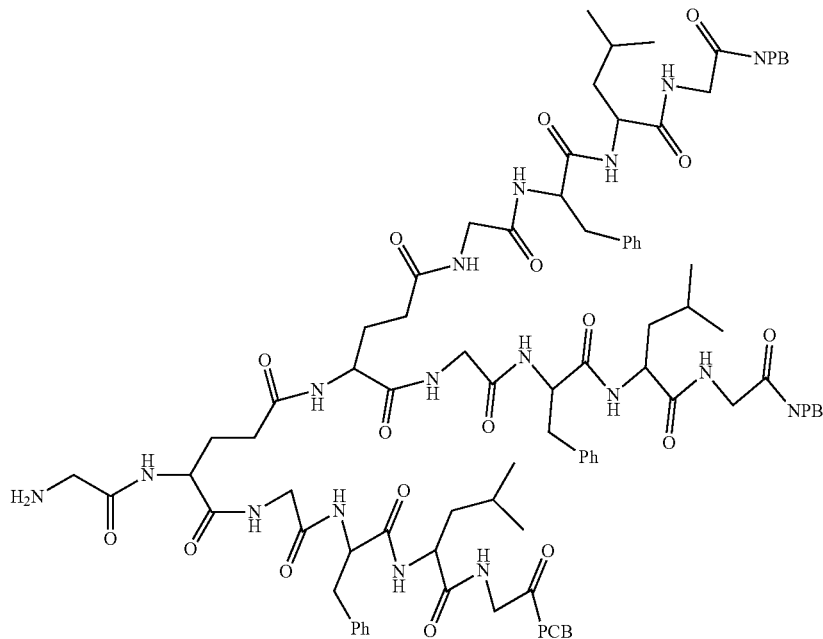

41-104 (5.8 g, 2.2598 mmol), and dichloromethane (20 mL) were added in a flask, TFA (5 mL, 67.2110 mL) was slowly added dropwise, and then the obtained solution was stirred to react at room temperature for 3 hours. At the end of the reaction, the dichloromethane was removed with a rotary evaporator, the obtained solution was precipitated with ethyl acetate (30 mL) and n-hexane (200 mL), and suction filtering was carried out many times. The obtained solid powder was transferred to a 500 mL round-bottomed flask, and evaporated to dryness, thus obtaining the product 5.5 g, yield 98%.

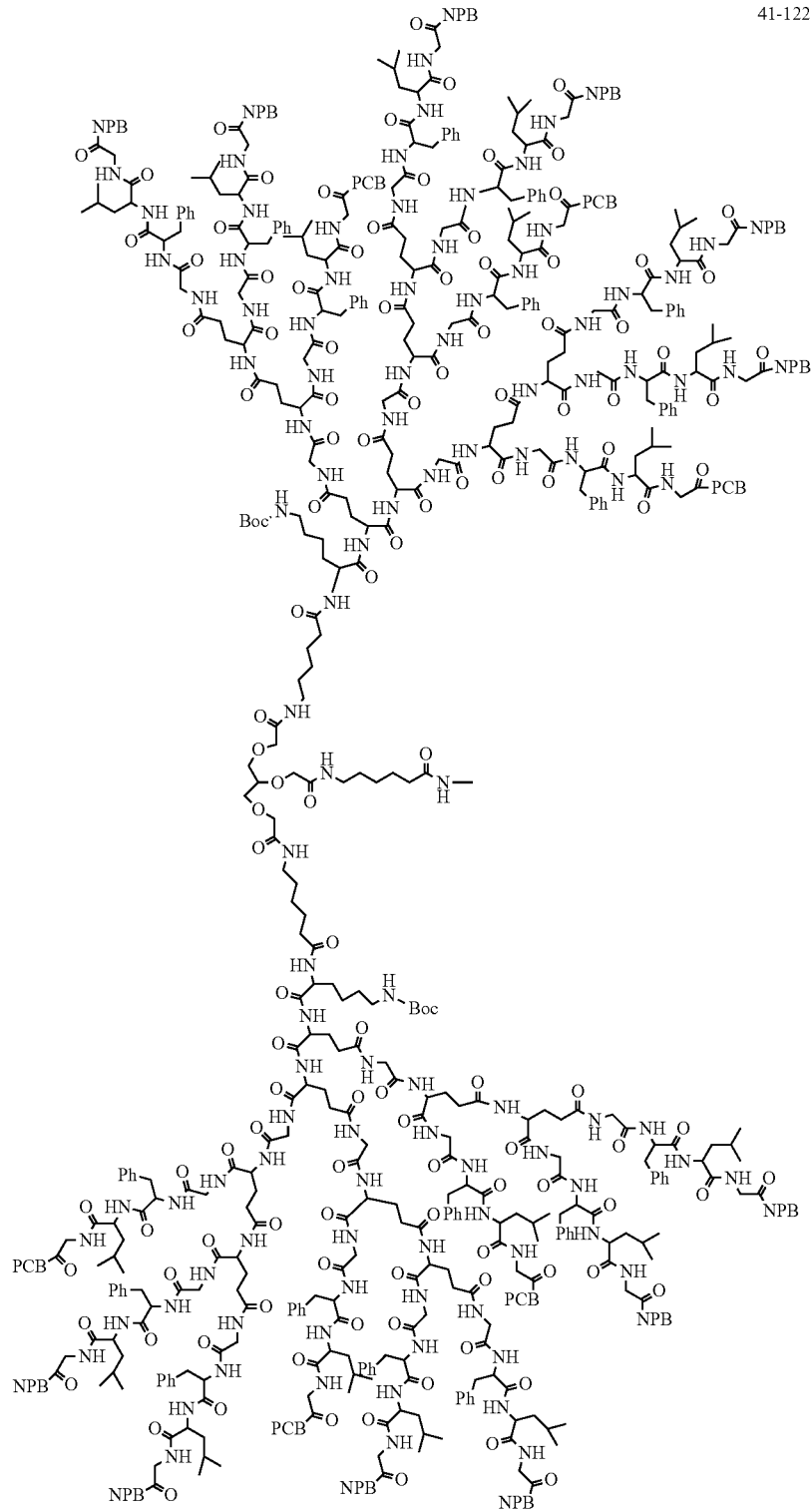
41-122

-continued

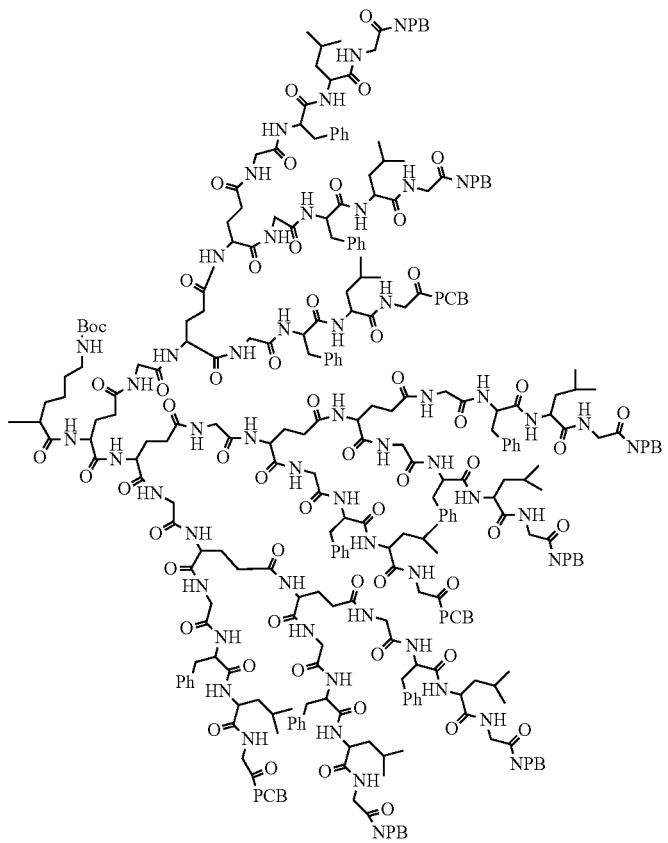

41-105 (0.8660 g, 0.3476 mmol), HBTU (0.1975 g, 0.5215 mmol), HOBT (0.0705 g, 0.5215 mmol) were added in a 250 mL flask, and dissolved with DMF solution of 41-120 (0.0348 mmol), and then the mixed solution was stirred at −5° C. for 30 minutes. Then DIEA (2 mL, 12.1005 mmol) was slowly added dropwise, and the obtained solution reacted at −5° C. overnight. At the end of the reaction, pure water was added to the reaction solution to separate out a solid, and suction filtering was carried out. The filter cake was dried, thus obtaining the product 0.84 g, yield 100%.

1161
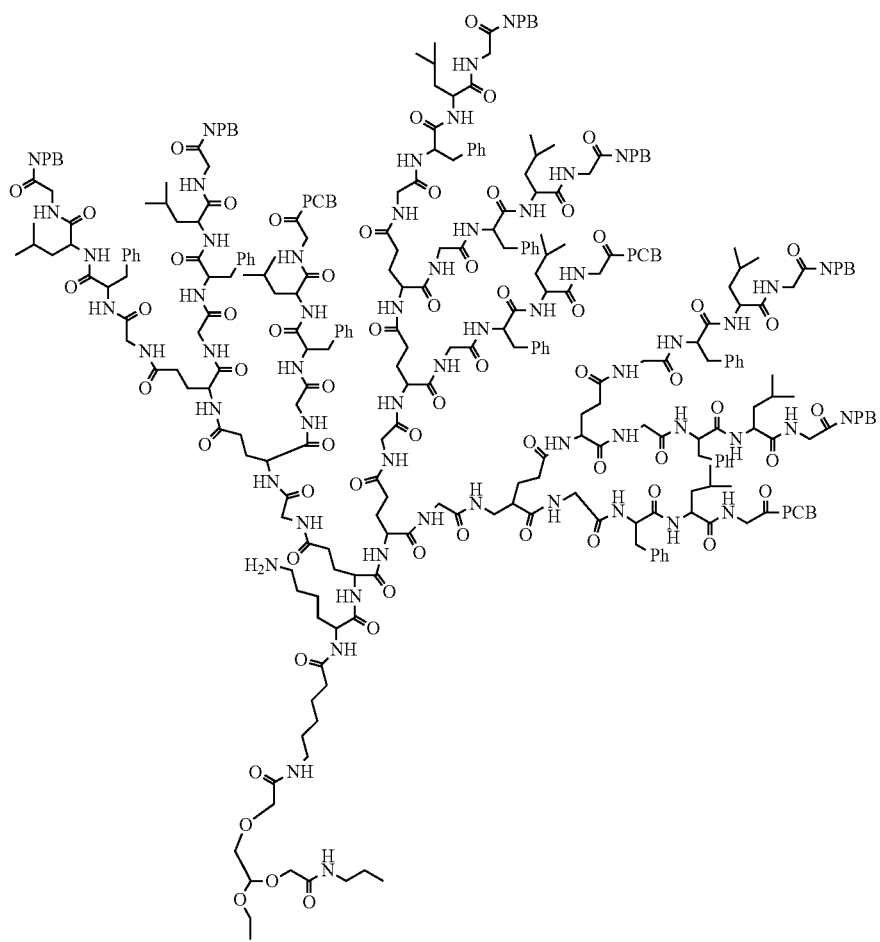
1162
41-125
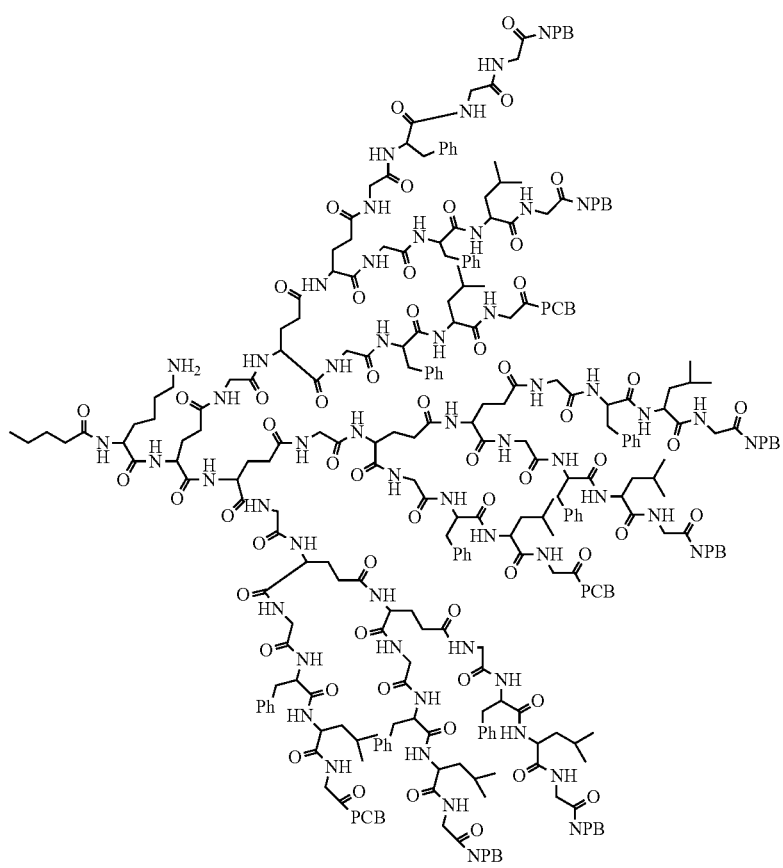

-continued

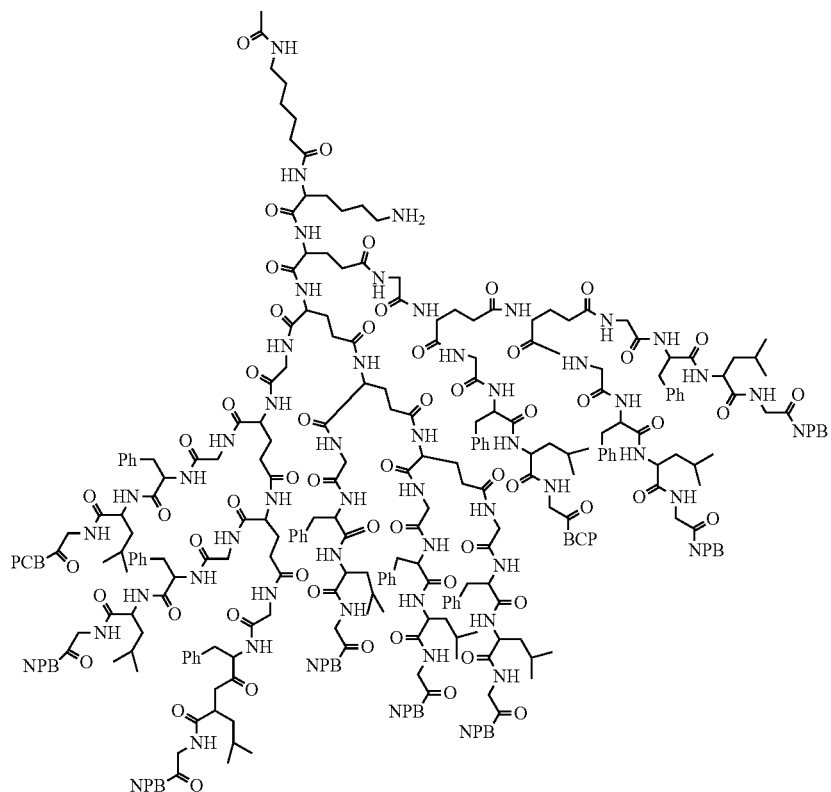

41-122 (0.84 g, 0.0348 mmol) was added in a 250 mL flask, and dissolved with dichloromethane (30 mL) in a condition of ultrasonic, TFA (0.3 mL, 0.2326 mmol) was added, and then the obtained solution was stirred at room temperature overnight. Next day, the reaction solution was first evaporated to remove the dichloromethane, methyl tert-butyl ether was then added for precipitation, and suction filtering was carried out. The filter cake was dried, thus obtaining the product 0.8 g, yield 100%.

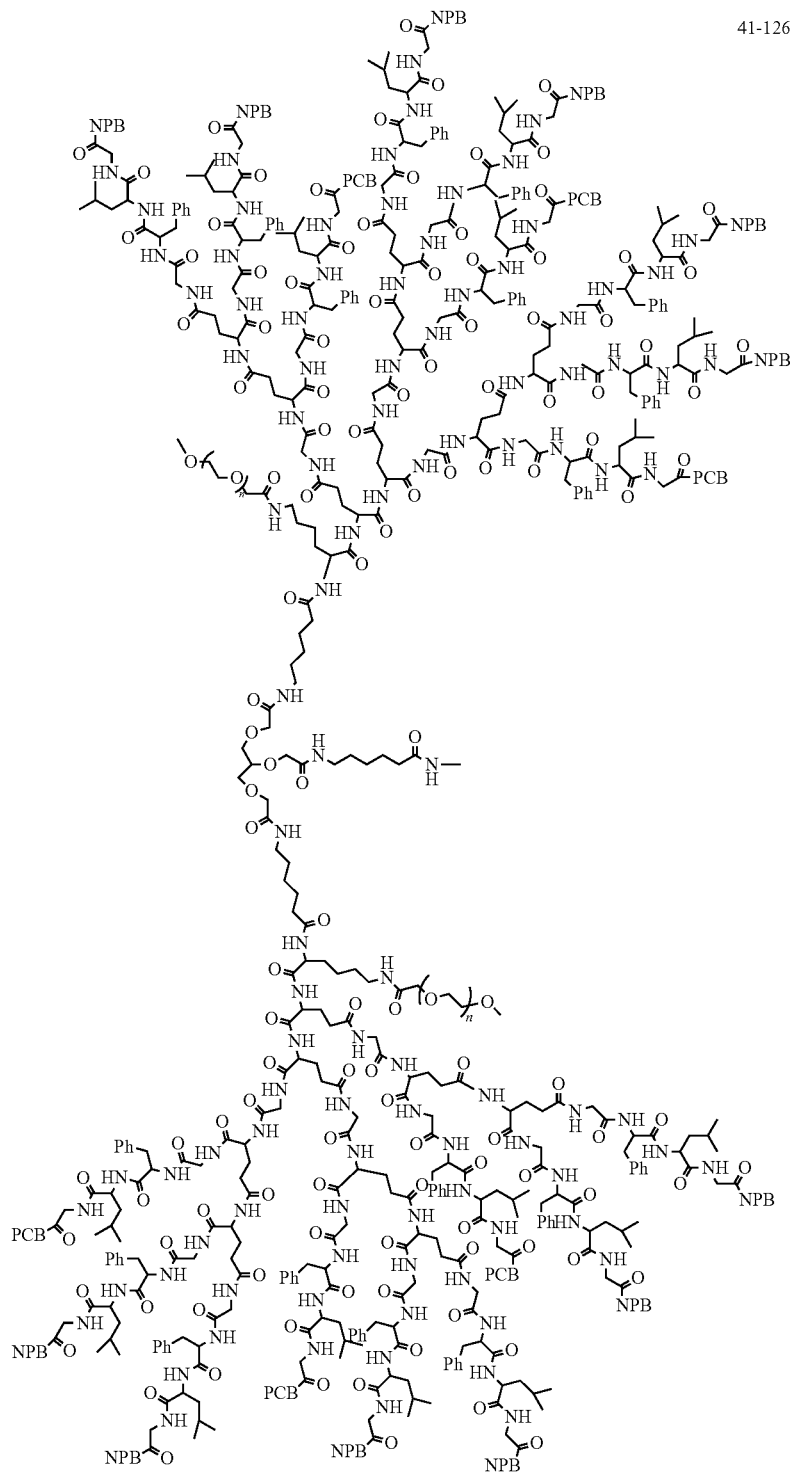
41-126

-continued

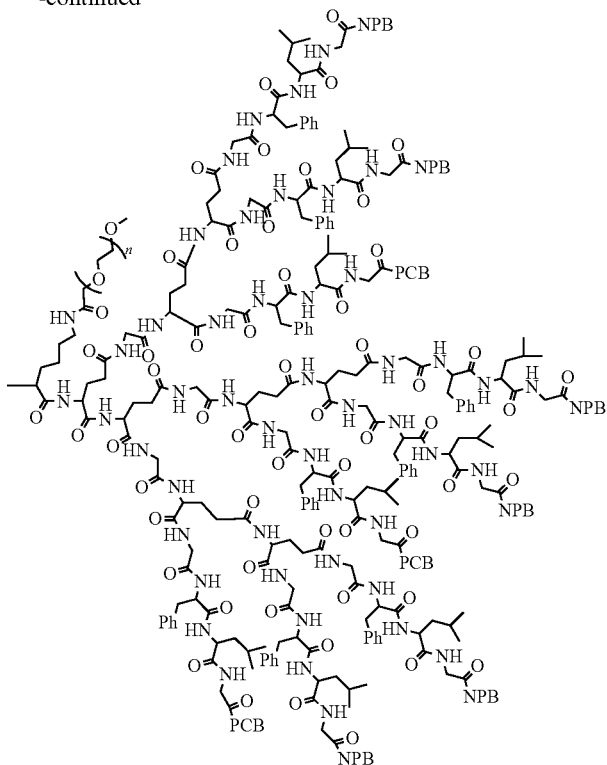

41-125 (0.8 g, 0.0348 mmol) was dissolved with DMF (20 mL) and M-SCM-10K (1.1058 g, 0.1044 mmol, purchased from JenKem) was added, and ultrasonic treatment was carried out to dissolve the reactants, and then the obtained solution reacted in the dark at a low speed of stirring. At the end of the reaction, methyl tert-butyl ether (150 mL), n-hexane (70 mL) were added to the reaction solution to separate out a solid, and suction filtering was carried out. The filter cake was dissolved with 20% methanol/dichloromethane, silica gel powder (3 g) was added, the operations of evaporation, column chromatography and gradient elution with 1% ammonia water+5%-10% methanol/dichloromethane were carried out, thus obtaining the product 0.35 g, yield 19.4%.

$^1$H-NMR (600 MHz, DMSO-$d_6$) δ 10.13-10.12 (m, 7H), 9.29-9.27 (m, 16H), 8.95-8.92 (m, 7H), 8.57-8.56 (m, 17H), 8.18-8.16 (m, 37H), 8.14-7.95 (m, 137H), 7.89-7.87 (m, 50H), 7.59-7.54 (m, 43H), 7.35-7.25 (m, 176H), 5.83-5.81 (m, 7H), 5.16-5.08 (m, 6H), 4.57-4.35 (m, 58H), 4.13-4.10 (m, 25H), 4.08-4.06 (m, 49H), 3.84-3.82 (m, 26H), 3.72-3.65 (m, 128H), 3.51-3.49 (m, 2888H), 3.24-3.19 (m, 30H), 3.13-3.10 (m, 44H), 3.06-3.02 (m, 40H), 2.91-2.90 (m, 14H), 2.78-2.74 (m, 35H), 2.65-2.60 (m, 26H), 2.41-2.30 (m, 47H), 2.21-1.96 (m, 84H), 1.83-1.75 (m, 91H), 1.64-1.39 (m, 156H), 1.20-1.16 (m, 24H), 0.90-0.85 (m, 162H).

26. Synthesis of 49-136 (Compound No. 26)

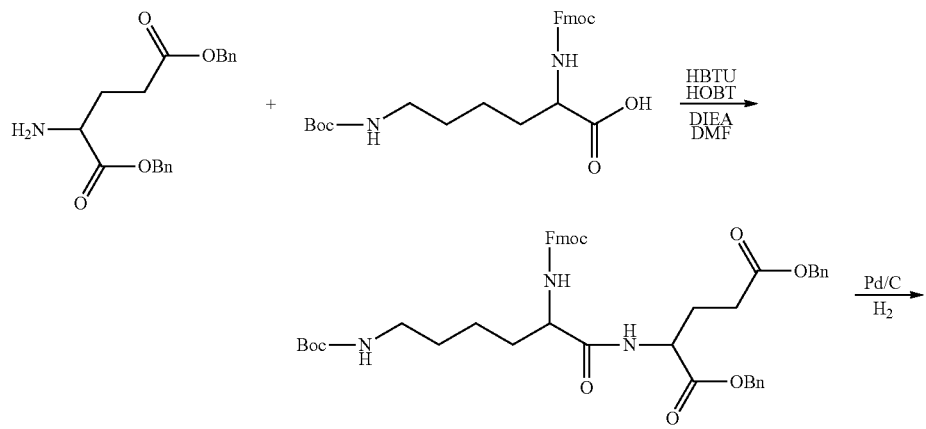

49-96

1169
-continued
1170
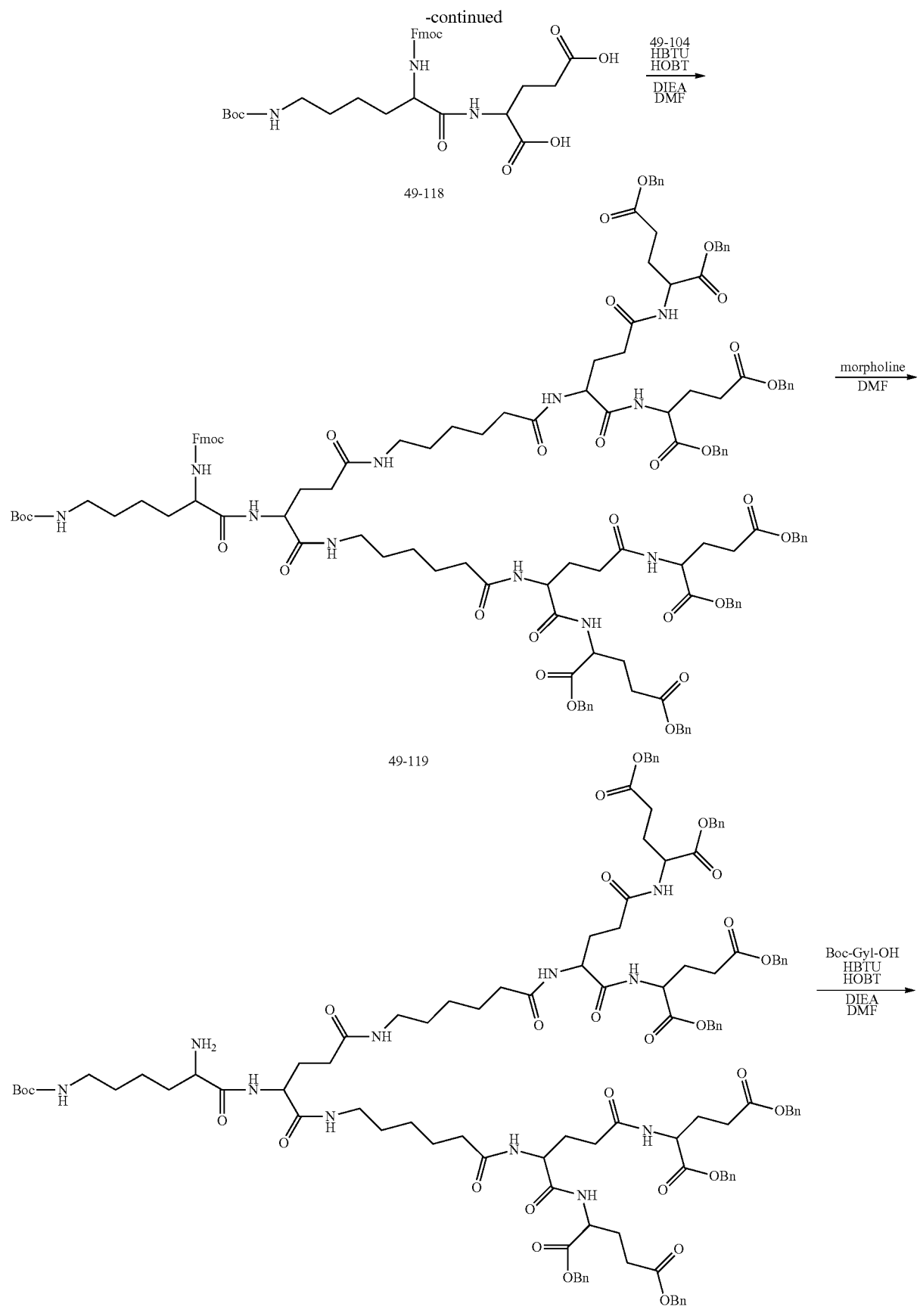

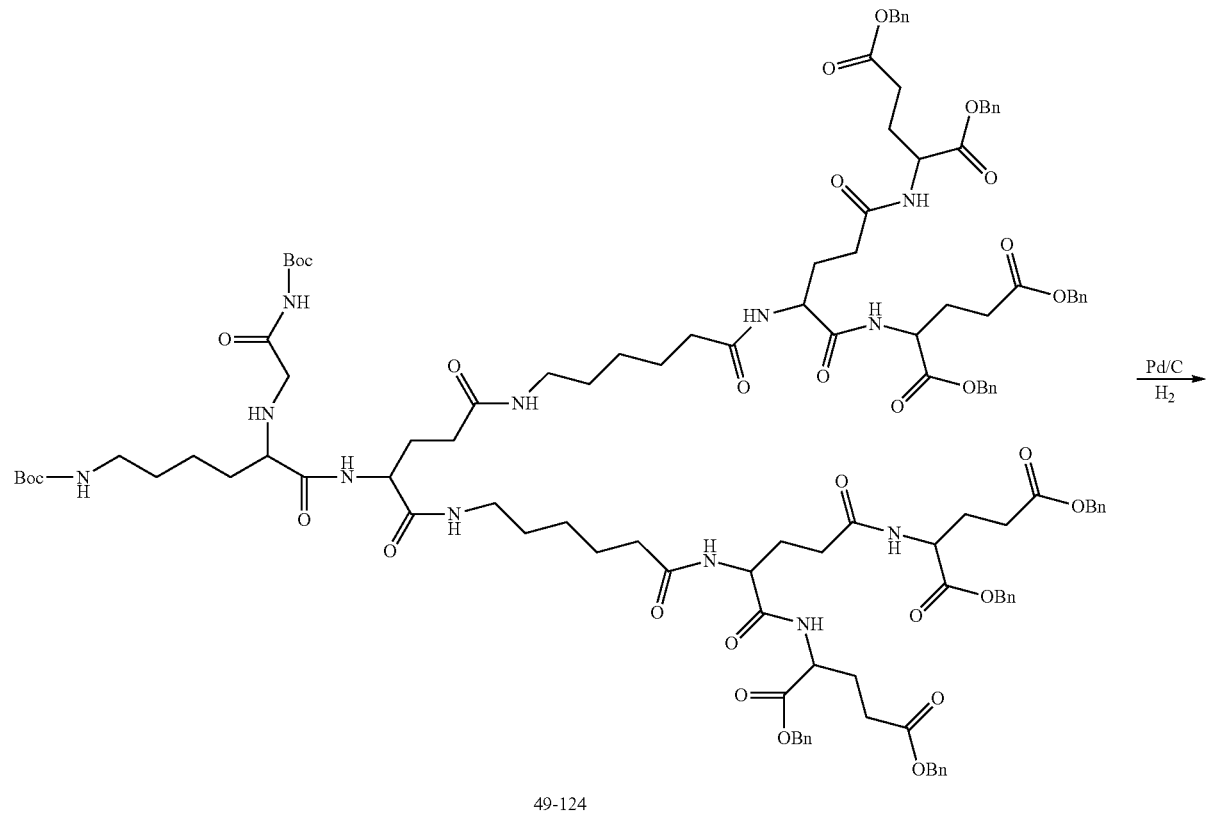
49-124
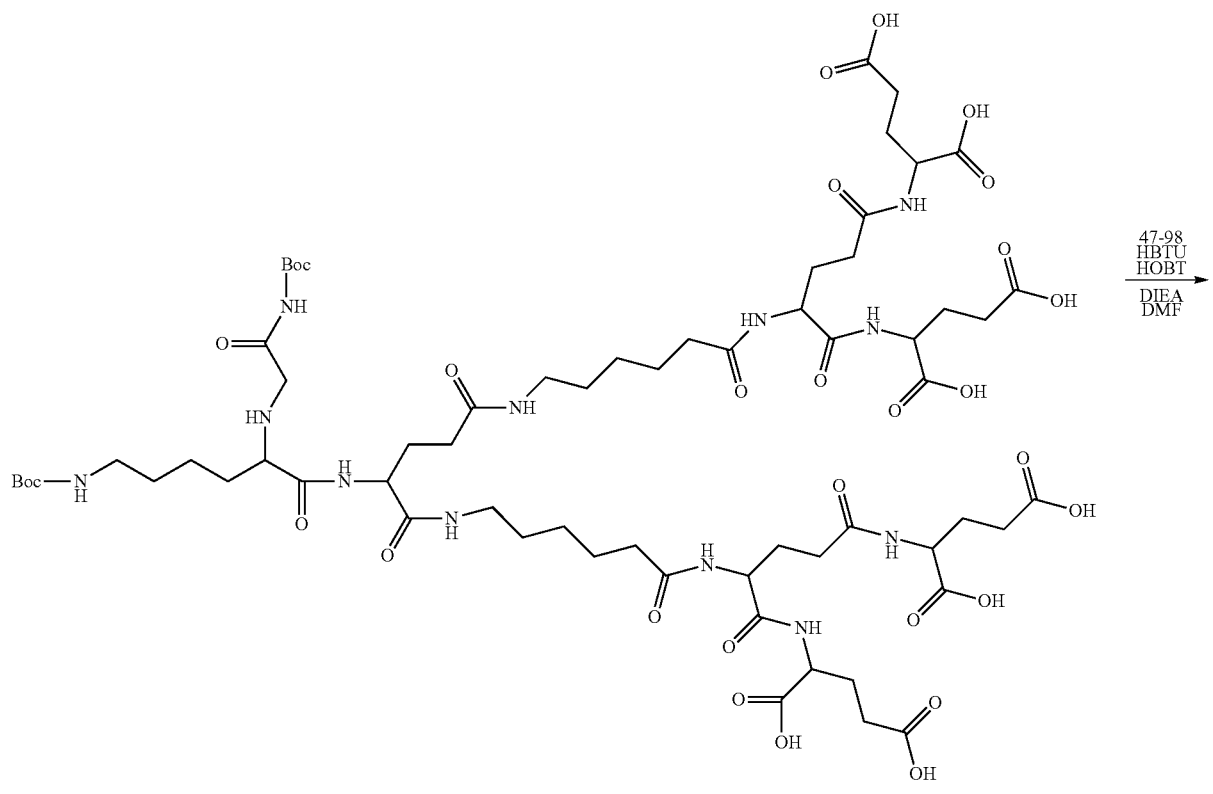
49-125

-continued
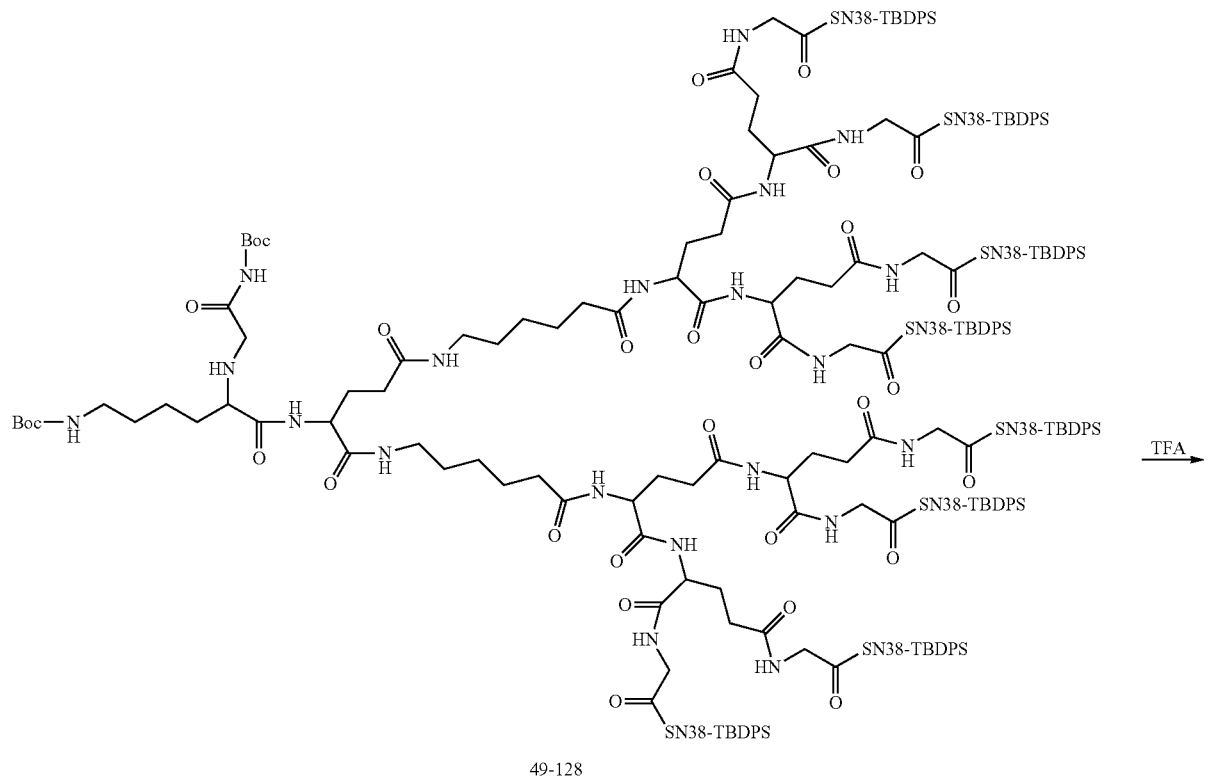
49-128
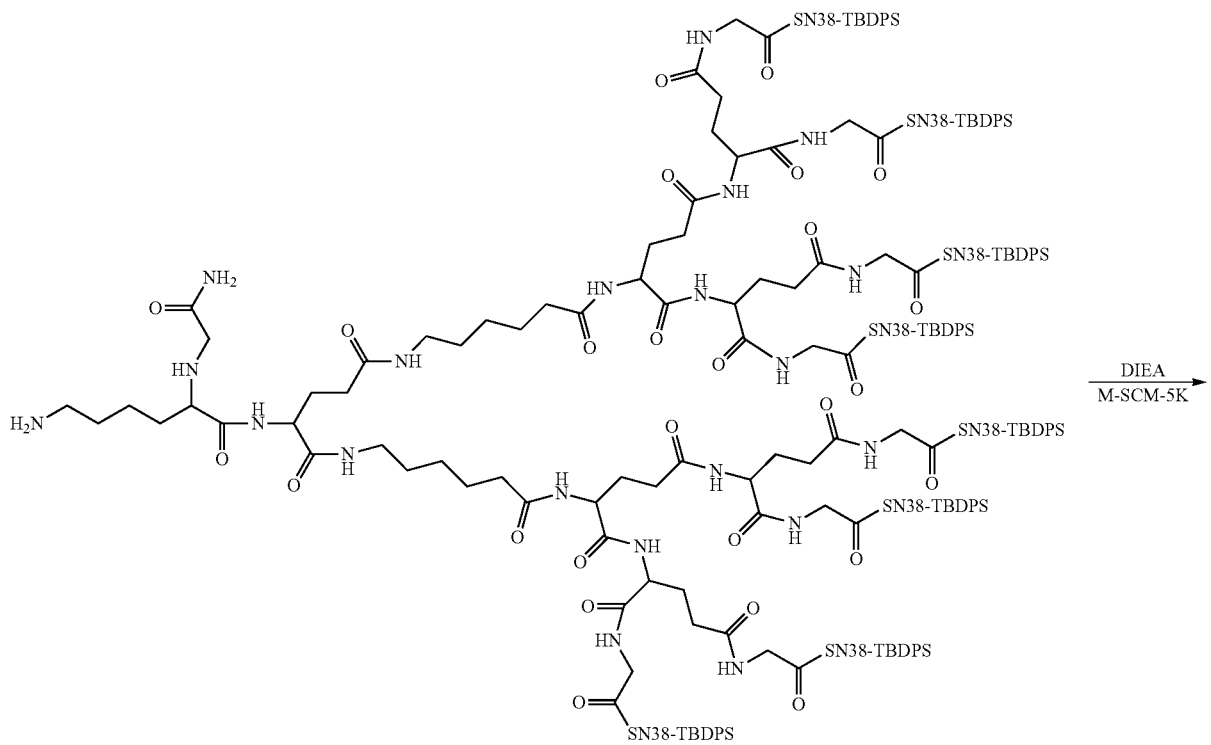
49-134

-continued
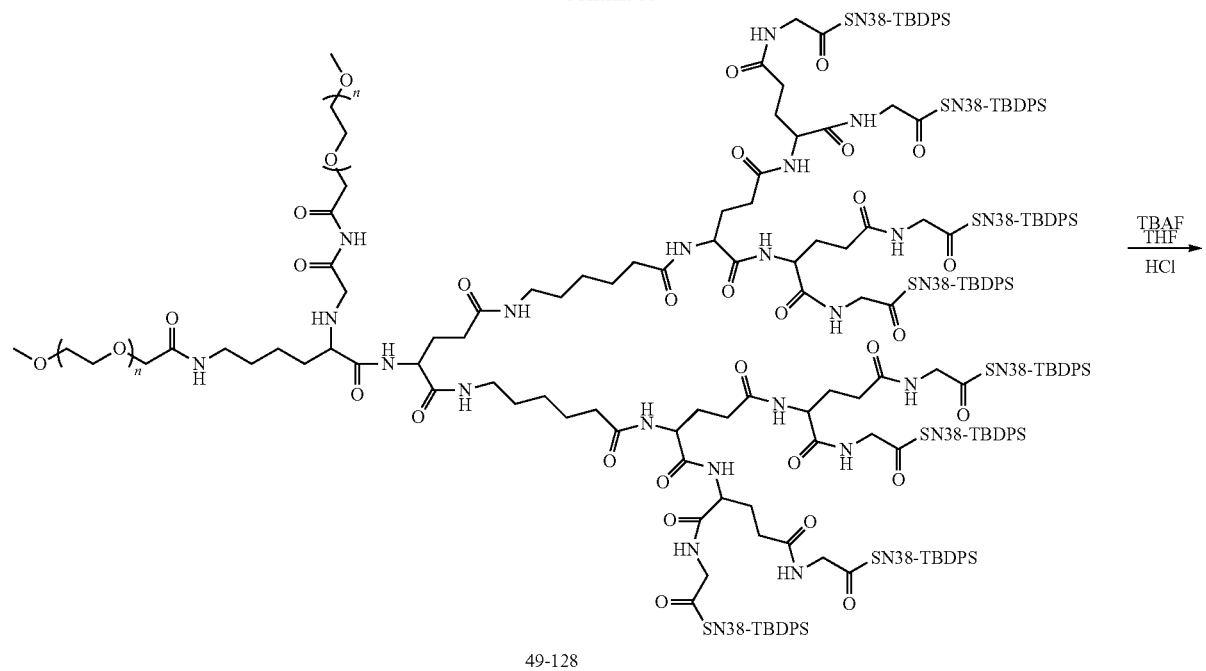
49-128
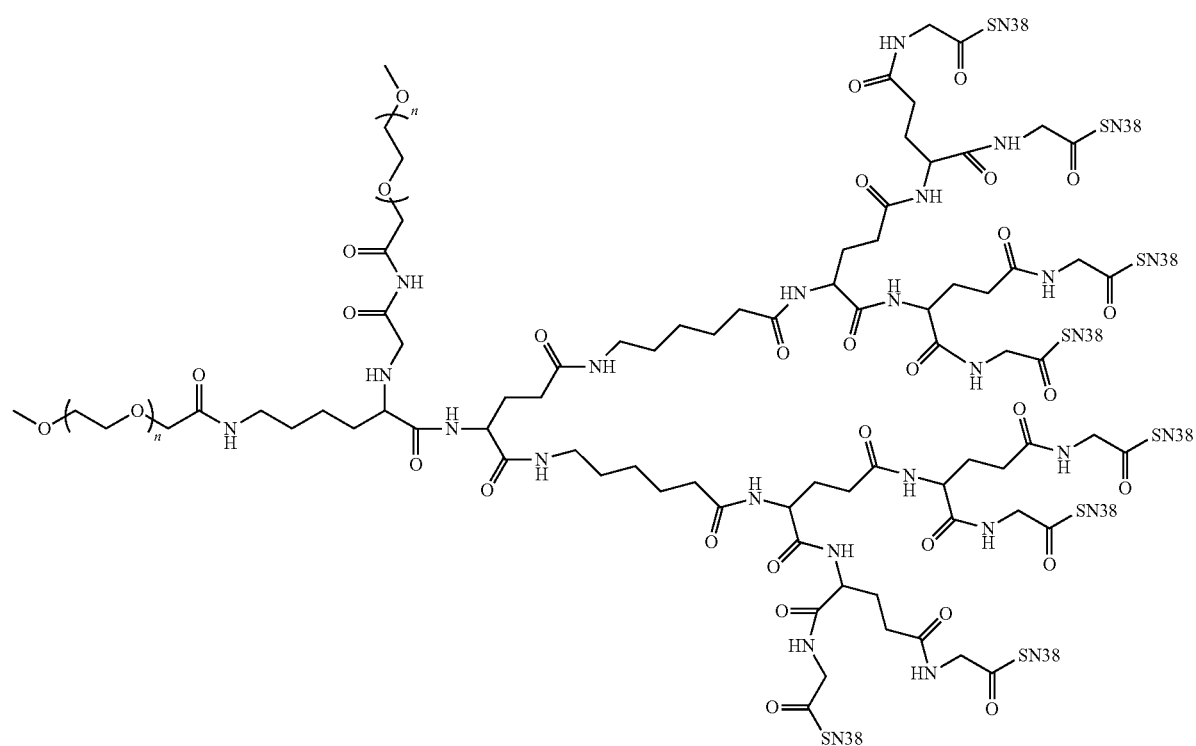
49-136
49-96
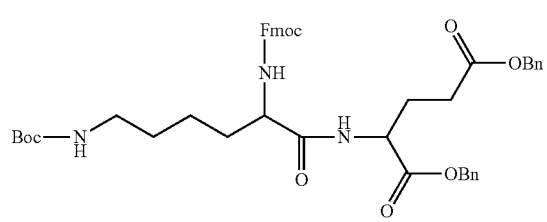

Fmoc-Lys (Boc) —OH (3 g, 6.4029 mmol, purchased from Accela), HBTU (3.64 g, 9.6044 mmol), HOBT (1.30 g, 9.6044 mmol) were added in a flask loaded with H-Glu (OBn)$_2$ (3.36 g, 6.7230 mmol, purchased from Ark Pharm), and dissolved with a proper amount of DMF, and then, at −5° C., DIEA (4.76 mL, 28.8131 mmol) was slowly added dropwise. At the end of the addition, the obtained solution reacted for half an hour, and was then moved to room temperature and stirred to react overnight. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, and dried in a vacuum oven, thus obtaining the product (6.96 g, extra-quota).

49-118

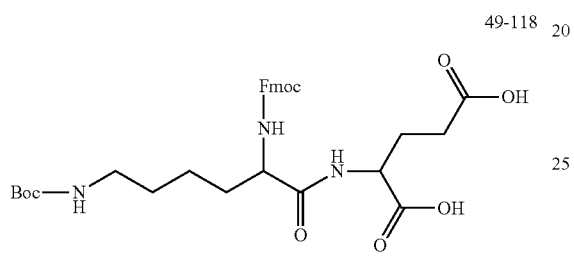

49-96 (2 g, 2.5710 mmol) and 10% Pd/C (0.05 g) were added in a hydrogenation reactor, and dissolved with DMF (20 mL), hydrogen was introduced to a pressure of 300 Psi, and then the mixed solution was stirred to react at room temperature overnight. At the end of the reaction, the reaction solution was filtered with diatomaceous earth. The filter cake was washed with DMF (15 mL×3) three times, and the filtrate was put into a 250 mL round-bottomed flask, thus obtaining the product as the raw material for the next reaction.

49-101

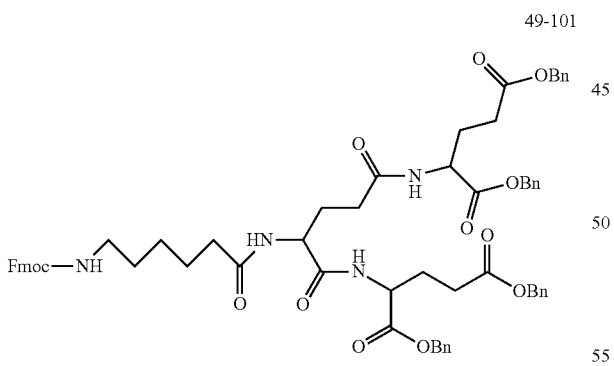

39-84 (8 g, 10.4459 mmol), HBTU (5.94 g, 15.6689 mmol), HOBT (2.12 g, 15.6689 mmol) were added in a flask loaded with 49-17 (3.69 g, 10.4459 mmol), and dissolved with a proper amount of DMF, and then, at −5° C., DIEA (7.77 mL, 47.0066 mmol) was slowly added dropwise. At the end of the addition, the obtained solution reacted for half an hour, and was then moved to room temperature and stirred to react overnight. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, the obtained solid was dissolved with a mixed solvent (100 mL) of methanol/dichloromethane (1:4), silica gel powder (100 mL) was added, and then the obtained mixture was evaporated to dryness to obtain a powdery solid. The operations of dry sample loading, column chromatography and elution with 100% dichloromethane were carried out. The elution product was then collected, concentrated, and dried in a vacuum oven, thus obtaining the product (9.6 g, 83.48%)

49-104

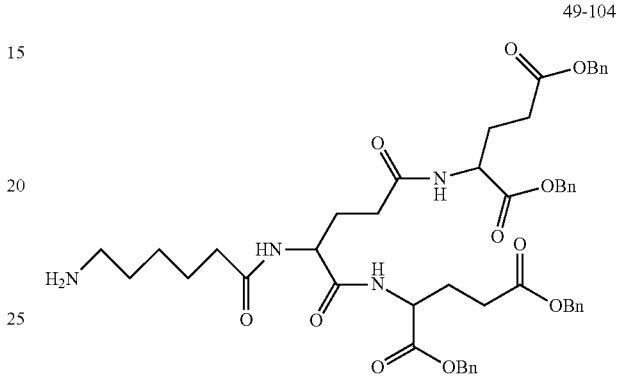

DMF was added in a flask loaded with 49-101 (9.6 g, 8.7193 mmol), ultrasonic vibration was carried out to completely dissolve the compound, morpholine (7.59 mL, 87.193 mmol) was added, and then the mixed solution was stirred to react at room temperature for 2 h. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, the obtained solid was dissolved with a mixed solvent (100 mL) of methanol/dichloromethane (1:4) solution, silica gel powder (100 mL) was added, and then the obtained mixture was evaporated to dryness to obtain a powdery solid. The operations of dry sample loading, column chromatography and elution with a dichloromethane mixed solution containing 3%-5% methanol were carried out. The elution product was then collected, concentrated, and dried in a vacuum oven, thus obtaining the product (5.3 g, 69.19%)

49-119

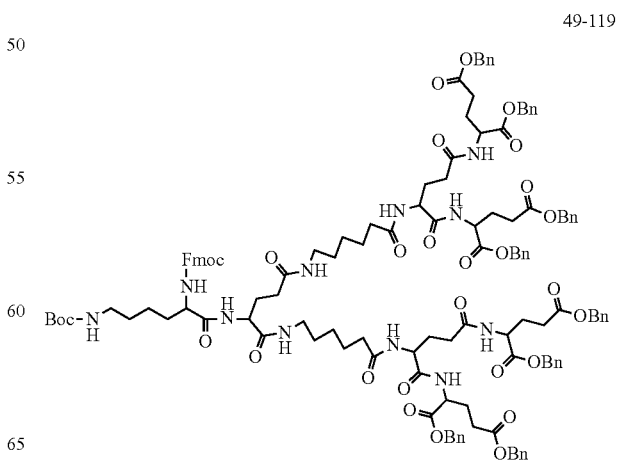

49-104 (4.74 g, 5.3991 mmol), HBTU (2.92 g, 7.7130 mmol), HOBT (1.04 g, 7.7130 mmol) were added in a flask loaded with 49-118 (1.53 g, 2.5710 mmol), and dissolved with a proper amount of DMF, and then, at −5° C., DIEA (4.76 mL, 28.8131 mmol) was slowly added dropwise. At the end of the addition, the obtained solution reacted for half an hour, and was then moved to room temperature and stirred to react overnight. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, and dried in a vacuum oven, thus obtaining the product (8.65 g, extra-quota)

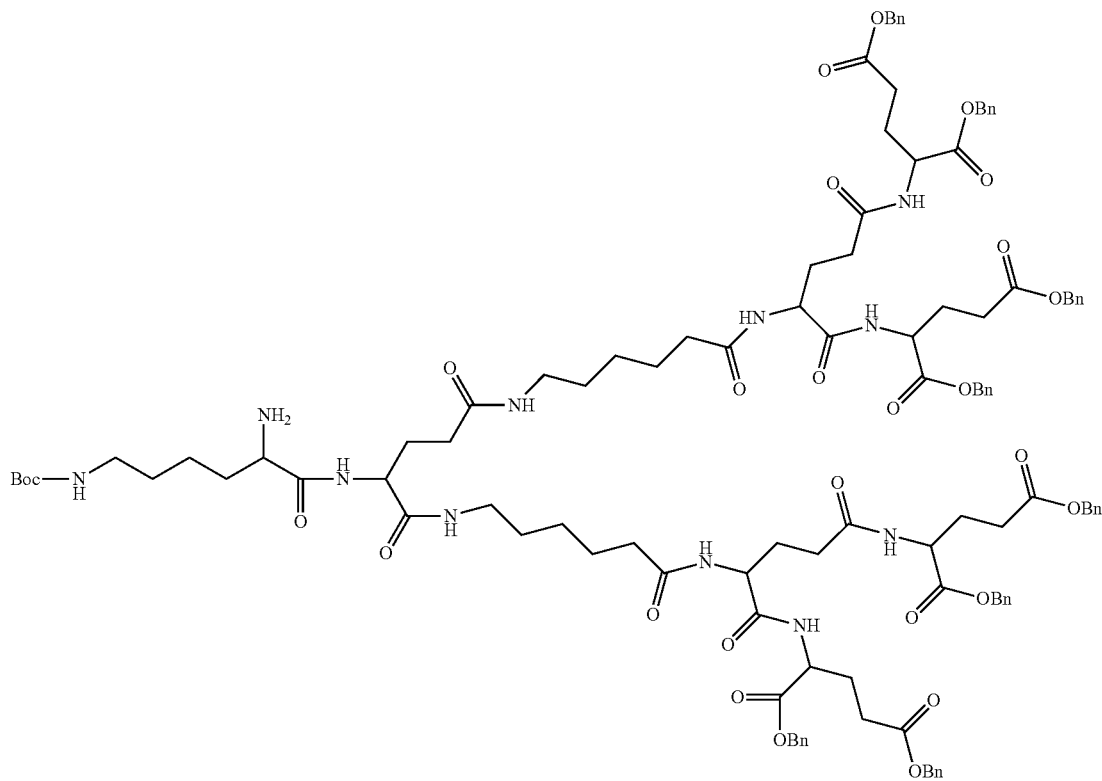

49-123

DMF was added in a flask loaded with 49-119 (5.96 g, 2.5710 mmol), ultrasonic vibration was carried out to completely dissolve the compound, morpholine (5.19 mL, 25.710 mmol) was added, and then the mixed solution was stirred to react at room temperature for 2 h. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, and dried in a vacuum oven, thus obtaining the product (7.6 g, extra-quota)

49-124

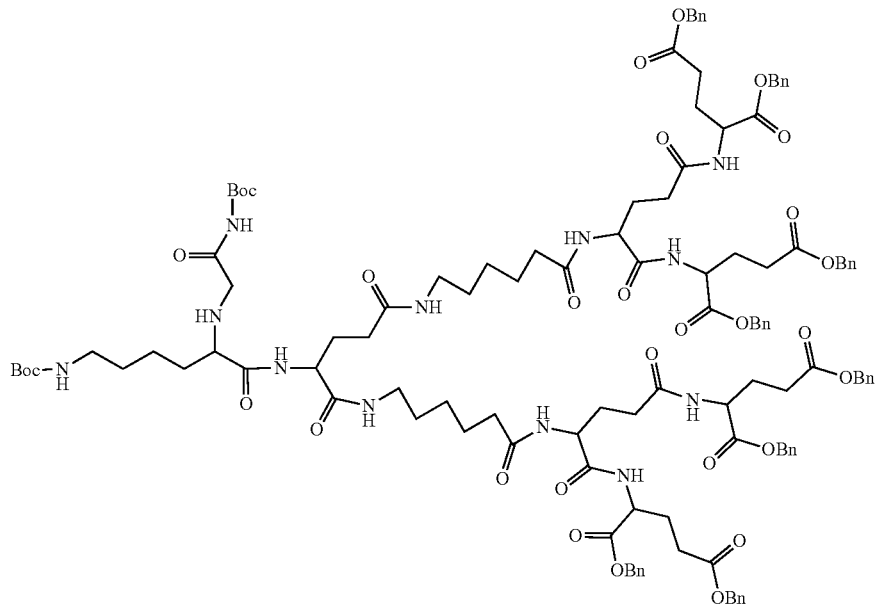

Boc-Gly-OH (0.49 g, 2.8281 mmol, purchased from Aladdin), HBTU (1.46 g, 3.8565 mmol), HOBT (0.52 g, 3.8565 mmol) was added in a flask loaded with 49-123 (5.39 g, 2.5710 mmol), and dissolved with a proper amount of DMF, and then, at −5° C., DIEA (4.76 mL, 28.8131 mmol) was slowly added dropwise. At the end of the addition, the obtained solution reacted for half an hour, and was then moved to room temperature and stirred to react overnight. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, the obtained solid was dissolved with a mixed solvent (100 mL) of methanol/dichloromethane (1:4), silica gel powder (100 mL) was added, and then the obtained mixture was evaporated to dryness to obtain a powdery solid. The operations of dry sample loading, column chromatography and elution with a dichloromethane mixed solution containing 2%-5% methanol were carried out. The elution product was then collected, concentrated, and dried in a vacuum oven, thus obtaining the product (3.2 g, 55.27%)

49-125

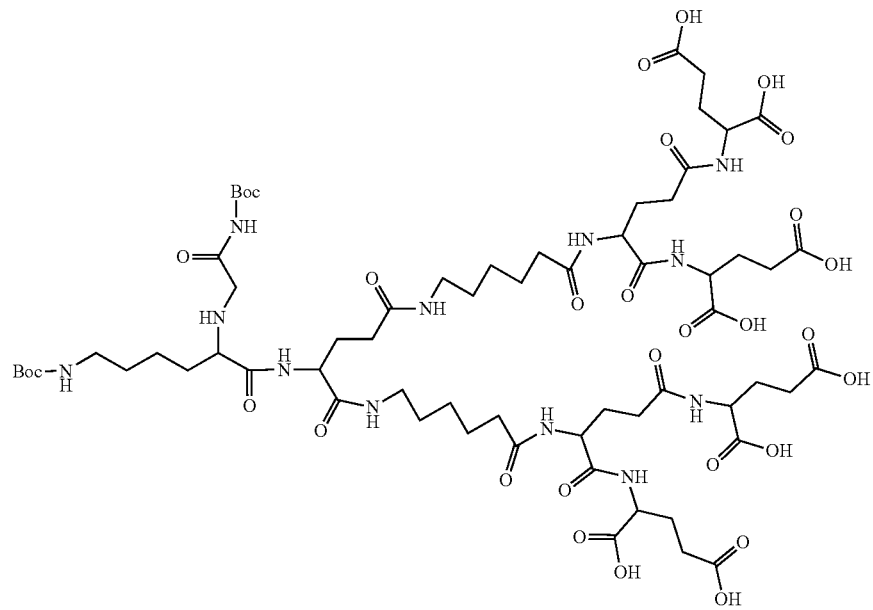

49-124 (1 g, 0.4437 mmol) and 10% Pd/C (0.05 g) were added in a hydrogenation reactor, and dissolved with DMF (20 mL), hydrogen was introduced to a pressure of 300 Psi, and then the mixed solution was stirred to react at room temperature overnight. At the end of the reaction, the reaction solution was filtered with diatomaceous earth. The filter cake was washed with DMF (15 mL×3) three times, and the filtrate was put into a 250 mL round-bottomed flask, thus obtaining the product, as the raw material for the next reaction.

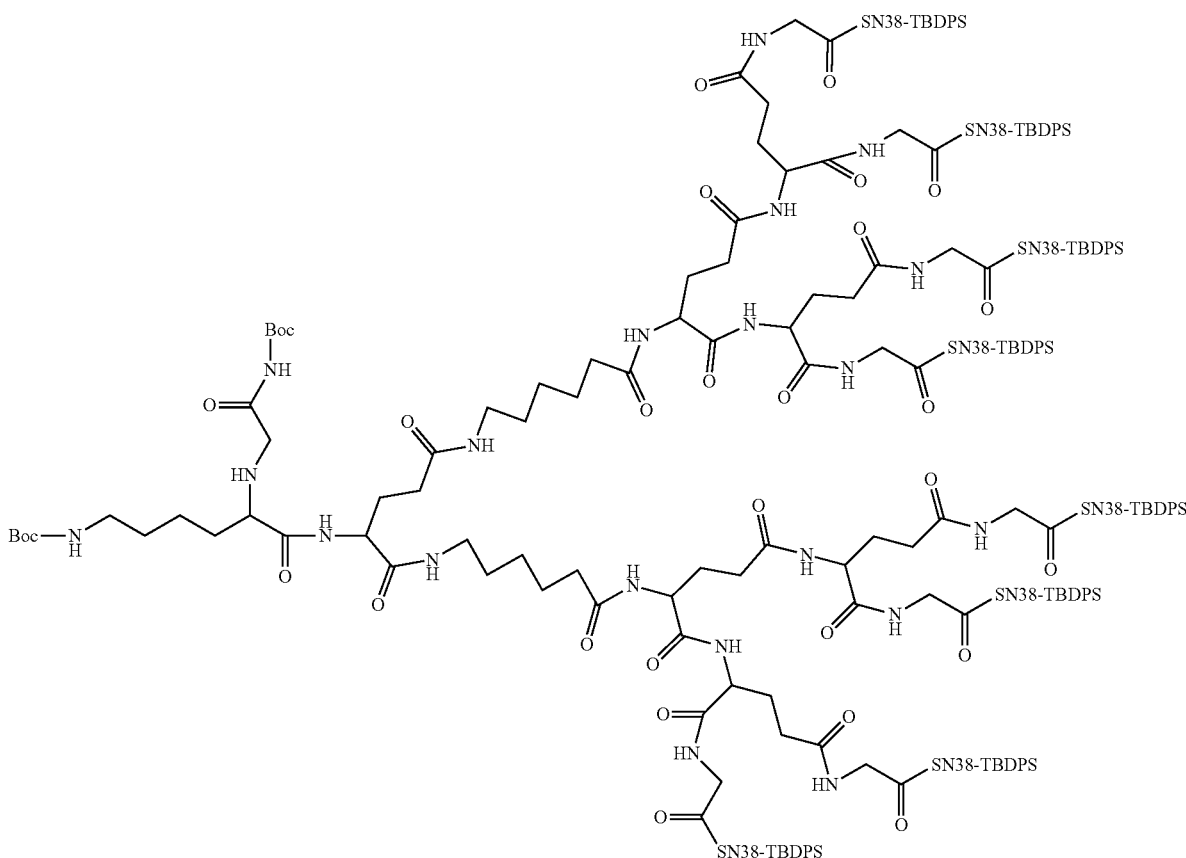

47-98 (2.56 g, 3.7271 mmol), HBTU (2.02 g, 5.3244 mmol), HOBT (0.72 g, 5.3244 mmol) were added in a flask loaded with 49-125 (0.68 g, 0.4437 mmol), and dissolved with a proper amount of DMF, and then, at −5° C., DIEA (2.64 mL, 15.9732 mmol) was slowly added dropwise. At the end of the addition, the obtained solution reacted for half an hour, and was then moved to room temperature and stirred to react overnight. At the end of the reaction, the reaction solution was extracted with saturated NaCl solution (200 mL) and EA (200 mL), and stood still to be layered, and the organic phase was separated. The aqueous phase was then washed with EA (200 mL×3), and the obtained organic phases were combined. The organic phase was evaporated to dryness, and dried in a vacuum oven, thus obtaining the product (4.3 g, extra-quota)

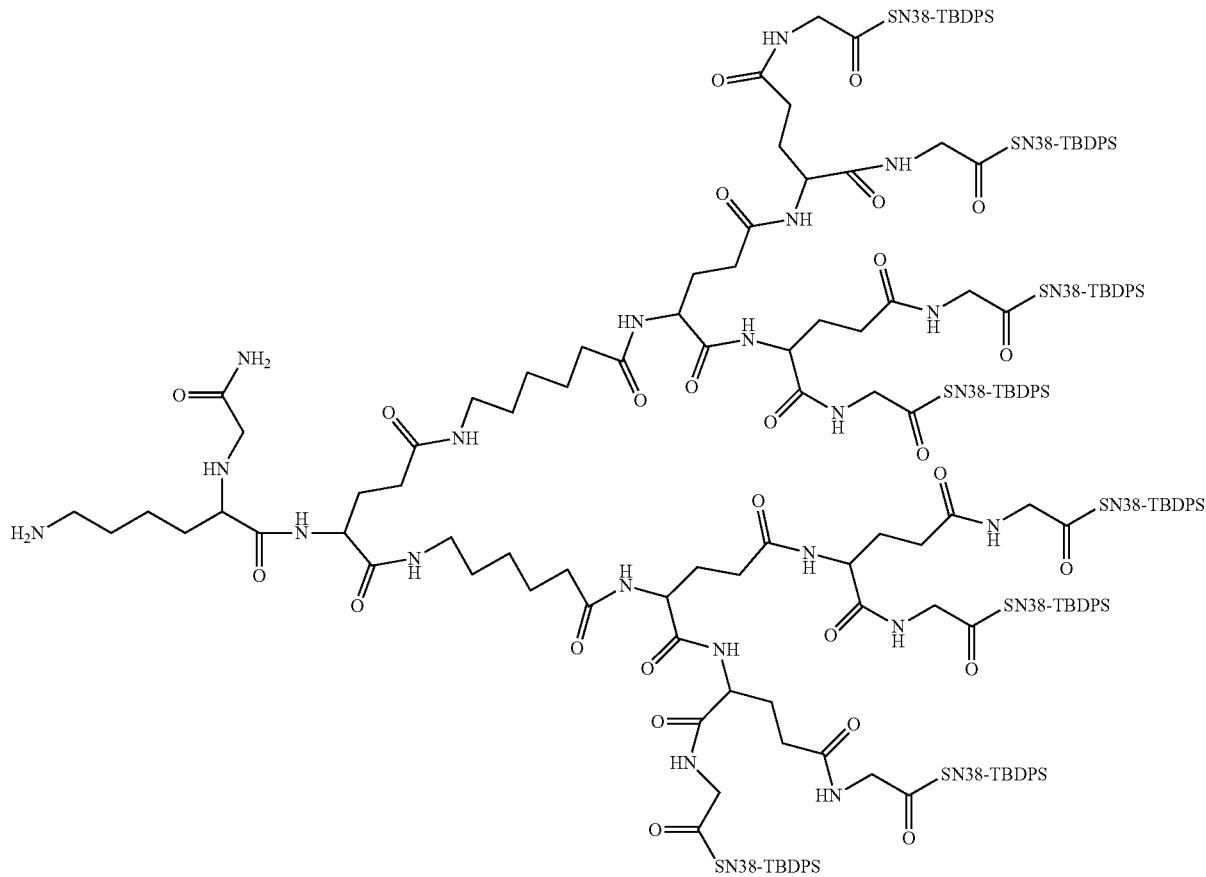

49-134

Dichloromethane was added in a flask loaded with 49-128 (3.06 g, 0.4437 mmol), ultrasonic vibration was carried out to completely dissolve the compound, TFA (2.27 mL, 4.437 mmol) was added, and then the mixed solution was stirred to react at room temperature overnight. At the end of the reaction, the reaction solution was evaporated to remove the dichloromethane and a majority of the TFA, then methyl tert-butyl ether (200 mL) was added to the obtained solution for precipitation, the supernatant was discarded. Such operations were repeated three times. Suction filtering was carried out, and a solid product was obtained. The obtained solid product was dissolved with a mixed solvent of dichloromethane and methanol. The operations of dry sample loading, column chromatography and elution with a dichloromethane mixed solution containing 3-6% methanol were carried out. The elution product was then collected, concentrated, and dried in a vacuum oven, thus obtaining the product (1.3 g, 43.92%). $^1$H NMR (400 MHz, DMSO-$d_6$) δ 10.39 (s, 4H), 8.05-7.98 (m, 24H), 7.81-7.36 (m, 99H), 7.10-7.04 (m, 6H), 5.39-5.24 (m, 14H), 3.16-2.65 (m, 122H), 1.37-1.16 (m, 62H), 1.05-0.80 (m, 72H).

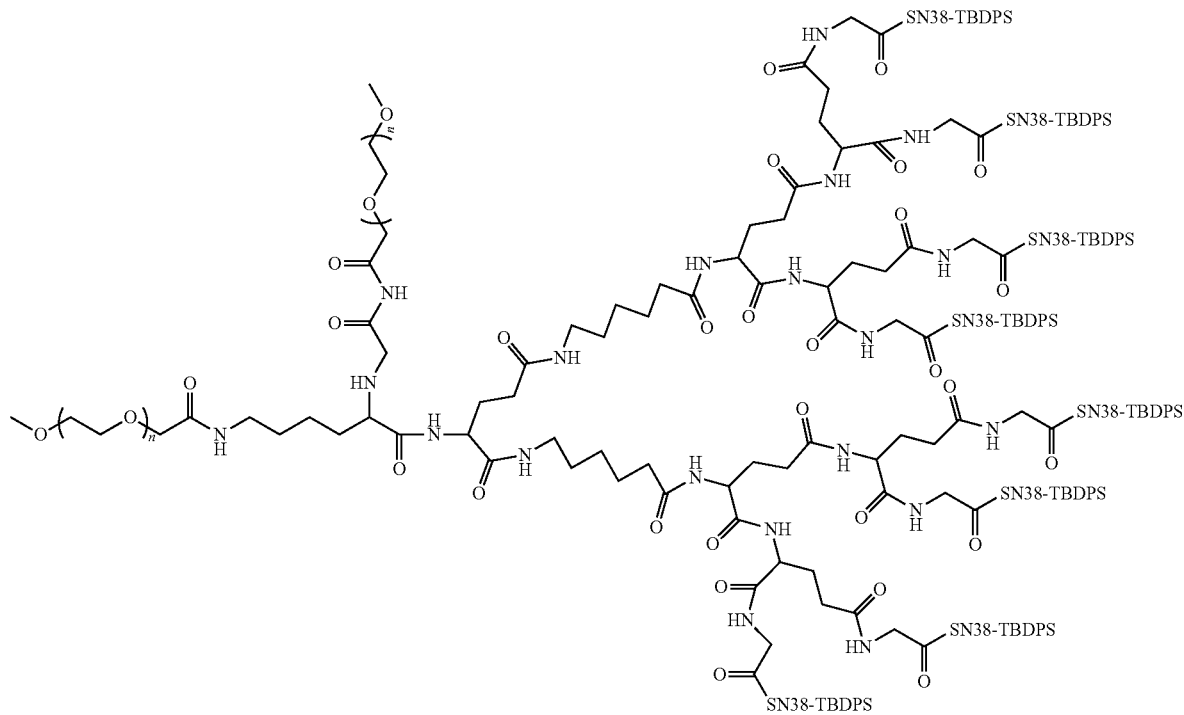

49-135

49-134 (1.3 g, 0.1943 mmol) was added in a 250 mL flask, and dissolved with DMF (20 mL), and M-SCM-5K (2.27 g, 0.4274 mmol, purchased from JenKem), ultrasonic vibration was carried out to dissolve the compound, and then, at −5° C., DIEA (0.90 mL, 5.4401 mmol) was slowly added dropwise. At the end of the addition, the obtained solution reacted for half an hour, and was then moved to room temperature and stirred to react in the dark for one week at a low speed. At the end of the reaction, n-hexane (25 mL) and methyl tert-butyl ether (200 mL) were added to the reaction solution for precipitation, the supernatant was discarded, and then n-hexane and methyl tert-butyl ether were added to the obtained solution for precipitation. Such operations were repeated three times. Suction filtering was carried out, and a solid product was obtained. The obtained solid product was dissolved with a mixed solvent of dichloromethane and methanol. The operations of dry sample loading, column chromatography and elution with a dichloromethane mixed solution containing 6-10% methanol were carried out. The elution product was then collected, concentrated, and dried in a vacuum oven, thus obtaining the product (2.1 g, 63.25%).

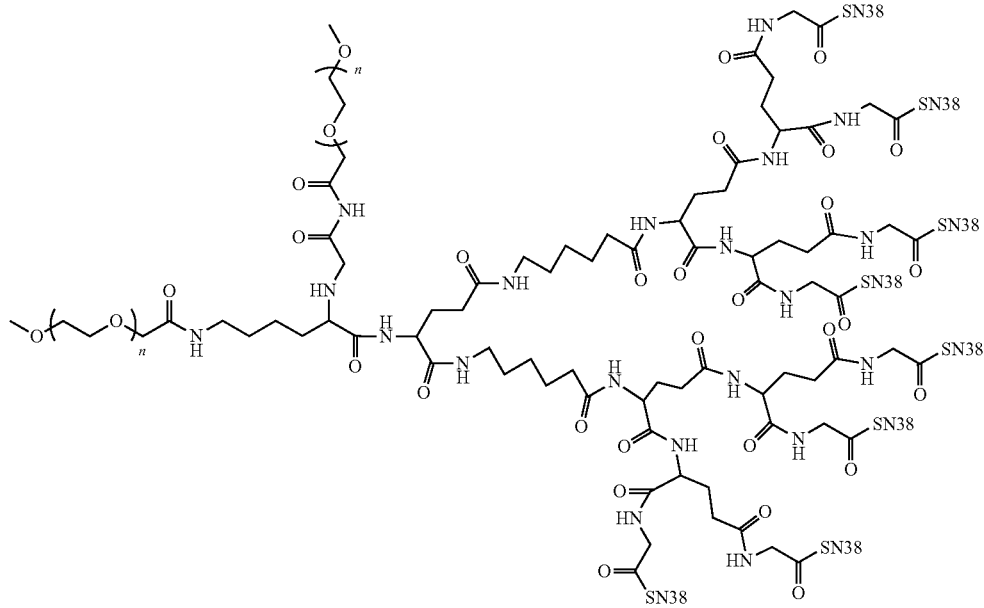

49-135 (2.1 g, 0.1229 mmol), TBAF (0.51 g, 1.9671 mmol), THF (20 mL) and diluted HCl (20 mL) were added in a 500 mL round-bottomed flask, and the mixed solution was stirred to react at room temperature overnight. At the end of the reaction, the reaction solution was concentrated under reduced pressure to obtain a solid product, the solid product was dissolved with DMF (5 mL), and isopropanol was added to the obtained solution for precipitation. Such operations were repeated three times. A solid product was obtained by filtering. The obtained solid product was dissolved with dichloromethane (10 mL), and methyl tert-butyl ether was added to the obtained solution for precipitation. Such operations were repeated three times to obtain a solid product. The solid product was dried, thus obtaining the product (1.2 g, 64.17%).

$^1$H NMR (600 MHz, DMSO-$d_6$) δ8.10-7.91 (m, 21H), 7.81-7.24 (m, 25H), 7.06-6.95 (m, 8H), 5.36-5.10 (m, 22H), 3.55-3.46 (m, 1056H), 3.18-2.36 (m, 133H), 1.37-1.16 (m, 62H).

27. Synthesis of 40-176 (Compound No. 27)

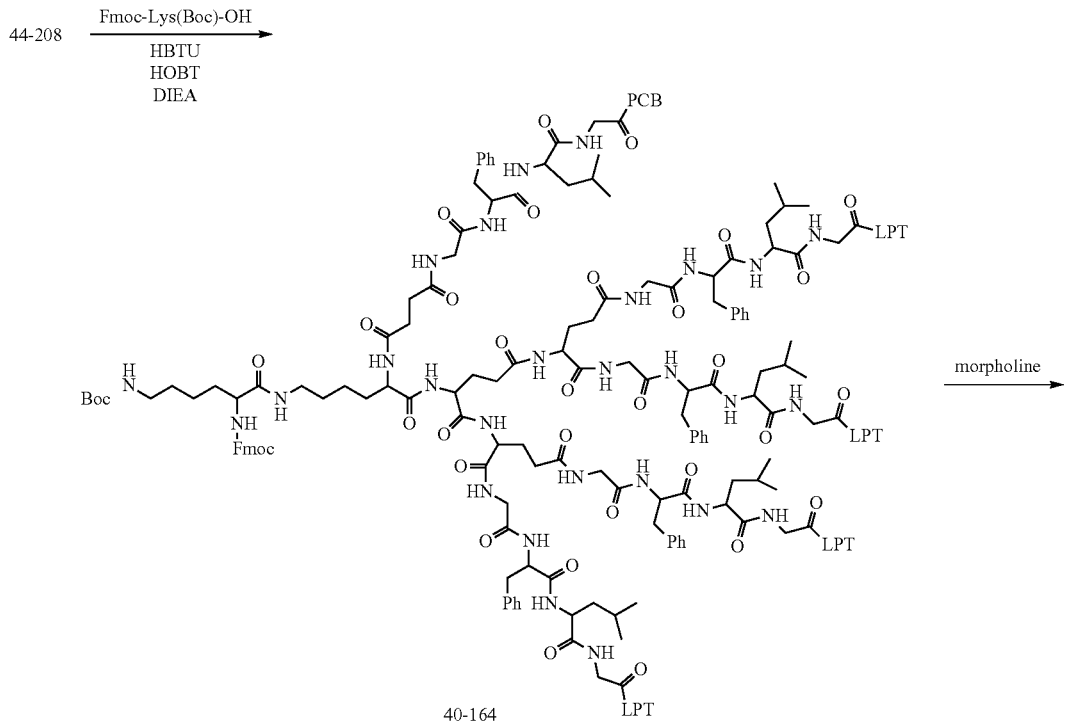

-continued
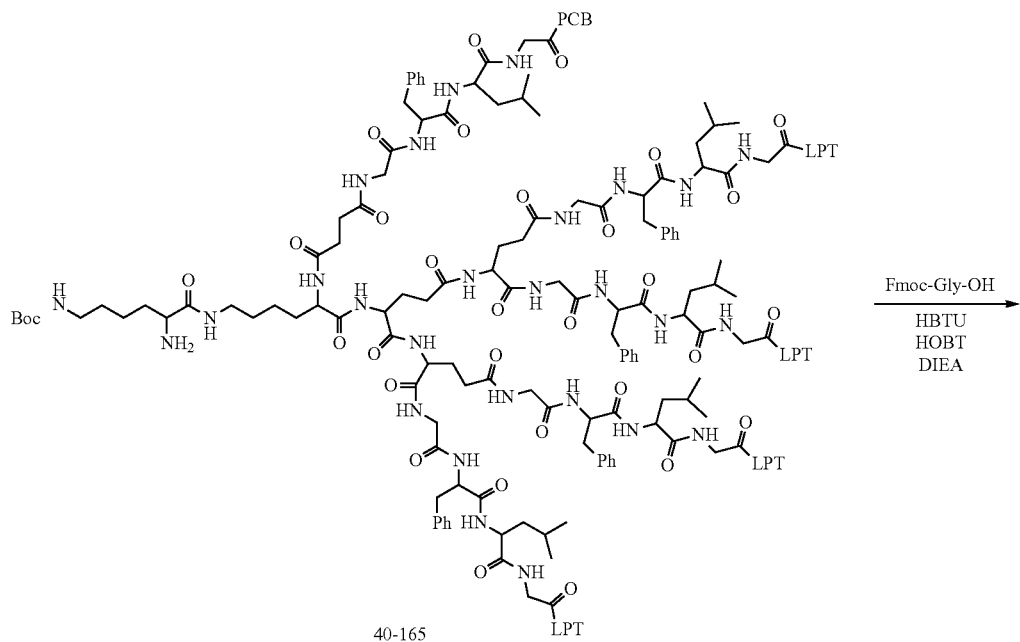
40-165
Fmoc-Gly-OH
HBTU
HOBT
DIEA
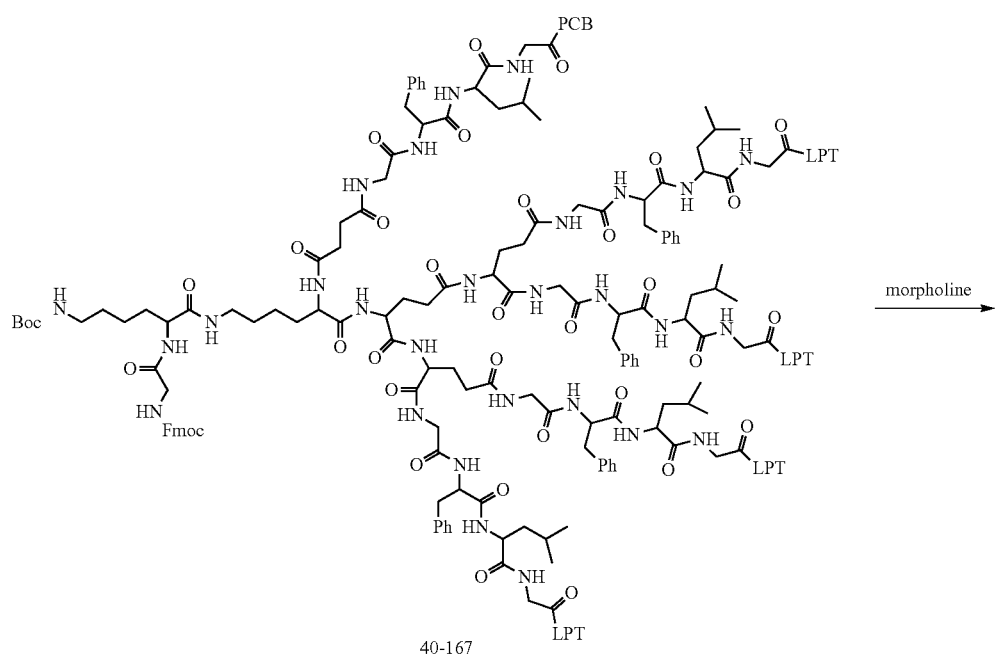
40-167
morpholine -continued
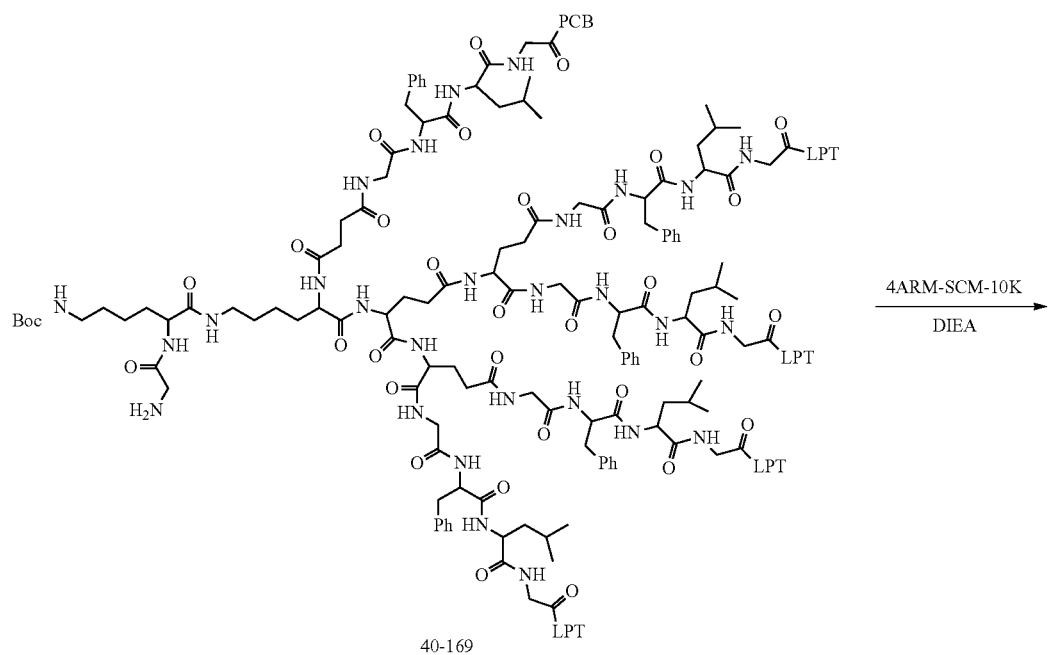
40-169
4ARM-SCM-10K / DIEA →
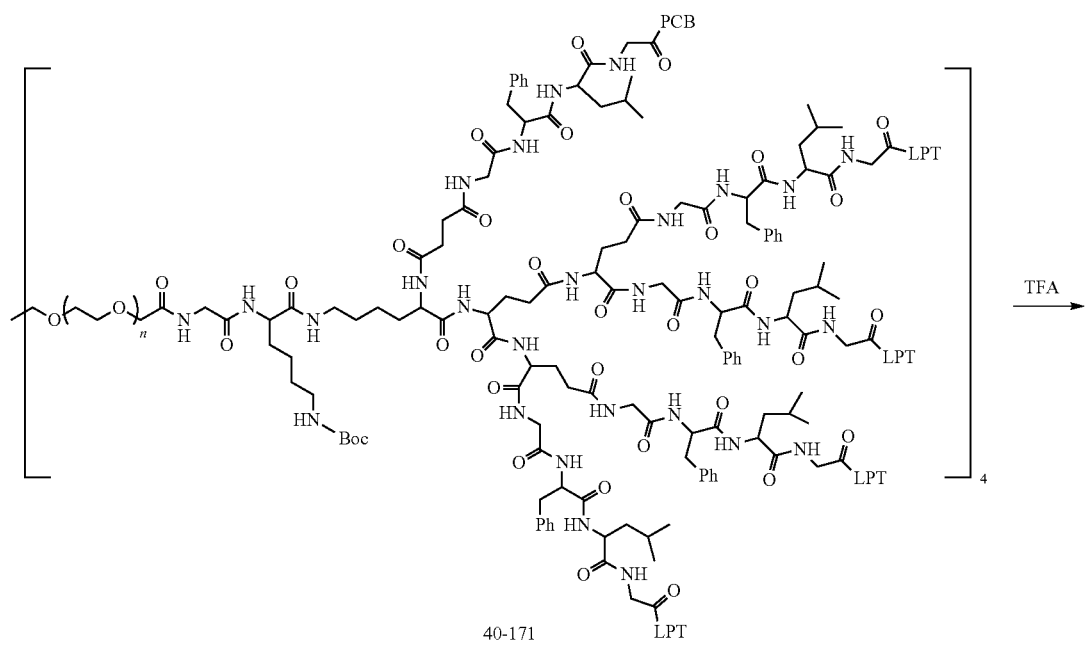
40-171
TFA →

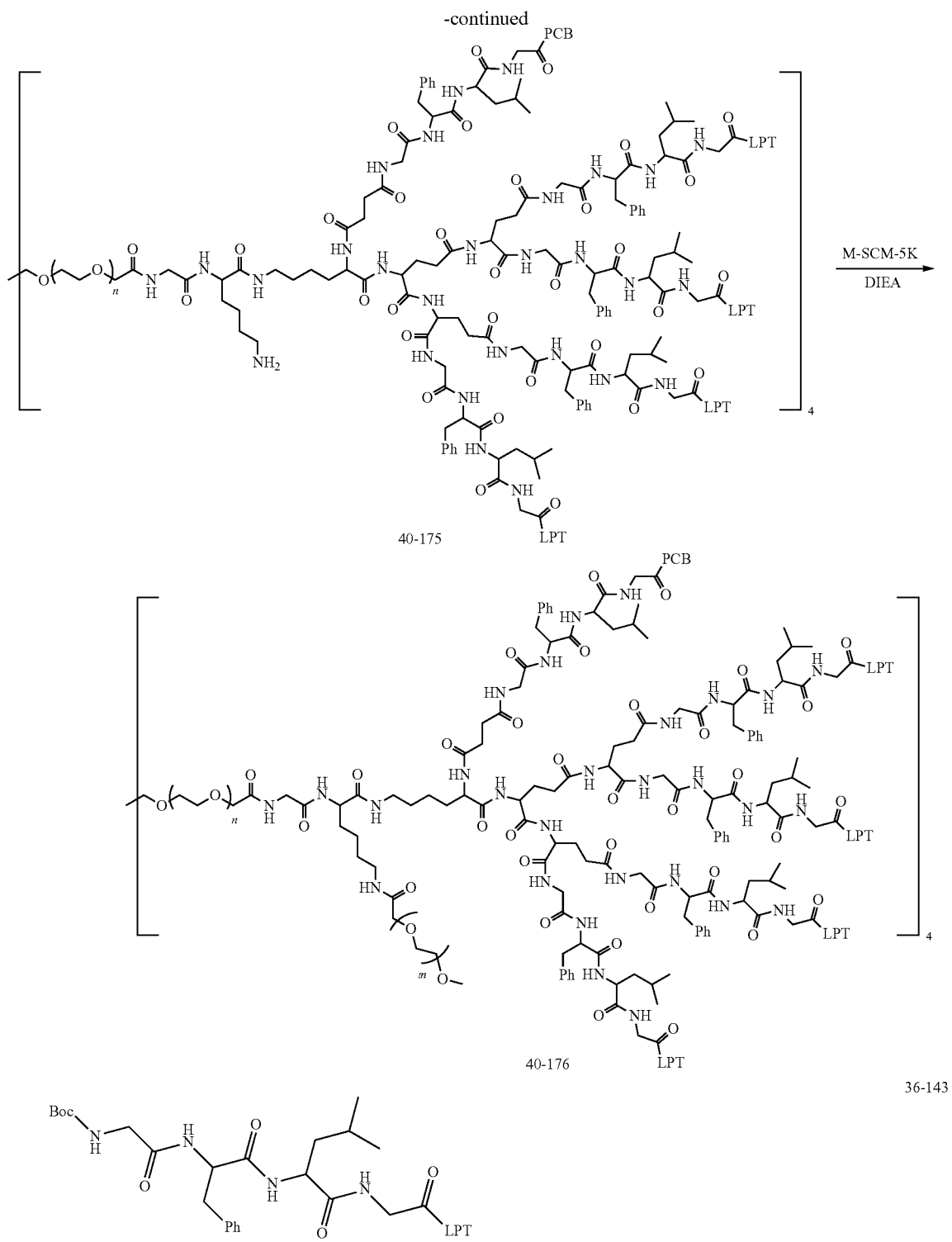

36-81 (8.45 g, 17.1618 mmol), Lapatinib (8.3 g, 14.3015 mmol, also referred to as LPT), HBTU (8.1 g, 21.4522 mmol), HOBT (2.9 g, 21.4522 mmol) were added in a 500 mL flask, and stirred at −5° C. for about 20 minutes. Then DIEA (10.6 mL, 64.3567 mmol) was slowly added dropwise, and the obtained solution continued to react at −5° C. for 1 hour, and was then moved to room temperature and stirred to react overnight. At the end of the reaction, the reaction solution was transferred to a 1 L separatory funnel, saturated NaHCO$_3$ solution (200 mL) and ethyl acetate (200 mL) were added for extraction, and the organic phase was separated. The aqueous phase was washed with ethyl acetate (200 mL×2), and the obtained organic phases were combined. The organic phase was washed with saturated saline solution (200 mL×2), and the obtained organic phases were combined. The organic phase was washed with saturated sodium chloride solution (100 ml×2), and evaporated to dryness, thus obtaining 36-143: 14 g, yield: 92.8%.

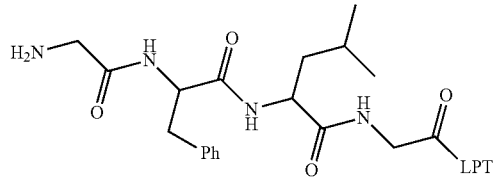

36-143 (14 g, 14.3015 mmol) was added in a 500 mL flask, and dissolved with dichloromethane (20 mL), TFA (10.6 mL, 143.015 mmol) was added, and then the mixed solution was stirred to react at room temperature overnight. At the end of the reaction, the reaction solution was concentrated to 10 mL, methyl tert-butyl ether (200 mL) was added to the obtained solution to separate out a powder product, and suction filtering was carried out. The filter cake was washed with methyl tert-butyl ether (50 mL×3), and dissolved with a mixed solvent (200 mL) of 20% methanol: 80% dichloromethane, silica gel power (60 ml) was added, and the obtained mixture was then evaporated to dryness to obtain a powder solid. The operations of dry sample loading, column chromatography and elution with a dichloromethane mixed solution containing 1% ammonia water: 5%-10% methanol were carried out. The elution product was then collected, concentrated and evaporated to dryness, thus obtaining the product 36-145: 6.2 g, yield 92.1%.

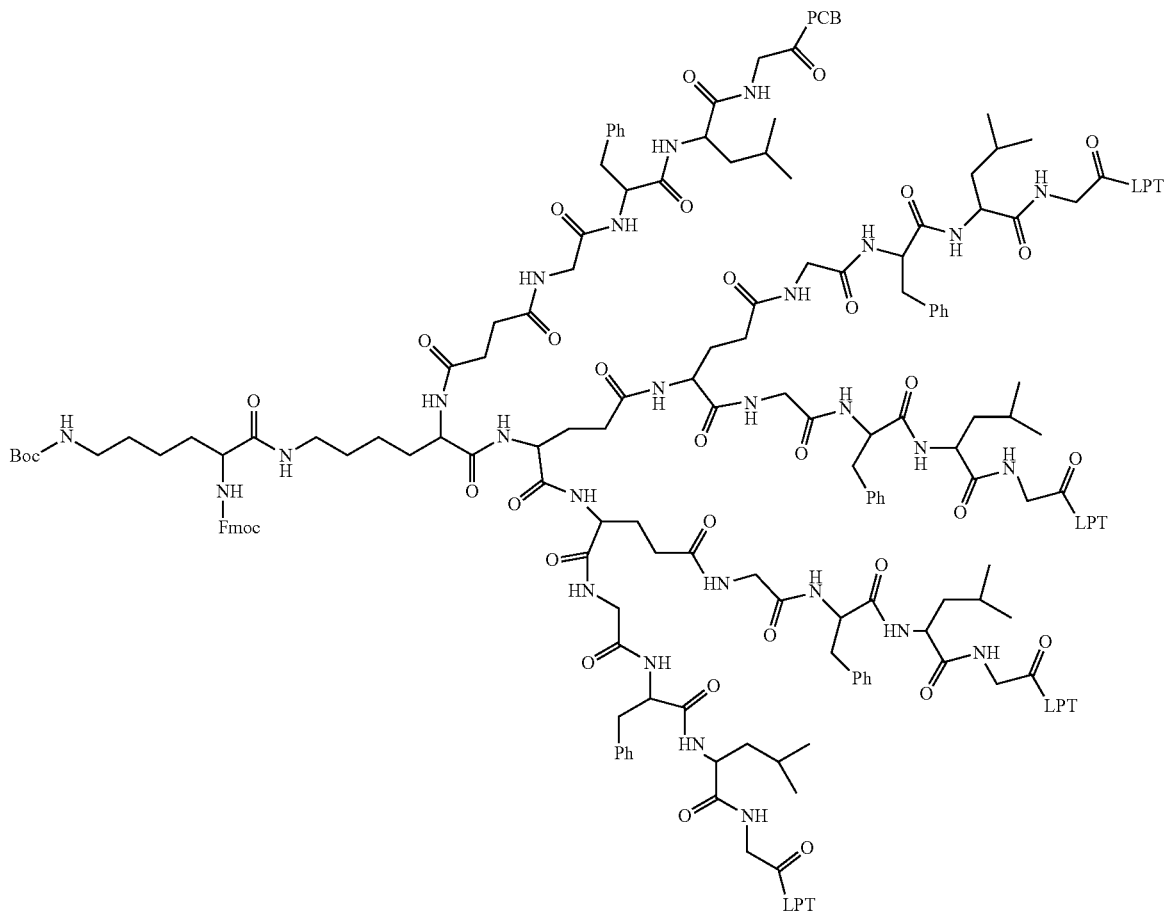

Fmoc-L-Lys(Boc)-OH (0.18 g, 0.3855 mmol, purchased from Accela), 44-208 (2 g, 0.3855 mmol, Compound No. 29), HBTU (0.2193 g, 0.5783 mmol), HOBT (0.0781 g, 0.5783 mmol) were added in a 250 mL flask, and dissolved with DMF (40 mL), and then the mixed solution was stirred at −5° C. for 30 minutes. DIEA (0.2878 mL, 1.7348 mmol) was slowly added dropwise, and then the obtained solution reacted at −5° C. overnight. At the end of the reaction, methyl tert-butyl ether and n-hexane were added to the reaction solution for precipitation, and suction filtering was carried out. The obtained solid was dissolved with 10% methanol/dichloromethane, silica gel powder was added, and the operations of evaporation, dry sample loading, column chromatography and gradient elution with 1% ammonia water+4%-8% methanol/dichloromethane were carried out, thus obtaining the product 1.8 g, yield 82.9%.

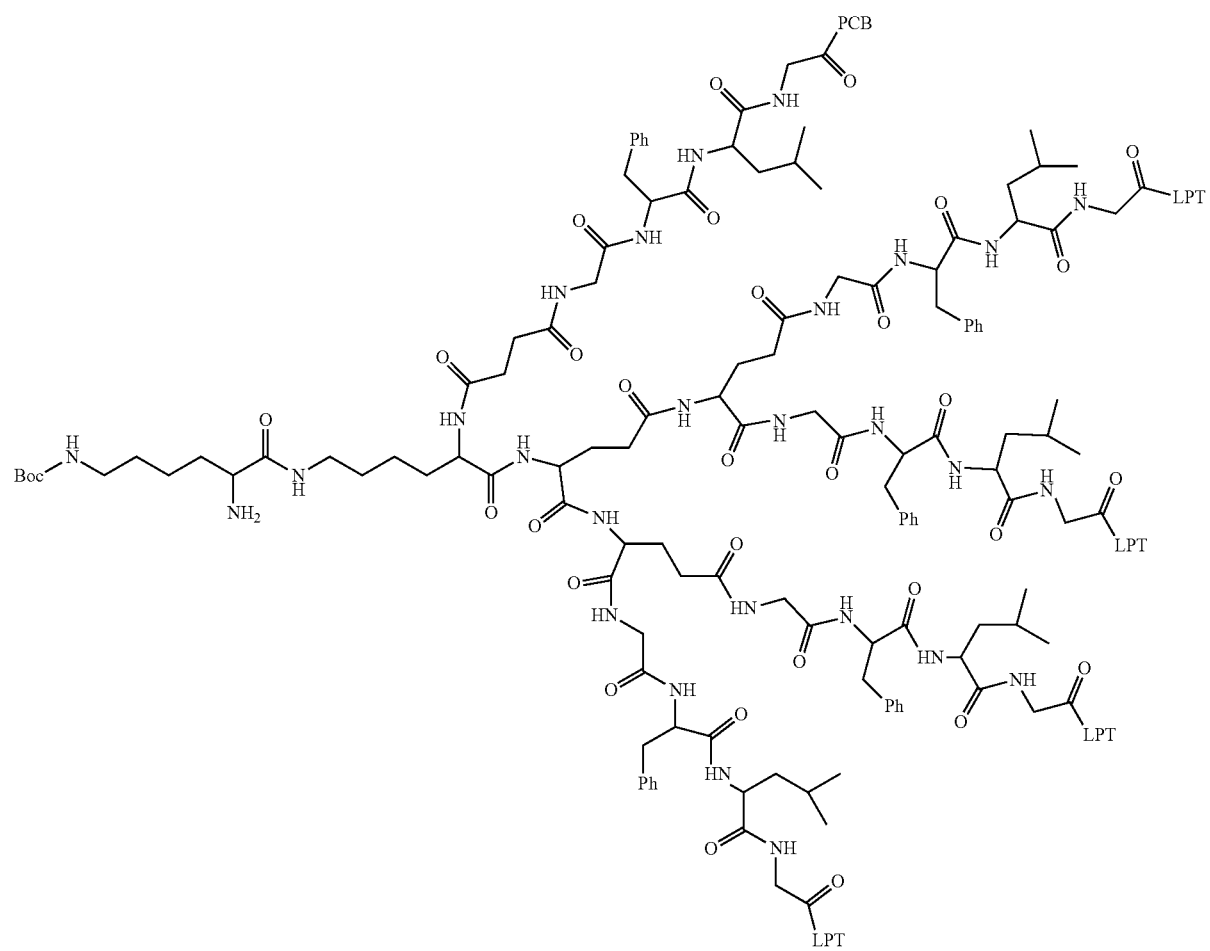

40-165

40-164 (1.8 g, 0.3193 mmol) was added in a 250 mL round-bottomed flask, and dissolved with DMF (30 mL), morpholine (0.5563 mL, 6.3852 mmol) was added, and ultrasonic treatment was carried out to completely dissolve the reactants, and then the mixed solution was stirred to react at room temperature. At the end of the reaction, methyl tert-butyl ether (150 mL) and n-hexane (100 mL) were added to the reaction solution to separate out a solid product, and suction filtering was carried out. The filter cake was dried, thus obtaining the product 1.7293 g, yield 100%.

40-167

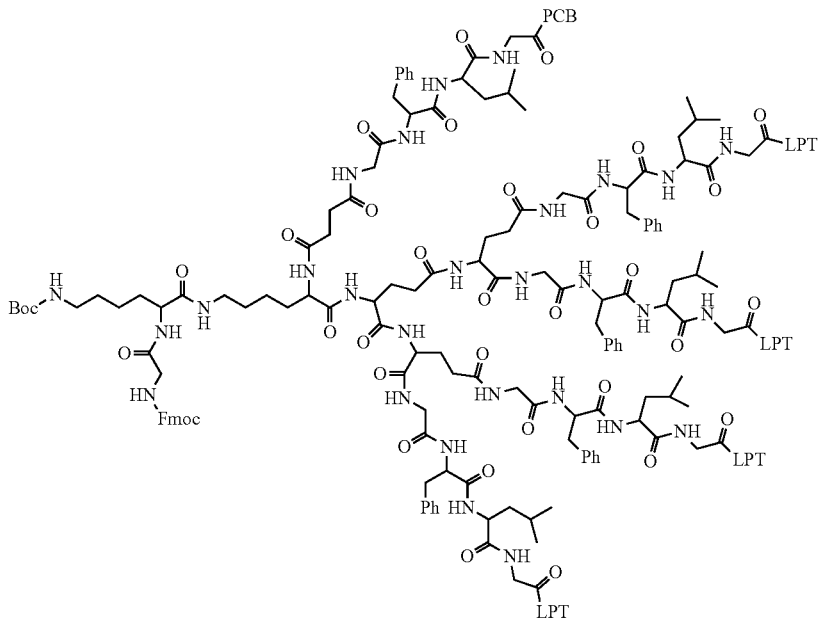

Fmoc-Gly-OH (0.0949 g, 0.3193 mmol, purchased from Accela), 40-165 (1.7 g, 0.3193 mmol), HBTU (0.1817 g, 0.4790 mmol), HOBT (0.0647 g, 0.4790 mmol) were added in a 250 mL round-bottomed flask, and dissolved with DMF (50 mL), and then the mixed solution was stirred at 0° C. for 30 minutes. Then DIEA (0.2384 mL, 1.4369 mmol) was slowly added dropwise. At the end of the addition, the obtained solution continued to react with stirring at 0° C. overnight. At the end of the reaction, methyl tert-butyl ether (150 mL) and n-hexane (100 mL) were added to the reaction solution to separate out a solid product, and suction filtering was carried out. The filter cake was dried, thus obtaining the product 1.8 g, yield, 100%.

40-169

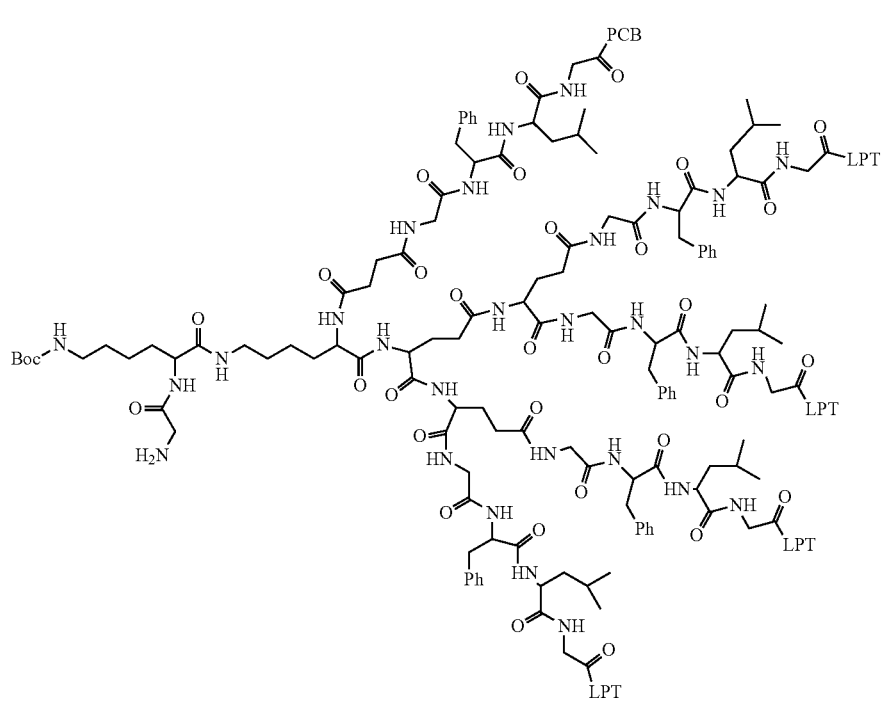

40-167 (1.8 g, 0.3193 mmol) was added in a 250 mL round-bottomed flask, and dissolved with DMF (30 mL), morpholine (0.5563 mL, 6.3852 mmol) was added, and ultrasonic treatment was carried out to completely dissolve the compound, and then the mixed solution was stirred to react at room temperature. At the end of the reaction, methyl tert-butyl ether (150 mL) and n-hexane (100 mL) were added to the reaction solution to separate out a solid product, and suction filtering was carried out. The obtained solid was dissolved with 10% methanol/dichloromethane, silica gel powder was added, and the operations of evaporation, dry sample loading, column chromatography and gradient elution with 1% ammonia water+4%-8% methanol/dichloromethane were carried out, thus obtaining the product 1.5 g, yield 85.85%.

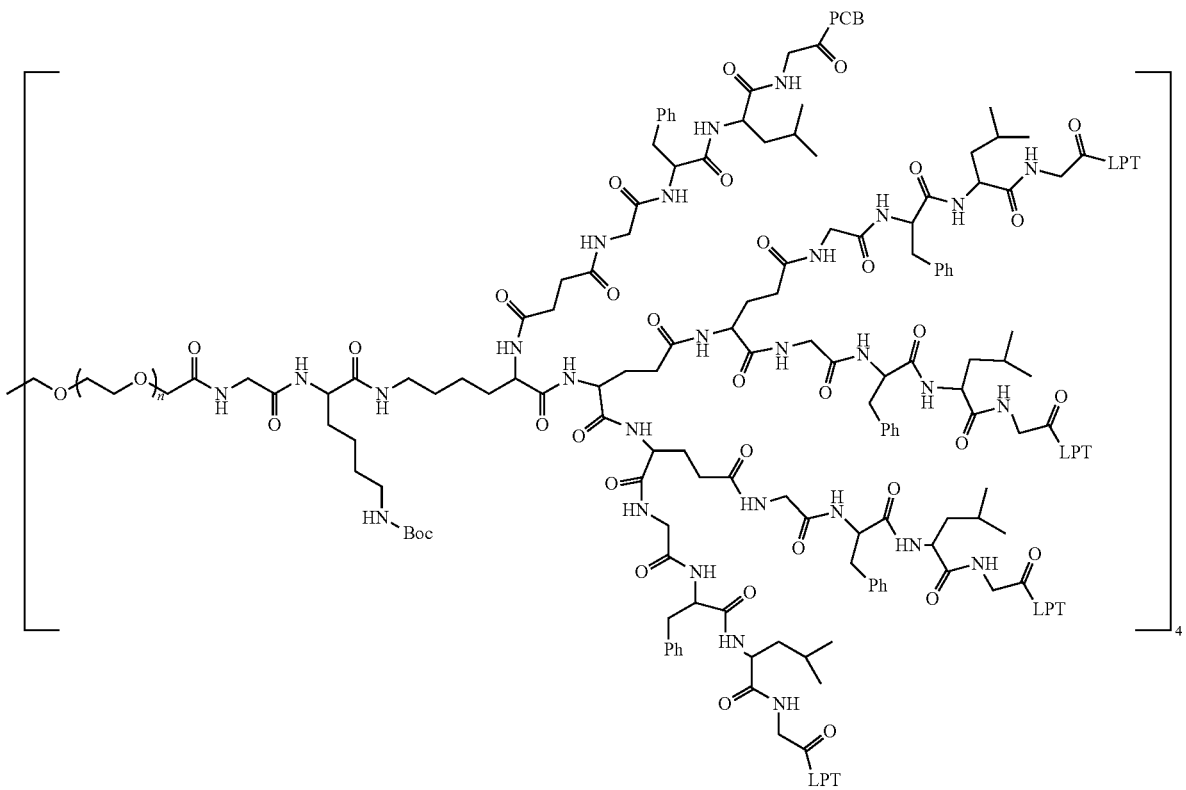

40-171

40-169 (1.5 g, 0.2741 mmol) was added in a 250 mL flask, and dissolved with DMF (20 mL), DIEA (0.1895 mL, 1.1420 mmol), and 4ARM-SCM-10K (0.6222 g, 0.0571 mmol) was added, and ultrasonic treatment was carried out to dissolve the reactants, and then the obtained solution reacted in the dark at a low speed. At the end of the reaction, methyl tert-butyl ether (200 mL) was added to the reaction solution to separate out a solid product, and suction filtering was carried out. The solid product was dissolved with 10% methanol/dichloromethane, silica gel powder (5 g) was added, and the operations of evaporation, column chromatography and gradient elution with 5%-15% methanol/dichloromethane were carried out, thus obtaining the product 1.2 g, yield 66.67%.

40-175

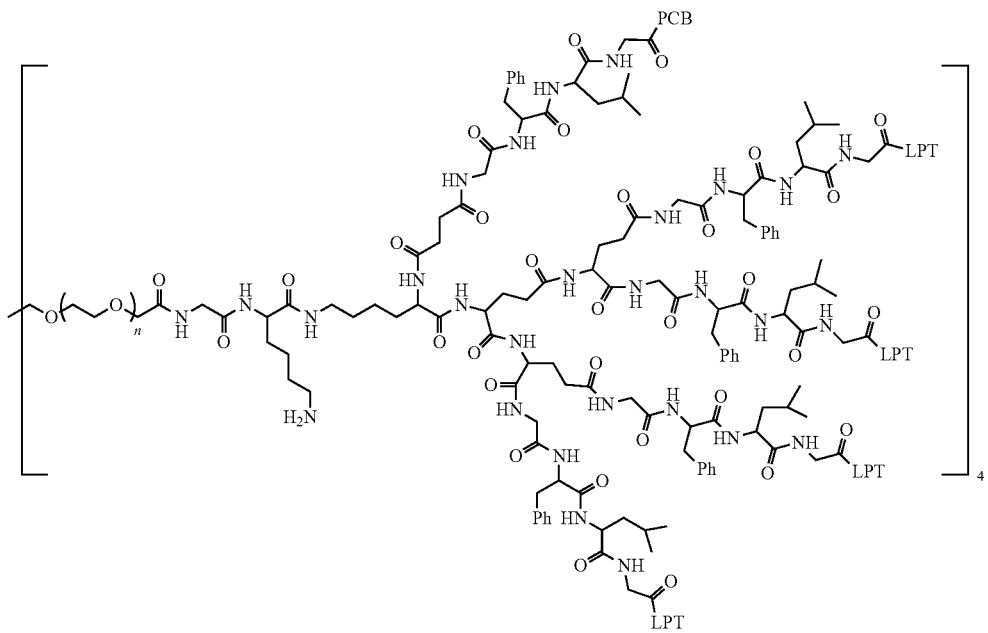

40-171 (1.2 g, 0.0371 mmol) was added in a 250 mL flask, and dissolved with dichloromethane (15 mL), TFA (0.1379 mL, 1.8562 mmol) was added, and ultrasonic treatment was carried out to completely dissolve the compound. A ground glass stopper was used, and the mixed solution was stirred to react at room temperature. At the end of the reaction, the reaction solution was evaporated to remove the dichloromethane, methyl tert-butyl ether (150 mL) was added, ultrasonic treatment was carried out for 2 minutes to separate out a solid product, and suction filtering was carried out. The solid product was dissolved with a mixed solvent of 20% methanol/dichloromethane, silica gel powder was added, and then the obtained mixture was evaporated to dryness with a rotary evaporator. The operations of dry sample loading, column chromatography and gradient elution with 1% ammonia water+5%-15% methanol/dichloromethane were carried out, thus obtaining the product 0.8 g, yield 80.21%.

$^1$H-NMR (600 MHz, DMSO-d$_6$) δ 10.15-9.90 (m, 14H), 9.05-9.03 (m, 1H), 8.94-8.93 (m, 2H), 8.76-8.71 (m, 12H), 8.61-8.55 (m, 11H), 8.25-7.58 (m, 155H), 7.52-7.41 (m, 16H), 7.36-6.99 (m, 198H), 6.71-6.63 (m, 10H), 6.57-6.50 (m, 4H), 5.29-5.22 (m, 26H), 4.80-4.52 (m, 39H), 4.42-4.10 (m, 58H), 4.06-3.89 (m, 14H), 3.86-3.74 (m, 31H), 3.70-3.56 (m, 65H), 3.54-3.42 (m, 907H), 3.22-2.98 (m, 81H), 2.91-2.60 (m, 37H), 2.43-2.09 (m, 68H), 1.93-1.44 (m, 124H), 1.39-1.14 (m, 144H), 0.90-0.75 (m, 120H).

40-176

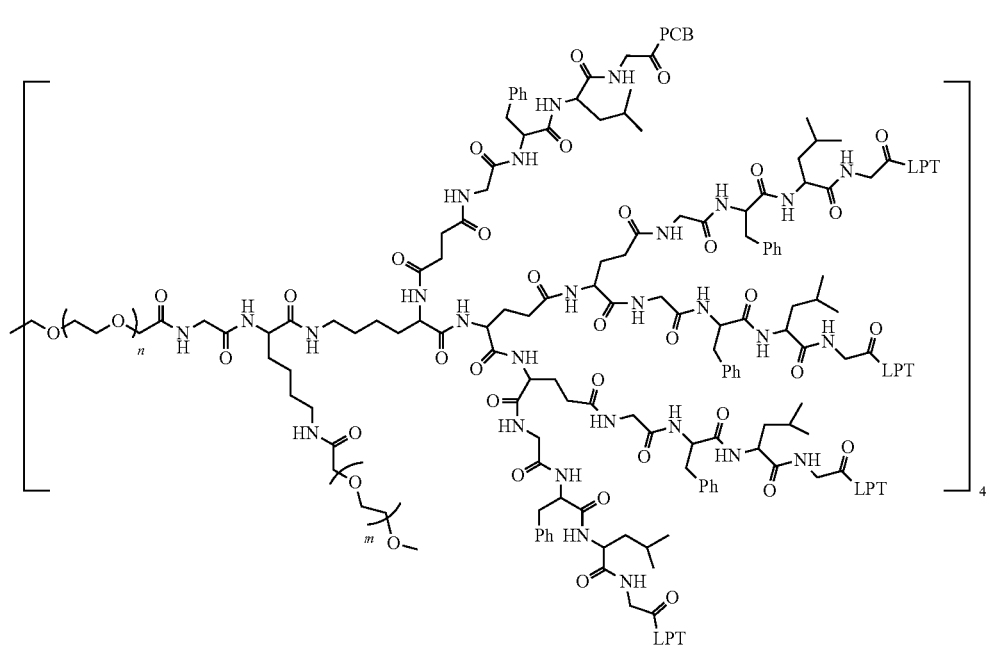

40-175 (0.8 g, 0.0282 mmol) was added in a 250 mL flask, and dissolved with DMF (20 mL), DIEA (0.0932 mL, 0.5640 mmol), and M-SCM-5K (0.6206 g, 0.1186 mmol) was added, and ultrasonic treatment was carried out to dissolve the reactants, and then the obtained solution reacted in the dark at a low speed. At the end of the reaction, methyl tert-butyl ether (150 mL) was added to the reaction solution to separate out a solid product, and suction filtering was carried out. The filter cake was dissolved with 10% methanol/dichloromethane, silica gel powder was added to the obtained solution, and the operations of evaporation, column chromatography and gradient elution with 5%-15% methanol/dichloromethane were carried out, thus obtaining the product 0.9 g, yield 69.23%.

$^1$H-NMR (600 MHz, DMSO-$d_6$) δ 9.88-9.81 (m, 9H), 8.94-8.55 (m, 17H), 8.21-7.98 (m, 61H), 7.87-7.71 (m, 21H), 7.47-7.45 (m, 12H), 7.23-7.14 (m, 292H), 6.67-6.53 (m, 11H), 5.26-5.23 (m, 19H), 4.75-4.57 (m, 17H), 4.35-4.19 (m, 35H), 3.51-3.33 (m, 2730H), 3.06-3.01 (m, 111H), 2.62-2.60 (m, 62H), 2.40-2.37 (m, 68H), 2.18-1.76 (m, 221H), 1.60-1.48 (m, 91H), 1.24-1.16 (m, 57H), 0.88-0.78 (m, 120H).

28. Synthesis of 46-51 (Compound No. 28)

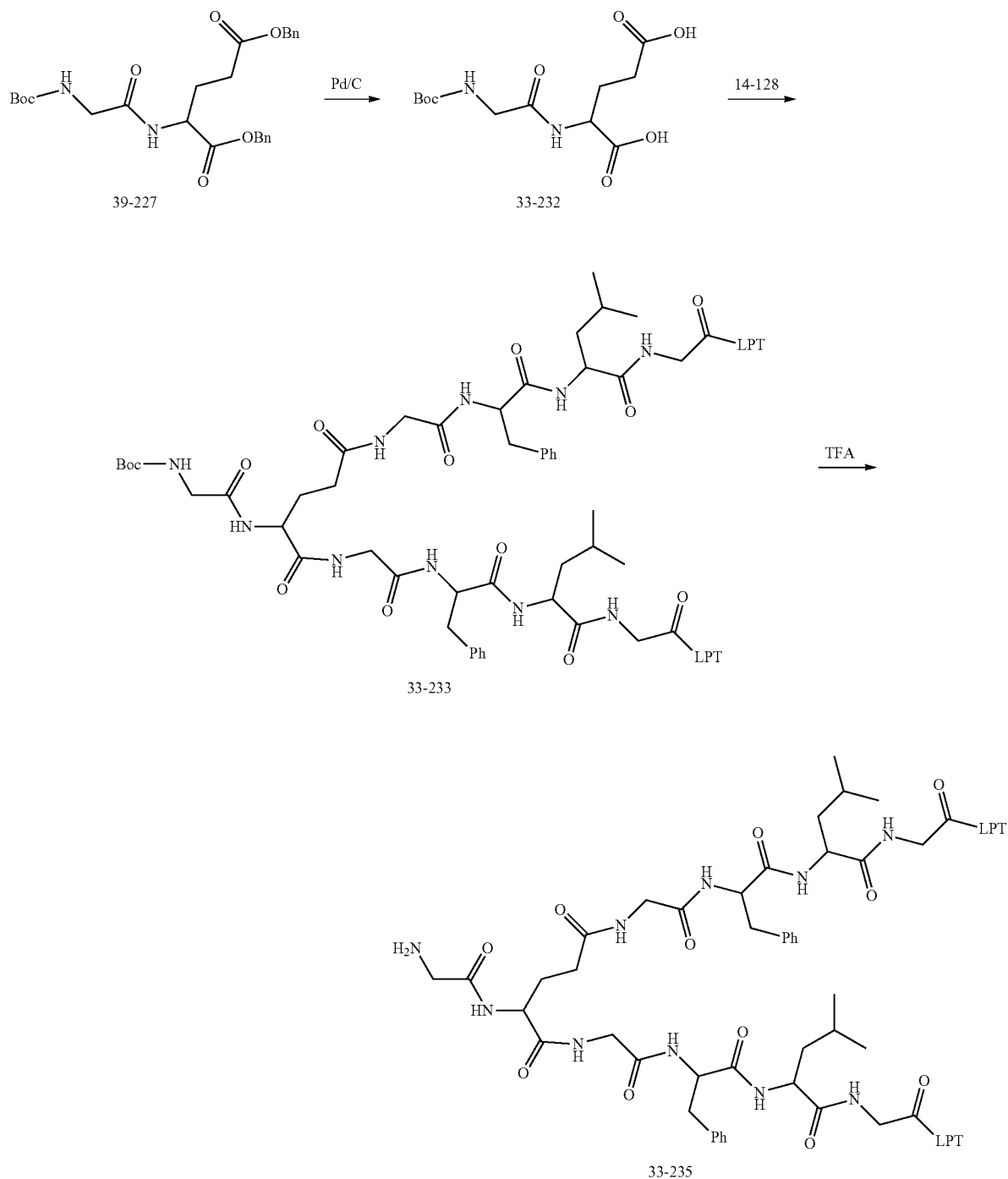

-continued
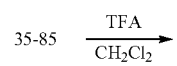
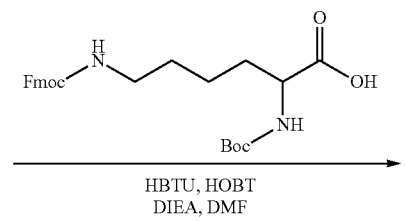
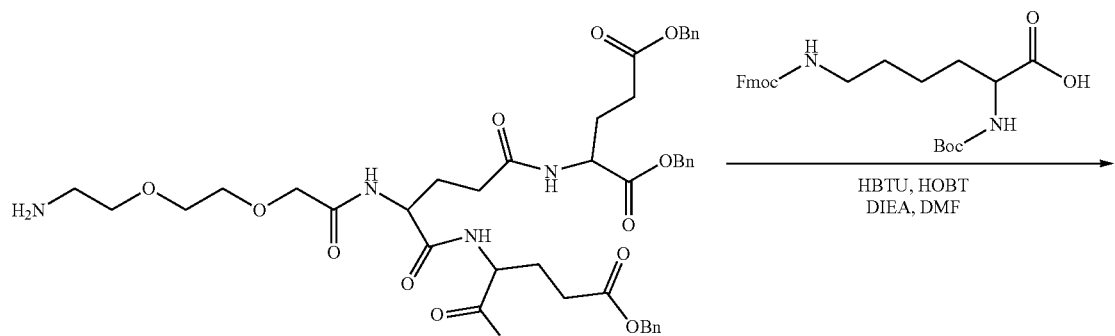
44-180
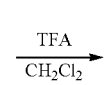
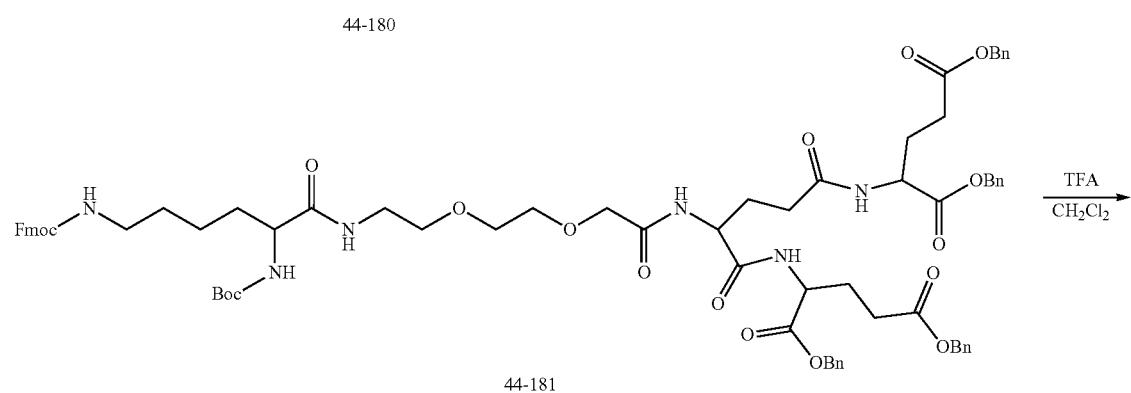
44-181
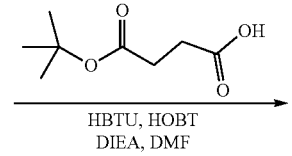
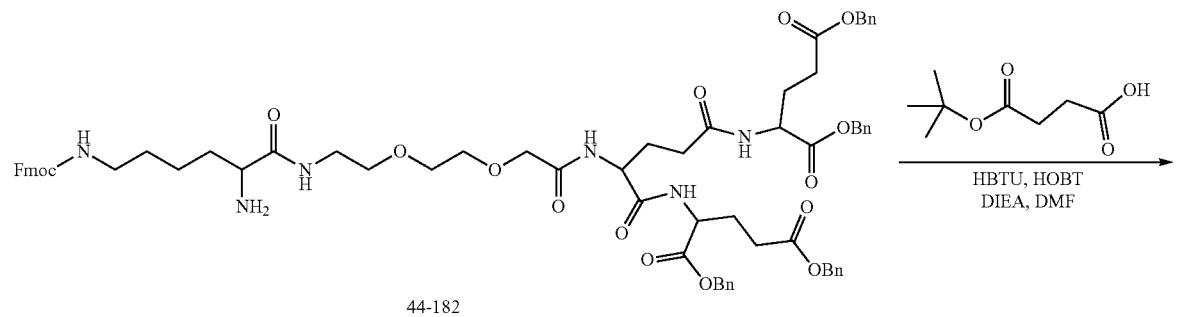
44-182
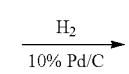
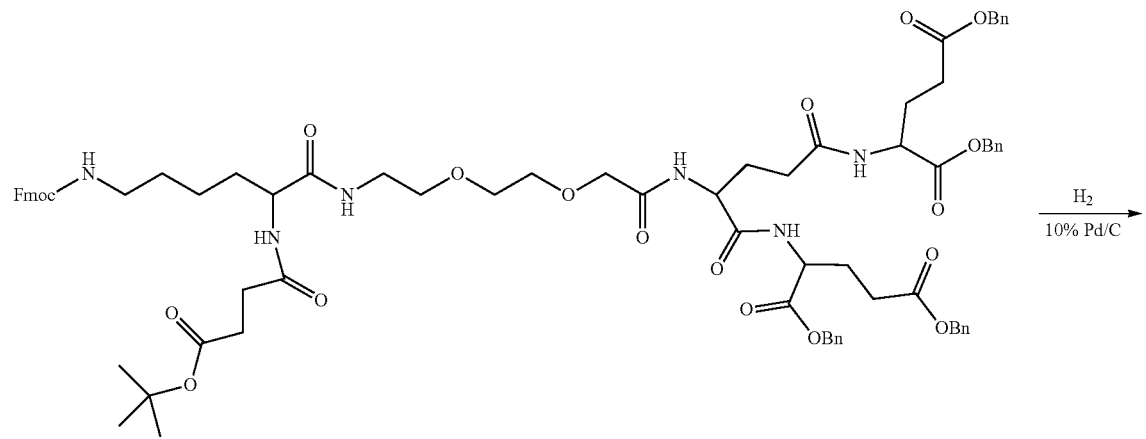
44-183

1211
1212
-continued
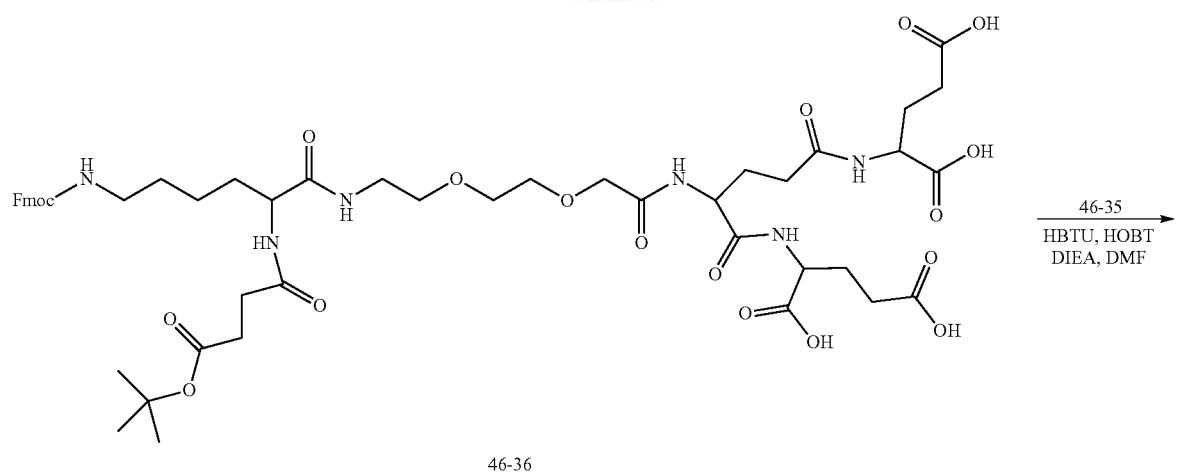
46-36
→ 46-35
HBTU, HOBT
DIEA, DMF
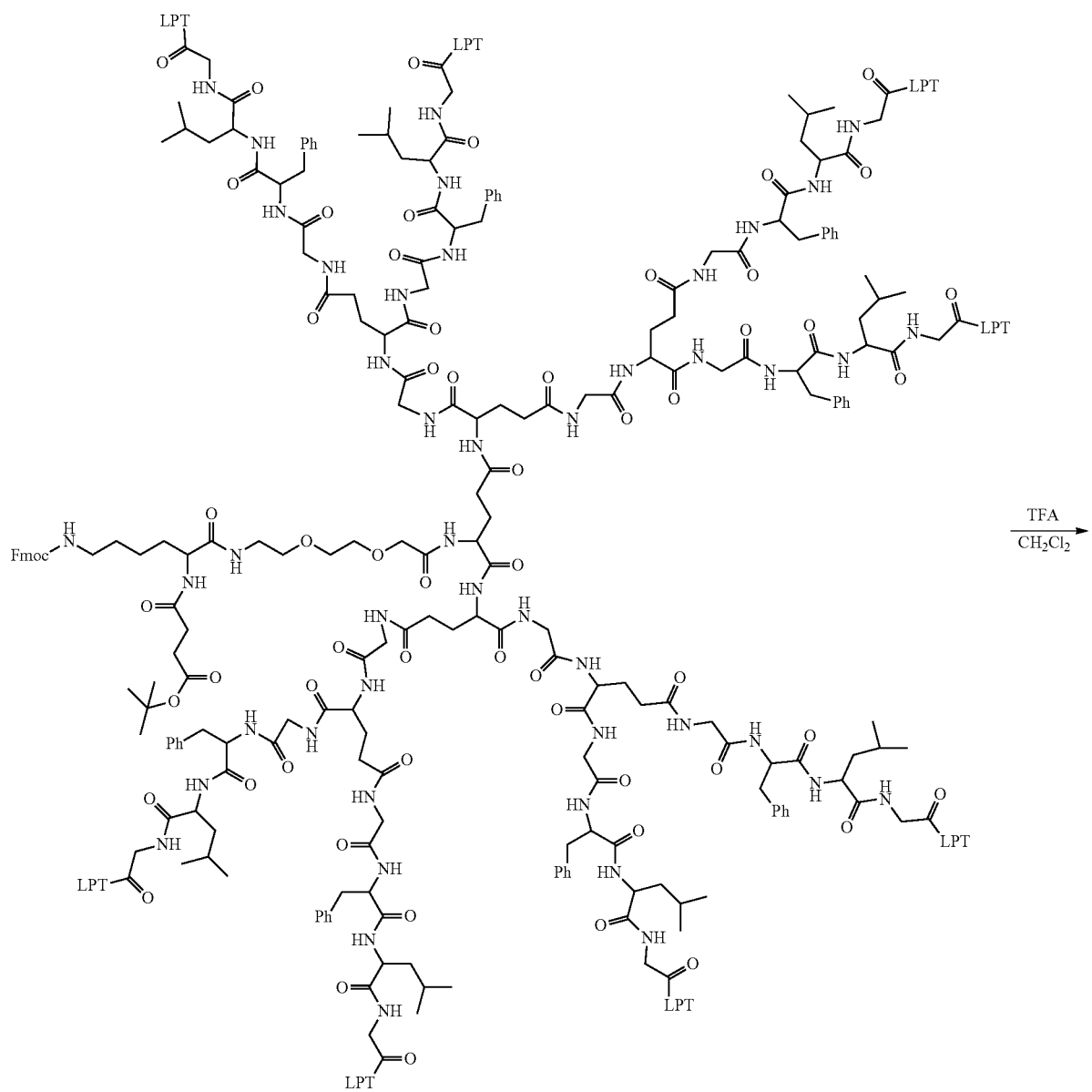
46-39
→ TFA
CH₂Cl₂

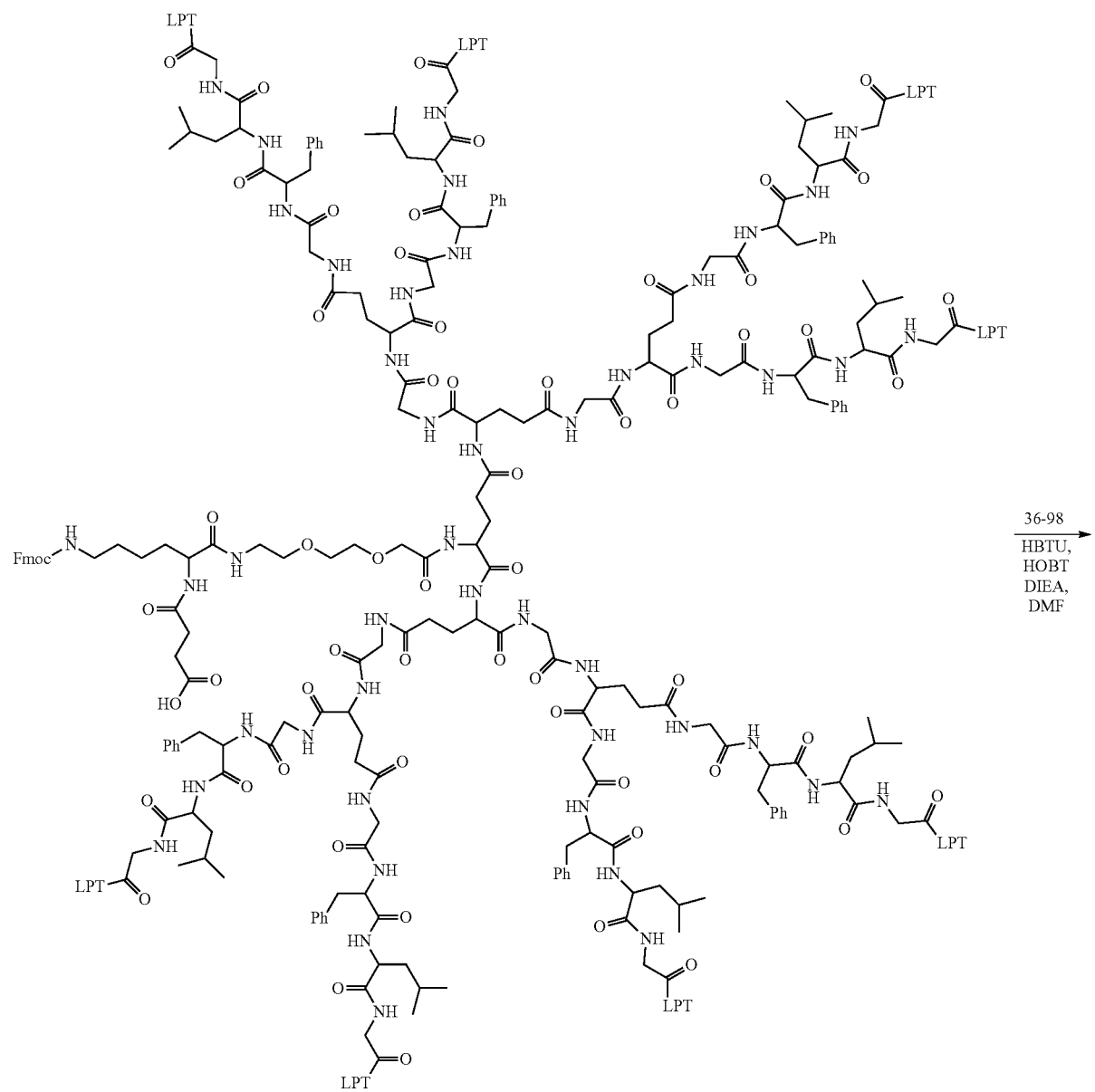
46-41

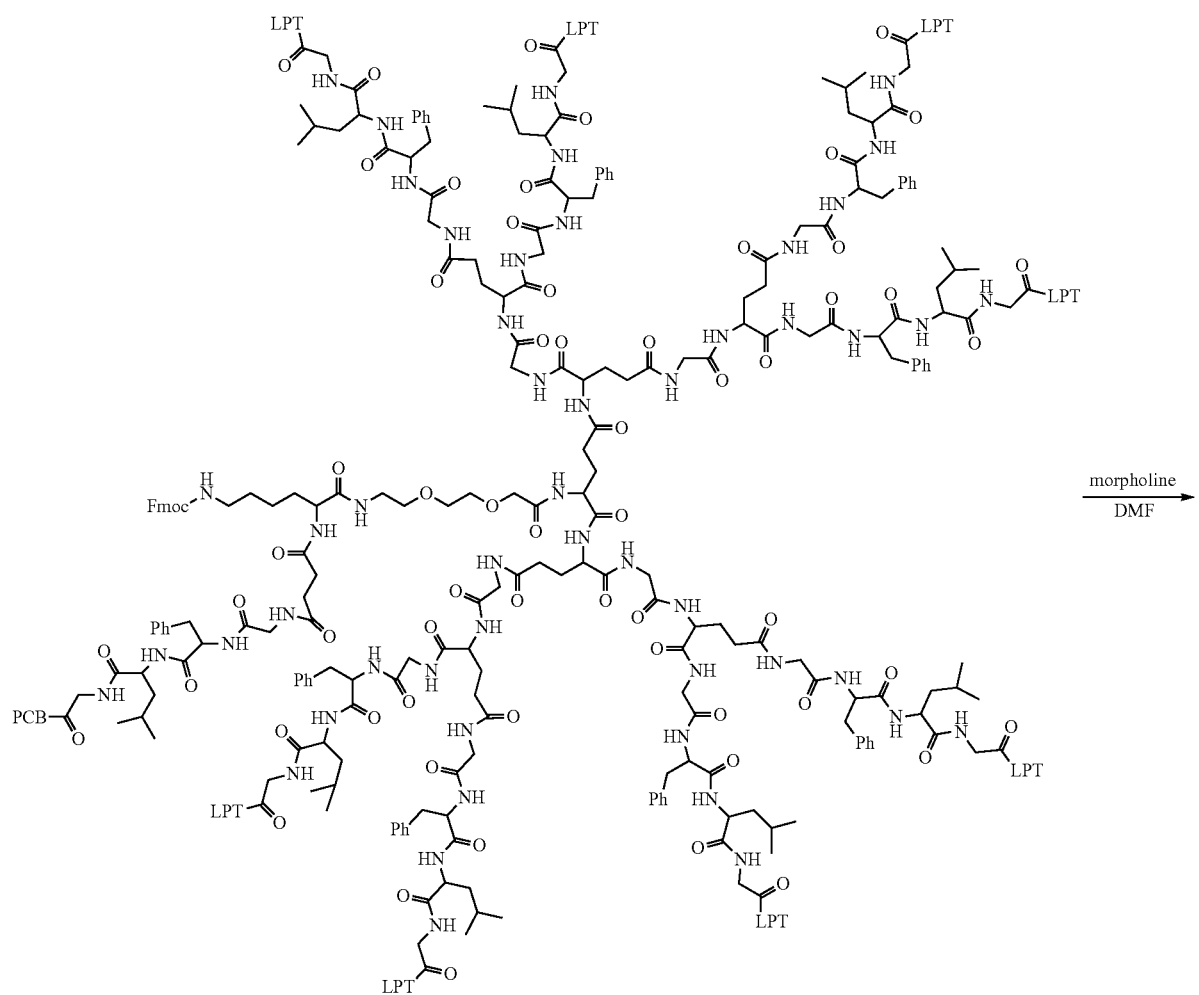
46-42

1217
-continued
1218
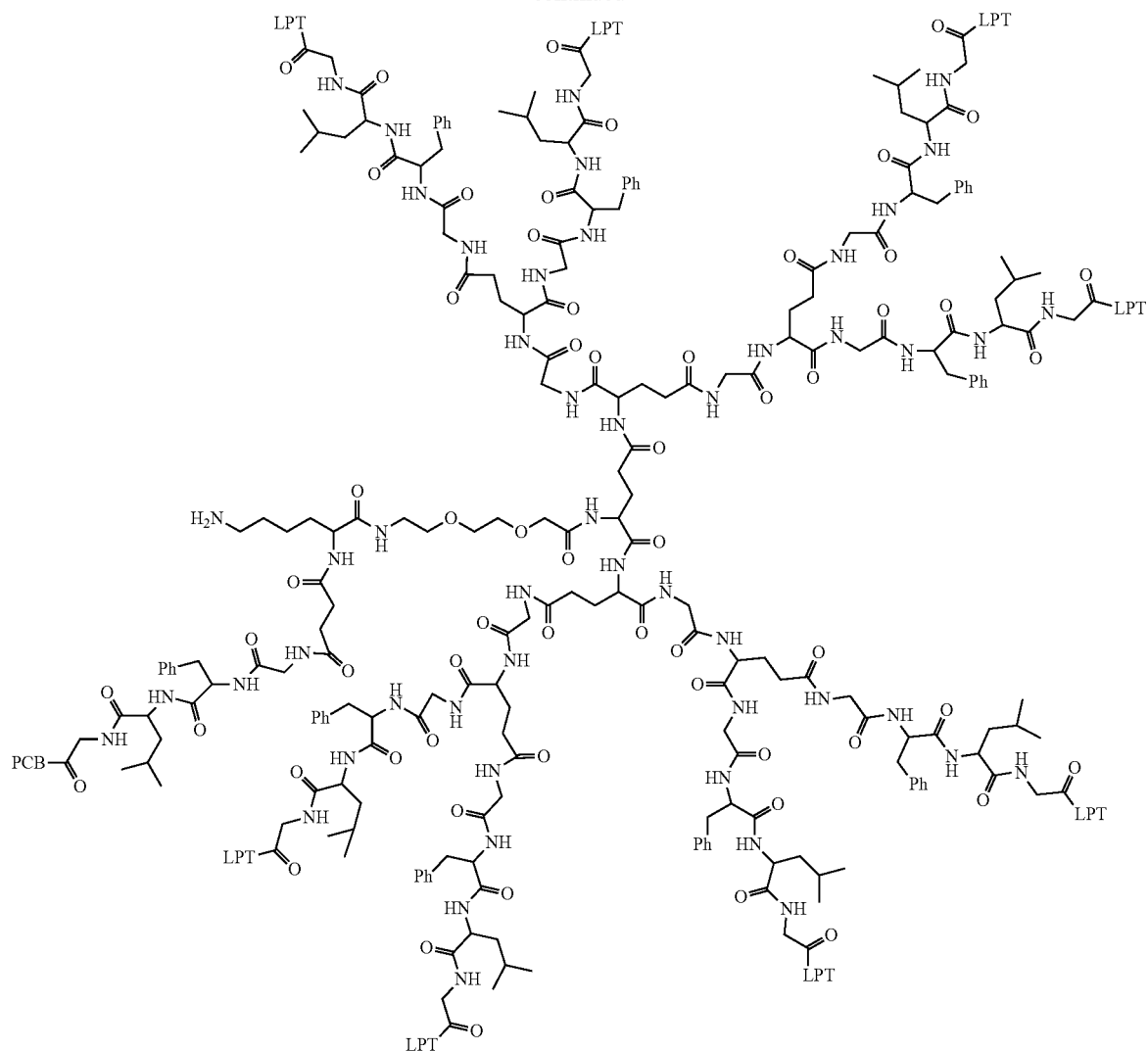
46-44
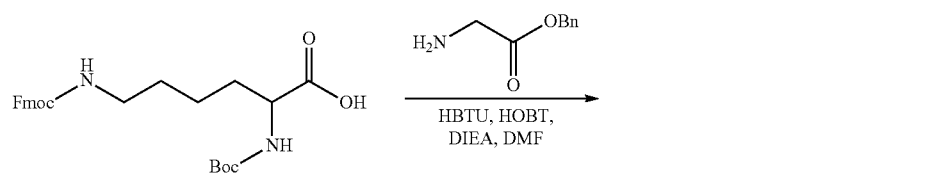
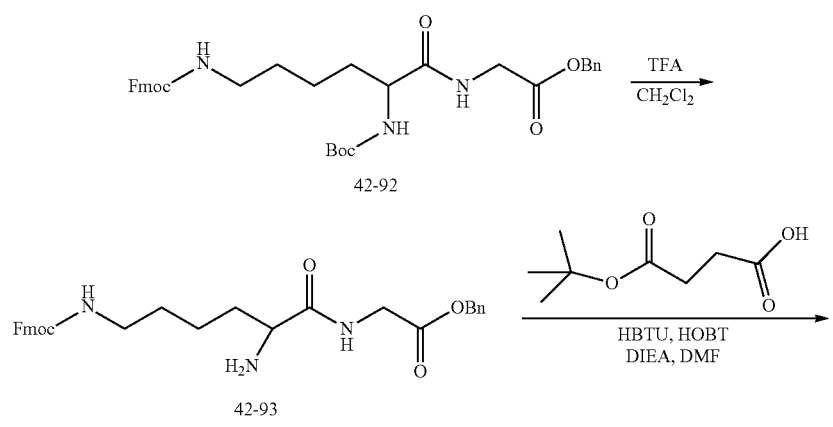
42-92
42-93

-continued
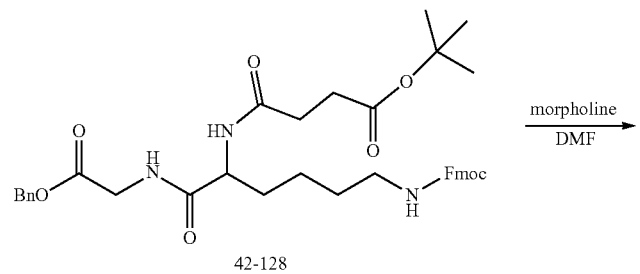
42-128
morpholine
DMF
→
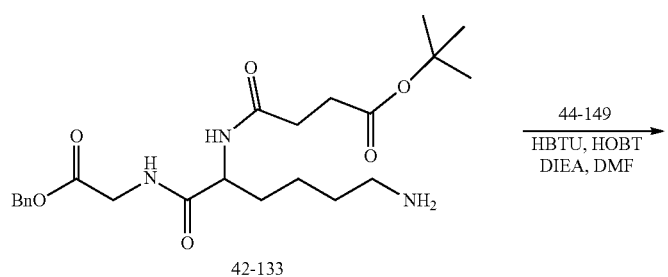
42-133
44-149
HBTU, HOBT
DIEA, DMF
→
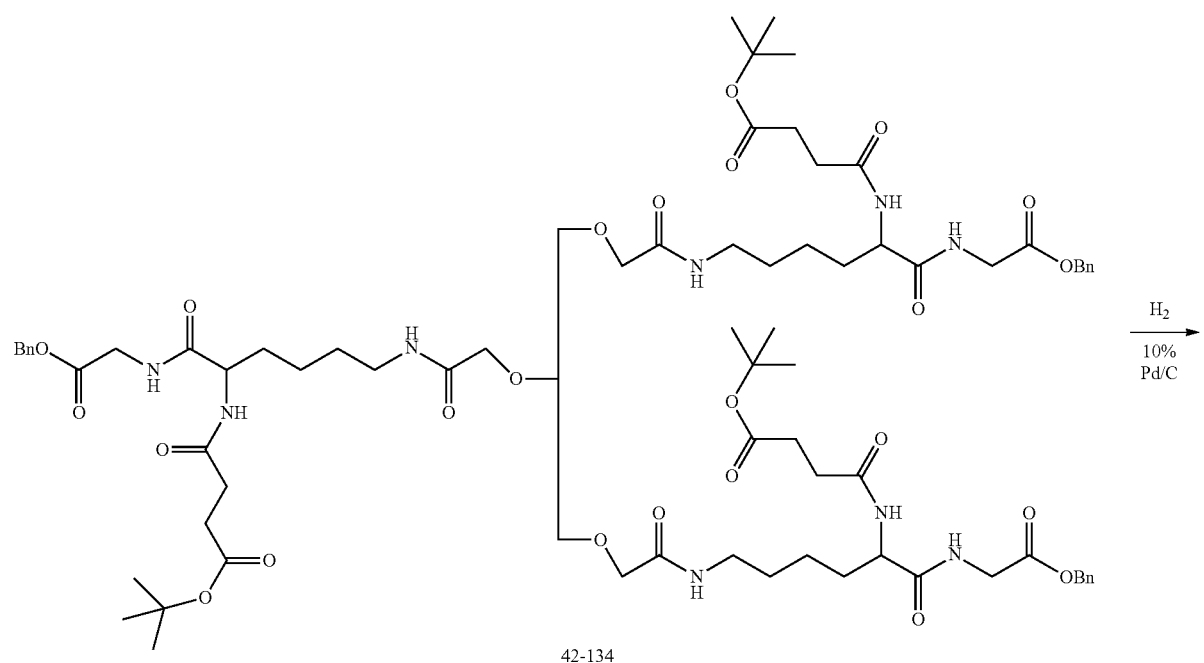
42-134
H₂
10%
Pd/C
→

1221                                   1222
-continued
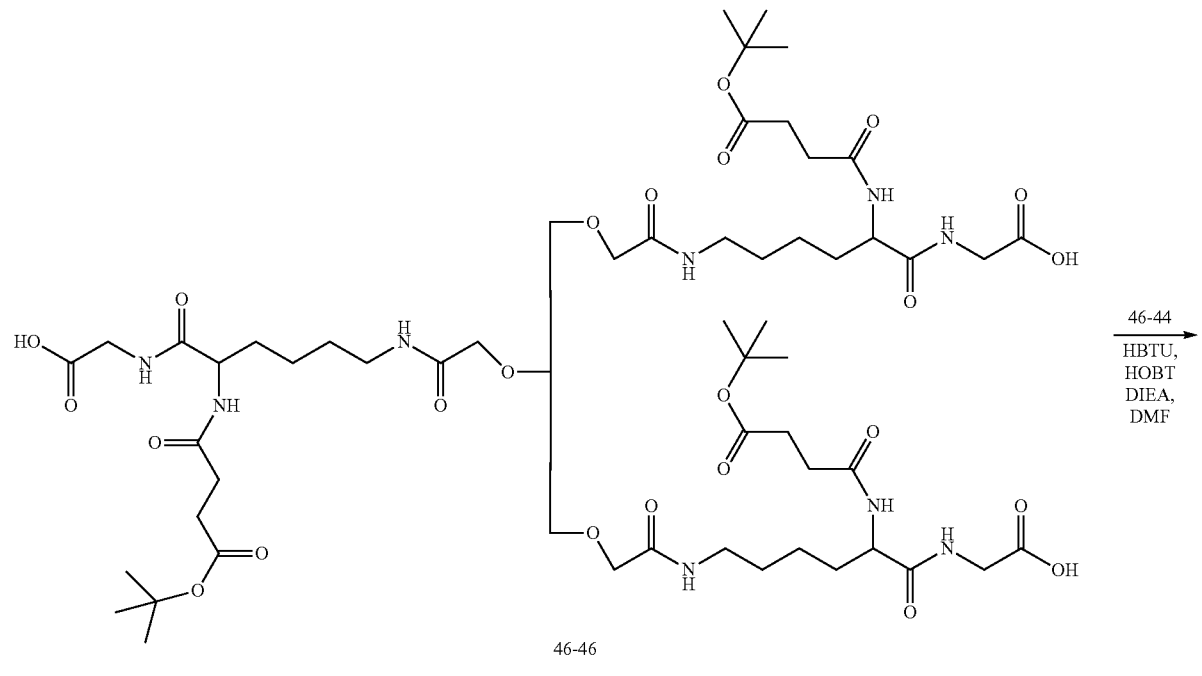 [SMILES: CC(C)(C)OC(=O)CCC(=O)NC(CCCCNC(=O)COCC(COCC(=O)NCCCCC(NC(=O)CCC(=O)OC(C)(C)C)C(=O)NCC(=O)O)OCC(=O)NCCCCC(NC(=O)CCC(=O)OC(C)(C)C)C(=O)NCC(=O)O)C(=O)NCC(=O)O]
46-46
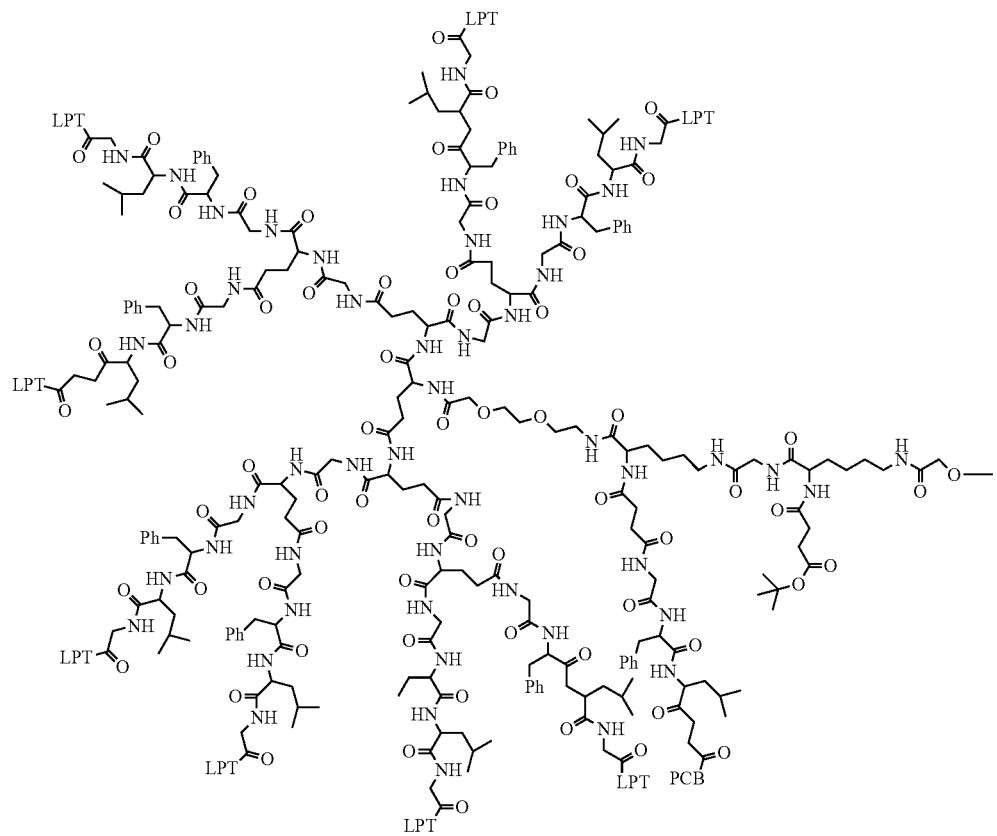

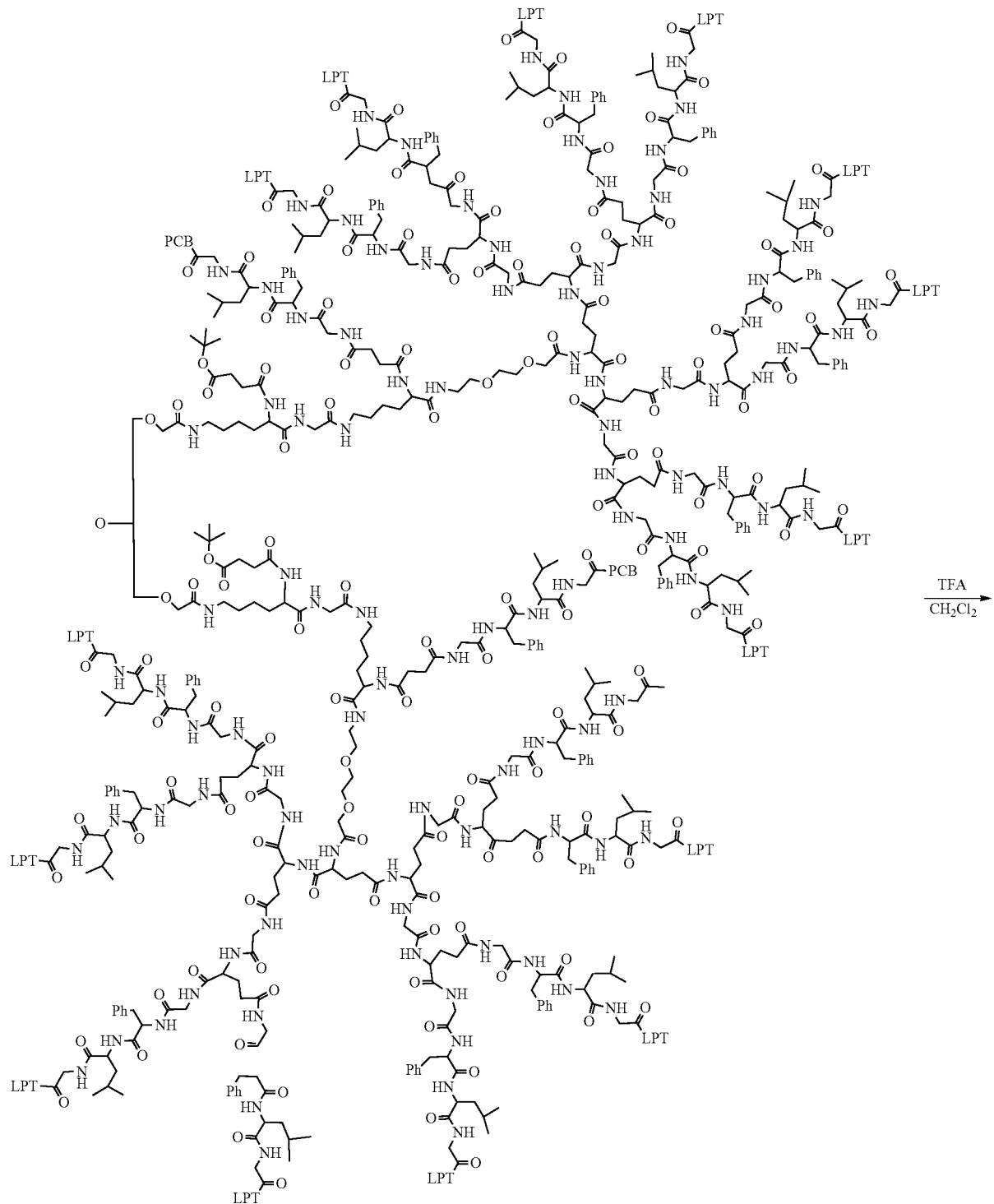

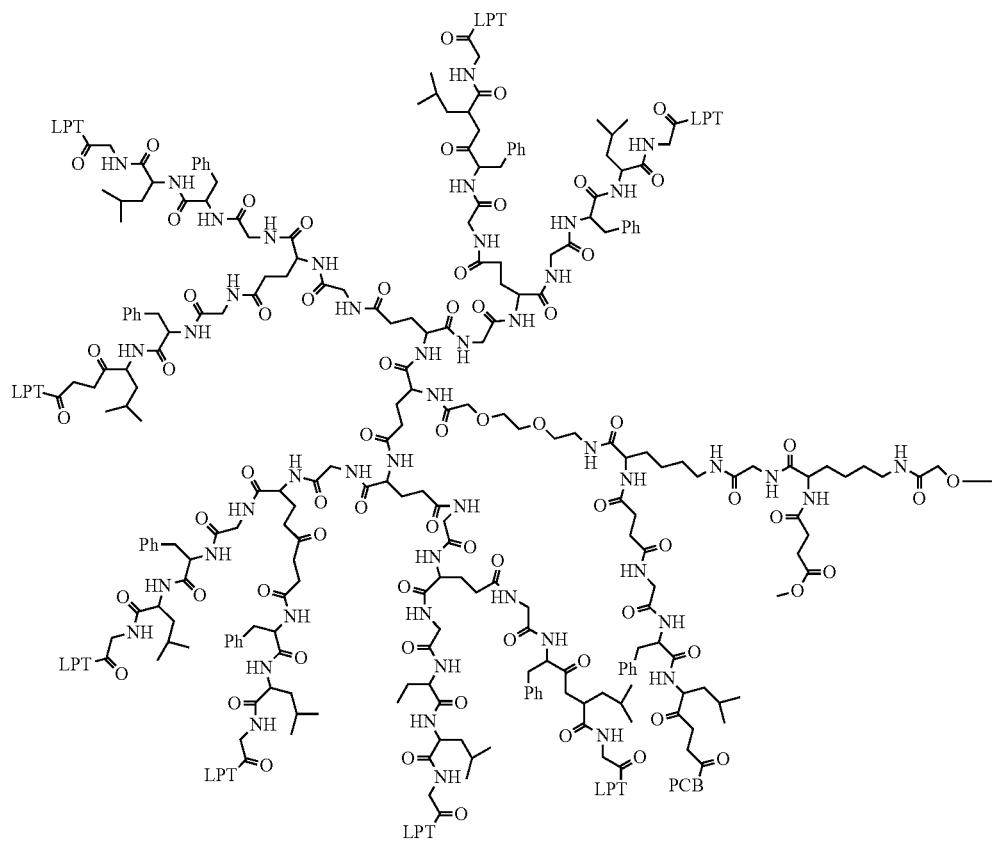

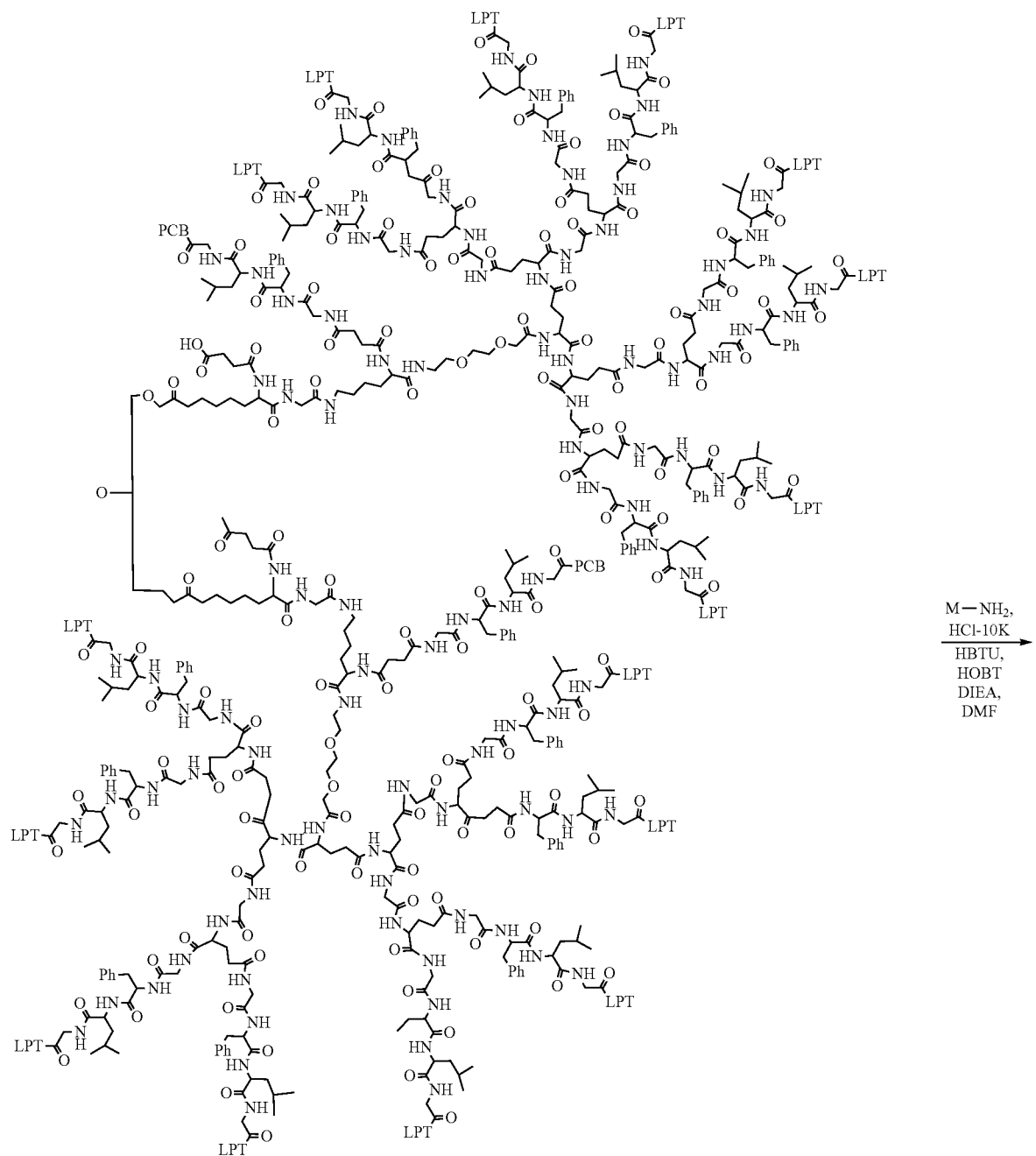
46-49

-continued
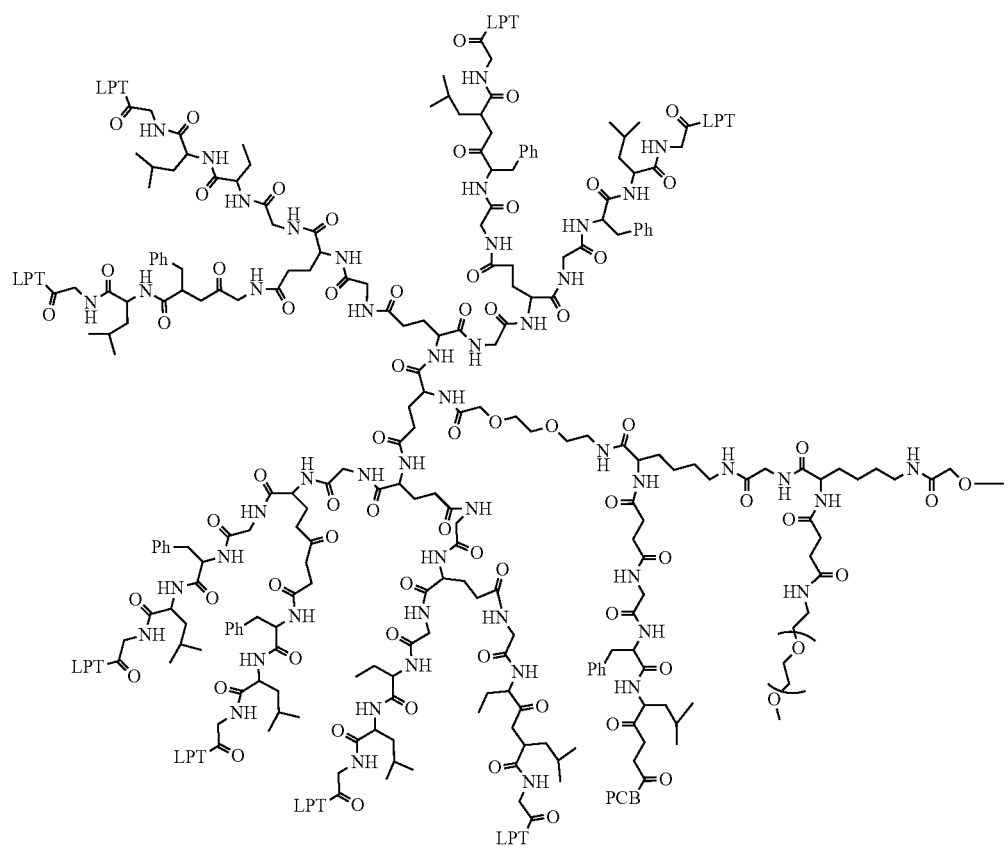

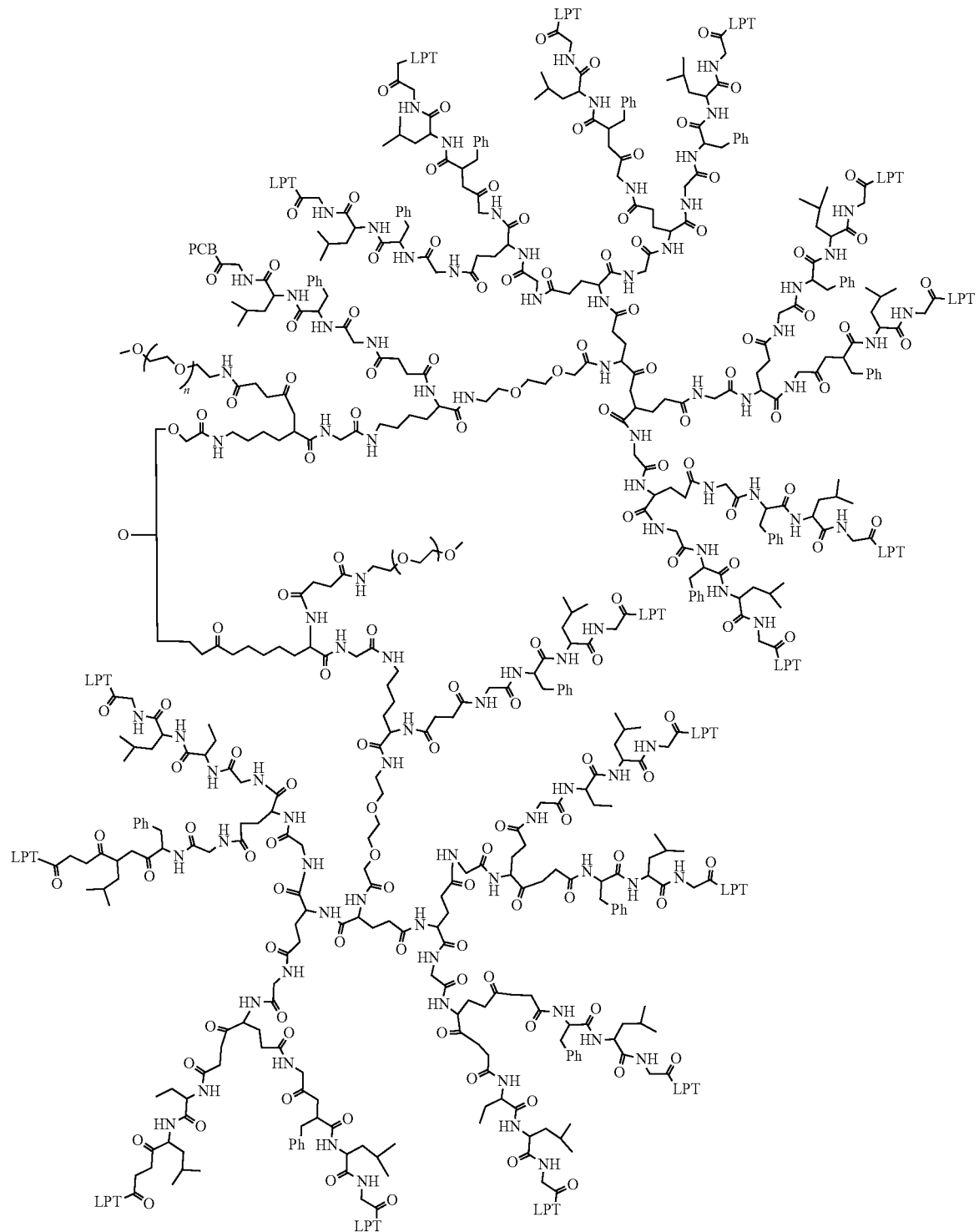
46-51

39-227

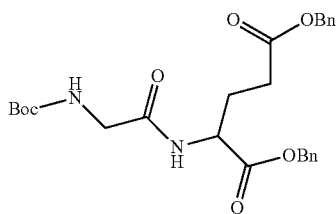

H-Glu (oBzl)-oBzl (15 g, 30.02 mmol), Boc-Gly-OH (5.25 g, 30.02 mmol), HBTU (6.08 g, 45.03 mmol), HOBT (17.07 g, 45.03 mmol) were added in a 250 mL flask, and dissolved with DMF (30 mL), and then the mixed solution was stirred to react at −5° C. for 30 minutes. Then DIEA (22.33 mL, 135.11 mmol) was slowly added dropwise. At the end of the addition, the obtained solution continued to react for 1 hour, and was then moved to room temperature and stirred to react overnight. At the end of the reaction, the reaction solution was transferred to a 1 L separatory funnel, pure water (200 mL) and ethyl acetate (200 mL) were added for extraction, and the organic phase was separated. The aqueous phase was washed with ethyl acetate (200 mL×2), and the obtained organic phases were combined. The organic phase was washed with saturated saline solution (200 mL×2), and the obtained organic phases were combined. The organic phase was washed with saturated sodium chloride solution (100 ml*2), and concentrated, and the operations of dry sample loading, column chromatography and gradient elution with 20%-50% ethyl acetate/petroleum ether were carried out, thus obtaining the product 10 g, yield 69%

33-232

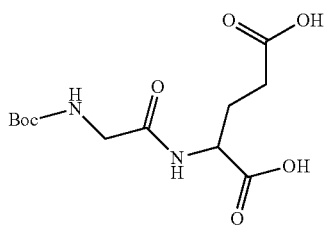

39-227 (2 g, 4.28 mmol) and 10% Pd/C (0.075 g) were added in a reactor, and dissolved with DMF (40 mL), hydrogen was introduced to a pressure of 0.16 MPa, and then the mixed solution was stirred to react at room temperature overnight. At the end of the reaction, the reaction solution was filtered with diatomaceous earth. The filter cake was washed with DMF (20 mL×3), and the DMF solutions were combined as the raw material for the next step.

33-233

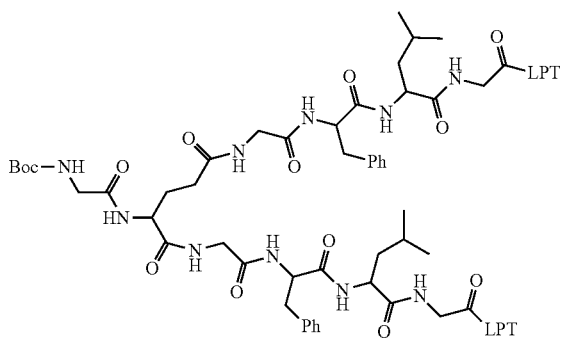

14-128 (6 g, 6.27 mmol), HBTU (3.2 g, 8.55 mmol), HOBT (1.15 g, 8.55 mmol) were added in a 250 mL flask, and dissolved with DMF (30 mL), and then the mixed solution was stirred to react at −5° C. for 30 minutes. Then DIEA (4.2 mL, 25.65 mmol) was slowly added dropwise. At the end of the addition, the obtained solution continued to react for 1 hour, and was then moved to room temperature and stirred to react overnight. At the end of the reaction, n-hexane (100 mL×3) was added for precipitation, the lower oily product was dissolved with a small amount of dichloromethane, and methyl tert-butyl ether was added to the obtained solution to separate out a solid product. The solid product was dried, thus obtaining the product 8 g, extraquota.

33-235

33-233 (8 g, 9.4 mmol) was added in a 500 mL flask, and dissolved with dichloromethane (20 mL), TFA (13 mL, 188 mmol) was added, and then the mixed solution was stirred to react at room temperature overnight. At the end of the reaction, the reaction solution was concentrated to 10 mL, methyl tert-butyl ether (200 mL) was added to the obtained solution to separate out a powder product, and suction filtering was carried out. The filter cake was washed with methyl tert-butyl ether (50 mL×3), and dissolved with a mixed solvent (200 mL) of 20% methanol: 80% dichloromethane, silica gel powder (100 mL) was added, and then the obtained mixture was evaporated to dryness to obtain a powder solid. The operations of dry sample loading, column chromatography and elution with a dichloromethane mixed solution containing 0.5%-1% ammonia water: 4%-7% methanol were carried out. The elution product was then collected, concentrated and evaporated to dryness, thus obtaining the product 6 g.

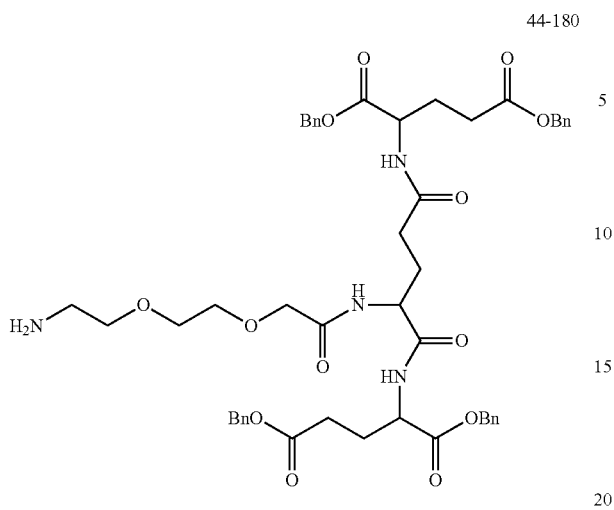

44-180

35-85 (5.4828 g, 5.4225 mmol) was added in a 250 mL round-bottomed flask, and dissolved with dichloromethane (10 mL), TFA (6.0 mL, 81.3375 mmol) was added with stirring, and then the mixed solution was stirred to react at room temperature. At the end of the reaction, the reaction solution was first concentrated under reduced pressure to remove the dichloromethane, the obtained solution was transferred to a 1 L separatory funnel, saturated sodium bicarbonate solution (400 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, deionized water (400 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 44-180: 4.7556 g, yield: 96.27%.

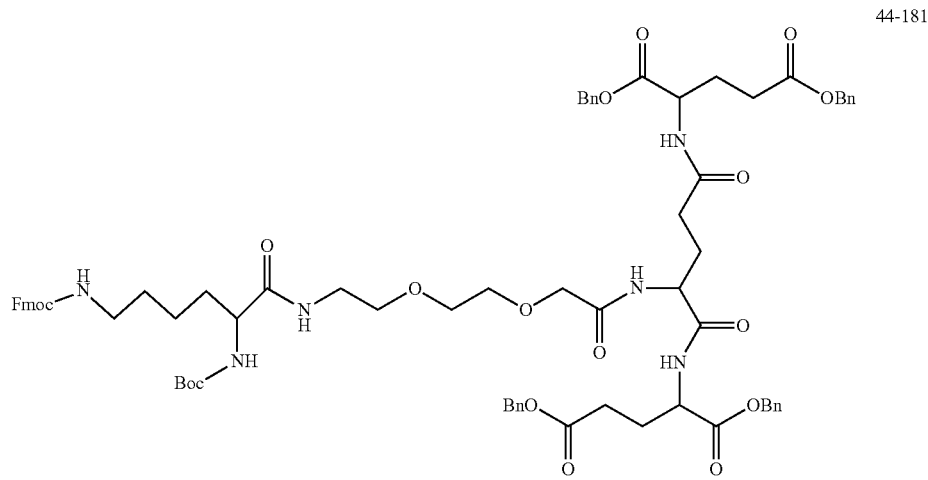

44-181

44-180 (4.7556 g, 5.2202 mmol), Boc-L-Lys (Fmoc)-011 (2.2235 g, 4.7456 mmol), HBTU (2.6996 g, 7.1185 mmol) and HOBT (0.9618 g, 7.1185 mmol) were added in a 500 mL round-bottomed flask, and dissolved with DMF (80 mL), and then the mixed solution was stirred at −5° C. for about 30 minutes. Then DIEA (4.7 mL, 46.1032 mmol) was slowly added dropwise. At the end of the addition, the obtained solution was stirred to react at −5° C. for 4 hours. At the end of the reaction, the reaction solution was transferred to a 1 L separatory funnel, saturated sodium chloride solution (400 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, saturated sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 44-181: 6.4613 g.

44-181 (6.4613 g, 4.7456 mmol) was added in a 250 mL round-bottomed flask, and dissolved with dichloromethane (10 mL), TFA (5.3 mL, 71.184 mmol) was added with stirring, and then the mixed solution was stirred to react at room temperature. At the end of the reaction, the reaction solution was first concentrated under reduced pressure to remove the dichloromethane, the obtained solution was transferred to a 1 L separatory funnel, saturated sodium chloride solution (300 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, saturated sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 44-182: 5.9861 g.

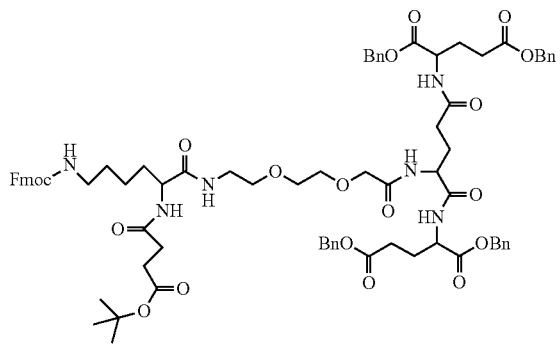

44-183

44-182 (5.9861 g, 4.7456 mmol), mono-tert-butyl succinate (0.9920 g, 4.7456 mmol), HBTU (2.6996 g, 7.1185 mmol) and HOBT (0.9618 g, 7.1185 mmol) were added in a 500 mL round-bottomed flask, and dissolved with DMF (80 mL), and then the mixed solution was stirred at −5° C. for 30 minutes. Then DIEA (4.7 mL, 46.1032 mmol) was slowly added dropwise. At the end of the addition, the obtained solution was stirred to react at −5° C. for 4 hours. At the end of the reaction, the reaction solution was transferred to a 1 L reparatory funnel, saturated sodium chloride

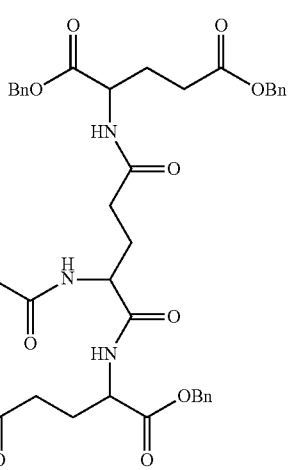

44-182

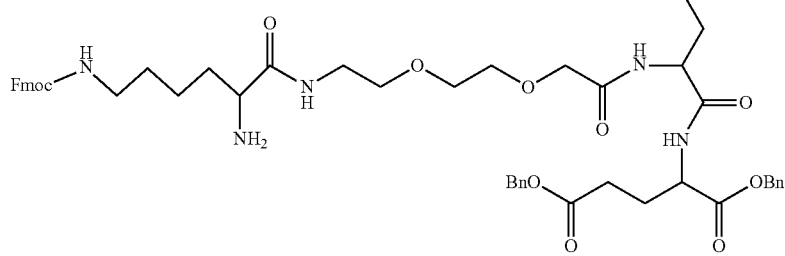

solution (400 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, saturated sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, and evaporated to dryness. The obtained dry product was dissolved with a mixed solvent (100 mL) of 20% methanol/dichloromethane, silica gel powder (60 mL) was added, and the operations of evaporation, dry sample loading, column chromatography, and elution with an elutent (1%-2% methanol: 99%-98% dichloromethane) were carried out. The elution product was then collected, concentrated, evaporated to dryness, and dried, thus obtaining the product 44-183: 4.6123 g, yield: 69.45%.

46-36

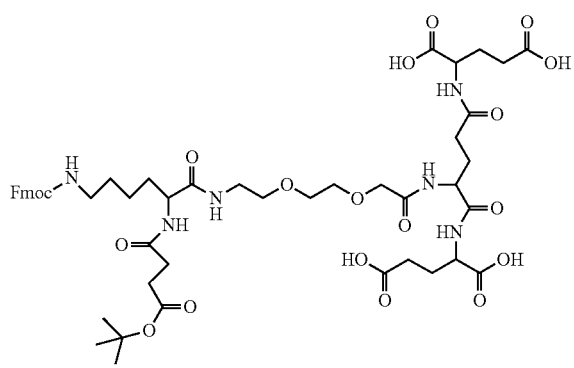

44-183 (1.9313 g, 1.3624 mmol) and 10% Pd/C (80 mg) were added in a hydrogenation reactor, and dissolved with DMF (30 mL). The hydrogenation reactor was sealed, hydrogen was introduced to a pressure of 2.0 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF until it did not contain any product, thus obtaining a reaction product solution.

46-39

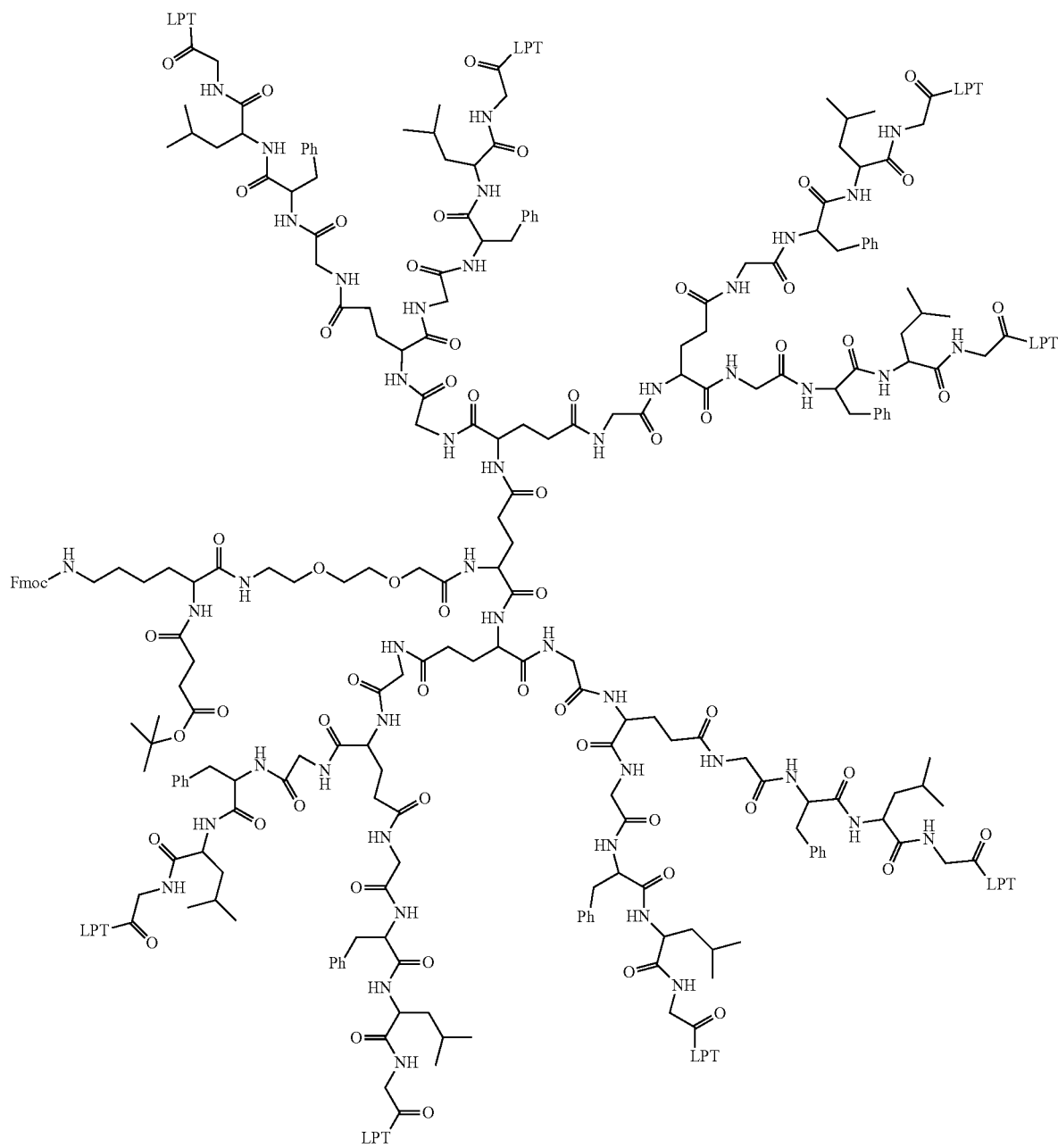

The solution of 46-36 (0.4349 g, 0.4114 mmol), 46-35 (4.1058 g, 1.9748 mmol, synthesized according to the method of synthesizing 33-235), HBTU (0.9361 g, 2.4684 mmol) and HOBT (0.3335 g, 2.4684 mmol) were added in a 500 mL round-bottomed flask, and dissolved with DMF (80 mL), and then the mixed solution was stirred at −5° C. for about 30 minutes. Then DIEA (1.2 mL, 7.4054 mmol) was slowly added dropwise. At the end of the addition, the obtained solution was stirred to react at −5° C. for 1 hour, and then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 46-39: 3.8267 g.

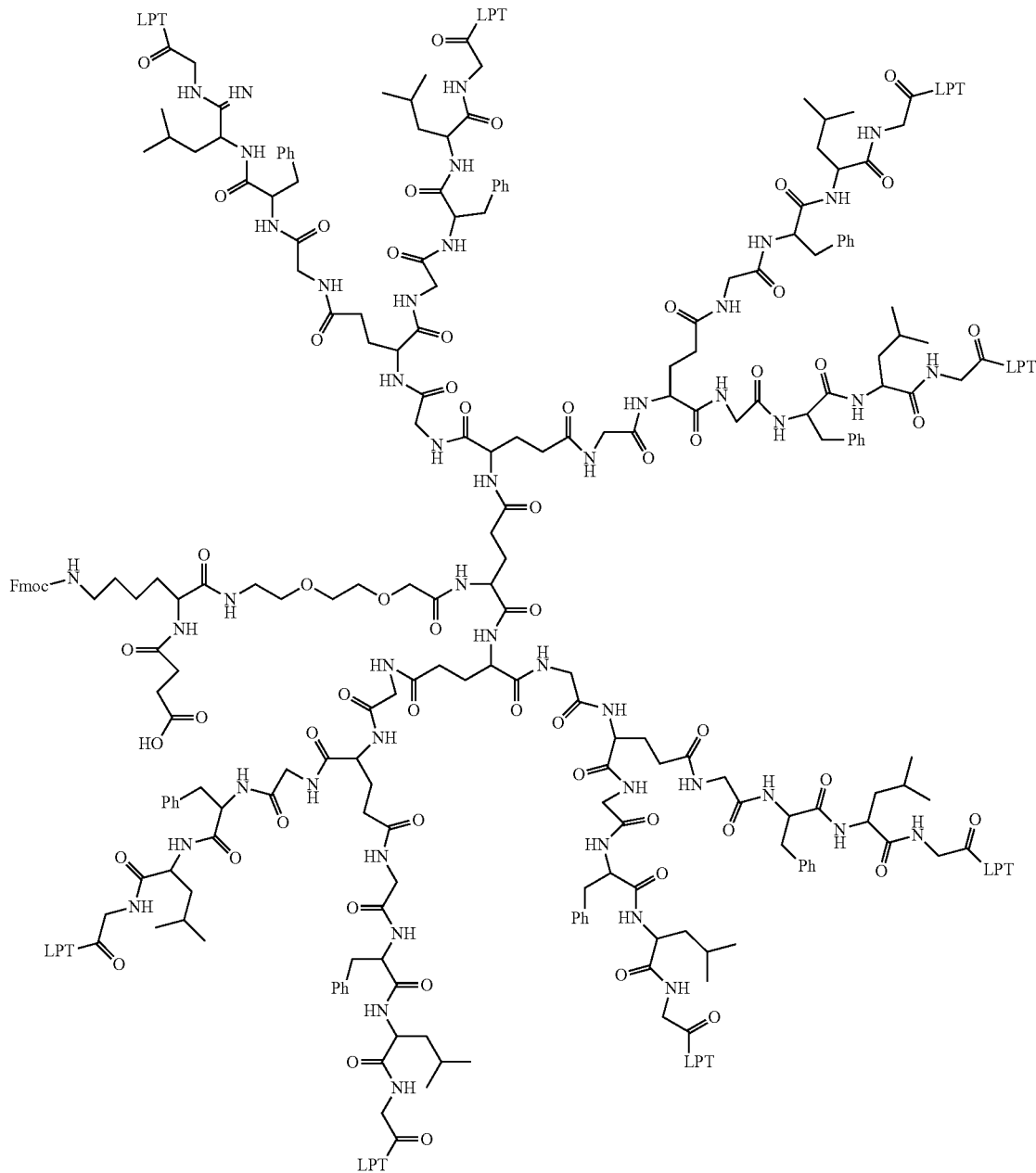

46-41

46-39 (3.8267 g, 0.4114 mmol) was added in a 500 mL round-bottomed flask, and dissolved with dichloromethane (10 mL), TFA (4.6 mL, 61.71 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), thus obtaining the product 46-41: 2.794 g, yield: 73.46%.

to react at −5° C. for 1 hour, and then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower

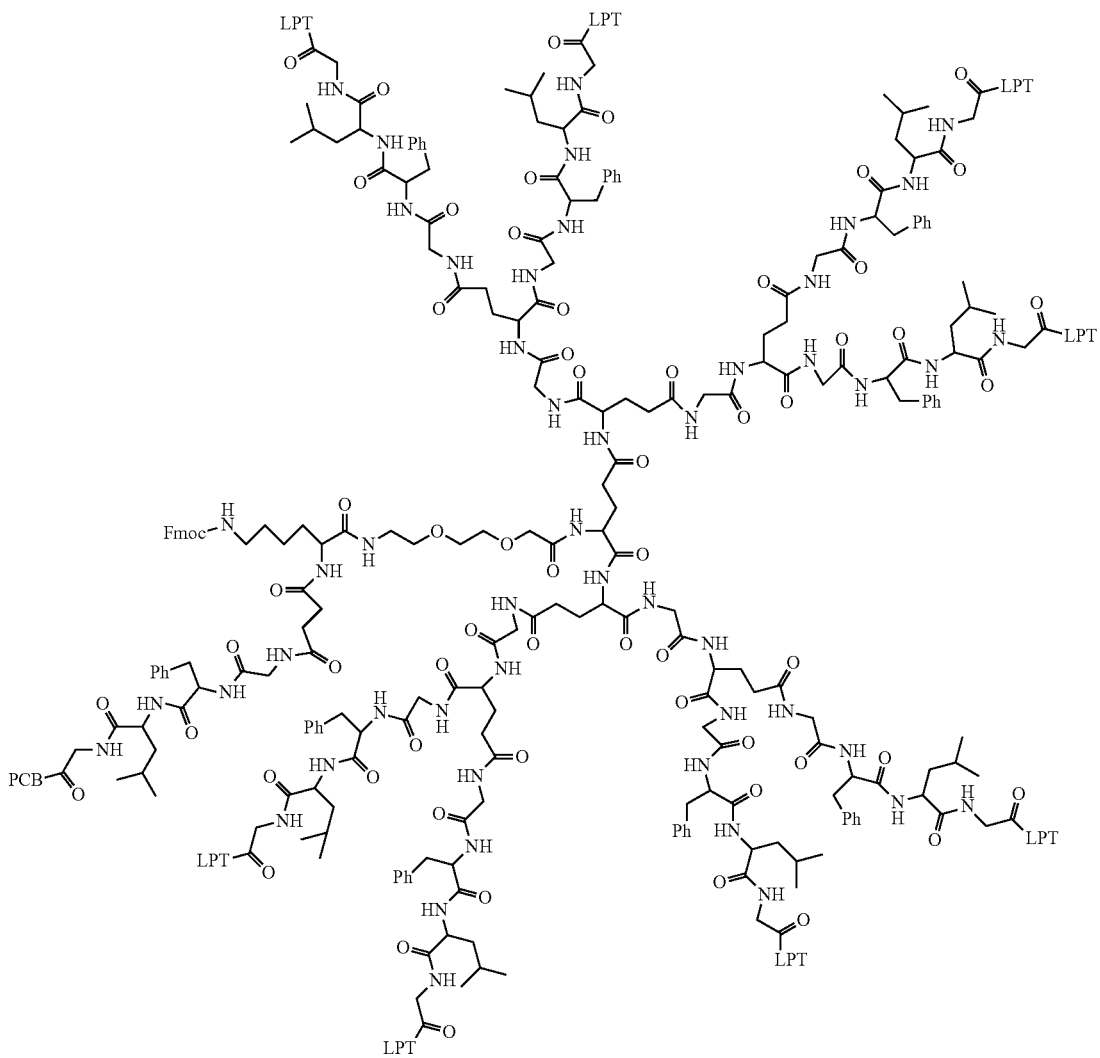

46-42

46-41 (2.794 g, 0.3022 mmol), 36-98 (0.3726 g, 0.0.4533 mmol), HBTU (0.1719 g, 0.4533 mmol) and HOBT (0.0613 g, 0.4533 mmol) were added in a 500 mL round-bottomed flask, and dissolved with DMF (80 mL), and then the mixed solution was stirred at −5° C. for about 30 minutes. Then DIEA (0.3 mL, 1.8132 mmol) was slowly added dropwise. At the end of the addition, the obtained solution was stirred oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 46-42: 3.0369 g.

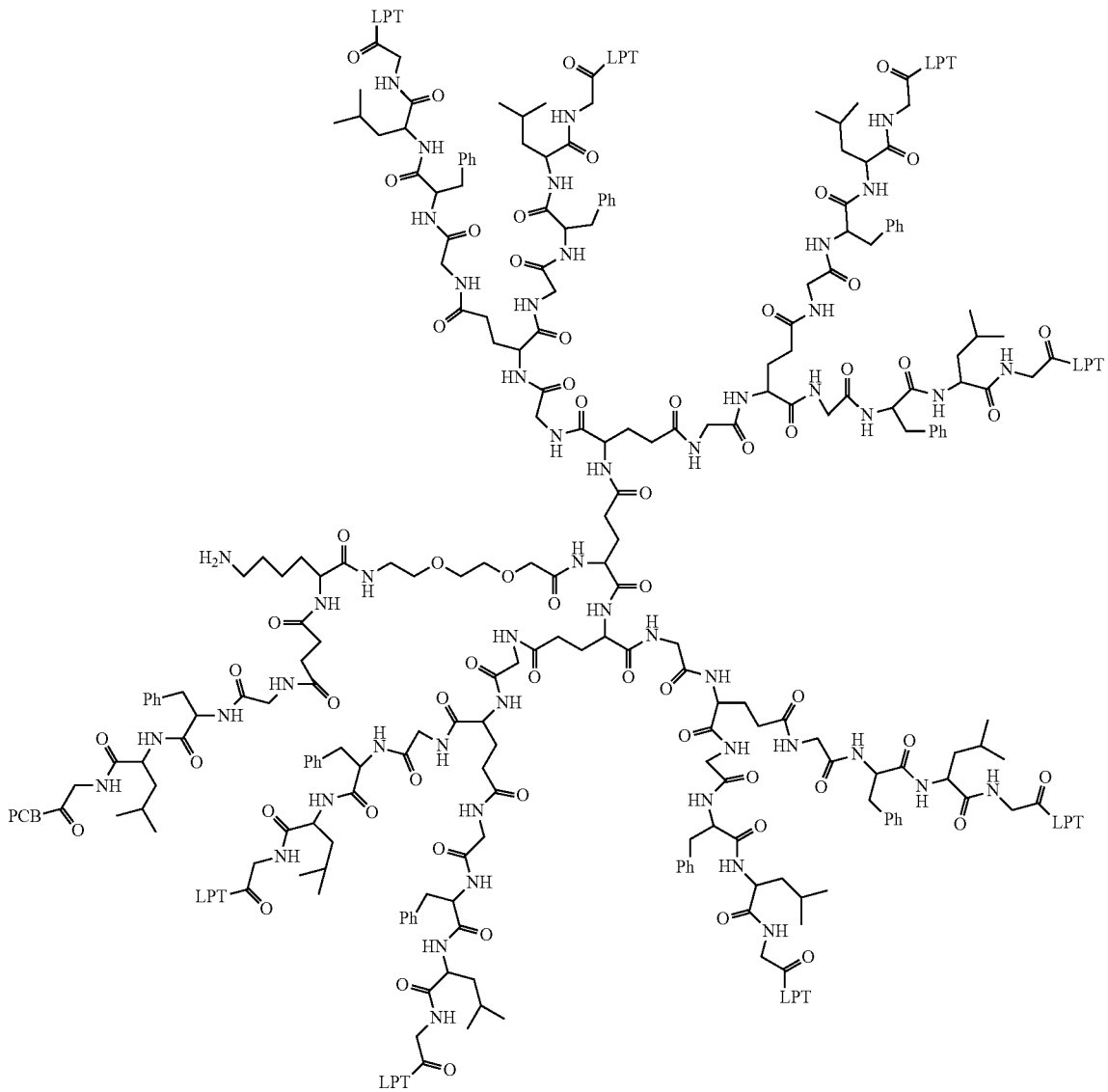

46-44

46-42 (3.0369 g, 0.3022 mmol) was added in a 500 mL round-bottomed flask, and dissolved with DMF (10 mL), morpholine (0.5 mL, 5.4395 mmol) was added with stirring, and then the mixed solution was stirred to react at room temperature for 2 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), thus obtaining the product 46-44: 0.4886 g, yield: 16.5%.

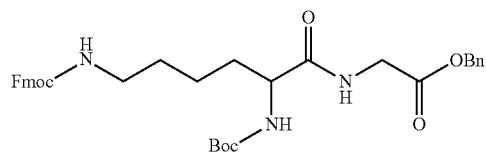

42-92

Boc-L-Lys (Fmoc)-OH (9.0 g, 19.2086 mmol), glycine benzyl ester hydrochloride (4.2608 g, 21.1295 mmol), HBTU (10.9270 g, 28.8129 mmol) and HOBT (3.8932 g, 28.8129 mmol) were added in a 500 mL round-bottomed flask, and dissolved with DMF (60 mL), and then the mixed solution was stirred at −5° C. for about 30 minutes. Then DIEA (14.3 mL, 86.4387 mmol) was slowly added dropwise. At the end of the addition, the obtained solution continued to react with stirring at −5° C. for 3 hours. At the end of the reaction, the reaction solution was transferred to a 1 L separatory funnel, saturated sodium chloride aqueous solution (300 mL) and ethyl acetate (200 mL) were added, the obtained solution was shaken for extraction, and the aqueous phase was separated. Ethyl acetate (100 mL) was then added to the aqueous phase, the obtained solution was shaken for extraction, and the aqueous phase was separated. The obtained organic phases were combined, saturated sodium chloride aqueous solution (300 mL) was then added to the organic phase, the obtained solution was shaken for extraction, and the aqueous phase was separated. Then, deionized water (300 mL) was added to the organic phase, the obtained solution was shaken for extraction, and the aqueous phase was separated. Finally, the organic phase was concentrated, evaporated to dryness, and dried in an oven, thus obtaining the product 42-92: 11.8271 g.

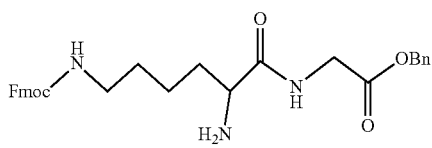

42-93

42-92 (11.8271 g, 19.2086 mmol) was added in a 500 mL round-bottomed flask, and dissolved with dichloromethane (40 mL), TFA (21.4 mL, 288.129 mmol) was added with stirring, and then the mixed solution was stirred to react at room temperature overnight. At the end of the reaction, the reaction solution was evaporated to remove the dichloromethane, and then precipitated with methyl tert-butyl ether (150 mL) to obtain a powdery solid, and filtering was carried out. The filter cake was washed with methyl tert-butyl ether (60 mL), and finally dried in an oven, thus obtaining the product 42-93: 9.9040 g.

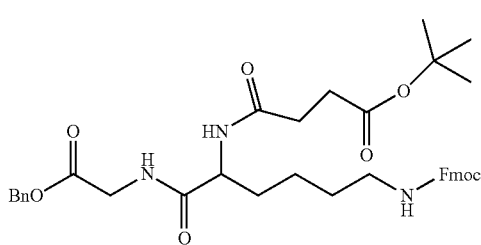

42-128

42-93 (9.9040 g, 19.2086 mmol), mono-tert-butyl succinate (3.6805 g, 21.1295 mmol), HBTU (10.9270 g, 28.8129 mmol) and HOBT (3.8932 g, 28.8129 mmol) were added in a 500 mL round-bottomed flask, and dissolved with DMF (100 mL), and then the mixed solution was stirred at −5° C. for about 30 minutes. Then DIEA (14.2 mL, 86.4387 mmol) was slowly added dropwise. At the end of the addition, the obtained solution was stirred to react at −5° C. for 1 hour, and then moved to room temperature and stirred to react. At the end of the reaction, the reaction solution was transferred to a 1 L separatory funnel, saturated sodium chloride aqueous solution (400 mL) and ethyl acetate (300 mL) were added, the obtained solution was shaken for extraction, and then the organic phase was separated from the aqueous phase. Ethyl acetate (200 mL) was then added to the aqueous phase, the obtained solution was shaken for extraction, and then the organic phase was separated from the aqueous phase. Then, the obtained organic phases were combined, aqueous sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 42-128: 12.9040 g.

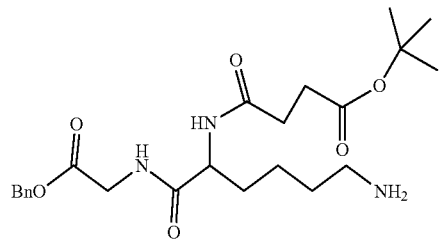

42-133

42-128 (12.9040 g, 19.2086 mmol) was added in a 500 mL round-bottomed flask, and dissolved with DMF (20 mL), morpholine (25.1 mL, 288.1290 mmol) was added with stirring, and then the mixed solution was stirred to react at room temperature for 2 hours. At the end of the reaction, the reaction solution was transferred to a 1 L separatory funnel, saturated sodium bicarbonate solution (400 mL) and ethyl acetate (300 mL) were added, the obtained solution was shaken for extraction, and then the organic phase was separated from the aqueous phase. Ethyl acetate (200 mL) was then added to the aqueous phase, the obtained solution was shaken for extraction, and then the organic phase was separated from the aqueous phase. Then, the obtained organic phases were combined, deionized water (400 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 42-133: 8.6350 g.

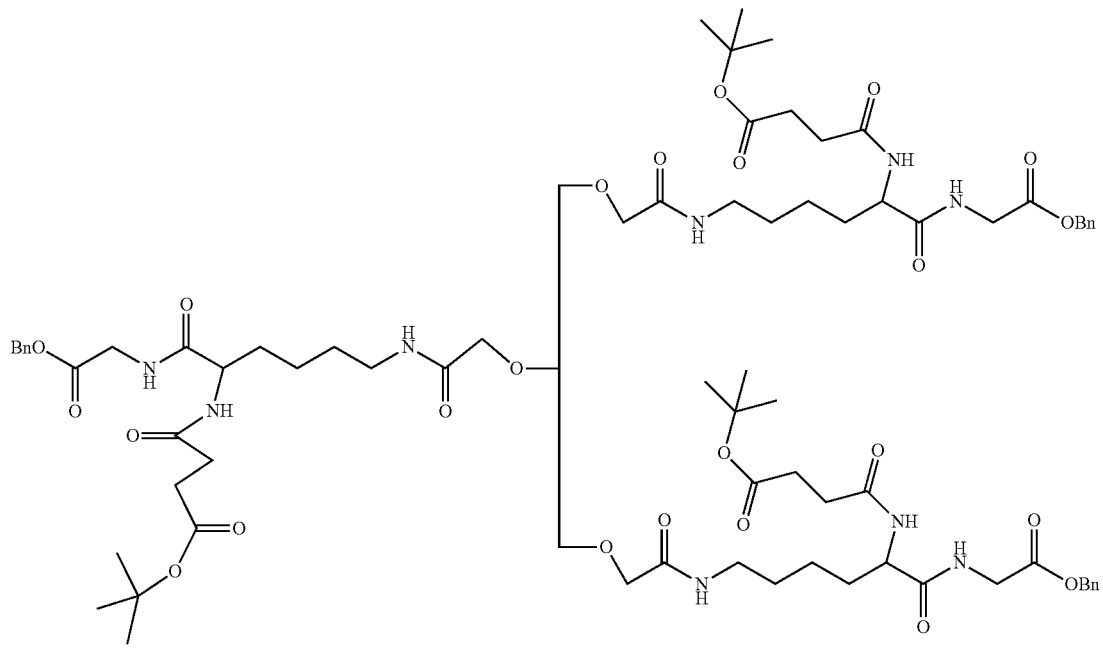

42-134

The solution of 42-133 (7.5191 g, 16.7263 mmol), 44-149 (that is, 36-186, 2.4930 g, 4.6462 mmol), HBTU (7.9291 g, 20.9079 mmol) and HOBT (2.8251 g, 20.9079 mmol) were added in a 500 mL round-bottomed flask, and dissolved with DMF (80 mL), and then the mixed solution was stirred at −5° C. for about 30 minutes. Then DIEA (10.4 mL, 62.7237 mmol) was slowly added dropwise. At the end of the addition, the obtained solution was stirred to react at −5° C. for 1 hour, and then moved to room temperature and stirred to react. At the end of the reaction, the reaction solution was transferred to a 1 L separatory funnel, saturated sodium bicarbonate solution (400 mL) and ethyl acetate (300 mL) were added, the obtained solution was shaken for extraction, and then the organic phase was separated from the aqueous phase. Ethyl acetate (200 mL) was then added to the aqueous phase, the obtained solution was shaken for extraction, and then the organic phase was separated from the aqueous phase. Then, the obtained organic phases were combined, deionized water (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, and the concentrated product was dissolved with a mixed solvent (60 mL) of 20% methanol/dichloromethane, silica gel powder (40 ml) was added to the obtained solution, and the operations of evaporation, dry sample loading, column chromatography, and elution with an elutent (2%-8% methanol: 98%-92% dichloromethane) were carried out. The elution product was then collected, concentrated, evaporated to dryness, and dried, thus obtaining the product 42-134: 4.8 g, yield: 66.19%.

$^1$H NMR (400 MHz, DMSO-$d_6$) δ 8.38-8.35 (m, 3H), 8.11-8.01 (m, 3H), 7.56 (t, J=5.2 Hz, 3H), 7.44-7.27 (m, 15H), 5.12 (s, 6H), 4.36-4.17 (m, 3H), 3.97-3.80 (m, 6H), 3.33 (s, 11H), 3.06 (m, 6H), 2.45-2.31 (m, 12H), 1.69-1.46 (m, 12H), 1.36 (m, 27H), 1.32-1.26 (m, 6H).

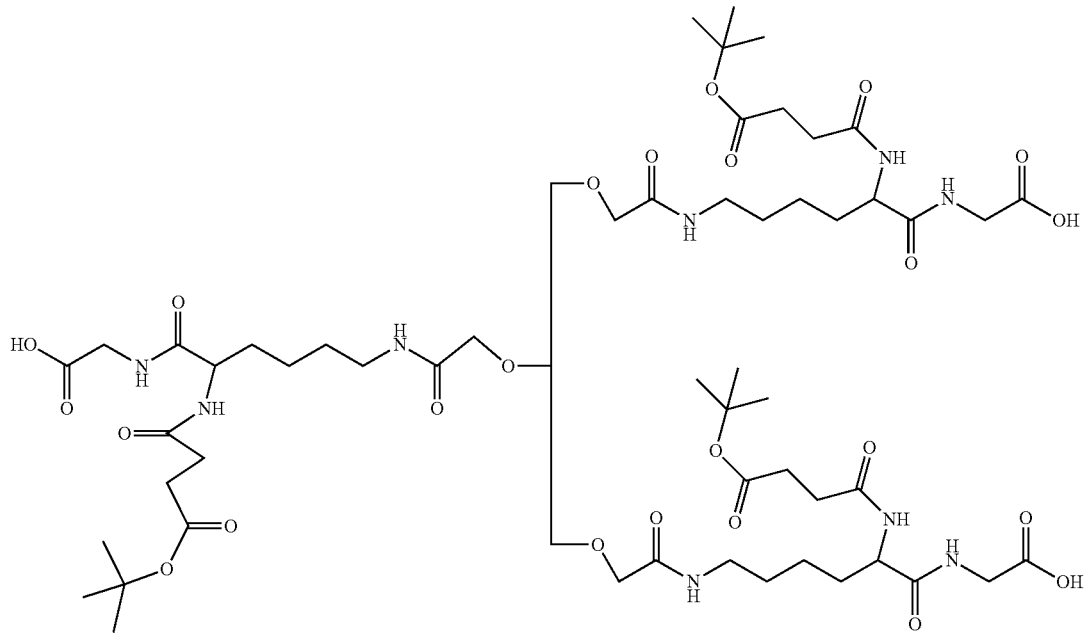

46-46

42-134 (0.5 g, 0.3204 mmol) and 10% Pd/C (50 mg) were added in a hydrogenation reactor, and dissolved with DMF (30 mL). The hydrogenation reactor was sealed, hydrogen was introduced to a pressure of 2.0 MPa, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF until it did not contain any product, thus obtaining a reaction product solution.

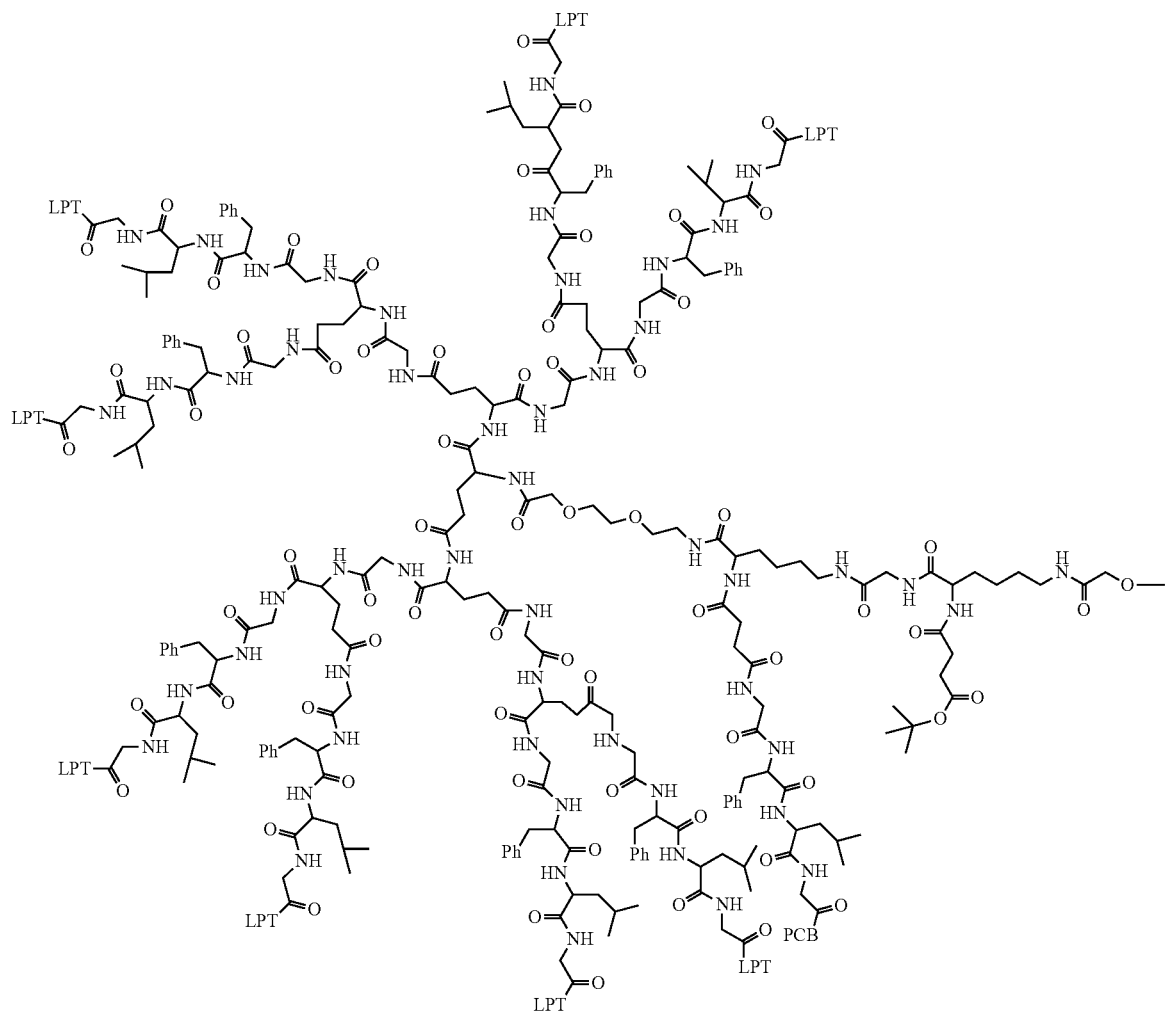
46-47

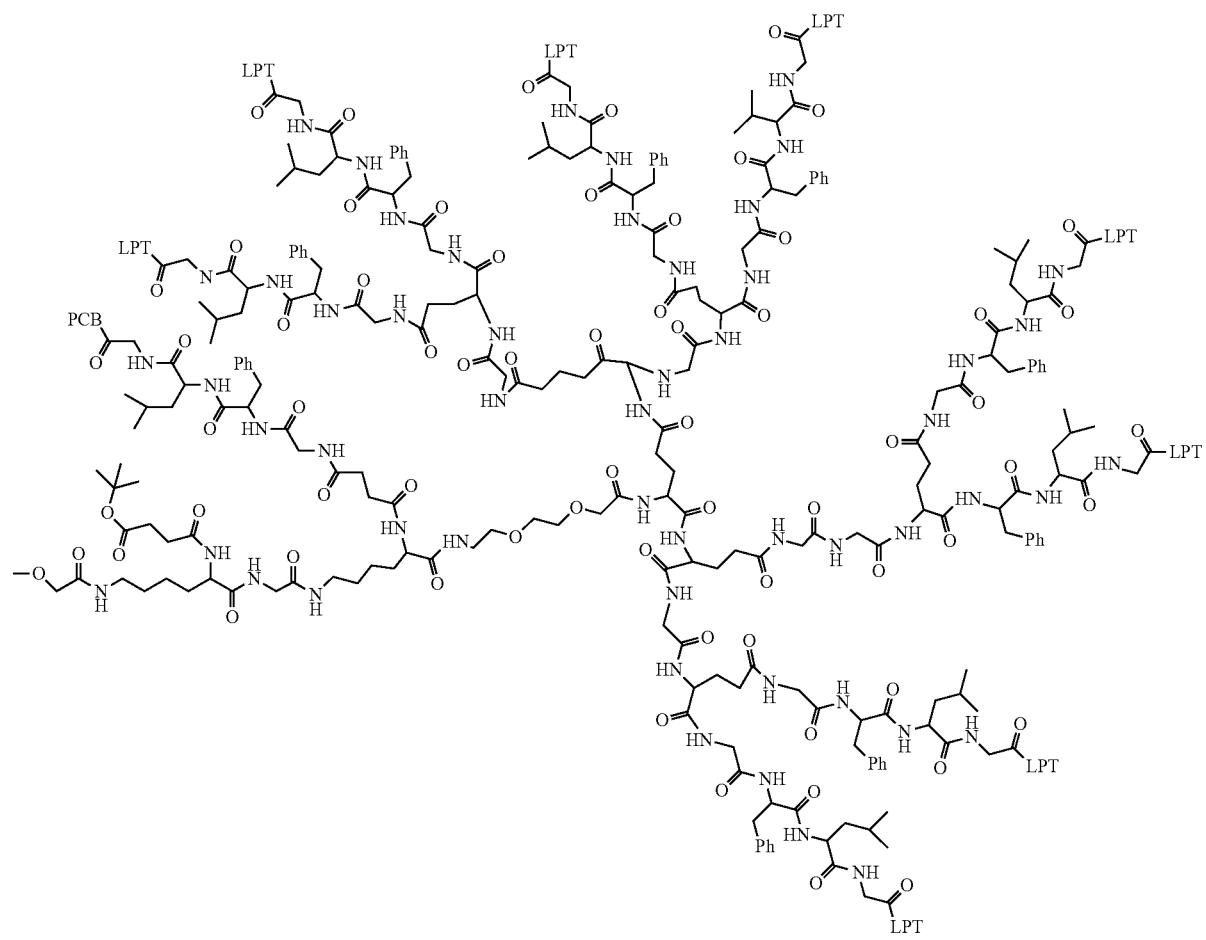

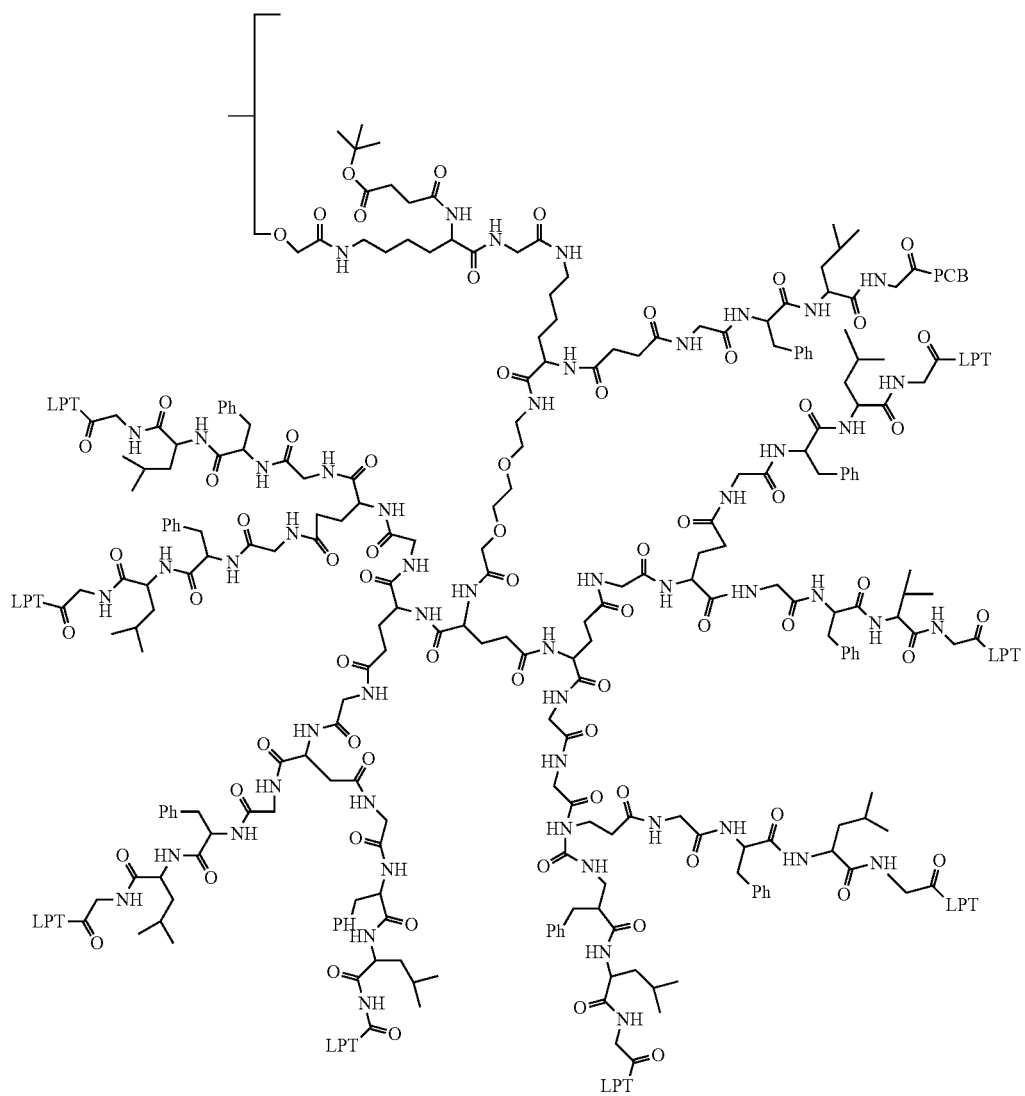

The solution of 46-46 (0.0194 g, 0.0151 mmol), 46-44 (0.4886 g, 0.0497 mmol), HBTU (0.0257 g, 0.0678 mmol) and HOBT (0.0092 g, 0.0678 mmol) were added in a 500 mL round-bottomed flask, and dissolved with DMF (100 mL), and then the mixed solution was stirred at −5° C. for about 30 minutes. Then DIEA (0.1 mL, 1.057 mmol) was slowly added dropwise. At the end of the addition, the obtained solution was stirred to react at −5° C. for 30 minutes, and then moved to room temperature and stirred to react overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 46-47: 0.4628 g.

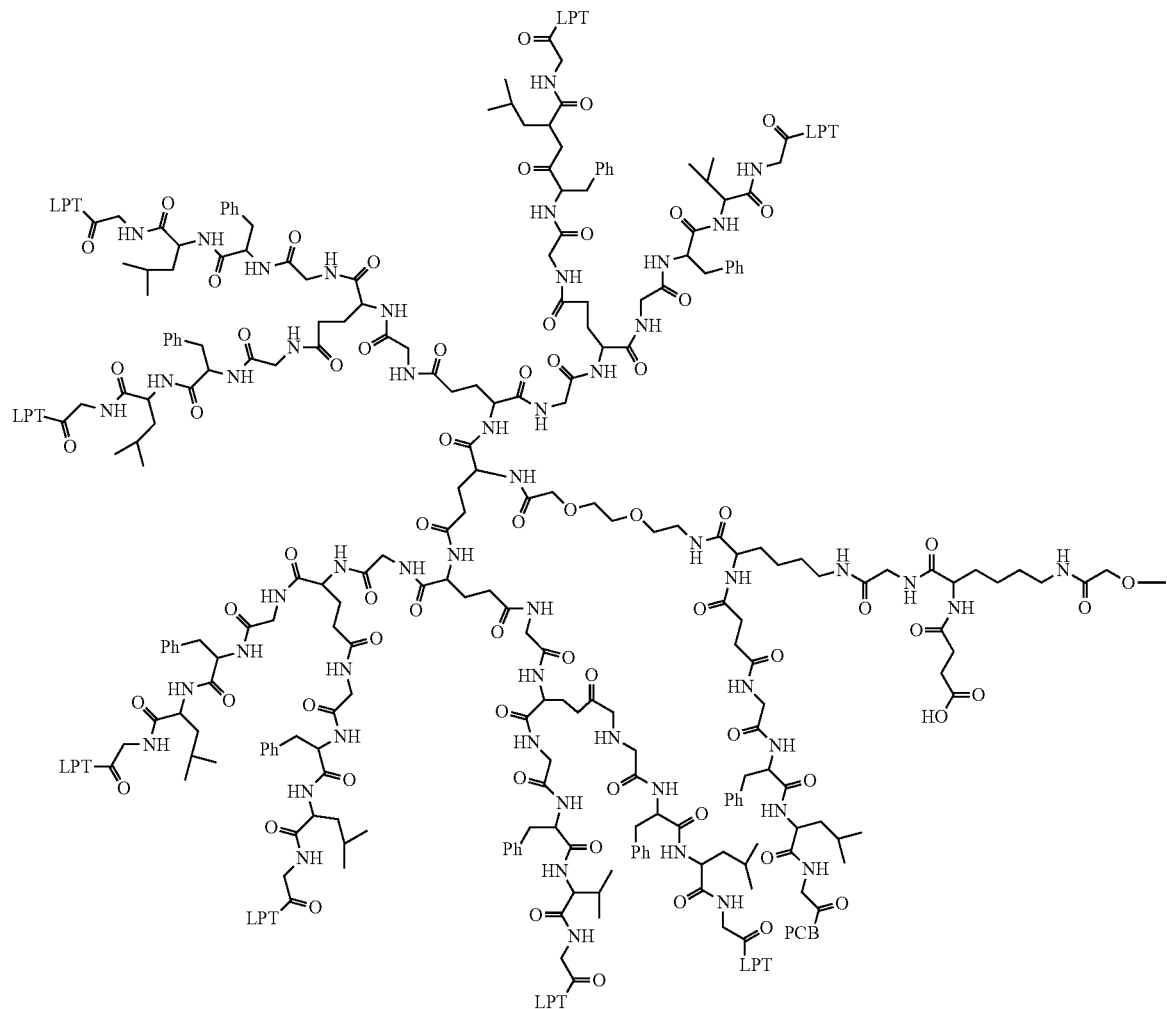

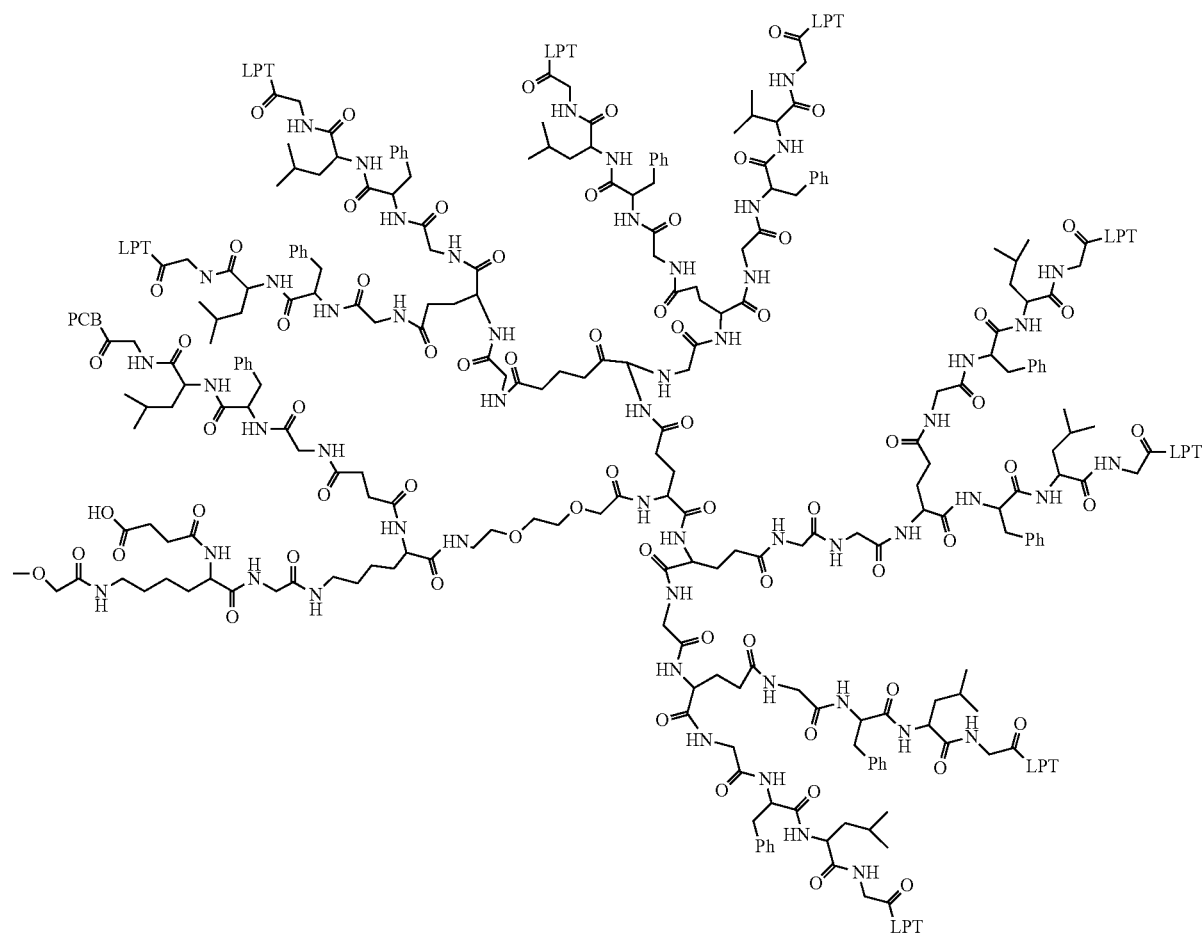

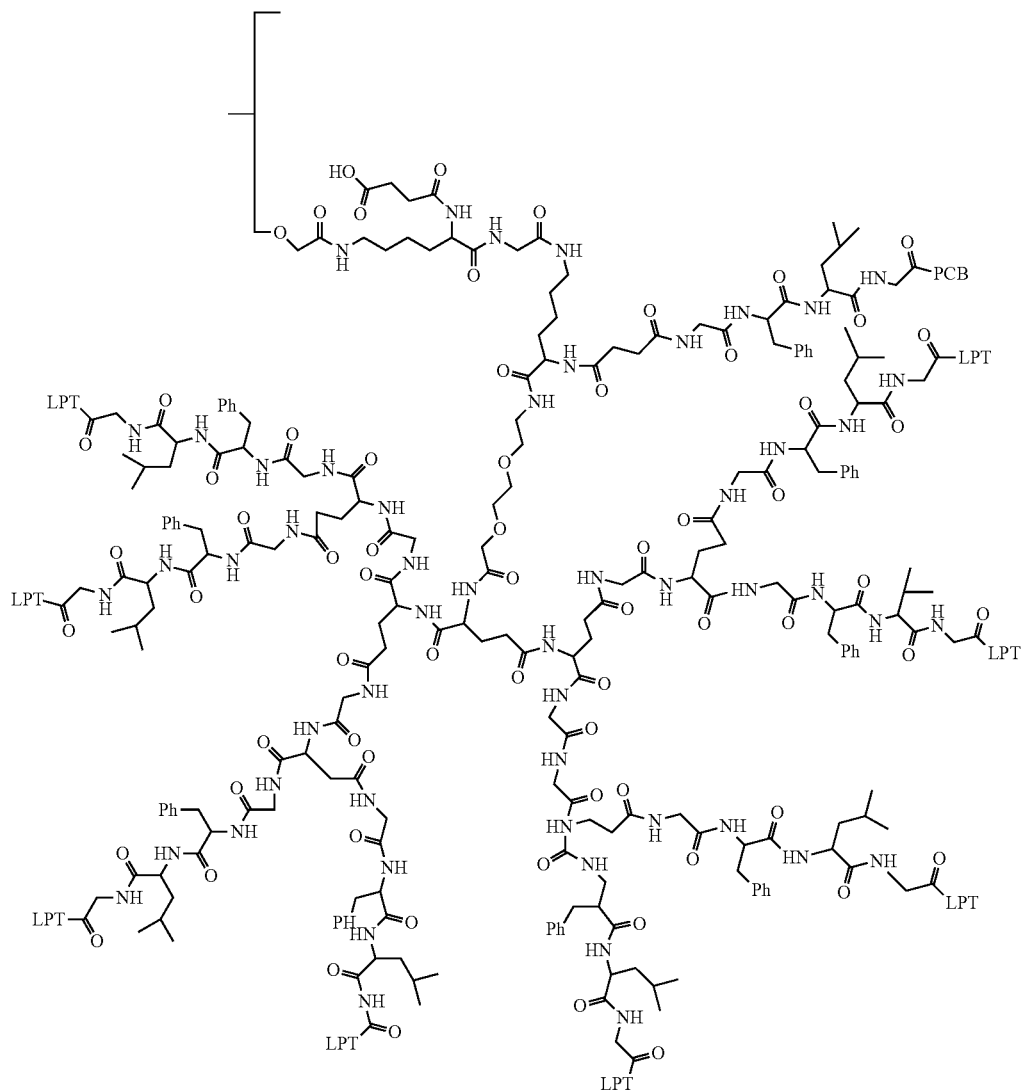

46-47 (0.4628 g, 0.0151 mmol) was added in a 250 mL round-bottomed flask, and dissolved with dichloromethane (10 mL), TFA (5 mL, 2.265 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), and dissolved with a mixed solvent (80 mL) of 20% methanol/dichloromethane, silica gel powder (50 mL) was added to the obtained solution, and the operations of evaporation, dry sample loading, column chromatography, and elution with an eluent (1% ammonia water: 6%-10% methanol: 93%-89% dichloromethane) were carried out. The elution product was then collected, concentrated, evaporated to dryness, and dried, thus obtaining the product 46-49: 0.2613 g, yield: 56.64%.

1265  1266
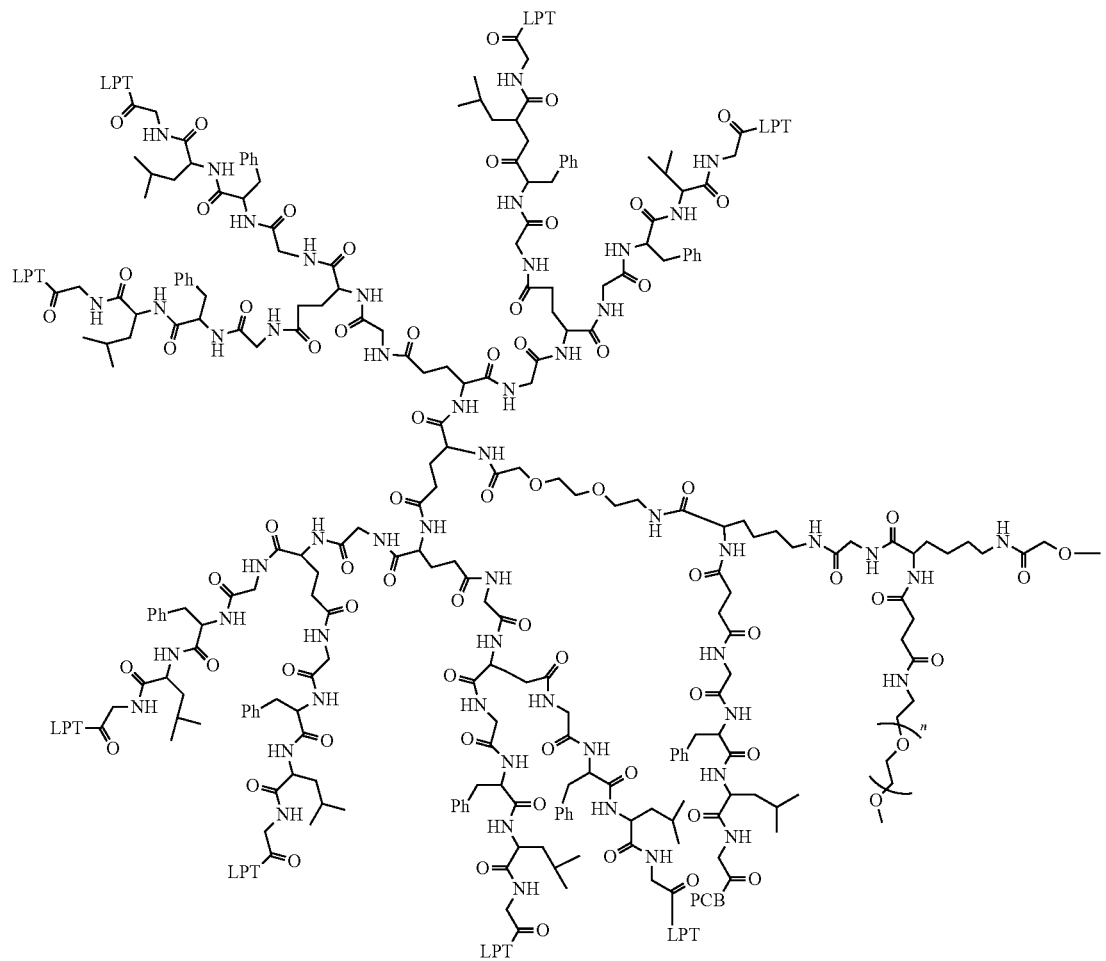
46-51

-continued
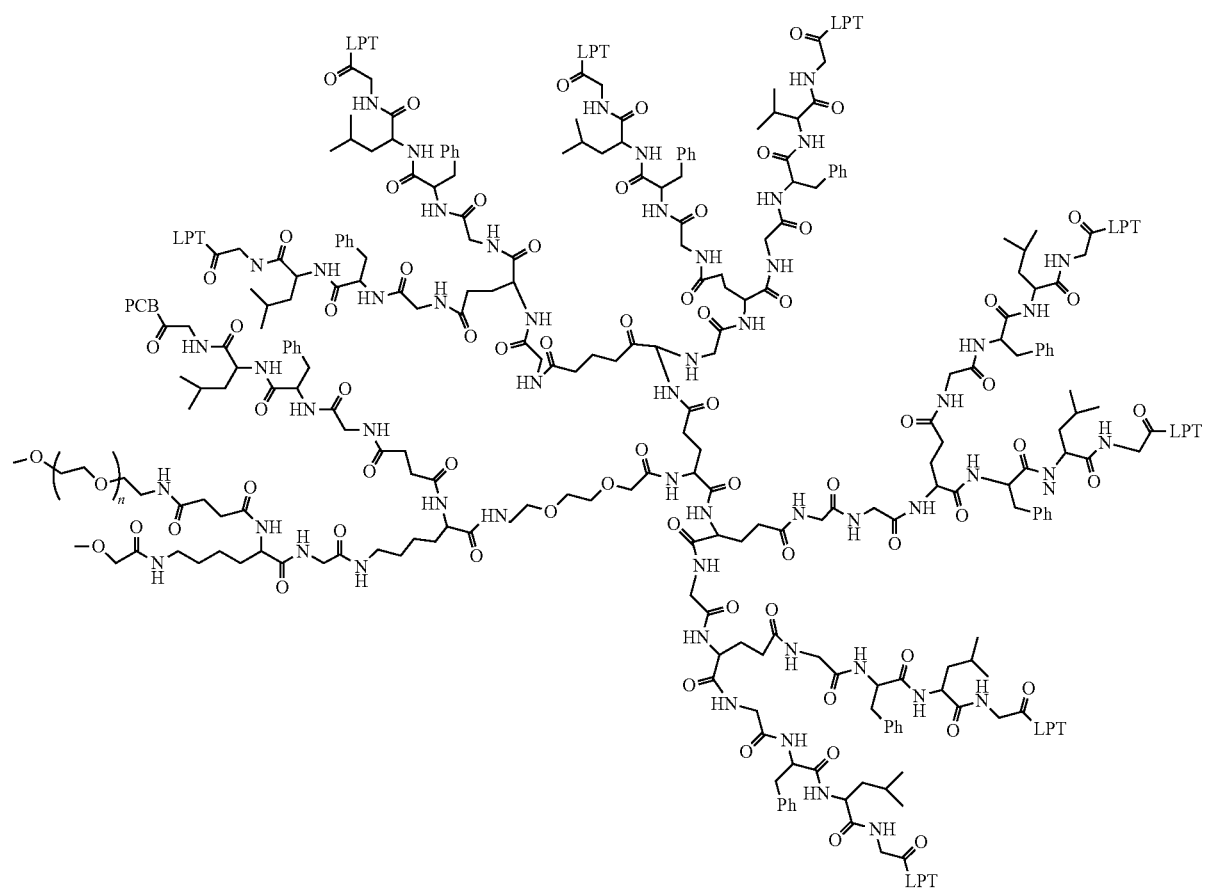

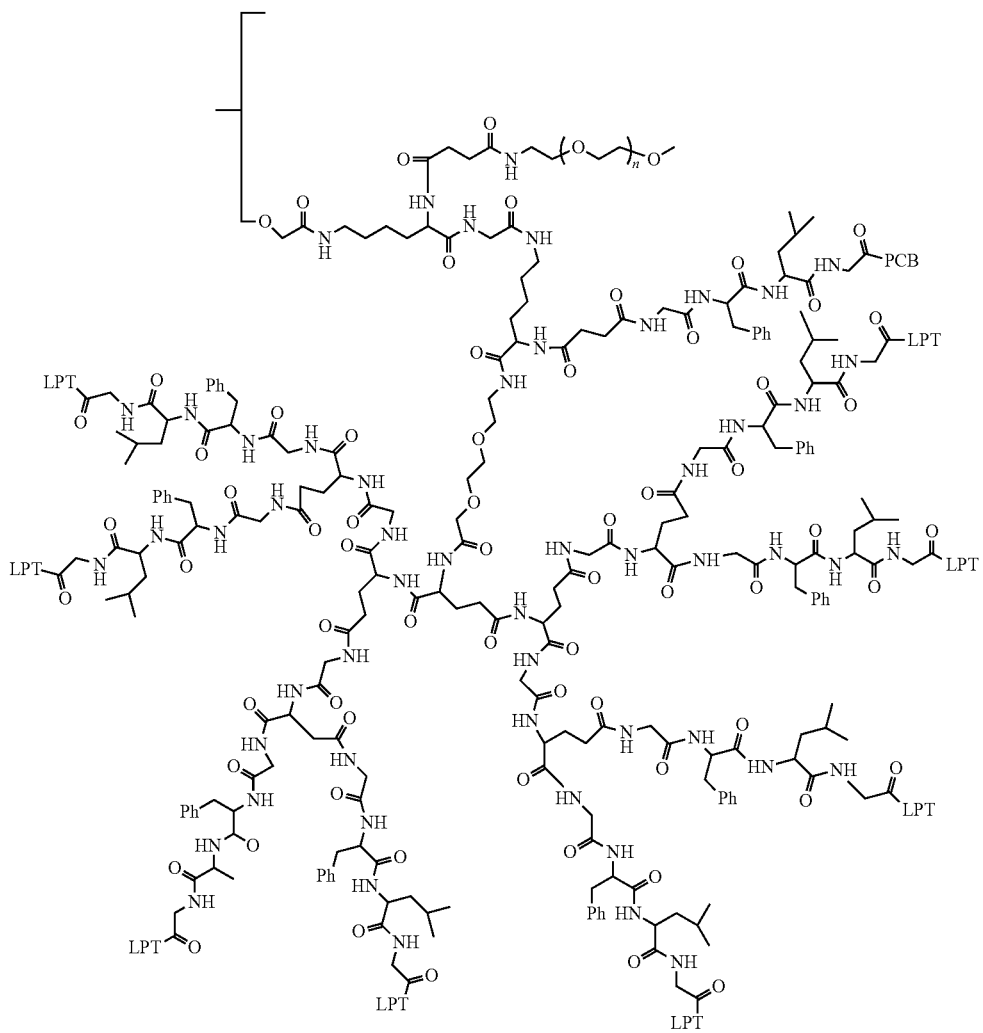

46-49 (0.2613 g, 0.0085 mmol), M-NH$_2$·HCl-10K (0.3253 g, 0.0308 mmol), HBTU (0.0146 g, 0.0385 mmol) and HOBT (0.0052 g, 0.0385 mmol) were added in a 250 mL round-bottomed flask, and dissolved with DMF (20 mL), and then the mixed solution was stirred at −5° C. for about 30 minutes. Then DIEA (0.1 mL, 1.9422 mmol) was slowly added dropwise. At the end of the addition, the obtained solution was stirred to react at −5° C. for 30 minutes, and then moved to room temperature and stirred to react in the dark at a low speed for one week. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated five times, to obtain a powdery solid, and a solid product was obtained by filtering. The solid product was washed with methyl tert-butyl ether (100 mL), and dissolved with a mixed solvent (60 mL) of 20% methanol/dichloromethane, silica gel powder (50 mL) was added to the obtained solution, and the operations of evaporation, dry sample loading, column chromatography, and elution with an elutent (1% ammonia water: 5%-15% methanol: 94%-84% dichloromethane) were carried out. The elution product was then collected, concentrated, evaporated to dryness, and dried, thus obtaining the product 46-51: 0.2251 g, yield: 42.66%.

$^1$H NMR (600 MHz, DMSO-d$_6$) δ 8.97-8.53 (m, 41H), 8.32-7.90 (m, 183H), 7.90-7.60 (m, 57H), 7.54-7.45 (m, 27H), 7.38-6.99 (m, 254H), 6.67-6.53 (m, 21H), 5.26-5.24 (m, 42H), 4.87-4.03 (m, 168H), 3.87-3.40 (m, 2876H), 3.24-3.11 (m, 110H), 3.10-2.93 (m, 142H), 2.92-2.70 (m, 108H), 2.69-2.61 (m, 20H), 2.43-2.00 (m, 104H), 1.86-1.47 (m, 162H), 1.23-1.11 (m, 61H), 0.99-0.66 (m, 162H).

29. Synthesis of 44-234 (Compound No. 29)
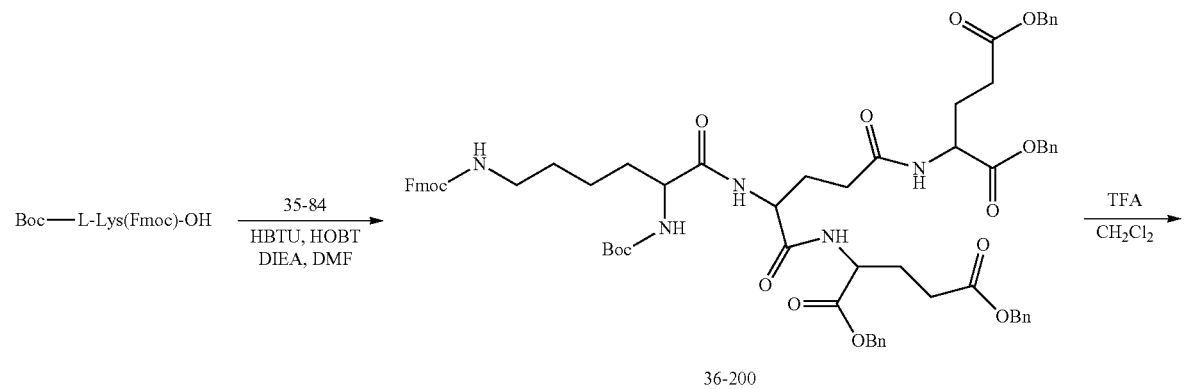
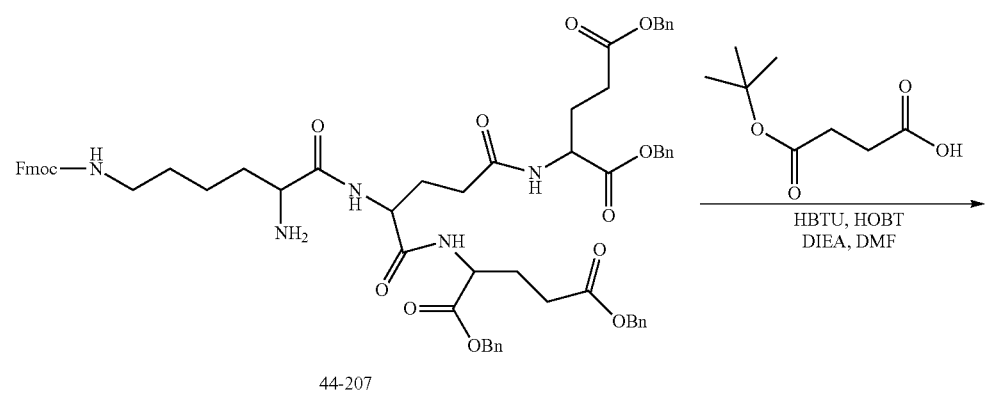
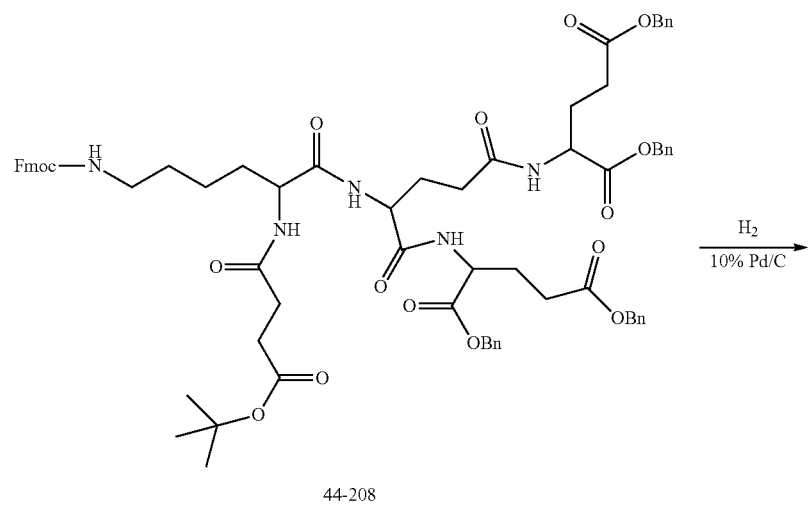

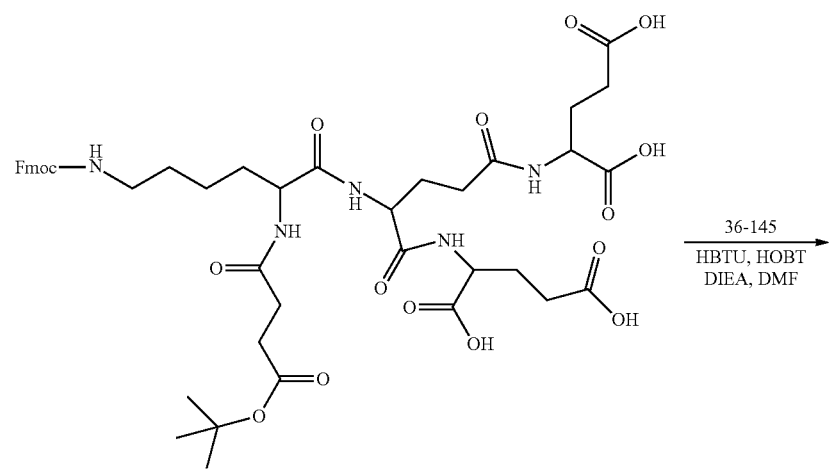
44-212
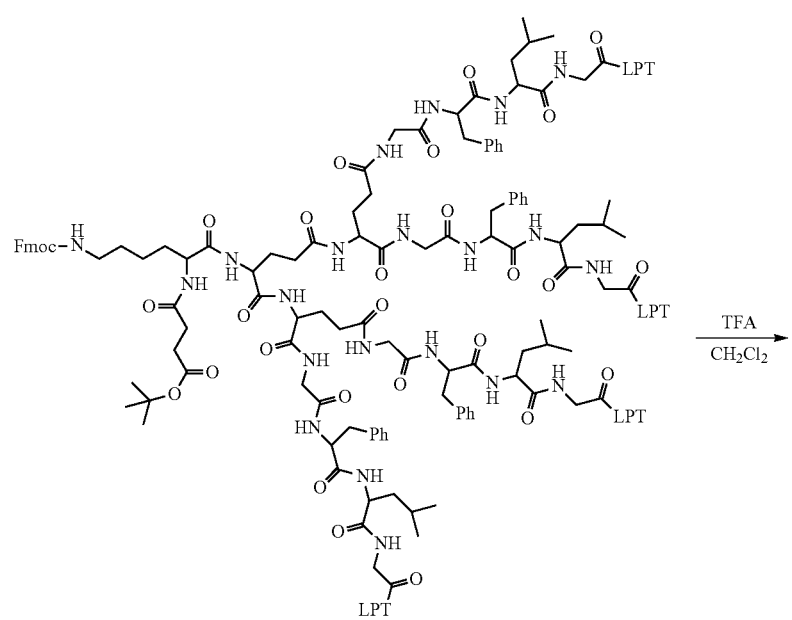
44-213

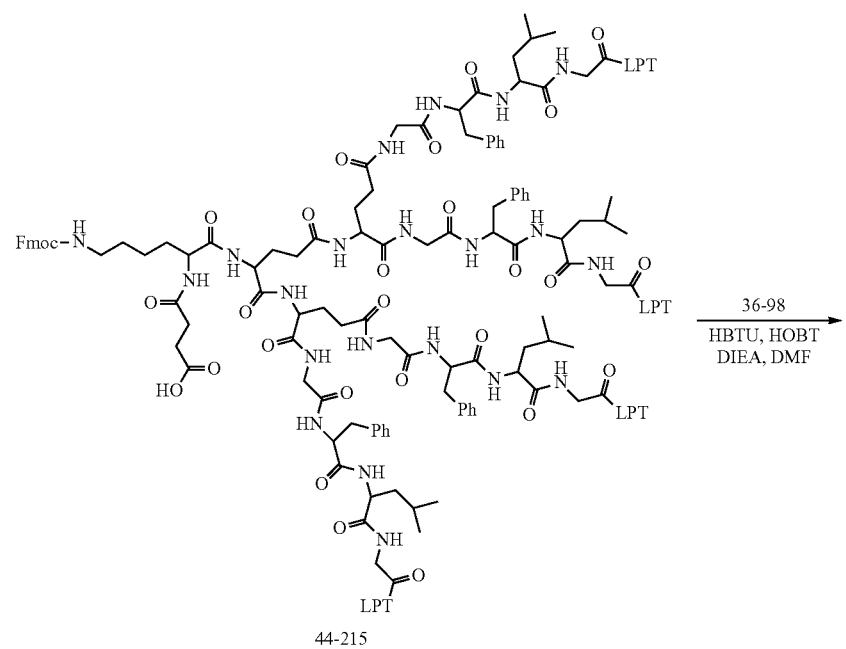
44-215
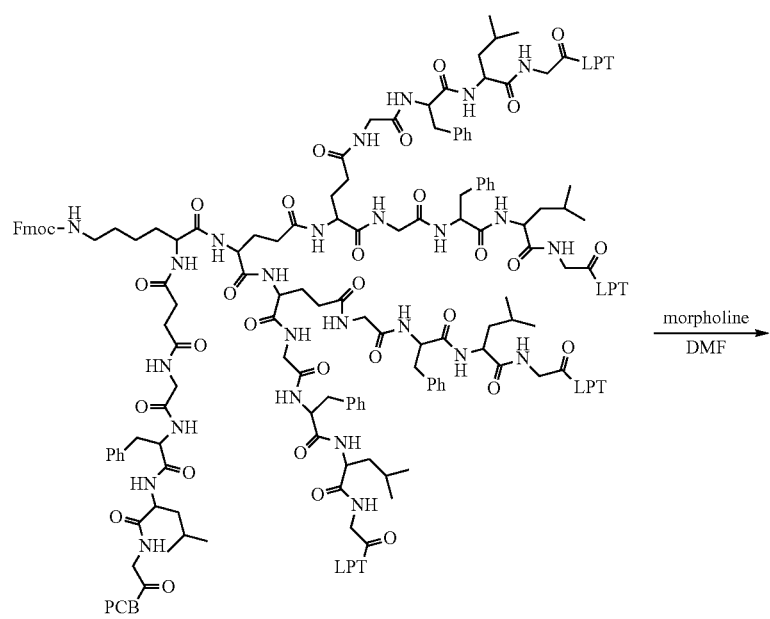
44-218

-continued
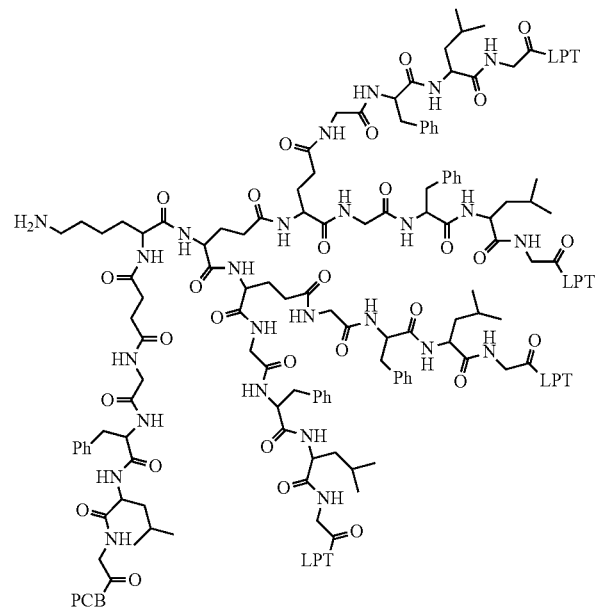
44-219
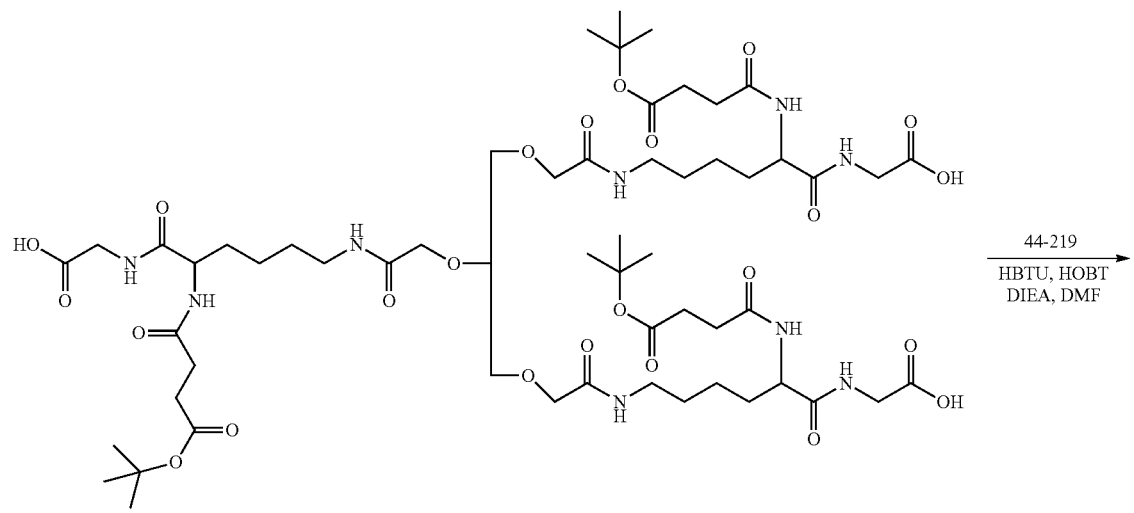
46-46

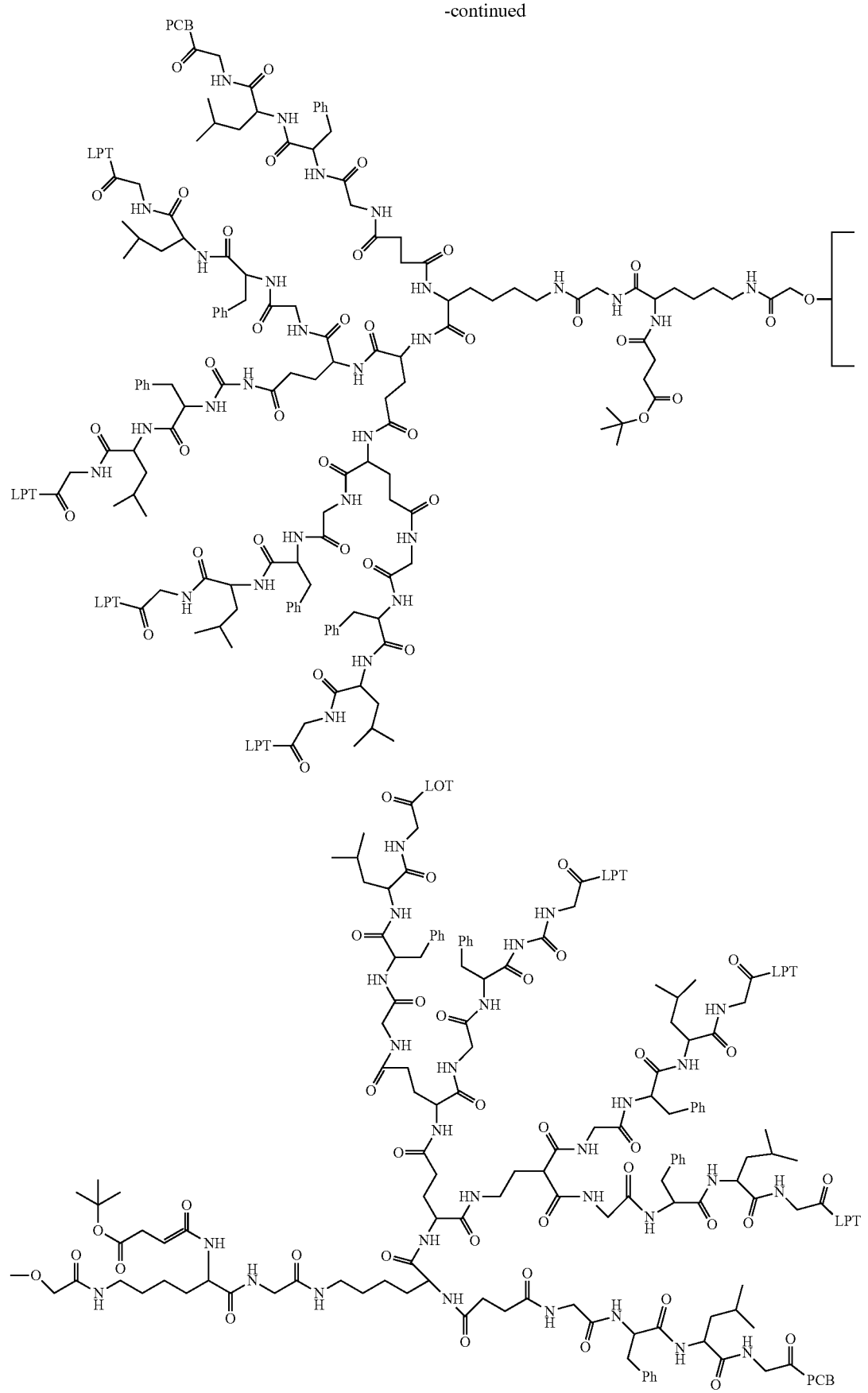

1281　-continued　1282
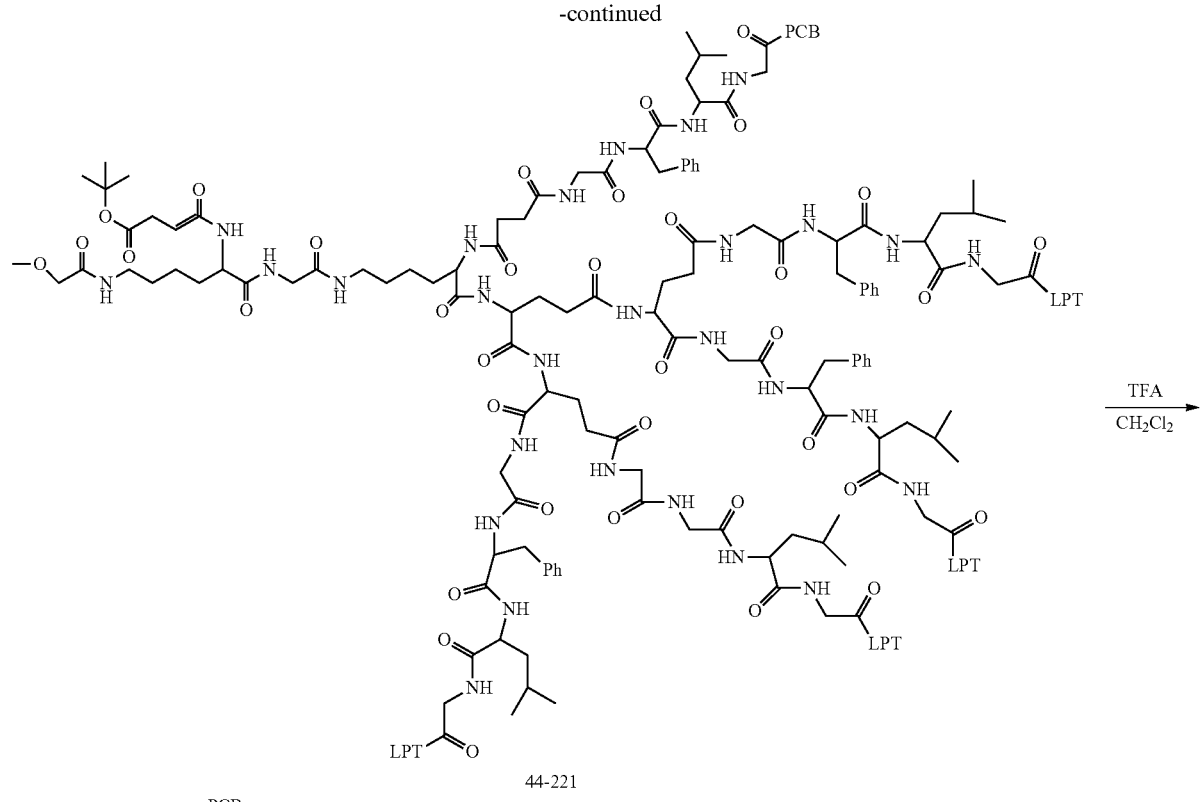
44-221
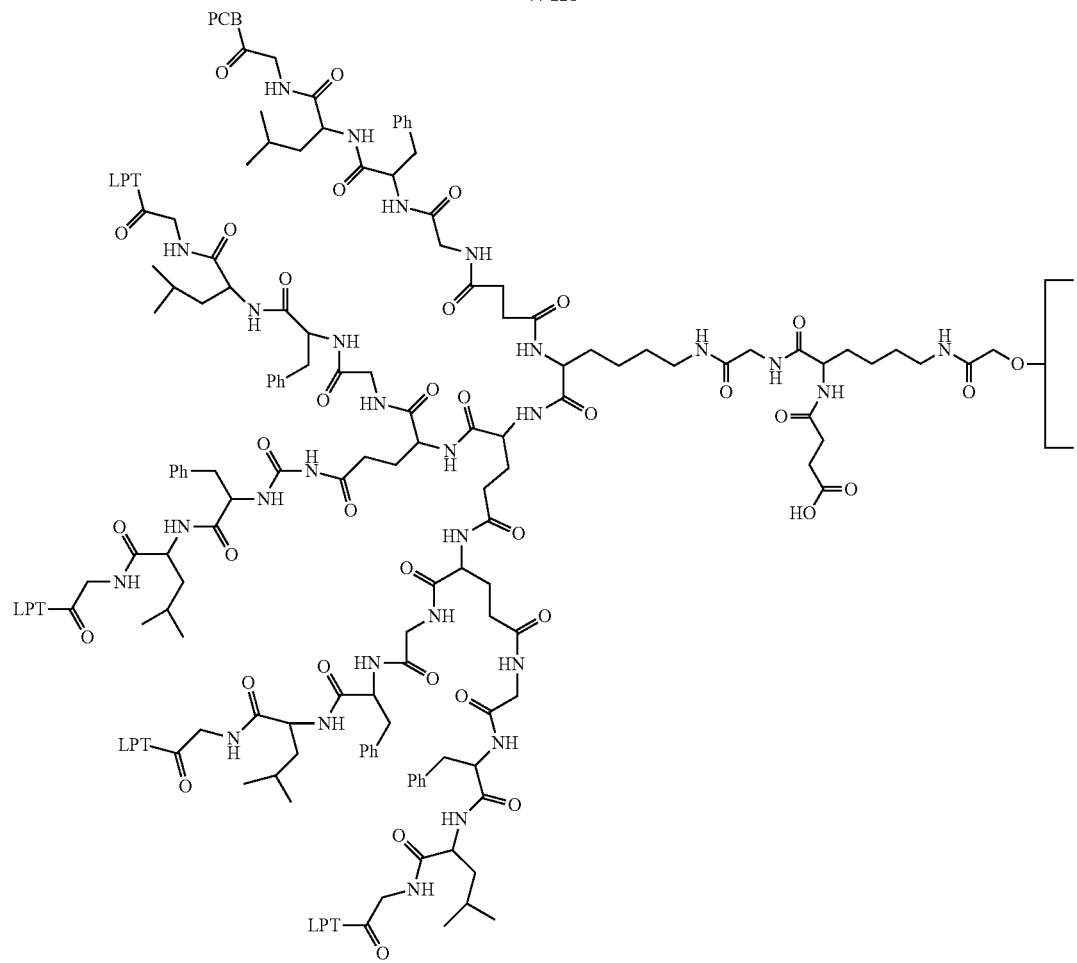

-continued
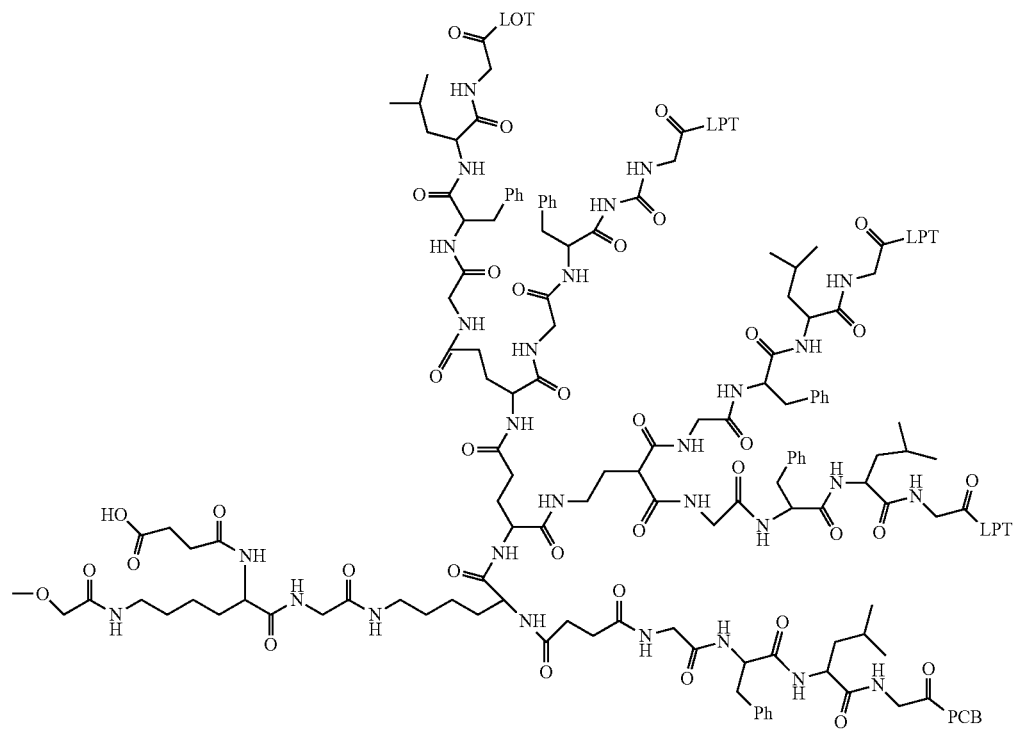
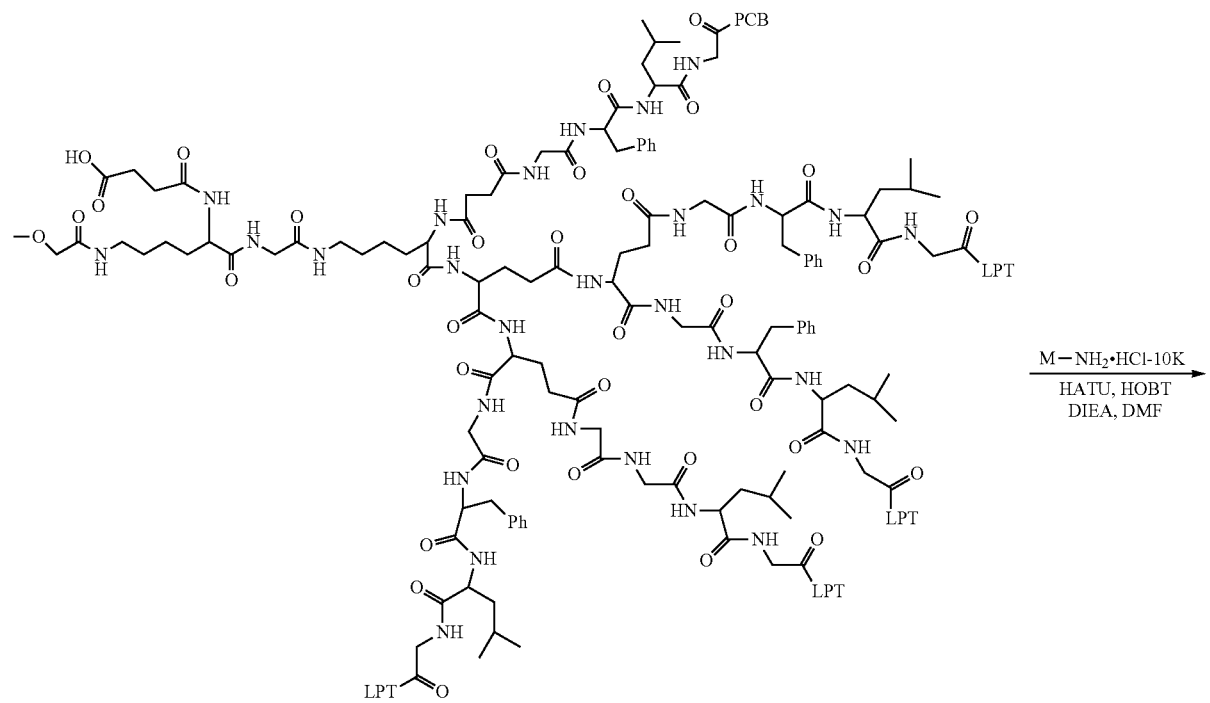
44-232
$\xrightarrow[\text{DIEA, DMF}]{\text{M—NH}_2\cdot\text{HCl-10K}}_{\text{HATU, HOBT}}$

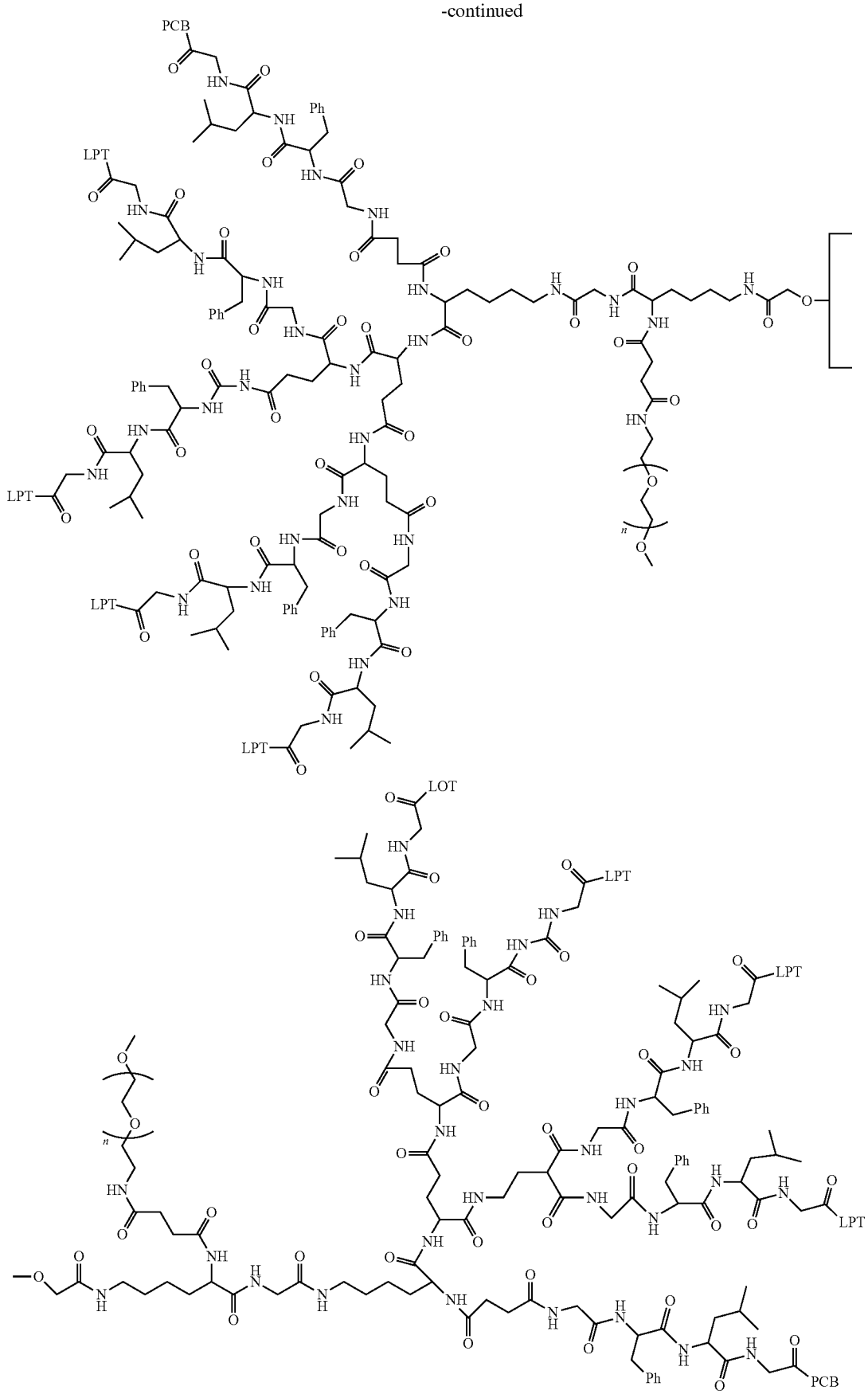

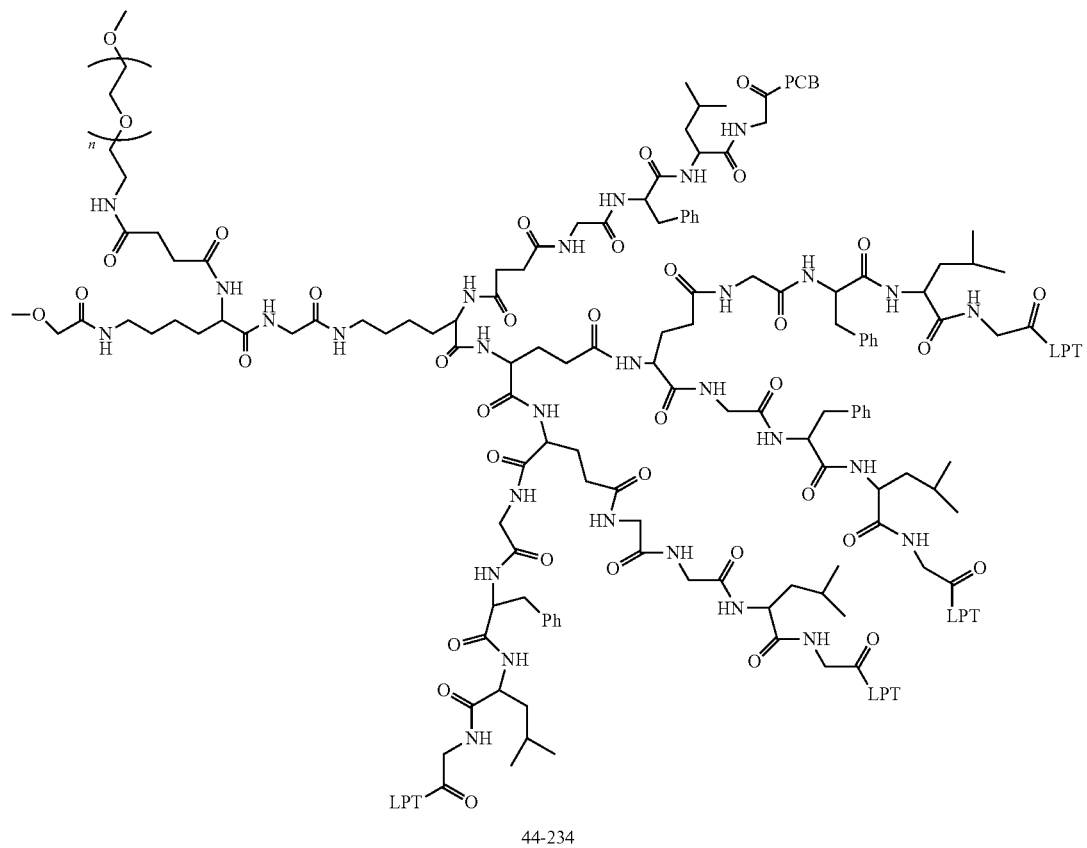

44-234

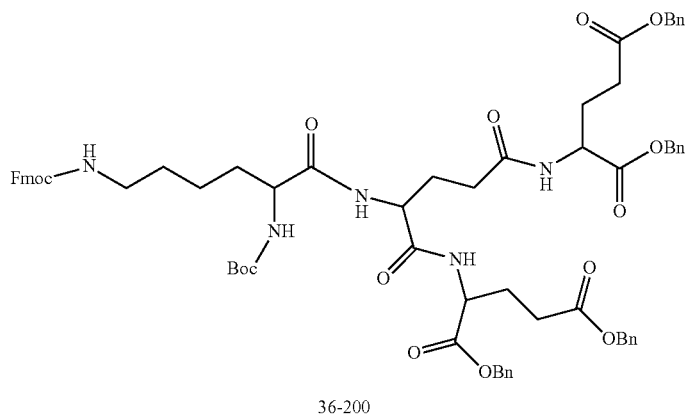

36-200

35-84 (8.99 g, 11.7386 mmol), Boc-L-Lys (Fmoc)-OH (5.0 g, 10.6714 mmol), HBTU (6.0706 g, 16.0072 mmol) and HOBT (2.1629 g, 16.0072 mmol) were added in a 500 mL round-bottomed flask, and dissolved with DMF (80 mL), and then the mixed solution was stirred at −5° C. for about 30 minutes. Then DIEA (10.6 mL, 64.0287 mmol) was slowly added dropwise. At the end of the addition, the obtained solution was stirred to react at −5° C. for 3 hours. At the end of the reaction, the reaction solution was transferred to a 1 L separatory funnel, saturated sodium chloride solution (300 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, saturated sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, evaporated to dryness, and dried, thus obtaining the product 36-200: 12.9804 g.

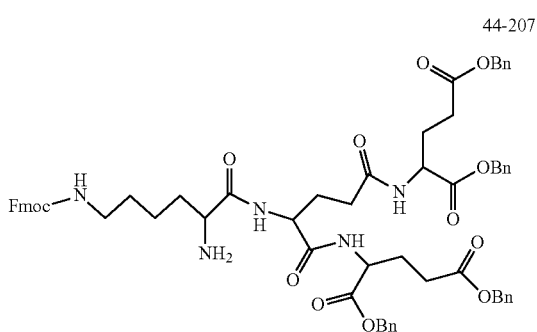

44-207

36-200 (11.9 g, 9.7832 mmol) was added in a 500 mL round-bottomed flask, and dissolved with dichloromethane (20 mL), TFA (10.9 mL, 146.748 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), thus obtaining the product 44-207: 8.351 g, yield: 76.47%.

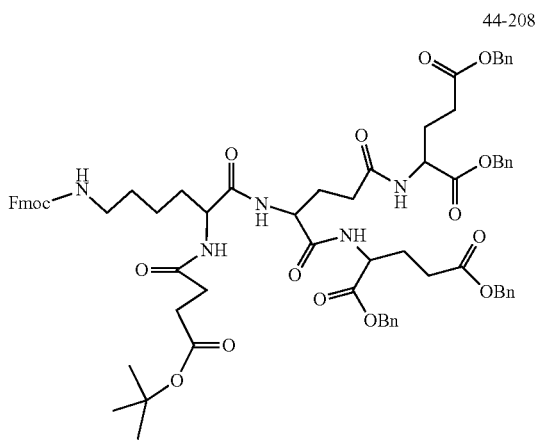

44-208

Mono-tert-butyl succinate (1.5638 g, 8.9775 mmol), 44-207 (8.351 g, 7.4812 mmol), HBTU (4.2558 g, 11.2218 mmol) and HOBT (1.5163 g, 11.2218 mmol) were added in a 500 mL round-bottomed flask, and dissolved with DMF (80 mL), and then the mixed solution was stirred at −5° C. for about 30 minutes. Then DIEA (9.9 mL, 59.8499 mmol) was slowly added dropwise. At the end of the addition, the obtained solution was stirred to react at −5° C. for 3 hours. At the end of the reaction, the reaction solution was transferred to a 1 L separatory funnel, saturated sodium chloride solution (300 mL) and ethyl acetate (200 mL) were added, the obtained solution was shaken for extraction, and then the organic phase was separated from the aqueous phase. Then ethyl acetate (100 mL) was added to the aqueous phase, the obtained solution was shaken for extraction, and then the organic phase was separated from the aqueous phase. Then, the obtained organic phases were combined, saturated sodium chloride solution (300 mL) was added to the organic phase, the obtained solution was shaken for extraction, and then the organic phase was separated from the aqueous phase. Then, deionized water (300 mL) was added to the organic phase, the obtained solution was shaken for extraction, and then the organic phase was separated from the aqueous phase. Finally, the organic phase was concentrated, and evaporated to dryness. The obtained dry product was dissolved with a mixed solvent (100 mL) of 20% methanol/dichloromethane, silica gel powder (50 mL) was added to the obtained solution, and the operations of evaporation, dry sample loading, column chromatography, and elution with an elutent (2%-8% methanol: 98%-92% dichloromethane) were carried out. The elution product was then collected, concentrated, evaporated to dryness, and dried, thus obtaining the product 44-208: 2.5268 g, yield: 35.85%.

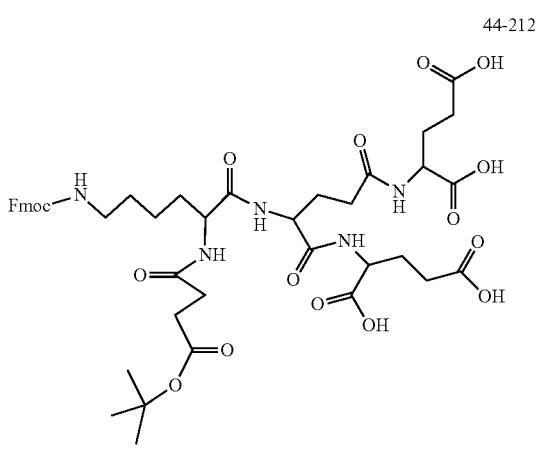

44-212

44-208 (2.5268 g, 1.9858 mmol) and 10% Pd/C (60 mg) were added in a hydrogenation reactor, and dissolved with DMF (30 mL). The hydrogenation reactor was sealed, hydrogen was introduced to a pressure of 2.2 MPa in the reactor, and then the mixed solution was stirred to react at room temperature overnight. At the end of the reaction, the reaction solution was taken out and evenly added dropwise to a sand core funnel filled with compacted diatomaceous earth, and then suction filtering was carried out. The diatomaceous earth was washed with DMF until it did not contain any product, thus obtaining a reaction product solution.

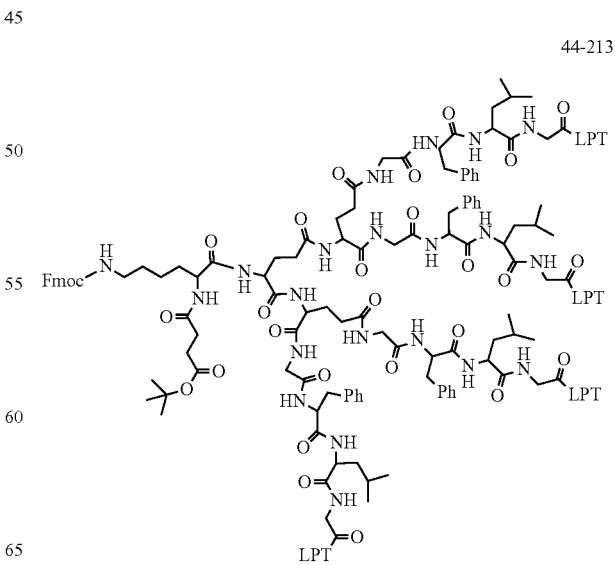

44-213

The solution of 44-212 (1.0846 g, 1.1893 mmol), 36-145 (5.0 g, 5.2329 mmol), HBTU (2.7062 g, 7.1358 mmol) and HOBT (0.9642 g, 7.1358 mmol) were added in a 500 mL round-bottomed flask, and dissolved with DMF (80 mL), and then the mixed solution was stirred at −5° C. for about 30 minutes. Then DIEA (3.5 mL, 21.4074 mmol) was slowly added dropwise. At the end of the addition, the obtained solution was stirred to react at −5° C. for 1 hour, and then moved to room temperature and stirred to react for 3 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 44-213: 5.5443 g.

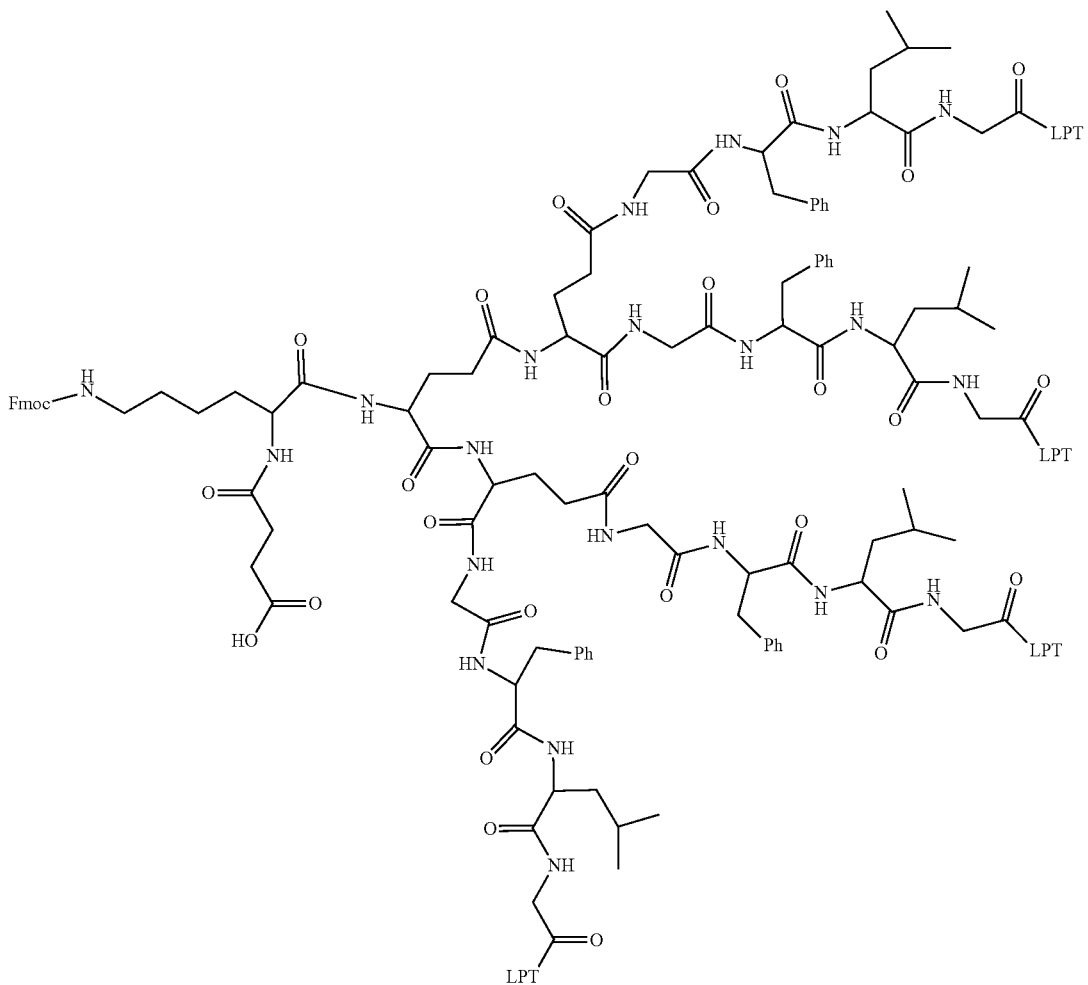

44-215

44-213 (5.5443 g, 1.1893 mmol) was added in a 500 mL round-bottomed flask, and dissolved with dichloromethane (20 mL), TFA (1.3 mL, 17.8395 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), thus obtaining the product 44-215: 5.0 g, yield: 91.28%.

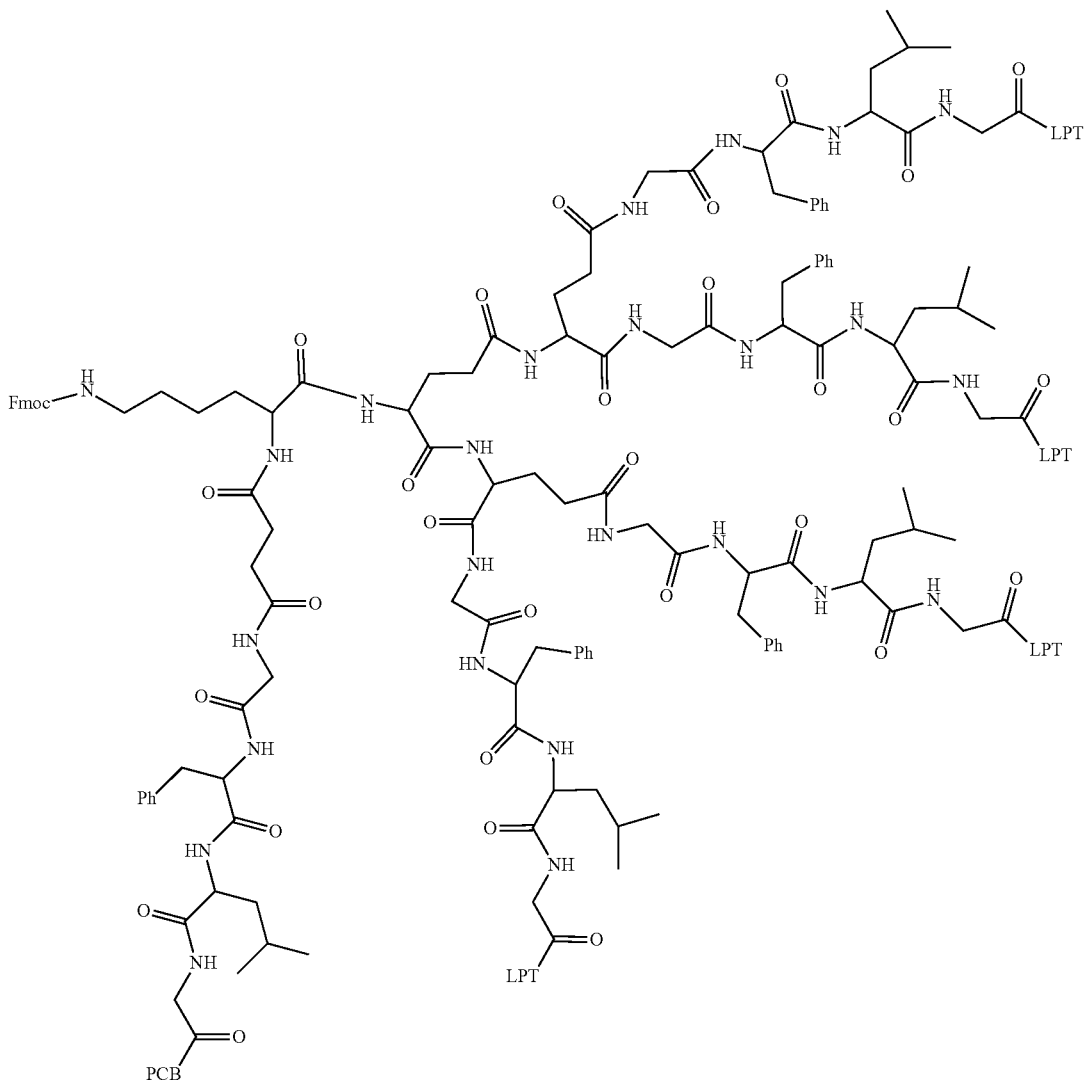

44-218

44-215 (5.0 g, 1.0856 mmol), 36-98 (1.16 g, 1.4113 mmol), HBTU (0.6176 g, 1.6284 mmol) and HOBT (0.22 g, 1.6284 mmol) were added in a 500 mL round-bottomed flask, and dissolved with DMF (80 mL), and then the mixed solution was stirred at −5° C. for bout 30 minutes. Then DIEA (1.1 mL, 6.5136 mmol) was slowly added dropwise. At the end of the addition, the obtained solution was stirred to react at −5° C. for 1 hour, and then moved to room temperature and stirred to react for 3 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 44-218: 5.8728 g.

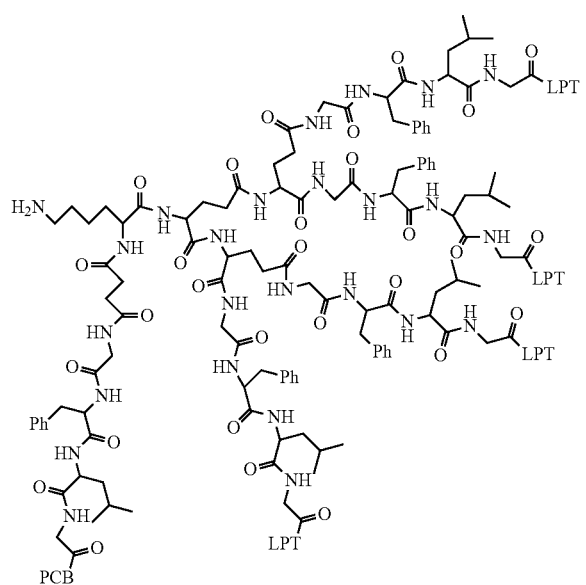

44-219

44-218 (5.8728 g, 1.0856 mmol) was added in a 500 mL round-bottomed flask, and dissolved with DMF (20 mL), morpholine (1.9 mL, 21.7120 mmol) was added with stirring, and then the mixed solution was stirred to react at room temperature for 2 hours. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated five times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dissolved with a mixed solvent (100 mL) of 20% methanol/dichloromethane, silica gel powder (60 mL) was added, and the operations of evaporation, dry sample loading, column chromatography, and elution with an elutent (1% ammonia water: 3%-15% methanol: 96%-84% dichloromethane) were carried out. The elution product was then collected, concentrated, evaporated to dryness, and dried, thus obtaining the product 44-219: 0.8841 g, yield: 15.7%.

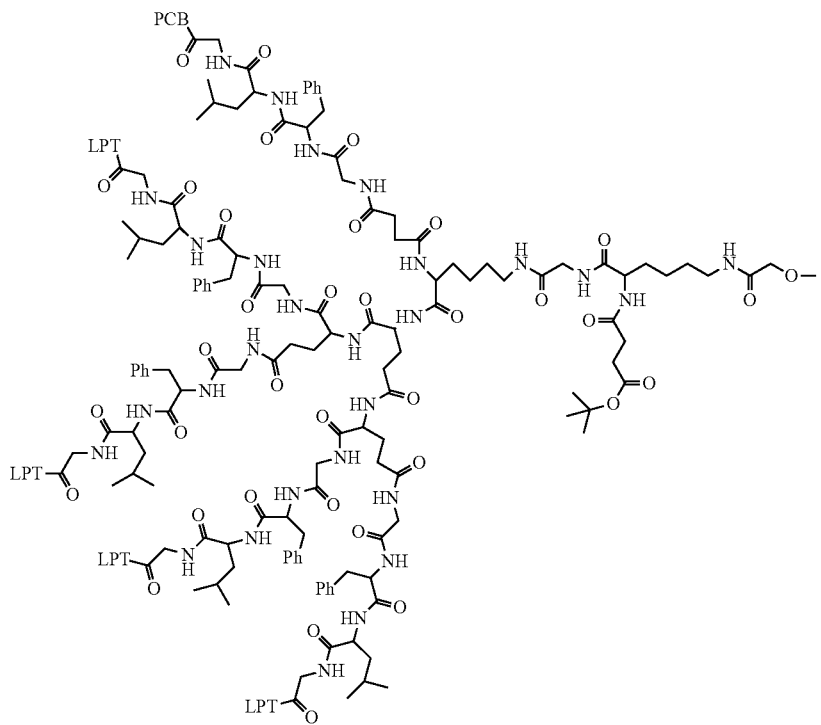

44-221

-continued
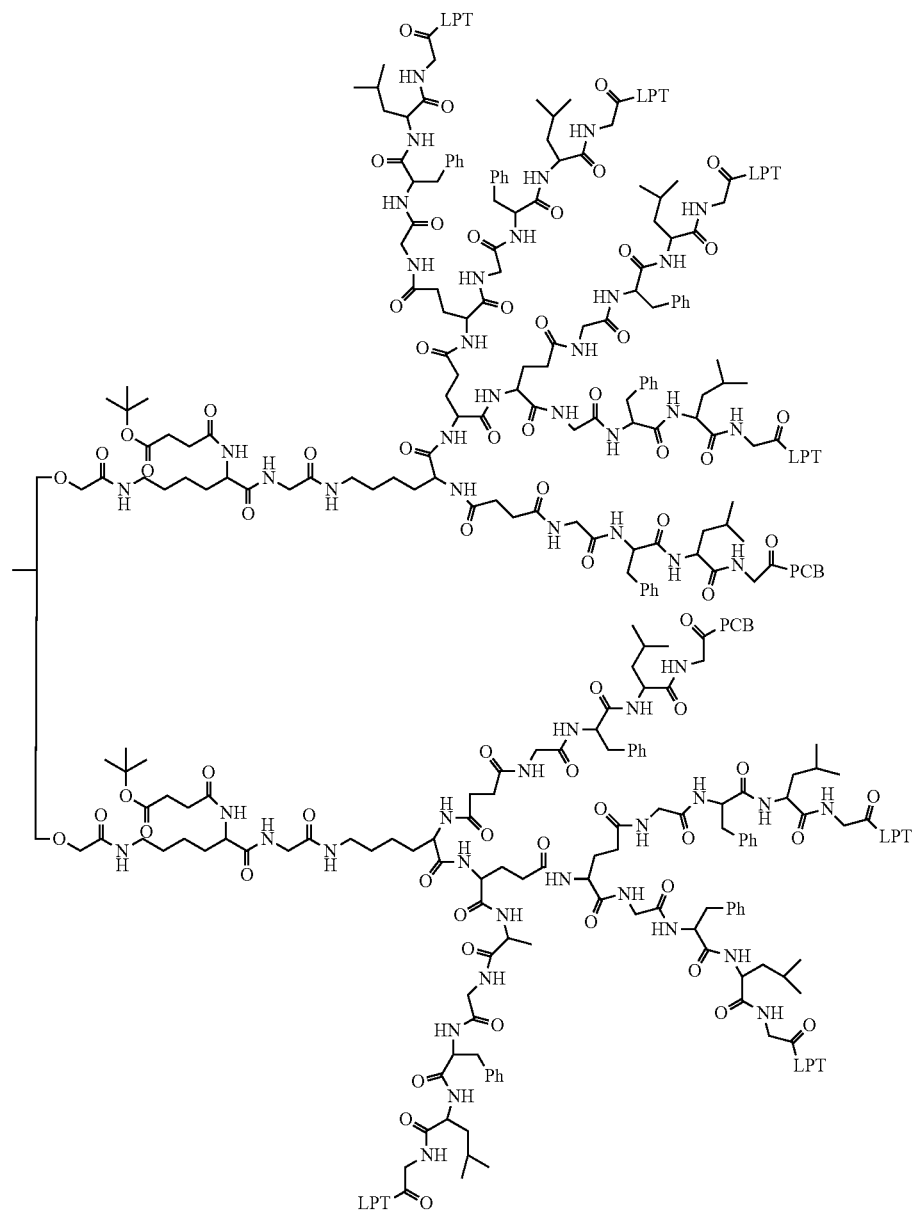

The solution of 46-46 (0.0611 g, 0.0473 mmol), 44-219 ((0.8841 g, 0.1704 mmol), HBTU (0.0808 g, 0.2130 mmol) and HOBT (0.0288 g, 0.2130 mmol) were added in a 500 mL round-bottomed flask, and dissolved with DMF (30 mL), and then the mixed solution was stirred at −5° C. for about 30 minutes. Then DIEA (0.1 mL, 0.6628 mmol) was slowly added dropwise. At the end of the addition, the obtained solution was stirred to react at −5° C. for 30 minutes, and then moved to room temperature and stirred in the dark overnight. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dried in an oven, thus obtaining the product 44-221: 0.7946 g.

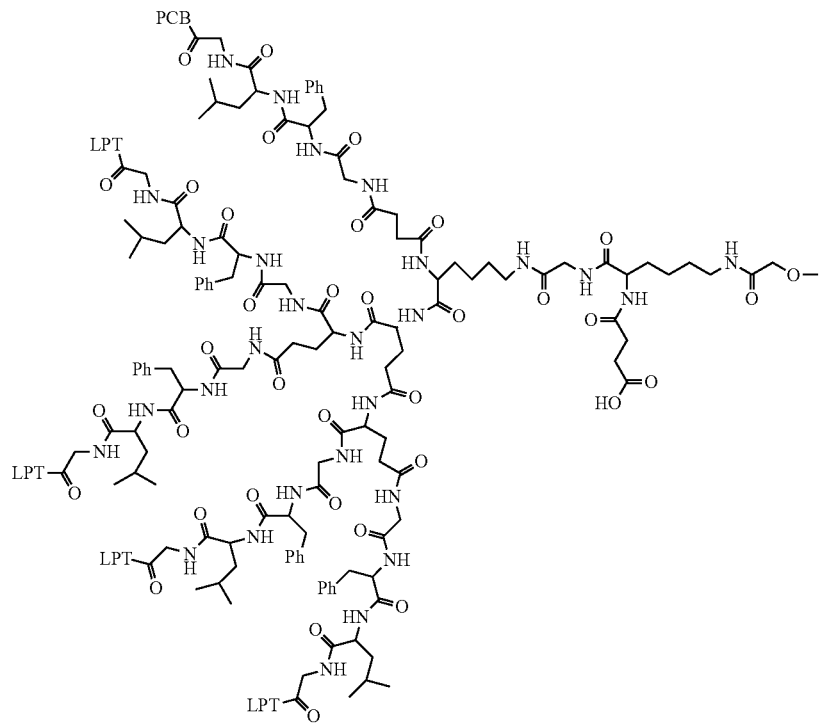

44-232

-continued
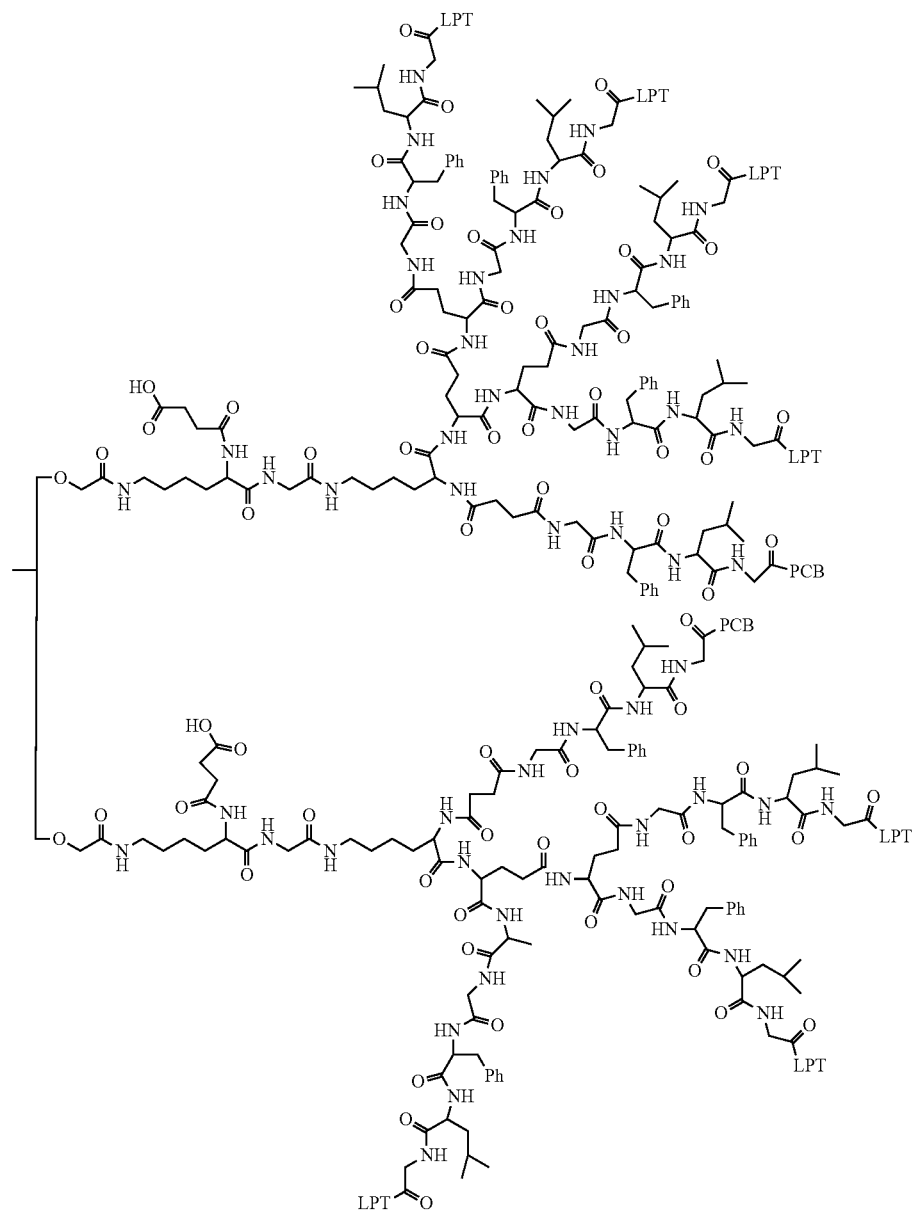

44-221 (0.7946 g, 0.0473 mmol) was added in a 250 mL round-bottomed flask, and dissolved with dichloromethane (20 mL), TFA (0.5 mL, 7.095 mmol) was added with stirring, and then the mixed solution was stirred to react at room temperature. At the end of the reaction, the reaction solution was first concentrated under reduced pressure to remove the dichloromethane, and then precipitated with methyl tert-butyl ether (150 mL) to obtain a powdery solid, and filtering was carried out. The solid product was washed with methyl tert-butyl ether (100 mL), and dissolved with a mixed solvent (60 mL) of 20% methanol/dichloromethane, silica gel powder (30 ml) was added to the obtained solution, and the operations of evaporation, dry sample loading, column chromatography, and elution with an elutent (1% ammonia water: 3%-10% methanol: 96%-89% dichloromethane) were carried out. The elution product was then collected, concentrated, evaporated to dryness, and dried, thus obtaining the product 44-232: 0.2239 g, yield: 28.46%.

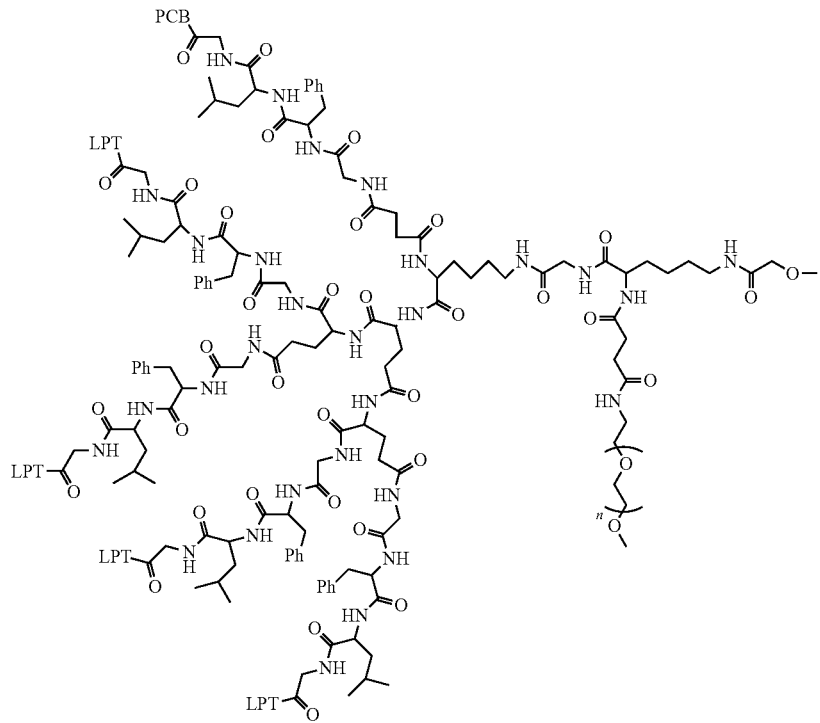

44-234

-continued

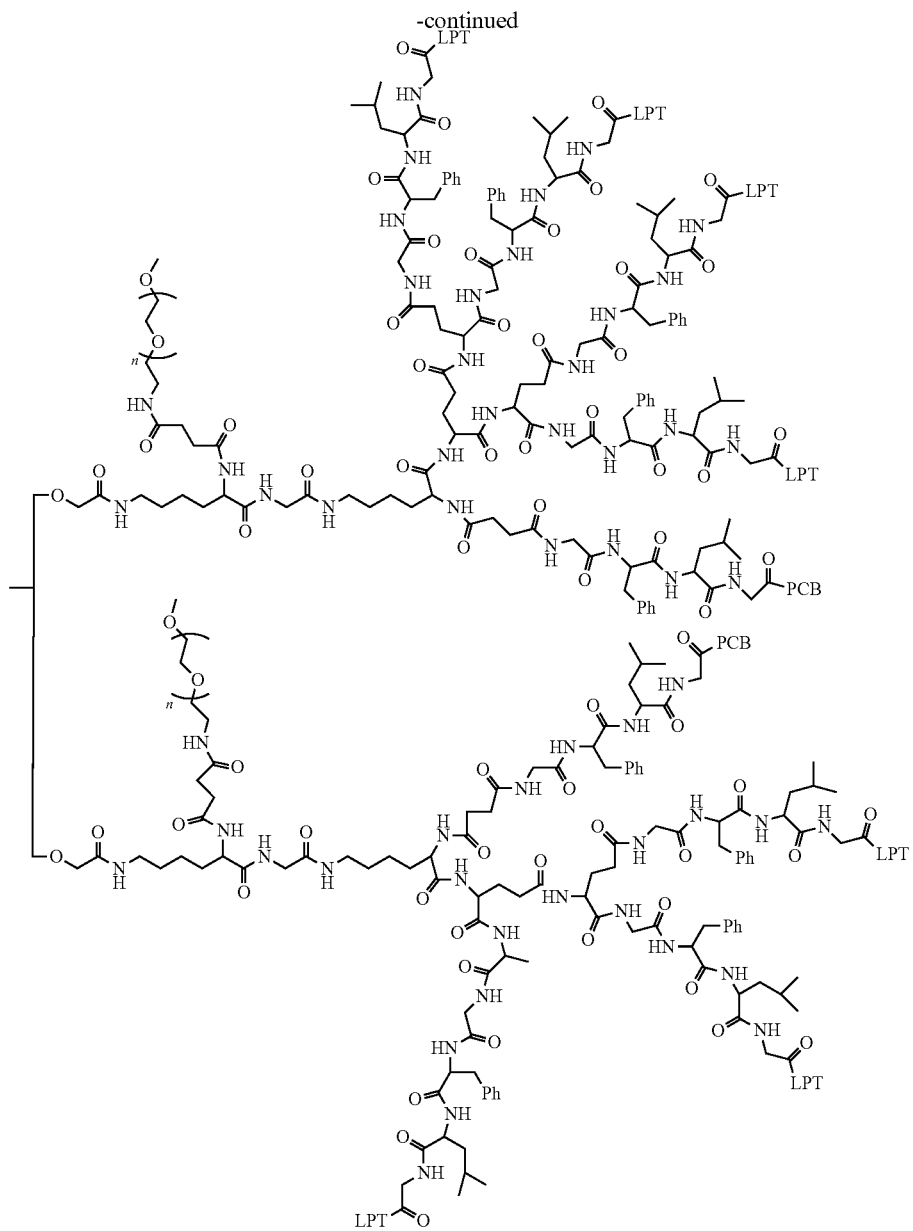

44-232 (0.2239 g, 0.0135 mmol), M-NH$_2$·HCl-10K (0.5547 g, 0.0525 mmol), HBTU (0.0230 g, 0.0606 mmol) and HOBT (0.0082 g, 0.0606 mmol) were added in a 250 mL round-bottomed flask, and dissolved with DMF (80 mL), and the mixed solution was stirred at −5° C. for about 30 minutes. Then DIEA (0.1 mL, 0.5385 mmol) was slowly added dropwise. At the end of the addition, the obtained solution was stirred to react at −5° C. for 1 hour, and then moved to room temperature and stirred in the dark for one week. At the end of the reaction, n-hexane (150 mL) and methyl tert-butyl ether (30 mL) were added to the reaction solution for precipitation, the supernatant was discarded, and n-hexane (150 mL) and methyl tert-butyl ether (30 mL) were then added to the lower oily solution for precipitation. Such operations were repeated three times, to obtain an oily solid. The oily solid was dissolved with dichloromethane (10 mL), the obtained solution was precipitated with methyl tert-butyl ether (150 mL) to separate out a powdery solid, and then a solid product was obtained by filtering. The solid product was washed with methyl tert-butyl ether (60 mL), and dissolved with a mixed solvent (100 mL) of 20% methanol/ dichloromethane, silica gel powder (50 mL) was added to the obtained solution, and the operations of evaporation, dry sample loading, column chromatography, and elution with an elutent (1% ammonia water: 3%-10% methanol: 96%-89% dichloromethane) were carried out. The elution product was then collected, concentrated, evaporated to dryness, and dried, thus obtaining the product 44-234: 0.2549 g, yield: 39.2%.

$^1$H-NMR (600 MHz, DMSO-d$_6$) δ 8.95-8.51 (m, 17H), 8.26-7.92 (m, 115H), 7.53-7.46 (m, 16H), 7.35-7.25 (m, 38H), 7.19-7.17 (m, 84H), 4.84-4.07 (m, 110H), 4.05-3.98 (m, 13H), 3.53-3.51 (m, 2874H), 3.25-2.94 (m, 117H), 2.89-2.85 (m, 73H), 2.77-2.73 (m, 47H), 2.69-2.61 (m, 16H), 2.41-2.29 (m, 52H), 2.23-1.75 (m, 71H), 1.59-1.48 (m, 77H), 1.34-1.23 (m, 30H), 0.85-0.83 (m, 60H)

30. Synthesis of 35-167 (Compound No. 32)
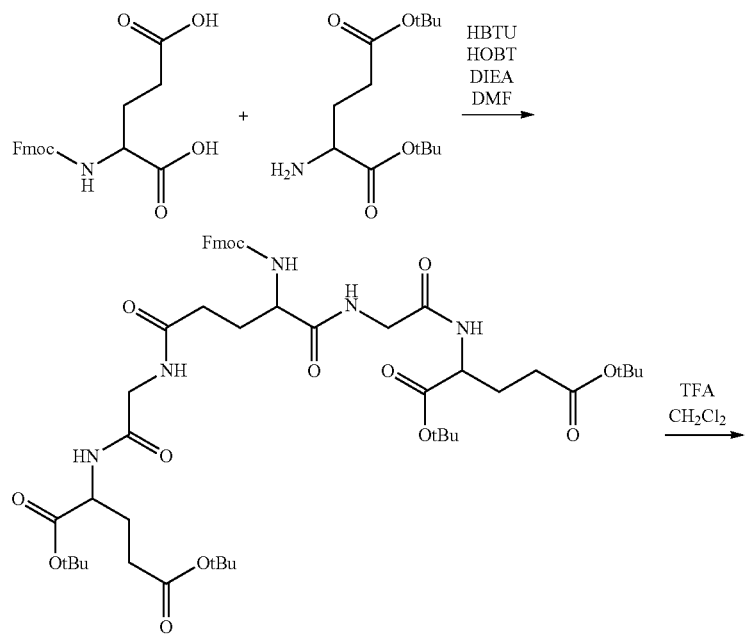
35-124
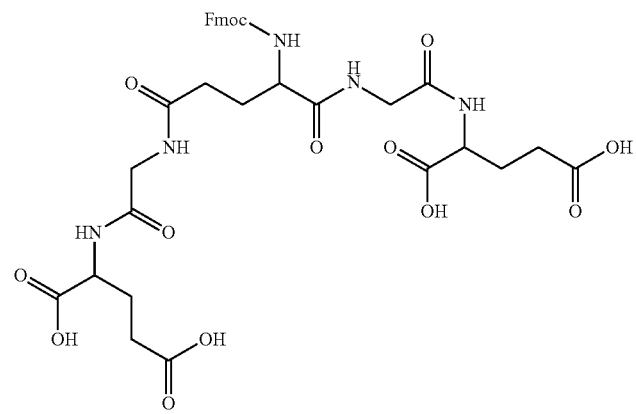
35-125
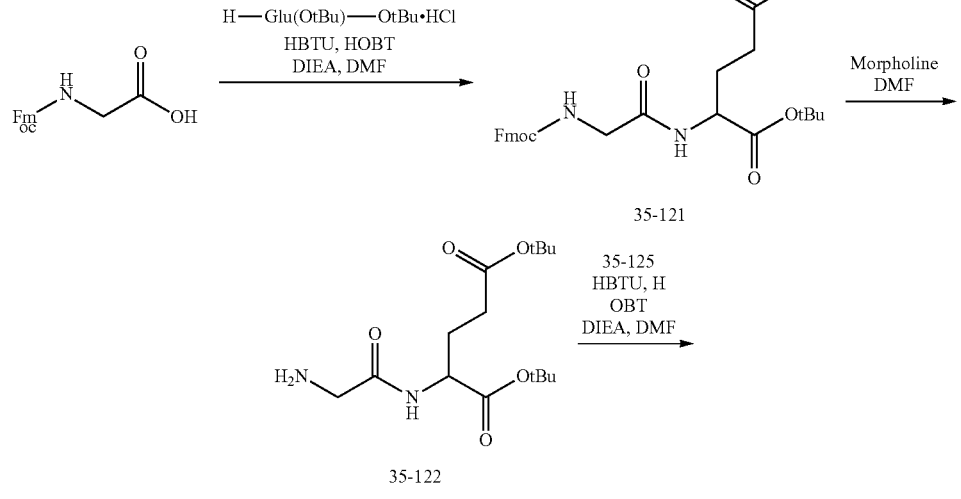

-continued
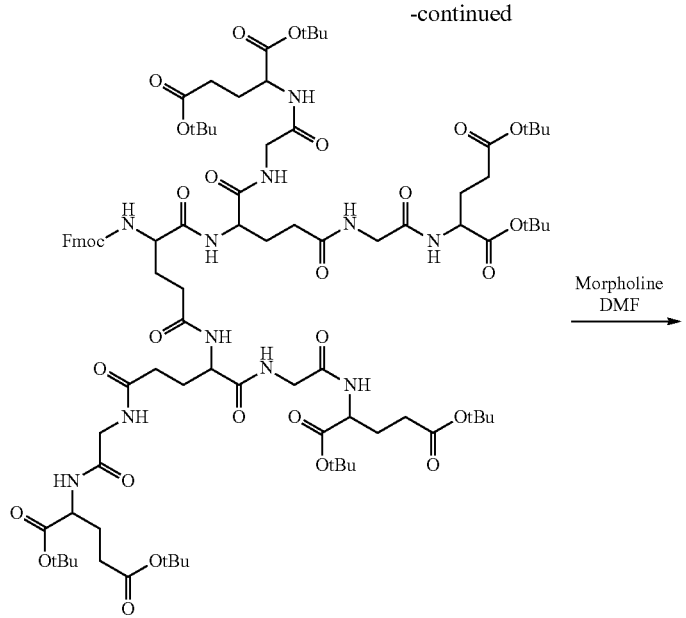
35-126
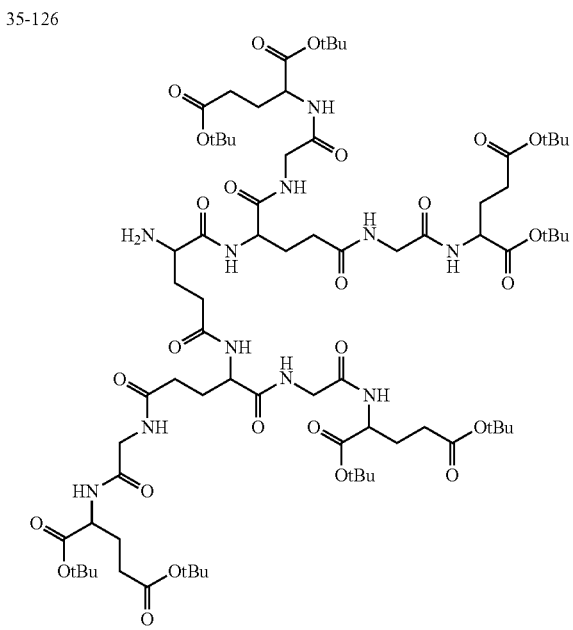
35-128
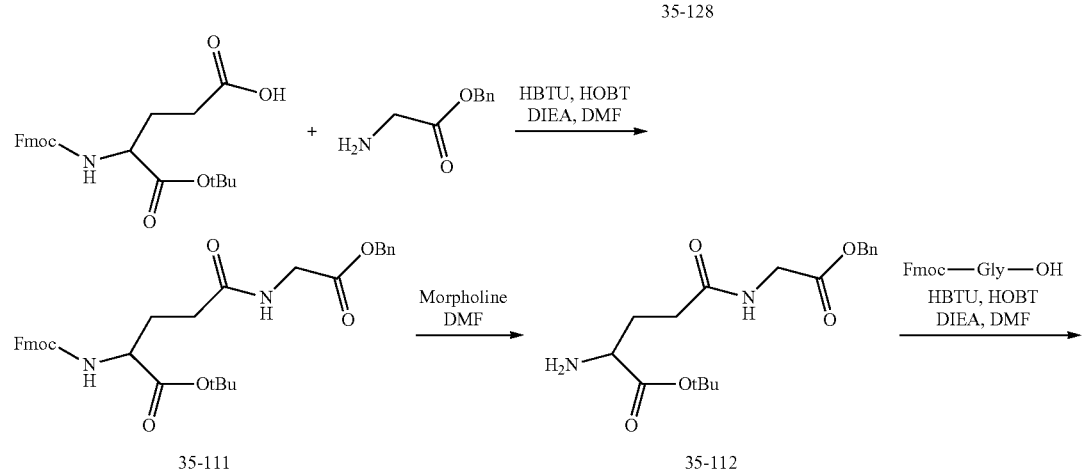
35-111    35-112

1311 1312
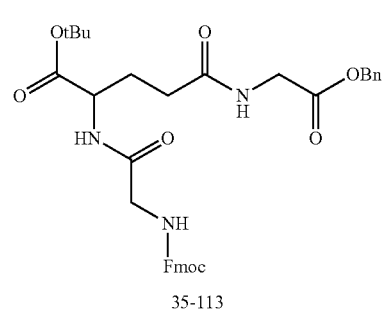
35-113
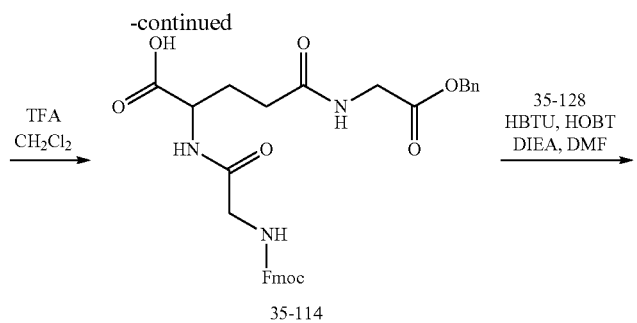
35-114
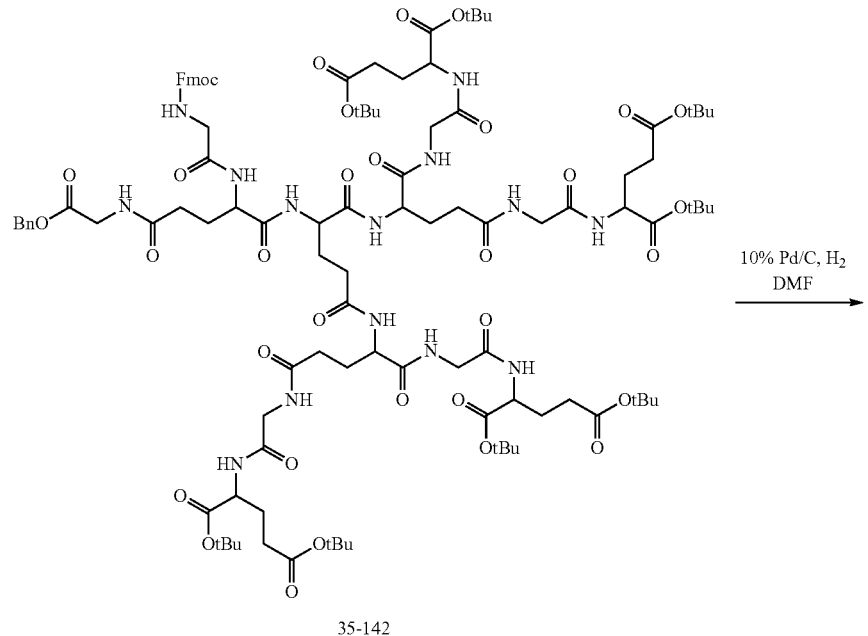
35-142
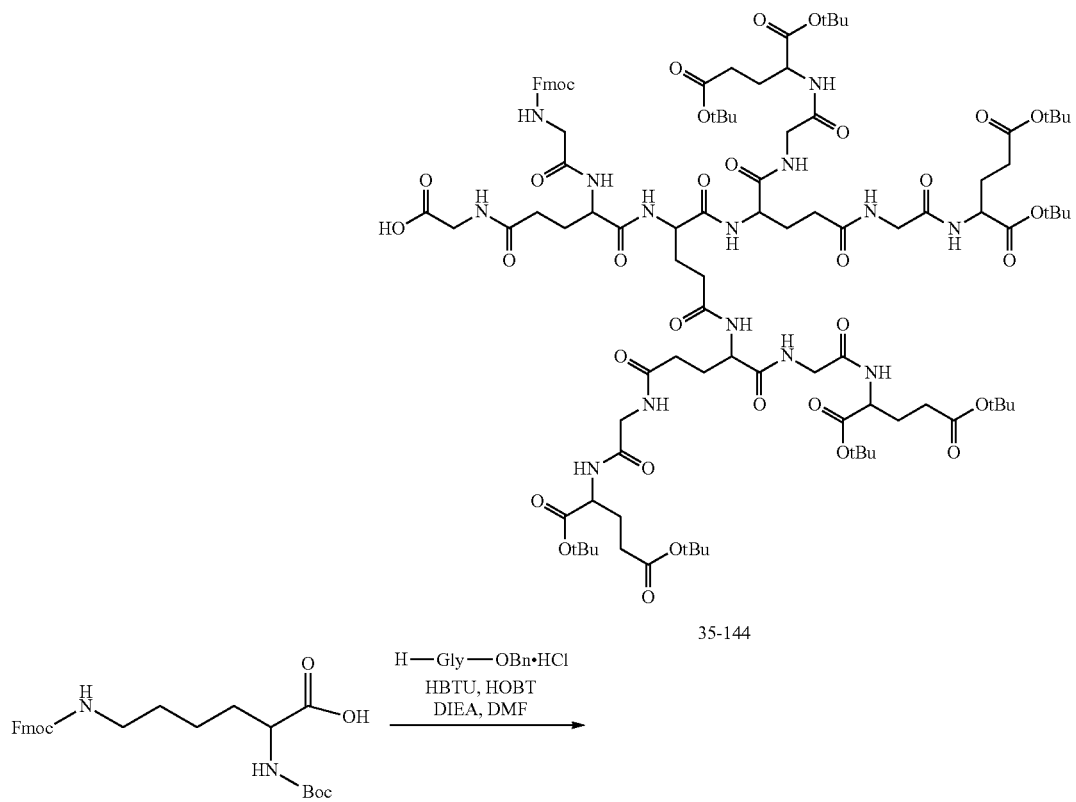
35-144

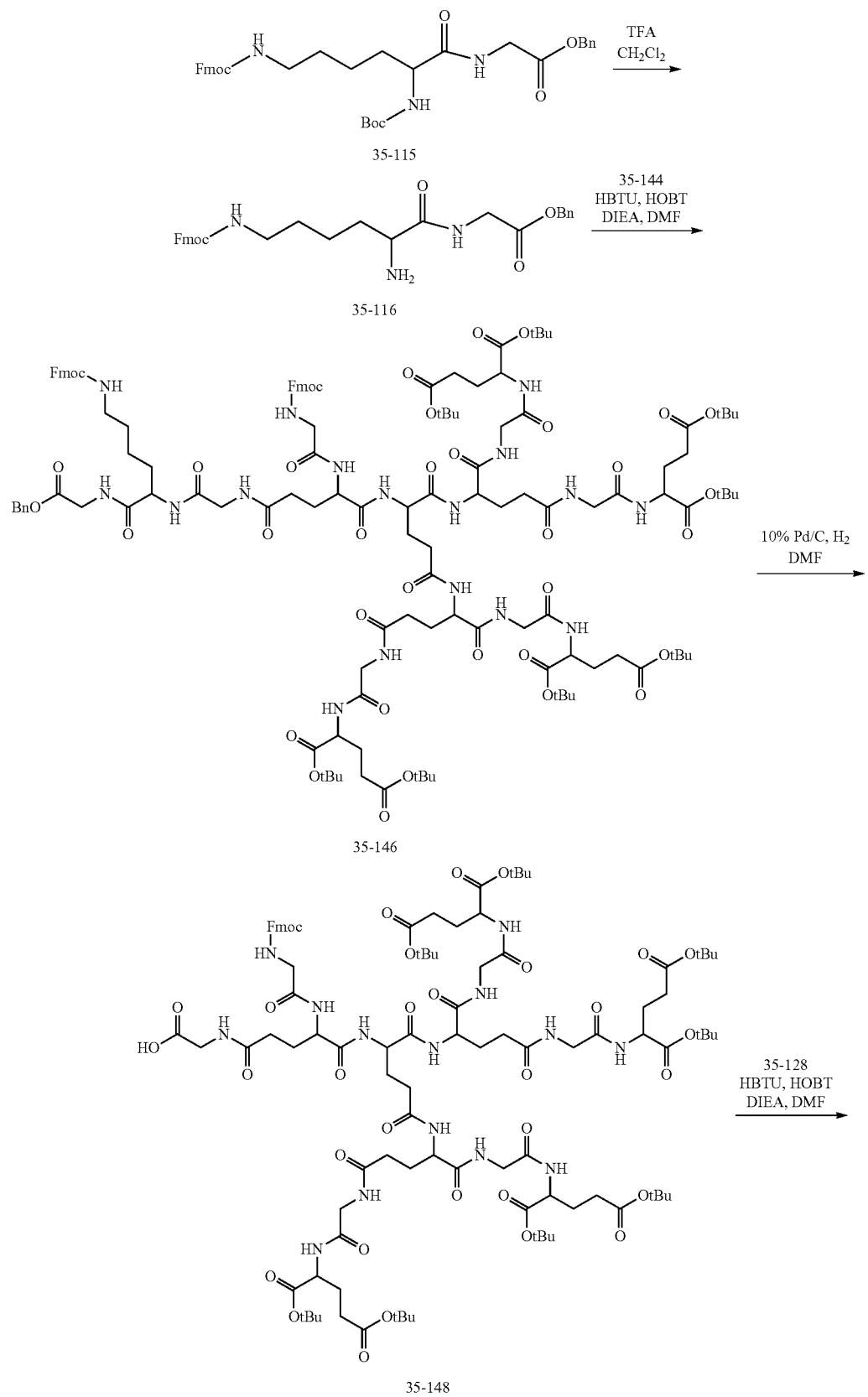

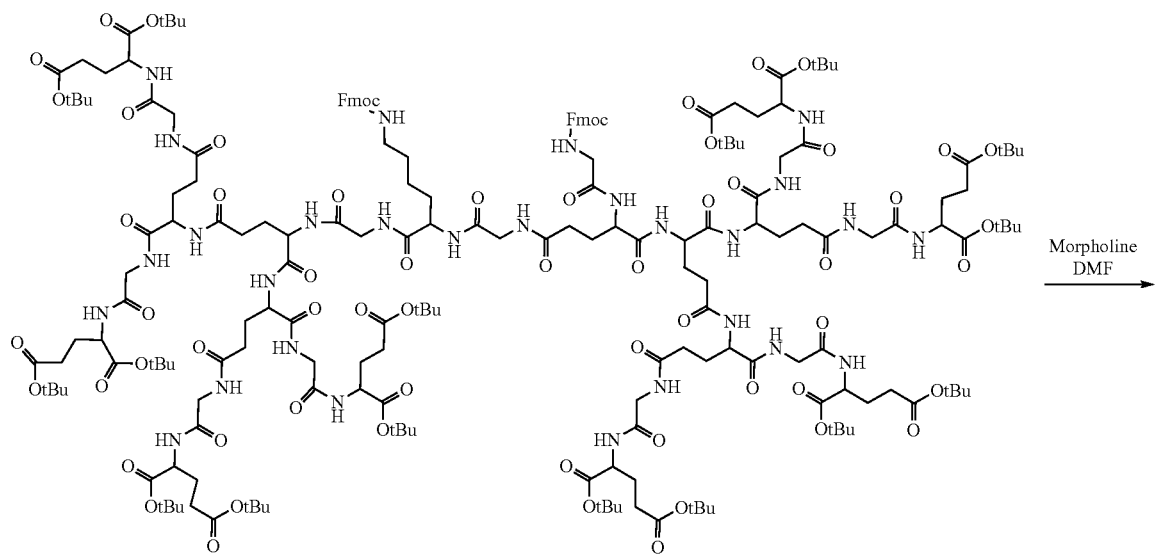
35-155
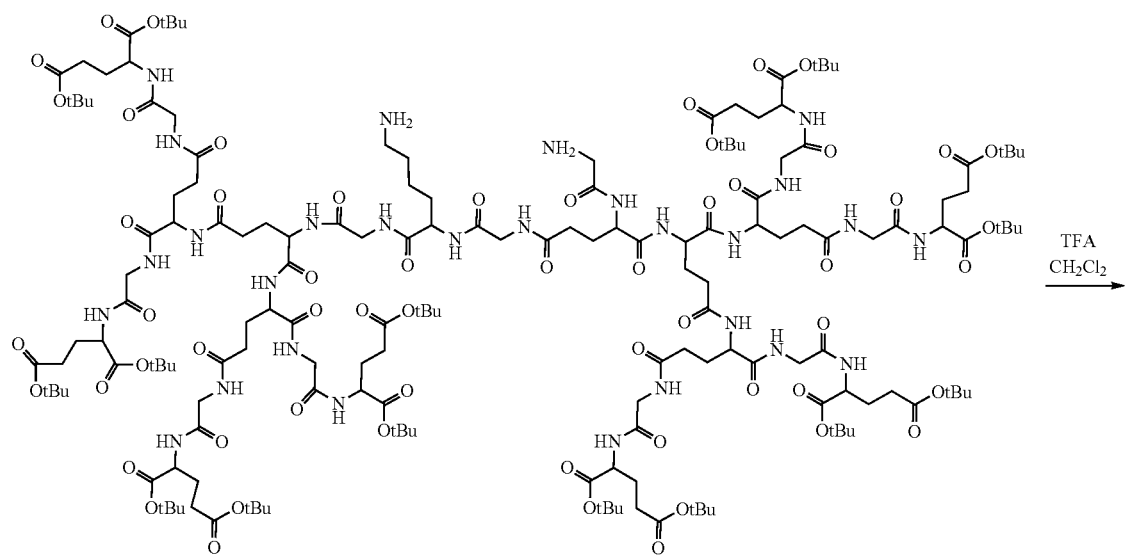
35-157

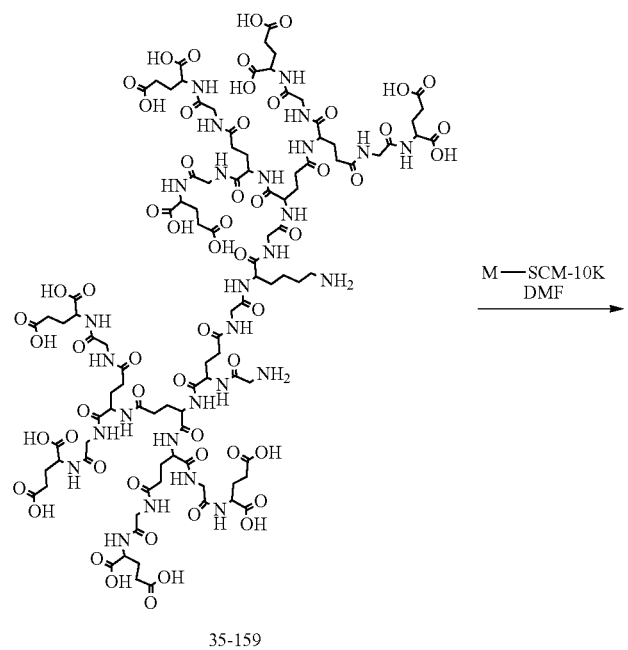
35-159
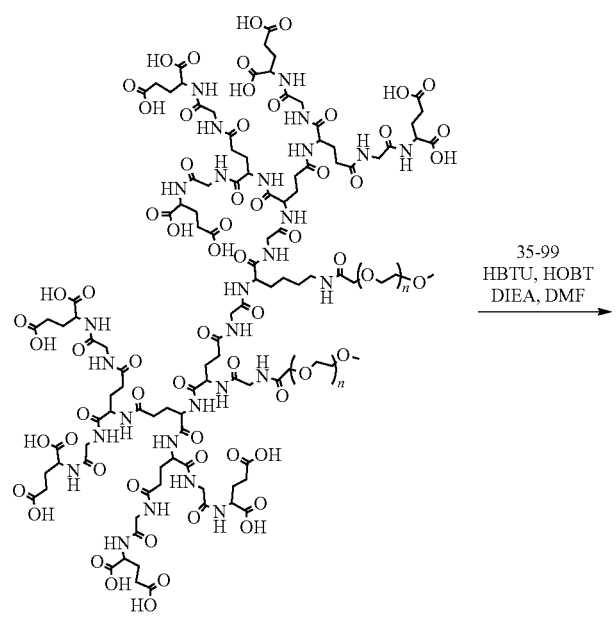
35-161

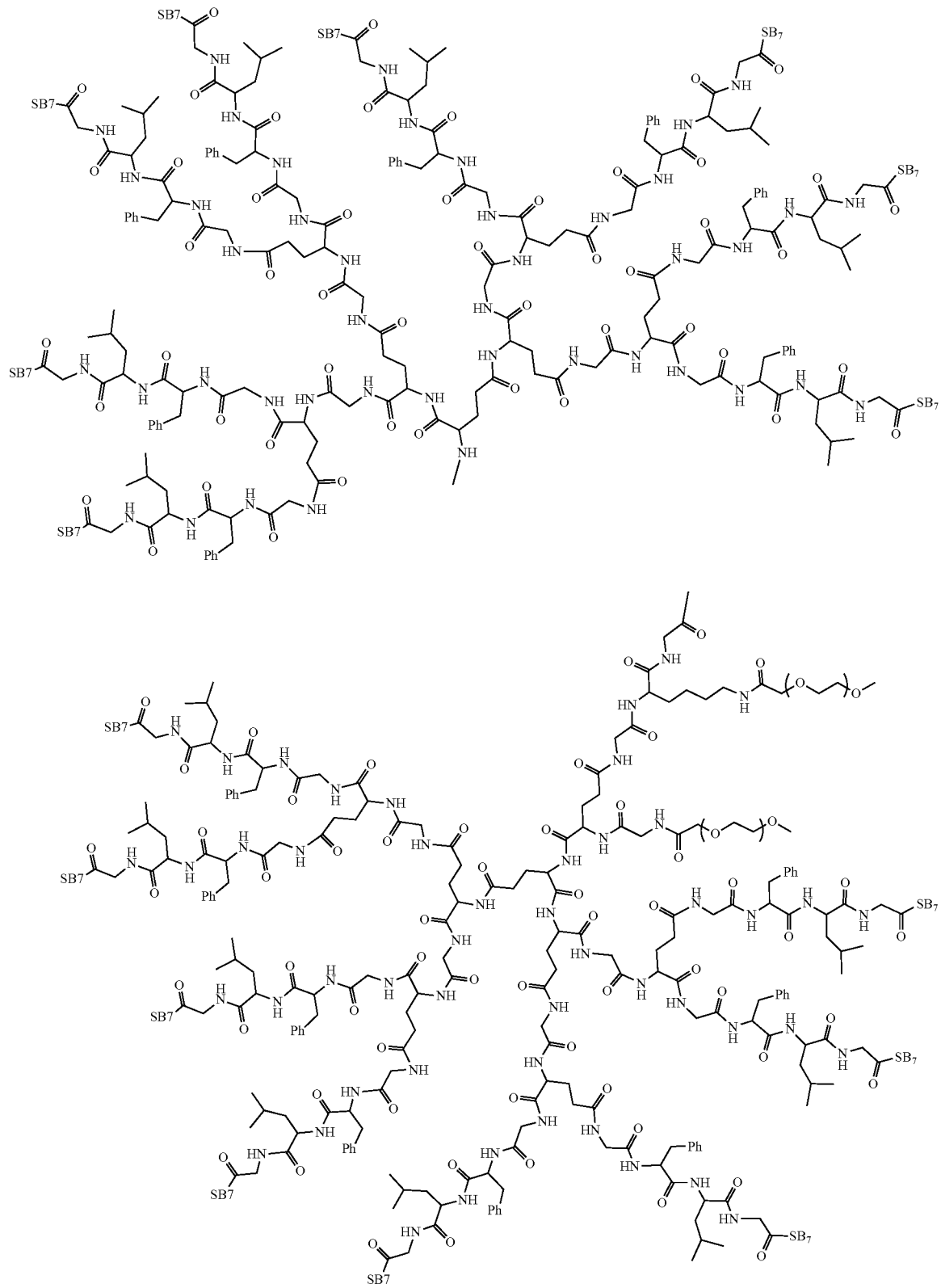
35-167

-continued 35-124

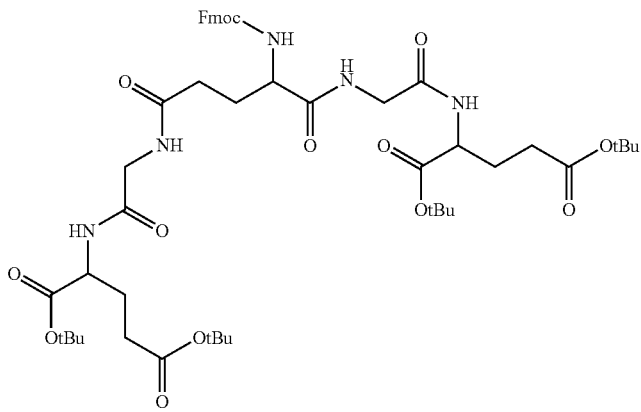

Fmoc-Gl-OH (3.57 g, 9.66 mmol), HBTU (10.99 g, 28.9 mmol), HOBT (3.91 g, 28.9 mmol) and H-Glu-(OtBu)-OtBu·HCl (6.57 g, 20.28 mmol) were added in a 500 mL flask, and dissolved with DMF (150 mL), and the mixed solution was stirred at 0° C. for about 30 minutes. Then DIEA (8.78 mL, 53.11 mmol) was slowly added dropwise. At the end of the addition, the obtained solution continued to react with stirring at 0° C. overnight. At the end of the reaction, the reaction solution was transferred to a 1 L separatory funnel, deionized water (200 mL) and ethyl acetate (250 mL) were added for extraction, the aqueous phase was washed with ethyl acetate (200 mL), and the obtained organic phases were combined. The organic phase was washed with saturated saline solution (200 mL), concentrated and evaporated to dryness, thus obtaining the product 35-124: 8.2 g.

35-125

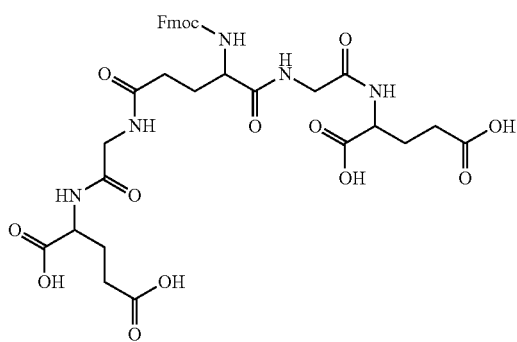

35-124 (8.2 g, 9.62 mmol) was added in a 500 mL flask, and dissolved with dichloromethane (30 mL), trifluoroacetic acid (21.4 mL, 288.6 mmol) was added, and then the mixed solution was stirred to react at room temperature overnight. At the end of the reaction, methyl tert-butyl ether (200 mL) was added to the reaction solution to separate out a solid, and filtering was carried out. The filter cake was washed with methyl tert-butyl ether (50 mL×2), and dried, thus obtaining the product 35-125: 6 g.

35-121

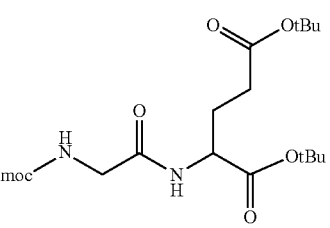

Fmoc-Gly-OH (9 g, 30.27 mmol), HBTU (16 g, 42.19 mmol), HOBT (6 g, 44.4 mmol) and H-Glu-(OtBu)-OtBu·HCl (8 g, 27.05 mmol) were added in a 500 mL flask, and dissolved with DMF (80 mL), and the mixed solution was stirred at 0° C. for about 30 minutes. Then DIEA (25 mL, 148.5 mmol) was slowly added dropwise. At the end of the addition, the obtained solution continued to react with stirring at 0° C. overnight. At the end of the reaction, the reaction solution was transferred to a 1 L separatory funnel, deionized water (200 mL) and ethyl acetate (300 mL) were added for extraction, the aqueous phase was washed with ethyl acetate (200 mL×2), and the obtained organic phases were combined. The organic phase was washed with saturated saline solution (200 mL×2), concentrated and evaporated to dryness, thus obtaining the product 35-121: 14 g, yield: 87.5%.

35-122

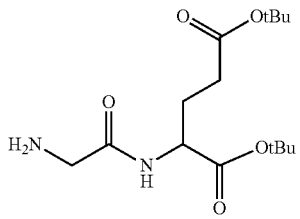

35-121 (14 g, 26 mmol) was added in a 250 mL flask, and dissolved with DMF (200 mL), morpholine (14 mL, 260 mmol) was added, and the mixed solution was stirred to react at room temperature for 1 hour. At the end of the reaction, the reaction solution was transferred to a 1 L separatory funnel, and extracted with deionized water (200 mL) and ethyl acetate (200 mL), and the organic phase was separated. The aqueous phase was washed with ethyl acetate (200 mL×2), and the obtained organic phases were combined. The organic phase was washed with saturated saline solution (200 mL×1), concentrated and evaporated to dryness, thus obtaining the product 35-122: 68.2 g.

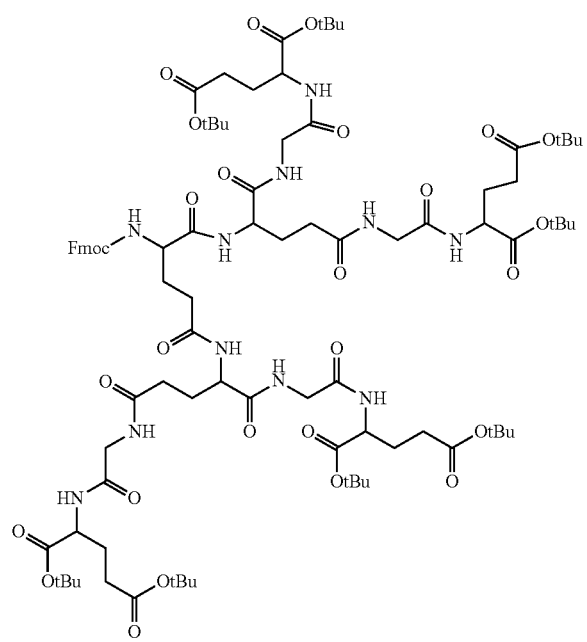

35-126

35-122 (8.1 g, 25.6 mmol), HBTU (12.1 g, 31.98 mmol), HOBT (4.3 g, 31.98 mmol) and 35-125 (3.35 g, 5.33 mmol) were added in a 500 mL flask, and dissolved with DMF (50 mL), and the mixed solution was stirred at 0° C. for about 20 minutes. Then DIEA (15.9 mL, 95.94 mmol) was slowly added dropwise. At the end of the addition, the obtained solution continued to react with stirring at 0° C. overnight. At the end of the reaction, the reaction solution was transferred to a 2 L separatory funnel, and extracted with deionized water (250 mL) and ethyl acetate (300 mL), the aqueous phase was washed with ethyl acetate (150 mL×1), and the obtained organic phases were combined. The organic phase was washed with saturated saline solution (200 mL×1), concentrated and evaporated to dryness. The obtained dry product was dissolved with methanol (20 mL) and dichloromethane (80 mL), silica gel powder (30 g) was added, and the obtained mixture was then evaporated to dryness to obtain a powdery solid. The operations of dry sample loading, column chromatography and elution with a dichloromethane mixed solution containing 5%-8% methanol were carried out, thus obtaining the product 35-126: 9.7 g.

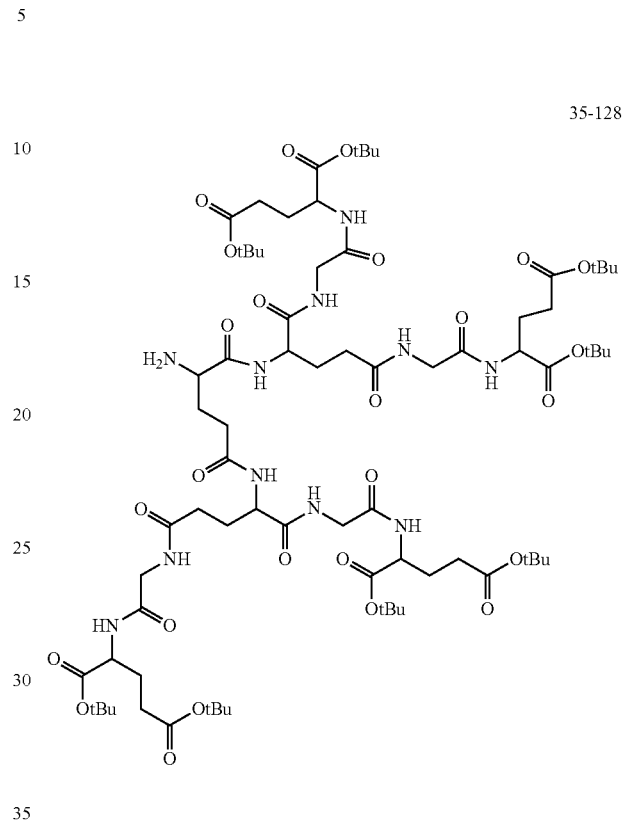

35-128

35-126 (9.7 g, 5.33 mmol) was added in a 250 mL flask, and dissolved with DMF (150 mL), morpholine (4.6 mL, 53.3 mmol) was added, and then the mixed solution was stirred to react at room temperature for 1 hour. At the end of the reaction, n-hexane (200 mL) and methyl tert-butyl ether (50 mL) were added to the reaction solution, the obtained solution was shaken to be layered, the supernatant was discarded, and n-hexane (200 mL) and methyl tert-butyl ether (50 mL) were then added to the lower oily solution. Such operations were repeated 4 times, to finally obtain an oily product. The oily product was dried, thus obtaining 35-128: 6.36 g, yield: 75%.

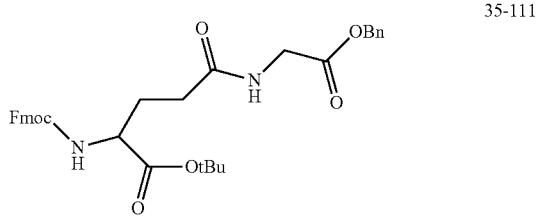

35-111

Fmoc-Gl-OtBu (5 g, 11.8 mmol), HBTU (6.7 g, 17.7 mmol), HOBT (2.4 g, 17.7 mmol) and H-Gly-OBn·HCl (2.5 g, 12.37 mmol) were added in a 500 mL flask, and dissolved with DMF (80 mL), and the mixed solution was stirred at 0° C. for about 30 minutes. Then DIEA (11 mL, 64.9 mmol) was slowly added dropwise. At the end of the addition, the obtained solution continued to react with stirring at 0° C. overnight. At the end of the reaction, the reaction solution was transferred to a 1 L separatory funnel, deionized water (200 mL) and ethyl acetate (300 mL) were added for extraction, the aqueous phase was washed with ethyl acetate (200 mL×2), and the obtained organic phases were combined. The organic phase was washed with saturated saline solution (200 mL×2), concentrated and evaporated to dryness, thus obtaining the product 35-111: 5.7 g.

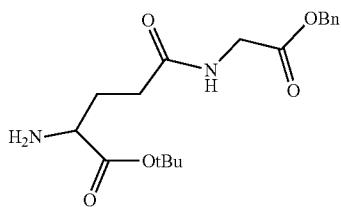

35-112

35-111 (6.7 g, 11.8 mmol) was added in a 250 mL flask, and dissolved with DMF (45 mL), morpholine (8.22 mL, 94.4 mmol) was added, and then the mixed solution was stirred to react at room temperature for 1 hour. At the end of the reaction, the reaction solution was transferred to a 1 L separatory funnel, deionized water (150 mL) and ethyl acetate (250 mL) were added for extraction, and the organic phase was separated. The aqueous phase was washed with ethyl acetate (200 mL×3), and the obtained organic phases were combined. The organic phase was washed with saturated saline solution (200 mL×1), concentrated and evaporated to dryness, thus obtaining the product 35-112: 3.2 g, yield 78%.

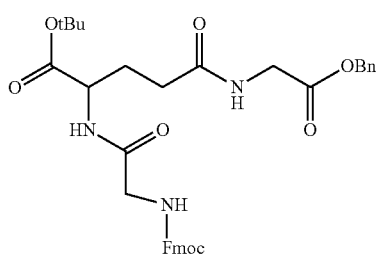

35-113

35-112 (3.2 g, 9.1 mmol), HBTU (5.2 g, 13.65 mmol), HOBT (1.8 g, 13.65 mmol) and Fmoc-Gly-OH (3.2 g, 10.92 mmol) were added in a 250 mL flask, and dissolved with DMF (30 mL), and the mixed solution was stirred at 0° C. for about 20 minutes. Then DIEA (7 mL, 42.39 mmol) was slowly added dropwise. At the end of the addition, the obtained solution continued to react with stirring at 0° C. overnight. At the end of the reaction, the reaction solution was transferred to a 2 L separatory funnel, and extracted with deionized water (250 mL) and ethyl acetate (300 mL), the aqueous phase was washed with ethyl acetate (150 mL×1), and the obtained organic phases were combined. The organic phase was washed with saturated saline solution (200 mL×1), concentrated and evaporated to dryness. The obtained dry product was dissolved with methanol (20 mL) and dichloromethane (80 mL), silica gel powder (30 g) was added, and the obtained mixture was then evaporated to dryness to obtain a powdery solid. The operations of dry sample loading, column chromatography and elution with an ethyl acetate mixed solution containing 30%-70% petroleum ether were carried out, thus obtaining the product 35-113: 5.7 g.

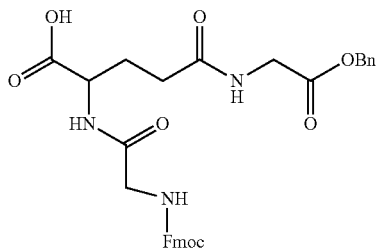

35-114

35-113 (5.7 g, 9.1 mmol) was added in a 250 mL flask, and dissolved with dichloromethane (30 mL), trifluoroacetic acid (20.4 mL, 273 mmol) was added, and then the mixed solution was stirred to react at room temperature overnight. At the end of the reaction, the reaction solution was concentrated to a small amount, n-hexane (150 mL) and methyl tert-butyl ether (40 mL) were added to layer the obtained solution, the supernatant was discarded, and n-hexane (150 mL) and methyl tert-butyl ether (40 mL) were added to the lower liquid, to obtain a viscous oily product. The oily product was dried, thus obtaining the product 35-114: 3.59 g, yield 68%.

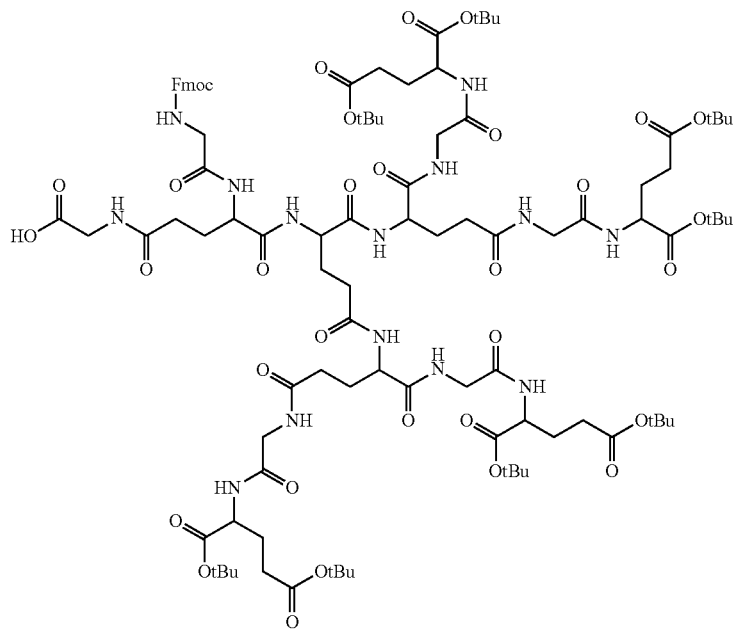

35-142

35-128 (10.2 g, 6.4 mmol), HBTU (1.36 g, 3.59 mmol), HOBT (0.49 g, 3.59 mmol) and 35-114 (3 g, 5.3 mmol) were added in a 250 mL flask, and dissolved with DMF (40 mL), and the mixed solution was stirred at 0° C. for about 20 minutes. Then DIEA (5 mL, 29.15 mmol) was slowly added dropwise. At the end of the addition, the obtained solution continued to react with stirring at 0° C. overnight. At the end of the reaction, the reaction solution was transferred to a 1 L separatory funnel, and extracted with deionized water (250 mL) and ethyl acetate (300 mL), the aqueous phase was washed with ethyl acetate (150 mL×1), and the obtained organic phases were combined. The organic phase was washed with saturated saline solution (200 mL×1), concentrated and evaporated to dryness. The obtained dry product was dissolved with methanol (20 mL) and dichloromethane (80 mL), silica gel powder (15 g) was added, and the obtained mixture was then evaporated to dryness to obtain a powdery solid. The operations of dry sample loading, column chromatography and elution with a dichloromethane mixed solution containing 4%-8% methanol were carried out, thus obtaining the product 35-142: 4 g, yield 81%.

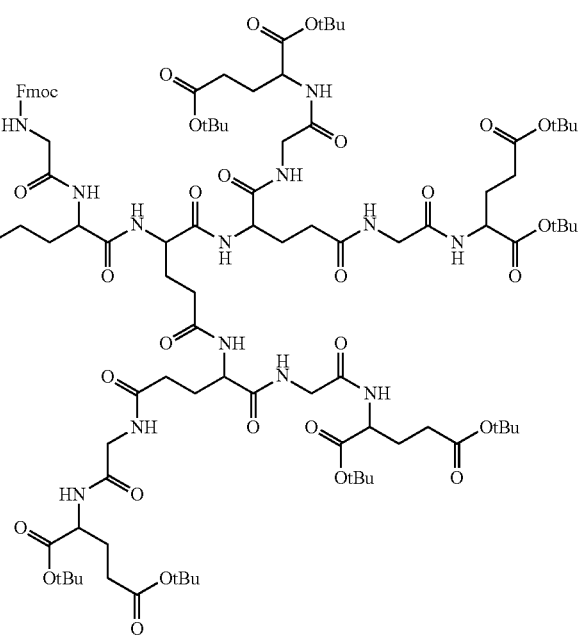

35-144

35-142 (9.2 g, 1.86 mmol) and 10% Pd/C (0.050 g) were added in a hydrogenation reactor, and dissolved with DMF (40 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

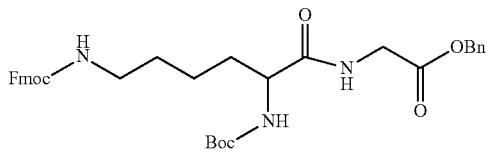

35-115

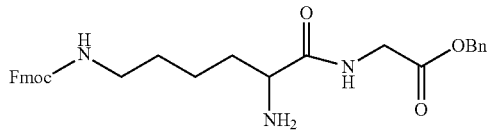

35-116

Boc-Lys (Fmoc) —OH (4.7 g, 10 mmol), HBTU (5.7 g, 15 mmol), HOBT (2.0 g, 15 mmol) and H-Gly-OBn·HCl (2.2 g, 11 mmol) were added in a 500 mL flask, and dissolved with DMF (50 mL), and the mixed solution was stirred at −5° C. for about 30 minutes. Then DIEA (9.1 mL, 55 mmol) was slowly added dropwise. At the end of the addition, the obtained solution continued to react with stirring at −5° C. for 1 hour, and was then moved to room temperature and stirred to react overnight. At the end of the reaction, the reaction solution was transferred to a 1 L separatory funnel, and extracted with saturated sodium chloride solution (200 mL) and ethyl acetate (250 mL), the aqueous phase was washed with ethyl acetate (200 mL×1), and the obtained organic phases were combined. The organic phase was washed with saturated saline solution (200 mL×2), concentrated and evaporated to dryness, thus obtaining the product 35-115: 6.5 g.

35-115 (7.9 g, 12.81 mmol) was added in a 250 mL flask, and dissolved with dichloromethane (20 mL), trifluoroacetic acid (7.4 mL, 100 mmol) was added with stirring, and then the mixed solution was stirred to react at room temperature overnight. At the end of the reaction, the reaction solution was concentrated to a small amount, and precipitated two times with n-hexane (150 mL) and methyl tert-butyl ether (40 mL), to obtain a viscous oily product. The oily product was dried, thus obtaining the product 35-116: 5.2 g.

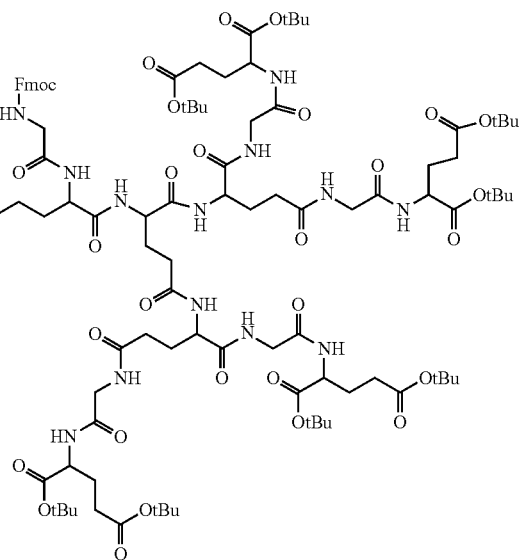

35-146

35-144 (8.9 g, 4.3 mmol), HBTU (2.45 g, 6.45 mmol), HOBT (0.9 g, 6.45 mmol) and 35-116 (2.7 g, 4.3 mmol) were added in a 250 mL flask, and dissolved with DMF (200 mL), and the mixed solution was stirred at 0° C. for about 20 minutes. Then DIEA (3.9 mL, 23.65 mmol) was slowly added dropwise. At the end of the addition, the obtained solution continued to react with stirring at 0° C. overnight. At the end of the reaction, n-hexane (200 mL) and methyl tert-butyl ether (40 mL) were added to layer the reaction solution, the supernatant was discarded, and n-hexane (200 mL) and methyl tert-butyl ether (40 mL) were added to the lower oily solution. Such operations were repeated three times, to obtain a viscous oily product. The oily product was dried, thus obtaining the product 35-146: 11 g.

35-148

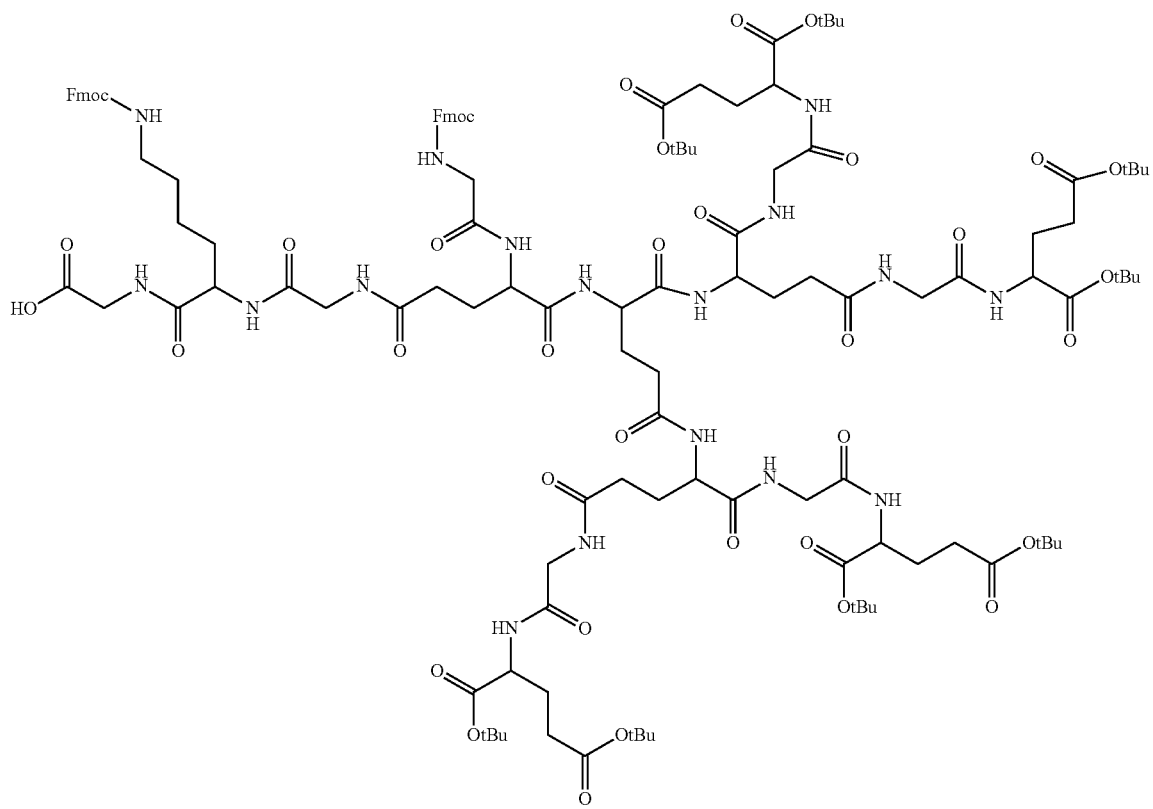

35-146 (11 g, 4.3 mmol) and 10% Pd/C (0.050 g) were added in a hydrogenation reactor, and dissolved with DMF (40 mL), hydrogen was introduced to a pressure of 1.8 MPa, and then the mixed solution was stirred to react at room temperature overnight. At the end of the reaction, the reaction solution was filtered with diatomaceous earth. The diatomaceous earth was then washed with DMF (20 mL×3), and the DMF solutions were combined as raw material for the next reaction.

35-148 (6.8 g, 2.75 mmol), HBTU (1.4 g, 3.75 mmol), HOBT (0.51 g, 3.75 mmol) and 35-128 (4 g, 2.5 mmol) were added in a 250 mL flask, and dissolved with DMF (150 mL), and the mixed solution was stirred at 0° C. for about 20 minutes. Then DIEA (1.86 mL, 11.25 mmol) was slowly added dropwise. At the end of the addition, the obtained solution continued to react with stirring at 0° C. overnight. At the end of the reaction, n-hexane (200 mL) and methyl tert-butyl ether (40 mL) were added to layer the reaction solution, the supernatant was discarded, and n-hexane (200 mL) and methyl tert-butyl ether (40 mL) were added to the lower oily solution. Such operations were repeated three times, to obtain a viscous oily product. The oily product was 35-155

dissolved with dichloromethane and methanol, silica gel powder (20 g) was added, and the obtained mixture was then evaporated to dryness to obtain a powdery solid. The operations of dry sample loading, column chromatography and elution with a dichloromethane mixed solution containing 0.5% ammonia water and 4%-10% methanol were carried out. The elution product was then collected, and dried, thus obtaining the product 35-155: 1.2 g, yield: 12%. $^1$H-NMR (600 MHz, DMSO-d$_6$) δ 8.13-8.05 (m, 22H), 7.85-7.55 (m, 8H), 7.38-7.28 (m, 8H), 4.71-4.33 (m, 7H), 4.31-4.09 (m, 14H), 3.85-3.42 (m, 12H), 3.18-2.35 (m, 4H), 2.31-2.29 (m, 32H), 2.07-1.91 (m, 26H), 1.89-1.55 (m, 6H), 1.45-1.38 (m, 144H), 1.25-1.11 (m, 21-1).

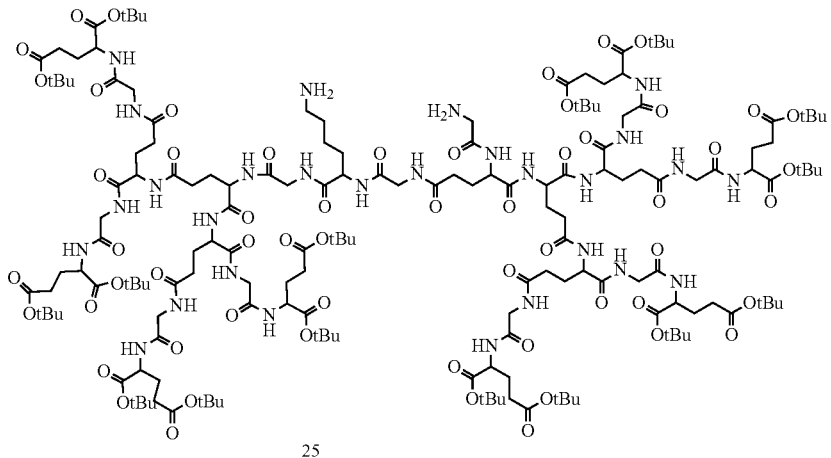

35-157

35-155 (1.2 g, 0.3 mmol) was added in a 250 mL flask, and dissolved with DMF (25 mL), morpholine (4 mL, 43.68 mmol) was added, and then the mixed solution was stirred to react at room temperature for 1 hour. At the end of the reaction, n-hexane (100 mL) and methyl tert-butyl ether (30 mL) were added to layer the reaction solution, the supernatant was discarded, and n-hexane (100 mL) and methyl tert-butyl ether (30 mL) were added to the lower oily solution. Such operations were repeated three times, to obtain a viscous oily product. The oily product was dried, thus obtaining the product 35-157: 1.02 g.

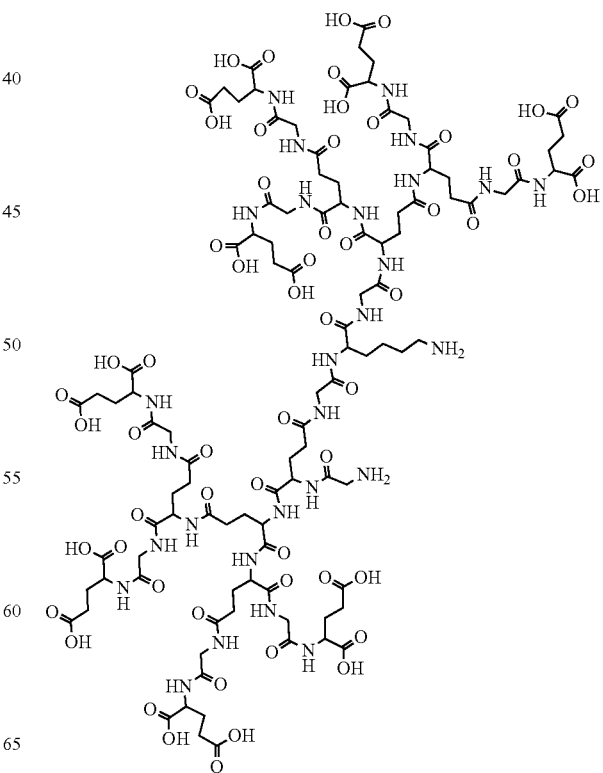

35-159

35-157 (1.02 g, 0.3 mmol) was added in a 250 mL flask, and dissolved with dichloromethane (30 mL) and trifluoroacetic acid (10 mL, 134 mmol), and the mixed solution was stirred to react at room temperature overnight. At the end of the reaction, the reaction solution was concentrated to a small amount, n-hexane (100 mL) and methyl tert-butyl ether (30 mL) were added to layer the obtained solution, the supernatant was discarded, and n-hexane (100 mL) and methyl tert-butyl ether (30 mL) were added to the lower liquid, to obtain a viscous oily product. The oily product was dried, thus obtaining the product 35-159: 0.8 g.

35-161

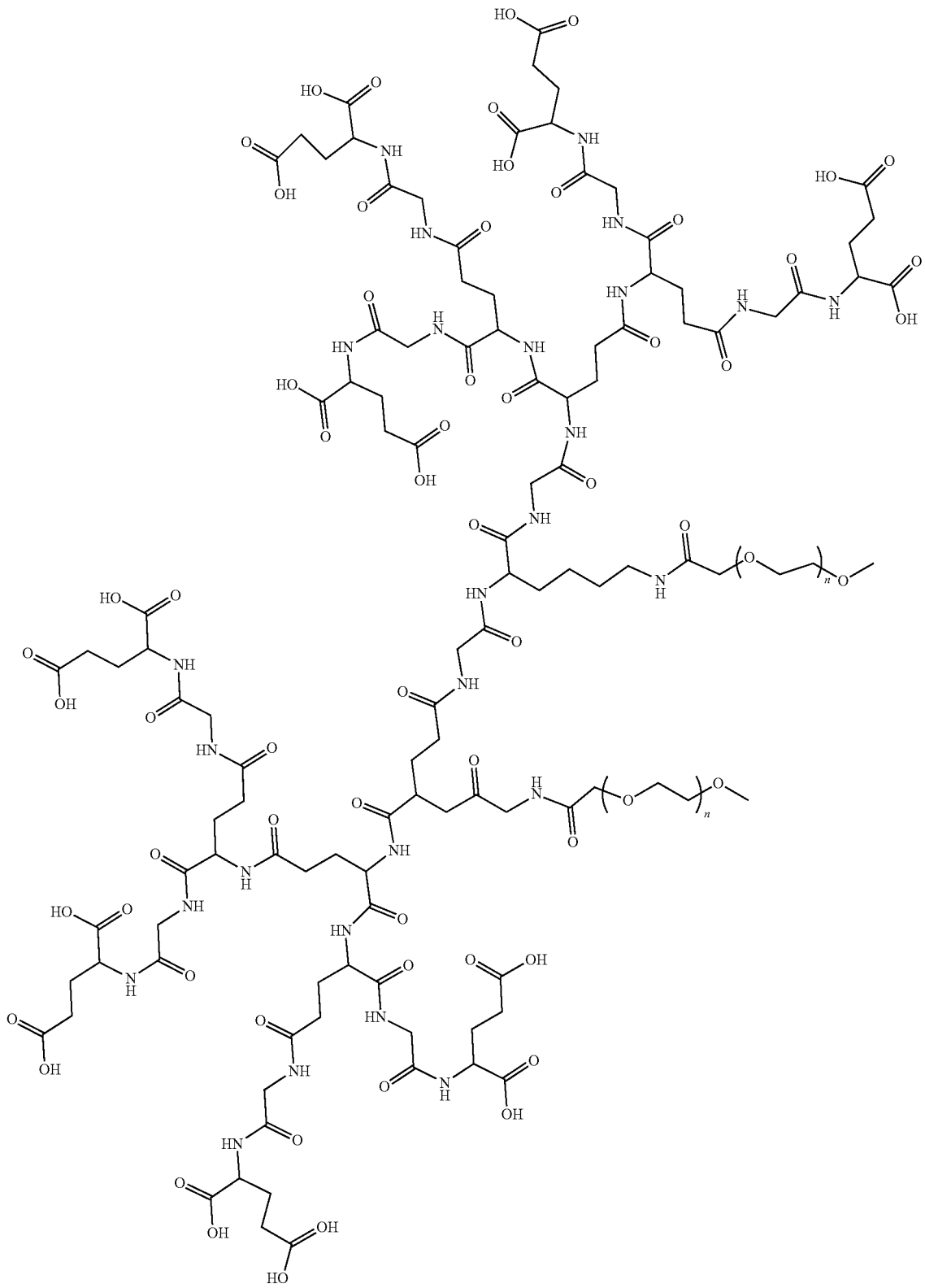

35-159 (0.1 g, 0.0367 mmol) was added in a 250 mL flask, and dissolved with DMF (20 mL). Then, DIEA (0.6 mL, 3.63 mmol) was added, the obtained solution was stirred for 30 minutes, M-SCM-10K (0.85 g, 0.081 mmol, purchased from JenKem) was added, and then the mixed solution was moved to room temperature and stirred to react in the dark for 7 days at a low speed. At the end of the reaction, n-hexane (100 mL) and methyl tert-butyl ether (30 mL) were added to layer the reaction solution, the supernatant was discarded, and n-hexane (100 mL) and methyl tert-butyl ether (30 mL) were added to the lower oily solution. Such operations were repeated three times, to obtain an oily product. The oily product was dissolved with methanol (30 mL) and dichloromethane (120 mL) solution, silica gel powder (20 g) was added, and the obtained mixture was then evaporated to dryness to obtain a powdery solid. The operations of dry sample loading, column chromatography and elution with a dichloromethane mixed solution containing 1% ammonia water and 6%-10% methanol were carried out. The elution product was then collected, concentrated, evaporated to dryness, and dried in a vacuum oven, thus obtaining the product 35-161: 0.87 g, yield: 58%.

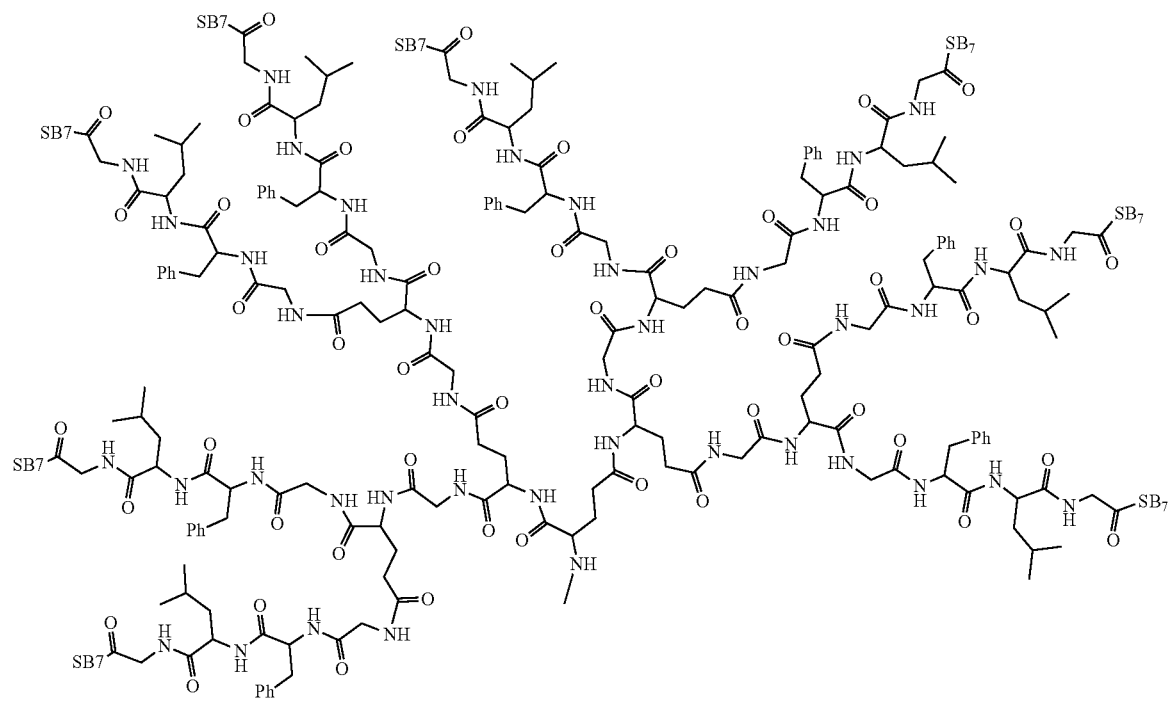

35-167

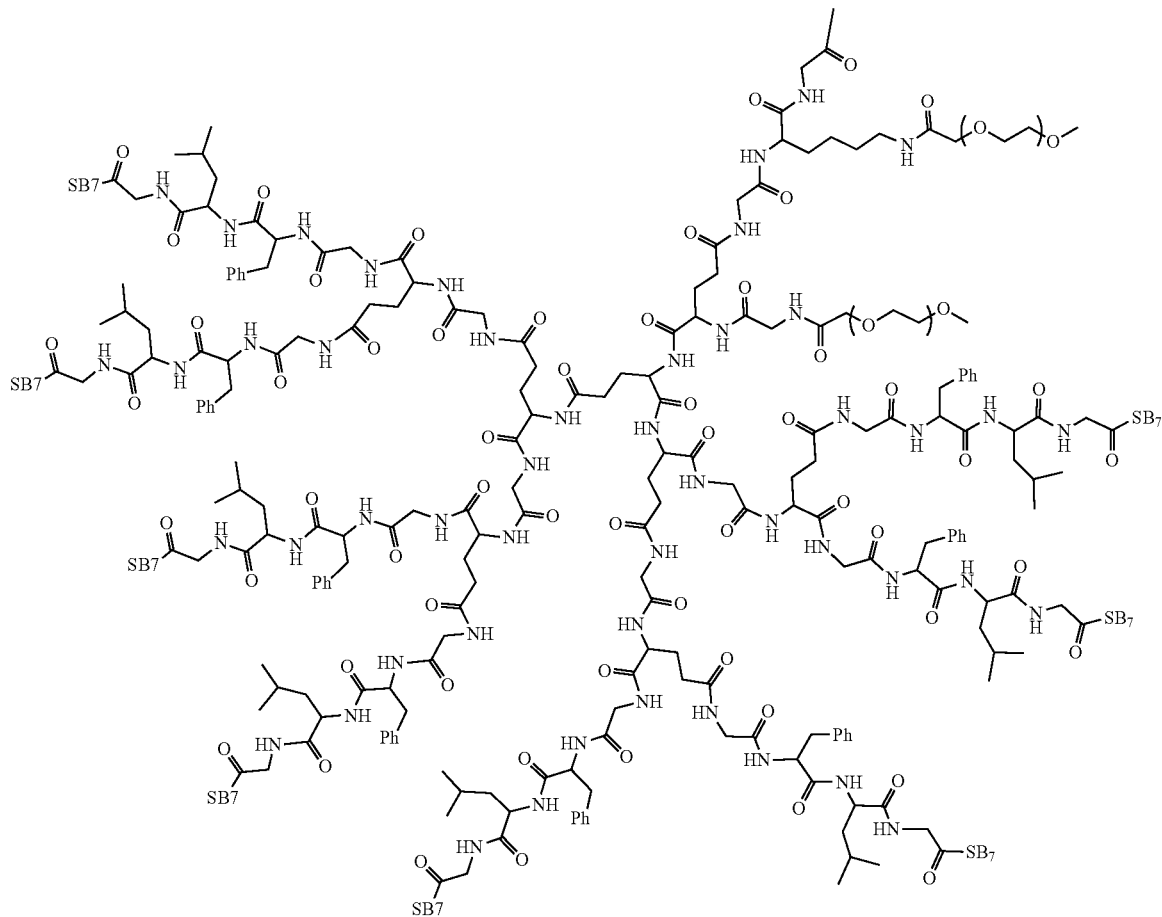

35-161 (0.5 g, 0.02 mmol), 35-99 (0.45 g, 0.5 mmol), synthesized according to the method of synthesizing 25-132), HBTU (0.15 g, 0.05 mmol), HOBT (0.06 g, 0.05 mmol) were added in a 250 mL flask, and dissolved with DMF (35 mL), and the mixed solution was stirred at −5° C. for 20 minutes. Then DIEA (0.22 mL, 1.4 mmol) was slowly added dropwise. At the end of the addition, the obtained solution was stirred to react at −5° C. for 30 minutes, and then moved to room temperature and stirred to react in the dark for 6 days at a low speed. At the end of the reaction, n-hexane (100 mL) and methyl tert-butyl ether (30 mL) were added to layer the reaction solution, the supernatant was discarded, and n-hexane (100 mL) and methyl tert-butyl ether (30 mL) were added to the lower oily solution. Such operations were repeated three times, to obtain a viscous oily product. The oily product was dissolved with methanol (30 mL) and dichloromethane (120 mL) solution, silica gel powder (15 g) was added, and the obtained mixture was then evaporated to dryness to obtain a powdery solid. The operations of dry sample loading, column chromatography and elution with a dichloromethane mixed solution containing 1% ammonia water and 7%-10% methanol were carried out. The elution product was then collected, concentrated, evaporated to dryness, and dried in a vacuum oven, thus obtaining the product. 35-167: 0.24 g, yield: 50%. $^1$H-NMR (600 MHz, DMSO-$d_6$) δ 9.04-9.03 (m, 2H), 8.37-8.34 (m, 29H), 8.18-8.02 (m, 42H), 8.01-7.80 (m, 48H), 7.61-7.59 (m, 38H), 7.39-7.36 (m, 25H), 7.27-6.95 (m, 190H), 6.69-6.66 (m, 4H), 4.67-4.49 (m, 13H), 4.38-4.23 (m, 16H), 4.19-4.12 (m, 10H), 3.90-3.87 (m, 11H), 3.79-3.75 (m, 9H), 3.70-3.68 (m, 16H), 3.61-3.58 (m, 20H), 3.51-3.49 (m, 1941H), 3.14-3.03 (m, 68H), 2.68-2.59 (m, 73H), 2.35-2.34 (m, 39H), 1.61-1.54 (m, 16H), 1.48 (m, 34H), 1.34-1.32 (m, 31H), 1.23-1.21 (m, 186H), 0.95-0.81 (m, 139H), 0.52-0.05 (m, 28H).

31. Synthesis of 41-137 (Compound No. 30)
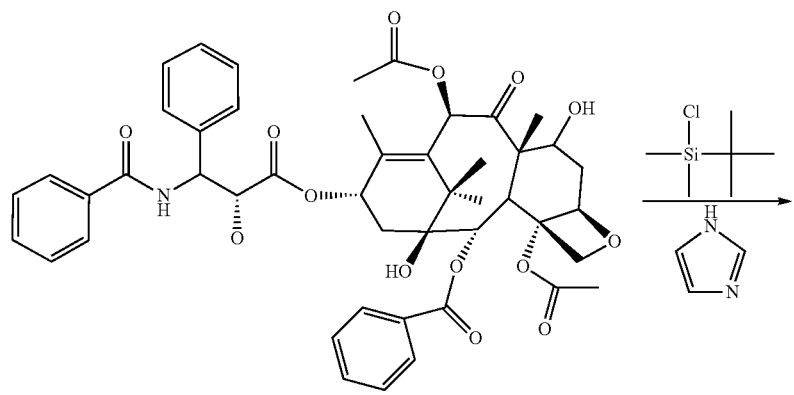
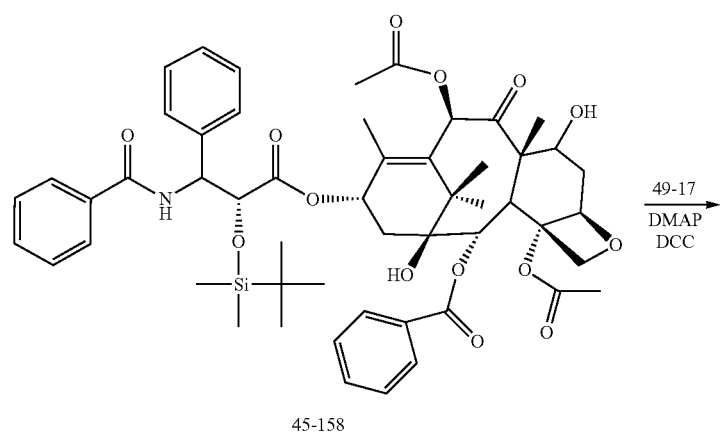
45-158
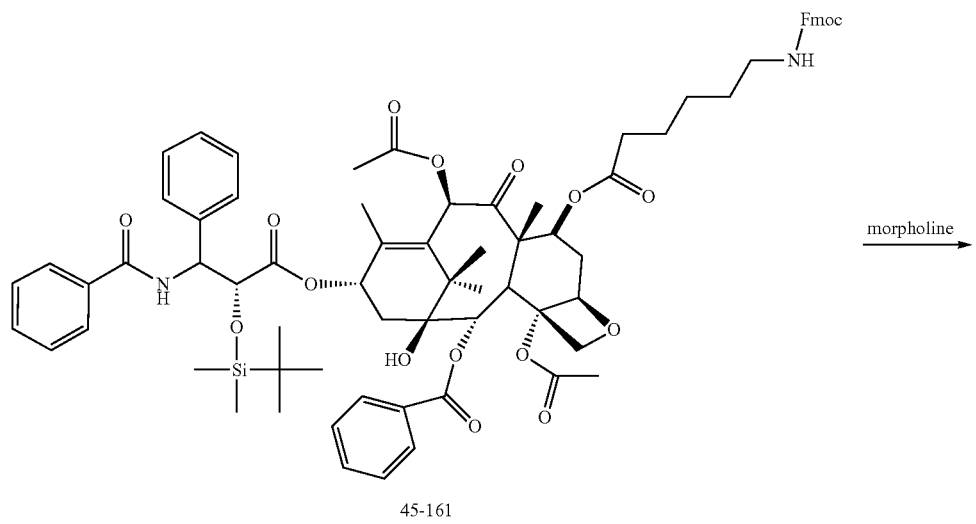
45-161

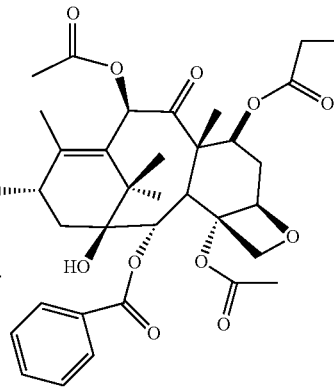
45-163
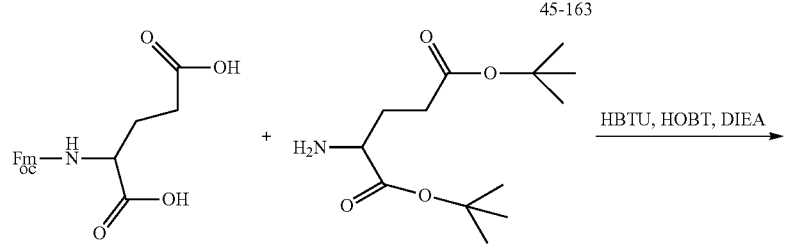
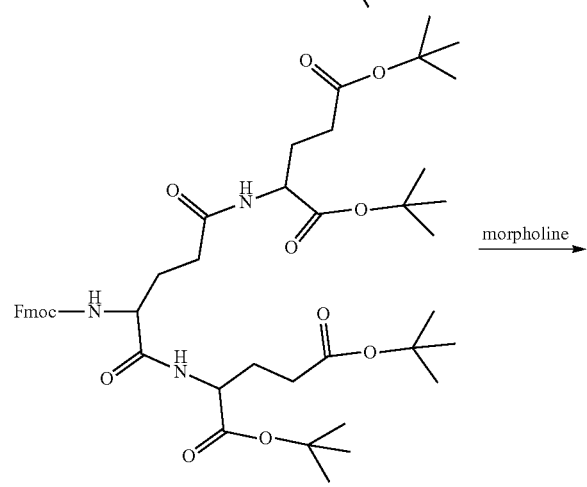
41-123
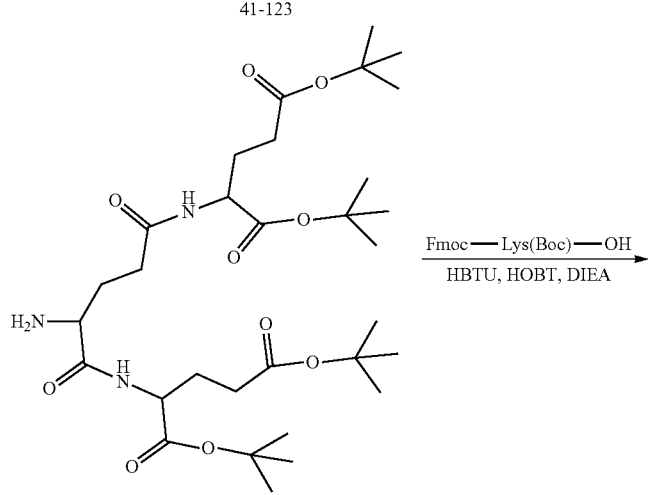
41-124

-continued
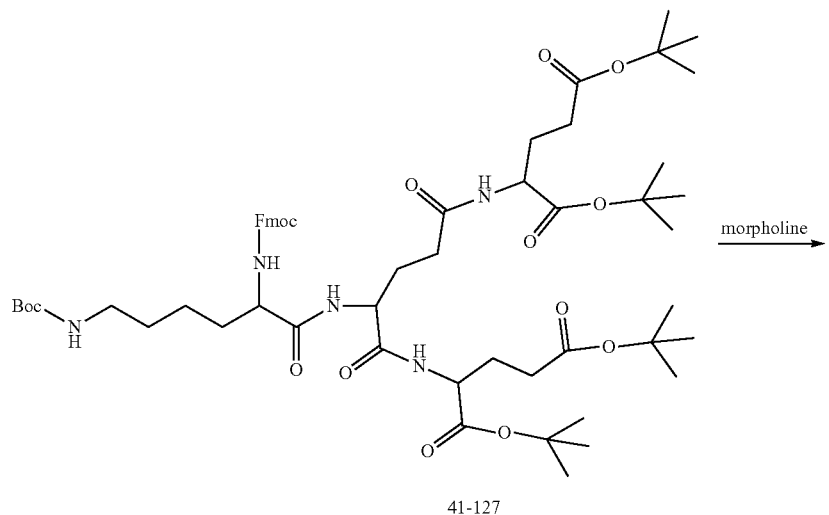
41-127
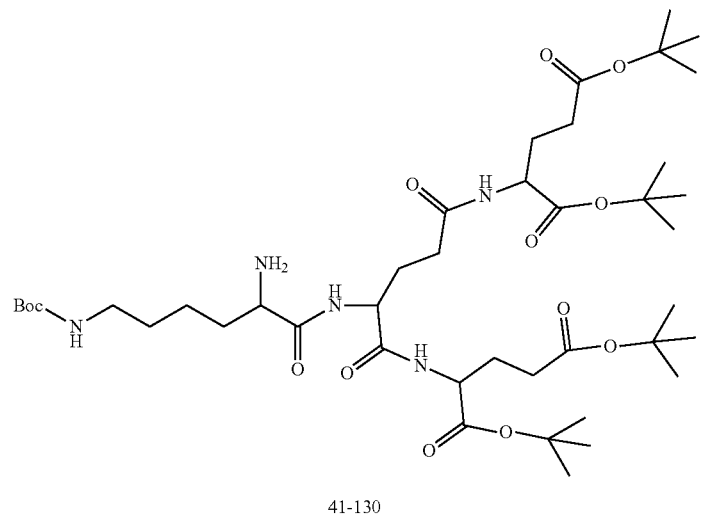
41-130
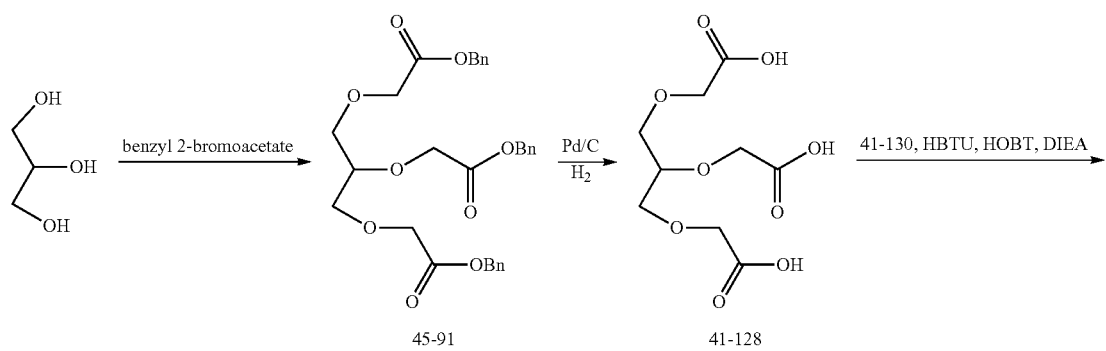

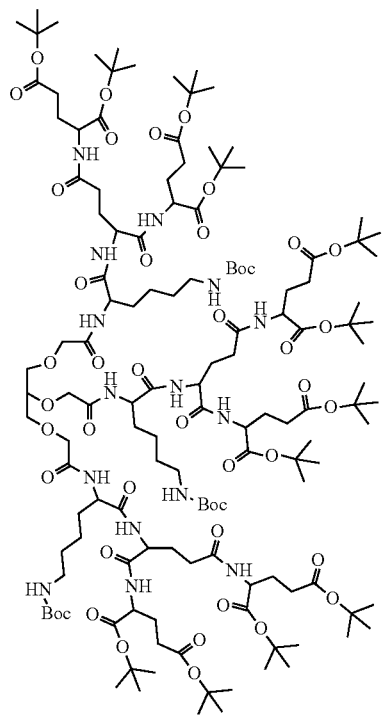
41-131
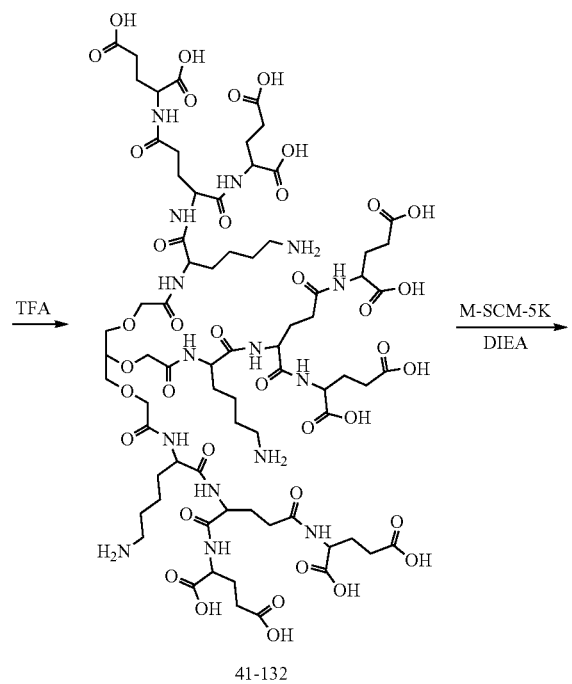
41-132
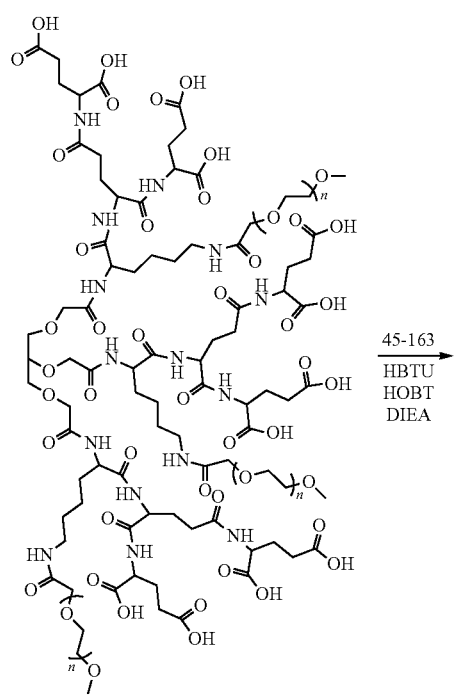
41-133

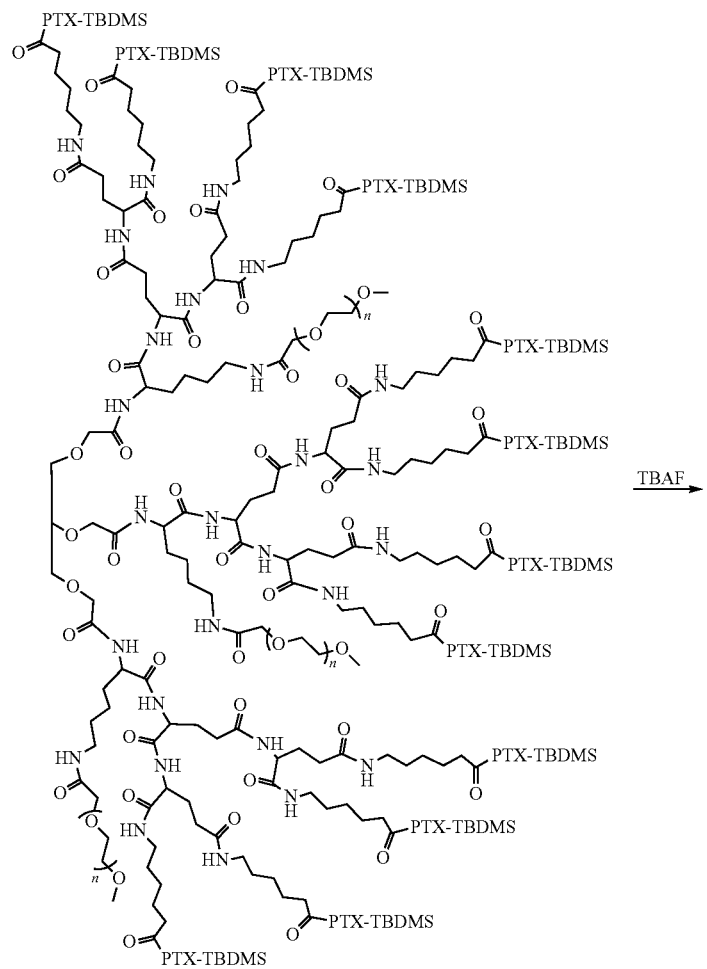
41-134

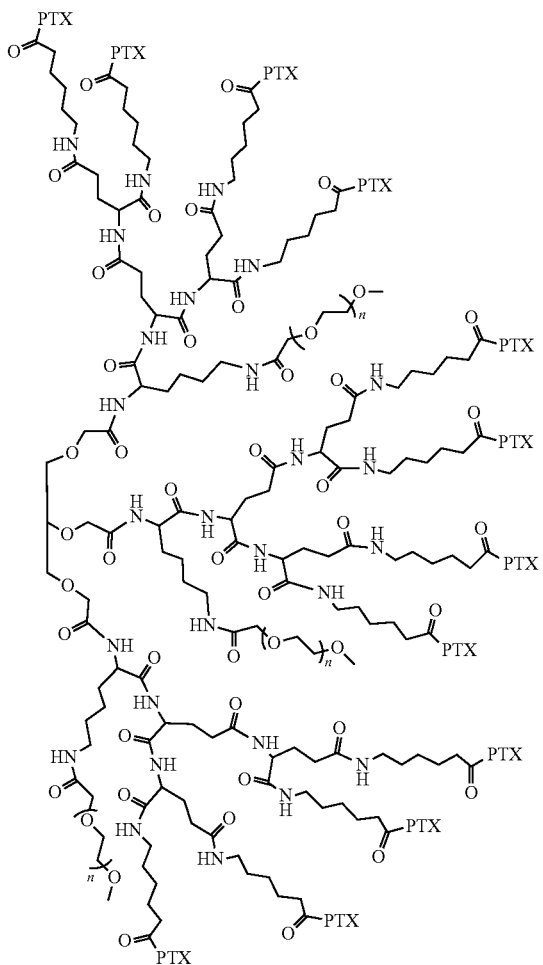

41-137

49-17

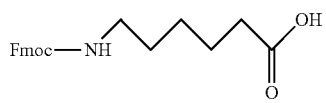

6-Amino caproic acid (4.61 g, 35.1407 mmol) was added in a 1 L flask, a mixed solution (150 mL) of THF:H$_2$O=1:1 was added to completely dissolve the compound, and the obtained solution was stirred at 0° C. A sodium carbonate solid (7.45 g, 70.2814 mmol) was then added, ultrasonic treatment was carried out to dissolve the compound, and the obtained solution was stirred to react at 0° C. for 30 minutes. Fmoc-Cl (10 g, 38.6548 mmol) was dissolved in 30 mL THF, and then slowly added dropwise to the reaction solution. At the end of the addition, the obtained solution was moved to room temperature and stirred to react. At the end of the reaction, 50 g citric acid was dissolved in 450 mL deionized water, and added to the reaction solution, to adjust the pH to 3. Then, the obtained solution was transferred to a 1 L separatory funnel, and extracted with EA (300 mL×3). The organic phase was collected, concentrated and evaporated to dryness. The obtained solid product was dissolved with a mixed solvent (100 mL) of methanol/dichloromethane (1:4), silica gel powder (50 mL) was added, and the obtained mixture was then evaporated to dryness to obtain a powdery solid. The operations of dry sample loading, column chromatography and elution with 2% methanol/dichloromethane solution were carried out. The elution product was then collected, concentrated, and dried in a vacuum oven, thus obtaining the product (7.7 g, 86.51%).

45-158

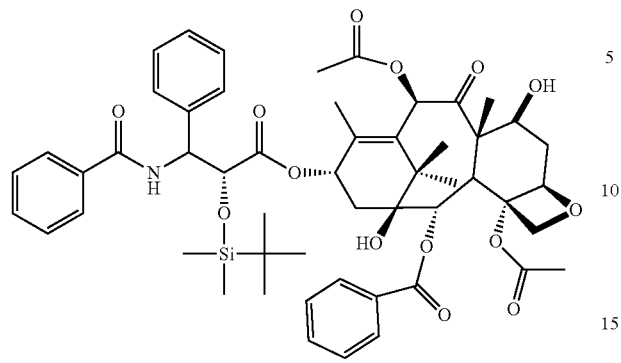

Paclitaxel (10 g, 11.71 mmol, also referred to as PTX, purchased from Beisheng, Chongqing), imidazole (3.986 g, 58.5 mmol, purchased from InnoChem) were added in a 500 mL flask, and dissolved with DMF (100 mL), tert-butyl dimethyl chlorosilane (10.59 g, 70.26 mmol, purchased from InnoChem) was added under the protection of nitrogen, and then the mixed solution was stirred to react at room temperature. At the end of the reaction, the reaction solution was extracted with saturated ammonium chloride solution and dichloromethane. The organic phase was concentrated and evaporated to dryness, thus obtaining the product 11.3 g, yield 100%.

45-161

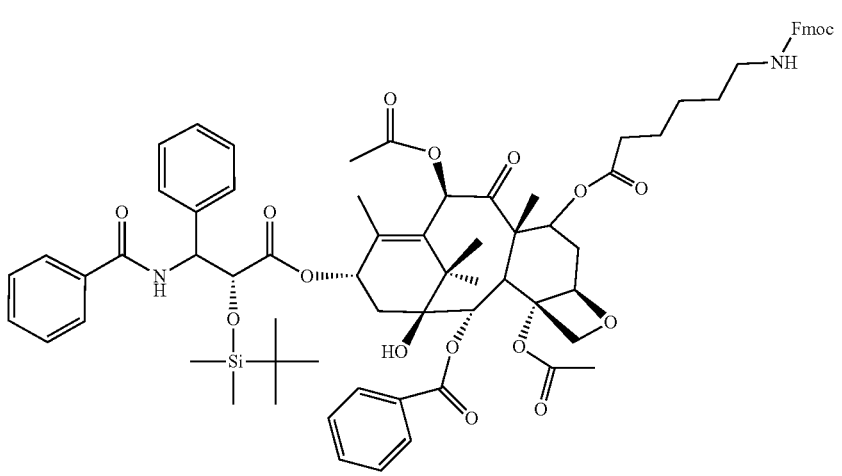

49-17 (4.2 g, 11.9297 mmol), 45-158 (11 g, 11.3616 mmol), DMAP (0.2776 g, 2.2723 mmol) were added in a 500 mL flask, and dissolved with dichloromethane (50 mL), DCC (11.7212 mL, 56.808 mmol) was added in batches under the condition of stirring at −5° C., and then the mixed solution reacted at −5° C. overnight. At the end of the reaction, the reaction solution was extracted with saturated sodium chloride solution and ethyl acetate, and the organic phase was separated. The aqueous phase was extracted one time with ethyl acetate, and the obtained organic phases were combined. The organic phase was washed two times with saturated sodium chloride solution, silica gel powder was added to the organic phase, and the operations of evaporation, sample loading, column chromatography and gradient elution with 20%-25% ethyl acetate/petroleum ether were carried out, thus obtaining the product 8 g, yield 54.05%.

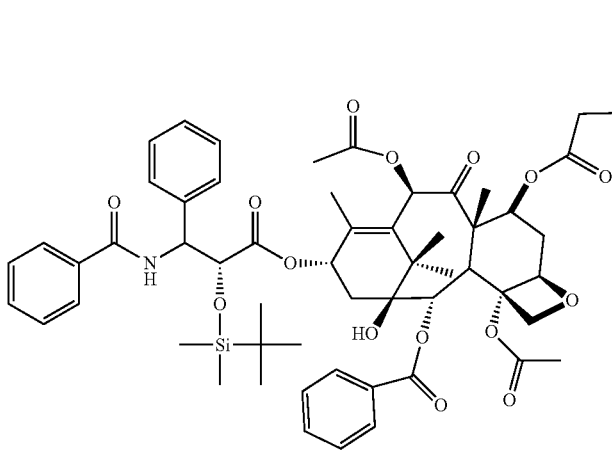

45-161 (7.5 g, 5.7535 mmol) was added in a 500 mL flask, and dissolved with DMF, morpholine (10.024 mL, 115.0695 mmol) was added, and then the mixed solution was stirred to react at room temperature for 2 hours. At the end of the reaction, the reaction solution was extracted with saturated sodium chloride solution and ethyl acetate, and the organic phase was separated. The aqueous phase was extracted one time with ethyl acetate, and the obtained organic phases were combined. The organic phase was washed two times with saturated sodium chloride solution, silica gel powder was added to the organic phase, and the operations of evaporation, sample loading, column chromatography and gradient elution with 20%-25% ethyl acetate/petroleum ether were carried out, thus obtaining the product 4.5 g, yield 72.58%.

solution was transferred to a 2 L separatory funnel, and extracted with ethyl acetate (150 mL) and deionized water (300 mL), and the organic phase was separated. The aqueous phase was extracted many times with ethyl acetate (300 mL) until there was no product in the aqueous phase, and the obtained organic phases were combined. The organic phase was concentrated, silica gel powder was added, and the operations of evaporation, column chromatography, and elution with 4% methanol/dichloromethane were carried out, thus obtaining the product 5 g, extra-quota 0.4 g.

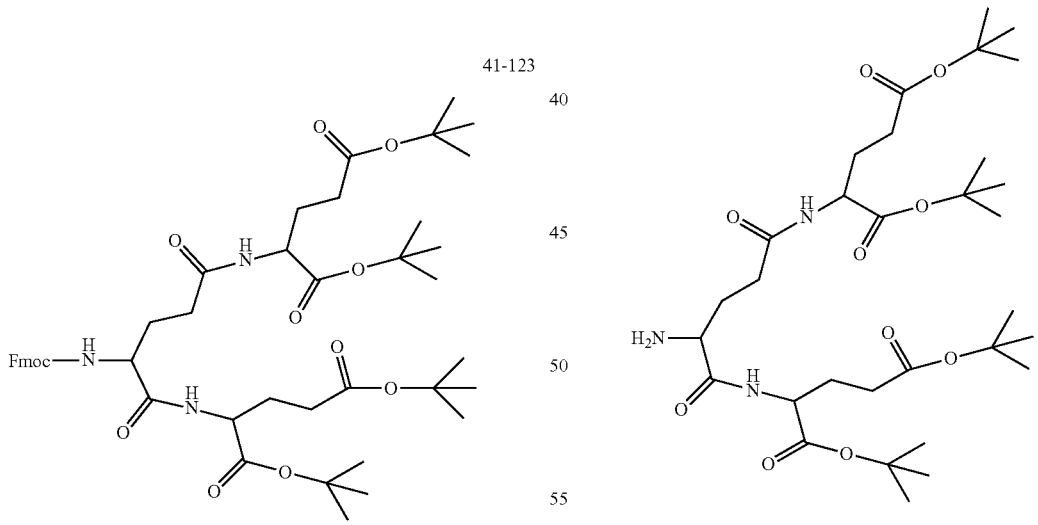

Fmoc-E (OH)$_2$ (2 g, 5.34142 mmol, purchased from Aladdin), E(OtBu)$_2$ (3.3632 g, 11.3698 mmol, purchased from Innochem), HBTU (6.1598 g, 16.2426 mmol), HOBT (2.1947 g, 16.2426 mmol) were added in a 250 mL flask, and dissolved with DMF (20 mL), and the obtained solution was stirred to react under low-temperature and constant temperature condition of 0° C. for 30 minutes. Then DIEA (8 mL, 48.7277 mmol) was slowly added dropwise, and the obtained solution continued to react with stirring under this condition for 3 hours. At the end of the reaction, the reaction 41-123 (5 g, 5.8684 mmol) was dissolved with DMF, morpholine (10.2 mL, 117.638 mmol) was added, and then the mixed solution was stirred to react at room temperature for 1 hour. At the end of the reaction, the reaction solution was precipitated with petroleum ether, the supernatant was discarded, pure water was added to the lower liquid, and suction filtering was carried out. The solids were collected and combined, and dissolved with DMF, pure water was added, and suction filtering was carried out. The filter cake was dried to obtain the product 3.3 g, yield 89%.

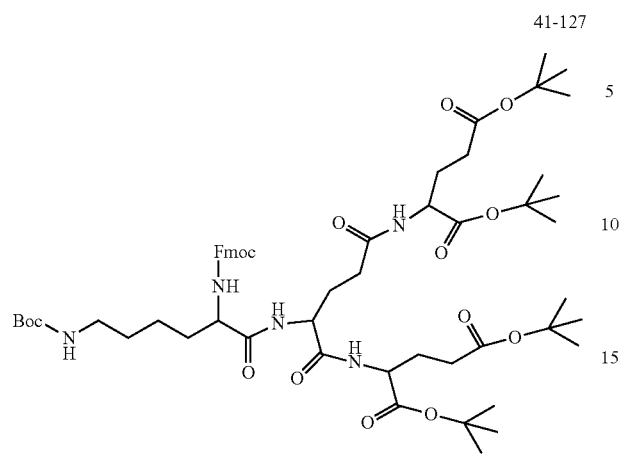

41-127

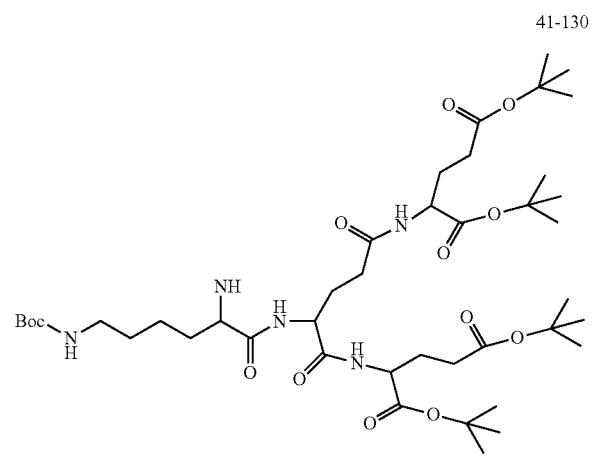 [SMILES: CC(C)(C)OC(=O)CCC(NC(=O)CCC(NC(=O)C(N)CCCCNC(=O)OC(C)(C)C)C(=O)NC(CCC(=O)OC(C)(C)C)C(=O)OC(C)(C)C)C(=O)OC(C)(C)C]

41-130

Fmoc-Lys(Boc)-OH (2.455 g, 5.2399 mmol, purchased from Aladdin), 41-124 (3.3 g, 5.2399 mmol), HBTU (2.9528 g, 7.8760 mmol), HOBT (1.0520 g, 7.8760 mmol) were added in a 250 mL flask, and dissolved with DMF (20 mL), and the obtained solution was stirred to react under low-temperature and constant temperature condition of 0° C. for 30 minutes. Then DIEA (3.9 mL, 23.5797 mmol) was slowly added dropwise, and the obtained solution continued to react with stirring under this condition for 3 hours. At the end of the reaction, the reaction solution was transferred to a 2 L separatory funnel, and extracted with ethyl acetate (150 mL) and deionized water (300 mL), and the organic phase was separated. The aqueous phase was extracted many times with ethyl acetate (300 mL) until there was no product in the aqueous phase, and the obtained organic phases were combined. The organic phase was concentrated, silica gel powder was added, and the operations of evaporation, column chromatography, and elution with 50% ethyl acetate/petroleum ether were carried out, thus obtaining the product 3.4 g, yield 77%.

41-127 (3.4 g, 4.0764 mmol) was dissolved with DMF, morpholine (7.1 mL, 81.5280 mmol) was added, and then the mixed solution was stirred to react at room temperature for 1 hour. At the end of the reaction, the reaction solution was transferred to a 2 L reparatory funnel, and extracted with ethyl acetate (150 mL) and deionized water (300 mL), and the organic phase was separated. The aqueous phase was extracted many times with ethyl acetate (300 mL) until there was no product in the aqueous phase, and the obtained organic phases were combined. The organic phase was dried, thus obtaining the product 3.49 g.

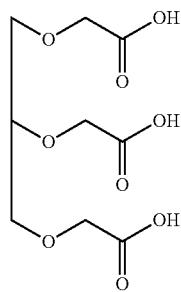

41-128

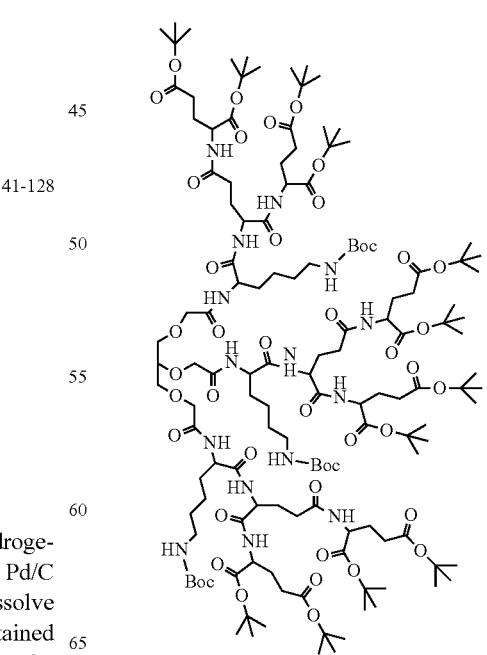

41-131

45-91 (0.6183 g, 1.1523 mmol) was added in a hydrogenation reactor; and dissolved with DMF (30 mL), 10% Pd/C (100 mg) was added, DMF (30 mL) was added to dissolve the reactant. H$_2$ (300 psi) was introduced, and the obtained solution was stirred overnight, thus obtaining the product for the next reaction.

41-130 (3.5 g, 4.0764 mmol), 41-128 (1.523 mmol), HBTU (1.9664 g, 5.1852 mmol), HOBT (0.7006 g, 5.1852 mmol) were added in a 250 mL flask, and dissolved with DMF (20 mL), and the obtained solution was stirred to react under low-temperature and constant temperature condition of 0° C. for 30 minutes. Then DIEA (2.6 mL, 15.5556 mmol) was slowly added dropwise, and the obtained solution continued to react with stirring under this condition for 3 hours. At the end of the reaction, the reaction solution was transferred to a 2 L separatory funnel, and extracted with ethyl acetate (150 mL) and deionized water (300 mL), and the organic phase was separated. The aqueous phase was extracted many times with ethyl acetate (300 mL) until there was no product in the aqueous phase, and the obtained organic phases were combined. The organic phase was evaporated to dryness, and dried, thus obtaining the product (3.5 g, extra-quota 0.3 g), for the next reaction.

276.552 mmol) was added, and then the obtained solution was stirred to react at room temperature overnight. At the end of the reaction, the reaction solution was first evaporated to remove a part of the TFA, and then precipitated with EA (200 mL) and n-hexane (200 mL), and suction filtering was carried out. The obtained solid powder was transferred to a 2 L round-bottomed flask, and evaporated to dryness, thus obtaining the product 2 g.

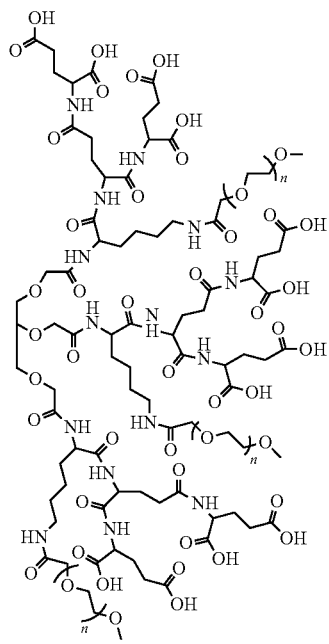

41-133

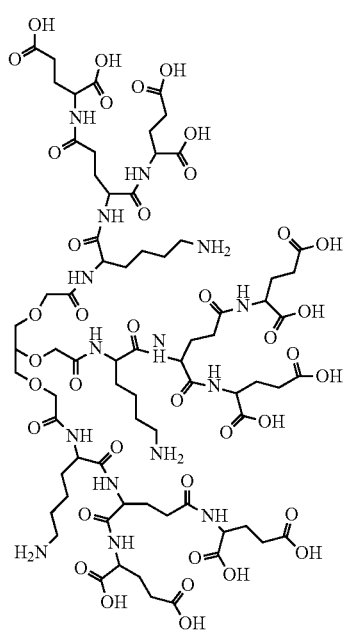

41-132

41-131 (3.2 g, 1.1523 mmol) was added in a flask, and dissolved with dichloromethane (20 mL), TFA (20 mL, 41-132 (0.28 g, 0.1545), M-SCM-5K (3.279 g, 0.6178 mmol, purchased from JenKem) were added in a 250 mL flask, and dissolved with DMF (30 mL), and then the obtained solution was stirred to react under low-temperature and constant temperature condition of 0° C. for 30 minutes. Then DIEA (1 mL, 6.0172 mmol) was slowly added dropwise, and the obtained solution was stirred to react at room temperature in the dark for one week. At the end of the reaction, the reaction solution was precipitated with methyl tert-butyl ether (200 mL) and n-hexane (50 mL), and suction filtering was carried out, to obtain a powder product 1 g, yield 38.46%.

41-134
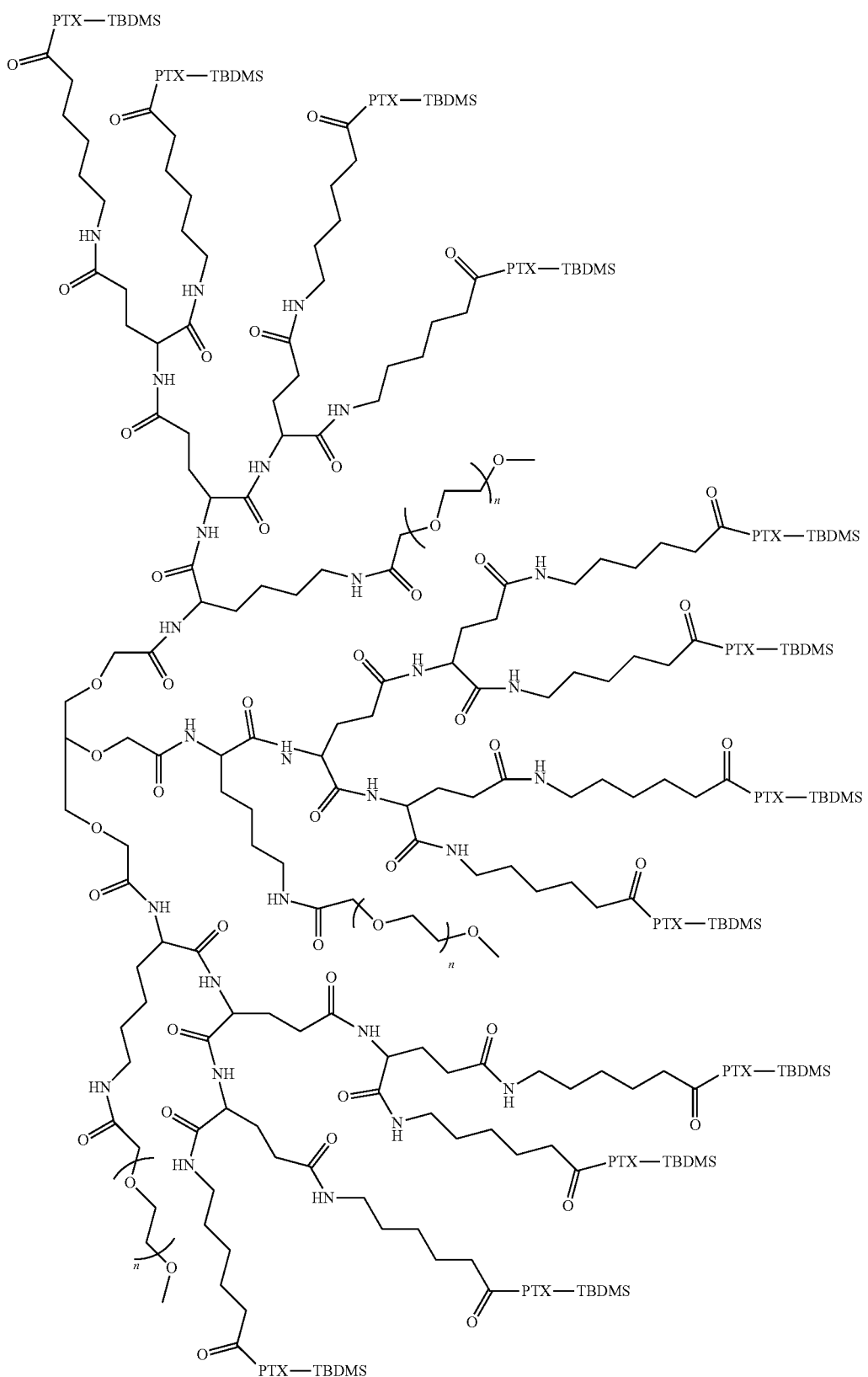
41-133 (0.1064 g, 0.0062 mmol), 45-163 (0.1 g, 0.0925 mmol), HBTU (0.0421 g, 0.1109 mmol), HOBT (0.0150 g, 0.1109 mmol) were added in a 100 mL flask, and dissolved with DMF (20 mL), and then the obtained solution was stirred to react under low-temperature and constant temperature condition of 0° C. for 30 minutes. Then DIEA (0.5 mL, 0.3329 mmol) was slowly added dropwise, and the obtained solution continued to react with stirring under this condition overnight. At the end of the reaction, the reaction solution was precipitated with methyl tert-butyl ether (200 mL) and n-hexane (50 mL), and filtered by suction to obtain a powder product. The obtained powder product was dissolved to obtain a solution. The obtained solution was concentrated, silica gel powder was added, and the operations of evaporation, column chromatography, and elution with 4% methanol/dichloromethane were carried out, thus obtaining the product 0.1 g, yield 55.56%.

41-137

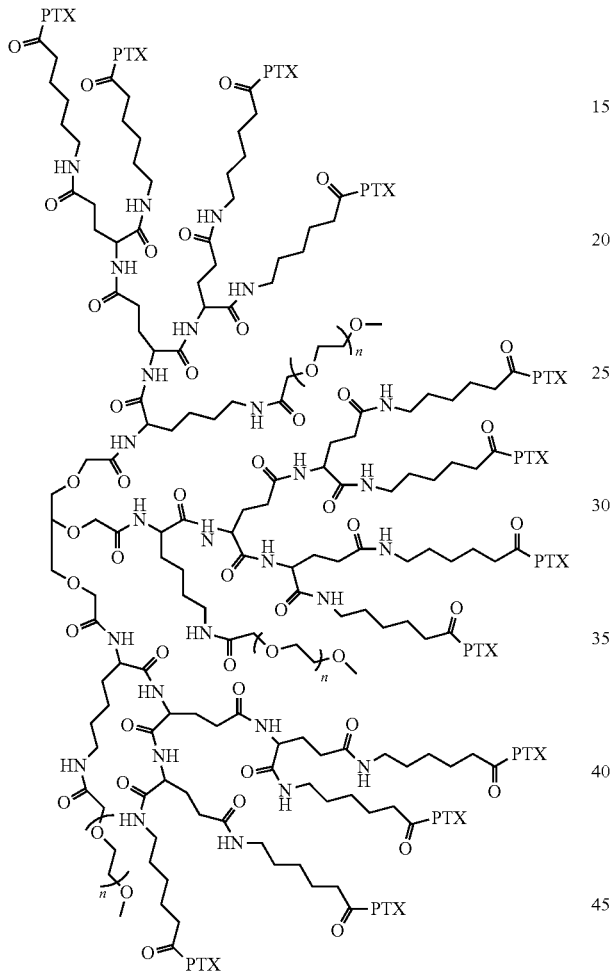

41-134 (0.7 g, 0.0234 mmol), TBAF (1.4684 g, 5.6160 mmol) were added in a 100 mL flask, and dissolved with THF (20 mL), and then the mixed solution was stirred to react at room temperature for 3 hours. At the end of the reaction, the reaction solution was precipitated with methyl tert-butyl ether (200 mL) and n-hexane (50 mL), and filtered by suction to obtain a powder product. The operations of dry sample loading, column chromatography and elution with 4% methanol/dichloromethane were carried out, thus obtaining the product 0.35 g, yield 50%.

$^1$H-NMR (600 MHz, DMSO-$d_6$) δ 8.55-8.54 (m, 8H), 7.96-7.94 (m, 3H), 7.82-7.80 (m, 7H), 7.57-7.39 (m, 21H), 7.29-7.24 (m, 18H), 7.22-7.21 (m, 28H), 6.97-6.90 (m, 48H), 6.78-6.61 (m, 86H), 5.77-5.76 (m, 9H), 5.37-5.32 (m, 3H), 5.09-5.04 (m, 5H), 4.52-4.42 (m, 3H), 4.35-4.23 (m, 9H), 3.51-3.49 (m, 1414H), 3.32-3.31 (m, 41H), 3.06-3.01 (m, 77H), 2.74-2.71 (m, 26H), 2.61-2.59 (m, 14H), 2.05-1.96 (m, 55H), 1.74-1.67 (m, 44H), 1.46-1.39 (m, 76H), 1.24-1.21 (m, 91H), 1.16-1.14 (m, 22H), 1.05-1.01 (m, 112H), 0.87-0.79 (m, 28H).

32. Synthesis of 49-166 (Compound No. 31)

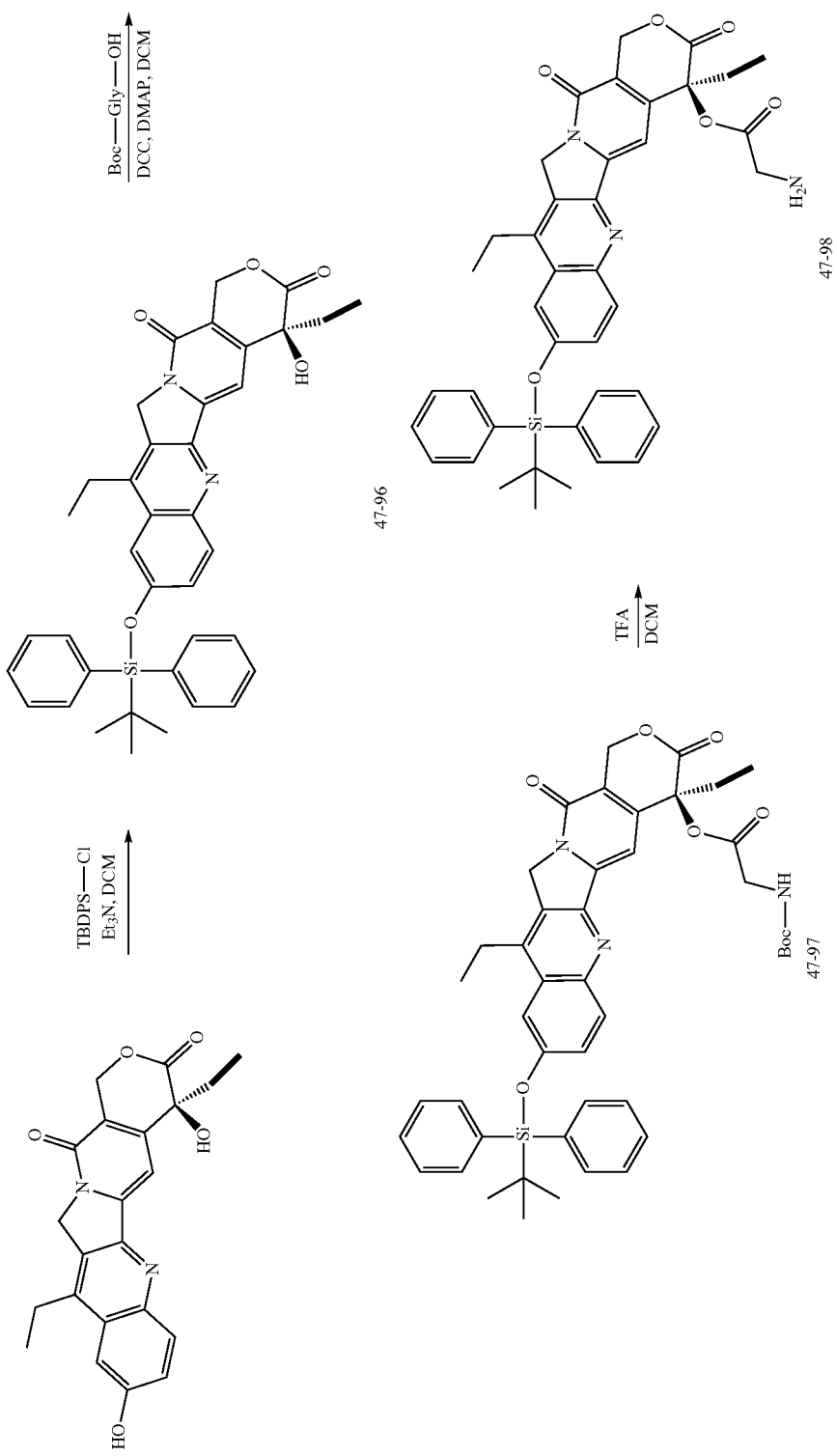

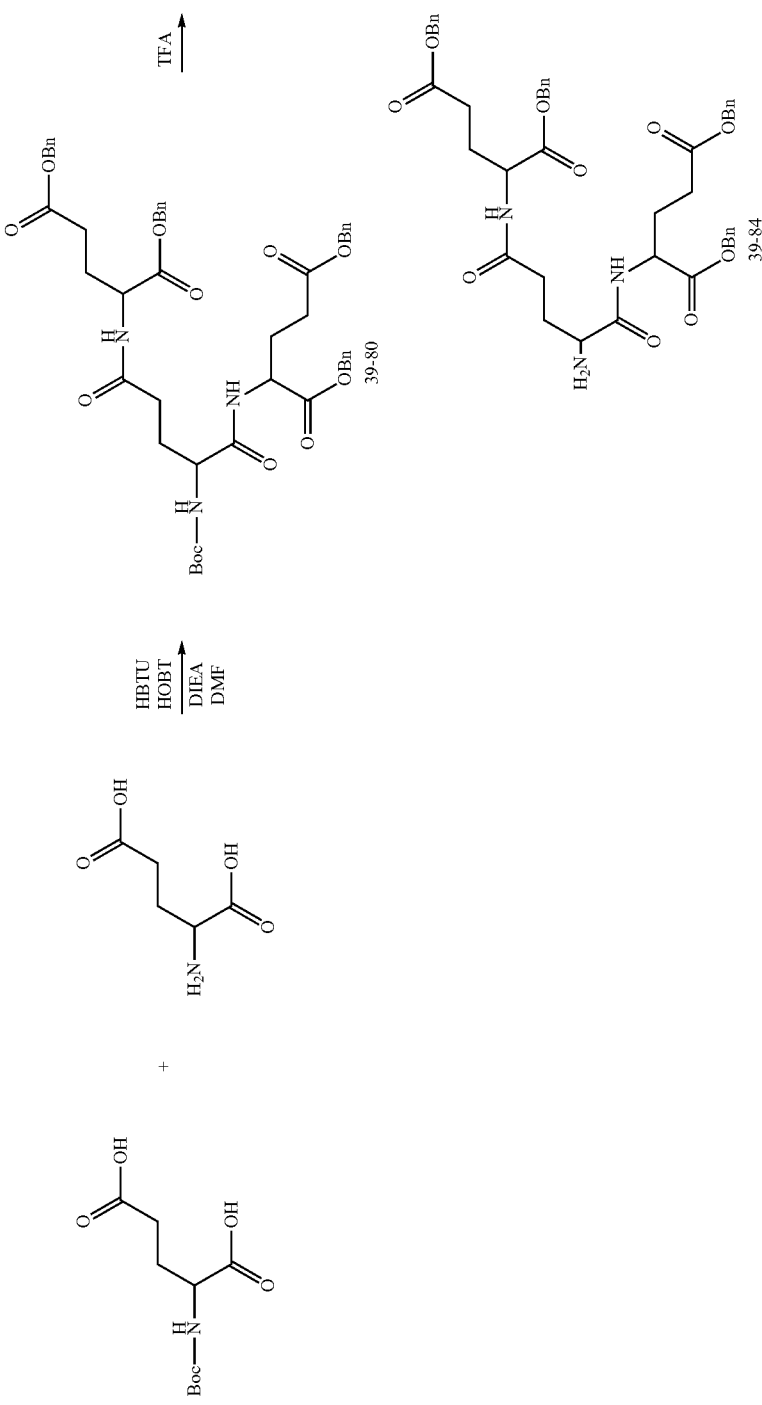

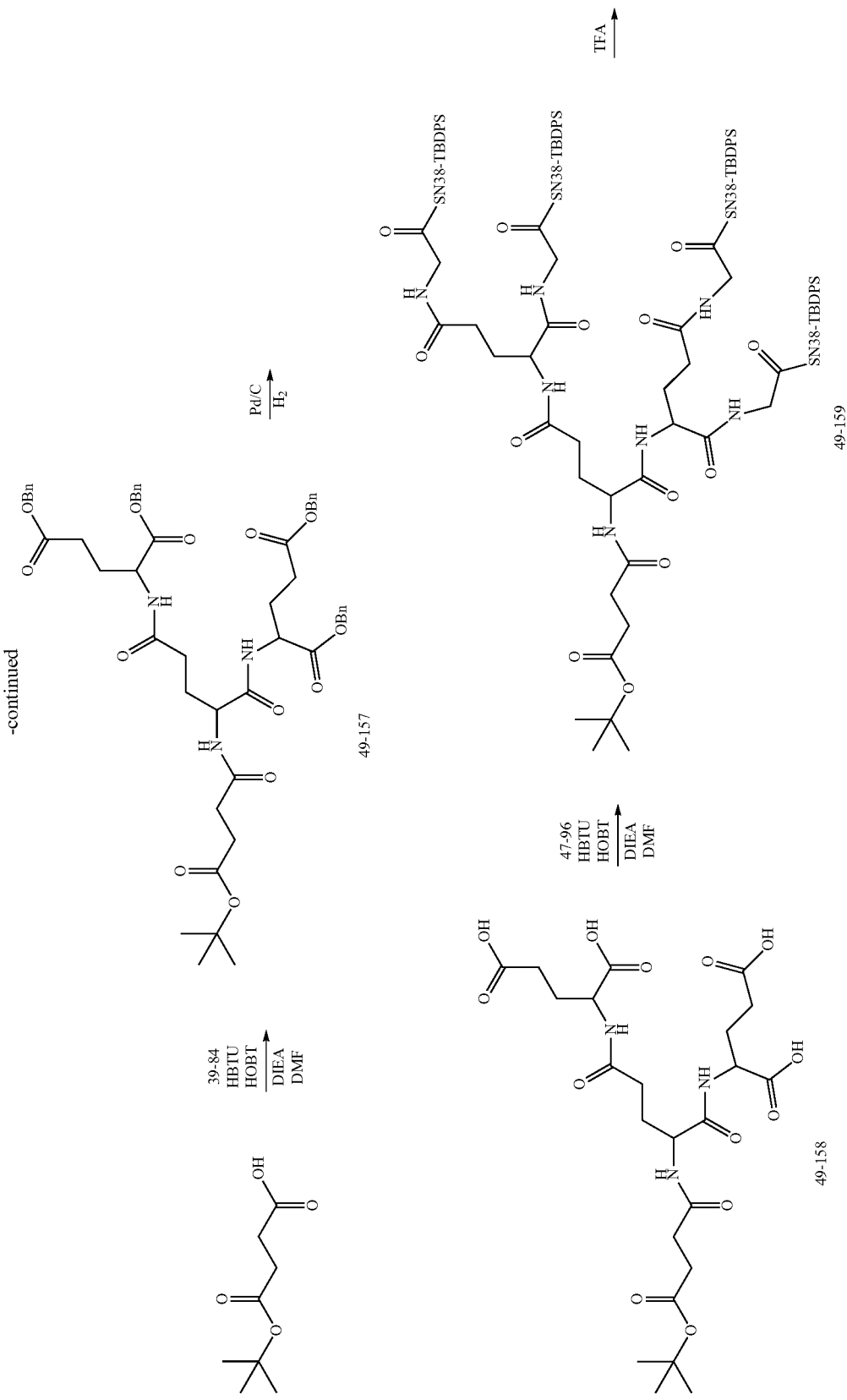

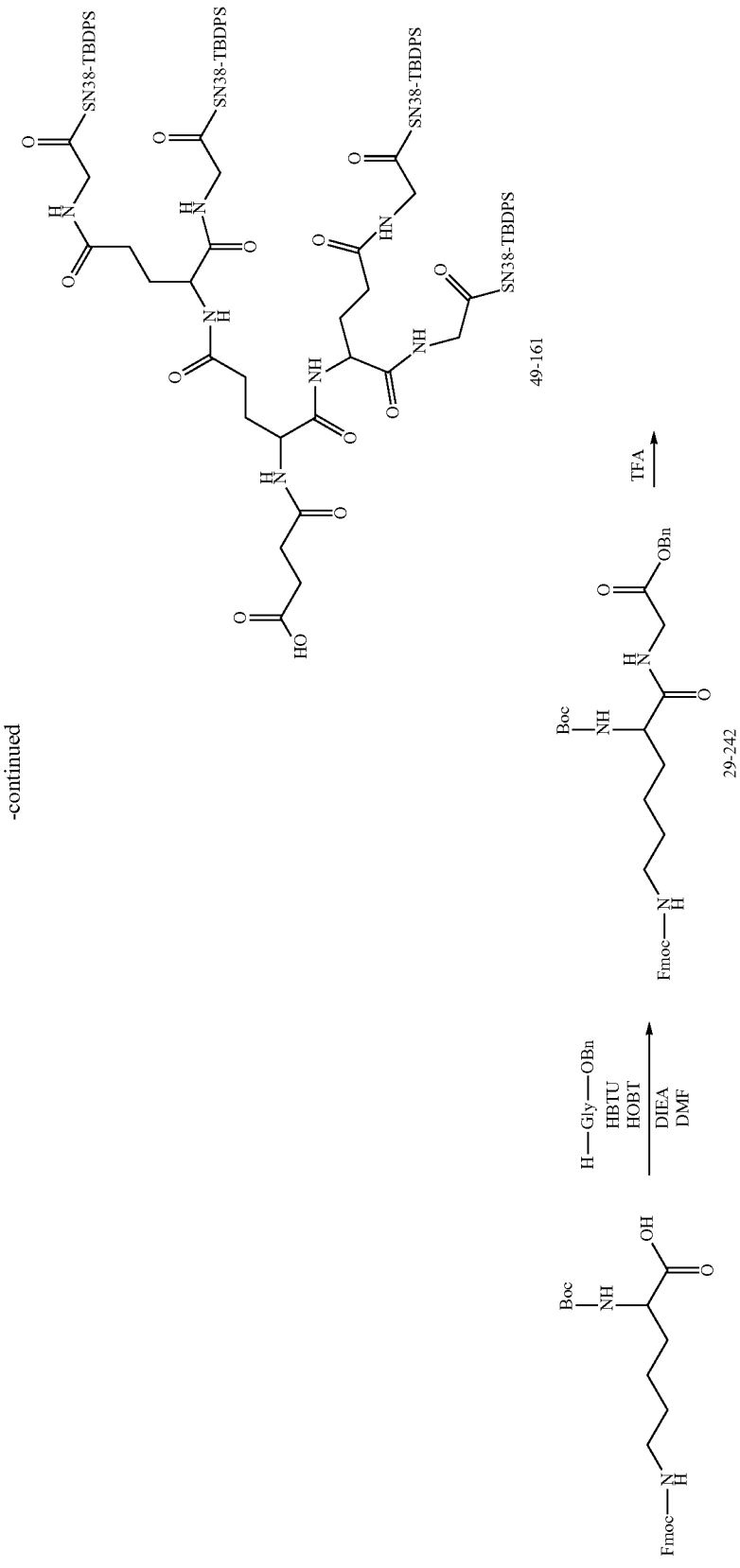

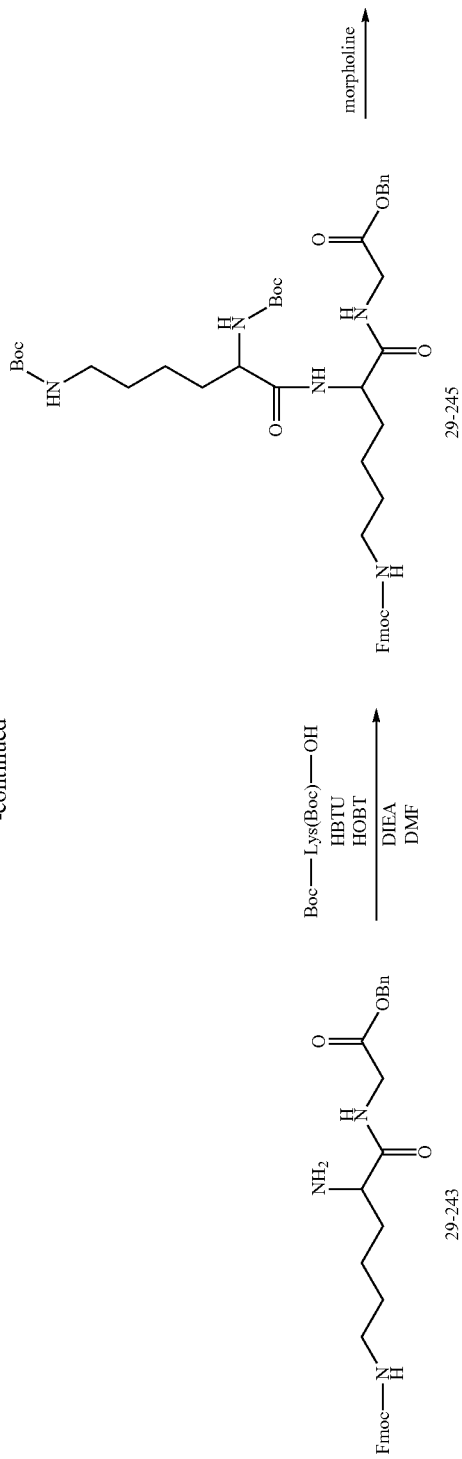

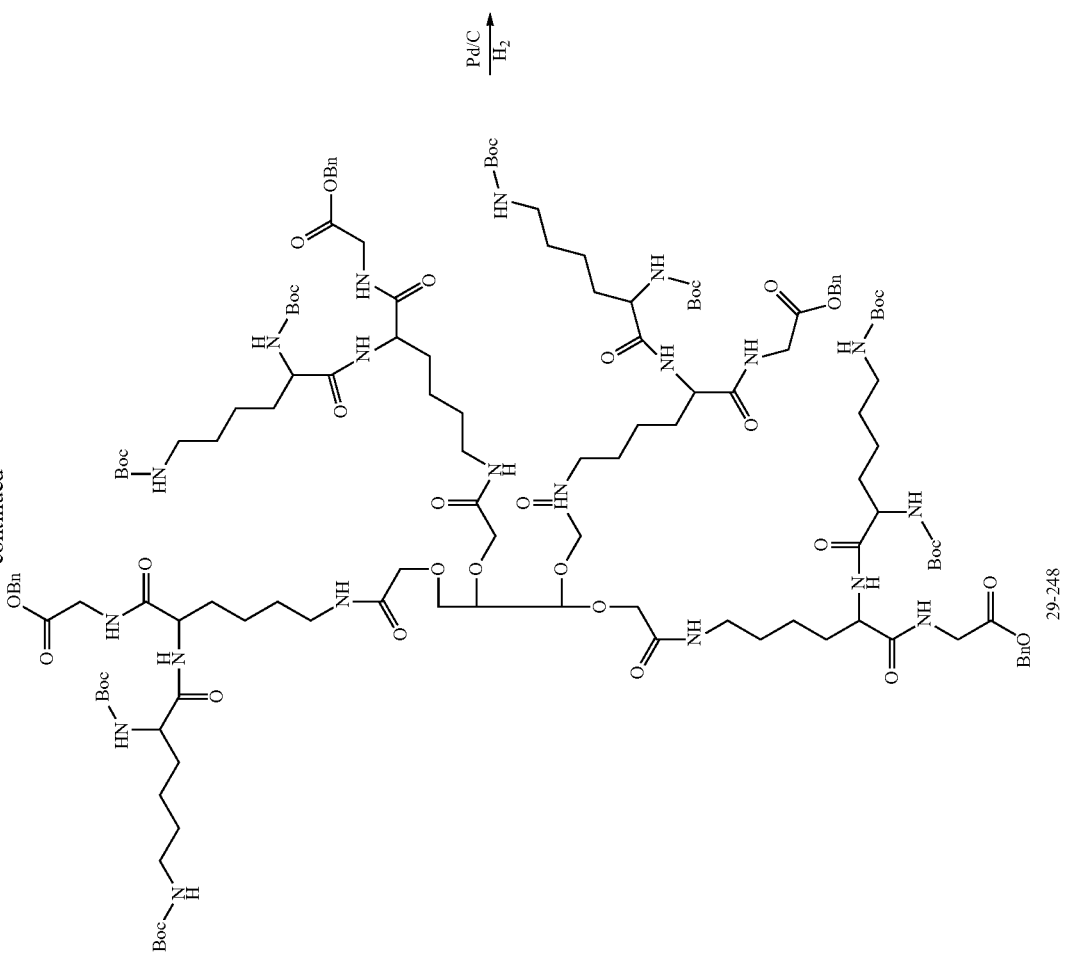

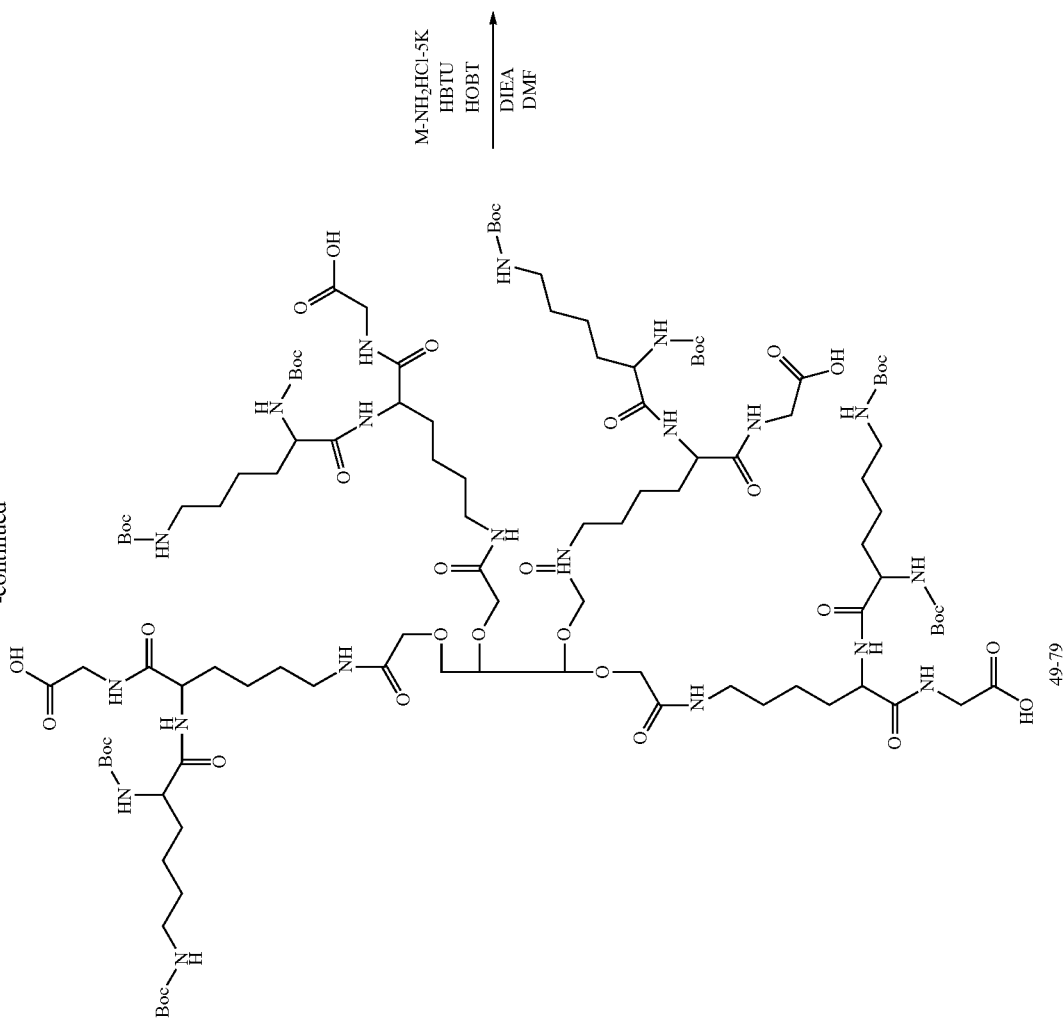

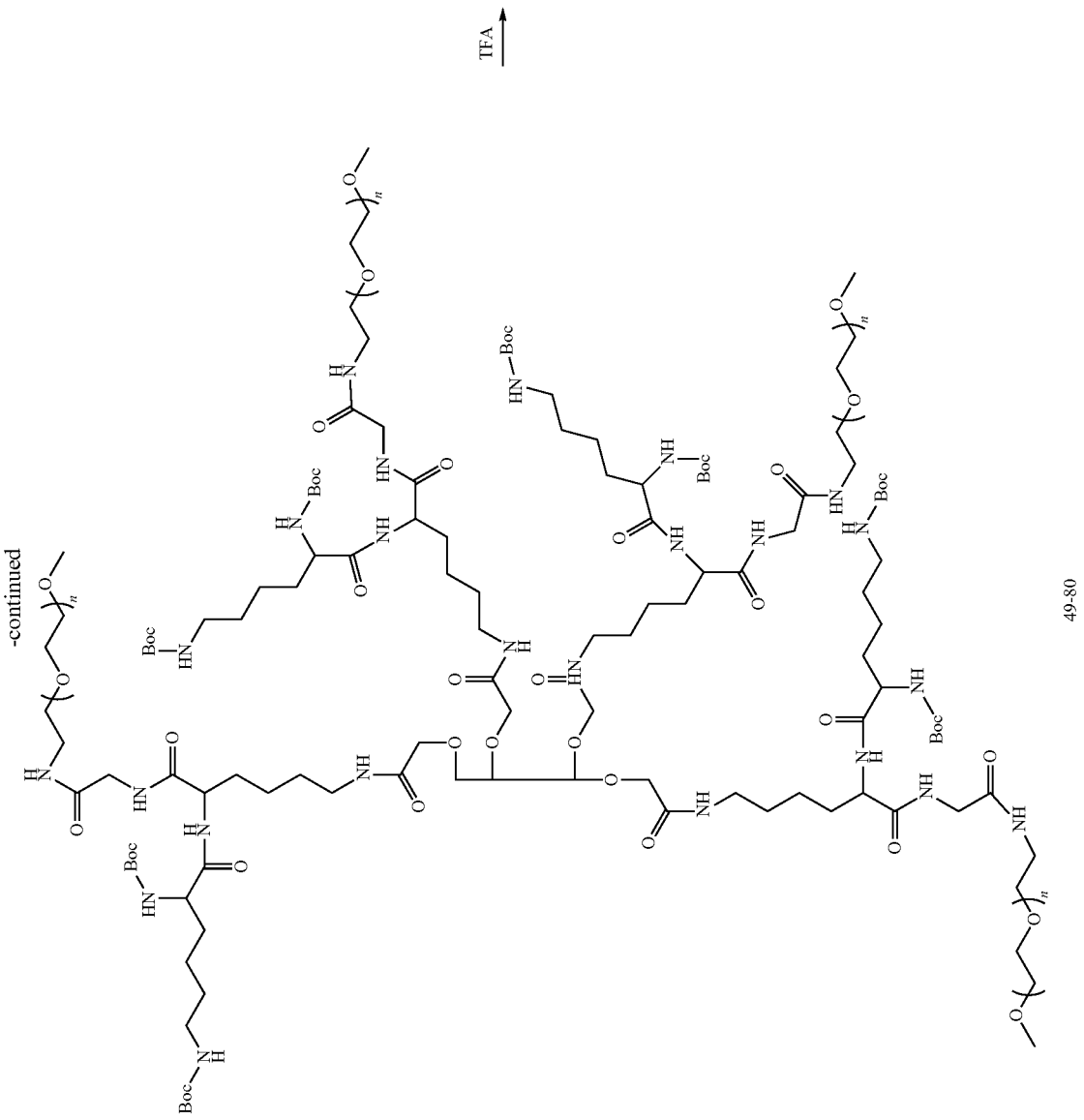

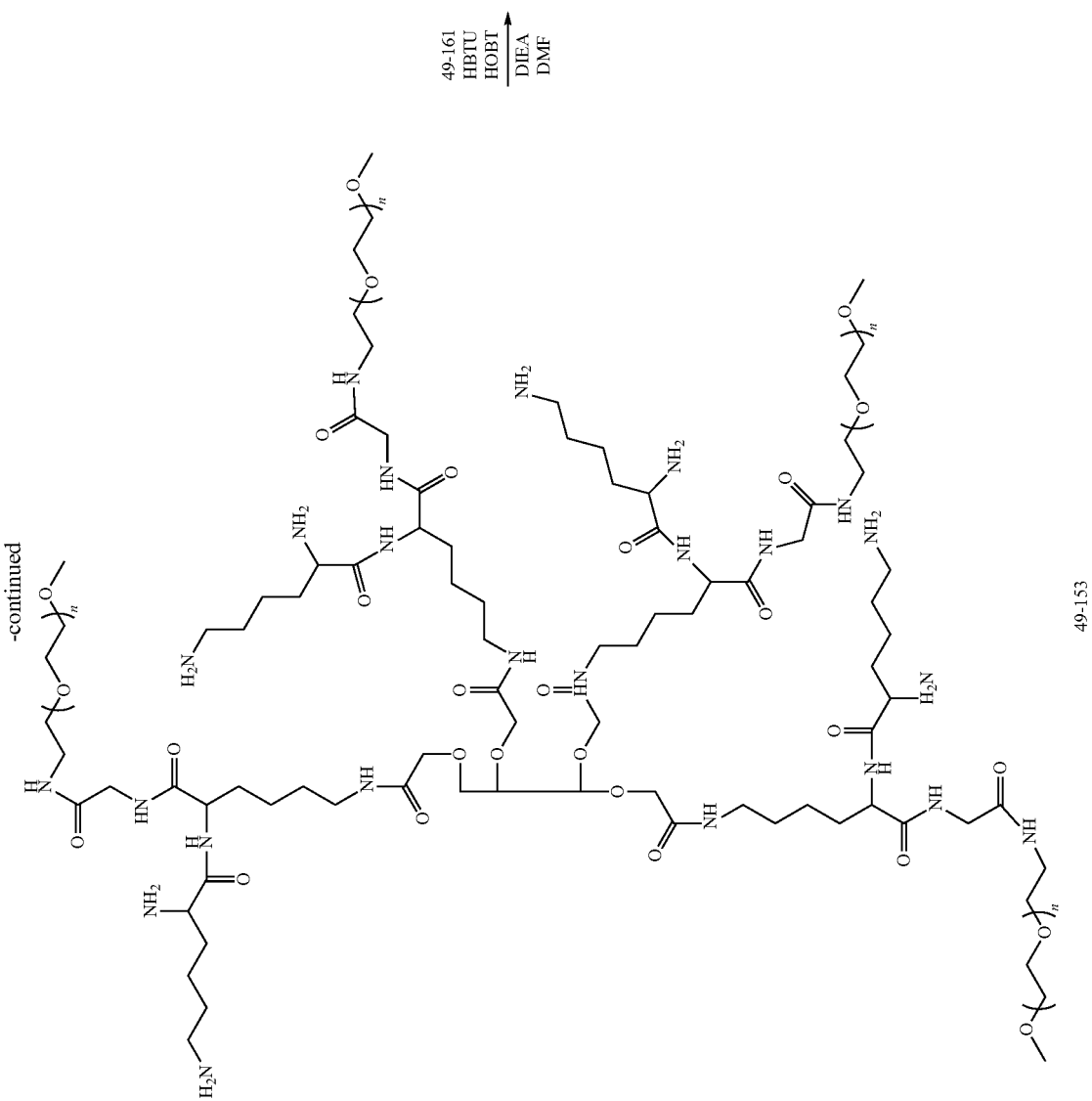

-continued
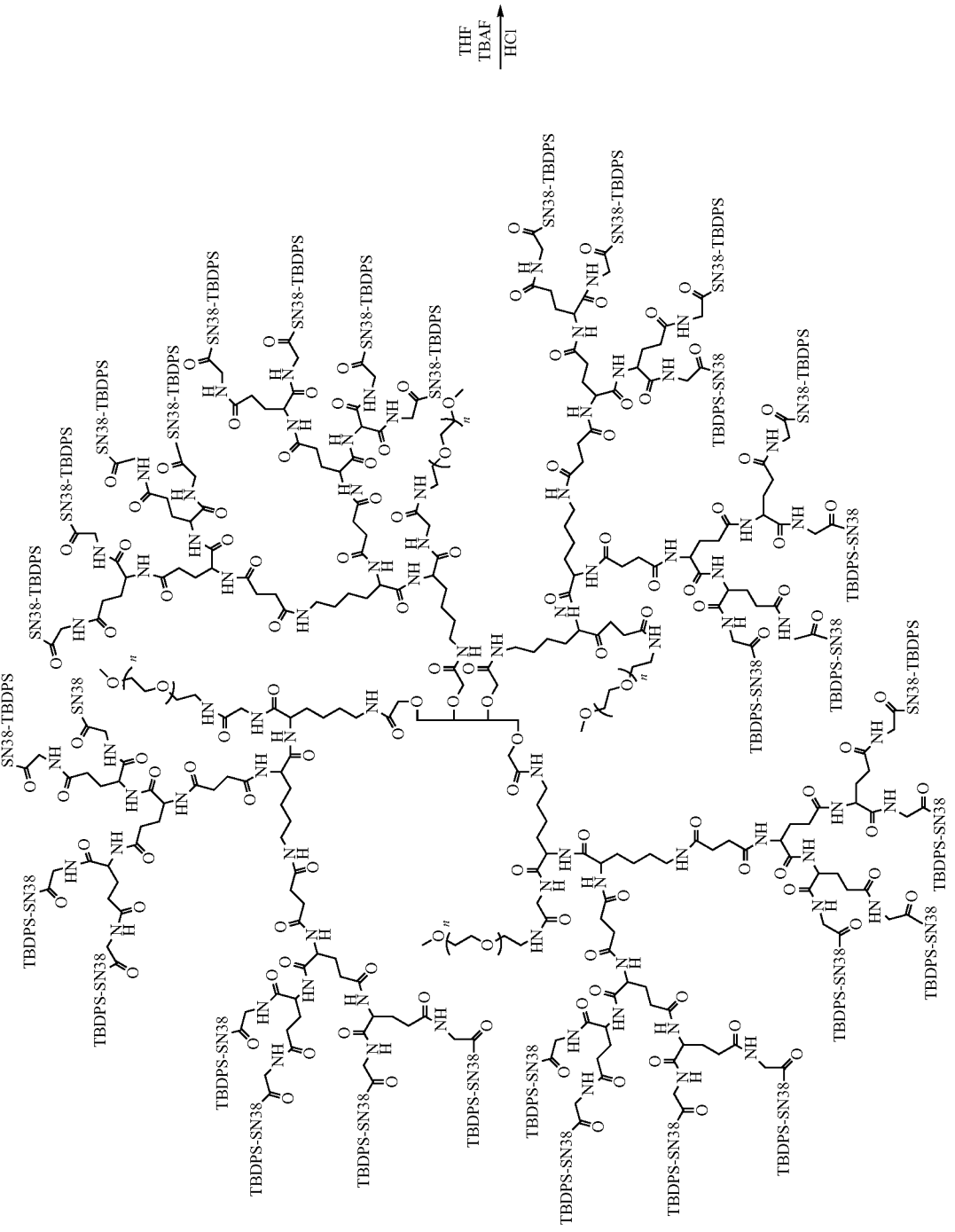
49-162

-continued
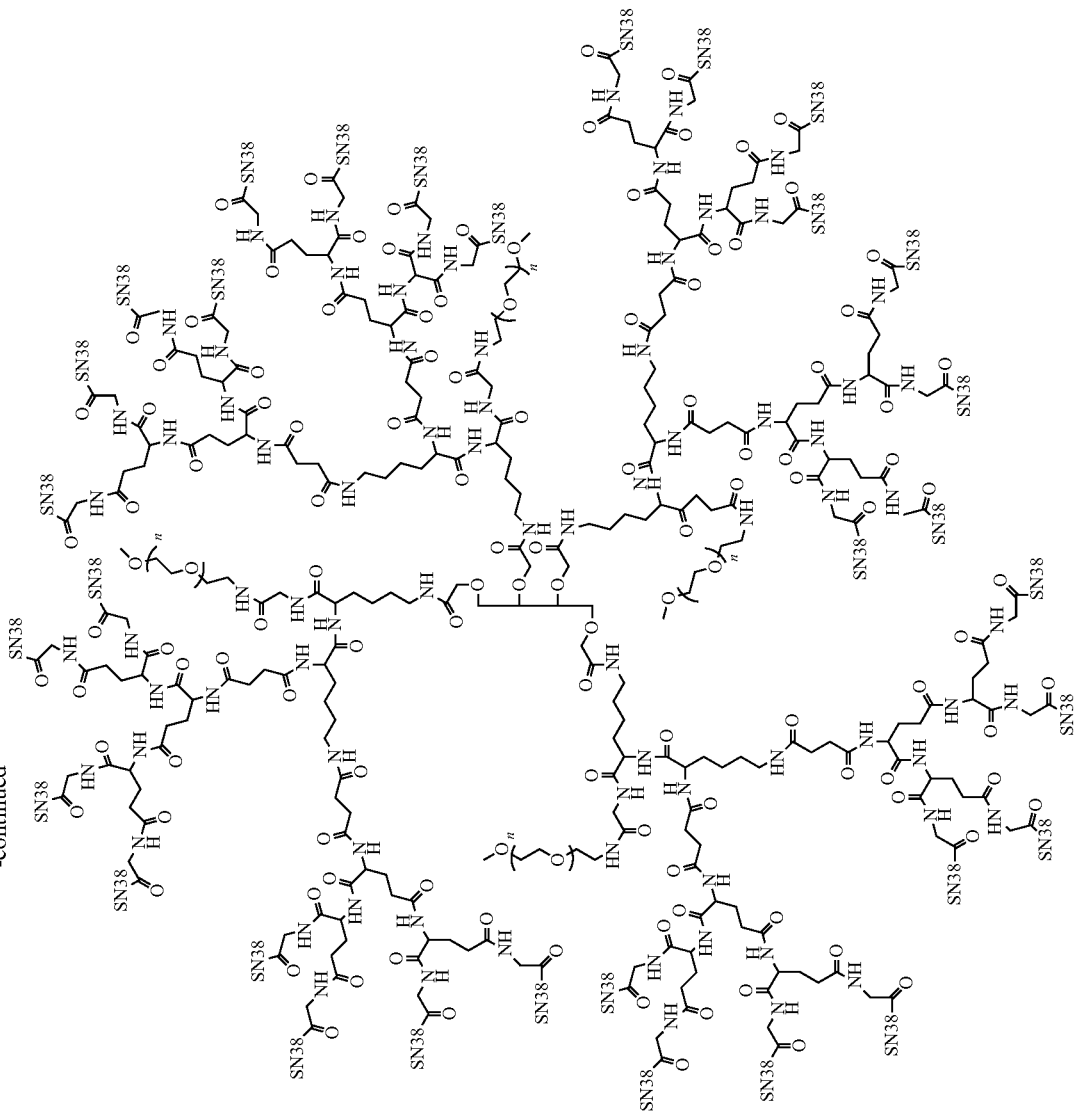

39-80
-continued
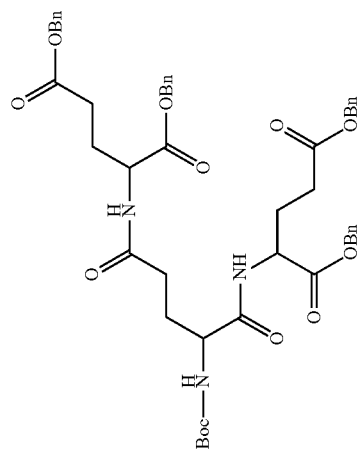

Boc-Glu-OH (5.0 g, 20.22 mmol, purchased from Aladdin), H-Glu (OBzl)-OBzl·TsOH (21.2 g, 42.46 mmol, purchased from Ark Pharm), HOBT (8 g, 60.66 mmol), HBTU (23 g, 60.66 mmol) were added in a 250 mL flask, and dissolved with DMF (80 mL), and ultrasonic treatment was carried out to completely dissolve the reactants, and then the obtained solution was stirred at −5° C. for 30 minutes. Then DIEA (30 mL, 181 mmol) was slowly added dropwise, and the obtained solution reacted at the low temperature under the reaction ended. At the end of the reaction, deionized water (100 mL) was added to the reaction solution, the obtained solution was extracted three times with ethyl acetate (100 mL×3), and the obtained organic phases were combined. The organic phase was washed two times with saturated sodium chloride solution (100 mL), concentrated and evaporated to dryness. The operations of dry sample loading, column chromatography and gradient elution with 40% ethyl acetate/petroleum ether-50% ethyl acetate/petroleum ether were carried out. The elution product was then collected, concentrated, and evaporated to dryness.

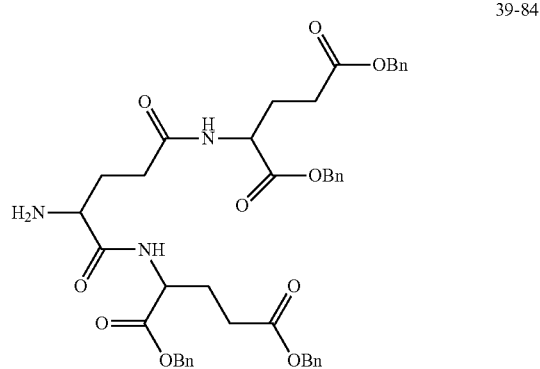 [SMILES: NC(CCC(=O)NC(CCC(=O)OCc1ccccc1)C(=O)OCc1ccccc1)C(=O)NC(CCC(=O)OCc1ccccc1)C(=O)OCc1ccccc1]

39-84

39-80 (19.2 mmol) was dissolved with dichloromethane (5 mL), TFA (14 mL, 192 mmol) was added, and ultrasonic treatment was carried out to completely dissolve the compound. A ground glass stopper was used, and the mixed solution was stirred to react at room temperature. At the end of the reaction, saturated sodium bicarbonate solution (300 mL) was added to the reaction solution, the obtained solution was extracted three times with ethyl acetate (100 mL×3), and the obtained organic phases were combined. The organic phase was washed two times with saturated sodium chloride solution (100 mL), concentrated and evaporated to dryness.

7-Ethyl-10-hydroxycamptothecin (15.00 g, 38.23 mmol, also referred to as SN38) was added in a 1000 mL round-bottomed flask, and dissolved with dichloromethane (150 mL), tert-butyl diphenylchlorosilane (59.64 ml, 229.36 mmol, purchased from Accela), triethylamine (31.88 ml, 229.36 mmol) were added, and then the obtained solution was placed in an oil bath at 37° C. and stirred to react overnight. At the end of the reaction, the reaction solution was evaporated to obtain a viscous solution, the viscous solution was precipitated with n-hexane (150 ml) to obtain a solid product, and suction filtering was carried out. The filter cake was dried, thus obtaining the product (23.15 g, 96%).

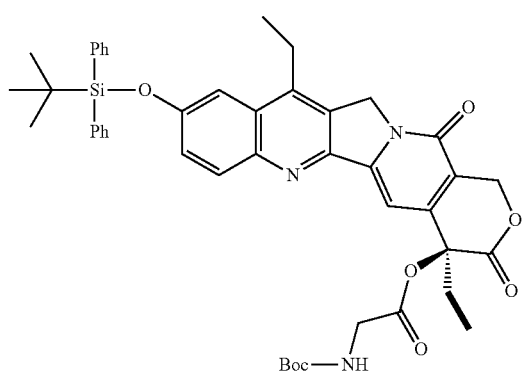

47-97

47-96 (23.15 g, 36.70 mmol), Boc-Gly-OH (8.71 g, 49.70 mmol, purchased from Aladdin), DMAP (0.94 g, 7.65 mmol) were added in a 1000 mL round-bottomed flask, and dissolved with dichloromethane (150 mL), and then the mixed solution was stirred at 0° C. for 30 minutes. Then, DCC (39.41 g, 191.15 mmol) was added in three batches, with an interval of 30 minutes each batch. At the end of the addition, the obtained solution reacted at 0° C. for 2 hours, and was then moved to room temperature and stirred to react overnight. At the end of the reaction, the reaction solution was precipitated with n-hexane (200 mL) and petroleum ether (50 mL). Such operations were repeated three times, and filtering was carried out to obtain a solid product. The solid product was dried in a vacuum oven, thus obtaining the product (27.53 g, 94%).

47-96

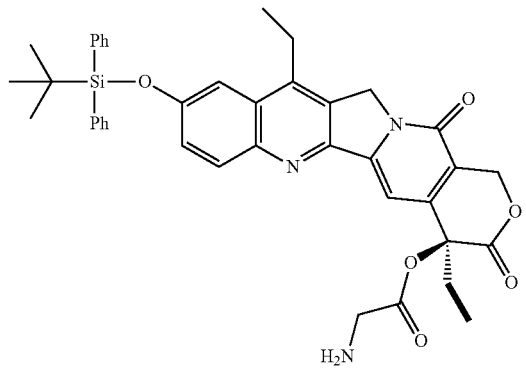

47-98

47-97 (27.53 g, 34.50 mmol) was added in a 1000 mL round-bottomed flask, and dissolved with dichloromethane (50 mL) and trifluoroacetic acid (28.40 ml, 382.30 mmol), and then the mixed solution reacted at room temperature. At the end of the reaction, deionized water (200 mL) was added to the reaction solution, the obtained solution was extracted with ethyl acetate (100 mL×3), and the obtained organic phases were combined. The organic phase was washed with saturated sodium chloride solution (200 mL×2), and concentrated, silica gel powder was added, and the obtained mixture was then evaporated to dryness to obtain a powdery product. The operations of column chromatography and gradient elution (with 1%-3% $CH_3OH$, the rest of $CH_2Cl_2$) were carried out. The elution product was then collected, and concentrated, thus obtaining the product (16.98 g, 72%).

29-242 (6.57 g, 10.6714 mmol) was added in a 500 mL flask, and dissolved with a proper amount of dichloromethane, TFA (7.9248 mL, 106.714 mmol) was added, and then the mixed solution was stirred to react at room temperature overnight. At the end of the reaction, the reaction solution was evaporated to obtain an oily solution, a saturated sodium bicarbonate solution was added to adjust pH until the solution became alkaline, the obtained solution was extracted with ethyl acetate (100 mL×3), and the obtained organic phases were combined. The organic phase was washed two times with saturated sodium chloride solution (200 mL), concentrated, evaporated to dryness, and dried in a vacuum oven, thus obtaining a crude product.

29-242

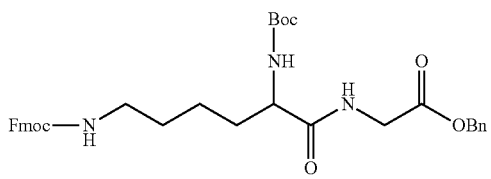

Fmoc-Lys (Boc) —OH (5.0 g, 10.6714 mmol, purchased from Aladdin), H-Gly-OBn (3.7802 g, 11.2050 mmol, purchased from Innochem), HBTU (6.0705 g, 16.0072 mmol), HOBT (2.1630 g, 16.0072 mmol) were added in a 500 mL flask, and dissolved with DMF (50 mL), and then the obtained solution was stirred to react at 0° C. for 30 minutes. Then DIEA (7.9371 mL, 48.0215 mmol) was slowly added dropwise, the obtained solution continued to react at 0° C. with stirring overnight. At the end of the reaction, deionized water (200 mL) was added to the reaction solution, the obtained solution was extracted with ethyl acetate (100 mL×3), and the obtained organic phases were combined. The organic phase was washed two times with saturated sodium chloride solution (200 mL), concentrated, evaporated to dryness, and dried in a vacuum oven, thus obtaining a crude product.

29-245

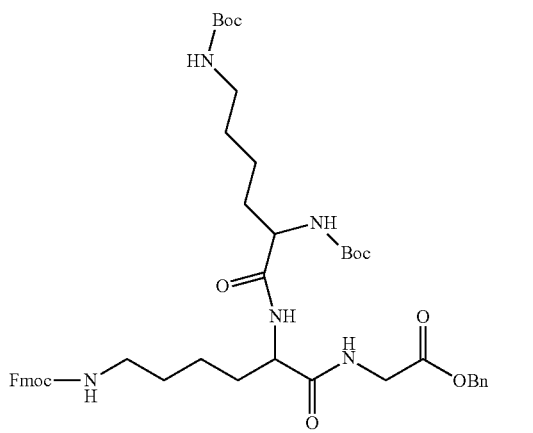

Boc-Lys (Boc) —OH (4.2805 g, 11.7385 mmol, purchased from Ark Pharm), 29-243 (5.50 g, 10.6714 mmol), HBTU (6.0705 g, 16.0072 mmol), HOBT (2.1630 g, 16.0072 mmol) were added in a 500 mL flask, and dissolved with DMF (50 mL), and then the mixed solution was stirred to react at 0° C. for 30 min. Then DIEA (7.9371 mL, 48.0215 mmol) was slowly added dropwise, the obtained solution continued to react at 0° C. overnight. At the end of the reaction, deionized water (200 mL) was added to the reaction solution, the obtained solution was extracted with ethyl acetate (100 mL×3), and the obtained organic phases were combined. The organic phase was washed two times with saturated sodium chloride solution (200 mL), concentrated, evaporated to dryness, and dried in a vacuum oven, thus obtaining a crude product.

29-243

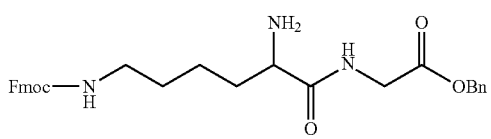

29-246

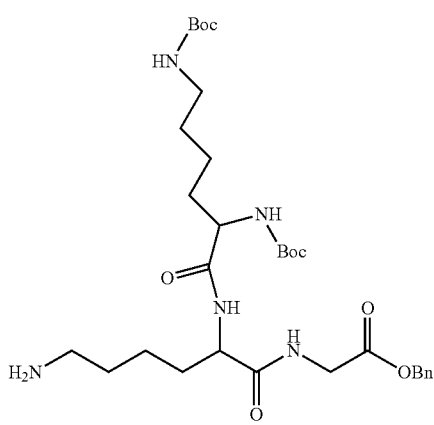

Morpholine (9.24 mL, 106.714 mmol) was added in a 500 ml flask loaded with 29-245 (9.0 g, 10.6714 mmol), and dissolved with DMF (10 mL), and then the mixed solution was stirred to react at room temperature for 1 hour. At the end of the reaction, deionized water (200 mL) was added to the reaction solution, the obtained solution was extracted with ethyl acetate (100 mL×3), and the obtained organic phases were combined. The organic phase was washed two times with saturated sodium chloride solution (200 mL), and concentrated, silica gel powder was added, and the obtained mixture was then evaporated to dryness to obtain a powdery product. The operations of column chromatography and gradient elution (with 1% ammonia water, 4%-5% methanol, the rest of dichloromethane) were carried out. The elution product was then collected, concentrated, thus obtaining the product 29-246: 3.7 g. Yield 56%.

Erythritol (4.5 g, 36.849 mmol) was added in a 500 mL two-neck flask, and dissolved with THF (60 mL) in a condition of ultrasonic, and then the obtained solution was stirred at 0° C. After introducing nitrogen for protective purpose, potassium tert-butoxide (200 mL, 184.245 mmol) was added, and the obtained solution was stirred at 0° C. for 2 hours. Then, benzyl bromoacetate (29.187 mL, 184.245 mmol) was added, and the obtained solution was stirred for 3 hours and then reacted at room temperature. At the end of the reaction, the reaction solution was extracted with pure water and ethyl acetate, and the organic phase was concentrated. The operations of dry sample loading, column chromatography and gradient elution with 1%-2% ethyl acetate/petroleum ether were carried out, thus obtaining the product 5 g, yield 20%.

38-120

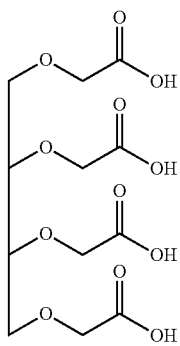

21-221

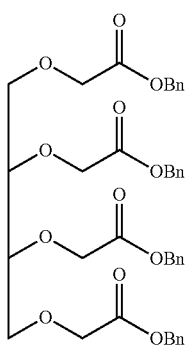

21-221 (0.64 g, 0.9793 mmol) and 10% Pd/C (100 mg) were added in a hydrogenation reactor, DMF (30 mL) was slowly added to dissolve the reactant with stirring, hydrogen was introduced to a pressure of 300 psi, and then the mixed solution was stirred to react at room temperature overnight. Next day, the reaction solution was filtered by suction through a sand core funnel filled with diatomaceous earth to remove the Pd/C, thus obtaining the DMF solution of the product, directly used for next reaction.

29-248

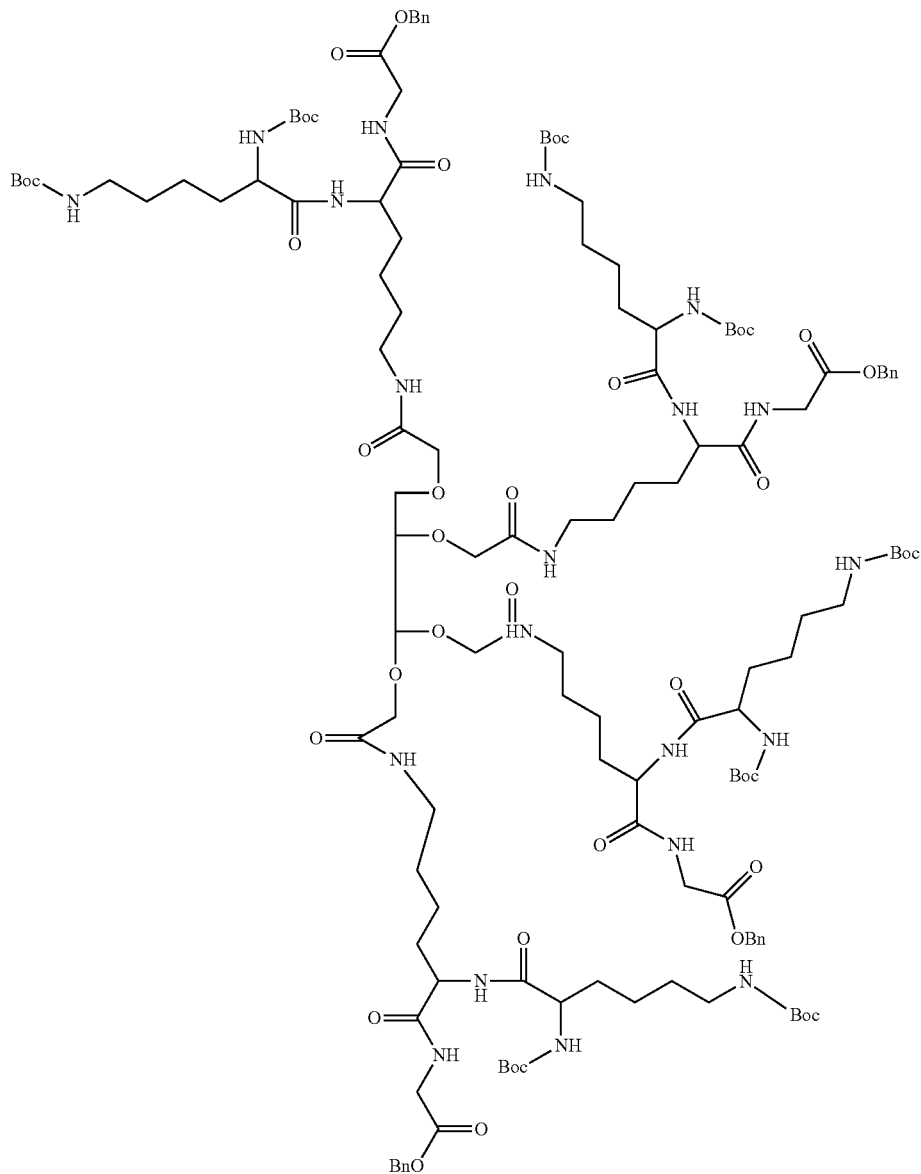

38-120 (0.39 g, 1.0966 mmol), 29-246 (3.0 g, 4.8249 mmol), HBTU (2.4951 g, 6.5795 mmol), HOBT (0.8891 g, 6.5795 mmol) were added in a 500 mL flask, and dissolved with DMF (50 mL), and then the mixed solution was stirred to react at −5° C. for about 30 minutes. Then DIEA (3.2624 mL, 19.7384 mmol) was slowly added dropwise, the obtained solution continued to react at −5° C. with stirring for 1 hour, and was then moved to room temperature and stirred to react overnight. At the end of the reaction, deionized water (200 mL) was added to the reaction solution, the obtained solution was extracted with ethyl acetate (100 mL×3), and the obtained organic phases were combined. The organic phase was washed two times with saturated sodium chloride solution (200 mL), and concentrated, silica gel powder was added, and the obtained mixture was then evaporated to dryness to obtain a powdery product. The operations of column chromatography and gradient elution (with 50%-80% ethyl acetate, the rest of petroleum ether) were carried out. The elution product was then collected, concentrated, thus obtaining the product (1.6 g, 53%).

49-79

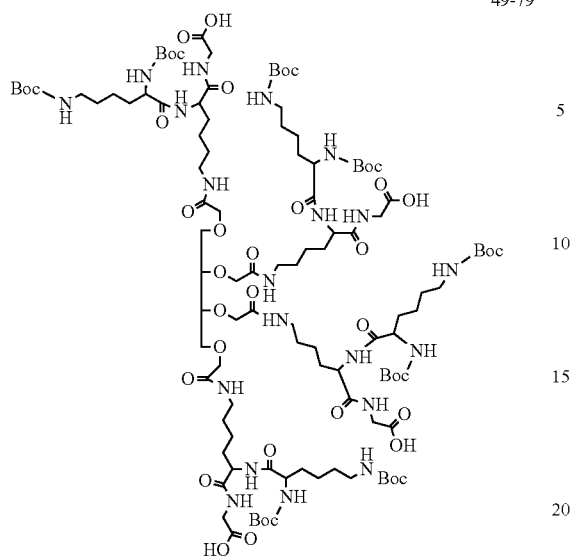

29-248 (0.52 g, 0.1878 mmol) and 10% Pd/C (0.0, 5 g) were added in a hydrogenation reactor, and dissolved with DMF (30 mL). The hydrogenation reactor was then sealed to perform the "three pumping and three charging" operation so that the pressure on the hydrogenation reactor was read as 0.18 MPa, and then the obtained solution reacted at room temperature overnight. At the end of the reaction, the reaction solution was filtered with diatomaceous earth. The filter cake was washed with DMF (20 mL×3), thus obtaining the DMF solution of the product, as the raw material for the next reaction.

49-80

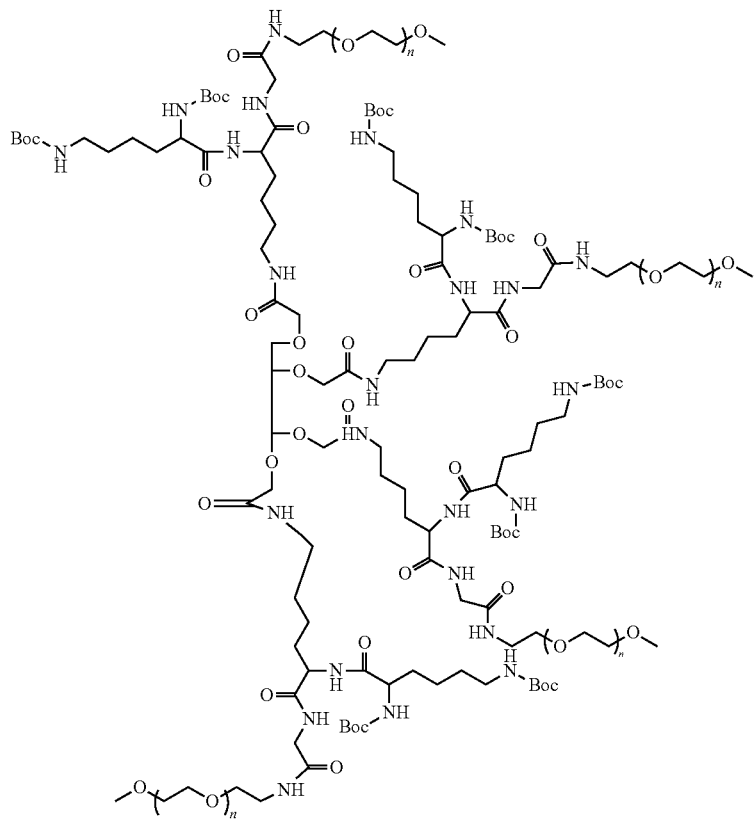

49-79 (0.45 g, 0.1878 mmol), M-NH$_2$HCl-5K (4.91 g, 0.9389 mmol, purchased from JenKem), HBTU (0.43 g, 1.1237 mmol), HOBT (0.15 g, 1.1267 mmol) were added in a 500 mL flask, and dissolved with DMF (60 mL), and then the mixed solution was stirred to react at −5° C. for about 30 minutes. Then DIEA (0.56 mL, 3.3780 mmol) was slowly added dropwise, and the obtained solution continued to react at −5° C. with stirring for 1 hour, and then reacted at room temperature in the dark for 3 days at a low speed of stirring. At the end of the reaction, the reaction solution was shaken with n-hexane (100 mL), and the supernatant was discarded. The above operations were repeated three times. The obtained solution was then shaken with methyl tert-butyl ether (80 mL) and a small amount of n-hexane (10 mL), and the supernatant was discarded. The above operations were repeated three times. A powdery solid was separated out of the reaction solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 1% ammonia water and 3%-7% methanol were carried out. The elution product was then collected, concentrated, and dried in a vacuum oven, thus obtaining the product (3.2 g, 73.73%).

49-80 (3.2 g, 0.1383 mmol) was added in a 250 mL flask, and dissolved with dichloromethane (5 mL) and TFA (0.82 mL, 11.0640 mmol), and then the mixed solution was stirred to react at room temperature in the dark overnight at a low speed. At the end of the reaction, the reaction solution was rotary evaporated to obtain an oily solution, and methyl tert-butyl ether (60 mL) was then added to the oily solution. A powdery solid was separated out of the obtained solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 3%-12% methanol were carried out. The elution product was then collected, concentrated, and dried in a vacuum oven, thus obtaining the product (1.74 g, 56.35%).

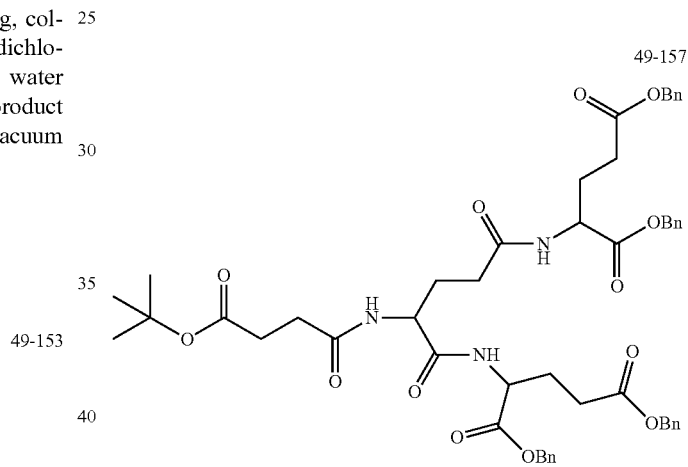

49-157

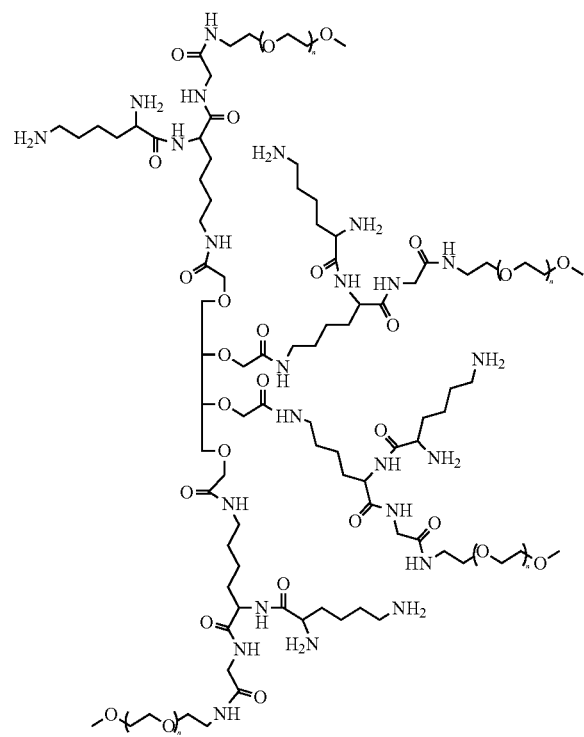

49-153

39-84 (5.16 g, 6.7433 mmol), mono-tert-butyl succinate (1.40 g, 8.0920 mmol, purchased from Accela), HBTU (3.84 g, 10.1149 mmol), HOBT (1.36 g, 10.1149 mmol) were added in a 500 mL flask, and dissolved with DMF (50 mL), and then the mixed solution was stirred to react at −5° C. for about 30 minutes. Then DIEA (10.03 mL, 60.6897 mmol) was slowly added dropwise, the obtained solution continued to react at −5° C. with stirring for 1 hour, and was then moved to room temperature and stirred to react overnight. At the end of the reaction, deionized water (200 mL) was added to the reaction solution, the obtained solution was extracted with ethyl acetate (100 mL×3), and the obtained organic phases were combined. The organic phase was washed two times with saturated sodium chloride solution (200 mL), and concentrated, silica gel powder was added, and the obtained mixture was then evaporated to dryness to obtain a powdery product. The operations of column chromatography and gradient elution (with 50%-90% ethyl acetate, the rest of petroleum ether) were carried out. The elution product was then collected, concentrated, thus obtaining the product (5.66 g, 90.99%).

49-158

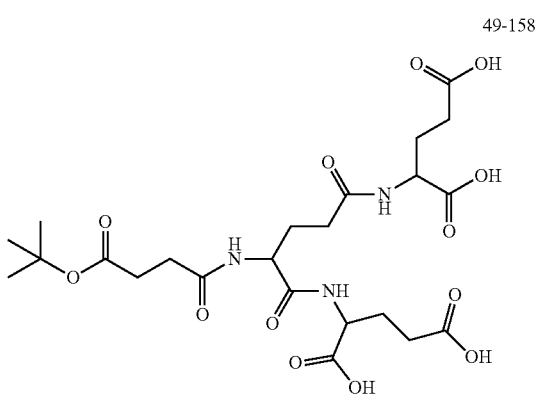 [SMILES: CC(C)(C)OC(=O)CCC(=O)NC(CCC(=O)NC(CCC(=O)O)C(=O)O)C(=O)NC(CCC(=O)O)C(=O)O]

49-157 (2.8 g, 3.0367 mmol) and 10% Pd/C (0.08 g) were added in a hydrogenation reactor, and dissolved with DMF (30 mL). The hydrogenation reactor was then sealed to perform the "three pumping and three charging" operation so that the pressure on the hydrogenation reactor was read as 0.18 MPa, and then the obtained solution reacted at room temperature overnight. At the end of the reaction, the reaction solution was filtered with diatomaceous earth. The filter cake was washed with DMF (20 mL×3), thus obtaining the DMF solution of the product as raw material for the next reaction.

49-159

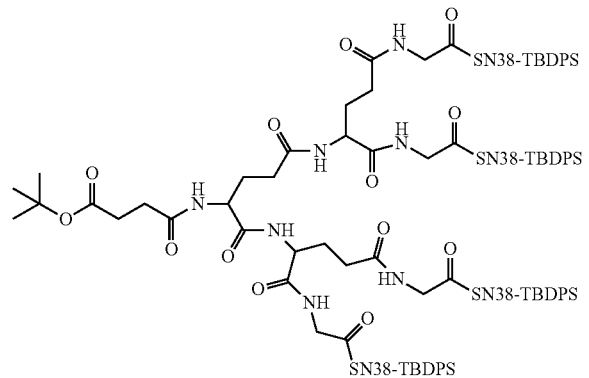

49-158 (1.71 g, 3.0367 mmol), 47-98 (8.77 g, 12.7541 mmol), HBTU (6.90 g, 18.2202 mmol), HOBT (2.46 g, 18.2202 mmol) were added in a 500 mL flask, and dissolved with DMF (60 mL), and then the mixed solution was stirred to react at −5° C. for about 30 minutes. Then DIEA (13 mL, 78.9542 mmol) was slowly added dropwise, and the obtained solution continued to react at −5° C. with stirring for 1 hour, and was then moved to room temperature and stirred to react overnight. At the end of the reaction, the reaction solution was shaken with n-hexane (100 mL), and the supernatant was discarded. The above operations were repeated three times. The obtained solution was then shaken with methyl tert-butyl ether (80 mL) and a small amount of n-hexane (10 mL), and the supernatant was discarded. The above operations were repeated three times. A powdery solid was separated out of the obtained solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (60 g) was added, and the obtained mixture was then evaporated to dryness to obtain a powdery solid. The operations of dry sample loading, column chromatography, and gradient elution with a dichloromethane mixed solution containing 3%-7% methanol were carried out. The elution product was then collected, concentrated, and dried in a vacuum oven, thus obtaining the product (11.3 g, extra-quota).

49-161

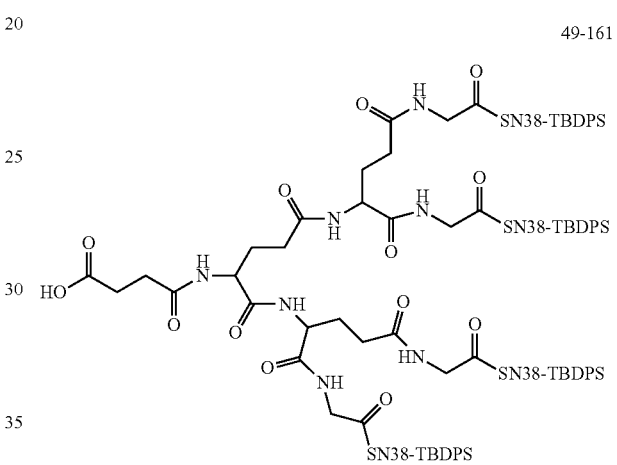

49-159 (9.84 g, 3.0367 mmol) was added in a 250 mL flask, and dissolved with dichloromethane (8 mL), TFA (8 mL) was added, and then the mixed solution was stirred to react at room temperature overnight. At the end of the reaction, the reaction solution was rotary evaporated to obtain an oily solution, and methyl tert-butyl ether (60 mL) was then added to the oily solution. A powdery solid was separated out of the obtained solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (60 g) was added, and the obtained mixture was then evaporated to dryness to obtain a powdery solid. The operations of dry sample loading, column chromatography and gradient elution with a dichloromethane mixed solution containing 1%-4% methanol were carried out. The elution product was then collected, concentrated, and dried in a vacuum oven, thus obtaining the product (2.7 g, 27.92%).

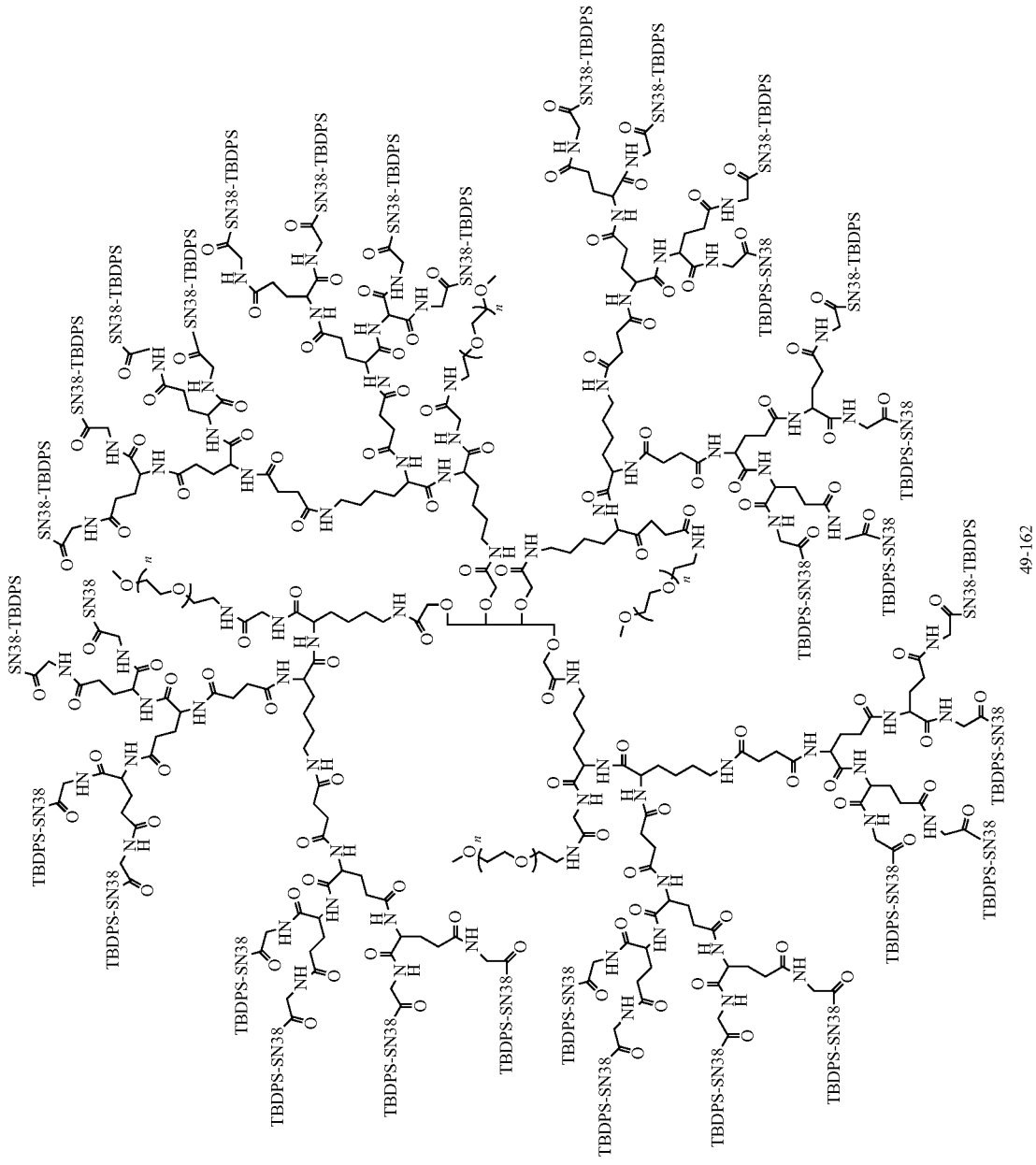

49-153 (1.19 g, 0.0535 mmol), 49-161 (1.5 g, 0.4710 mmol), HBTU (0.24 g, 0.6422 mmol), HOBT (0.08 g, 0.6422 mmol) were added in a 500 mL flask, and dissolved with DMF (60 mL), and then the mixed solution was stirred to react at −5° C. for 30 minutes. Then DIEA (0.60 mL, 3.6395 mmol) was slowly added dropwise, and the obtained solution continued to react at −5° C. with stirring for 1 hour, and then reacted at room temperature in the dark overnight at a low speed of stirring. At the end of the reaction, the reaction solution was shaken with n-hexane (100 mL), and the supernatant was discarded. The above operations were repeated three times. The obtained solution was then shaken with methyl tert-butyl ether (80 mL) and a small amount of n-hexane (10 mL), and the supernatant was discarded. The above operations were repeated three times. A powdery solid was separated out of the obtained solution, and suction filtering was carried out. The filter cake was washed with methyl tert-butyl ether (40 mL×3), the washed filter cakes were collected, and dissolved with a mixed solvent (100 mL) of methanol/dichloromethane (1:4), silica gel powder (20 g) was added, and the obtained mixture was then evaporated to dryness to obtain a powdery solid. The operations of dry sample loading, column chromatography and gradient elution with a dichloromethane mixed solution containing 3%-15% methanol were carried out. The elution product was then collected, concentrated, and dried in a vacuum oven, thus obtaining the product (0.95 g, 37.25%).

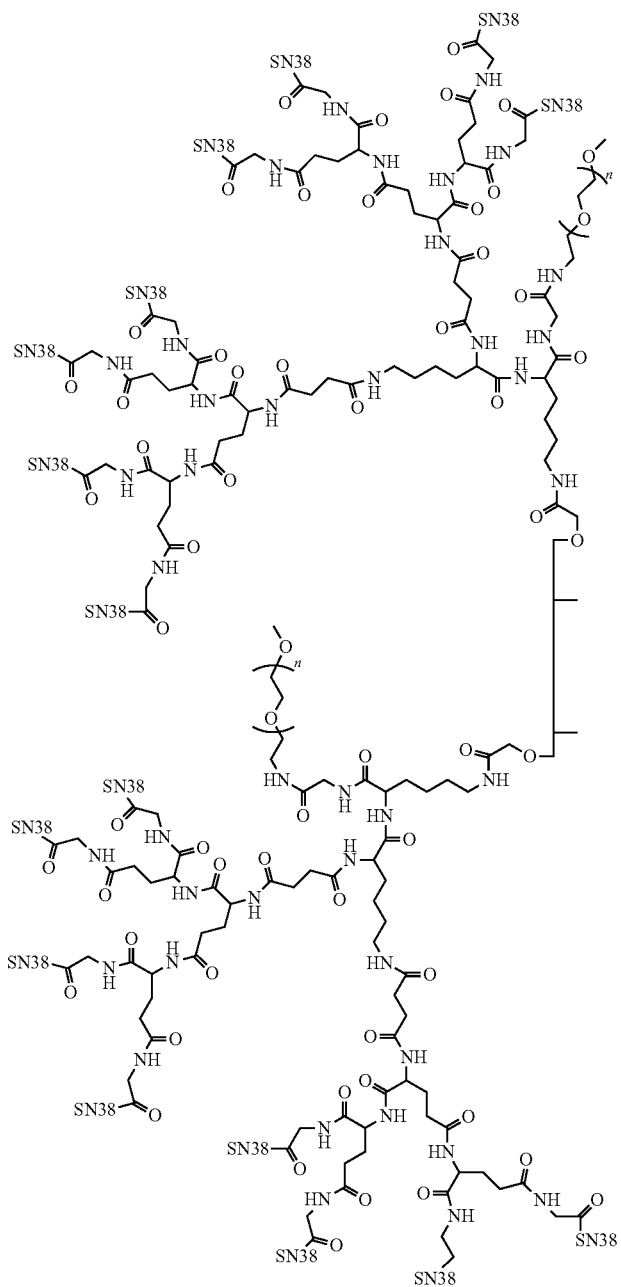

49-166

-continued

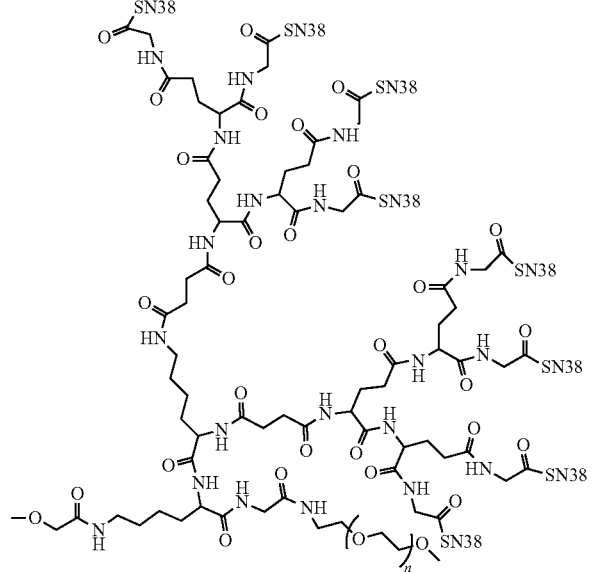

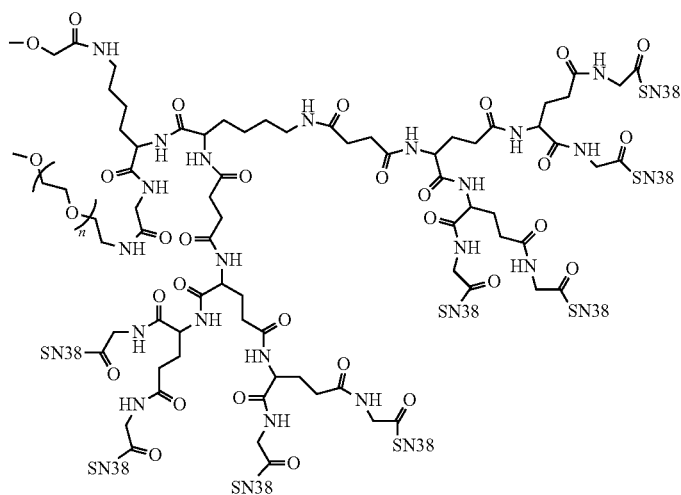

49-162 (0.95 g, 0.0199 mmol) was added in a 500 ml flask, and dissolved with THF (10 ml) and diluted hydrochloric acid (10 ml, 0.05 mmol/L) by ultrasonic, TBAF (0.5 g, 1.9133 mmol) was added, and then the mixed solution was stirred to react at room temperature in the dark for 3 hours. At the end of the reaction, the reaction solution was evaporated to dryness. The obtained dry product was dissolved with DMF (5 ml), and the obtained solution was precipitated with isopropanol. Such operations were repeated three times. The precipitate was dissolved with anhydrous ethanol and a small amount of dichloromethane, and the obtained solution was precipitated with methyl tert-butyl ether. Such operations were repeated three times. The obtained solid was then collected, and dried in a vacuum oven, thus obtaining the product (0.75 g, 93.75%).

$^1$H NMR (600 MHz, DMSO-$d_6$) δ 8.36-8.18 (m, 32H), 8.12-7.89 (m, 56H), 7.81-7.76 (m, 16H), 7.35 (s, 100H), 7.05-6.96 (m, 27H), 5.95-5.18 (m, 124H), 4.25-3.81 (m, 156H), 3.53-3.49 (m, 3706H), 3.12-2.78 (m, 123H), 2.08 (s, 109H), 1.47-1.20 (m, 211H), 0.99-0.78 (m, 136H).

Example 2 Activity Assay 27-134 (Compound No. 18), 44-2 (Compound No. 3) were taken as examples below, while the test method for other compounds was the same, and the inhibitory effect on cancer cells was also significant.

I. Experimental Materials:
1. Customer samples: Colo205, MDA-MB-231 cancer cell, 2 drugs (27-134, 44-2)
2. Experimental equipment and reagent: PerkinElmer multifunctional microplate reader, CCK8 cell proliferation and cytotoxicity detection kit II. Experimental Method Drug formulation: the drugs were formulated into 0.1 g/ml with physiological saline, corresponding to a molar concentration of 7.4537 mM for each drug.

1. Cells were cultivated and digested by trypsin. The cells were blown into a single cell suspension with the corresponding medium. The suspension was inoculated into a 96-well plate with 100 μl per well, the cell density being about 10-15%. Cultivation continued in an incubator at 37° C. and 5% $CO_2$ for 6 hours until the cells are attached to the wall, yet to be treated.

Figures 1, 2:
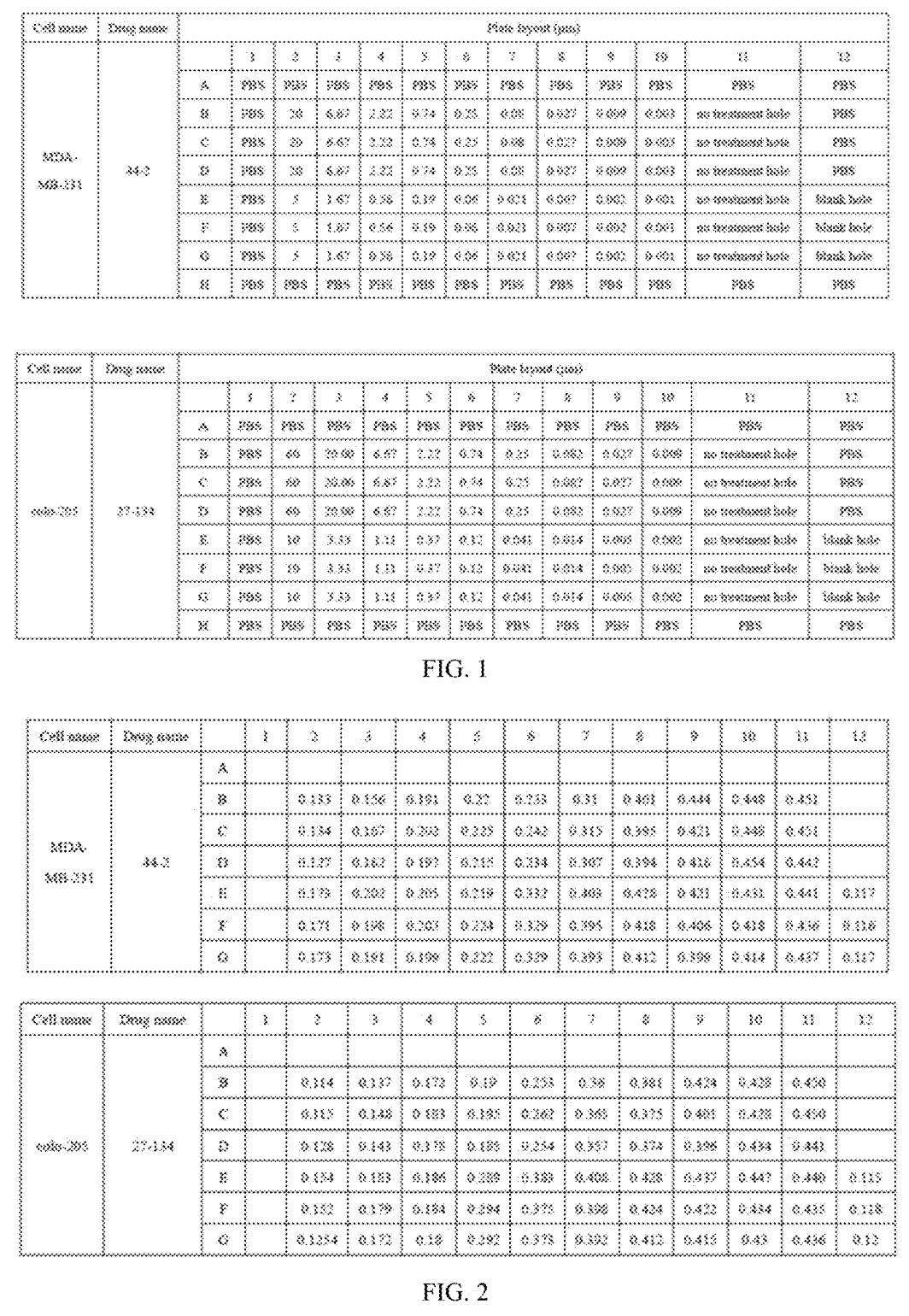

2. According to the requirement of drug concentration, drug-containing culture media with different concentrations were prepared by a multiple dilution method. Two groups of different gradient combinations of the same drug were screened on one plate, as shown in FIG. 1.
3. Drug gradient: 100 μl of the fresh culture media (the total volume was 200 μl, the drug concentration was shown in FIG. 1) containing the corresponding drugs prepared in the step 2 were respectively added, and cultivation continued for 48 hours.
4. After 48 hours of drug treatment, the original medium was discarded.
5. 100 μl of a medium (containing 10% CCK8) was added to each well and cultivation continued in the cell incubator for 2 hours.
6. The absorbance was measured at 450 nm, with the results shown in FIG. 2.

III. Analysis of the Experimental Results:
1. The cell inhibition rate at each drug concentration was calculated from the readings as follows:

| 96% | 86% | 76% | 69% | 64% | 41% | 15% | 6% | −1% | 0% |
|---|---|---|---|---|---|---|---|---|---|
| 20 | 6.67 | 2.22 | 0.74 | 0.25 | 0.08 | 0.027 | 0.009 | 0.003 | 0 |
| 83% | 75% | 73% | 67% | 34% | 13% | 6% | 9% | 5% | 0% |
| 5 | 1.67 | 0.56 | 0.19 | 0.06 | 0.021 | 0.007 | 0.002 | 0.001 | 0 |
| 100% | 92% | 82% | 78% | 58% | 26% | 21% | 12% | 5% | 0% |
| 60 | 20.00 | 6.67 | 2.22 | 0.74 | 0.25 | 0.082 | 0.027 | 0.009 | 0 |
| 92% | 81% | 79% | 45% | 19% | 12% | 5% | 4% | 0% | 0% |
| 10 | 3.33 | 1.11 | 0.37 | 0.12 | 0.041 | 0.014 | 0.005 | 0.002 | 0 |

2. Plot:
The inhibitory effect of drug 44-2 on MDA-MB-231 cancer cells, as shown in FIG. 3.
The inhibitory effect of drug 27-134 on Colo205 cancer cells, as shown in FIG. 4.
3. Calculation of $IC_{50}$ for individual drug
The results are shown in FIG. 5.

Example 3 In Vivo Anti-Tumor Efficacy Pre-Test of Multiple Test Samples on NPG Mouse Subcutaneous Transplantation Tumor Models of Human Breast Cancer BT474 Cells I. Experimental Materials:
Preparation Methods:
Test sample diluent: a proper amount of PEG300 and absolute alcohol was taken, and sodium chloride injection was added to make that the content of PEG300 and absolute alcohol was 20% (v/v).
Test samples: 41-32, 41-40 and 39-55 were respectively taken in a proper volume, and a proper amount of each of the test sample diluent was added, to respectively prepare solutions with the concentrations of 8.3 mg/mL, 4.6 mg/mL and 5.5 mg/mL.
SB7·HCL: a proper amount of SB7·HCL (conversion factor: 93.4%) was taken, a certain volume of ethanol (5%, V/V) was added for dissolving, and, after complete dissolution, a proper amount of sodium chloride injection was added, to prepare a solution with a concentration of 0.5 mg/mL.

LPT: a proper amount of LPT was taken, and a certain volume of 0.5% CMC-Na solution was added, followed by uniform stirring on a magnetic stirrer to prepare a solution with a concentration of 0.56 mg/mL.
Negative control: the test sample diluent was directly used.
Preservation and treatment of the prepared solutions: the prepared test samples and control sample were preserved at 2-8 V or in an ice box before administration, and the residual test samples and control sample after administration were treated as medical waste.
Human breast cancer cell BT474: it was from the Cell Resource Center of Shanghai Institutes for Biological Sciences of Chinese Academy of Sciences, cultured under the conditions of RPMI1640+10% FBS, 37° C., 5% $CO_2$.
Animal species & strain: NPG mice
Animal level: SPF level
Animal source: Beijing Vitalstar Biotechnology Co., Ltd.
Animal age at tumor inoculation: about 4-5 weeks.
Animal weight at tumor inoculation: about 15-18 g. The weights of animals of the same sex were between 80-120% of the average weight.
Animal sex and number: female, 60 mice, 36 modeling animals were screened for final experiments, and the remaining animals were either transferred to veterinarian or euthanasia.
Animals were reared in an independent ventilation system (IVC), at most 6 animals of the same group in each cage, and an SPF level animal house was provided, with the environmental conditions controlled as follows: room temperature 20-26° C., 40-70% of relative humidity and illumination with 12 hour light dark alternation.
Feed: qualified mouse feed (manufacturer: Beijing Keao Xieli Feed Co., Ltd.) was provided each day. The animals ate freely and drunk water freely.
2. Experimental Method:
BT474 cells were revived, and cell passage amplification was carried out. When amplified to a sufficient number, the cells in the logarithmic growth phase were collected for cell inoculation. An estrogen sustained-release tablet (17 beta-ESTRADIOL, product No.: SE-121, Innovative Research of America) was embedded under the skin at the neck back of NPG mice before cell inoculation. A BT474 cell suspension with the concentration of $7.5 \times 10^7$/mL and a Matrigel Basement membrane Matrix (BD Co.) were mixed according to the volume ratio of 1:1 to obtain a cell suspension with the concentration of $3.75 \times 10^7$/mL. 0.2 mL of the cell suspension was inoculated into the right mammary fat pad of the mice. The tumor growth was observed after inoculation, and 36 tumorigenic animals with the tumor volume of 66.83-324.35 $mm^3$ were finally screened and used for the test.
The tumorigenic animals were randomly divided into 6 groups according to the tumor volume and the body weight, including: group 1 (negative control group, test sample diluent), group 2 (LPT, 20 mg/kg), group 3 (SB7+LPT, 5+5.6 mg/kg), group 4 (41-32, i.e., Compound No. 20, 83 mg/kg), group 5 (41-40, i.e., Compound No. 13, 46 mg/kg) and group 6 (39-55, i.e., Compound No. 12, 55 mg/kg), 6 animals in each group, with the administration volume of 10 mL/kg. The negative control, SB7, 41-32, 41-40 and 39-55 were intravenously injected; LPT was intragastrically administered. The groups 2 and 4 were administered one time every 3 days (the administration was stopped once at D19 due to insufficient drug dosage), while the rest groups were administered one time/week, for a duration of 4 weeks, at D29 the animals were euthanized. During the experiment, the general clinical symptoms of the animals were observed 2 times every day, and the body weight and tumor diameter were measured two times every week. The tumor was stripped after euthanization, and the tumor weight was weighed. The tumor volume, relative tumor volume RTV, relative tumor proliferation rate T/C % and tumor weight inhibition rate $IR_{TW}$ % were calculated. The relative tumor proliferation rate T/C %≤40% of the administration group and the RTV of that group being significantly different compared with the RTV of the negative control group (P≤0.05) were considered to be effective, and the $IR_{TW}$≥60% was taken as an effectiveness auxiliary reference indicator.

A. Measurement of Tumor Diameter:

Test animal: all animals

Test time: the day of grouping (i.e., D1, the day of first administration), 2 times per week after first administration, and before euthanasia, the long and short diameters of tumor were measured using a slide caliper and recorded, and the tumor volume was calculated.

The tumor volume was calculated according to the following formula:

$$V = \frac{1}{2} \times \text{long diameter} \times \text{short diameter}^2$$

B. Evaluation of Therapeutic Efficacy Based on the Tumor Volume

The relative tumor volume (RTV) and the relative tumor proliferation rate T/C % were calculated according to the following formula:

$$RTV = V_t/V_0$$

$V_t$: tumor volume obtained by measuring tumor every day $V_0$: initial tumor volume (before administration)

T/C %=average RTV of the administration group/average RTV of the control group×100%

If T/C % was ≤40%, and the RTV of the administration group was different in statistics compared with the RTV of the control group (P<0.05), tumor growth inhibition effect was achieved; on the other hand, if T/C % was >40%, tumor growth was not inhibited.

C. Evaluation of Therapeutic Efficacy Based on the Tumor Weight

After the experiment, tumor nodules were stripped and weighed, and the differences in tumor weight among the groups were compared to further calculate the tumor inhibition rate $IR_{TW}$. $IR_{TW}$>60% was taken as an effective reference indicator. The calculation was conducted according to the following formula:

$$IR_{TW}(\%) = (W_{Control\ group} - W_{Administration\ group})/W_{Control\ group} \times 100\%$$

3. Experimental Results:

Throughout the experiment, 1 animal in the group 2 died at D19; 2 animals in the group 3 died at D15 and D25, respectively, of which 1 animal was observed after dissection to have white sand-like particles filled in the bladder, the cause of death being considered to be related to the inoculation of estrogen tablet; the cause of death of other 2 animals was presumed to be related to the toxicity of the control. The weights of the animals in the groups 1-6 all gradually increased, and no significant difference (P>0.05) was observed among the groups.

In the negative control group (the group 1), the tumor gradually increased throughout the experiment, by the end of the experiment (D29), the group 1 had an average tumor volume of 1938.55±511.20 mm³ and an average RTV of 14.98±8.63; the average tumor volumes of the groups 2-6 were 1313.80±241.46 mm³, 1463.75±1088.95 mm³, 1232.77±652.36 mm³, 1616.52±985.05 mm³, 346.96±203.35 mm³ respectively, and the average RTVs thereof were 8.13±2.92, 8.80±3.57, 8.27±3.92, 11.61±8.28, 2.26±1.32 respectively, and the tumor volumes of the group 6 during D15-D29 were significantly lower than that of the group 1 (P≤0.05); the RTV of the group 6 at D12 was significantly lower than that of the group 1 (P≤0.05), and no significant difference in tumor volume and RTV was observed among other groups (P>0.05).

Figure 7:
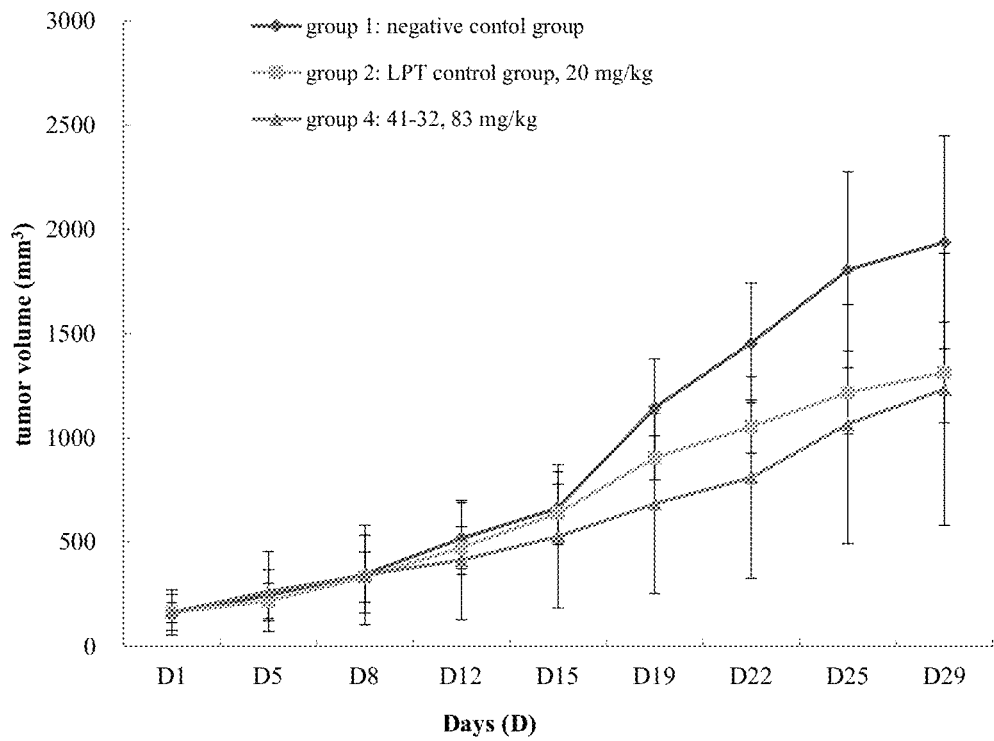
Figure 8:
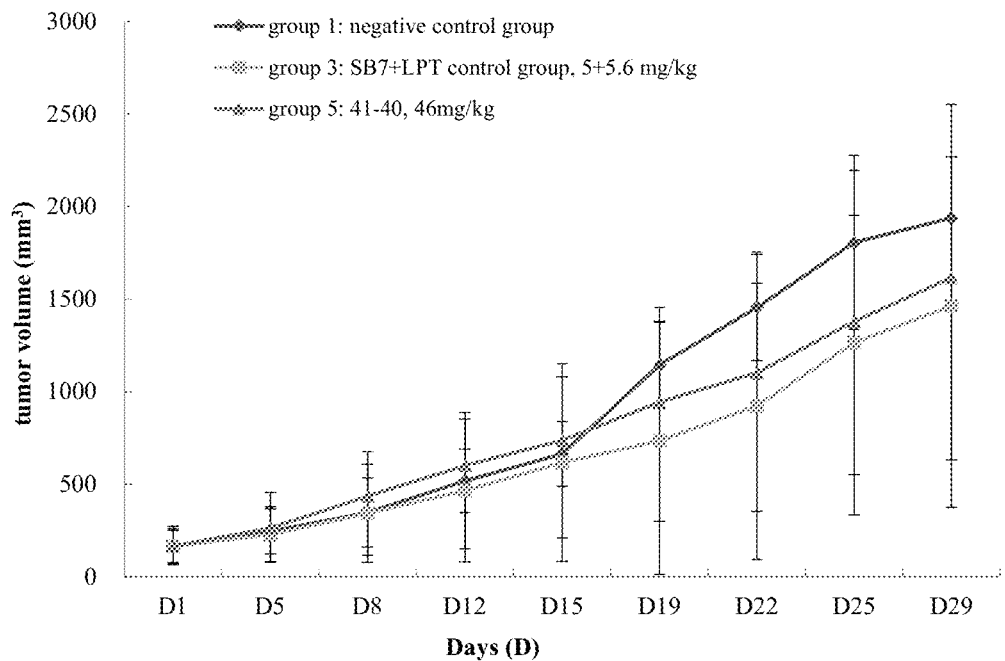

The tumor growth trend of each group is shown in FIG. 6, FIG. 7 and FIG. 8.

By the end of the experiment (D29), the T/C % values of the groups 2-6 were 54.27%, 58.74%, 55.21%, 77.54% and 15.07%, respectively, and the $IR_{TW}$ % values thereof were 45.73%, 41.26%, 44.79%, 22.46% and 84.93%, respectively, and the T/C % of the group 6 was reduced to less than 40% during D12-D29.

At the end of the experiment, the tumors of the animals were weighed after euthanasia. The average tumor weights of the groups 1-6 were 1.807±0.350 g, 1.226±0.370 g, 1.185±0.934 g, 0.899±0.428 g, 1.287±0.746 g, 0.266±0.167 g, respectively, the tumor weight of the group 6 being significantly lower than that of the group 1 (P≤0.05). The $IR_{TW}$ % of the groups 2-6 were 32.15%, 34.42%, 50.25%, 28.78%, 85.28%, respectively.

Figure 9:
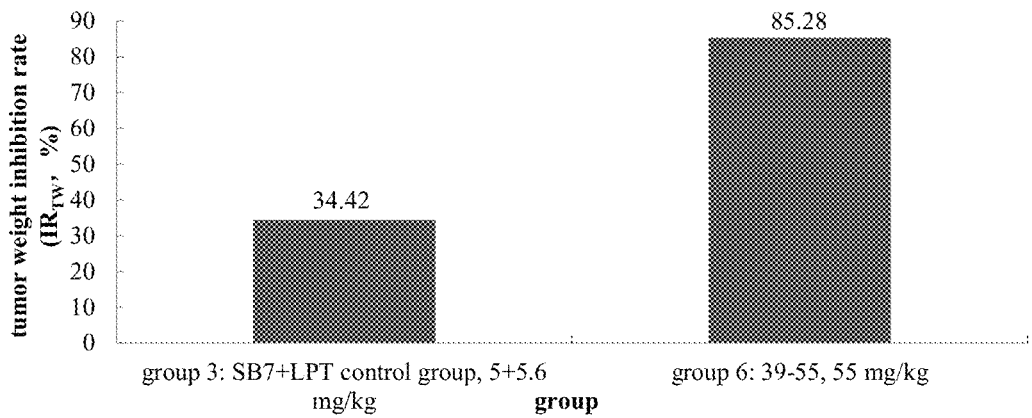
FIG. 9, FIG. 10 and FIG. 11 are schematic diagrams of the tumor weight inhibition rate of each group in Example 3.
Figure 10:
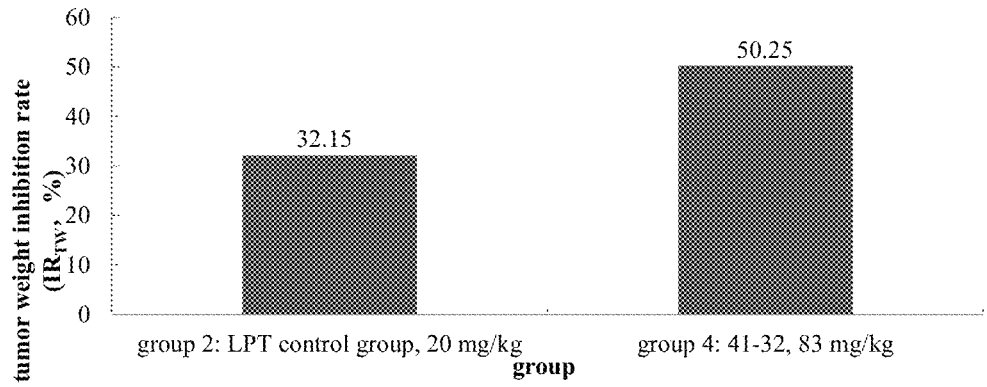
Figure 11:
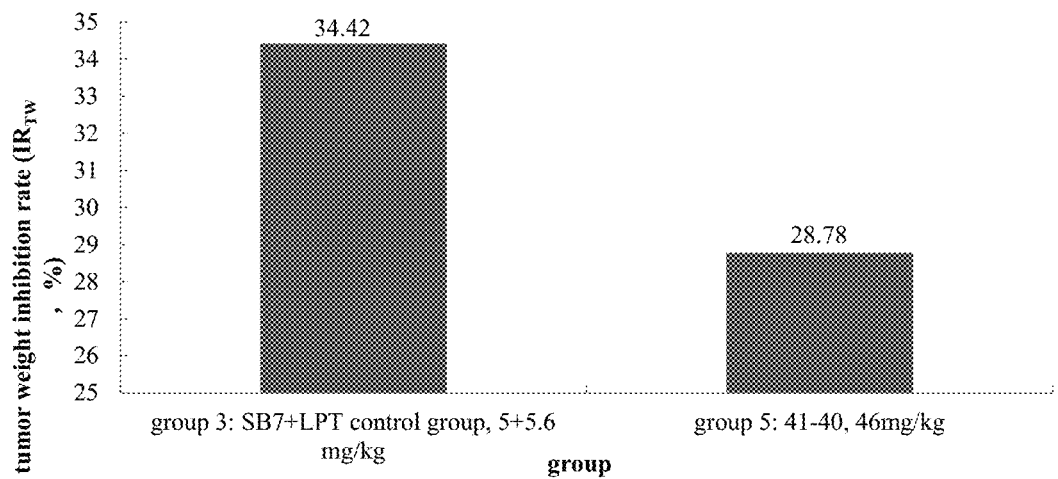
Figure 12:
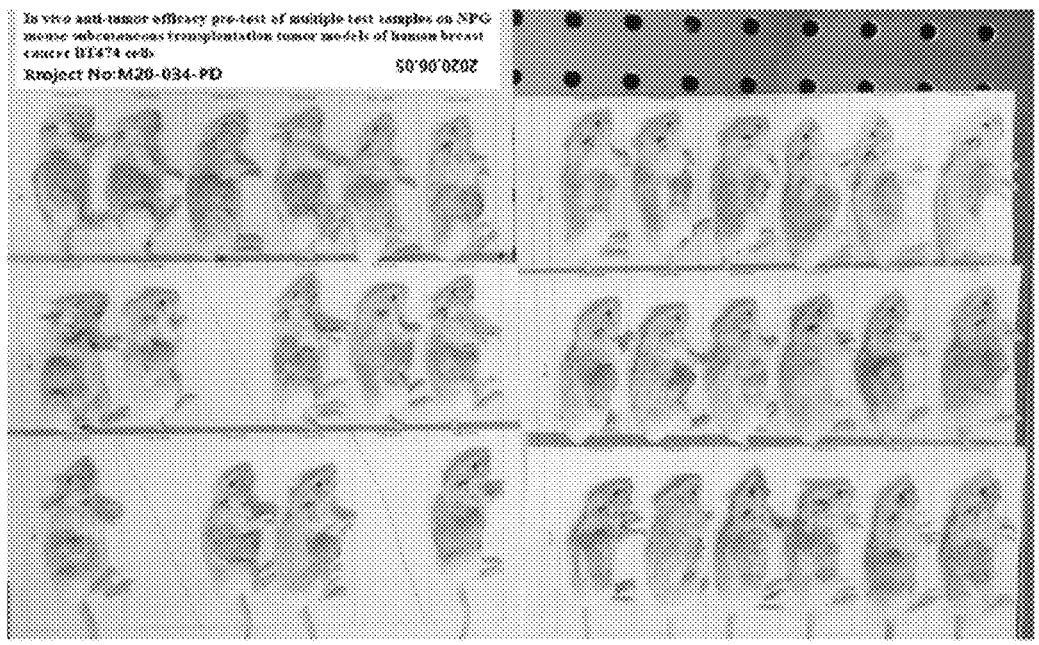
FIG. 12 shows the photos of euthanized animals of each group in Example 3.
Figure 13:
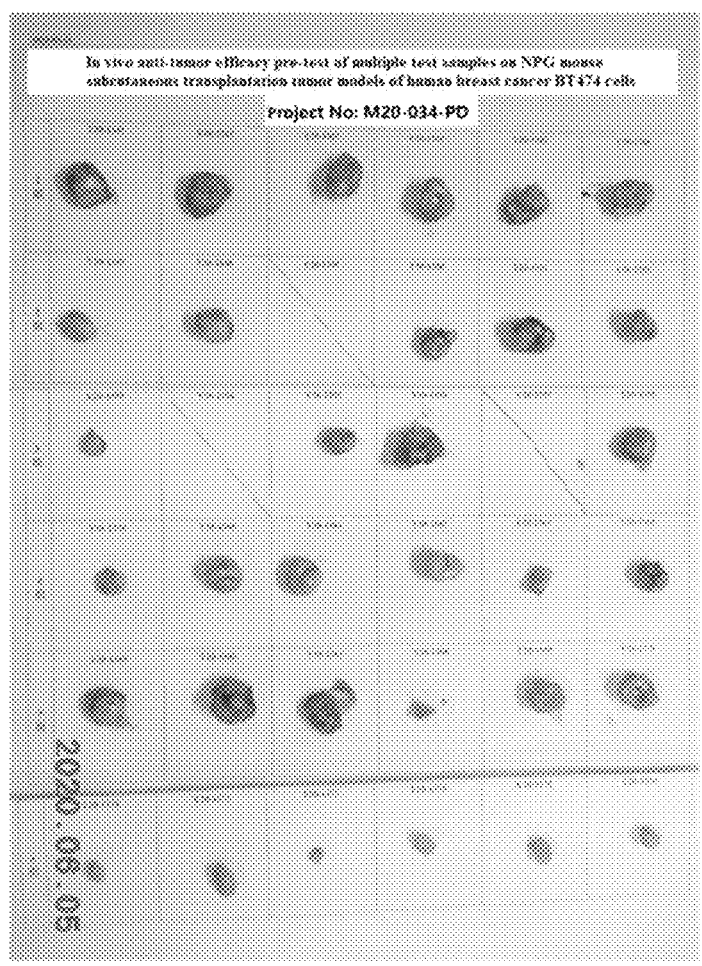
FIG. 13 shows the photos of tumors of each group in Example 3.

The schematic diagrams of the tumor weight inhibition rate of each group are shown in FIG. 9, FIG. 10 and FIG. 11. FIG. 12 shows the photos of euthanized animals of each group. FIG. 13 shows the photos of tumors of each group.

Conclusion: under the experimental conditions, the administration groups all had tumor growth inhibition effects of different degrees on NPG mouse subcutaneous transplantation tumor models of human breast cancer BT474 cells. The test sample 39-55, which was administered by tail vein injection at a dose of 55 mg/kg, had an obvious inhibition effect on the tumor growth of the NPG mouse subcutaneous transplantation tumor models of human breast cancer BT474 cells, and the effect was superior to that of the combination of SB7 which was administered by tail vein injection at a dose of 5 mg/kg and LPT which was intragastrically administered at a dose of 5.6 mg/kg. LPT which was intragastrically administered at a dose of 20 mg/kg, 41-32 which was administered by intravenous injection at a dose of 83 mg/kg and 41-40 which was administered by intravenous injection at a dose of 46 mg/kg had certain inhibition effects on NPG mouse subcutaneous transplantation tumor models of human breast cancer BT474 cells.

Example 4 In Vivo Anti-Tumor Efficacy Pre-Test of Test Samples on BALB/c Nude Mouse Subcutaneous Transplantation Tumor Models of Human Colon Cancer COLO-205 Cells 1. Experimental Materials Test Sample Name: 39-17 (i.e., Compound No. 14); concentration: 10 mg/mL.

Vehicle/Negative Control

Name: sodium chloride injection; lot No.: 4B19091206; specification: 100 mL: 0.9 g; character: colorless and clear liquid; preservation condition: preserved in a sealed container; manufacturer: Shandong Qidu Pharmaceutical Co., Ltd.

Preparation of the test sample and the control:

Preparation Methods:

Test sample: directly used, without dilution.

SB7·HCL: a proper amount of SB7·HCL (conversion factor: 93.4%) was taken, a certain volume of ethanol (5%, V/V) was added for dissolving, and, after complete dissolution, a proper amount of sodium chloride injection was added, to prepare a solution with a concentration of 0.3 mg/mL.

PCB: a proper amount of PCB was taken, and a certain volume of 0.5% CMC-Na solution was added, followed by uniform stirring on a magnetic stirrer to prepare a solution with a concentration of 1.04 mg/mL.

Negative control: sodium chloride injection was directly used.

Preservation and treatment of the prepared solutions: the prepared test samples and control sample were preserved at 2-8° C. or in an ice box before administration, and the residual test samples and control sample after administration were treated as medical waste.

Human colon cancer COLO-205 cell: it was from the Cell Resource Center of Institute of Basic Medicine of Chinese Academy of Medical Sciences, cultured under the conditions of RPMI1640+10% FBS, 37° C., 5% $CO_2$.

Animal species & strain: BALB/c nude mice
Animal level: SPF level
Animal source: Beijing Charles River Laboratory Animal Technology Co., Ltd.
Animal age at tumor inoculation: about 4-5 weeks.
Animal weight at tumor inoculation: about 15-18 g. The weights of animals of the same sex were between 80-120% of the average weight.
Animal sex and number: male, 25 mice, 18 modeling animals were screened for final experiments, and the remaining animals were either further reared or euthanized.

Animals were reared in an independent ventilation system (IVC), at most 6 animals of the same group in each cage, and an SPF level animal house was provided, with the environmental conditions controlled as follows: room temperature 20-26° C., 40-70% of relative humidity and illumination with 12 hour light dark alternation.

Feed: qualified mouse feed (manufacturer: Beijing Keao Xieli Feed Co., Ltd.) was provided each day. The animals ate freely and drunk water freely.

2. Experimental Method:

COLO-205 cells were revived, and cell passage amplification was carried out. When amplified to a sufficient number, the cells in the logarithmic growth phase were collected for cell inoculation. According to the actual cell number, the cells were adjusted to have a concentration of $5 \times 10^7$/mL, and inoculated subcutaneously in the right armpit of 25 mice at 0.2 mL per mouse. The tumor growth after inoculation was observed. When the tumor volume was about 100-300 $mm^3$, the animals were screened according to the size of the tumor volume, excluding those that had too large tumor volume and those that were non-tumorigenic, and finally 18 tumorigenic animals were screened for test.

The 18 tumorigenic animals were randomly divided into 3 groups, including: group 1 (negative control group, sodium chloride injection), group 2 (SB7+PCB, 3+10.4 mg/kg), and group 3 (39-17, 153 mg/kg), 6 animals in each group, with the administration volume of 10 mL/kg for the negative control, SB7, PCB, and 15.3 mL/kg for 39-17. The negative control, SB7 and 39-17 were intravenously injected, and PCB was intragastrically administered, one time/week, for a duration of 3 weeks, at D22 the animals were euthanized. During the experiment, the general clinical symptoms of the animals were observed 2 times every day, and the body weight and tumor diameter were measured two times every week. The tumor was stripped after euthanization, and the tumor weight was weighed. The tumor volume, relative tumor volume RTV, relative tumor proliferation rate T/C % and tumor weight inhibition rate $IR_{TW}$ % were calculated. The relative tumor proliferation rate T/C %≤40% of the administration group and the RTV of that group being significantly different compared with the RTV of the negative control group (P≤0.05) were considered to be effective, and the $IR_{TW} \geq 60\%$ was taken as an effectiveness reference indicator.

A. Measurement of Tumor Diameter:
Test animal: all animals
Test time: the day of grouping (i.e., D1, the day of first administration), 2 times per week after first administration, and before euthanasia, the long and short diameters of tumor were measured using a slide caliper and recorded, and the tumor volume was calculated.

The tumor volume was calculated according to the following formula:

$$V = \tfrac{1}{2} \times \text{long diameter} \times \text{short diameter}^2$$

B. Evaluation of Therapeutic Efficacy Based on the Tumor Volume

The relative tumor volume (RTV) and the relative tumor proliferation rate T/C % were calculated according to the following formula:

$$RTV = V_t / V_0$$

$V_t$: tumor volume obtained by measuring tumor every day
$V_0$: initial tumor volume (before administration)
T/C %=average RTV of the administration group/average RTV of the control group×100

If T/C % was ≤40%, and the RTV of the administration group was different in statistics compared with the RTV of the control group (P<0.05), tumor growth inhibition effect was achieved; on the other hand, if T/C % was >40%, tumor growth was not inhibited.

C. Evaluation of Therapeutic Efficacy Based on the Tumor Weight

After the experiment, tumor nodules were stripped and weighed, and the differences in tumor weight among the groups were compared to further calculate the tumor inhibition rate $IR_{TW}$. $IR_{TW} > 60\%$ was taken as an effective reference indicator. The calculation was conducted according to the following formula:

$$IR_{TW}(\%) = (W_{Control\ group} - W_{Administration\ group}) / W_{Control\ group} \times 100$$

3. Experimental Results:

Throughout the experiment, 1 animal in the group 3 died at D8, and the weight of the animal after death was 14.5 g, the weight loss of the animal before death being greater, which was presumed to be related to the toxicity of 39-17; 2 animals in the group 1 died at D19 and D20 respectively, wherein tumor ulceration was observed for 1 animal before death, which was presumed to be related to the larger tumor load. The weight of the animal in the group 1 gradually decreased, the weight of the animal in the group 2 slightly increased and then decreased, and the weight of the animal in the group 3 gradually increased. The weight of the animal in the group 3 was obviously higher than that in the group 1 (P≤0.05) during D8-D22, and was significantly higher than that in the group 2 (P≤0.05) during D12-D22.

In the negative control group (group 1), the tumor gradually increased throughout the experiment, by the end of the experiment (D22), the group 1 had an average tumor volume of 1900.58±489.19 $mm^3$ and an average RTV of 16.03±6.43; the average tumor volumes of the groups 2-3 were 774.06±228.43 $mm^3$, 33.83±37.01 $mm^3$ respectively, and the average RTVs thereof were 6.38±1.81, 0.24±0.21 respectively, the tumor volumes of the group 2 during D5-D22 were significantly lower than that of the group 1 (P≤0.05), and the tumor volumes of the group 3 during D5-D22 were significantly lower than those of the groups 1 and 2 (P≤0.05); the RTVs of the group 2 during D5-D19 were significantly lower than that of the group 1 (P≤0.05), and the tumor volumes of the group 3 during D5-D22 were significantly lower than those of the groups 1 and 2 (P≤0.05).

Figure 14:
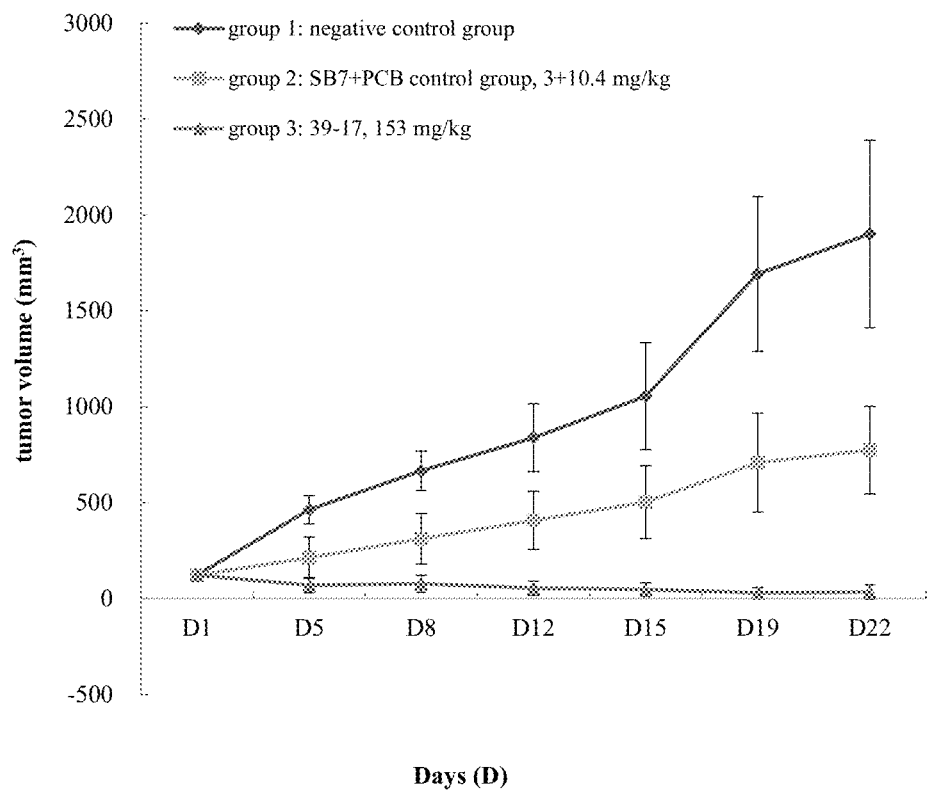
FIG. 14 shows the tumor growth trend of each group in Example 4.

The tumor growth trend of each group is shown in FIG. 14.

By the end of the experiment (D22), the T/C % values of the groups 2-3 were 59.68%, 1.88%, respectively, and the $IR_{TW}$ % values thereof were 40.32%, 98.12%, respectively. The T/C % of the group 3 was reduced to less than 40% during D5-D22, and was significantly lower than that of the group 1 (P≤0.05).

At the end of the experiment, the tumors of the animals were weighed after euthanasia. The average tumor weights of the groups 1-3 were 1.551±0.290 g, 0.607±0.173 g, 0.036±0.036 g, respectively, the tumor weights of the groups 2-3 being significantly lower than that of the group 1 (P≤0.05). The $IR_{TW}$ % of the groups 2-3 were 60.86%, 97.68%, respectively.

Figure 15:
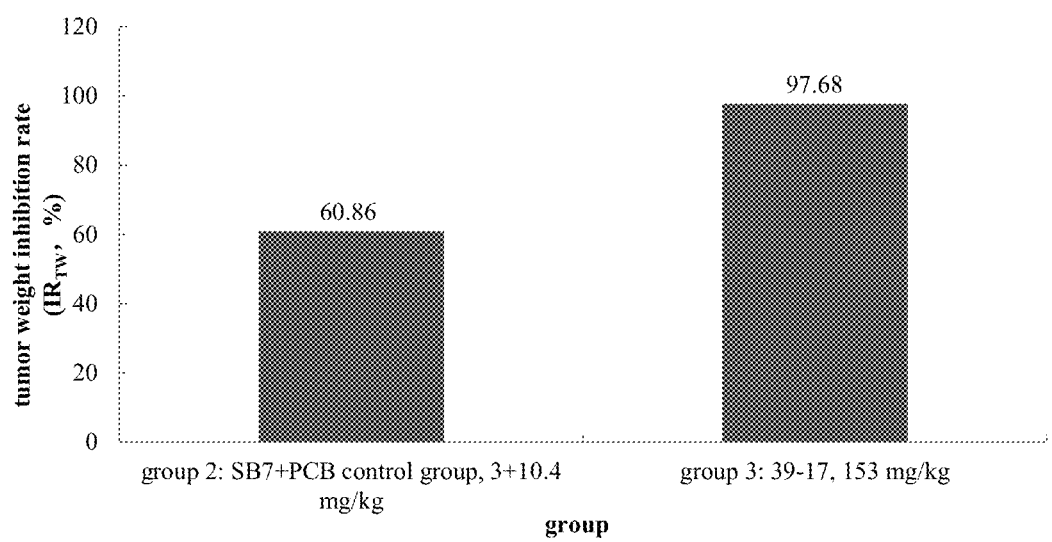
FIG. 15 is a schematic diagram of the tumor weight inhibition rate of each group in Example 4.

The schematic diagram of the tumor weight inhibition rate of each group is shown in FIG. 15.

Conclusion: under the experimental conditions, the test sample 39-17, which was administered by tail vein injection at a dose of 153 mg/kg, had an obvious inhibition effect on the tumor growth of the subcutaneous transplantation tumor models of human colon cancer COLO-205 cells, and the combination of SB7 which was administered by tail vein injection at a dose of 3 mg/kg and PCB which was intragastrically administered at a dose of 10.4 mg/kg also had an obvious inhibition effect on the tumor growth of the tumor models. The effect of 39-17 was obviously superior to that of the combination of PCB and SB7.

Although the specific embodiments of the disclosure have been described in detail, those skilled in the art will understand that various modifications and changes can be made to the details according to all the teachings that have been disclosed, and these changes are within the protection scope of the disclosure. The full scope of the disclosure is given by the appended claims and any equivalents thereof.

The invention claimed is:

1. A polyethylene glycol conjugated drug of formula (I) or a pharmaceutically acceptable salt thereof,

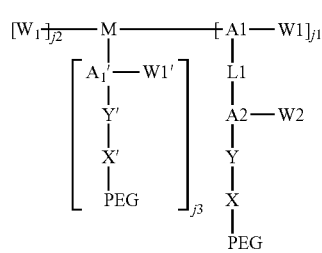

(I)

wherein:

M is —C(=O)—$C_{1-6}$ alkylene-C(=O)—, —C(=O)—, —NH—$C_{1-6}$alkylene-NH—, —C(=O)—$C_{1-6}$ alkylene-NH—,

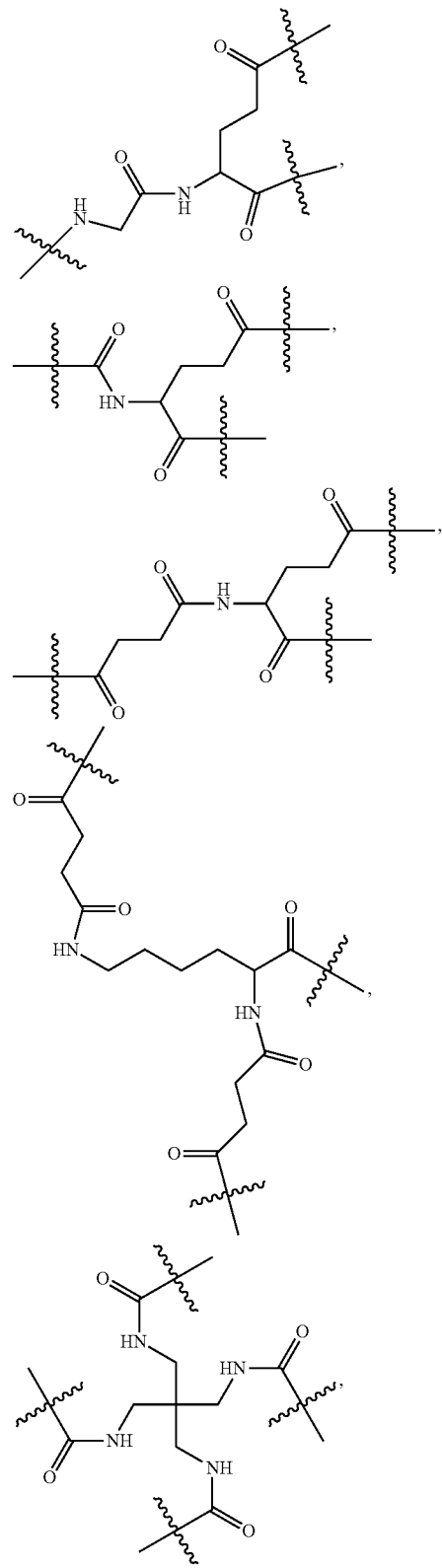

1417
-continued
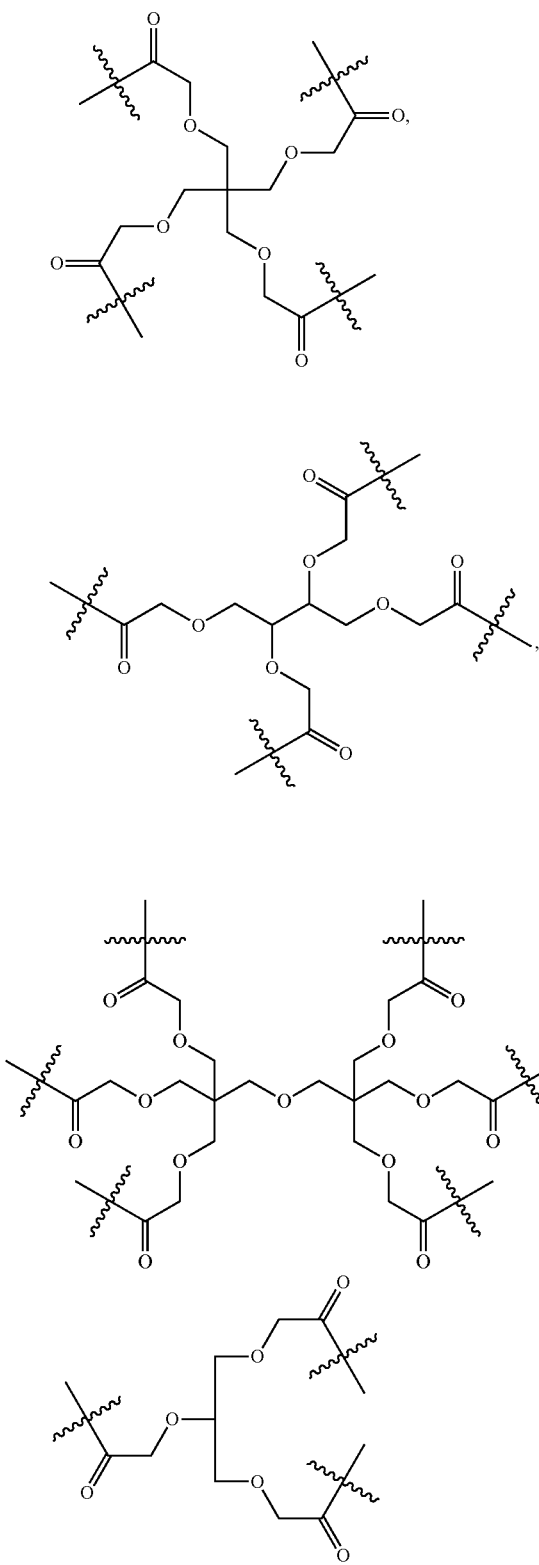
or PEG$_m$; wherein, PEG$_m$ is a single-arm or multi-arm polyethylene glycol segment, and its number-average molecular weight is 5k-40k;
1418
A1, A1' each independently are
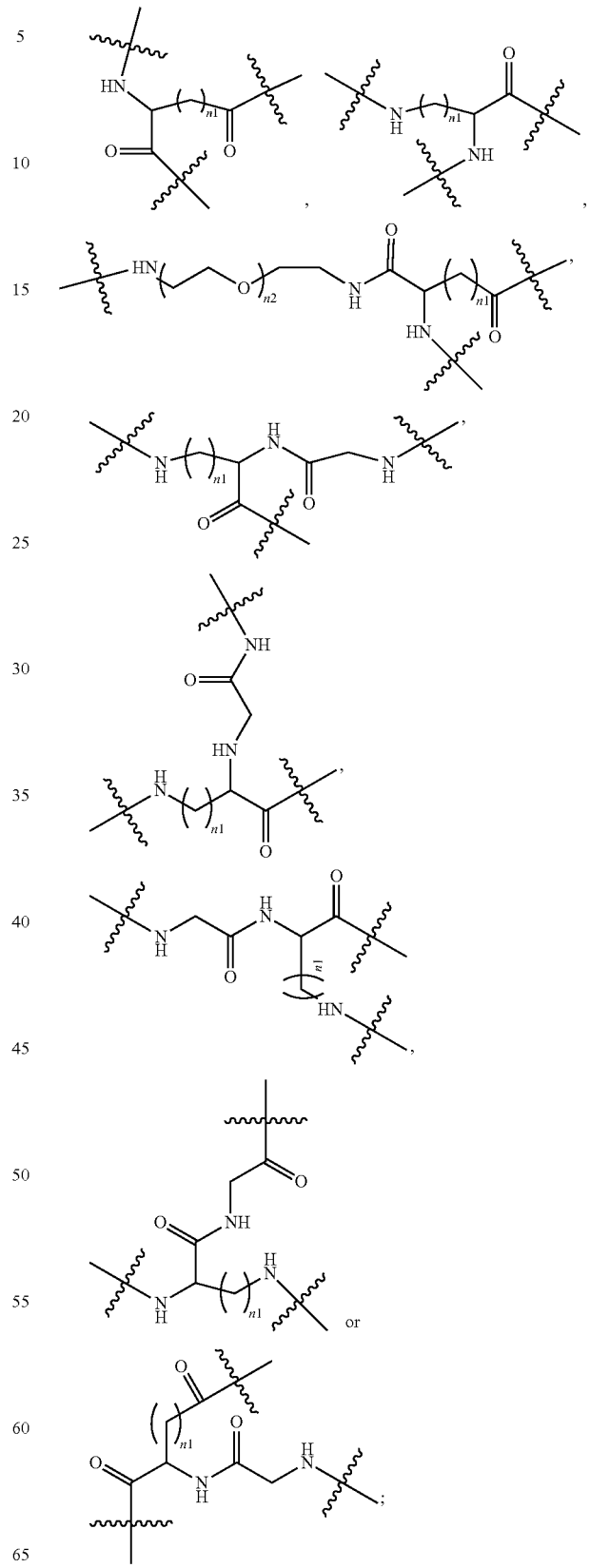

A2 independently is a direct bond or

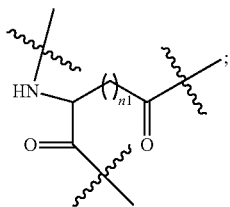

L1 independently is a direct bond or —C(=O)—C$_{1-6}$ alkylene-C(=O)—;

W1, W1', W2 each independently are Q1,

—Z4—(Z3—(Z2—Z1—(Z0—(Q2)$_2$)$_2$)$_2$)$_2$,

—Z2—(Z1—(Z0—Q2)$_2$)$_2$ with Q1 substituent,

—Z2—(Z1—(Z0—(Q)$_2$)$_2$)$_2$,    —Z1—(Z0—(Q1)$_2$)$_2$,

—Z4—(Z3—(Z2—(Q2)$_2$)$_2$)$_2$,

—Z2—(Z1—(Z0—(Q2)$_2$)$_2$)$_2$,    —Z0—(Q1)$_2$,

—Z3—(Z2—(Z1—(Q2)$_2$)$_2$)$_2$,    —Z1—(Z0—(Q2)$_3$)$_3$,

—Z1—(Z0—(Q)$_2$)$_2$,    —Z$_2$—(Z$_1$—Z$_0$—(Q$_1$)$_2$)$_3$ with Q$_2$ substituent, —Z$_2$—Z$_1$—(Z$_0$—(Q$_1$)$_2$)$_2$ with Q$_2$ substituent   or —Z$_3$—Z$_2$—(Z$_1$—(Z$_0$—(Q$_1$)$_2$)$_2$)$_2$ with Q$_2$ substituent;

Z4, Z3, Z2, Z1, Z0 each independently are

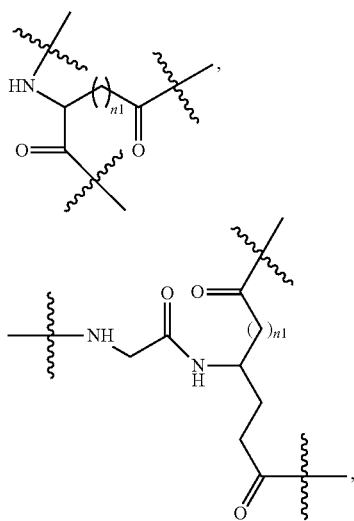

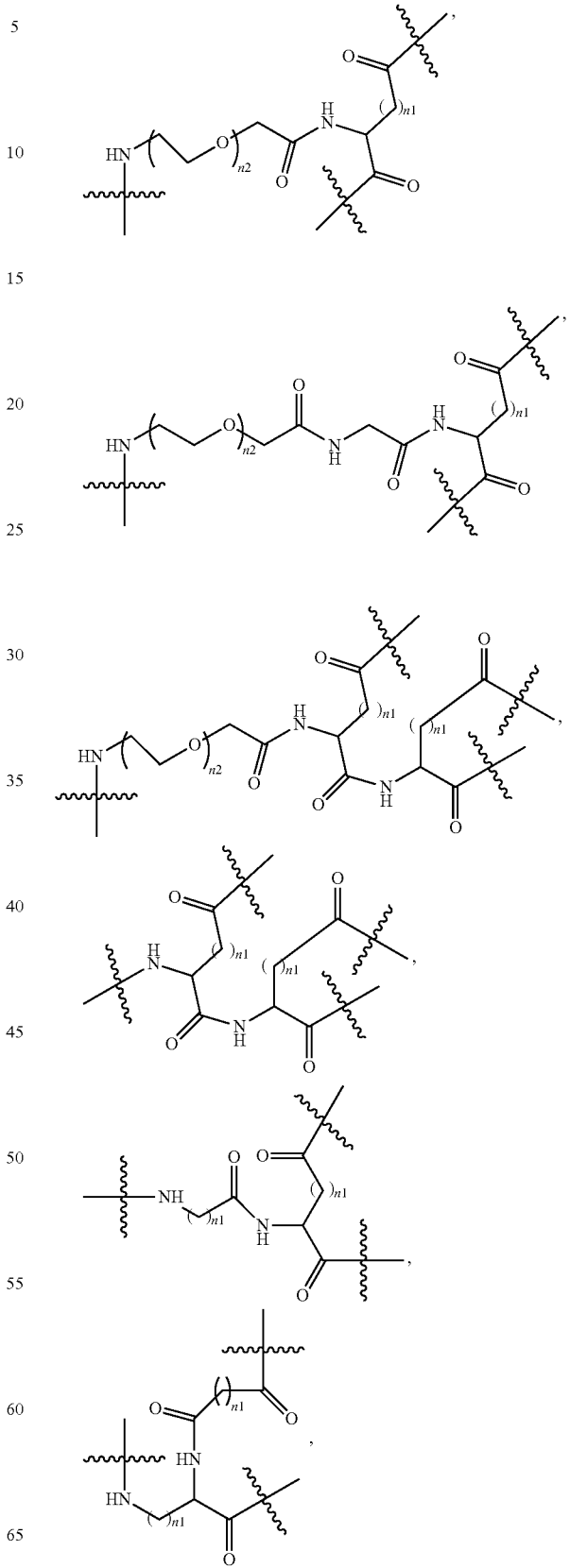

1421

-continued

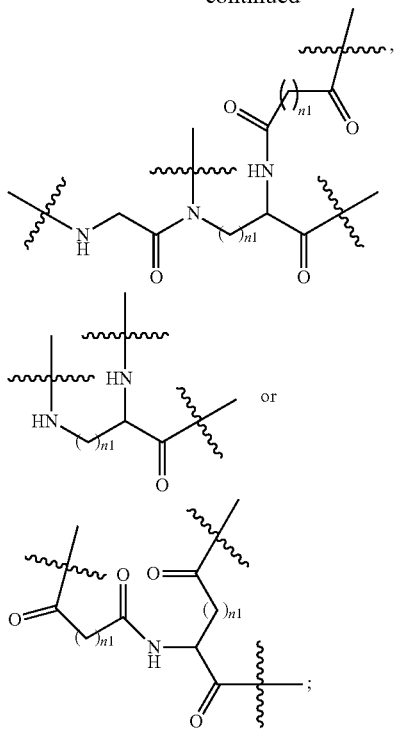

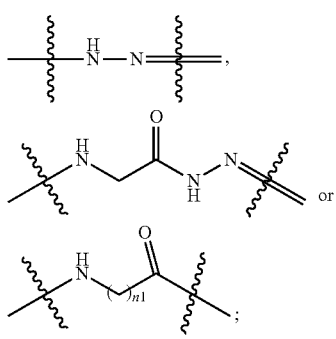

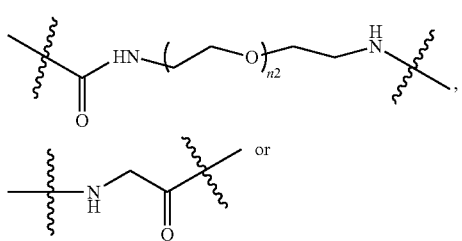

Q is —N-AC;
Q1 is —N1-AC1;
Q2 is —N2-AC2;
N, N1, N2 each independently are GFLG, G, AC, AC1, AC2 each independently are drug molecules;
n1, n2 each independently are 0, 1, 2, 3, 4, 5 or 6;
Y, Y' each independently are a direct bond, GLFG, —C(=O)—C$_{1-6}$ alkylene-C(=O)—,

1422

-continued

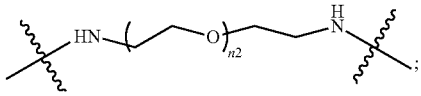

X, X' each independently are

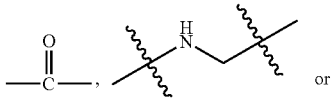

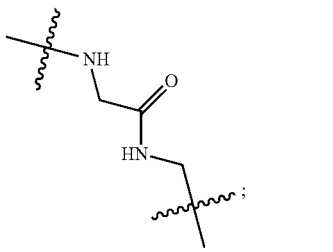

PEG is a single-arm polyethylene glycol segment, and its number-average molecular weight independently is 5k-40k;

j1 is 1, 2, 3, 4, 5 or 6;

j2, j3 each independently are 0 or 1.

2. The polyethylene glycol conjugated drug or a pharmaceutically acceptable salt thereof according to claim 1, the polyethylene glycol conjugated drug having the structure represented by the formula (II), $$M \underset{\underset{\underset{PEG}{|}}{\overset{\overset{Y}{|}}{X}}}{\overline{\left[ A1-W1 \right]_{j1}}} \quad (II)$$

wherein:

M is —C(=O)—C$_{1-6}$ alkylene-C(=O)—,

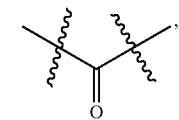 [SMILES: *C(*)=O]

—NH—C$_{1-6}$alkylene-NH—,
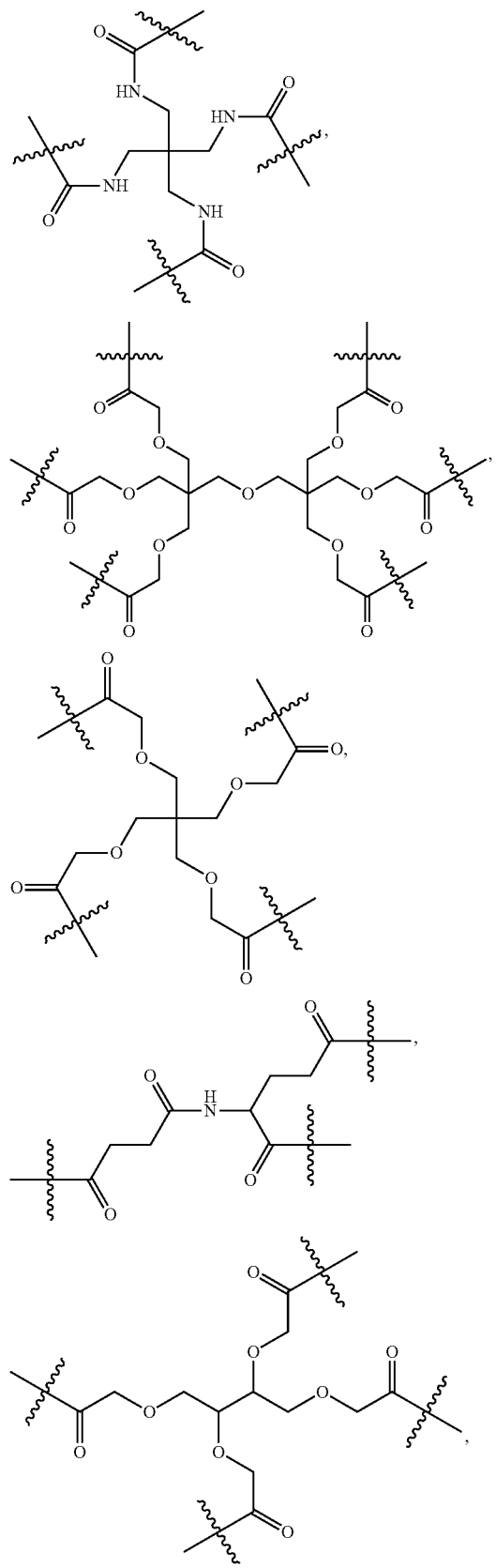
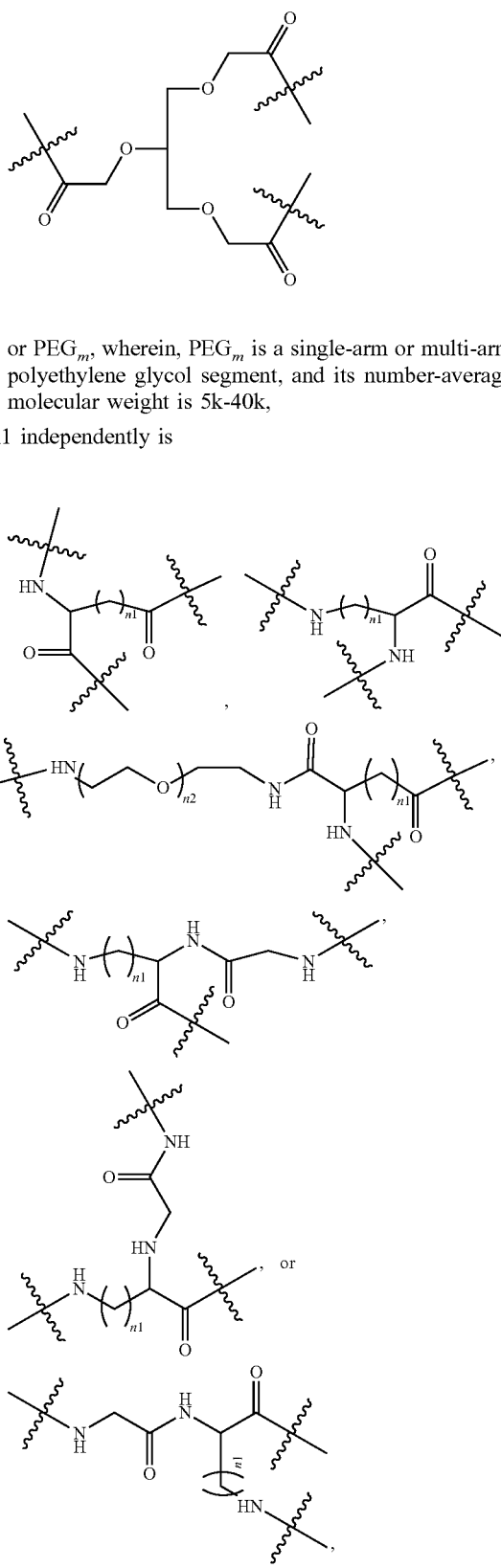
or PEG$_m$, wherein, PEG$_m$ is a single-arm or multi-arm polyethylene glycol segment, and its number-average molecular weight is 5k-40k,
A1 independently is Y independently is a direct bond,
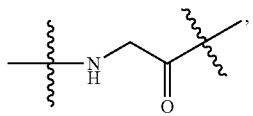 [SMILES: *NCC(*)=O]
GLFG, —C(=O)—C$_{1-6}$ alkylene-C(=O)—,
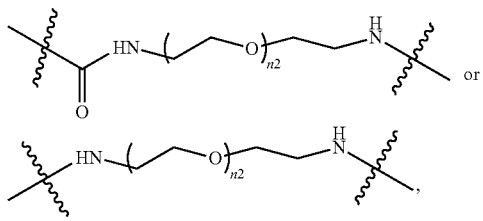
X independently is
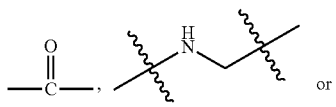
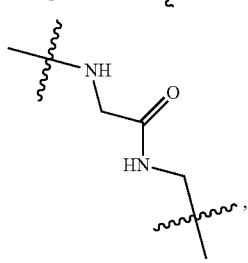
W1 independently is
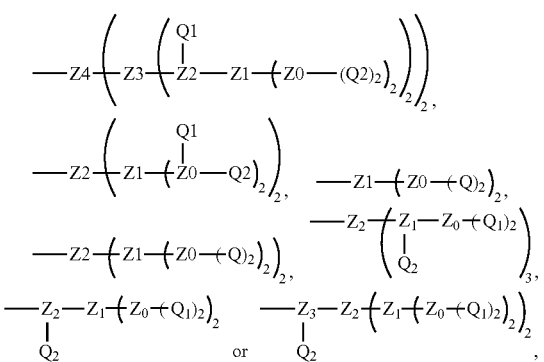
Z4, Z3, Z2, Z1, Z0 each independently are
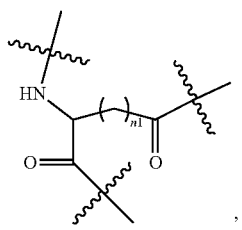
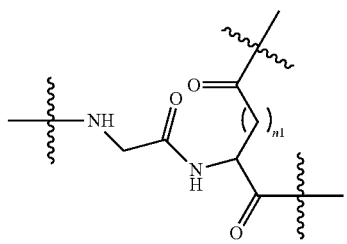
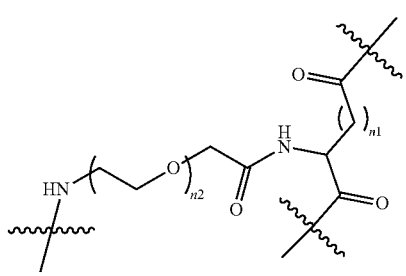
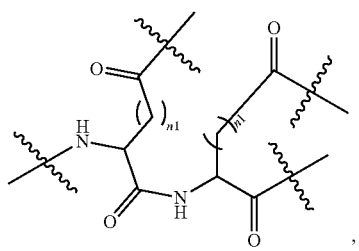
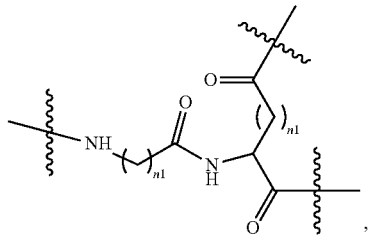
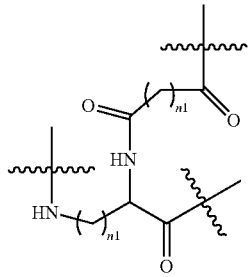
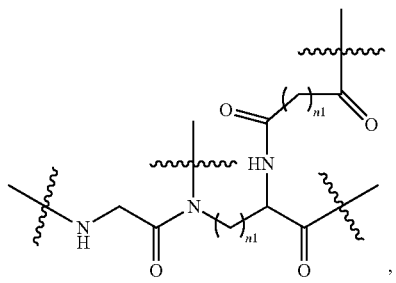

-continued

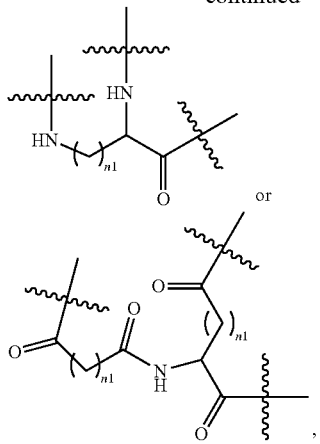
or

Q is —N-AC,
Q1 is —N1-AC1,
Q2 is —N2-AC2,
N, N1, N2 each independently are G, GFLG,

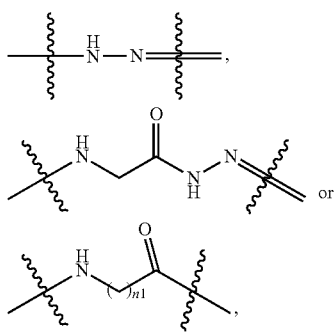
or

AC, AC1, AC2 each independently are SN38, PKA, PCB, LPT, SB7, PTX or NPB, the number-average molecular weight of PEG independently is 5k-40k.

3. The polyethylene glycol conjugated drug or a pharmaceutically acceptable salt thereof according to claim 2, wherein:

M is —C(=O)—C$_{1-6}$alkylene-C(=O)—, A1 is

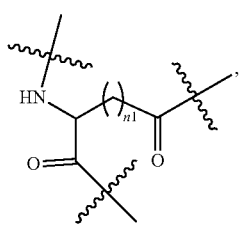

Y is

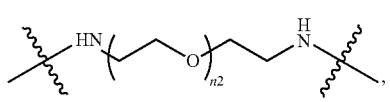,

X is

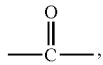,

W1 is

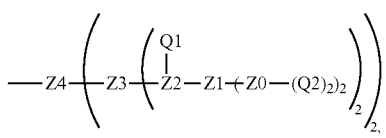

Z4, Z2 and Z1 are

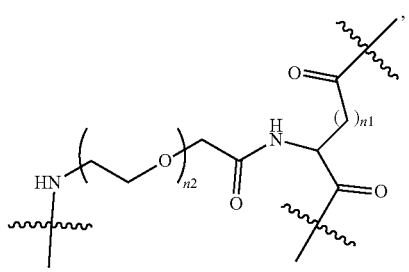

Z3 and Z0 are

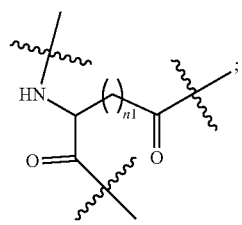

-or, M is —NH—C$_{1-6}$ alkylene-NH—, A1 is

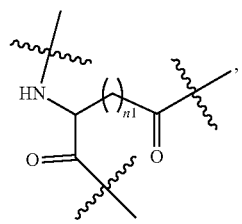,

Y is GLFG, X is

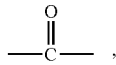,

W1 is
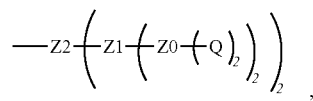
Z2 is
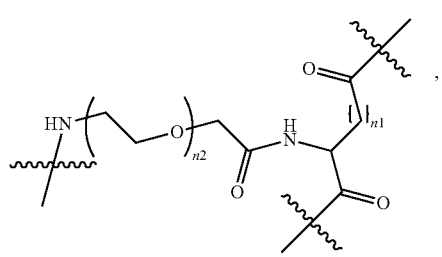
Z1 is
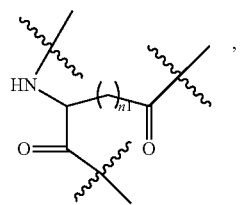
Z0 is
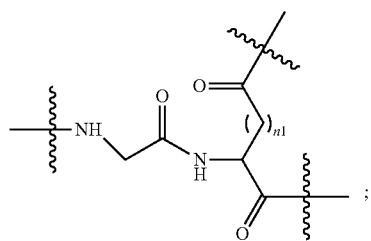
or, M is
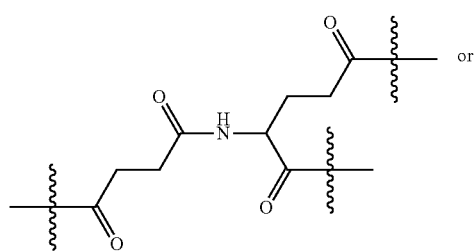
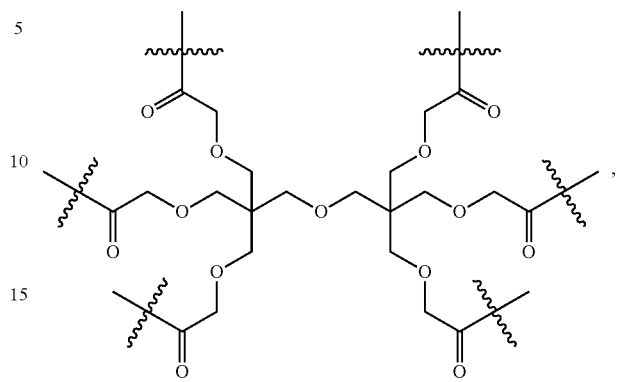
A1 is
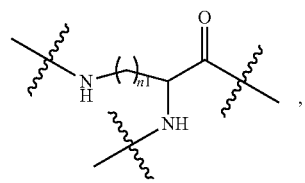
Y is a direct bond or —C(=O)—C$_{1-6}$ alkylene-C(=O)—, X is
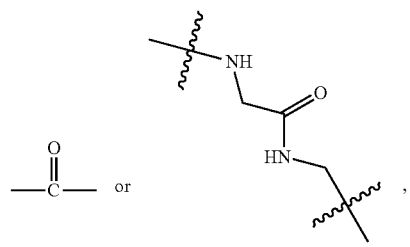
W1 is
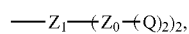
Z1 is
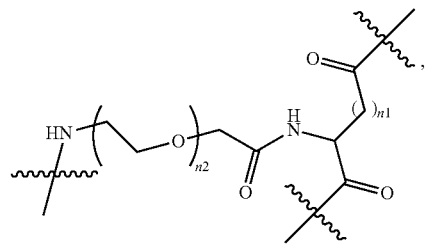

Z0 is
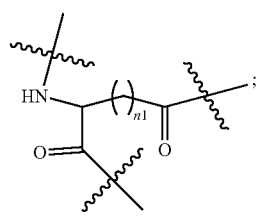
or, M is
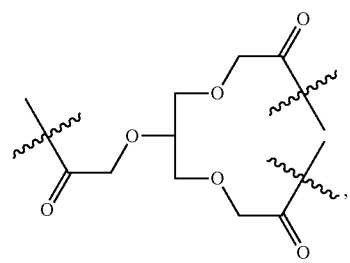 [SMILES: *C(=O)COCC(COCC(*)=O)OCC(*)=O]
A1 is
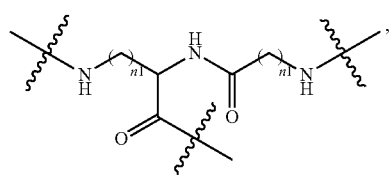
Y is a direct bond, X is
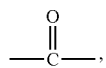
W1 is
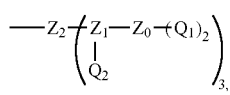
Z2 is
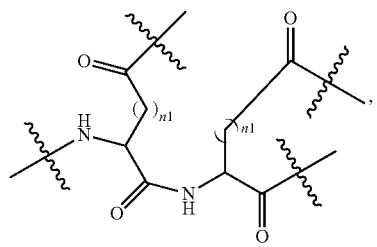
Z1 is
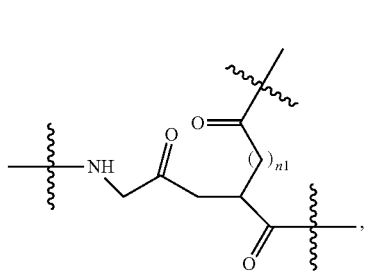
Z0 is
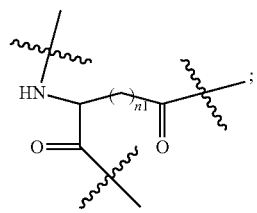
or, M is PEGm, $PEG_m$ is a single-arm polyethylene glycol segment, and its number-average molecular weight is 5k-40k,
A1 is
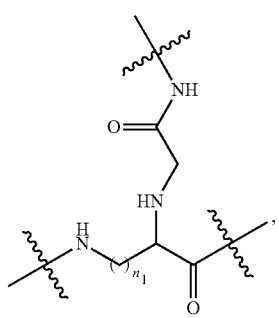
Y is a direct bond, X is
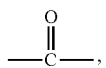
W1 is
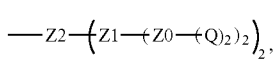

Z2 is
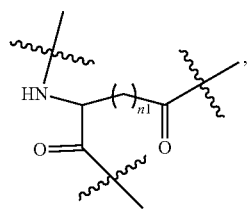
Z1 is
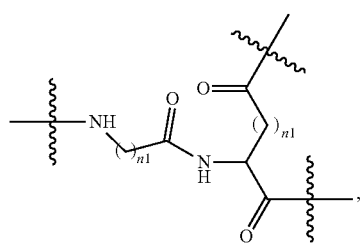 [SMILES: *NCC(=O)NC(CC(*)=O)C(*)=O]
Z0 is
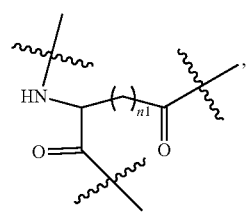
or, M is PEGm, PEG$_m$ is a multi-arm polyethylene glycol segment, and its number-average molecular weight is 5k-40k,
A1 is
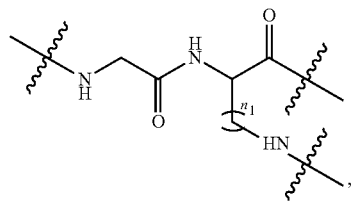
Y is a direct bond, X is
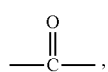
W1 is
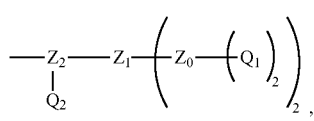
Z2 is
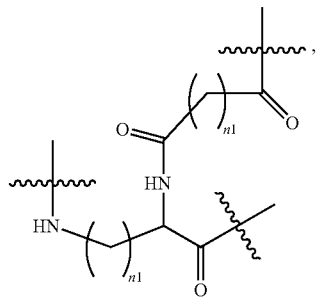
Z1 is
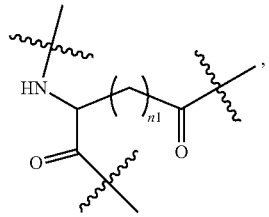
Z0 is
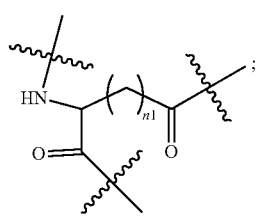
or, M is
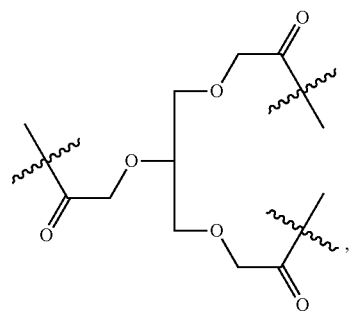 [SMILES: *C(=O)COCC(COCC(*)=O)OCC(*)=O]
A1 is
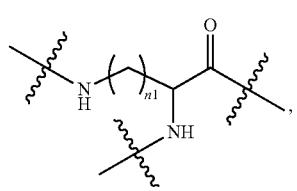

Y is
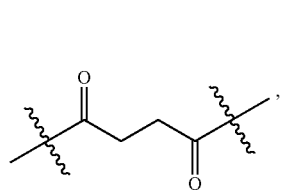 [SMILES: *C(=O)CCC(*)=O]
X is
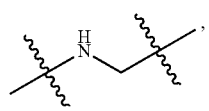
W1 is
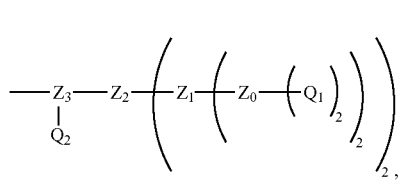
Z3 is
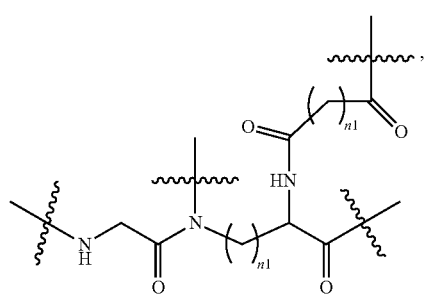
Z2 is
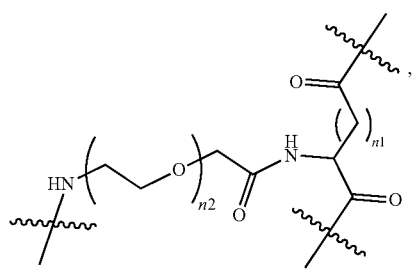
Z1 is
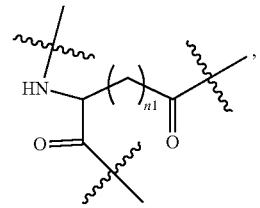
Z0 is
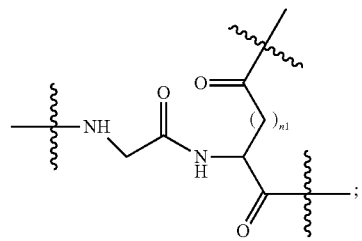 [SMILES: *NCC(=O)NC(CC(*)=O)C(*)=O]
-or, M is
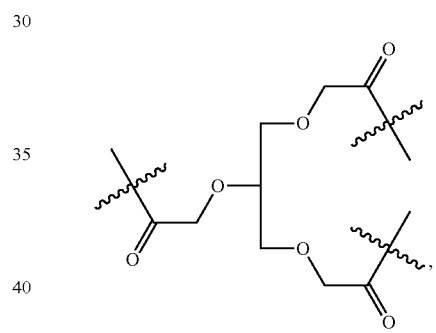
A1 is
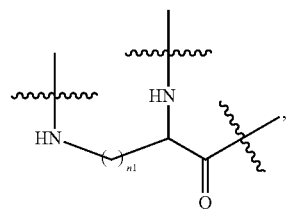 [SMILES: *NCC(N*)C(*)=O]
Y is
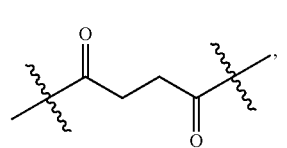 [SMILES: *C(=O)CCC(*)=O]

X is
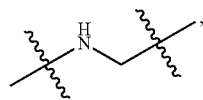
W1 is
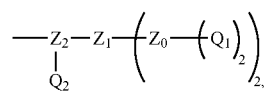
Z2 is
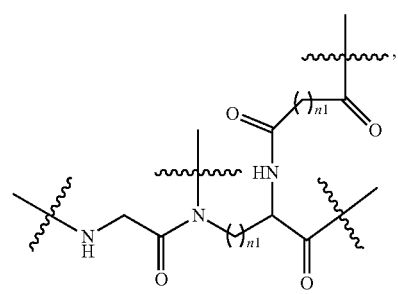
Z1 is
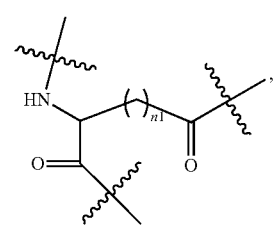
Z0 is
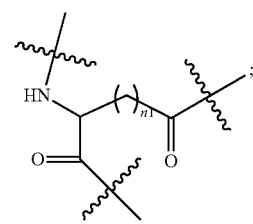
or, M is
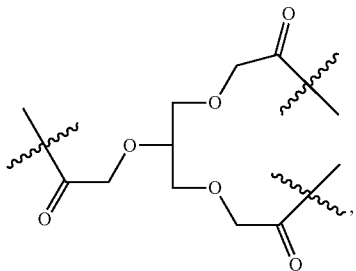 [SMILES: *C(=O)COCC(COCC(*)=O)OCC(*)=O]
A1 is
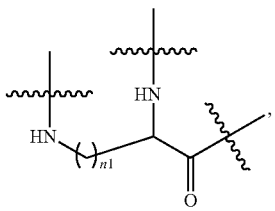
Y is a direct bond, X is
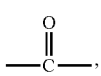
W1 is
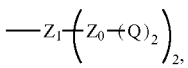
Z1 is
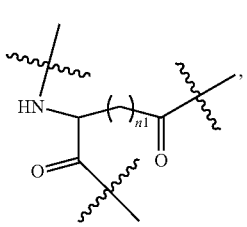
Z0 is
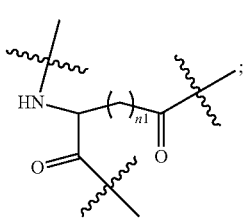

or, M is
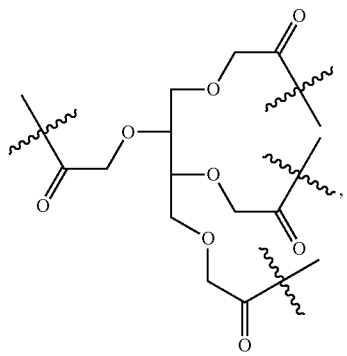 [SMILES: *C(=O)COCC(OCC(*)=O)C(COCC(*)=O)OCC(*)=O]
A1 is
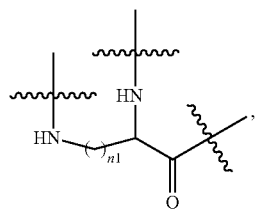 [SMILES: *NCC(N*)C(*)=O]
Y is
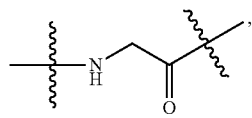 [SMILES: *NCC(*)=O]
X is
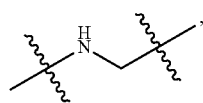
W1 is
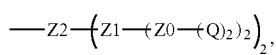
Z2 is
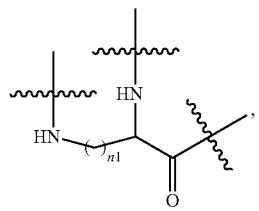 [SMILES: *NCC(N*)C(*)=O]
Z1 is
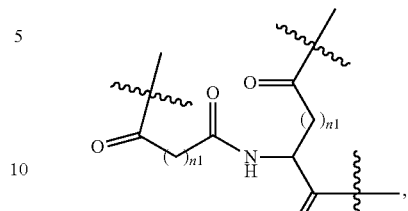
Z0 is
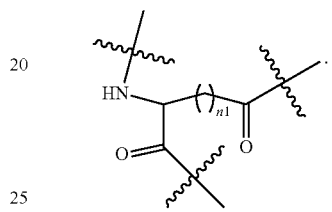
4. The polyethylene glycol conjugated drug or a pharmaceutically acceptable salt thereof according to claim 2, wherein:
M is
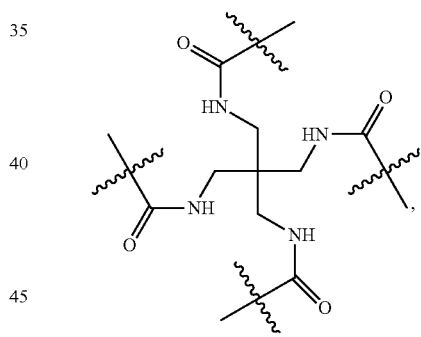
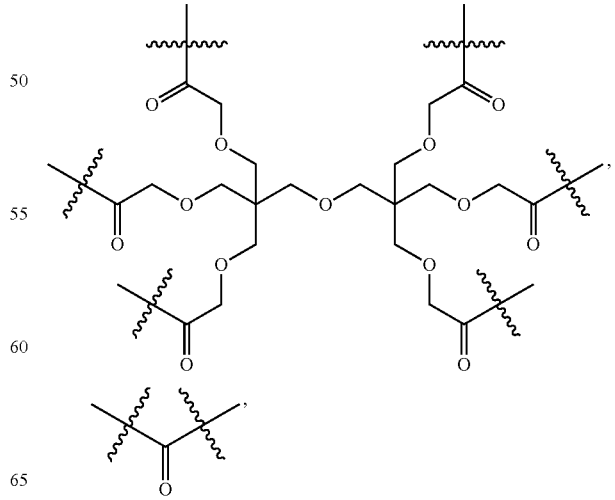

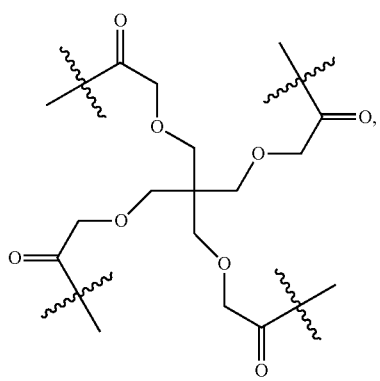
—C(=O)—C$_{1-6}$ alkylene-C(=O)—,
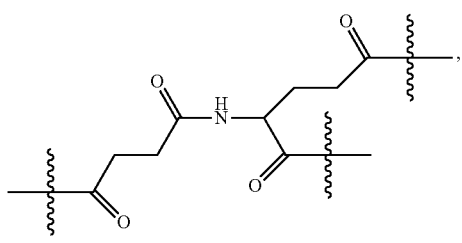
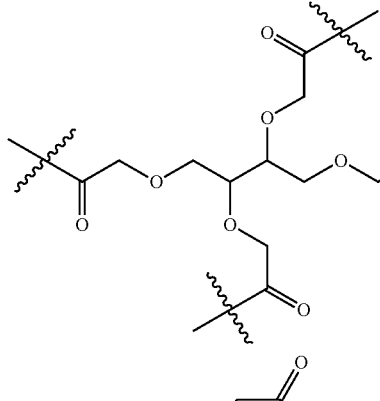
, or
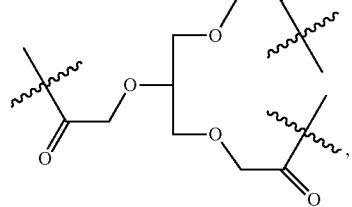
A1 is
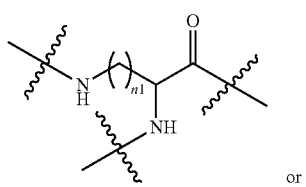
or
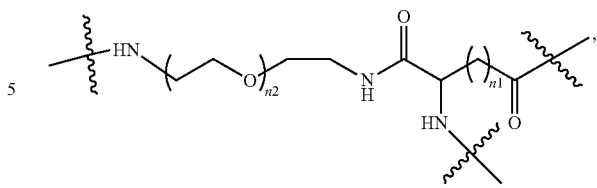
Y is a direct bond, GLFG, —C(=O)—C$_{1-6}$ alkylene-C(=O)— or
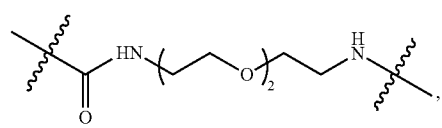
X is
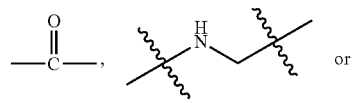
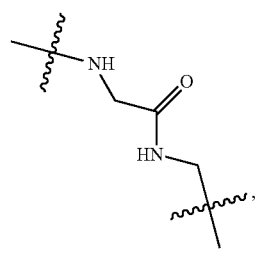
W1 is
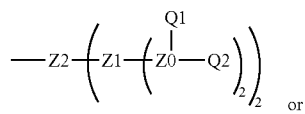
or
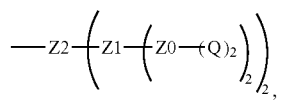
Z2 is
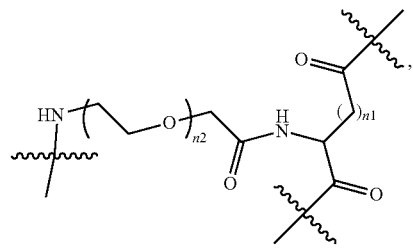

Z1 is

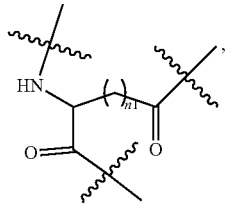

Z0 is

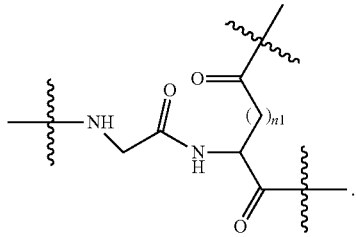

5. The polyethylene glycol conjugated drug or a pharmaceutically acceptable salt thereof according to claim 1, the polyethylene glycol conjugated drug having the structure represented by the formula (III), $$
\begin{array}{l}
\text{M} \text{—} [\text{A1} \text{—} \text{W1}]_{j1} \\
|\\
\text{A1}' \text{—} \text{W1}' \quad \text{Y} \\
| \qquad\qquad | \\
\text{Y}' \qquad\qquad \text{X} \\
| \qquad\qquad | \\
\text{X}' \qquad\qquad \text{PEG} \\
| \\
\text{PEG}
\end{array} \quad (\text{III})
$$

wherein:

M is

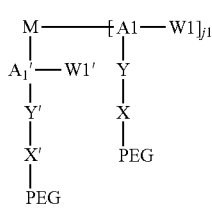

—C(=O)—$C_{1-6}$ alkylene-NH— or —C(=O)—$C_{1-6}$ alkylene-C(=O)—,

A1, A1' each independently are

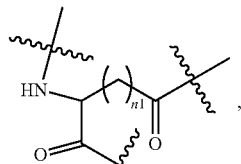

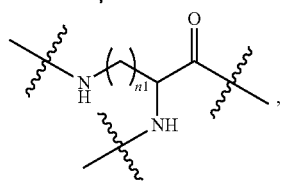

 or

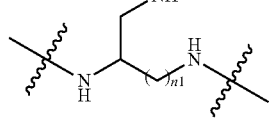

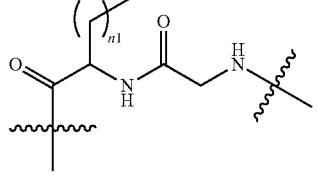

Y, Y' each independently are a direct bond or

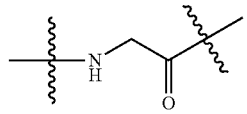

X and X' are

W1, W1' each independently are

—Z2—(Z1—(Z0—(Q)$_2$)$_2$)$_2$,

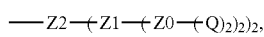
—Z1—(Z0—(Q1)$_2$)$_2$, —Z4—(Z3—(Z2—(Q2)$_2$)$_2$)$_2$,

—Z2—(Z1—(Z0—(Q2)$_2$)$_2$)$_2$, —Z0—(Q1)$_2$,

—Z3—(Z2—(Z1—(Q2)$_2$)$_2$)$_2$ or —Z1—(Z0—(Q2)$_3$)$_3$,

Z4, Z3, Z2, Z1, Z0 each independently are

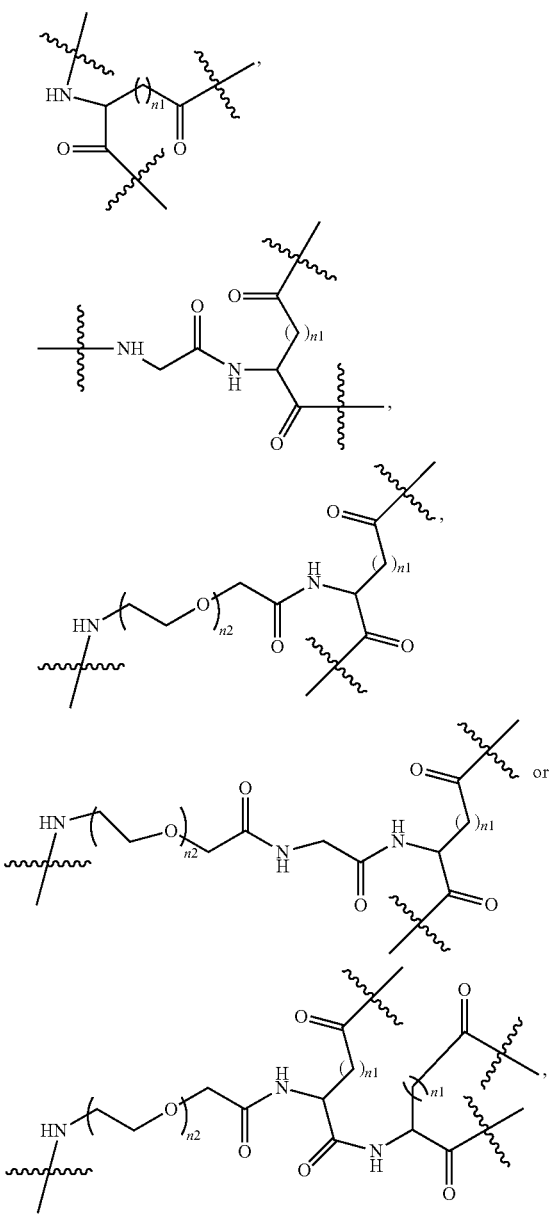

Q is —N-AC,
Q1 is —N1-AC1,
Q2 is —N2-AC2,
N, N1, N2 each independently are GFLG, G,

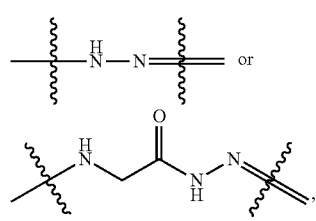

AC, AC1, AC2 each independently are SN38, PKA, PCB, PTX, LPT, SB7 or DOX, the number-average molecular weight of PEG independently is 5k-40k.

6. The polyethylene glycol conjugated drug or a pharmaceutically acceptable salt thereof according to claim 5, wherein:

M is

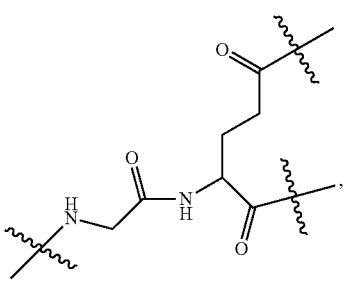 [SMILES: *NCC(=O)NC(CCC(*)=O)C(*)=O]

A1 is

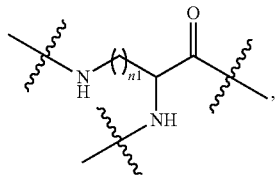

A1' is

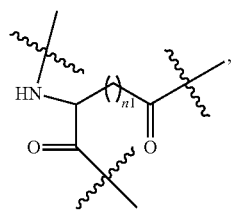

Y is a direct bond, Y' is

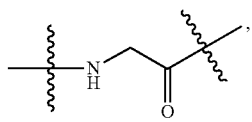 [SMILES: *NCC(*)=O]

W1 is

—Z4—(Z3—(Z2—(Q2)$_2$)$_2$)$_2$,

W1' is

—Z1—(Z0—(Q1)$_2$)$_2$,

1447
Z4, Z2 and Z0 are
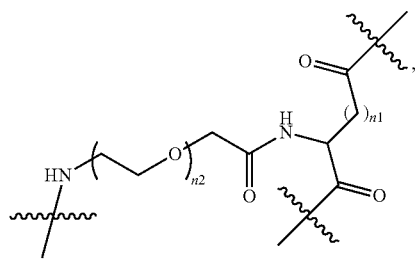
Z3 and Z1 are
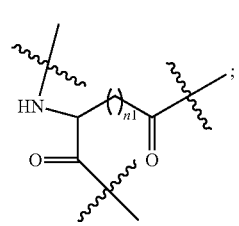
or, M is —C(=O)—$C_{1-6}$alkylene-NH—, A1 is
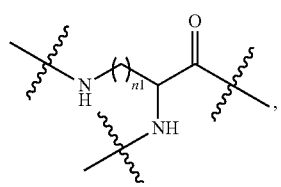
A1' is
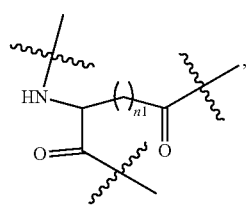
Y is a direct bond, Y' is
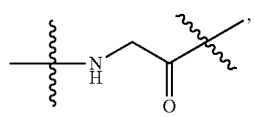 [SMILES: *NCC(*)=O]
W1 is
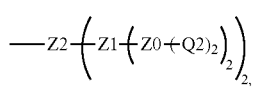
1448
W1' is Q1, Z2 and Z0 are
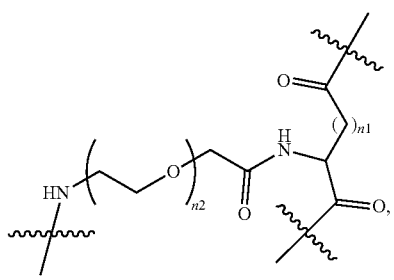
Z1 is
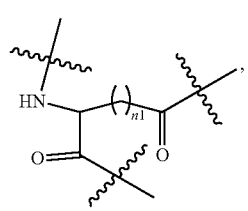
or, M is —C(=O)—$C_{1-6}$ alkylene-C(=O)—, A1 and A1' are
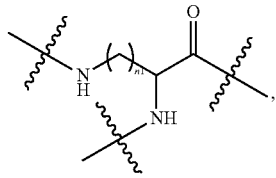
Y and Y' are a direct bond, W1 is
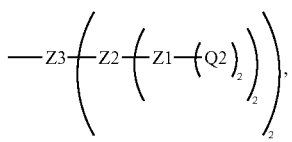
W1' is —Z0-(Q1)$_2$, Z3 and Z1 are
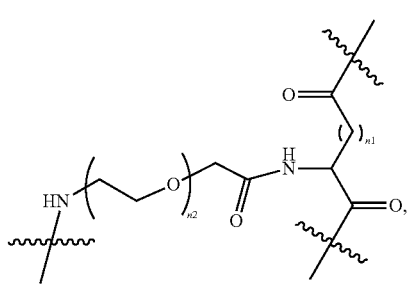

Z2 and Z0 are

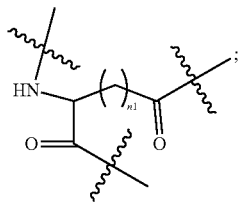

or, M is —C(=O)—$C_{1-6}$ alkylene-C(=O)—, A1 and A1' are

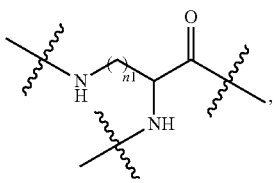

Y and Y' are a direct bond, W1 is

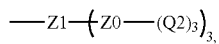

W1' is Q1, Z1 and Z0 are

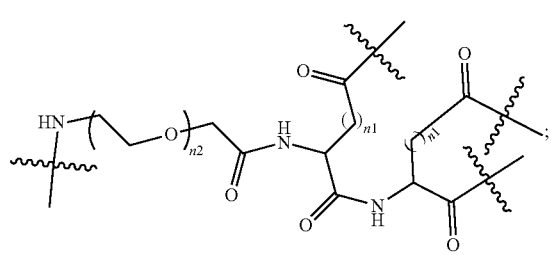

or, M is —C(=O)—$C_{1-6}$alkylene-NH—, A1 is

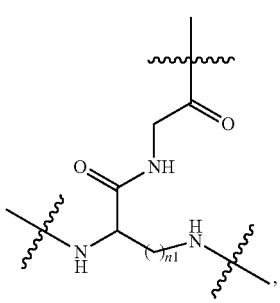

A1' is

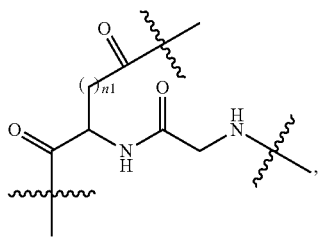

Y and Y' are a direct bond, W1 and W1' are

Z2 is

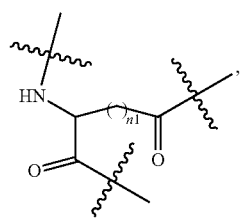

Z1 is

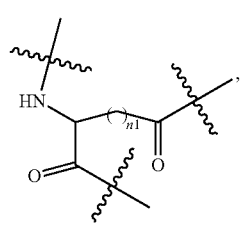

Z0 is

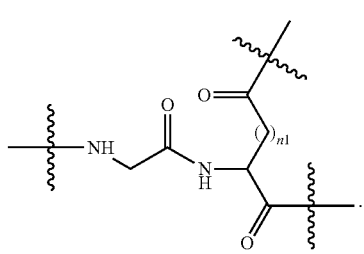

7. The polyethylene glycol conjugated drug or a pharmaceutically acceptable salt thereof according to claim 1, the polyethylene glycol conjugated drug having the structure represented by the formula (IV),

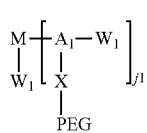
wherein:
M is
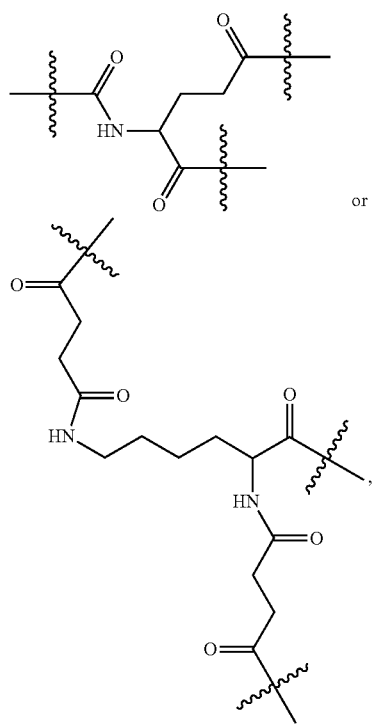
A1 is preferably
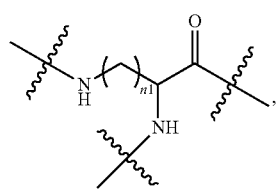
X is
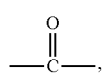
W1 independently is
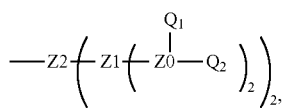
-continued
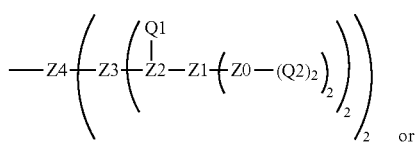 or
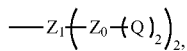
Z4, Z3, Z2, Z1, Z0 each independently are
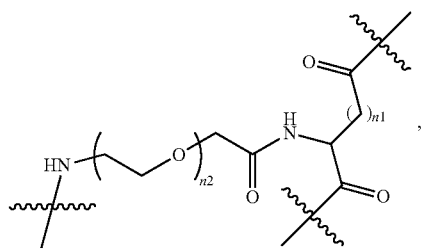
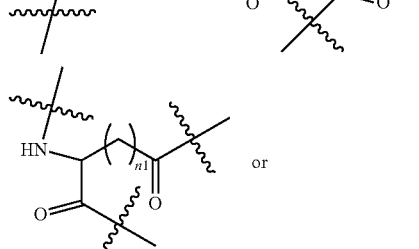 or
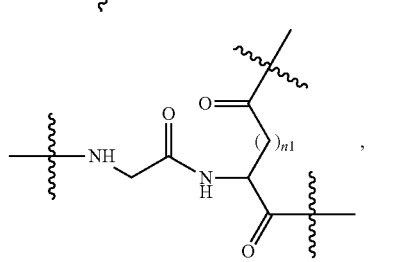
Q is —N-AC,
Q1 is —N1-AC1,
Q2 is —N2-AC2,
N1 and N2 are GFLG,
AC1, AC2 each independently are PCB, SB7, LPT, PKA, the number-average molecular weight of PEG independently is 5k-40k.
8. The polyethylene glycol conjugated drug or a pharmaceutically acceptable salt thereof according to claim 7, wherein:
M is
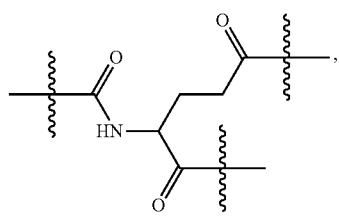 [SMILES: *C(=O)CCC(NC(*)=O)C(*)=O]

W1 is
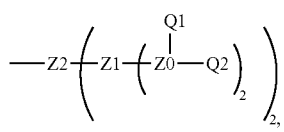
Z2 is
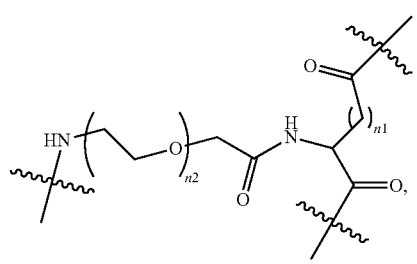
Z1 is
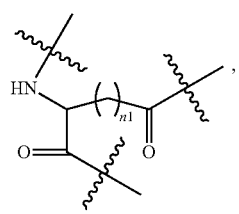
Z0 is
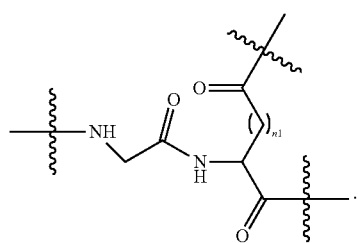
or, M is
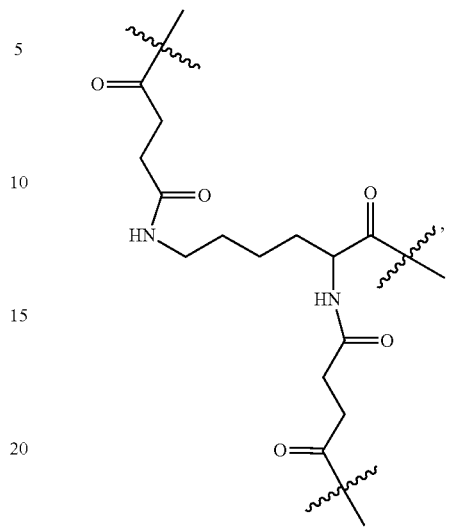
W1 is
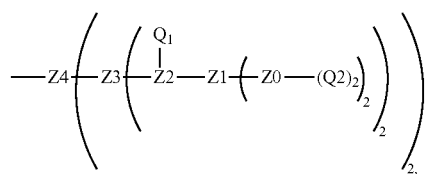
Z4 and Z1 are
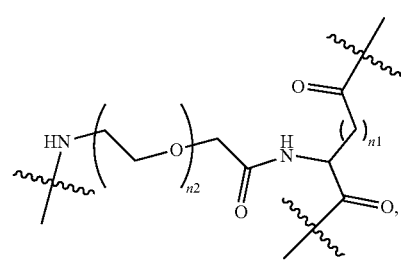
Z3, Z2 and Z0 are
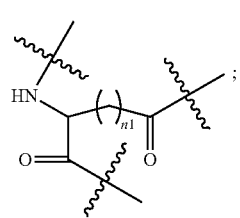

or, M is
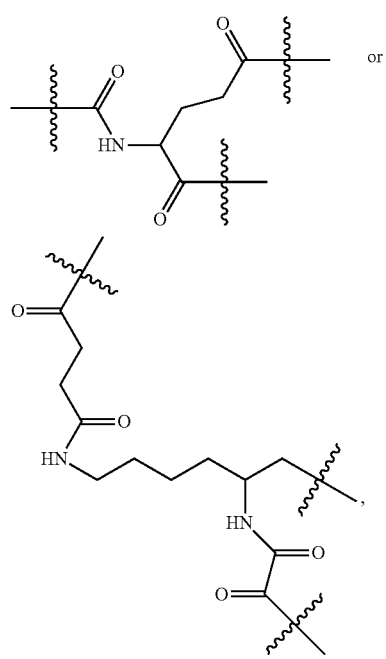
W1 is
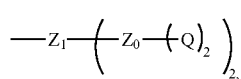
Z1 is
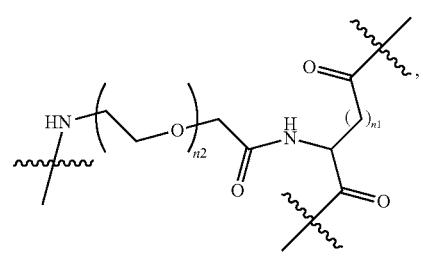
Z0 is
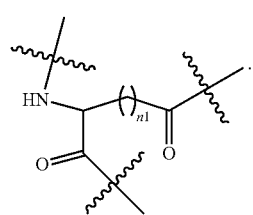
9. The polyethylene glycol conjugated drug or a pharmaceutically acceptable salt thereof according to claim 1, the polyethylene glycol conjugated drug having the structure represented by the formula (V),
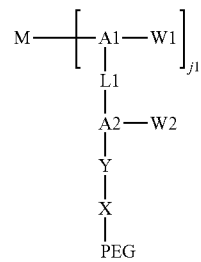
(V)
wherein:
L1 is —C(=O)—C$_{1-6}$ alkylene-C(=O),
A2 is
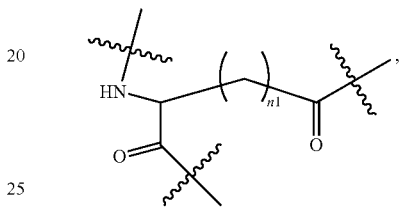
M is
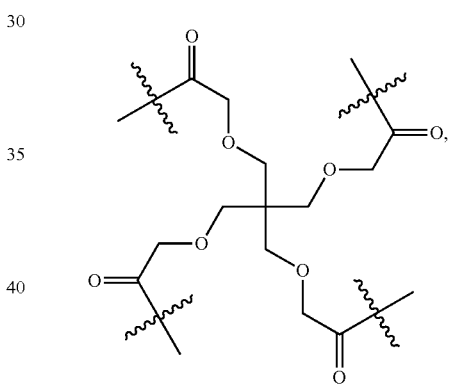
A1 is
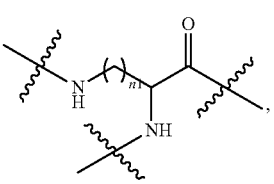
Y is
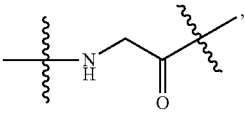 [SMILES: *NCC(*)=O]

X is

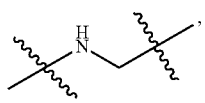 [SMILES: *CN*]

W1, W2 each independently are

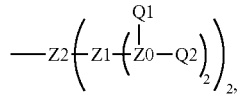

Z2, Z1, Z0 each independently are

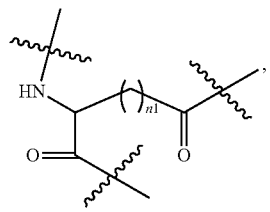

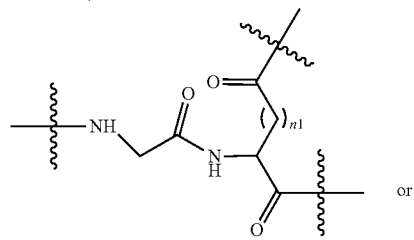

or

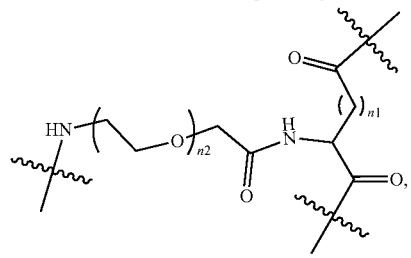

Q1 is —N1-AC1,
Q2 is —N2-AC2,
N1 and N2 are GFLG,
AC1, AC2 each independently are PCB or SB7,
the number-average molecular weight of PEG is 5k-40k.

10. The polyethylene glycol conjugated drug or a pharmaceutically acceptable salt thereof according to claim 9, wherein:
W1 and W2 are

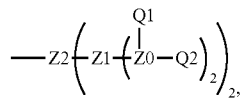

Z2 is

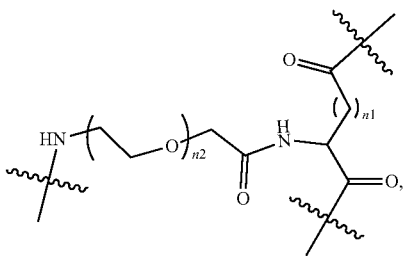

Z1 is

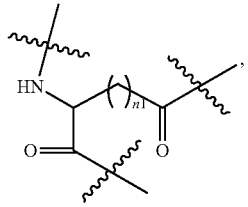

Z0 is

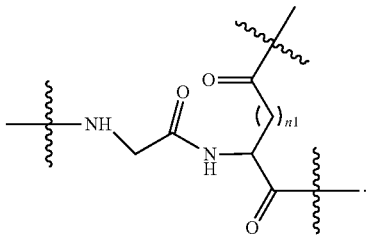

11. A polyethylene glycol conjugated drug or a pharmaceutically acceptable salt thereof, wherein the polyethylene glycol conjugated drug is selected from:

-continued
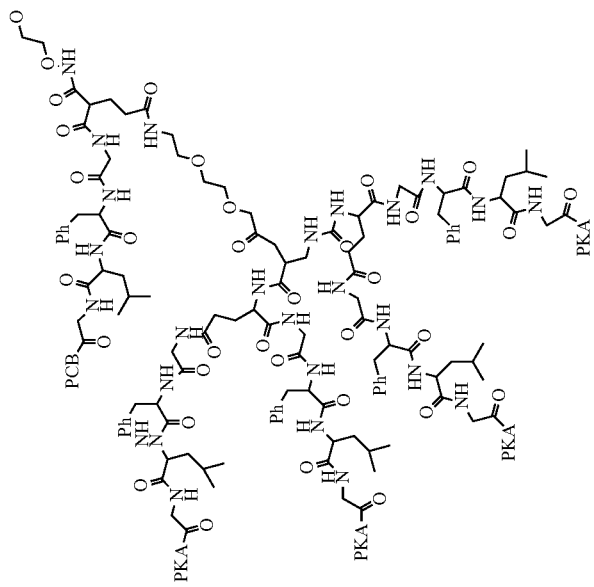

-continued
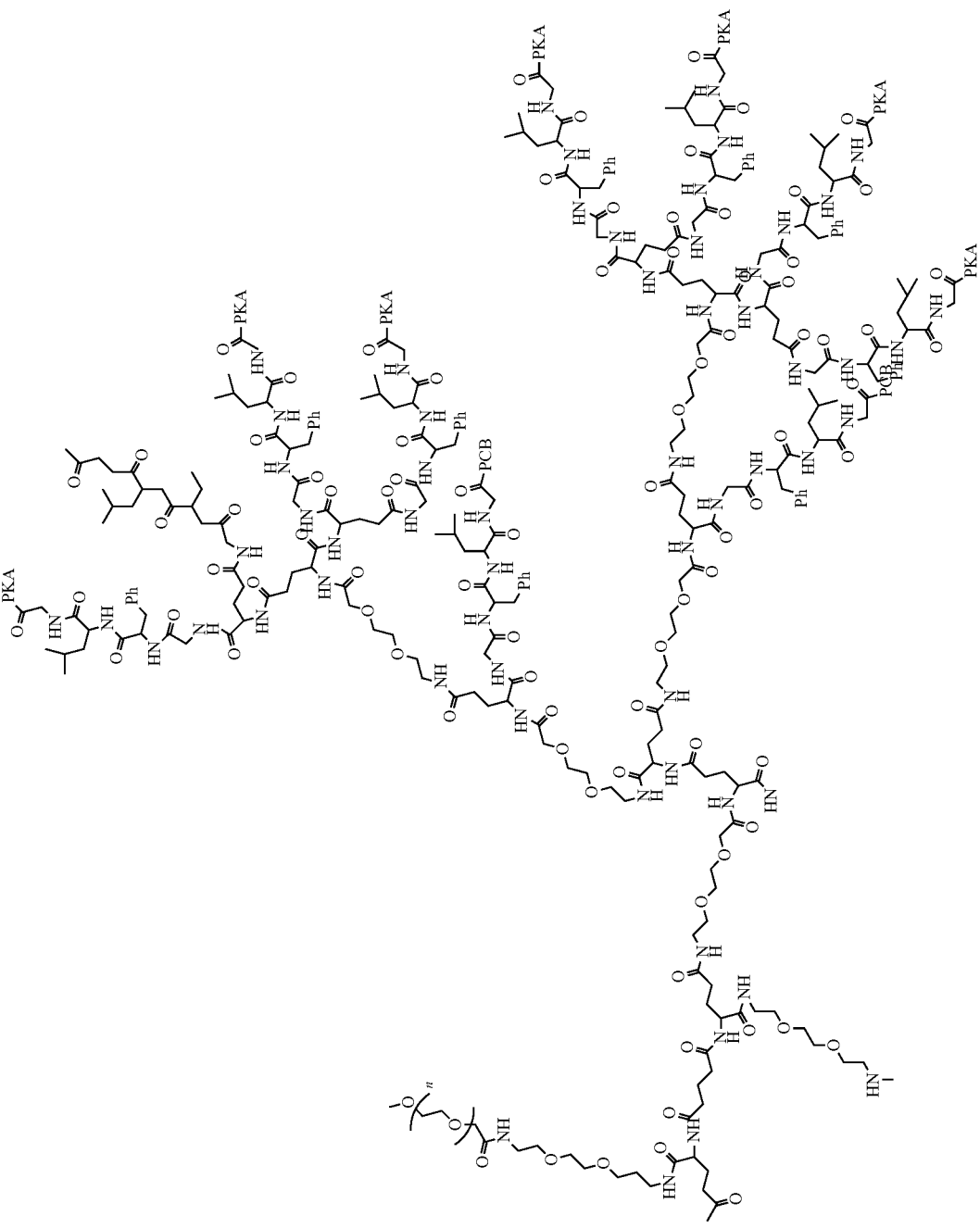

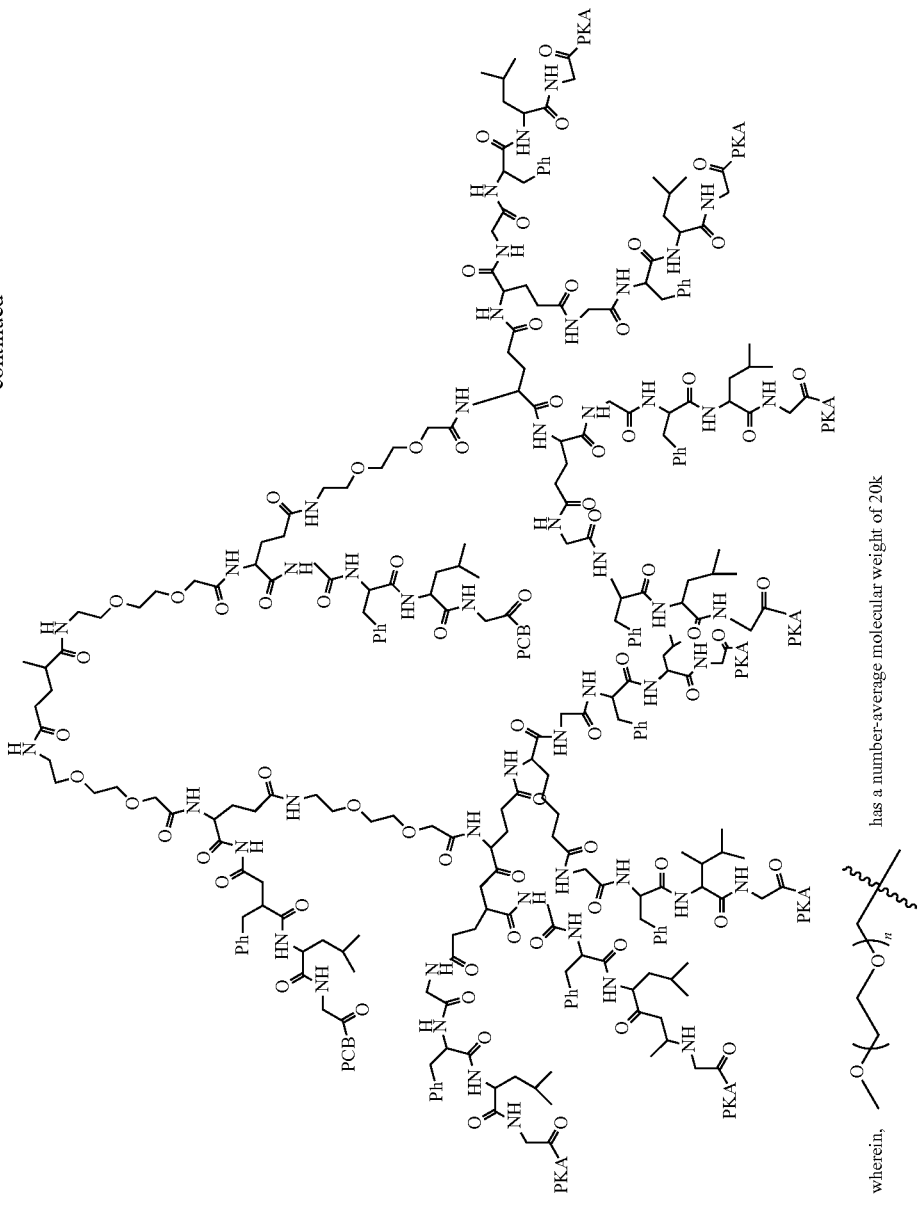

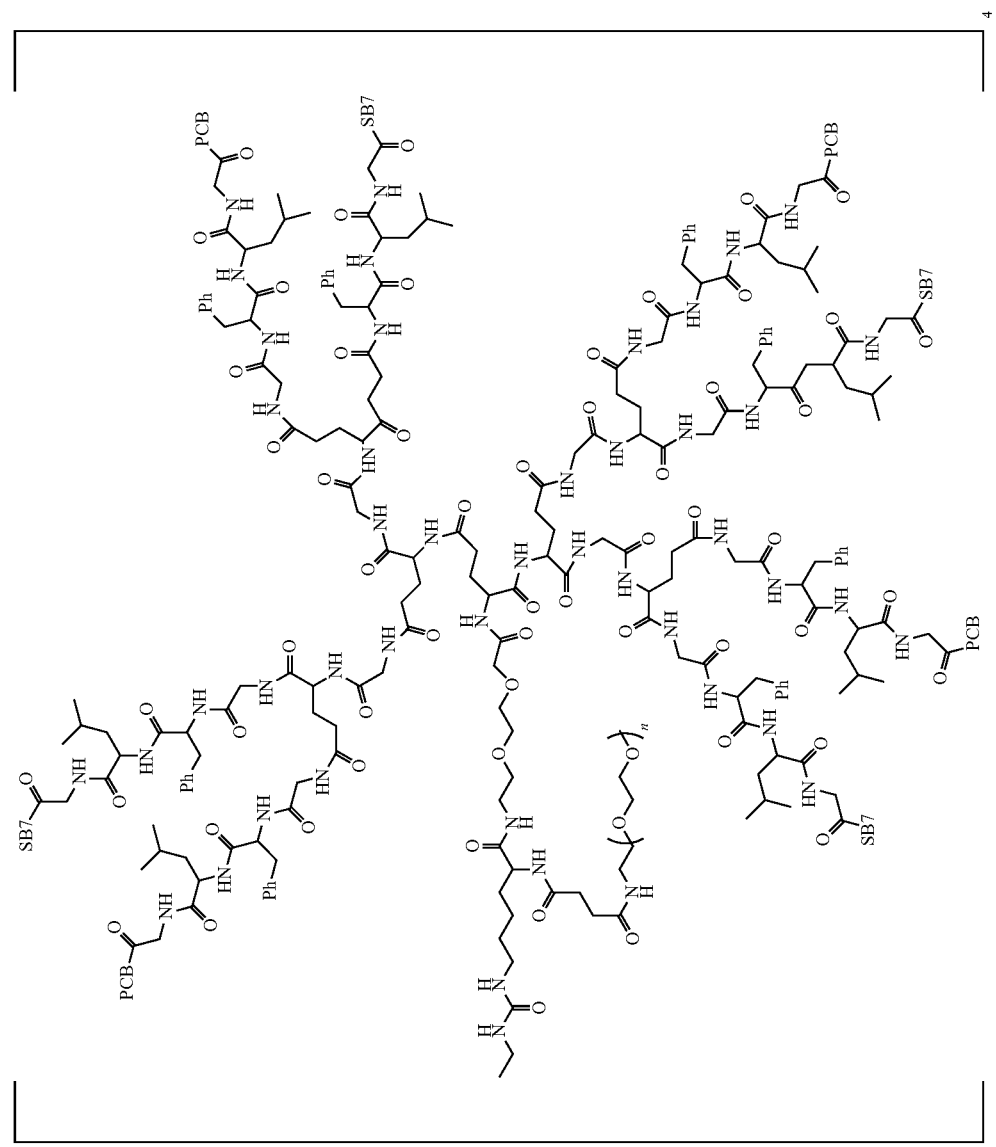
wherein,  has a number-average molecular weight of 5k

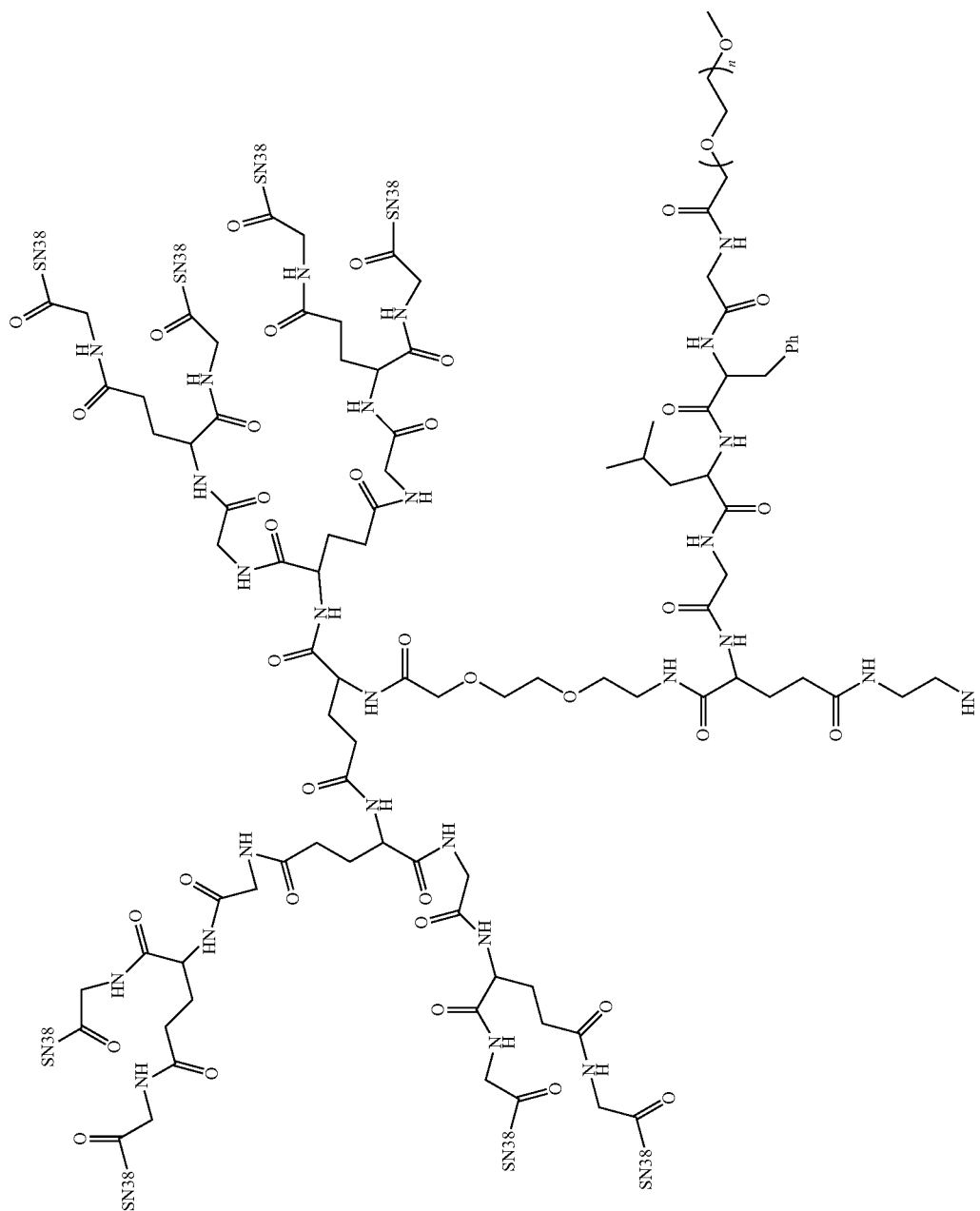

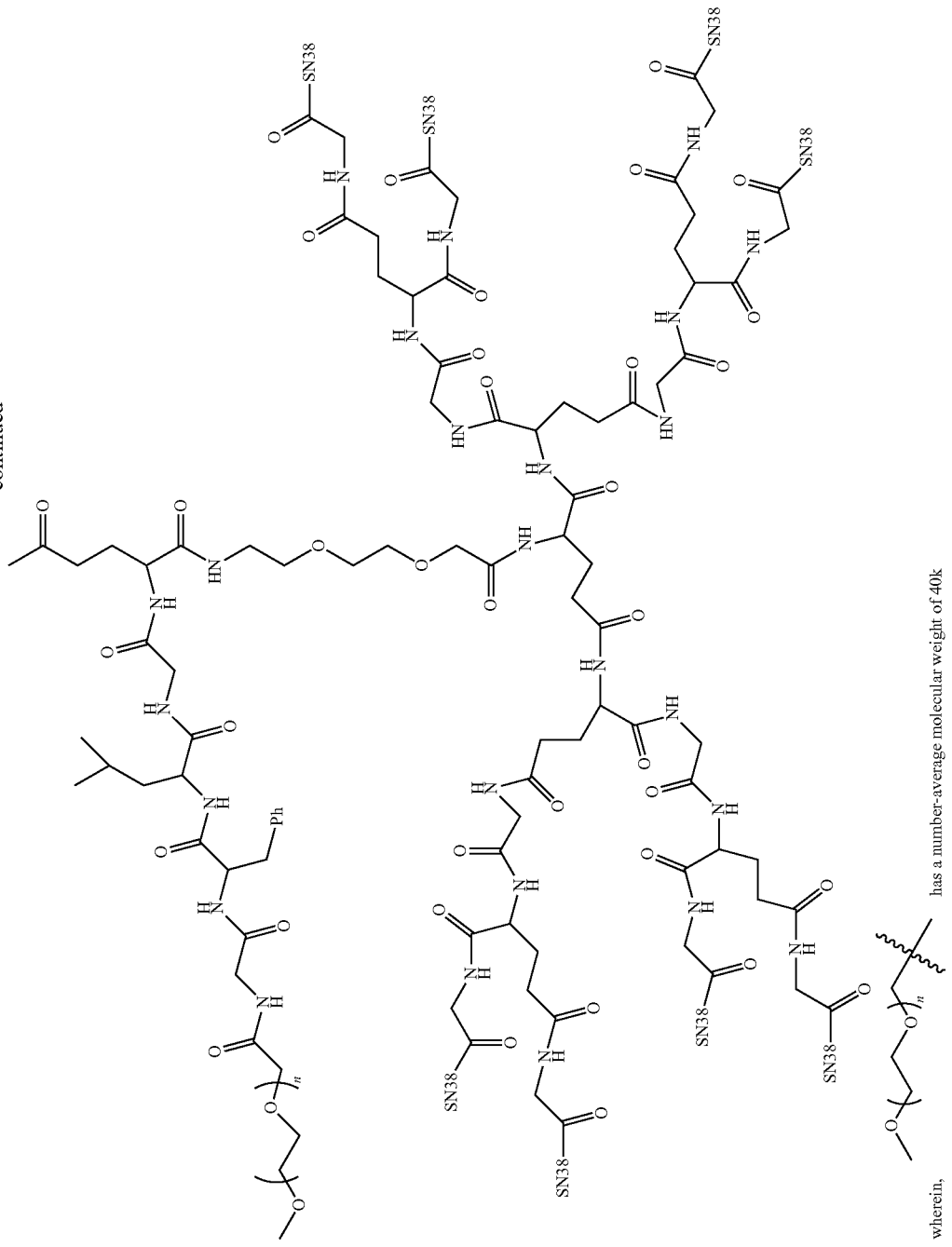
wherein, has a number-average molecular weight of 40k

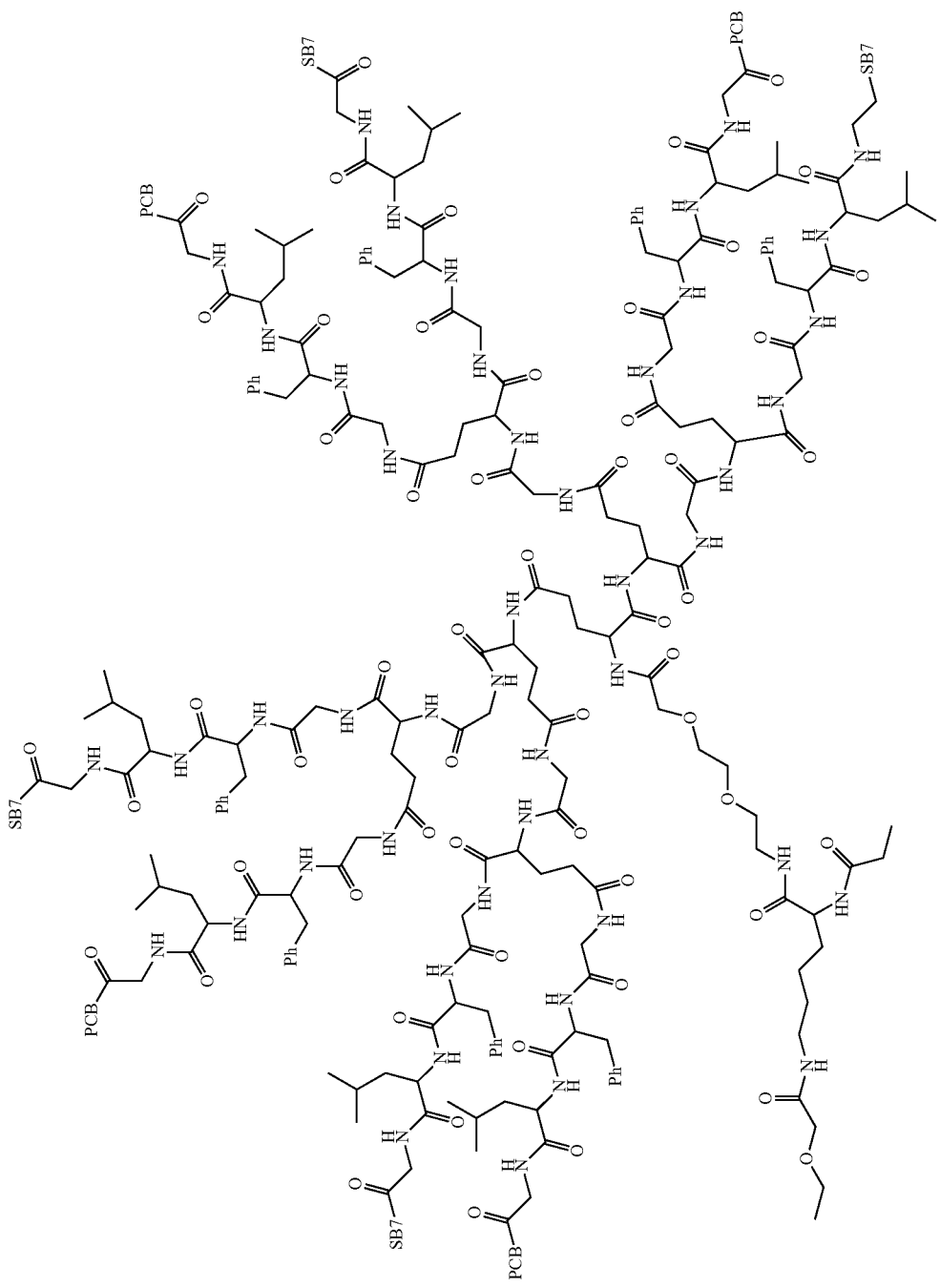

-continued
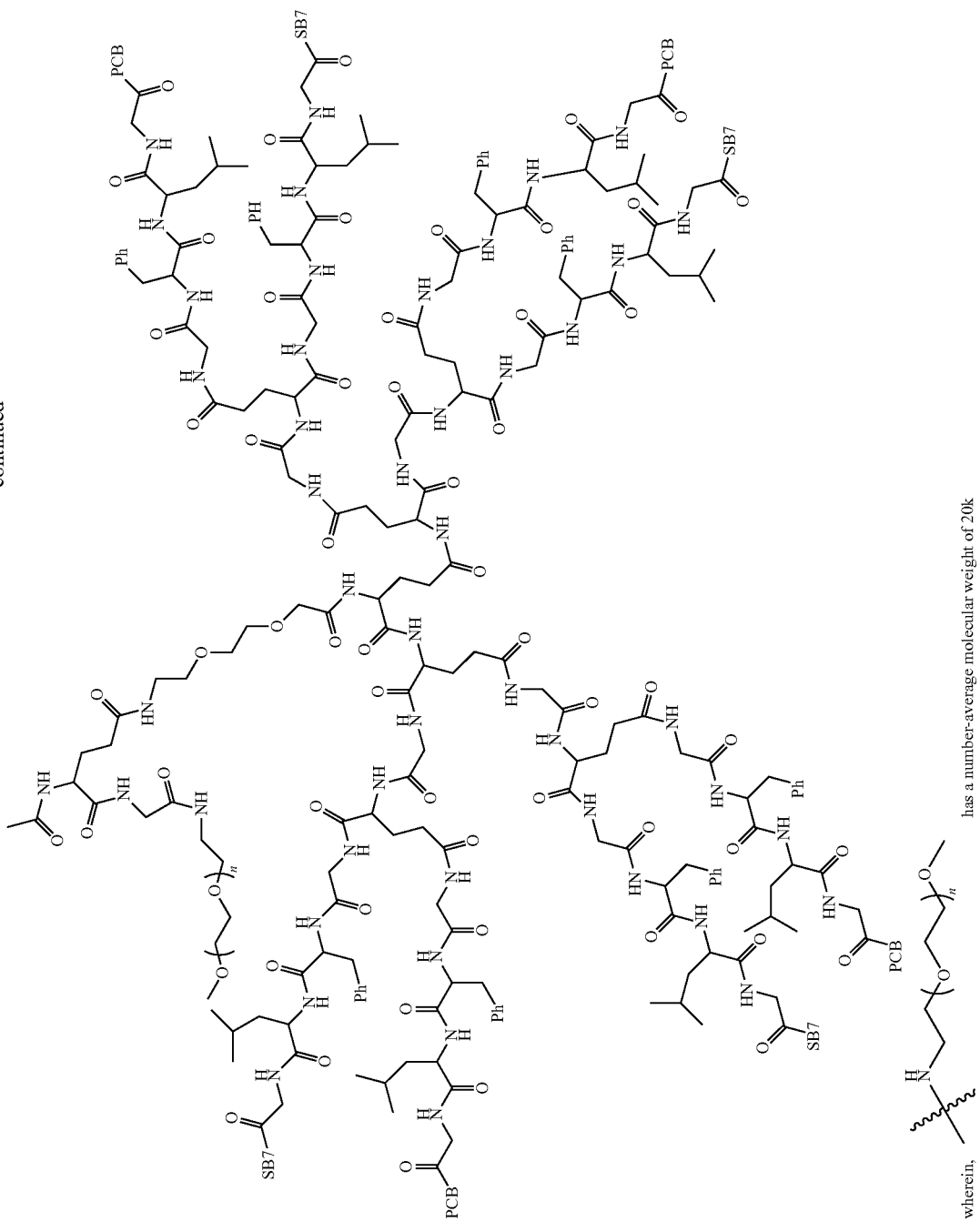
wherein, has a number-average molecular weight of 20k

-continued
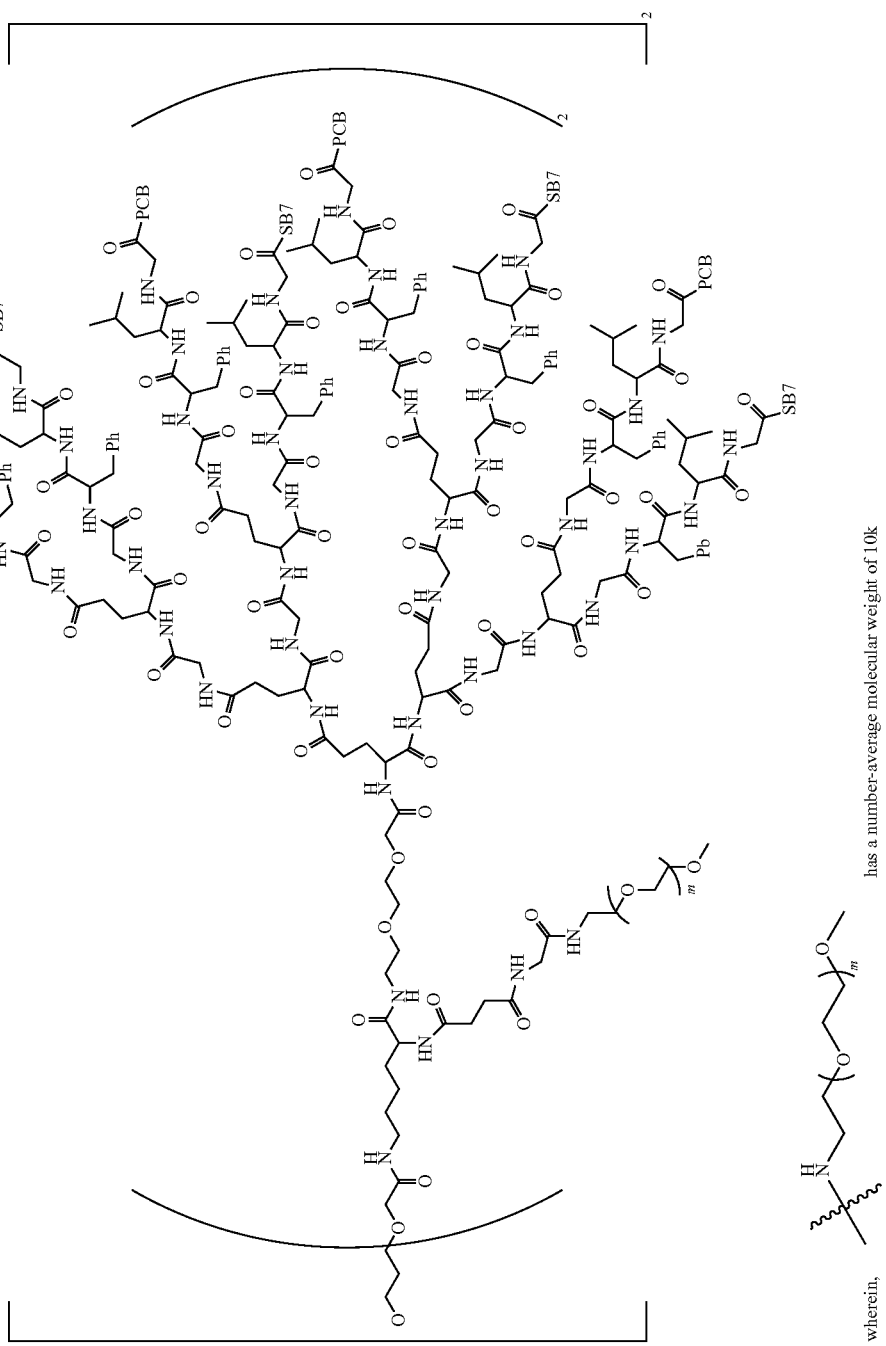
wherein,

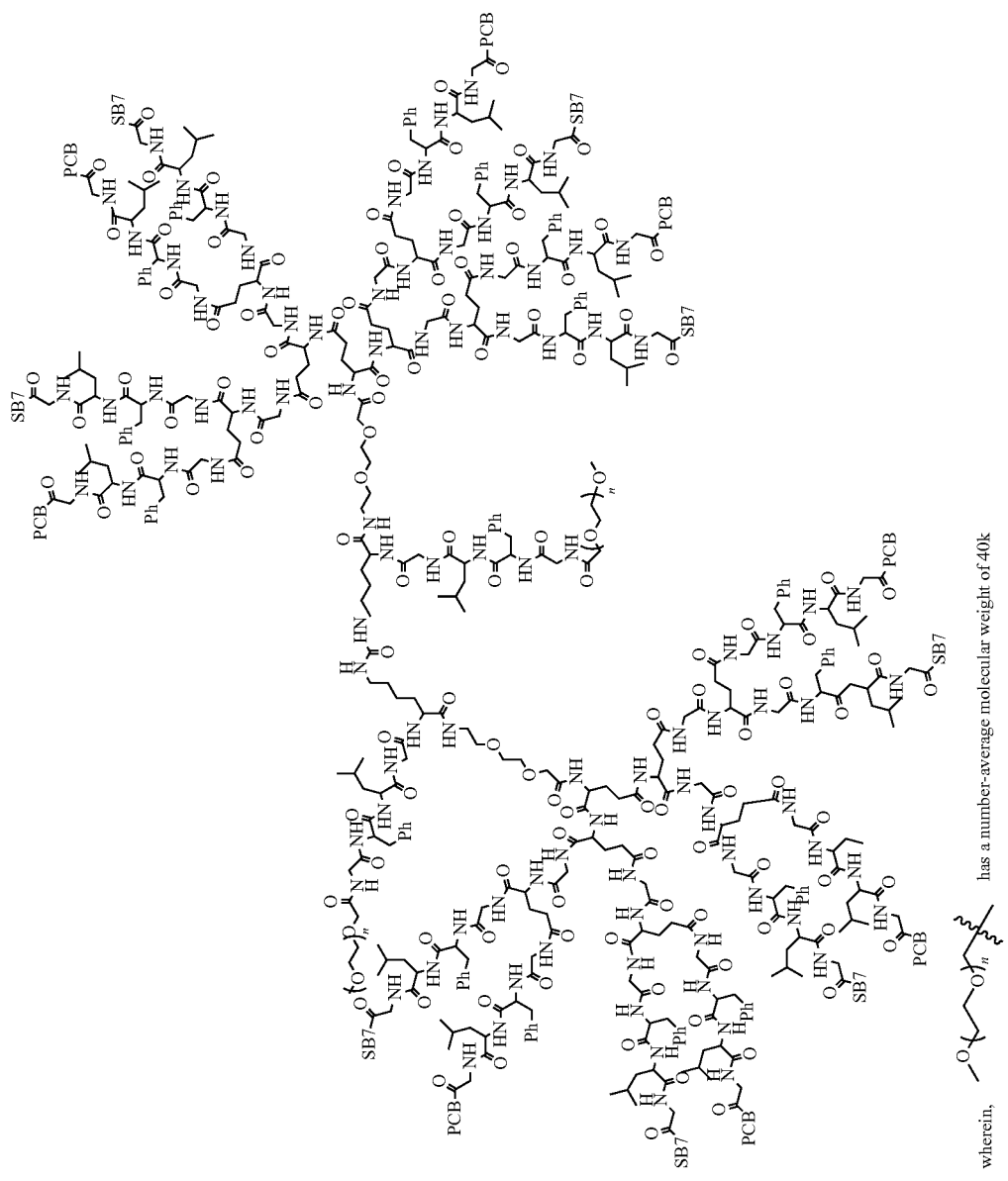
wherein, ~O~n has a number-average molecular weight of 40k

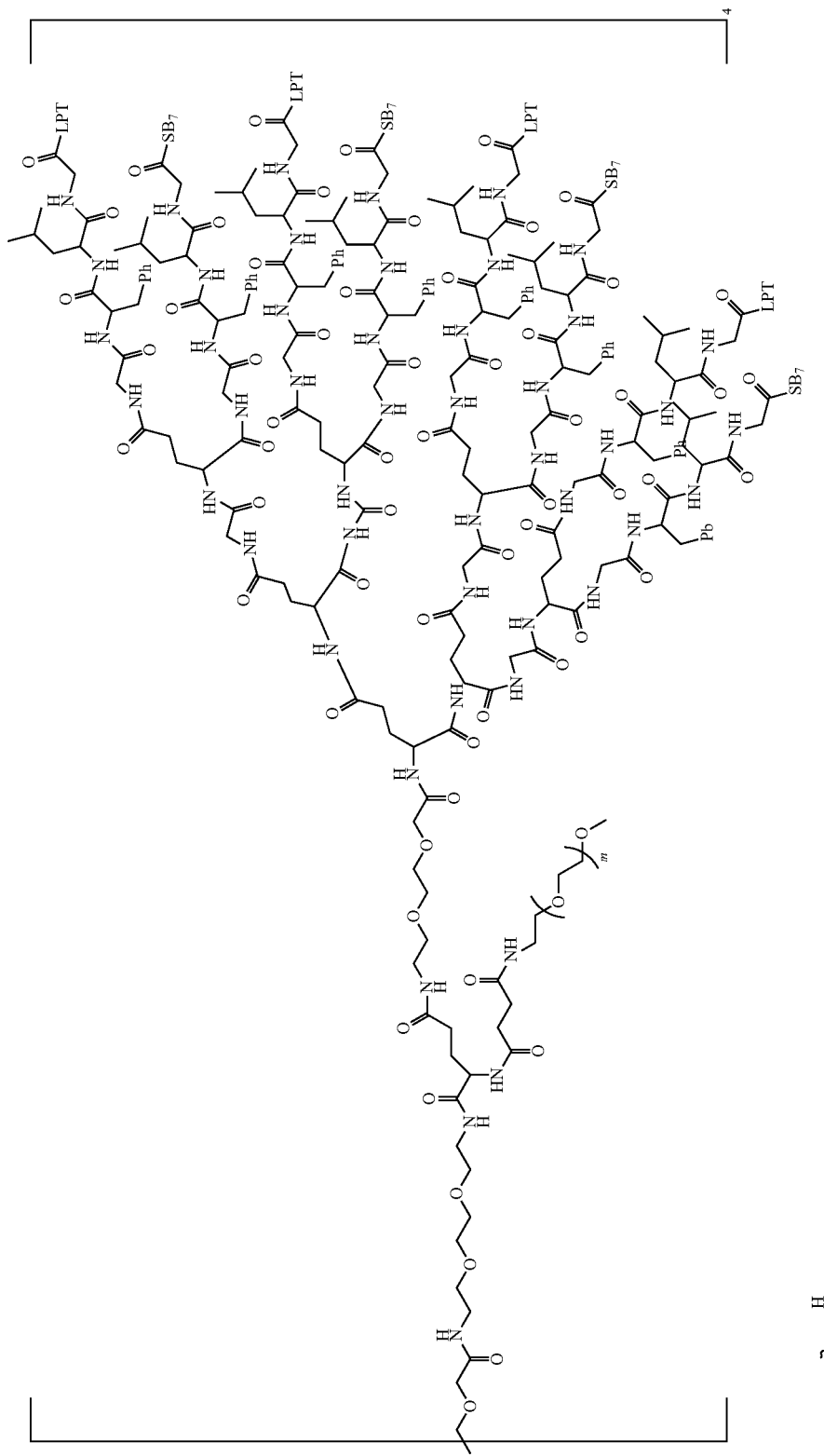
-continued
wherein, has a number-average molecular weight of 10k

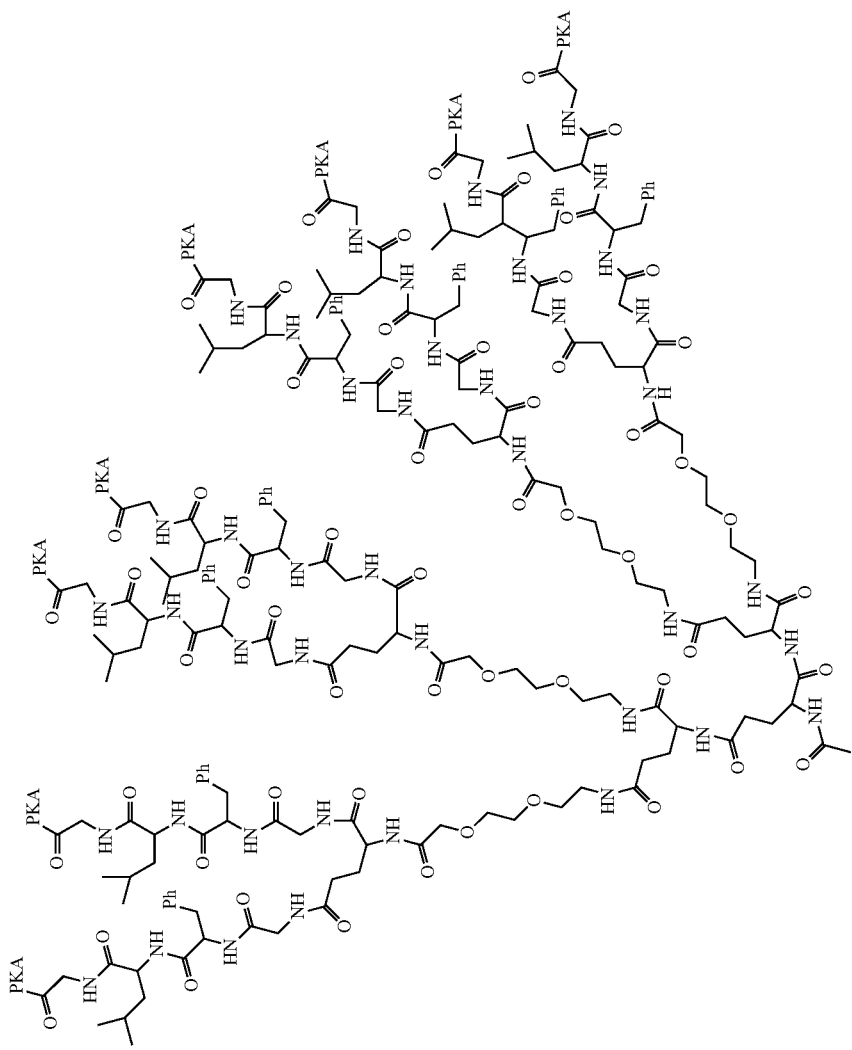

-continued
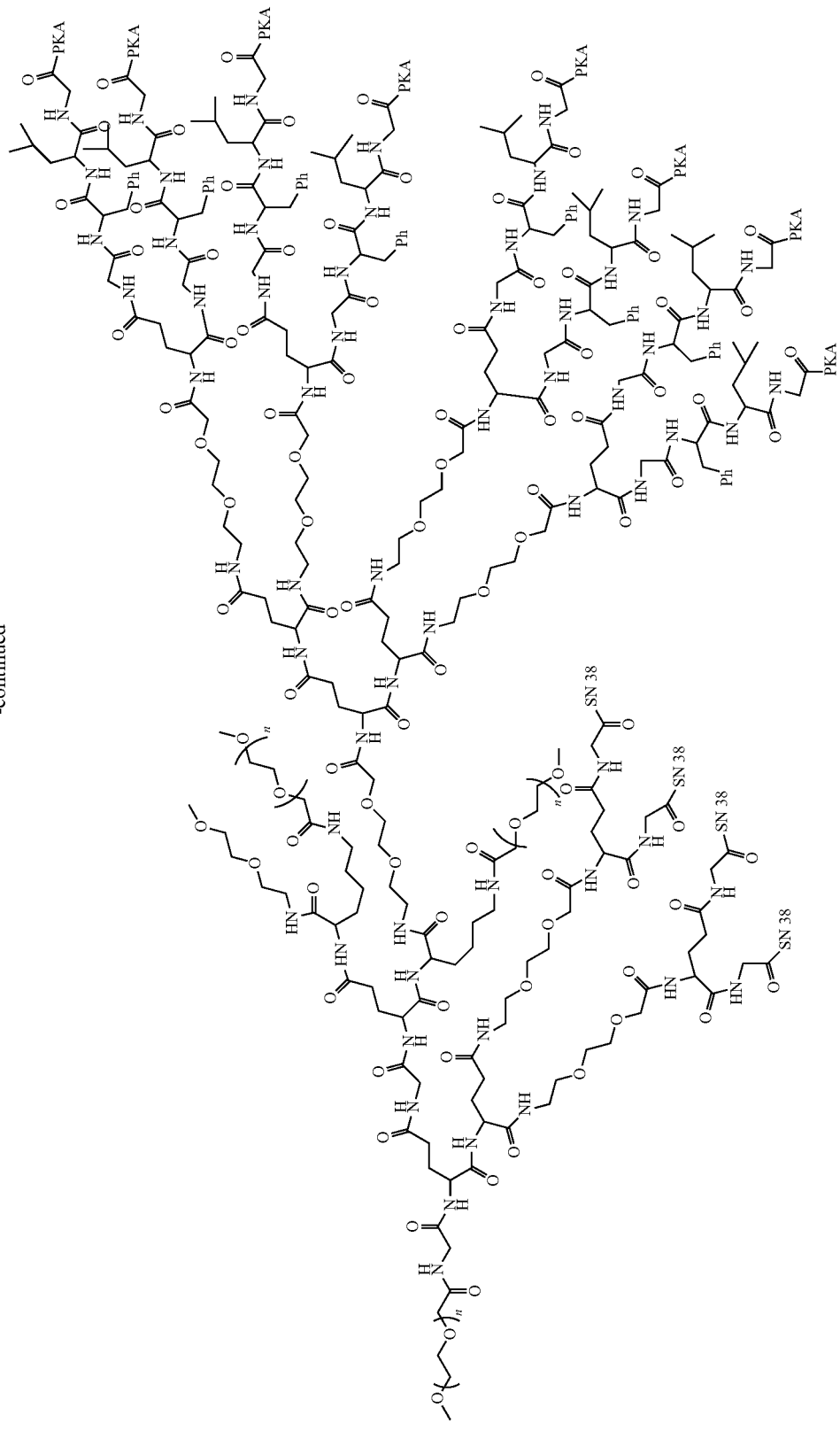
wherein, ~~~O~~~ has a number-average molecular weight of 5k

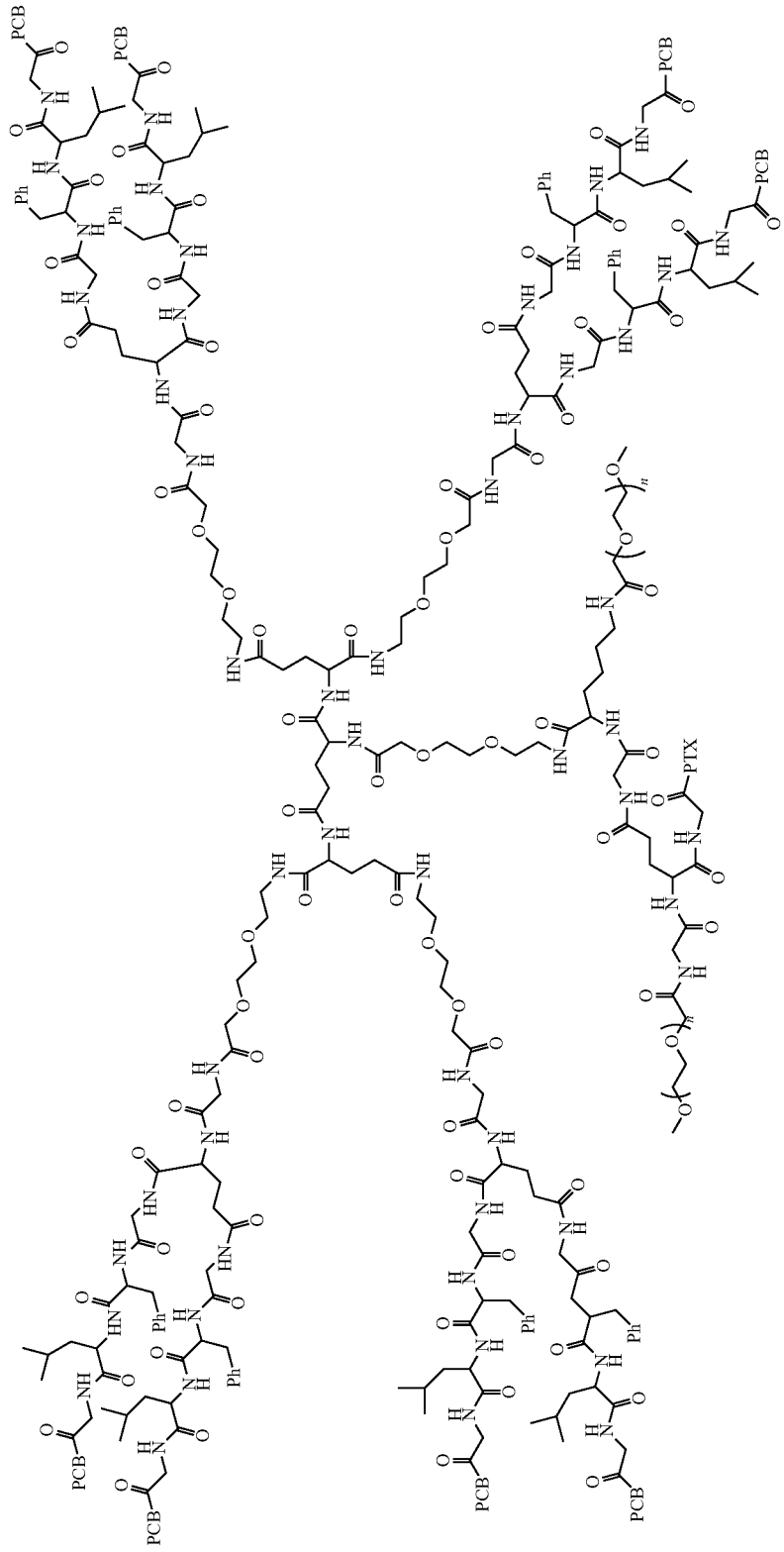
-continued
wherein, ～～⟨O⟩ₙ~ has a number-average molecular weight of 5k

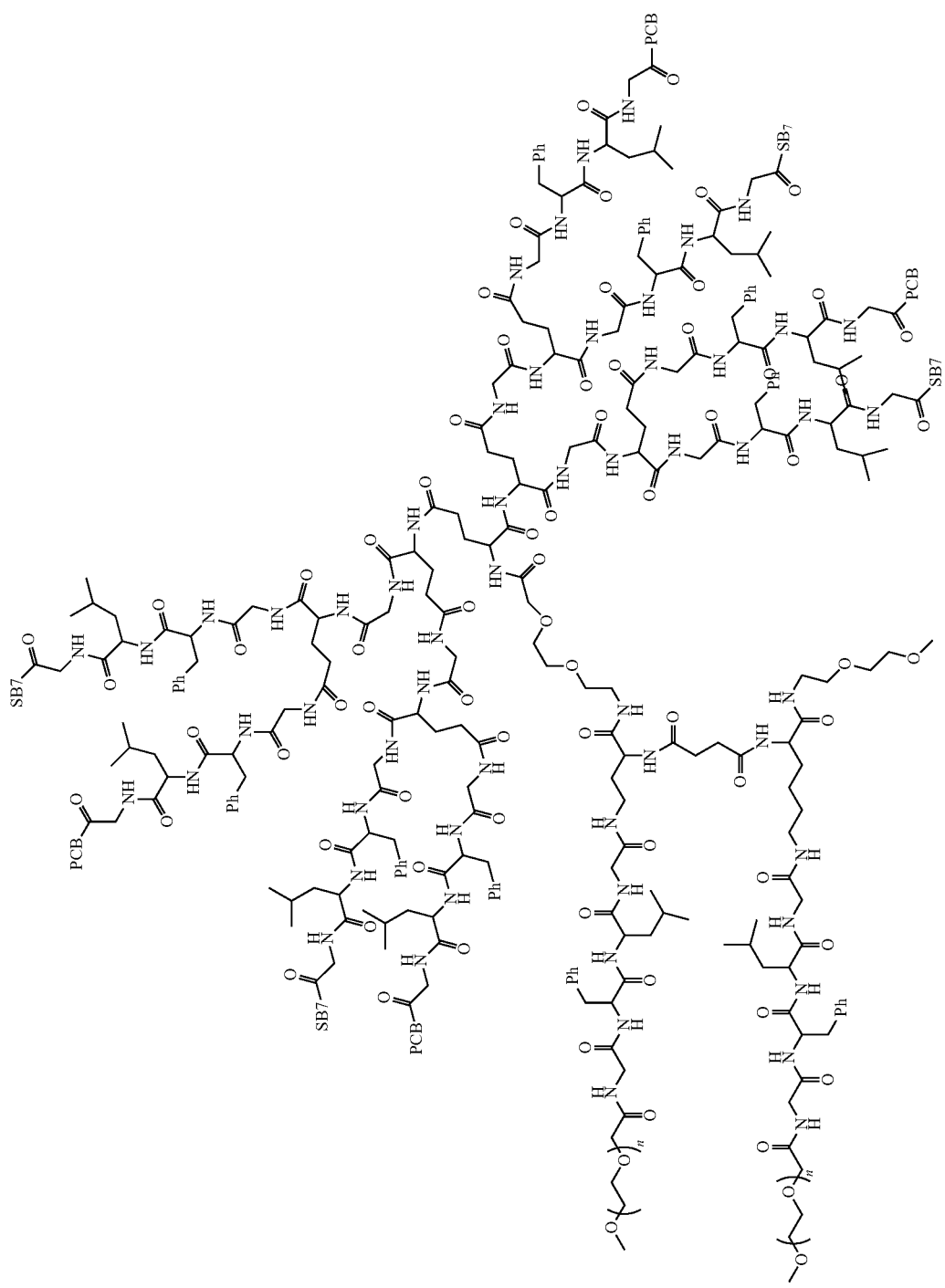

-continued
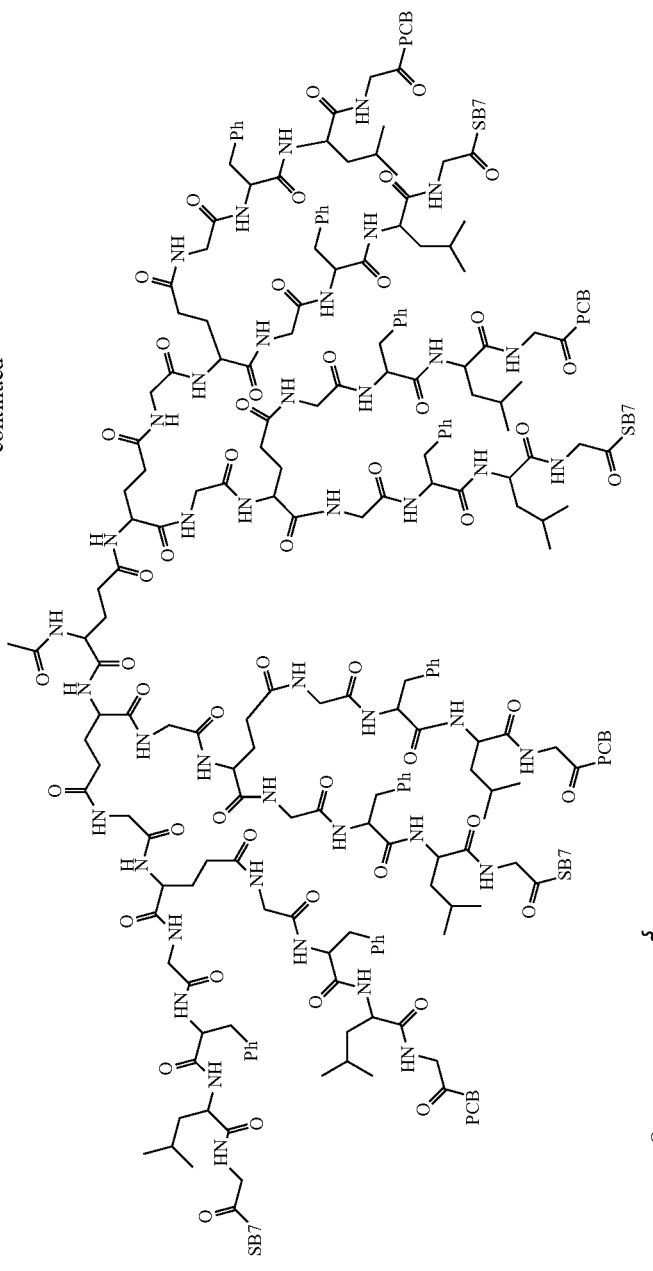
wherein, has a number-average molecular weight of 40k

-continued
11
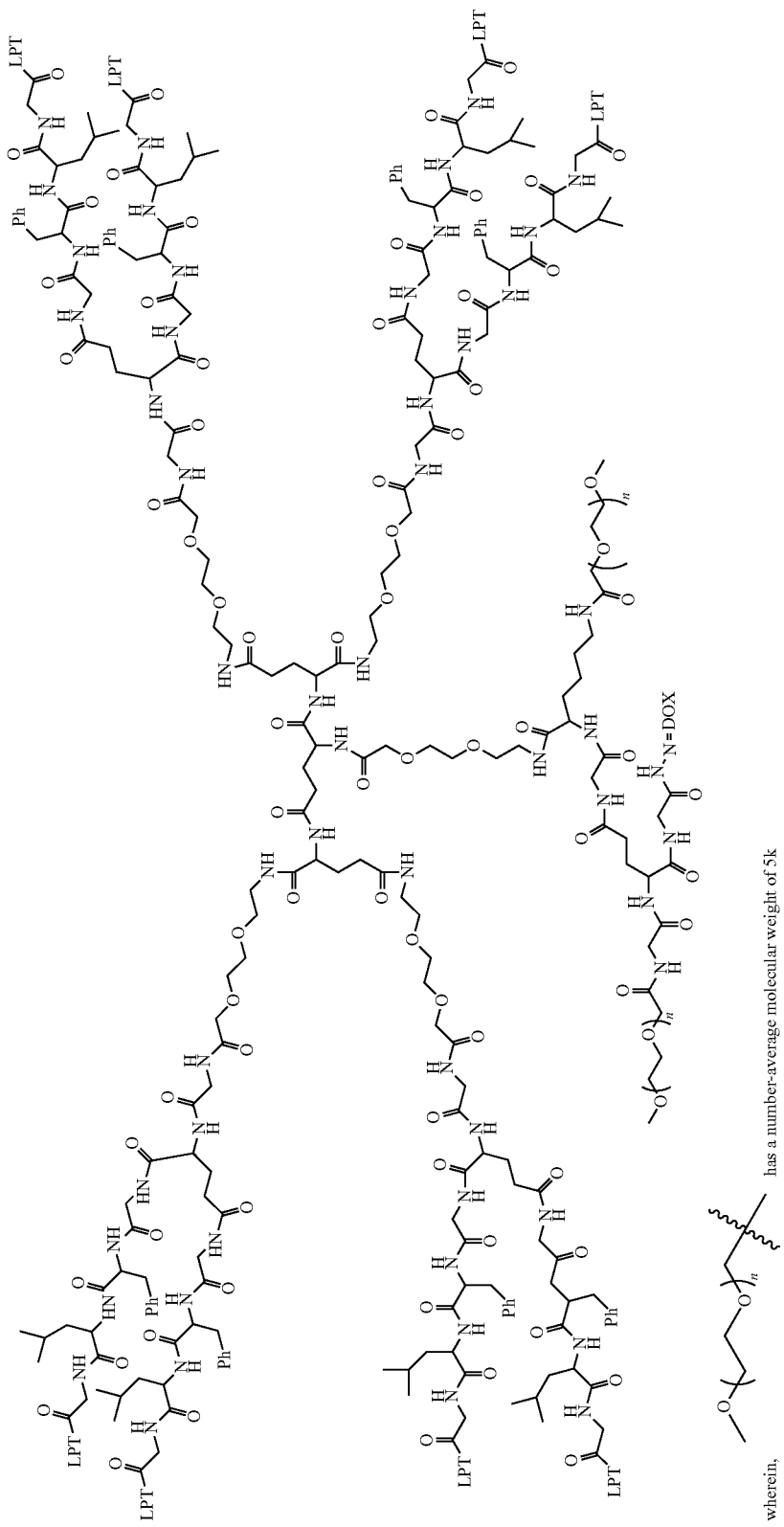
wherein,
~~~O~~~ has a number-average molecular weight of 5k -continued
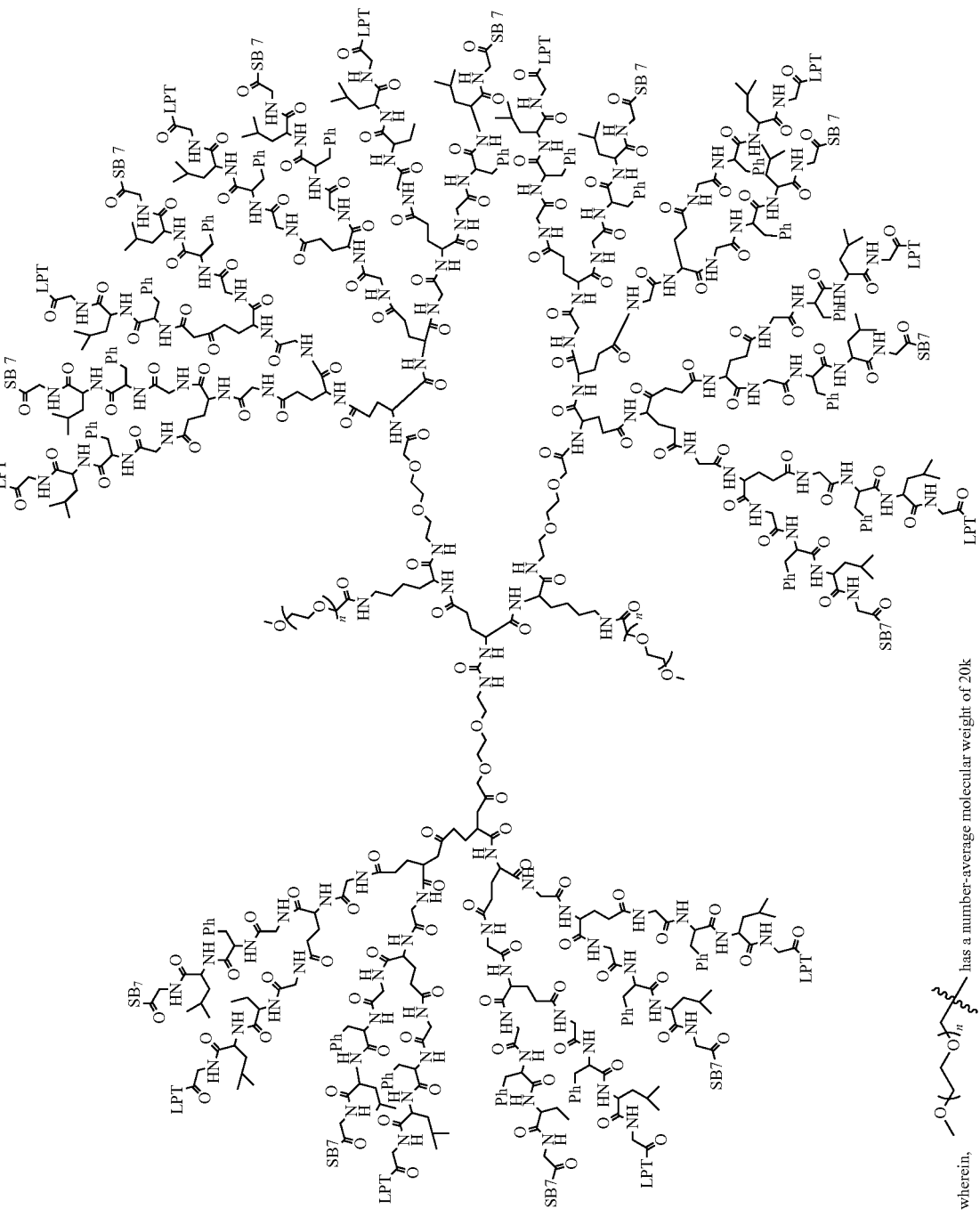
wherein, $\xi\!\!\!\sim\!\!\!\{\mathrm{O}\!\!\sim\!\!\}_n\mathrm{O}-$ has a number-average molecular weight of 20k -continued

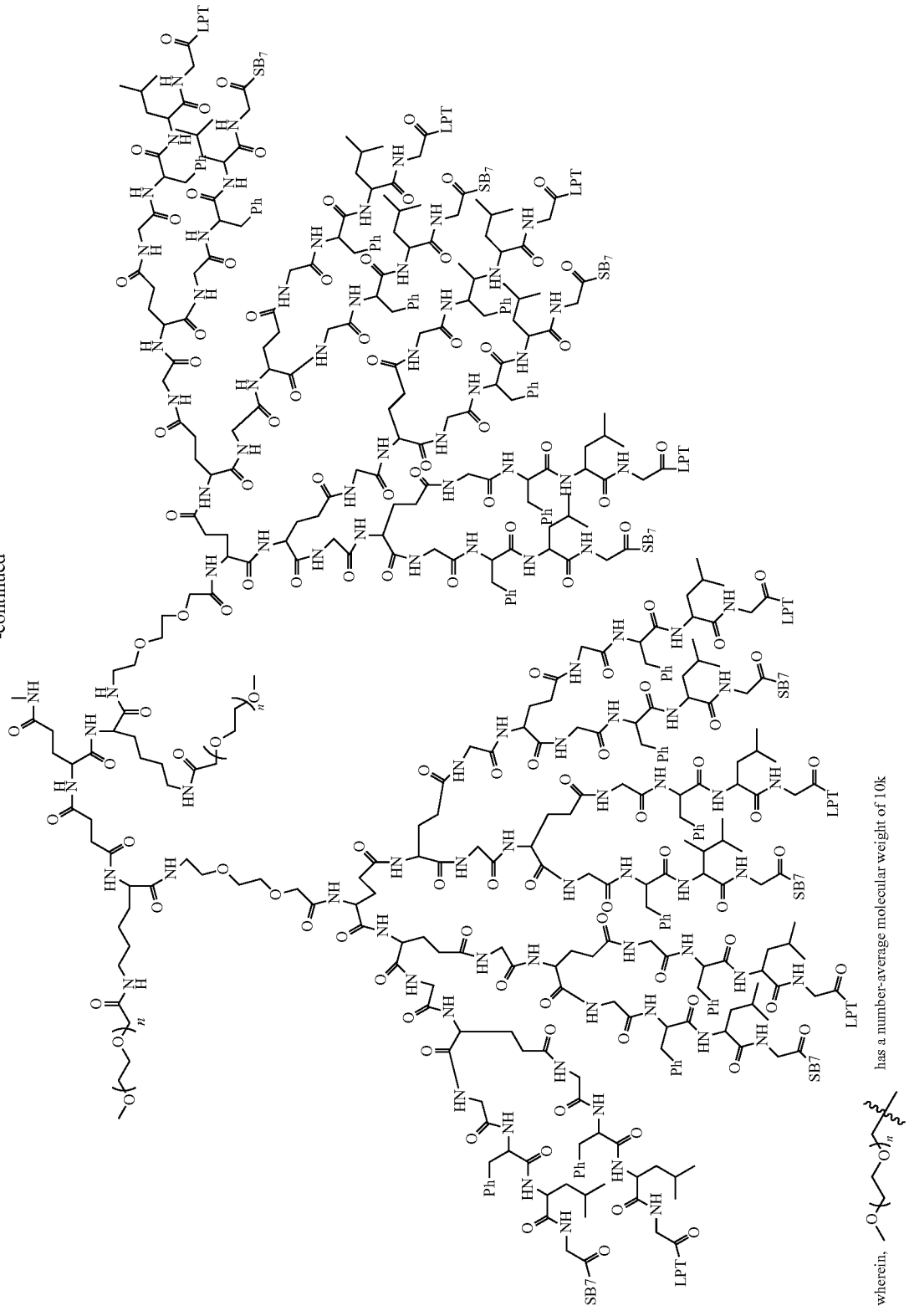

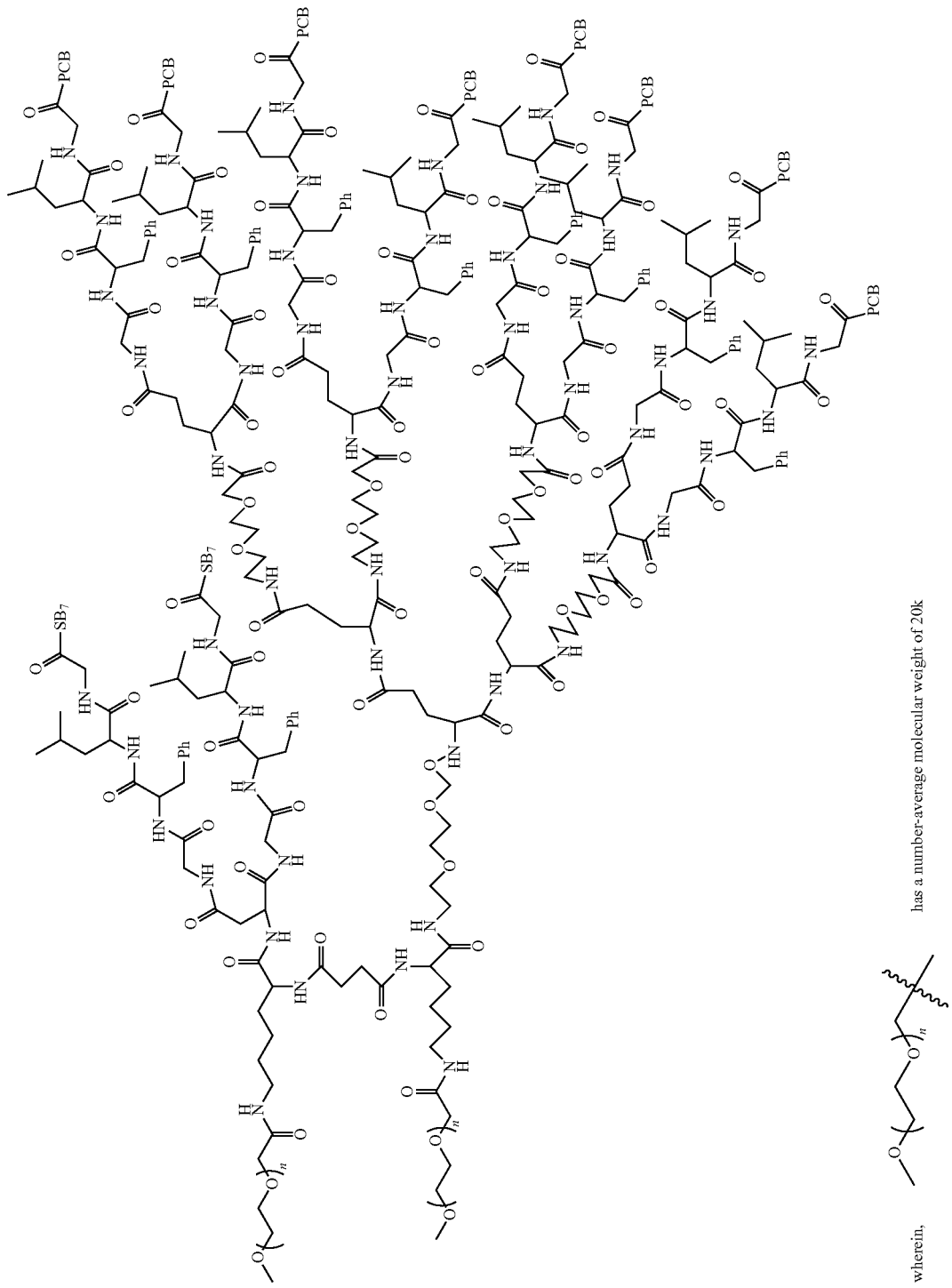
wherein, has a number-average molecular weight of 20k 1503                                                    1504
-continued
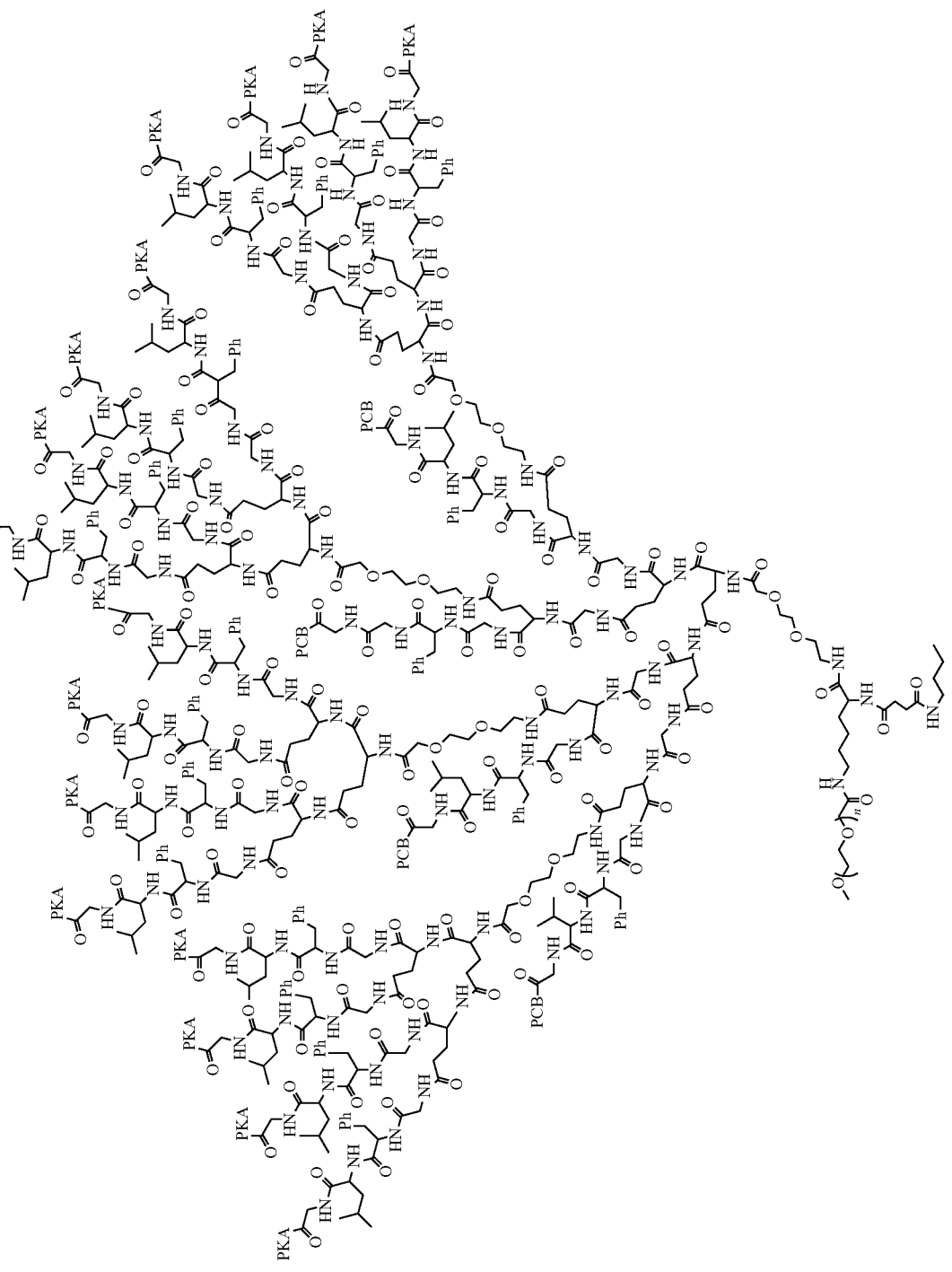

-continued
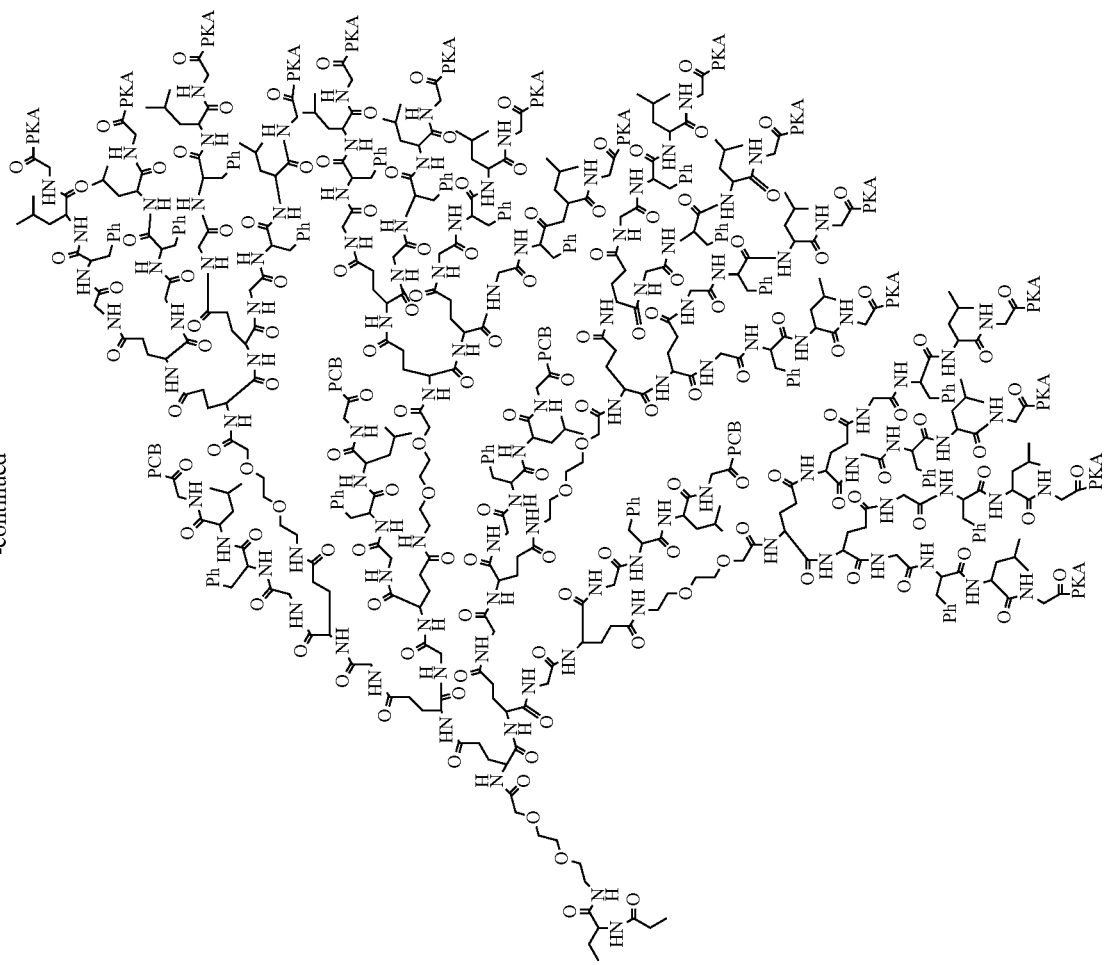

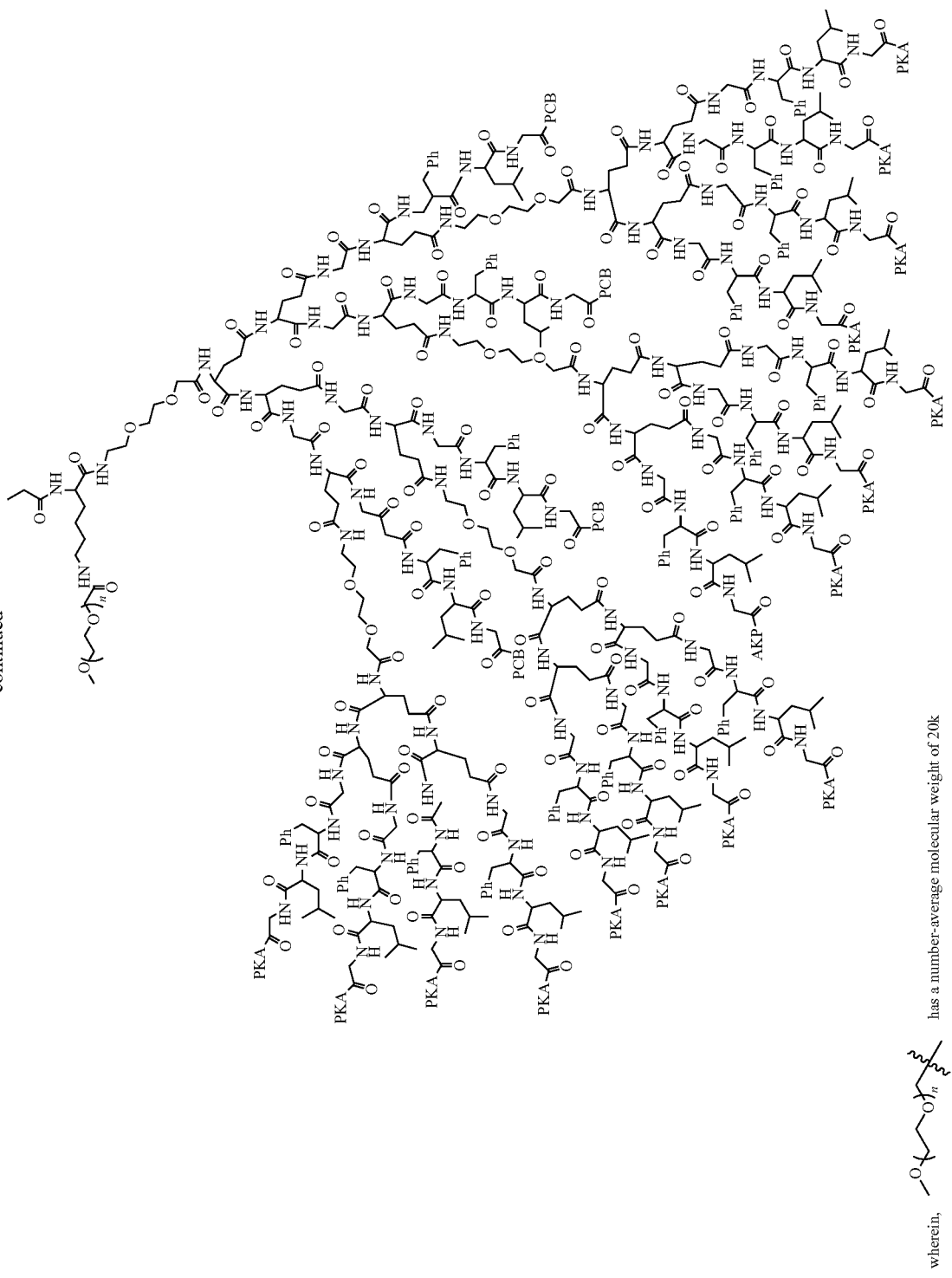
wherein,  has a number-average molecular weight of 20k

-continued
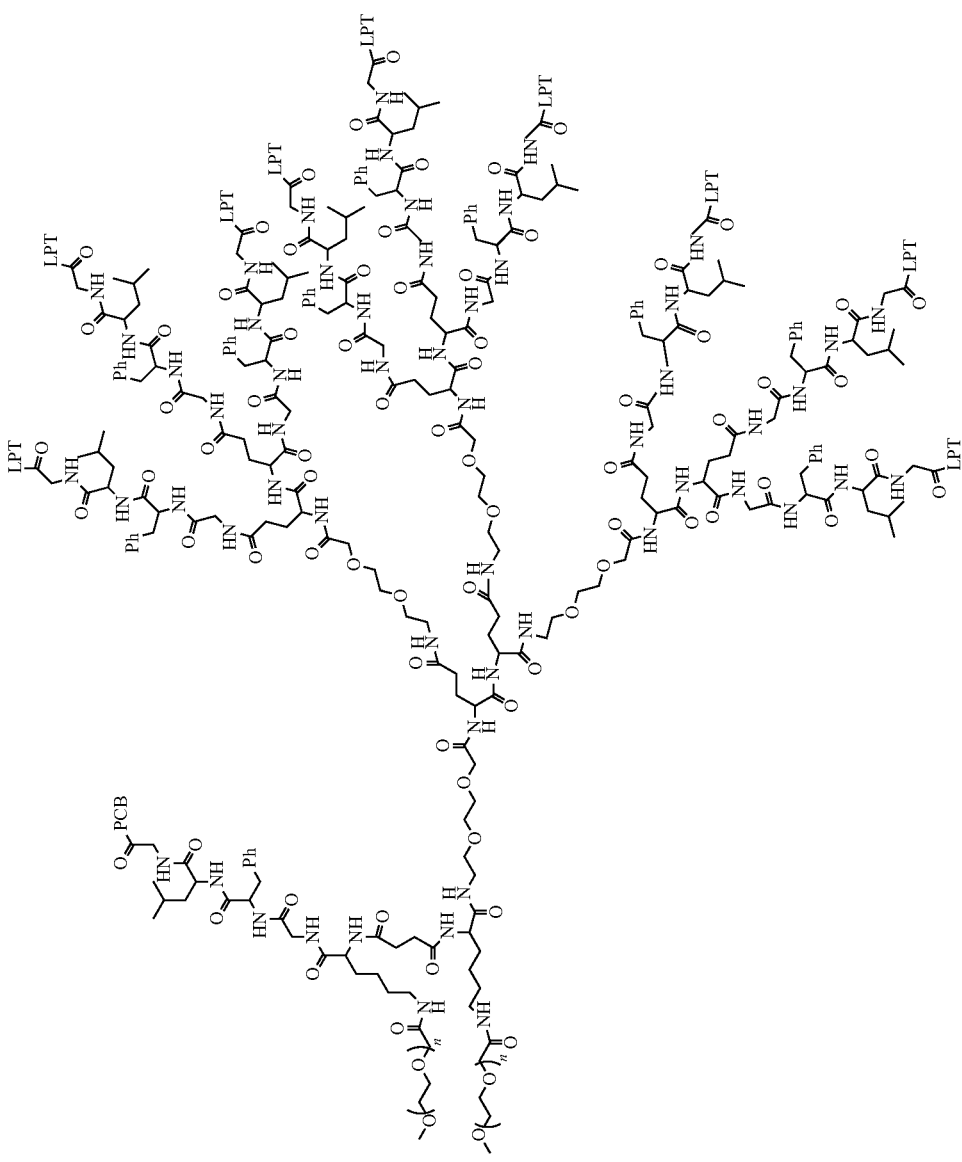

-continued
1511 1512
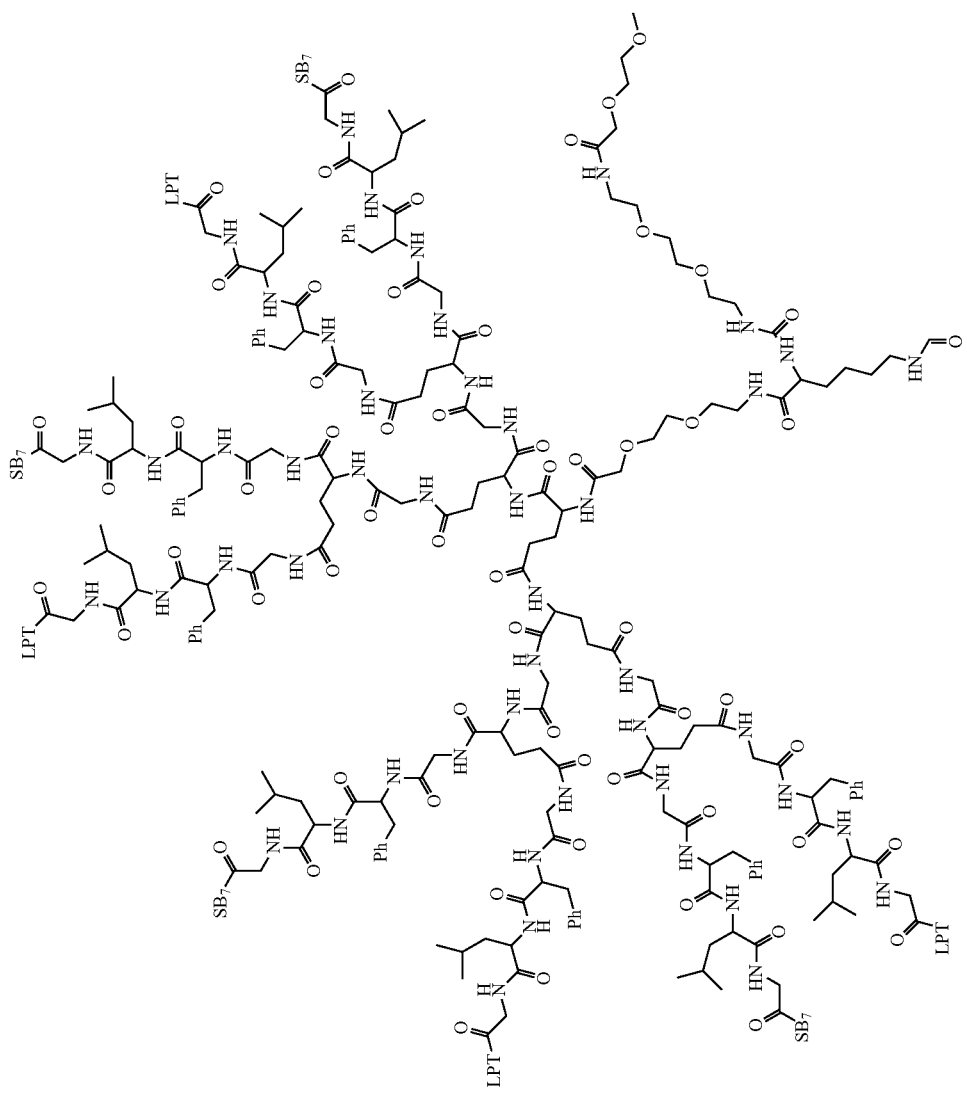

1513 1514
-continued
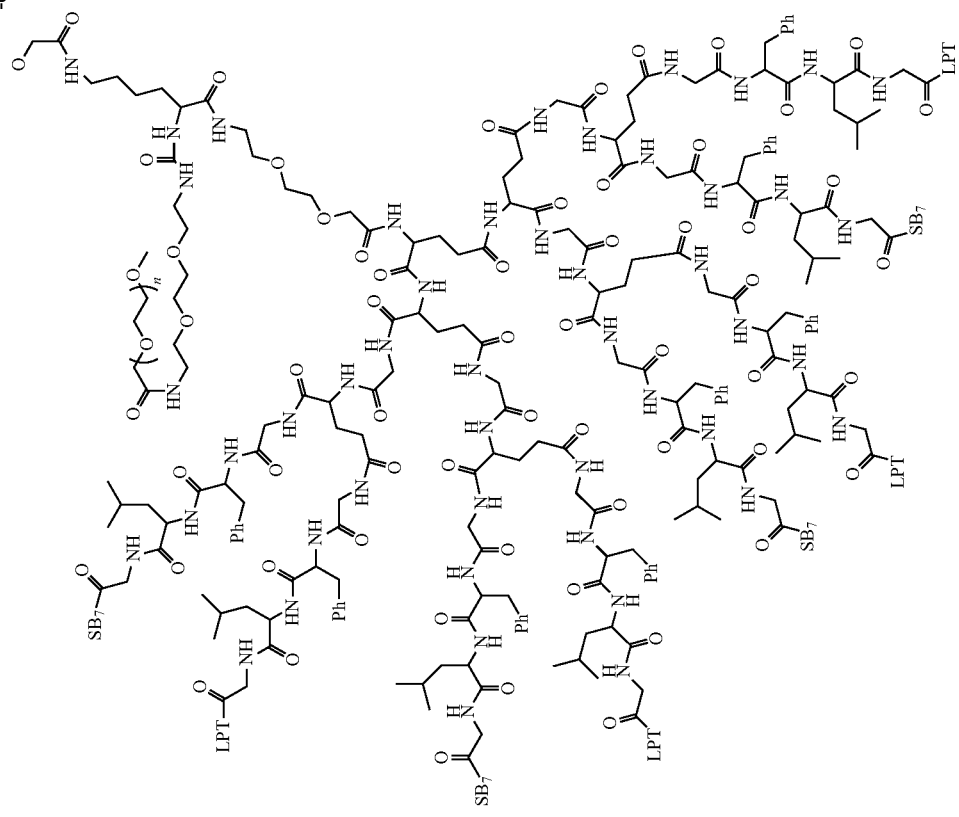

-continued
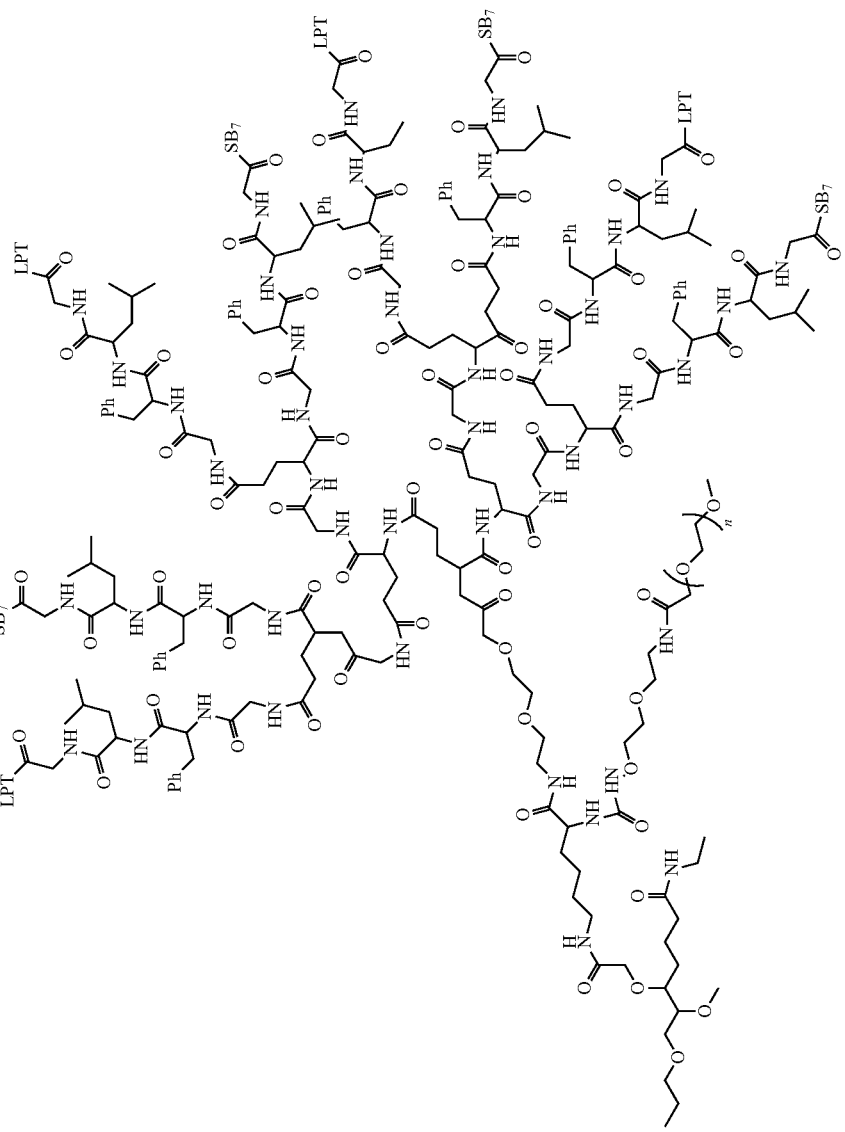

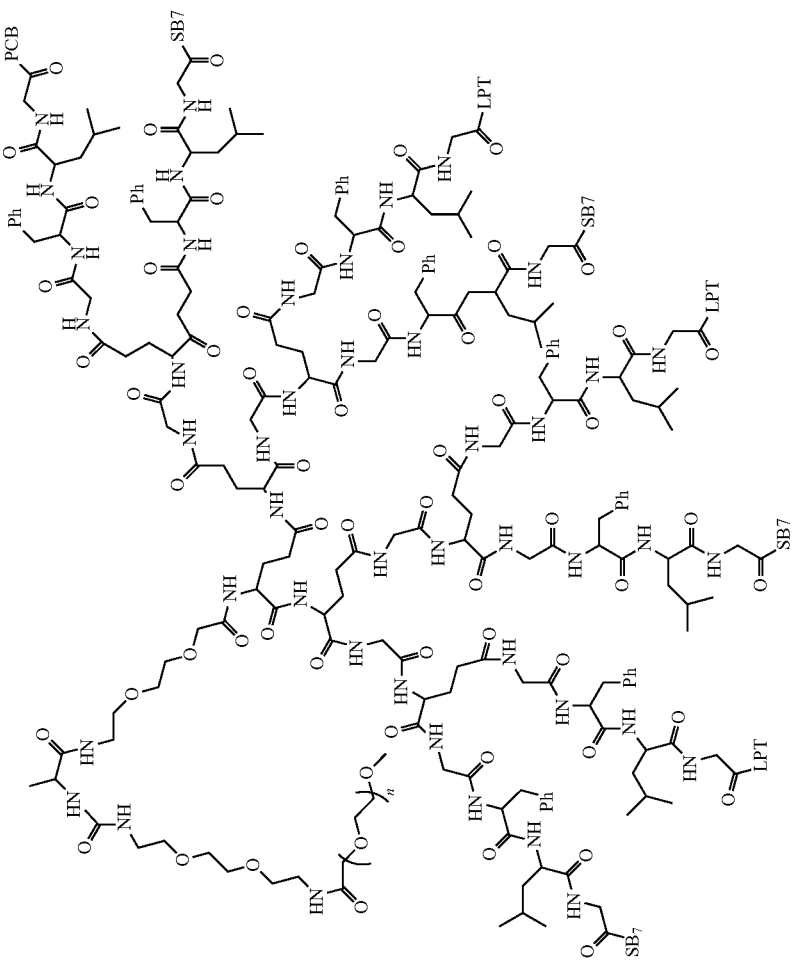

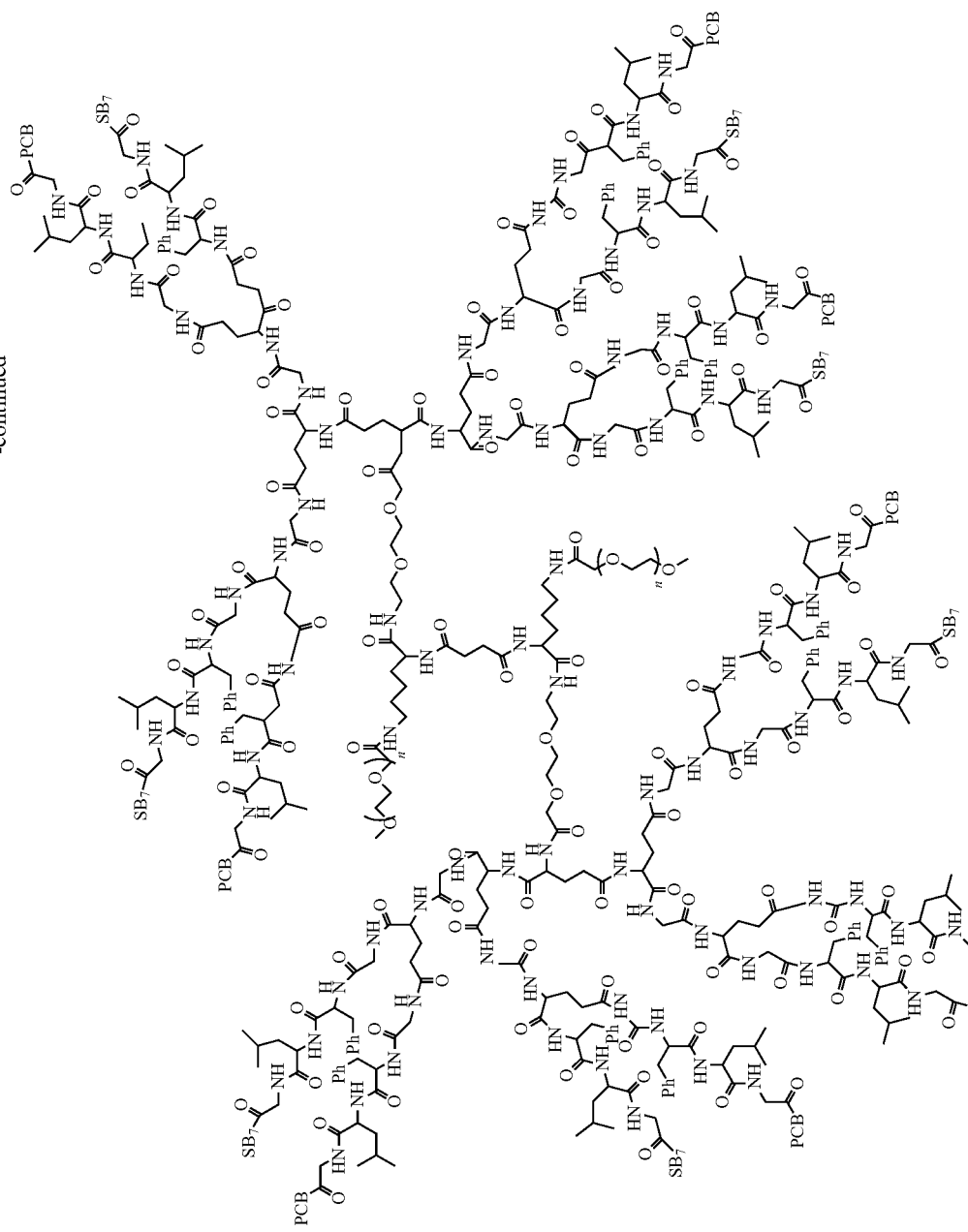

1521 1522
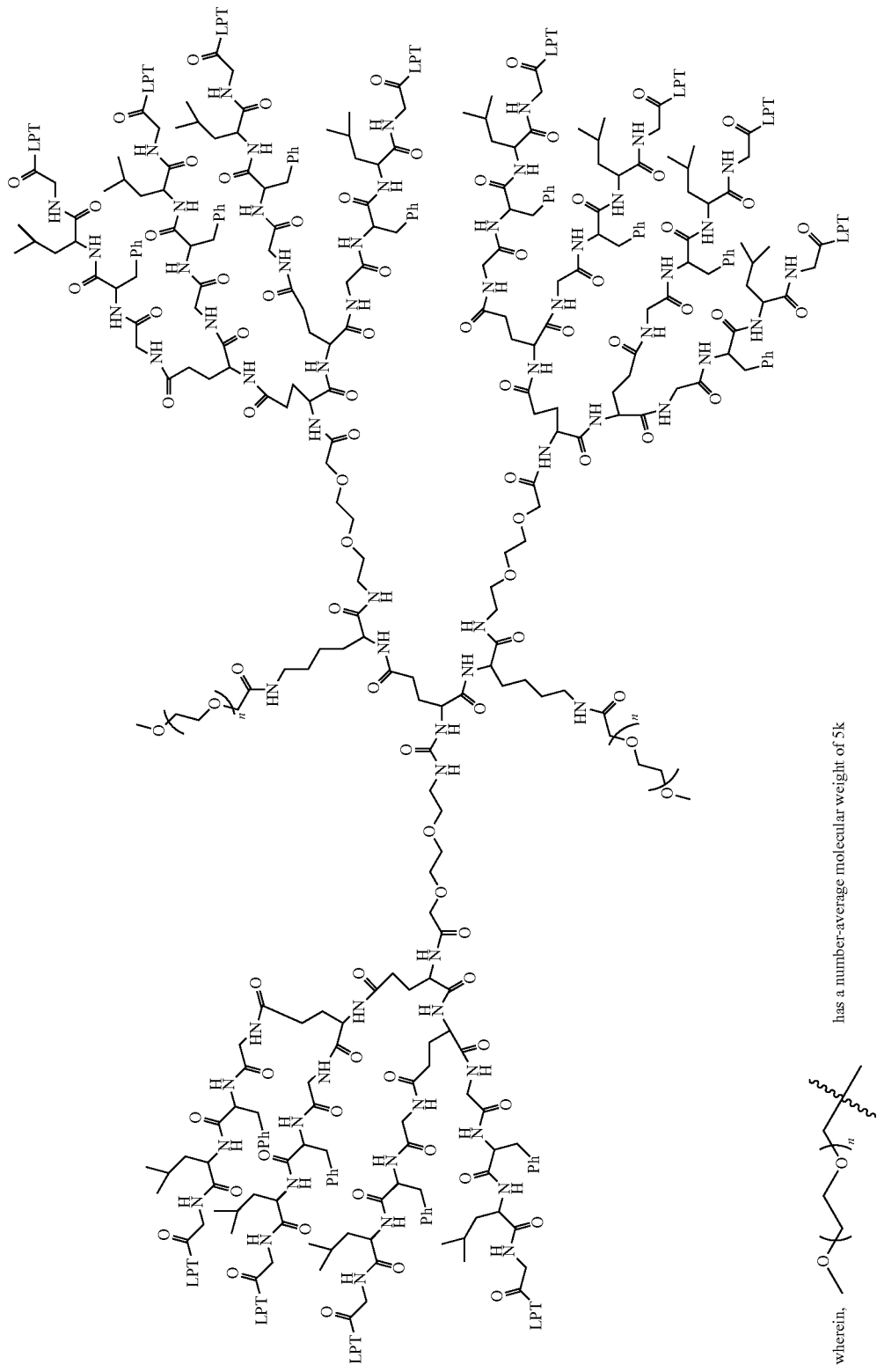

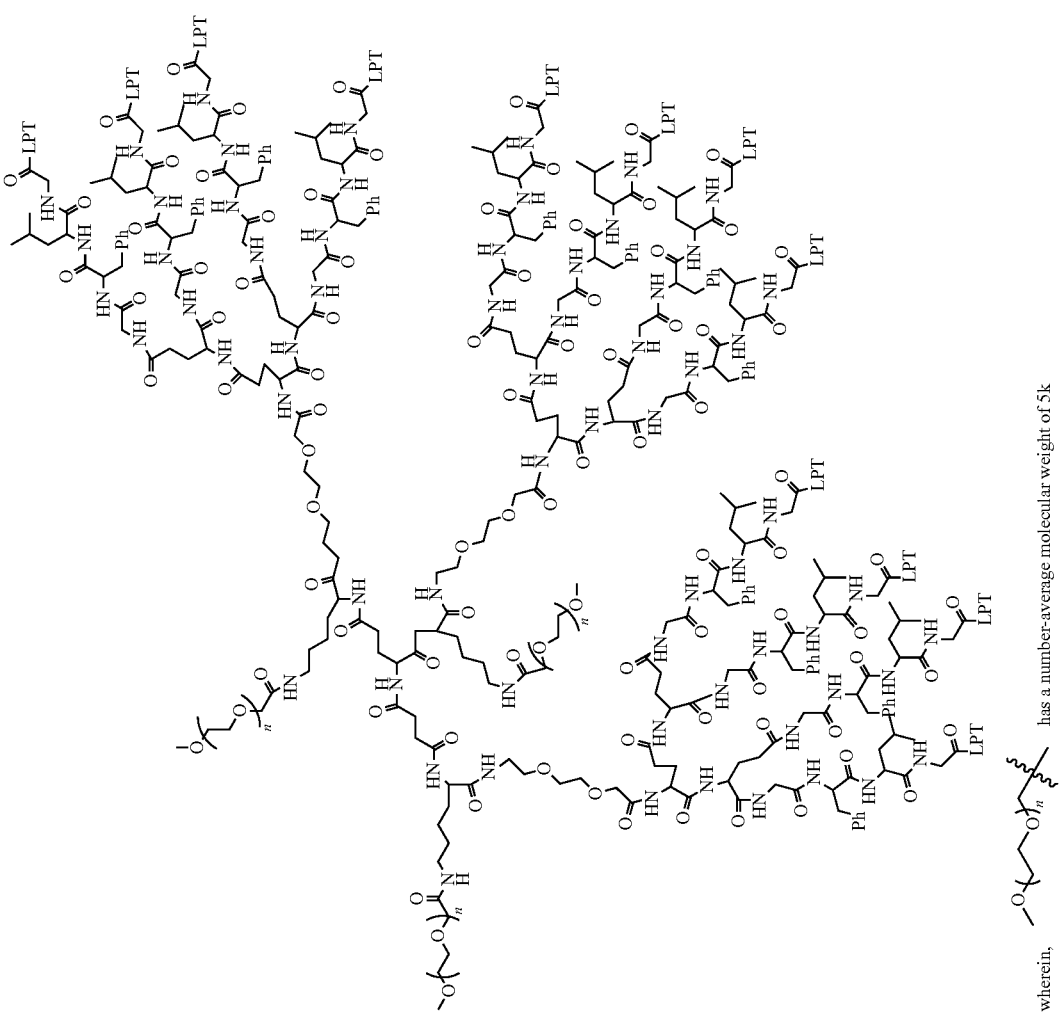
wherein, has a number-average molecular weight of 5k

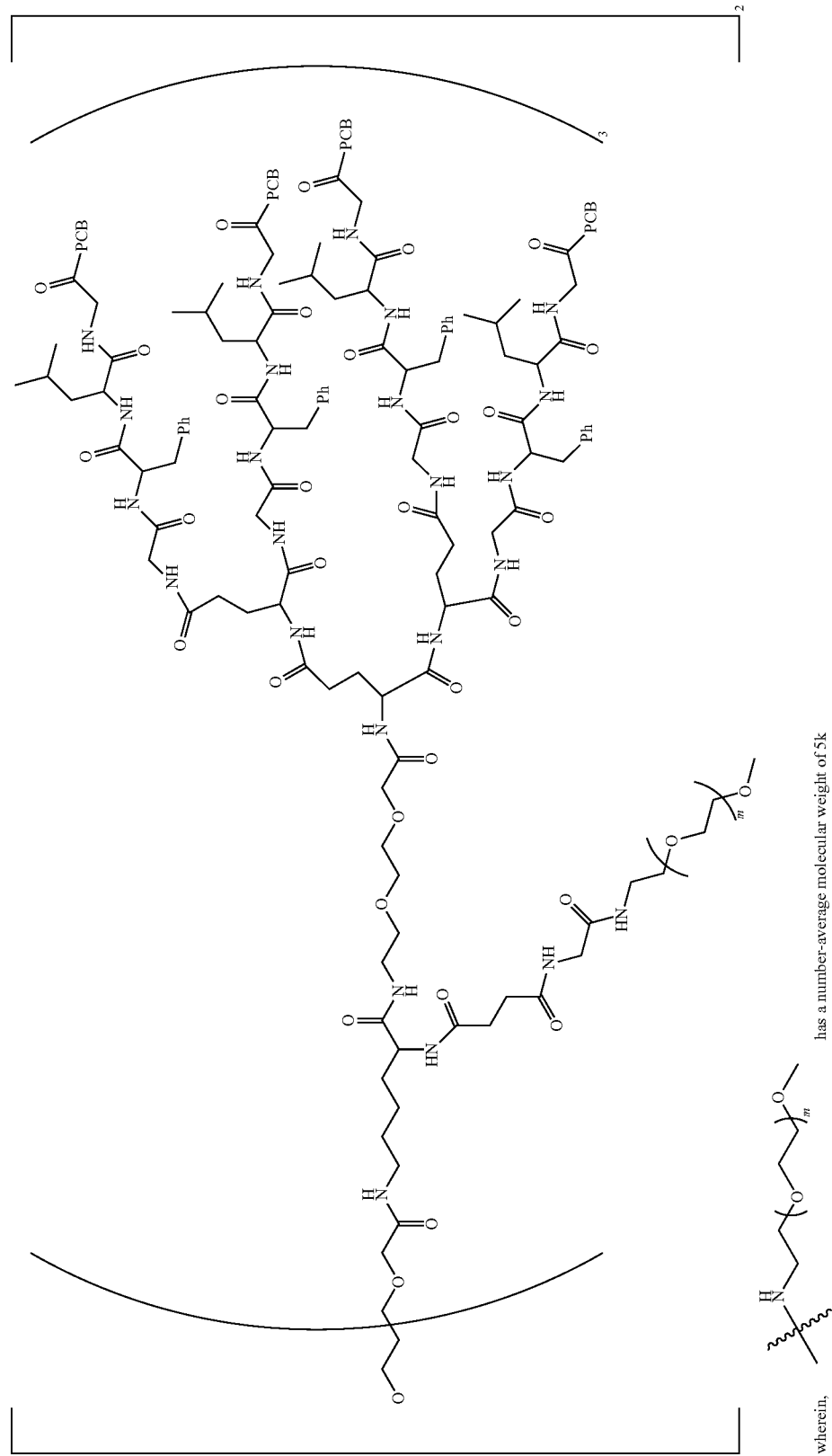
wherein,

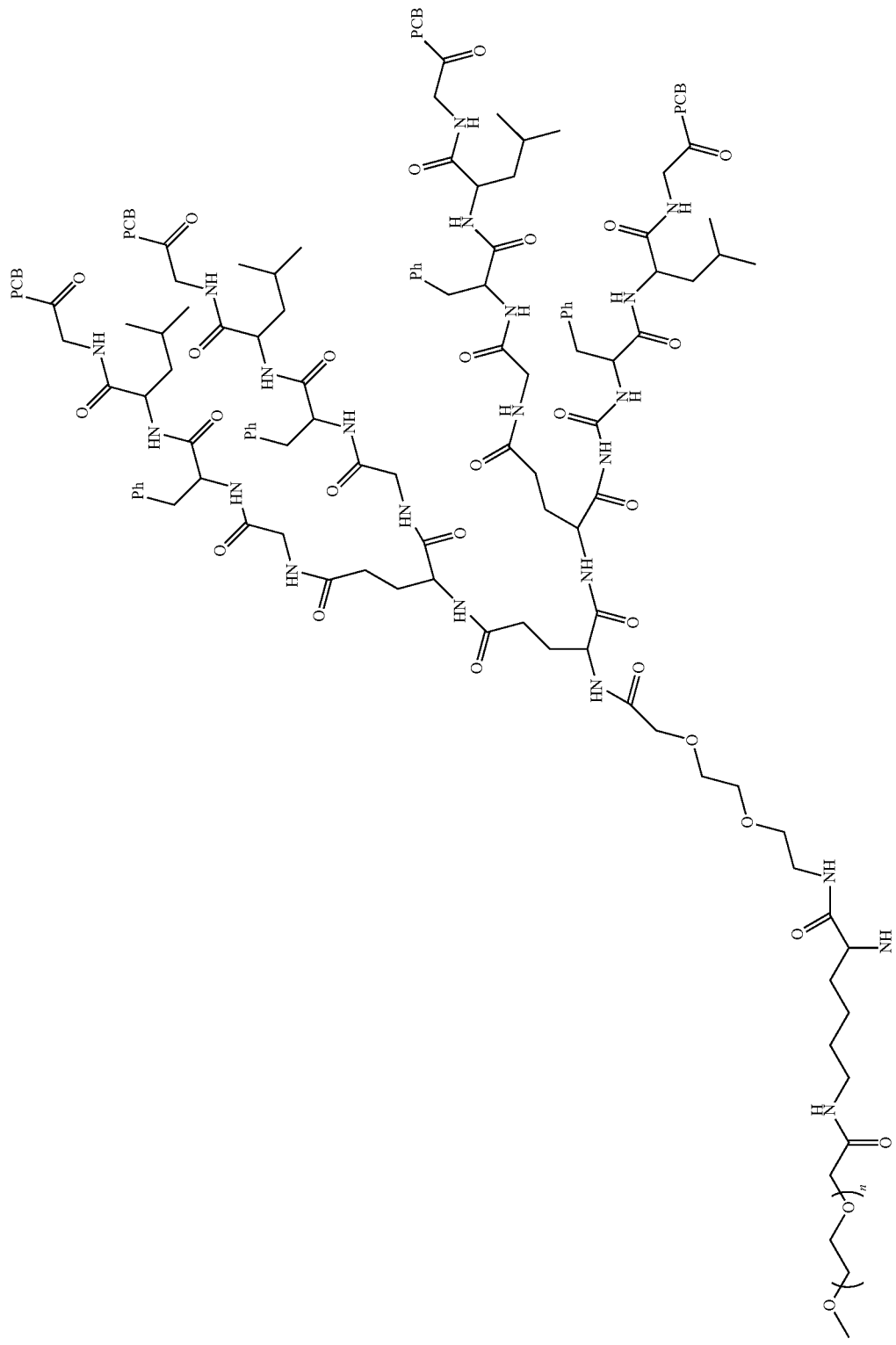

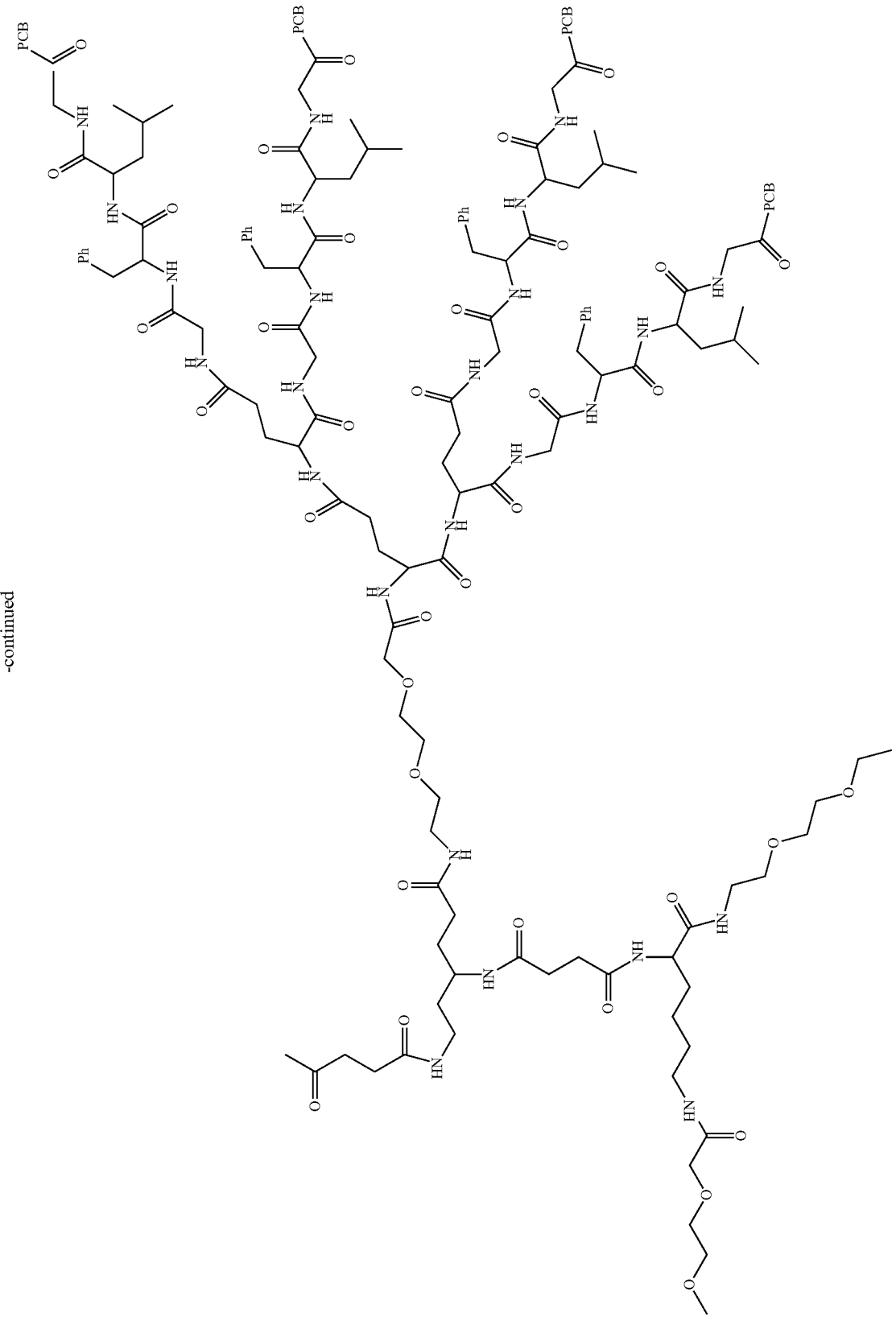

-continued
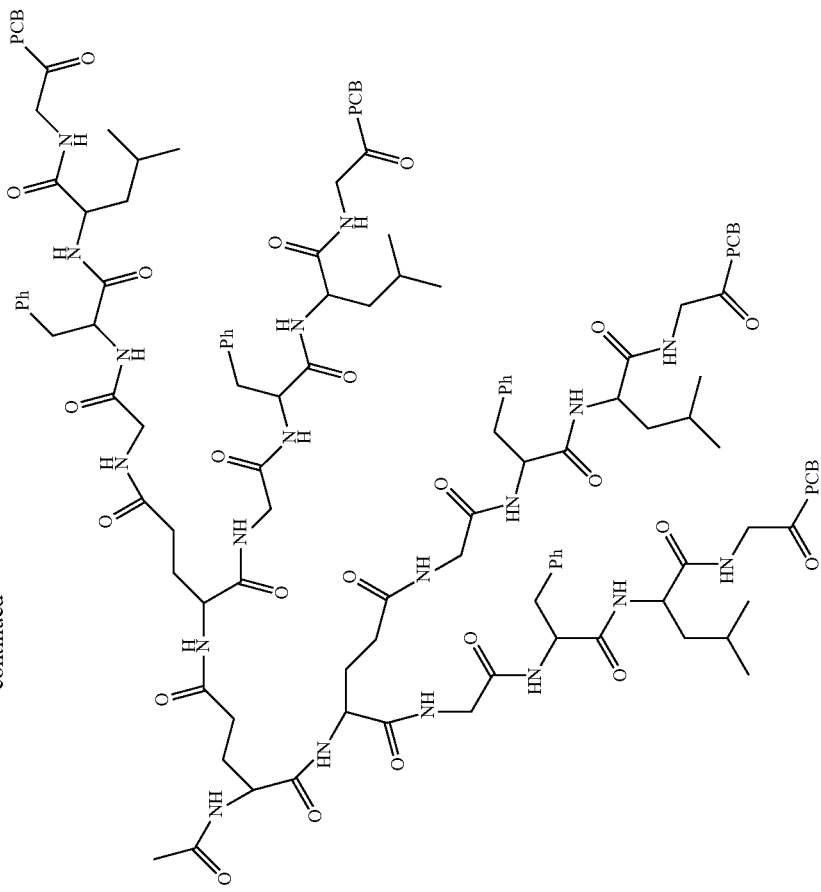
wherein,  has a number-average molecular weight of 10k

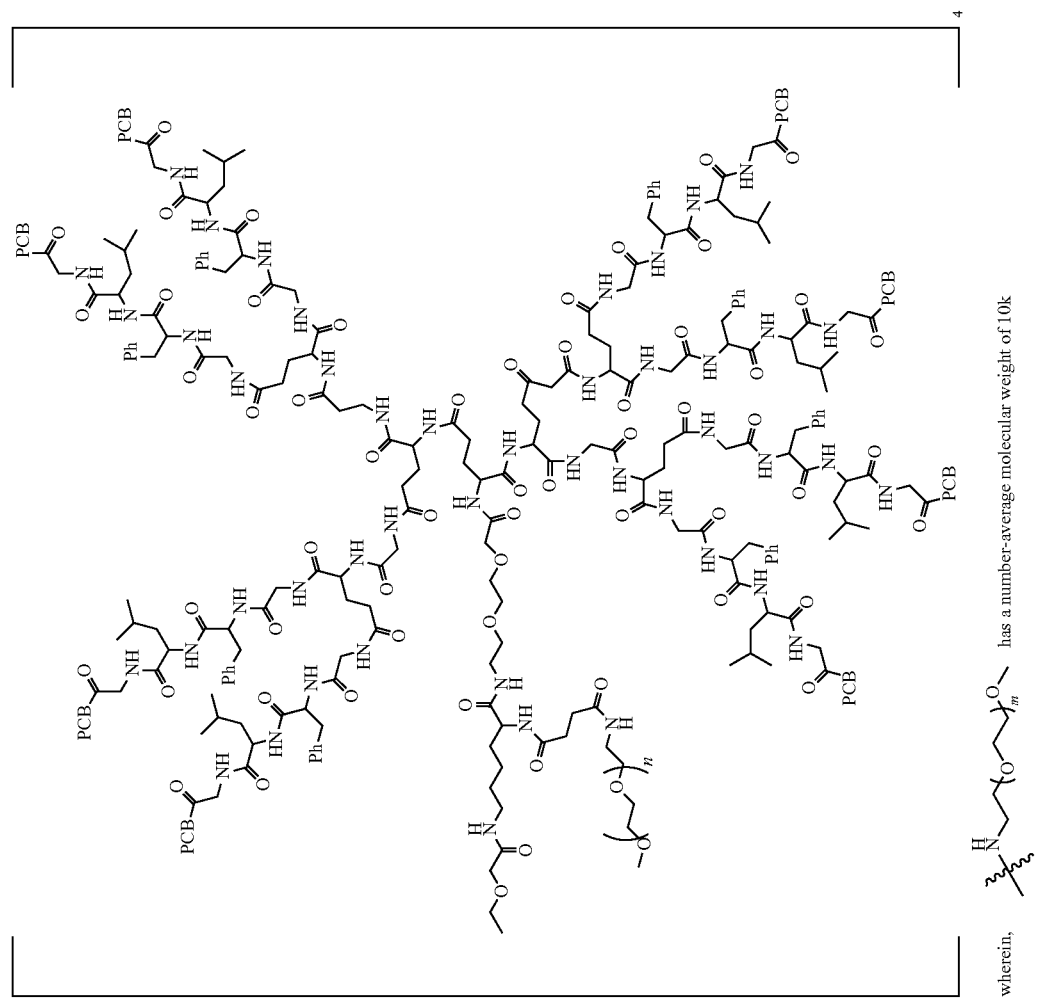

1535 1536
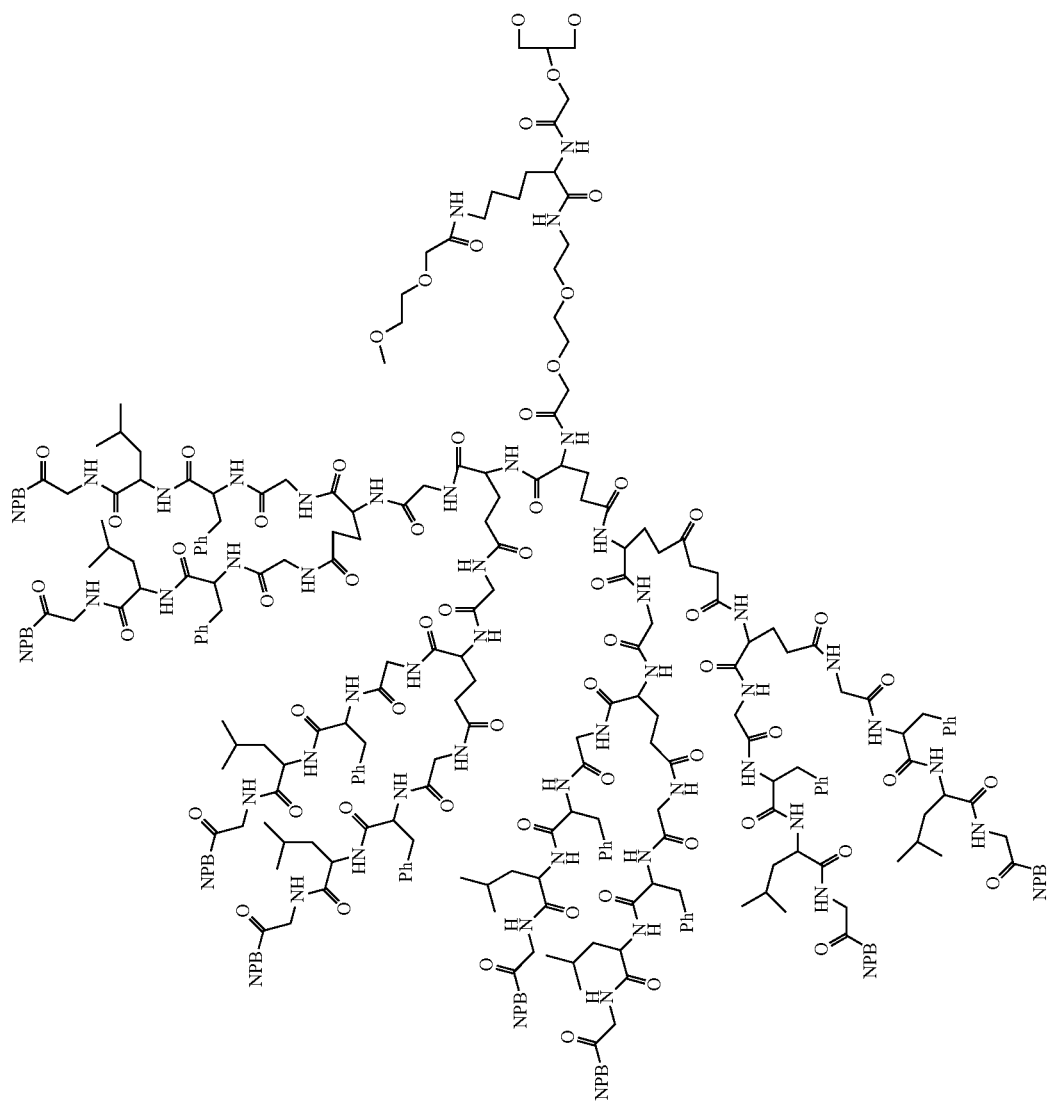

-continued
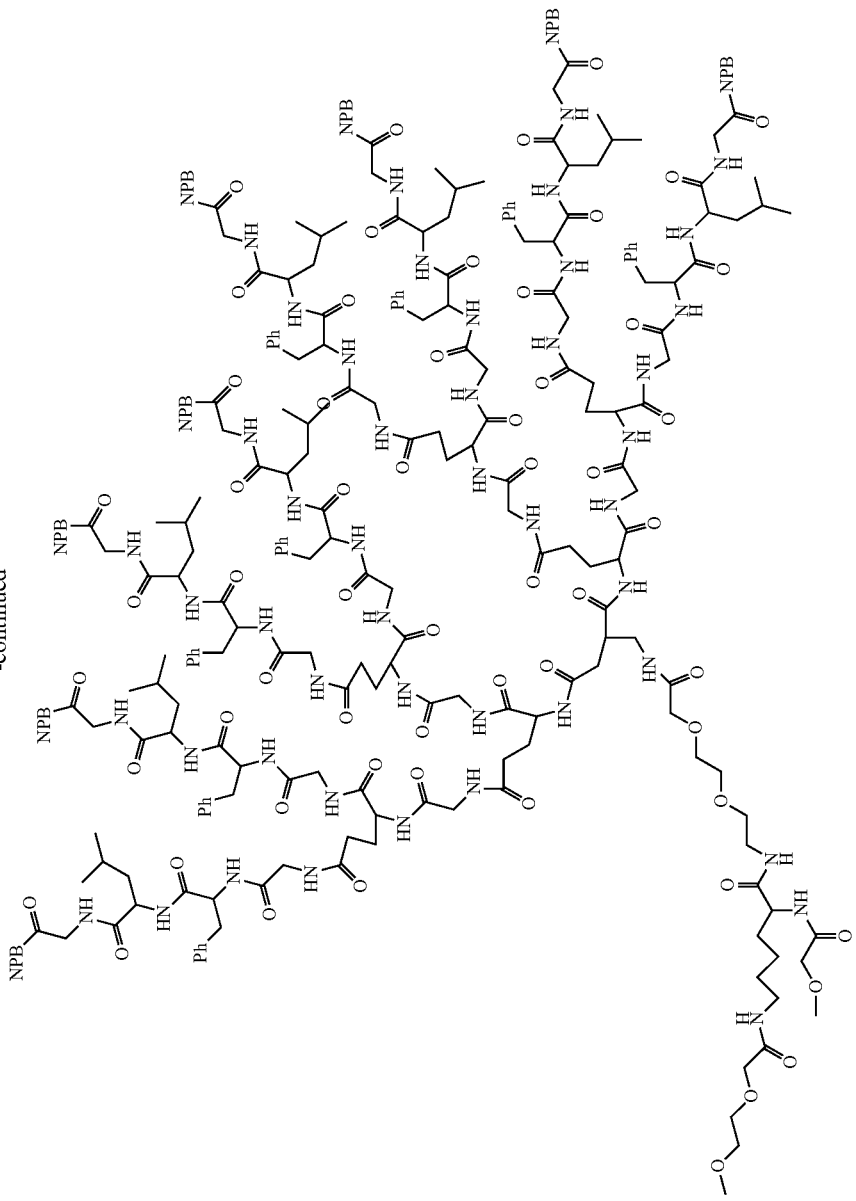

-continued
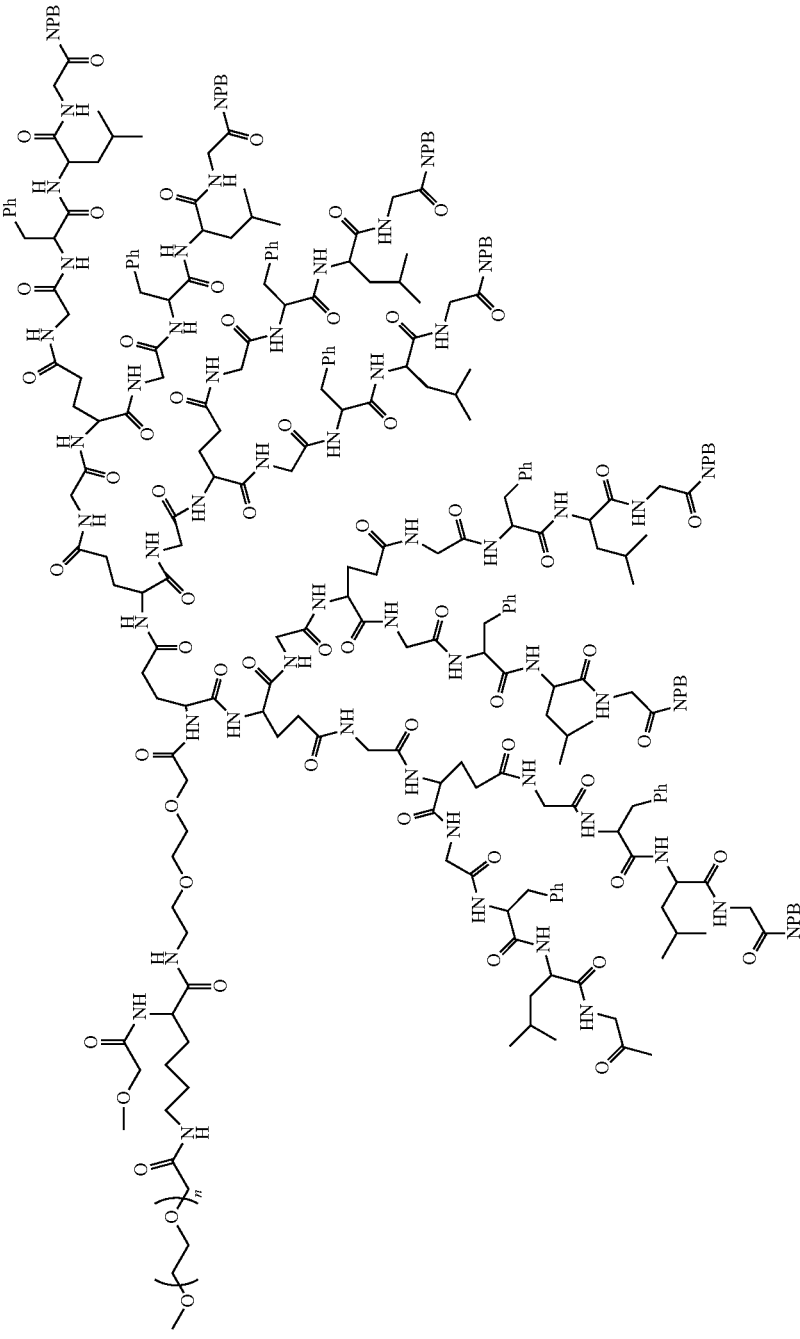
has a number-average molecular weight of 10k
wherein,

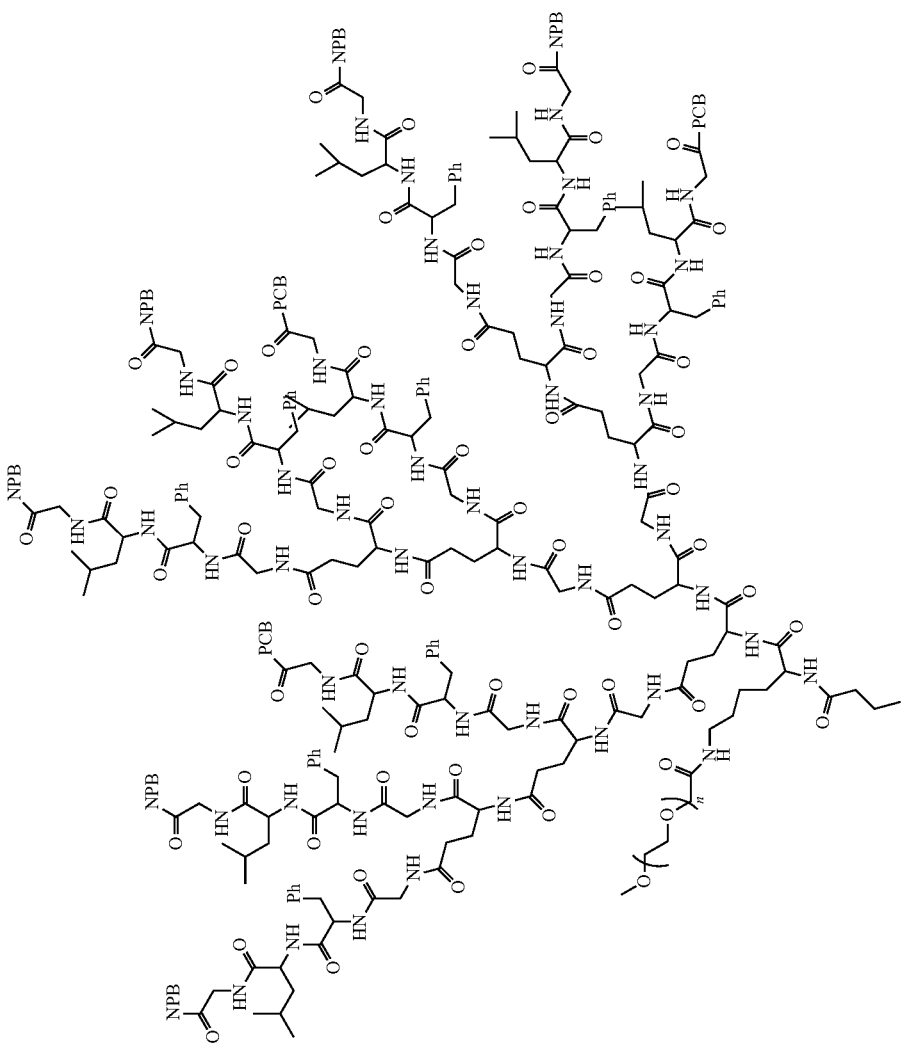

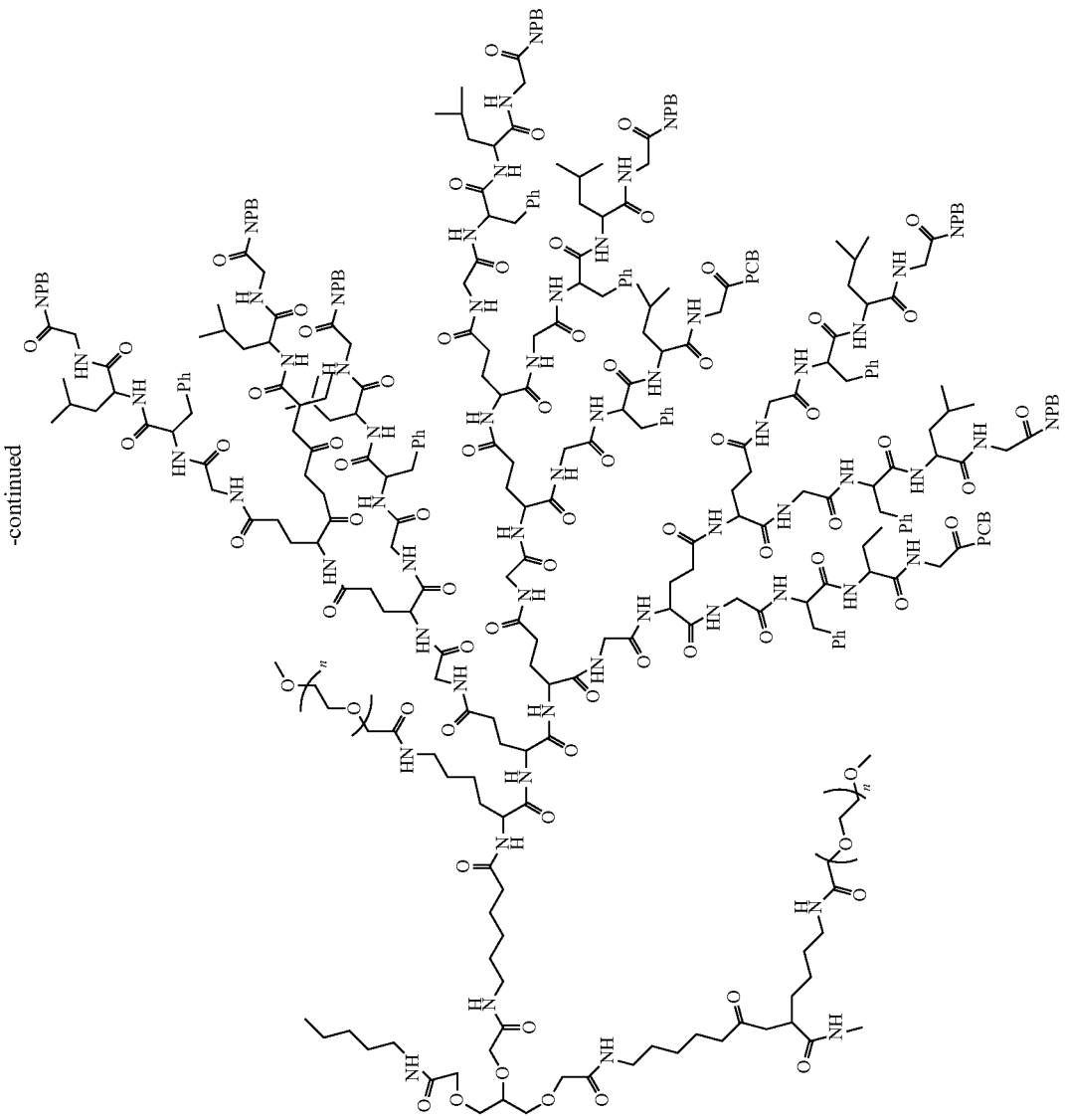
-continued

-continued
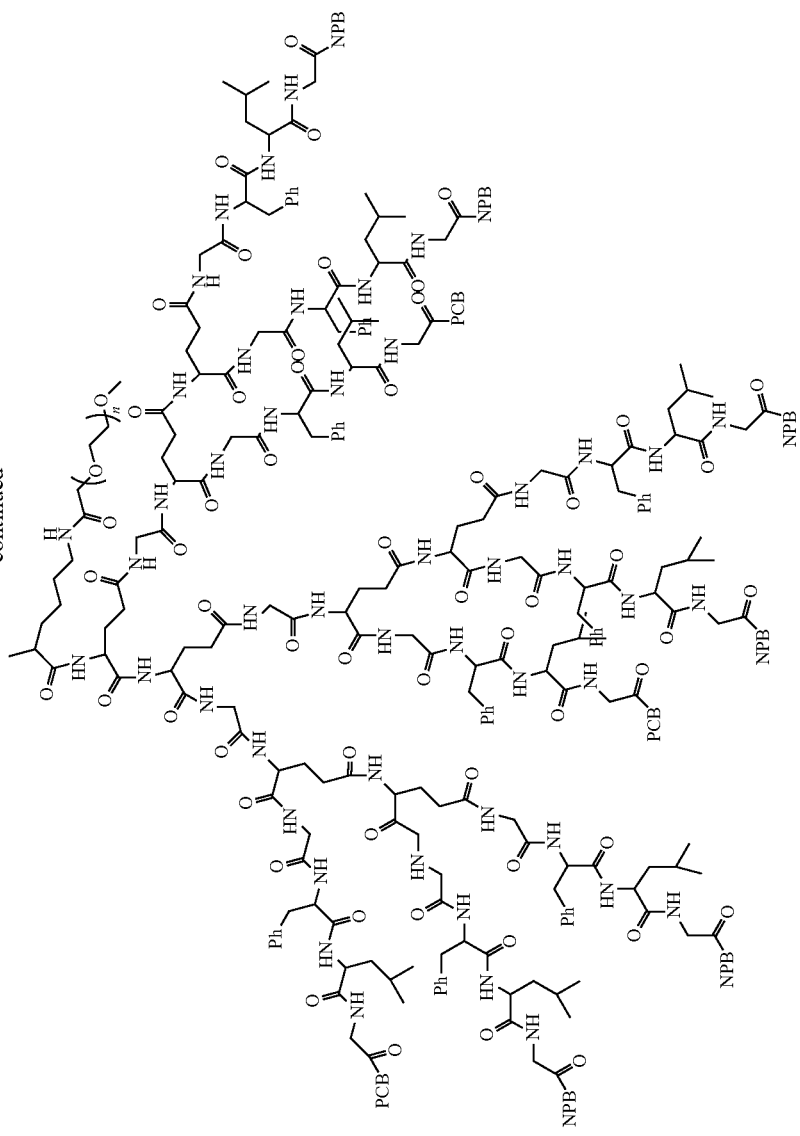
wherein, has a number-average molecular weight of 10k

-continued
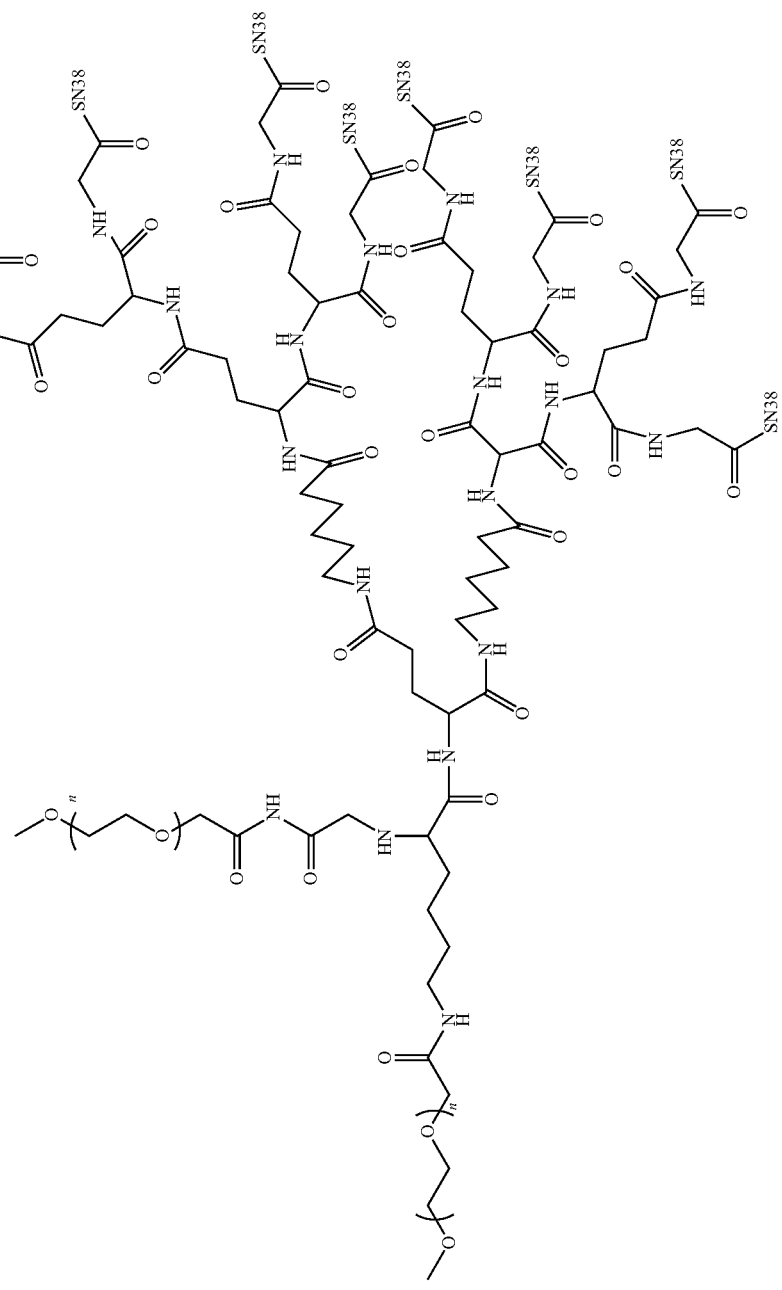
wherein,
has a number-average molecular weight of 5k -continued
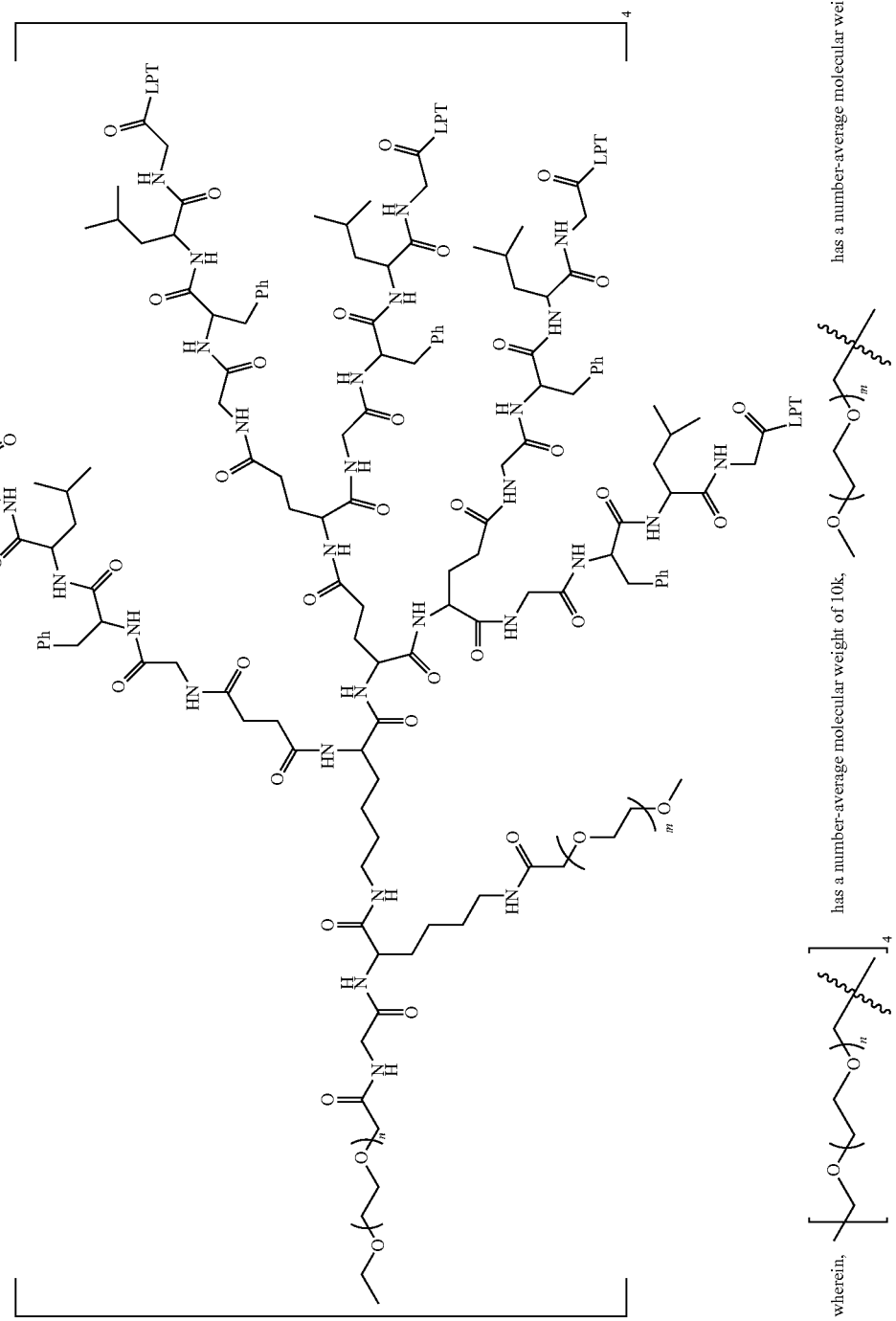
wherein, has a number-average molecular weight of 10k, has a number-average molecular weight of 5k, 1551 1552
-continued
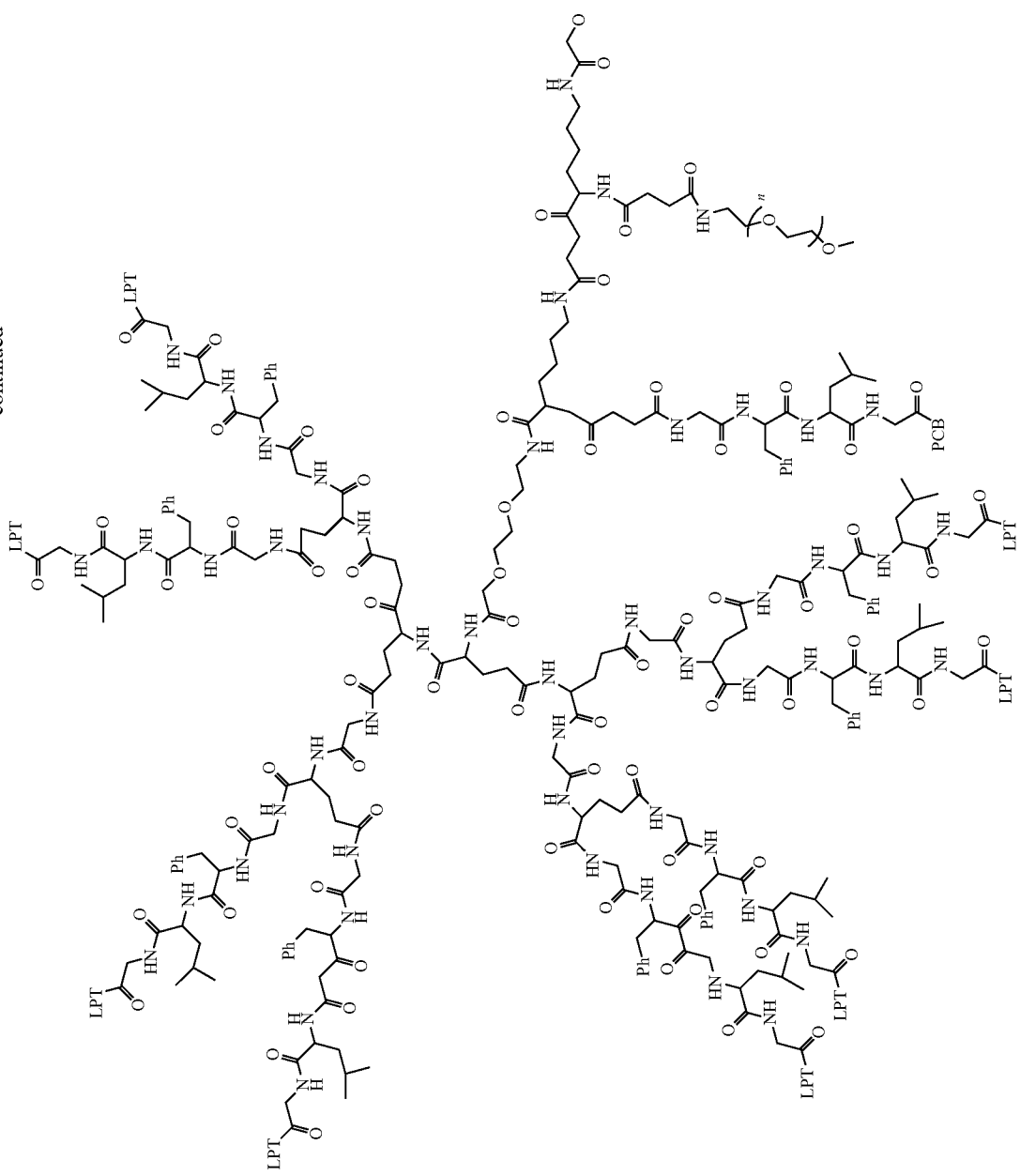

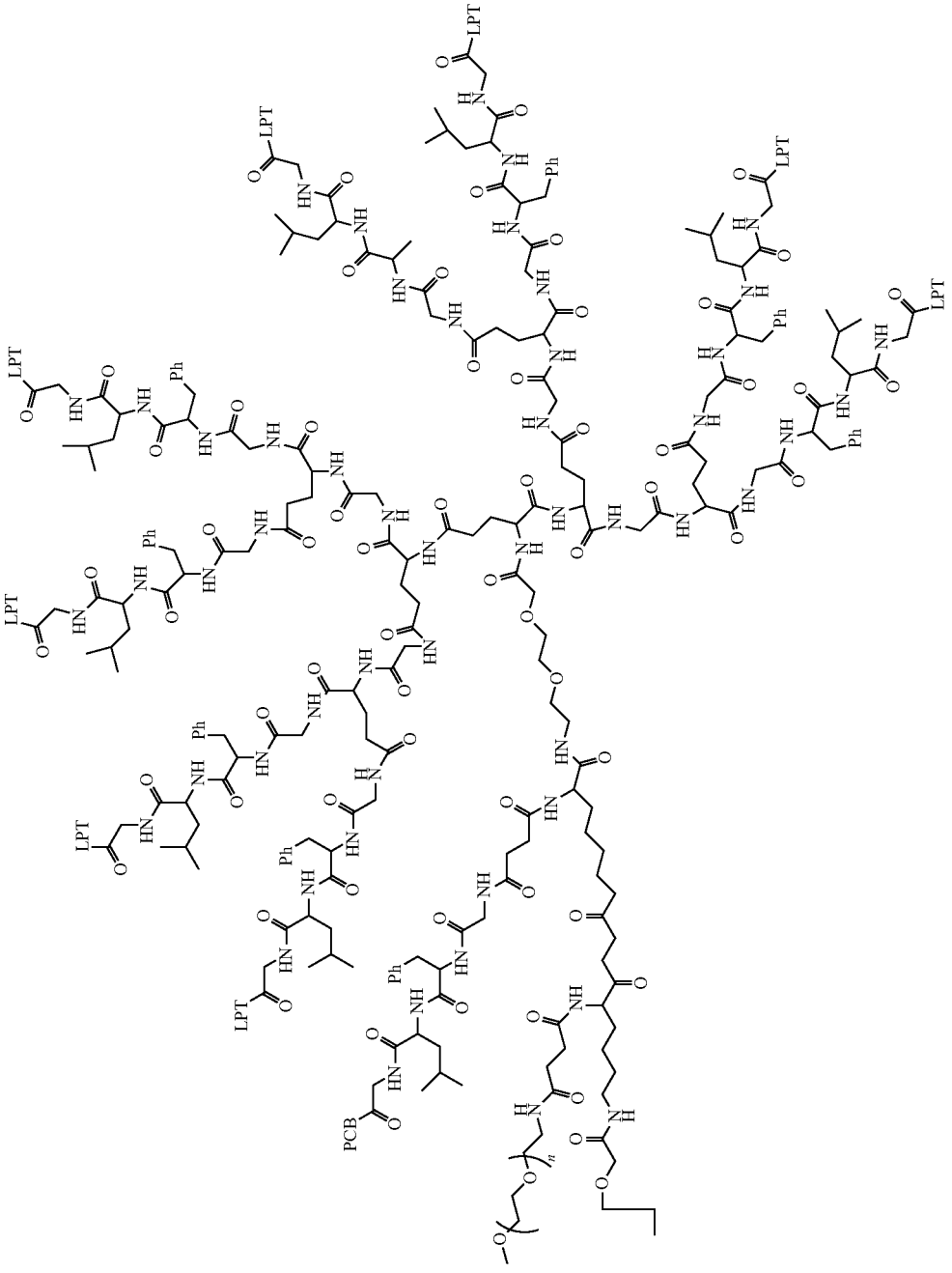
-continued

-continued
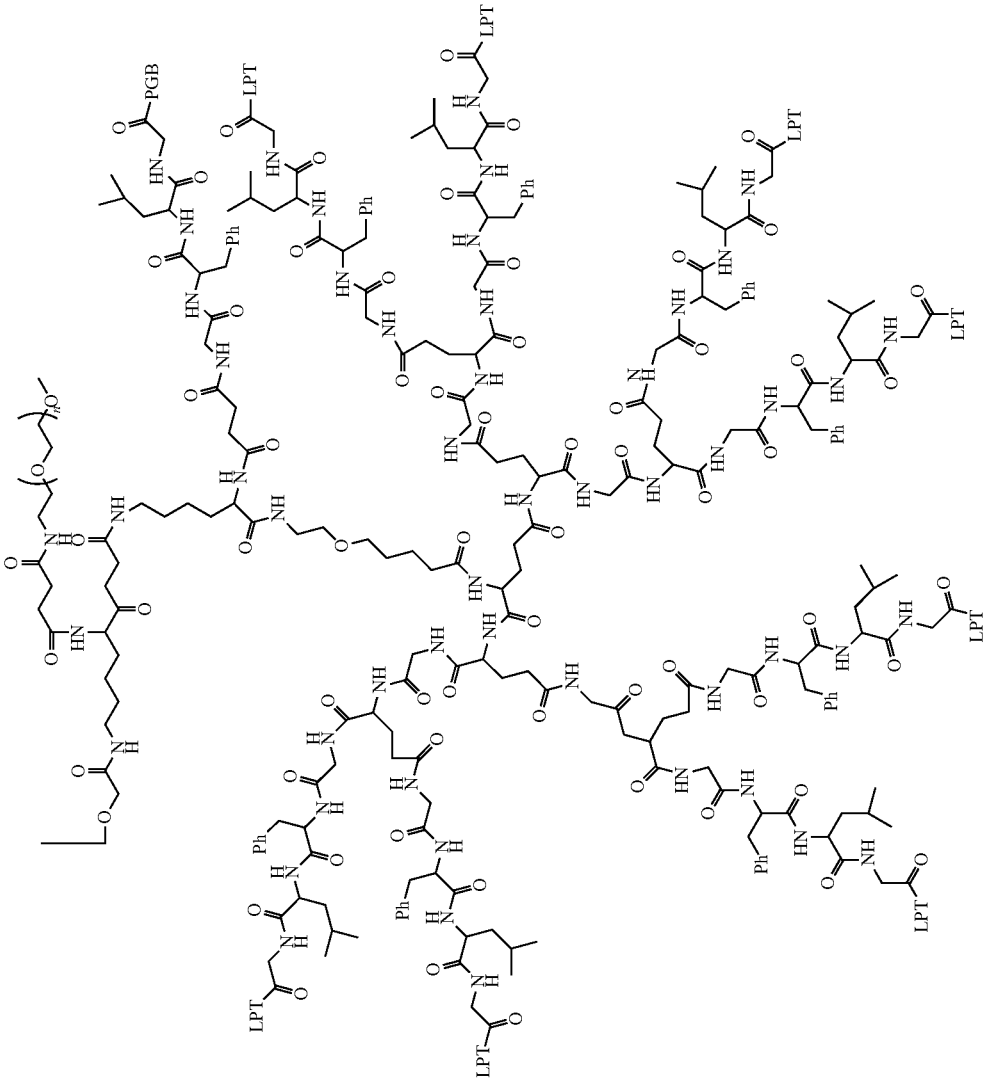
wherein,
has a number-average molecular weight of 10k -continued
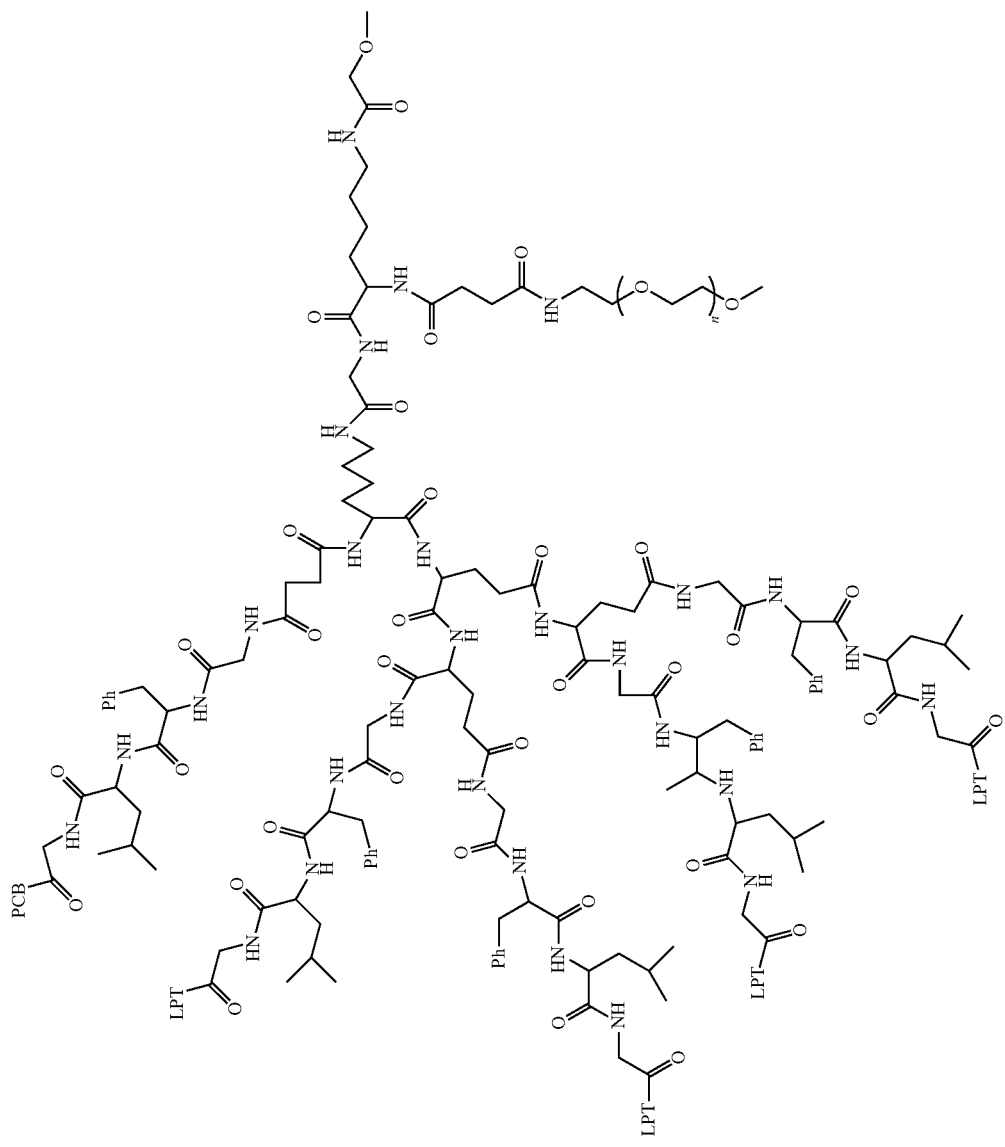

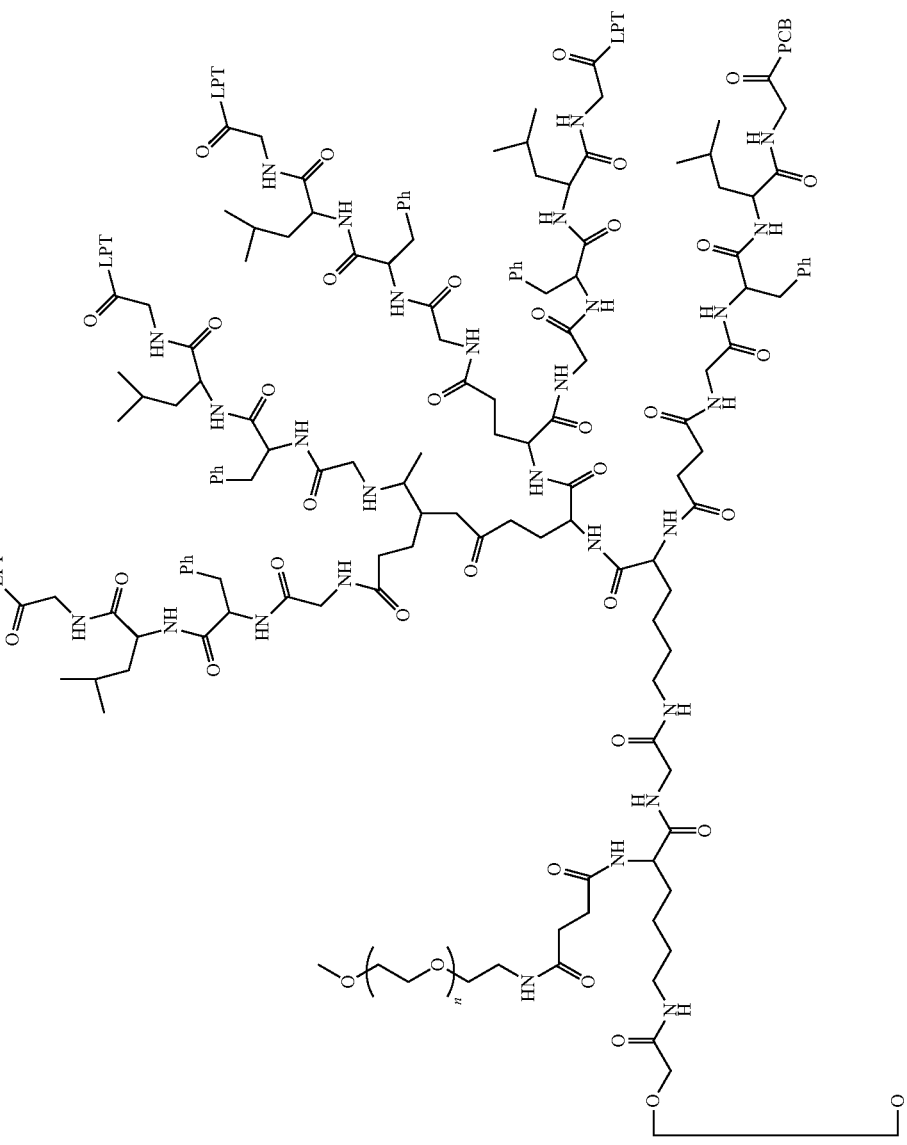

-continued
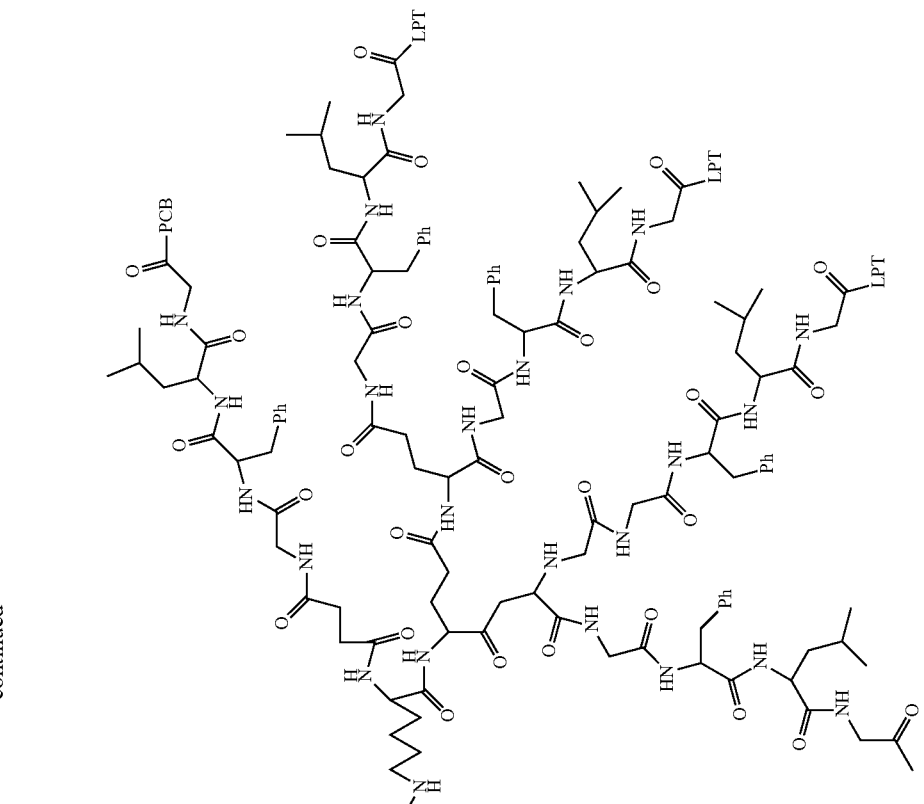
has a number-average molecular weight of 10k
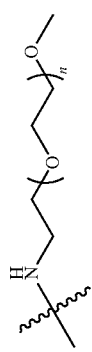
wherein, 1563 1564
-continued
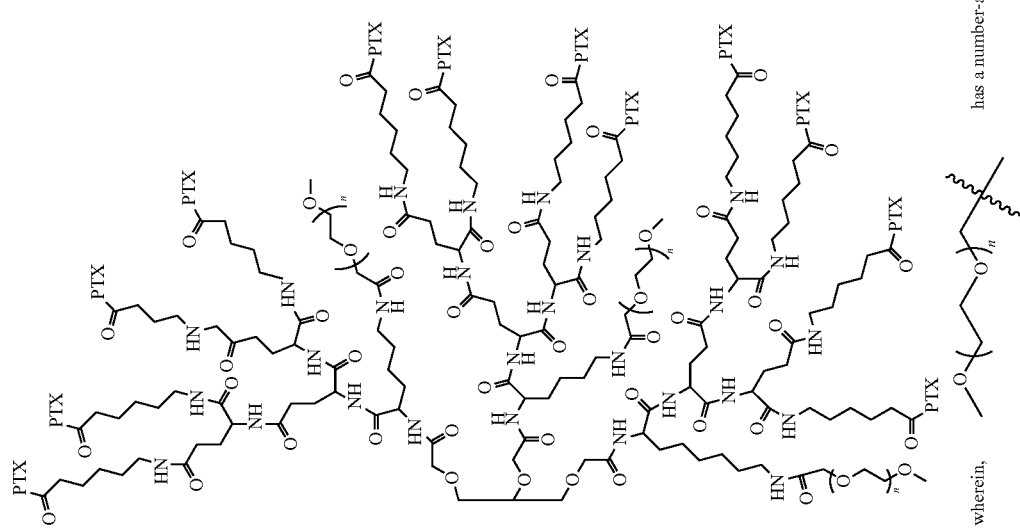
wherein,
has a number-average molecular weight of 5k -continued
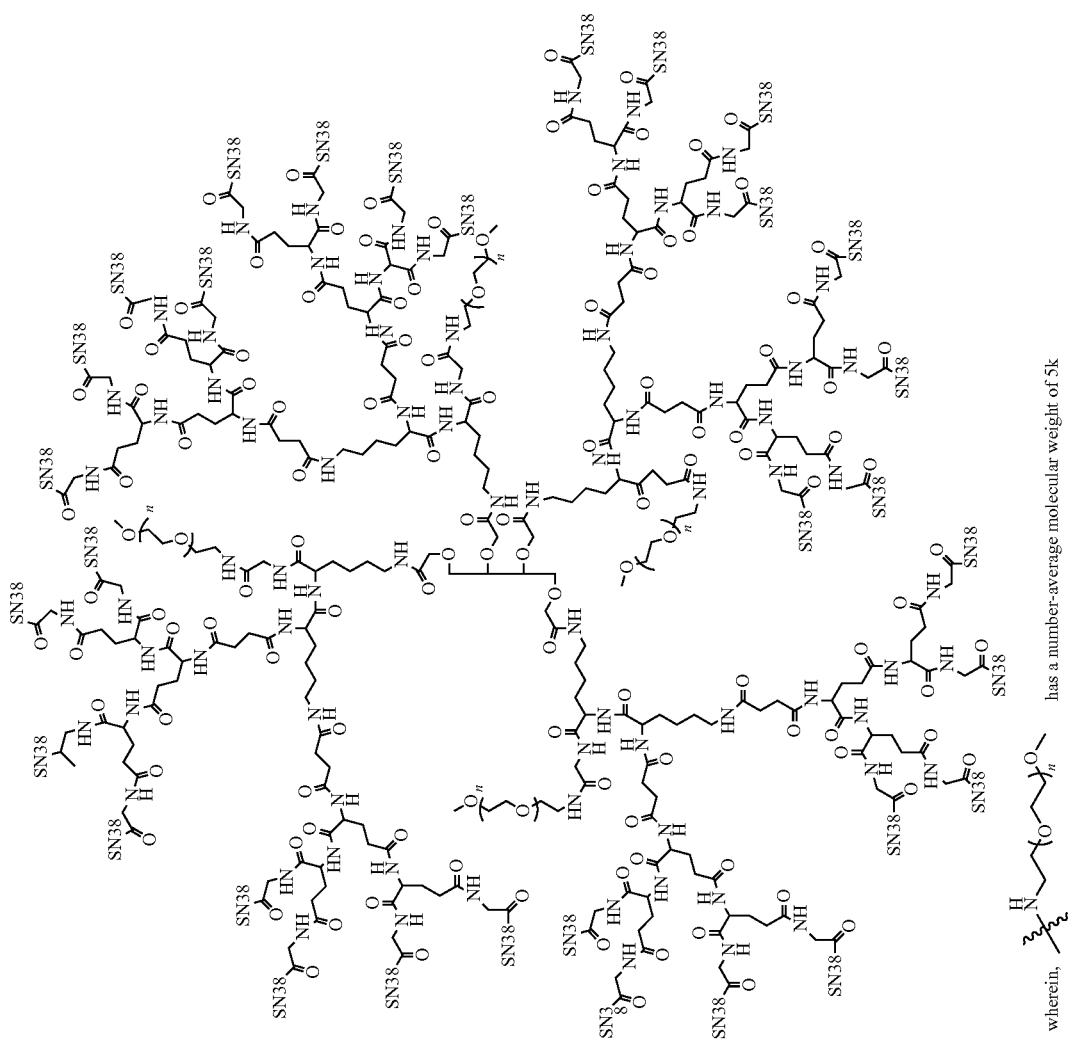
wherein, has a number-average molecular weight of 5k

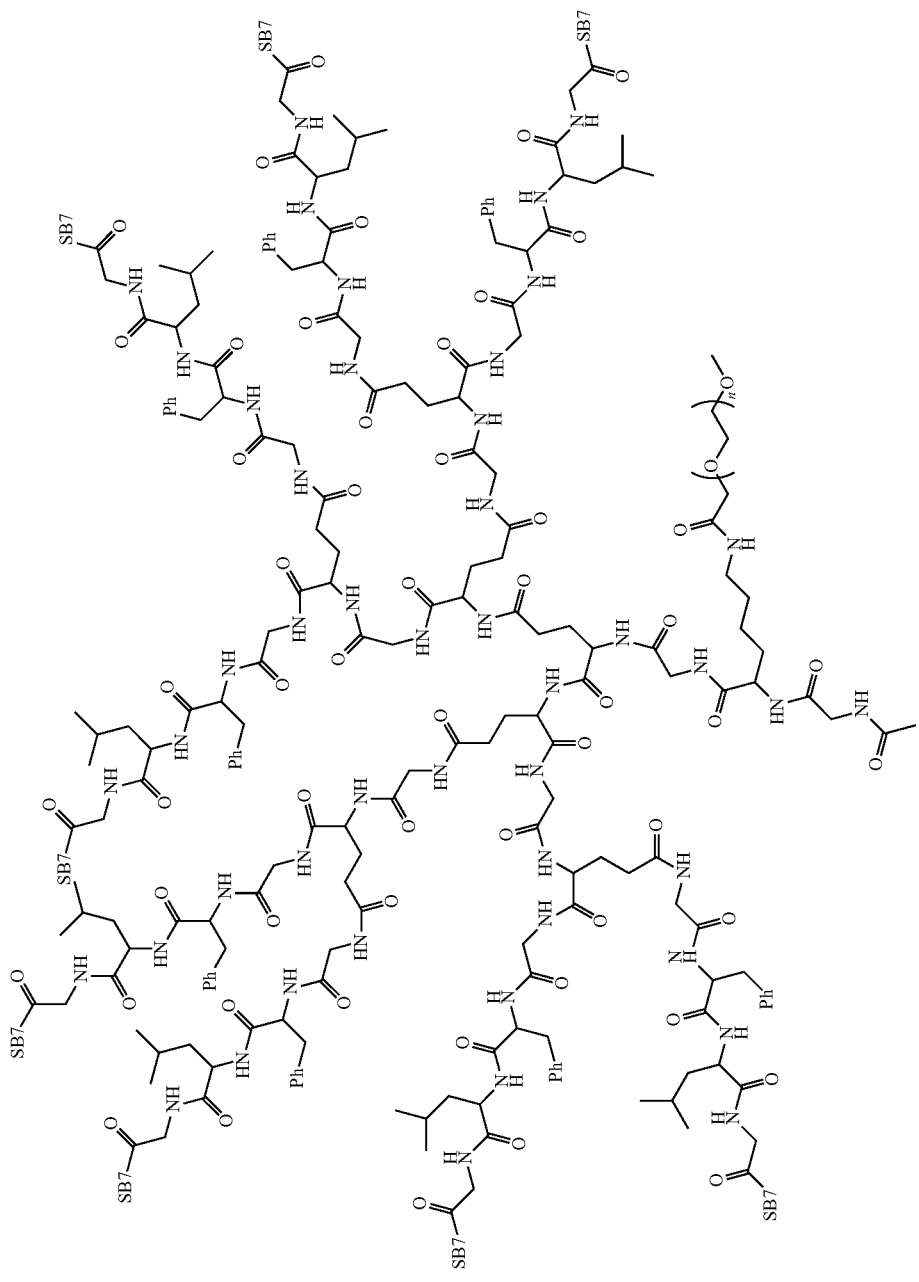

-continued
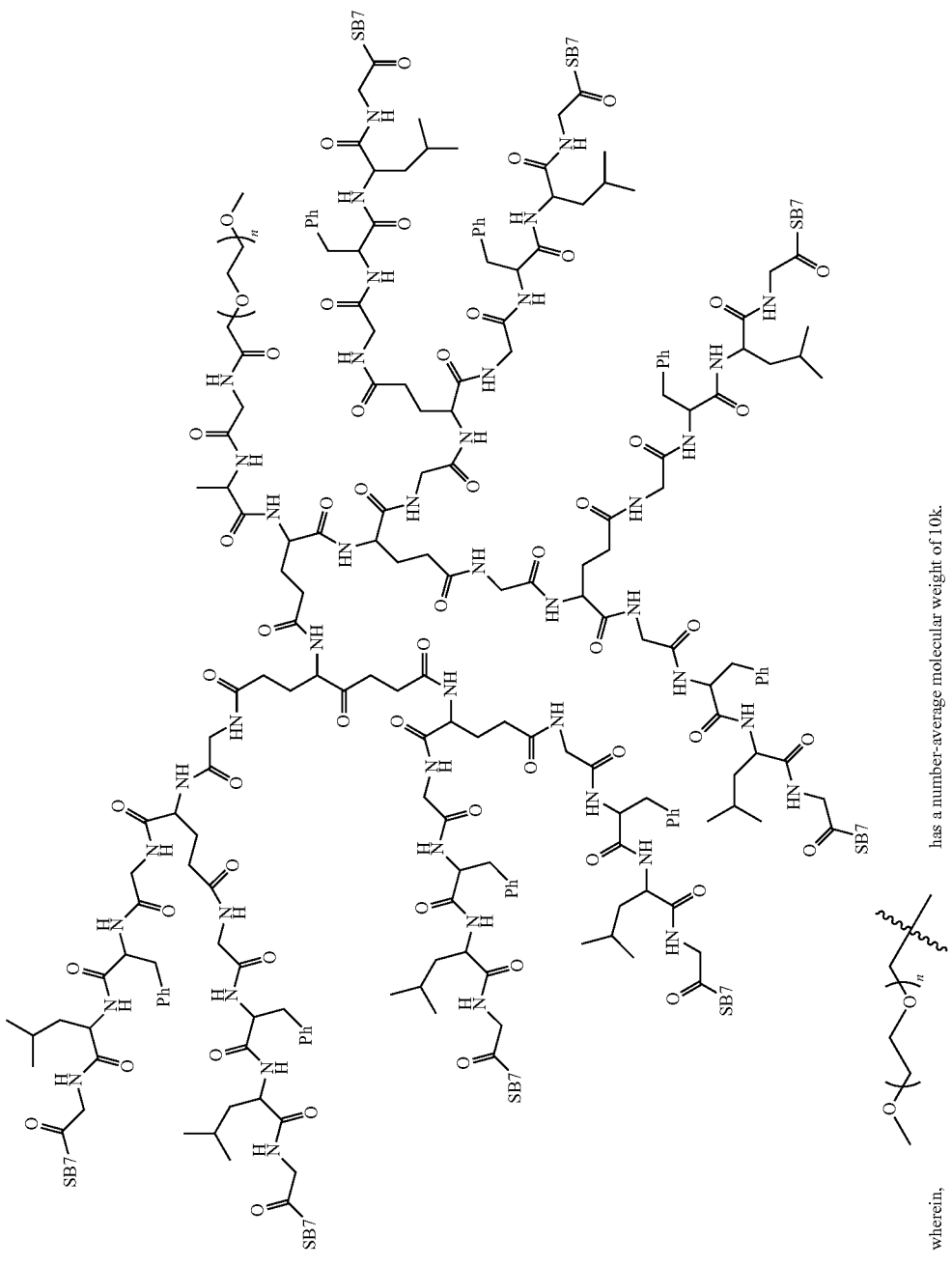
has a number-average molecular weight of 10k.
wherein,

12. An intermediate for preparing the polyethylene glycol conjugated drug or a pharmaceutically acceptable salt thereof according to claim 2, wherein the intermediate is selected from:

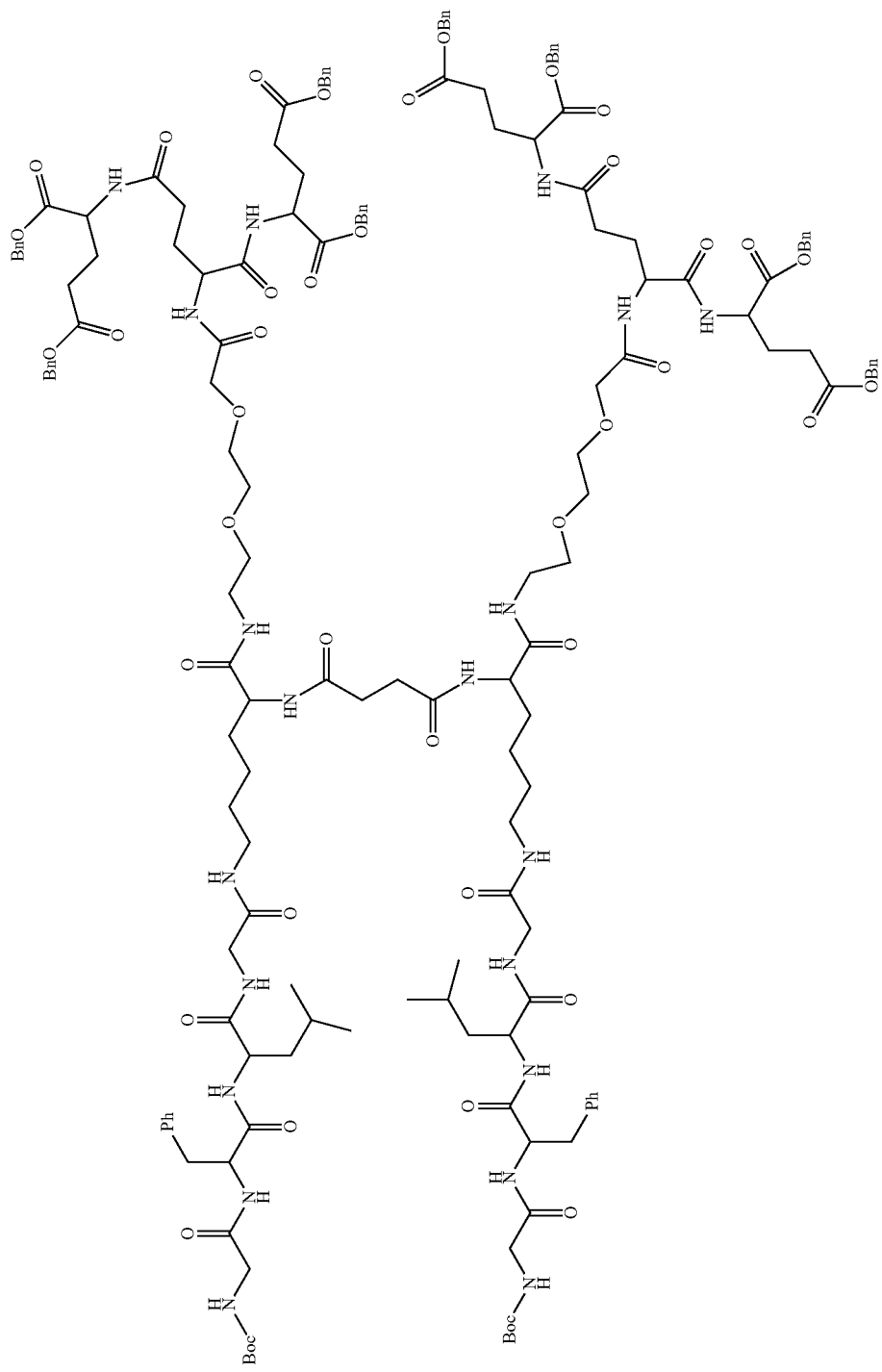

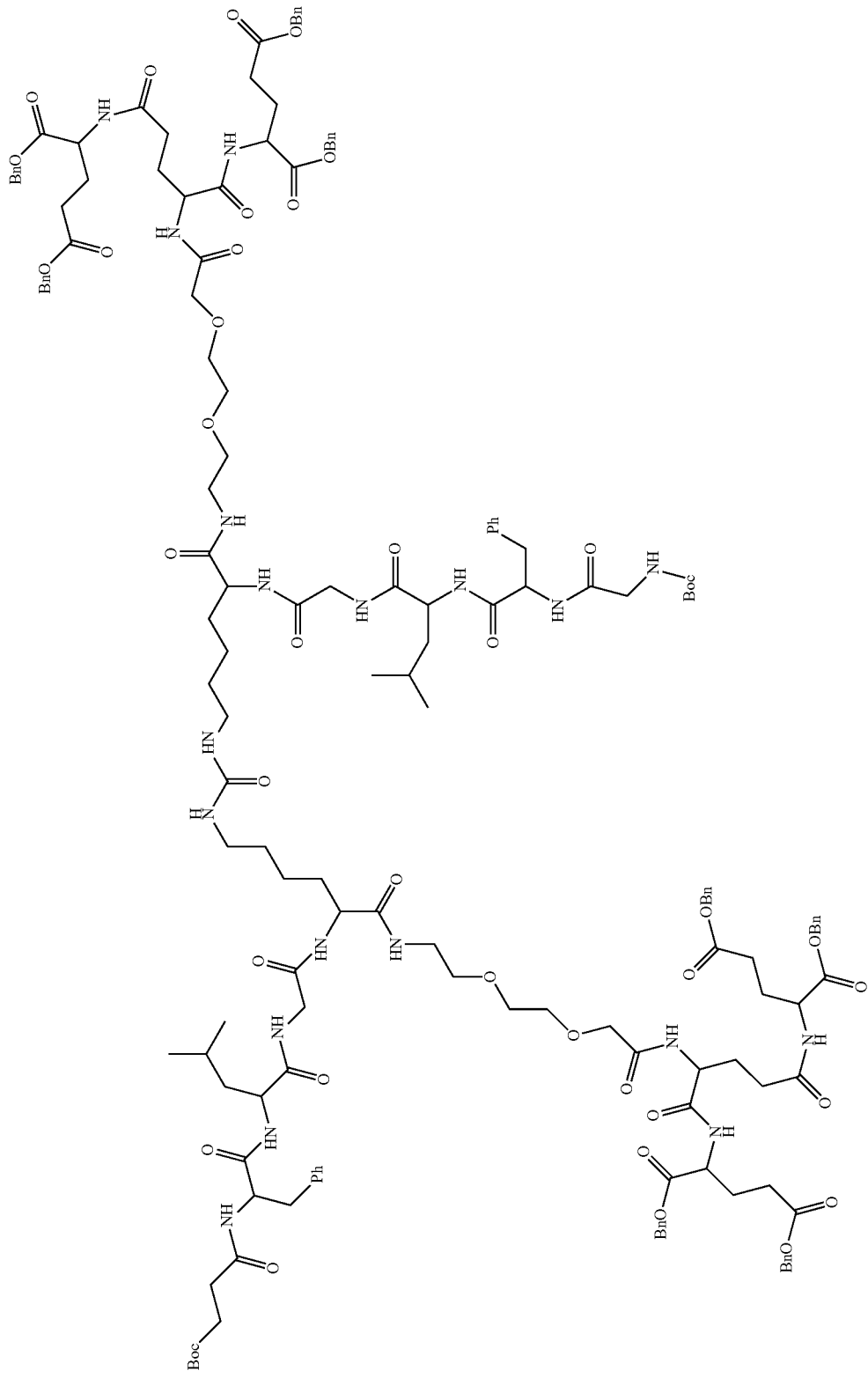

27-121
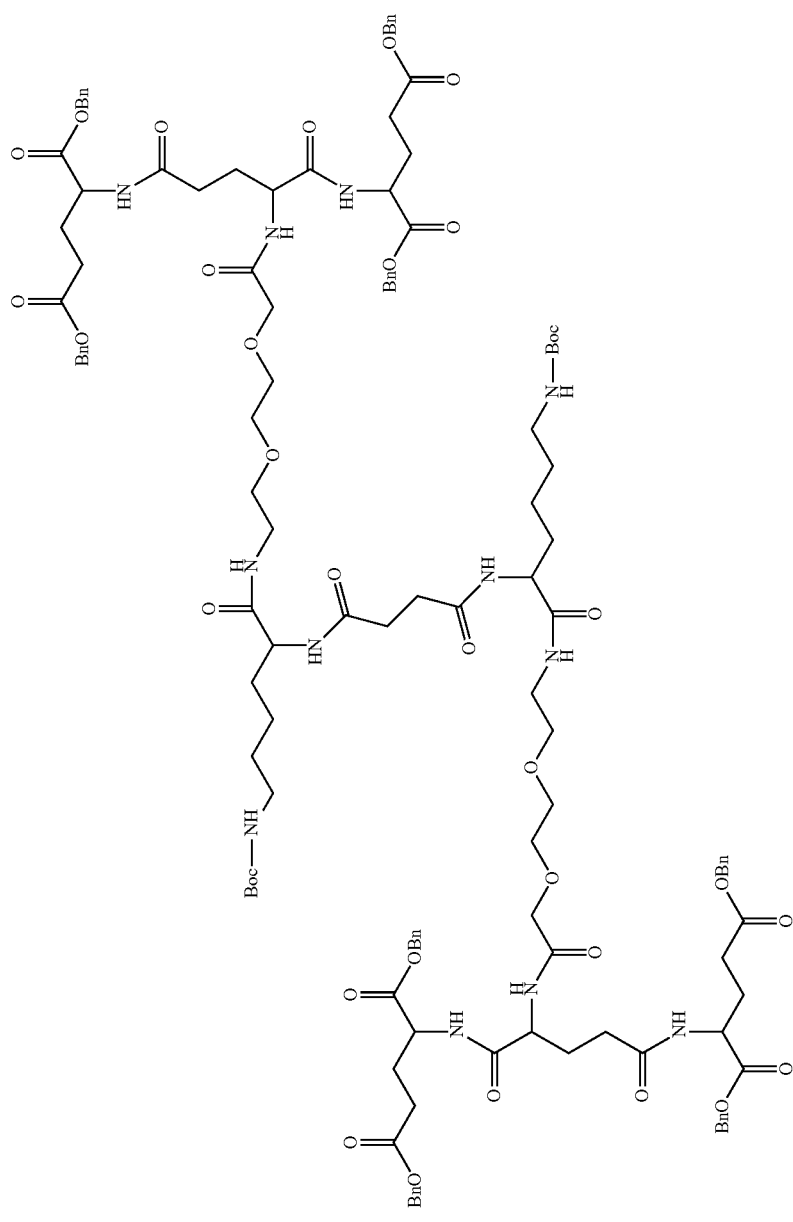

1579  1580
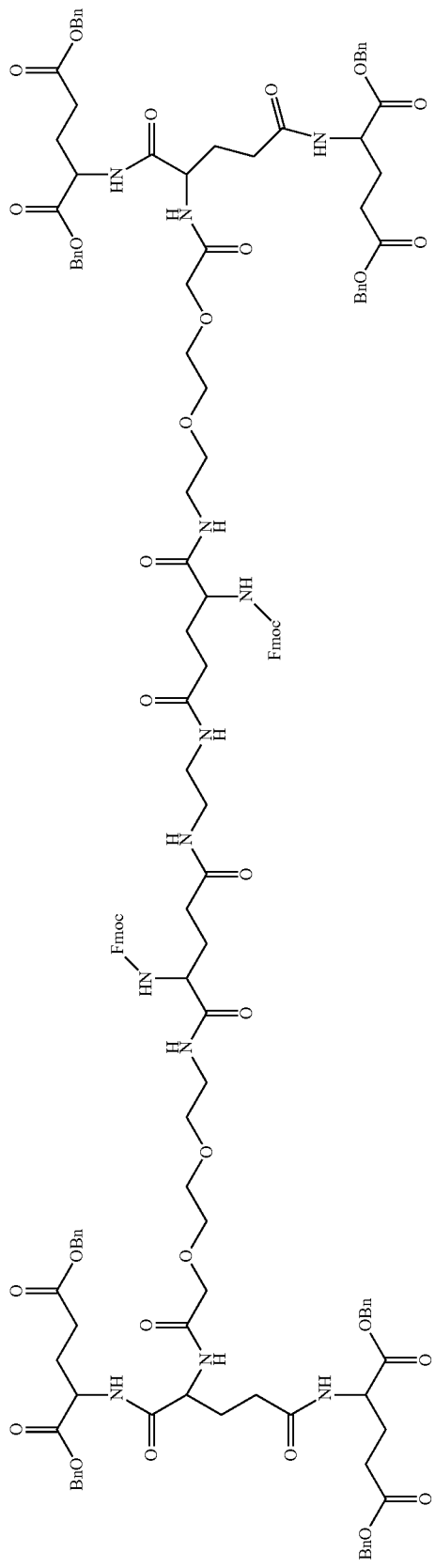
25-221
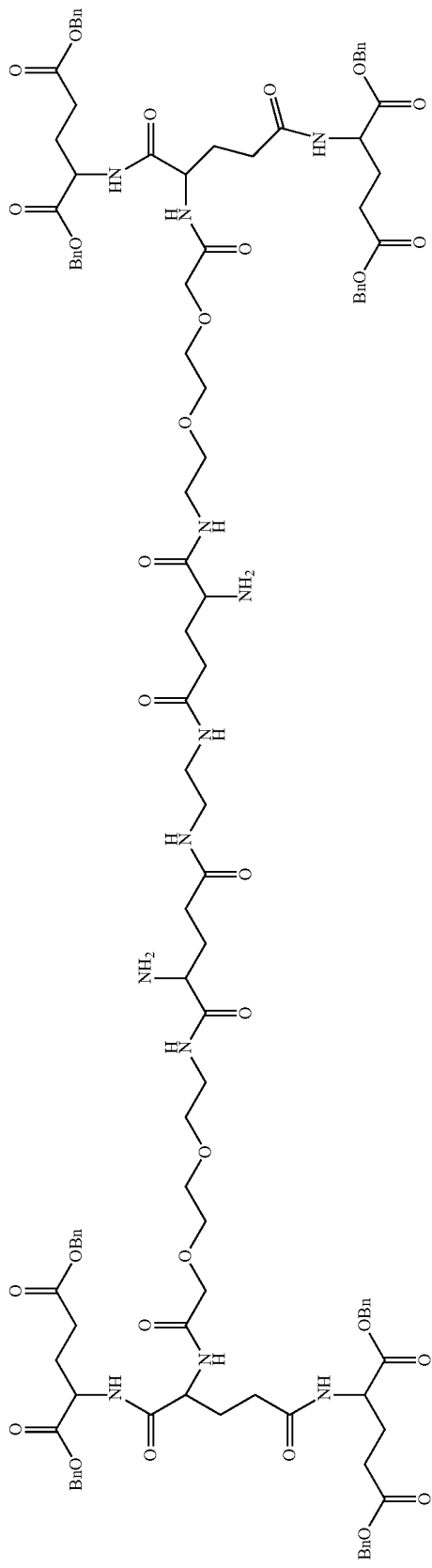
25-226

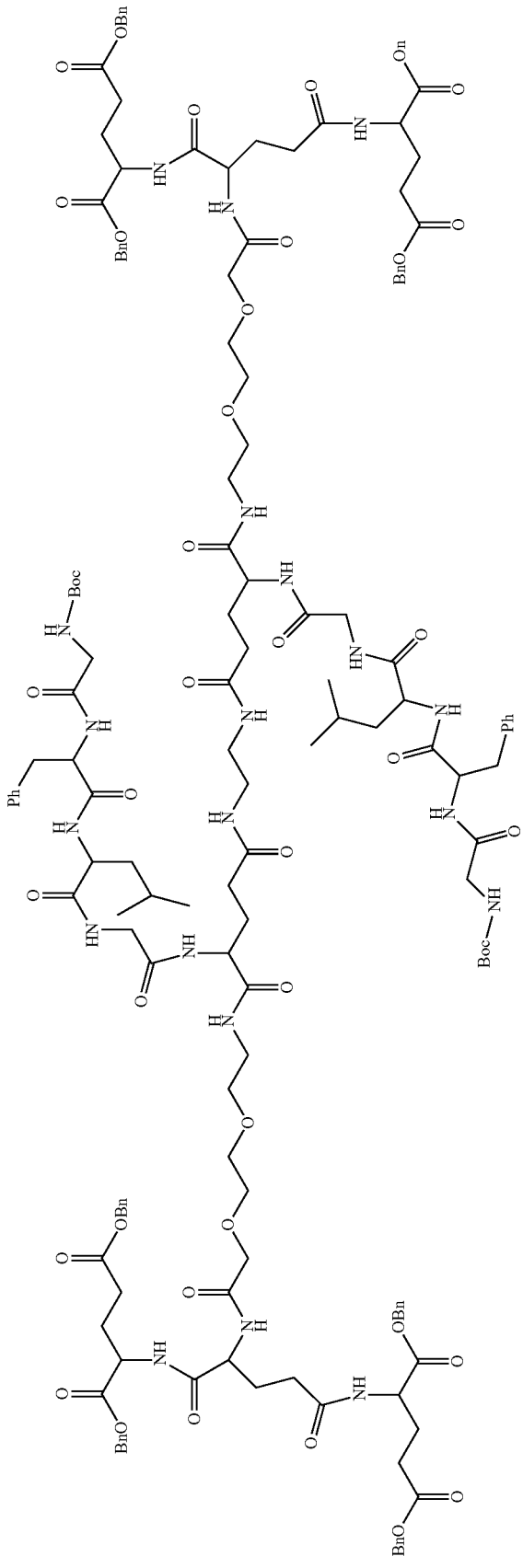

42-34
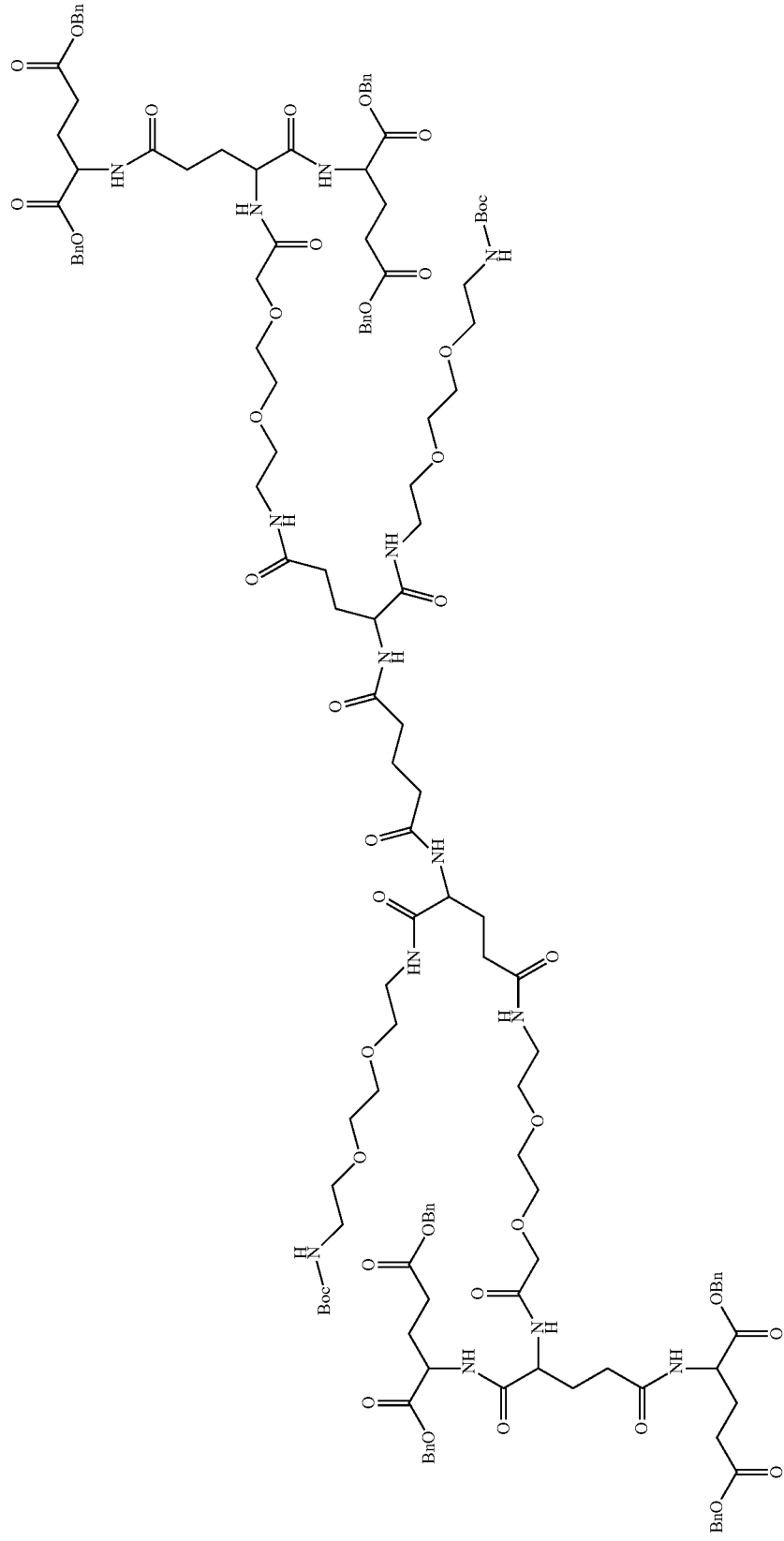

37-45
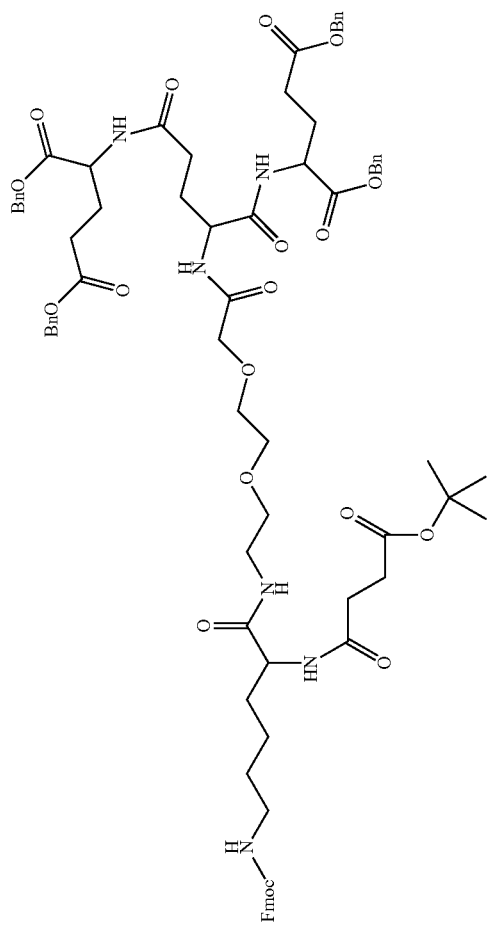

1587
46-6
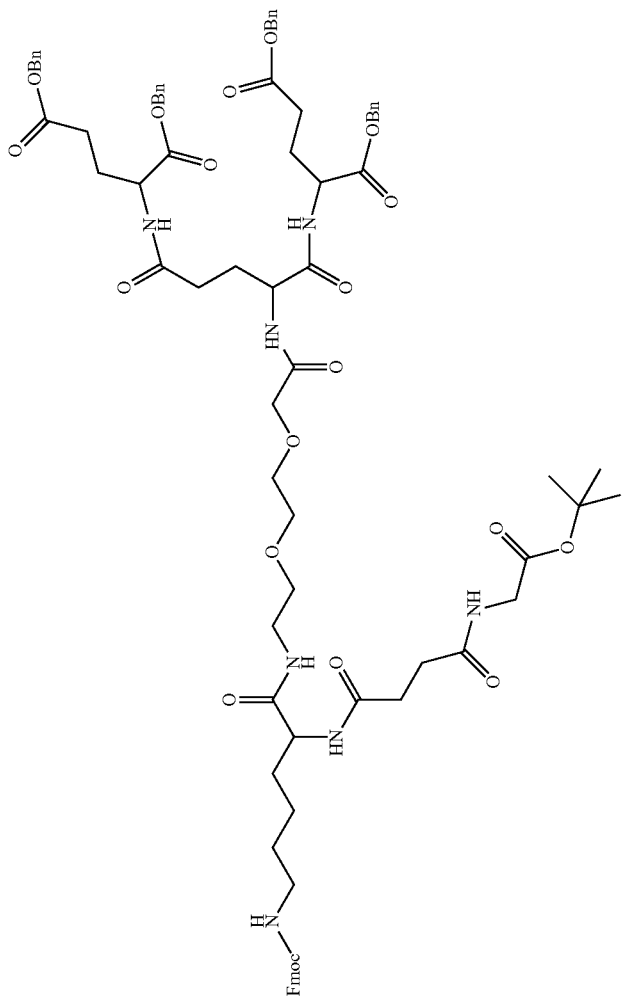
-continued
1588
45-9
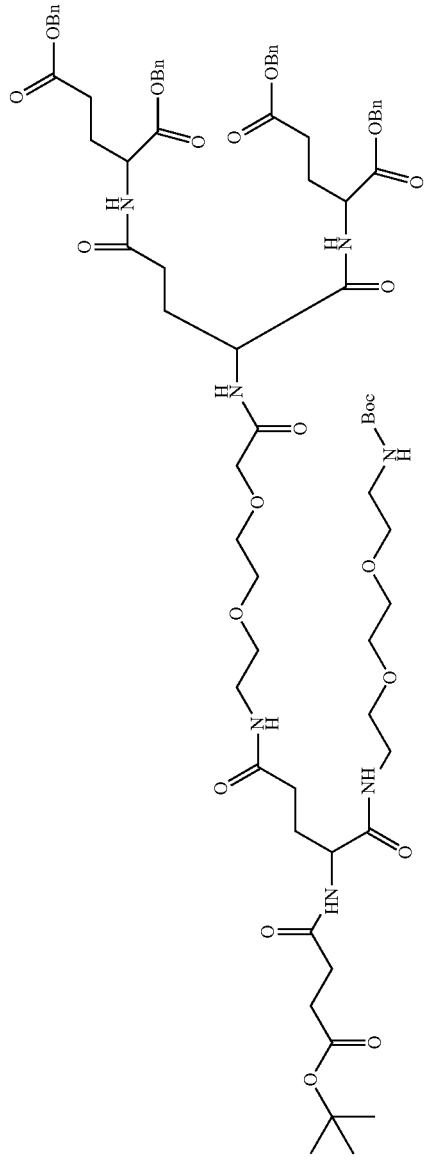

1589 1590
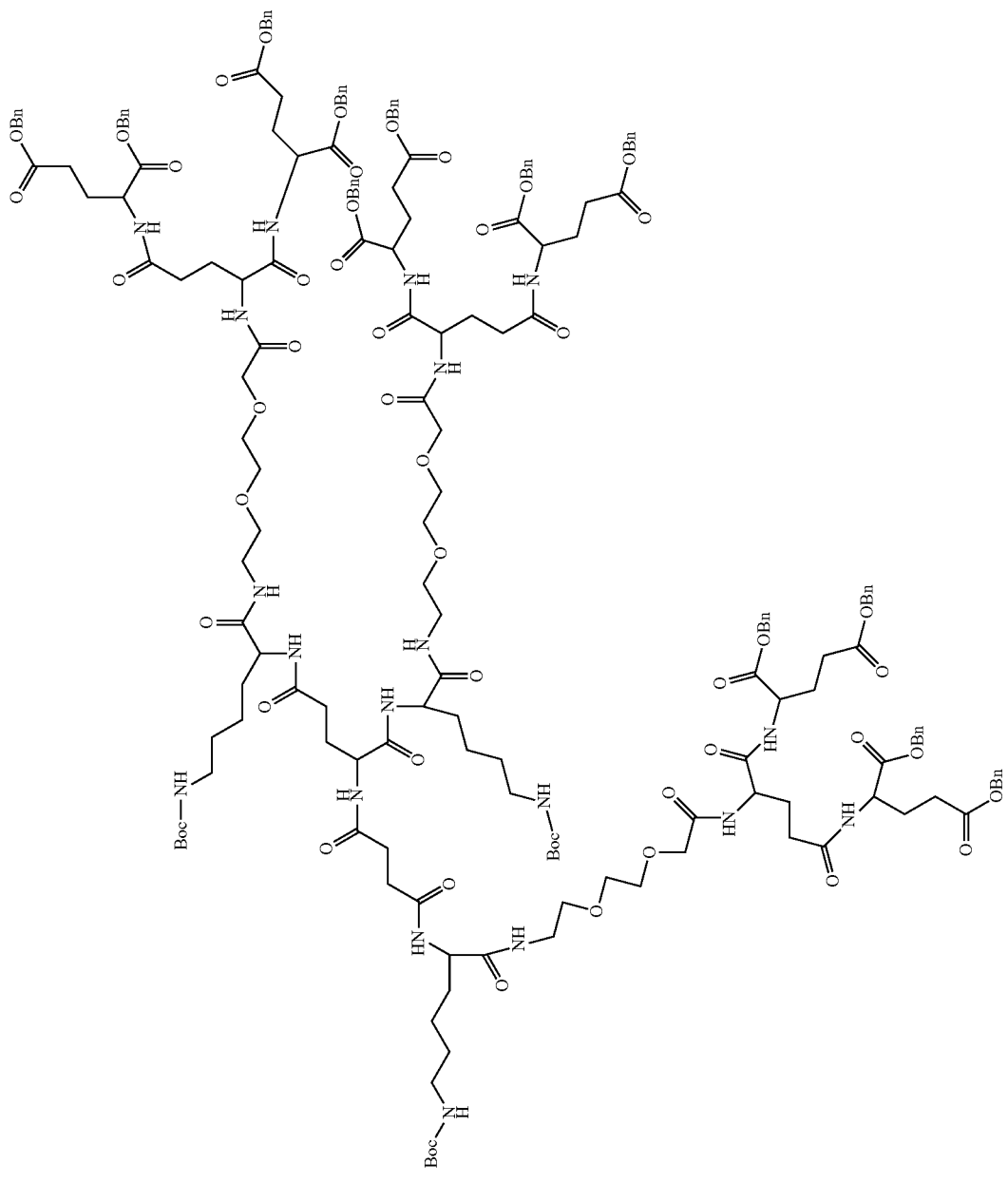

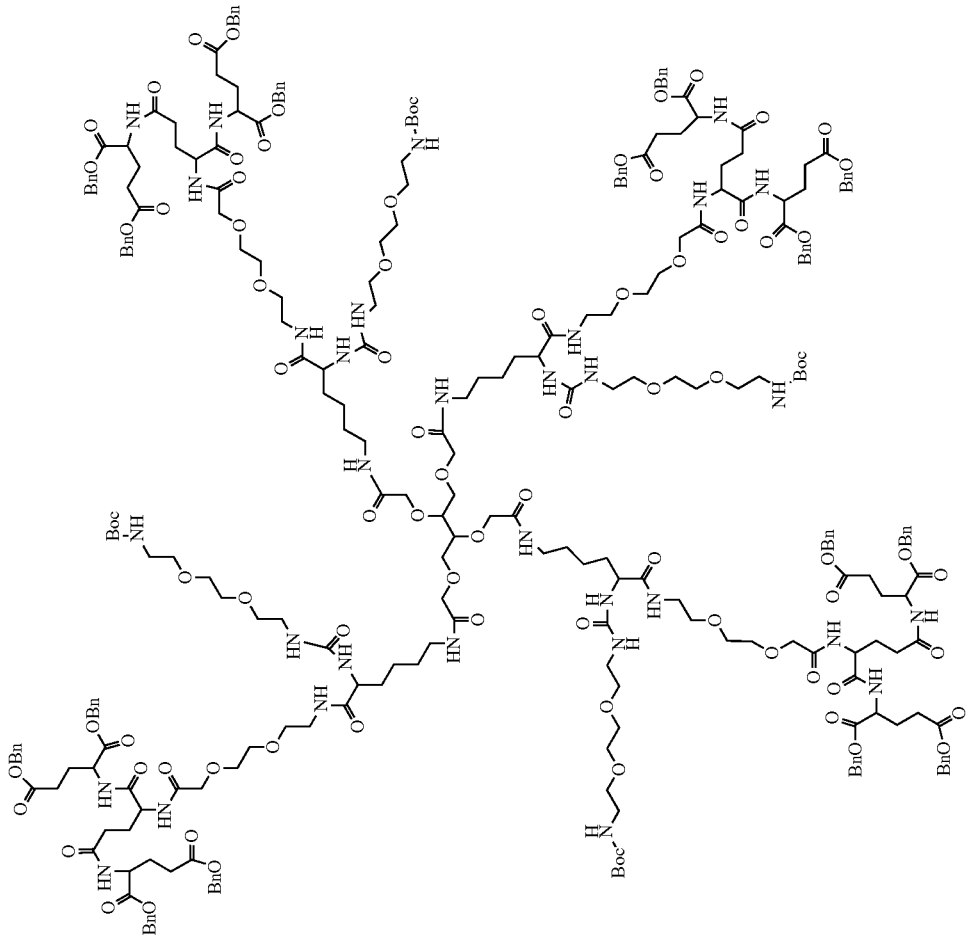

35-90
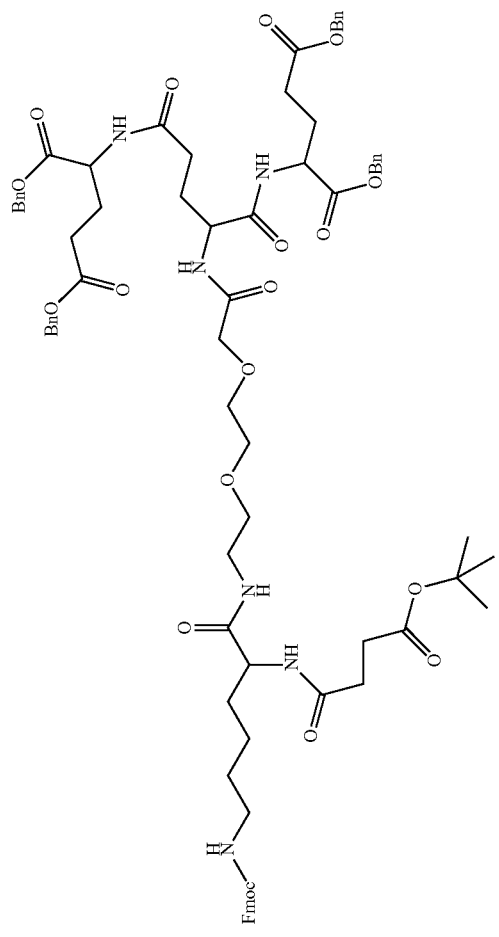

44-161
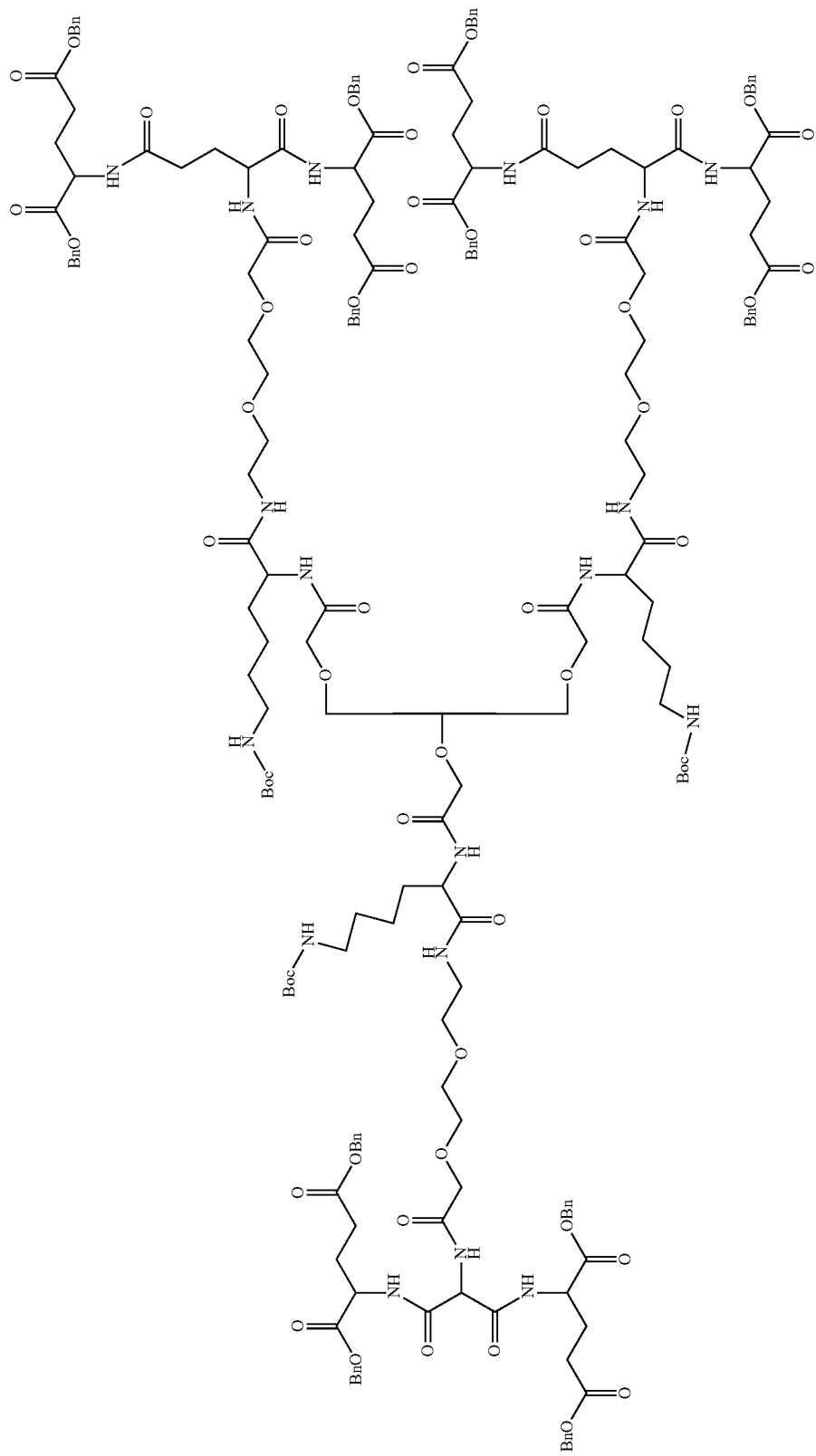

1597 1598
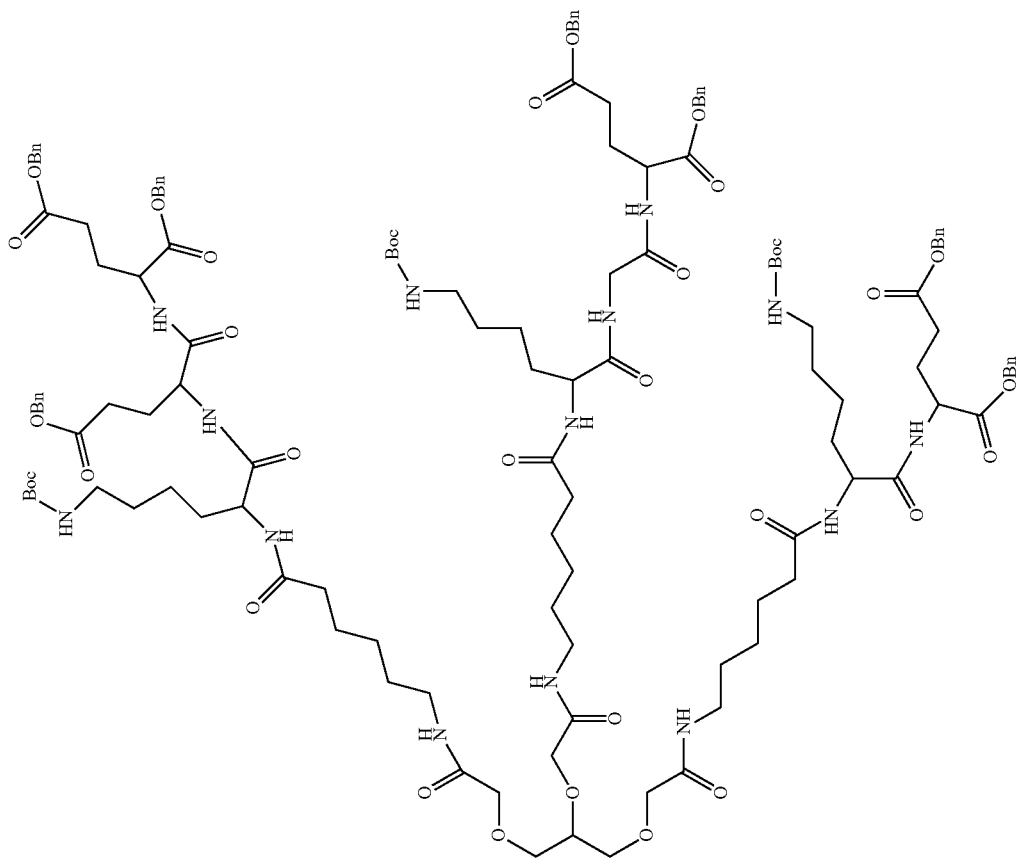

49-124
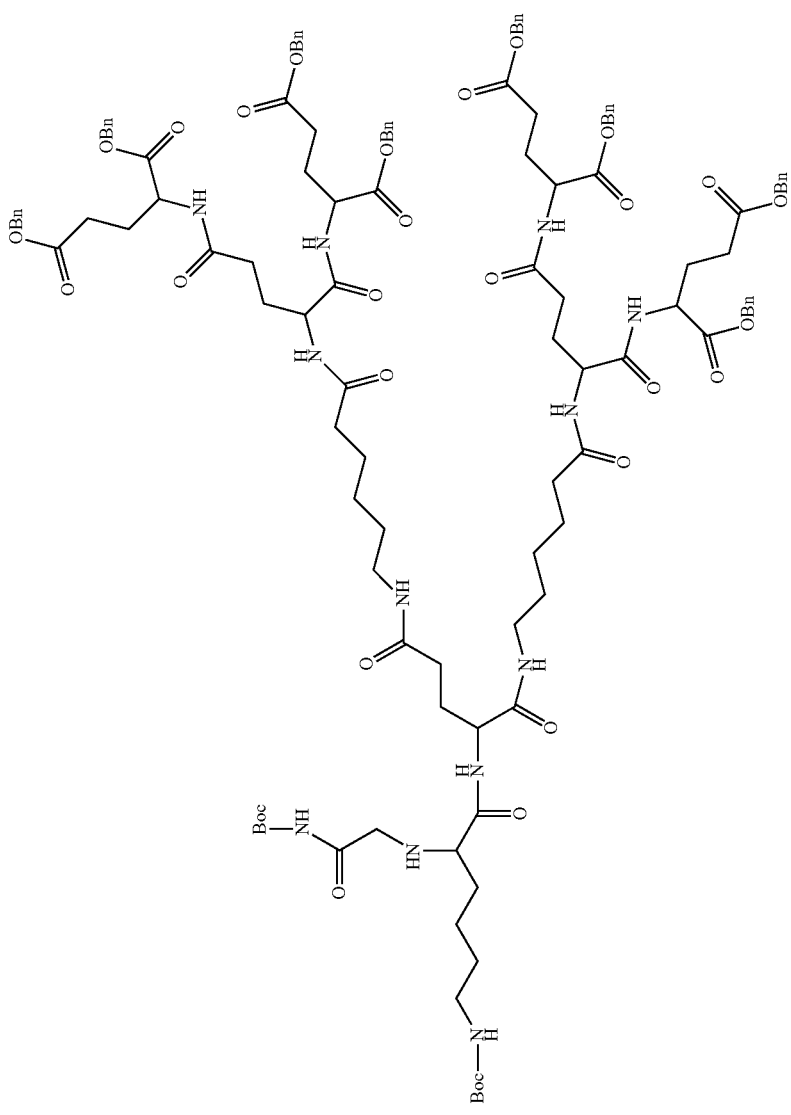

1601 1602
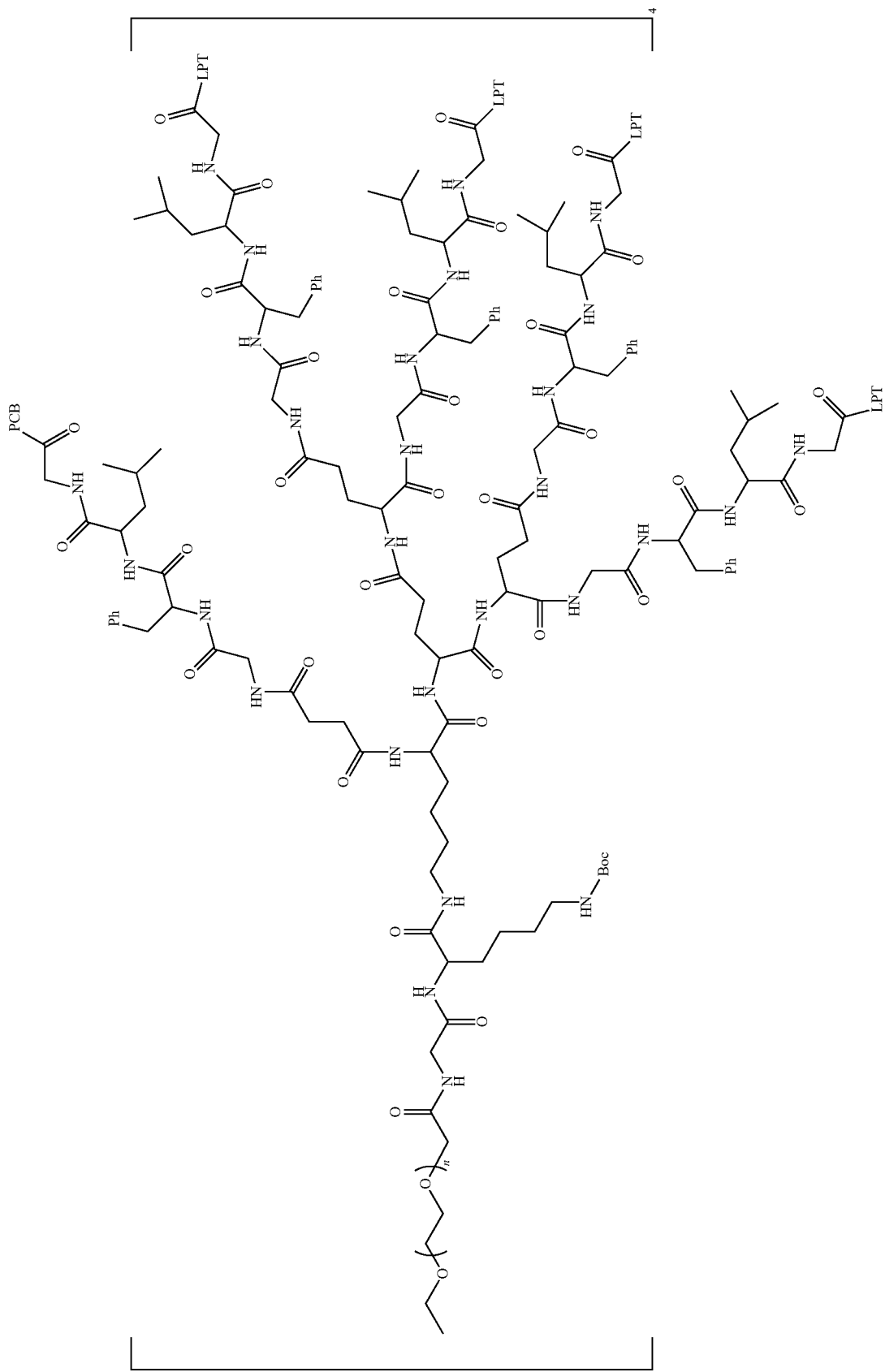

1603 1604
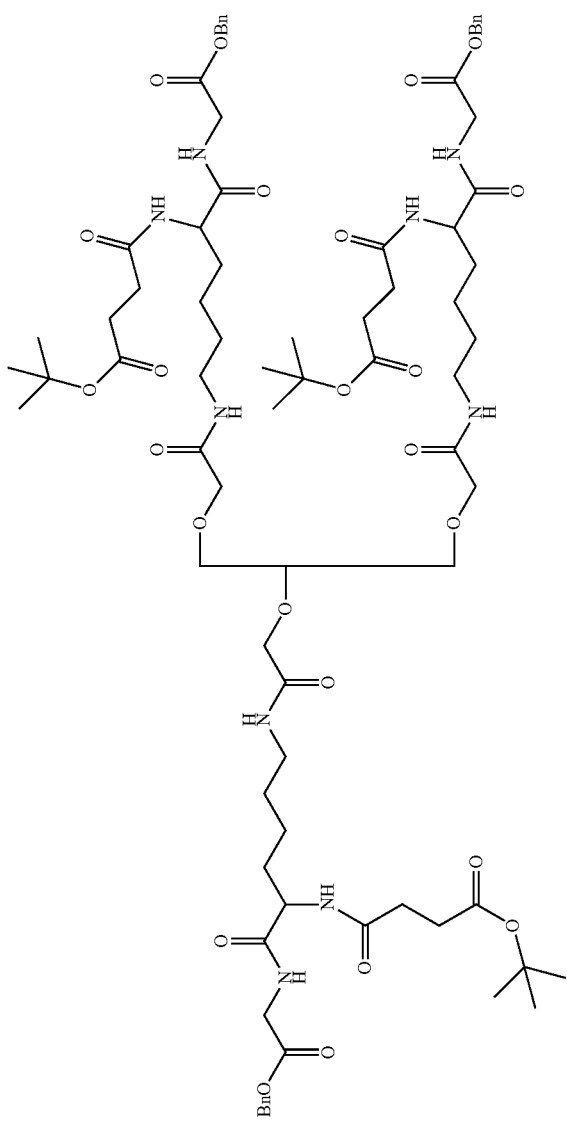

1605 1606
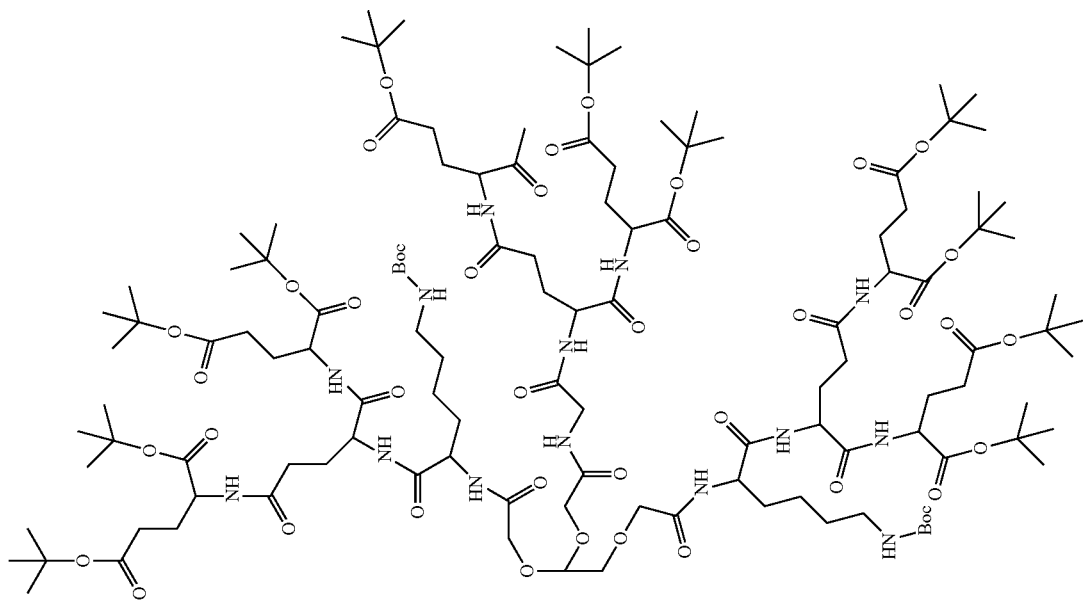

-continued
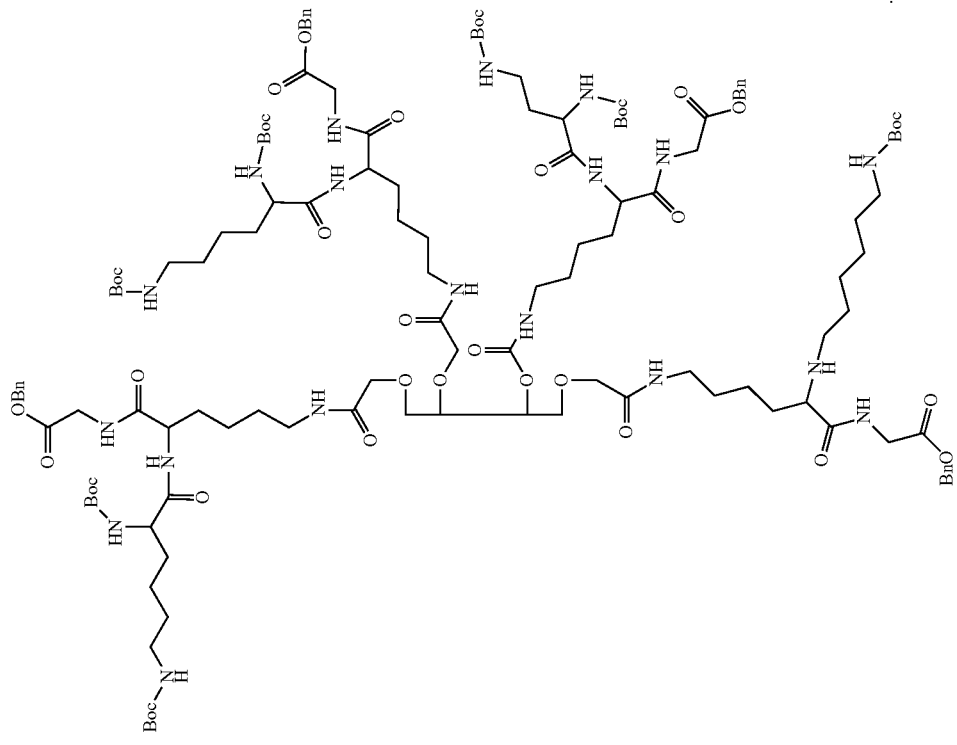

13. A method for preparing the polyethylene glycol conjugated drug or a pharmaceutically acceptable salt thereof according to claim 2, comprising the following steps:

(1) preparing the intermediate

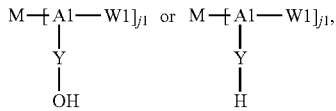

M, A1, W1, Y and j1 being as defined in claim 2, wherein:
in the preparation of the intermediate

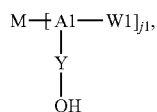

when Y is other than a direct bond, —Y—OH has a terminal carboxyl group, when Y is a direct bond,

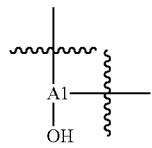

has a terminal carboxyl group,
in the preparation of the intermediate

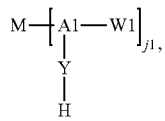

when Y is other than a direct bond, —Y—H has a terminal amino group, when Y is a direct bond,

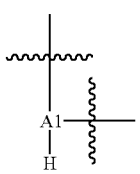

has a terminal amino group;

(2) allowing the PEG with amino group or activated amino group and the intermediate

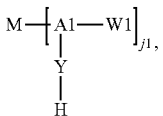

to carry out amidation reaction, or, allowing the PEG with carboxyl group or activated carboxyl group and the intermediate

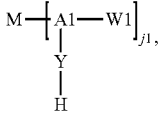

to carry out amidation reaction, to obtain the polyethylene glycol conjugated drug as defined in claim 2.

14. An intermediate for preparing the polyethylene glycol conjugated drug or a pharmaceutically acceptable salt thereof according to claim 5, wherein the intermediate is selected from:

1611 1612
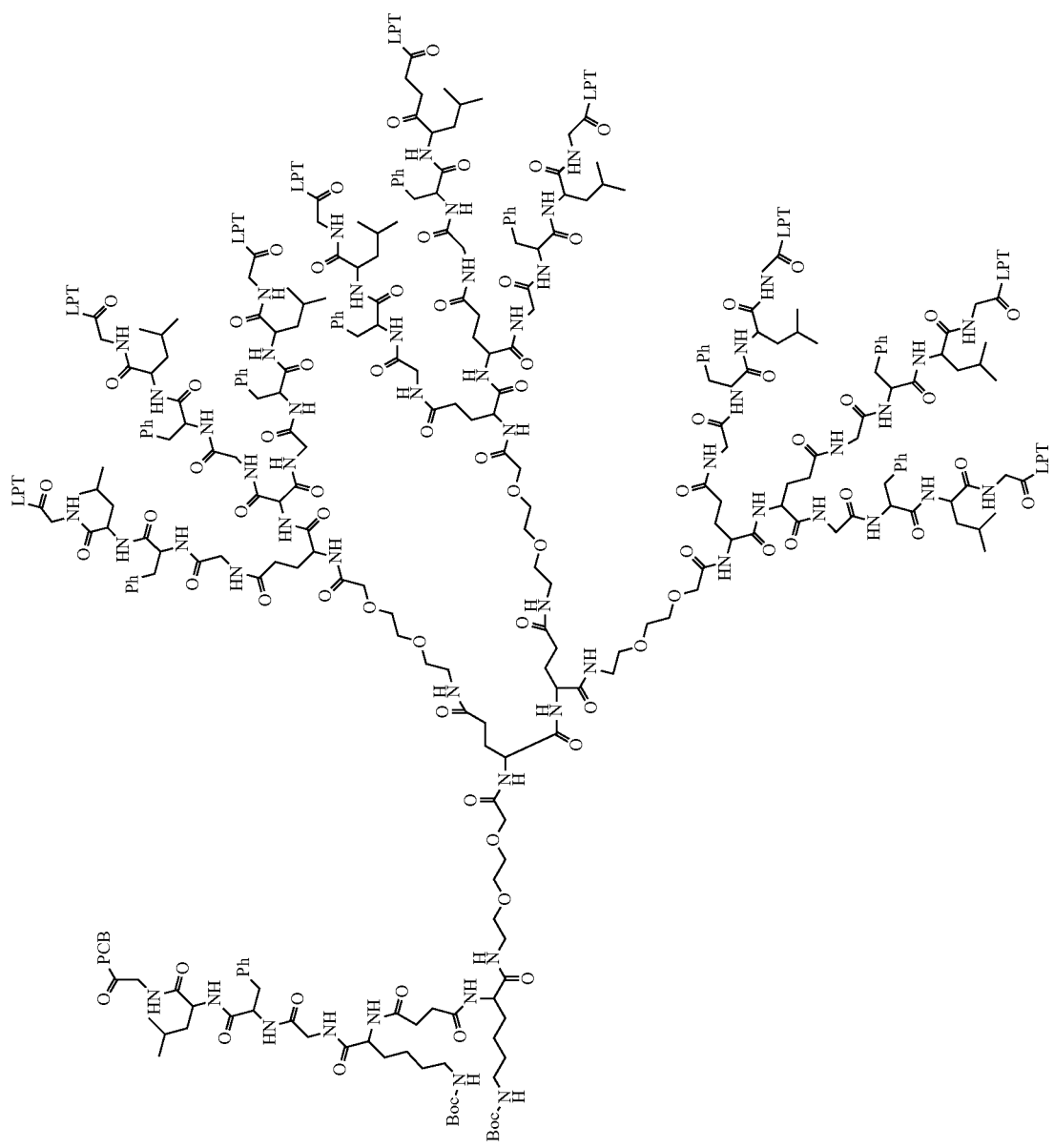

1613 1614
-continued
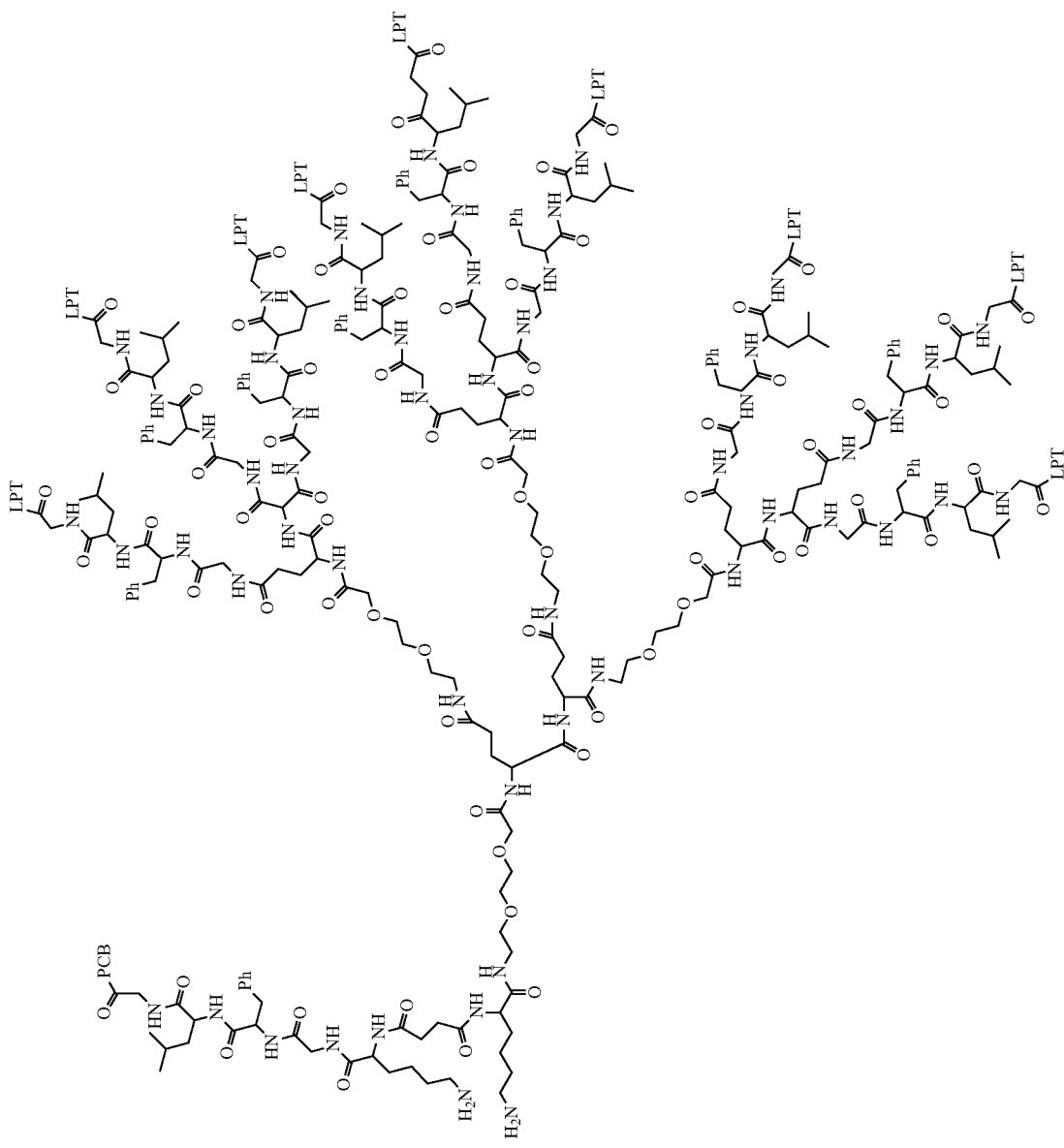

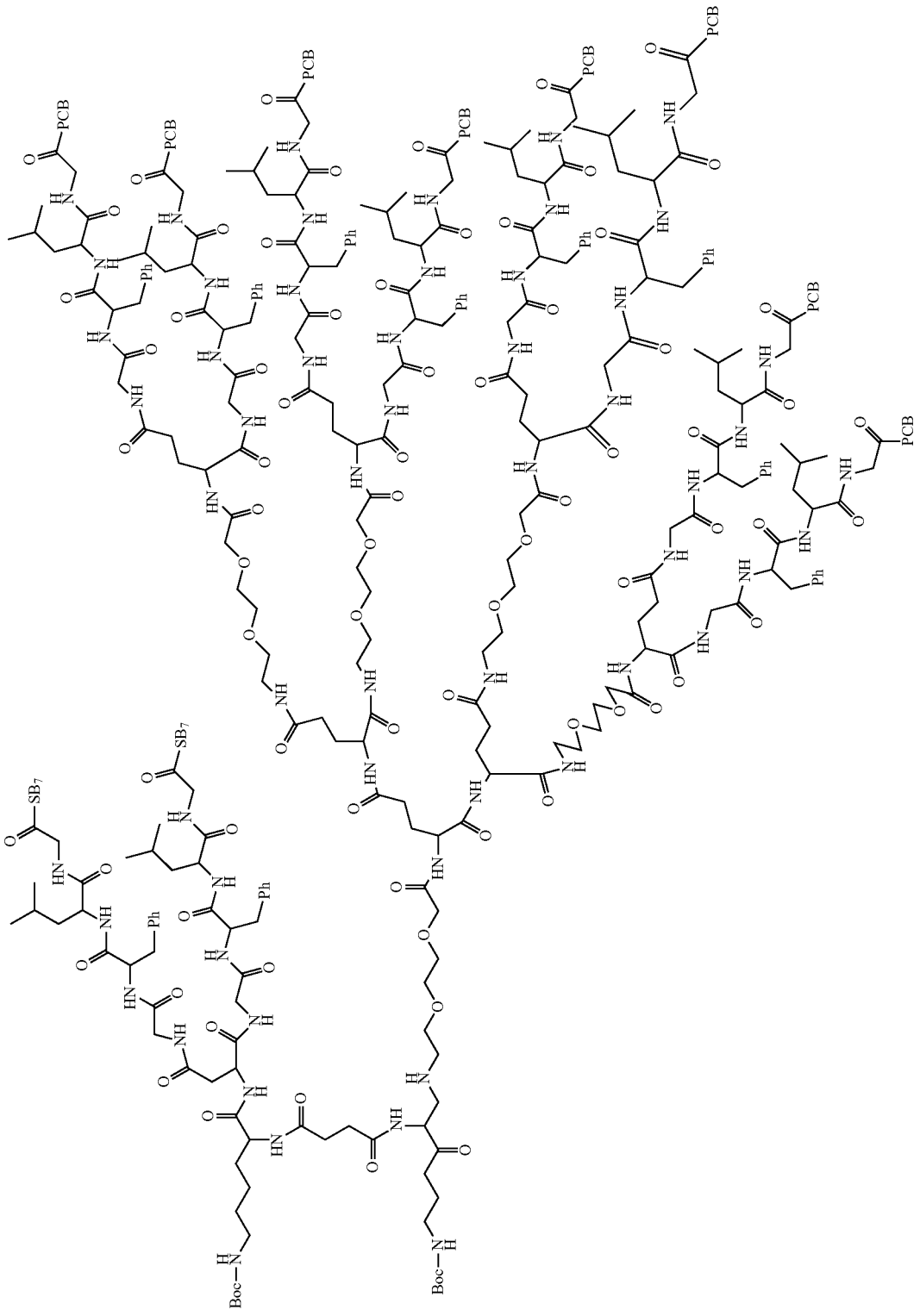

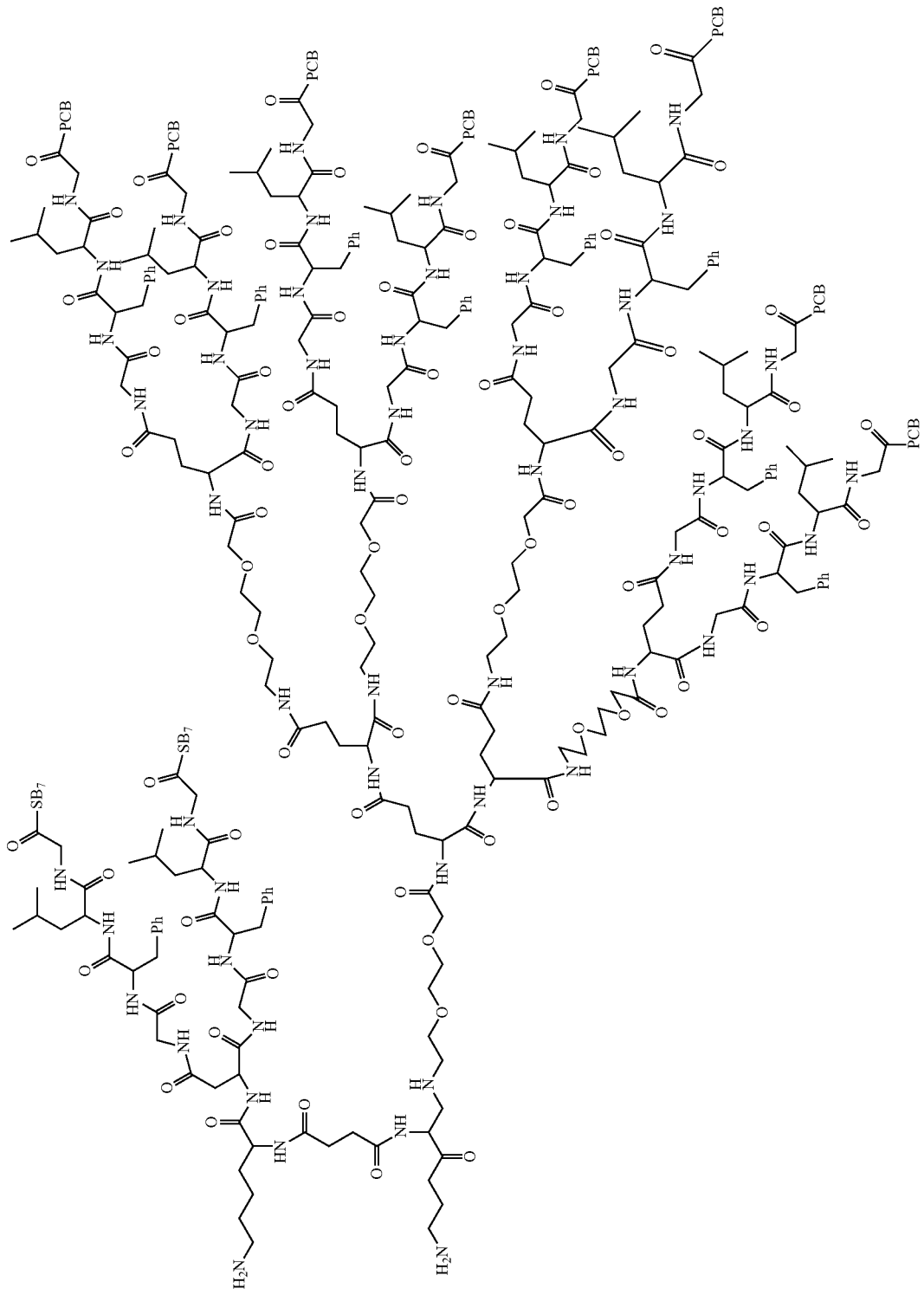

1621 1622
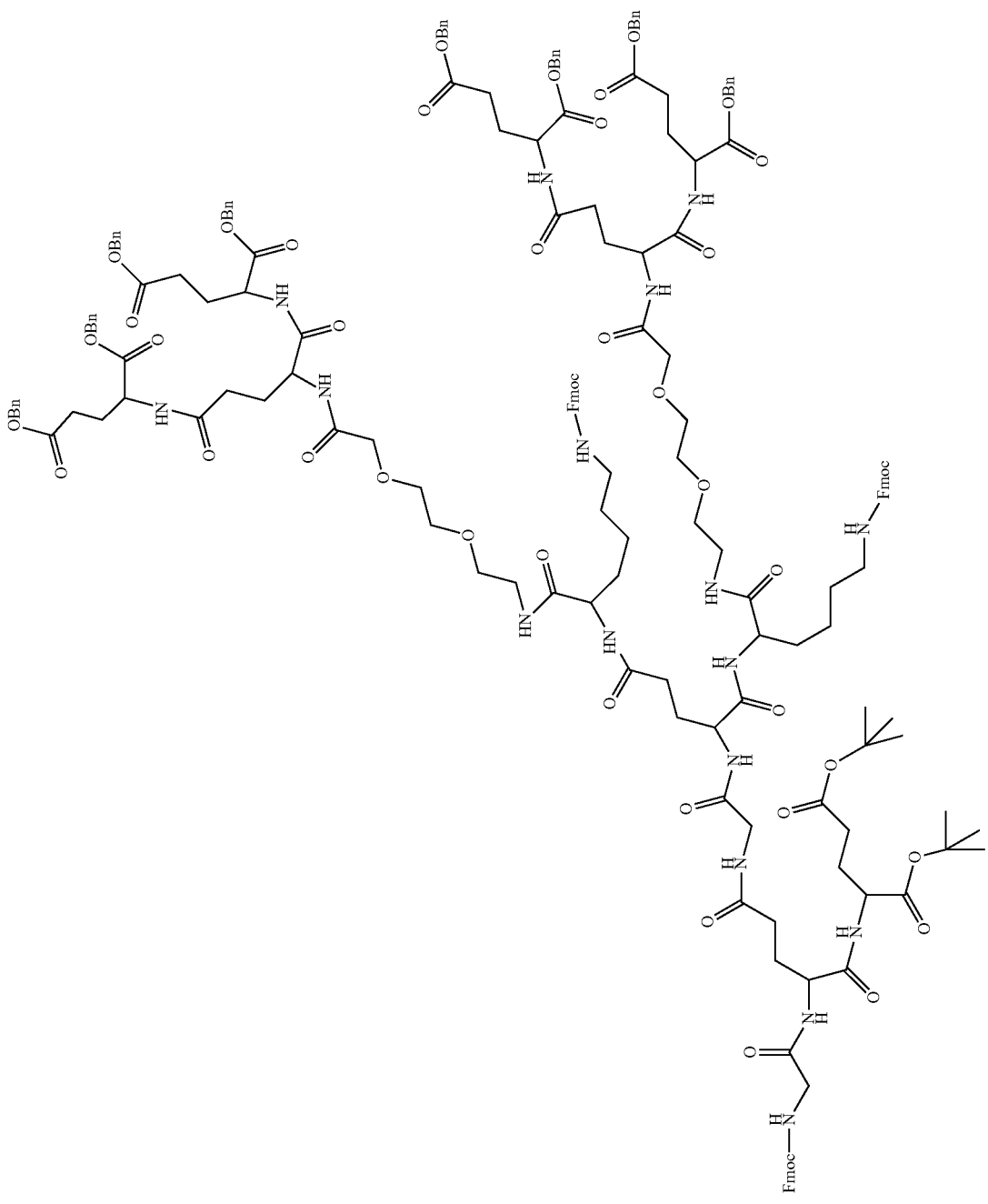

1624
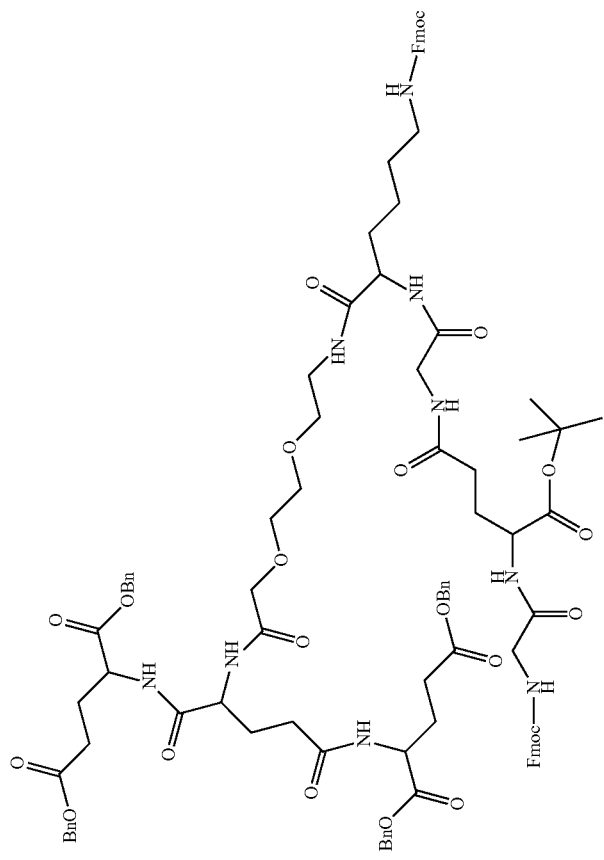

1625 1626
-continued
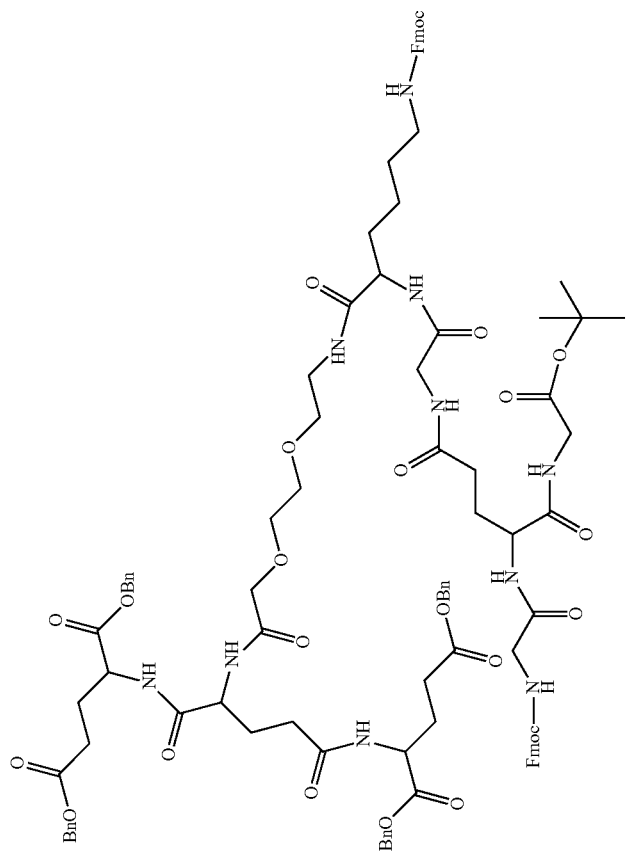

1627 1628
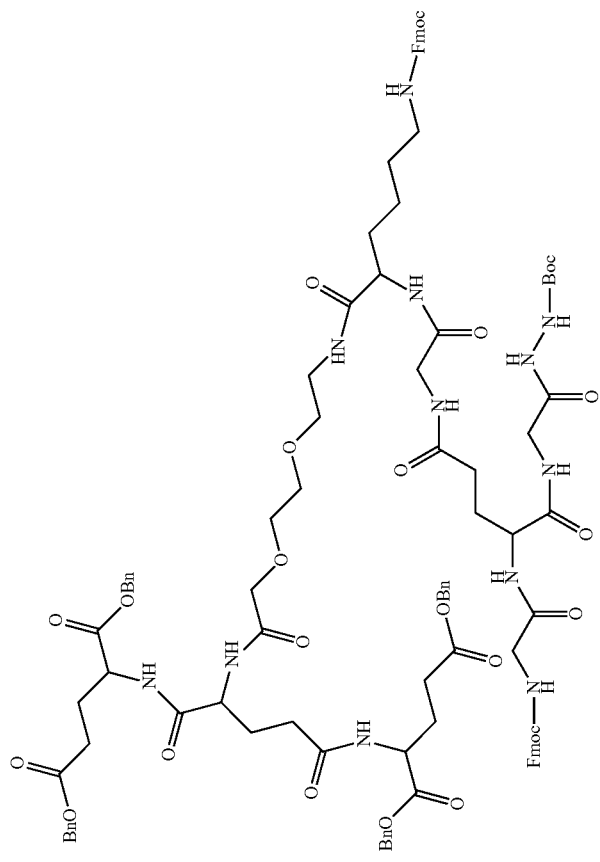

35-155
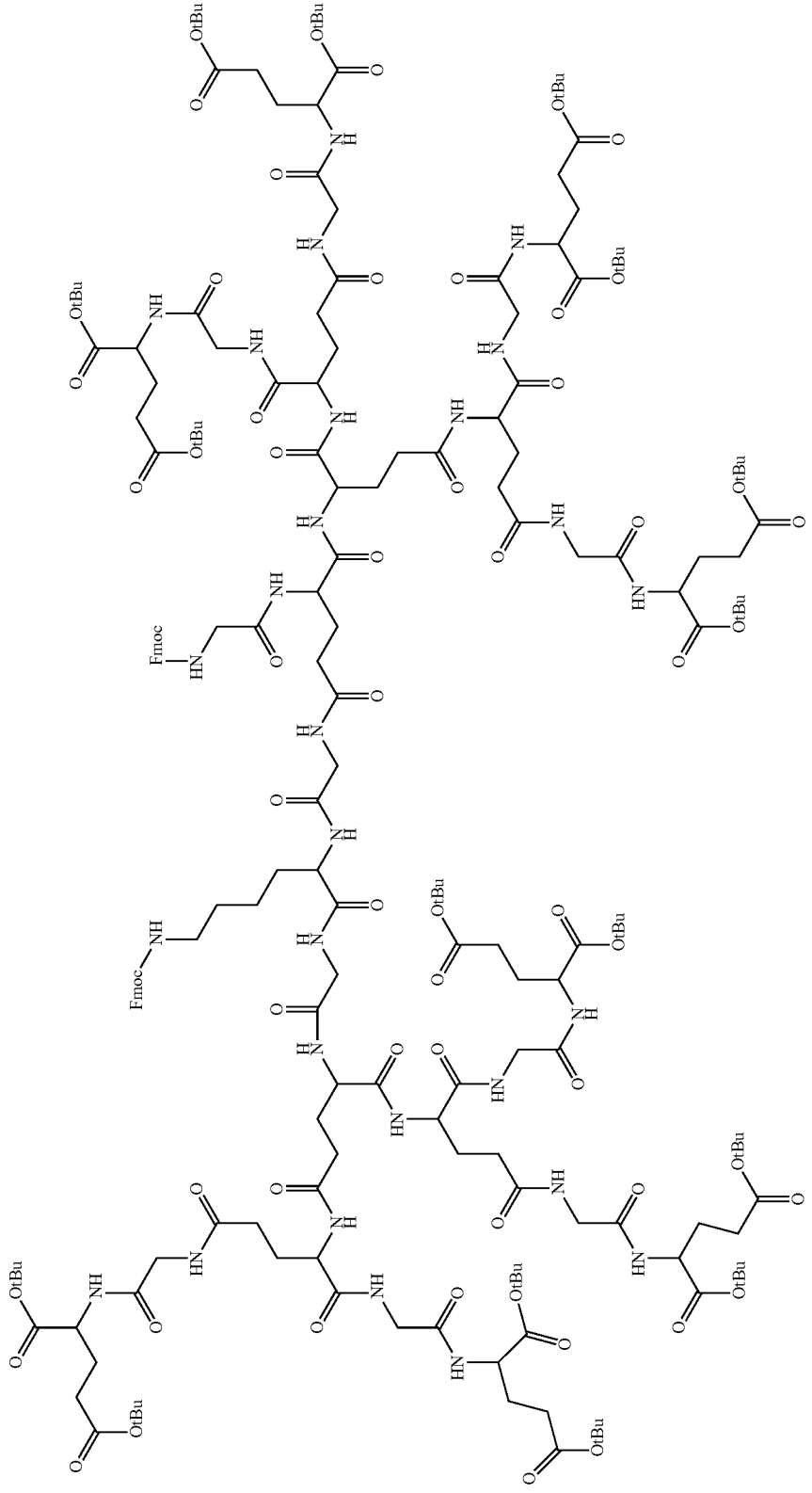

15. A method for preparing the polyethylene glycol conjugated drug or a pharmaceutically acceptable salt thereof according to claim 5, comprising the following steps:

(1) preparing the intermediate

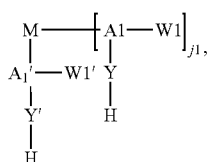

M, A1, A1', W1, W1', Y, Y' and j1 being as defined in claim 5, wherein:
when Y or Y' is other than a direct bond, —Y—H or —Y'—H has a terminal amino group,
when Y or Y' is a direct bond,

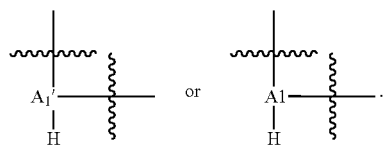

has a terminal amino group;

(2) allowing the PEG with carboxyl group or activated carboxyl group and the intermediate

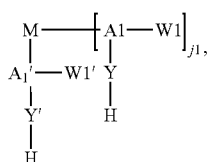

to carry out amidation reaction, to obtain the polyethylene glycol conjugated drug as defined in claim 5.

16. An intermediate for preparing the polyethylene glycol conjugated drug or a pharmaceutically acceptable salt thereof according to claim 7, wherein the intermediate is selected from:

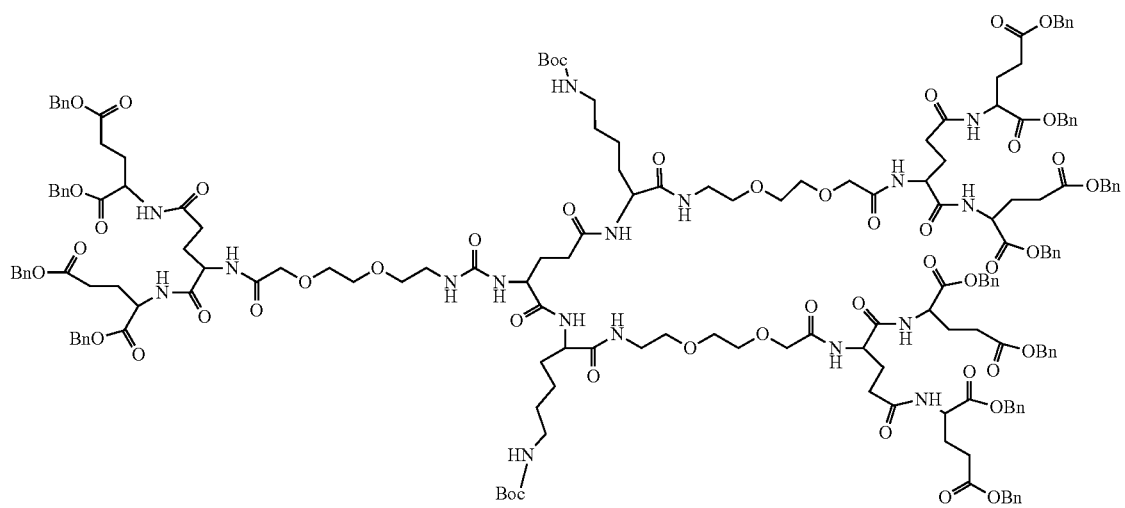

39-30

-continued 26-258

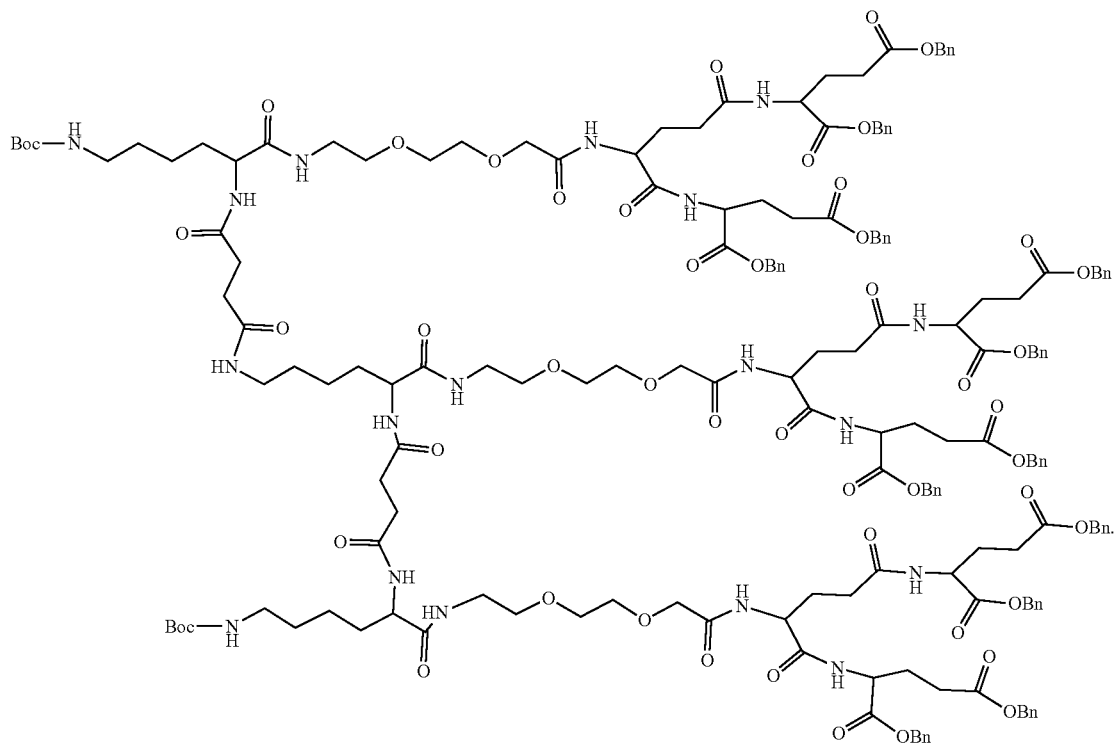

17. A method for preparing the polyethylene glycol conjugated drug or a pharmaceutically acceptable salt thereof according to claim 7, comprising the following steps:

(1) preparing the intermediate

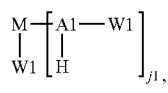

M, A1, W1 and j1 being as defined in claim 7, wherein,

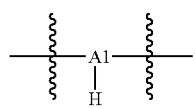

has a terminal amino group;

(2) allowing the PEG with carboxyl group or activated carboxyl group and the intermediate

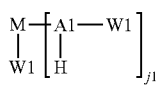

to carry out amidation reaction, to obtain the polyethylene glycol conjugated drug as defined in claim 7.

18. An intermediate for preparing the polyethylene glycol conjugated drug or a pharmaceutically acceptable salt thereof according to claim 9, wherein the intermediate is selected from:

35-36

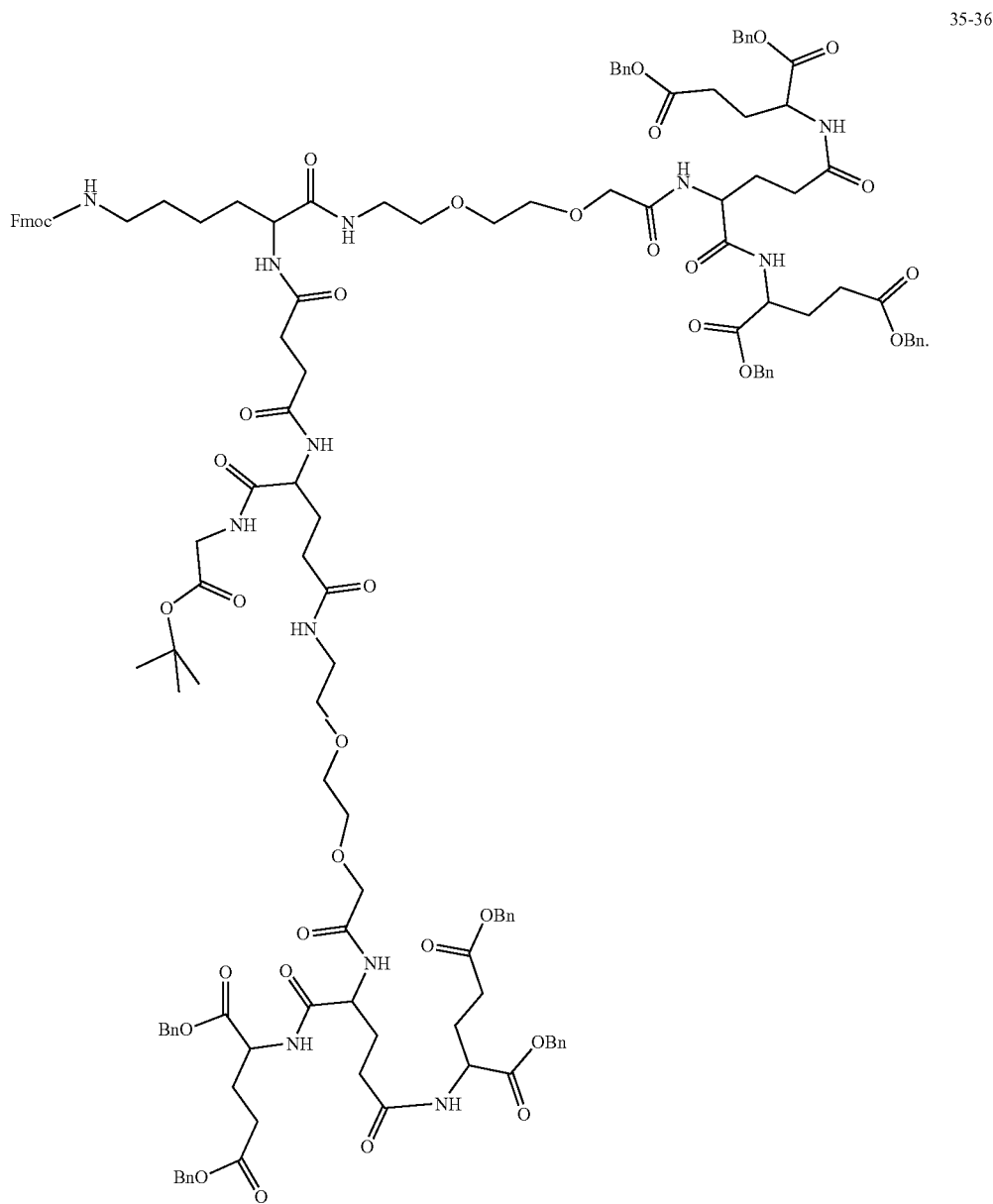

19. A method for preparing the polyethylene glycol conjugated drug or a pharmaceutically acceptable salt thereof according to claim 9, comprising the following steps:
(1) preparing the intermediate

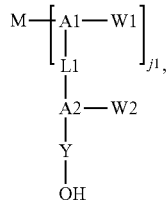

M, A1, A2, W1, W2, L1, Y and j1 being as defined in claim 9, wherein, —Y—OH has a terminal carboxyl group;

(2) allowing the PEG with amino group or activated amino group and the intermediate

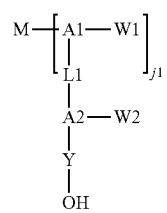

to carry out amidation reaction, to obtain the polyethylene glycol conjugated drug as defined in claim 9.

20. A pharmaceutical composition, comprising a therapeutically effective amount of the polyethylene glycol conjugated drug or a pharmaceutically acceptable salt thereof according to claim 1; the composition further comprises one or more pharmaceutically acceptable excipients.

21. A method for treating a cancer, comprising administering an effective amount of the polyethylene glycol conjugated drug or a pharmaceutically acceptable salt thereof according to claim 1 to an individual in need thereof, wherein the cancer refers to a cancer treated by the active ingredient in the polyethylene glycol conjugated drug.

22. The method according to claim 21, wherein the cancer is selected from colon cancer, leukemia, lymphoma, bladder cancer, bone cancer, brain tumor, medulloblastoma, glioma, breast cancer, adenoma/carcinoid, adrenal cortical cancer, pancreatic islet cell cancer, cervical cancer, endometrial cancer, ovarian cancer, colorectal cancer, skin cancer, esophageal cancer, eye cancer, gallbladder cancer, stomach cancer, head and neck cancer, liver cancer, melanoma, Kaposi's sarcoma, kidney cancer, oral cancer, lung cancer, nasopharyngeal cancer, neuroblastoma, ovarian cancer, pancreatic cancer, thyroid cancer, parathyroid penile cancer, prostate cancer, urethral cancer, vaginal cancer, vulvar cancer, anal cancer, and sarcoma, as well as metastasis of these cancers.

\* \* \* \* \*